US012577589B2

(12) United States Patent
Hauser et al.

(10) Patent No.: US 12,577,589 B2
(45) Date of Patent: Mar. 17, 2026

(54) VACCINES AND USES THEREOF TO INDUCE AN IMMUNE RESPONSE TO SARS-CoV2

(71) Applicant: GeoVax, Inc., Smyrna, GA (US)

(72) Inventors: Mary Jo Hauser, Marietta, GA (US); Arban Domi, Atlanta, GA (US); Farshad Guirakhoo, Atlanta, GA (US)

(73) Assignee: GeoVax, Inc., Smyrna, GA (US)

( * ) Notice: Subject to any disclaimer, the term of this patent is extended or adjusted under 35 U.S.C. 154(b) by 720 days.

(21) Appl. No.: 17/888,131

(22) Filed: Aug. 15, 2022

(65) Prior Publication Data

US 2022/0396810 A1      Dec. 15, 2022

Related U.S. Application Data

(63) Continuation of application No. PCT/US2021/018033, filed on Feb. 12, 2021.

(60) Provisional application No. 63/026,580, filed on May 18, 2020, provisional application No. 62/992,710, filed on Mar. 20, 2020, provisional application No. 62/977,402, filed on Feb. 16, 2020, provisional application No. 62/976,913, filed on Feb. 14, 2020.

(51) Int. Cl.
*C12N 15/863* (2006.01)
*C07K 14/005* (2006.01)

(52) U.S. Cl.
CPC ........ *C12N 15/8636* (2013.01); *C07K 14/005* (2013.01); *C12N 2710/24143* (2013.01)

(58) Field of Classification Search
None
See application file for complete search history.

(56) References Cited

U.S. PATENT DOCUMENTS

| | | | |
|---|---|---|---|
| 6,998,252 | B1 | 2/2006 | Moss et al. |
| 7,015,024 | B1 | 3/2006 | Moss et al. |
| 7,045,136 | B1 | 5/2006 | Moss et al. |
| 7,045,313 | B1 | 5/2006 | Moss et al. |
| 8,288,125 | B2 | 10/2012 | Howley et al. |
| 8,309,326 | B2 | 11/2012 | Howley et al. |
| 8,414,900 | B2 | 4/2013 | Howley et al. |
| 8,435,543 | B2 | 5/2013 | Howley et al. |
| 8,916,172 | B2 | 12/2014 | Moss et al. |
| 9,133,478 | B2 | 9/2015 | Moss et al. |
| 9,133,480 | B2 | 9/2015 | Moss et al. |
| 9,453,239 | B2 | 9/2016 | Moss et al. |
| 9,879,231 | B2 | 1/2018 | Moss et al. |
| 10,421,978 | B2 | 9/2019 | Moss et al. |
| 10,519,186 | B2 | 12/2019 | Moussa et al. |
| 10,960,070 | B2 | 3/2021 | Graham et al. |
| 2005/0069869 | A1 | 3/2005 | Ambrosino et al. |
| 2007/0092936 | A1 | 4/2007 | Haynes |
| 2007/0105193 | A1 | 5/2007 | Vilalta et al. |
| 2008/0118530 | A1 | 5/2008 | Kew et al. |
| 2008/0193483 | A1 | 8/2008 | Moss et al. |
| 2012/0263750 | A1 | 10/2012 | Moss et al. |
| 2013/0344100 | A1 | 12/2013 | D'Aoust et al. |
| 2015/0266929 | A1 | 9/2015 | Compans et al. |
| 2016/0040135 | A1 | 2/2016 | Moss et al. |
| 2019/0030158 | A1 | 1/2019 | Protzer et al. |
| 2019/0290745 | A1 | 9/2019 | Robinson et al. |
| 2020/0030432 | A1 | 1/2020 | Ciaramella et al. |
| 2020/0325182 | A1 | 10/2020 | Keller et al. |
| 2021/0246170 | A1 | 8/2021 | Langedijk et al. |
| 2021/0275664 | A1 | 9/2021 | Graham et al. |
| 2021/0299245 | A1 | 9/2021 | Prow et al. |

FOREIGN PATENT DOCUMENTS

| | | | |
|---|---|---|---|
| CH | 568392 | A5 | 10/1975 |
| CN | 1840188 | A | 10/2006 |
| CN | 1918288 | A | 2/2007 |
| EP | 0538496 | A1 | 5/1993 |
| EP | 2402451 | A2 | 1/2012 |
| EP | 3045181 | B1 | 11/2018 |
| EP | 3928789 | A1 | 12/2021 |
| WO | WO 1994/012617 | A1 | 6/1994 |
| WO | WO 1998/008539 | A1 | 3/1998 |
| WO | WO 1999/063062 | A1 | 12/1999 |
| WO | WO 2000/003030 | A2 | 1/2000 |
| WO | WO 2002/072754 | A2 | 9/2002 |
| WO | WO 2003/078640 | A2 | 9/2003 |
| WO | WO 2003/097845 | A1 | 11/2003 |
| WO | WO 2004/048582 | A2 | 6/2004 |
| WO | WO-2005021713 | A2 | 3/2005 |

(Continued)

OTHER PUBLICATIONS

Mukherjee, R. et al. Global efforts on vaccines for COVID-19: Since, sooner or later, we all will catch the coronavirus. Journal of Biosciences, Springer India, New Delhi. 45(1):1-10, May 7, 2020.
Padron-Regalado, E. Vaccines for SARS-CoV-2: Lessons from Other Coronavirus Strains. Infectious Diseases and Therapy. 9(2):255-274, Apr. 23, 2020.
Shi, Y. et al. An overview of COVID-19. Journal of Zheijiang University-Science. 21(5):343-360, May 1, 2020.
Supplementary European Search Report. European Application No. EP21809653.5. Mailed Jun. 12, 2024.
Tse, L. V. et al. The Current and Future State of Vaccines, Antivirals and Gene Therapies Against Emerging Coronaviruses. Frontiers in Microbiology. 11:1-26, Apr. 24, 2020.
US, 2019/0117758, A1, U.S. Appl. No. 15/543,139, filed Apr. 25, 2019, Robinson et al.
US, U.S. Pat. No. 11,052,148, B2, U.S. Appl. No. 16/305,305, filed Jul. 6, 2021, Guirakhoo et al.

(Continued)

*Primary Examiner* — M Franco G Salvoza
*Assistant Examiner* — Ruixue Wang
(74) *Attorney, Agent, or Firm* — Knowles Intellectual Property Strategies, LLC

(57) ABSTRACT

Provided herein are recombinant modified vaccinia Ankara (rMVA) viral vectors comprising heterologous nucleic acid inserts encoding one or more SARS-CoV2 proteins, peptides, or fragments thereof, operably linked to a promoter compatible with poxvirus expression systems that, upon expression, are capable of inducing protective immunity. The compositions can be used in a priming vaccination strategy or in a prime/boost vaccination strategy to provide immunity to SARS-CoV2 and variants thereof.

28 Claims, 191 Drawing Sheets

Specification includes a Sequence Listing.

(56)                References Cited

FOREIGN PATENT DOCUMENTS

| WO | WO 2005/048957 A2 | 6/2005 |
|----|-------------------|--------|
| WO | WO 2006/026667 A2 | 3/2006 |
| WO | WO-2006022215 A1 | 3/2006 |
| WO | WO 2006071250 A2 | 7/2006 |
| WO | WO 2007/012691 A1 | 2/2007 |
| WO | WO 2008/142479 A2 | 11/2008 |
| WO | WO 2010/062757 A1 | 6/2010 |
| WO | WO 2011/047031 A2 | 4/2011 |
| WO | WO 2011/103417 A2 | 8/2011 |
| WO | WO 2013/059498 A1 | 5/2013 |
| WO | WO 2014/005958 A1 | 1/2014 |
| WO | WO 2015/009946 A1 | 1/2015 |
| WO | WO 2015/066715 A1 | 5/2015 |
| WO | WO 2015/175340 A1 | 11/2015 |
| WO | WO 2016/034678 A2 | 3/2016 |
| WO | WO 2016/068919 A1 | 5/2016 |
| WO | WO 2016/115116 A1 | 7/2016 |
| WO | WO-2016/116398 A1 | 7/2016 |
| WO | WO 2017/120577 A1 | 7/2017 |
| WO | WO 2017/136419 A1 | 8/2017 |
| WO | WO 2017/143016 A1 | 8/2017 |
| WO | WO 2017/210181 A1 | 12/2017 |
| WO | WO 2018/195447 A1 | 10/2018 |
| WO | WO 2019/018501 A1 | 1/2019 |
| WO | WO 2019/040846 A1 | 2/2019 |
| WO | WO 2019/060356 A1 | 3/2019 |
| WO | WO 2020/247547 A1 | 12/2020 |
| WO | WO 2021/158565 A2 | 8/2021 |
| WO | WO 2021/163365 A1 | 8/2021 |
| WO | WO 2021/165667 A1 | 8/2021 |
| WO | WO 2021/181100 A1 | 9/2021 |
| WO | WO 2021/188969 A1 | 9/2021 |
| WO | WO 2021/194826 A1 | 9/2021 |
| WO | WO 2021174142 A1 | 9/2021 |
| WO | WO 2021/198706 A1 | 10/2021 |
| WO | WO 2021216743 A2 | 10/2021 |
| WO | WO 2021/236550 A1 | 11/2021 |
| WO | WO 2022/169895 A1 | 8/2022 |

OTHER PUBLICATIONS

US, U.S. Pat. No. 11,278,607, B2, U.S. Appl. No. 16/068,527, filed Mar. 22, 2022, Robinson et al.

US, U.S. Pat. No. 11,098,086, A1, U.S. Appl. No. 16/077,215, filed Aug. 24, 2021, Robinson, Harriet.

US, 2020/0171141, A1, U.S. Appl. No. 16/631,489, filed Jun. 4, 2020, Guirakhoo et al.

US, U.S. Pat. No. 11,311,612, B2, U.S. Appl. No. 16/648,693, filed Apr. 26, 2022, Guirakhoo et al.

US, 2021/0220469, A1, U.S. Appl. No. 16/641,728, filed Jul. 22, 2021, Guirakhoo, Farshad.

US, U.S. Pat. No. 11,413,341, B2, U.S. Appl. No. 16/796,350, filed Aug. 16, 2022, Robinson et al.

US, 2021/0100891, A1, U.S. Appl. No. 17/000,768, filed Apr. 8, 2021, Guirakhoo et al.

US, 2022/0118082, A1, U.S. Appl. No. 17/368,761, filed Apr. 21, 2022, Guirakhoo et al.

US, 2022/0112248, A1, U.S. Appl. No. 17/409,574, filed Apr. 14, 2022, Robinson, Harriet.

US, 2022/0160853, A1, U.S. Appl. No. 17/542,100, filed May 26, 2022, Guirakhoo et al.

US, 2022/0152190, A1, U.S. Appl. No. 17/584,231, filed May 19, 2022, Robinson et al.

US, 2022/0313808, A1, U.S. Appl. No. 17/726,254, filed Oct. 6, 2022, Guirakhoo et al.

U.S. Appl. No. 17/876,682, filed Jul. 29, 2022, Robinson, Harriet.

U.S. Appl. No. 17/950,989, filed Sep. 22, 2022, Guirakhoo, Farshad.

Arora, K. et al. Multi-Antigenic Virus-like Particle of SARS CoV-2 produced in *Saccharomyces cerevisiae* as a vaccine candidate. BIORXIV. 1-9(May 19, 2020).

Bisht, H. et al. Severe acute respiratory syndrome coronavirus spike protein expressed by attenuated vaccinia virus protectively immunizes mice. Proc Natl Acad Sci U S A. 101(17):6641-6646(Apr. 27, 2004).

Chen, Z. et al. Recombinant modified vaccinia virus Ankara expressing the spike glycoprotein of severe acute respiratory syndrome coronavirus induces protective neutralizing antibodies primarily targeting the receptor binding region. J Virol. 79(5):2678-2688(Mar. 2005).

Czub, M. et al. Evaluation of modified vaccinia virus Ankara based recombinant SARS vaccine in ferrets. Vaccine. 23(17-18):2273-2279(Mar. 18, 2005).

Hu, B. et al. Discovery of a rich gene pool of bat SARS-related coronaviruses provides new insights into the origin of SARS coronavirus. PLoS Pathog. Nov. 30, 2017;13(11):e1006698.

Wennier, S.T. et al. A novel naturally occurring tandem promoter in modified vaccinia virus ankara drives very early gene expression and potent immune responses. PLoS One. 8(8):e73511(Aug. 12, 2013).

Zhu, N. et al. China Novel Coronavirus Investigating and Research Team. A Novel Coronavirus from Patients with Pneumonia in China, 2019. N Engl J Med. 382(8):727-733(Feb. 20, 2020).

US, U.S. Pat. No. 11,638,750, B2, U.S. Appl. No. 17/000,768, filed May 2, 2023, Guirakhoo et al.

US, U.S. Pat. No. 11,701,418, A1, U.S. Appl. No. 15/543,139, filed Jul. 18, 2023, Robinson et al.

US, U.S. Pat. No. 11,801,299, B2, U.S. Appl. No. 17/368,761, filed Oct. 31, 2023, Guirakhoo et al.

US, U.S. Pat. No. 11,857,611, B2, U.S. Appl. No. 17/726,254, filed Jan. 2, 2024, Guirakhoo et al.

US, U.S. Pat. No. 11,896,657, B2, U.S. Appl. No. 17/584,231, filed Feb. 13, 2024, Robinson et al.

US, U.S. Pat. No. 11,897,919, B2, U.S. Appl. No. 17/409,574, filed Feb. 13, 2024, Robinson, Harriet.

US, 2022/0031817, A1, U.S. Appl. No. 17/502,101, filed Feb. 3, 2022, Parker et al.

US, 2022/0396810, A1, U.S. Appl. No. 17/888,131, filed Dec. 15, 2022, Hauser et al.

US, 2022/0040403, A1, U.S. Appl. No. 17/876,682, filed Feb. 9, 2023, Robinson, Harriet.

US, 2022/0256088, A1, U.S. Appl. No. 17/950,989, filed Aug. 17, 2023, Guirakhoo, Farshad.

U.S. Appl. No. 18/229,070, filed Aug. 1, 2023, Hauser et al.

U.S. Appl. No. 18/394,555, filed Dec. 22, 2023, Robinson et al.

U.S. Appl. No. 18/394,580, filed Dec. 22, 2023, Guirakhoo et al.

US, 2024/0156940, A1, U.S. Appl. No. 18/394,555, filed May 16, 2024, Robinson et al.

Ahmed, S.F. et al. Preliminary identification of potential vaccine targets for the COVID-19 coronavirus (SARS-CoV-2) based on SARS-CoV immunological studies. bioRxiv, Feb. 12, 2020 (Feb. 12, 2020), pp. 1-20.

Assarsson, E. et al. Kinetic analysis of a complete poxvirus transcriptome reveals an immediate-early class of genes. PNAS 2008; 105(6):2140-2145.

ATCC #VR-1508. MVA 1974/NIH Clone 1 Vaccinia Virus.

Broyles, SS. Vaccinia virus transcription. J Gen Virol. 2003;84(Pt 9):2293-2303.

Chakrabarti, S. et al. Compact, synthetic, vaccinia virus early/late promoter for protein expression. Biotechniques. 1997;23(6):1094-1097.

Cochran, M.A. et al. In vitro mutagenesis of the promoter region for a vaccinia virus gene: evidence for tandem early and late regulatory signals. J Virol. 1985;54(1):30-37.

Coupar, B.E. et al. Effect of in vitro mutations in a vaccinia virus early promoter region monitored by herpes simplex virus thymidine kinase expression in recombinant vaccinia virus. J Gen Virol. 1987;68(Pt 9):2299-2309.

De Haan, C.A.M. et al. Assembly of the coronavirus envelope: homotypic interactions between the M proteins. J Virol. 2000;74(11):4967-78.

(56)             References Cited

OTHER PUBLICATIONS

Doolan, D. L. et al. Circumventing genetic restriction of protection against malaria with multigene DNA immunization: CD8+ cell-, interferon gamma-, and nitric oxide-dependent immunity. J. Exp. Med. 183:1739-1746 (1996).

Geiben-Lynn, R. et al., Kinetics of recombinant adenovirus type 5, vaccinia virus, modified vaccinia ankara virus, and DNA antigen expression in vivo and the induction of memory T-lymphocyte responses. Clin Vaccine Immunol. 2008; 15(4):691-696.

GenBank Accession No. AFV31202.1. Membrane glycoprotein [Marburg Marburgvirus].

GenBank Accession No. AFV31201.1. viral protein 40 (VP40) [Marburg marburgvirus].

GenBank Accession No. JX458834. Marburg marburgvirus isolate MARV/*H. sapiens*-tc/COD/2000/24 DRC, complete genome.

GenBank Accession No. MN908947.3. Severe acute respiratory syndrome coronavirus 2 isolate Wuhan-Hu-1, complete genome.

GenBank Accession No. MT039888.1. Severe acute respiratory syndrome coronavirus 2 isolate SARS-CoV-2/human/USA/MA-CDC-03038398-001/2020, complete genome.

GenBank Accession No. QHD43416. Surface glycoprotein [Severe acute respiratory syndrome coronavirus 2].

GenBank Accession No. QHD43418. Envelope protein [Severe acute respiratory syndrome coronavirus 2].

GenBank Accession No. QHD43419. Membrane glycoprotein [Severe acute respiratory syndrome coronavirus 2].

GenBank Accession No. U94848.1. Vaccinia virus strain Ankara, complete genomic sequence.

Hammond, J.M. et al. A synthetic vaccinia virus promoter with enhanced early and late activity. J Virol Methods. 1997;66(1):135-1380.

Hu, D. et al. Genomic characterization and infectivity of a novel SARS-like coronavirus in Chinese bats. Emerging Microbes & Infections, Sep. 12, 2018 (Sep. 12, 2018), vol. 7, No. 154, pp. 1-10. entire document.

International Search Report and Written Opinion from PCT Patent Application No. PCT/US2021/018033, issued Jul. 1, 2021. 30 pages.

Kirchdoerfer, R.N. et al., Pre-fusion structure of a human coronavirus spike protein. Nature. Mar. 3, 2016; 531(7592):118-21.

Levy, D. COVID-19 Vaccines Latest Facts and Fallacies. University of Nebraska Medical Center. Feb. 9, 2020 (Feb. 9, 2020), pp. 1-25.

Li, W. et al., 2003. Angiotensin-converting enzyme 2 is a functional receptor for the SARS coronavirus. Nature 426:450-454.

Li, F. 2016. Structure, Function, and Evolution of Coronavirus Spike Proteins. Annu Rev Virol 3:237-261.

Mayr, A. et al. 1975 Infection 3:6-14.

Meyer, H. et al. Mapping of deletions in the genome of the highly attenuated vaccinia virus MVA and their influence on virulence. 1991 J Gen Virol 72: 1031-1038.

Mortola, E. & Roy, P. Efficient assembly and release of SARS coronavirus-like particles by a heterologous expression system. FEBS Lett. 2004;576(1-2):174-8.

Moss, B. et al. Reflections on the early development of poxvirus vectors. Vaccine, 2013, 31(39), 4220-4222.

Naskalska, A. et al. Functional Severe Acute Respiratory Syndrome Coronavirus 2 Virus-Like Particles From Insect Cells. Front Microbiol. Oct. 20, 2021;12:732998.

Neuman, B.W. et al., A structural analysis of M protein in coronavirus assembly and morphology. J Struct Biol. 2011;174(1):11-22.

Nieto-Torres, J.L. et al., Subcellular location and topology of severe acute respiratory syndrome coronavirus envelope protein. Virology. 2011;415(2):69-82.

Ober, B.T. et al. Immunogenicity and Safety of Defective Vaccinia Virus Lister: Comparison with Modified Vaccinia Virus Ankara. J. Virol., Aug. 2002 (p. 7713-7723).

Orubu, T. et al., Expression and cellular immunogenicity of a transgenic antigen driven by endogenous poxviral early promoters at their 25 authentic loci in MVA. PLoS One. 2012;7(6):e40167.

Perkus, M.E. et al., Cloning and expression of foreign genes in vaccinia virus, using a host range selection system. J Virol. 1989;63(9):3829-3836.

Perlman, S. & Netland, J., Coronaviruses post-SARS: update on replication and pathogenesis. Nature Reviews Microbiology 2009; 7:439-450).

Perlman, S. Another Decade, Another Coronavirus. NEJM (Jan. 24, 2020); doi:10.1056/NEJMe200112610.

Prideaux, C.T. et al. Comparative analysis of vaccinia virus promoter activity in fowlpox and vaccinia virus recombinants. Virus Res. 1990; 16(1):43-57.

Raz, E. et al., PNAS (USA) 91 :9519-9523 (1994).

Sancho, M.C. et al., The block in assembly of modified vaccinia virus Ankara in HeLa cells reveals new insights into vaccinia virus morphogenesis. J Virol. 2002;76(16):8318-8334.

Schmitt, J.F. et al., Sequence and transcriptional analysis of the vaccinia virus HindIII I fragment. J Virol. 1988;62(6):1889-1897.

Sedegah, M. et al. Protection against malaria by immunization with plasmid DNA encoding circumsporozoite protein. PNAS (USA) 91 :9866-9870 (1994).

Sutter, G. and Moss, B. Nonreplicating vaccinia vector efficiently expresses recombinant genes. 1992 PNAS USA 89: 10847-10851.

Tascon, R. C. et al. Vaccination against tuberculosis by DNA injection. Nat. Med. 2:888-892 (1996).

Tripathy, D.N. et al. Regulation of foreign gene in fowlpox virus by a vaccinia virus promoter. Avian Dis. 1990;34(1):218-220.

Ulmer, J. B. et al. Heterologous protection against influenza by injection of DNA encoding a viral protein. Science 259: 1745-1749 (1993).

Venkatagopalan, P. et al., Coronavirus envelope (E) protein remains at the site of assembly. Virology. 2015;478:75-85.

Wan, Y. et al., Receptor recognition by novel coronavirus from Wuhan: An analysis based on decade-long structural studies of SARS, J. Virol. Apr. 2020 94(7):e00127-20.

Weir, J.P. & Moss, B. Determination of the promoter region of an early vaccinia virus gene encoding thymidine kinase. Virology. 1987;158(1):206-210.

Wittek, R. et al. Mapping of a gene coding for a major late structural polypeptide on the vaccinia virus genome. J Virol. 1984;49(2):371-378.

Wu, F. et al. A new coronavirus associated with human respiratory disease in China. Nature, Feb. 3, 2020 (Feb. 3, 2020), vol. 579, pp. 265-269.

Wu, J.T. et al., Nowcasting and forecasting the potential domestic and international spread of the SARS-CoV2 outbreak originating in Wuhan, China: a modelling study. The Lancet (Jan. 31, 2020); doi: 10.1016/S0140-6736(20)30260-9.

Wyatt, L.S. et al. Correlation of immunogenicities and in vitro expression levels of recombinant modified vaccinia virus Ankara HIV vaccines. Vaccine. 2008;26(4):486-493.

Wyatt, L.S. et al., Development of a replication-deficient recombinant vaccinia virus vaccine effective against parainfluenza virus 3 infection in an animal model. Vaccine. 1996; 14(15):1451-1458.

Yang, Z. et al., Genome-wide analysis of the 5' and 3' ends of vaccinia virus early mRNAs delineates regulatory sequences of annotated and anomalous transcripts. J Virol. 2011;85(12):5897-5909.

Zhou, P. et al., A pneumonia outbreak associated with a new coronavirus of probable bat origin, Nature. Feb. 3, 2020;1-4; doi:10.1038/s41586-020-2012-7.

Tripp, Ralph A. et al., "Monoclonal antibodies to SARS-associated coronavirus (SARS-CoV): identification of neutralizing and antibodies reactive to S, N, M and E viral proteins." Journal of virological methods 128.1-2, 21-28, 2005.

Altenburg, A. F. et al., "Modified Vaccinia Virus Ankara Preferentially Targets Antigen Presenting Cells *In Vitro, Ex Vivo and In Vivo*" Sci. Rep., 7:8580, Aug. 17, 2017.

Buchholz, U. J. et al., "Contributions of the structural proteins of severe acute respiratory syndrone coronavirus to protective immunity" PNAS, vol. 101, No. 26, 9804-9809, Jun. 29, 2004.

Gasteiger, G. et al., "Cross-Priming of Cytotoxic T Cells Dictates Antigen Requisites for Modified Vaccinia Virus Ankara Vector Vaccines" JVI, vol. 81, No. 21, 1195-11936, Nov. 2007.

(56)  References Cited

OTHER PUBLICATIONS

Liu, L. et al., "Dendritic Cells are preferentially targeted among hematolymphocytes by Modified Vaccinia Virus Ankara and play a key role in the induction of virus-specific T cell responses in vivo" BMC Immunol., 9:15, Apr. 15, 2008.

Stone, S. et al., "Multi-Antigen Viral-Vectored Vaccine Protects Against SARS-CoV-2 and Variants in a Lethal hACE2 Transgenic Mouse Model" Vaccines, 13, 411, Apr. 15, 2025.

Full Length S-M-E (SEQ ID NO: 46)

Vaccinia mH5 promoter                                                                 Kozak AAAATTGAAAATAAATACAAAGGTTCTTGAGGGTTGTGTTAAATTGAAAGCGAGAAATAATCATAA | gccacc Start of S ATG | TTCGTGTCGTTCCTAGTCCTACTACCGGCTAGTCTTCTCAGTGTGTAAACCTAACAACGAGAACACAACTACCACCGG
CGTACACCAATTCTTTCACAGAGGAGTATATTACCCGGACAAGGTGTTCAGATCCTCCGTACTACATTCTACACAGA
CCTATTCCTACCGTTCTTCTCTAACGTAACATGGTTCCACGCGATCCATGTCTCTCTGGAACAAACGAAGGAAGATTC
GATAAACCCGGTCTTGCCGTTCAACGATGGTGTATACTTTGCGTCCACCGAGAGTCCAACATCATCAGAGGATGGATCT
TCGGAACCACCTTGGATTCTAAGGACCCAGTCCTTGCTAATCGTCAACAAGCGACAACAAGTCCTGGATGGAATCTGCGA
ATTCCAGTTCTGTAACGACCCGTTCTTGGGAGTCTACTACCACAGAACAACAAGTCCTGGATGGAATCCGAGTTCAGA
GTCTACTCTTCCCGCGAACAACTGGCACCTTGCGAATATGTATCTCAGCCGGTTCCTAATGGACCTAGAGGGAAAGCAGGGAA
ACTTCAAGAACCTAAGAGAGTTCGTATTCAAGAACATCGACGGATCTTCAAGATCTACTCCAAGCCACACTCCGATCAA
CCTAGTTAGAGATCTACCGCAAGGATTCTCTGCGGCTAGAACCGTTAGTAGATTTGCCGATCGGAATCAACATCACCAGA
TTCCAGACAACTACTAGCGCTACACAGATCTTACCTAACGCCGGGAGATTCTTCTTCTGATGGACTGCTGGTGCTGCGG
CTTATTATGTAGGATACCTACAGCCGGAGAACCTTCCTATTGAAGTACAAACGAAACCATCACCGATGCCGGTAG
ATTGTGTCTCTAGATCCGCTATCCGAAACGAAGTGCACCCTAAAGTCTTTCACCGTCGAGAAGGGAATCTACCAGACCTC
CAACTTTAGAGTACAGCCGACCGGAATCCATCGTCGTCAGATTTCCGAACATCATCGTTCCGGTTCCGTTCGGAGAAGTGTTC
AACGGCGGACAAGATTTGGCGTCGTGTCTATGCGGTGGAACAGAAAAAGAATCAGTAACTGGTCGCGGACTACTCCGTCCTAT
ACAACTCTGCCTCTTTCTCCACGTTCAAATGCTACGGTGTATCTCCGACAAAGCTAAACGATCTATGCTTCACCAACGTC
TACGCGGACTCCTTCGTAATCAGAGGAGATGAAGTTAGACAGATTGGCGCGGGACAAACTGGAAAGATCGCGGATTAT
AACTACAAGTCTACCGGACGACTTCACCGGAGGACTTCAGGAGGATGTAATTGGCGTGGAAGCCTAAAGCCGTTCGAGAGAGACATCTCCACGCAAATCTATC
AGGCTGGATCTACACCGTGTAATGGTGTCGAAGGATTCAACTGCTACTTCCCGCGTACTACACTACGGAGCAGTATGTGGA
AAACGGTGTAGGATATGCTCAGCCGTACAGAGTCGGTAAATGCCGTAAAAGTCCAACTGCTCAACTTAACTTCAACGGACTTC
ACGGAATCTAACAGAGAAGTTTCTACGGTTCCAGCAGTTCGGAAGAGATATGCGGGAAGAGATACAACAGACGCTGTCAGAGAT
CCGCAAACCTTGGAGATCCTAGATATCACACCGTGTCTTCGGTGGTCTCGTAATTACTCCGGGAACGAACACCT
CCAATCAAGTAGCGGTACTATACCAGGACGTGAACTGTACAGAAGTACCGGTAGTATTCACGCGGATCAACTAACAC
CAACTTGGAGAGTGTACTCCACCGGATCTAACGTATTCCAAACAAGAGGCGGGATGTCTAATCGGGAGCGGGAACACGTAA

FIG. 1B

ACAACTCCTACGACGAATGTGATATCCCGATTGGAGCGGGGAATCTGTGCGTCTTACCAAACACAAACAAACTCTCCGAGAA
GAGCGGAGATCTGTAGCCTCTCAATCTATTATCGCCTACACCATGTCCTTGGGAGCCGAAAATTCTGTCGGCGTACTCCAA
CAATTCTATCGCGATCCCGACAAACTTCACCATCTCTGTAACAACCGAGATCCTACCGGTGTCTCATGGATCCAAGACATCT
GTCGATTGCACCATGTACATCTGCGGAGATTCCACCGGGAGTTCCAACCTACTACTACAGTACGGATCTTTCGTACCC
AGCTAAACAGAGCGGTTGACTGGAATCGCTGTAGAGCAGGATAAGAACACTCAAGAGGTATTCGCGCAGTCAAGCAG
ATCTATAAGACTCCGCCGATCAAGGACTTCGGAGGTTTCAACTTCTCTCAGATCTTGCCGGATCCGTCCAAACCGTCTA
AGAGATCTTTCATCGAGGACTACTATTCAACAAAGTCACCCTAGCTGACGCGGGATTCATCAAACAATACGGAGATTG
CTTGGGAGACATTGCGGCGGCGAGAGATCTAATTTGCGCGCAGAAGTTTAACGGATTGACAGTACTACCGCCGCTACTAACC
GATGAGATGATTGCGCAGTACACGTCTGCTCTATTGGGGAACAATTACAAGTGATGGACATTGGAGCGGTGCC
GCTCTACAAATTCCGTTTGCTATGCAAATGGGCGTACAGATTCAATCGCGAACCAGTTCAATTCCGCGATCGGAAAGATCCAGGA
ACCAGAAGCTAATCGCGAACCAGTTCAATTCCGCGATCGGAAAGATCCAGGACACAGTCTATCTTCTACTGCTTCGGCGTT
GGGAAAGCTACAGGATGTAGTAAATCAAAAACGCGCAGGCGCTAAACACCTTGGTCAAGCAACTATCCTCTAACTTCGG
AGCGGATCTCGTCCGTCCGTCCTAAAGACATCTTATCCAGACGTAACAGCCTACGTAACAGCAACTACTAGATCGATAGAGACTAAT
CACTGGAAGATTGCAGTCCCTACAGACCTACGTTGGGACAATGTGTCTTGGGACAATGTGTCTTGCGGAGATTAGAGCCCTGCTAA
TCTAGCTGCGACCAAGATGTCCGAATTGTCGCGCGGCCATGTGCCATGTGGAAAGGGATACCACCT
AATGTCTTTCCCACAATCTCGCGCCGCGCATGTATCCTACTACATGTCCGGGCCGCAAGAAAGAACTTC
ACAACAGTCCAGCGATCTGCCATGATGGAAAAGCTCATTCCCGAGAGAGGGAGTCTTTGTCTCTAACGGAACTCATT
GGTTCGTCACCCAGAGAAAACTTCTACGGAGAAAGCCGCAGATCTCTACGATACCGTCGGATGTGGGAGACTGGGACG
TGGTCATCGGAATCGTAAACAATACCGTCTAAACATCCGTCTACGATCTCCGGATGTGGGAGACTTCAAAGAAGAGTTGGACA
AGTACTTCAAGAACCACACCTCTCCGATGTGGACTTGGGAGATATCTCTGGAATCAACGGCGTCCGTCGTCAACATCCA
GAAAGAAATCGATAGATTGAACGAGGTCGCGAAGAACTTGAACGAGTCCCTATCTGCTGTGGGAGACTAATTGGGAGATCAAGAGCTAGGAAAAT
ACGAGCAGTACACATCAAGTGGCCCGTGGCCGTGGTACATCTGCTAGGATTCATTGGTCTGGCTGGACTAATTGCTGGACTAAGACAGTCCATGGTCACCAT
CATGCTATGCGTGTATGACCTCCGTGTTGCTCCGTGTCTAAAGGGATGGTTGTTCCTGCGGATCCGTGTTGCAAGTT

End of S   C-tag gagccagaggct TAATAAttttatc

CGATGAAGATGATAGTGAACCGGTCCTAAAGGGTGTCAAGCTGTCAAGCTACACTACACTACACTgagccagaggct...

Vaccinia P11 promoter          Kozak Start of E

TTTCATTTTGTTTTGTTTTCTATGCTATAA gccacc ATG TACTCCTTCCGTGTCCGAAGAAACCGGAACCTTGATCGTCAACTCC
GTCCTACTATTCCTACGGCGTTCGTTCGTTCCTACTAGTAACCCTAGCTATCCTAACCTAGTATCCTAACCGGCGCTAAGACTATGTGGCGTACTG
CTGCAACATCGTCAACGGTCGTCCCTAGTGAAGCCGGTCCGTCTACTTCTACTCCAGAGTCAAGAACCTAA

FIG. 1C

End of E    C-Tag                                         C-Tag    End M

ACTCCTCTAGAGTCCCGGACCTACTAGTT|gagccagaggct|TAATTAAataaaaaTTATTA|agcctctggctc|CTGGACTAGTAGAGCGAT
ATTATCGGAAACTGGAGGAGTGGTCGGTGTTAGCTTGTTAGTTCCGATTCTGTATCTGTAGTTCTCTAGAATACGCCGCAAATCCAGAA
TCTCCCGGCGACTCTTTGAGAGGCTCCCAACTTATAGTACGATAGGGGTTCTAGAGGTCGCTACGGTGATCTCCTTCGGTA
GGTCCTTGATGTCACATCTTCCTAGGTGTCCCGCAATTCTTAGATGTCCTCTTAGGGGTACGTTCAATGTGTCCGATAACCAAT
TCGGATTCCAATAGCGGTCTCGGTTAGGATGGTCCATGTAGGGGTCCATGTCAATAGGGATGTTCGTCTCCGGGTTGAACG
ACCACACATAGATCTGGTTCTCGCGAATAGTCTGAAGGAGGCGGATGAAGTAGGATAGCCACATTAGTCCTACTAGACAAG
CCATAGGCGATCGGCCATTCCACCTGTGATCCAGTTGATTCTGTAGACCGCGCAGAACGAAGCAGGCCAAGTGACCG
GCCATAGTAGCCATAGGAAGATTAGCTTGATGATGTACAAGAATCTGTTCCGTTCCGCGAACTGTAGTAGGCA
GATCCAGGTTAGGAATAGGAATCCGATGACTAGGTTCCACTGCTCTAGTAG

Start of M Kozak

CTTCTTCAACTCTTCGACGGTGATGGTTCCGTTAGAATCCGC|CAT|ggtggc|TTATGATTATTTCTCGCTTTCAATTTAACAC

Vaccinia mH5 promoter

AACCCTCAAGAACCTTTGTATTTATTTCAATTTTT

FIG. 1D

Full Length S-M-E (SEQ ID NO: 47)

| Vaccinia mH5 promoter | SmaI | Kozak |
| --- | --- | --- |

AAAAATTGAAAATAAATACAAAGGTTCTTGAGGGTTGTGTTAAATTGAAAGGCGAGAAATAATCATAA|CCCGGGgcacc

Start of S

ATG TTCGGTGTTCCTAGTTCTTCTACCGGCTAGTCTTCTCAGTGTGTAAACCTAACAACGAGAACACCTACCACCGG
CGTACACCAATTCTTCACAAGAGGAGTATATTACCCGGACAAGGTGTTCAGATCCTCCGTACTACATTCTACACAGA
CCTATTCCTACCGGTCTTCTCTAACGTAACATGGTTCCACGCGATCCATGTCTCTGGAACAAACGAAGAGATTC
GATAAACCCGGTCTTGCCGTTCAACGATGGTGTATACTTTGGCGTCCACCGAGAAGTCCAACATCATCAGAGGATGGATCT
TCGGAACCACCTTGGATTCTAAGACCCAGTCCTTGCTAATCGTCAACAACGCGACAACGTCGTCATCAAAGTCTGCGA
ATTCCAGTTCTGTAACGACCCGTTCTTGGGAGTCTACTACCACACAGAACAACAAGTCCTGGAATCCGAGTTCAGA
GTCTACTCTTCCCGCGAACAACTGACACCTTCGTATTCAAGAACATCGACGGATACTTCAAGATCTCCAAGCACACTCCGATCAA
ACTTCAAGAACCTAAGAGAGTTCGTTCTCTGCGCTAGAACCGTTAGTAGATTTGCCGATCGGAATCAACATCACCAGA
CCTAGTTAGAGATCTACCGCAAGGATCTCTGCGCTAGAACCGTTAGTAGATTTGCCGATCGGAATCAACATCACCAGA
TTCCAGACAACTACTAGCGCTACACAGATCTTACCTAACGCCGGGAGATTCTTCTCTGGACTGCTGCTGGTGCTGCGG
CTTATTATGTAGGATACCTACAGCCGAGAACCTTCCTATTGAAGTACAAACGAACCATCACCGATGCCGGTAG
ATTGTGTCTAGATCCGCTATCCGAAACGAAGTGCACCCTAAAGTCTTTCACCGTCGAGAAGGAATCTACCAGACCTC
CAACTTTAGAGTACAGCCGACCGAATCCATCGTCAGATTCCGAACATCATCACGCAACCTATGTCCGTTCGGAGAAGTGTTC
AACGGGACAAGATTTGGGTCTGTCGTTATGCGTGGAACAGAAAAGAATCAGTAACTGGCGTCGGCGACTACTCCGTCCTAT
ACAACTCTGCCTCTTCTCCACGTTCAAATGCTACGGTGTATCTCCGACAAAGCTAAACGATCTATGCTTCACCAACGTC
TACGCGGACTCCTGGTCTTCGTAATCAGAGGAGATGAAGTTAGACAGATTGCGCGGGACAAACTGAAAGATCGGGATTAT
AACTACAAGTCTACCGGACGACTTCACCGGAATTGGCGTGGAATTCAACAACCTAGACTCCAAGTCGGAGGA
AACTACAACTACTTGTACAGACTATTCAGAAAGTCCAACCTAAAGCCGTTCGAGAGAGACATCTCCACCGAAATCTATC
AGGCTGGATCTACACCGTGTAATGGTGTCGAAGGATTCAACTGCTACTTCCCGCTACACTACAGTCTTACGGATTTCAACCGAC
AAACGGTGTAGGATATCAGCCGTACAGAGTCGGTCGTACTATCCTTCGAACTACATCGGCGGATACAACAGAGCGCTGTCAGAT
CCGCAAACCTTGGAGATCCTAGATATCACACCGTGTCTTCGGTGGTCTCTGTAATTACTCCGGGAACGAACACCT
CCAATCAAGTAGCGGTACTATACCAGGACGTGAACTGTACAGAACGTAAGTACCGGTAGCTATTCACGCGGATCAACTAACAC
CAACTTGGAGAGTGTACTCCACCGGATCTAACGTATTCCAAACAAGAGGCGGGATGTCTAATCGGCGGGAACACGTAA

FIG. 1E

ACAACTCCTACGACGAATGTGATATCCCGATTGGAGCGGGGAATCTGTGCGTCTTACCAAACACAAACAAACTCTCCGAGAA
GAGCGGAGATCTGTAGCCTGCTCTCAATCTATTATCGCCTACACCATGTCCTTGGGAGCCGAAAATTCTGTCGGCGTACTCCAA
CAATTCTATCGCGATCCCGACAAACTTCACCATCTCTGTAACAACCGAGATCCTACCGGTGTCTATGGACCAAGACATCT
GTCGATTGCACCATGTACATCTGCGGAGATTCCACGGAGTTGCTCAACCTACTACTACAGTACGGATCTTTCGTACCC
AGCTAAACAGAGCGGTTGACTGGAATCGCTGTAGAGCAGGATAAGAACACTCAAGAGGTATTCGCGCAGTCAAGCAG
AITCTATAAGGACTCCGCCGATCAAGGACTTCGGAGGTTTCAACTTCTCTCAGATCTTGCCGGATCCGTCCAAACCGTCTA
AGAGATCTTTCATCGAGGACTACTATTCAACAAAGTCACCCTAGCTGCGCGGGATTCATCAAACAATACGGAGATTG
CTTGGGAGACAATTGCGGCGGAGAGATCTAATTTGCCGCGCAGAAGTTAACGGATTGACAGTACTACCGCCGCTACTAACC
GATGAGATGATTGCGCAGTACACGTCTCTATTGGGGAACAATTACAAGTGGATGGACAATTGGAGCGGTGCC
GCTCTACAAATTCCGTTTGCTATGCAAATGGCGTACAGATTCAATGCGTAACCCAGAACGTCTTGTACGAGA
ACCAGAAGCTAATCGCGAACCAGTTCAATTCCGCGATCGGAAAGATCCGGAGCACCTTGGTCAAGCAACACCTTGGTCTTCGGCGTT
GGGAAAGCTACAGGATGTAGTAAATCAAAAACGCGCAGGCGCTAAACACCTTGGTCAAGCAACTATCCTCTAACTTCGG
AGCGGATCTCGTCCGTCCTAAAGACATCTTATCCAGACCTACGTAACACAGCCAACTAGTAAGGTCGAAGGCGAGGTCCAGATCGATAGACTAAT
CACTGGAAGATTGCAGTCCCTACAGAACCTACGTAACAGCAACTAATTAGAGCGGCGGAGATTAGAGCCCTGCTAA
TCTAGCTGCGACCAAGATGTCCGAAGATCCGAATTGTGTCTGGGACAATCCAAGAGAGTGACTTCTGCGGGAAAGGGATACCACCT
AATGTCTTTCCCACAATCTCGCGCGCCCATGGTCGTATCCTCTACACATGTAACATATGTCCGGGCCGCAAGAAAAGAACTTC
ACAACAGTCCAGCGATCTGCCATGATGGAAAAGCTCATTCCCGAGAGAGGGAGTCTTTGTCTCTAACGGAACTCATT
GGTTCGTCACCCAGAGAAACTTCTACGAGAAACCGTCTACGATACCGTCTCCGGATGTGGACTTGGGAGAACTGGGACG
TGGTCATCGGAATCGTAAACAATACCGTCTAAACATCTCCGATGGACTTGGGAGGAATCTGGAGGAGTCGTCAACATCCA
AGTACTTCAAGAACCACACACTCTGAAGAGGTCGCGAAGAACTTGAAGGTCCCTAATCGACCTACAAGAGCTAGGAAAAT
GAAAGAAATCGATAGATTGAAGCGGCCGTGGTACATCTGCTAGGATTCATTGCTGACTAATTGCGATCGTCATGGTCACCAT
ACGAGCAGTACATCAAGTGGCCGGTACATCCAGGATTCATTGCTAGGATTCATTGCTGACTAATTGCGATCGTCATGGTCACCAT
CATGCTATGCTGTATGACCTCCGTGTTCCCTGTTGCTCCTGTCTAAAGGGATGTTGTTCCTGCGGATCCTGTGTTGCAAGTT

End of S    C-tag

CGATGAAGATGATAGTGAACCGGTCCAAAGGGTGTCAAGCTACCACTACACTACACA ┌gcagcagaggct┐TAATAAttttatc

Vaccinia P11 promoter

┌TTTCATTTTGTTTTTTCTATGCTATAA┐gccacc┌ATG┐tACTCCTTCGGTCCGAAGAAAACCGGAACCTTGATCGTCAACTCC
Kozak  Start of E
GTCCTACTATTCCTACTAGCGTTCGTTCCTACTAGTAACCCTAGCTATCCTAACCGGCGCTAAGACTATATGTGGTACTG
CTGCAACATCGTCAACGTGTCCCTAGTGAAGCCGGTCCTTCTACTCCACTCCAGAGTCAAGAACCTAA

FIG. 1F

End of E    C-Tag                                        C-Tag    End M

ACTCCTCTAGAGTCCCGGACCTACTAGTT|gagccagaggct|TAATAAAataaaaTTATTA|agcctctggctc|CTGGACTAGTAGAGCGAT ATTATCGGAACTGGAGGAGTGGTCGGTGTTAGCTTGTAGTTCCCGATTCTGTATCTAGAATACGCCGCAAATCCAGAA
TCTCCCGGCGACTCTTGAGAGGCTCCCAACTTATAGTACGATAGGGTTCTAGAGGTCGCTACGGTGATCTCCTTCGGTA
GGTCCTTGATGTCACATCTTCCTAGGTGGTCCCGCAATTCTTAGATGTCCCTCTTAGGATGACCGCTCCGATAACCAAT
TCGGATTCCAATAGCGGTCTCGGTTAGGATGGTTCCATGTAGCGGTCACGTTCAATAGGGATGTTCGTCCGGGTTGAACG
ACCACATAGATCTGGTTCTCGCGAATAGTCTGAAGGAGGGCGATGAAGTAGGATAGCCACATTAGTCCTACTAGACAAG
CCATAGGCGATCGGCGATTCCACCTGTGATCCAGTTGATTCTGTAGACGCAGTTGATGATGTACAAGAATCTGTTCCTGT
GCCATAGTAGCCATAGGAAGATTAGCTTGATGATGTAGCTTGACGCTAGTGTCGGAACTGTGTAGTAGGCA
GATCCAGGTTAGGAATAGGAATCCGATGACTAGGTTCCACTGCTCTAGTAG

Start of M Kozak

CTTCTTCAACTCTTCGACGGTGATGGTCCGTTAGAATCCGC|CAT|ggtggc|TTATGATTATTTCTCGCTTTCAATTTAACAC

Vaccinia mH5 promoter

|AACCCTCAAGAACCTTTGTATTTATTTCAATTTTT|

FIG. 1G

Full Length S-M-E (SEQ ID NO: 156)

Vaccinia mH5 promoter                                                              SmaI

AAAAATTGAAAATAAATACAAAGGTTCTTGAGGGTTGTGTAAATTGAAAGGCGAGAAATAATCATAA|ATAAGCCCGGG

Kozak Start of S gcacc|ATG|TTCGTTGTGTTCCTAGTCCTACTACCGGCTAGTCTCTTCTCAGTGTGTAAACCTAACAACGAGAACACAACTACCA
CCGGCGTACACCAATTCTTCACAAGAGGAGTATATTACCCGGACAAGGTGTTCAGATCCTCCGTACTACATTCTACAC
AGGACCTATTCCTACCGGTCTTCTCTAACGTAACATGGTTCCACGCGATCCATGTCTCTGGAACAAACGGAACGGAAGAG
ATTCGATAACCCGGTCGTCTTGCCGTCCGTTCAACGATGGTGTATACTTTGCGTCCACCGAGAAGTCCAACATCATCAGAGGATGG
ATCTTCGGAACCACCTTGGATTCTAAGACCCAGTCCTTGCTAATCGTCAACAAGAACAACAAGTCCTGGAATCCGAGTT
GCGAATTCCAGTTCTGTAACGACCCGGTTCTTGGGAGTCTACTACCACAAGAAGTCAATATGTATCTCAGCCCGTTCTAATGGACCTAGAGGGAAAGCAG
GAAAACTTCAAGAAACCTAAGAGAGTCGTATTCAAGAACATCGACGATACTTCAAGATCTACTCCAAGCACTCCG
ATCAACCTAGTTAGAGATCTACCGCAAGGATTCTCGCGCTAGAACATCTACCTACGACCGTTAGTAGATTGCCGATCGGAATCAACATCA
CCAGATTCCAGACACTACTAGCGCTACACAGATCTACCTACGACCGGGAGATTCTTCTTCTGATGGACTGCTGGTGC
TGCGGGCTTATTATGTAGGATACCTACACAGCCGAGAACCTTCCTATTGAAGTACAACGGAACCATCACCGATGCC
GTAGATTGTGCTCTAGATCCGCTATCGGAAAACGAAGTGCACCCTAAAGTCTTTCACCGTCGAGAAGGGAATCTACCAGA
CCTCCAACTTTAGAGTACAGCCGACCGAATCCATCGTGAACATCCGAACATCACGAACCTATGTCCGTTCGGAGAAGT
GTTCAACGGGACAAGATTTGCGTCGTCTATGGCGTGGAACAGAAAAAGAATCAGTAACTGGCGTCGGCGGACTACTCCGTC
CTATACAACTCTGCCTCTTTCTCCACGTTCAAATGCTACGGTGTATCTCCGACAAAGCTAAACGATCTATGTTCACCAA
CGTCTACGCGGACTCCTGCTAATCAGAGGAGATGAAGTTAGACAGATTGCGCGGGACAAACTGGAAAGATCGGCGGA
TTATAACTACAAGCTACCGGACGACTTCACCGGATGTGTAAATTGCGTGAAATCCAACAACCTAGACTCCAAAGTCGGA
GGAAACTACAACTACTTGTACAGACTATTCAGAAAGTCCAACCTAAAGCCGTTCGAGAGAGACATCTCCACCGAAATC
TATCAGGCTGGATCTGACACCGTGTAATGGTGTCGAAGGATTCAACTGCTACTTCCCGCTACTCCGGGCTACAGTATG
CGACAAACGGTGTAGGATATCAGCCGTACAGACGTCGGTACTACTACCATGCTCCGGGGCACAGTATG
TGGACGGCAAAAGTCTAACAAGAAGTTTCTACCGTTCGGGAAGAGATATCGCGGAAGTTCCAGCAGTTGTCAG
CCTAACCGAATCTAACAAGTAGCGGTCTAGATCCTAGATATCACACCCGGTCTCTGTAATTACTCCGGGAACGAAC
AGATCCGCAAACCTTGGAGATCCGAGAACTGTACAGGACGTGAACTGTACAGAAGTACCGGTAGTATTCACGCGGATCAACTA
ACCTCCAATCAAGTAGCGGTAGTGTACTATCCACCGGATCTAAGTATTCCAAACAAGAGCGGGATGTCTAATGGGAGGGGAACAC
GTAA

FIG. 1H

ACAACTCCTACGACGAATGTGATATCCCGGATTGGAGCGGGGAATCTGTGTGCGTCTTACCAAACACAAACAACAAACTCTCCGAGAA
GAGCGGAGATCTGTAGCCTCTCAATCTATTATCGCCTACACCAATGTCCTTGGGAGCCGAAAATTCTGTCGCGTACTCCAA
CAATTCTATCGCGATCCCGACAAACTTCACCATCTCTGTAACAACCGAGATCCTACCGGTGTCTATGGACCAAGACATCT
GTCGATTGCACCATGTACATCTGCGGGAGATTCCACCGAGTGCTCAACCTACTACAGTACGGATCTTTCGTACCC
AGCTAAACAGAGCGGTTGACTGGAATCGCTGTAGAGCAGGATAAGAACACTCAAGAGGTATTCGCGCAGTCAAGCAG
ATCTATAAGACTCCGCCGATCAAGGACTTCGGAGGTTCAACTTCTCTCAGATCTTGCCGGATCCGTCCAAACCGTCTA
AGAGATCTTTCATCGAGGACCTACTATTCAACAAAGTCACCCTAGCTAGCGCGGGATTCATCAAACAATACGGAGATTG
CTTGGGAGACATTGCGGCGGAGAGATCTAATTTGCCGCGCAGAAGTTAACGGATTGACAGTACTACCGCCGCTACTAACC
GATGAGATGATTGCGCAGTCAGTGATTGCACACGTCTGCTCTATTGGGCGTCTATTGCAAATGGCGTACAGATTCAAGCGT
GCTCTACAAATTCCGTTTGCTATGCAAATGGCGTACAGATTCAAGCGTACACAGATCCGCGATCGGAAAGATCGGAGTAACGTCTTGTACGAGA
ACCAGAAGCTAATCGCGAACCAGTTCAATTCCGCGATCGGAAAGATCGGAGTAAACACCTGGTCAACTATCCTCTACTTCGG
GGGAAAGCTACAGGATGTAGTAAATCAAAAACGCGCAGGCGCTAAACACCTGGTCAACTATCCTCTAACTTCGG
AGCGGATCTCGTCCGTCCGTAAAGACACATCTTATCCAGATCTAACGACTAGATAAGGTCGAAGCGGGAGGTCCAGATCGATAGACTAAT
CACTGGGAAGATTGCAGTCCCTACAGAACGTAACAGCAACTACGTAACACAGCAATCCAAGAGAGTGGACTTCTGCGGGAAAGGGATACCACCT
TCTAGCTGCGACCAAGATGTCCGAATGTCGGGGACAATGTGTCTTGGGACAATGTGCCGGGCGCAAGAAAAGAACTTC
AATGTCTTTCCCACAATCTCGCCGCCGCATGGTCGTATCCTACACATGTAACATATGTGCCGGGCGCAAGAAAAGAACTTC
ACAACAGTCCAGCGATCTGCCATGATGGAAAAGCTCATTCCCGAGAGAGGGAGTCTTTGTCTCTAACGGAACTCATT
GGTTCGTCACCCAGAGAAACTTCTACGAGAAAGCTCTACGTCTACGCCGTTGGGAGCCGCAGATATCTCGGAATCAACATCCA
TGGTCATCGGAATCGTAAACAATACCGTAAACAATACCGTCCGGATGTGGGAGCCGCAGATATCTCGGAATCAACATCCA
AGTACTTCAAGAACCACACCTCTCCGGATGTGACCGTAGGTCGCGAAGAACTTGAACATCGAAGAGCTAGGAAAAT
GAAAGAAATCGATAGATTGAAACGAGGTCGCGAAGAACTTGAACATCGAAGAGCTAGGAAAAT
ACGAGCAGTACATCAAGTGGCCGCCGTGGTACATCTGCTAGGTACATCTGCTGACTAATTGCTGGTCATCGATCGTCATGGTCCACCAT
CATGCTATGCTGTATGACCTCCTGTTGCGTCCGTGTTCCTGGGATGTTGTTCCTGCGGATCCTGTGTTGCAAGTT

End of S   C-tag

CGATGAAGATGATAGTGAACCGGTCGAACCGGTCCTAAAGGGTGTCAAGCTACACTACACA gagccagagggc TAATAA tttttatgtcgacc

Vaccinia P11 promoter   Kozak   Start of E

TTTCATTTTGTTTTTTTCTATGCTATAA gccacc ATG TACTCCTTCGGTCCGTGTCCGGAAGAAACCGGAAGCCTTGATCGTCAACTCC
GTCCTACTATTCCTACGGTTCGTTCGTTCCTACTAGTAACCCTAGCTATCCTAACCGGCGCTAAGACTACATGTGCGGTACTG
CTGCAAACATCGTCAACGTGTCCCTAGTGAAGCCGGTCCTTCTACTCCACTCCAGAGTCAAGAACCTAA

FIG. 1I

End of E    C-Tag      C-Tag    End M

ACTCCTCTAGAGTCCCGGACCTACTAGTT|gagccagaggct|TAATAAaataaaaaTTATTA|agcctctggctc|CTGGACTAGTAGAGCGAT ATTATCGGAACTGGAGGAGTGGTCGGTGTGTTAGCTTGTTGTAGTTCCCGATTCTCGTATCGTAGAATACGGCGCAAATCCAGAA
TCTCCCGCGACTCTTGAGAGCGCTCCCAACTTATAGTACGATAGGGTTCTAGAGGTCGCTACGGTGATCTCCTTCGGTA
GGTCCTTGATGTCACATCTTCCTAGGTGGGTGCCCGCAATTCTTAGATGTCCCTCTTAGGATGACCGCTCCGATAACCAAT
TCGGATTCCAATAGGCGGTCGGTTAGGATGGTTCCATGTAGCCGGTACGTTCAATAGGATGTTCGTCTCCGGGTTGAACG
ACCACATAGATCTGGTTCTCGCGAATAGTCTGAAGGAGGCGATGAAGTAGGATAGCCACATTAGTCCTACTAGACAAG
CCATAGGCGATCGGCGATTCCACCTGTGATCCAGTTGATTCTGTAGACCGCAGCTAGAGAAGCGAGGCCAAGGTGACCG
GCCATAGTAGCCATAGGAAGATTAGCTTGATGATGTACAAGAATCTGTTCCTGTTCGGCGTACGCGAACTGTAGTAGGCA
GATCCAGGTTAGGAATAGGAATCCGATGACTAGGTTCCACTGCTCTAGTAG

Start of M Kozak

CAT|ggtggc|TTATGATTATTCTCGCTTCAATTAACAC

CTTCTTCAACTCTTCGACGGTGATGGTTCCGTTAGAATCCGC

Vaccinia mH5 promoter

AACCCTCAAGAACCTTTGTATTTATTTTCAATTTTT|ctgcag

FIG. 1J

Stabilized S-M-E (SEQ ID NO: 48)

Vaccinia mH5 promoter                                                                 Kozak

AAAATTGAAAATAAATACAAAGGTTCTTGAGGGTTGTGTTAAATTGAAAGCGAGAAATAATCATAA | gccacc

Stabilized S Start

ATGTTCGTTGTTCCTAGTCTTCTCAGTGTGTAAACCTAACAACGAGAACTAACAACTACCACCGG
CGTACACCAATTCTTCACAAGAGGAGTATATTACCCGGACAAGGTGTTCAGATCCTCCGTACTACATTCTACACAGA
CCTATTCCTACCGGTTCTTCTCTAACGTAACATGGTTCCACGCGATCCATGTCTCTGGAACAAACGAACGAAGAGATTC
GATAAACCCGGTCTTGCCGTTCAACGATGGTGTATACTTTGCGTCCACCGAGAAGTCCAACATCATCAGAGGATGGATCT
TCGGAACCACCTTGGATTCTAAGAACGTCCTTGCTAATCGTCAACAAGAACAACAAGTCCTGGATGGAATCCGAGTTCGA
ATTCCAGTTCTGTAACGACCCGTTCTTGGGAGTCTACTAACCACACAAGTCCGAATATGTATCTCAGCCGGT
GTCTACTCTTCCCGCGAACAACTGCACCTTCGTATTCAAGAACATCGACGGATACTTCAAGATCTACTCCAAGCCACTCCGATCAA
ACTTCAAGAACCTAAGAGAGTTCGTATCTCTGCGGTAGAAGCCGTTAGTAGTACAACCGTTAGTTGCCGATTCAGTAGATCACCAGA
CCTAGTTAGAGATCTACCGCAAGGATCTCTGCGGCTAGAACCGTTAGTAGTACAACCGTTAGTTGCCGATCGGAATCAACATCACCAGA
TTCCAGACAACTACTAGCGCTACACAGATCTTACCTAACGCCGGGAGATTCTTCTTCTGATGGACTGCTGCGTGCTGCGG
CTTATTAATGTAGGATACCTACCAGCCGGAGAACCTTCCTATTGAAGTACAACGGAACCATCACCGATGCCGTAG
ATTGTGTCTCTAGATCCGCTATCCGAAACGAAGTGCACCCTAAAGTCTTTCACCGTCGAGAAGGGAATCTACCAGACCTC
CAACTTTAGAGTACAGCCGACCGAATCCATCGTCGTCAGATTTCCGAACATCACGAACCTATGTCCGTTCGGAGAAGTGTTC
AACGGGACAAGATTTGGCGTCGTCGTCTATGCGGTGAACAGAAAAGAATCAGTAACTGGCGTCGCGGACTACTCCGTCCTAT
ACAACTCTGCCTCTTCTCCACGTCAAATGCTACGGTGTATCTCCGACAAAGCTAAACGATCTATGCTTCACCAACGTC
TACGCGGACTCCTTCGTAATCAGAGGAGATGAAGTTAGACAGATTGCGGGACAAACTGAAAAGATCGCGGATTAT
AACTACAAGCTACCGGACGACTTCACCGGATGTGTAATTGCGTGAACAACCTAGAACTCCAAGTCGGAGGA
AACTACAACTACTTGTACAGACTATTCAGAAAGTCCAACCTAAAGCCGTTCGAGAGAGACATCTCCACGAAATCTATC
AGGCTGGATCTACACCGTGTAATGGTGTCGAAGGATTCAACTGCTACTTCCCGCTACAGTCTTACGGATTTCAACCGAC
AAACGGTGTAGGATATATCAGCCGTACAGAGTCGGCTACTACACGGAGCAGTATGTGGA
CCGAAAAGTCTAACAAGAAGTTTCTACCGGTTCCAGCAGTTCGGAAGAGATATCGCGGATACAACAGAGCGTGTCAGAGAT
CCGCAAACCTTGGAGATCCTAGATATCACACCGTGTTCTTGCGGTGTCTCTGTAATTACTCCGGGAACGAACACCT
CCAATCAAGTAGCGGTACTATACCAGGACGTGAACTGTACAGAAGTACCGGTAGCTATTCACGCGGATCAACTAACAC
CAACTTGGAGAGTGTACTCCACCGGATCTAACGTATTCCAAACAAGAGGCGGGATGTCTAATCGGGGAACACGTAA

FIG. 2B

ACAACTCCTACGACGAATGTGATATCCCGATTGGAGCGGGAATCTGTGCGTCTTACCAAACACAAACAAACTCTCCGAGAA
GAGCGGAGATCTGTAGCCTGCTCTCAATCTATTATCGCCTACACCATGTCCTTGGGAGCCGAAAATTCTGTCGCGTACTCCAA
CAATTCTATCGCGATCCCGACAAACTTCACCATCTCTGTAACAACCGAGATCCTACCGGTGTCTATGACCAAGACATCT
GTCGATTGCACCATGTACATCTGCGGAGATTCCACCGGGAGATTCCAACCTACTACTACAGTACGGATCTTTCGTACCC
AGCTAAACAGAGCGGTTGACTGGAATCGCTGTAGAGCAGGATAAGAACACTCAAGAGGTATTCGCGCAGTCAAGCAG
ATCTATAAGACTCCGCCGATCAAGGACTTCGGAGACTTCGGAGGTTTCAACTTCTCTCAGATCTTGCCGGATCCGTCCAAACCGTCTA
AGAGATCTTTCATCGAGGACTACTATTCAACAAAGTCACCCTAGCTGACGCGGGATTCATCAAACAATACGGAGATTG
CTTGGGAGACATTGCGGCGGAGAGATCTAATTTGCGCGCAGAAGTTAACGGATTGACAGTACTACCGCGCTACTAACC
GATGAGATGATTGCGCAGTCAGTGACACGTCTGCTCTATTGGGGAACAATTACAAGTGATGGACATTGGAGCGGTGCC
GCTCTACAAATTCCGTTTGCTATGCAAATGGCGTACAGATTCAACGGCGTAACCCAGAAGCGTCTTGTACGAGA
ACCAGAAGCTAATCGCGAACCAGTTCAATTCCGCGATCGGAAAGATCCAGGACCAGTCTATCTTCTACTGCTTCGGCGTT
GGGAAAGCTACAGGATGTAGTAAATCAAAAACGCGCAGGCGCTAAACACCTTGGTCAACTATCCTCTAACTTCGG
AGCGGATCTCGTCCCGTCCTAAACGACACATCTTATCCAGATCTTATCCAGACTAGAT[CCACCG]GAAGCGGAGGTCCAGATCGATAGACTAAT
CACTGGAAGATTGCAGTCCCTACGACCTACGTAACACAGCAACTAATTAGAGCGGCGGAGATTAGAGCCTCTGCTAA
TCTAGCTGCGACCAAGAGTGTCCGAATGTCTGGGACAATCCAAGAGAGTGACTTCTGCGGGAAAGGGATACCACCT
AATGTCTTTCCCACAATCTCGGCCCGCATGGTATTCCTCACATGTAACATATGTGGCGCAAGAAAAGAACTTC
ACAACAGCTCCAGCGATCTGCCATGATGGAAAAGCTCATTCCCGAGAGAGGAGCAACACCACCAGGAGTCTTTGTCTCTCTAACGAACTCATT
GGTTCGTCACCCGAGAAAACTTCTACGGAGCCGCAGATCATCCACCAGTCGCTGCGACCG
TGGTCATCGGAATCGTAAACAATACCGTCTACGATCCGTTGGGAGATATCTGGAGATATCTTGGAATCAAGGTCCCTAATCGACACATCCA
AGTACTTCAAGAACCACACCTCCCGATGTGGACTTGGGAGATGTCGGCGAAGAACTTGAACGAGGTCCCTAATCGACCTACAAGAGCTAGGAAAAT
ACGAGCAGTACATCAAGGTGCCGTGGTACATCTGGCTAGGATTCATTGCTGACTAATTGCGACTAATTGGTCACCAT
CATGCTATGCGTGATGACCTCGTGCTGTTCCTGTTCCTGTACCTCCTGTCCTGTTCCTGTGCTCCCTGTTGCTCCTGTGCTCCCTGTCCTGATCCGTGTTGCAAGTT

End of S   C-tag

CGATGAAGATGATAGTGAACCGGTCCTAAAGGGTGTCAAGTACTACACTACACA[agagccagaggct][TAATAAtttttatc]
Vaccinia P11 promoter          Kozak  Start of E
[TTTCATTTTGTTTTTTTCTATGCTATAA][gccacc][ATG]TACTCCTTCGTGTCCGAAGAAACCGGAAGAAACCGGAAACCTTGATCGTCAACTCC
GTCCTACTATTCCTAGCGGTTCGTTCGTTCCTACTAGTAACCCTAGCTATCCTAACCGGGCTAAGACTAATGTGTGCGTACTG
CTGCAACATCGTCAACGTGTCCCTAGTGAAGCCGTCCTTCTACGTCTACTCCAGAGTCAAGAACCTAA

FIG. 2C

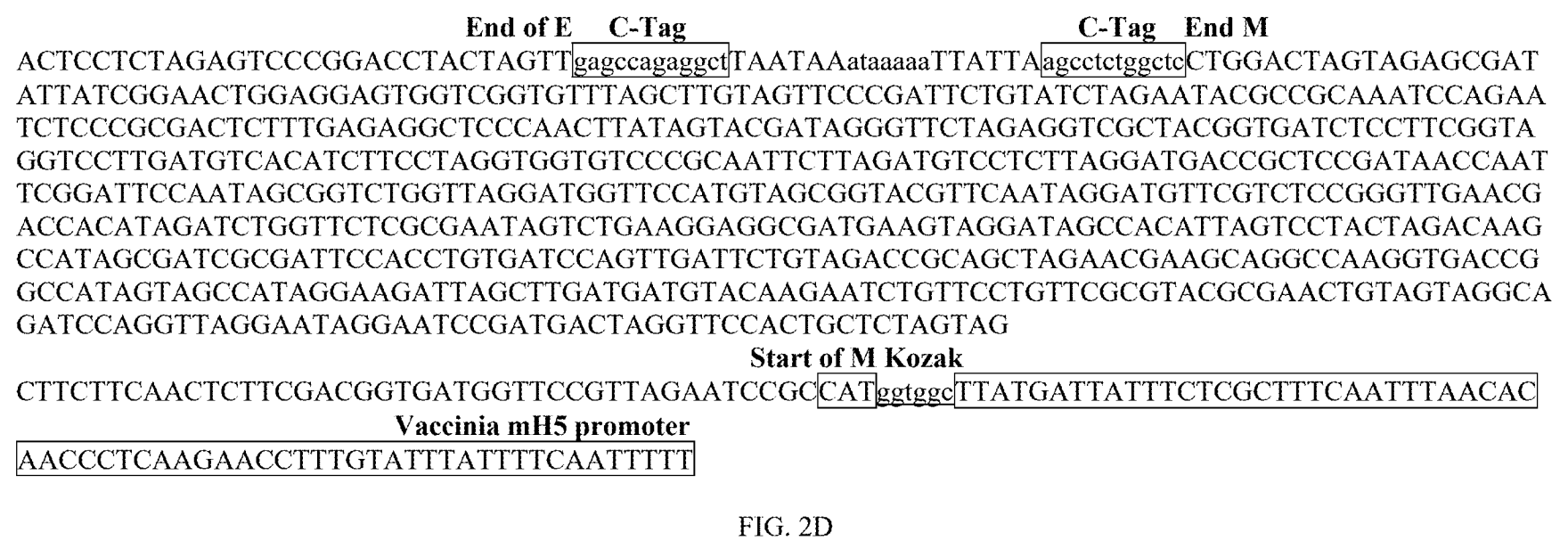

End of E    C-Tag        C-Tag    End M

```
ACTCCCTCTAGAGTCCCGGACCTACTAGTT|gagccagaggct|TAATAAAataaaaaTTATTA|agcctctggctc|CTGGGACTAGTAGAGCGAT
ATTATCGGAACTGGAGGAGTGGTCGGTGTTGTTTAGCTTGTAGTTCCCGATTCTGTAGTTCTGTATCTAGAATCCGCCGCAAATCCAGAA
TCTCCCGCGACTCTTGAGAGGCTCCCAACTTATAGTACGATAGGGTTCTAGAGAGGTCGCTACGGTGATCTCCTTCGGTA
GGTCCTTGATGTCACATCTTCCTAGGTGGTGCCCGCCAATTCTTAGAGTGTCCTCTTAGGATGACCGGCTCCGATAACCAAT
TCGGATTCCAATAGCGGTCTCGGTTAGGATGGTTCCATGTAGCGGTACGTTCCATGGATGTTCGTCTCCGGGTTGAACCG
ACCACATAGATCTGGTTCTCGGGAATAGTCTGAAGGGAGGGCGATGAAGTAGGATAGCCACATTAGTCCTACTAGACAAG
CCATAGGCGATCGCGATTCCACCGTGATCCGGTCGTGTAGATCTGTAGACCCGAGTCTAGCAACGAAGCAGGCCAAGGTGACCG
GCCATAGTAGCCATAGAAGATTAGCTTGATGATGTACAAGAATCTGTTCCGCGTACGCGCAACTGTGTAGTAGGCA
GATCCAGGTTAGGAATAGGAATCCGATGACTAGGTTCCACTGCTCTAGTAG
```

Start of M Kozak

```
CTTCTTCAACTCTTCGACGGTGATGGTCCGTTAGAATCCGC|CAT|ggtggc|TTATGATTATTTCTGCTTTCAATTAACAC
```

Vaccinia mH5 promoter

```
AACCCTCAAGAACCTTTGTATTTATTTTCAATTTTT
```

FIG. 2D

Stabilized S-M-E (SEQ ID NO: 49)

Vaccinia mH5 promoter　　　　　　　　　　　　　　SmaI/Kozak

AAAATTGAAAATAAATACAAAGGTTCTTGAGGGTTGTGTTAAATTGAAAGGCGAGAAATAATCATAA|CCCGGGgcacc

Start of Stabilized S

ATG|TCGTGTGTTCCTAGTCCTACTACCGGCTAGTCTTCTCAGTGTGTAAACCTAACAACGAGAACTACCACCGG
CGTACACCAATTCTTCACAAGAGGAGTATATTACCCGGACAAGGTGTTCAGATCCTCCGTACTACATTCTACACAGA
CCTATTCCTACCGTTCTTCTCTAACGTAACATGGTTCCACGCGATCCATGTCTCTGGAACAAACGAAGGAAGAGATTC
GATAAACCCGGTCTTGCCGTCAACGATGGTGTATACTTTGCGTCCACCGAGAAGTCCAACATCATCAGAGGATGGATCT
TCGGAACCACCTGGATTCTAAGACCCAGTCCTTGCTAATCGTCAACAAGCGACAACAAGCAGTCCTGGATGGAATCCGA
ATTCCAGTTCTGTGTAACGACCCGTTCTTGGGAGTCTACTACCACACAAGAACAAGTCCTGGATGGAATCCGAGTTCAGA
GTCTACTCTTCCCGCGAACAACTGCACCTTCGTATTCAAGAACATCAGCCGGTTCCTAATGGACCTAGAGGGAAAGCAGGGAA
ACTTCAAGAAACCTAAGAGAGTTCGTATTCAAGAACATCAGCCGGTACTTCAAGATCTAGTAGTTTGCCGATCGGAATCAACATCACCAGA
CCTAGTTAGAGATCTACCGCAAGGATTCTCTGCGGCTAGAACCGTTAGTAGATTTGCCGATCGGAATCAACATCACCAGA
TTCCAGACAACTACTAGCGCTACTACACAGATCTTACCTAACGCCGGGAGATTCTTCTCTGAGGACTGCTGCTGTGCTGCGG
CTTATTATGTAGGATACCTACAGCCGAGAACCTTCCTATTGAAGTACAAACGAACCATCACCGATGCCGGTAG
ATTGTGTCTCTAGATCCGCTATCCGAAACGAAGTGCACCCTAAAGTCTTTCACCGTCGAGAAGGGAATCTACCAGACCTC
CAACTTTAGAGTACAGCCGACCGAATCCATCGTCGTCAGATTTCCGAACATCACGAACCTATGTCCGTTCGGAGAAGTGTTC
AACGGCGACAAGATTTGGCGTCGTGTCTATGCGGTGGAACAGAAAAGAATCAGTAACTGGTCGCGGACTACTCCGTCCTAT
ACAACTCTGCCTCTTTCTCCACGTTCAAATGCTACGGTGTATCTCCGACAAAGCTAAACGATCTATGCTTCACCAACGTC
TACGCGGACTCCTTCGTAATCAGAGGAGATGAAGTTAGACAGATTGGCGGGACAAACTGGAAAGATCGCGGATTAT
AACTACAAGCTACCGGACGACTTCACCGGGATATGGCGTGGAATTGGCGTGGAATGTGTAAATTGGCGTGGAATGTAGACTCCAAGTCGGAGGA
AACTACAACTACTTGTACAGACTATTCAGAAAGTCCAACCTAAAGCCGTTCGAGAGAGACATCTCCACGAAATCTATC
AGGCTGGATCTACACCGTGTAATGGTGTCGAAGGATTCAACTGCTACTTCCCGCTACACTACAGTCTTACGGATTTCAACCGAC
AAACGGTGTAGGATATCAGCCGTACAGAGTCGGAAGAACAAATGCGTCAACTTAACTTCAACGGTTCGGAAGATATGGGAAGAATATGGCGTTCAACGGTATGTGGA
CCGAAAAAGTCTAACAGAAGTTTCTACCGTTCCAGCAGTTCGGAAGAGATATCGCGGAAGAGATATCGCGGAGATGCTGTCAGAGAT
ACGGAATCTAACCTTGGAGATCCTAGATATCCACACCGTGTCTTCGGTGGTGTCTCGTAATTACTCCGGGAACGAACACCT
CCGCAAACCTTGGAGATCCTAGATATCCACACCGTGTCTTCGGTGGTGTCTCGTAATTACTCCGGGAACGAACACCT
CCAATCAAGTAGCGGTACTATACCAGGACGTGAACTGTACAGAACTGTACAGAAGTAGCGGTACTATACCAGGACGTGAACTGTACAGAAGTAGCGGTATTCAACTAACAC
CAACTTGGAGAGTGTACTCCACCGGATCTAACGTATTCCAAACAACAAGAGCGGGATGTCTAATCGGAGGCGGAACACGTAA

FIG. 2E

ACAACTCCTACGACGAATGTGATATCCCGATTGGAGCGGGGAATCTGTGCGTCTTACCAAACACAAACAAACTCTCCGAGAA
GAGCGGAGATCTGTAGCCTGCTCTCAATCTATTATGCCTACACCATGTCCTTGGGAGCCGAAAATTCTGTCGGTACTCCAA
CAATTCTATCGCGATCCCGACAAACTTCACCATCTCTGTAACAACCGAGATCCTACCGGTGTCTATGACCAAGACATCT
GTCGATTGCACCATGTACATCTGCGGAGATTCCACGGAGTTGCTCAACCTACTACTACAGTACGGATCTTTCGTACCC
AGCTAAACAGAGGGTTGACTGGAATCGCTGTAGAGCAGGATAAGAACACTCAAGAGGTATTCGCGCAGTCAAGCAG
AICTATAAGACTCCGCCGATCAAGGACTTCGGAGGTTTCAACTTCTCTCAGATCTTGCCGGATCCGTCCAAACCGTCTA
AGAGATCTTTCATCGAGGACTACTATTCAACAAAGTCACCCTAGCTGACGCGGGATTCATCAAACAATACGGAGATTG
CTTGGGAGACAATTGCGGCGGCGAGAGATCTAATTTGCCGCGCAGAAGTTAACGGATTGACAGTACTACCGCGCTACTAACC
GATGAGATGATTGGCGCAGTAGGTACACGTCTGCTCTATTGGGGGAACAATTACAAGTGATGGACATTGGAGCGGTGCC
GCTCTACAAATTCCGTTTGCTATGCAAATGGGCGTACAGATTCAAGTGAATCAAGCGTCTTCTACTGCTTCGGCGTT
ACCAGAAGCTAATCGCGAACCAGTTCAATTCCCGCGATCGGAAAGATCCAGGACACAGTCTATCTTCTACTGCTTCGGCGTT
GGGAAAGCTACAGGATGTAGTAAATCAAAAACGCGCAGGCGCTAAACACCTTGGTCAAGCAACTATCCTCTAACTTCGG
AGCGGATCTCGTCCCGTCCTAAACGACATCTTATCCAGACTAGAT CCACCG GAAGCGGAGGTCCAGATCGATAGACTAAT
CACTGGAAGATTGCAGTCCCTACAGACCTACGTAACACCAGCAACTAATTAGAGCGGCGGAGATTAGAGCCTCTGCTAA
TCTAGCTGCGACCAAGAGTGTCCGAATGTCTTGGGACAATCCAAGAGAGGTGGACTTCTGCGGAAAGGGGATACCACCT
AATGTCTTTCCCACAATCTGGCGCCGCATGGTATCCTACATGTAACATATGTGGGCGCAAGAAAAGAACTTC
ACAACAGCTCCAGCGATCTGCCATGAATGGGAAAAGCTCATTCCCGAGAGAGGGAGTCTTTGTCTCTAACGGAACTCATT
GGTTCGTCACCGAGATCTTACGAGCGCAGAAACTTCTACGAGCGGCGCAGATCATCACCGACAACACATTCGTCTCGGGAAACTGCGACG
TGGTCATCGGAATCGTAAACAATACCGTTCTACGATCCGTTGCAGCCGGGAGATATCTCTGGAATCAAGCGGTCCGTCGTCAACATCCA
AGTACTTCAAGAACCACACCTCCCGATGTGACCTCCCGATGTGGGAGACTTGGGAGAACTTGAAGGTCCTAATGCACTAGAGAGCTAGGAAAAT
GAAAGAAATCGATAGATTGAACGAGGTCGCGAAGAACTTGAAGCGATTCATTGCTGGACTAATTGCGATCGTCATGGTCACCAT
CATGCTATGCTGTATGACCTCTGTTCCTGTTCCTGCTCCGTGCTCCTGTTCCTGATCCGTGTGCAAGTT

End of S   C-tag

CGATGAAGATGATAGTGAACCGGTCCTAAAGGGTGTCAAGCTACACTACACA gagccagaggct TAATA attttatc

Vaccinia P11 promoter   Kozak Start of E

TTTCATTTTGTTTTTTTCTATGCTATAA gccacc ATG tACTCCTTCGGTGTCCGAAGAAACCGGAACCTTGATCGTCAACTCC
GTCCTACTATTCCTAGCGTTCGGTCGTTCCTACTAGTAACCCTAGCTATCCTAACCGGCTAAGACTATGTGCGTACTG
CTGCAACATCGTCAACGTGTCCCTAGTGAAGCCGTCCTTCTACGTCTACTCCAGAGTCAAGAACCTAA

FIG. 2F

End of E C-Tag C-Tag End M

ACTCCCTCTAGAGTCCCCGGACCTACTAGTT[gagccagaggct]TAATAAAataaaaaTTATTA[agcctctggctc]CTGGACTAGTAGAGCGAT
ATTATCGGAACTGGAGGAGTGGTGCGGTCGGTGTTGTTTAGCTTGTAGTTCCCGATTCTGTATCTAGAATACGCCGCAAATCCAGAA
TCTCCCGCGACTCTTTGAGAGGCTCCCAACTTATAGTACGATAGGGTTCTAGAGAGGTCGCTACGGTGATCTCCTCGTA
GGTCCTTGATGTCACATCTTCCTAGGTGGTGCCCGCAATTCTTAGATGTCCTCTTAGGATGACCGGCTCCGATAACCAAT
TCGGATTCCAATAGCGGTCTCGGTTAGGATGGTTCCATGTAGCGGTACGTTCCATGGATGTTCGTCTCCGGGTTGAACG
ACCACATAGATCGGATCGGTTCTCGGAATAGTCTGAAGGAGGCGATGAAGTAGGATAGCCACATTAGTCCTACTAGACAAG
CCATAGGCGGATCGCGATTCCACCGTGATCCAGTTGATTCTGTAGACCCGCAGTAGTGTTCCTAGAACGAGCAGGCCAAGGTGACCG
GCCATAGTAGCCATAGAAGATTAGCTTGATGATGTACAAGAATCTGTTCGGCGTACGCGCAACTGTAGTAGTAGGCA
GATCCAGGTTAGGAATAGGAATCCGATGACTAGGTTCCACTGCTCTAGTAG

Start of M Kozak

CTTCTTCAACTCTTCGACGGTGATGGTTCCGTTAGAATCCGC[CAT][ggtggc]TTATGATTATTTCTCGCTTTCAATTAACAC

Vaccinia mH5 promoter

[AACCCTCAAGAACCTTTGTATTTATTTTTCAATTTTT]

FIG. 2G

Stabilized S-M-E (SEQ ID NO: 50) (K417T, E484K, N501Y)

Vaccinia mH5 promoter                                                   SmaI/Kozak AAAATTGAAAATAAATACAAAGGTTCTTGAGGGTTGTGTTAAATTGAAAGGCGAGAAATAATCATAA CCCGGGgcacc

Start of Stabilized S

ATGTTCGTGTTCCTAGTCTTCCTACCGCTAGTCTCTTCTCAGTGTGTAAACCTAACAAGCAGAACACAACTACCACCGG
CGTACACCAATTCTTCACAAGAGGAGTATATTACCCGGACAAGGTGTTCAGATCGTTCAGATCCTCCGTACTACATTCTACACAGA
CCTATTCCTACCGTTCTTCTCTAACGTAACATGGTTCCACGCGATCCATGTCTCTGGAACAAACGAAGGAAGAGATTC
GATAAACCCGGTCTTGCCGTTCAACGATGGTGTATACTTTGCGTCCACCGAGAAGTCCAACATCATCAGAGGATGGATCT
TCGGAACCACCTTGGATTCTAAGACCCAGTCCTTGCTAATCGTCAACAAGCAACAAGTCCTGGATGGAATCCGAGTTCGCGA
ATTCCAGTTCTGTGTAACGACCCGTTCTTGGGAGTCTACTACCACACAGAACAAGTCCTAGAGAGGAAAGCAGGGAA
GTCTACTCTTCCGCGAACAACTGCACCTTCGTATTCAAGAACATCGACGGATACTTCAAGATCTACTCCAAGCACACTCCGATCAA
ACTTCAAGAACCTAAGAGAGTTCGTATTCAAGAACATCGACGGATACTTCAAGATCTTCAAGATTTAGTAGATTTGCCGATCGGAATCAACATCACCAGA
CCTAGTTAGAGATCTACCGCAAGGATCTCTGCGCTAGAACCGTTAGTAGATTTGCCGATCGGAATCAACATCACCAGA
TTCCAGACACTACTAGCGCTGCTACACAGATCTTACCTAACGCCGGGGAGATTCTTCTGCTGTGGTGCTGCTGCGGG
CTTATTATGTAGGATACCTACAGCCGAGAACCTTCCTATTGAAGTACAAACGAAACCATCACCGATGCCGGTAG
ATTGTGTCTCTAGATCCGCTATCCGAAACGAAGTGCACCCTAAAGTCTTTCACCGTCGAGAAGGGAATCTACCAGACCTC
CAACTTTAGAGTACAGCCGACCGAATCCATCGTCAGATTCCGAACATCATCGTCCGTTCGGAGAAGTGTTC
AACGGCGACAAGATTTGCGTCGTCTGTCTATGCGTGGAACAGAAAAAGAATCAGTAACTGTAACTGCGCGTCGCGACTACTCCGTCCTAT
ACAACTCTGCCTCTTTCTCCACGTCAAATGCTACGGTGTATCTCCGACAAAGCTAAACGATCTATGCTTCACCAACGTC
TACGCGGACTCCTTCGTAATCGAGGAGATGAAGTTAGACAGATTGGCGCGGGACAACTGGaacgATCGCGGATTATA
ACTACAAGTACCGGACGACTTCACCGGATGGTAATTGCGTGGAATTCGAACAACCTAGACTCCAAAGTCGGAGGAA
ACTACAACTACTTGTACACCGGTAATGGTGTCaagGGATTCAACTGCTCAACTGCTACATCCTTCGAACTACTACACGGACATac
GGCTGGGATCTACACCGGTAATGGTGTCaagGGATTCAACTGCTACATCTCCCGGCTACACTACACGGACAGTATGTGGACCGA
GGTGTAGGATATCAGCGGTACAGAGTAGTGAACAAACAAATGCGTCAAGAACAAATGCGTCAGTTCGGAAGAGATATCGCGGAAGAGATATCGGCGGA
AAAAGTCTACCAACCTAGTCAAGAACAAATGCGTCAACTTAACTTCAAGGAAGAGAACCGGTGTCCTAACCG
AATCTAACAAGAAGTTTCTACCGTTCCAGCAGTTCGGAAGAGATATGGCGGAAGAGATATCGGGAAGATCCGC
AAACCTTGGAGTCGGATCCTAGATATCACCACCGTGTCTTTCGGTGTCTTGTAATTACTCCGGGAACGAACACCTCCAA
TCAAGTAGCGGTACTATCCAGGACGTGAACTGTACAGAAGTACCGGTAGCTATTCACGCGGATCAACTAACACCAAC
TTGGAGAGTGTACTCCACCGGATCTAACGTATTCCAAACAAGAGGGGGATGTCTAATCGGAGCGGAACACGTAAACAA

FIG. 2H

CTCCTACGAATGTGATATCCCGATTGGAGCGGGGAATCGTGTGCGTCTTACCAAACACAAACAAACTCTCCGAGAAGAGC
GAGATCTGTAGCCTCTCAATCTATTATCGCCTACACCATGTCCTTGGGAGCCGAAAATTCTGTGCGTACTCCAACAATT
CTATCGCGATCCCGACAAACTTCACCATCTCTGTAACAACCGAGATCCTACCGGTGTCTATGACCAAGACATCTGTCGA
TTGCACCATGTACATCTGCGGAGATTCCACCGAGTGCTCCAACCTACTACTACAGTACGGATCTTTCTGTACCCAGCTA
AACAGAGCGGTTGACTGAAATCGCTGTGTAGAGCAGGATAAGAACACTCAAGAGGTATTCGGCGCAAGTCAAGCAGATCTAT
AAGACTCCGCCGATCAAGGACTTCGGAGTTTCAACTTCTCTCAGATCTTGCCGGATCCGTCCAAACCGTCTAAGAGAT
CTTTCATCGAGGACCTACTATTCAACAAAGTCACCCTAGCTGACGCGGGATTCATCAAACAATACGGAGATTGCTTGGG
AGACATTGGCGGCGAGAGATCTAATTTGCCGCCAGAAGTTAACGGATTGACAGTACTACCGCCCGTACTAACCGATGA
GATGATTGGCGCAGTCACACGTCTGCTCTATTGGGGAACAATTACAAGTGGATGGACATTTGGAGCCGGTGCCGCTCTA
CAAATTCCGTTTGCTATGCAAATGGGCGTACAAATGCCAGTTCAATTCCCGCGATCGGAAAGATCCAGGACAGTCTATCTTCTACTGCTTCGGCGTTGGGAA
AGTACAGGATGTAGTAGTAAATCAAAACGCGCAGGGGCTAAACACCTTGGTCAAGCAACCTTGGTCAACTTCGGAGCGA
TCTCGGTCCGTCCTAAACGACACATCTTATCCAGACTAGATccaccgGAAGCGGAGGTCCAGATAGCAACTAATCACTGAA
GATTGCAGTCCCTACGTAACAGCAACTACGTAACCAGCAACTAATTAGAGCGGCGGAGATTGGGAAAGGGGATACCACCTAATGTCTTTC
GACCAAGATGTCCGAATGTGTCTGGGACAATCCAAGAGAGTGGACTTCTGCGGAAAGGGGATACCACCTAATGTCTTTC
CCACAAATCTGCGCCGCCATGGCTATTCCTACATGTAACATATGTAACCATATGTGCCGGCGCAAGAAAAGAACTTCACAACAGCTC
CAGCGATCTGCCATGATGGAAAAGCTCATTCCCGAGAGAGGGGAGTCTTTGTCTCTAACGAACTCATTGGTTCGTCAC
CCAGAGAAACTTCTACGGAGCCGGCAGATCATCACCACCGACAACACATAGACTCGTCTCGGGAAACTGCGACGTGGTCATCGG
AATCGTAAACAATACCGTCACCGTCTACGATCCGTTGCAGCCGGAACTAGACTCCTTCAAAGAAGAGTTGGACAAGTACTTCAA
GAACCACCACCTCTCCGGATGTGGACTTGGGAGATATCTCTGGAATCAACGGCGTCCGTCGTCAACATCCAGAAAGAAAT
CGATAGATTGAACGAGGTCGGCGAAGAACTTGAACGAGTCCCTAACGAGTCCTACAAGAGCTAGGAAAATACGAGCAGTA
CATCAAGTGGCCGGTACTACATCTGCTAGGATTCATTGCTGACTAAATTGCTGACTAATGGCTAGGATTCATTGCTGACTAATGCTCACCATCATGCTATGC
TGTATGACCTCCGTGTTGCTCCGTGTCTCTGTCTAAAGGGGATGTTGTTCCTGCGGATTCCTGCGGATTCCTGCGTTGCAAGTT

End of S    C-tag

...CTACACTACACA|gagccagaggct|TAATAAtttttatc

Vaccinia P11 promoter          Kozak Start of E

CGATGAAGATGATAGTGAACCGGTCCTAAAGGGTCCTAAAGGGTGTCAAGCTCAAGCTGTCAAGCTACACTACACAgagccagaggctTAATAAtttttatc
|TTTCATTTTGTTTTGTTTTCTATGCTATAA|gccacc|ATG|tACTCCTTCCGTGTCCGGAAGAAACCGGAACCTTGATCGTCAACTCC
GTCCTACTATTCCTAGCGGTTCGTCGTTCCTACTAGTAACCCTAGCTATCCTAACCCTAGCTATCCTAACCCGGCGCTAAGACTATGTGGTACTG
CTGCAACATCGTCAACGGTCCGTCCTTCTACTCCTAGCGTCTACTCCAGAGTCAAGAACCTAA

FIG. 2I

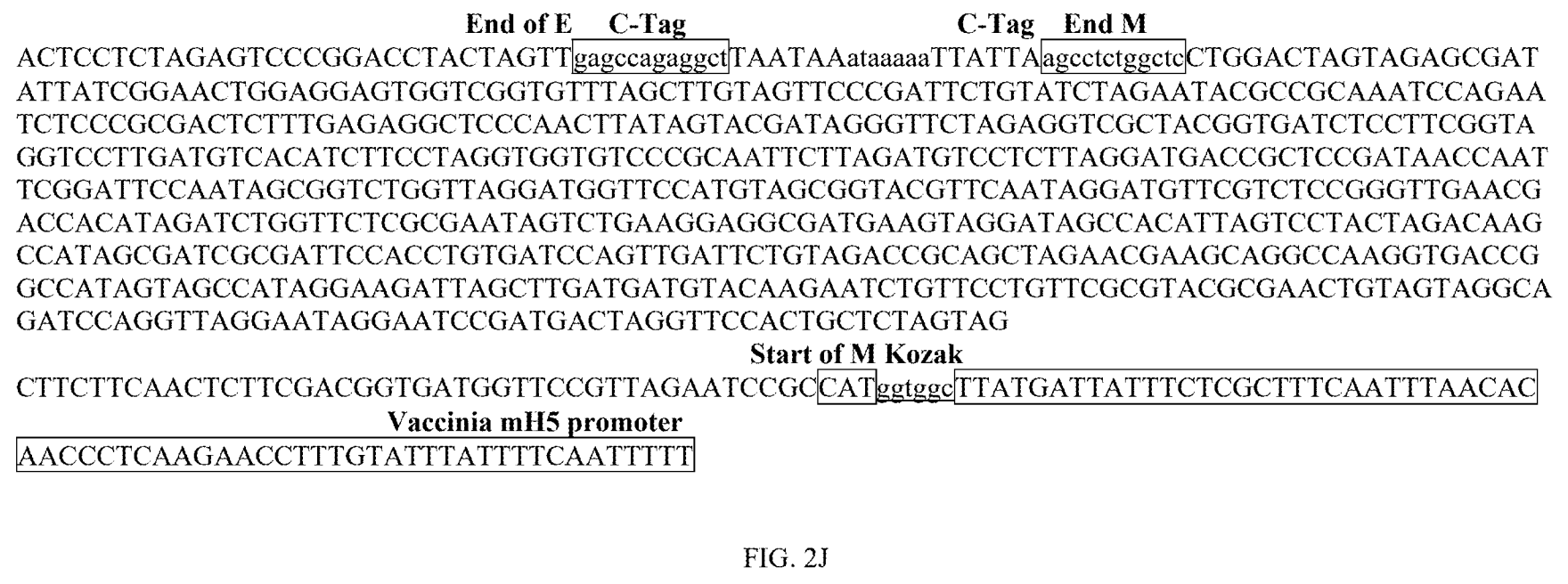

End of E    C-Tag        C-Tag    End M

ACTCCTCTAGAGTCCCGGACCTACTAGTTgagccagaggctTAATAAAataaaaaTTATTAagcctctggctcCTGGACTAGTAGAGCGAT
ATTATCGGAAACTGGAGGAGTGGTCGGTCGGTGTTGTTAGCTTGTTGTGTAGTTCCGATTCTGTGTATCTAGAATACGCCGCAAATCCAGAA
TCTCCCGGCGACTCTTTGAGAGGCTCCCAACTTATCGATATAGTTCTAGAGGGTTCTAGAGGGTGCTACGGGTGATCTCCTTCGGTA
GGTCCTTGATGTCACATCTTCCTAGGTGGTGCCCGCAATTCTTAGATGTCCTCTTAGGATGACCGCCTCCGATAACCAAT
TCGGATTCCAATAGCGGGTCTCGGTTAGGATGGTTCCATGTAGGCGGTACGTTCAATAGGATGTTCGTCTCCGGGTTGAACG
ACCACACATAGATCTGGTTCTCTGCGCGAATAGTCTGAAGGAGGCGATGAAGTAGGATAGCCACATTAGTCCTACTAGACAAG
CCATAGGCGATCGGCCATTCCACCTGTGATCCAGTTGATTCTGTGAGACCGCAGTAGAACGAAGCAGGCCAAGGTGACCG
GCCATAGTAGCCATAGGAAGATTAGCTTGATGATGTACAAGAAATCTGTTCCTGTTCCGCGGTACGCGAACTGTAGTAGGCA
GATCCAGGTTAGGAATAGGAATCCGATGACTAGGGTTCCACTGCTCTAGTAG

Start of M Kozak

CTTCTTCAACTCTTCGACGGTGATGGTTCCGGTTAGAATCCGCCATggtggcTTATGATTATTTCTCGCTTTCAATTTAACAC

Vaccinia mH5 promoter

AACCCTCAAGAACCTTTGTATTTATTTCAATTTTT

FIG. 2J

Stabilized S-M-E (SEQ ID NO: 157)

Vaccinia mH5 promoter                                     SmaI

AAAAATTGAAATAAATAAATACAAAGGTTCTTGAGGGTGTGTTAAATTGAAAGCGAGAAATAATCATAA|ATAAGCCCGGG

Kozak Start of S stabilized gccacc|ATG|TTCGTGTTCCTAGTCCTACTACCGGCTAGTCTCTTCTCAGTGTGTAAACCTAACAACGAGAACACAACTACCA
CCGGGCGTACACCAATTCTTTCACAAGAGGAGTATATTACCCGGACAAGGTGTTCAGATCCTCCGTACTACATTCTACAC
AGGACCTATTCCTACCGGTTCTTCTCTAACGTAACATGGTTCCACGCGATCCATGTCTCTGGAACAAACGAACGAAGAG
ATTCGATAAACCCGGTCTCTTGCCGGTCAACGATGGTGTATACTTTGGCGTCCACGAGAGTCCAACATCATCAGAGGATGG
ATCTTTCGGAACCACCACCTTGGATTCTAAGAACCCAGTCCTTGCTAATCGTCAACAAGCGGACCAACGTCGTCATCAAAGTCT
GCGAATTCCAGTTCTCGTAACGACCCGGTTCTTGGGAGTCTACTACCACAAGAACAACAAGTCCTGGATGGAATCCGAGTT
CAGAGTCTACTCTTCCGCGAACAACTAAGAGAGTCGTATTCAAGAACATGCACCTTCGAATATGTATCTCAGCCGTTCCTAATGGACCTAGAGGGAAAGCAG
GGAAACTTCAAGAACCTAAGAGAGTCGTATTACCGCGAGTCGTTCTCTGCGCTAGAACCGTTAGTAGATTTGCCGATCAACATCA
CCAGATTCCAGACACTACTAGGCGCTACACAGATCTTACCTAACGCCGGGAGAATCCTACCTAATGGAACCATCACCGATGCC
TGCGGCTTATTATGTAGGATACCGCTATCGGATACCCGAGAAACGAAGTGCACCCTAAAGTCTTCACCGTTCACCGAACCATCACCGATGCC
GTAGATTGTGTCTCTAGATCCGCTATCGGAAACGAAGGAAGTGCACCCTAAAGTCTTCACCGTTCACCGAACCATCTTTCACCGAACCATCACCAGA
CCTCCAACTTTAGAGTACAGCCGACCGAATCCATCGTCAGATTCCGAACCATCACGAACCTATGTCCGTTCGGAGAAGT
GTTCAACGGCGACAAGATTGCGTCGTCGTGTCTATGCGGTGAACAGAAAAAGAATCAGTCGGCGTCGCGGACTACTCCGTC
CTATACAACTCTGCCTCTTCTCCACGTTCAAATGCTACGGTGTATCTCCGACAAGCTAAACGATCTATGCTTCACCAA
CGTCTACGCGGACTCCTTCGTAATCAGAGGAGATGAAGTTAGACAGATTGCGCGGGACAAACTGGAAAGATCGCGGA
TTATAACTACAAGCTACGGACGACTTCACCGGATGTGTAATTGCGTGAATTCGAACAACCTAGACTCCAAAGTCGGA
GGAAACTACAACTACTTGTACAGAATATTCAGAAAGTCCAACCTAAAGCCGTTCGAGAGAGACATCTCCACGGAAATC
TATCAGGCTGGATCTACACCGGTGTAATGGTGTCGAAGGATTCAACTGCTACTCCCGCTACAGTCTTACGGATTTCAAC
CGACAAACGGTGTAGGATATCAGCCGTACAGAGTCGTCGTACTATCCTTCGAACTACCATGCTCCGGCGACCAGTATG
TGGACCGGAAAAAGTCTACCACCTAGTCAAGAACAAATGCGTCAACTTTAACTTCAACGGACTAACCGGAACCGGTGT
CCTAACGCGAATCTAACAAGAGAAGTTTCTACCGTTCGGAAGAGATATCGCGGATACAACAGACGCTGTCAG
AGATCCG

FIG. 2K

CAAACCTTGGAGATCCTAGATATCACACCCGTGTCTTCGGTGGTGTCTCTGTAATTACTCCGGGAACGAACACCTCCA
ATCAAGTAGCGGTACTATACCAGGACGTGAACTGTACAGAAGTACCGGTAGCTATTCACGCGGATCAACTAACACCAA
CTTGGAGAGTGTACTCCACCGGATCTAACGTATTCCAAACAACAGAGCGGGATGTCTAATCGGAGCGGAACACGTAAACA
ACTCCTACGAATGTGATATCCCGATTGGAGCGGGAATCTGTGCGTCTTACCAAACCAAACAAACTCTCCGAGAAGAG
CGAGATCTGTAGCCTCTCAATCTATTATCGCCTACACCATGTCCTTGGGAGCCGAAAATTCTGCGCTACTCCAACAAT
TCTATCGCGATCCCGACAAACTTCACCATCTCTGTAACAACCGAGATCCTACCGGTGTCTATGACCAAGACATCTGTCG
ATTGCACCATGTACATCTGCGGAGATTCCACCGAGATCCAACCTACTACTACTCAAGAGGTATTCGGGCAAGTCAAGCAGATCTA
AAACAGAGCGGTTGACTGGAATCGCTGTAGAGCAGGATAAGAACACTCAAGAGGTATTCGGGCAAGTCAAGCAGATCTA
TAAGACTCCGCCGATCAAGGGACTTCGGGAGGTTCAACTTCTCTCAGATCTTGCCGGATCCGTCCAAACCGTCAAGAGA
TCTTTCATCGAGGGACCTACTATTCAACAAAGTCACCCTAGCTGACGCGGGGATTCATCAAACAATACGGGAGATTGCTTGG
GAGACATTGCGGGCGAGAGATCTAATTTGCGCGCAGAAGTTAACGGATTGACAGTACTACCGCCGCTACTAACCGATG
AGATGATTGCGCAGTACACCGTCGTCTATTGGCGGGAACAATTACAAGTGGACATTTGGAGCCGGTGCCGCTCT
ACAAATTCCGTTGCTATGCAAATGGCGTACAGATTCAACGGAATCGGAGTAACCCAGAACGTCTTGTACGAGAACCA
GAAGCTAATCGGGAACCAGTCAATTCCGGATCGGAAAGATCCAGGACAGTCTATCTTCTACTGCTTCGGGCGTTGGGA
AAGCTACAGGATGTAGTAGTAAATCAAAACGGGCCAGGCGCTAAACACCTTGGTCAAGCAACTATCTCTAACTTCGGAGCG
ATCTCGTCCGTCCTAAACGACACATCTTATCCAGACTAGATCCACCGGAGGTCCAGATCGATAGACTAATCACTG
GAAGATTGCAGTCCCCTACAGACCTACGTAACACAGCAACTAATTAGAGCGGCGGAGATTAGAGCCCTCGCTAATCTAG
CTGCGACCAAGATGTCCGAATGTGTCTTGGGACAATCCAAGAGAGTGGACTTCTGCGGAAAGGGATACCACCTAATGT
CTTTCCCACAATCTGGCGCCGCATGGTGTCGTATTCCTACACATGTAACATATGTGCGGGCGCAAGAAAAGAACTTCACAAC
AGCTCCAGCGACATCTGCCATGATGGAAAAGCTCATTCCCGAGAGAGGGAGTCTTTGTCTCTAACGGAACTCATTGGTTC
GTCACCCAGAGAAAACTTCTACGAGCCGCAGATCATCACCGACAACACATTCGGTCTCGGGAAACTGCGACGTGGTC
ATCGGAATCGTAAACAATAACCGGTTACGACGTCTACGGTTGCAGCCGGAACTAGACTCCTTCAAAGAAGAGAGTTGGACAAGTAC
TTCAAGAACCACCACCTCTCCGGATGTGGGGACTTGGGAGATATCTCTGGAATCAACGCGTCCGTCCGTCAACATCCAGAAAAG
AAATCGATAGATTGAACGAGGTCGCGAAGAACTTGAACGAGTCCCTAATCGACTACAAGAGCTAGGAAAATACGAGC
AGTACATCAAGTGCCGTGGTACATCTGGTAGGATTCATTGCTGGACTAATTGCGATCGTCATGGTCACCATCATGCT
ATGCTGTATGAGCTT

FIG. 2L

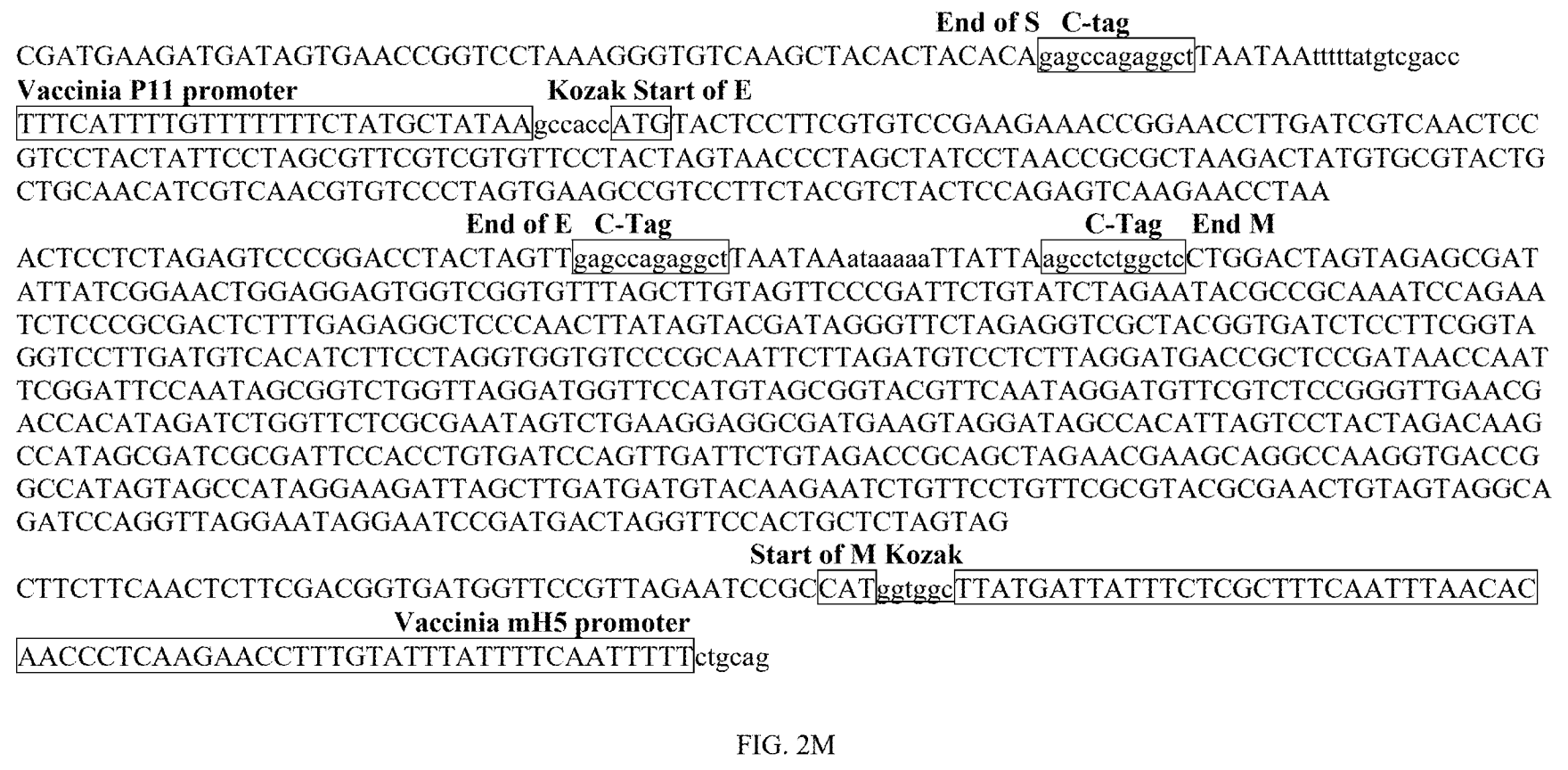

End of S    C-tag

CGATGAAGATGATAGTGAACCGGTCCTAAAGGGGTGTCAAGCTACACTACACAgagccagaggctTAATAAttttatgtcgacc Vaccinia P11 promoter                    Kozak Start of E TTTCATTTTGTTTTTTCTATGCTATAAgccaccATGTACTCCTTCGTGTCCGAAGAAACCGGAACCTTGATCGTCAACTCC
GTCCTACTATTCCTAGCGGTTCGTCGTGTCCTAGTAACCCTAGCTATCCTAACCGGCGCTAAGACTATGTGCGGTACTG
CTGCAACATCGTCAACGTGTCCCTAGGTCAAGCCGTCCTTCTACGTCTACTCCAGAGTCAAGAACCTAA End of E    C-Tag ACTCCCTCTAGAGTCCCGGACCTACTAGTTgagccagaggctTAATAAataaaaaTTATTAagcctctggctcCTGGACTAGTAGAGCGAT
ATTATCGGAACTGGAGGAGTGGTGCGGTGTTTAGCTTGGTTGTAGTTCCCGATTCGTATCTAGAATACGGCGCAAATCCAGAA
TCTCCCGCGACTCTTGAGAGCTCCAACTATAGTACGATAGGGTTCTAGAGGTCGCTACGGTGATCTCCTTCGGTA
GGTCCTTGATGTCACATCTTCCTAGGTGGTGTCCCGCAATTCTTAGATGTCCCTCTTAGGATGACCGGCTCCGATAACCAAT
TCGGATTCCAATAGGCGTCTGGTTAGGATGGTTCCATGTAGGCGGTACGTTCAATGGATGTTCGTCTCCGGGTTGAACG
ACCACATAGATCGTTGGTTCTCGCGAATAGTCTGAAGGAGGCGATGAAGTAGGATAGCCACATTAGTCCTACTAGACAAG
CCATAGGGATCGGCGATTCCACCTGTGATCCAGTTGATTCTGTAGAGCCAGCTAGAAGAATCTGTTCCTGTTCGCGTACGGCGAACTGTAGTAGGCA
GATCCAGGTTAGGAATAGGAAATCCGATGACTAGGTTCCACTGCTCTAGTAG C-Tag    End M Start of M Kozak CTTCTTCAACTCTTCGACGGTGATGGTTCGGTTCCGTTAGAAATCCGCCATggtggcTTATGATTATTTCTCGCTTCAATTAACAC Vaccinia mH5 promoter AACCCTCAAGAACCTTTGTATTTATTTTCAATTTTTctgcag

FIG. 2M

Stabilized S-M-E (SEQ ID NO: 159) (K417T, E484K, N501Y)

Vaccinia mH5 promoter                                                                                           SmaI

```
AAAAATTGAAAATAAAATACAAAGGTTCTTGAGGGTTGTGTTAAATTGAAAGGCGAGAAATAATCATAA|AATACCCGGG
```

Kozak Stabilized S Start

```
gccacc[ATG]TTCGTTGGTGTTCCTAGTCCTACTACCGGTCCTAGTCTCTTCTCAGTGTGTAAACCTAACAACGAGAACACAACTACCA
CCGGCGTACACCACCAATTCTTCACAAGAGGAGTATATTACCCGGACAAGGTGTTCAGATCCTCCGTACTACATTCTACAC
AGGACCTATTCCTACCGGTCTTCTCTAACGTAACATGGTTCCACGCGGATCCATGGTCTCTGGAACAAACGGAACGAAGAG
ATTCGATAACCCGGTCTTGCCGTTCAACGATGGTGTATACTTTGGCGTCCACCGAGAAGTCCAACATCATCAGAGGATGG
ATCTTCGGAACCACCTTGGATTCTAAGACCCAGTCCTTGCTAATCGTCAACAAGAACAACAAGTCCTGGATGGAATCGAGTT
GCGAATTCCAGTTCTGTAACGACCCGGTTCTTGGGAGTCTACTACCACAAGAACAAGTCCTAATGGACCTAGAGGGAAGCAG
CAGAGTCTACTCTTCCGCGAACAACCTAAGAGAGAGTCGTATTCAAGAACATGACGATACTTCAAGATCTACTCCAAGCACTCCG
GGAAACTTCAAGAACCTAAGAGATCTACCGCAAGGATTCTCGCGCTAGAACGTTAGTAGATTGCCGATCGGAATCAACATCA
ATCAACCTAGTTAGAGATCTACCGCTACAGCGCTACCACTACTAGCGCTACTAACGCCGGGGAGATTCTTCTTCTGGACTGCTGGTGC
CCAGATTCCAGACCACTACTAGCGCTACCACAGATCTTACCTACCTAGCCGGAGAACCTTCCTATTGAAGTACAACGAACCATCACCGATGCC
TGCGGCTTATTATGTAGGATACCTACACCAGCCGGAGAACCTTCTATTGAAGTACAACGAACCATCACCGATGCC
GTAGATTGTGTCTCTAGATCCGGCTATCCGAAAACGAAGTGCACCCTAAGTCTTTCACCGTCGAGAAGGGAATCTACCAGA
CCTCCAACTTTAGAGTACAGCGAGCCGACCGAATCCATCGTCAGATTCCGAACATCACGAACCTATGTCCGTTCGGAGAAGT
GTTCAACGGGACAAGATTTGGCGTCGTCTATGGCGTGGAACAGAAAAAGAATCAGTAACTGGCGTCGCGGACTACTCCGTC
CTATACAACTCTGCCTCTTCTTCTCCACGTTCAAATGCTACGGTGTATCTCCGACAAAGCTAAACGATCTATGCTTCACCAA
CGTCTACGCGGGACTCCCTTCGTAATCAGCCGGACGACTTCACCGGATGTGTAATTGGCGTGGAATTCGAACAACCTAGACTCCAAAGTCGGA
TATAACTACAAGCTACAACTACTTGTACAGAGCTATTCAGAAAGTCCAACCTAAAGCCGTTCAACTGCTACTTCCCGCTACTCACATCTCCACCGAAATC
TATCAGGCTGGATCCACACCGTGTAATGGTGTCaagGGATTCAACTGCTACTTCCCGCTACTCACATGTCTTACGGATTTCAACCG
ACAtacGGTGTAGGATATCAGCCGTACAGAGTCGTCGTACAGACAAATGCGTCAACTTAACTTCAACGGACTACATGGATCCACATGGTGG
ACCGAAAAAGTCTACCAACCTAGTCACAAGAAGTTTCTACCGTTCGGAAGAAGGTATCGGCGGATACAACAGACGCGTGTCAGAGA
AACCGAATCTAACAAGAAGTTTCTACCGTTCGGAAGAAGGTATCGGCGGATACAACAGACGCGTGTCAGAGA
TCCGCAAACCTTGGAGATCCTAGATATCACCAACGTGTTCTTCGGTGGTGTCTCTGTAATTACTCCGGGAACGAACACCT
CCAATCAAGTAGCGGTACTATACCAGGACGTGAACTGTACAGAGAAGTACCGGTAGCTATTCACGCGGGATCAACTAACAC
CAACTTGGAGAGTGTACTCCACCGGATCTAACGTATTCCAAACAACAGAGCGGGATGTCTAATCGGTCTAATGCGGGAACACGTAA
ACAA
```

FIG. 2N

CTCCTACGAATGTGATATCCCGATTGGAGCGGGGAATCTGTGCGTCTTACCAAACACAAACAAACTCTCCGAAGAGAGC
GAGATCTGTAGCCTCTCAATCTATTATCGCCTACACCATGTCCTTGGGAGCCGAAAATTCTGTCGCGTACTCCAACAATT
CTATCGCGATCCCGACAAACTTCACCATCTCTGTAACAACCGAGATCCTACCGGTGTCTATGACCAAGACATCTGTCGA
TTGCACCATGTACATCTGCGGGAGATTCCACCGAGTGCTCCAACCTACTACTACAGTACGGATCTTTCTGTACCCAGCTA
AACAGAGCGGTTGACTGAATCGCTGTAGAGCAGGATAAGAACACTCAAGAGGTATTCGGCAAGTCAAGCAGATCTAT
AAGACTCCGCCGATCAAGGACTTCGGACTTCAACTTCTCTCAGATCTTGCCGGGATTCCGTCCAAACCGTCTAAGAGAT
CTTTCATCGAGGACCTACTATTCAACAAAGTCACCCTAGCTGACGCGGGATTCATCAAACAATACGGAGATTGCTTGGG
AGACATTGCGGCGAGAGATCTAATTTGCCGCGCAGAAGTTAACGGATTGACAGTACTACCGCCGTACTAACCGATGA
GATGATTGGCCAGTACACGTCTGCTCTATTGGGGAACAATTACAAGTGGATGGACATTTGGAGCCGGTGCCGCTCTA
CAAATTCCGTTTGCTATGCAAATGGCGTACAGATTCAAACGGTAACGGAATCAAACGTCTTGTACGAGAACCAG
AAGCTAATCGCGAACCAGTTCAATTCCCGCGATCGGAAAGATCCCAGGACAGTCTATCTTCTACTGCTTCCGGCGTTGGGAA
AGCTACAGGATGTAGTAAATCAAAACGCGCAGGCGCTAAACACCTTGGTCAACTATCCCTCTAACTTCGGAGCGA
TCTCGGTCCCGTCCTAAACGACATCTTATCCAGACTAGAT ccaccg GAAGCGGGAGGTCCAGATCGATAGACTAATCACTGGA
AGATTGCAGTCCCTACGAGATGTCCGAATGTGTCTTGGGACAATCCAAGAGAGAGTGGGACTTCTGCGGAAAGGGATACCCACCTAATGTCT
GCGACCAAGATGTCCGGCCGCCATGGAATCTCGGCGGCATGGTGTCGTATTCCTACATGTAACATATATGTCCGGCCAAGAAAGAACTTCACAACAG
TTCCCACCAATCTCGGCGCCGATCTGATGGAAAAGCTCATTTCCCGAGAGAGGGAGTCTTTGTCTCTAACGGAACTCATTGGTTCGT
CTCCAGCGATCTGCCATGATGGAGCCGCAGATCATCACCACCGACAACACATTCGTCTCGGGAAACTGGCGACGTGGTCAT
CACCCAGAGAAACTTCTACGAGCCGCTTACGATCCGGTTGGCAGCCGGAACTAGACTCCTTCAAAGAAGAGTTGGACAAGTACTT
CGGAATCGTAAACAATACCGTTCCGGATGTGGCGGAAGAACTTGAAGAACTTGAACTGAAGATCAAGAGCGAGCA
CAAGAACCACACCTCTCCGGATGTGTCTGGTACATCCGGCGACTGGCTAGGATTCATTGCTGGACTAATTGCATCCACCATCATGCTA
GTACATACCAGTGGCCGCCGTGTACATCTGGCTGGACTGGAGTGTTGGGAGATATCTCGGAGAACTTGAACGAGGTCCCTAATGCCTTAGGAAAATACGAGCA
TGCTGTATGACCTCGTGTTCCTGTCTCGTCTCTAAAGGGATGTTGTTCCTGCCGGATTCCTGTTGCAAGTT

End of S    C-tag

CGATGAAGATGATAGTGAACCGGTCGAACCGGTCCTAAAGGGTGTCAAGCTAGTCAAGCTACACTACACTACAACAG agccagaggct TAATAA tttttatgtcgacc

Vaccinia P11 promoter          Kozak Start of E

TTTCATTTTGTTTTTTTCTATGCTATAA gccacc ATG TACTCCTTCGTGTCCGAAGAAACCGGAAACCTTGATCGTCAACTCC
GTCCTACTATTCCTAGCGGTTCGTTCGTTCCTACTAGTAACCCTAGTATCCTAACCGGCGCTAAGGCTAAGACTATATGTGCGTACTG
CTGCAACATCGTCAACGTGTCCCTAGTGAAGCCGTCCTTCTACGTCTACTCCAGTGTCACTCCAGAGTCAAGAACCTAA

FIG. 20

End of E    C-Tag        C-Tag    End M

ACTCCTCTAGAGTCCCGGACCTACTAGTT gagccagaggct TAATTAAAataaaaaTTATTA agcctctggctc CTGGACTAGTAGAGCGAT
ATTATCGGAAACTGGAGGAGTGGTCGGTGTTGTGGTGTTAGCTTGTTAGTTCCCGATTCTGTGTATCTAGAATACGCGCAAATCCAGAA
TCTCCCGGCGACTCTTTGAGAGGCTCCCAACTTATATAGTACGATAGGGTTCTAGAGGTCGCTACGGGTGATCTCCTTCGGTA
GGTCCTTGATGTCACATCTTCCTAGGTGGTGTCCCGCAATTCTTAGATGTCCTCTTAGGGGTACGGTCCTCCGATAACCAAT
TCGGATTCCAATAGCGGTCTGGTTAGGATGGTTCCATGGTCCATGTGTAGCGGTACGGTCCATGTGTCGTCCGGGTTGAACG
ACCACACATAGATCTGGTTCTCGGCGAATAGTCTGAAGGAGGCGATGAAGTAGGATAGCCACATTAGTCCTACTAGACAAG
CCATAGCGATCGGCATTCCACCTGTGATCCAGTTGATTCTGTAGACCGCGATTAGTGTACAAGAAATCTGTTCCTGTTCGGCCAAGGTGACCG
GCCATAGTAGCCATAGGAAGATTAGCTTGATGATGTAGCTTGATGATGTACCGCGAACTGTAGTAGTAGGCA
GATCCAGGTTAGGAATAGGAATCCGATGACTAGGTTCCACTGCTCTAGTAG

Start of M   Kozak

CTTCTTCAACTCTTCGACGGTGATGGTTCCGTTAGAATCCGC CAT ggtggc TTATGATTATTTCTCGCTTTCAATTTAACAC

Vaccinia mH5 promoter

AACCCTCAAGAACCTTTGTATTTATTTTCAATTTT ctgcag

FIG. 2P

Stabilized S-M-E (SEQ ID NO: 160) (K417T, E484K, N501Y)

Vaccinia mH5 promoter           SmaI
AAAAATTGAAAATAAATACAAAGGTTCTTGAGGGTTGTGTTAAATTGAAAGGCGAGAAATAATCATAA|ATAAGcccgggg Kozak   Start of S stabilized
ccacc|ATG|TTCGTTGTTCCTAGTCCTACTACCGGCTAGTCTCTTCTCCAGTGTGTAAACCTAACAACGAGAACACAACTACCAC
CGGCGTACACCAATTCTTCACAAGAGGAGTATATTACCCGGACAAGTGTTCAGATCCTCCGTACTACATTCTACACA
GGACCTATTCCTACCGGTTCTCCGGTTCTCTAACGTAACATGGTTCCACGGATCCATGGTTCTCTGGAACAAACGAACGAAGAGA
TTCGATAAACCCGGTCTTGCCGGTTCAACGATGGTGTATACTTTGCGTCCACGGAAGTCCAACATCATCAGAGGATGGA
TCTTCGGAACCACCTTGGATTCTAAGACCCAGTCCTTGCTAATCGTCAACAACGCGACCAACGTCGTCATCAAGTCTG
CGAATTCCAGTTCTGTAACGACCCGGTTCTTGGGAGTCTACTACCACAAGAAGAACAACAAGTCCTGGATGGAATCCGAGTTC
AGAGTGCTACTCTTCCGCGAAACCTAAGAGAGTTCGTATTCAAGAACATCGACGGATACTTCAAGATCTACTCCAAGCACACTCCGA
GAAACTTCAAGAACCTAAGAGAGTTCGTATTCAAGAACATCGACGGATACTTCAAGATCTACTCCAAGCACACTCCGA
TCAACCTAGTTAGAGATCTACCGCAAGGATTCTCTGCGCTAGAACCGTTAGTAGATTGCCGATCGGAATCAACATCAC
CAGATTCCAGACACTACTAGCGCTACACAGATCTTACCTAAGCGCGGGAGATTCTTCTTCTGGATGGACTGCTGGTGCT
GCGGCTTATTATGTAGGATACCTACACAGCCGGAGAACCTTCCTATTGAAGTACAACCTTCCTATTGAAGTACAACGGAACCATCACCGATGCC
GTAGATTGTGCTCTAGATCCGCTATCCGAAACGAAGTGCACCCTAAAGTCTTCACCGTCGAGAAGGGAATCTACCAGA
CCTCCAACTTTAGAGTACAGCCGGACCGAATCCATGTCAGATTTCCGAACATCAACGAACCTATGTCCGTTCGGAGAAGT
GTTCAACGGCGACAAGATTTGGCGTCGTCTATGGCGTGGAACAGAAAAAGAATCAGTAACTGGCGTCGCGGACTACTCCGTC
CTATACAACTCTGCCTCTTCTTCCCAGTTCAAATGCTACGGTGTATCTCGACAAAGCTAAACGATCTATGCTTCACCAA
CGTCTACGGCGGACTCCTCGTAATCAGAGGAGATGAAGTTAGACAGATTGGCGCGGGACAAACTGGAacgATCGCGGAT
TATAACTACAAGTCACCGGACGACTCACCGGATGTGTAATTGCGTGGAATTCGAACAACCTAGACTCCAAAGTCGGA
GGAAACTACAACTACTTGTACAGACTATTCAGAAAGTCCAACCTAAAGCCGTTCGAGAGAGACATCTCCACCGAAATC
TATCAGGCTGGATCCGTTCACACCGTGTAATGGTGTCaagGGATTCAACTGCTACTTCCCGCTACTCACAGTCTTACGGATTTCAACCG
ACAtacGGTGTAGGATATCAGCCGTACAGAGTCGTCGTACTATCCTTCGAACTACTCACATGTCTCCGGCGACAGTATGTGG
ACCGAAAAAGTCTACCAACCTAGTCAAGAACAAATGCGTCAACTTAACTTCAACGGACTAAACGGACTAACGCGGTGTCCT
AACCGAATCTAACAAGAAGTTTCTACCGTTCCAGCAGTTCGGAAGAGAGATATCGCGGATACAACAGAGCGGCTGTCAGAGA
TCCGCAAACCTTGGAGATCCTAGATATCACCACGTGTTCTTTCGGTGTCTGTAATTACTCCGGAACGAACACCT
CCAATCAAGTAGCGGTACTATCCAGAACGTGAACCTGTACAGAAGTACCGGTAGCTATTCACGCGGGATCAACTAACAC

FIG. 2Q

```
CAACTTGGAGAGTGTACTCCACCGGATCTAACGTATTCCAAACAAGAGAGCGGGATGTCTAATGCGGAGGCGGAACACGTAA
ACAACTCCTACGAATGTGATATCCGGATTGGAGCGGGAATCTGTGCGTCTTACCAAACACAAACAAACTCTCCGAGAA
GAGCGAGATCTGTAGCCTCTCAATCTATTATCGCCTACACCATGTCCTTGGGAGCCGAAATTCTGTCGCGCTACTCCAA
CAATTCTATCGCGATCCGACAAACTTCACCATCTCGTAACAACGAGATCCTACCGGTGTCTATGACCAAGACATCT
GTCGATTGCACCATGTACATGTACATCTGCGGAGATTCCACCGAGATTCGCTGTGAATCGCGCTGACTGGAATCGCGCTTGACTGGAATCGC
AGCTAAACAGAGCGGTTGACTGGAATCGCGCTGACTGGAATCGCTGTGAGTAGAGGTATTCGCGCAAGTCAAGCAG
ATCTATAAGACTCCCGCCGATCAAGGACTTCGGAGGTTCAACTTCTCTCAGATCTTGCCGGATCCGTCCAAACCGTCTA
AGAGATCTTTCATCGAGGACCTACTATTCAACAAAGTCACCCTAGCTGACGCGGGATTCATCAACAATACGGAGATTG
CTTGGGAGACATTGCGGCGAGAGATCTAATTTGCGCGCAGAAGTTTAACGGATTGACAGTACTACCGCGCTACTAACC
GATGAGATGATTGGCGCAGTACACGTCCAGTCTATTGGCGGGAACAATTACAAGTGGATGGACATTTGGAGCCGGTGCC
GCTCTACAAATTCCGTTTGCTATGCAAATGGCGTACAGATTCAACGAATCGGAGTAACCCAGAACGTCTTGTACGAGA
ACCAGAAGCTAATCGCGGAACCAGTTCAATTCCGCGATCGGAAAAGATCGGAAAGATCCGGAAAGATCCAGGACAGTCTATCTTCTGCTTCGGCGTT
GGGAAAGCTACAGGATGTAAATCAAAAACGCGCAGGCGCTAAACACCTTGGTCAAGCAACTATCCTCTAACTTCGG
AGCGGATCTCCGTCCGTCCTAAACGACATCTTATCCAGACTAGAT caccg GAAGCGGAGGTCCAGATCGATAGACTAATCA
CTGGAAGATTGCAGTCCCTACAGACCTGAAGTCCGGAGAGTCCGGAGAGTTGGCGGAGATTAGAGCGCTCTGCTAATC
TAGCTGCGACCAAGAGTCCGAATGTGTCTTGGGACAATCCAAGAGAGTGGACTTCTGCGGAAAGGGATACCACCTAA
TGTCTTTCCCACAATCTGCGCCGCATGGTGTCGTATTCCTACACGTGTAACATATGTGCCGGCGCAAGAAAAGAACTTCAC
AACAGTCCAGGATCTGCCATGATGGAAAAGCTCATTTCCCGAGAGAGGGAGTCTTTGTCTCTAACGGAACTCATTGG
TTCGTCACCCAGAGAAACTTCTACGAGGCGCAGATCTACACCGTCTACGATCTCACCGGAGAATCAACTGCGACGTG
GTCATCGGAATCGTAAACAATACCGTCTACGATCCGGTTGCAGCCGGAACTAGACTCCTTCAAAGAAGAGTTGGACAAG
TACTTCAAGAACCACACCTCTCCGGATGTGGGACTTGGGAGATATCTCGGAATCAACGGCGTCCGTCGTCAACATCCAGA
AAGAAATCGATAGATTGAACGAGGTCGGCGAAGACGGTCCCTAATCGACCTAACGAGTCCTACAAGAGCTAGGAAATAC
GAGCAGTACATCATCAAGTGGCCGTGTACATCTGGCTAGGATTCATTGCTGACTAATTGCGATCGTCATGGTCACCATCA
TGCTATGCGTGTATGACCTCGTTCCTGTTCCTGTCTCTAAAGGGGATG TTGTTCCTGGCGGATCCTGGTTGCAAGTTCGATGAAGATGAATGAGTGAACCGGTCCTAAAGGGGTGTCAAGCTACACTACACA
```

End of S Stabilized

```
TAATAAtttttatgcggccggagctc CGCTTTTTATAGTAAGTTTTTCACCCATAAATAAATACAATAATTAATTTCTCGTAAA
```

Vaccinia p7.5

Kozak Start of M

```
AGTAGAAAATATATTCTAATTTATTGCACGGT gccacc ATG GCGGGATTCTAACGGAACCATCACCGTCGAAGAGTTGAAG
```

FIG. 2R

```
AAGCTACTAGAGAGCAGTGGAACCTAGTCATCGGATTCATTCCTATTCCTAACCTGGATCTGCCTACTACAGTTCGGCGTACGGCGA
ACAGGAACAGATTCTTGTACATCATCAAGCTAATCTTCCTATGGCTACTATGGCCGGTCACCTGGCCTTGGCCTGCTTCGTTCTA
GCTGCGGTCTACAGAATCAACTGGATCACAGGTGGAATCGCGATCGCTATGGCTTGTCTAGTAGGACTAATGTGGCTAT
CCTACTTCATCGGCCTCCTTCAGACTATTCGGGAGAACCAGATCTATGTGGTCGTTCAACCCGGAGACGAACATCCTATT
GAACGTACCGCTACATGGAACCATCCTAACCAGACCGGCTATTGGAATCCGACCGGCTATCGGAGCGGGTCATCCTAAGA
GGACATCTAAGAATTGCGGGACACCACCTAGGAAGATGTGACATCAAGGACCTACCGAAGGAGATCACCGTAGCGAC
CTCTAGAACCCTATCGTACTATAAGTTGGGAGCCCTCAAAGAGTCGCGGGAGATTCGGGATTTGCGGGGGTATTCTAGA
```

End of M

```
TACAGAATCGGGAACTACAAGCTAAACACCGACCACCTCCTCCAGTTCCGATAATATCGCTCTACTAGTCCAGTAATAAtt
``` p11 promoter        Kozak Start of E

```
tttatatgcatccgcgcg|TTTCATTTTTGTTTTTTTTCTATGCTATAAAT|gccacc|ATG|TACTCCTTCGTTCCGAAGAAACCGGAACCTTG
ATCGTCAACTCCGTCCTACTATTCCTAGCGGTTCGTCGTTCCTACTAGTAACCTAGCTATCCTAACCGGCGCTAAGACT
ATGTGCGTACTGCTGCAACATCGTCAACGTGTCCCTAGTGAAGCCGTCCTTCTACGTCTACTCCAGAGTCAAGAACCTA
```

End of E

```
AACTCCCTCTAGAGTCCCGGACCTACTAGTTTAATAAttttttatgtcgac
```

FIG. 2S

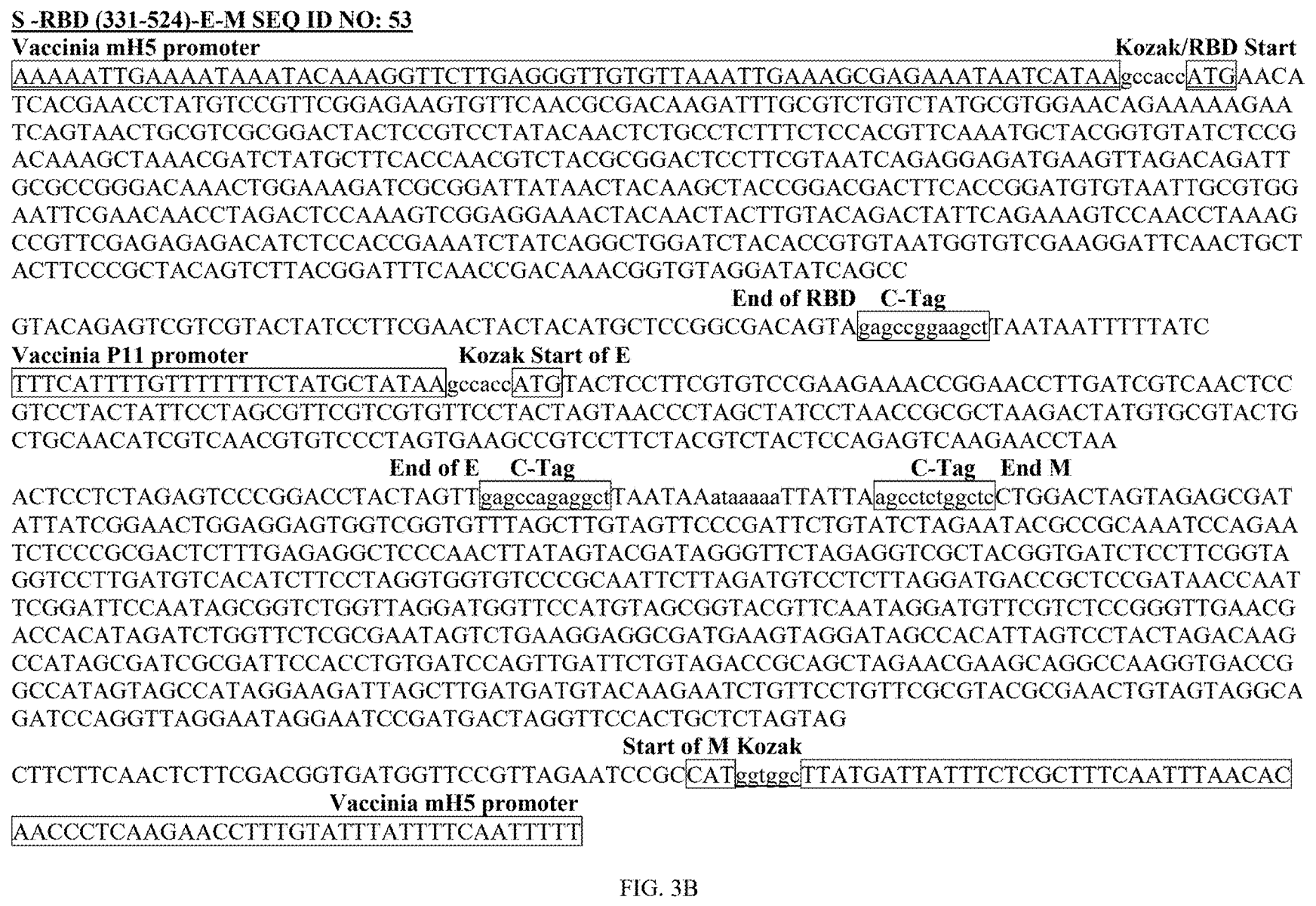

S_-RBD (331-524)-E-M SEQ ID NO: 53

Vaccinia mH5 promoter                            Kozak/RBD Start

AAAAATTGAAAATAAATACAAAGGTTCTTGAGGGTTGTGTTAAATTGAAAGGCGAGAAATAATCATAAgccaccATGAACA
TCACGAACCTATGTCCGTTCGGGAGAAGTTCAACGGACAAGATTGCGTCTGTCGTGGAACAGAAAAAGAA
TCAGTAACTGGCGTGCGGGACTACTCCGTTCCTATACAACTCTGCCTCTTTCTCCACGTTCAAATGCTACGGTGTATCTCCG
ACAAAGCTAAACGATCTATGTCACCAACGTCACCAACGTCGGATTATAACTACAAGCTACCGGACGATT
GCGCCGGGACAAACTGGAAAGATCGGCGATTATAACTACAAGCTACCGGACGATGTAATTGGCGTGG
AATTCGAACAACCTAGACTCGGAGGAAACTACAACTACTTGTACACCGTGTCGAAGATTCAACCTAAAG
CCGTTCGAGAGAGACATCTCCACGGAAATCTATCAGGCTGACTCACACCGTGTAATGGTGTCGAAGATTCAACTGCT
ACTTCCCGTACAGTCTTACGGATTCAACGACAAACGGTGTAGGATATCAGCC

End of RBD    C-Tag

GTACAGAGTCGTCGTACTATCCTTCGAACTACTACATGCTCCGGCGACAGTAgagccggaagctTAATAATTTTTATC

Vaccinia P11 promoter                     Kozak Start of E

TTTCATTTTGTTTTTTTCTATGCTATAAgccaccATGTACTCCTTCGTGTCCGAAGAAACCGGAACCTTGATCGTCAACTCC
GTCCTACTATTCCTAGCGTTCGTTCCTACTAGTAACCCTAGTAACCCGCTATCCTAGTAACGACTATGTGCGTACTG
CTGCAACATCGTCAACGTGTCCCTAGTGAAGCCCTGTCCTTCTACGTCCTCTACTCCAGAGTCAAGAACCTAA

End of E    C-Tag

ACTCCTCTAGAGTCCCGGACCTACTAGTTgagccagaggctTAATAAaataaaaTTATTAagcctctggctcCTGGACTAGTAGAGCGGAT
ATTATCGGAACTGGAGGAGTGGTCGGTGTTAGCTTGTAGTTCCGATTCGTATCTAGAATACGGCCGCAAATCCAGAA
TCTCCCGGACTCTTTGAGAGGCTCCCAACTTATAGTACGATACGGGTTCTAGAGGTCGCTACGGTGATCTCCTTCGGTA
GGTCCTTGATGTCACATCTCCAGTGGTGTGCCCGCAATTCTAGATGTCCTCTAGATGCCGCTCCGATAACCAAT
TCGGATTCCAATAGGCGGTCTGGTTAGGAGATGGTTCCATGGAGGGTACGTTCAATAGGATGTTCGTCCGGGTTGAACG
ACCACATAGATCTGTTCTCGCGAAATAGTCTGAAGGAGGCGATGAAGTAGGATAGCCACATTAGTCCTACTAGACAAG
CCATAGCGATCGCGATTCCACCTGATTCCAGTTGATTCGTAGAGGTGTACAAGAATCTGTTCCGTTCGCGGTAGCAGGTGACCG
GCCATAGTAGCCATAGGAAGATTAGCTTGATGATGTACAAGAATCGGTCCACTGCTCTAGTAG

Start of M Kozak

GATCCAGGTTAGGAATAGGAATCCGATGACTAGGTTCCACTGCTCTAGTAG

Vaccinia mH5 promoter                  C-Tag    End M

CTTCTTCAACTCTTCGACGGTGATGGTTCCGTTAGAATCCGCCATgctggcTTATGATTATTTCTCGCTTTCAATTTAACAC
AACCCTCAAGAACCTTTGTATTTATTTATTTTCAATTTTT

FIG. 3B

S_-RBD (331-524)-E-M SEQ ID NO: 54

Vaccinia mH5 promoter                                                                                        SMAI/Kozak AAAAATTGAAAATAAATACAAAGGTTCTTGAGGGTTGTGTTAAATTGAAAGCGAGAAATAATCATAA|CCCGGGgccacc RBD Start ATG|AACATCACGAACCTATGTCCGTTCGGAGAAGTGTTCAACGCGACAAGATTTGCGTCTGTCTATGCGTGGAACAGA
AAAGAATCAGTAACTGCCGTGCCGGACTACTCCGTCCATACAACTCTGCCTCTTTCTCCACGTTCAAATGCTACGGTGT
ATCTCCGACAAAGCTAAACGATCTATGCTTCACCAACGTCTACGCGGACTCCTTGTAATCAGAGGAGATGAAGTTAGA
CAGATTGGCGCGGGACAAACTGGAAAGATCGCGGATTATAACTACAAGCTACCGGACTTCACGGATGTGTAATT
GCGGTGGAATTCGAACAACTGCGAACCAGAGTCCAAAGTCGGAGGAAAAACTACTTGTACAGACTATTCAGAAGTCCAAC
CTAAAGCCGTTGAGAGGAGAGACATCTCCACGAAATCTATCAGGTGGATCTACACCGTGTAATGGTGTCGAAGGATTCA
ACTGCTACTTCCCGCTACAGTCTTACGGATTCAACCGACAAACGGTGTAGGATATCAGCC End of RBD    C-Tag GTACAGAGTCGTCGTACTATCCTTCGAACTACTACACATGCTCCGGCGCGACAGTA|GagcccggaagcT|AATAATTTTATC Vaccinia P11 promoter                               Kozak Start of E TTTCATTTTGTTTTTCTATGCTATAA|gccacc|ATG|TACTCCTTCGTCGTGTCCGTGTCCGAAGAAACCGGAACCTTGATCGTCAACTCC
GTCCTACTATTCCTAGCGGTTCGTCGTGTTCCTACTAGTAACCCTAGTCATCTCTACTCTTCTACGTCTAACCGGCTAAGACTATGTGGCTACTG
CTGCAACATCGTCAACGTGTCCCTAGTGAAGCCGTCCTTCTACGTCTACTCCAGAGTCAAGAACCTAA End of E    C-Tag                                C-Tag    End M ACTCCTCTAGAGTCCCGGACCTACTAGTT|gagccagaggctT|AATAAaataaaaaTTATTA|agcctctggctc|CTGGACTAGTAGAGGGAT
ATTATCGGAACTGGAGGAGAGTGGTCGGTGTTAGCTTGTAGTTCCCGATTCGTTGTAGTTCCCGATTCTGTATCTAGAATACGGCGCAAATCCAGAA
TCTCCCGCGACTCTTGAGAGCTCCAACTTATAGTACGATAGGGTTCTAGAGGTTCTAGAGTCGCTACGGTGATCTCCTTCGGTA
GGTCCTTGATGTCACATCTTCCTAGGTGGTCCCGCAATTCTTAGATGTCCTTAGGATGTCCGGCTACCGGATGACCGGCTAACCAAT
TCGGATTCCAATAGCGGTCTGGTTAGGATGGTCTCCCATGTAGCCGGTACGTTCAATGGTACGTTCGTCTCCGGGTTGAACG
ACCACATAGATCTGGTTCTCGCGAATAGTCTGAAGGAGGGCGATGAAGTAGGATAGCCACATTAGTCCTACTAGACAAG
CCATAGGCGATCGCGATTCCACCTGATTCCAGTTGATTCGTTGTAGACCGCGAGTAGAATCGTTCCTGGTCTAGAGGTGACCG
GCCATAGTAGCCATAGGAATCCGATGAGTAGGTTCCACTGCTCTAGTAG Start of M Kozak CTTCTTCAACTCTTCGACGGTGATGGTTCCGTTAGAATCCGC|CAT|ggtggc|TTATGATTATTTCTGCTTCAATTTAACAC Vaccinia mH5 promoter

AACCCTCAAGAACCTTGTATTTATTTTCAATTTTT|

FIG. 3C

S -RBD (aa 327-524)-E-M SEQ ID NO: 51

Vaccinia mH5 promoter                                                                 Kozak

AAAATTGAAAATAAATACAAAGGTTCTTGAGGGTTGTGTTAAATTGAAAGCGAGAAATAATCATAA|gccacc

RBD Start

AT|GGTCAGATTTCCGAACATCACGAACCTATGTCCGTTCGGGAGAAGTGTTCAAGCGCGACAAGATTTGGCGTCTGTCTATG
CGTGGAACAGAACAGAAGAATCAGTAACTGGCGTCGGGACTACTCCGTCCTATACAACGTCTGCCTCTTTCTCCACGTTCAA
ATGCTACGGGTGTATCTCCGACAAAGCTAAACGATCTATGCTTCACCAACGTCTTCACCAACGTCTTCGTAATCAGAGGA
GATGAAGTTAGACAGATTGCGCCGGGACAAACTGGAAAGATCGGGAATTATAACTACAAGCTACCGGACGACTTCACC
GGATGTGTAATTGCGGTGGAATTCGAACAACCTAGACTCGAACAAAGTCGGAGGAAAACTACAACTACTTGTACAGACTATTC
AGAAAGTCCAACCTAAAGCCGTTCAAGCCATCTCCACGGATTTCAACCACGGTGATCTATCAGGCTGGATCTCACCGTGTAATGGT
GTCGAAGGATTCAACTGCTACTTCCCGCTACGGATTCAGCTTACGGATTCAACCACAACGGTGTAGGATATCAGCC

End of RBD     C-Tag

GTACAGAGTCGTCGTACTATCCTTCGAACTACTACATGCTCCGGGCGACAGTA|gagcccggaagct|TAATAATTTTTATC

Vaccinia P11 promoter                     Kozak Start of E

TTTCATTTGTTTGTTTTTCTATGCTATAA|gccacc|ATG|TACTCCTTCGTGTCCGAAGAAACCGAACCTTGATCGTCAACTCC
GTCCTACTATTCCTAGCGGTTCGTCGTTCCTACTAGTAACCCTAGTATCTCGTATAACCTAGTTCTAACCGGCGCTAAGACTATGTGCGTACTG
CTGCAACATCGTCAACGTGTCCCAGTGAAGCCGGTCCTTCTACGGTCAAGCCGGTCCTTCTACGTCTACTCCAGAGTCAAGAACCTAA

End of E     C-Tag

ACTCCTCTAGAGTCCCGGACCTACTAGTT|gagccagaggct|TAATAAataaaaaTTATTA|ataaaaaTTATTA... ATTATCGGAACTGGAGGAGTGGTGGTCGGTGTTAGCTTGAGTTCCGATTCTGTTAGTTCCGATTCGTATCGTATCTGAGAATCGTCTGTATCTAGAATACGCCGCAAATCCAGAA
TCTCCCGCGACTCTTGAGAGCTCCAAACTTATAGTACGATAGGGTTCGTCGCTACGGTGATCTCCTTCGGTA
GGTCCTTGATGTCACATCTTCCTAGGGTGTGCCCGCAATTCTTAGATGTCCCTCTTAGATGGATGTCCCGTCTCGGGTTGAACG
TCGGATTCCAATAGGCGGTTCGTCGGTTAGGATGGTTCCATGTTAGGATGGTTCCATGTGTAGGCGGTCAATAGTTCAATAGGAGGCGATGAAGGTGAGGAGGCGATGAAGTAGGAGGCGAGTAGGAGGCGATGAAGTAGGAGGAGGCGATGAGGAGGCGAGTAGGAGGCGATGAAGTAGGAGGAGGCGATGAGGAGGCGAGTAGGAGGCGATGAAGTAGGAGGAGGCGATGAGGAGGCGAGTAGG... 
CCATAGGGATCGGCGATTCCACCTGTAGGATTTCGATGGGATTCGATGTGTAGACCGCGCAAGGTGACCG
GCCATAGTAGCCATAGCCATAGGAAGATTAGCTTGATGATGTACAAGAATCTGTTCCTGTTCCGGTACGCGCAACTGTAGTAGGCA
GATCCAGGTTAGGAATAGGAATCCGATGACTAGGTTCCACTGCTCTAGTAG

Start of M Kozak                                         Vaccinia mH5 promoter

CTTCTTCAACTCTTCGACGGTGATGGTTCCGTTAGAATCCGC|CAT|ggtggc|TTATGATTATTTCTCGCTTTCAATTTAACAC
AACCCTCAAGAACCTTTGTATTTATTTCAATTTT

FIG. 3E

S -RBD (aa 327-524)-E-M SEQ ID NO: 52

Vaccinia mH5 promoter                                                           SMAI/Kozak
AAAATTGAAAATAAACAAAGGTTCTTGAGGGTTGTGTTAAATTGAAAGGGAGAAATAATCATAA CCCGGGccacc

RBD Start
ATG GTCAGATTCCGAACATCACGAACCTATGTCCGTTCGGAGAGAAGTGTTCAACGCGACAAGATTTGCGTCGTCTATG
CGTGGAACAGAAAAAGAATCAGTAACTGCGTCGGGACTAACTCTGCCTCTTTCTCCACGTTCAA
ATGCTACGGGTGTATCTCCGACAAAGCTAAACGATCTATGTTCACCAACGTCTACGCGGACTCCTTCGTAATCAGAGGA
GATGAAGTTAGACACAGATTGCGCCGGGACAAACTGGAAAGATCGCGGATTATAACTACAAGCTACCGGACGACTTCACC
GGATGTGTAATTGGCGTGGAATTGAACAACCTAGAACTCGGGAGGAAACTACAACTACTTGTACAGACTATTC
AGAAAGTCCAACCTAAAGCCGTTCGGAGAGAGACAATCTCCACCGGAAATCTATCAGGCTGGATCTACACCGTGTAATGGT
GTCGAAGGATTCAACTGCTACTTCCCGCTACTTCCCGGATTCAACCGACAAACGGGTGTAGGATATCAGCC

End of RBD    C-Tag
GTACAGAGTCGTCGTACTATCCTTCGAACTACTACACATGCTCCGGCGACAGTA Agagccggaagct TAATAATTTTATC

Vaccinia P11 promoter          Kozak Start of E
TTTCATTTTGTTTTTTCTATGCTATAA gccacc ATG TACTCCTTCGTGTCCGAAGAAACCTTGATCGTCAACTCC
GTCCTACTATTCCTAGCGGTCGTTCGTGTTCGTTCCTACTAGTAACCCTAGCTATCCTAACCGGGCTAAGACTATGTGGTACTG
CTGCAACATCGTCAAGTGTCCCTAGTGAAGCCGTCCTTCAGTCGCCGGTCCTTCTACTCCCAGAGTCAAGAACCTAA

End of E    C-Tag
ACTCCTCTAGAGTCCCGGACCTACTAGT T gagccagagct TAATAAAaataaaaTTATTA Aagcctctggctc CTGGACTAGTAGAGCGAT
ATTATCGGAACTGGAGGAGTGGTCGGTGTTTAGCTTGTGTGAGTTCCGATTCGTATCGTGTAATACGCGCAAATCCAGAA
TCTCCCGGACTCTTGAGAGGCTCCCAACTTATAGTACGATAGGGTTCTAGAGGTCGCTACGGTGATCTCCTTCGGTA
GGTCCTTGATGTCACATCTCCTAGTGGTCCCGCAATTCTTAGATGTCCTTAGGATGTCCTTCCGATAACCAAT
TCGGATTCCAATAGCGGTCTCGGTAGGATGGTCTCCATGGTACGTTCAATGTAGGCGGTACGTTCGTCTCCGGGTTGAACG
ACCACATAGATCGTGTTCTCGCGAATAGTAGTCTGAAGGAGGCGATGAAGTAGGATAGCCACACATTAGTCCTACTAGACAAG
CCATAGCGATCGGCCATTCCACCTGTGATCCAGTTGATTCTGTAGACCGCAGCTAGAATACGCCGCAAGGTGACCG
GCCATAGTAGCCATAGGAAGATTAGCTTGATGATGTACAAGAATCTGTTCCTGTTCCGTGTTCGGCGAACTGTAGTAGGCA
GATCCCAGGTTAGGAATAGGAATCCGATGACTAGGTTCCACTGCTCTAGTAG

Start of M Kozak          C-Tag    End M
CCGCCAT ggttggc TTATGATTATTTCTGCTTTCAATTTAACAC

Vaccinia mH5 promoter
CTTCTTCAACTCTTCGACGGTGATGGTTCCGTTAGAATCCGGTTGTATTTATTTGTATTATTTTCAATTTTT
AACCCTCAAGAACCTTGTATTATTTCAATTTTT

FIG. 3F

S.-SP-RBD (aa 327-524)-TM-E-M SEQ ID NO: 69 mH5 vaccinia promoter                     Kozak   Signal

AAAAATTGAAAATAAATACAAAGGTTCTTGAGGGTTGTGTTAAATTGAAAGCGAGAAATAATCATAA|gccacc|ATGTTCG RBD Start TGTTCCTAGTCCTACTACCGGCTAGTCTCTTCT|GTCAGAATTCCGAACATCACGAACCTATGTCCGTTCGGAGAAGTGTTC
AACGGGACAAGATTTGGCGTCGTGTCTATGCGTGGAACAGAAAAAGAATCAGTAACTGCGGTCGGGGACTACTCCGTCCTAT
ACAACTCTGCCTCTTCTCCACGTTCAAATGCTACGGTGTATCTCCGACAAAGCTAAACGATCTATGCTTCACCAACGTC
TACGGGGACTCCTTCGTAATCAGAGGAGATGAAGTTAGACAGATTGGCGCGGGACAAACTGGAAAGATCGGGGATTAT
AACTACACAAGTCACCGGACGACTTCACCGGCGGATGTGTAATTGGCGTGGAATTCGAACAACCTAGACTCCAAGTCGGAGA
AACTACAACTACTTGTACAGACTATTCAGAAAGTCCAACCTAAAGCCGTTCGAGAGGACACATCTCCACGAAATCTATC
AGGCTGGATCTCACACCGGTGTAATGGTGTCGAAGGATTCAACTGCTACTTCCCGCTACCAGTCTTACGGATTTCAACCGAC
AAACGGTGGAGATATCAGCGGTACACGGCGTCGTTCGTACTACATCCTTCGAACTACTACACATGCTCCG RBD end CoV19 Tm-Ct GCGACAGTA|TGGTACATCTGGCTAGGATTCATTGCTGCTGGACTAATTGCGATCGTCACCATCATGCTATGCTGTA
TGACCTCCGTGTTGCCTGTGTCTAAAGGGATGTTGTTCCTGCGGATCCTGTTGCAAGTTCGATGAAGATGATAGTGAACC
GGTCCTAAAGGGTG C-Tag            P11 vaccinia promoter            Kozak E Start TCAAGCTACACTACACA|gagcccggaagcttaataatttatc|TTTCATTTTGTTTTTTCTATGCTATAA|gccacc|ATGTACTCCTTCGTGT
CCGAAGAAACCGGAACCTTGATCGTCAACTCCGTCCTACTATTCCTAGCGTTCGTCGTGTTCCTACTAGTAACCCTAGCT
ATCCTAACCGGCGCTAAGACTATGTGCTGCAACATCGTCAACGGTGTCCCTAGTGAAGCCGTCCTTCTACGTCT
ACTCCA E End     C-Tag                          C-Tag GAGTCAAGAGAACCTAAACTCCCTCTAGAGTCCCGGACCTACTAGT|gagccagagggctTAATAAataaaaaTTATTAagcctctggctc M end CTGGACTAGTAGAGCGATATTATCGGAACTGGAGGAGTGGTCGGTGTTAGCTTGTTCCGATTCTGTATCTAGAA
TACGCCGCAAATCCAGAAATCTCCGCGACTCTTGAGAGCTCCAACTTAGTACGATAGGGTTCTAGAGGTCGCTA
CGGTGATCTCCTTCGGTAGGTCCTTGATGTCACATCTCTAGGGGTGTCCGCAATTCTTAGATGTCCTCTTAGGATG
ACCGGCTCCGATAACCAATTCGGATTCCAATAGGCGGTCTGGTTAGGATGGTCCATGTAGGGGTACGTTCAATAGGATGT
TCGTCTCCGGGTTGAACGACCACCACATAGATCTCGGTTCTCGCGAATAGTCTGGTTCTCGGAATAGTCTGGATAGCCACA
TTAGTCCTACTAGACAACAAGCACCATAGGCGATCGCGCATTCCACCTGTGATTCTGTATCGGCGCTAGAACGAA

FIG. 3I

GCAGGCCAAGGTGACCGGCCATAGTAGTAGCCATAGGAAGAGATTAGCTTGATGATGTACAAGAATCTGTTCCTGTTCGCGTA

CGCGAACTGTGAGTAGGCAGATCCAGGTTAGGAATAGGAATCCGATGACT

M Start    kozak

AGGTTCCACTGCTCTAGTAGCTTCTTCAACTCTTCGACGGGTGATGGTTCCGTTAGAATCCGCCAT ggtggc TTATGATTATT mH5 promoter

TCTCGCTTTCAATTTAACACAACCCTCAAGAACCTTTGTATTTATTTTCAATTTT

FIG. 3J

S_-SP-RBD (aa 327-524)-TM-E-M SEQ ID NO: 70 mH5 vaccinia promoter    SMAI/Kozak

AAAATTGAAAATAAATACAAAGGTTCTTGAGGGTTGTGTAAATTGAAAGGCGAGAAATAATCATAA|CCCGGGgccacc

Signal    RBD start

ATGTTCGTTGTGTTCCTAGTCCTACTACCGCTAGTCTCTTCT|GTCAGATTTCCGAACATCACGAACCTATGTCCGTTCGGAGA

AGTGTTCAACGCGACAAGATTTGCGTCTGTCTATGCGGTGAACACAGAAAAAGAATCAGTAACTGCGTCGCGGACTACTC

CGTCCTATACAACTCTGCCTCTTCCACGTTCAAATGCTTCAAAGAGGAGATGAAGTTAGACAGATTGGCGCGGGACAAACTGAAAGATCG

CCAACGTCTACGCGGACTCCTTCGTAATCAGAGGAGAGTGAAGTTAGACAGATTGGCGCGGGACAAACTGAAAGATCG

CGGATTATAACTACAAGCTACCGGACGACTTCACCGGACGATTGTAATTGCGTGGAATTCGAACAACCTAGACTCCAAAGT

CGGAGGAAACTACAACTACTTGTACAGACTATTCAGAAAAGTCCAACCTAAAGCCGTTCGAGAGAGACATCTCCACCGA

AATCTATCAGGTGACGATCTACACCGTGTAATGGTGTGCAAGGATGGTGTTCCTGCGGATCCTGTTGCAAGTTCGATGAGATGAGTGAACC

AACCGACACAAACGGTGTAGGATATCAGCCGTCGTACAGAGTCGTACTATCCTTCGAACTACTACATGCTCCG

RBD end    CoV19 Tm-Ct

GCGACAGTA|TGGTACATCTGGCTAGGATTCATTGCTGGACTAATTGCGGATCGTCACCATCATCATGTGTGTA

TGACCTCCTGTTGCTGCTCTGTGTCTAAAGGGATGTTGTTCCTGCCGATCCTGTTGCAAGTTCGATGAGATGAGTGAACC

GGTCCTAAAGGGTG|

C-Tag

TCAAGCTACACTACACA|gagccggaagcttaataattttatc|TTTCATTTGTTTTTTCTATGCTATAA|gccacc|ATGTACTCCTTCGTGT

CCGAAGAACCGAACCTTGATCGTCAACTTCCGTCCTACTATTCCGTCGTTCGTCTTCTACTAGTAACCCTAGCT

ATCCTAACCGGCGCTAAGACTATGTGCTAGCTATGTGCTGCTGCAACATCGTCAACGTGTCCCTAGTGAAGCGCCGTCCTTCTACGTCT

ACTCCA|

P11 vaccinia promoter    Kozak E start

E end    C-Tag    C-Tag

GAGTCAAGAACCTAAACTCCCTCTAGAGTCCCGGACCTACTAGTT|gagccagagggctTAATAAataaaaaTTATTAagcctctggctc

M end

CTGGACTAGTAGAGGCGGATATTATCGGAACTGGAGGAGTGGTCGGTGTGTTTAGCTTGTGTAGTTCCGATTCTGTATCTAGAA

TACGGCCGCAAATCCAGAATCTCCCGCGACTCTTTGAGAGGCTCCCAACTTATAGTACGATAGGGTTCTAGAGGTCGCTA

CGGTGATCTCCTTCGGTAGTCGTAGTTCCTTGATGTCACATCGTCGTCCCGCAATTCTTAGATGTCCTCTTAGGATG

ACCGGCTCCGATAACCAATTCGGATTCCAATAGCGGTGTCGGTTCCATGTAGGATGGTTCCATGTAGGGTACGTTCAATAGGATGT

FIG. 3K

TCGTCTCCGGGTTGAAGGACCACCATAGATCTGGTTCTCGCGAATAGTCTGAAGGAGGCGATGAAGTAGGATAGCCACA

TTAGTCCTACTAGACAAGCCATAGGCGGATCGGGGATTCCACCTGTGATCCAGTTGATTCTGTAGACCGGCAGCTAGAAGCGAA

GCAGGGCCAAGGTGACCGGCCATAGTAGCCATAGGAAGATTAGCTTGATGATGTACAAGAATCTGTTCCTGTTCGCGTA

CGCCGAACTGTAGTAGGCAGATCCCAGGTTAGGAATAGGAATCCGATGACT

AGGTTCCACTGCTCTAGTAGCTTCTTCAACTCTTCGACGGTGATGGTTCCGTTAGAATCCGCCAT ggtggc TTATGATTATT mH5 promoter M start Kozak

TCTCGCTTTCAATTTAACACAACCCTCAAGAACCTTTGTATTTATTTTCAATTTTT

FIG. 3L

S.-SP-RBD (aa 331-524)-TM-E-M SEQ ID NO: 71 mH5 vaccinia promoter                                    Kozak  Signal

AAAAATTGAAAATAAATACAAAGGTTCTTGAGGGTTGTGTTAAATTGAAAGCGAGAAATAATCATAA|gccacc|ATGTTCG RBD start TGTTCCTAGTCCTACTACCGCTAGTCTCTTCT|AACATCACGAACCTATGTCCGTTCGGAGAAGTGTTCAACGGCGACAAG
ATTGGCGTCTGTCTGTCTATGCGTGGAACAGAGAAAAAGAATCAGTAACTGCGTCGCGGACTACTCCGTCCTATACAACTCTGCC
TCTTTCTCCACGTTCAAATGCTACGGTGTATCCGACAAAGCTAAACGATCTATGCTTCACCAACGTCTACGGGACTC
CTTCGTAATCAGAGGAGAGATGAAGTTAGACAGATTGCGCGCGGGACAAACTGGAAAGATCGCGGATTATAACTACAAGCT
ACCGGACGACTTCACCGGATGTGTAATTGCGTGGAATTCGAACAACCTAGACTCCAAGTCGGGAGGAAACTACAACTA
CTTGTACAGACTATTCAGAAAGTCCAACCTAAAGCCGTTCGAGAGAGACATCTCCACGGATTTCAACCGACACCGTAATGGTGTCGAAGGTGTAATGGTGTCGAAGGTATTCAACCGACAAACGGTGTAG RBD/end CoV19 Tm-Ct GCGACAGTA|TGGTACATCTGGCTAGGATTCATTGCTGGACTAATTGCGATCGTCACCATCATGCTGTGTA
TGACCTCCTGTTGCTCCGTGTCTAAAGGGATGTTGTTCCTGCGATCCGTGTTGCAAGTTCGATGAAGATGATAGTGAACC C-Tag

GGTCCTAAAGGGTG

C-Tag

TCAAGCTACACTACACA|gagccgccggaagcttaataatttttatc|TTTCATTTGTTTTTTCTATGCTATAA|gccacc|ATGTATCCTTCGTGT P11 vaccinia promoter          Kozak E Start CCGAAGAAACCGGAACCTTGATCGTCAACTCCGTCCTACTATTCCTAGCGTTCGTCGTCCTACTAGTAACCCTAGCT
ATCCTAACCGGCGCTAAGACTATGTGCGTAAGACTATGTGCTGCAACATCGTCAACGTGTCCCTAGTGAAGCCGTCCTTCTACGTCT
ACTCCA E end C-Tag.                              C-Tag GAGTCAAGAACCTAAACTCCTCTAGAGTCCCGGACCTACTAGT|gagccgccagaggctTAATAAataaaaaTTATTAagcctctggctc CTGGACTAGTAGAGGCGATATTATCGGAACTGGAAGTGGTCGGTGTTTAGCTGGTGTTAGCTGGTGGTGGAGGAGGAGTGGTCCGGAGTGGTCGGTGTTTAGCTGGTGTTAGCTGGTGGTGGAGGAGGAGTGGTCGGAGTTCTAGAA
TACGCGGCAAATCCAGAATCTCCCCGGACTCTTTGAGAGGCTCCAACTTATAGTACGATAGGGTTCTAGAGGTCGCTA
CGGTGATCTCCTTCGGGTAGGTCGTAGTGTCACATCTTCCTAGGTGGTGTCCCGCAATTCTTAGAGATGTCCTTAGGATG M end

FIG. 3M

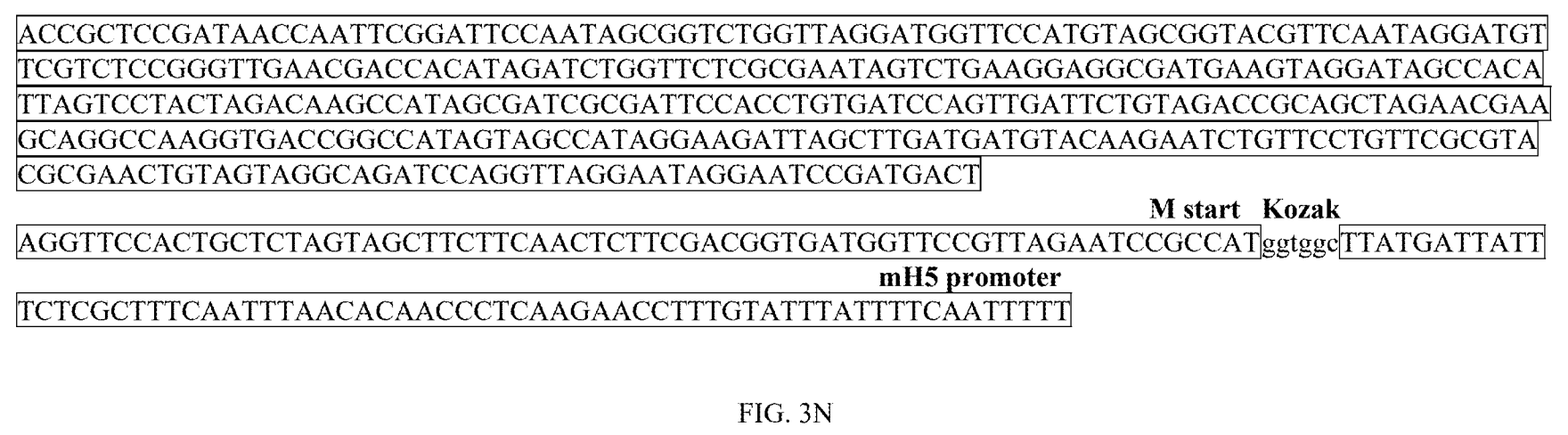

ACGGCTCCGATAACCAATTCGGATTCCAATAGCGGTCTGGTTAGGATGGTTCCATGTAGGCGGTACGTTCAATAGGATGT

TCGTCTCGGGGTTGAAGGACCACATAGATCTGGTTCTCGGAATAGTCTGAAGGAGGCGATGAAGTAGGATAGCCACA

TTAGTCCTACTAGACAAGCCATAGGCATCGGGATTCCACCTGTGATCCAGTTGATTCGTAGACCGGCAGCTAGAACGAA

GCAGGGCCAAGGTGACCGGCCATAGTAGCCATAGGAAGATTAGCTTGATGATGTACAAGAATCTGTTCCTGTTCGCGTA

CGCGAACTGTAGTAGGCAGATCCAGGTTAGGAATAGGAATCCGATGACT

AGGTTCCACTGCTCTAGTAGCTTCTTCAACTCTTCGACGGTGATGGTTCCGTTAGAATCCGCCAT|ggtggc|TTATGATTATT

| | M start | Kozak | mH5 promoter

TCTCGGCTTTCAATTTAACACAACCCTCAAGAACCTTTGTATTTATTTCAATTTT

FIG. 3N

S_-SP-RBD (aa 331-524)-TM-E-M SEQ ID NO: 72 mH5 vaccinia promoter                                                     SMAI    Kozak AAAAATTGAAAATAAATACAAAGGTTCTTGAGGGTTGTGTTAAATTGAAAGGCGAGAAATAATCATAA CCCGGG gccacc RBD start ATGTTCGTGTCGTTCCTACTACCGCTAGTCTCTTCT AACATCACGAACCTATGTCCGTTCGGAGAAGTGTTCAACGC
GACAAGATTTGGCGTCTGCGTCTGTCTATGCGGTGGAACAGAAAAAGAATCAGTAACTGCGTCGCGGACTACTCCGTCCTATACAAC
TCTGCCTCTTTCTCCACGTTCAAATGCTGTGTATCTCCGACAAAGCTAAACGATCTATGCTTCACCAACGCTACGC
GGACTCCTTCGTAATCAGAGGAGAGATGAAGTTAGACAGATTGGCGCGGGACAAACTGAAAGAGATCGGGGATTATAACTA
CAAGCTACCGGACGACTTCACCGGATGTGTAATTGCGTGGAATTCCAAGTCCAAGTCCGAGGAAACTA
CAACTACTTGTACAGAGTATTCAGAAAGTCCAACTAAAGCCGGTTGCGAAGGATTCAACGTCTACTTCCCGCGTACAGTCTTACGGATTTCAACGACAAACG
GTGTAGGATATCAGCCGTACAGAGTCGTCGTACTATCCTTCGAACTACTACATGCTCCG RBD end   CoV19 Tm-Ct GCGACAGTA TGGTACATCTGGCTAGGATTCATTGCTGGACTAATTGCGATCGTCACCATCATGCTGTGTA
TGACCTCCTGTTGCTCGTGTCTAAAGGGATGTTGTTCCTGCGGATCCTGTTGCAAGTTCGATGAAGATGATAGTGAACC
GGTCCTAAAGGGTG C-Tag                                                                    Kozak E start TCAAGCTACACTACACA gagccggaagcttaataatttatc TTTCATTTGTTTTTTCTATGCTATAA gccacc ATGTACTCCTTCGTGT
CCGAAGAAACCGGAACCTTGATCGTCAACTCCGTCCTACTATTCCTAGCGTTCGTCGTTCCTACTAGTAACCCTAGCT
ATCCTAACCGGCGCTAAGACTATGTGCGCTAAGACTATGTGTCCCTAGTGAAGCCGTCCTTCTACGTCT
ACTCCA E end   C-Tag GAGTCAAGAACCTAAACTCCTCTAGAGTCCCGGACCTACTAGTT gagccagaggctTAATAAataaaaaTTATTAagcctctggctc M end CTGGACTAGTAGAGGCGATATTATCGGAACTGGAGGAGAGTGGTCGGTGTTAGCTTGTTAGTTCCGATTCGTGTATCTAGAA
TACGCCGCAAATCCAGAATCTCCCGGACTCTTTGAGAGGCTCCAACTTATAGTACGATAGGGTTCTAGAGGTCGCTA
CGGTGATCTCCTTCGGTAGTCCTTGATGTCACATCTTCCTAGGTGGTGTCCCGCAATTCTTAGAGTGTCCTTCTTAGGATG

S -SP-RBD (aa 327-598)-E-M SEQ ID NO: 158 mH5 vaccinia promotor                                            SMAI

AAAATTGAAAATAAATACAAAGGTTCTTGAGGGTTGTGTAAATTGAAATTGAAAGGCGAGAAATAATCATAA|ATAAGCCCGGG

Kozak S Signal                                     RBD Start gccacc|ATGTTCGGTGTTCCTACTACCGGTCCTACTACCGGTAGTCTCTTCT|GTCAGATTCCGAACATCACGAACCTATGTCCGTTCG

GAGAAGTGTTCAACGCGACAAGATTTGCGTCTGTCTATGCGGTGGAACAGAAAAAGAATCAGTAACTGGCGTGCGGACT

ACTCCGTCCTATACAACTCTGCCCTTCTCCACGTTCAAATGCTACGGTGTATCCGACAAAGCTAAACGATCTATGC

TTCACCAACGTCTACGGGACTCCTTGGTAATCAGAGGAGAGTAGACAGATTGAGTTAGACAGATTGGCGCGGGACAAACTGGAAAG

ATCGCGGATTATAACTACAACTACAAGCTACCGACGACTTCACCGGATGTGTAATTGCGTGGAATTCGAACAACCTAGACTCCA

AAGTCGGAGGAAACTACAACTACTTGTACAGACTATTCAGAAAGTCCAACCTAAAGCCGTTCGAGAGACATCTCCA

CCGAAATCTATCAGGCTGGATCTACACCGGTGTCGAAGGATTCAACTGCTACTTCCCGCTACCAGTCTTACGG

ATTTCAACCGACAAACGGGTGTAGGATATCAGCCGTACAGAGTCGTCGTACTATCCTTCGAACTACTACATGCTCCGGCG

ACAGTATGTGGACCGGAAAAAGTCTACCAACCTAGTCAAGAACAAATGCGTCAACTTTAACTTCAACGGACTAACCGGA

ACCGGTGTCCTAACCGAATCTAACAAGAAGTTCTACCGGTCCAGCAGTTCGGAAGAGATATCGCGGATACAACAGAC

RBD End c-Tag

GCTGTCAGAGATCCGCAAACCTTGGAGATCCTAGATATCACACCGTGTTCTTTCGGTGGTGTCTCTGTAATT|gagccagaggct

Start of E

P11 Promoter

TAATAAtttt|atgtcgacc|TTCATTTGTTTTTTCTATGCTATAA|gccacc|ATG|TACTCCTTCGTGTCCGAAGAAACCGGAACCTT GATCGTCAACTCCGTCCTACTATTCCTAGCGGTTCGGTCGGTGTTCCTACTAGTAACCCTAGTATCCTAACCGCGCTAAGAC TATGTGCGTACTGCTGCAACATCGTCAACGTGCCCTAGTGAAGCCGTCCTTAGTGAAGCCGTCCTTAGTCTCTACTCTCTACGTCTCAAGAACCT

End of E    c-Tag                      c-Tag      End of M

AAACTCCCTCTAGAGTCCCGGACCTACTAGTT|gagccagaggct|TAATAAataaaaaTTATTAagcctctggtc|CTGGACTAGTAGAGCG ATATTATCGGAACTGGAGGAGTGGTCGGTGTTTAGCTTGGTAGCTTGTGTAGTTCCCGATTCTCTAGAATACGCCGCAAATCCAG

AATCTCCCGGACTCTTTGAGAGGCTCCCAACTTATAGTACGGTTCTAGAGGTTCGGTGATCTCCTTCGG

TAGGTCCTTGATGTCACATCTTCCTAGGTGGTGTCCCGCAATTCTTAGATGTCCTCTTAGGATGACCGCTCCGATAACCA

ATTCGGATTCCAATAGCGGTCGGTTAGGATGGGTACGTTCAATAGGATGTTCGTCTCCGGGTTGAA

CGACCACATAGATCTGGTTCTCGCGAATAGTCTGAAGGAGGCGATGAAGTAGGATAGCCACATTAGTCCTACTAGACA

AGCCCATAGCGATCGCGATTCCACCTGTGATCCAGTTGATTCTGTAGACCGACCAGTTCTGTAGACCGAGCCAGCCAAGGTGAC

FIG. 3U

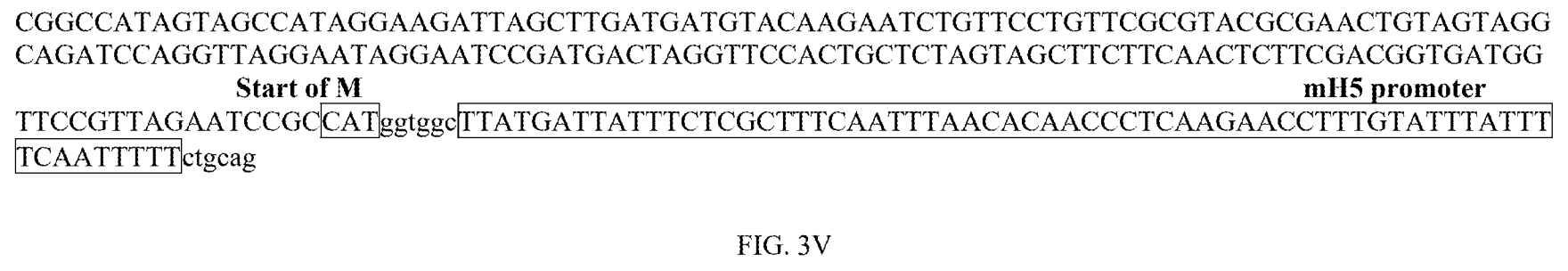

CGGCCATAGTAGCCATAGGAAGAGATTAGCTTGATGATGTACAAGAATCTGTTCCTGTTCGGCGTACGGCGAACTGTAGTAGG
CAGATCCAGGTTAGGAATAGGAATCCGATGACTAGGTTCCACTGCTCTAGTAGCTTCTTCAACTCTTCGACGGTGATGG mH5 promoter

Start of M

TTCCGTTAGAATCCGC|CAT|ggtggc|TTATGATTATTTCTCGCTTTCAATTTAACACAACCCTCAAGAACCTTTGTATTTATTT

|TCAATTTTT|ctgcag

FIG. 3V

Tandem Repeat-E-M (SEQ ID NO: 73)

Vaccinia mH5 promoter                                                                                    Kozak
AAAAATTGAAAATAAATACAAAGGTTCTTGAGGGTTGTGTTAAATTGAAAGGGAGAAATAATCATAA|gccacc
epitope 504-524
ATG|TGGACGACCTGCTGCTTCTTCATCTCCCTAATCCTAGGGAATCAAGACCCTATATCAGCCGTACAGAGTCGTCG TACTATCCTTCGAACTACTACATGCTCCGGGCGACAGTAggtcctgaccGgtTATCAGGCTGGATCTACACCGTGTAA
                                            Linker        epitope 473-490
                                                  Linker      epitope 504-524
TGGTGTGCGAAGGATTCAACTGCTACTTCggtcctggacccggtTATCAGCCGTACAGAGTCGTCGTACTATCCTTCG
                                    linker      epitope 473-490
AACTACTACATGCTCCGGGCGACAGTAggtcctggacccggtTATCAGGCTGGATCTACACCGTGTAATGGTGTGCGAA
                                linker      epitope 504-524
GGATTCAACTGCTACTTCggtcctggacccggtTATCAGCCGTACAGAGTCGTCGTACTATCCTTCGAACTACTACA
                                linker      epitope 473-490
TGCTCCGGGCGACAGTAggtcctgacccggtTATCAGGCTGGATCTACACCGTGTAATGGTGTCGAAGGATTCAACT
                            linker      epitope 504-524
GCTACTTCggtcctggacccggtTATCAGCCGTACAGAGTCGTCGTACTATCCTTCGAACTACTACATGCTCCGGCG
                    linker      epitope 473-490
ACAGTAggtcctgacccggtTATCAGGCTGGATCTACAGAGTCGTCGTACTATCCTTCGAACTACTACATGCTCCGGCG
          linker      epitope 504-524
tcctggacccggtTATCAGCCGTACAGAGTCGTCGTACTATCCTTCGAAGGATTCAACTGCTACTTCgg
linker      epitope 473-490                                                        C-Tag
ctggacccggtTATCAGGCTGGATCTACACCGTGTAATGGTGTCGAAGGATTCAACTGCTACTTCAACTGCTACTTC|gagccggaagct|TAATAAttttatc
vaccinia promoter P11          Kozak E Start
TTTCATTTGTTTTTTTCTATGCTATAA|gccacc|ATG|TACTCCTTCGTGTCCGAAGAAACCGGAACCTTGATCGTCAACTCC
GTCCTACTATTCCTAGTGGTTGTCGTGTCCTACTAGTAACCCTAGTGGCTATCCTAACCGCGCTAAGACTATGTGGTACTG
CTGCAACATCGTCAACGTGTCCCTAGTGAAGCCGTCCTTCTACGTCTACTCCTACGAGTCAAGAACCTAA
                End of E    C-Tag                              C-Tag    End M
                                        |gagccagaggct|TAATAAataaaaaTTATTAgcctctggctc|CTGGACTAGTAGAGCGAT
ACTCCCTCTAGAGTCCCGGACCTACTAGTT

FIG. 4B

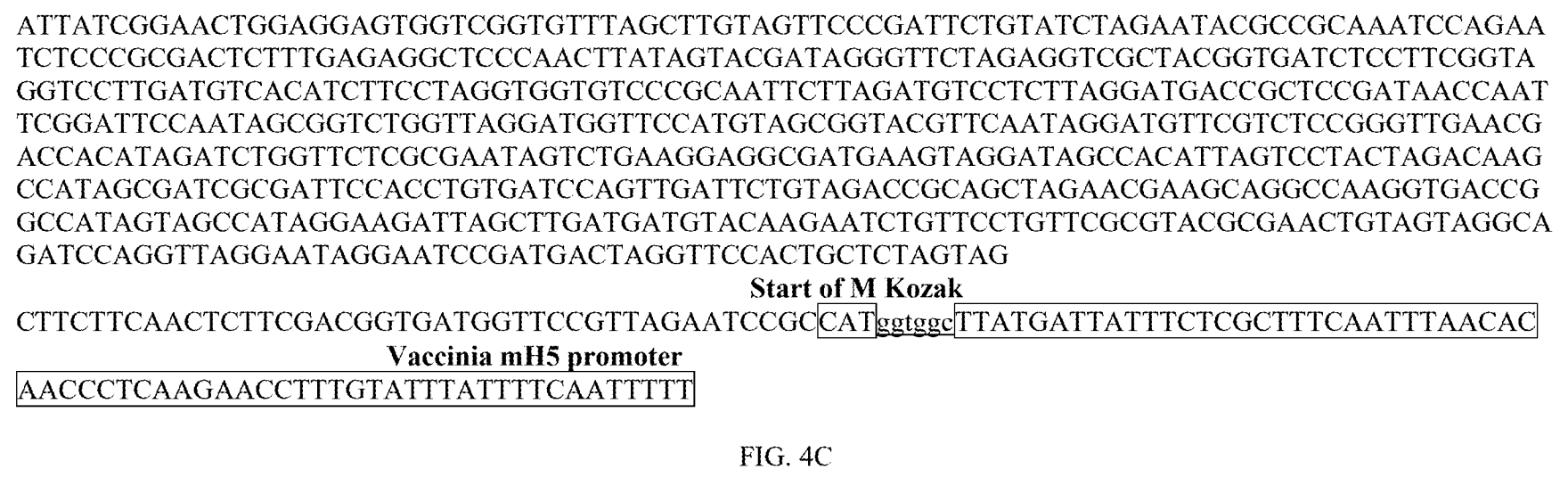

ATTATCGGAACTGGAGGAGTGGTCGGTGTGTTAGCTTGTAGTTCCCGATTCTCGTATCTAGAATACGCCGCAAATCCAGAA

TCTCCCGCGACTCTTGAGAGGCTCCCAACTTATAGTACGATAGGGTTCTAGAGGTCGCTACGGTGATCTCCTTCGGTA

GGTCCTTGATGTCACATCTTCCTAGGTGGTGCCCGCAATTCTTAGATGTCCCTCTAGAGTGACCGCTCCGATAACCAAT

TCGGATTCCAATAGCGGGTCTCGGTTAGGATGGTTCCATGTAGCGGTCGGTACGTTCAATAGGATGTTCGTTCTCCGGGTTGAACG

ACCACATAGATCTGGTTCTCGCGAATAGTCTGAAGGAGGCGATGAAGTAGGATAGCCACATTAGTCCTACTAGACAAG

CCATAGGCGATCGGCGATTCCACCTGTGATCCAGTTGATTCTGTGAGACCGGCTAGAACGCAGGCCAAGGTGACCG

GCCATAGTAGCCATAGGAAGATTAGCTTGATGATGTACAAGAAATCTGTTCCGGTACGCGAACTGTAGTAGGCA

GATCCAGGTTAGGAATAGGAATCCGATGACTAGGTTCCACTGCTCTAGTAG

Start of M Kozak

CTTCTTCAACTCTTCGACGGTGATGGTTCCGTTAGAATCCGC|CAT|ggtggc|TTATGATTATTTCTCGCGTTTCAATTTAACAC

Vaccinia mH5 promoter

|AACCCTCAAGAACCTTTGTATTTATTTTCAATTTTT|

FIG. 4C

Tandem Repeat-E-M (SEQ ID NO: 74)

Vaccinia mH5 promoter        SmaI  Kozak

AAAAATTGAAAATAAATACAAAGGTTCTTGAGGGTTGTGTTAAATTGAAAGGGAGAAATAATCATAA|CCCGGG|gccacc epitope 504-524

ATG|TGGACGACCTGCTGCTTCTTCATCTCCCTAATCCTAATCCAGGGAATCAAGACCCTATATCAGCCGTACAGAGTCGTCG

Linker   epitope 473-490

TACTATCCTTCGAACTACTACATGCTCCGGGCGACAGTAggtcctgacccggtTATCAGGCTGGATCTACACCGTGTAA

Linker  epitope 504-524

TGGTGTGCGAAGGATTCAACTGCTACTTCggtcctggacccggtTATCAGCCGTACAGAGTCGTCGTACTATCCTTCG linker  epitope 473-490

AACTACTACATGCTCCGGGCGACAGTAggtcctggacccggtTATCAGGCTGGATCTACACCGTGTAATGGTGTGCGAA linker  epitope 504-524

GGATTCAACTGCTACTTCggtcctggacccggtTATCAGCCGTACAGAGTCGTCGTACTATCCTTCGAACTACTACA linker  epitope 473-490

TGCTCCGGGCGACAGTAggtcctggacccggtTATCAGGCTGGATCTACACCGTGTAATGGTGTCGAAGGATTCAACT linker  epitope 504-524

GCTACTTCggtcctggacccggtTATCAGCCGTACAGAGTCGTCGTACTATCCTTCGAACTACTACATGCTCCGGGCG linker  epitope 473-490

ACAGTAggtcctggacccggtTATCAGGCTGGATCTACAGAGTCGTCGTACTATCCTTCGAACTACTACATGCTCCGGGACAGTAggtc linker  epitope 504-524         C-Tag tcctggacccggtTATCAGCCGTACAGAGTCGTCGTACTATCCTTCGAACTGCTCCGGGACAGTAggtc|gagccggaagct|TAATAATtttatc linker  epitope 473-490    Kozak E Start ctggacccggtTATCAGGCTGGATCTACACCGTGTAATGGTGTCGAAGGATTCAACTGTCAACTGCTACTTC|gccacc|ATG|TACTCCTTCGTGTCCGAAGAAACCGGAACCTTGATCGTCAACTCC vaccinia promoter P11

|TTTCATTTGTTTTTTTCTATGCTATAA|gccacc|ATG|TACTCCTTCGTGTCCGAAGAAACCGGAACCTTGATCGTCAACTCC

GTCCTACTATTCCTAGCGTGTCGTGTCCTACTAGTAACCCTAGTAATCCTAGCTATCCTACCGGCGCTATGTGGCTACTG

CTGCAACATCGTCAACGTCAAGTCCAGTGAAGGCGGTCCTTCTACGTCTACTTCCAGTCAAGAACCTAA

End of E C-Tag            C-Tag End M

ACTCCCTAGAGTCCCGGACCTACTAGTT|gagccagaggct|TAATAAataaaaTTATTA|agcctctggctc|CTGGACTAGTAGAGCGAT

FIG. 4D

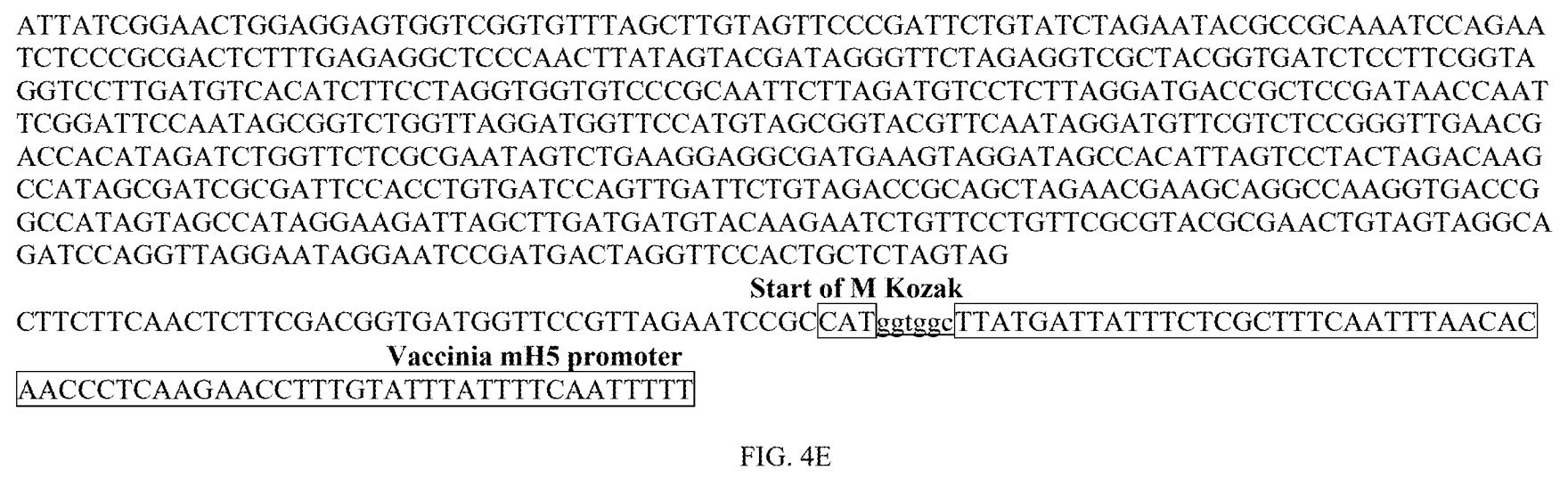

ATTATCGGAACTGGAGGAGTGGTCGGTGTGTTAGCTTGTGTAGTTCCCGATTCTCGTATCTAGAATACGCCGCAAATCCAGAA
TCTCCCGCGACTCTTGAGAGCTCCCAACTTATAGTACGATAGGGTTCTAGAGGTCGCTACGGTGATCTCCTTCGGTA
GGTCCTTGATGTCACATCTTCCTAGGTGGTGCCCGCAATTCTTAGATGTCCCTCTAGGATGACCGCTCCGATAACCAAT
TCGGATTCCAATAGCGGGTCTCGGTTAGGATGGTTCCATGTAGCGGTACGTTCAATAGGATGTTCGTTCTCCGGGTTGAACG
ACCACATAGATCTGGTTCTCGCGAATAGTCTGAAGGAGGCGATGAAGTAGGATAGCCACATTAGTCCTACTAGACAAG
CCATAGGCGATCGGCGATTCCACCTGTGATCCAGTTGATTCTGTAGACCGGATCTGTAGAGAATCTGTTCCGGCTGTCGG
GCCATAGTAGCCATAGGAAGATTAGCTTGATGATGTACAAGAATCTGTTCGGTACGCGAACTGTAGTAGGCA
GATCCAGGTTAGGAATAGGAATCCGATGACTAGGTTCCACTGCTCTAGTAG

Start of M Kozak

CTTCTTCAACTCTTCGACGGTGATGGTTCCGTTAGAATCCGC CAT ggtggc TTATGATTATTTCTCGCTTTCAATTAACAC

Vaccinia mH5 promoter

AACCCTCAAGAACCTTTGTATTTATTTTTCAATTTTT

FIG. 4E

SP-Tandem Repeat-TM-E-M (SEQ ID NO: 81)

Vaccinia mH5 promoter　　　　　　　　　　　　　　　　　　　Kozak
AAAAATTGAAAATAAATACAAAGGTTCTTGAGGGTTGTGTTAAATTGAAAGCGAGAAATAATCATAA gccacc

CoV signal peptide
                                                      epitope 504-524
ATGTTCGTGTCCTAGTCCTACTACCGCTACTACCGCTAGTCTCTTCT TATCAGCCGTACAGAGTCGTGTACTATCCTTCGAACTACT Linker　　epitope 473-490
ACATGCTCCGGCGACAGTA ggtcctggacccggt TATCAGCCTGGATCTACACCGTGTAATGGTGTCGAAGGATTCAA Linker　　epitope 504-524
CTGCTACTTC ggtcctggacccggt TATCAGCCGTACAGAGTCGTCGTACTACTACATGCTCCGG Linker　　epitope 473-490
CGACAGTA ggtcctggacccggt TATCAGCCTGGATCTACACCGTGTAATGGTGTCGAAGGATTCAACTACTACTTC

Linker
ggtcctggacccggtggtgg TATCAGCCGTACAGAGTCGTCGTACTATCCTTCGAACTACTACATGC

Linker　　epitope 473-490
TCCGGCGACAGTA ggtcctggacccggt TATCAGCCTGGATCTACACCGTGTAATGGTGTCGAAGGATTCAACTGCT Linker　　epitope 504-524
ACTTC ggtcctggacccggt TATCAGCCGTACAGAGTCGTCGTACTATCCTTCGAACTACTACATGCTCCGGGCGACA Linker　　epitope 473-490
GTA ggtcctggacccggt TATCAGCCTGGATCTACACCGTGTAATGGTGTCGAACTACTACATGCTCCGG Linker　　epitope 504-524
tggacccggtggtggtggacccggt TATCAGCCGTACAGAGTCGTCGTACTATCCTTCGAACTACTACATGCTATGCGTCGAAGGATTCAACTGCTAC Linker　　epitope 473-490
CGACAGTA ggtcctggacccggt TATCAGCCTGGATCTACACCGTGTAATAATGGCGATCGTCATGGTCACCATCATGCTATGCGTATGAC

CoV Tm.Ct
TTC TGGTACATCTGGCTAGGATTCATTGCTGGACTAATTGGCGATCGTCATGGTCACCATCATGCTATGCGTGTATGAC

FIG. 4G

CTCCTGTTGCTCCTGTCTAAAGGGATGTTGTTCCTGCGGATCCTGTTGCAAGTTCGATGAAGATGATAGTGAACCGG

P11 vaccinia promoter

C-Tag

TCCTAAAGGGTGTCAAGCTACACTACACAgagcccggaagcttaataatttatcTTTCATTTGTTTTTTTCTATG

Kozak Start of E

CTATAAgccaccATGTACTCCTTCGGTCGTCCGAAGAAACCGGAACCTTGATCGTCAACTCCGTCCTACTATTCCTAGCGTTC GTCGTGTTCCTACTAGTAACCCTAGCTATCCTAACCGCGCTAAGACTATGTGCTAGACTATGTGCTGCAACATCGTCAACGTGTC

CCTAGTGAAGCCGTCCTTCTACGTCTACTCCTACGTCTCCAGATGCAAGAACCTAAACTCCCTCTAGAGTCCCGGACCTA

End of E    C-Tag

CTAGTTgagccagaggctTAATAAaataaaaaTTATTAaataaaaaTTATTAagcctctggctcCTGGACTAGTAGAGCGATATTATCGGAACTGGAGGAGTGGT

CGGTGTTAGCTTGTAGTTCCGATTCTGTATCTAGAATACGCGCAAATCCAGAATCTCCGGCACTCTTGAGAGGCT

CCCAACTTATAGTAGTACGATAGGGTTCTAGAGGTCGGCTACGGTGTCGGTAGGTCCTTGATGTCACATCTTCCTAG

GTGGTGTCCCGCAATTCTTAGATGTCCTCTAGAGATGTCCTCGATAACCAATTCGGATTCCAATAGCGGTCTGGTTA

GGATGGTTCCATGTAGCGGGTACGTTCAATAGGGATAGGATAGCCACATTAGTCCTACTAGACAAGATCTGGTTCTCGCGAA

TAGTCTGAAGGAGGGGGGATGAAGTAGGATAGCCGCAGCTAGAACGCAGCCAGGCCAAGGTGACCGGCCATAGGAAGATTAG

GATCCAGTTGATTCTGTAGACCGCCAGTAGAACGCAGGCCAAGCGCAGCGAGATCCAGTTAGAACGCAGCTAGCCATAGCTAGCCATAGGAAGATTAG

CTTGATGATGTACAAGAATCTGTTCCTGTTCCGGTACGGGAACTGTAGTAGGCAGATCCAGGTTAGGAATAGGAATCCG

ATGACTAGGTTCCACTGCTTCCACTCTCTCCAACTCTTCGACGGTGA

M Start Kozak

Vaccinia mH5 promoter

TGGTTCCGTTAGAATCCGCCATggtggcTTATGATTATTTCTCGCTTTCAATTTAACACAACCCTCAAGAACCTTGTATTT

ATTTTCAATTTTT

FIG. 4H

SP-Tandem Repeat-TM-E-M (SEQ ID NO: 82)

Vaccinia mH5 promoter                                                      SmaI    Kozak

AAAAATTGAAAATAAATACAAAGGTTCTTGAGGGTTGTGTTAAATTGAAAGCGAGAAATAATCATAA|CCCGGG|gccacc

CoV signal peptide                                        epitope 504-524

ATGTTCGTGTCCTAGTCCTACTACCGCTAGTCCTCTTCT|TATCAGCCGTACAGAGTCGTCGTACTATCCTTCGAACTACT

Linker       epitope 473-490

ACATGCTCCGGCGACAGTA|ggtcctggacccggt|TATCAGGCTGGATCTACACCGTGTAATGGTGTCGAAGGATTCAA Linker       epitope 504-524

CTGCTACTTC|ggtcctggacccggt|TATCAGCCGTACAGAGTCGTCGTACTATCCTTCGAACTACTACATGCTCCGG

Linker    epitope 473-490

CGACAGTA|ggtcctggacccggt|TATCAGGCTGGATCTACACCGTGTAATGGTGTCGAAGGATTCAACTACTACATTC

Linker            epitope 504-524 ggtcctggacccggtggtgg|TATCAGCCGTACAGAGTCGTCGTACTATCCTTCGAACTACTACATGC

Linker    epitope 473-490

TCCGGCGACAGTA|ggtcctggacccggt|TATCAGGCTGGATCTACACCGTGTAATGGTGTCGAAGGATTCAACTGCT

Linker       epitope 504-524

ACTTC|ggtcctggacccggt|TATCAGCCGTACAGAGTCGTCGTACTATCCTTCGAACTACTACATGCTCCGGGCGACA Linker    epitope 473-490

GTA|ggtcctggacccggt|TATCAGGCTGGATCTACACCGTGTAATGGTGTCGAAGGATTCAACTACTACATGCTCCGG Linker       epitope 504-524 tggacccggtggtggt|TATCAGCCGTACAGAGTCGTCGTACTATCCTTCGAACTACTACATGCTACTTC|ggtcc

Linker    epitope 473-490

CGACAGTA|ggtcctggacccggt|TATCAGGCTGGATCTACACCGTGTAATAATGGTGTCGAAGGATTCAACTGCTAC

CoV Tm.Ct

TTC|TGGTACATCTGGCTAGGATTCATTGCTGGACTAATTGGCGATCGTCACGATCGTCATTGCTGTATGTGTATGAC

FIG. 4I

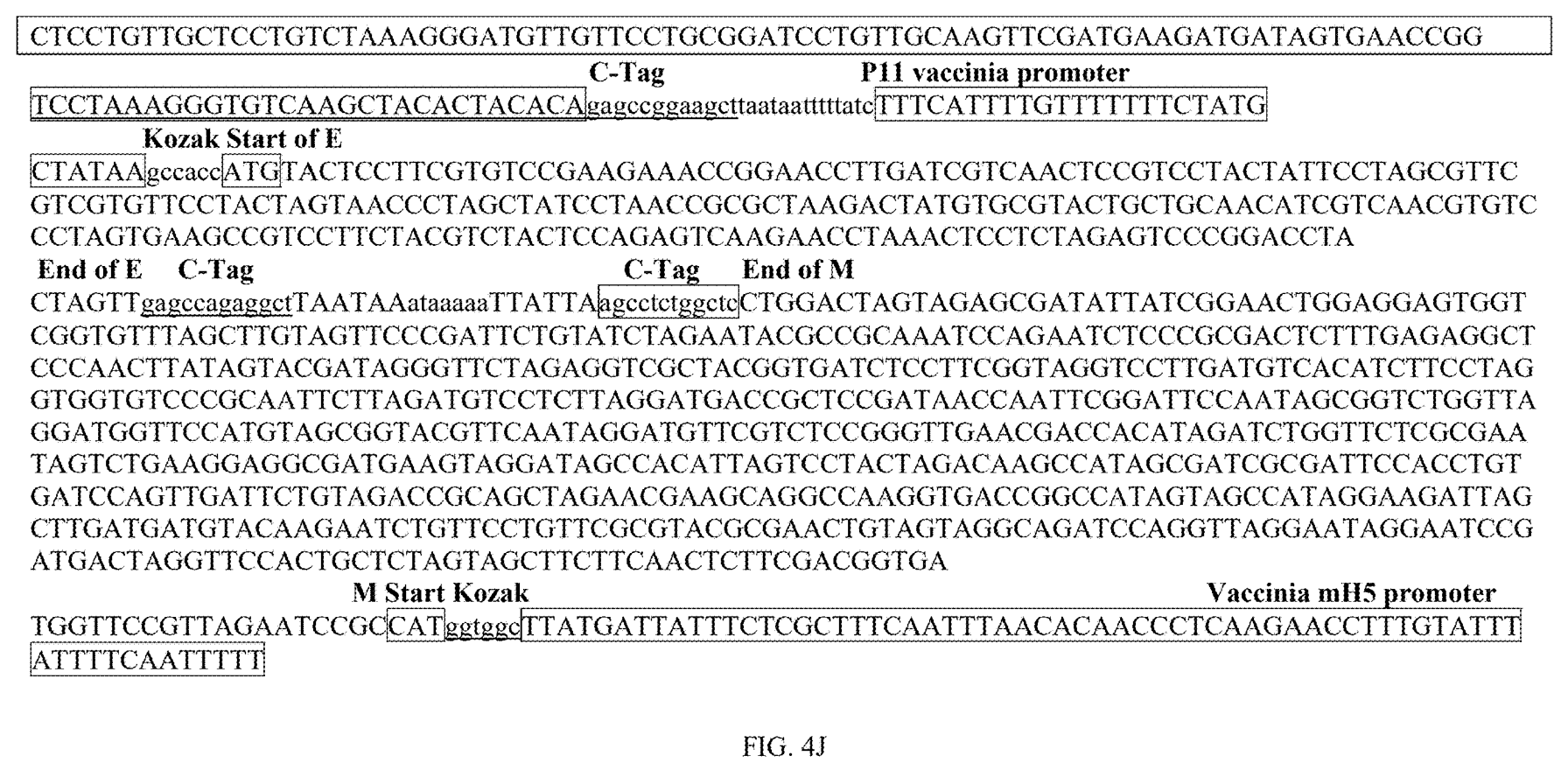

CTCCTGTTGCTCCTGTCTAAAGGGATGTTGTTCCTGCGGATCCTGTTGCAAGTTCGATGAAGATGATAGTGAACCGG

P11 vaccinia promoter

C-Tag

TCCTAAAGGGTGTCAAGCTACTACACA gagcccggaagcttaataattttatc TTCATTTGTTTTTTTCTATG

Kozak Start of E

CTATAA gccacc ATG TACTCCTTCGGTCCGAAGAAACCGGAACCTTGATCGTCAACTCCGTCCTACTATTCCTAGCGTTC
GTCGTGTTCCTACTAGTAACCCTAGCTATCCTAACCGGCGCTAAGACTATGTGCGTACTGCTGCAACATCGTCAACGTGTC
CCTAGTGAAGCCGTCCTTCTACGTCTACTCCCAGAGTCAAGAAACCTAAACTCCTCTAGAGTCCCGGACCTA

End of E    C-Tag    End of M

CTAGTT gagccagaggct TAATAA aataaaaa TTATTA agcctctggctc CTGGACTAGTAGAGCGATATTATCGGAACTGGAGGAGTGGT
CGGTGTTAGCTTGTAGTTCCGATTCTGTATCTAGAATACGCGCAAATCCAGAATCTCCGGCACTCTTGAGAGGCT
CCCAACTTATAGTACGATAGGGTTCTAGAGGTCGCTACGGTGATCCTCGGTAGGTCCTTGATGTCACATCTTCCTAG
GTGGTGTCCCGCAATTCTTAGATGTCCTCTAGGATGACCGCTCCGATAACCAATTCGGATTCCAATAGCGGTCTGGTTA
GGATGGTTCCATGTAGCGGGTACGTTCAATAGGATAGTCGTTCGTCCGGGTTGAACGACCACATAGATCTGGTTCTCGCGAA
TAGTCTGAAGGAGGGGGATGAAGTAGGATAGCCACCATTAGTCCTACTAGACAACAAGCCATAGCGGCGATTCCACCTGT
GATCCAGTTGATTCTGTGACCGCTAGAACGAAGCAGGCCAAGGTGACCGGCCATAGTAGCCATAGGAAGATTAG
CTTGATGATGTACAAGAATCTGTTCCTGGCGTACGGGCGAACTGTAGTAGGCAGATCCAGGTTAGGAATAGGAATCCG
ATGACTAGGTTCCACTGCTTCCAGTCTAGCGTTCTTTCAACTCTTCGACGGTGA

Vaccinia mH5 promoter

M Start Kozak

TGGTTCCGTTAGAATCCGCCAT ggtggc TTATGATTATTTCTCGCTTTCAATTTAACACAACCCTCAAGAACCTTGTATTT
ATTTTCAATTTT

FIG. 4J

Truncated S-E-M (SEQ ID NO: 83)

Vaccinia mH5 promoter                                                    Kozak/S start AAAATTGAAAATAACAAAGGTTCTTGAGGGTTGTGTTAAATTGAAAGGCGAGAAATAATCATAA|gccacc|ATG|TTCG
TGTTCCTAGTCCTACTACCGGCTAGTCTTCTTCTCAGTGTGTAAACCTAACAACGAGAACACAACTACCACCGGCGTACAC
CAATTCTTTCACAAGAGGAGTATATTACCCGGACAAGGTGTTCAGATCCTCCGTACTACCATTCTACACAGAGGACCTATTC
CTACCGGTTCTTCTTCTTAACGTAACATGGTTCCACGCGATCCATGTCTCTGGAACAAACGAACGAAGAGATTCGATAACC
CGGTCTTGCCGGTTCAACGATGGTGTATACTTTGCGTCCACCGAGAAGTCCAACATCATCAGAGGATGGATCTTCGGAAC
CACCTTGGATTCTAAGGACCCAGTCCTTGCTAATCGTCAACAAGAACAACAAGTCCTGGAATCCGAGTTCAGAGTCTACT
TTCTGTAACGACCCGGTTCTTGGGGAGTCACCTCCGAATATGTATCTCAGCCGTTCCTAATGGACCTAGAGGGAAGCAGGGAAACTTCAA
CTTCCGGCGAACAACTGCACCTTCGTATTCAAGAACATCGACGGATTCAAGATCTCTCAGCGCACACTCCGATCAACCTAGTT
GAACCTAAGAGAGTTCGTATTCAAGAACATCGACGGATTCAAGATCTCTCAGCGCACACTCCGATCAACCTAGTT
AGAGATCTACCGCAAGGATTCTCTGGCTAGAACCGTTAGTAGATTTGCCGATCGGAATCAACATCACCAGATTCCAGA
CACTACTAGCGCTACACAGATCTTACCTAACGCCGGGAGATTCTTCTTCTGGACTGCTGGTTGCTGGCGGCTTATTAT
GTAGGATACCTACACAGCCGAGAACCTTCTATTGAAGTACAACGGAACCATCACCGATGCCGTAGATTGTGCT
CTAGATCCGGCTATCCGAAACGAAGTGCACCCTAAAGTTCTTTCACCGTCGAACATCACGAAGAATCTACCAGACCTCCAACTTTA
GAGTACAGCCGACCGAATCCATCGTTCAGATTTCCGAACACATCACGAAATCAGTAACTGCGCGGACTACTCCGTCCTATACAACTC
CAAGATTTGCCGTCGTCTATGCGGTGGAACAGAAAAAGAATCAGTAACTGCGCGGACTACTCCGTCCTATACAACTC
TGCCTCTTTCTCCAGTTCAAATGCTACGGGTGTATCTCCGACAAAGTAAAGCTATGTCTTCACCGGGATTATAACTACA
ACTCCTTCGTAATCAGAGGAGATGAAGTTAGACAGATTGCGCGGGACCAAACTGGAAGATCGGGAGGAAACTACA
AGCTACCGGACGACTTCACCGGAGTGTGTAATTGGCGTGGAATTCGAACAACCTAGACTCCAAAGTCGGGAGGAAACTACA
ACTACTTGTACAGATCATTCAGAAGTCGAACCTAAAGCCGTTCAGAACTACTACCTTCGAACTACTACCTTCACCGAACTATCAGGCTGG
ATCTACCGGTGTAATGGTGTCGAAGGATTCAACTGCTACTTCCCGCTACTTCCCGGACCAGTATGTGGACCGAAAA
GTAGGATATCAGCCGGTACAGAGTCGTACTAGAGTCGTCGTACTATCCTTCGAACTACTTCAACGGACTTCAACGGACAAACGGT
AGTCTACCAACCTAGTCAGTAACAACAAATGCGTCAACTTTAACTTCAACGGACTTAACTTCAACGGACGTCCTAACCGAAT
CTAACAAGAAGTTCTACCGTTCCAGCAGTTCGGAAGAGATATCGCGAATACCAACAGACGCGTCAGAGATCCGCAAA
CCTTGGAGATCCTAGATATCACACACCGTTCTTTCGGTGGTGTCTCGTAATTACTCCGGGAACGAACACCTCCAATCAA
GTAGCGGTACTATACCAGGACGTGAACTGTACAGAAGTACCGGTAACTGTCAATTCACGCGCGATCAACTAACCACCTTGG
AGAGTGTACTCCACGGGATCTAACGTATTCCAAACAAGAGCGGGGATGCTAATCGGAGCGGAACACGTAAACAACTCC
TACGAATGTGATATCCCGGATTGGGAGCGGGGAATCTGTGCGTCTTACCAACACAACAAACTCTCCGAGAGAGGGAGA

FIG. 6B

TCTGTAGCCTCTCAATCTCTATTATCGCCTACACCATGTCCTTGGGAGCCGAAAATTCTGTCGGCGTACTCCAACAATTCTAT
CGGGATCCCGACAAACTTCACCATCTCTGTAACAACCGAGATCCTACCGGGTGTCTATGACCAAGACATCTGTCGATTGC
ACCATGTACATCTGCGGAGATTCCACCGAGTGCTCCAACTACTACTACGAGGTATTCGCGCAAGTCAAGCAGATCTATAAACA
GAGCGGTTGACTGGAATCGCTGTAGAGCAGGATAAGAACACTCAAGAGGTATTCGCGCAAGTCAAGCAGATCTATAAGA
CTCCGCCGATCAAGGACTTCGGAGGTTTCAACTTCTCTCAGATCTTGCCGGATCCGTCCAAACCGTCTAAGAGATCTTTC
ATCGAGGACCTACTATTCAACAAAGTCACCCTAGCTGCGACGCGGGATTCATCAACAATACGCGGAGATTGCTTGGGAGAC
ATTGCGGCGAGAGATCTAATTTGCGCGCAGAAGTTAACGGATTGACACAGTACTACCCGCGCTACTAACCGATGAGATG
ATTGCGCAGTACACGTCTGCTCTATTGCGGGAACAATTACAAGTGGACATTTGGAGCGCGGTGCCGCTCTACAAA
TTCCGTTTGCTATGCAAATGGCGTACAGATTCAAGGCGTACAGAGTCTATCTTCTACTGCTTCGGGCGTTGGGAAAGCT
TAATCGGGAACCAGTTCAATTCCGCGATCGGAAAGATCCAGGACAGTCTATCTTCTACTGCTTCGGGCGTTGGGAAAGCT
ACAGGATGAGTAAATCAAAACGCGCAGGCGCTAAACACCTTGGTCAAGCAACTATCCTCAACTTCGAGCGATCTC
GTCCGTCCTAAACGACATCTTATCCAGACTAGATAAGGTCGAAGCGGAGGTCCAGATCGATAGACTAATCACTGGAAG
ATTGCAGTCCCTACAGACCTACGTACGTAACAGCAACTAATCCAAGAGAGTTAGAGCGGGATTAGAGCCCTGCTAATCTAGCTGCG
ACCAAGATGTCCGAATGTGTCTTGGGACAATCCAAGAGGTACTTCTGCGGAAAGGGATACCACCTAATGTCTTTCC
CACAATCTGGCGCCGCATGGGTGTCCATTATTCCTACATGTAACATATGTGCGGGCAAGAAAAGAACTTCACAACAGCTCC
AGCGGATCTGCCATGATGGAAAAGCTCATTTCCCGAGAGAGGGAGTCTTGTCTCTAACGGAACTCATGGTTCGTCACC
CAGAGAAACTTCTACGAGCCGCAGATCATCACCACCGACAACAACATTCGTCTCGGGAAACTGCGACGTGGTCATCGGA
ATCGTAAACAATACCGTCTCCGGATGTGGGACTTGGGAGATATCTCTGGAATCAACGCCGTCGTCAACATCCAGAAAGAAATC
AACCACACCTCTCCGGATGGGACTTGGGAGATATCTCTGGAATCAACGCCGTCGTCAACATCCAGAAAGAAATC
GATAGATTGAACGAGGTCGCGAAGAACTTGAACGAGCTCAATGCACCTAACAAGAGCTAGGAAAATACGAGCAGT

C-Tag
ACATCAAGTGGCCCGgagccggaagctTAATAAttttatcTTTCATTTGTTTTTTCTATGCTATAAgccaccATGTACTCCTTCGTGTC
CGAAGAAACCGGAACCTTGATCGTCAACTCCGTCGTACTATTCCTAGCGTTCGTTGCTTGTAGTTCCGATTCTGTATCTAG
TCCTAACCGGGCTAAGACTATGTGGCTACTATGTGCTGCAACATCGTCAACGTGTCCCTAGTGAAGCCGTCCTTCTACGTCT

Kozak/E Start (boxed)

E end    C-Tag
ACTCCAGAGTCAAGAACCTAAACTCCTCTAGAGTCCCGGACCTACTAGTTgagccagagagctTAATAAataaaaaTTATTAaggcctctg
M end
gctcCTGAACTAGTAGAGCGGATATTATCGGAACTGGAACTGGTCGGTGTTAGCTTGTAGTTCCGATTCTGTATCTAG
AATACGCCGCAAATCCAGAAATCTCCCGCGACTCTTTGAGAGGTTCCAACTTATAGTACGATAGGGTTCTAGAGGTCGC
TACGGTGATCTCCTTCGGTAGGTCGTTGATGTCACATCTCCTAGGTGGTGGTTCCCGCAATTCTTAGATGTCCTCTAGGA

C-Tag

FIG. 6C

TGACCGGCTCCGATAACCAATTCGGATTCCAATAGCGGTCGGTCTGGTTAGGATGGTTCCATGTAGCGGTACGTTCAATAGGAT
GTTCGTCTCCGGGGTTGAACGACCACATAGATCTGGTTCTCGGCGAATAGTCTGAAGGAGGCGATGAAGTAGGATAGCCA
CATTAGTCCTACTAGACACAAGCCATAGGCGATCGGCGATTCCACCTGGTCGTGTAGACCGCAGCTAGAACG
AAGCAGGCCAAGGTGACCGGCCATAGTAGCCATAGGAAGATTAGCTTGATGATGTACAAGAATCTGTTCCGTTCGCG
TACGGGAACTGTGTAGTAGGCAGGATCCCAGGTTAGGAATAGGAATCCGATGACTAGGTTCCCACTGCTCTAGTAGCTTCTTCA

M start    Kozak

ACTCTTCGACGGTGATGGTTCCGTTAGAATCCGCCATgggtggcTTATGATTATTTCTCGCTTTCAATTAACACAACCCTCA mH5 promoter

AGAACCTTTGTATTTATTTTCAATTTT

FIG. 6D

Truncated S-E-M (SEQ ID NO: 84)

Vaccinia mH5 promoter                                    SmaI   Kozak

AAAAATTGAAAATAAATACAAAGGTTCTTGAGGGTGTGTTAAATTGAAAGGCGAGAAATAATCATAA CCCGGGgccacc S Start ATG TTCGTGTTCCTAGTCCTACTACCGGCTAGTCTCTTCTTCTCAGTGTGTAAACCTAACAACGAGAACACAACTACCACCGG
CGTACACCAATTCTTCACAAGAGGAGTATATTACCCGGACAAGGTGTTCAGATCCTCCGTACTACATTCTACACAGA
CCTATTCCTACCGTTCTTCTCTAACGTAACATGGTTCCACGCGGATCCATGTCTCTGGAACAAACGGAAGAGATTC
GATAACCCGGTTCTTGCCGTTCAACGATGGTGTATACTTTGCGTCCACCGAGAAGTCCAACATCAGAGGATGGATCT
TCGGAACCACCTTGGATTCTAAGGACCCCAGTCCTTGCTAATCGTCAACAAGAACAACAAGTCCTGGATGGAATCCGAGTTCAGA
ATTCCAGTTCTGTAACGACCCGTTCTTGGGAGTCTACTACCACAAGAACAACAAGTCCTGGATGGAATCCGAGTTCAGA
GTCTACTCTTCCGCGAACAACTGCACCTTCGAATATGTATCTCAGCCGTCCTAATGGACCTAGAGGGAAAGCAGGGAA
ACTTCAAGAACCTAAGAGAGTTCGTATTCAAGAACATCGACGGATACTTCAAGATCTACTCCAAGCACACTCCGATCAA
CCTAGTTAGAGATCTACCGCAAGGATTCTCTGCGCTAGAACCGTTAGTAGATTCGGCGATCGGAATCAACATCACCAGA
TTCCAGACACTACTAGCGCTACTACAGATCTTACCTAACGCCGGAGATTCTTCTCTGGATGGACTGCTGGTGCTGCGG
CTTATTATGTAGGATACCTACAGCCGGAGAACCTTCCTATTGAAGTACAAACGAAAACGAACCATCACCGATGCCGGTAG
ATTGTGCTCTAGATCCGCTATCCGAAACGAAGTGCACCCTAAAGTCTTTCACCGTCGAGAAGGGAATCTACCAGACCTC
CAACTTTAGAGTAGTACAGCCGACCGAATCCATCGTCAGATTTCCGAACATCACGAGAACAACTGCGTTCCGACGGTGTTC
AACGGACAAGAGATTTGCGTCGTCGTCTATGCGGTGGAACAGAAAAAGAATCAGTAACTGCTAAACGTAAACGATCTATGCGGCGGACTACTCCGTCCTAT
ACAACTCTGCCTCTTCTCCACGTCAGTTCAAATGCTCAAATGCGGGAAATGCGGGACTAAACGATCTATGCTTCACCACGTC
TACGCGGGACTCCTGGAACTCACCGGACTTCAGACTCAGGACTCACCGACTTCAGACTATTCAGAGATGAAGTTAGAGTCGGGATTAT
AACTACAAGCTACCGGACGACTTCACCGACTTCAGACTATTCAGAGATGGCGTGAATTCGAACAACTAGACTCCAAGTCGGAGGA
AACTACAACTACTTGTACACCGTGTAATGGTGTCGAAGAGTCCAACTAAAGCCGTTCGAGAGAGACATCTCCACGAAATCTATC
AGGCTGGATCGTCACACCGTGTAATGGTGTCGAAGAGTCCAACTAAAGCCGTTCGAGAGAGACATCTCCACGAAATCTATC
AAACGGTGTAGGATATCAGCCGTACAGAGTCGTCGTACTACTTCGAACTACATCCTTCGAACTTCAACGGACTAACAGACGCTGTCAGAGAT
CCGAAAAAGTCTACCAACTAGTCAAGAACAAATGCGTCAACTTTAACTTCAACGGACTAACAGACGCTGTCAGAGAT
ACCGAATCTAACAAGAAGTTTCTACCGTTCAGCAGTTCGGAAGAGATATCGCGGAGAACAGAGCGTGTCAGAGAT
CCGCAAACCTTGGAGATCCTAGATATCACACCGTCGGTTCTTCGGTGTCTCGTATTACTCCGGAACGAACACCT
CCAATCAAGTAGCGGATCGTACTATACCAGGACGTGAACTGTACAGAAGTACCGGTGAACTGTACAGAAGTAACGCTGTCAACTAACAC

FIG. 6E

```
CAACTTGGAGAGTGTACTCCACCGGATCTAACGTATTCCAAACAAGAGCGGGATGTCTAATCGGAGCGGAACACGTAA
ACAACTCCTACGAATGTGATATCCCGATTGGAGCGGGGAATCTGTGCGTCTTACCAAACACAAACAAACTCTCCGAGAA
GAGCGGAGATCTGTAGCCTCTCAATCTATTATCGCCTACACCATGTCCTTGGGAGCCGAAAATTCTGTCGGTACTCCAA
CAATTCTATCGCGCATCCCGACAAACTTCACCATCTCTGTAACAACCGAGATCCTACCGGTGTCTATGACCAAGACATCT
GTCGATTGCACCATGTACATCTGCGGAGATTCCACCGGAGTGCTCCAACCTACTACTACAGTACGGATCTTTCGTACCC
AGCTAAACAGAGCGGTTGACTGGAATCGCTGTAGAGCAGGATAAGAACACTCAAGAGGTATTCGGCAGTCAAGCAG
AICTATAAGACTCCGCGATCAAGGACTTCGGAGGTTCAACTTCTCTCAACTTCTCGAGATCTTGCCGGATCCGTCCAAACCGTCTA
AGAGATCTTTCATCGAGGACCTACTATTCAACAAAGTCACCCTAGCTGACGCGGGATTCATCAAACAATACGGAGATTG
CTTGGGAGACATTGCGGCGGAGAGATCTAATTTGCGCGCAGAAGTTTAACGGATTGACAGTACTACCGCGCTACTAACC
GATGAGATGATTGCGCAGTCAGTACACGTCGCTCTATTGGCGGGAACAATTACAAGTGGATGGACAATTGGAGCGGTGCC
GCTCTACAAATTCCGTTTGCTATGCAAATGGGCGTACAGATTCAACGGAGTAACCCAGAAACGTCTTGTACGAGA
ACCAGAAGCTAATCGCGAACCAGTTCAATTCCGCGATCGGAAAGATCCCAGGACACAGTCTATCTTCTACTGCTTCGGCGTT
GGGAAAGCTACAGGATGTAGTAATCAAAAACGCGCAGGCGCTAAACACCTTGGTCAAGCAACTATCCTCTAACTTCGG
AGCGGATCTCGTCCGTCCGTCCTAAAGCACATCTTATCCAGACCTACGTAACACAGCAACTACGATATCGATAGACTAAT
CACTGGAAGATTGCAGTCCCTACAGACCCGAATGTGTCTTGGGACAATCCAAGAGAGTGGAACGGATACCACCT
TCTAGCTGCGACCAAGATGTCCGAATCTGCGCCCGCCATGGTTGTATCCTAGTTGCGTATTCCTACACATGTAACAATGTGCCGGCGCAGAAAAGAACTTC
AATGTCTTTCCCACAATCTCGGCGGCCGCCATGGTTGTATCCTAGTTGCGTATTCCTACATGTAACATGTGCCGGCGCAGAAAAGAACTTC
ACAACAGTCCCAGCGATCTGCCATGATGGAAAAGCTCATTCCCGAGAGAGGGAGTCTTTGTCTCTAACGGAACTCATT
GGTTCGTCACCCAGAGAAAACTTCTACGAGCCGCAGATCATCCGGCGTCTACGGATCCGTTGGGAAACTGCGACG
TGGTCATCGGAATCGTAAACAATACCGTTACGGATGTGGACTTGGGAGATATCTCTGGAGAATCAAGGCGTCGTCAACATCCA
AGTACTTCAAGAACCACACCTCTCCGATGTGAAGCGTCGCGAAGAACTTGAAGAACTTGAACGAGTCCCTAATCGACCTACAAGAGCTAGGAAAAT
GAAAGAAATCGATAGATTGAACGAGGTCGCGAAGAGTCGCGAAGAACTTGAACGAGTCCCTAATCGACCTACAAGAGCTAGGAAAAT
ACGAGCAGT
```

C-Tag        vaccinia P11 promoter        Kozak/E Start

```
ACATCAAGTGGGCCG|gagccggaagct|TAATAAAttttttatc|TTTCATTTTGTTTTTTTCTATGCTATAA|gccaccATGTACTCCTTCGTGTC
CGAAGAAACCCGGAACCTTGATCGTCAACTCCGTCTACTATTCCTAGCGTTCGTCGTTCCTACTAGTAACCCTAGCTA
TCCTAACCGCGCTAAGACTATGTGCGTGCTGCAACATCGTCAAGTGTCCCTAGTGAAGCCGTCCTTCTACGTCT
```

E end    C-Tag                C-Tag

```
ACTCCAGAGTCAAGAACCTAAACTCCTCTAGAGTCCCGGACCTACTAGTT|gagccagaggct|TAATAAAataaaaaTTATTAagcctctg
```

FIG. 6F

M end gctcCTGGACTAGTAGTAGAGAGGCGATATTATCGGAACTGGAGGAGTGGTCGGTGTGTTAGCTTGTGTAGTTCCCGATTCTGTATCTAG AATACGCCCGCAAATCCAGAATCTCCCGCGACTCTTTGAGAGGCTCCCAACTTATAGTACGGATAGGGTTCTAGAGGTCGC

TACGGTGATCTCCTTCGGTAGGTCCTTGATGTCACATCTTCCTAGGTGGTGCCCGCAATTCTTAGATGTCCTCTTAGGA

TGACCGCTCCGATAAACCAATTCGGATTCCAATAGCGGTCGGTTAGGATGGTTCCATGTAGCGGTACGTTCAATAGGAT

GTTCGTCTCCGGGTTGAACGACCACATAGATCTGGTTCTCGCGAATAGTCTGGTTCTCGCGAATAGTCTGAAGGAGGCGATGAAGTAGGATAGCCA

CATTAGTCCTAGACGACAAGCCATAGGCGGATCGCGATTCCACCTGTGATCTCAGTTGATTCTGTAGACCGCAGCTAGAACG

AAGCAGGCCAAGGTGACCGGCCATAGTAGCCATAGGAAGATTAGCTTGATGATGTACAAGAATCTGTTCCTGTTCGCG

TACGCGAACTGTAGTAGGCAGATCCAGGTTAGGAATAGGAATCCGATGACTAGGTTCCACTGCTCTAGTAGCTTCTTCA

M start   Kozak

ACTCTTCGACGGTGATGGTTCCGTTAGAATCCGCCATggtggcTTATGATTATTTCTCGCTTTCAATTAACACAACCCTCA mH5 promoter

AGAACCTTTGTATTTATTTTCAATTTTT

FIG. 6G

Truncated S +K986P and V987P-E-M (SEQ ID NO: 85)

Vaccinia mH5 promoter                                                Kozak/S start

```
AAAAATTGAAAATAAATACAAAGGTTCTTGAGGTTGTGTTAAATTGAAAGCGAGAAATAATCATAA|gccacc|ATG|TTCG
TGTTCCTAGTCCTACTACCGCTAGTCTCTTCTCAGTGTCTCAGTGTGTAAACCTAACAACGAGAACCACAACTACCACCGGCGTACAC
CAATTCTTTCACAAGAGGAGTATATTACCCGGACAAGGTGTTCAGATCCTCCGTACTACATTCTACACAGGACCTATTC
CTACCGTTCTTCTTAACGTAACGATGGTTCCACGCGATCCATGTCTCTGGAACAAACGAACGAAGAGATTCGATAACC
CGGTCTTGCCGTTCAACGATGGTGTATACTTTGGCGTCCACGAGAAGTCCAACATCATCAGAGGATGGATCTTCGGAAC
CACCTTGGAATCTAAGAACGACCCAGTCCTTGCTAATCGTCAACAAGAACAAGTCCTGGAATCCGAGTTCAGAGTCTACT
TTCTGTAACGACCCGGTTCTTGGGAGTTCTTGGGAGTCTGAATATGTATCTCAGCCGTTCCTAATGGACCTAGAGGGAAAGCAGGGAAACTTCAA
GAACCTAAGAGAGTTCGTATTCAAGAACCATCGACGGATACTTCAAGATATCTGCGCTAGAACCGTTAGTAGTTTGCCGATCAACCTAGTT
AGAGATCTACCGCAAGGATTCTCTGCGCTAGAACCGTTAGTAGATTTGCCGATGGAATTCAACATCACCAGATTCCAGA
CACTACTAGCGGCTACACAGATCTTACCTAACGCCGGGGAGATTCTTCTCTGGACTGGTGCGGCTTATTAT
GTAGGATACCTACAGCCGAGAACCTTCCTATTGAAGTACAACGAAAAACGGAACCATCACCGATGCCGTAGATTGTGCT
CTAGACTACCGCTATCCGAAAACGAAGTGCACCCTAAAGTCTTTCACCGTCGAGAAGGGAATCTACCGACCTCCAACTTTA
GAGTACAGCCGACCGAATCCATCGTCAGATTTCCGAACATCACGAACCTATGTCCGTTCGGAGAAGTGTTCAACGCGA
CAAGATTTGCGCTGTCGTCTATGCGGTGGAACAGAAAAAGAATCAGTAGTCCGTCGCGTCCGGACTACTCCGTATACAACTC
TGCCCTTCTTCCTCCACGTTGTAAATGCTACGGGTATCTCCGACAAAGTATCCCCGACAAAGTTCACCAAGGTCTTCACCAAGGTTCACCAAGGTTACGGCGG
ACTCCTTCGTAATCAGAGGAGATGAAGTTAGACAGATTAGACAGTGTGCGCGGGAATTCGGTGGAATTGTGTTTAGCACTGGTATAACTACA
AGCTACCGGACGACTTCACCGGGATGGTGTGTATTGGCGTGGAATTCGAACAACCTAGACTCGGAGGAAACTACA
ACTACTTGTACAGATTATTCAGAAGGATCAGGATCATTCAGAAAGTCAACTGCTACTCAACTGCTACTCACCGAATCGGAGAGAAACTACA
ATCTACACCGTGTAATGGTGTCAGAGTCGTGAAGGATTCAACTGCTACTTCCCGGCTACTCACATGCTCCGGCGACAGTATGTGGACCGGAAAAA
GTAGGATATCAGCCGTACAGAGTCGTACAACAAATGCGTCAACTTAACTTCAAGGACTACAACCGGTGTCCTAACCGAAT
AGTCTACCAACCTAGTCAACAACAAATGCGTCAACTTAACTTCAAGGAAGAGATATCGCGGAAGATCCGCAAA
CTAACAAGAAGTTCTACCGGTTCCAGCAGTTCGGAAGAGTCGTTCGGTGTCTTTCGGTGTCTTTCGGTGTTCTTTCTGTACAGATCCGCAAA
CCTTGGAGATCCTAGATATCCACCGTGTTCTTCGGTGTCTTTCTGTAATTACTCCGGTAGCTATTCACGCGGTAGCTATTCACGCGGATCTCCAATCAA
GTAGCGGTACTATACCAGGATAATGCTAACGTATTCCAAACAAGAGCGGGATGTCTAATCGGAGGCGAACACGTAAACAACTCC
TACGAATGTGATATCCCGATTGGGAGCGGGAATCTGTGCGTCTTACCAAACACAACAAACTCTCCGAGAGGGGAGA
```

FIG. 6I

TCTGTTAGCCTCTCAATCTATTATCGCCTACACCATGTCCTTGGGAGCCGGGAAAAATTCTGTCGGCTACTCCAACAATTCTAT
CGGGATCCCGACAAACTTCACCATCTCTGTAACAACCGAGGATCCTACCGGGTGTCTATGACCAAGACACATCTGTCGATTGC
ACCATGTACATCTGCGGGAGATTCCACCGAGTGCTCCAACCTACTACTACGATCTTTCTGTACCCAGCTAAACA
GAGCGGTTGACTGGAATCGCTGTAGAGCAGGATAAGAACACTCAAGAGGTATTCGGCGCAAGTCAAGCAGATCTATAAGA
CTCCGCCGATCAAGGACTTCGGAGGTTTCAACTTCTCTCAGATCTTGCCGGATCCGTCCAAACCGTCTAAGAGATCTTTC
ATCGAGGACCTACTATTCAACAAAGTCACCCTAGCTGACGCGCGGGATTCATCAAACAATACGGAGATTGCTTGGGAGAC
ATTGCGGCGGAGAGATCTCAAATTTGGCGCAGAAGTTAACGGATTGACAGTACTACCGGCGCTACTAACCGATGAGATG
ATTGCGCAGTACACGTCTGCTCTATTGGCGGGAACAATTACAAGTGGATGGACAATTTGGAGCGGCGGTGCCGCTCTACAAA
TTCCGTTTGCTATGCAAATGGCGTACAGATTCAACGGAATCCAGGACAGTCTATCTTCTACTGCTTCGGGCGTTGGGAAAGCT
TAATCGGGAACCAGTTCAATTCCGCGATCGGAAAGATCCAGGAAAGATTCAAGGCGCAGCGCTAAACACCTTGGTCAAGCAACTATCTTCTACTGCTTCGGAGCGATCTC
ACAGGATGTAGTAAATCAAAACGCGCAGCGCTAAACACCTTGGTCAAGCAACTATCTTCTACTGCTTCGGAGCGATCTC
GTCCGTCCTAAACGACATCTTATCCAGACTAGAT CCACCG GAAGCGGGAGGTCCAGATCGATAGACTAATCACTGGAAG
ATTGCAGTCCCTACAGACCTACGTAACAGCAACTAATTAGAGACGGGCGGCGAGATTAGAGCCGCCTGCTAATCTAGCTGCG
ACCAAGAGATGTCCGAATGTGTCTTGGGACAATCCAAGAGAGTGGACTTCTGCGGCGAAGGGATACCACCTAATGTCTTTCC
CACAATCTCTGCGCCGCCATGTTGCTGGTGTCGTATTCCTACACATATGTGCGGCGGCGCAAGAAAAGAACTTCACAACAGCTCC
AGCGGATCTGCCATGATGGAAAAGCTCATTCCGGAGAGAGGAGTCTTGTCTCTAACGGAACTCATTGGTTCGTCACC
CAGAGAAACTTCTACGAGCCGCAGATCATCACCACCGACAACACATTCGTCTCGGAAACTGCGACGTGGTCATCGGA
ATCGTAAACAATACCGTCTACGATACGGTCCGGTTGCAGCCGGAACTAGACTCCTTCAAAGAAGAGTTGGACAAGTACTTCAAG
AACCACACCTCCGGAGACTTGGGAGATATCTCTGGAATCAACAAGCGGTCCGTCGTCAACATCCAGAAAGAAATC
GATAGATTGAACGAGGTGAACGAAGAACTTGAACGAGCTCCCTAATCGACCTACAAGAGTAGGAAAATACGAGCAGT

ACATCAAGTGGCCG gagccggaagct TAATAAtttttatc TTTCATTTTGTTTTTTTTCTATGCTATAAgccaccATGTACTCCTTCGTGTC vaccinia P11 promoter     Kozak/E Start

CGAAGAAACCGGAACCTTGATCGTCAACTCCGTCCTACTATTCCTAGCGTTCGTCGTGTTCCTACTACTAGTAACCCTAGCTA
TCCTAACCGCGCTAAGACTATGTGCGTACTAGTCGGCAAAGTCCAACGTGTCCCTAGTGAAGCCGTCCTTCCTTCTACGTCT

E end     C-Tag     C-Tag

ACTCCAGAGTCAAGAACCTAAACTCCTCTAGAACTCCTCTAGAGTCCCGGACCTACTAGTTgagccagagagctTAATAAataaaaaTTATTAagcctctg
M end gctcCTGGACTAGTAGAGCGGATATTATCGGAACTGGAACTGGAGGAGGAGTGGTCGGTCGTTTAGCTTGTGTTTAGCTTGTCGTGTATCTAG
AATACGCCGCAAATCCAGAAATCCCGCGACTCTTGAGAGGCTCCAACTTATAGTACGATAGGGTTCTAGAGGTCGC
TACGGTGATCTCCTTGTGGTCCTTGATGTCGCAATTCTTCACATCTCTCAGGTGGTGTCCGCAATTCTTCAGTGTCCTCTTAGGA

FIG. 6J

TGACCGGCTCCGATAACCAATTCGGATTCCAATAGCGGTCGGTCTGGTTAGGATGGTTCCATGTAGCGGTACGTTCAATAGGAT

GTTCGTCTCCGGGGTTGAACGACCACATAGATCTGGTTCTCCGGAATAGTCTGGCGAGGCGATGAAGTAGGATAGCCA

CATTAGTCCTACTAGACACAAGCCATAGCCATAGCGGCGATTCCACCTGTGATCCAGTTGATTCTGTAGACCGCAGCTAGAACG

AAGCAGGCCAAGGTGACCGGCCATAGTAGCCATAGGAAGATTAGCTTGATGATGTACAAGAATCTGTTCCTGTTCGCG

TACGGGAACTGTGTAGTAGGCAGGCAGATCCAGGTTAGGAATAGGAATCCGATGACTAGGTTCCCACTGCTCTAGTAGCTTCTTCA

M start　Kozak

ACTCTTCGACGGTGATGGTTCCGTTAGAATCCGCCATgggtggcTTATGATTATTTCTCGCTTTCAATTTAACACAACCCTCA mH5 promoter

AGAACCTTTGTATTTATTTTCAATTTTT

FIG. 6K

Truncated S +K986P and V987P-E-M (SEQ ID NO: 86)

Vaccinia mH5 promoter                                                    SmaI   Kozak AAAAATTGAAAATAAATACAAAGGTTCTTGAGGGTTGTGTTAAATTGAAAGCGAGAAATAATCATAA [CCCGGG] gccacc S Start

[ATG]TTCGTGTTCCTAGTCCTACTACCGGCTAGTCTTCTCTCTCAGTGTGTAAACCTAACAACGAGAACACAACTACCACCGG
CGTACACCAATTCTTTCACAAGAGGAGTATATTACCCGGACAAGGTGTTCAGATCCTCCGTACTACATTCTACACAGGA
CCTATTCCTACCGTTCTCTCTAACGTAACATGGTTCCACGCGATCCATGTCTCTGGAACAAACGGAACGAAGAGATTC
GATAACCCGGTCTGCGTTCAACGATGGTGTATACTTTGGCGTCCACGGAGTCCAACATCATCAGAGGATGGATCT
TCGGAACCACCTTGGATTCTAAGACCCAGTCCTTGCTAATCGTCAACAACGGCGACCAACGTGCTCATCAAAGTCTGCGA
ATTCCAGTTCTGTAACGACCCGTTCTTGGGAGTCTACTACCACAAGAACAACAAGTCCTGGATGAATCCGAGTTCAGA
GTCTACTCTTCCGGGAACAACTGCACCTTGAATATGTATCTCAGCCGTTCCTAATGGACCTAGAGGGAAAGCAGGGAA
ACTTCAAGAAACCTAAGAGAGTTCGTATTCAAGAACATCGACGGATACTTCAAGATCTACTTCAAGCACACTCCGATCAA
CCTAGTTAGAGATCTACCGCAAGGATTCTCTGCGCTAGAACCGTTAGTAGATTTGCCGATCGGAATCAACATCACCAGA
TTCCAGACAACTACTAGGCGCTACACAGATTCTTACCTAACGCCGGGAGATTCTTCTCGGATGGACTGCTGGTGCTGCGG
CTTATTATGTAGGATACCTACAGCCGGAGAACCTTCCTATTGAAGTAACAACGAAAACGGAACCATCACCGATGCCGTAG
ATTGTGTCTCTAGATCCGCTATCCGAAACGAAGTGCACCCTAAAGTCTTTCACCGTCGAGAAGGGAATCTACCAGACCTC
CAACTTTAGAGTACAGCCGGACCGGAATCCATCGTCAGATTTCCGAACATCACGAACCTATGTCCGTTCGGGAGAAGTGTTC
AACGGCGACAAGATTTGCGTCGTCTGTCTATGCGGTGGAACAGAAAAAGAATCAGTAACTGCCGTCGCGACTACTCCGTCCTAT
ACAACTCTGCCTCTTCTTCTCCACGTTCAAATGCTAAACGGGTGTATCTCCGACAAAGCTAAACGATCTATGTTCACCAACGTC
TACGCGGACTCCTTCGTAATCAGAGGAGATGAAGTTAGACAGATTGGCGCGGGACAAACTGGAAAGATCGGGATTAT
AACTACAAGTACCGGACGACTTCACCGGATGTGTAATTGCGTGGAATTCGAACAACCTAGACTCCAAGTCGGAGGA
AACTACAACTACTTGTACAGACTATTCAGAAAGTCCAACCTAAAGGCCGGTTCGAGAGACATCTCCACGAAATCTATC
AGGCTGGATCTACACCGGTGTAATGGTTGTCGAAGAGTTCGTGTCTACAGAGTCGTACTACATGTCCGGCGACAGTATGTGGA
AAACGGGTGTAGGATATCAGCCGTACAGAGTCGTGTCAAGAACAAACAAATGCCGTCAACTTTAACTTCAAGGGACTAACCGAC
CCGAAAAAGTCTAACAAGAAGTTTCTACCGTTCCAGCAGTTCGGGAAGAGAGATATCGCGGATACAACAGACGCGTGTCAGAGAT
ACCGGAATCTAACAAGAAGTTTCTACCGTTCCAGCAGTTCGGGAAGAGAGATATCGCGGATACAACAGACGCGTGTCAGAGAT
CCGGCAAACCTTGGGAGATCCTAGATATCACACCGTGTCTCTGTAATTACTCCGGGAACGAACACCT

FIG. 6L

CCAATCAAGTAGCGGTACTATACCAGGACGTGAACTGTACAGAAGTACCGGTAGCTATTCACGCGGATCAACTAACAC
CAACTTGGAGAGTGTACTCCACGGATCTAACGTATTCCAAACAAGAGCGGGATGTCTAATCGGAGCGGGAACACGTAA
ACAACTCCTACGAAATGTGATATCCCGATTGGAGCGGGAATCTGTGCGTCTTACCAAACACAAACAAACTCTCCGAGAA
GAGCGGAGATCTGTAGCCTCTCAATCTATTATGCCTACACCCATGTCCTTGGGAGCCGAAAATTCTGTCGCGTACTCCAA
CAATTCTATCGGCGATCCCGACAAACTTCACCATCTCTGTAACAACCGAGATCCTACCGGTGTCTATGACCAAGACATCT
GTCGATTGCACCATGTACATCTGCCGGAGATTCCACCGAGTGCTCCAACCTACTACTACAGTACGGATCTTTCTGTACCC
AGCTAAACAGAGCGGTTGACTGGAATCGCTGTGTAGAGCAGGATAAGAACACTCAAGAGGTATTCGCGCAAGTCAAGCAG
ATCTATAAGACTCCGCCGATCAAGGACTTCGGAGGTTTCAACTTCTCTCCAGATCTTGCCGGATCCGTCCAAACCGTCTA
AGAGATCTTTCATCGAGGACCTACTATTCAACAAAGTCACCCTAGCTGACGCGGGATTCATCAAACAATACGGAGATTG
CTTGGGAGACATTGCGCGGCGGAGAGATCTAATTTGCGCGCAGAAGTTTAACGGATTGACAGTACTACCGCGCTACTAACC
GATGAGATGATTGCGCAGTACAGTCACGTCTGCTCTATTGGCGGGAACAATTACAAGTGGATGGAACATTTGGAGCCGGTGCC
GCTCTACAAATTCCGTTTGCTATGCAAATGGCGTACAGATTCAACGGCGTACAGATCTGGGAAAGATCCAGGACAGTCTATCTTCTACTGCTTCGGCGTT
ACCAGAAGCTAATCGGCAACCAGTCAATTCCGCGGGATCGGAAAGATCTAAACACCTTGGTCAAGCAACTATCCTCTAACTTCGG
GGGAAAGCTACAGGATGTAGTAAATCAAAAACGCGCAGGCGCTAACACCTTGGTCAAGCAACTATCCTCTAACTTCGG
AGCGGATCTCGTCCGTCCTAAACGACATCTTATCCAGACTAGAT[CCACCG]GAAGCGGAGTCCAGATCGATAGACTAAT
CACTGGAAGATTGCAGTCCCTACAGACCTAGTAACACAGCAACTAATTAGAGCGGCGGGAGATTAGAGCCTCGCTAA
TCTAGCTGCGACCAAGAGTCCGAATGTGTCTTGGGACAATCCAAGAGAGTGGACTTCTGCGGAAAGGGATACCACCT
AATGTCTTTCCCACACAATCTGCGCCGCCATGGTGTCGTATTCCTACATGTAACATATGTCCGGCGCGCAAGAAAGAACTTC
ACAACAGTCCAGGCGGATCTGCCATGATGGAAAAGCTCATTTCCCGGAGAGAGGAGCACAACACATTCGTCTCTAACGGAACTCATT
GGTTCGTCACCCAGGAAACTTCTACGGAACCGCAGATCTCTACGGACTCCTTCAAAGAAGAGTTGGACA
TGGTCATCGGAATCGTAAACAATACCGTCTACGATCCGTTGCAGCCGGAACTAGACTCCTTCAAAGAAGAGTTGGACA
AGTACTTCAAGAACCACACCCTCTCCGGATGTGGGAGATATCTCTGGAATCAAGCGGTCCGTCGTCAACATCCA
GAAAGAAATCGATAGATTGAACGAGGTCGCGAAGAACTTGAACGAGGTCCCTAATCGACCTACAAGAGCTAGGAAAAT
ACGAGCGAGT

C-Tag                vaccinia P11 promoter              Kozak/E Start
ACATCAAGTAGCGCCG[gagccgggaagct][TAATAAAtttttatc][TTTCATTTTGTTTTTTTCTATGCTATAA][gccaccATGTACTCCTTCGTGT]

FIG. 6M

CCGAAGAAACCGGAACCTTGATCGTCAACTCCGTCCTCCTACTATTCCTAGGCGGTTCGTCGTGTTCCTACTAGTAACCCTAGCT

ATCCTAACCGGCGCTAAGACTATGTGGCTACTGCTGCAACATCGTCAACGTGTCCCTAGTGAAGCCGGTCCTTCTACGTCT    C-Tag

ACTCCAGAGTCAAGAACCTAAACCTCCCTCTAGAGTCCCGGACCTACTAGTTgagccagaggctTAATAAataaaaaTTATTAagcctctg

E end     C-Tag

M end gctcCTGGACTAGTAGAGCGGGATATTATCGGAACTGGAGGAGTGGTCGGTGTTAGCTTGGTTCCGATTCTGTATCTAG

AATACGCGCAAATCCAGAAATCTCCCGCGACTCTTGAGAGGCTCCAACTTATAGTACGATAGGGTTCTAGAGGTCGC

TACGGTGATCTCCTTCGGTAGTCTCCTTGATGTCACATCTTCCTAGGTGGTCTCCGCAATTCTTAGATGTCCTTAGGA

TGACCGCTCCGATAAACCAATTCGGATTCCAATAGCGGTCGGTTAGGATGGTTCCATGTGGGTTACGTTCAATAGGAT

GTTCGTCTCCGGGTTGAACGACCACATAGATCTGGTTCTCCGCGAATAGTCTGAAGGAGGCGATGAAGTAGGATAGCCA

CATTAGTCCTACTAGACAAGCCATAGCGATGCGATCCACCTGTGATTCGTGTAGACCGCAGTAGAACG

AAGCAGGCCAAGGTGACCGGCCATAGCCATAGTAGGAAGATTAGCTTGATGATGTACAAGAATCTGTTCCTGTTCGCGG

TACGCGAACTGTAGTAGGCAGATCCAGGTTAGGAATAGGAATCCGATGACTAGGTTCCACTGCTGCTCTAGTAGCTTCTTCA

M start    Kozak

ACTCTTCGACGGGTGATGGTTCCGTTAGAATCCGCCATggtggcTTATGATTATTTCTCGCTTTCAATTAACACAACCCTCA mH5 promoter

AGAACCTTTGTATTTATTTTCAATTTTT

FIG. 6N

RBD(aa 331-524)-(MAR/SP-GP-Tm)-ME (SEQ ID NO: 103)

Vaccinia mH5 promoter

Kozak

AAAATTGAAATAAATACAAAGGTTCTTGAGGGTTGTGTTAAATTGAAAGGCGAGAAATAATCATAAgccacc

MAR Signal Peptide                                                          Start of RBD ATGTGGACGACCTGCTTCTTCATCTCCTAATCCTAGGGAATCAAGACCTAAACATCACGACAACCTATGTCCGT
TCGGAGAAGTGTTCAACGCGACAAGATTGGCGTCTGCTGGAACAGAAAAAGAATCAGTAACTGCGTCGCGG
ACTACTCCGTCCTATACAACTCTGCCTCTTTCTCCACGTTCAAATGCTACGGTGTATCTCGACAAAGCTAAACGATCTA
TGCTTCACCAACGTCTACGCGGACTCCTTCGTAATCAGAGGAGATGAAGTAGACAGATTGCGCGGGACAAACTGGA
AAGATCGGGATTATAACTACAAGCTACCGGACGACTTCACCGGATGTGTAATTGCGTGGAATTCGAACAACCTAGAC
TCCAAAGTCGGGAGGAAAACTACAACTACTTGTACACCGTGTAATGGTGTCGAAGGATTCAACTGCTACTTCCCGCTACAGTCTT
ACGGATTTCAACGACAAACGGTGTAGGGATATCAGCCGTACAGAGTCGTGTACAGAGTCGTGTACTACATGCTCC End of RBD        MAR-Tm

GGCGACAGTATGTGGTGGACCTCCGATTGGGGAGTACTAACAACCTAGGAATCCTACTACTATTGTCGATGCGGGTCCTA

MAR-Ct                                                        Vaccinia P11 promoter C-Tag ATCGGCTATCCTGTATCTGTAGAATCTTCACCAAGTACATCGGAgagccggaagctTAATAATTTTATCTTTCATTTTGTTT Kozack E start TTTTCTATGCTATAAgccaccATGTACTCCTTCGTCGTGTCCGAAGAAAACCTGATCGTCAACTCCGTCCTACTATTCC
TAGGGTTCGGTGCGTGTTCCTACTAGTAAACCCTAGCTATCCTAAGCCGGCTAAGACTATGTGCGTACTGCTGCAACATCGTC
AACGTGTCCCTAGTGAAGCCGTCCTTCTCAGTCTACTCCAGTCTACTCCAGTCAAGAACCTAA End of E        C-Tag                C-Tag        End M ACTCCTCTAGAGTCCCGGACCTACTAGTTgagccagagagctTAATAAataaaaTTATTAgcctctggctcCTGGACTAGTAGAGCGAT
ATTATCGGAACTGGAGGAGGAGTGGTCGGTGCGGTGTTAGCTTGTGTAGTTCCGATTCTGTATCTGAGAATACGGCCGCAAATCCAGAA
TCTCCCGGCGACTCTTTGAGAGGCCCACTTATAGTACGATAGGGTTCTAGAGGTGCTACGGTGATCTCCTTCGGTA
GGTCCTTGATGTCACATCTTCCTAGGTGGTGTCCCGCAATTCTTAGATGTCCCTCTTAGGATGACCGGCTCCGATAACCAAT
TCGGATTCCAATAGCGGTCTGGTTAGGATGGTCCATGTAGCGGTCCATGTGTTCTCCGGGTTGAACG
ACCACATAGATCTGGTTCTCGCGAATAGTCTGAAGGAGGCGATGAAGTAGGATAGCCACATTAGTCCTACTAGACAAG
CCATAGCGGATCGCGATTCCACCTGTGATCCAGTTGATTCTGTAGACCGCTAGAACGAAGCAGCAGCCAAGGTGACCG

FIG. 7C

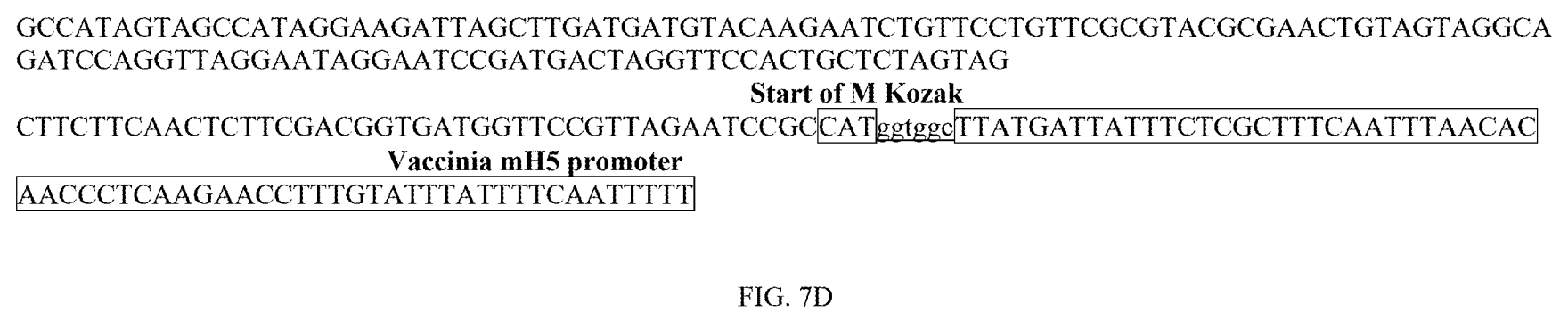

GCCATAGTAGTAGCCATAGGAAGAGATTAGCTTGATGATGTACAAGAATCTGTTCCTGTTCGGCGTACGCGAACTGTAGTAGGCA
GATCCAGGTTAGGAATAGGAATCCGATGACTAGGTTCCACTGCTCTAGTAG

Start of M Kozak

CTTCTTCAACTCTTCGACGGTGATGGTTCCGTTAGAATCCGC|CAT|ggtggc|TTATGATTATTTCTCGCTTTCAATTTAACAC

Vaccinia mH5 promoter

AACCCTCAAGAACCTTGTATTTATTTTCAATTTT

FIG. 7D

RBD(aa 331-524)-(MAR/SP-GP-Tm)-ME (SEQ ID NO: 104)

Vaccinia mH5 promoter    SmaI    Kozak

AAAAATTGAAAATAAATACAAGGTTCTTGAGGGTTGTGTTAAATTGAAAGGCGAGAAATAATCATAA CCCGGG gccacc MAR Signal Peptide    Start of RBD ATGTGGACGACCTGCTTCTTCATCTCCCTAATCCTAATCCAGGGAATCAAGACCCTA AAC ATCACGACGAACCTATGTCCGT
TCGGAGAAGTGTTCAACGCGACAAGATTTGCGTCTCTGTCTATGCGTGGAACAGAAAAAGAATCAGTAACTGCGTCGCGG
ACTACTCCGTCCTATACAACTCTGCCTTTCTCCACGTTCAAATGCTACGGTGTATCCGACAAAGCTAAACGATCTA
TGCTTCACCAACGTCTACGCGGACTCCTTCGTAATCAGAGGAGATGAAGTTAGACAGATTGCGCGGGACAAACTGGA
AAGATCGCGGATTATAACTACAAGCTACCGGACGACTCACCGGACGCTGTGTAATTGCGTGGAATTCGAACAACCTAGAC
TCCAAAGTCGGGAGGAAACTACAACTACTTGTACAGACTATTCAGAAAGTCCAAACTCAAAGCCGTTCGAGAGAGACATC
TCCACCGAAATCTATCAGGCTGGATCTACACCGGTAATGGTGTCGAAGGATTCAACTGCTACTTCCCGCTACAGTCTT
ACGGATTTCAACGACGACAAACGGTGTAGGATATCAGCCGTACTACAGAGTCGTCGTACTACTCCTTCGAACTACTACATGCTCC End of RBD    MAR-Tm GGCGACAGTA TGGTGGGACCTCCGATTGGGGAGTACTAACAACAAACCTAGGAATCCTACTACTATTGTCGATCGCGGTCCTA MAR-Ct    C-Tag    Vaccinia P11 promoter ATCGCGGCTATCCTGTATCTGT AGAATCTTCACCAAGTACACATCGGA gagccggaagct TAATAATTTTTATCTTTCATTTTGTTT Kozack E start TTTTCTATGCTATAA gccacc ATG TACTCCTTCGTGTCCGAAGAGAAACCCGAACCTTGATCGTCAACTCCGTCCTATTCC
TAGCGGTTCGTCGTTCCTACTAGTAACCCTAGCTATCCTAACCGGCTATCCTAACCGGCTAAGACTATGTGCTACTATGTGCAACATCGTC
AACGGTGTCCCTAGTGAAGCCGGTCCCTTCTACGTCTCCTTCTACTCCTCTACTCCAGAGTCCAGAACCTAA End of E    C-Tag gagccagagct TAATAA ataaaaaTTATTA agcctctggct CTGGACTAGTAGAGCGAT
ATTATCGGAACTGGAGGAGTGGTCGGTGTTTAGCTTGTAGTTCCCGATTCTGTATCTAGAATACGCCGCAAATCCAGAA
TCTCCCGCGACTCTTTGAGAGGCTCCCAACTTATAGTACGATAGGGTTCGCACGGTGATCTCCTTCGGTA
GGTCCTTGAGTGTCACATCTTCCTAGGTGGTCCCGCAATTCTTAGATGTCCTCTTAGGATGACCGGTCCCGATAACCAAT
TCGGATTCCAATAGGCGGTCTGGTTAGGATGGTTCCATGTAGCGGTACGTTCAATGTGTCTCCGGGGTTGAACG
ACCACATAGATCGGTCTTCTCCGGAATAGTCTGAAGGAGGCGATGAAGTAGGATAGCCACATTAGTCCTACTAGACAAG
CCATAGGGATCGCGGATTCCACCTGTGATCCAGTTGATTCTGTAGACCGTAGAACGAAGCGAGCCAGCCAAGGTGACCG C-Tag    End M

FIG. 7E

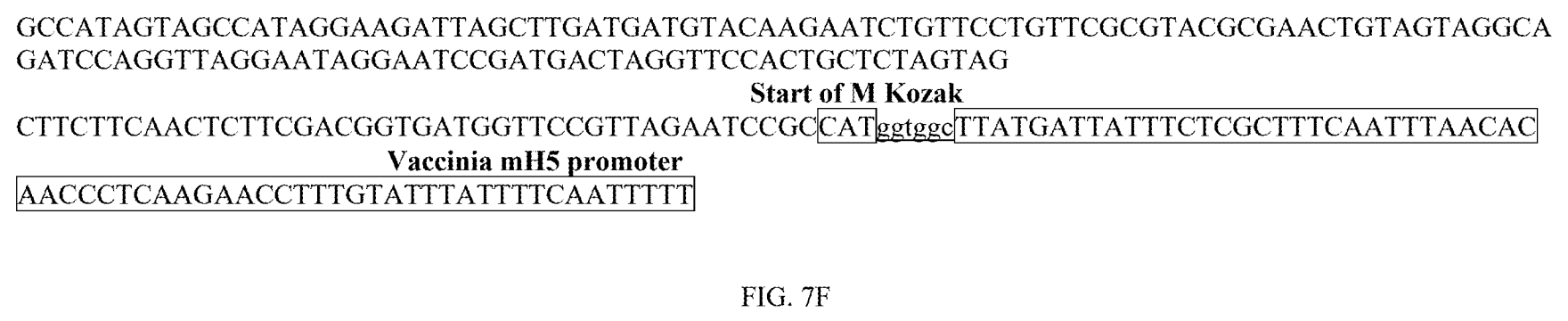

GCCATAGTAGTAGCCATAGGAAGAGATTAGCTTGATGATGTACAAGAATCTGTTCCTGTTCGGCGTACGCGAACTGTAGTAGGCA

GATCCAGGTTAGGAATAGGAATCCGATGACTAGGTTCCACTGCTCTAGTAG

Start of M Kozak

CTTCTTCAACTCTTCGACGGTGATGGTTCCGTTAGAATCCGC CAT ggtggc TTATGATTATTTCTCGCTTTCAATTTAACAC

Vaccinia mH5 promoter

AACCCTCAAGAACCTTTGTATTTATTTTTCAATTTTT

FIG. 7F

RBD(aa 327-524)-(MAR/SP-GP-Tm)-ME (SEQ ID NO: 101)

Vaccinia mH5 promoter                                                                  Kozak

AAAATTGAAATAATACAAAGGTTCTTGAGGGTTGTGTTAAATTGAAAGCGAGAAATAATCATAA|gccacc

MAR Signal Peptide                                  Start of RBD

ATGTGGACGACCTGCTTCTTCATCTCCCTAATCCTAATCCAGGGAATCAAGAGACCCTAG|GTC|AGATTTCCGAACATCACGA
ACCTATGTCCGTTCGGAGAAGTGTTCAACGGCGACAAGATTTGCGTCGTGTCTATGCGTGGAACAGAAAAGAATCAGTA
ACTGCGGTCGCGGACTACTCCGTCGTATACAACTCTGCCCTCTTTCTCCACGTTCAAATGCTACGGTGTATCCGACAAAG
CTAAACGATCTATGTCGTTCACCAACGTCTACGGGGACTCCTTCGTAATCAGAGGAGAAGTTAGACAGATTGGCGCGG
GACAAACTGGAAAGATCGGCGGATTATAACTACAACTACAAGCTACCGGACGACTTCACCGGATGTGTAATTGCGTGGAATTCGA
ACAACCTAGACTCCAAAGTCGGAGGAAACTCATCAGGCTGGATCTACACCGTGTAATGGTCGTCGAAGGATTCAACTGCTACTTCCC
AGAGAGACATCTCCACGAAATCTATCAGGCTGGATCTACACCGTGTAATGGTCGTCGAAGGATTCAACTGCTACTTCCC
GCTACAGTCTTACGGATTCAACCGACAAACGGTGTAGGATATCAGCC

End of RBD    MAR-Tm

GTACAGAGTCGTCGTACTATCCTTCGAACTACTACATGCTCCGGCGACAGTA|TGGTGGACCTCCGATTGGGGAGTAC

MAR-Ct

TAACAAACCTAGGAATCCTACTACTATTGTCGATCGCGGGTCCTAATCGCGCTATCCTGTATCTGT|AGAATCTTCACC

Vaccinia P11 promoter                     Kozak/ E start

AAGTACATCGGA|gagccggaagct|TAATAATTTTTATC|TTTCATTTTGTTTTTTTTCTATGCTATAA|gccacc|ATG|TACTCCTTCGTG
TCCGAAGAAACCGGAACCTTGATCGTCAACTCCGTCCTACTATTCCTAGGTTCCTACTAGTAACCCTAGC
TATCCTAACCGGCGCTAAGACTATGTGGCTACTATGTCCTAGTGCAACATCGTCAACGTGCCGTCCTTCTACGTCT
ACTCCAGAGTCAAGAACCTAA

End of E    C-Tag

ACTCCTCTAGAGTCCCGGACCTACTAGTT|gagccagaggct|TAATAAAataaaaaTTATTA|agcctctggctc|CTGGACTAGTAGAGCGAT
ATTATCGGAACTGGAGGAGTGGTCGGTGTTTAGCTTGTAGTTCCCGATTCTGTATCTAGAATCTAGAATACGCGCAAATCCAGAA
TCTCCCGGCGACTCTTGAGAGGCTCCAACTATAGTACGATAGGGTTCTAGAGGTCGCTACGGTGATCTCCTTCGTA
GGTCCTTGATGTCACATCTTCCTAGGTGGTGTCCCGCCAATTCTTAGAGTGTCCTCTTAGGATGACCGGTCCGGTCCGATAACCAAT

C-Tag

AAGTACATCGGA|gagccggaagct|...

C-Tag    End M

FIG. 7H

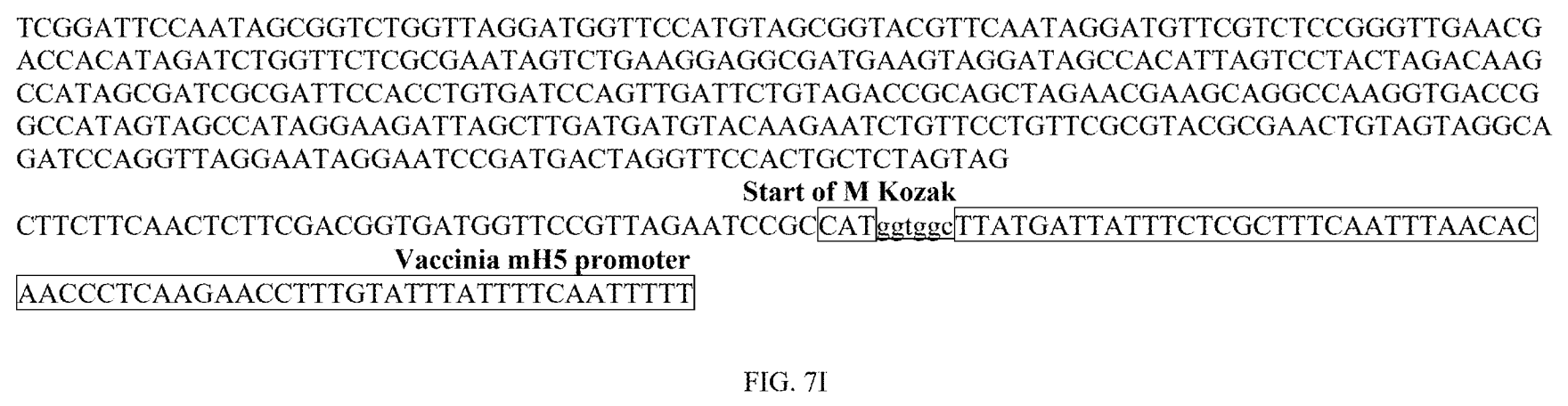

TCGGATTCCAATAGCGGCGGTCTCGGTTAGGATGGTTCCATGTGTAGCGGGTACGTTCAATAGGATGTTCGTCTCCGGGTTGAACG
ACCACATAGATCTGGTTCTCGCGAATAGTCTGAAGGAGGCGATGAAGTAGGATAGCCACATTAGTCCTACTAGACAAG
CCATAGGCGATCGCGATTCCACCTGTGATCCAGTTGATTCTGTAGACCGCTAGAACGAAGCAGGCAAGGTGACCG
GCCATAGTAGCCATAGGAAGATTAGCTTGATGATGTACAAGAATCTGTTCCTGTTCGCGAACTGTGTAGTAGGCA
GATCCAGGTTAGGAATAGGAATCCGATGACTAGGTTCCACTGCTCTAGTAG

Start of M Kozak

CTTCTTCAACTCTTCGACGGTGATGGTTCCGTTAGAATCCGC CAT ggtggc TTATGATTATTTCTCGCTTTCAATTTAACAC

Vaccinia mH5 promoter

AACCCTCAAGAACCTTTGTATTTATTTTCAATTTTT

FIG. 7I

RBD(aa 327-524)-(MAR/SP-GP-Tm)-ME (SEQ ID NO: 102)

Vaccinia mH5 promoter              SmaI    Kozak

AAAATTGAAAATAAATACAAAGGTTCTTGAGGGTTGTGTTAAATTGAAAGCGAGAAATAATCATAA|CCCGGG|gccacc MAR Signal Peptide       Start of RBD ATGTGGACGACCTGCTTCTTCATCTCCCTAATCCTAATCCAGGGAATCAAGAGACCCTA|GTC|AGATTTCCGAACATCACGA
ACCTATGTCCGTTCGGAGAAGTGTTCAACGGCGACAAGAATTTGGCTGCTGTCTATGCGTGGAACAGAAAAAGAATCAGTA
ACTGGGTGCGGACTACTCCGTCCTATACAAACTCTGCCCTCTTTCTCCACGTTCAAATGCTACGGGTGTATCCGACAAAG
CTAAACGATCTATGTGCTTCACCAACGTCTACGGGACTCCTTCGTAATCAGAGGAGATGAAGTTAGACAGATTGGCGCGG
GACAAACTGGAAAGATCGGCGGATTATAACTACAAGCTACCGGACGACTTCACCGGATGTGTAATTGCGTGGAATTCGA
ACAACCTAGACTCGAAAGTCGGAGGAAACTACAACTACTGTACAGGCTGGATCATTCAGAAAGTCCAACCTAAAGCCGTTCG
AGAGAGACATCTCCACGAAAATCTATCAGGCTGGGATCTACACCGGTGTAATGGTGTCGAAGGATTCAACTGCTACTTCCC
GCTACAGTCTTACGGATTCAACCGACAAACGGGTGTAGGGATATCAGCC End of RBD    MAR-Tm

GTACAGAGTCGTCGTACTATCCTTCGAACTACTACATGCTCCGGCGACAGTA|TGGTGGACCTCCGATTGGGGAGTAC

MAR-Ct

TAACAAACCTAGGAATCCTACTACTATTGTCGCGGGTCCTAATCGCGGCTATCCTGTATCGTGT|AGAATCTTCACC

Vaccinia P11 promoter       Kozak/ E start

AAGTACATCGGA|gagccggaagct|TAATAATTTTTATC|TTTCATTTTGTTTTTTTCTATGCTATAA|ATG|TACTCCTTCGTG
C-Tag
TCCGAAGAAACCGGAACCTGGAACCTTGATCGTCAACTCCGTCCGTCTACTATTCCGTCAACTCCGTTCCTACTAGTAACCCTAGC
TATCCTAACCGGCGGCTAAGACTATGTGGCTACTATGTGTCCTAGTCAACATCGTCAACGTGTCCTAGTGAAGCCGTCCTTCTACGTCT
ACTCCAGAGTCAAGAACCTAA End of E    C-Tag            C-Tag     End M ACTCCTCTAGAGTCCCGGACCTACTAGTT|gagccagaggct|TAATAAAATaataaaaTTATTA|agcctctggctc|CTGGACTAGTAGAGCGAT
ATTATCGGAACTGGAGGAGTGGTCGGTGTTAGCTTGGTGTGTTAGCTTGTCCGATTCGTGTATCTAGAATACGCGCCAAATCCAGAA
TCTCCCGGCGACTCTTGAGAGGCTCCCAACTTATACGATAGGGTTCTAGAGGTCGCTACGGTGATCTCCTTCGTA
GGTCCTTGATGTGCACATCTTCCTAGGTGGTGTCCCGGCGCAATTCCTAGGATGACCGCTCCGATAACCAAT

FIG. 7J

TCGGATTCCAATAGCGGGTCTGGTTAGGATGGTTCCATGTGTAGGGGTACGTTCAATAGGATGTTCGTCTCCGGGTTGAACG
ACCACATAGATCTGGTTCTCGCGGAATAGTCTGAAGGAGGGCGATGAAGTAGGATAGGCCACATTAGTCCTACTAGACAAG
CCATAGGCGATCGGCGATTCCACCTGTGATCCAGTTGATTCTGTAGACCGCTAGAACGAAGCAGGCAAGGTGACCG
GCCATAGTAGCCATAGGAAGATTAGCTTGATGATGTACAAGAATCTGTTCCTGTTCGGCGTACGCGAACTGTGTAGTAGGCA
GATCCAGGTTAGGAGGAATAGGAATCCGATAGGTTCCACTGCTCTAGTAG

Start of M Kozak

CTTCTTCAACTCTTCGACGGTGATGGTTCCGTTAGAATCCGCCAT|ggtggc|TTATGATTATTTCTCGCTTTCAATTTAACAC

Vaccinia mH5 promoter

AACCCTCAAGAACCTTTGTATTTATTTTCAATTTT

FIG. 7K

GPS-Tandem Repeat (5x)-GPTM-E-M (SEQ ID NO: 111)

Vaccinia mH5 promoter                                                                 Kozak
AAAATTGAAAATAAATACAAAGGTTCTTGAGGGTTGTGTTAAATTGAAAGCGAGAAATAATCATAA|gccacc

MAR Signal peptide                                    epitope 504-524
A|TGTGGACGACCTGCTGCTTCTTCATCTCCCTAATCCTCATCTCCCTAATCCTAA|TGGACGACCTGCTGCTTCTTCATCTC
CCTAATCCTAATCCAGGGAATCAAGACCCTATATCAGCCGTACAGAGTCGTCGTACTATCCTTCGAACTACTACATGC linker        epitope 473-490
TCCGGGGGACAGTAggtcctggaccggtTATCAGGCTGGATCTACACCGTGTAATGGTGTCGAAGGATTCAACTGCT linker        epitope 504-524
ACTTCggtcctggaccggtTATCAGCCGGTACAGAGTCGTCGTACTATCCTTCGAACTACTACATGCTCCGGGCGACA linker        epitope 473-490
GTAggtcctggaccggtTATCAGGCTGGATCTACACCGTGTAATGGTGTCGAAGGATTCAACTGCTACTTCggtcc linker        epitope 504-524
tggaccggtTATCAGCCGGTACAGAGTCGTCGTACTATCCTTCGAACTACTACATGCTCCGGGCGACAGTAggtcctg linker
epitope 473-490
gaccggtTATCAGGCTGGATCTACACCGTGTAATGGTGTCGAAGGATTCAACTGCTACTTCggtcctggaccggt epitope 504-524                                                      linker
TATCAGCCGGTACAGAGTCGTCGTACTATCCTTCGAACTACTACATGCTCCGGGCGACAGTAggtcctggaccggtTA epitope 473-490              linker      epitope 504-524
TCAGGCTGGATCTACACCGTGTAATGGTGTCGAAGGATTCAACTGCTACTTCggtcctggaccggtTATCAGCCGT linker      epitope 473-490
ACAGAGTCGTCGTACTATCCTTCGAACTACTACATGCTCCGGGCGACAGTAggtcctggaccggtTATCAGGCTGGA

MAR-TM                                                                 MAR-Ct
TCTACACCGTGTAATGGTGTCGAAGGATTCAACTGCTACTTC|TGGTGGACATCTGACTGGGGAGTCCTAACGAACCT

AGGAATCCTACTACTATTGTCGATCGGGGTCCTAATCGGCTATCCTGTATCTGT|AGAATCTTCACCAAGTACATCG

C-Tag                                    vaccinia P11 promoter              Kozak
GA|gagccgcggaagct|TAATAAttttat|TAATAAttttttatTAATAAttttttatTAATAAtttttatc|TTTCATTTGTTTTTTCTATGCTATAA|gccacc

FIG. 8B

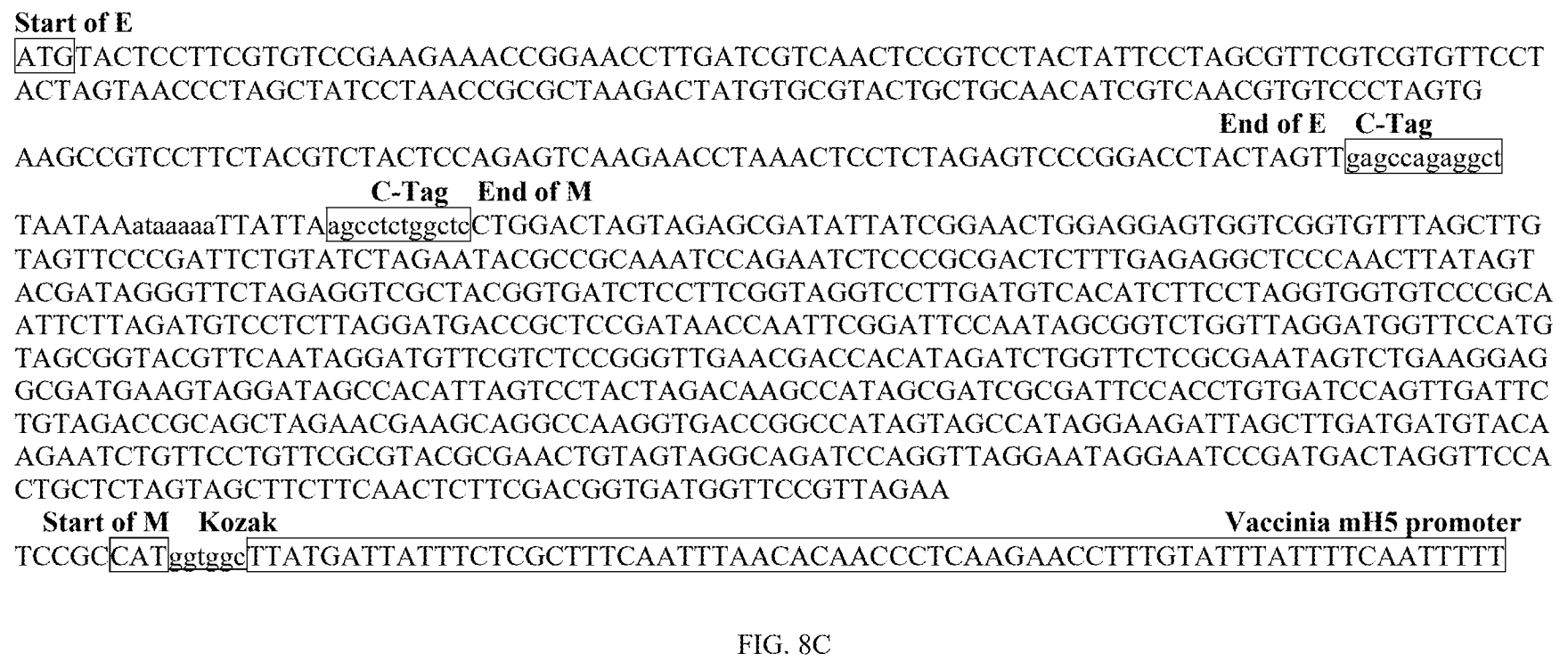

Start of E

ATG TACTCCTTCGGTGTCCGAAGAAACCGGAACCTTGATCGTCAACTCCGTCCTACTATTCCTAGGCGTTCGTCGTGTTCCT

ACTAGTAACCCTAGCTATCCTAACCGGCGCTAAGACTATGTGCGTACTGCTGCAACATCGTCAACGTGTCCCTAGTG

End of E     C-Tag

AAGCCGTCCTTCTACGTCTACTCCAGAGTCAAGAACCTAAACTCCTCTAGAGTCCCGGACCTACTAGTT gagccagaggct C-Tag     End of M TAATAAataaaaaTTATTA agcctctggctc CTGGACTAGTAGAGCGGATATTATCGGAACTGGAGGAGTGGTCGGTGTTAGCTTG

TAGTTCCCGATTCTGTATCTAGAATACGCCGCAAATCCAGAATCCCGCGACTCTTGAGAGCTCCAACTATAGT

ACGATAGGGTTCTAGAGGGTTCTACGGTCGCTACGGTCGATCTCCTTCGGTATGTCACATCTTCCTAGGTGGTGTCCCGCA

ATTCTTAGATGTCCCTCTTAGGATGACGACCGGTCCGATAACCAATTCGGATTCCAATAGCCGGTCTGGTTCTCGCGAATGGTTCCATG

TAGCGGGTACGTTCAATAGGATGTTCGTCTCCGGGTTGAACGACCACATAGATCTGGTTCTCGCGAATAGTCTGAAGGAG

GCGATGAAGTAGGATAGCGCCACATTAGTCCTACTAGACAAGCCATAGCGGCCATAGGACCGGCCATAGTAGCTTGATCCAGTTGATTC

TGTAGACCGCAGCTAGAACGAAGCAGCGCAAGGTGACGGCCATAGGAAGATTAGCTTGATGATGTACA

AGAATCTGTTCCTGTTCGGCGTACGGCAGATCTGTAGTAGGCAGAACTGTAGTAGGCAGATCCAGGTTAGGAATAGGAATCCGATGACTAGGTTCCA

CTGCTCTAGTAGCTTCTTCAACTCTTCGACGGTGATGGTTCCGTTAGAA

Start of M     Kozak                    Vaccinia mH5 promoter

TCCGCC CAT ggtggc TTATGATTATTTCTCGCTTTCAATTTAACACAACCCTCAAGAACCTTGTATTTATTTTCAATTTTT

FIG. 8C

GPS-Tandem Repeat (5x)-GPTM-E-M (SEQ ID NO: 112)

Vaccinia mH5 promoter                                                                 SmaI    Kozak

AAAAATTGAAAATAAATACAAAGGTTCTTGAGGGTTGTGTTAAATTGAAAGCGAGAAATAATCATAA|CCCGGG|gccacc

MAR Signal peptide                                                    epitope 504-524

ATGTGGACGACCTGCTTCTTCATCTCCCTAATCCTAATCCAGGGAATCAAGACCTA|TGGACGACCTGCTTCTTCATCTC

CCTAATCCTAATCCAGGGAATCAAGACCCTATATCAGCCGTACAGAGTCGTCGTACTATCCTTCGAACTACTACGTGC linker      epitope 473-490

TCCGGGACAGTAggtcctggacccggtTATCAGGCTGGATCTACACCGTGTAATGGTGTCGAAGGATTCAACTGCT linker      epitope 504-524

ACTTCggtcctggacccggtTATCAGCCGGTACAGAGTCGTCGTACTATCCTTCGAACTACTACGTGCTCCGGGACA linker      epitope 473-490

GTAggtcctggacccggtTATCAGGCTGGATCTACACCGTGTAATGGTGTCGAAGGATTCAACTGCTACTTCggtcc linker      epitope 504-524 tggacccggtTATCAGCCGGTACAGAGTCGTCGTACTATCCTTCGAACTACTACGTGCTCCGGGACAGTAggtcctg linker      epitope 473-490                                         linker gacccggtTATCAGGCTGGATCTACACCGTGTAATGGTGTCGAAGGATTCAACTGCTACTTCggtcctggacccggt epitope 504-524                                                                 linker

TATCAGCCGTACAGAGTCGTCGTACTATCCTTCGAACTACTACGTGCTCCGGGACAGTAggtcctggacccggtTA epitope 473-490                         linker      epitope 504-524

TCAGGCTGGATCTACACCGTGTAATGGTGTCGAAGGATTCAACTGCTACTTCggtcctggacccggtTATCAGCCGT linker      epitope 473-490

ACAGAGTCGTCGTACTATCCTTCGAACTACTACGTGCTCCGGGACAGTAggtcctggacccggtTATCAGGCTGGA

MAR-TM

TCTACACCGTGTAATGGTGTCGAAGGATTCAACTGCTACTTC|TGGTGGACATCTGACTGGGGAGTCCTAACGAACCT

MAR-Ct

AGGAATCCTACTACTATTGTCGGGCTCCTAATCGGGCTATCCTGTATCTGT|AGAATCTTCACCAAGTACATCG

C-Tag                       vaccinia P11 promoter                 Kozak

GA|gagccggaagct|TAATAAttttatTAATAAtttttatc|TTTCATTTGTTTTTTCTATGCTATAA|gccacc

FIG. 8D

Start of E

ATG|TACTCCTTCGTGTCCGAAGAAACCGGAACCTTGATCGTCAACTCCGTCCTACTATTCCTAGGCGTTCGTCGTGTTCCT
ACTAGTAACCCTAGCTATCCTAACCCGCGCTAAGACTATGTGCGTACTGCTGCAACATCGTCAACGTGTCCCTAGTG

End of E    C-Tag |gagccagaggct|

AAGCCGTCCTTCTACGTCTACTCCAGAGTCAAGAACCTAAACTCCTCTAGAGTCCCGGACCTACTAGTT|gagccagaggct|

C-Tag    End of M

TAATAAataaaaaTTATTA|agcctctggctc|CTGGACTAGTAGAGCGGATATTATCGGAACTGGAGGAGTGGTCGGTGTTAGCTTG
TAGTTCCCGATTCTGTATCTAGAATACGCGCCAAATCCAGAATCTCCCGGACTCTTGAGAGGCTCCCAACTATAGT
ACGATAGGGGTTCTAGAGGTCGCTACGGTCGATCTCCTTCGGTAGGTCCTTGATGTCACATCTTCCTAGGTGGTGTCCCGCA
ATTCTTAGATGTCCCTCTTAGGATGACCGGCTCCGATAACCAATTCGGATTCCAATAGCGGTCTCTGGTTAGGATGGTTCCATG
TAGCGGGTACGTTCAATAGGATGTTCGTCTCCGGGTTGAACGACCACATAGATCTGGTTCTCGCGAATAGTCTGAAGGAG
GCGATGAAGTAGGATAGCGCCACCATTAGTCCTACTAGACAAGCCATAGCGGCCATAGCCGTGTGATCCAGTTGATTC
TGTAGACCGCAGCTAGAACGAAGCAGGCCAAGGTGACGGCCATAGTAGCTTGATGATGTACA
AGAATCTGTTCCGTTCGGTACGGCGAACTGTAGTAGGCAGATCCAGGTTAGGAATAGGAATCCGATGACTAGGTTCCA
CTGCTCTAGTTCGTTCTTCAACTCTTCGACGGTGATGGTTCCGTTAGAA

Start of M    Kozak |ggtggc|                                      Vaccinia mH5 promoter

TCCGC|CAT|TTATGATTATTTCTCGCTTTCAATTTAACACAACCCTCAAGAACCTTGTATTTATTTTCAATTTTT|

FIG. 8E

GPS-truncated S-GPTM, the E protein, and the M protein (SEQ ID NO: 119)

Vaccinia mH5 promoter       Kozak

AAAAATTGAAAATAAAATACAAAGGTTCTTGAGGGTTGTGTTAAATTGAAAGCGAGAAATAATCATAA|gccacc

MAR signal       Truncated S

```
ATGTGGACGACCTGCTTCTTCATCTCCCTAATCCTCCAGGGAATCAAGACCCTA|TTCGTGTCCTAGTCCTACTACC
GCTAGTCTCTTCTCAGTGTGTAAACCTAACAACGAGAACAACTACCACCGGCGTACACCAATTCTTTCACAGAGGA
GTATATTACCCGGACAAGGTGTTCAGATCCTCCGTACTACATTCTACACAGGACCTATTCCTACCGGTTCTTCTTAACGT
AACATGGTTCCACGCGATCCATGTCTCTGGAACAAAACGAAGAAGAGATTCGATAAACCCGGTCTTGCCGTTCAACGAT
GGTGTATACTTTGCGGTCCACCGAGAAGTCCAACATCATCAGAGGATGGATCTTCCGGAACCACCTTGGATTCTAAGACCC
AGTCCTTGCTAATCGTCAACAAGACGACCAACGTCATCAAAGTCTGCGAATTCCAGTTCGTGTAAGCGACCCGTTCTT
GGGAGTCACTACCACCACAGAGAACAACAAGAACCAAGTCCTGGATGGAATCCGAGTTCAGAGTGCTACTCTTCCGCGGAACAACTGCAC
CTTCGAATATGTATCTCAGCCGGTTCCTAATGGACCTAGAGGGAAAGCCAGGGAAACTTCAACCTAGTTAGAGATCTACCGCAAGG
ATTCAAGAACATGACGATCTCAGCGGATACTTCAGAATCTCAAGCCGTTAGTAGATTTGCCGAATCAACACCAGATTCCAGCACTAGCGCTACAC
ATTCTCTGCGCTAGAACCGGTTAGTAGATTTGCCGAATCAACACCAGATTCCAGCACTAGCGCTACAC
AGATCTTACCTAACGCGCGGAGATTCTTCTGGATGGAACCATCACCGATGCCGTAGATTGGTGCTCTAGATCCGCTATCCGA
CGAGAACCTTCCTATTGAAGTACAACGAAAAACGGAACCATCACCGATGCCGTAGATTGGTGCTCTAGATCCGCTATCCGA
AACGAAGTGCACCTAAAGTCTTCACCGGTCGAGAAGGGAATCTCCAACTTAGAGTACAGCCGACCGA
ATCCATCGTCAGATTTCCGAACATCACGAACCTATGTCCGTTCGGGAGAAGTGTTCAAGCGACAAGATTTGCGGTCTGTC
TATGCGGTGGAACAGAGAAAAAGAAATCAGTAACTGCGTAAACGATCTATGCTTCAACGTCTACGCGACTCCTTCTCCACGT
TCAAATGCTACGGTGTGTCTCCGACAAAGTCAAACGATCTATGCTTCAACGTCTACGCGACTCCTTCTCCACGT
AGGAGATGAAGTTAGACAGATTGCGCCGGGACAAACTGGAAAGATCGCGGATTATAACTACAAGCTACCGGACGACTT
CACCGGATGTGTAATTGCGTGGAATTCGAACAACCTAGACTCGGAGGAAACTACAACTACTTGTACAGACT
ATTCAGAAAGTCCAACCTAAAGCCGTTCGAGAGAGACATCTCCACGAAATCTATCAGCCTGGATCTCACACCGTGTAAT
GGTGTGCGAAGGATTCAACTGCTACTTCCCGCTACGTTCCCGTACTACATGCTCCGGCGACCAGTATGTGGACCGAAAAAGTCTACCAACCTAGT
ACAGAGTCGTGCTACTATCCTTCGAACTACTACGTGCTCCGGCGACCAGTATGTGGACCGAAAAAGTCTACCAACCTAGT
CAAGAACAAATGCGTCAACTTTAACTTCAAGCGGACTAACACCGGACTAACACCGGTGTCCTAACCGAATCTAACAAGAAGTTTCT
ACCGGTTCCAGCAGTTCGGAAGAGAGATATCGGGGATATCCGGGAATCCGCAAACCTTGGAGATCCTAGA
TATCACACCGTGTTCTTTCGGTGGTGTCTCTGTAATTACTCCGGAACGAACACCTCCAATCAAGTTAGCGGTACTATACC
AGGACGTGAACTGTACAGAGTACCGGTATTCACGGAGAAGTCAACTAACACCAACTGGAGAGTGTACTCCACCG
```

FIG. 9B

GATCTAACGTATTCCAAACAAGAGAGCGGGATGTCTAATCGGAGCGGAACACGTAAACAACTCCTACGAATGTGATATCC
CGATTGGAGCGGGGAATCTGTCGCGTCTTACCAACAACAAACTCCGAGAGAGCGAGATCTGTAGCCTCTCAAT
CTATTATCGGCCTACCACCATGTCCTTGGGAGCCGAAAATTCTGTCGGCGTACTCCAACAATTCTATCGGGATCCCGACAAA
CTTCACCATCTCTGTAACAACCGAGATCCTACCGGTGTCTATGACCAAGACATCTGTCGATTGCACCATGTACATCTGC
GGAGATTCCACCGAGTGCTCCAACCTACTACTACAGTACGGATCTTTCTGTACCCAGCTAAACAGAGAGGGTTGACTGGAA
TCGCTGTGTAGAGCAGGATAAGAACACTCAAGAGGTATTCGGCGCAAGTCAAGCAGATCTATAAGACTCCGCCGATCAAGG
ACTTCGGAGGTTCAACTTCTCTCAGATCTTGCCGGATCCGTCCAAACCGTCTAAGAGATCTTTCATCGAGACCTACTA
TTCAAACAAAGTCACCCTAGCTGACGCGGGATTCATCAAACAATACGGAGATTGCTTGGGAGACATTGCGGCGGAGAT
CTAATTTGCGCGCAGAAGTTAACGGATTGACAGTACTACCGCCGCTACTAACCGATGAGATGATTGGCGCAGTACACGT
CTGCTCTATTGGCGGGAACAATTACAAGTGGATGGACATTTGGAGCCGGTGCCGCTCTACAAATTCCGTTTGCTATGCA
AATGGGGTACAGATTCAACGGAATCGGAGTAACCCAGAAGCGTCTTGTACGGAGAGAAGCTAATCGCGAACCAGTT
CAATTCCGCGATCGGAAAGATCCAGGACCAGTCTATCTTCTACTGCTTCGGCGTTGGGAAAGCTACACAGGATGTAGTAAAT
CAAAACGCGCAGCCGCTAAACACCTGGTCAAGCAACTATCCTGGTCAAGCAACTATCAACTGGAAGATTGCAGTCCCTACAGA
TCTTATCCAGACTAGATAAGGTCGAAGCGGAGGTCCAGATTAGAGCGGCGGAGATTAGAGCCTCTGTAATCTAGC
GTGTCTTGGGACAATCCAAGAGAGTGGACTTCTGCGGAAAGGGATACCACCTAATGTCTTTCCCACAATCTCGGCGCA
TGGTGTCGTATTCCTACATGTAACATATGTGCCGGCGCAAGAAAAGAACTTCACAACAGCTCCAGCGATCTGCCATGAT
GGAAAGCTCATTTCCCGAGAGAGGGAGTCTTGTCTCTAACGGAGTCTTTGTCTCAAGGAACTCATTGGTTGCGTCACCCAGGAAACTTCTACG
AGCCGCAGATCATCACCACGACAACACATTCGTCTCGGGAAACTCGGACGTGTCATCGGAATCGTAAACAATACCG
TCTACGATCCGTTGCAGCCGGAACTAGACTCCTTCAAAGAAGAGTTGGACAAGTACTTCAAGAACCACACCTCTCCGG
ATGTGGACTTGGGAGATATCTCTGAATCAACGCGTCCGTCAACATCCAGAAAGAAATCGATAGATTGAACGAGG
TCGGCGAA

GAACTTGAACGAGTCCCTAATCGACCTACAAGAGCTAGGAAAATACGAGCAGTAGGAAAATACGAGCAGTACATCAAGTGGCCG|TGGTGGACATC

MAR-Ct                          C-Tag        P11 vaccinia promoter.        Kozak/ Start E

TGACTGGGGAGTCCTAAGCGAACCTAGGAATCCTACTACTATTGTGTGATCGCGGCTATCCTGTATCTGT

AGAATCTTCACCCAAGTACACATCGGA|gagccggaagct|TAATAAttttatc|TTTCATTTGTTTTTTTCTATGCTATAA|gccaccATGTAC

FIG. 9C

TCCTTCGTGTCCGAAGAAACCGGAACCTTGATCGTCAACTCCGTCCTACTATTCCTAGCGGTTCGTCGTCGTTCCTACTAGT
AACCCTAGCTATCCTAACCGCGCTAAGACTATGTGCGTACTGCTGCAACATCGTCAACGTGTCCCTAGTGAAGCCGTCC
TTCTACGTCTACTCCAGAGTCAA

End E    C-Tag                    C-Tag    End of M

GAACCTAAACTCCCTCTAGAGTCCCGGACCTACTAGTTgagccagaggctTAATAAAataaaaaTTATTAagcctctggctcCTGGAC
TAGTAGAGCGGATATTATCGGAACTGGAGGAGTGGTCGGTGTTAGCTTGTAGTTCCCGATTCTGTATCTAGAATACGCC
GCAAATCCAGAATCTCCCGCGACTCTTTGAGAGGCTCCAACTTATAGTACGATAGGGTTCTAGAGGTCGCTACGGTGA
TCTCCTTCGGTAGGTCCTTGATGTCACATCTTCCTAGGTGGGTGGTCCCGCAATTCTTAGATGTCCTCTTAGGATGACCGCT
CCGATAACCAATTCGGATTCCAATAGCGGTCTGGTTCTCGCGAATAGTGGTTCCATGTTAGCGGTACGTTCAATAGGATGTTCGTCT
CCGGGTTGAACGACCACATAGATCTGGTTCTCGCGAATAGTCTGAAGGAGGCGATGAAGTAGGATAGCCACATTAGTC
CTACTAGACAAGCCATAGGCGATCCACCTGGATTCCACCTGTGATCCAGTTGATTCTGTAGACCGCAGCTAGAACGAAGCAGG
CCAAGGTGACCGGCCATAGTAGCCATAGGAAGATTAGCTTGATGATGTACAAGAATCTGTTCCGTTCCGGTACGCGAA
CTGTAGTAGGCAGATCCAGGTTAGGAATAGGAATCCGATGACTAGGTTCC Start of M    Kozak ACTGCTCTAGTAGCTTCTTCAACTCTTCGACGGTGATGGTTCCGTTAGAATCCGCCATggtgggcTTATGATTATTTCTCGCT mH5 vaccinia promoter

TTCAATTTAACACAACCCTCAAGAACCTTTGTATTTATTTTCAATTTT

FIG. 9D

GPS-truncated S-GPTM, the E protein, and the M protein (SEQ ID NO: 120)

Vaccinia mH5 promoter                    Smal    Kozak

AAAAATTGAAAATAAATACAAAGGTTCTTGAGGGTTGTGTTAAATTGAAAGCGAGAAATAATCATAA|CCCGGG|gccacc MAR signal          Truncated S

```
ATGTGGACGACCTGCTTCTTCATCTCCCTAATCCTCAGGGAATCAAGACCCTA|TTCGTGTCCTAGTCCTACTACC
GCTAGTCTCTTCTCAGTGTGTAAACCTAACAACGAGAACAACTACCACCGGCGTACACCAATTCTTTCACAAGAGGA
GTATATTACCCGGACAAGGTGTTCAGTATCCTCCGTACTACACAGGACCTATTCCTACCGGTTCTTCTTCTTAACGT
AACATGGTTCCACGCGATCCATGTCTGGAACAAAACGAAGAGAGATTCGATAAACCCGGTCTTGCCGTTCAACGAT
GGTGTATACTTTGCGTCCACCGGTCCGAGAAGTCCAACATCATCAGAGGATGGATCTTCCGGAACCACCTGGATTCTAAGACCC
AGTCCTTGCTAATCGTCAACAAGCGACCAAGCGTCATCAAAGTCTGGAATTCCAGTTCGTGTAAGCGACCCGTTCTT
GGGAGTCGCTACTACCACCACAAGAACAACAAGAAGTCCTGGAATCCGAGTTCAGAGTCTACTCTTCCGGCGAACAACTGCAC
CTTCGAATATGTATCTCAGCCGGTTCCTAATGACCGTAGAGGGAAAGCCAGGGAAACTTCAACCTAGTTAGAGATCTACCGCAAGG
ATTCAAGAACATCGACGGATACTTCAGATCTCAACCAGATTCCAGGAATCAACATCACCAGATTCCAGACACTACTAGCGCTACAC
ATTCTCTGCGCTAGAACCGTTAGTAGATTTGCCGATCGGATGGACTGCTGGTGCTGGTGCGCTTATTATGTAGGATACCTACAGC
AGATCTTACCTAACGCCGGGAGATTCTTCTCTGGATGGAACCATCACCGATGCCGTAGATTGGTGCTCTAGATCCGCTATCCGA
CGAGAACCTTCCTATTGAAGTACAACGAAAACGGAACCATCACCGATGCCGTAGATTGGTGCTCTAGATCCGCTATCCGA
AACGAAGTGCACCCTAAAGTCTTTCACGGTCGAGAAGGGAATCACCAGACCTCCAACTTAGAGTACAGCCGACCGA
ATCCATCGTCAGATTTCCGAACATCACGAACCTATGTCCGTTCGGGAGAAGTGTTCAAGCGACAAGATTTGGGTCTGTC
TATGCGGTGGAACAGAGAAAAGAAATCAGTAACTCAGTAACGTAAACGATCTATGCTTCACCAAGTCTACGCGGACTACAG
TCAAATGCTACGGGTGTCATCCGACAAAGTCAAACGATCTATGCTTCACCAAGTCTACGCGGACTACAG
AGGAGATGAAGTTAGACAGATTGGCGCCGGGACAAACTGGAAAGATCGGAGATTATAACTACAAGCTACCGGACGACTT
CACCGGATGTGTAATTGCGTGGAATTCGAACAACCTAGACTCGGAGGAAAACTACTACTTGTACAGACT
ATTCAGAAAGTCCAACCTAAAGGCCGTTCGAGAGAACATCTCCACGGAAATCTATCAGGCTGGATCTCTACACCGTGTAAT
GGTGTGTGGAAGGATTCAAACTGCTACTTCCCGCTACGGTCTTACGGGATTTCAACGACAAAGGGTGTAGGGATATCAGCCGT
ACAGAGTCGTCGTACTACTATCCTTCGAACTACTACATGCTCCGGCGACAGTATGTGGACCGAAAAAGTCTACCAACCTAGT
CAAGAACAAATGCGTCAACTTTAACTTCAAGCGGACTAACTTAACCGAGACCGTTGTCCTAACCGAATCTAACAAGAAGTTTCT
ACCGGTTCCAGCAGTTCGGAAGAGAGATATCGCGGGGAATATCCGGCAAACACCTCCAATCCAAGTCAAGTAGCCGGTACTATACC
TATCACACCGGTGTTCTTTCGGTGGTGTCTGTAATTACTCCGGAACGAACACCTCCAATCAAGTAGCGGTACTATACC
AGGACGGTGAACTGTACAGAAGTACCGGTACCGGTAGCTATTCACGCGGATCAACTAACACCAACTGGAGAGTGTACTCCACCG
```
```

FIG. 9E

GATCTAACGTATTCCAAACAAGAGAGGCGGGATGTCTAATCGGAGCGGGAACCACGTAAACAACTCCTACGATTGTGATATCC
CGATTGGAGCGGGGAATCTGTGCGTCTTACCAAACACAAACAAACTCTCCGAGAGAGGCGAGATCTGTAGCCTCTCAAT
CTATTATCGCCTACACCATGTCCTTGGGAGCCGAAAATTCTGTCGCTACTCCAACAATTCTATCGCGATCCCGACAAA
CTTCACCATCTCTGTAACAACCGAGATCCTACCGGTGTCTATGACCAAGACATCTGTCGATTGCACCATGTACATCTGC
GGAGATTCCACGAGTGCTCCAACCTACTACTACAGTACGGATCTTTCTGTACCCAGCTAAACAGAGAGGTTGACTGGAA
TCGCTGTGTAGAGCAGGATAAGAACACTCAAGAGGTATTCGCGCAAGAGTCTATAAGACTCCGCCGATCAAGG
ACTTCGGAGGTTTCAACTTCTCTCAGATCTTGCCGGATCCGTCCAAACCGTCTAAGAGATCTTTCATCGAGGACCTACTA
TTCAACAAAGTCACCCTAGCTGACGAAGTTAACGGATTGACAGTACAGTCATCAAACAATACCGCGCTACTCAACCGAGAGAT
CTAATTTGCGCGCAGAAGTTAACGGATTGACAGTACAGTCATCAAACAATACCGCGCTACTAACCGAGTGGCAGTACACGT
CTGCTCTATTGGCGGGAACAATTACAAGTGGATGGACATTTGGAGCCGGTGCCCGTCTACAAATTCCGTTTGCTATGCA
AATGGCGTACAGATTCAACGAATCGGAGTAACCCAGAACGTCTGTACGAGAACGTAATCGCGAACAGTCAATCGCGAACCAGTT
CAATTCCGGATCGGAAAGATCCAGGACCAGTCTATCTTCTACTGCTTCGGGGAAAGCTACAGGATGTAGTAAAT
CAAAACGGGCGCAGGCGCTAAACACCTTGGTCAAGCAACTATCCTCTAAGCAACTATCCTCTAACCGTCCGTCCTAAACGACA
TCTTATCCAGACTAGATAAGGTCGAAGCGGAGGTCCAGATCGATAGACTAATCACTGAAGATTGCAGTCCCTACAGA
CCTACGTAACACAGCAACTAATTAGAGGGGCGGGAGATTAGAGCCCTCGTAATCTAGTCGTGCGACCAAGATGTCGAAT
GTGTCTTGGGACAATCCAAGAGAGTGGACTTCTCGCGGGAAAGGGATCCCCCACAATCTGGCGCGCA
TGGTGTGCGTATTCCTACACATGTAACATATGTGCCGCGCAAGAAAAGAACTTCACAACAGCTCCAGCTCGCCATGAT
GGAAAAGCTCATTTCCCGAGAGAGGGAGTCTTTGTCTCTAAGGAACTCATTGGTCGTCACCGAGAAACTTCTACG
AGCCGCAGATCATCACCACCGACAACACACATTCGTCTCGGGAAATCGGGGAATCGTAAACAATACCG
TCTACGATCCGGTGCAGCCGGAACTGAGACTCCTTCAAAGAAGAGTTGGACAAGTAGTCACTTCAAGAACCACACCTCCGG
ATGTGGACTTGGGAGATATCTCTGGAATCAACGGTCCGTCAACGGTCCGTCAACATCCAGAAGAAATCGATAGATTGAACGAGG
TCGCGAA

MAR-Ct

GAACTTGAACGAGTCCCTAATCGACCTACAAGAGCTAGGAAAATACGAGCAGTACATCAAGTGGCCGTGGTGGACATC

TGACTGGGGGAGTCCTAACGAACCTAGGAATCCTACTACTATTGTGATCGCGGTCCTAATCGGCGTCATCCTGTATCTGT

MAR-Tm

MAR-Ct C-Tag P11 vaccinia promoter.

AGAATCTTCACCAAGTACATCGGAgagccggaagctTAATAAttttatcTTTCATTTTGTTTTTCTATGCTATAAgccaccATGTAC

Kozak/ Start E

TCCTTCCGTGTCCGAAGAAACCGGAACCTTGATCGTCAACTCCGTCCTACTATTCCTACGCGGTTCGTGTTCCTACTAGT

AACCCTAGCTATCCTAACCGCGCTAAACCGCGCTATGTGCGTAAGACTATGTGCCAACATCGTCAACGTGTCCCTAGTGAAGCCGTCC

TTCTACGTCTACTCCAGAGTCAA

FIG. 9F

End E   C-Tag          C-Tag   End of M

GAACCTAAACTCCTCTAGAGAGTCCCGGACCTACTAGTTgagccagaggctTAATAAataaaaaTTATTAagcctctggctcCTGGAC

TAGTAGAGCGGATATTATCGGAACTGGAGGAGTGGTCGGTGTTAGCTTGTTCCCGATTCTGTATCTAGAATACGCC

GCAAATCCAGAATCTCCCGCGACTCTTTGAGAGGCTCCCAACTTATAGTACGATAGGGTTCTAGAGGTCGCTACGGTGA

TCTCCTTCGGTAGGTCCTTGATGTCACATCTTCCTAGGTGGTGGTCCCGCAATTCTTAGCGGTCCTCTTAGGATGACCGCT

CCGATAACCAATTCGGATTCCAATAGCGGTCTCGGTTAGGATGGTTCCATGTCAGCGGTACGTTCAATAGGATGTTCGTCT

CCGGGTTGAACGACCACACATAGATCTGGTTCTCGCGAATAGTCTGAAGGAGGCGATGAAGTAGGATAGCCACATTAGTC

CTACTAGACAAGCCATAGGCGATCGGCCATTCCACCTGTAGATCCAGTTGATGTCGTAGACCGCAGCTAGAACGAAGCAGG

CCAAGGTGACCGGCCATAGTAGCCATAGGAAGATTAGCTTGATGATGTACAAGAATCTGTTCCTGTTCCGTACGCGAA

CTGTAGGCAGATCCAGGTTAGGAATAGGAATCCGATGACTAGGTTCC

Start of M  Kozak

ACTGCTCTAGTAGCTTCTTCAACTCTTCGACGGGTGATGGTTCCGTTAGAATCCGCCATggtggcTTATGATTATTTCTCGCT mH5 vaccinia promoter

TTCAATTTAACACAACCCTCAAGAACCTTTGTATTTATTTTCAATTTT

FIG. 9G

GPS-truncated S + K986P and V987P-GPTM, the E protein, and the M protein (SEQ ID NO: 121)

Vaccinia mH5 promoter                                                                    Kozak AAAAATTGAAAATAAATACAAAGGTTCTTGAGGGTTGTGTTAAATTGAAAGCGAGAAATAATCATAA|gccacc MAR signal                          Truncated S ATGTGGACGACCTGCTTCTTCATCTCCCTAATCCTAATCCAGGGAATCAAGACCCTA|TTCGTGTTCCTAGTCCTACTACC
GCTAGTCTCTTCTCAGTGTGTAAACCTAACAACGAGAACAACTACCACCGGCGTACACCAATTCTTTCACAGAGGA
GTATATTACCCGGACAAGGTGTTCAGATCCTCCGTACTACACAGGACCTATTCCTACCGGTCTTCTTCTTCTTAACGT
AACATGGTTCCACGCGATCCATGTCTCTGGAACAAACGAAGAGAGAGATTCGATAAACCCGGTCTTGCCGTTCAACGAT
GGTGTATACTTTGCGTCCGGTCCACCGAGAAGTCCAACATCATCAGAGGATGGATCTTCGGAACCACCTGGATTCTAAGACCC
AGTCCTTGCTAATCGTCAACAAGCGACCAACAACAAGTCCAGTTCCAGTTCGTGTAAGCGACCCGTTCTT
GGGAGTCACTACCACCACAAGAGAACAACAAGAAGTCCTGGAATCCGAGTCAGAGTCACTCTTCCGGAACAACTGCAC
CTTCGAATATGTATCTCAGCGGATACTTCCAAGATCTCAAGAGAGGGAAAGCCAGGGAAACTTCAACCTAAGAGAGTTCGT
ATTCAAGAACATCGACGGATACTTCAGATCGGAATCAACACCAGATTCAACAACTAGTCCAGACTAGCGGCTACAC
ATTCTCTGCGCTAGAACCGTTAGTAGATTGCCGATCGGAATGGACTGGCTGCGCGTATTATGTAGGATACCTACAGC
AGATCTTAACGCGCGGGAGATTCTTCTCTGGATGGACAACCATCACCGCGTGCGTAGATTGGTGCTCTAGATCCGCTATCCGA
CGAGAACCTTCCTATTGAAGTACAACGAAAAACGGAACCATCCAACCTCCAACTTAGAGTACAGCCGACCGA
AACGAAGTGCACCTAAAGTCTTTCACCGTCAAGCTAAGTGCTAAGTACAGCCGACCGA
ATCCATCGTCAGATTTCCGAACATCACGAACCTATGTCGGGAGAAGTGTTCAACGGCGACAAGATTTGCGGTCTGTC
TATGCGGTGGAACAGAAAAAGAATCAGTAACTCAGTAAACGATCTATGCTTCACCGACTCCTCCTTCTCCCACGT
TCAAATGCTACGGGTGTGTATCTCCGACAAAGTAAACGATCTATCTCCGACGTCTACGCGGACTCCTTCGTAATCAG
AGGAGATGAAGTTAGACAGATTGCGCGGGACAAACTGGAAAGATCGCGAGATTATAACTACAAGCTACCGGACGACTT
CACCGGATGTGTAATTGCGTGGAATTCGAACAACTAGACTCCAAAGTCGGAGGAAACTACAACTACTTGTACAGACT
ATTCAGAAAGTCCAACCTAAAGCCGTTCGTCGAGAGAACATCTCCACGAAATCTATCAGGCTGGATCTCACCGTGTAAT
GGTGTGTCGAAGGATTCAACTGCTACTTCCCGCTACTTCCCGCTACTACATGTCTCCGGCGACAGTATGGACCGA
ACAGAGTCGTCGTACTATCCTTCGAACTACTACTTCAACTTAAGCGGACTAAACCGGAAAAAGTCTACCAACCTAGT
CAAGAACAAATGCGTCAACTTTAACTTCAACGGACTAACTTAACCGGACTAAACTCTAACCAAGAAGTTTCT
ACCGGTTCCAGCAGTTCGGAAGAGAGATATCGCGGGATACAACAACAGACGCGGCAAACCTTGGAGATCCTAGA
TATCACACCGTGTTCTTCGGTGGTCTTGTGAATTACTCCGGAACGAACACCTCCAATCAAGTAGCGGTACTATACC
AGGACGGTGAACTGTACAGAAGTACCGGTATTCACGCGGGATCAACTGCAACAACCAACTGGAGAGTGTACTCCACCG

FIG. 9I

```
GATCTAACGTATTCCAAACAAGAGAGCGGGATGTCTAATCGGAGGCGGAACACGTAAACAACTCCTACGAATGTGATATCC
CGATTGGAGCGGGGAATCTGTGCGTCTTACCAAACACAAACAAACTCTCCGAGAGAGCGAGATCTGTAGCCTCTCAAT
CTATTATCGCCTACACCATGTCCTTGGGAGCCGAAATTCTGTCGCGATCCAACAATTCTATCGCGATCCCGACAAA
CTTCACCATCTCTGTAACAACCGAGATCCTACGGTGTCTATGACCAAGACATCTGTCGATTGCACCATGTACATCTGC
GGAGATTCCACCGAGTGCTCCAACCTACTACTACGAGAGGTTTCTGTACCCAGCTAAACAGAGAGGTTGACTGGAA
TCGCTGTGTAGAGCAGGATAAGAACACTCAAGAGGTATTCGCGCAAGAGTCTATAAGACTCCGCGATCAAGG
ACTTCGGAGGTTTCAACTTCTCTCAGATCTTGCCGGATCCGTCCAAACCGTCTAAGAGATCTTTCATCGAGGACCTACTA
TTCAACAAAGTCACCCTAGCTGACGAAGTTAACGGATTGACAGTCATCAAACAATACGGAGATTGCTTGGGAGACATTGCTGGCGGAGAGAT
CTAATTTGCGCGCAGAAGTTAACGGATTACAAGTGGACAATTACAAGTGGATGGACACATTTGGAGCCCGGTGCCGTCTTACAAATTCCGTTTGCTATGCA
CTGCTCTATTGGCGGGAACAATTACAAGTGGACAATTACAAGTGGATGGACACATTTGGAGCCCGGTGCCGTCTTACAAATTCCGTTTGCTATGCA
AATGGCGTACAGATTCAACGAATCGGAGTAACCCAGAACGTCTGTACGAGAACGTCTGTCTTCTACTGTTCGGAGAAGCTAATCGCGAACCAGTT
CAATTCCGGATCGGAAAGATCCAGGACAGTCTATCTTCTACTGTTCGGAGAAGCTAATCGCGAACCAGTT
CAAAACGGCGCAGGCGTAAACACCTGGTCAAGCAACTATCCTCTAACTTCGGAGATCTCGCGTCCTAAACGACA
TCTTATCCAGACTAGATCCACCGGAAGCGGAGGTCCAGATCGATAGACTAATCACTGGAAGATTGCAGTCCTACAGA
CCTACGTAACACAGCAACTAATTAGAGCGGGGAGATTAGAGCCCTGCTAATCTAGCTGCGACCAAGAGTCGAAT
GTGTCTTGGGACAATCCAAGAGAGTGGACTTCTCGCGGAAAGGGATCCTTCCCACCATCTGCGGCCGCA
TGGTGTCGTATTCCTACACATGTAACATATGTCGCGCGCAAGAAAAGAACTTCACAACAGCTCCAGCTCGCCATGAT
GGAAAAGCTCATTTCCCGAGAGAGGGAGTCTTTGTCTCTAACGGAACTCATTGGTCGTCACCCAGAGAAACTTCTACG
AGCCGCAGATCATCACCACCGACAACACATTCGTCGTCTCGGGAAACTGGTCATCGGACGTGGTAAACAATACCG
TCTACGATCCGGTTGCAGCCGGAACTAGACTCCTTCAAAGAAGAGTTGACAAGTACTTCAAGAACCACACCTCTCCGG
ATGTGGACTTGGGAGATATCTCTGGAATCAACGGGTCCGTCAACATCCAGAAGAAATCGATAGATTGAACGAGG
TCGCGAA
```

Labeled section:

```
                                                                    MAR-Tm
GAACTTGAACGAGTCCCTAATCGACCTACAAGAGTCTAGGAAAATACGAGCAGTACATCAAGTGGCCG[TGGTGGACATC
TGACTGGGGAGTCCTAACGAACCTAGGAATCCTACTACTATTGTGATCGGCGTCTAATCGGCCTATCCTGTATCTGT]
MAR-Ct                        C-Tag          P11 vaccinia promoter.      Kozak/ Start E
AGAATCTTCACCAAGTACATCGGA[gagcccggaagct]TAATAAttttatc[TTTCATTTTGTTTTTTTCTATGCTATAA]gccaccATGTAC
TCCTTCCGTGTCCGAAGAAACCGGAAGCCTTGATCGTCAACTCCGTCCTACTATTCCTACTACTTCGTTCCTACTAGT
AACCCTAGCTATCCTCAACCGCGCTAAGACTATGTGCGTAAGACTATGTGCCAACATCGTCAACGTGTCCCTAGTGAAGCCGTCC
TTCTACGTCTACTCCAGAGTCAA
```

End E     C-Tag

C-Tag     End of M

GAACCTAAACTCCTCTAGAGTCCCGGACCTACTAGTTgagccagaggctTAATAAataaaaaTTATTAagcctctggctcCTGGAC
TAGTAGAGCGATATTATCGGAACTGGAGGAGTGGTCGGTGTTAGCTTGTAGTTCCCGATTCTGTATCTAGAATACGCC
GCAAATCCAGAAATCTCCCGCGACTCTTTGAGAGGCTCCCAACTTATAGTACGATAGGGTTCTAGAGGTCGCTACGGTGA
TCTCCTTCGGTAGGTCCTTGATGTCACATCTTCCTAGGTGGGTGGTCCCGCAATTCTTAGAGTGTCCTCTTAGGATGACCGCT
CCGATAACCAATTCGGATTCCAATAGCGGTCTCGGTTAGGATGGTTCCATGTAGCGGTACGTTCAATAGGATGTTCGTCT
CCGGGTTGAACGACCACCACATAGATCTGGTTCTCGCGAATAGTCTGAAGGAGGCGATGAAGTAGGATAGCCACATTAGTC
CTACTAGACAAGCACCATAGCGGCCATCGGCGATTCCACCTGTGATCCAGTTGATTCTGTAGACCGCAGCTAGAACGAAGCAGG
CCAAGGTGACCGGCCATAGTAGCCATAGGAAGATTAGCTTGATGATGTACAAGAATCTGTTCCTGTTCCGTACGCGAA
CTGTAGTAGGCAGATCCAGGTTAGGAATAGGAATCCGATGACTAGGTTCC

Start of M  Kozak

ACTGCTCTAGTAGCTTCTTCAACTCTTCGACGGGTGATGGTTCCGTTAGAATCCGCCATggtggcTTATGATTATTTCTCGCT mH5 vaccinia promoter

TTCAATTTAACACAACCCTCAAGAACCTTTGTATTTATTTTCAATTTTT

FIG. 9K

GPS-truncated S + K986P and V987P-GPTM, the E protein, and the M protein (SEQ ID NO: 122)

Vaccinia mH5 promoter　　　　　　　　　　　　　　　　　　　　　　　　SmaI　　Kozak

AAAAATTGAAAATAAAATACAAAGGTTCTTGAGGGTTGTGTTAAATTGAAAGCGAGAAATAATCATAA|CCCGGG|gccacc

MAR signal　　　　　Truncated S

ATGTGGACGACCTGCTTGTTCTTCATCTCCCTAATCCTCCTAATCCTAAGGGAATCAAGACCCTA|TTCGTGTTCCTAGTCCTACTACC
GCTAGTCTCTTCTCAGTGTGTAAACCTAACAACGAACAACTACCACCGGCGTACACCAATTCTTTCACAGAGGA
GTATATTACCCGGACAAGGTGTTCAGATCCTCCGTACTACATTCTACACACAGGACCTATTCCTACCGTTCTTCTCTAACGT
AACATGGTTCCACGCGATCCATGTCTCTGGAACAAACGGAACGAAGAGATTCGATAAACCCGGTCTTGCCGTTCAACGAT
GGTGTATACTTTGCGTCCACCGTCCACCGAGAAGTCCAACATCATCAGAGGATGGATCTTCGGAACCACCTGGATTCTAAGACCC
AGTCCTTGCTAATCGTCAACAAGAACAACAAGAATCGTCTGGAATTCCAGTTCGTGTAACGACCCGTTCTT
GGGAGTCACTACCACCACAGAGAACAACAAGAATCCTGGATGGAATCGAGAGGGAAAGCCAGGGAAACTAAGAGAGTTCGT
CTTCGAATATGTATCTCGACGGATACTTCAGAATCTCAGATGACCTAGAGGGAAAGCCAGGGAAACTAAGAGAGTTCGT
ATTCAAGAACATCGACGGATACTTCAGAATCTCAAGATCCGGAATCAACATCACCACCAGATTCCAGACCAGTTCGTGTCTCTCTAGCC
ATTCTCTGCGCTAGAACCGGTTAGTAGATTTGCCGATCGGAATGGACTGCTGGTGCGCGTTATTATGTAGGATACCTACAGC
AGATCTTACCTAACGCCGGAGATTCTTCTGGATGGAACCATCACCGATGCCGTGAGATTGGTGCTCTAGATCCGCTATCCGA
CGAGAACCTTCCTATTGAAGTACAACGAAAACGGAACCATCACCGATGCCGTGAGATTGGTGCTCTAGATCCGCTATCCGA
AACGAAGTGCACCCTAAAGTCTTTCACGGTCGAGAAGGGAATCACCAGACCTCCAACTTAGAGTACAGCCGACCGA
ATCCATCGTCAGATTTCCGAACATCACGAACCTATGTCCGTTCGGGAGAAGTGTTCAACGGGACAAGATTTGGGTCTGTC
TATGCGGTGGAACAGAAAAAGAATCAGTAACTGGCTAAACGATCTATGCTTCACCAACGTCTACGCGGACTCCTTCTCCACGT
TCAAATGCTACGGGTGTATCTCCGACAAAAGTAAACGATCTATGCTTCACCAACGTCTACGCGGACTCCTTCTCCACGT
AGGAGATGAAGTTAGACAGATTGCGCGGGACAAACTGGAAAGATCGCGGATTATAACTACAAGCTACGGACGACTT
CACCGGATGTGTAATTGCGTGGAATTCGAACAACCTAGACTCGGAGGAAACTACAACTACTTGTACAGACT
ATTCAGAAAGTCCAACCTAAAGCCGTTCGAGAGAACATCTCCACGGAAATCTATCAGCTGGATCTCACCGTGTAAT
GGTGTGCGAAGGATTCAACTGGCTACTTCCCGCTACGGTTCAAACGGTAGGGATATCAGCCGT
ACAGAGTCGTCGTACTATCCTTCGAACTACTACGTGCTCCGGCGACCGGACAGTATGTGGACCGAAAAAGTCTACCAACCTAGT
CAAGAACAAATGGCGTCAACTTAACTTCAACGGTCCTAACCGAATCTAACAAGAAGTTTCT
ACCGGTCCAGCAGTTCGGAAGAGAGATATGCGGGATACAACAGAGATCCGCAAACCTTGGAGATCCTAGA
TATCACACCGTGTTCTTTCGGTGGTGTCTCTGTAATTACTCCGGAACGAACACCTCCAATCAAGTAGCGGTACTATACC
AGGACGTGAACTGTACAGAGAAGTACCGGTATTCACGCGGATCAACTAACACCAACTGGGAGAGTGTACTCCACCG

FIG. 9L

```
GATCTAACGTATTCCAAACAAGAGAGCGGGATGTCTAATCGGAGGAGCGGGAACACGTAAACAACTCCTACGAATGTGATATCC
CGATTGGAGCGGGGAATCTGTGCGTCTTACCAAACACAAACAAACTCTCCGAGAGAGCGGAGATCTGTAGCCTCTCAAT
CTATTATCGCCTACACCATGTCCTTGGGAGCCGAAAATTCTGTCGCGAAATTCTATCGCGATCCCGACAAA
CTTCACCATCTCTGTAACAACCGAGATCCTACCGGTGTCTATGACCAAGACATCTGTCGATTGCACCATGTACATCTGC
GGAGATTCCACCGAGTGCTCCAACCTACTACTACGAGTCTTTCGTACCCAGCTAAACAGAGAGGGTTGACTGGAA
TCGCTGTGTAGAGCAGGATAAGAACACTCAAGAGGTATTCGCGCAAGAGTCTATAAGACTCCGCGATCAAGG
ACTTCGGAGGTTTCAACTTCTCTCAGATCTTGCCGGATCCGTCCAAACCGTCTAAGAGATCTTTCATCGAGGACCTACTA
TTCAACAAAGTCACCCTAGCTGACGAGAGTTCATCAAACAATACGGAGATTGCTTGGGAGACATTGCGGCGAGAGAT
CTAATTTGCGCGCAGAAGTTAACGGATTGACAGTCATACCGCGCTACTAACCGATGAGATGATTGCGCAGTACACGT
CTGCTCTATTGGCGGGAACAATTACAAGTGGATGGACATTTGGAGCCGGTGCCCGTCTACAAATTCCGTTTGCTATGCA
AATGGCGTACAGATTCAACGAATCGGAGTAACCCAGAACGTCTTGTACGGAACGAGAGCTAATCGCGAACCAGTT
CAATTCCGGATCGGAAAGATCCAGGACAGTCTATCTTCTACTGCTTCGGCGGTTGGGAAAGCTACAGGATGTAGTAAAT
CAAAACGGCGCAGGCGCTAAACACCTGGTCAAGCAACTATCCTCTAACTTCGGAGCGATCTCGTCCGTCCTAAACGACA
TCTTATCCAGACTAGATCCACCGGAAGCGGAGGTCCAGATCGATAGACTAATCCACTGGAAGATTGCAGTCCCTACAGA
CCTACGTAACACAGCAACTAATTAGAGCGGGGGAGATTAGAGCCCTGCTAATCTAGCTGCGACCAAGAGTCCGAAT
GTGTCTTGGGACAATCCAAGAGAGTGGACTTCTGCGGGAAAGGGATACCACCTACTTGTCTTCCCACCATCTGCGGCGCA
TGGTGTGCGTATTCCTACATGTAACATATGTGCCGCGCAAGAAAAGAACTTCACAACAGCTCCAGCGATCTGCCATGAT
GGAAAAGCTCATTTCCCGAGAGAGGGAGTCTTTGTCTCTAAGGAACTCATTGGTCGTCACCGAGAAACTTCTACG
AGCCGCAGATCATCACCACCGACAACACACATCGTCGTCCGGGAATCGTCATCGGAATCGTAAACAATACCG
TCTACGATCCGTTGCAGCCGGAACTGGAACTCCTTCAAAGAAGAGTTGACAAGAGTTGGACAAGTACTTCAAGAACCACACCTCCGG
ATGTGGACTTGGGAGATATCTCTGGAATCAACGGGTCCGTCAACATCCAGAAGAAATCGATAGATTGAACGAGG
TCGCGAA
```

MAR-Ct

```
GAACTTGAACGAGTCCCTAATCGACCTACAAGAGCTAGGAAAATACGAGCAGTACATCAAGTGGCCG[TGGTGGACATC]
[TGACTGGGGAGTCCTAACGAACCTAGGAATCCTACTACTATTGTCGATCGCCTAATCGGCGTCATCCTGTATCTGT]
```
MAR-Tm

```
MAR-Ct                          C-Tag              P11 vaccinia promoter.          Kozak/ Start E
AGAATCTTCACCAAGTACATCGGA[gagcccggaagct]TAATAAtttttatc[TTTCATTTTGTTTTTCTATGCTATAA]gccaccATGTAC
TCCTTCCGTGTCCGAAGAAACCGGAAACCTTGATCGTCAACTCCGTCCTACTATTCCTAGCGTTCGGTTCGGTTCCTACTAGT
AACCCTAGCTATCCTAACCGCGCTAAGACTATGTGCCTAAGACATCGTCAACATCGTCCGTCAACGTGTCCCTAGTGAAGCCGTCC
TTCTACGTCTACTCCAGAGTCAA
```

FIG. 9M

End E    C-Tag                                                    C-Tag    End of M

GAACCTAAACTCCTCTAGAGTCCCGGACCTACTAGTTgagccagaggctTAATAAataaaaaTTATTAagcctctggctcCTGGAC
TAGTAGAGCGATATTATCGGAAGACTGGAGGAGTGGTCGGTGTTAGCTTGTTAGTTCCCGATTCTGTATCTAGAATACGCC
GCAAATCCAGAATCTCCCGCGACTCTTTGAGAGGCTCCCAACTTATAGTACGATAGGGTTCTAGAGGTCGCTACGGTGA
TCTCCTTCGGTAGGTCCTTGATGTCACATCTTCCTAGGTGGTGGTCCCGCAATTCTTAGATGTCCTCTTAGGATGACCGCT
CCGATAACCAATTCGGATTCCAATAGCGGTCTGGTTAGGATGGTTCCATGTAGCGGTACGTTCAATAGGATGTTCGTCT
CCGGGTTGAACGACCACACATAGATCTGGTTCTCGCGAATAGTCTGAAGGAGGCGATGAAGTAGGATAGCCACATTAGTC
CTACTAGAGACAAGCCATAGGCGATCCATAGGCCAATTCCACCTGATCCAGTTGATCTGATGTCGTAGACCGCAGCTAGAACGAAGCAGG
CCAAGGTGACCGGCCATAGTAGCCATAGGAAGATTAGCTTGATGATGTACAAGAATCTGTTCCTGTTCCGTACGCGAA
CTGTAGTAGGCAGATCCAGGTTAGGAATAGGAATCCGATGACTAGGTTCC

Start of M   Kozak

ACTGCTCTAGTAGCTTCTTCAACTCTCTTCGACGGGTGATGGTTCCGTTAGAATCCGCCATggtggcTTATGATTATTTCTCGCT mH5 vaccinia promoter

TTCAATTTAACACAACCCTCAAGAACCTTTGTATTTATTTTTCAATTTT

FIG. 9N

GPS-truncated S-GPTM (SEQ ID NO: 123)

Vaccinia mH5 promoter                                                                Kozak AAAAATTGAAAATAAATACAAAGGTTCTTGAGGGTTGTGTTAAATTGAAAGGCGAGAAATAATCATAA|gccacc MAR signal                              Truncated S ATGTGGACGACCTGCTTCTTCATCTCCTAATCTCCTAGTCCTACTACC
GCTAGTCTCTTCTCAGTGTGTAAACCTAACAACGAGAACAACTACCACGGCGTACCAATTCTTCACAAGAGGA
GTATATTACCCGGACAAGGTGTTCAGATCCTCCGTACTACATTCTACACAGGACCTATTCCTACCGTTCTTCTTAACGT
AACATGGTTCCACGCGATCCATGTCTGGAACAAAACGGAAGAGAGATTCGATAACCCGGTCTTGCCGTTCAACGAT
GGTGTATACTTGCGTCCGTCCACCGGAAGTCCAACATCATCAGAGGATGGATCTTCGGAACCACCTTGGATTCTAAGACCC
AGTCCTTGCTAATCGTCAACAACGGACCAACGTCGTCATCAAAGTCTGCGAAGTCCAGTTCTGTAACGACCCGTTCTT
GGGAGTCTACTACCACACAAGAACAACAAGTCCTGGAATGCAAGTCCGAGTTCAGAGTCAGGGGAAACAACTGCAC
CTTCGAATATGTATCTCAGCCGTTCCTAATGGACCTAGAGGGAAAGCCAGGGAAACTTCAAGAACCTAAGAGAGTTCGT
ATTCAAGAACATGACGGATACTTCAAGATCTACTCCAAGCACACTCCGATCAACACTCAGTTAGAGATCTACCGCAAGG
ATTCTCGCGCTAGAACCGTTAGTAGTTGCCGATCGGAATCAACACCACCAGATTCCAGACACTACTAGCGCTACAC
AGATCTTACCTAACGCCGGGAGATTCTTCTTCTGGATGGACTGCTGCGCCGTTATTATGTAGGATACCTACAGC
CGAGAACCTTCCTATTGAAGTACAACGAAAACGGAACCATCACCAGGAACATCTAGATTGTGTCTCTAGATCCGATCCGA
AACGAAGTGCACCTAAAGTCTTCACCGTCGAGAAGAAGGGAATCTCCAACTTTAGAGTACACAGCCGACCGA
ATCCATCGGTCAGATTTCCGAACATCACGAACCTATGTCCGTTCGGAGAAGTGTTCAACGGGACAAGATTTGCGTCTGTC
TATGCGGTGGAACAGAAAAAGAATCAGTAACTGCGGCTACTCCGTTCCTATACAACTCTGCCTCTTCTTCTCCACGT
TCAAATGCTACGGGTGTATCTCCGACAAAGCTAAACGATCTATGCTTCACCAGTCTTACGCGGACTCCTTCGTAATCAG
AGGAGATGAAGTTAGACAGATTGGCGCCGGGACAAACTGGAAAGATCGGCGGATTATAACTACAAGTCTACGGACGACTT
CACCGGATGTGTAATTGCGGTGAATTCGAACCTAGACTCGAGAGACACATCTCCAAAGTCGGAGGAAAATCATCAGGCTGGATCTACACCGTGTAAT
ATTCAGAGAAAGTCCAACTAAAGCCGTTCGAGAGAGACCGTTCGAGATTCAACCGACAAACGGTGTAGGATATCAGCCGT
GGTGTCGAAGGATTCAACTGCTACTTCCCGCTACTACTACAGTCTTACGGATTTCAACGACAAACGGTGTAGGATATCAGCCGT
ACAGAGTCGTCGTACTATCCTTCGAACTACTACACGTGCTCCGGCGACAGTATGTGGACCGAGAAAAGTCTACCAACCTAGT
CAAGAACAAATGGGTCAACTTTAACTTCAACGGGACTAACCGGAACCGGGTGTCCTAACGGAATCTAACAAGAAGTTTCT
ACCGTTCCAGCAGTTCGGAAGAGATATCGCGGTCTCTGTAATTACTCGGGGAACACCTCAAGTAGCGGTGTACTCCACCG
TATCACACCGTGTTCTTTCGGTGTCTCCGGTAGCTATTCACGCGGATCTATTCAACGGGTCTATTCCAAGCTTGGAGATCCTATACC
AGGACGTGAACTGTACAGAAGTACCGGTACGAAGCGGGATGCTATTCACGCGGATCTATTCACGAGAGTGTACTCCACCG
GATCTAACGTATTCCAAACCAGAGAGCGGGATGTCTAATCGGAGCGACACGTAACAACTCCTACGAATGTGATATCC

FIG. 10B

CGATTGGAGCGGGGAATCTGTGCGTCTTACCAAACACAAACAAACTCTCCGAGAGAGAGGCGAGATCTGTGAGCCTCTCAAT
CTATTATCGGCCTACACCATGTCCTTGGGAGCCGGAAAATTCTGTGCGTACTCCAACAATTCTATCGGCGATCCCGACAAA
CTTCACCATCTCTGTAAACAACGAGATCCTACCGGTGTCTATGACCAAGACATCTGTCGATTGCACCATGTACATCTGC
GGAGATTCCACCGAGTGCTCCACCTACTACTACAGTACGGATCTTTCTGTACCCAGCTAAACAGAGCGTTGACTGGAA
TCGCTGTAGAGCAGGATAAGAACACTCAAGAGGTATTCGCGCAACACTCAAGTCAAGCAGATCTATAAGACTCCGCCGATCAAGG
ACTTCGGAGGTTCAACTTCTCTCAGATCTTGCCGGATCCGTCCAAACCGTCTAAGAGATCTTCATCGAGGACCTACTA
TTCAACAAGTCACCCTAGCTGACGCGGGATTCATCAAACAATACGCCGCCTCAACAGTACAGTGATTGCTTGGGAGACATTGCGCGCGAGAGAT
CTAATTTGGCGCAGAAGTTAACGGATTGACAGTACAAGTGGACATTGGAGCCGGTGCCCGCTACAAATTCCGTTTGCTATGCA
CTGCTCTATTGGCGGGGAACAATTACAAGTGGACAATTCAACGAACTCCAGAACGTCTTGTACGAACCAGAAGCTAATCGCGAACCAGTT
AATGGCGTACAGATTCAACGGAAAGATCCAGGACAGTCTATCTTCTACTGCTTCGGCGTTGGGAAAGCTACAGGATGTAGTAAAT
CAATTCCCGGATCGGGAAAGATCCAGGACGCGCTAACACCTGGTCAACAACTATCCTCTAACTTCGGAGCGATCTCGTCCGTCCGTCCTAAACGACA
CAAAACGGGCCAGGCGCTAACACCTGGTCAACAACTATCCTCTAACTTCGGAGCGATCTCGTCCGTCCGTCCTAAACGACA
TCTTATCCAGACTAGATAAGGTCGAAGCGGAGTCCAGATCGGAATCGATCATCACTGAGACTAATCACTGCAGTCCTACAGA
CCTACGTAACACAGCAACTAATTAGAGCGGGCGAGATTAGAGCCTCGTGCTAATCTAGCTGCGACCAAGATGTCCGAAT
GTGTCTTGGGACAATCCAAGAGAGGTGGACTTCTGCGGAAAGGGATCCCACCTATGTCTTTCCCACAATCTCGCGCCGCA
TGGTGTCGTATTCCTACACATGTAACATATGTGCCGGCGCAAGAAAAAGAACTTCACAACAGCTCAGCTGATCTGCCATGAT
GGAAAAGCTCATTTCCCGAGAGAGGGAGTCTTTGTCTCTAACGGAACTCATTGGTTCGTCACCCAGAGAAACTTCTACG
AGCCGCAGATCATCACCGACAACACATTCGTCGTCTCGCGGAAACTGCGACGTGTCATCGGAATCGTAAACAATACCG
TCTACGATCCGTTGCAGCCGGAACTAGACTTCTGGACTTCAAAGAAGAGTTGGACAAGTACTTCAAGAACCACACCTCTCCGG
ATGTGGACTTGGGAGATATCTCTGGAATCAACGCGTCCGTCAACATCCAGAAAGAAATCGATAGATTGAACGAGG
TCGGCGAAACTTGAACGAGTCCCTAATCGACCTACACAAGAGCTAGGAAAATACGAGCAGTACATCAAGTGGCCG

MAR-Tm
TGGTGGACATCTGACTGGGGAGTCCTAACGAACCTAGGAATCCTACTACTATTGTCGATCGCGGGTCCTAATCGCGCTAT

MAR-Ct
CCTGTATCTGT AGAATCTTCACCCAAGTACATCGGA

C-Tag
gagccggaagct TAATAAttttat

FIG. 10C

GPS-truncated S-GPTM (SEQ ID NO: 124)

| Vaccinia mH5 promoter | SmaI | Kozak |
|---|---|---|
| AAAAATTGAAATAAAATACAAAGGTTCTTGAGGGTTGTGTTAAATTGAAAGGCGAGAAATAATCATAA | CCCGGG | gccacc |

MAR signal / Truncated S

```
ATGTGGACGACCTGCTTCTTCATCTCCTAATCCTAATCCTCCTACTACC TTCGTGTTCCTAGTCCTACTACC
GCTAGTCTTCTTCAGTGTGTAAACCTAACAACGAGAACCAACACCACCGGCGTACCACCGGTACCAATTCTTCACAAGAGGA
GTATATTACCCGGACAAGGTGTTCAGATCCTCCGTACTACAGGACCTATTCCTACCGGTTCTTCTAACGT
AACATGGTTCCACGGCGATCCATGTCTCTGGAACAAACGGAAGAGATTCGATAACCGGTCTCTTGCCGGTCTTGCCGGTCAACGAT
GGTGTATACTTTGCGGTCCACCGAGAAGTCCAACATCATCAGAGGATGGATCTTCGGAACCTTGGAATTCTTGGATTCTAAGACCC
AGTCCTTGCTAATCGTCAACAACGGACCAACGTCGTCATCAAAGTCTGCAAGTCCGAGTTCAGAGTTCAGAACGACCCGTTCTT
GGGAGTCTACTACCACAAGAACAACAACAAGTCCTGGAATGGAATCCGAGTTCAGAGTTCAGAGGAAACCTAAGAACAACTGCAC
CTTCGAATATGTATCTCAGCCGTTCCTAATGGACCTAGAGGGAAAGCAGGGAAAGCCTAAGAACCTAAGAGAGTTCGT
ATTCAAGAACATGACGGATACTTCAAGATCTCACTCCAAGCACACTCCGATCAACCTAGTTAGAGATCTACCGCAAGG
ATTCTCGCGCTAGAACCGTTAGTAGATTGCCGATCGGAATCAACATCACCACCGGAATCCAGATTCCAGACTAGCGCTACAC
AGATCTTACCTAACGCGCGGGAGATTCTTCTTCTGGATGGACTGCGGCTGTGGCTTATTATGTAGGATACCTACAGC
CGAGAACCTTCCTATTGAAGTACAACGAAAACGGAACCATCACCACCGGCCGTAGATTGTGCTCTAGATCCGCTATCCGA
AACGAAGTGCACCCTAAAGTCTTTCACCGTCGAGAAGAGGAATCTCCAACTTAGAGTACAGCCGACCGA
ATCCATCGTCAGATTTCCGAACATCACGAACCTATGTCCGTTCGGGAGAAGTGTTCAACGGCACAAGATTGGCGTCTGTC
TATGCGGTGGAACAGAAAAAGAATCAGTAACTCAGCGGGACTACTCCGTCCTATACTAACCGCTGGATCTACACCGTGTAAT
TCAAATGCTACGGGTGTATCTCCGACAAAGCTAAACGATCTATGTGCTCACCAGTCTACGCGCGACTCCTTCGTAATCAG
AGGAGATGAAGTTAGACAGATTGGCGCGGGAATTCGAACAAAACTGGAAAGATCGGCGGATTATAACTACAAGCTACGGACGACTT
CACCGGATGTGTAATTGCCGTGAATTCGGAATTCGAACCTAAAGCCGTTCAAGTCGGAGAAATCTATCGGCTGGATCTACACCGTGTAAT
ATTCAGAAAGTCCAACCTAAAGCCGTACTACGTCTACCCGCTACTACTAGGCGGATCTACACCGACGGATATCAGCCGT
GGTGTCGAAGGATTCAACTGCTACTATCCTCCGCGTACTACTCCGACGGATATGGGACCGAAAAAGTCTACCAACCTAGT
ACAGAGTCGTGAACTGTACAGAAGTACCGGTATGTGGACCAGTATGTGGACGCCGAAATCTAACGAATCTAACAAGAAGTTTCT
CAAGAACAAATGGCGTCAACTTTAACTTCAACGGACTAACCGGGTGTCCTAACGAATCCAACCTTGGAGATCCTAGA
ACCGTTCCAGCAGTTCGGAAGAGTATATGCGGGAGATATCGGCGGATATCGGCGGTGTCAGAGATCCGGAGATCCTATACC
TATCACACCGTGTTCGGTGGTCTTCGGTCTCGTAATTACTCCGGGAACGAACACCTCCAATCAACCAACTTGGAGAGTGTACTCCACCG
AGGACGGTGAACTGTACAGAAGTACCGGTATGTGGACGCCGAAATCTAACGAATCTAACAAGAAGTTTCT
GATCTAACGTATTCCAAACAAGAGAGCGGGATGTCTAATGGAGCGGGAACCAACAACTCCTACGAATGTGATATCC
```

FIG. 10D

CGATTGGAGCGGGGAATCTGTGCGTCTTACCAAACACAAACAAACTCTCCGAGAGAGAGCGAGATCTGTAGCCTCTCAAT
CTATTATCGGCCTACACCATGTCCTTGGGAGCCGAAAATTCTGTGCGTACTCCAACAATTCTATCGGCGATCCCGACAAA
CTTCACCATCTCTGTAAACAACGAGATCCTACCGGTGTCTATGACCAAGACATCTGTCGATTGCACCATGTACATCTGC
GGAGATTCCACCGAGTGCTCCACCTACTACACGATCTTTCGTACCCAGCTAAACAGAGCGTTGACTGGAA
TCGCTGTAGAGCAGGATAAGAACACTCAAGAGGTATTCGCGCAAGTCAAGCAGATCTATAAGACTCCGCCGATCAAGG
ACTTCGGAGGTTTCAACTTCTCTCAGATCTTGCCGGATCCGTCCAAACCGTCTAAGAGATCTTCATCGAGGACCTACTA
TTCAACAAAGTCACCCTAGCTGACGCGGGATTCATCAAACAATACGGAGATTGCTTGGGAGACATTGCGGCGAGAGAT
CTAATTGGCGCGCAGAAGTTAACGGATTGACAGTACTACCGCCGCTACTAACCGATGAGATGATTGGCGCAGTACACGT
CTGCTCTATTGGCGGGGAACAATTACAAGTGGACATTTGGAGCCGGTGCCGCTACAAATTCCGTTTGCTATGCA
AATGGCGTACAGATTCAACGGAATCGGAGTAACCCAGAACGTCTTGTACGAACCAGAAGCTAATCGCGAACCAGTT
CAATTCCCGGATCGGGAAAGATCCAGGACAGTCTATCTTCACTGCTTCGGCGTTGGGAAAGCTACAGGATGTGAGTAAAT
CAAAACGGCGCAGGCGCTAACACCTTGGTCAACGCTAATCCTCTAACTTCGAGCGATCTCGTCCGTCCTAAACGACA
TCTTATCCAGACTAGATAAGGTCGAAGCGGAGGTCCAGATCGATCGAGACTAATCACTGAAGATTGCAGTCCCTACAGA
CCTACGTAACACAGCAACTAATTAGAGCGGGGAGATTAGAGCCTCTGCTAATCTAGCTGGGACCAAGATGTCCGAAT
GTGTCTTGGGACAATCCAAGAGAGTGGACTTCTGCGGAAAGGGATACCACCTATGTCTTTCCCACAATCTGCGCCGCA
TGGTGTCGTATTCCTACACATGTAACATATGTGCCGGCGCAAGAAAAGAACTTCACAACAGCTCCAGGATCTGCCATGAT
GGAAAAGCTCATTTCCCGAGAGAGGGAGTCTTTGTCTCTAACGGAACTCATTGGTTCGTCACCCAGAGAAACTTCTACG
AGCCCGAGATCATCACCGACAACACACATTCGTCGTCCTTCGCGGAAACTGCGACGTGCCGACGTGAATCGTAAACAATACCG
TCTACGATCCGTTGCGCGGAACTAGACTTCTCGGAGATATCTCTGGAATCAACGCGTCCGTCAACATCCAGAAGAGTTGGACAAGTACTTCAAGAACCACCTCCGG
ATGTGGACTTGGGAGATATCTCTGGAATCAACGCGTCCGTCAACATCCAGAAAGAATCGATAGATTGAACGAGG
TCGCGAAGAACTTGAACGAGTCCCTAATCGACCTACAAGAGCTAGGAAATACGAGCAGTACATCAAGTGGCCG

MAR-Tm

TGGTGGACATCTGACTGGGGAGTCCTAACGAACCTAGGAATCCTACTACTATTGTCGATCGCGGTCCTAATCGCGCTAT

MAR-Ct                               C-Tag

CCTGTATCTGT AGAATCTTCACCCAAGTACACATCGGA gagccggaagct TAATAAttttat

FIG. 10E

GPS-truncated S + K986P and V987P-GPTM (SEQ ID NO: 125)

Vaccinia mH5 promoter

Kozak

AAAAATTGAAAATAAATACAAAGGTTCTTGAGGGTTGTGTTAAATTGAAAGCGAGAAATAATCATAA | gccacc

MAR signal

Truncated S

ATGTGGACGACCTGCTTCTTCATCTCC | TTCGTGTTCCTAGTCCTACTACC
GCTAGTCCTCTTCTCAGTGTGTAAACCTAACAACGAGAACAACTACCACCGGCGTACACCAATTCTTTCACAAGAGGA
GTATATTACCCGGACAAGGTGTTCAGATCCTCCGTACTACTACACACGGACCTATTCCTACCGGTTCTCTTCTTAACGT
AACATGGTTCCACGCGGATCCATGTCTGGAACAAACGAAGGAAGAGATTCGATAACCCGGTCTTGCCGTTCAACGAT
GGTGTATACTTTGCGTCCGGTCCACCGAGAAGTCCAACATCATCAGAGGATGGATCTTCGGAACCACCTGGATTCTAAGACCC
AGTCCTTGCTAATCGTCAACAAGAACAACAACAAGTCCTGGATGGAATCGTCATCAAAGTCTGCGAATTCCAGTTCGTGTAACGACCCGTTCTT
GGGAGTCGTACTACCACAACAGAACAACAAGTCCTGGAATCGTCAGAGTCCAGAGTTCAGAAGCTACCTCCGGGAACAACTGCAC
CTTCGAATATGTATCTCAGCCGGATACTTCAGATCTCAAGTGACCTAGAGGGAAAGCCAGGGAAACTTCAAGAACCTAAGAGAGTTCGT
ATTCAAGAACATCGACGGGATACTTCAGATCTCAAGTGACCTAGAGGGCACACTCCGATCAACACCACCAGATTCCAGACACTAGCGGCTACAC
ATTCTCTGCGCTAACGCGCGGAGATTTGCCGAATCGGAACCAACCGGTGGTGCGCGCTTATTAGTGTTGTGCTCTAGATCCGGCTATCCGA
AGATCTTACCTAACGCGCGGAGATTTGCCGAATCGGAACCAACCGGTGGTGCGCGCTTATTAGTGTTGTGCTCTAGATCCGGCTATCCGA
CGAGAACCTTCCTATTGAAGTACAACGAAAACGGAACCATCACCGGAGAAGGGAATCTCCAGACCTCCAACTTAGAGTACAGCGGACCGA
AACGAAGTGCACCCTAAAGTCTTTCACGGTCGAGAAGTCCGGTCGGAGAAGTGTTCAAGCGGACAAGATTTGGGTCTGTC
ATCCATCGTCAGATTTCCGAACATCACGAACCTATGTCGGCGGAGAAGTTCGGTCCGTCCTATACACCTCTGCCCTCTTTCTCCACGT
TATGCGGTGGAACAGAAAAAGAAATCAGTAACTGCGGTAAACGATCTATGCTTCACCAACGTCTACGCGACTCCTTCGTAATCAG
TCAAATGCTACGGTGTGTCTCCGACAAGTCAAAGTCGAAAGTCGGAAGATCGCGGGACAAACTGGAAAGATCGCGGATTATAACTACAAGTACACGGACGACTT
AGGAGATGAAGTTAGACAGATTGCGCGGGGACAAACTGGAAAGATCGCGGATTATAACTACAAGTACACGGACGACTT
CACCGGATGTGTAATTGCGTGGAATTCGAACAACCTAGACTCGGAGGAAACTACAACTACTTGTACAGACT
ATTCAGAAAGTCCAACCTAAAGCCGTTCGAGAGGACAACATCTCCACCGAAATCATCAGCGCTGGATCTCACCGTGTAAT
GGTGTGCGAAGGATTCAACTGCTACTTCCCGCTACGGCTTCACGAGTCTTCAACCGACAAACGGGTAGGGATATCAGCCGT
ACAGAGTCGTCGTACTACTTCCTTCGAACTACTACTGCTCCGGCGACAGTATGTGGACCGAAAAAGTCTACCAACCTAGT
CAAGAACAAATGCGTCAACTTAACTTCAACGGACTAACTTCAACGGACTAACGCTCCTAACCGAACGTCCTAACCGAATCTAACAAGAAGTTTCT
ACCGGTTCCAGCAGTTCGGAAGAGAGATATCGGGGATATCCGGGGAAGTCGCAAACCTTGGAGATCCTAGA
TATCACACCGTGTTCTTTCGGTGGTGTCTCTGTAATTACTCCGGAACGCTATTCAAGCTAGCTCAAGTAGCGGTGTACTCCACCG
AGGACGTGAACTGTACAGAAGTACCGGTAACTTCAACGGACTAACAACACCAACCTGGAGTAGTGTACTCCACCG
GATCTAACGTATTCCAAACAGAGGCGGGGATGTCTAATCGGACGGAACACGTAAACAACTCCTACGAATGTGTATCC

FIG. 10G

```
CGATTGGAGCGGGGAATCTGTGCGTCTTACCAAACACAAACAAACTCTCCGAGAGAGAGCGAGATCTGTAGCCTCTCAAT
CTATTATCGGCCTACACCACCATGTCCTTGGGAGCCGGAAAATTCTGTCGCGTACTCCAACAATTCTATCGGCGATCCCGACAAA
CTTCACCATCTCTGTAAACAACGAGATCCTACCGGTGTCTATGACCAAGACATCTGTCGATTGCACCATGTACATCTGC
GGAGATTCCACCGAGTGCTCCAACCTACTACTACAGTACGGATCTTTCGTACCCAGCTAAACAGAGCGTTGACTGGAA
TCGCTGTGTAGAGCAGGATAAGAACACTCAAGAGGTATTCGCGCAAGTCAAGCAGATCTATAAGACTCCGCCGATCAAGG
ACTTCGGAGGTTTCAACTTCTCTCAGATCTTGCCGGATCCGTCCAAACCGTCTAAGAGATCTTCATCGAGGACCTACTA
TTCAACAAGTCACCCTAGCTGACGCGGGATTCATCAAACAATACGGAGATTGCTTGGGAGACATTGCGGCGAGAGAT
CTAATTTGGCGGCAGAAGTTAACGGATTGACAGTACTACCGCCGCTACTAACCGATGAGATGATTGGCAGTACACGT
CTGCTCTATTGGCGGGGAACAATTACAAGTGGATGGACATTTGGAGCCGGGTGCCGCTTACAAATTTCCGTTTGCTATGCA
AATGGCGTACAGATTCAACGGAATCGGAGTAACCCAGAACGTCTTGTACGGAACCAGAAGCTAATCGCGAACCAGTT
CAATTCCCGGATCGGGAAAGATCCAGGACAGTCTATCTTCTACTGCTTCGGCGTTGGGAAAGCTACAGGATGTAGTAAAT
CAAAACGGCGCAGGCGCTAACACCTTGGTCAAGCAACTATCCTCCTAACTTCGGAGCGATCTCGTCCGTCCTAAACGACA
TCTTTATCCAGACCACCGGAAGGTCGAAGCGGAGGTCGAGATTAGAGCGGGCGGAGATTAGAGCCCTGCTAATCTAGCTGGACCAAGATGTCCGAAT
CCTACGTAACACAGCAACTAATTAGAGCGGGCGGAGATTAGAGCCCTGCTAATCTAGCTGGACCAAGATGTCCGAAT
GTGTCTTGGGACAATCCAAGAGAGTGGACTTCTGCGGAAAGGGATCCACCTATGTCTTTCCCACAATCTCGCCGCGCA
TGGTGTCGTATTCCTACATGTAACATATGTGCCGGCGCAAGAAAAGAACTTCACAACAGCTCACCAGCTCTGCCATGAT
GGAAAAGCTCATTTCCCGAGAGAGGGAGTCTTTGTCTCTAAACGGAACTCATTGGTTCGTCACCCAGAGAAACTTCTACG
AGCCGCAGATCATCACCGACAACACATTCGTCGTCCGGGAAACTGCGACGTGGTCATCGGGAAATCGTAAACAATACCG
TCTACGATCCGGTTGCAGCCGGAACTGAGACTTCCTTCAAAGAAGAGAGTTGGACAAGTACTTCAAGAACCACCTCTCCGG
ATGTGGACTTGGGAGATATCTGTGAATCAACGCGTCCGTCAACATCCAGAAAGAAATCGATAGATTGAACGAGG
TCGCGAAGAACTTGAACGAGAGTCCCTAATCGACCTACAGAGCTAGGAAAATACGAGCAGTACATCAAGTGGCCG
```

MAR-Tm

```
TGGTTGGACATCTGACTGGGGAGTCCTAACGAACCTAGGAATCCTACTACTATTGTCGATCGCGGTCCTAATCGCGCTAT
```

MAR-Ct

```
CCTGTATCTGTAGAATCTTCACCCAAGTACATCGGA gagccggaagct TAATAA tttttat
```

C-Tag

FIG. 10H

GPS-truncated S + K986P and V987P-GPTM (SEQ ID NO: 126)

Vaccinia mH5 promoter                                                    SmaI      Kozak AAAAATTGAAAATAAATACAAAGGTTCTTGAGGGTTGTGTTAAATTGAAAGCGAGAAATAATCATAA|CCCGGG|gccacc MAR signal                          Truncated S ATGTGGACGACCTGCTGCTTCTTCATCTCCTAATCCTAACGA|TTCGTGTTCCTAGTCCTACTACC
GCTAGTCTCTTCTCAGTGTGTAAACCTAACAACGAGAACAACTACCACCGGCGTACACCAATTCTTTCACAGAGGA
GTATATTACCCGGACAAGGTGTTCAGATCCTCCGTACTACACCAGGACCTATTCCTACCGGTCTTCTTCTTAACGT
AACATGGTTCCACGCGATCCATGTCTCTGGAACAAACGGAACGAAGAGATTCGATAACCCGGTCTTGCCGTTCAACGAT
GGTGTATACTTTGCGTCCACCGGTCCACCGAGAAGTCCAACATCATCAGAGGATGGATCTTCCGGAACCACCTGGATTCTAAGACCC
AGTCCTTGCTAATCGTCAACAAGAACAACAACAAGTCCTGGAATTCCAGTTCGTGTAAGCCCGTTCTT
GGGAGTCTACTACCACCAACAGAACAACAAGTCCTGGATGGAATCGCTGGAAGTCAGATCTCAGTTCCGGAACCAACTGCAC
CTTCGAATATGTATCTCAGCCGGATACTTCAGATCTCAAGGGATATTTGCCGACCGTTAGTAGATTTGCCGAACCAACTAAGAGAGTTCGT
ATTCAAGAACATCGACGGATACTTCAAGATCTCCAAGCACACTCCGATCAACACCAGTTAGTACACTAGCGCTACAC
ATTCTCTGCGCTAACGCCGGGAGATTCTTTCTGGATGGACTGCTGGTGCTGCCGTGAGATTGTGCTCTAGATCCGCTATCCGA
AGATCTTACCTAACGCCGGGAGATTCTTTGAAGTACAACGAAAACGGAACCATCACCGGAATCTACCAGACCTCCAACTTAGAGTACAGCCGACCGA
CGAGAACGAAGTGCACCCTATTGAAGTACAAGTCTTTCACCGGTCGAGAAAGGGAATCTAAACGTCTACGCGACTCCTTCGTAATCAG
AACGAAGTGCACCCTATTGAAGTCTTTCACCGGTCGAGAAAGGGAATCTAAACGTCTACGCGACTCCTTCGTAATCAG
ATCCATCGTCAGATTTCCGAACATCACGAACCTATGTCCGTTCGGGAGAAGTGTTCAAGCGGACAAGTTGGGTCGTGTC
TATGCGGTGGAACAGAAAAAGAATCAGTAACTAGTAACCAGTAAACGATCTATGCTTCACCGGCGACTCCTTCTACAGT
TCAAATGCTACGGGTGTCTACGGGAGATTCCGACAAAGTCAAACGATCTATGCTTCACCGGCGACTCCTTCGTAATCAG
AGGAGATGAAGTTAGACAGATTGCGCCGGGACAAACTGGAAAGATCGGGAATATAACTACAAGCTACCGGACGACTT
CACCGGATGTGTAATTGCGTGGAATTCGAACAACCTAGACTCGGAGGAAACTACAACTACTTGTACAGACT
ATTCAGAAAGTCCAACCTAAAGCCGGTTCGGAGAGAACATCTCCACCGAAATCATCAGCGCTGGATCTCTACACCGTGTAAT
GGTGTGCGAAGGATTCAACTGCTACTTCCCGCTACAGTTCTTACGGGATATTCAACGACAAACGGGTAGGATATCAGCCGT
ACAGAGTCGTGCTACTATCCTTCGAACTACTACATGTCTCCGGCGACAGTATGTGGACCGAAAAAGTCTACCAACCTAGT
CAAGAACAAATGCGTCAACTTAACTTCAACGGACTAACTTAACCGGAATCTAACAAGAAGTTTCT
ACCGGTCCAGCAGTTCGGAAGAGAGATATCGGGAAGATATCGCGGATCAACAAGAACGGCTGTCAGAGTCGCAAACCTTGGAGATCCTAGA
TATCACACCGTGTTCTTTCGGTGGTGTCTGTAATTACTCCGGACAACAACCTCCAATCAAGTAGCGGTGTACTCCACCG
AGGACGCTGAACTGTACAGAAGTACCGGTATTCACGGGATCAACTAACCAACCTGGAGAGTGTACTCCACCG
GATCTAACGTATTCCAAACGAACCAAGAGCGGGGATGTCTAATCGGAGCGGAACACGTAAACAACTCCTACGAATGTGATATCC

FIG. 10I

CGATTGGAGCGGGAATCTGTGCGTCTTACCAAACACAAACAAACTCTCCGAGAGAGGCGAGATCTGTAGCCTCTCAAT
CTATTATCGCCTACACCATGTCCTTGGGAGCCGAAAATTCTGTGCGTACTCCAACAATTCTATCGCGATCCCGACAAA
CTTCACCATCTCTGTAAACAACGAGATCCTACCGGTGTCTATGACAAGACATCTGTCGATTGCACCATGTACATCTGC
GGAGATTCCACCGAGTGCTCCAACCTACTACTACGATCTTTCGTACCCAGCTAAACAGAGCGTTGACTGGAA
TCGCTGTGTAGAGCAGGATAAGAACACTCAAGAGGTATTCGCGCAAGTCAAGCAGATCTATAAGAGACTCCGCCGATCAAGG
ACTTCGGGAGGTTCAACTTCTCTCAGATCTTGCCGGATCCGTCCAAACCGTCTAAGAGATCTTCATCGAGGACCTACTA
TTCAACAAAGTCACCCTAGCTGACGCGGGATTCATCAAACAATACGGAGATTGCTTGGGAGACATTGCGCGCGAGAGAT
CTAATTTGCGCGCAGAAGTTAACGGATTGACAGTACTACCGCCGCTAACCGATGAGATGAGTACGCAGTACACGT
CTGCTCTATTGGCGGGGAACAATTACAAGTGGACATTTGGAGCCGGTGCCGCTCTACAAATTCCGTTGCTATGCA
AATGGCGTACAGATTCAACGGAATCCAGGACAGTCTATCTTCGGGCGTTGGGAAAGCTAATCGCGAACCAGTT
CAATTCCCGGATCGGGAAAGATCCAGGACGTCTAACGACAGTCTATCTCCTCTAACTTCGGACGATCTCGGGTGGGAAAGCTACAGGATGTAGTAAAT
CAAAACGGCGCAGGCGCTAACACCTTGGTCAACAACTATCCTCCTAAGCAACTTCGGACGATCTCGTCCGTCCTAAACGACA
TCTTATCCAGACTAGATCTCCACCGGAAGCGGGAGGTCCAGATCGAAGCGGGAGATTGCAGTCCCTACAGA
CCTACGTAACACAGCAACTAATTAGAGCGGGCGGAGATTAGAGCCCTGCTAATCTAGCTGCGACCAAGATGTCCGAAT
GTGTCTTGGGACAATCCAAGAGAGTGGACTTCTGCGGAAAGGGGATCCACCTATGTCTTTCCCACAATCTGCGCGCGCA
TGGTGTCGTATTCCTACATGTAACATATGTGCCGGCGCAAGAAAAGAACTTCACAACAGCTCCAGGATCTGCCATGAT
GGAAAAGCTCATTTCCCGAGAGAGGGAGTCTTTGTCTCTAAACGGAACTCATTGGTTCGTCACCCAGAGAAACTTCTACG
AGCCGCAGATCATCACCACCGACAACACATTCGTCTGCGGGAAACTGCGACGTCGTCATCGGAATCGTAAACAATACCG
TCTACGATCCGTTGCGACCGGGAACTAGACTTCTTCAAAGAAGGAGTTGGACAAGTACTTCAAGAACCACACCTCTCCGG
ATGTGGACTTGGGAGATATCTCTGGAATCAACGCGTCCGTCAACATCCAGAAAGAAATCGATAGATTGAACGAGGAGG
TCGGCGAAGAACTTGAACGAGTCCCTAATCGACCTACAAGAGCTAGGAAAATACGAGCAGTACATCAAGTGGCCG

MAR-Tm
TGGTGGACATCTGACTGGGGAGTCCTAACGAACCTAGGAATCCTACTACTATTGTCGATCGCGGTCCTAATCGCGCTAT

MAR-Ct
CCTGTATCTGT|AGAATCTTCACCAAGTACACATCGGA

C-Tag
gagccggaagct|TAATAAattttat

FIG. 10J

GPS-truncated S-GPTM-Marv VP40 (SEQ ID NO: 127)

Vaccinia mH5 promoter                                                                 Kozak AAAAATTGAAATAAAATACAAAGGTTCTTGAGGGTTGTGTTAAATTGAAAGGCGAGAAATAATCATAA|gccacc MAR signal                              Truncated S ATGTGGACGACCTGCTTCTTCATCTCCTAATCTCCTAATCCCAGGGAATCAAGAGACCCTA|TTCGTGTTCCTAGTCCTACTACC
GCTAGTCTCTTCTCAGTGTGTAAACCTAACAACGAGAACAACTACCACCGGCGTACACCAATTCTTCACAAGAGGA
GTATATTACCCGGACAAGGTGTTCAGATCCTCCGTACTACATTCTACACAGGACCTATTCCTACCGTTCTCTCTAACGT
AACATGGTTCCACGCGATCCATGTCTCTGGAACAAACGGAAGAGAGATTCGATAACCCGGTCTTGCCGGTTCAACGAT
GGTGTATACTTGCGTCCACCGGAAGTCCAACGACCAACGTGGTCATCCAGTTCTGGAATCTTCGGAATCTTAAGACCC
AGTCCTTGCTAATCGTCAACAACGGACCAACGTGTCATCAAAGTCTGCGAATTCCAGTTCTGTAACGACCCGTTCTT
GGGAGTCTACTACCACAAGAACAACAACAAGTCCTGGAATGGAATCAAGGTCAGAGTTCAGAATCCGAGTCTTCCGCGAACAACTGCAC
CTTCGAATATGTATCTCAGCCGTTCCTAATGGACCTAGAGGGAAAGCAGGGAAACTTCAAGAACCTAAGAGAGTTCGT
ATTCAAGAACACATGACGGGATACTTCAAGAGATCTCAAGATCTACTCCAAGCACACTCCGATCAACCTAGTTAGAGATCTACCGCAAGG
ATTCTCTGCGCTAGAACCGGTTAGTAGATTGCCAGATTGGCCAGATTCCAGATTCCAGAGATTCCACACTACTAGCGCTACAC
AGATCTTACCTAACGGCGCGGGAGATTCTTCTTCTGGATGGACTGGCTGCGAGCCGTTATTATGTAGGATACCTACAGC
CGAGAACCTTCCTATTGAAGTACAACGAAAACGGAACCATCACCGATGCCGTAGATTGTGTGCTCTAGATCCGCTATCCGA
AACGAAGTGCACCCTAAAGTCTTTCACCGTCGAGAAGAGGAATCTCCAACTTTAGAGTACACAGCGCCGACCGA
ATCCATCGTCAGATTTCCGAACATCAGAACGAACCTATGTCCGTTCGGGAGAAGTGTTCAACGGGACAAGAGATTGGCGTCTGTC
TATGCCGTGGAACAGAAAAGAAAGAATCAGTAACTCAGTACTCCGTCCTATACAACTCTGCCTCTTCTTCTCCACGT
TCAAATGCTACGGGTGTATCTCCGACAAAGCTAAACGATCTATGCTTCACCAAGTCTACGCGGACTCCTTCGTAATCAG
AGGAGATGAAGTTAGACAGATTGGCGCGGGACAAACTGGAAAGATCGGCGGATTATAACTACAAGCTACGGGACGACTT
CACCGGATGTGTAATTGCGTGGAATTCGAACAACCTAGACTCGGAGGAAAATCTATCAGGCTGGATCTACACCGTGTAAT
ATTCAGAAAAGTCCAACCTAAAGCCGTTCGGAGAGAGACAGTCTTACGGGATTTCAACCGACAAACGGTTAGGATATCAGCCGT
GGTGTCGAAGGATTCAACTGCTACTTCCGCGTACTACTACATGCTCCGGCGACCAGTAGTGTAGGGATATCAGCCGGT
ACAGAGTCGTCGAACTGTACAGAAGAAGTACCGGTATTCAACGGGAACGCGAAAAGTCTACCAACCTAGT
CAAGAACAAATGCGTCAACTTTAACTTCAAGGGACTAACCGGAACCGGTGTCCTAACGAATCTAACAAGAAGTTCT
ACCGGTTCCAGCAGTTCGGAAGAGATATCGGGAAGATATCCGGATACAACAGACGCTGTCAGAGATCCGAAACCTTGGAGATCCTAGA
TATCACACCGGTGTTCTTTCGGTGGTGTCTCGTAATTACTCCGGGAACGCGAATCCAATCAAGTTGGGCGGTACTATACC
AGGACGTGAACTGTACAGAAGTACCGGTAGCTATTCACGCGGATCAACCTAACCAACTTGGAGAGTGTACTCCACCG
GATCTAACGTATTCCAAACAAGAGCGGGATGTCTAATCGGACGGGATGTCTAATCTCCTACGAATGTGATATCC

FIG. 10L

CGATTGGAGCGGGGAATCTGTGTGCGGTCTTACCAAACACAAACAAACTCTCCGAGAAGAGCGGAGATCTGTAGCCTCTCAAT
CTATTATCGGCCTACCACCATGTCCTTGGGAGCCGGAAAATTCTGTCGCGTACTCCAACAATTCTATCGGCGATCCCGACAAA
CTTCACCATCTCTGTAACAACCGAGATCCTACCGGTGTCTATGACCAAGACATCTGTCGATTGCACCATGTACATCTGC
GGAGATTCCACGAGTGCTCCAACTACTACTACAGTACGGATCTTTCTGTACCCAGCTAAACGAGCGGTTGACTGGAA
TCGCTGTGTAGAGCAGGATAAGAACACTCAAGAGGTATTCGGCGCAAGTCAAGCAGTCTATAAGACTCCGCCGATCAAGG
ACTTCGGAGGTTTCAACTTCTCTCAGATCTTGCCGGATCCGTCCAAACCGTCTAAGAGATCTTTCATCGAGGACCTACTA
TTCAACAAAGTCACCTCCAGCTGACGCGCGGGATTCATCAAACAATACGGAGATTGCTTGGGAGACATTGCGGCGGAGAT
CTAATTTGGCGCGCAGAAGTTAACGGATTGACAGTACTACCGGCGCGCTACTAACCGATGAGATGATTGGCCAGTACACGT
CTGCTCTATTGGCGGGAACAATTACAAGTGGATGGACATTTGGAGCCGGTGCCGCTCTACAAATTCCGTTGCTATGCA
AATGGCGGTACAGATTCAACGGAAGATCCAGGAGTAACCCAGAACGTCTTGTACGAGAAGCTAATCGGGAACCAGTT
CAATTCCCGGATCGGAAAGATCCAGGACAGTCGTATCTTCTACTGCTTCGGGGCCGTTGGGAAAGCTACACAGGATGTAGTAAAT
CAAAACGCGCCAGCGCTAAACACCTTGGTCAAGCAACTATCCTCTAACTTCTCTAACTATCCTCTAACGACA
TCTTATCCAGACTAGATAAGGTCGAAGCGGAGGTCCAGATGACTAATCACTGGAAGATTGCAGTCCCTACAGA
CCTACGTAACACAGCAACTAATTAGAGCGGGCGGGAGATTAGAGCCTGCTAATCTAGCTGCGACCAAGATGTCCGAAT
GTGTCTTGGGACAATCCAAGAGAGTGGACTTCTGCGGAAAGGGATCCTGCGGAAAGGGATCCCCACAATCTGCGCGCA
TGGTGTCGTATTCCTACACATGTAACATATGTCGCGGCGCAAGTCTTTGTCTCTAACATGTCCAGGATCTGCCATGAT
GGAAAAGCTCATTCCCGAGAGAGGGAGTCTTTGTCTCTAACGGAAGAAACTTCACCGAGAAACTTCTACG
AGCCGCAGATCATCACCACCGACAAACACATTCGTCTCGGGAAACTGCGACGTGGTCATCGGAATCGTAAACAATACCG
TCTACGATCCGTTGCAGCCGGAACTAGACTCCTTCAAAGAAGAGTTGGACAAGTACTTCAAGAACCACCCTCTCCGG
ATGTGGACTTGGGAGATATCTGAATCAAGCCGTCCGTCAACATCGAGAAAGAAATCGATAGATTGAACGAGG
TCGCGAAGAACTTGAACGAGTCCCTAATCGACCTACAAGAGCTAGGAAAATACGAGCAGTACATCAAGTGGCCG

MAR-Tm

TGGTGGACATCTGACTGGGAGTCCTAACGAACCTAGGAATCCTACTACTATTGTCGATCGCGGTCCTAATCGCGCTAT

MAR-Ct   C-Tag   MCS   End of VP40

CCTGTATCTGTAGAATCTTCACCAAGTACATCGGAgagcccggaagctTAATAAttttatctgcaggtcgacTTATTA|TAT|CGCAGATAGT
GTTGGATTCGCATACGCTAGTACTACTTGTCTATTATTAAAACCATTCAATGGAAAATTTCTGGCGCTTGAAAAATATAC
TACTGGAGAAGATTCTCTCTCTTTTCTTCATCATTCCTTCTTTACAGAAAACATATCCGCTGGTAGAGAATTCTAAACA
AAGATGTCTTTTCTGGTACCTTTCTACTCTTAGTTGATTGAGAATGTAAGTGGTCCATTATTTGGA
TTCTTATGTGTCTATACGCTTGTTTCTTTACAGTTGGTGGTACTACTTGGTTGTGGTAGTACTATTGGGATGAAATAGAAATCGCTGG

FIG. 10M

ATGCATTGTATTCCAATTAGTTTATCTTTAGATGGTCTCCAAGCATCATCTGGTAGCTTTGTACAGATAGTACTAGAT
TAGTTAGATTATAAGTAAACTGATTGTGAGAGAAATTTCTGGAATAACCATATTTGAATAAAGCTTGATTCCTTCT
CTTAGCATTCTTAGTGGATGGCGCTGGTATTCCAGTTCCTAGTCTATTTACTCTAACAAACTTTGTCCATTATGTGTAAAC
TGTGTAATTGTATAAGATCCTGTCAATAGGCGCCGCTACTGTATGCGCTAGTGGATATTCAAAATTAGACATAATTCCTA
GTGGGTAGCCAAGCTGGTACACCTTTACTGTTCTTTCATTATACGCAGAAATATCAATAATCGCTTCTAGTGTAAACGCA
TGACAAACATTTCCTTTAAACTGATCATCTAGATTCATCTAGATTCATCTAGATTAGATCTCCAACATAATTTGGTGTAATTCCATGTTGATTAGATAG
TTGATCCGCTGGAATTAGTTGATTAGCACCATGATCCGCATATGGTGGTGGATTTA

Start of MAR VP40

GATATTGCATATAAGTATTATAATTAGAACTAGACGC[CAT]cccgggcttatTTATGATTATTTCTCGCTTTCAATTT

Vaccinia virus mH5 promoter

AACACAACCCTCAAGAACCTTTGTATTTATTTTCAATTTTT

FIG. 10N

GPS-truncated S-GPTM-Marv VP40 (SEQ ID NO: 128)

Vaccinia mH5 promoter SmaI Kozak

AAAAATTGAAATAAATACAAAGGTTCTTGAGGGTTGTGTTAAATTGAAAGCGAGAAATAATCATAA|CCCGGG|gccacc

MAR signal Truncated S

ATGTGGACGACCTGCTTCTTCATCTCCCTAATCCTCCTAGTCCTACTACC|TTCGTGTTCCTAGTCCTACTACC

GCTAGTCCTCTTCTCAGTGTGTAAACCTAACAACGAACAACTACCACCGGCGTACACCAATTCTTTCACAAGAGGA

GTATATTACCCGGACAAGGTGTTCAGATCCTCCGTACTACATTCTACACACAGGACCTATTCCTACCGGTCTTCTTCTTAACGT

AACATGGTTCCACGCGATCCATGTCTCTGGAACAAACGAAGAGAGATTCGATAAACCCGGTCTTGCCGTTCAACGAT

GGTGTATACTTTGCGTCCACCGGTTCCACCGGAAGTCCAACATCATCAGAGGATGGATCTTCCGGAACCACCTGGATTCTAAGACCC

AGTCCTTGCTAATCGTCAACAAGAACAACAAGCGACCAACGTCGTCATCAAAGTCTGCGAAATTCCAGTTCGTGTAACGACCCGTTCTT

GGGAGTCGTACTACCACCACAGAGAACAACAAGTCCTGGAATGGAATCGGAAAGCCACTGCAC

CTTCGAATATGTATCTCAGCCGGTTCCTAATGACCTAGAGGGAAATCGGAAAGCACACTCCGATCAACCTAAGGAGTTCGT

ATTCAAGAACATCGACGGATACTTCAAGATCTCAAGATCTAGAGGTTAGAGATCTACCGCAAGG

ATTCTCTGCGCTAACGCCGGGAGATTCTTCTTCTGGATGGACTGCTGGTGCTGCCGTGAGATTGGTGCTCTAGATCCGCTATCCGA

AGATCTTACCTAACGCCGGGAGATTCTTCTTCTGGATGGACTGCTGGTGCTGCCGTGAGATTGGTGCTCTAGATCCGCTATCCGA

AACGAAGTGCACCTTCACCCTAAGTCTTCCGAACATCACGAACCTATGTCGGGGACTAACTCTGCCCTCTTCTCCACGT

ATCCATCGTCAGATTTCCGAACATCACGAACCTATGTCGGCGGGACTAACTCTGCCCTCTTCTCCACGT

TATGCGGTGGAACAGAGAAAAGAATCAGTAACTGCGTAAACGATCTATGCTTCACCAAGTCTACCGCGACTACT

TCAAATGCTACGGGTGTATCTCCGACAAAGTAAACGTCTACGCGACTCCTTCGTAATCAG

AGGAGATGAAGTTAGACAGATTGCGCCGGGACAAACTGGAAAGATCGGCGGATTATAACTACAAGCTACCGGACGACTT

CACCGGATGTGTAATTGCGTGGAATTCGAACAACCTAGACTCCAAAGTCGGAGGAAACTACAACTACTTGTACAGACT

ATTCAGAAAGTCCAACCTAAAGCCGTTCGAGAGAACAATCTATCAGGCTGGATCTACACCGTGTAAT

GGTGTGCGAAGGATTCAACTGCTACTTCCCGCTACGGTTCAACGCTGTAGGATATCAGCCGT

ACAGAGTCGTCGTACTATCCTTCGAACTACTACATGCTCCGGCGACAGTATGTGGACCGAAAAAGTCTACCAACCTAGT

CAAGAACAAATGCGTCAACTTAACTTACTTAACTTCAAGCGGACTAACCGGTGTCCTAACCGAATCTAACAAGAAGTTTCT

ACCGGTTCCAGCAGTTCGGAAGAGAGATATCGGGGGGATACAAACAAGACGGCTGTCAGATCCGCAAACCTTGGAGATCCTAGA

TATCACACCGTGTTCTTTCGGTGGTGTCTCTGTAATTACTCCGGAACGAACACCTCCAATCAACTTAGCGGTACTATACC

AGGACGTGAACTGTACGAAGTACCGGTATTCACGGGCTATTCAGCGGAACACGTAAACAACTCCTACGAATGTGATATCC

GATCTAACGTATTCCAAACAAGAGAGCGGGGATGTCTAATCGGAGGGAACACGTAAACAACTCCTACGAATGTGATATCC

FIG. 10O

CGATTGGAGCGGGGAATCTGTGTGCGGTCTTACCAAACACAAACAAACTCTCCGAGAAGAGCGGAGATCTGTAGCCTCTCAAT
CTATTATCGGCCTACACCATGTCCTTGGGAGCCGGAAAATTCTGTCGCGTACTCCAACAATTCTATCGGCGATCCCGACAAA
CTTCACCATCTCTGTAACAACCGAGATCCTACCGGTGTCTATGACCAAGACATCTGTCGATTGCACCCATGTACATCTGC
GGAGATTCCACCGAGTGCTCCAACTACTACTACAGTACGGATCTTTCTGTACCCAGTCAAACAGAGCGGTTGACTGGAA
TCGCTGTGTAGAGCAGGATAAGAACACTCAAGAGGTATTCGCGCAAGTCAAGCAGTATAAGACTCCGCCGATCAAGG
ACTTCGGAGGTTTCAACTTCTCTCAGATCTTGCCGGATCCGTCCAAACCGTCTTTCATCGAGAGATCTTTCATCGAGAGACCTACTA
TTCAACAAAGTCACCTCCAGCTGACGCGCGGGATTCATCAAACAATACGGAGATTGCTTGGGAGACATTGCGGCGAGAGAT
CTAATTTGGCGCGCAGAAGTTAAACGGATTGACACAGTACTACCGCCGCTACTAACCGATGAGATGGCCAGTACACGT
CTGCTCTATTGGCGGGAACAATTACAAGTGGATGGACATTTGGAGCCGGTGCCGCTCTACAAATTCCGTTGCTATGCA
AATGGCGGTACAGATTCAACGGAAGATTCAAGGAAATCCAGAGCAGTCTTGTACGAGAAGCTAATCGGAACCAGTT
CAATTCCCGCGATCGGAAAGATCCAGGAAAGATCTCATCTTCTACTGCTTCGGCGGTTGGGAAAGCTACAGGATGTAGTAAAT
CAAAACGCGCAGCGCTAAACACCTTGGTCAAGCAACTATCCTCTAACTTCGGAGCGATCTCGTCCGTCCTAAACGACA
TCTTATCCAGACTAGATAAGGTCGAAGCGGAGGTCCAGATGACTAATCACTGGAAGATTGCAGTCCCTACAGA
CCTACGTAACACAGCAACTAATTAGAGCGGGCGGGAGATTAGAGCCTCCTAATCTAGCTGCGACCAAGATGTCCGAAT
GTGTCTTGGGACAATCCAAGAGAGTGGACTTCTGCGGAAAGGGATACCACCTAATGTCTTCCCACAATCTGCGCGCA
TGGTGTCGTATTCCTACACATGTAACATATGTGCGGGCAAGAACTCCAGCGTCGTCCAGAGAAACTTCTACG
GGAAAAGCTCATTCCCGAGAGAGGGAGTCTTTGTCTCTAACGGAACTGCGACGTGGTCATCGGAAATCGTAAACAATACCG
AGCCGCAGATCATCACCACCGACAAACACATTCGTCGTCCGGAAGTCCTTCAAGAAGAGAGTTGGACAAGTACTTCAAGAACCACCTCTCCGG
TCTACGATCCGGTTGCAGCCGGAACTAGACTCCTTCAAAGAAGAGAATCGATAGAAATCGCATTTTGGA
ATGTGGACTTGGGAGATATCTGGAAGCCCTAAATCGACTTACAAGAAATTCAAGAAATCGATAGTTGAACGAGG
TCGCGAAGAACTTGAACGAGTCCCTAATCGACCTACAAGAGCTAGGAAAAATACGAGCAGTACATCAAGTGGCCG

MAR-Tm

MAR-Ct     C-Tag     MCS     End of VP40

TGGTGGACATCTGACTGGGACTGGGAGGAATCCTAACGGAACCTAGGAATCCTACTACTATTGTCGATCGGGTCCTAATCGCGCTAT
CCTGTATCTGT|AGAATCTTCACCAAGTACATCGGA|gagcccggaagct|TAATAAttttttatctgcaggtcgac|TTATTA|TAT|CGCAGATAGT
GTTGGATTCGCATACGCTAGTACTACTGTCTATTATTAAAACCATTCAATGGAAAATTTCTGGCGCTTGAAAATATAC
TACTGGAGAAGATTCTCTCTTTTTCTTCATCATTCCTTCTTTACAGAAAACATATCCGCTGGTAGAGAATTCTAAACA
AAGATGTCTTTTCTGGTACCTTTTCTACTCTTAGTTGATGTTAGAATTCCAGAAATCGGCCAATAGTGGTCCATTTTTGGA
TTCTTATGTGTCTATACGCTTGTTCTTTACAGTGGTAGTACTATTGGTGGTGGTAGATTGGATGAATAGAAATCGCTGG

FIG. 10P

ATGCATTGTATTCCAATTAGTTATCTTTAGATGGTCTCCAAGCATCATCTGGTAGCTTTGTACAGATAGTACTAGAT
TAGTTAGATTATAAGTAAACTGATTGTGAGAGAAATTTCTTGGAATAACCATATTTGAATAAAAGCTTGATTCCTTCT
CTTAGCATTCTTAGTGGATGGCGCTGGTATTCCAGTTCCTAGTCTATTTACTCTAACAAACTTTTGTCCATTATGTGTAAAC
TGTGTAATTGTATAAGATCCTGTCAATAGGCGCCGCTACTGTATGCGCTAGTGCTGATATTCAAAATTAGACATAATTCCTA
GTGGTAGCCAAGCTGGTACACCTTTACTGTTCTTTCATTATACGGCAGAAATATCAATAATCGCTTCTAGTGTAAACGCA
TGACAAACATTTCCTTTAAACTGATCATCTAGATTTAGATCTCCAACATAATTTGGTGTAATTCCATGTTGATTAGAGATAG
TTGATCCGCTGGAATTAGTTGATTAGCACCATGATCCGCCATGATCCGGCATATGGGTGGTGGATTTA

Start of MAR VP40

GATATTGCATATAAGTATTATAATTAGAACTAGACGCGCCATcccgggcttatTTATGATTATTTCTCGCTTTCAATTT

Vaccinia virus mH5 promoter

AACACAACCCTCAAGAACCTTTGTATTTATTTTCAATTTTT

FIG. 10Q

GPS-truncated S + K986P and V987P-GPTM-MARV VP40 (SEQ ID NO: 129)

Vaccinia mH5 promoter       Kozak

MAR signal       Truncated S

```
AAAAATTGAAAATAAATACAAAGGTTCTTGAGGGTTGTGTTAAATTGAAAGCGAGAAATAATCATAA gccacc

ATGTGGACGACCTGCTTCTTCATCTCCCTAATCCTA                       TTCGTGTTCCTAGTCCTACTACC
GCTAGTCCTTCTTCAGTGTGTAAACCTAACAACGAGAACAACTACCACCGGCGTACCAATTCTTTCACAGAGGA
GTATATTACCCGGACCAAGGTGTTCAGTCCTCCGTACTACACAGGACCTATTCCTACCGGTCTCTTCTTCTAACGT
AACATGGTTCCACGCGGATCCATGTCGTCTGGAACAAACGAAGGAGATTCGATAAACCCGGTCTTGCCGTTCAACGAT
GGTGTATACTTTGCGGTCCACCGAGAAGTCCAACATCATCAGAGGATGGATCTTCCGGAACCACCTGGATTCTAAGACCC
AGTCCCTTGCTAATCGTCAACAAGAACAACAAGCGACCAACGTCATCAAAGTCTGCGAATTCCAGTTCTGTAACGACCCGTTCTT
GGGAGTCACTACCACCACAAGAACAACAAGAGTCCTGGATGGAATCTGCGAGTCAGAATCCGAGTTCAGAGGGAAAGCAACAACTGCAC
CTTCGAATATGTATCTCAGCCGGATACTTCCTAATGGACCGTTCCTAGAGACCTAGAGGGAAAGCAGGGAAAGCCAGGTTAGAGAGTTCGT
ATTCAAGAACATCGACGGATACTTCAGATCTTCAGAATCGGAATCAACATCACCAGATTCCAGCACTACTAGCGCTACAC
ATTCTCTGCGCTAACGCCGGGAGAATCTAGTTAGTAGATTTGCCGATGGACTGCTGGTGCGCGTTATTATGTAGGATACCTACAGC
AGATCCTTACCTAACGCCGGGAGATTCTTCTTGGATGGAACCATCACCGATGCCGTAGATTGTGCTCTAGATCCGCTATCCGA
CGAGAACCTTCCTATTGAAGTACAACGAAAACGGAAACTACCAGAGCTCCAACTTAGAGTACAGCCGACCGA
AACGAAGTGCACCCTAAAGTCTTTCCGGTCCGGTCGAGAAGGGAATCAGTCAACGGCGACAAGATTTGCGGTCTGTC
ATCCATCGTCAGATTTCCGAACATCACGAACCTATGTCCGTTCGGGAGAAGTGTTCAAGCGGACAGTATGGCGGATTATCCGA
TATGCGGTGGAACAGAGAAAAAGAATCAGTAACTCAGTAAACGATCTATGCTTCACCAACGTCTACGCGGACTCCTTCGTGTAATCAG
TCAAATGCTACGGGTGTATCTCCGACAAAGTAAACGATCTCCGACGAAAGATCGGAAAGATCGGCGGATTATAACTACAAGCTACCGGACGACTT
AGGAGATGAAGTTAGACAGATTGCGCGGGGGACAAACTGGAAAGATCGGAAAGATCCAAAGTCGGAGGAAACTACAACTACTTGTACAGACT
CACCGGATGTGTAATTGCGTGGAATTCAGAACAACCTAGACTCGAACAAGTCGGAGGAAACTCCAAAGTCTACACCGTGTAAT
ATTCAGAAAGTCCAACCTAAAGCCGTTCGGTGTGCGAAGGATTCAACCGCTGAGAGAGACATCTCCACCGGGATCTACACCGTGTAAT
GGTGTGCGAAGGATTCAACTGCTACTTTCCCGCTACTCCTTCGAACTACTACATGTCTCCGGCGACCAGTATGTGGACCGAAAAAGTCTACCAACCTAGT
ACAGAGTCGTGCTACTATCCTTCGAACTACTACTTCGAACTTCAACGGACTAACCGGAACCGGAACCGAATCTAACAAGAAGTTTCT
CAAGAACAAATGCGTCAACTTTAACTTCAACGGACTAACCGGACTAACAAGAGACAGACCGGTCCTAACGAATCTAACAAGAAGTTTCT
ACCGGTTCCAGCAGTCGGAAGAGAGATATCCGGGAGATATCCGCAAACCTTGGAGATCCTAGA
TATCCACACCGTGTTCTTCGGTGTCTCTGTAATTACTCCGGACGAACACCTCCAATCAAGTAGCGGTACTACTACC
AGGACCGTGAACTGTACAGAAGTACCGGTGAACTGAACTAACAACACCAACGGAGAGCGGAGAGTGTACTCCACCG
GATCTAACGTATTCCAAACAAGAGAGCGGGGGATGTCTAATCGGAGACGGGAACACGTAAACAACTCCTACGAATGTGTATATCC
```

FIG. 10S

MAR-Tm

CGATTGGAGCGGGGAATCTGTGTGCGTCTTACCAAACACAAACAAACTCTCCGAGAAGAGGCGAGATCTGTAGCCTCTCAAT
CTATTATCGGCCTACACCATGTCCTTGGGAGCCGAAAATTCTGTCGCGGTACTCCAACAATTCTATCGGCGATCCCGACAAA
CTTCACCATCTCTGTAACAACCGAGATCCTACCGGTGTCTATGACCAAGACATCTGTCGATTGCACCATGTACATCTGC
GGAGATTCCACGAGTGCTCCAACCTACTACTACAGAGGTACGGATCTTTCTGTACCAGCTAAACAGAGCGGTTGACTGGAA
TCGCTGTAGAGCAGGATAAGAACACTCAAGAGTATTCGCGCAAGTCAAGCAGATCTATAAGAACTCCGCCGATCAAGG
ACTTCGGAGGTTCAACTTCTCTCAGATCTTGCCGGATCTCGAGATCTCAGAGATCTTTCATCGAGGACGACTACTA
TTCAACAAAGTCACCCTAGCTGACGGATTAACGGATTGACAGTACTAACCGCCGCTACTAACCGATGAGATGATTGCGCAGTACACGT
CTAATTTGCGGCGCAGAAGTTAACGGGGAACAATTACAAGTGGATGGACATTGGAGCGCGGTGCCGCTCTACAAATTCCGTTGCTATGCA
CTGCTCTATTGGCGGGAACAATTCAACGAGAATCGGAGTAACCAGAACGTCTTGTACGAGAGAACCAGAAGCTAATCGCGAACCAGTT
AATGGCGTACAGATTCAACGGAATCCGGACACAGTCTATCTTCTACTGCTTCGGCGTTGGGAAAGCTACAGGATGTAGTAAAT
CAATTCCGCGATCGGAAAGATCCAGGACACAGTCTATCTTCTACTGCTTCGGCGTTGGGAAAGCTACAGGATGTAGTAAAT
CAAAACGGCGCAGGCGCTAAACACCTTGGTCAAGCAACTATCCTCTAACTTCGGAGCGATCTCGGTCCTAAACGACA
TCTTATCCAGACTAGATCCACCGGAAGCGGAGGTCCAGATGCAACTAATCACTGGAAGATTGCAGTCCCTACAGA
CCTACGTAACACAGCAACTATTAGAGCGGCGGAGATTAGAGCCTCGTAATCTAGCTGCGACCAAGATGTCCGAAT
GTGTCTTGGGACAATCCAAGAGAGTGGACTTCTGGGGAAAGGGATACCACCTAATGTCTTTCCCACAATCTGGCGCA
TGGTGTCGTATTCCTACACATGTAACATGTGTGCCGGCGCAAGAAAAGAACTTCACAACAGTCCAGCATCTGCCATGAT
GGAAAAGCTCATTTCCCGAGAGAGGGAGTCTTTGTCGTCTAACGGAACTCATTGGTCGTCACCCAGAGAAACTTCTACG
AGCCGCAGATCATCACCACCGACAACACACTAGACTCGTCTCGGGAAACTGGCGACGTGGTCATCGGAATCGTAAACAATACCG
TCTACGATCCGGTTGCGCAGCGGTACTGCTGGGAGATATCTCTGGAATCAAGCGTCGCAACATCCGTCAACGCGTAAGAACTCTCCGG
ATGTGGACTTGGGGAGAGATCTCTGGAGATATCGTCGTCCGTCAACATCCGTCAACGCGTAGATTGAACGAGG
TCGGCGAAGAACTTGAACGAGTCCCTAATCGACCTACAAGAGCTAGGAAAATACGAGCAGTACATCAAGTGGCCG

MAR-Ct

TGGTGGACACATCGACTGGGGAGTCCTAACGAACCTAGGAATCCTACTACTATTGTGCGATCGGCGTCCTAATCGCGCTAT
CCTGTATCTGTAGAATCTTCACCAAGTACACCAAGTACACATCGGA agagccggaagct TAAT AAtttatctgcagggtcgacTTATTATCGCAGATAGT
GTTGGATTCGCATACGCTAGTACTTGTCTATTATTAAAACCATTCAATGGAAATTTCTGGCGCTTGAAAATATAC
TACTGGAGAAGATTCTCTTTTCTTCATCATTCCTTCTTTACAGAAAAACATATCCGCTGGTAGAGAAATTCTAAACA
AAGATGTCTTTTCTGGTACCTTTTCTACTCTTAGTTGATGTAGAATTCCAGAAATCCAGAAATCGCCAATAGTGGTCCATTATTTGGA
TTCTTATGTTGTCTATACGCTTGTTCTTTACAGTTGCTTTTACAGTACTATTGGTGGTAGTACTATTGGTGATACTATTGGTGATAGAAATCGCTGG

C-Tag    MCS    End of VP40

TAT

FIG. 10T

ATGCATTGTATTCCAATTAGTTTATCTTTAGATGGTCTCCAAGCATCATCTGGTAGCTTTTGTACAGATAGTACTAGAT
TAGTTAGATTATAAGTAAACTGATTGTGAGAGAAATTTCTGGAATAACCATATTTGAATAAAAGCTTGATTCCTTCT
CTTAGCATTCTTAGTGGATGGCGCTGGTATTCCAGTTCCTAGTCTATTTACTCTAACAAACTTTTGTCCATTATGTGTAAAC
TGTGTAATTGTATAAGATCCTGTCAATAGCGCCGCTACTGTATGCGCTAGTGGATATTCAAAATTAGACATAATTCCTA
GTGGGTAGCCAAGCTGGTACACCTTTACTGTTCTTTCATTATACGCAGAAATATCAATAATCGCTTCTAGTGTAAACGCA
TGACAAACATTTCCTTTAAACTGATCATCTAGATTTAGATCTCCAACATAATTTGGTGTAATTCCATGTTGATTAGATAG
TTGATCCGCTGGAATTAGTTGATTAGCACCATGATCCGCATATGGTGGTGGATTTA

Start of MAR VP40

GATATTGCATATAAGTATTATAATTAGAACTAGACGC[CAT]cccgggcttatTTATGATTATTTCTCGCTTTCAATTT

Vaccinia virus mH5 promoter

AACACAACCCTCAAGAACCTTTGTATTTATTTTCAATTTTT

FIG. 10U

GPS-truncated S + K986P and V987P-GPTM-MARV VP40 (SEQ ID NO: 130)

Vaccinia mH5 promoter                                                                 SmaI      Kozak AAAAATTGAAAATAAAATACAAAGGTTCTTGAGGGTTGTGTTAAATTGAAAGCGAGAAATAATCATAA|CCCGGG|gccacc MAR signal                                       Truncated S ATGTGGACGACCTGCTTCTTCATCTCCCTAATCCTCCTAATCCTCCTA|TTCGTGTTCCTAGTCCTACTACC
GCTAGTCCTTCTCAGTGTGTAAACCTAACAACGAACAACTACCACCGGCGTACACCAATTCTTTCACAGAGGA
GTATATTACCCGGACAAGGTGTTCAGATCCTCCGTACTACACACAGGACCTATTCCTACCGGTTCTTCTTCTAACGT
AACATGGTTCCACGCGATCCATGTTCTTGGAACAAAACGAAGAGAGATTCGATAAACCCGGTCTTGCCGTTCAACGAT
GGTGTATACTTTGCGGTCCACCGAGAAGTCCAACATCATCAGAGGAAGTGGATGGATCTTCGGAACCACCTGGATTCTAAGACCC
AGTCCTTGCTAATCGTCAACAAGAACAACAAGCGACCAACGTCATCAAAGTCTGCGAATTCCAGTTCTGTAACGACCCGTTCTT
GGGAGTCACTACCACCAGAGAACAACAAGCCTGGAATGGAATCCAGAGGGAAAGCCAGGGAAACTTCAAGAACCTAAGAGAGTTCGT
CTTCGAATATGTATCTCAGCCGTTCCTAATGGACCCGTTCCTAATGGACCGAGAGGGAAAGCAGGGAAACTTCAAGAACCTAAGAGAGTTCGT
ATTCAAGAACATGCAGCGGATACTTCAGAATCTCAAGGACCGGATCTTAGTAGTATTGCCGACTGCTAGTCCAGATTCCAGCACTAGCGGCTACAC
ATTCTCTGCGCTAGAACCGTTAGTAGATTTGCCGAATCAACATCACACCAGATTCCAGCACTACTAGCGGCTACAC
AGATCTTACCTAACGCCGGAGATTCTCTCTGGATGGACTGCTGGTGCGCGTAGATTGGTGCTCTAGATCCGGCTATCCGA
CGAGAACCTTCCTATTGAAGTACAACGAAAAACGGAACCATCACACGGAATCCACCAGAGGAATCCACCTTAGAGTACAGCCGACCGA
AACGAAGTGCACCTAAAGTCTTTCACCGGTCAAGTACAACGAACTATGCCGGGAGTTCCGTTCGGGACAAGATTTGGGTCTGTC
ATCCATCGTCAGATTTCCGAACATCACGAACCTATGTCGGGAGAAGTGTTCAAGGCGACAAGATTTGGGTCTGTC
TATGCGGTGGAACAGAGAAAAAGAATCAGTAACTAGTAACTCAGTAACTCGTATACACCTGCGTATACAACTCGTATACAACTCGCCTCTTTCCACGT
TCAAATGCTACGGGTGTATCTCCGACAAAGTAAACGATCTATGCTTCACCAACGTCTACGCGACTCCTTCGTAATCAG
AGGAGATGAAGTTAGACAGATTGCGCCGGGACAAACTGGAAAGATCGGCGGATTATAACTACAAGCTACCGGACGACTT
CACCGGATGTGTAATTGCGTGGAATTCGAACAACCTAGACTCGGAGGAAACTACAACTACTTGTACAGACT
ATTCAGAAAGTCCAACCTAAAGCCGTTCGAGAGAGAGATTCGAGAGAGAGATCTCCACCGTGATCTATCAGGCTGGATCTCTACACCGTGTAAT
GGTGTGCGAAGGATTCAACTGCTACTTCCCGCTACTTCCCGGCTACTTCCCGGATATTCAACGACAAACGGGTAGGGATATCAGCCGT
ACAGAGTCGTCGTACTACTATCCTTCGAACTACTACATGCTCCGGCGACCAGTATGTGGACCGAAAAGTCTACCAACCTAGT
CAAGAACAAATGCGTCAACTTAACTTAACTTAACTTAACCGGACTAACTTAACAAGAAGTTTCT
ACCGGTTCCAGCAGTCGGAAGAGAGATATCGGGATATCGGGGATATCCGCAAACCTTGGGAGATCCTAGA
TATCACACCGTGTTCTTTCGGTGGTGTCTCGTGTCTCTGTAATTACTCCGGAACGAACAACACCTCCAATCAAGTAGCGGTACTATACC
AGGACGTGAACTGTACAGAAGTACCGGTATTCAACGACTAACCAACTTGGAGGAGTGTACTCCACCG
GATCTAACGTATTCCAAACAGTATCCAAACAGGCGGGATGTCTAATCGGAGGCGGAACAACTCCTACGAATGTGTATCC

FIG. 10V

CGATTGGGAGCGGGGAATCTGTTGTGCGGTCTTACCAAACAACAAACAACAAACTCTCCGAGAAGAGCGGAGATCTGTAGCCTCTCAAT
CTATTATCGGCTACACCATGTCCTTGGGAGCCGGGAAAATTCTGTCGGCGTACTCCAACAATTCTATCGGCGATCCCGACAAA
CTTCACCATCTCTGTAACAACCGAGATCCTACCGGTGTCTATGACCAAGACATCTGTCGATTGCCACCATGTACATCTGC
GGAGATTCCACCGAGTGCTCCAACTACTACTACAGTACGGATCTTTCTGTACCCAGTCAAACAGAGCGGTTGACTGGAA
TCGCTGTGTAGAGCAGGATAAGAACACTCAAGAGGTATTCGGCGCAAGTCAAGCAGTCTATAAGACTCCGCCGATCAAGG
ACTTCGGAGGTTTCAACTTCTCTCAGATCTTGCCGGATCCCGATCCGTCCAAACCGTCTAAGAGATCTTTCATCGAGGACCTACTA
TTCAACAAAGTCACCCTAGCTGACGCGGGATTCATCAAACAATACGGAGATTGCTTGGGAGACATTGCGGCGGAGAT
CTAATTTGGCGCGCAGAAGTTAACGGATTGACACAGTACTACCGGCCGCTACTAACCGGATGAGATGATTGGCGCAGTACACGT
CTGCTCTATTGGCGGGAACAATTACAAGTGGATGGACATTTGGACAAGTCGTCTTGTACGAGAAACGTAATCGGGAACCAGTT
AATGGCGGTACAGATTCAACGGGAGTAAACCAGAACGTCTTGTACGAGAAGCTAATCGGGAACCAGTT
CAATTCCCGGATCGGAAAGATCCAGGACAGTCTATCTTCTACTGTTCCGGCGTTGGGAAAGCTACACAGGATGTAGTAAAT
CAAAACGCGCAGCGCTAAACCTTGGTCAAGCAACTATCCTCTAACTTCGGAGCGATCTCGTCCGTCCTAAACGACA
TCTTATCCAGACTAGATCTCCACCGGAAGCGGGAGGTCCAGATCGATAGACTAATCACTGGAAGATTGCAGTCCCTACAGA
CCTACGTAACACAGCAACTAATTAGAGCGGGCGGGAGATTAGAGCCTGCTAATCTAGCTGCGACCAAGATGTCCGAAT
GTGTCTTGGGACAATCCAAGAGAGGTGGACTTCTGCGGAAAGGGATCCGAAAGGGATACCACCTAATGTCTTCCCACAATCTGCGCGCA
TGGTGTCGTATTCCTACACATGTAACATATGTGCGCGGCAAGTCTTTGTTGTCTCTAACGGAGTCTTGTCACCGGAAACTTCTACG
GGAAAAGCTCATTCCCGAGAGAGGGAGTCTTGTCTCTAACGGAACTCATGGTTCGTCACCGGAATCGTAAACAATACCG
AGCCGCAGATCATCACCACCGACAAACACATTCGTCTCGGAACTGCGACGTGGTCATCGGAATCGTAAACAATACCG
TCTACGATCCGTTGCAGCGGGAACTAGACTCCTTCAAAGAAGAGTTGGACAAGTACTTCAAGAACCACACCTCTCCGG
ATGTGGACTTGGGAGAGTATCTGCAGGAGATATCTTCGAATCAACGCGTCCGTCGTCAACATCCAGAAAGAAATCGATAGTTGAACGAGG
TCGCGAAGAACTTGAACGAGTCCCTAATCGACCTACAAGAGCTAGGAAAATACGAGCAGTACATCAAGTGGCCG

MAR-Tm

MAR-Ct

TGGTGGACATCTGACTGGGACTGGGGAGTCCTAACGGAACCTAGGAATCCTACTACTATTGTCGATCGCGGTCCAATCGCGCTAT

CCTGTATCTGTAGAATCTTCACCAAGTACATCGGAAGAATCTTCACCAAGTACTACTTGTCTATTATTAAAACCATTCAATGGAAATTTCTGGCGTTGAAAATATAC

GTTGGATTCGGCATACGCTAGTACTACTTGTCTATTATTAAAACCATTCAATGGAAATTTCTGGCGTTGAAAATATAC
TACTGGGAGAAGATTCTCTCCTCTTTCTTCATCATTCCTTCTTTACACAGAAAACATATCCGCTGGTAGAGAATTCTAAACA
AAGATGTCTTTTCTGGTACCTTTCTACTCTTAGTTGATGTAGAAATCGCCAATAGCCGCCAATAGTGGTCCATTATTTGGA
TTCTTATGTTGTCTATACGCTTGTTGTTCTTTTACAGTTGGTAGTAGTTGGTGGTAGTACTATTGGTGGTGGTAGAATAGAAATCGCGTGG

C-Tag    MCS    End of VP40

FIG. 10W

ATGCATTGTATTCCAATTAGTTTATCTTTAGATGGTCTCCAAGCATCATCTGGTAGCTTTTGTACAGATAGTACTAGAT
TAGTTAGATTATAAGTAAACTGATTTGTAGAGAAATTTCTGGAATAACCATATTTGAATAAAAGCTTGATTTCCTTCT
CTTAGCATTCTTAGTGGATGGCGCTGGTATTCCAGTTCCTAGTCTATTTACTCTAACAAACTTTTGTCCATTATGTGTAAAC
TGTGTAATTGTATAAGATCCGTGCAATAGCGCCGCTACTGTATGCGCTAGTGGATATTCAAAATTAGACATAATTCCTA
GTGGTAGCCAAGCTGGTACACCTTTTACTGTTCTTTCATTATACGCAGAAATATCAATAATCGCTTCTAGTGTGTAAACGCA
TGACAAACATTTCCTTTAAACTGATCATCTAGATTTAGATCATCTCCAACATAATTTGGTGTAATTCCATGTTGATTAGATAG
TTGATCCGCTGGAATTAGTTGATTAGCACCATGATCCGCATATGGTGGTGGATTTA

Start of MAR VP40

GATATTGCATATAAGTATTATAATTAGAACTAGAACGCCATcccgggcttatTTATGATTATTTCTCGCTTTCAATTT

Vaccinia virus mH5 promoter

AACACAACCCTCAAGAACCTTTGTATTTATTTTCAATTTTT

FIG. 10X

RBD (aa 331-524)-(MAR/SP-GP-Tm) (SEQ ID NO: 133)

Vaccinia mH5 promoter                                                                          Kozak AAAAATTGAAAATAAAATACAAAGGTTCTTGAGGGTTGTGTTAAATTGAAAGCGAGAAATAATCATAA|gccacc MAR Signal Peptide                                  Start of RBD

ATGTGGACGACCTGCTTCTTCATCTCCCTAATCCTCAGGGAATCAAGACCCTA|AAC|ATCACGAACCTATGTCCGT

TCGGAGAAGTGTTCAACGCGACAAGATTTGGCTCGTGTCTGTGTATGCGTGGAACAGAAAAAGAATCAGTAACTGCGTCGCGG

ACTACTCCGTCCTATACAACTCTGCCTCTTCTCCACGTTCAAATGCTACGGTGTATCTCCGACAAGCTAAACGATCTA

TGCTTCACCAACGTCTACGCGGACTCCTTCGTAATCAGAGGAGATGAAGTTAGACAGATGGCGCGGACAAACTGA

AAGATCGGGATTATAACTACAAGCTACCGGACGACTTCACCGGATGGTAATTGCGTGGAATTCGAACAACCTAGAC

TCCAAAGTCGGAGGAGAAACTACAACTACTGTACAGACTATTCAGAAAGTCCAACCTAAAGCCGTTCGAGAGAGACATC

TCCACCGAAATCTATCAGGCTGGATCTACACCGTGTAATGGTGTGTCGAAGGATTCAACTGCTACTTCCCGCTACAGTCTT

ACGGATTTCAACCGACAAACGGTGTAGGATATCAGCC

End of RBD     MAR-Tm

GTACAGAGTCGTCGTACTATCCTTCGAACTACTACACATGCTCCGGCGACAGTA|TGGTGGACCTCCGATTGGGGAGTAC

MAR-Ct

TAACAAACCTAGGAATCCTACTACTATTGTCGATCGCGGTCCTAATCGCGCTATCGTGTATCCTGTATCGT|AGAATCTTCACC

C-Tag

AAGTACATCGGA|gagccggaagct|TAATAATTTTTAT

FIG. 11C

RBD (aa 331-524)-(MAR/SP-GP-Tm) (SEQ ID NO: 134)

Vaccinia mH5 promoter                                                                    SmaI    Kozak

AAAAATTGAAATAAATACAAAGGTTCTTGAGGGTGTGTTAAATTGAAAGGCGAGAAATAATCATAAATAACCCGGG

Kozak MAR Signal Peptide                                                              Start of RBD gccaccATGTGGACGACCTGCTTCTTCATCTCCCTAATCCTCCAGGGAATCAAGAGACCCTAAACATCACGAACCTATGT
CCGTTCGGAGAAGTGTTCAACGCGACAAGAATTTGCGTCTGTCTATGCGTGGAACAGAAAAAGAATCAGTAACTGCGTC
GCGGACTACTCCGTCCTATACAACTCTGCCTCTTTCTCCACGTTCAAATGCTACGGTGTATCCGACAAAGCTAAACG
ATCTATGCTTCACCAACGTCTACGGCGACTCCTTCGTCGTAATCAGAGGAGATGAAGTTAGACAGATTGGCGCGGGACAAA
CTGGAAAGATCGCGGATTATAACTACAAGCTACCGACGACTTCACCGGATGTGTAATTGCGTGGAATTCGAACAACC
TAGACTCCAAAGTCGGGAGGAAAGTCGGAGGAAACTACAACTACTTGTACGACTATTCAGAAAGTCCAACCTAAAGGCCGTTCGAGAGAG
ACATCTCCACCGAAATCTATCAGCGTGATCTACACCGTGTAATGGTGTCGAAGGATTCAACTGCTACTTCCCGCTACA
GTCTTACGGATTTCAACGACAAACGGTGTAGGATATCAGCC End of RBD    MAR-Tm

GTACAGAGTCGTCGTACTATCCTTCGAACTACTACATGCTCCGGGACAGTATGGTGGACCTCCGATGGGGGAGTAC

MAR-Ct

TAACAAACCTAGGAATCCTACTACTATTGTCGATCGCGGTCCTAATCGCGCTATCCTGTATCTGTAGAATCTTCACC

C-Tag

AAGTACATCGGAgagccggaagctTAATAATTTTTAT

FIG. 11D

RBD (aa 327-524)-(MAR/SP-GP-Tm) (SEQ ID NO: 131)

Vaccinia mH5 promoter            Kozak

AAAATTGAAAATAAATACAAAGGTTCTTGAGGGTTGTGTTAAATTGAAAGCGAGAAATAATCATAAgccacc

MAR Signal Peptide       Start of RBD

ATGTGGACGACCTGCTTCTTCATCTCCCTAATCCTAATCCAGGGAATCAAGAGACCCTAGTCAGATTTCCGAACATCACGA

ACCTATGTCCGTTCGGAGAAGTGTTCAACGCGACAAGATTTGCGTCTCTGTCTATGCGTGGAACAGAAAAAGAATCAGTA

ACTGCGTGCGGACTACTCCGTCCTATACAACTCTGCCTCTTTCTCCACGTTCAAATGCTACGGTGTATCTCGACAAAG

CTAAACGATCTATGCTTCACCAACGTCTACGGCGACTCCTTCGTAATCAGAGGAGATGAAGTTAGACAGATTGGCGCGG

GACAAACTGGAAAGATCGGCGGATTATAACTACAAGCTACCGGACGACTTCACCGGATGTGTAATTGGCGTGGAATTCGA

ACAACCTAGACTCCAAAGTCGGAGGAAACTACAACTACTTGTACAGGACTATTCAGAAAGTCCAACCTAAAGCCGTTCG

AGAGAGACATCTCCACGAAAATCTATCAGGCTGGATCTACACCGGTGTAATGGGTGTGACAAGGATTCAACTGCTACTTCCC

GCTACAGTCTTACGGATTTCAACCGACAAACGGGTGTAGGATATCAGCC

End of RBD     MAR-Tm

GTACAGAGTCGTCGTACTATCCTTCGAACTACTACACATGCTCCGGCGACAGTATGGTGGACCTCCGATTGGGGAGTAC

MAR-Ct

TAACAAACCTAGGAATCCTACTACTATTGTCGATCGCGGTCCTAATCGGCTATCCTGTATCTGTAGAATCTTCACC

C-Tag

AAGTACATCGGAgagcccggaagctTAATAATTTTTAT

FIG. 11F

RBD (aa 327-524)-(MAR/SP-GP-Tm) (SEQ ID NO: 132)

Vaccinia mH5 promoter                                                                                          SmaI     Kozak AAAAATTGAAAATAAATACAAAGGTTCTTGAGGGTTGTGTTAAATTGAAAGCGAGAAATAATCATAA|CCCGGG|gccacc MAR Signal Peptide                               Start of RBD

ATGTGGACGACCTGCTTCTTCATCTCCCTAATCCTAGGGAATCAAGACCCTA|GTC|AGATTTCCGAACATCACGA

ACCTATGTCCGTTCGGAGAAGTGTTCAAGGCGACAAGATTTGGCGTCGTCTATGCGGTGAACAGAAAAGAATCAGTA

ACTGGCGTCGCGGACTACTCCGTCGTCCTATACAACTCTGCCTCTTTCTCCACGTTCAAATGCTACGGTGTATCCGACAAAG

CTAAACGATCTATGCTTCACCAACGTCTACGCGGACTCCTTCGTAATCAGAGGAGATGAAGTTAGACAGATTGCGCCGG

GACAAACTGGAAAGATCGGCGATTATAACTACAAGCTACCGGACGACTTCACGGATGTAATTGCGTGGAATTCGA

ACAACCTAGACTCCAAAGTCGGAGGAAACTACAACTACTTGTACAGACTATTCAGAAAGTCCAACCTAAAGCCGTTCG

AGAGAGACATCTCCACGGAAATCTATCAGGTGGATCTACACCGTGTAATGGTGTCGAAGGATTCAACTGCTACTTCCC

GCTACAGTCTTACGGATTTCAACCGACAAACGGGTGTGAGGATATCAGCC

End of RBD     MAR-Tm

GTACAGAGTCGTCGTACTATCCTTCGAACTACTACACATGCTCCGGCGACAGTA|TGGTGGACCTCCGATTGGGGAGTAC

MAR-Ct

TAACAAACCTAGGAATCCTACTACTATTGTCGATCGGCGTCCTAATCGGCGTATCCTGTATCTGT|AGAATCTTCACC

C-Tag

AAGTACATCGGA|gagccggaagct|TAATAATTTTTTAT

FIG. 11G

RBD (aa 331-524)-(MAR/SP-GP-Tm/VP40) (SEQ ID NO: 137)

Vaccinia mH5 promoter　　　　　　　　　　　　　　　　　　　　Kozak

AAAATTGAAAATAAATACAAAGGTTCTTGAGGGTTGTGTTAAATTGAAAGGCGAGAAATAATCATAA|gccacc|

MAR Signal Peptide　　　　　　　　　　　Start of RBD

ATGTGGACGACCTGCTTCTTCATCTCCTAATCCAGGAATCAAGACCCTA|AAC|ATCACGACAACCTATGTCCGT
TCGGAGAAGTGTTCAACGGCGACAAGATTGGCGTCTGTCTATGCGGTGGAACAGAAAAAGAATCAGTAACTGGCGTCGCGGG
ACTACTCCGTCCTATACAACTCTGCCTCTTCTCCACGTTCAAATGCTGTATCTCCGACAAAGCTAAACGATCTA
TGCTTCACCAACGTCTACGCGGACCTACGCGGACCTCCTTCGTAATCAGAGGAGATGAAGTTAGACACAGATTGCGCCGGGACAAACTGGA
AAGATCGGCGGATTATAACTACAAGCTACCGGACGACTTCACCGGACTTCACGGATGTGTAATTGCGTGGAATTGCGTTAATGGCGTGGAACAACCTAGAC
TCCAAAGTCGGGAGGAAACTACAACTACTTGTACAGAATCAGAAAGTCCAACGATTCAACTGCTACTTCCCGCTACCAGTCTT
ACGGATTTCAACGACAAACGGTGTAGGGATATCAGCC

End of RBD　　MAR-Tm

GTACAGAGTCGTCGTACTATCCTTCGAACTACTACATGCTCCGCGGACAGTA|TGGTGGGACCTCCGATTGGGGAGTAC|

MAR-Ct

TAACAAACCTAGGAATCCTACTACTATTGTCGATCGCGGGTCCTAATCGGGCTATCCTGTATCTGT|AGAATCTTCACC|

MCS　　　End of VP40

AAGTACATCGGA|agagccggaagct|TAATAATTTTTATctgcagtcgacTTATTA|TAT|CGCAGATAGTGTTGGATTCGCATACGCTA
GTACTACTTGTCTATTATTAAAACCATTCAATGGAAAATTTCTGGCGCTTGAAAATATACTACTGGAGAAGATTCTCCT
CTTTcTTCATCATTCCTTCTTTACAGAAAAACATATCCGCTGGTAGAGAAATTCTAAACAAAGATGtcTTTCTGGTACc
TTTTCTACTCTTAGTTGATGTAGAAATCCGCAAATCCAGAATCGGCCAATAGTGGTCCATTATTGGATTcTTATGTGTCTATACGCT
TGTTTcTTTACAGTTGGTAGTACTATTGGTGGTAGTACTATTGGTGGTAGcTTTTGTACAGATAGTAGTAGATTATAAGTAAACT
TTTATCTTTAGATGGTCTCCAAGCATCCATCGGTAGcTTTTGTACAGATAGTAGTAGATTATAAGTAAACT
GATTGTAGAgAGAATTCTGGAATAAACCATATTTTGAATAAAAGCTTGAICTCTTAGCATTCTTAGTGGATGC
GCTGGTATTCCAGTTCCTAGTCTATTTACTCTAACAAAcTTTGTCCATTATGTGTAAACTGTGTAATTGTATAAGATCCT
GTCAATAGCGCGCTACTGTATGCGCTAGTGCTGCTAGTGTTGCATTAGACATAATTCCTAGTGGTGCCAAGCTGTACAC
CTTTACTGTTCTTTCATTATACGCAGAAATATCAATAAATCGCTTCTAGTGTAAACGGACAAACATTCCTTTAAAC
TGATCATCTAGATTTAGATCTCCAACATAATTTGGTGTAATTCCATGTTGATTGATTAGATAGTTGATCCGCTGGAATTAGTTG
ATTAGCACCATGATCCGCATATGGTGGTGGATTTA

FIG. 11J

Start of MAR VP40

GATATTGCATATAAGTATTATATAATTAGAACTAGAACGC CAT cccggggcttat TTATGATTATTTCTCGCTTTCAATTT

Vaccinia virus mH5 promoter

AACACAACCCTCAAGAACCTTGTATTTATTTTCAATTTT

FIG. 11K

RBD (aa 331-524)-(MAR/SP-GP-Tm/VP40) (SEQ ID NO: 138)

Vaccinia mH5 promoter

SmaI     Kozak

AAAAATTGAAAATAAATACAAAGGTTCTTGAGGGTTGTGTTAAATTGAAAGGCGAGAAATAATCATAA|CCCGGG|gccacc Start of RBD MAR Signal Peptide ATGTGGACGACCTGCTTCTTCTTCATCTCCCTAATCCTAATCCAGGGAATCAAGACCCTA|AAC|ATCACGAACCTATGTCCGT
TCGGAGAAGTGTTCAACGCGACAAGATTGCGTCTCTGTCGTGGAACAGAAAAAGAATCAGTCAGTGCGTCGCGG
ACTACTCCGTCCTATACAACTCTGCCTCTTTCTCCACGTTCAAATGCTACGGTGTATCTCCGACAAAGCTAAACGATCTA
TGCTTCACCAACGTCTACGCGGACTCCTTCGTAATCAGAGGAGATGAAGTTAGACACAGATTGCCGCGGACAAACTGGA
AAGATCGGCGGATTATAACTACAAGCTACCGGACGACTCACCGGATGTGTAATTGCGTGAAATCGAACAACCTAGAC
TCCAAAGTCGGGAGGAAACTACAAACTACAACTACTTGTACAGACTATTCAGAAAGTCCAACCGTTCGAGAGAGACATC
TCCACCGAAATCTATCAGGCTGGATCTACACCGTGTAATGGTGTCGAAGGATTCAACTGCTACTTCCCGCTACCAGTCTT
ACGGATTTCAACCGACAAACGGTGTAGGGATATCAGCC End of RBD     MAR-Tm GTACAGAGTCGTGTACTATCCTTCGAACTACTACACATGCTCCGGCGACAGTA|TGGTGGACCTCCGATTGGGGAGTAC
MAR-Ct TAACAAACCTAGGAATCCTACTACTATTGTCGATCGCGGTCCTAATCGCGGTCCTATCGGCTATCTGT|AGAATCTTCACC C-Tag                                   End of VP40

AAGTA|CACATCGGA|gagccggaagct|TAATAAATTTTTATctgcagtcgac|TTATTA|TAT|CGCAGATAGTGTTGGATTCGCATACGCTA
GTACTACTTGTCTATTATTAAACCATTCAATGGAAAATTTCTGGCGCTTGAAAATATACTACTGGAGAAGATTCTCCT
CTTTcTTCATCATCCTTCTTTACAGAAAACATATCCGCTGGTAGAGAAATTCTAAACAAAGATGTcTTTTCTGGTACc
TTTTCTACTCTTAGTTGATGTAGAATTCCAGAAATCGCCAATAGTGGTCCATTATTGGATTcTTATGTTGTCTATACGCT
TGTTTcTTTACAGTTGGTAGTACTATTGGTGGTAGATTGGTAGATTGGATGAATAGAAAATCGCTGGATGCATTGTAGTTCCAATTAG
TTTATCTTTTAGATGGTCTCCAAGCATCATCGGTAGcTTTTGTACAGATAGTAGTTAGATTATAAGTAAACT
GATTTGTAGAgAAATTTCTGGAATAACCATATTTTGAATAAAAGCTTGAATTCCTTCTCTTAGCATTCTTAGTGGATGC
GCTGGTATTCCAGTTCCTAGTCTATTTACTCCTAACAAAcTTTTGTCCATTATGTAAACTGTGTAAACTGTGTATAAGATCCT
GTCAATAGCGCCGCTACTGTATGCGCTAGTGATATTCAAAATTAGACATAATCAATAATCAATATTTGGTGTGTAAACGTGGTACAC
CTTTACTGTTCTTTCATTATACGCAGAAATATCAATAATTTGGTGTAAATCGCTTCTAGTGTAAACGATGACAAACATTCCTTTAAAC
TGATCATCTAGATTTAGATCTCCAACATAAATTTGGTGTAAATTCCATGTTGTGATTAGATAGTTGATCCGCTGGAATTAGTTG
ATTAGCACCATGATCCGCATATGGGTGGTGATTTA

FIG. 11L

Start of MAR VP40

GATATTGCATATAAGTATTATAATTAGAACTAGACGC CAT cccgggcttat TTATGATTATTTCTCGCTTTCAATTT

Vaccinia virus mH5 promoter

AACACAACCCTCAAGAACCTTGTATTTATTTTCAATTTT

FIG. 11M

RBD (aa 327-524)-(MAR/SP-GP-Tm/VP40) (SEQ ID NO: 135)

Vaccinia mH5 promoter                                                                    Kozak
AAAATTGAAAATAAATACAAAGGTTCTTGAGGGTTGTGTAAATTGAAAGGCGAGAAATAATCATAA|gccacc MAR Signal Peptide                                                       Start of RBD
ATGTGGACGACCTGCTTCTTCATCTGCCTAATCCTAGGGAATCAAGACCCTAG|GTC|AGATTTCCGAACATCACGA
ACCTATGTCCGTTCGGAGAAGTGTTCAAGCGGACAAGATTTGGCGTCTGTCATGCGTGGAACACAGAAAAAGAAATCAGTA
ACTGGGTGCGCGGACTACTCCGTCCTATACAAACTCTGCCTCTTTCTCCACGTTCAAATGCTACGGTGTATCTCCGACAAAG
CTAAACGATCTATGCTTCACCAACGTCTACGCGGACTCCTCGTAATCAGAGGAGACAGATTGAAGTTAGACACAGATTGGCGCCGG
GACAAACTGGAAAGATCGCGGATTATAACTACAAGTACACAACTACAACTACTGTACAGACTATTGGCGGTAATTGCGTTCGA
ACAACCTAGACTCCAAAGTCGGAGGAAACTACAAATCTATCAGGCTGGATCTACACCGTGAATGGTGCGAAGGATTCAACTGCTACTTCCC
GCTACAGTCTACGGATTCAACCGACAAACGGTGTAGGATATCAGCC End of RBD    MAR-Tm
GTACAGAGTCGTCGTACTATCCTTCGAACTACTACATGCTCCGGCGACAGTA|TGGTGGGACCTCCGATTGGGGAGTAC|

MAR-Ct
TAACAAACCTAGGAATCCTACTACTATTGTGCGATCGCGGCTCCTAATCGGGCTATCCGTATCTGT|TAT|AGAATCTTCACC

MCS        End of VP40
AAGTACACATCGGA|agccgggaagct|TAATAATTTTTATctgcaggtcgacTTATTATATcgcGCAGATAGTGTTGGATTCGCATACGCTA
                C-Tag
GTACTACTTGTCTATTATTAAAACCATTCAATGGAAAATTTTCTGGCGCTTGAAAATATACTACTGGAGAAGATTCTCCT
CTTTcTTCATCATTCTTCTTTTACAGAAAACATATCCGCTGGTAGAGAAACATTCTAAACAAGATGTcTTTTCTGGTACc
TTTTCTACTCTTAGTTGATGTAGAATTCCAGAAATCGGGGTCCATTATTGGATTcTTATGTGTCTATACGGCT
TGTTTcTTTACAGTTGGTAGTAGTACTATTGGTGGTAGTATTGGATGAATAGAAATCGCTGGATGCATTGTATTTCCAATTAG
TTTATCTTTAGATGGTCTCCAAGCATCATCGTGGTAGcTTTTGTACAGATAGTACTACTAGTAGTTAGATTATAAGTAAACT
GATTGTAGAGAAATTTCTGGAATAACCATATTTGAATAAAAGCTGATTCCTTCTTCTTAGCATTCTTAGTGGATGC
GCTGGTATTCCAGTTCCTAGTCTATTTACTCTAACAAAcTTTTGTCCATTATGTAAACTGTGTAAATTGTATAAGATCCT
GTCAATAGCGCCGCTACTGTCATGCGGCTAGTGGATGTGTTCAGTGGTGCCAAGCTGTACAC
CTTTTACGTTCTTTCATTATACGCAGAAATATCAATAAATGCGTTCTCTAGTGTAAAACGTACACAACATTCCTTTAAAC
TGATCATCTAGATTTAGATCTCCAACATAATTTGGTGTAATTCCATGTTGATTGATTAGATAGTTGATCCGCTGGAATTAGTTG
ATTAGCACCATGATCCGCATATGGGTGGTGGATTTA

FIG. 110

Start of MAR VP40

GATATTGCATATAAGTATTATTAATTAGAACTAGAGGC CAT cccgggcttat TTATGATTATTTCTCGCTTTCAATTT

Vaccinia virus mH5 promoter

AACACAACCCTCAAGAACCTTGTATTTATTTTCAATTTT

FIG. 11P

RBD (aa 327-524)-(MAR/SP-GP-Tm/VP40) (SEQ ID NO: 136)

Vaccinia mH5 promoter                                                    SmaI     Kozak AAAAATTGAAAATAAATACAAAGGTTCTTGAGGGTTGTGTTAAATTGAAAGGCGAGAAATAATCATAA|CCCGGG|gccacc MAR Signal Peptide                    Start of RBD ATGTGGACGACCTGCTTCTCATCTCCCTAATCCTCAGGGAATCAAGACCCTA|GTC|AGATTTCCGAACATCACGA
ACCTATGTCCGTTCGGAGAAGTGTTCAAGCGACAAGATTTGCGTCGTCTGTATGCGTGGAACCAGAAAAAGAATCAGTA
ACTGGCGTCGGGACTACTCCGTCCTATACAACTCTGCCTCTTTCTCCACGTTCAAATGCTACGGTGTATCCGACAAAG
CTAAACGATCTATGCTTCACCAACGTCTACGCGGACTCCTCGTAATCAGAGGAGGAGTTAGACAGATTGGCGCCGG
GACAAACTGGAAAGATCGCGGGATTATAACTACAAGCTTACCGGACGACTTCACCGGATGTGTAATTGGCTGGAATTCGA
ACAACCTAGACTCCAAAGTCGGAGGAAACTACAACTACTTGTACAGACTATTCAGAAGTCCAACCTAAAGCCGTTCG
AGAGAGACATCTCCACCGGAAATCTATCAGGCTGGATCTCACACCGTGTAATGGTGTCGAAGGATTCAACTGCTACTTCCC
GCTACAGTTCTTACGGATTTCAACGACAAACGGTGTGTAGGATATCAGCC End of RBD    MAR-Tm

GTACAGAGTCGTCGTACTATCCTTCGAACTACTACATGCTCCGGCGACAGTA|TGGTGGACCTCCGATTGGGGAGTAC

MAR-Ct

TAACAAACCTAGGAATCCTACTACTATTGTCGATCGCGGTCCTAATCGGCGTATCCTGTATCCTGT|AGAATCTTCACC

C-Tag           MCS          End of VP40

AAGT|ACATCGGA|gagccggaagct|TAATAATTTTTAT|ctgcaggtcgac|TTATTA|TAT|CGCAGATAGTGTTGGATTCGCATACGCTA
GTACTACTTGTCTATTATTAAAACCATTCAATGGAAAATTTTCTGGCGCTTGAAAATATACTACTGGAGAAGATTCTCCT
CTTTTcTTCATCATCCTTCTTTACAGAAAACATATCCGCTGGTAGAGAAACTATCTAAACAAAGATGTcTTTTCTGGTACc
TTTTCTACTCTTAGTTGATGTAGAATTCCAGAAATCGGCAAATAGTGGTCCATTATTTGGATTcTTATGTGTCTATACGCT
TGTTTcTTTACAGTTGGTAGTACTATTGGTGGTAGATTTGGATGCATTGTATTTCCAATTAG
TTATCTTTAGATGGTCTCCAAGCATCATCCGGTAGcTTTTGTACAGATAGTAGTTAGATTATAAGTAAACT
GATTTGTAGAGAgAAATTTCTGGAATAACCATATTTGAATAAAAGCTTGATTCCTTCTCTTAGCATTCTTAGTGGATGC
GCTGGTATTCCAGTTCCTAGTCTATTTACTCTAACAAAcTTTTGTCCATTATGTGTAAACTGTGTAAATTGTATAAGATCCT
GTCAATAGCGCCGCTACTGTATGCGCTACTATACGGCAGAAAATATCAATAAATCGCTTCTAGTGTAAACAATTCCTTTAAAC
CTTTTACTGTTCTTCATTATACGCGCAGAAAATATCAATAAATTTGGTGTAATTCCATGTTGATTAGATAGTTGATCCGGTGGTACAC
TGATCATCTAGATTTAGATCTCCAACATAATTTGGTGTAATTCCATGTTGATTAGATAGTTGATCCGCTGGAATTAGTTG
ATTAGCACCATGATCCGGCATATGGTGGTGGATTTA

FIG. 11Q

Start of MAR VP40

GATATTGCATATAAGTATTATTATAATTAGAACTAGACGC CAT cccgggcttat TTATGATTATTTCTCGCTTTCAATTT

Vaccinia virus mH5 promoter

AACACAACCCTCAAGAACCTTGTATTATTTTCAATTTT

FIG. 11R

GPS-Tandem Repeat (5x)-GPTM (SEQ ID NO: 139)

Vaccinia mH5 promoter                                                                 Kozak
AAAAATTGAAAATAAAATACAAAGGTTCTTGAGGGTTGTGTTAAATTGAAAGGCGAGAAATAATCATAA|gccacc

MAR Signal peptide                                  epitope 504-524
ATGTGGACGACCTGCTTCTTCATCTCCCTAATCCTAATCCAGGGAATCAAGAGACCCTA|TGGACGACCTGCTTCTTCATCTC
CCTAATCCTAATCCAGGGAATCAAGAGACCCTATATCAGCCGTACAGAGTCGTCGTACTATCCTTCGAACTACTACATGC linker      epitope 473-490
TCCGGGCGACAGTAggtcctggacccggtTATCAGGCTGGATCTACACCGGTGTAATGGTGTCGAAGGATTCAACTGCT linker      epitope 504-524
ACTTCggtcctggacccggtTATCAGCCGTACAGAGTCGTCGTACTATCCTTCGAACTACTACATGCTCCGGGCGACA linker      epitope 473-490
GTAggtcctggacccggtTATCAGGCTGGATCTACACCGGTGTAATGGTGTCGAAGGATTCAACTGCTACTTCggtcc linker      epitope 504-524
tggacccggtTATCAGCCGTACAGAGTCGTCGTACTATCCTTCGAACTACTACATGCTCCGGGCGACAGTAggtcctg linker
gacccggtTATCAGGCTGGATCTACACCGGTGTAATGGTGTCGAAGGATTCAACTGCTACTTCggtcctggacccggt linker
epitope 504-524
TATCAGCCGTACAGAGTCGTCGTACTATCCTTCGAACTACTACATGCTCCGGGCGACAGTAggtcctggacccggtTA epitope 473-490             linker      epitope 504-524
TCAGGCTGGATCTACACCGGTGTAATGGTGTCGAAGGATTCAACTGCTACTTCggtcctggacccggtTATCAGCCGT linker
                                    epitope 473-490
ACAGAGTCGTCGTACTATCCTTCGAACTACTACATGCTCCGGGCGACAGTAggtcctggacccggtTATCAGGCTGGA epitope 473-490
TCTACACCGGTGTAATGGTGTCGAAGGATTCAACTGCTACTTC|TGGTGGACATCGGACTGGGGAGTCCTAACGAACCT

MAR-TM
                                                  MAR-Ct
AGGAATCCTACTACTATTGTCGATCGCGGTCCTAATCGGCGTATCCTGTATCGT|AGAATCCTTCACCAAGTACATCG
GA|agcccggaagct|TAATAAttttaf TAATAAttttat

C-Tag

FIG. 12B

GPS-Tandem Repeat (5x)-GPTM (SEQ ID NO: 140)

Vaccinia mH5 promoter　　　　　　　　　　　　　　　　　　　　SmaI　　Kozak
AAAATTGAAAATAAATACAAAGGTTCTTGAGGGTTGTGTTAAATTGAAAGGGAGAAATAATCATAA|CCCGGG|gccacc

MAR Signal peptide　　　　　　　　　　　　　　　　　epitope 504-524
|ATGTGGACGACCTGCTTCTTCATCTCCCTAATCCTAATCCTAATCCAGGGAATCAAGACCCTA|TGGACGACCTGCTTCTTCATCTC
CCTAATCCTAATCCAGGGAATCAAGACCCTATATCAGCCGTACAGAGTCGTCGTACTATCCTTCGAACTACTACATGC linker　　　epitope 473-490
TCCGGCGACAGTAggtcctggacccggtTATCAGCCTGGATCTACACCGTGTAATGGTGTCGAAGGATTCAACTGCT linker　　　epitope 504-524
ACTTCggtcctggacccggtTATCAGCCGTACAGAGTCGTCGTACTATCCTTCGAACTACTACATGCTCCGGCGACA linker　　　epitope 473-490
GTAggtcctggacccggtTATCAGCCTGGATCTACACCGTGTAATGGTGTCGAAGGATTCAACTGCTACTTCggtcc linker　　　epitope 504-524
tggacccggtTATCAGCCGTACAGAGTCGTCGTACTATCCTTCGAACTACTACATGCTCCGGCGACAGTAggtcctg linker　　　　　　　　　　　　　　　　　　linker
gacccggtTATCAGCCTGGATCTACACCGTGTAATGGTGTCGAAGGATTCAACTGCTACTTCggtcctggacccggt epitope 504-524
TATCAGCCGTACAGAGTCGTCGTACTATCCTTCGAACTACTACATGCTCCGGCGACAGTAggtcctgacccggtTA epitope 473-490　　linker　　　epitope 504-524
TCAGGCTGGATCTACACCGTGTAATGGTGTCGAAGGATTCAACTGCTACTTCggtcctggacccggtTATCAGCCGT linker
ACAGAGTCGTCGTACTATCCTTCGAACTACTACATGCTCCGGCGACAGTAggtcctggacccggtTATCAGGCTGGA epitope 473-490
TCTACACCGTGTAATGGTGTCGAAGGATTCAACTGCTACTTC|GGTGGACATCTGACTGGGGAGTCCTAACGAACCT

MAR-TM　　　　　　　　　　　　　　　　　　　MAR-Ct
|GGTGGACATCTGACTGGGGAGTCCTAACGAACCT|AGAATCTTCACCAAGTACATCG

C-Tag
GA|gagccgggaagct|TAATAAttttafTAATAAttttat

FIG. 12C

GPS-Tandem Repeat (5x)-GPTM-VP40 (SEQ ID NO: 141)

Vaccinia mH5 promoter                                                                 Kozak
AAAATTGAAAAATAAACAAAGGTTCTTGAGGGTTGTGTTAAATTGAAAGCGAGAAATAATCATAA|gccacc MAR Signal peptide                                              epitope 504-524
A|TGTGGACGACCTGCTTCTTCATCTCCCTAATCCTAATCCAGGGAATCAAGACCTA|TGGACGACCTGCTTCTTCATCTC
CCTAATCCTAATCCAGGGAATCAAGACCCTATATCAGCCGTACAGAGTCGTCGTACTATCCTTCGAACTACTACATGC linker        epitope 473-490
TCCGGGGACAGTAggtcctggacccggtTATCAGGCTGGATCTACACCGGTGTAATGGTGTCGAAGGATTCAACTGCT linker        epitope 504-524
ACTTCggtcctggacccggtTATCAGCCGTACAGAGTCGTCGTACTATCCTTCGAACTACTACATGCTCCGGGGACA linker        epitope 473-490
GTAggtcctggacccggtTATCAGGCTGGATCTACACCGGTGTAATGGTGTCGAAGGATTCAACTGCTACTTCggtcc linker          epitope 504-524
tggacccggtTATCAGCCGTACAGAGTCGTCGTACTATCCTTCGAACTACTACATGCTCCGGGACAGTAggtcctg linker                                linker
gacccggtTATCAGGCTGGATCTACACCGGTGTAATGGTGTCGAAGGATTCAACTGCTACTTCggtcctggacccggt linker
epitope 504-524
TATCAGCCGTACAGAGTCGTCGTACTATCCTTCGAACTACTACATGCTCCGGGGACAGTAggtcctggacccggtTA linker        epitope 504-524
epitope 473-490
TCAGGCTGGATCTACACCGGTGTAATGGTGTCGAAGGATTCAACTGCTACTTCggtcctggacccggtTATCAGCCGT linker
ACAGAGTCGTCGTACTATCCTTCGAACTACTACATGCTCCGGGGACAGTAggtcctggacccggtTATCAGGCTGGA MAR-TM
epitope 473-490
TCTACACCGGTGTAATGGTGTCGAAGGATTCAACTGCTACTTC|TGGTGGACATCTGGGGAGTCCTAACGAACCT MAR-Ct
                                    End of VP40
|TGGTGGACATCTGTATCCTGTATCGT|AT|CGCAGATAGTGTTGGATTCGCATACGCTAGTACT MCS
AGGAATCCTACTACTATTGTCGATCGGGGTCCTAATCGGCTATCGT|AGGAATCCTACTACTATTGTCGATCGGGGTCCTAATCGGCTATCGT C-Tag
GA|agccggaagct|TAATAAttttatTAATAAtttttatctgcaggtcgacTTATTA
ACTTGTCTATTATTAAAACCATTCAATGGAAAAATTTCTGGCGTTGAAAAATATACTACTGGAGAAGATTCTCCTCTTT

FIG. 12E

CTTCATCATTCCTTCTTTTACAGAAAACATATCCGGCTGGTAGAGAAATTCTAAACAAAGATGTCTTTCTGGTACCTTTT
CTACTCTTAGTTGATGTAGAGAATTCCAGAAATCGCCAATAGTGGTCCATTATTTGGATTCTTATGTTGTCTATACGCTTGT
TTCTTTACAGTTGGTAGTACTATTGGTGGTGGTAGATTTGGATGAATAGAAATCGCTGGATGCATTGTATTTCCAATTAGTTT
ATCTTTAGATGGTCTCCAAGCATCATCTGGTAGCTTTTGTACAGATAGTAGTACTAGATTATAAGTAAACTGAT
TTGTAGAGAAATTTCTTGGAATAACCATATTTTGAATAAAAGCTTGATTTCCTTCTTAGCATTCTTAGTGGATGCGCT
GGTATTCCAGTTCCTAGTTCGTCTATTTACTCTAACAAACTTTTGTCCATTAGTGTAAACTGTGTAATTGTATAAGATCCTGTC
AATAGGCGCGCTACTGTATGCGCTAGTGGATATTCAAAATTAGACATAATTCCTAGTGGGTAGCCAAGCTGGTACACCTT
TTACTGTTCTTTCATTATACGCAGAAATATCAATAATCGCTTCTAGTGTAAACGCATGACAAACATTTCCTTTAAACTGA
TCATCTAGATTAGATCTCCAACATAATTTGGTGTAATTCCATGTTGATTAGATAGTAGTTGATCCGGCTGGAATTAGTTGATT
AGCACCATGATCCGCATATGGGTGGTGGATTTA

Start of MAR VP40

GATATTGCATATAAGTATTATAATTAGAACTAGAGCGC|CAT|cccgggcttat|TTATGATTATTTCTCGCTTTCAATTT|

Vaccinia virus mH5 promoter

|AACACAACCCTCAAGAACCTTTGTATTTATTTTCAATTTT|

FIG. 12F

GPS-Tandem Repeat (5x)-GPTM-VP40 (SEQ ID NO: 142)

Vaccinia mH5 promoter                                                                SmaI    Kozak
AAAAATTGAAAATAAATACAAAGGTTCTTGAGGGTTGTGTTAAATTGAAAGCGAGAAATAATCATAACCCGGGgccacc MAR Signal peptide                                          epitope 504-524
ATGTGGACGACCTGCTCTTCTTCATCTCCCTAATCCTAATCCAGGGAATCAAGACCCTATGGACGACCTGCTCTTCATCTC
CCTAATCCTAATCCAGGGAATCAAGACCCTATATCAGCCGTACAGAGTCGTCGTACTATCCTTCGAACTACTACAGC linker         epitope 473-490
TCCGGGGACAGTAggtcctgaccggtTATCAGGCTGGATCTACACCGTGTAATGGTGTCGAAGGATTCAACTGCT
              linker         epitope 504-524
ACTTCggtcctgaccggtTATCAGCCGTACAGAGTCGTCGTACTATCCTTCGAACTACTACATGCTCCGGGCGACA linker         epitope 473-490
GTAggtcctgaccggtTATCAGGCTGGATCTACACCGTGTAATGGTGTCGAAGGATTCAACTGCTACTTCggtcc
linker         epitope 504-524
tggacccggtTATCAGCCGTACAGAGTCGTCGTACTATCCTTCGAACTACTACATGCTCCGGGCGACAGTAggtcctg linker                                   linker                              linker
gacccggtTATCAGGCTGGATCTACACCGTGTAATGGTGTCGAAGGATTCAACTGCTACTTCggtcctggacccggt
                        epitope 504-524
TATCAGCCGTACAGAGTCGTCGTACTATCCTTCGAACTACTACATGCTCCGGGCGACAGTAggtcctgaccggtTA
epitope 473-490              linker         epitope 504-524
TCAGGCTGGATCTACACCGTGTAATGGTGTCGAAGGATTCAACTGCTACTTCggtcctggacccggtTATCAGCCGT linker
ACAGAGTCGTCGTACTATCCTTCGAACTACTACATGCTCCGGGCGACAGTAggtcctggacccggtTATCAGGCTGGA
epitope 473-490                                                 MAR-TM
TCTACACCGTGTAATGGTGTCGAAGGATTCAACTGCTACTTCTGGTGGACATCTGGGGAGTCCTAACGAACCT MAR-Ct
TGGTGGACATCTGTATCCTGTATCGTGGGCTATCGTGGGCTATCCTGTATCGTAGAATCTTCACCAGTACATCG C-Tag                            MCS         End of VP40
GAagcccggaagctTAATAAttttatTAATAAttttatctgcaggtcgacTTATTATACGCAGATAGTGTTGGATTCGCATACGCTAGTACT
ACTTGTCTATTATTAAAACCATTCAATGGAAAATATACTCTGGCGCTTGAAAATATACTACTGGAGAAGAATTCTCCTTTTT

FIG. 12G

CTTCATCATTCCTTCTTTTACAGAGAAAAACATATCCGGCTGGTAGAGAAATTCTAAACAAAGATGTCTTTCTGGTACCTTT
CTACTCTTAGTTGATGTAGAAATTCCAGAAATCGCCAATAGTGGTCCATTATTTGGATTCTTATGTTGTCTATACGCTTGT
TTCTTTACAGTTGGTAGTACTATTGGTGGTAGATTTGGATGAATAGAAATCGCTGGATGCATTGTATTTCCAATTAGTTT
ATCTTTAGATGGTCTCCAAGCATCATCTGGTAGCTTTTGTACAGATAGTAGTTAGATTATAAGTAAACTGAT
TTGTAGAGAAATTTCTTGGAATAACCATATTTTGAATAAAAAGCTTGATTTCCTTCTCTTAGCATTCTTAGTGGATGGCT
GGTATTCCAGTTCCTAGTTCTTATTTACTCTAACAAACTTTGTCCATTAGTGTAAACTGTGTAATTGTATAAGATCCTGTC
AATAGGCGCGCTACTGTATGCGCTAGTGGATATTCAAAATTAGACATAATTCCTAGTGGTAGCCAAGCTGGTACACCT
TTACTGTTCTTTCATTATACGCAGAAATATCAATAATCATATTGGTGTAAACGCTTCTAGTGTAAACGCATGACAAACATTCCTTTAAACTGA
TCATCTAGATTAGATCTCCAACATAATTTGGTGTAATTCCATGTTGATTAGATAGTAGTTGATCCGCTGGAATTAGTTGATT
AGCACCATGATCCGCATATGGGTGGTGGATTTA

Start of MAR VP40

GATATTGCATATAAGTATTATAATTAGAACTAGACGC[CAT]cccgggcttat[TTATGATTATTTCTCGCTTTCAATTT

Vaccinia virus mH5 promoter
[AACACAACCCTCAAGAACCTTTGTATTTATTTCAATTTTT]

FIG. 12H

Full Length S (SEQ ID NO: 143)

Vaccinia mH5 promoter                                                                    Kozak AAAAATTGAAATAAATACAAAGGTTCTTGAGGGTTGTGTTAAATTGAAAGCGAGAAATAATCATAA  gccacc S Start ATG TTCGGTGTTCCTAGTCTTCTCAGTGTGTAAACCTAACAAGCAGAACAACTAACTACCACCGG
CGTACACCAATTCTTCACAGAGGAGTATATTACCCGGACAAGGTGTTCAGATCGTTCCGTACTACATTCTACACAGA
CCTATTCCTACCGTTCTTCTCTAACGTAACATGGTTCCACGCGATCCATGTCTCTGGAACAAACGAACGAAGAGATTC
GATAAACCCGGTCTTGCCGTTCAACGATGGTGTATACTTTGCGTCCACCGAGAAGTCCAACATCATCAGAGGATGGATCT
TCGGAACCACCTTGGATTCTAAGACCAGTCCTTGCTAATCGTCAACAAGCGACCAACGTCGTCATCAAGTCTGCGA
ATTCCAGTTCTGTAACGACCCGTTCTTGGGAGTCTACTACCACACAAGAACAACAAGTCCTGGAATCCGAGTTCAGA
GTCTACTCTTCCCGCGAACAACTAAGAGAGTTCGTATTCAAGAACATCAGCCGGTCCTAATGGACCTAGAGGGAAAGCAGGGAA
ACTTCAAGAACCTAAGAGAGTTCGTATTCAAGAACATCAGCCGGATACTTCAAGATCTACTCCAAGCACACTCCGATCAA
CCTAGTTAGAGATCTACCGCAAGGATTCTCTGCGGCTAGAACCGTTAGTAGACCGTTAGTTGCCGATCGGAATCAACATCACCAGA
TTCCAGACAACTACTAGCGCTACTACACAGATCTTACCTAACCGCCGGGAGATTCTTCTTCTGGAGGACTGCTGCTGCGG
CTTATTATGTAGGATACCTACAGCCGAGAACCTTCCTATTGAAGTACAAACGAAACCATCACCGATGCCGGTAG
ATTGTGTCTCTAGATCCGCTATCCGAAACGAAGTGCACCCTAAAGTCTTTCACCGTCGAGAAGGGAATCTACCAGACCTC
CAACTTTAGAGTACAGCCGACCGAATCCATCGTCGTCAGATTTCCGAACATCATCGTTCCGTTCGGAGAAGTGTTC
AACGGGAAGATTGGCGTCGTGTTCTATGCGGTGGAACAGAAAAAGAATCAGTAACTGCGTCGCGGACTACTCCGTCCTAT
ACAACTCTGCCTCTTCTCCACGTTCAAATGCTACGGTGTATCTCCGACAAAGCTAAACGATCTATGCTTCACCAACGTC
TACGCGGACTCCTTCGTAATCAGAGGAGATGAAGTTAGACAGATTGGCGTCGGGACAAACTGAAAGATCGCGGATTAT
AACTACAAGCTACCGGACGACTTCACCGGATGTGTAATTGGCGTGGAATTCGAACAACCTAGAACTCCAAAGTCGGAGGA
AACTACAACTACTTGTACAGACTATTCAGAAAGTCCAACCTAAAGCCGTTCGAGAGAGACATCTCCACCGAAATCTATC
AGGCTGGATCTACACCGTGTAATGGTGTCGAAGGATTCAACTGCTACTTCCCGCTACTACACAGTCTTACGGATTTCAACCGAC
AAACGGTGTAGGATATCAGCCGTACAGAGTCGGTCGTACAGAGTACACTTAACTTCAACTTAACTTCAACCGGACTAACCGGTGTCCTA
CCGAAAAAGTCTACCAACTAGTCAAGAACAAATGCGTCAACTTAACTTCAACCGGAAGAGATATCGCGGAAGATCGGAAGAGACGCGTGTCAGAT
ACGGAATCTAACAGAAGTTTCTACCGTTCCAGTTCGGAAGAGATATCGCGGAAGATATGCGGGAAGACAGAGACGCGTGTCAGAT
CCGCAACCTTGGAGATCCTAGATATCACACCGTGTCTTCGGTCGTCTCTGTAATTACTCCGGGAACGAACACCT
CCAATCAAGTAGCGGTACTATACCAGGACGTGAACTGTACAGAGTACCGGTGAACTGTAGCTATTCACGCGGATCAACTAACAC
CAACTTGGAGAGTGTACTCCACCGGATCTAACGTATTCCAAACAAGAGGCGGGGATGTCTAATCGGGAGGCGGAAGAACGTAA

FIG. 13B

ACAACTCCTACGAATGTGATATCCCGATTGGAGCGGGAATCTGTGCGTCTTACCAAACACAAACAAACTCTCGAGAA
GAGCGGAGATCTGTAGCCTCTCAATCTATTATCGGCCTACACCATGTCCTTGGGAGCCGAAAATTCTGTCGGTACTCCAA
CAATTCTATCGGCGATCCCGACAAACTTCACCATCTCTGTAACAACCGAGATCCTACCGGTGTCTATGACCAAGACATCT
GTCGATTGCACCATGTACATCTGCGGAGATTCCACCGAGTGCTCCAACCTACTACAGTACGGATCTTTCTGTACCC
AGCTAAACAGAGCGGTTGACTGGAATCGGCTGTGTAGAGCAGGATAAGAACACTCAAGAGGTATTCGGCGCAAGTCAAGCAG
ATCTATAAGACTCCGCCGATCAAGGACTTCGGGAGGTTCAACTTCTCTCAGATCTTGCCGGATCCGTCCAAACCGTCTA
AGAGATCTTTCATCGAGGACCTACTATTCAACAAAGTCACCCTAGCTGACGCGGGGATTCATCAAACAATACGGAGATTG
CTTGGGAGACATTGCGGGCGGAGAGATCTAATTTGCGCGCAGAAGTTAACGGATTGACAGTACTACCGCCGCTACTAACC
GATGAGATGATTGCGCAGTCGATTACACGTCTATTGGCGGGAACAATTACAAGTGGATGGACATTGGAGCCGGTGCC
GCTCTACAAATTCCGTTTGCTATGCAAATGGCGTACAGATTCAAGCGGAGTAACCCAGAACGTCTTGTACGAGA
ACCAGAAGCTAATCGGCAACCAGTTACATCCCGGATCGGAAAGATCCAGGACAGTCTATCTTCTACTGCTTCGGCGTT
GGGAAAGCTACAGGATGTAGTAAATCAAAACGCGCAGGCGCTAAACACCTTGTCAAGCAACTATCCTCTAACTTCGG
AGCGGATCTCGTCCGTCCTAAAGACATCTTATCCAGACTAGATAAGGTCGAAGCGGAGGTCCAGATCGATAGACTAAT
CACTGGAAGATTGCAGTCCCTACAGACCTACGTAACACAGCAATCAATTAGAGCGGCGACTTCTGCGGAAGGGATACCACCT
TCTAGCTGCGACCAAGATGTCCGAATGTCTTGGGACAATCCAAGAGAGTGACTTGCGGGCGCAAGAAAGAACTTC
AATGTCTTTCCCACAATCTGCGCCGACATGGGTCGTATTCCTACATGTAACATATGTGCGGGCGCAAGAAAGAACTTC
ACAACAGCTCCAGCTCCGATCGCCATGATGGAAAAGCTCATTCCCGAGAGAGGGAGTCTTTGTCTCTAACGGAACTCATT
GGTTCGTCACCCAGAGAAAACTTCTACGAGCCGCAGATCATCACCCGACAACACATTCGTCTCGGGAAACTGCGACG
TGGTCATCGGAATCGTAAACAATACCGTTCTACGATCCGTTGCAGCCGGAACTAGACTCCTTCAAAGAAGAGTTGGACA
AGTACTTCAAGAACCACACCTCTCCGATGTGGACTGGGAGATATCTCTGGAATCAACGCGTCCGTCGTCAACATCCA
GAAAGAAAATCGATAGATTGAACGAGGTCGGCGAAGAACTTGAACGAGTCCCTAATGCAACAAGAGCTAGGAAAAT
ACGAGCAGTACATCAAGTGGCCCGTGGTACATCTGGCTAGGATTCATTGCTGGACTAATTGCGATCGTCATGGTCACCAT
CATGCTATGCTGTATGACCTCGTGTCCTGCTCCTGTTGCTCCTGCGGATCCTGTTGCAAGTT

End of S  C-tag agccagaggct[TAATAA]tttttat

CGATGAAGATGATAGTGAACCGGTCCTAAAGGGGTGTCAAGCTACAACTACACAGagccagaggct[TAATAA]tttttat

FIG. 13C

Full Length S (SEQ ID NO: 144)

| Vaccinia mH5 promoter | SmaI | Kozak |
|---|---|---|

AAAAATTGAAATAAATACAAAGGTTCTTGAGGGTTGTGTT|AAATTGAAAGGCGAGAAATAATCATAA|CCCGGG|gccacc

S Start

ATG TTCGGTGTTCCTAGTCCTACCGGCTCGTCTTCTCAGTGTGTAAACCTAACAACGAGAACTAACTACCACCGG
CGTACACCAATTCTTCACAGAGAGGAGTATATTACCCGGACAAGGTGTTCAGATCCTCCGTACTACATTCTACACAGA
CCTATTCCTACCGGTCGTTCTTCTCTAACGTAACATGGTTCCACGCGATCCATGTCTCTGGAACAAACGAAGGAGATTC
GATAACCCGGTCTTGCGGTCAACGATGGTGTATACTTTGCGGTCCACCGGAGAAGTCCAACATCATCAGAGGATGGATCT
TCGGAACCACCTTGGATTCTAAGGACCCAGTCCTTGCTAATCGTCAACAACGCGACAACAAGTCCTGGAATCCGAGTTCGA
ATTCCAGTTCTGTAACGACCCGGTTCTTGGGAGTCTACTACCACAGAACAACAAGTCCTAATGGACCTAGAGAGGAAAGCAGGGAA
GTCTACTCTTCCCGCGAACAACTGCACCTTCGTATTCAAGAACATCGACGGATACTTCAAGATCTACTCCAAGCACACTCCGATCAA
ACTTCAAGAACCTAAGAGAGTTCGTTCTCAAGAACCGTTAGTAATGTATCTCAGCCGTCCTCAAGATCTTCAAGATTTGCCGATCGGAATCAACATCACCAGA
CCTAGTTAGAGATCTCACCGCAAGGATCTCTGCGCTAGAACCGTTAGTAGATTTGCCGATTGGCCGATCGGAATCAACATCACCAGA
TTCCAGACAACTACTAGCGCTGCTACACAGATCTTACCTAACGCCGGGAGATTCTCTTCTGAGTGACTGCTGCTGGTGCTGCGG
CTTATTATGTAGGATACCTACAGCCGGAGAACCTTCCTATTGAAGTACAACGAAACCATCACCGATGCCGGTAG
ATTGTGCTCTAGATCCGCTATCCGAAACGAAGTGCACCCTAAAGTCTTTCACCGTCGAGAAGGGAATCTACCAGACCTC
CAACTTTAGAGTACAGCCGACCGAATCCATCGTCGTCAGATTTCCGAACATCATCACGAACCTATGTCCGTTCGGAGAAGTGTTC
AACGGGACAAGAGATTTGGCGTCGTGTCTATGCGGGAACAGAAAAAGAATCAGTAACTGCGTCGCGGACTACTCCGTCCTAT
ACAACTCTGCCTCTTCTTCTCCACGTCAAATGCTACGGTGTATCTCCGACAAAGCTAAACGATCTATGCTTCACCAACGTC
TACGCGGACTCCTTCGTAATCAGAGGAGATGAAGTTAGACAGAGATTGCGCGGACAAACTGAAAGATCGCGGATTAT
AACTACAAGTCACCGGAGACGACTTCACCGGATGTGTAATTGCGTGGAATTGGCGTGGTAATTCCAACCTAAAGTCGGAGGA
AACTACAACTACTTGTACAGACTATTCAGAAAAGTCCAACCTAAAGCCGTTCGAGAGAGACATCTCCACGAAATCTATC
AGGCTGGATCCTACACCGTGTAATGGTGTCGAAGGATTCAACTGCTACTTCCCGCTACACTACCAGTCTTACGGATTTCAACCGAC
AAACGGTGTAGGATATCAGCCGTACAGAGTCGGTCGTACTTCCTTCGAACTACTACACATGTCCGGCGACAGTATGTGGA
CCGAAAAAGTCTACCAACTAGTCAAGAACAAATGCGTCAACTTAACTTCAACGGACTAACCGGACTACAGACGCGTGTCAGAT
ACGGAATCTAACAGAAGTTTCTACGGTTCCAGCAGTTCGGAAGAGATATCGCGGGAAGATATGCGGACTACAACAGAGCGCTGTCAGAGAT
CCGCAAACCTTGGAGATCCTAGATATCACACCGTGTCTTCGGTGGTCTCTGTAATTACTCCGGGAACGAACACCT
CCAATCAAGTAGCGGTACTATACCAGGACGTGAACTGTACAGAACTGTACAGGTAGCTATTCACGCGGATCAACTAACAC
CAACTTGGAGAGTGTACTCCACCGGATCTAACGTATTCCAAACAAGAGGCGGGGATGTCTAATCGGGAGCGGGAACACGTAA

FIG. 13D

ACAACTCCTACGAATGTGATATCCGATTGGAGCGGGAATCTGTGCGTCTTACCAAACACAAACAAACTCTCGAGAA
GAGCGGAGAATCTGTAGCCTCTCAATCTATTATCGGCTACCATGTCCTTGGGAGCCGAAAATTCTGTCGCGTACTCCAA
CAATTCTATCGCGATCCCGACAAACTTCACCATCTCGTAACAACCGAGATCCTACCGGTGTCTATGACCAAGACATCT
GTCGATTGCACCATGTACATCTGCGGAGATTCCACCGAGTGCTCCAACCTACTACAGTACGGATCTTTCTGTACCC
AGCTAAACAGAGAGGCGTTGACTGGAATGCGCTGTAGAGCAGGATAAGAACACTCAAGAGGTATTCGCGCAAGTCAAGCAG
ATCTATAAGACTCCGCCGATCAAGGACTTCGGAGGTTCAACTTCTCTCAGATCTTGCCGGATCCGTCCAAACCGTCTA
AGAGATCTTTCATCGAGGACCTACTATTCAACAAAGTCACCCTAGCTGACGGCGGGATTCATCAAACAATACGGAGATTG
CTTGGGAGACATTGCGGGCGAGAGATCTAATTTGCGCGCAGATCTAATTTGCGCGCAGAAGTTAACGGATTGACAGTACTACCGCCGCTACTAACC
GATGAGATGATTGCGCAGTGATTGCGCAGTACACGTCTATTGGCGGGAACAATTACAAGTGGATGGACATTGGAGCCGGTGCC
GCTCTACAAATTCCGTTGCTATGCAAATGGGCGTACAGATTCAACGGAATCGGAGTAACCCAGAAACGTCTTGTACGAGA
ACCAGAAGCTAATCGGCAACCAGTTCAATTCCGGATCGGAAAGATCCGGAAAGATCCGGAAAGATCCTCAACCACTTGTCAAGCAACTATCCTCTAACTTCGG
GGGAAAGCTACAGGATGTAGTAAATCAAAACGCGCAGGCGCTAAACACCTTGTCAAGCAACTATCCTCTAACTTCGG
AGCGGATCTCGTCCGTCCTAAAGACATCTTATCCAGACTAGATAAGGTCGAAGCGGAGGTCCAGATCGATAGACTAAT
CACTGGAAGATTGCAGTCCCTACAGACTACGTAACACAGCTAACACACAGCAACTAATTAGACGCGGCGGGAGATTAGAGCCTCTGCTAA
TCTAGCTGCGACCAAGATGTCCGAATGTGTCTTGGGACAATCCAAGAGAGTGGACTTCTGCGGAAAGGGATACCACCT
AATGTCTTTCCCACAATCTGCGCCGGCGCCATGGGTGCGTATTCCTACATGTAACATATGTGCGGGCGCAAGAAAAGAACTTC
ACAACAGCTCCAGCTCCGATCGCCATGATGGAAAAGCTCATTCCCGAGAGAGGGAGTCTTTGTCTCTAACGGAACTCATT
GGTTCGTCGTCACCCAGAGAAACTTCTACGAGCCGCAGATCATCACCACCGACAACACATTCGTCTCGGGAAACTGCGACG
TGGTCATCGGAATCGTAAACAATACCGTTCTACGATCCGTTGCAGCCGGAACTAGACTCCTTCAAAGAAGAGTTGGACA
AGTACTTCAAGAACCACACCTCTCCGATGTGACTTGGGAGATATCTGGAGATATCTGGAGATGTGACTTGGGAGATATCTGGAGATCTCGGAATCAAGCGGTCCGTCGTCAACATCCA
GAAAGAAAATCGATAGATTGAACGAGGTCGGCGAAGAACTTGAACGAGTCCCTAATTGCTGGACTCCCTAATTGCTGGACTCATCTGGCTAGGAAAAT
ACGAGCAGTACATCAAGTGGCCGGTACATCTGGTACATCTGGCTAGGATTCATTGCGACTAATTGCGATCGTCATGGTCACCAT
CATGCTATGCTGTATGCATGTGTATGCTGTATGCATGTTCCTGCGGATCCTGTTGCAAGTT

End of S    C-tag

CGATGAAGATGATAGTGAACCGGTCCTAAAGGGGTGTCAAGCTACACTACACAG[agccagaggct]TAATAAtttttat

FIG. 13E

Stabilized S (SEQ ID NO: 145)

Vaccinia mH5 promoter                                                                 Kozak AAAAATTGAAAATAAATACAAAGGTTCTTGAGGGTTGTGTTAAATTGAAAGCGAGAAATAATCATAA|gccacc|

Stabilized S start

ATGTTCGTTGTTCCTAGTCTTCTCAGTGTGTAAACCTAACAAGGAGAACTAACAACTACCACCGG
CGTACACCAATTCTTCACAAGAGGAGTATATTACCCGGACAAGGTGTTCAGATCCTCCGTACTACATTCTACACAGA
CCTATTCCTACCGTTCTTCTCTAACGTAACATGGTTCCACGGGATCCATGTCTCTGGAACAAACGAAGAGATTC
GATAAACCCGGTCTTGCCGTTCAACGATGGTGTATACTTTGCGTCCACCGAGAAGTCCAACATCATCAGAGGATGGATCT
TCGGAACCACCTTGGATTCTAAGAACGACCCAGTCCTTGCTAATCGTCAACAAGCGACCAACGTCGTCATCAAAGTCTGCGA
ATTCCAGTTCTGTGTAACGACCCGGTTCTTGGGGAGTCTACTACCACACAAGAACAACAAGTCCTGGAATCCGAGTTCAGA
GTCTACTCTTCCGCGAACAACTGAGCACCTTCGAATATGTATCTCAGCCGGTTCCTAATGGACCTAGAGGGAAAGCAGGGAA
ACTTCAAGAAACCTAAGAGAGTTCGTATTCAAGAACATCGACGGATACTTCAAGATCTACTCCAAGCACACTCCGATCAA
CCTAGTTAGAGATCCACGCAAGGATCTCTGCGGCTAGAACCGTTAGTAGATTTGCCGATCGGAATCAACATCACCAGA
TTCCAGACAACTACTAGCGCTACACAGATCTTACCTAACGCCGGGAGATTCTTCTCTGAGGACTGCTGGTGCTGCGGG
CTTATTAGTAGGATAACCTACAGCCGAGAACCTTCCTATTGAAGTACAACGAAACCATCACCGATGCCGTAG
ATTGTGCTCTAGATCCGCTATCCGAAACGAAGTGCACCCTAAAGTCTTTCACCGTCGAGAAGGGAATCTACCAGACCTC
CAACTTTAGAGTACAGCCGACCGAATCCATCGTCGTCAGATTTCCGAACATCATCAGTCCGTTCGGAGAAGTGTTC
AACGGGACAAGATTTGGCGTCGTCTGTCTATGCGGTGGAACAGAAAAAGAATCAGTAACTGGTCGCGTCGGACTACTCCGTCCTAT
ACAACTCTGCCTCTTCTTCTCCACGTCAAATGCTACGGTGTATCTCCGACAAAGCTAAACGATCTATGCTTCACCAACGTC
TACGCGGACTCCTTCGTAATCAGAGGAGATGAAGTTAGACAGATTGGCGTGAAGTTAATTGCGTGAAATCGCAAGATCGGGATTAT
AACTACAAGTCACCGGACGACTTCACCGGAGTCTCAACCGGATGTGTAATTGCGTGAAGTGTAAGTCCAAAGTCGGAGGA
AACTACAACTACTGTACAGACTATTCAGAAAGTCCAACCTAAAGCCGTTCGAGAGACATCTCCACGAAATCTATC
AGGCTGGATCTACACCGTGTAATGGTGTCGAAGGATTCAACTGCTACTTCCCGCTACACTACAGTCTTACGGATTTCAACCGAC
AAACGGTGTAGGATATAGCCGTACAGAGTCGTGGAAGAACAAATGCGTCAACTTAACTTCAACGGACTAACCGGTGTCCTA
ACGGAATCTAACAAGAAGTTTCTACCGTTCCAGCAGTTCGGAAGAGATATGCGGGAAGAGATACAACAGAGCGCTGTCAGAGAT
CCGCAAACCTTGGAGATCCTAGATATCACACCGTGTCTTCGGTGGTCTCTGTAATTACTCCGGGAACGAACACCT
CCAATCAAGTAGCGGTACTATACCAGACGTGAACTGTACAGAAGTAACCGGTAGCTATTCACGCGGATCAACTAACAC
CAACTTGGAGAGTGTACTCCACGGATGTCTAATCGGTATTCCAAACAAGAGGCGGGGATGTCTAATCGGGGAACACGTAA
ACA

FIG. 14B

ACTCCTACGAATGTGATATCCCGATTGGAGCGGGGAATCTGTGCGTCTTACCAAACACAAACAAACTCTCCGAGAAGAG
CGAGATCTGTAGCCTCTCAATCTATTATGCCTACACCATGTCCTTGGGAGCCGGAAATTCTGTCGCGTACTCCAACAAT
TCTATCGGGATCCCGACAAACTTCACCATCTCTGTAACAACCGAGATCCTACCGGTGTCTATGACCAAGACATCTGTCG
ATTGCACCATGTACATCTGCGGAGATTCCACCGAGTGCTCCAACCTACTACTACAGTACGGATCTTTCTGTACCCAGCT
AAACAGAGGCGTTGACTGGAATCGCTGTGAGCAGGATAAGAACACTCAAGAGGTATTCGGCAAGTCAAGCAGATCTA
TAAGACTCCGCCGATCAAGGACTTCGGAGGTTCAACTTCTCTCAGATCTTGCCGGATCCGTCCAAACCGTCTAAGAGA
TCTTTCATCGAGGACCTACTATTCAACAAGTCACCTAGCTGACGCGGGATTCATCAACATACGGAGATTGCTTGG
GAGACATTGCGGCGGAGAGATCTAATTGCGCGCAGAAGTTTAACGGATTGACAGTACTACCGCCGCTACTAACCGATG
AGATGATTGCGCAGTACACGTCGTCTGCTCTATTGGCGGGAACAATTACAAGTGATGGACATTTGGAGCCGGTGCCGTCT
ACAAATTCCGTTGCTATGCAAATGGCGTACAGATTCAACGGCGTACAGATTCAAGGAGTAACCCAGAACGTCTTGTACGAGAACCA
GAAGCTAATCGGGAACCAGTTCAATTCGCGGATCGGAAAGATCCAGGACAGTCTATCTTCTACTGCTTCGGGGTTGGGA
AAGCTACAGGATGTAGTAAATCAAAACGGCGCAGGCGCTAAACACCTTGGTCAACGACCTATCCTCTCTAACTTCGGAGCG
ATCTCGTCCGTCTAAACGACATCTTATCCAGACTAGATCCCACCGGAAGCGGGAGGTCCAGATCGATAGACTAATCACT
GGAAGATTGCAGTCCCTACAGACCTACGTAACACAGCAACTAATTAGAGCGGGGAGATTAGAGCCTCTGCTAATCTA
GCTGCGACCAAGATGTCCGAATGTGTCTTGGGACAATCCAAGAGAGTGGACTTCTGCGGAAAGGGATACCCACCTAATG
TCTTTCCCACAATCTGCGCCGCATGGTCGTATTCGTACACATATGTGCCGGCGCAAGAAAAGAACTTCACAA
CAGCTCCAGCGATCGCATGCCATGATGGAAAAGCTCATTCCCGAGAGAGGGAGTCTTTGTCTCTAACGGAACTCATTGGTT
CGTCACCCAGAGAAACTTCTACGGCCAGATGGCCGCAGATCCAGCCGCACAACACACCATTCGTCTCGGAAAACTGCGACGTGGT
CATCGGAATCGTAAACAATACCGTCTACGATCCGGATGTGGACTTGGGAGATATCTCTGGAATCAACGGCTCCGTGCTCAACATCCAGAAA
CTTCAAGAACCACACCTCTCCCGGATGTGAACGAGGTCGCGAAGAACTTGAACGAGTCCCTAATCGACCTACAAGAGCTAGGAAAATACGA
GAAATCGATAGATTGAACGAGGTGCCGGTGGTACATCGGCCGTGGTACATCATTGCTAGGATTCATTGCTGACTAATTGCTGACATCCAGAA
GCAGTACATCAAGTGGCCGTGGTACATCGGGCTAGGATTCATTGCTGACATGGTCATGCGGATCCGTCACCATCATG
CTATGCTGTGATGACCTCGTATGACCTCCGTGCTCCTGTCTAAAGGGTGTCTAAGTCTACCACTACACTGCTGTTGCAAGTT

CGATGAAAGATGATAGTGAACCGGGTCCTAAAGGGGTGTCAAGCTACACTACACTGCTGTTGTTCCTGCGGATCCTGTTGCAAGTT

End of S    C-tag | gagccagaggct | TAATAAtttttat

FIG. 14C

Stabilized S (SEQ ID NO: 146)

Vaccinia mH5 promoter                                                    SmaI     Kozak AAAATTGAAAATAAAATACAAAGGTTCTTGAGGGTTGTGTTAAATTGAAAGCGAGAAATCATAA|CCCGGG|gccacc Stabilized S start ATG|TTCGTGTTCCTAGTCCTACTACCGGCTAGTCTCTTCTCAGTGTGTAAACCTAAACAACGAGAACACAACTACCACCGG
CGTACCACCAATTCTTTCACAAGAGGAGTATATTACCCGGACAAGGTGTTCAGATCCTCCGTACTACATTCTACACAGGA
CCTATTCCTACCGTTCTTCTTAACGTAACATGGTTCCACGCGATCCATGTCTCTGGAACAAACGGAACGAAGAGATTC
GATAAACCCGGTCTTGCCGTTCAACGATGGTGTATACTTTGCGTCCACGGAGAGTCAACATCATCAGAGGATGGATCT
TCGGAACCACCTTGGATTCTAAGACACCAGTCCTTGCTAATCGTCAACAAGCGACCAACGTCGTCATCAAGTCTGCGA
ATTCCAGTTCTGTAACGACCGGTTCTTGGGAGTCTACTACCACAAGAACAACAAGTCCTGGATGAATCCGAGTTCAGA
GTCTACTCTTCCGCGAACAACTGCACCTTCGTATTCAAGAACATGTATCTCAGCCGGTCCTAATGGACCTAGAGGGAAAGCAGGGAA
ACTTCAAGAACCTAAGAGAGTTCGTATTCAAGAACATCACGACGGATACTTCAAGATCTACTCCAAGCACACTCCGATCAA
CCTAGTTAGAGATCTACCGCAAGGATTCTCTGCGCTAGAACCGTTAGTAGTTGCCGATCGGAATCAACATCACCAGA
TTCCAGACACTACTAGCGCTACACAGATCTTACCTTACCTCCTATTGAAGTACAACGCCGGGAGATTCTTCTGGACTGCTGGTGCGGG
CTTATTATGTAGGATACCTCTAGATCCGCTATCGGAACGAAGTGCACCTAAAGTCTTTCACCGTCGGAAGGGAATCTACCAGACCTC
ATTGTGTCTAGATCCGCTATCCGAAACGAAGTGCACCTAAAGTCTTTCACCGTCGGAAGGGAATCTACCAGACCTC
CAACTTTAGAGTACAGCCGACCGAATCCATCGTCAGATTTCCGAACACATCACGAACCTATGTCCGTTCGGGAAGTGTTC
AACGCGACAAGAGATTGGCGTCTGCGTCTATGCGGTGGAACAGAAAAAGAATCAGTAACTCAGTAACTCCGTCGCGGACTACTCCGTCCTAT
ACAACTCTGCCTCTTCTCCAGTTCTCCAGTTCAAATGCTACGGTGTATCTCCGACAAAGCTAAACGATCTATGCTTCACCAACGTC
TACGCGGACTCCTTCGTAATCAGAGGAGATGAAGTTAGACAGATTGCGCCGGGACAAACTGGAAAGATCGGGATTAT
AACTACAAGCTACCGGACGACTTCACCGGACGACTTCACCGGATTGTAATTGCGGTGGAATTCGAACAACCTAGACTCCAAGTCGGAGGA
AACTACAACTACTACTGGTACACAGAGATCAGAAAGTCCAACCTAAAGCCGTTCGAGAGAGACATCTCCACGAAATCTATC
AGGCTGGATCTACACCGTGTAATGGTGTCGAAGGATTCAACTGCTACTTCCCGCTACACAGTCTTACGGATTTCAACCGAC
AAACGGTGTAGGATATCAGCCGTACGAGTCGTCGTACTATCCTTCGAACTACATGCTCCGCGACAGTATGTGGA
CCGAAAAGTCTACCAACCTAGTCAGAGAACAAATGGCTGTTCGGAAGATATCGCGAAGAGATATCGCGGATACAACCGGTGTCCTA
ACCGAATCTAACAAGAAGTTCTACCGTTCCAGCAGTTCGGAAGAGATATCGCGGATACAACAGACGCTGTCAGAT
CCGCAAACCTTGGAGATCCTAGATATCCAGATATCGCGTCTCTGGTGTCTTTCGGTGTCTTTCGGTGTCTTTCGGTGAATTACTCCGGGAACGAACACCT
CCAATCAAGTAGTAGCCGGTACTATACCAGGACGTGAACTGTACAGAAGTACCGGGTACTATTCACGCGGGATCCAACTAACAC

FIG. 14D

CAACTTGGAGAGTGTACTCCACCGGATCTAACGTATTCCAAACAAGAGCGGGATGTCTAATCGGAGCGGAACACGTAA
ACAACTCCTACGAATGTGATATCCCGATTGGAGCGGGAATCTGTGCGTCTTACCAAACAACAACAACTCTCCGAGAA
GAGCGGAGATCTGTAGCCTCTCAATCTATTATCGCCTACACCATGTCCTTGGGAGCCGAAAATTCTGTCGCGTACTCCAA
CAATTCTATCGCGATCCCGACAAACTTCACCACCATCTCTGTAACAACCGAGATCTACGGTGTCTATGCCAAGACATCT
GTCGATTGCACCATGTACATTGCGGAGATTCCACCGGAGTCGCCAACCTACTACTACAGTACGGATCTTTCTGTACCC
AGCTAAACAGAGCGGTTGACTGGAATCGCTGTAGAGCAGGATAAGAACACTCAAGAGGTATTCGCGCAAGTCAAGCAG
ATCTATAAGAACTCCGCGATCAAGGACTTCGGAGGTTTCAACTTCTCTCAGATCTGCGGGATCCGTCCAAACCGTCTA
AGAGATCTTTCATCGAGGACCTACTATTCAACAAAGTCACCCTAGCTGACGGGGATTCATCAAACAATACGGAGATTG
CTTGGGAGACATTGCGGCGAGAGATCTAATTTGCGCGCAGAGTTTAACGGATTGACAGTACTACCGCGCTACTAACC
GATGAGATGATTGGGCAGTACACGTCTGCTCTATTGGCGGGAACAATTACAAGTGGATGGACATTGGAGCGGGTGCC
GCTCTACAAATTCCGTTTGCTATGCAAATGGGCGTACAGATTCAACGGAATCGGAGTAACCCAGAACGTCTTGTACGAGA
ACCAGAAGCTAATCGCGAACCAGTTCAATTCAAACAAACGGCGGCGGTAAACACCTTGGTCAAGCAACTATCCTCTAACTTCGG
GGGAAAGCTACAGGATGTAGTAATCAAAACGACGGCGGGCGCTAAACACCTTGGTCAAGCAACTATCCTCTAACTTCGG
AGCGGATCTCGTCCGTCCTAAACGACATCTTATCCAGACTAGATCCACCGGAAGCGGGAGGTCCAGATCGATAGACTAAT
CACTGGGAAGATTGCAGTCCCTACAGACCTACGTAACACAGCAACTAATTAGAGCGGCGGAGATTAGAGCCTCGCTAA
TCTAGCTGCGACCAAGAGTGCCAAGATCCGAATGTGTCTTGGGACAATCCAAGAGAGTGGACAATATGTGCCGGAAAGGGATACCACCT
AATGTCTTTCCCACAACTCTCGCGCCCGCATGGTCGTATTCCTACACATGTAACATATGTGCCGGGCGCAAGAAAAGAACTTC
ACAACAGTCCAGCGATCTGCCATGATGGAAAAGCTCATTCCCGAGAGAGGGAGTCTTTGTCTCTAACGAACTCATT
GGTTCGTCACCCAGAGAAACTTCTACGAGCCGCAGATCATCACCGACAACACATTCGTCTCGGGAAACTGGGACG
TGGTCATCGATGGCAAATCGTAAACAATACCGTCTACGATCCGTTGCAGCGGGACTTGGGAGATATCTCTGGAATCAAAGAGAGTTGGACA
AGTACTTCAAGAACCACACCTCTCCGATGTGGCCGCGTGTCGGGAAGAACTTGAACGAGGTCGCCTACAAGAGCTAGGAAAAT
GAAAGAAATCGATAGATTGAACGGACGTCGCGAAGAACTTGAACGAGGTCCCTAATCGACCTACAAGAGCTAGGAAAAT
ACGAGCAGTACATCACAGTGCGCCGGTTACATCTGGCTAGGATTCATTGCTGACTAATTGCGATCGTCATGGTCACCAT
CATGCTATGCTGTATGACCTCCGTGTTCCTGTCTAAAGGGATTGTTCCTGCGGATCCGTGTTGCAAGTT

End of S   C-tag [agccagaggct]TAATAAtttttat

CGATGAAGATGATAGTGAACCGGTCCTAAAGGGTGTCAAGTCTACAAGCTACACTACACACAG

FIG. 14E

Truncated S (SEQ ID NO: 147)

Vaccinia mH5 promoter                          Kozak

AAAAATTGAAAATAAATACAAAGGTTCTTGAGGGTTGTGTTAAATTGAAAGCGAGAAATAATCATAAgccacc

Truncated S Start

ATGTTCGTTCGTGTTCCTAGTCCTACTACCGGTCCTAGTCTCTTCTCAGTGTGTAAACCTAACAACGAGAACACAACAACTACCACCGG
CGTACACCAATTCTTCACAAGAGGAGTATATTACCCGGACAAGGTGTTCAGATCCTCCGTACTACATTCTACACAGA
CCTATTCCTACCGGTCTTCTCTCTAACGTAACATGGTTCCACGGGATCCATGTCTCTGGAACAAACGAAGGAAGAGATTC
GATAAACCCGGTCTTGCCGTTCAACGATGGTGTATACTTTGCGTCCACCGAGAAGTCCAACATCATCAGAGGATGGATCT
TCGGAACCACCTTGGATTCTAAGACCCAGTCCTTGCTAATCGTCAACAAGAACAACAAGTCCTGGATGAATCCGAGTTCAGA
ATTCCAGTTCTGTAACGACCCGGTTCTTGGGAGTCTACTACCACAAGAACCGTCCTAATATGTATCTCAGCCGGTCCTAAGGA
GTCTACTCTTCCCGCGAACAACCTAAGAGAGTTCGTATTCAAGAACATCAGACGGATACTTCAAGATCTACTCCAAGCCACACTCCGATCAA
CCTAGTTAGAGATCTACCGCAAGGATTCTCTGCGGCTAGAACCGTTAGTAGATTTGCCGATTCGGAATCAACATCACCAGA
TTCCAGACACTACTAGCGCGCTACACAGATCTTACCTAACGCCGGGAGATTCTTCTCGATGGACTGCTGCTGCGCGG
CTTATTATGTAGGATACCTACAGCCGAGAACCTTCCTATTGAAGTACAACGAAACCATCACCGATGCCGGTAG
ATTGTGCTCTAGATCCGCTATCCGAAACGAAGTGCACCCTAAAGTCTTTCACCGTCGAGAAGGGAATCTACCAGACCTC
CAACTTTAGAGTACAGCCGACCGAATCCATCGTCGTCAGATTCCGAACATCATCGTCCGTTCGGGAGAAGTGTTC
AACGGGACAAGATTTGGGTCTGTCGTCTATGCGGTGGAACAGAAAAAGAATCAGTAACTGTAACTGTACTCCGTCCTAT
ACAACTCTGCCTCTTCTTCTCCACGTCAAATGCTACGGTGTATCTCCGACAAAGCTAAACGATCTATGCTTCACCAACGTC
TACGCGCGACTCCTGACTTCGTAATCAGAGGAGATGAAGTTAGACAGATTGCGCGGACAAACTGAAAGATCGCGGATTAT
AACTACAAGTCACCGGACGACTTCACCGGATGTGTAATTGCGTGGAAATTGGCGTAGAACTCCAAGTCGGAGGA
AACTACAACTACTTGTACAGAACTATTCAGAAAGTCCAACCTAAAGCCGTTCGAGAGAGACATCTCCACGAAATCTATC
AGGCTGGATCTACACCGGTAATGGTGTCGAAGGATTCAACTGCTACTTCCCGCTACTACACCGGATTTCAACCGAC
AAACGGTGTAGGATATCAGCCGTACAGAGAGTCCGTACGAGAACAAATGCGTCAACTTAACTTCAACGGACTAACCGGTGTCCTA
ACCGAATCTAACAAGAAGTTTCTACCGTTCCAGCAGTTCGGAAGAGATATCGCGGAAGATACAACAGAGCGCTGTCAGAGAT
CCGCAAACCTTGGAGATCCTAGATATCACACACCGTGTTCTTCGGTGGTCTGTCTGTAATTACTCCGGGAACGAACACCT
CCAATCAAGTAGCGGTACTATACCAGGACGTGAACTGTACAGAACTGGTAGAGAAGTACCGGTAGCTATTCACGCGGATCAACTAACAC
CAACTTGGAGAGTGAGTGTACTCCACCGGATCTAACGTATTCCAAACAGAGGCGGGATGTCTAATCGGGGAGCGGGAACACGTAA

FIG. 15B

ACAACTCCTACGAATGTGATATCCGATTGGAGCGGGAATCTGTGCGTCTTACCAAACACAAACAAACTCCGAGAA
GAGCGAGAGATCTGTAGCCTCCTCTCATTCTATTATCGGCCTACACCATGTCCTTGGGAGCCGAAAATTCTGTCGGCGTACTCCAA
CAATTCTATCGCGATCCGACAAACTTCACCATCTCTGTAACAACCGAGATCCTACCGGTGTCTATGACCAAGACATCT
GTCGATTGCACCATGTACATCTGCGGAGATTCCACCGGAGATTCCAACCTACTACTACAGTACGGATCTTTCTGTACCC
AGCTAAACAGAGCGTTGACTGGAATGCGTGTAGAGCAGGATAAGAACACTCAAGAGGTATTCGCGCAGTCAAGCAG
ATCTATAAGAGACTCCGCGATCAAGGACTTCGGAGGTTCAACTTCTCCAGATCTTGCCGGATCCGTCCAAACCGTCTA
AGAGATCTTTCATCGAGGAGGACCTACTATTCAACAAAGTCACCCTAGCTGACGCGGGGATTCATCAAACAATACGGAGATTG
CTTGGGAGACATTGCGGCGGAGAGAGATCTAATTTGCCGGCGCAGAAGTTTAACGGATTGACAGTACTACCGGCGCTACTAACC
GATGAGATGATTGCGCAGTACACGTCTCTATTGGCGGTACAGATTCAACGGAATCAATTACAAGTGGATGGACATTGGAGCCGGTGCC
GCTCTACAAAATTCCGTTTGCTATGCAAATGGGCGTACAGATTCCCGCGATCGGAAAGATCCAGGACAGTCTATCTTCTACTGCTTCGGCGTT
ACCAGAAGCTAATCGCGAACCAGTTCAATTCCCGCGATCGGAAAGATCCAGGACAGTCTATCTTCTACTGCTTCGGCGTT
GGGAAAGCTACAGGATGTAGTAATCAAAACGCGCAGGCGTAAACACCTTGGTCAAGCAACTATCCTCTAACTTCGG
AGCGGATCTCGTCCGTCCTAAACGACATCTTATCCAGACTAGGTCGAAGGGAGGTCCAGATCGATAGACTAAT
CACTGGAAGATTGCAGTCCCTACAGACTCCCTACGACTACGTAACACAGCAACTAATTAGAGCGCGGAGATTAGAGCCCTCTGCTAA
TCTAGCTGCGACCAAGATGTCCGAATGTCTTGGGACAATCCAAGAGAGTGGACTTCTGCGGAAAGGGATACCACCT
AATGTCTTTCCCACAATCTCGCGCCGCATGGTGTCGTATTCCTACATGTAACATATGTGCCGGGCGCAAGAAAAGAACTTC
ACAACAGCTCCAGCGCTCCAGCGATCTGCCATGATGGAAAAGCTCATTTCCCGAGAGAGGAGAGTCTTTGTCTCTAACGGAACTCATT
GGTTCGTCGTCACCCAGAGAAACTTCTACGAGCCGCAGATCATCACCAACAACATTCGTCTCGGGAAACTGGGACG
TGGTCATCGGAATCGTAAACAATACCGTCTACGATCCGTTGCAGCCGGAACTAGACTCCTTCAAAGAAGAGTTGGACA
AGTACTTCAAGAACCACCACCCTCTCCGATGTGGGACTTGGGAGGATATCTCGGAGAATCAACGCGTCCGTCGTCAACATCCA
GAAAGAAATCGATATAGATAGATTGAACGAGTCGCGAAGAACTTGAACGAGTCCCTAATCGACCTACAAGAGACTAGAGAAAAT
ACGAGCGAGT

Truncated S end C-Tag
ACATCAAGTGGCCG|gagccggaagct|TAATAAAtttttat

FIG. 15C

Truncated S (SEQ ID NO: 148)

Vaccinia mH5 promoter                                    SmaI    Kozak
AAAATTGAAAATAAATACAAAGGTTCTTGAGGGTTGTGTTAAATTGAAAGCGAGAAATAATCATAA CCCGGG gccacc Truncated S Start
ATG TTCGTTGGTGTTCCTAGTCCTACTACCGGTCTAGTCTCTTCTCAGTGTGTAAACCTAACGAGAACAACTACCACCGG
CGTACACCAATTCTTCACAAGAGGAGTATATTACCCGGACAAGGTGTTCAGATCCTCCGTACTACATTCTACACAGA
CCTATTCCTACCGGTTCTTCTCTAACGTAACATGGTTCCACGGATCCATGTCTCTCGGAACAAACGAAGGAGAGATTC
GATAAACCCGGTCTTGCCGTTCAACGATGGTGTATACTTTGCGTCCACCGAGAAGTCCACAACATCATCAGAGGATGGATCT
TCGGAACCACCTGGATTCTAAGACCAGTCCTTGCTAATCGTCAACAAGAACAACAAGTCCTGGAATCCGAGTTCAGA
ATTCCAGTTCTGTAACGACCCGTTCTTGGGAGTCTACTACCACCAGAACATATGTATCTCAGCCGGTCCTAATGGACCTAGAGG
GTCTACTCTTCCCGCGAACAACTAAGAGAGTTCGTATTCAAGAACATCGACGGATCACTTCAAGATCTACTACTCCAAGCACTCCGATCAA
ACTTCAAGAACCTAAGAGAGTTCGTATTCAAGAACATCGACGGATCACTTCAAGATCTACTAGTGGAATCGGAATCAACATCACCAGA
CCTAGTTAGAGATCTACCGCAAGGATCTCTGCGCTAGAACCGTTAGTAGAACCGTTAGTTGCCGATTCAGTTGCCGTGCTGCGGG
TTCCAGACACTACTAGCGCTACACAGATCTTACCTAACCGCCGGGAGATTCTTCTCTGATGGACTGCTGCTGGTGCTGCGGG
CTTATTATGTAGGATACCTACAGCCGGAGAACCTTCCTATTGAAGTACAAACGAAACCATCACCGATGCCGGTAG
ATTGTGCTCTAGATCCGCTATCCGAAACGAAGTGCACCCTAAAGTCTTTCACCGTCGAGAAGGGAATCTACCAGACCTC
CAACTTTAGAGTACAGCCGACCGAATCCATGTCGTCAGATTTCCGAACATCATCACGACAACCTATGTCCGTTCGGAGAAGTGTTC
AACGGGACAAGATTTGGCGTCGTGTCTATGCCGTGGAACAGAAAAGAATCAGTAACTGTAACTCAGCGTCGCGACTACTCCGTCCTAT
ACAACTCTGCCTCTTCTTCTCCACGTCAAATGCTACGGTGTATCTCCGACAAAGCTAAACGATCTATGCTTCACCAACGTC
TACGCGGACTCCTTCGTAATCAGAGGAGATGAAGTTAGACAGATTGGCGTGAAGTTAGAAGATCGCGGATTAT
AACTACAAGTCACCGGACGACTTCACCGGAGTGGAATTGCGTGGAATTCGAACAACTAGACTCCAAGTCGGAGGA
AACTACAACTACTTGTACAGACTATTCAGAAAGTCCAACCTAAAGCCGTTCGAGAGAGACATCTCCACGAAATCTATC
AGGCTGGATCTACACCGTGTAATGGTGTCGAAGGATTCAACTGCTACTTCCCGCTACTACATCGGATTTCAACCGAC
AAACGGTGTAGGATATGCAGCCGTACAGAGTCGTACGTAATGGCGAAGAACAAATGCGTCAACTTAACTTCAACCGGTGTCCTA
ACGGAATCTAACAAGAAGTTTCTACCGTTCCAGCAGTTCGGAAGAGATATGCGGGATACAACAGAGCGCTGTCAGAGAT
CCGCAAACCTTGGAGATCCTAGATATCACCACCGTGTCTTTCGGTGGTCTCTGTAATTACTCCGGGAACGAACACCT
CCAATCAAGTAGCGGTGTACTATACCAGGACGTGAACTGTACAGAACTGTACAGAGGTACCGGTAGCTATTCACGCGGATCAACTAACAC
CAACTTGGGAGAGTGTACTCCACCGGATCTAACGTATTCAACCGGATCTAACGTATTCCAAACAAGAGGCGGGATGTCTAATCGGGGAACACGTAA

FIG. 15D

ACAACTCCTACGAATGTGATATCCGATTGGAGCGGGAATCTGTGCGTCTTACCAAACACAAACAAACTCCGAGAA
GAGCGAGAGTCTGTAGCCTCTCAATCTATTATCGGCCTACACCATGTCCTTGGGAGCCGAAAATTCTGTCGGCGTACTCCAA
CAATTCTATCGCGATCCCGACAAACTTCACCATCTCTGTAACAACCGAGATCCTACCGGTGTCTATGACCAAGACATCT
GTCGATTGCACCATGTACATCTGCGGAGATTCCACCGGAGATCCAACCTACTACAGTACGGATCTTTCTGTACCC
AGCTAAACAGAGCGGTTGACTGGAATGCGTGTAGAGCAGGATAAGAACACTCAAGAGGTATTCGCGCAGTCAAGCAG
ATCTATAAGACTCCGCCGATCAAGGACTTCGGAGGTTCAACTTCTCAGATCTTGCCGGATCCGTCCAACCGTCTA
AGAGATCTTTCATCGAGGACCTACTATTCAACAAAGTCACCCTAGCTGACGGCGGGATTCATCAAACAATACGGAGATTG
CTTGGGAGACATTGCGGCGGAGAGATCTAATTTGCCGCGCAGAAGTTTAACGGATTGACAGTACTACCGCCGCTACTAACC
GATGAGATGATTGCGCAGTACACGTCTCATTGGCGGAACAATTACAAGTGGATGGACATTGGAGCCGGTGCC
GCTCTACAAATTCCGTTTGCTATGCAAATGGCGTACAGATTCAACGGAGTAACCCAGAACGTCTTGTACGAGA
ACCAGAAGCTAATCGCGAACCAGTTCAATTCCCGCGATCGGGAAAGATCCAGGACAGTCTATCTTCTACTGCTTCGGCGTT
GGGAAAGCTACAGGATGTAGTCAAATCAAAACGCGCAGGCGTAAACACCTTGGTCAAGCAACTATCCTCTAACTTCGG
AGCGGATCTCGTCCGTCCTAAACGACATCTTATCCAGACTAAGGTCGAAGGGAGGTCCAGATCGGATAGACTAAT
CACTGGAAGATTGCAGTCCCTACAGACTCCGAATGTGTCTTGGGACAATGTTAACACAGCAACTAATTAGAGCGCCTCTGCTAA
TCTAGCTGCGACCAAGATGTCCGAATGTCTTGGGACAATCGCAAGGAGAGTGGACTTCTGCGGAAAGGGATACCACCT
AATGTCTTTCCCACAATCTCGCGCGCCGCATGGTTGTCGTATTCCTACACATATGTGCCGGGCGCAAGAAAAGAACTTC
ACAACAGCTCCAGCGATCTGCCATGTGCCATGATGGAAAAGCTCATTCCCGAGAGAGGGAGTCTTTGTCTCTAACGAACTCATT
GGTTCGTCGTCACCCAGAGAAACTTCTACGAGCCGCAGATCATCACCACGACAACACATTCGTCTCGGGAAACTGGGACG
TGGTCATCGGAATCGTAAACAATACCGTCTACGATCCGTTGCAGCCGAACTAGACTCCTTCAAAGAAGAGTTGGACA
AGTACTTCAAGAACCACCACCCTCTCCGATGTGGGACTTGGGACTTGGGAGATATCTCTGGGAGGTCGTCAACATCCA
GAAAGAAATCGATAGATAGATTGAAACGAACTTGAAGCTCCCTAATCGACCTACAAGAGCTAGGAAAAT
ACGAGCAGT

Truncated S end     C-Tag
ACATCAAGTGTGGCCCG|gagccggaagct|TAATAAttttat

FIG. 15E

Truncated S + K986P and V987P (SEQ ID NO: 149)

Vaccinia mH5 promoter        Kozak

AAAAATTGAAAATAAAAATACAAAAGGTTCTTGAGGGTTGTGTTAAATTGAAAGCGAGAAATAATCATAA | gccacc

Truncated S Start

ATG | TTCGTGTGTTCCTAGTCCTACTACCGCTAGTCCTCCTTCTCAGTGTGTGTAAACCTAACAACGAGAACAACTACCACCGG
CGTACACCAATTCTTTCACAAGAGGAGTATATTACCCGGACAAGGTGTTCAGATCCTCCGTACTACATTCTACACAGGA
CCTATTCCTACCGTTCTTCTCTAACGTAACATGGTTCCACGCGATCCATGTCTCTGGAACAAACGGAACGAAGAGATTC
GATAACCCGGTCTTGCCGTTCAACGATGGTGTATACTTTGGCGTCCACCGAGAAGTCCAACATCATCAGAGGATGGATCT
TCGGAACCACCTTGGATTCTAAGAACCAGTCCTTGCTAATCGTCAACAACGCGACCAACAAGTCCTGGATGAATCCGCGA
ATTCCAGTTCTGTAACGACCCGTTCTGGGAGTCTACTACCACAAGAACAACAAGTCCTGGAATCCGAGTTCAGA
GTCTACTCTTCCGGCGAACAACTGCACCTTCGAATCATCTCCGCCGTATTCAAGAACATCGACGGATACTTCAAGATGGAAAGCAGGAA
ACTTCAAGAAACCTAAGAGAGTTCGTATCTACCGCAAGGATTCTCTGCGCTAGAGTCTAGAACGCGTAGTCCGATCAA
CCTAGTTAGAGATCTACCGGCGTACACAGATCTTACCTAACGCCGGGAGATTCTCTTGGACTGCTGGTGCTGCGG
TTCCAGACACTACTAGGATAACCTACCAGCCGAGAACCTTCCTATTGAAGTACAACGGAACCATCACCGATGCCGTAG
ATTGTGCTCTAGATCCGCTATCCGAAACGAAGTGCACCCTAAAGTCTTTCACCGTCGAGAAGGGAATCTACCAGACCTC
CAACTTTAGAGTACAGCCGACCGGAATCCCATCGTCGTCAGATTTCCGAACACAGAAAAAGAATCAGTAACTGGGAGAAGTGTTC
AACGGGACAAGATTGGCGTCGTCTATGCGGAACAGAAAAAGAATCTCCGACAAAGCTAAACGATCTATGCTTCACCAACGTC
ACAACTCTGCCCTCTTCTCCACGTCAAATGCTACGGGTGTATCTCCGACAAAGCTAAACGATCTATGCTTCACCAACGTC
TACGCGCGACTCCTTCGTAATCAGAGGAGAGAAGTTAGACACAGATTGCGCCGGGACAAACTGGAAAGATCGCGGATTAT
AACTACAAGCTACCGGACGACTTCACCGGATGTAATTGGCGTGAATTGGGAATTGGAATTGTGCCAGTCGGAGGA
AACTACAACTACTTGTACAGACTATTCAGAAGACTATTCAGAAGTCCAACCTAAAGCCGTTCGAGAGAGACATCTCCACGAAATCTATC
AGGCTGGATCTACACCGTGTAATGGTGTGCGAAGGATTCAACTGCTACTTCCCGCTACTACATGGACTACTACATGGACTACAGTATGTGGA
AAACGGGTGTAGGATATCAGCCGTACAGAGTCGGTACAGAGTCGGTACTATCCTTCGAACTACATCCTTCGAACTTAACTTCAACGGACTAACGGGTCCTA
CCGAAAAAGTCTACCAACCTAGTCAAGAACAAATGCGTCAACTTAACTTCAACGGACTAACGGCGTGTCAGAGAT
ACCGAATCTAACAAGAAGTTTCTACCGTTCCAGCAGTTCGGAAGAGATATCGCGGAATACAACAGAGCGTGTCAGAGAT
CCGCAAACCTTGGAGATCCTAGATATCACCAGGACGTGAACTGTACAGAAGTACCGGTGAACTGTACAGAAGTACCGGTCTCGTAATTACTCCGGGAACGAACACCT
CCAATCAAGTAGCGGTACTATACCAGGACGTGAACTGTACAGAAGTACCGGTAGCTATTCACGCGGATCAACTAACAC
CAACTTGGAGAGTGTTACTCCACCGGATCTAACGTCTATTCCAAACAAGAGGCGGGATGTCTAATCGGCTAACGGGAACACGTAA

FIG. 15G

ACAACTCCTACGAATGTGATATCCGATTGGAGCGGGAATCTGTGCGTCTTACCAAACACAAACAAACTCCGAGAA
GAGCGGAGATCGTAGCCTGCTCTCAATCTATTATCGCCTACACACCATGTCCTTGGGAGCCGAAAATTCTGTCGGCGTACTCCAA
CAATTCTATCGCGATCCGACAAACTTCACCATCTCGTAACAACCGAGATCCTACCGGTGTCTATGACCAAGACATCT
GTCGATTGCACCATGTACATCTGCGGAGATTCCACCGAGTGCTCCAACCTACTACTACAGTACGGATCTTTCTGTACCC
AGCTAAACAGAGCGTTGACTGGAATCGCTGTAGAGCAGGATAAGAACACTCAAGAGGTATTCGCGCAGTCAAGCAG
ATCTATAAGACTCCGCCGATCAAGGACTTCGGGAGGTTCAACTTCTCTCAGATCTTGCCGGATCCGTCCAAACCGTCTA
AGAGATCTTTCATCGAGGACCTACTATTCAACAAAGTCACCCTAGCTGACGCGGGATTCATCAAACAATACGGAGATTG
CTTGGGAGACATTGCGCGGCAGAGATCTAATTTGCGCGCAGAAGTTTAACGGATTGACAGTACTACCGCGCCTACTAACC
GATGAGATGATTGCGCAGTACACGTCTGCTCTATTGGCGGGAACAATTACAAGTGGATGGACATTGGAGCCGGTGCC
GCTCTACAAATTCCGTTTGCTATGCAAATGGGGTACAGATTCAACGGAATCGGAGTAACCCAGAAACGTCTTGTACGAGA
ACCAGAAGCTAATCGCGAACCAGTTCAATTCCGCGATCGGAAAGATCCCAGGACCAGTCTATCTTCTTCTACTGCTTCGGCGTT
GGGAAAGTCTACAGGATGTAGTAAATCAAAACGCGCAGGCGCTAAACACCTTGGTCAAGCAACTATCCTCTAACTTCGG
AGCGGATCTCCGTCCGTCCTAAACGACATCTTATCCAGACTAGAT[CCACCG]GAAGCGGGAGGTCCAGATCGATAGACTAAT
CACTGGAAGATTGCAGTCCCTACCAGACCTACGTAACACACAGCAACTAATTAGAGCGGCGGAGATTAGAGCCTCTGCTAA
TCTAGCTGCGACCAAGAGATGTCGGAACAATCCAAGAGAGTGCGACTTCTGCGGAAAGGGATACCACCT
AATGTCTTTCCCACAATCTGCGCCGCATGGTGTCGTATTCCTACACATGTAACATATGTGCGGGCGCAAGAAAAGAACTTC
ACAACAGCTCCAGCGATCTGCCATGATGGAAAAGCTCATTCCCGAGAGGGAGTCTTTGTCTCTAACGGAACTCATT
GGTTCGTCACCCAGAGAAAACTTCTACGGAGCCGCAGATCACCACCGACAACACATTCGTCTCGGGAAACTGCGACG
TGGTCATCGGAATCGTAAACAATACCGTCTACGATCCGTTGCAGCCGGAACTAGACTCCTTCAAAGAAGAGTTGGACA
AGTACTTCAAGAACCACCACCCTCTCCGGATGTGGGACTTGGGAGATATCTCTGAATCAACGGCGTCCGTCGTCAACATCCA
GAAAGAAATCGATAGATTGAACGAGGTCGGCGAAGAACTTGAACGAGTCCCTAATCGACCTACAAGAGCTAGGAAAAT
ACGAGCAGT

Truncated S end    C-Tag
ACATCAAGTGGCCC[G][gagccggaagct][TAATAAttttat]

FIG. 15H

Truncated S + K986P and V987P (SEQ ID NO: 150)

Vaccinia mH5 promoter                                          SmaI    Kozak

AAAAATTGAAAATAAAATACAAAGGTTCTTGAGGGTTGTGTTAAATTGAAAGCGAGAAATAATCATAA|CCCGGG|gccacc Truncated S Start ATG|TTCGTGTGTTCCTAGTCCTACCGGTCCTAGTCTCTCTTCTCAGTGTGTGTAAACCTAACAACGAGAACAACTACCACCGG
CGTACACCAATTCTTTCACAAGAGGAGTATATTACCCGGACAAGGTGTTCAGATCCTCCGTACTACATTCTACACAGGA
CCTATTCCTACCGTTCTTCTCTAACGTAACATGGTTCCACGCGATCCATGTCTCTGGAACAAACGGAACGAAGAGATTC
GATAACCCGGTCTTGCCGTTCAACGATGGTGTATACTTTGGCGTCCACGGAAGTCCAACATCATCAGAGGATGGATCT
TCGGAACCACCTTGGATTCTAAGGACCCAGTCCTTGCTAATCGTCAACAACGCGACCAACGTCGTCATCAAAGTCTGCGA
ATTCCAGTTCTGTAACGACCCGTTCTGGGAGTCTACTACCACAAGAACAACAAGTCCTGGATGGAATCCGAGTTCAGA
GTCTACTCTTCCCGGCGAACAACTGCACCTTCGAATATGTATCTCAGCCGTCCTAATGGACCTAGAGGGAAAGCAGGGAA
ACTTCAAGAACCTAAGAGAGTTCGTATTCAAGAACATCGACGGATCTTCAAGATCTACTCCAAGCACACTCCGATCAA
CCTAGTTAGAGATCTACCGCAAGGATTCTCTGCGCTAGAACGTTAGTAGTTGCCGATCGGAATCAACATCAACCAGA
TTCCAGACACTACTAGCGCTACCTACACAGCCGGTACCTATCCGAAGTACCTTCCTATTGAAGTACAAACGGAACCATCACCGATGCCGGTAG
CTTATTATGTAGGATAACCTACAGCCAGCTAGATCCGCTATCCGACCGGAATCCCATCGTCGTCAGATTTCCGAACGAAGGGAATCTACCAGACCTC
AACGGGACAAGATTGCGTCGTCGTCTATGCGGTGGAACAGAAAAAGAATCAGTAACTGCGACTACTCCGTCCTAT
ACAACTCTGCCCTCTTTCTCCACGTCAAATGCTACGGTGTATCTCCGACAAAGCTAAACGATCTATGCTTCACCAACGTC
TACGCGCGACTCCTTCCTTCGTAATCAGAGGAGTGAAGTTAGACACAGATTGCGCCGGGACAAACTGGAAAGATCGCGGATTAT
AACTACAAGCTACCGACGACTTCACCGGATGGTAATTGGCGTGGAATTGCAACAACCTAGACTCCAAAGTCGGGAGGA
AACTACAACTACTTGTACAGACTATTCAGAAGCTATTCAGAAAGTCCAACCTAAAGCCGTTCGAGAGAGACATCTCCACGAAATCTATC
AGGCTGGATCTACACCGTGTAATGGTGTCGAAGGATTCAACTGCTACTTCCCGCTACTACAGTCTTACGGATTTCAACCGAC
AAACGGGTGTAGGATATCAGCCGTACAGAGTCGGTCGTCTATCCTTCGAACTATCCTTCAACTTCAACGGACTAACGCAGTATGTGGA
CCGAAAAAAGTCTACCAACCTAGTCAAGAACAAATGCGTCAACTTCAACGGACTAACCGGTGTCCTA
ACCGAATCTAACAAGAAGTTTCTACCGTTCGGAAGAGAGAGATATCGCGGAAGATACAACAGAGCGCTGTCAGAGAT
CCGCAAACCTTGGAGATCCTAGATATCACCAGGACGTGAACTGTACAGAAGTACCGGTCTCGTAATTACTCCGGGAACACACCT
CCAATCAAGTAGCCGGTACTATACCAGGACGTGAACTGTACAGAAGTACCGGTCTATTCACGCGGATCAACTAACAC
CAACTTGGAGAGTGTACTCCACCGGATCTAACGTCTATTCCAAACAAGAGGGGGGATGTCTAATGCGGTGTAATCGGAGCGGGAACGTAA

FIG. 15I

```
ACAACTCCTACGAATGTGATATCCCGGATTGGAGCGGGGAATCTGTGCGTCTTACCAAACACAACAAACAAACTCCGAGAA
GAGCGGAGATCTGTAGCCTCTCAATCTATTATGCGCTACACCATGTCCTTGGGAGCCGAAAATTCTGTCGGCGTACTCCAA
CAATTCTATCGCGATCCCGACAAACTTCACCATCTCTGTAACAACCGAGATCCTACCGGTGTCTATGACCAAGACATCT
GTCGATTGCACCATGTACATCTGCGGGAGATTCCACCGAGGTGCTCCAACCTACTACTACAGTACGGATCTTTCTGTACCC
AGCTAAACAGAGACGGTTGACTGGAATCGCTGTAGAGCAGGATAAGAACACTCAAGAGGTATTCGCGCAGTCAAGCAG
ATCTATAAGACTCCGCCGATCAAGGACTTCGGGAGGTTCAACTTCTCTCAGATCTTGCCGGATCCGTCCAAACCGTCTA
AGAGATCTTTCATCGAGGACCTACTATTCAACAAAGTCACCCTAGCTGACGCGGGATTCATCAAACAATACGGAGATTG
CTTGGGAGACATTGCGCGGCGAGAGATCTAATTTGCGCGCAGAAGTTTAACGGATTGACAGTACTACCGCGCCTACTAACC
GATGAGATGATTGCGCAGTACACGTCTGCTCTATTGGGCGGGAACAATTACAAGTGGATGGACATTGGAGCCGGTGCC
GCTCTACAAATTCCGTTTGCTATGCAAATGGGGTACAGATTCAACGGAGTAACCCAGAACGTCTTGTACGAGA
ACCAGAAGCTAATCGCGAACCAGTTCAATTCCCGCGATCGGAAAGATCCCAGGACCAGTCTATCTTCTACTGCTTCGGCGTT
GGGAAAGTACAGGATGTAGTAAATCAAAAACGGCGCAGGCGCTAAACACTTGGTCAAGCAACTATCCTCTAACTTCGG
AGCGGATCTCGTCCGTCCTAAACGACATCTTATCCAGACTAGAT[CCACCG]GAAGCGGAGGTCCAGATCGATAGACTAAT
CACTGGAAGATTGCCAGTCCCTACCAGACTAACACAGCAACTAATTAGAGCGGCGGAGATTAGAGCCTCTGCTAA
TCTAGCTGCGACCAAGAGATGTCCGAATGTCTTGGGACAATCCAAGAGAGTGCGGACTTCTGCGGAAAGGGATACCACCT
AATGTCTTTCCCACACAATCTGCGCCCGCATGGGTGTCGTATTCCTACACATGTAACATATGTGCCGGGCGCAAGAAAAGAACTTC
ACAACAGCTCCAGCGATCTGCCATGATGGAAAAGCTCATTCCCGAGAGAGGAGTCTTTGTCTCTAACGGAACTCATT
GGTTCGTCACCCAGAGAAACTTCTACGGAGCCGCAGATCATCACCACGACAACACATTCGTCTCGGGAAACTGGCGACG
TGGTCATCGGAATCGTAAACAATACCGTCTACGATCCGTTGCAGCCGGAACTAGACTCCTTCAAAGAGGAGTTGGACA
AGTACTTCAAGAACCACCACCTCTCCGGATGTGGGAGACTGGGGAGATATCTCTGAATCAACGGCTCCGGTCCGTCAACATCCA
GAAAGAAATCGATAGATTGAACGAGGTCGCGAAGAACCTTGAACGAGTCCCTAATCGACCTACAAGAGCTAGGAAAAT
ACGAGCCAGT
```

Truncated S end    C-Tag

ACATCAAGTGGCCCG[gagccggaagct][TAATAA]Attttat

VACCINES AND USES THEREOF TO INDUCE AN IMMUNE RESPONSE TO SARS-CoV2

CROSS-REFERENCE TO RELATED APPLICATIONS

This application is a continuation of International Patent Application No. PCT/US2021/018033, filed Feb. 12, 2021, which claims benefit of and priority to U.S. Provisional Application No. 62/976,913, filed on Feb. 14, 2020; U.S. Provisional Application No. 62/977,402, filed on Feb. 16, 2020; U.S. Provisional Application No. 62/992,710, filed on Mar. 20, 2020, and U.S. Provisional Application No. 63/026, 580, filed on May 18, 2020, each of which is incorporated by reference herein in its entirety.

FIELD OF THE INVENTION

The invention provides compositions for inducing an immune response in a host to severe acute respiratory syndrome-coronavirus 2 (SARS-CoV2), and methods of using and manufacturing such compositions. In particular, the compositions described herein are recombinant modified vaccinia Ankara (MVA) viral constructs encoding one or more SARS-CoV2 antigens. The compositions can be used in a priming vaccination strategy or in a prime/boost vaccination strategy to provide immunity to a wide range of SARS-CoV2 variants.

INCORPORATION BY REFERENCE

The contents of the XML file named "19101-002WO1US1_SequenceListing_ST26.2" which was created on Jan. 18, 2023 and is 415 KB in size, are hereby incorporated by reference in their entirety.

BACKGROUND OF THE INVENTION

Coronaviruses (CoVs) (order Nidovirales, family Coronaviridae, subfamily Coronavirinae) are enveloped viruses with a positive sense, single-stranded RNA genome. Comparatively, CoVs have a large genome for an RNA virus, ranging in size from 26 to 32 kilobases (kb) in length. The CoV genome encodes four major structural proteins: the spike(S) protein, nucleocapsid (N) protein, membrane (M) protein, and the envelope (E) protein, all of which are required to produce a structurally complete viral particle. See, e.g., P S Masters, The molecular biology of coronavirus. Adv. Virus Res. 2014:101:105-12. Each major CoV structural protein plays a role in the structure of the virus particle and may be involved in other aspects of the replication cycle. Based on genetic and antigenic criteria, CoVs have been organized into three groups: α-CoVs, β-CoVs, and γ-CoVs (van Regenmortel et al., editors. Virus taxonomy: Classification and nomenclature of viruses Seventh report of the International Committee on Taxonomy of Viruses. San Diego: Academic Press; 2000. p. 835-49. ISBN 0123702003).

Coronaviruses primarily infect birds and mammals, but can also infect humans (see, e.g., Bande et al., Progress and challenges toward the development of vaccines against avian infectious bronchitis. J Immunol Res. 2015; 2015; van der Hoek L. Human coronaviruses: What do they cause? Antiviral Therapy. 2007; 12 (4 Pt B): 651). Coronaviral infections in humans are varying in severity, ranging from upper respiratory tract infections resembling the common

2 cold, to lower respiratory tract infections such as bronchitis, pneumonia, and even severe acute respiratory syndrome (SARS).

Some CoVs were originally found as enzootic infections, limited only to their natural animal hosts, but have crossed the animal-human species barrier and progressed to establish zoonotic diseases in humans. See, e.g., Lau et al., Severe acute respiratory syndrome coronavirus-like virus in Chinese horseshoe bats. PNAS 2005; 102 (39): 14040-5; Rest et al., SARS associated coronavirus has a recombinant polymerase and coronaviruses have a history of host-shifting. Infect Genet Evol. 2003; 3 (3): 219-25. Cross-species barrier jumps have allowed CoVs such as the SARS CoV and the Middle Eastern respiratory syndrome CoV (MERS) to manifest as virulent human viruses. Schoeman and Fielding, Coronavirus envelope protein: current knowledge. Virology 2019; 16:69. For example, the 2003 SARS CoV led to 8096 confirmed cases, with 774 deaths reported worldwide, for a fatality rate of 9.6%. World Health Organization WHO. Summary of probable SARS cases with onset of illness from 1 Nov. 2002 to 31 Jul. 2003 2003. Available from: http://www.who.int/csr/sars/country/table2004_04_21/en/index-.html. There have been 2229 confirmed cases of MERS reported since April 2012, with 792 associated deaths, resulting in a fatality rate of 35.5%. World Health Organization WHO. WHO MERS-CoV Global Summary and Assessment of Risk, August 2018 (WHO/MERS/RA/August18). Available from: http://www.who.int/csr/disease/coronavirus_infections/risk-assessment-august-2018.pdf?ua=1.

Recently, a novel coronavirus—SARS-CoV2—has been implicated in an outbreak which started in Wuhan, China. See Statement on the second meeting of the International Health Regulations (2005) Emergency Committee regarding the outbreak of novel coronavirus (SARS-CoV2), World Health Organization. 30 Jan. 2020. Archived from the original on 31 Jan. 2020, available at https://www.who.int/news-room/detail/30-01-2020-statement-on-the-second-meeting-of-the-international-health-regulations-(2005)-emergency-committee-regarding-the-outbreak-of-novel-coronavirus-(SARS-CoV2). Many early cases were linked to a large seafood and animal market in the Chinese city of Wuhan, and the virus is thought to have a zoonotic origin. Perlman, Another Decade, Another Coronavirus. NEJM (24 Jan. 2020); doi: 10.1056/NEJMe200112610; C Wu, Joseph et al., Nowcasting and forecasting the potential domestic and international spread of the SARS-CoV2 outbreak originating in Wuhan, China: a modelling study. The Lancet (31 Jan. 2020); doi: 10.1016/S0140-6736 (20) 30260-9. Comparisons of the genetic sequences of this virus and other virus samples have shown similarities to SARS-CoV (79.5%) and bat coronaviruses (96%) (Zhou, et al., A pneumonia outbreak associated with a new coronavirus of probable bat origin, Nature (Feb. 3, 2020; 1-4; doi: 10.1038/s41586-020-2012-7), and the SARS-CoV2 clusters with the betacoronaviruses, forming a distinct clade in lineage B of the subgenus Sarbecovirus together with two bat-derived SARS-like strains. The origin of the virus is not clear yet. Similar to SARS-CoV, a recent study confirmed that Angiotensin Converting Enzyme 2 (ACE 2), a membrane exopeptidase, is the receptor used by SARS-CoV2 for entry into the human cells.

In an attempt to control the spread of the outbreak, quarantine and travel restrictions have been put in place throughout the world. Nonetheless, as of February 2021, over 107 million individual cases had been reported worldwide, and over 2.3 million deaths. with an estimated fatality rate for the virus of about 0.7%.

The history of creating therapeutic vaccines for a human coronavirus illustrates the complexity and challenges of the problem. There are still no commercial vaccines against MERS-CoV and SARS-CoV, despite the fact that the viruses were discovered in 2012 and 2003, respectively. The selection of the framework and antigenic components that achieve the desired results of safety, tolerability and the necessary length of immunogenicity is difficult and can involve multiple failures.

A number of vaccines are in development to reduce or prevent SARS-CoV2 infections. On Dec. 11, 2020, the Food and Drug Administration (FDA) issued an Emergency Use Authorization (EUA) for Pfizer-BioNTech COVID-19 vaccine (BNT162b2) in persons aged 16 years and older for prevention of COVID-19. On Dec. 18, 2020, the U.S. Food and Drug Administration issued an Emergency Use Authorization (EUA) for the second vaccine for the prevention of coronavirus disease 2019 (COVID-19) caused by severe acute respiratory syndrome coronavirus 2 (SARS-CoV-2). The emergency use authorization allows the ModernaTX, Inc. COVID-19 Vaccine (mRNA-1272) to be distributed in the U.S for use in individuals 18 years of age and older. Both the Pfizer and Moderna vaccines are mRNA vaccines that encode only for the SARS-CoV2 spike protein.

SARS-CoV2, like other SARS-related coronaviruses, has shown a high mutation rate, and this mutation rate drives SARS-CoV2 evolution and genome variability, thereby potentially enabling SARS-CoV2 to escape host immunity and immunity provided by current vaccines. Since the original report of the SARS-CoV2 genomic sequence, a large number of SARS-CoV2 variants have been identified, which may potentially affect the therapeutic efficacy of various vaccination strategies. For example, the large number of mutations recently identified in the structural spike protein has raised concerns that vaccine strategies may be rendered ineffective due to mutational escape. Recent mutations to the spike protein have raised significant concerns about the effectiveness of current vaccines. For example, in a small clinical trial, the Oxford-AstraZeneca vaccine was shown to have reduced effectiveness against the South African variant 501Y.V2. It is feared that the E484K mutation, which is present in the 501Y.V2 variant, may render current vaccines less effective, resulting in potential escape mutants.

The high mortality rate of SARS-CoV2, along with its ease and speed of transmission and mutation rate, highlights the need for the development of effective SARS-CoV2 vaccines.

It is therefore an object of the present invention to provide a therapeutic vaccine against SARS-CoV2, and associated plasmids and constructs, as well as their use to impart immunogenicity to humans at risk of infection.

SUMMARY OF INVENTION

Provided herein are recombinant modified vaccinia Ankara (rMVA) viral vectors comprising heterologous nucleic acid inserts encoding one or more SARS-CoV2 proteins, peptides, or fragments thereof, operably linked to a promoter compatible with poxvirus expression systems that, upon expression, are capable of inducing protective immunity. The compositions described herein can be used in a priming vaccination strategy or in a prime/boost vaccination strategy to provide immunity to a wide range of SARS-CoV2 variants, including potential escape mutants.

In one aspect, the rMVA viral vectors are designed to express SARS-CoV2 antigens—for example the Spike(S), Membrane (M) and Envelope (E) proteins—in the form of a virus-like particle (VLP) in a recipient host cell (see, e.g., FIG. 20), wherein the expression and formation of the VLP is sufficient to provide protective immunity against mutant lineages due to enhanced display of potential immunologically dominant epitopes. By expressing a wider range of SARS-CoV2 antigens displayed as VLPs following expression, a more robust humoral and cellular response can be generated across multiple antigens, reducing the risks of mutant immune escape by SARS-CoV2 variants. For example, by expressing coronavirus VLPs which include the S, M, and E protein, a more robust immune response can be generated compared to vaccines directed to the S protein alone, thus reducing the potential of immune escape by the virus through mutations, including, for example amino acid substitutions within the S protein receptor binding domain (RBD), including, for example those of K417T, K417N, E484K and/or N501Y.

In some embodiments, the rMVA expresses SARS-CoV2 antigens so that two distinct populations of VLPs are produced. In some embodiments, the rMVA expresses one or more SARS-CoV2 antigens as a fusion protein with a non-coronavirus viral glycoprotein and separately expresses a viral matrix protein, wherein the SARS-CoV2 polypeptide antigen-glycoprotein fusion and matrix protein are capable of forming a VLP.

In some embodiments, an rMVA viral vector is provided containing one or more nucleic acid sequences which encode the membrane (M) protein, the envelope (E) protein, and the spike(S) protein of the SARS-CoV2, wherein, upon expression of the M, E, and S protein, a VLP is formed (see, e.g., FIG. 20). In some embodiments, the rMVA contains a nucleic acid sequence which encodes the full-length S protein, E protein, and M protein, for example, as exemplified in FIG. 1A. In some embodiments, the rMVA encodes an amino acid sequence comprising SEQ ID NOS: 1, 40, and 43. In some embodiments, the rMVA comprises nucleic acid sequences comprising SEQ ID NOS: 3, 42, and 45. In some embodiments, the rMVA comprises a nucleic acid sequence comprising SEQ ID NOS: 46, 47, or 156. In some embodiments, the rMVA contains a nucleic acid sequence which encodes the full-length S protein further comprising substitutions at K417T, E484K, and N501Y. In some embodiments, the rMVA encodes an amino acid sequence comprising SEQ ID NOS: 6, 40, and 43.

In some embodiments, an rMVA viral vector is provided containing one or more nucleic acid sequences which encode the membrane (M) protein, the envelope (E) protein, and the spike(S) protein of the SARS-CoV2, wherein, upon expression of the M, E, and S protein, a VLP is formed, and wherein the S protein comprises one or more amino acid proline substitutions that stabilize the S protein trimer in the prefusion conformation. In some embodiments, the S protein contains one or more proline substitutions at or near the boundary between a Heptad Repeat 1 (HR1) and a central helix of the promoters of the S ectodomain trimer. In some embodiments, the proline substitutions occur between amino acid residues 970 to 990 of the promoters in the trimer. In some embodiments, the S protein is expressed as a full-length protein and contains two proline substitutions at amino acids K986 and V987, for example, as exemplified in FIG. 2A. In some embodiments, the rMVA encodes an amino acid sequence comprising SEQ ID NOS: 8, 40, and 43. In some embodiments, the rMVA comprises nucleic acid sequences comprising SEQ ID NOS: 10, 42, and 45. In some embodiments, the S protein is expressed as a full-length protein and contains substitutions K986P, V987P, and one or more of K417T, E484K, and N501Y. In some embodiments, the S protein is expressed as a full-length protein and contains substitutions K986P, V987P, K417T, E484K, and N501Y. In some embodiments, the S protein is expressed as an amino acid comprising SEQ ID NO: 11. In some embodiments, the S protein is encoded by a nucleic acid comprising SEQ ID NO: 12. In some embodiments, the rMVA encodes an amino acid sequence comprising SEQ ID NOS: 11, 40, and 43. In some embodiments, the rMVA comprises nucleic acid sequences comprising SEQ ID NO: 12, 42, and 45. In some embodiments, the rMVA comprises nucleic acid sequences comprising SEQ ID NO: 157. In some embodiments, the rMVA comprises nucleic acid sequences comprising SEQ ID NO: 159. In some embodiments, the rMVA comprises nucleic acid sequences comprising SEQ ID NO: 50. In some embodiments, the rMVA comprises nucleic acid sequences comprising SEQ ID NO: 160.

In alternative embodiments of the above, the rMVA viral vector contains one or more nucleic acid sequence that encode the membrane (M) protein, the envelope (E) protein, and a linear epitope of the spike(S) protein, wherein upon expression of the M, E, and a linear epitope of the S protein, a VLP is formed. In a particular embodiment, the linear epitope of the S protein encoded by the rMVA is the receptor biding domain (RBD) of the SARS-CoV2 S protein. In some embodiments, the linear S epitope encoded comprises amino acids 331 to 524 of the S protein (RBD aa 331-524), as exemplified in FIG. 3A. In some embodiments, the rMVA expresses the linear epitope comprising SEQ ID NO: 21. In some embodiments, the linear S epitope encoded comprises amino acids 327 to 524 of the S protein (RBD aa 327 to 524), as exemplified in FIG. 3D. In some embodiments, the rMVA expresses the linear epitope comprising SEQ ID NO: 20. In some embodiments, the RBD peptide comprises substitutions K417T, E484K, and N501Y. In some embodiments, the rMVA expresses the linear epitope comprising SEQ ID NO: 33. In some embodiments, the rMVA expresses the linear epitope comprising SEQ ID NO: 32. In some embodiments, the rMVA encodes an amino acid sequence comprising SEQ ID NOS: 20, 40, and 43. In some embodiments, the rMVA comprises nucleic acid sequences comprising SEQ ID NOS: 24, 42, and 45. In some embodiments, the rMVA encodes an amino acid sequence of SEQ ID NOS: 21, 40, and 43. In some embodiments, the rMVA comprises nucleic acid sequences comprising SEQ ID NOS: 25, 42, and 45. In some embodiments, the rMVA encodes amino acid sequences of SEQ ID NOS: 32, 40, and 43. In some embodiments, the rMVA encodes amino acid sequences comprising SEQ ID NOS: 33, 40, and 43.

In some embodiments, the nucleic acid insert encodes a linear S epitope which further comprises a signal peptide and a transmembrane peptide derived from the S protein, for example, as exemplified in FIG. 3G and FIG. 3H. The S protein signal peptide can comprise or be derived from, for example, amino acids 1-13 (MFVFLVLLPLVSS) (SEQ ID NO: 55) of the SARS-CoV2 S protein. The S protein transmembrane domain, which can also include the cytoplasmic tail, can comprise, or be derived from, for example, amino acids 1214-1273 (SEQ ID NO: 57). In some embodiments, the S protein encoded comprises an RBD consensus sequence, as exemplified in FIG. 5A. In some embodiments, the RBD consensus sequence further comprises an S protein signal peptide, for example derived from SEQ ID NO: 55, and an S protein transmembrane peptide, for example derived from SEQ ID NO: 57, for example, as exemplified in FIG. 5B. In some embodiments, the rMVA expresses the linear epitope comprising SEQ ID NO: 61. In some embodiments, the rMVA expresses the linear epitope comprising SEQ ID NO: 62. In some embodiments, the RBD peptide comprises substitutions K417T, E484K, and N501Y. In some embodiments, the rMVA expresses the linear epitope comprising SEQ ID NO: 67. In some embodiments, the rMVA expresses the linear epitope comprising SEQ ID NO: 68. In some embodiments, the rMVA encodes an amino acid sequence comprising SEQ ID NOS: 61, 40, and 43. In some embodiments, the rMVA comprises nucleic acid sequences comprising SEQ ID NO: 65, 42, and 45. In some embodiments, the rMVA encodes an amino acid sequence of SEQ ID NOS: 62, 40, and 43. In some embodiments, the rMVA comprises nucleic acid sequences comprising SEQ ID NOS: 66, 42, and 45. In some embodiments, the rMVA encodes amino acid sequences of SEQ ID NOS: 67, 40, and 43. In some embodiments, the rMVA encodes amino acid sequences comprising SEQ ID NOS: 68, 40, and 43.

In some embodiments, the nucleic acid insert encodes a linear S epitope which further comprises a signal peptide, the E protein, and the M protein (see, e.g., FIG. 3Q, FIG. 3R, FIG. 3S, FIG. 3T). The S protein signal peptide can comprise or be derived from, for example, amino acids 1-13 (MFVFLVLLPLVSS) (SEQ ID NO: 55) of the SARS-CoV2 S protein. In some embodiments, the S protein encoded comprises an RBD consensus sequence. In some embodiments, the RBD consensus sequence further comprises an S protein signal peptide, for example derived from SEQ ID NO: 55. In some embodiments, the rMVA expresses the linear RBD epitope comprising amino acids 327-524. In some embodiments, the rMVA expresses the amino acid sequences comprising SEQ ID NOS: 55 and 20. In some embodiments, the rMVA expresses the linear RBD epitope comprising amino acids 331-524. In some embodiments, the rMVA expresses the amino acid sequences comprising SEQ ID NOS: 55 and 21. In some embodiments, the rMVA expresses the linear RBD epitope comprising amino acids 327-598. In some embodiments, the rMVA expresses the amino acid sequences comprising SEQ ID NOS: 55 and 161. In some embodiments, the rMVA expresses the linear RBD epitope comprising amino acids 331-598. In some embodiments, the rMVA expresses the amino acid sequences comprising SEQ ID NOS: 55 and 162. In some embodiments, the RBD peptide comprises substitutions K417T, E484K, and N501Y. In some embodiments, the rMVA expresses the amino acid sequences comprising SEQ ID NOS: 55 and 32. In some embodiments, the rMVA expresses the amino acid sequences comprising SEQ ID NOS: 55 and 33. In some embodiments, the rMVA expresses the amino acid sequences comprising SEQ ID NOS: 55 and 163. In some embodiments, the rMVA expresses the amino acid sequences comprising SEQ ID NOS: 55 and 164. In some embodiments, the rMVA encodes an amino acid sequence comprising SEQ ID NOS: 55, 20, 40, and 43. In some embodiments, the rMVA encodes an amino acid sequence of SEQ ID NO: 55, 21, 40, and 43. In some embodiments, the rMVA encodes amino acid sequences of SEQ ID NOS: 55, 32, 40, and 43. In some embodiments, the rMVA encodes amino acid sequences comprising SEQ ID NOS: 55, 33, 40, and 43. In some embodiments, the rMVA encodes amino acid sequences comprising SEQ ID NOS: 55, 161, 40, and 43. In some embodiments, the rMVA encodes amino acid sequences comprising SEQ ID NOS: 55, 162, 40, and 43. In some embodiments, the rMVA encodes amino acid sequences comprising SEQ ID NOS: 55, 163, 40, and 43. In some embodiments, the rMVA encodes amino acid sequences comprising SEQ ID NOS: 164, 33, 40, and 43. In some embodiments, the rMVA comprises SEQ ID NO: 158.

7

In some embodiments, the rMVA viral vector contains a nucleic acid sequence that encodes two or more linear epitopes of the S protein, wherein the two or more linear epitopes are separated by a spacer, for example a GPGPG spacer polypeptide, and wherein the rMVA viral vector also contains one or more nucleic acid sequence that encode the SARS-CoV2 envelope (E) and membrane (M) proteins. In some embodiments, the sequence inserted into the rMVA viral vector encodes S protein linear epitopes separated by a spacer, wherein the linear epitopes include different S protein RBD peptide sequences, for example (RBD Seq. 1-spacer-RBD Seq. 2), wherein RBD Seq. 1 is a first S protein RBD peptide, and RBD Seq. 2 is a second S protein RBD peptide. In some embodiments, the sequence inserted into the MVA viral vector encodes a tandem repeat sequence, for example (RBD Seq. 1-spacer-RBD Seq.2-spacer) x, wherein x=2, 3, 4, 5, 6, 7, 8, 9, 10. In some embodiments, the nucleic acid sequence encodes a tandem repeat sequence is flanked by an S peptide signal peptide, for example as derived from SEQ ID NO: 55, on the NH-terminus and an S protein transmembrane domain, for example derived from SEQ ID NO: 57, on the carboxy terminus. In some embodiments, the RBD peptide is selected from one or more peptides derived from amino acids 331 to 524, or alternatively amino acids 327 to 524, of the SARS-CoV2 S protein. In some embodiments, the linear epitopes encoded by the nucleic acid sequence in the rMVA are selected from the amino acids 504 to 524 and amino acids 473 to 490 of the SARS-CoV2 S protein. In some embodiments, the linear epitopes encoded by the nucleic acid sequence in the rMVA are the amino acids 504 to 524 and amino acids 473 to 490 of the SARS-CoV2 S protein. In some embodiments, the sequence inserted into the MVA viral vector encodes an S protein RBD peptide containing the tandem repeat sequence ((aa504-524)-GPGPG-(aa473-490)-GPGPG) x, wherein x=2, 3, 4, 5, 6, 7, 8, 9, 10, for example, as exemplified in FIG. 4A. In some embodiments, x=3-7. In some embodiments, x=5. In some embodiments, the sequence inserted into the MVA viral vector encodes an S protein RBD peptide containing the tandem repeat sequence ((aa504-524)-GPGPG-(aa473-490)-GPGPG) x, wherein x=2, 3, 4, 5, 6, 7, 8, 9, 10, and wherein the tandem repeat is flanked by an S protein signal peptide, for example as derived from SEQ ID NO: 55, on the NH-terminus and an S protein transmembrane domain, for example, as derived from SEQ ID NO: 57, on the carboxy terminus, for example, as exemplified in FIG. 4F. In some embodiments, x=3-7. In some embodiments, x=5. In some embodiments, the aa473-490 RBD peptide comprises E484K.

In alternative embodiments of the above, the rMVA viral vector contains one or more nucleic acid sequences that encode the SARS-CoV2 membrane (M) protein, envelope (E) protein, and a modified spike(S) protein lacking the carboxy terminus of the S protein. The modified S protein comprises S1+S2 truncated, wherein upon expression of the M, E, and truncated S protein, a VLP is formed. In a particular embodiment, the modified S protein encoded by the rMVA comprises amino acids (1-1213) of the SARS-CoV2 S protein, for example, as exemplified in FIG. 6A. Alternatively, the rMVA viral vector contains one or more nucleic acid sequences that encode the SARS-CoV2 membrane (M) protein, envelope (E) protein, and an S1+S2 truncated protein fragment having one or more proline substitutions, wherein upon expression of the M, E, and truncated S protein, a VLP is formed. In a particular embodiment, the modified S protein encoded by the rMVA comprises amino acids (1-1213) of the SARS-CoV2 S protein,

8 wherein the S1+S2 truncated fragment contains two proline substitution at amino acids K986 and V987 (S1+S2 truncated+K986P and V987P), for example, as exemplified in FIG. 6H. In some embodiments, the S1+S2 peptide further comprises substitutions K417T, E484K, and N501Y.

In an alternative aspect, provided herein is a rMVA viral vector designed to express one or more SARS-CoV2 S protein antigenic peptides as a fusion protein, wherein the fusion protein comprises an envelope glycoprotein signal peptide (GPS), a SARS-CoV2 S protein or protein fragment, and a transmembrane domain of an envelope glycoprotein (GPTM), wherein the envelope glycoprotein is not derived from a coronavirus. The rMVA viral vector is constructed to further express the membrane (M) protein and the envelope (E) protein of the SARS-CoV2, and a matrix protein derived from the same virus as the envelope glycoprotein. By expressing both the M and E proteins, an S protein fragment in a fusion with a GP, and a matrix protein, two distinct VLPS can be formed: the first containing the SARS-CoV2 M and E proteins, and the second containing the S protein fragment in concert with the GP and matrix protein. By providing two VLPs, enhanced epitope presentation may be possible. Suitable glycoproteins for use in the present invention include, but are not limited to, those derived from: a Filoviridae, for example Marburg virus, Ebola virus, or Sudan virus; a Retroviridae, for example human immunodeficiency virus type 1 (HIV-1); an Arenaviridaea, for example Lassa virus; a Flaviviridae, for example Dengue virus and Zika virus. In particular embodiments, the glycoprotein is derived from Marburg virus (MARV). In particular embodiments, the glycoprotein is derived from the MARV GP protein (Genbank accession number AFV31202.1). In particular embodiments, the MARV GPS domain comprises amino acids 1 to 19 of the glycoprotein (MWTTCFFISLILIQGIKTL) (SEQ ID NO: 88) and the GPTM domain comprises amino acid sequences 644-681 of the glycoprotein (WWTSDWGVLTNLGILLLLSIA-VLIALSCICRIFTKYIG) (SEQ ID NO: 90). In some embodiments, the S protein or protein fragment-GP fusion protein comprises an S protein receptor biding domain (RBD), for example as exemplified in FIG. 7A. In some embodiments, the RBD peptide is derived from amino acids 331 to 524 of the S protein. In some embodiments, the linear S epitope comprises amino acids 331 to 524 of the S protein, for example, as exemplified in FIG. 7B. In some embodiments, the RBD peptide is derived from amino acids 327 to 524 of the S protein. In some embodiments, the linear S epitope comprises amino acids 327 to 524 of the S protein, for example, as exemplified in FIG. 7G. In some embodiments, the linear S epitope comprises a coronavirus consensus sequence. In some embodiments, the RBD peptide comprises substitutions K417T, E484K, and N501Y. In some embodiments, the rMVA encodes amino acid sequences comprising SEQ ID NOS: 95, 40, and 43. In some embodiments, the rMVA comprises nucleic acid sequences comprising SEQ ID NOS: 97, 42, and 45. In some embodiments, the rMVA encodes amino acid sequences comprising SEQ ID NOS: 96, 40, and 43. In some embodiments, the rMVA comprises nucleic acid sequences comprising SEQ ID NOS: 98, 42, and 45. In some embodiments, the rMVA encodes amino acid sequences comprising SEQ ID NOS: 99, 40, and 43. In some embodiments, the rMVA encodes amino acid sequences comprising SEQ ID NOS: 99, 40, and 43.

In some embodiments, the rMVA contains one or more nucleic acid sequences which encode the E protein, the M protein, and two or more linear epitopes of the S protein fused with a viral glycoprotein, for example the MARV GP, wherein the two or more linear epitopes are separated by a spacer, for example a GPGPG spacer polypeptide, and wherein the GPS flanks the two or more linear epitopes' NH terminus and the GPTM flanks its carboxy terminus, and a matrix protein derived from the same virus as the glycoprotein, for example, the MARV VP40 matrix protein. In some embodiments, two or more linear epitopes of the S protein are fused with the MARV GP, wherein the linear epitopes include different S protein RBD peptides, for example (RBD Seq. 1-spacer-RBD Seq.2), wherein RBD Seq. 1 is a first S protein RBD peptide, and RBD Seq. 2 is a second S protein RBD peptide. In some embodiments, two or more linear epitopes of the S protein are fused with the MARV GP, wherein the epitopes are contained in a tandem repeat sequence, for example (RBD Seq. 1-spacer-RBD Seq.2-spacer) X, wherein x=2, 3, 4, 5, 6, 7, 8, 9, 10, or more than 10. In some embodiments, the RBD peptide is selected from one or more peptides derived from amino acids 331 to 524 or amino acids 327 to 524 of the SARS-CoV2 S protein. In some embodiments, the linear epitopes encoded by the rMVA are selected from the amino acids 504 to 524 and amino acids 473 to 490 of the SARS-CoV2 S protein. In some embodiments, the linear epitopes encoded by the tandem repeat are the amino acids 504 to 524 and amino acids 473 to 490 of the SARS-CoV2 S protein. In some embodiments, the tandem repeat sequence encodes ((aa504-524)-GPGPG-(aa473-490)-GPGPG) x, wherein x=2, 3, 4, 5, 6, 7, 8, 9, 10, or more than 10. In some embodiments, x=3 to 7. In some embodiments, x=5, for example, as exemplified in FIG. 8A. Where a tandem repeat is utilized, the MARV GPS peptide flanks the tandem repeat on the NH-terminus, and the MARV GPTM peptide flanks the tandem repeat on the carboxy-terminus. In some embodiments, the aa473-490 RBD peptide comprises E484K.

In some embodiments, the rMVA encodes, along with the E protein and M protein, a modified S protein comprising an S1+S2 truncated protein fused with a viral glycoprotein, for example the MARV GP, wherein the GPS flanks the S1+S2 truncated S protein's NH terminus and the GPTM flanks its carboxy terminus, and a matrix protein derived from the same virus as the glycoprotein, for example, the MARV VP40 matrix protein. In a particular embodiment, the modified S S1+S2 truncated protein encoded by the rMVA comprises amino acids 1-1213 of the SARS-CoV2 S protein, for example, as exemplified in FIG. 9A. In some embodiments, the S protein fragment encoded by the rMVA along comprises a modified S protein comprising an S1+S2 truncated protein comprising one or more proline substitutions, for example, proline substitutions at K986P and V987P, for example as exemplified by FIG. 9B. In some embodiments, the S1+S2 peptide further comprises substitutions K417T, E484K, and N501Y In an alternative aspect, provided herein is a rMVA viral vector designed to express one or more SARS-CoV2 antigenic peptides as a fusion protein, wherein the fusion protein comprises a signal peptide of an envelope glycoprotein (GPS), SARS-CoV2 S protein fragment, and a transmembrane domain of an envelope glycoprotein (GPTM), wherein the envelope glycoprotein is not derived from a coronavirus, and wherein the rMVA viral vector further expresses a matrix protein derived from the same virus as the glycoprotein. The SARS-CoV2 peptide-GP fusion protein is designed to allow for the formation of VLPs in conjunction with the matrix protein, which display the SARS-CoV2 antigenic peptide. Suitable glycoproteins domains and matrix proteins for use in the present invention include, but are not limited to, those derived from: a Filoviridae, for example Marburg virus, Ebola virus, or Sudan virus; a Retroviridae, for example human immunodeficiency virus type 1 (HIV-1); a Arenaviridaea, for example Lassa virus; a Flaviviridae, for example Dengue virus and Zika virus. In particular embodiments, the GP and matrix proteins are derived from Marburg virus (MARV). In particular embodiments, the glycoprotein is derived from the MARV GP protein (Genbank accession number AFV31202.1). In particular embodiments, the MARV GPS domain comprises amino acids 1 to 19 of the glycoprotein (MWTTCFFISLILIQGIKTL) (SEQ ID NO: 88), the GPTM domain comprises amino acid sequences 644-681 of the glycoprotein (WWTSDWGVLTNLGILLLLSIAVLIALSCIC RIFT-KYIG) (SEQ ID NO: 90). In some embodiments, the glycoprotein-S protein fusion and viral matrix protein are contained in the rMVA as nucleic acids inserted at different locations. In some embodiments, the glycoprotein-s protein or protein fragment fusion and viral matrix protein are contained in the rMVA as a bicistronic nucleic acid inserted at the same location. In some embodiments, the SARS-CoV2 protein fused to the glycoprotein is the S protein or a fragment thereof. In some embodiments, the S protein is a fragment comprising a modified S protein comprising an S1+S2 truncated protein. In some embodiments, the modified S protein fragment encoded by the rMVA comprises amino acids 2 to 1213 of the SARS-CoV2 S protein, for example, as exemplified in FIGS. 10A and 10C. In some embodiments, the modified S protein fragment encoded by the rMVA comprises amino acids 2 to 1213 of the SARS-CoV2 S protein containing one or more proline substitutions, for example, at K986P and V987P, for example as exemplified in FIGS. 10F and 10D. In some embodiments, the S1+S2 peptide further comprises substitutions K417T, E484K, and N501Y. In some embodiments, the fused S protein is a linear epitope of the S protein. In a particular embodiment, the linear epitope of the S protein is the receptor biding domain (RBD) of the SARS-CoV2 S protein, for example as exemplified in FIG. 11A and FIG. 11H. In some embodiments, the linear S epitope comprises an RBD peptide derived from amino acids 331 to 524 of the S protein. In some embodiments, the linear S epitope comprises amino acids 331 to 524 of the S protein, for example, as exemplified in FIG. 11B and FIG. 11I. In some embodiments, the linear S epitope comprises an RBD peptide derived from amino acids 327 to 524 of the S protein. In some embodiments, the linear S epitope comprises amino acids 327 to 524 of the S protein, for example, as exemplified in FIG. 11E and FIG. 11N. In some embodiments, the RBD peptide further comprises substitutions K417T, E484K, and N501Y. In some embodiments, the linear S epitope comprises a coronavirus consensus sequence. In some embodiments, two or more linear epitopes of the S protein are fused with the MARV GP, wherein the two or more linear epitopes are separated by a spacer, for example a GPGPG spacer polypeptide. In some embodiments, the linear epitopes include different S protein RBD peptides, for example (RBD Seq.1-spacer-RBD Seq.2), wherein RBD Seq. 1 is a first S protein RBD peptide, and RBD Seq. 2 is a second S protein RBD peptide. In some embodiments, the fused S protein includes two or more linear epitopes of the S protein, wherein the epitopes are contained in a tandem repeat sequence, for example (RBD Seq. 1-spacer-RBD Seq.2-spacer) x, wherein x=2, 3, 4, 5, 6, 7, 8, 9, 10, or more than 10. In some embodiments, the RBD peptide is selected from one or more peptides derived from amino acids 331 to 524 of the SARS-CoV2 S protein. In some embodiments, the linear epitopes encoded by the rMVA are selected from the amino acids 504 to 524 and amino acids 473 to 490 of the SARS-CoV2 S protein. In some embodiments, the linear epitopes encoded by the tandem repeat are the amino acids 504 to 524 and amino acids 473 to 490 of the SARS-CoV2 S protein. In some embodiments, the tandem repeat sequence encodes ((aa504-524)-GPGPG-(aa473-490)-GPGPG) x, wherein x=2, 3, 4, 5, 6, 7, 8, 9, 10, or more than 10. In some embodiments, x=3 to 7. In some embodiments, x=5. Where the S protein fragment is provided as a tandem repeat, the GPS flanks the NH-terminus of the tandem repeat and the GPTM flanks the carboxy terminus of the tandem repeat, as exemplified, for example, in FIGS. 12A and 12B. In some embodiments, the RBD peptide further comprises substitution E484K. In some embodiments, the rMVA encodes amino acid sequences comprising SEQ ID NOS: 92 and 95. In some embodiments, the rMVA comprises nucleic acid sequences comprising SEQ ID NOS: 93 or 94, and 97. In some embodiments, the rMVA encodes amino acid sequences comprising SEQ ID NOS: 92 and 96. In some embodiments, the rMVA comprises nucleic acid sequences comprising SEQ ID NOS: 93 or 94, and 98. In some embodiments, the rMVA encodes amino acid sequences comprising SEQ ID NOS: 92 and 99. In some embodiments, the rMVA encodes amino acid sequences comprising SEQ ID NOS: 92 and 100. In some embodiments the rMVA encodes an amino acid sequence comprising SEQ ID NO: 134.

In an alternative aspect of the present invention, provided herein is a recombinant MVA viral vector encoding a full-length S protein, for example, as exemplified in FIG. 13A. In some embodiments, the S protein is a full-length stabilized protein, wherein one or more proline substitutions have been made at or near the boundary between a Heptad Repeat 1 (HR1) and a central helix of the promoters of the S ectodomain trimer. In some embodiments, the proline substitutions occur between residues 970 to 990 of the promoters in the trimer. In some embodiments, the S protein is stabilized and is expressed as a full-length protein and contains two proline substitutions at amino acids K986 and V987, for example, as exemplified in FIG. 14A. In some embodiments, the S protein is expressed as a truncated S protein comprising the S1+S2 domains of the S protein, and lacking the carboxy terminus of the S protein. In some embodiments, the truncated S protein comprises amino acids 1 to 1213 of the S protein, as exemplified in FIG. 15A. In some embodiments, the truncated S protein includes two proline substitutions at amino acids K986 and V987, as exemplified in FIG. 15F. In some embodiments, the S peptide further comprises one or more substitutions selected from K417N, K417T, E484K, and N501Y. In some embodiments, the S peptide further comprises substitutions K417T, E484K, and N501Y.

In some aspects, provided herein is a method of reducing or preventing a SARS-CoV2 infection in a subject, for example a human, comprising administering an rMVA viral vector described herein. In some embodiments, the rMVA viral vector is prophylactically administered as a prime vaccine to a subject that has not previously been infected with SARS-CoV2. In some embodiments, the rMVA viral vector is administered as a boost vaccine to a subject that has previously been infected with SARS-CoV2. In some embodiments, the rMVA viral vector is administered as a boost vaccine in a subject that has previously been administered a SARS-CoV2 vaccine. In some embodiments, the previously administered SARS-CoV2 vaccine is an rMVA viral vector described herein. In some embodiments, the previously administered vaccine is non-MVA viral vector vaccine. In some embodiments, the vaccine is an mRNA-based vaccine, an adenovirus vaccine, a non-replicating vaccine, a DNA vaccine, a live attenuated vaccine, a plant-based adjuvant vaccine, a multiepitope peptide-based vaccine, an inactivated virus, a peptide vaccine. In some embodiments, the previously administered vaccine is selected from one or more of mRNA-1273 (MODERNA COVID-19 VACCINE; Moderna, Inc.), AZD-1222 (COVIDSHIELD; AstraZeneca and University of Oxford), BNT162 (COMIRNATY; Pfizer and BioNTech), Sputnik V (Gamaleya Research Institute, Acellena Contract Drug Research and Development), Corona Vac (Sinovac), NVX-CoV 2372 (NovoVax), SCB-2019 (Sanofi and GSK), ZyCoV-D (Zydus Cadila), BBIBP-CorV (Beijing Institute of Biological Products; China National Pharmaceutical Group (Sinopharm)), EpiVacCorona (Federal Budgetary Research Institution State Research Center of Virology and Biotechnology), Convidicea (CanSino Biologics), Covid-19 Vaccine (Wuhan Institute of Biological Products; China National Pharmaceutical Group (Sinopharm), JNJ-78436735 (Johnson & Johnson), ZF2001) Anhui Zhifei Longcom Biopharmaceutical, Institute of Microbiology of the Chinese Academy of Sciences), CVnCoV (CureVac; GSK), INO-4800 (Inovio Pharmaceuticals), VIR-7831 (Medicago; GSK; Dynavax), Covid-19 adenovirus bases vaccine (ImmunityBio; NantKwest), UB-612 (COVAXX), or CoVaxin (Bharat Biotech).

In some aspects, the rMVA viral vectors described herein are administered to a subject, for example a human, in an immunization protocol using one or more additional vaccinating agents other than the rMVA described herein.

Also provided herein are shuttle vectors comprising the nucleic acid sequences to be inserted into the MVA as described herein, as well as isolated nucleic acid sequences comprising the nucleic acid sequence inserts described herein. Further provided herein are cells, such as a chicken embryo fibroblast cell or DF1 cell, comprising an rMVA as described herein.

BRIEF DESCRIPTION OF FIGURES

FIG. 1B-1C-1D is an exemplary rMVA nucleic acid insert of SEQ ID NO: 46 encoding the full-length SARS-CoV2 S, M, and E proteins. Also exemplified and identified within the sequence are the vaccinia mH5 promoters, vaccinia P11 promoter, start codons, Kozak regulatory sequences, and c-tag sequences.

FIG. 1E-1F-1G is an exemplary rMVA nucleic acid insert of SEQ ID NO: 47 encoding the full-length SARS-CoV2 S, M, and E proteins. Also exemplified and identified within the sequence are the vaccinia mH5 promoters, vaccinia P11 promoter, start codons, Kozak regulatory sequences, SmaI restriction site, and c-tag sequences.

FIG. 1H-1I-1J is an exemplary rMVA nucleic acid insert of SEQ ID NO: 156 encoding the full-length SARS-CoV2 S, M, and E proteins. Also exemplified and identified within the sequence are the vaccinia mH5 promoters, vaccinia P11 promoter, start codons, Kozak regulatory sequences, SmaI restriction site, and c-tag sequences.

FIG. 2B-2C-2D is an exemplary rMVA nucleic acid insert of SEQ ID NO: 48 encoding the full-length stabilized SARS-CoV2 S, M, and E proteins comprising the amino acid substitutions K986P and V987P. Also exemplified and identified within the sequence are the vaccinia mH5 promoters, vaccinia P11 promoter, start codons, Kozak regulatory sequences, and c-tag sequences.

FIG. 2E-2F-2G is an exemplary rMVA nucleic acid insert of SEQ ID NO: 49 encoding the full-length stabilized SARS-CoV2 S, M, and E proteins comprising the amino acid substitutions K986P and V987P. Also exemplified and identified within the sequence are the vaccinia mH5 promoters, vaccinia P11 promoter, SmaI restriction site, start codons, Kozak regulatory sequences, and c-tag sequences.

FIG. 2H-2I-2J is an exemplary rMVA nucleic acid insert of SEQ ID NO: 50 encoding the full-length stabilized SARS-CoV2 S, M, and E proteins comprising the amino acid substitutions K986P, V987P, K417T, E484K, and N501Y. Also exemplified and identified within the sequence are the vaccinia mH5 promoters, vaccinia P11 promoter, SmaI restriction site, start codons, Kozak regulatory sequences, and c-tag sequences.

FIG. 2K-2L-2M is an exemplary rMVA nucleic acid insert of SEQ ID NO: 157 encoding the full-length stabilized SARS-CoV2 S, M, and E proteins comprising the amino acid substitutions K986P and V987P. Also exemplified and identified within the sequence are the vaccinia mH5 promoters, vaccinia P11 promoter, SmaI restriction site, start codons, Kozak regulatory sequences, and c-tag sequences.

FIG. 2N-2O-2P is an exemplary rMVA nucleic acid insert of SEQ ID NO: 159 encoding the full-length stabilized SARS-CoV2 S, M, and E proteins comprising the amino acid substitutions K986P, V987P, K417T, E484K, and N501Y. Also exemplified and identified within the sequence are the vaccinia mH5 promoters, vaccinia P11 promoter, SmaI restriction site, start codons, Kozak regulatory sequences, and c-tag sequences.

FIG. 2Q-2R-2S is an exemplary rMVA nucleic acid insert of SEQ ID NO: 160 encoding the full-length stabilized SARS-CoV2 S, M, and E proteins comprising the amino acid substitutions K986P, V987P, K417T, E484K, and N501Y. Also exemplified and identified within the sequence are the vaccinia mH5 promoters, vaccinia P11 promoter, SmaI restriction site, start codons, and Kozak regulatory sequences.

FIG. 3B is an exemplary rMVA nucleic acid insert of SEQ ID NO: 53 encoding an RBD (aa 331-524) region of the S protein, an E protein, and an M protein. Also exemplified and identified in the sequence are the vaccinia mH5 promoters, vaccinia P11 promoter, start codons, Kozak regulatory sequences, and c-tag sequences.

FIG. 3C is an exemplary rMVA nucleic acid insert of SEQ ID NO: 54 encoding an RBD (aa 331-524) region of the S protein, an E protein, and an M protein. Also exemplified and identified in the sequence are the vaccinia mH5 promoters, vaccinia P11 promoter, SmaI restriction site, start codons, Kozak regulatory sequences, and c-tag sequences.

FIG. 3E is an exemplary rMVA nucleic acid insert of SEQ ID NO: 51 encoding an RBD (aa 327-524) region of the S protein, an E protein, and an M protein. Also exemplified and identified in the sequence are the vaccinia mH5 promoters, vaccinia P11 promoter, start codons, Kozak regulatory sequences, and c-tag sequences.

FIG. 3F is an exemplary rMVA nucleic acid insert of SEQ ID NO: 52 encoding an RBD (aa 327-524) region of the S protein, an E protein, and an M protein. Also exemplified and identified in the sequence are the vaccinia mH5 promoters, vaccinia P11 promoter, SmaI restriction site, start codons, Kozak regulatory sequences, and c-tag sequences.

FIG. 3I-3J is an exemplary rMVA nucleic acid insert of SEQ ID NO: 69 encoding a S protein signal peptide (SP)-S protein RBD (aa 327-524)-S protein transmembrane domain (STM) fusion protein, an E protein, and an M protein. Also exemplified and identified in the sequence are the vaccinia mH5 promoters, vaccinia P11 promoter, start codons, Kozak regulatory sequences, and c-tag sequences.

FIG. 3K-3L is an exemplary rMVA nucleic acid insert of SEQ ID NO: 70 encoding a S protein signal peptide (SP)-S protein RBD (aa 327-524)-S protein transmembrane domain (STM) fusion protein, an E protein, and an M protein. Also exemplified and identified in the sequence are the vaccinia mH5 promoters, vaccinia P11 promoter, SmaI restriction site, start codons, Kozak regulatory sequences, and c-tag sequences.

FIG. 3M-3N is an exemplary rMVA nucleic acid insert of SEQ ID NO: 71 encoding a S protein signal peptide (SP)-S protein RBD (aa 331-524)-S protein transmembrane domain (STM) fusion protein, an E protein, and an M protein. Also exemplified and identified in the sequence are the vaccinia mH5 promoters, vaccinia P11 promoter, start codons, Kozak regulatory sequences, and c-tag sequences.

FIG. 3O-3P is an exemplary rMVA nucleic acid insert of SEQ ID NO: 72 encoding a S protein signal peptide (SP)-S protein RBD (aa 331-524)-S protein transmembrane domain (STM) fusion protein, an E protein, and an M protein. Also exemplified and identified in the sequence are the vaccinia mH5 promoters, vaccinia P11 promoter, SmaI restriction site, start codons, Kozak regulatory sequences, and c-tag sequences.

FIG. 3U-3V is an exemplary rMVA nucleic acid insert of SEQ ID NO: 158 encoding a S protein signal peptide (SP)-S protein RBD (aa 331-524)-S protein transmembrane domain (STM) fusion protein, an E protein, and an M protein. Also exemplified and identified in the sequence are the vaccinia mH5 promoters, vaccinia P11 promoter, start codons, Kozak regulatory sequences, and c-tag sequences.

FIG. 4B-4C is an exemplary rMVA nucleic acid insert of SEQ ID NO: 73 encoding a tandem repeat of S protein RBD derived amino acids, an E protein, and an M protein. Also exemplified and identified in the sequence are the vaccinia mH5 promoters, vaccinia P11 promoter, start codons, Kozak regulatory sequences, linker sequences, and c-tag sequences.

FIG. 4D-4E is an exemplary rMVA nucleic acid insert of SEQ ID NO: 74 encoding a tandem repeat of S protein RBD derived amino acids, an E protein, and an M protein. Also exemplified and identified in the sequence are the vaccinia mH5 promoters, vaccinia P11 promoter, SmaI restriction site, start codons, Kozak regulatory sequences, linker sequences, and c-tag sequences.

FIG. 4G-4H is an exemplary rMVA nucleic acid insert of SEQ ID NO: 81 encoding a signal peptide of the S protein amino acids 1-13 (SP)-S protein RBD tandem repeat-S protein transmembrane domain (STM) fusion protein, an E protein, and an M protein. Also exemplified and identified in the sequence are the vaccinia mH5 promoters, vaccinia P11 promoter, start codons, Kozak regulatory sequences, and c-tag sequences.

FIG. 4I-4J is an exemplary rMVA nucleic acid insert of SEQ ID NO: 82 encoding a signal peptide of the S protein amino acids 1-13 (SP)-S protein RBD tandem repeat-S protein transmembrane domain (STM) fusion protein, an E protein, and an M protein. Also exemplified and identified in the sequence are the vaccinia mH5 promoters, vaccinia P11 promoter, Smal restriction site, start codons, Kozak regulatory sequences, and c-tag sequences.

FIG. 6B-6C-6D is an exemplary rMVA nucleic acid insert of SEQ ID NO: 83 encoding truncated amino acids 1-1213 derived from the S protein (S1+S2 truncated), an E protein, and M protein. Also exemplified and identified in the sequence are the vaccinia mH5 promoters, vaccinia P11 promoter, start codons, Kozak regulatory sequences, and c-tag sequences.

FIG. 6E-6F-6G is an exemplary rMVA nucleic acid insert of SEQ ID NO: 84 encoding truncated amino acids 1-1213 derived from the S protein (S1+S2 truncated), an E protein, and M protein. Also exemplified and identified in the sequence are the vaccinia mH5 promoters, vaccinia P11 promoter, SmaI restriction site, start codons, Kozak regulatory sequences, and c-tag sequences.

FIG. 6I-6J-6K is an exemplary rMVA nucleic acid insert of SEQ ID NO: 85 encoding truncated amino acids 1-1213 derived from the S protein (S1+S2 truncated) with two proline substitutions at amino acids 981 and 982, an E protein, and M protein. Also exemplified and identified in the sequence are the vaccinia mH5 promoters, vaccinia P11 promoter, start codons, Kozak regulatory sequences, and c-tag sequences.

FIG. 6L-6M-6N is an exemplary rMVA nucleic acid insert of SEQ ID NO: 86 encoding truncated amino acids 1-1213 derived from the S protein (S1+S2 truncated) with two proline substitutions at amino acids 981 and 982, an E protein, and M protein. Also exemplified and identified in the sequence are the vaccinia mH5 promoters, vaccinia P11 promoter, SmaI restriction site, start codons, Kozak regulatory sequences, and c-tag sequences.

FIG. 7C-7D is an exemplary rMVA nucleic acid insert of SEQ ID NO: 103 encoding a signal glycoprotein (Signal GP)-S protein RBD (aa 331-524) consensus-glycoprotein transmembrane domain sequence (GP TM) fusion protein, an E protein, and an M protein. Also exemplified and identified in the sequence are the vaccinia mH5 promoters, vaccinia P11 promoter, start codons, Kozak regulatory sequences, and c-tag sequences.

FIG. 7E-7F is an exemplary rMVA nucleic acid insert of SEQ ID NO: 104 encoding a signal glycoprotein (Signal GP)-S protein RBD (aa 331-524) consensus-glycoprotein transmembrane domain sequence (GP TM) fusion protein, an E protein, and an M protein. Also exemplified and identified in the sequence are the vaccinia mH5 promoters, vaccinia P11 promoter, SmaI restriction site, start codons, Kozak regulatory sequences, and c-tag sequences.

As exemplified, adjacent to the Signal GP-S RBD (aa 327-524) consensus-GP TM fusion encoding sequence is a nucleic acid sequence encoding the full-length E protein, in a left-to-right orientation, which is operably linked to, for example, a p11 promoter. The E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a mH5 promoter (pmH5). The M protein nucleic acid sequence can also include appropriate translation initiation sequences such as a Kozak sequence, as well as a nucleic acid sequence encoding a tag at the 3' terminus of the coding sequence prior to the stop codon. As exemplified, a nucleic acid sequence encoding a non-coronavirus matrix protein, for example Marburgvirus matrix protein VP40, is inserted between, for example, MVA genes A50R and B1R. The nucleic acid sequence encoding the matrix protein is operably linked to, for example, a mH5 promoter (pmH5). Similar to the fusion protein, the matrix protein nucleic acid sequence can also include appropriate translation initiation sequences such as a Kozak sequence, as well as a nucleic acid sequence encoding a tag at the 3' terminus of the coding sequence prior to the stop codon.

Figure 7A:
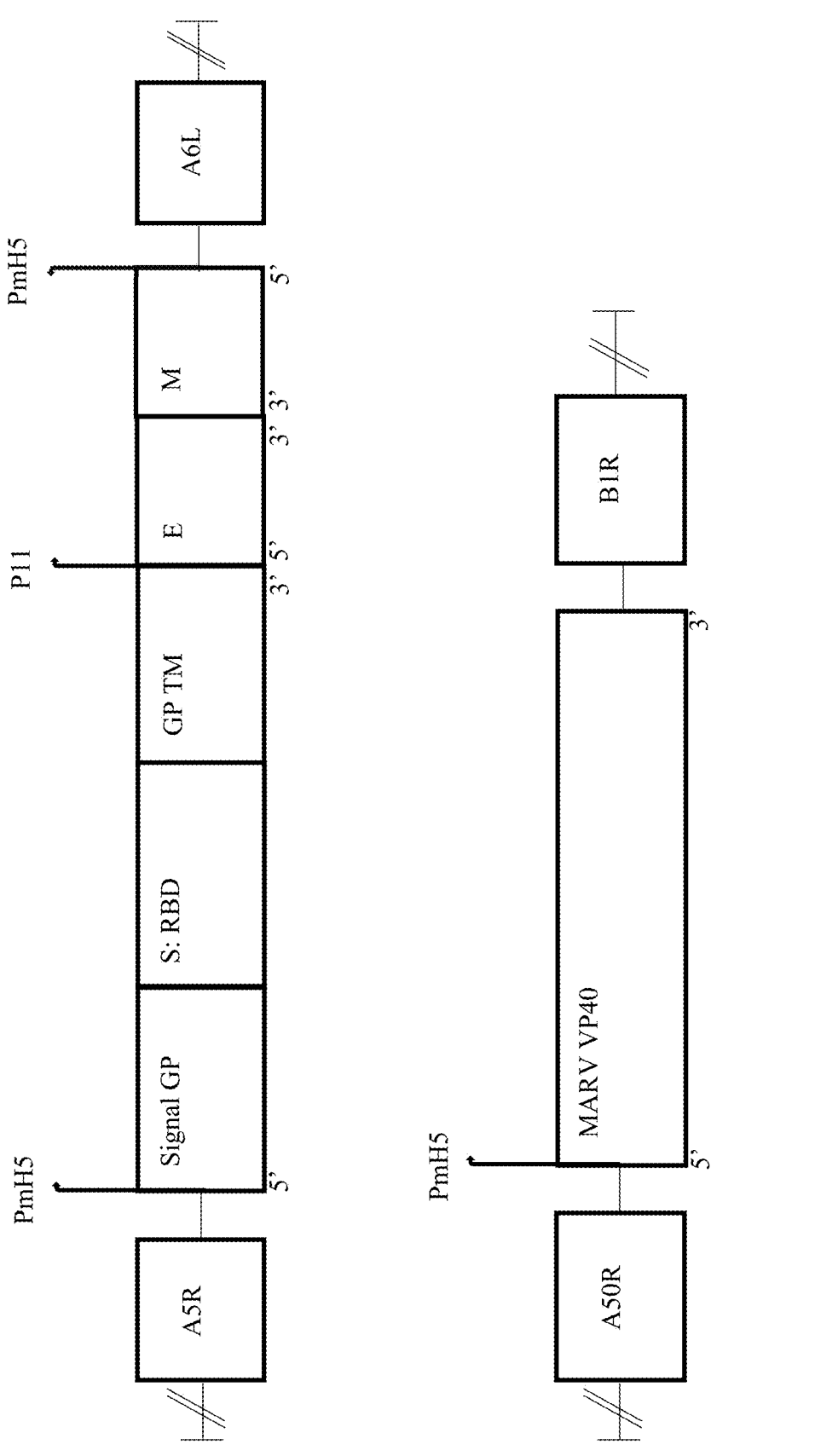
FIG. 7A provides an exemplary linear schematic of an exemplary recombinant MVA viral vector comprising a nucleic acid sequence encoding a signal glycoprotein (Signal GP)-S protein RBD consensus-glycoprotein transmembrane domain sequence (GP TM) fusion protein, an E protein, and an M protein inserted between MVA genes A5R and A6L. As exemplified, a mH5 promoter (pmH5) is operably linked to a nucleic acid encoding a fusion protein, wherein the fusion protein includes a signal peptide from a non-coronavirus signal glycoprotein (Signal GP), an S protein RBD consensus peptide, and a transmembrane domain of the glycoprotein (GP TM), in a left-to-right orientation. A start codon is provided 5' to the Signal GP-S RBD consensus-GP TM fusion encoding nucleic acid. The insert may include a translation initiation sequence, for example a Kozak sequence, prior to the start codon of the signal peptide encoding sequence. In addition, a nucleic acid sequence encoding a tag, for example a C-affinity tag, may be included at the 3' terminus of the Signal GP-S RBD consensus-GP TM fusion, prior to the stop codon. As exemplified, adjacent to the Signal GP-S RBD consensus-GP TM fusion encoding sequence is a nucleic acid sequence encoding the full-length E protein, in a left-to-right orientation, which is operably linked to, for example, a p11 promoter. The E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a mH5 promoter (pmH5). The M protein nucleic acid sequence can also include appropriate translation initiation sequences such as a Kozak sequence, as well as a nucleic acid sequence encoding a tag at the 3' terminus of the coding sequence prior to the stop codon. As exemplified, a nucleic acid sequence encoding a non-coronavirus matrix protein, for example Marburgvirus matrix protein VP40, is inserted between, for example, MVA genes A50R and B1R. The nucleic acid sequence encoding the matrix protein is operably linked to, for example, a mH5 promoter (pmH5). Similar to the fusion protein, the matrix protein nucleic acid sequence can also include appropriate translation initiation sequences such as a Kozak sequence, as well as a nucleic acid sequence encoding a tag at the 3' terminus of the coding sequence prior to the stop codon.

FIG. 7H-7I is an exemplary rMVA nucleic acid insert of SEQ ID NO: 101 encoding a signal glycoprotein (Signal GP)-S protein RBD (aa 327-524) consensus-glycoprotein transmembrane domain sequence (GP TM) fusion protein, an E protein, and an M protein. Also exemplified and identified in the sequence are the vaccinia mH5 promoters, vaccinia P11 promoter, start codons, Kozak regulatory sequences, and c-tag sequences.

FIG. 7J-7K is an exemplary rMVA nucleic acid insert of SEQ ID NO: 102 encoding a signal glycoprotein (Signal GP)-S protein RBD (aa 327-524) consensus-glycoprotein transmembrane domain sequence (GP TM) fusion protein, an E protein, and an M protein. Also exemplified and identified in the sequence are the vaccinia mH5 promoters, vaccinia P11 promoter, SmaI restriction site, start codons, Kozak regulatory sequences, and c-tag sequences.

Figure 8A:
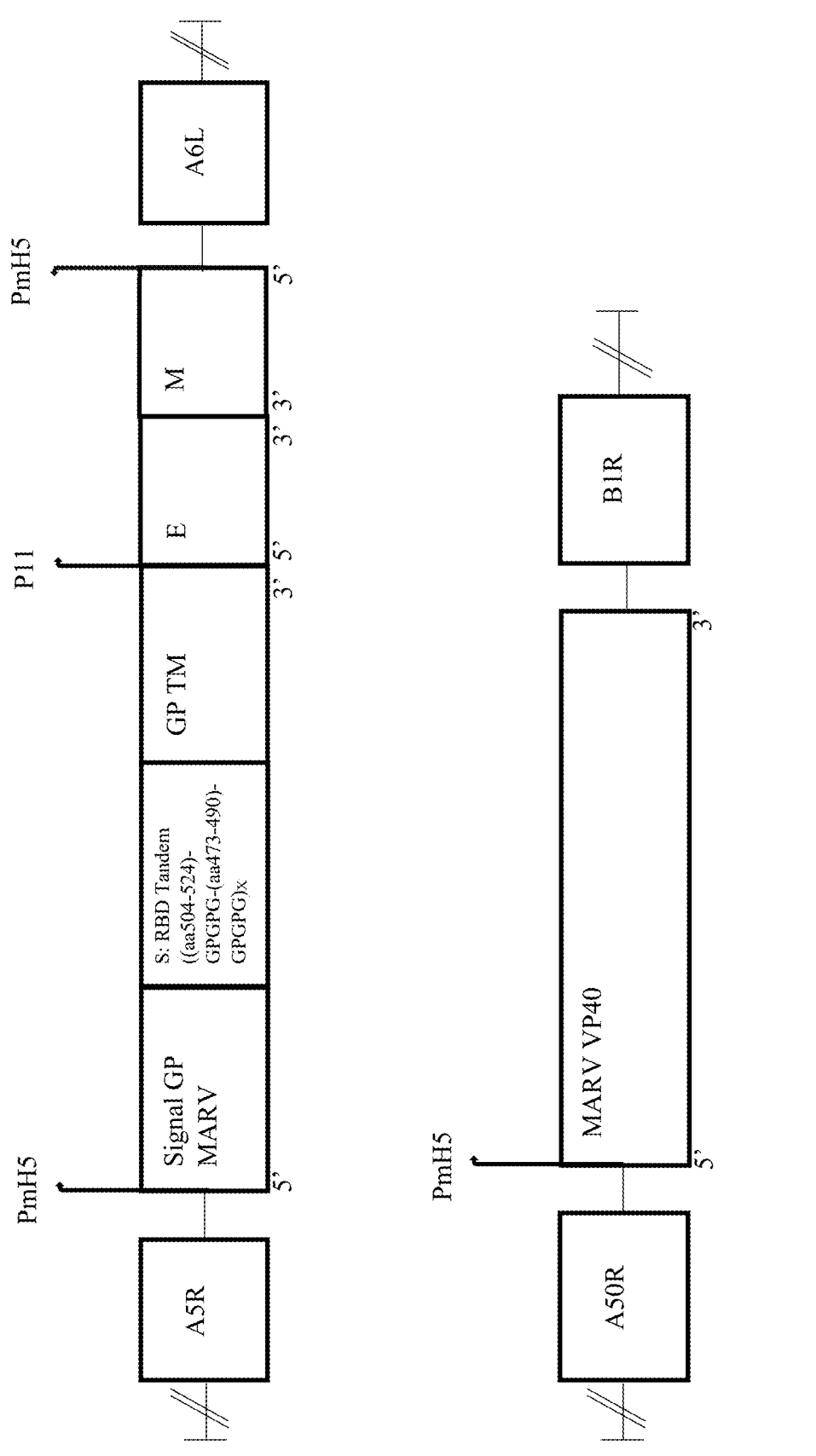

FIG. 8A provides an exemplary linear schematic of an exemplary recombinant MVA viral vector comprising a nucleic acid sequence encoding a glycoprotein (Signal GP MARV)-tandem repeat of S protein RBD derived amino acid-transmembrane domain of the glycoprotein (GP TM) fusion protein, an E protein, and an M protein inserted between, for example, MVA genes A5R and A6L. As exemplified, a mH5 promoter (pmH5) is operably linked to a nucleic acid encoding a fusion protein, wherein the fusion protein includes a signal peptide from a non-coronavirus glycoprotein (Signal GP MARV), S RBD tandem repeat ((aa504-524)-GPGPG-(aa473-490)-GPGPG) 5, and a transmembrane domain of the glycoprotein (GP TM), in a left-to-right orientation. A start codon is provided 5' to the Signal GP MARV-S RBD tandem repeat-GP TM fusion encoding sequence. The insert may include a translation initiation sequence, for example a Kozak sequence, prior to the start codon of the Signal GP MARV-S RBD tandem repeat-GP TM fusion sequence. In addition, a nucleic acid sequence encoding a tag, for example a C-affinity tag, may be included at the 3' terminus of the fusion protein, prior to the stop codon. As exemplified, adjacent to the fusion protein is a nucleic acid sequence encoding the full-length E protein, in the left to right orientation, which is operably linked to, for example, a p11 promoter. Similar to the fusion protein, the E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a mH5 promoter (pmH5). The M protein nucleic acid sequence can also include appropriate translation initiation sequences such as a Kozak sequence, as well as a nucleic acid sequence encoding a tag at the 3' terminus of the coding sequence prior to the stop codon. As exemplified, a nucleic acid sequence encoding a non-coronavirus matrix protein, for example Marburgvirus matrix protein VP40, is inserted between, for example, MVA genes A50R and B1R. The nucleic acid sequence encoding the matrix protein is operably linked to, for example, a mH5 promoter (pmH5). Similar to the fusion protein, the matrix protein nucleic acid sequence can also include appropriate translation initiation sequences such as a Kozak sequence, as well as a nucleic acid sequence encoding a tag at the 3' terminus of the coding sequence prior to the stop codon.

FIG. 8B-8C is an exemplary rMVA nucleic acid insert of SEQ ID NO: 111 encoding a glycoprotein (Signal GP MARV)-tandem repeat of S protein RBD derived amino acid-transmembrane domain of the glycoprotein (GP TM) fusion protein, an E protein, and an M protein. Also exemplified and identified in the sequence are the vaccinia mH5 promoters, vaccinia P11 promoter, start codons, Kozak regulatory sequences, linker sequences, and c-tag sequences.

FIG. 8D-8E is an exemplary rMVA nucleic acid insert of SEQ ID NO: 112 encoding a glycoprotein (Signal GP MARV)-tandem repeat of S protein RBD derived amino acid-transmembrane domain of the glycoprotein (GP TM) fusion protein, an E protein, and an M protein. Also exemplified and identified in the sequence are the vaccinia mH5 promoters, vaccinia P11 promoter, SmaI restriction site, start codons, Kozak regulatory sequences, linker sequences, and c-tag sequences.

Figure 9A:
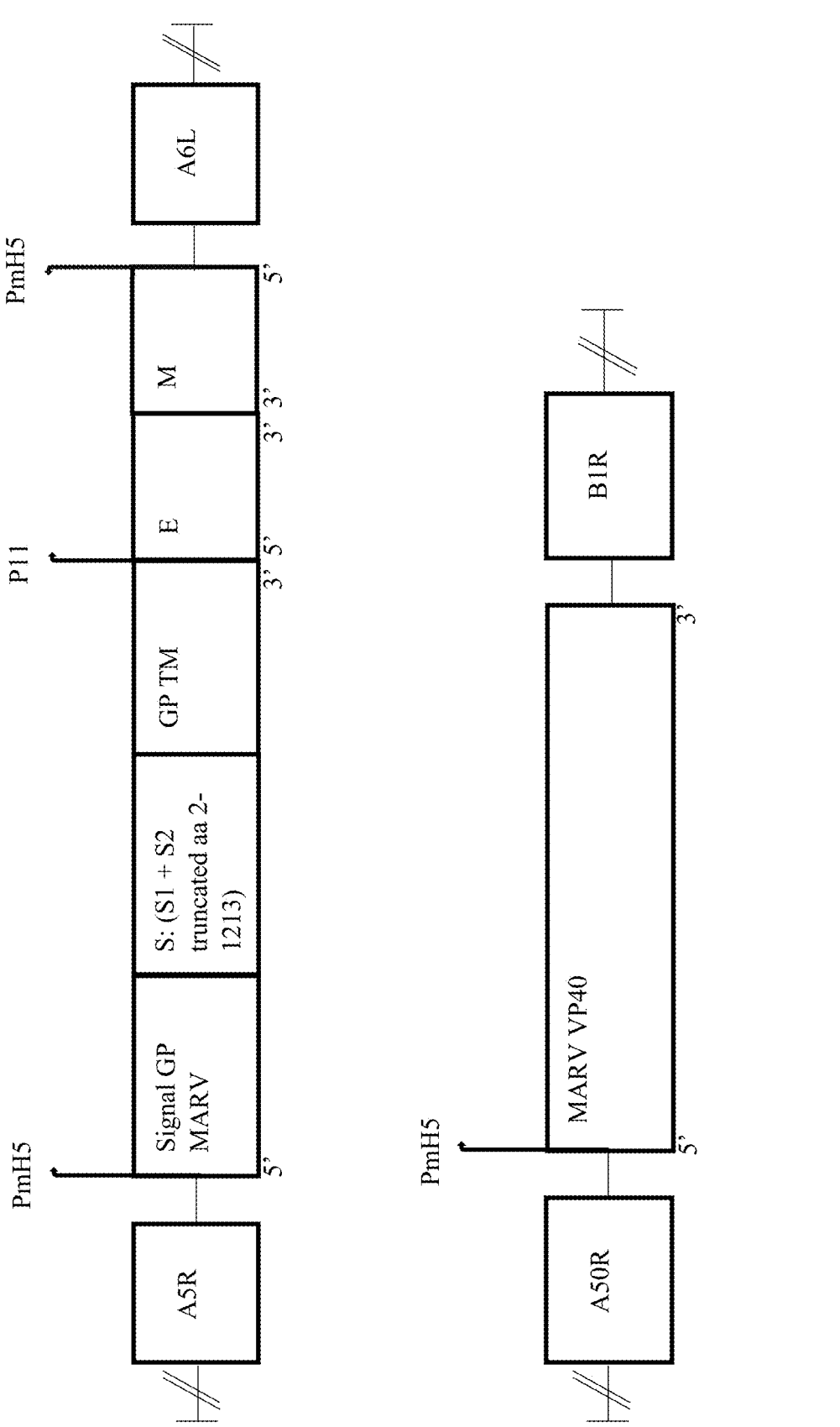

FIG. 9A provides an exemplary linear schematic of an exemplary recombinant MVA viral vector comprising a nucleic acid sequence encoding a glycoprotein (Signal GP MARV)-truncated amino acids 2-1213 derived from the S protein (S1+S2 truncated)-transmembrane domain of the glycoprotein (GP TM) fusion protein, an E protein, and an M protein inserted between, for example, MVA genes A5R and A6L. As exemplified, a mH5 promoter (pmH5) is operably linked to a nucleic acid encoding a fusion protein, wherein the fusion protein includes a signal peptide from a non-coronavirus glycoprotein (Signal GP MARV), the S protein (S1+S2 truncated), and a transmembrane domain of the glycoprotein (GP TM), in a left-to-right orientation. A start codon is provided 5' to the Signal GP MARV-S protein truncated (S1+S2 truncated)-GP TM fusion encoding sequence. The insert may include a translation initiation sequence, for example a Kozak sequence, prior to the start codon of the Signal GP MARV-S protein (S1+S2 truncated)-GP TM fusion sequence. In addition, a nucleic acid sequence encoding a tag, for example a C-affinity tag, may be included at the 3' terminus of the fusion protein, prior to the stop codon. As exemplified, adjacent to the fusion protein is a nucleic acid sequence encoding the full-length E protein, in the left to right orientation, which is operably linked to, for example, a p11 promoter. Similar to the fusion protein, the E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a mH5 promoter (pmH5). The M protein nucleic acid sequence can also include appropriate translation initiation sequences such as a Kozak sequence, as well as a nucleic acid sequence encoding a tag at the 3' terminus of the coding sequence prior to the stop codon. As exemplified, a nucleic acid sequence encoding a non-coronavirus matrix protein, for example Marburgvirus matrix protein VP40, is inserted between, for example, MVA genes A50R and B1R. The nucleic acid sequence encoding the matrix protein is operably linked to, for example, a mH5 promoter (pmH5). Similar to the fusion protein, the matrix protein nucleic acid sequence can also include appropriate translation initiation sequences such as a Kozak sequence, as well as a nucleic acid sequence encoding a tag at the 3' terminus of the coding sequence prior to the stop codon.

FIG. 9B-9C-9D is an exemplary rMVA nucleic acid insert of SEQ ID NO: 119 encoding a glycoprotein (Signal GP MARV)-truncated amino acids 2-1213 derived from the S protein (S1+S2 truncated)-transmembrane domain of the glycoprotein (GP TM) fusion protein, an E protein, and an M protein. Also exemplified and identified in the sequence are the vaccinia mH5 promoters, vaccinia P11 promoter, start codons, Kozak regulatory sequences, and c-tag sequences.

FIG. 9E-9F-9G is an exemplary rMVA nucleic acid insert of SEQ ID NO: 120 encoding a glycoprotein (Signal GP MARV)-truncated amino acids 2-1213 derived from the S protein (S1+S2 truncated)-transmembrane domain of the glycoprotein (GP TM) fusion protein, an E protein, and an M protein. Also exemplified and identified in the sequence are the vaccinia mH5 promoters, vaccinia P11 promoter, SmaI restriction site, start codons, Kozak regulatory sequences, and c-tag sequences.

Figure 9H:
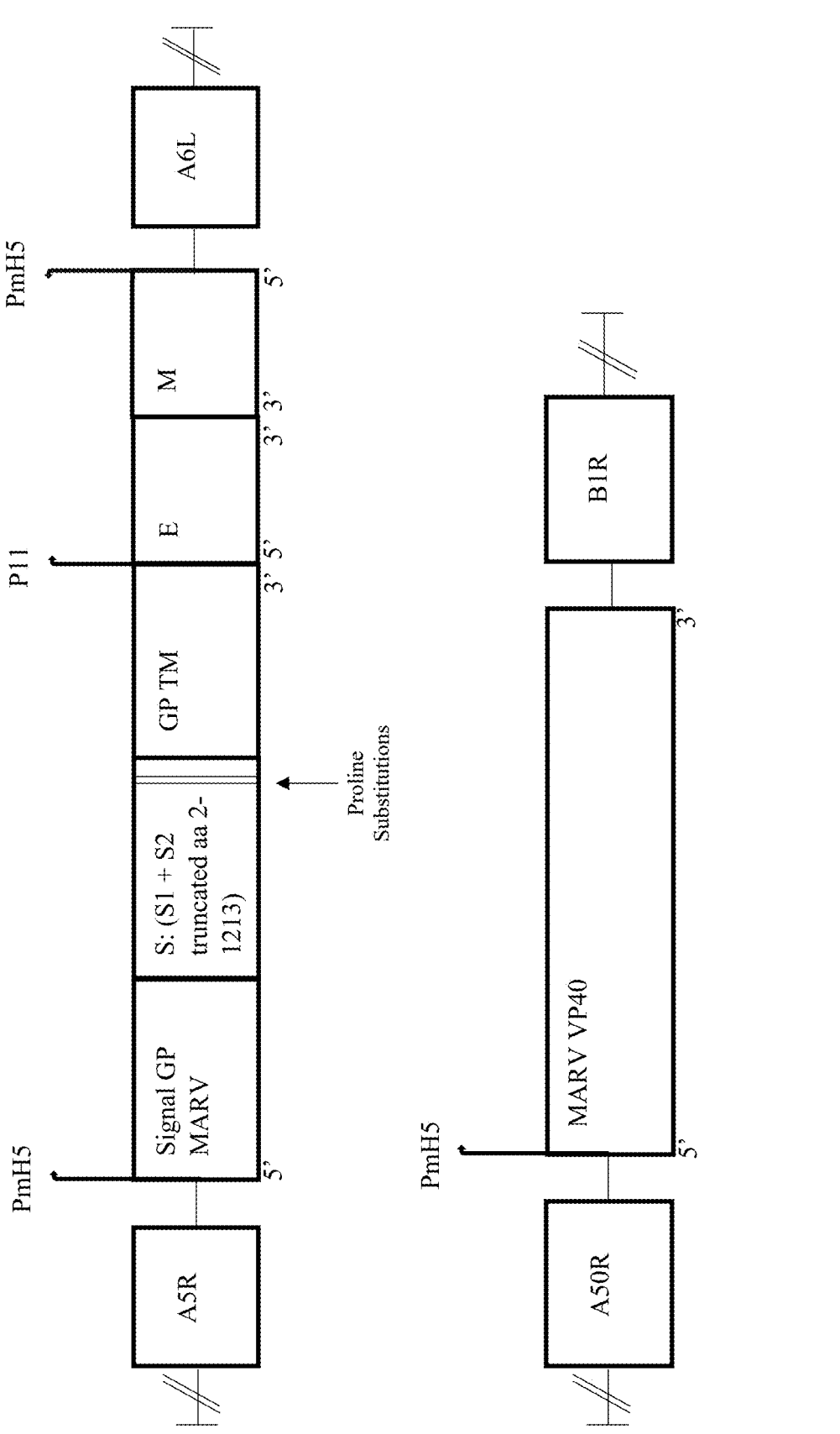

FIG. 9H provides an exemplary linear schematic of an exemplary recombinant MVA viral vector comprising a nucleic acid sequence encoding a glycoprotein (Signal GP MARV)-truncated amino acids 2-1213 derived from the S protein (S1+S2 truncated+K986P and V987P)-transmembrane domain of the glycoprotein (GP TM) fusion protein, an E protein, and an M protein inserted between, for example, MVA genes A5R and A6L. As exemplified, a mH5 promoter (pmH5) is operably linked to a nucleic acid encoding a fusion protein, wherein the fusion protein includes a signal peptide from a non-coronavirus glycoprotein (Signal GP MARV), the S protein (S1+S2 truncated+K986P and V987P), and a transmembrane domain of the glycoprotein (GP TM), in a left-to-right orientation. A start codon is provided 5' to the Signal GP MARV-S protein truncated (S1+S2 truncated+K986P and V987P)-GP TM fusion encoding sequence. The insert may include a translation initiation sequence, for example a Kozak sequence, prior to the start codon of the Signal GP MARV-S protein (S1+S2 truncated+K986P and V987P)-GP TM fusion sequence. In addition, a nucleic acid sequence encoding a tag, for example a C-affinity tag, may be included at the 3' terminus of the fusion protein, prior to the stop codon. As exemplified, adjacent to the fusion protein is a nucleic acid sequence encoding the full-length E protein, in the left to right orientation, which is operably linked to, for example, a p11 promoter. Similar to the fusion protein, the E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a mH5 promoter (pmH5). The M protein nucleic acid sequence can also include appropriate translation initiation sequences such as a Kozak sequence, as well as a nucleic acid sequence encoding a tag at the 3' terminus of the coding sequence prior to the stop codon. As exemplified, a nucleic acid sequence encoding a non-coronavirus matrix protein, for example Marburgvirus matrix protein VP40, is inserted between, for example, MVA genes A50R and B1R. The nucleic acid sequence encoding the matrix protein is operably linked to, for example, a mH5 promoter (pmH5). Similar to the fusion protein, the matrix protein nucleic acid sequence can also include appropriate translation initiation sequences such as a Kozak sequence, as well as a nucleic acid sequence encoding a tag at the 3' terminus of the coding sequence prior to the stop codon.

FIG. 9I-9J-9K is an exemplary rMVA nucleic acid insert of SEQ ID NO: 121 encoding a glycoprotein (Signal GP MARV)-truncated amino acids 2-1213 derived from the S protein (S1+S2 truncated+K986P and V987P)-transmembrane domain of the glycoprotein (GP TM) fusion protein, an E protein, and an M protein. Also exemplified and identified in the sequence are the vaccinia mH5 promoters, vaccinia P11 promoter, start codons, Kozak regulatory sequences, and c-tag sequences.

FIG. 9L-9M-9N is an exemplary rMVA nucleic acid insert of SEQ ID NO: 122 encoding a glycoprotein (Signal GP MARV)-truncated amino acids 2-1213 derived from the S protein (S1+S2 truncated+K986P and V987P)-transmembrane domain of the glycoprotein (GP TM) fusion protein, an E protein, and an M protein. Also exemplified and identified in the sequence are the vaccinia mH5 promoters, vaccinia P11 promoter, SmaI restriction site, start codons, Kozak regulatory sequences, and c-tag sequences.

Figure 10A:
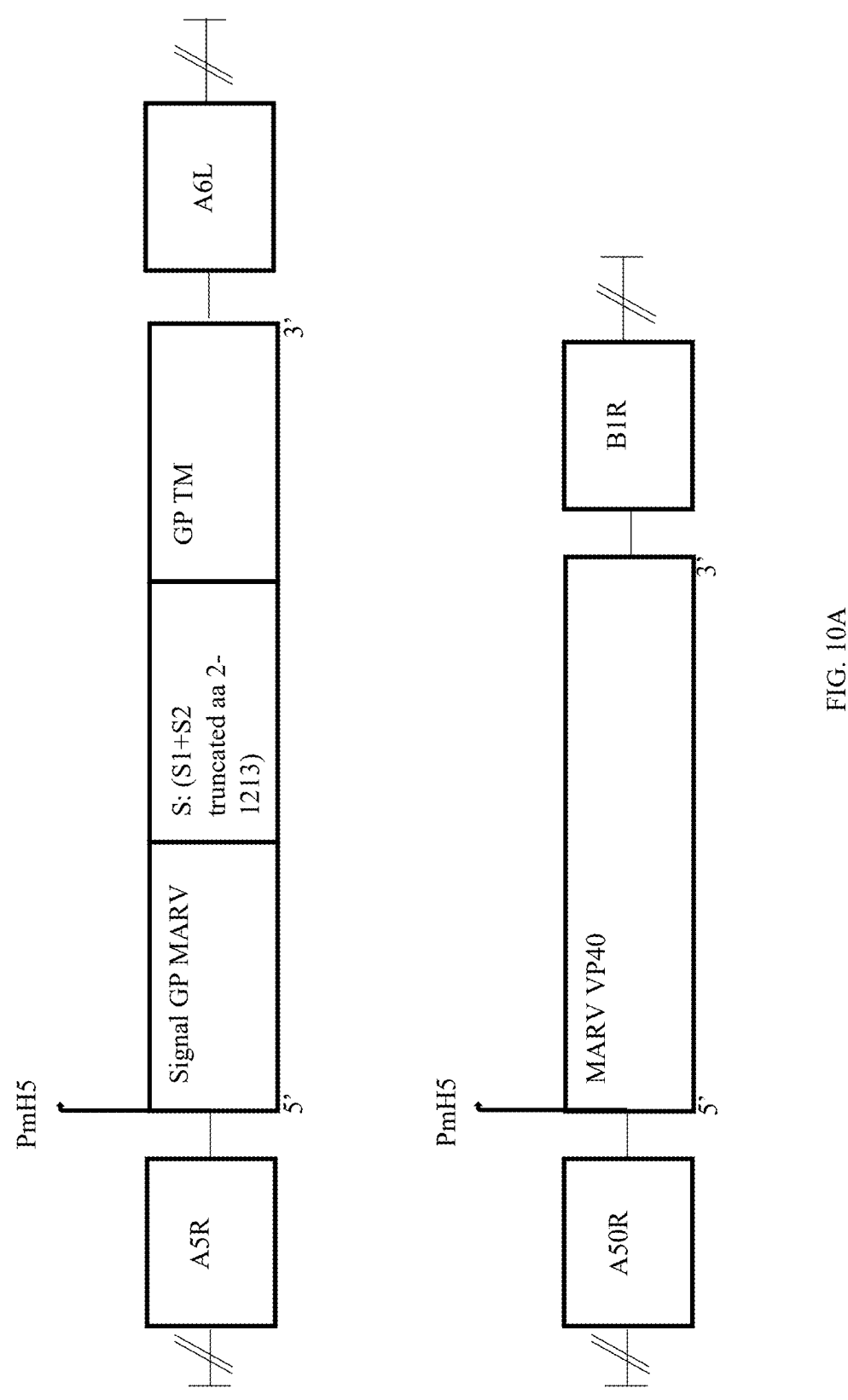

FIG. 10A provides an exemplary linear schematic of an exemplary recombinant MVA viral vector comprising a nucleic acid sequence encoding a glycoprotein (Signal GP MARV)-S protein truncated S1+S2-transmembrane domain of the glycoprotein (GP TM) fusion protein inserted between MVA genes A5R and A6L, and a nucleic acid sequence encoding a non-coronavirus matrix protein inserted between MVA genes A50R and B1R. As exemplified, a mH5 promoter (pmH5) is operably linked to a nucleic acid encoding a fusion protein, wherein the fusion protein includes a signal peptide from a non-coronavirus glycoprotein (Signal GP MARV), truncated amino acids 2-1213 derived from the S protein (S1+S2 truncated), and a transmembrane domain of the glycoprotein (GP TM), in a left-to-right orientation. A start codon is provided 5' to the Signal GP MARV-S protein (S1+S2 truncated)-GP TM fusion encoding nucleic acid in a left-to-right orientation. The insert may include a translation initiation sequence, for example a Kozak sequence, prior to the start codon of the Signal GP MARV-S protein (S1+S2 truncated)-GP TM fusion sequence. In addition, a nucleic acid sequence encoding a tag, for example a C-affinity tag, may be included at the 3' terminus of the fusion protein, prior to the stop codon. As exemplified, a nucleic acid sequence encoding a non-coronavirus matrix protein, for example Marburgvirus matrix protein VP40, is inserted between MVA genes A50R and B1R. The nucleic acid sequence encoding the matrix protein is operably linked to, for example, a pmH5 promoter. Similar to the fusion protein, the matrix protein nucleic acid sequence can also include appropriate translation initiation sequences such as a Kozak sequence, as well as a nucleic acid sequence encoding a tag at the 3' terminus of the coding sequence prior to the stop codon.

FIG. 10B-10C is an exemplary rMVA nucleic acid insert of SEQ ID NO: 123 encoding a glycoprotein (Signal GP MARV)-S protein truncated S1+S2-transmembrane domain of the glycoprotein (GP TM) fusion protein. Also exemplified and identified in the sequence are the vaccinia mH5 promoters, vaccinia P11 promoter, start codons, Kozak regulatory sequences, and c-tag sequences.

FIG. 10D-10E is an exemplary rMVA nucleic acid insert of SEQ ID NO: 124 encoding a glycoprotein (Signal GP MARV)-S protein truncated S1+S2-transmembrane domain of the glycoprotein (GP TM) fusion protein. Also exemplified and identified in the sequence are the vaccinia mH5 promoters, vaccinia P11 promoter, SmaI restriction site, start codons, Kozak regulatory sequences, and c-tag sequences.

Figure 10F:
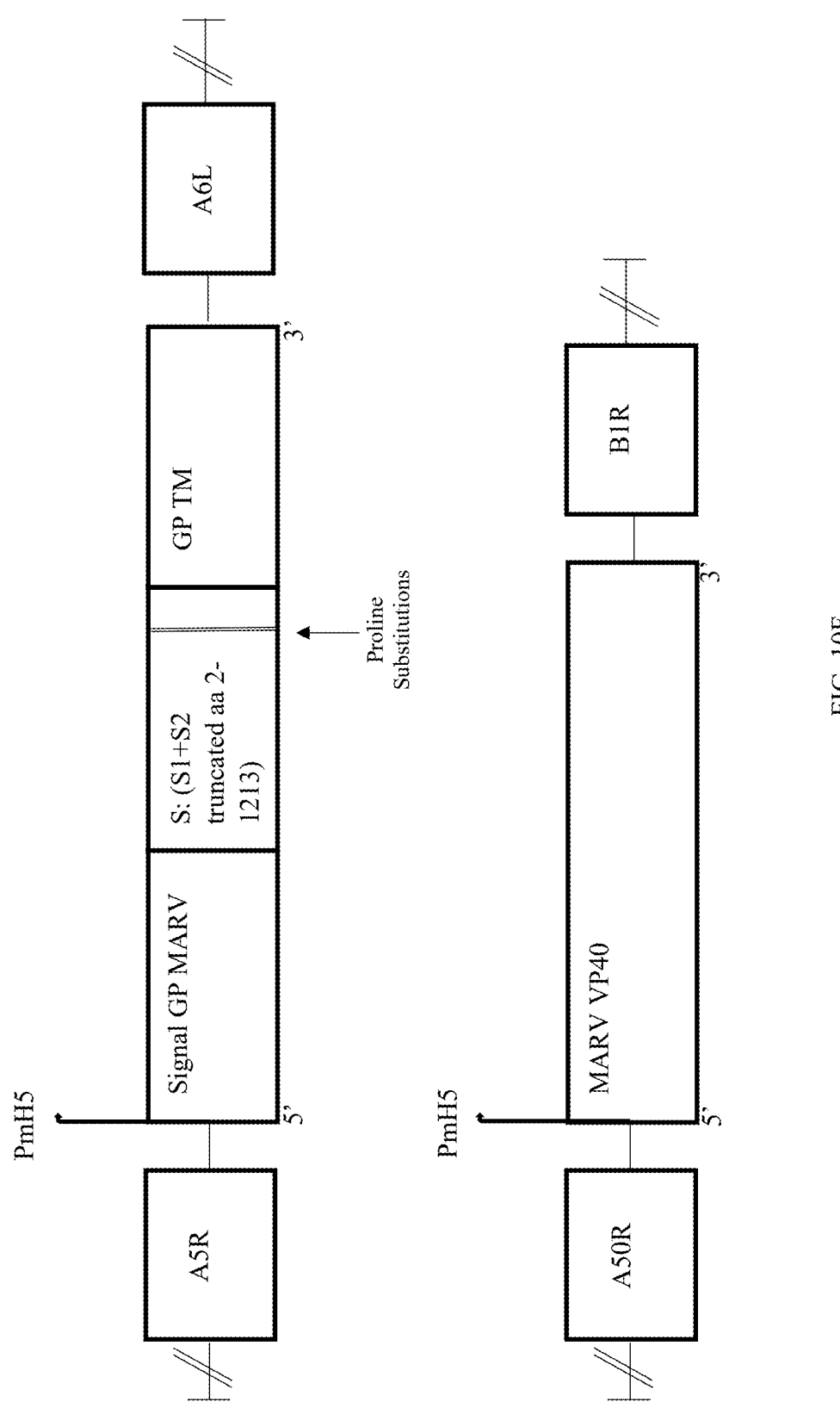

FIG. 10F provides an exemplary linear schematic of an exemplary recombinant MVA viral vector comprising a nucleic acid sequence encoding a glycoprotein (Signal GP MARV)-S protein S1+S2 truncated+K986P and V987P-transmembrane domain of the glycoprotein (GP TM) fusion protein inserted between MVA genes A5R and A6L, and a nucleic acid sequence encoding a non-coronavirus matrix protein inserted between MVA genes A50R and B1R. As exemplified, a mH5 promoter (pmH5) is operably linked to a nucleic acid encoding a fusion protein, wherein the fusion protein includes a signal peptide from a non-coronavirus glycoprotein (Signal GP MARV), truncated amino acids 2-1213 derived from the S protein (S1+S2 truncated) plus two proline substitutions at amino acids 981 and 982, and a transmembrane domain of the glycoprotein (GP TM), in a left-to-right orientation. A start codon is provided 5' to the Signal GP MARV-S protein (S1+S2 truncated)-GP TM fusion encoding nucleic acid in a left-to-right orientation. The insert may include a translation initiation sequence, for example a Kozak sequence, prior to the start codon of the Signal GP MARV-S protein (S1+S2 truncated+K986P and V987P)-GP TM fusion sequence. In addition, a nucleic acid sequence encoding a tag, for example a C-affinity tag, may be included at the 3' terminus of the fusion protein, prior to the stop codon. As exemplified, a nucleic acid sequence encoding a non-coronavirus matrix protein, for example Marburgvirus matrix protein VP40, is inserted between, for example, MVA genes A50R and B1R. The nucleic acid sequence encoding the matrix protein is operably linked to, for example, a pmH5 promoter. Similar to the fusion protein, the matrix protein nucleic acid sequence can also include appropriate translation initiation sequences such as a Kozak sequence, as well as a nucleic acid sequence encoding a tag at the 3' terminus of the coding sequence prior to the stop codon.

FIG. 10G-10H is an exemplary rMVA nucleic acid insert of SEQ ID NO: 125 encoding a glycoprotein (Signal GP MARV)-S protein S1+S2 truncated+K986P and V987P-transmembrane domain of the glycoprotein (GP TM) fusion protein. Also exemplified and identified in the sequence are the vaccinia mH5 promoters, vaccinia P11 promoter, start codons, Kozak regulatory sequences, and c-tag sequences.

FIG. 10I-10J is an exemplary rMVA nucleic acid insert of SEQ ID NO: 126 encoding a glycoprotein (Signal GP MARV)-S protein S1+S2 truncated+K986P and V987P-transmembrane domain of the glycoprotein (GP TM) fusion protein. Also exemplified and identified in the sequence are the vaccinia mH5 promoters, vaccinia P11 promoter, SmaI restriction site, start codons, Kozak regulatory sequences, and c-tag sequences.

Figure 10K:
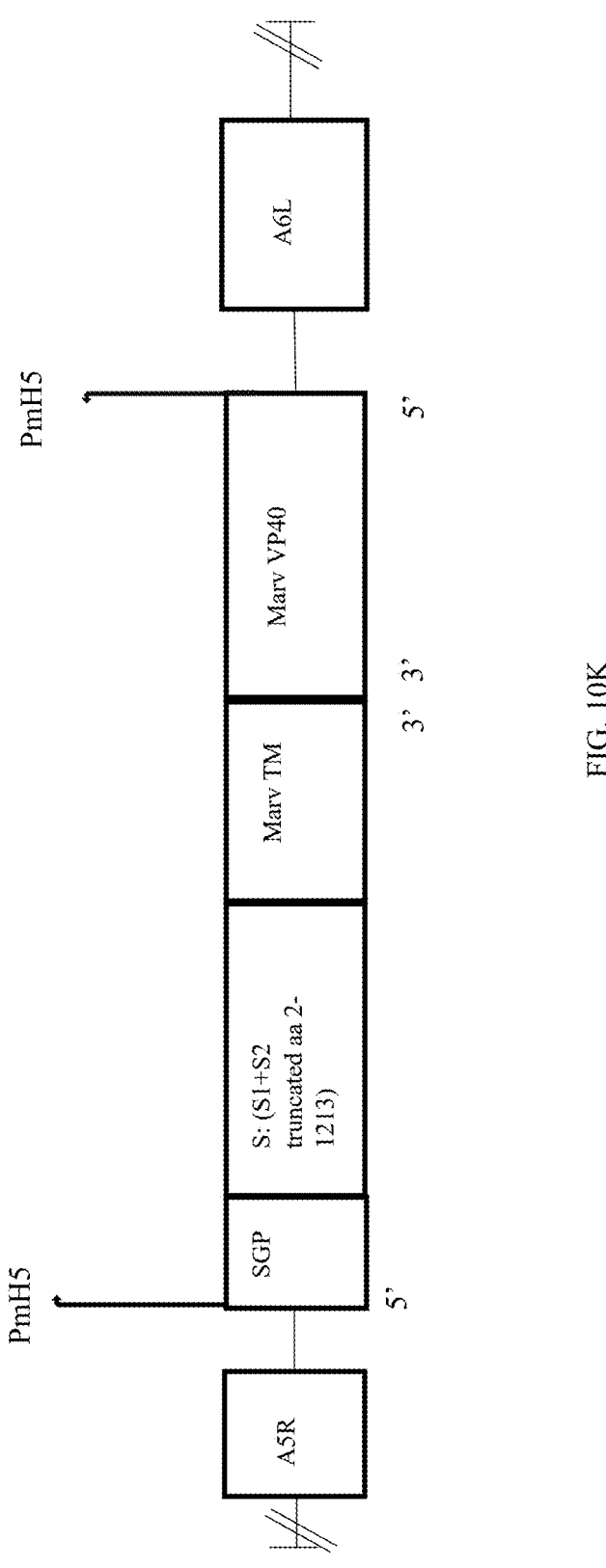

FIG. 10K provides an exemplary linear schematic of an exemplary recombinant MVA viral vector comprising a nucleic acid sequence encoding a glycoprotein (Signal GP MARV)-S protein truncated S1+S2-transmembrane domain of the glycoprotein (GP TM) fusion protein and a nucleic acid sequence encoding a non-coronavirus matrix protein inserted between, for example, MVA genes A5R and A6L. As exemplified, a mH5 promoter (pmH5) is operably linked to a nucleic acid encoding a fusion protein, wherein the fusion protein includes a signal peptide from a non-coronavirus glycoprotein (Signal GP MARV), truncated amino acids 2-1213 derived from the S protein (S1+S2 truncated), and a transmembrane domain of the glycoprotein (GP TM), in a left-to-right orientation. A start codon is provided 5' to the Signal GP MARV-S protein (S1+S2 truncated)-GP TM fusion encoding nucleic acid in a left-to-right orientation. The insert may include a translation initiation sequence, for example a Kozak sequence, prior to the start codon of the Signal GP MARV-S protein (S1+S2 truncated)-GP TM fusion sequence. In addition, a nucleic acid sequence encoding a tag, for example a C-affinity tag, may be included at the 3' terminus of the fusion protein, prior to the stop codon. As exemplified, a nucleic acid sequence encoding a non-coronavirus matrix protein, for example Marburgvirus matrix protein VP40, is also inserted as, for example, a bicistronic sequence. The nucleic acid sequence encoding the matrix protein is operably linked to, for example, a pmH15 promoter and is oriented in a 3' to 5' orientation. Similar to the fusion protein, the matrix protein nucleic acid sequence can also include appropriate translation initiation sequences such as a Kozak sequence, as well as a nucleic acid sequence encoding a tag at the 3' terminus of the coding sequence prior to the stop codon.

FIG. 10L-10M-10N is an exemplary rMVA nucleic acid insert of SEQ ID NO: 127 encoding a glycoprotein (Signal GP MARV)-S protein truncated S1+S2-transmembrane domain of the glycoprotein (GP TM) fusion protein and the MARC VP40 protein. Also exemplified and identified in the sequence are the vaccinia mH5 promoters, vaccinia P11 promoter, start codons, Kozak regulatory sequences, and c-tag sequences.

FIG. 10O-10P-10Q is an exemplary rMVA nucleic acid insert of SEQ ID NO: 128 encoding a glycoprotein (Signal GP MARV)-S protein truncated S1+S2-transmembrane domain of the glycoprotein (GP TM) fusion protein and the MARC VP40 protein. Also exemplified and identified in the sequence are the vaccinia mH5 promoters, vaccinia P11 promoter, SmaI restriction site, start codons, Kozak regulatory sequences, and c-tag sequences.

Figure 10R:
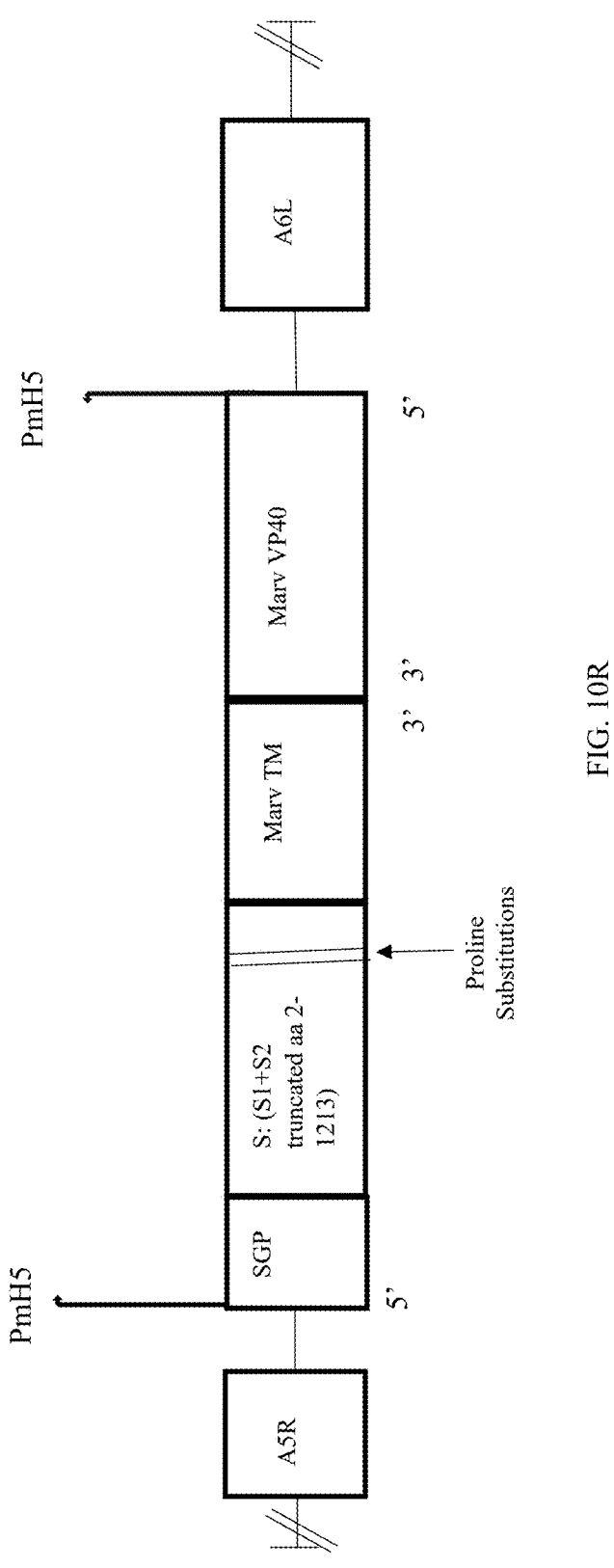

FIG. 10R provides an exemplary linear schematic of an exemplary recombinant MVA viral vector comprising a nucleic acid sequence encoding a glycoprotein (Signal GP MARV)-S protein truncated S1+S2 plus two proline substitutions at amino acids 981 and 982-transmembrane domain of the glycoprotein (GP TM) fusion protein and a nucleic acid sequence encoding a non-coronavirus matrix protein inserted between, for example, MVA genes A5R and A6L. As exemplified, a mH5 promoter (pmH5) is operably linked to a nucleic acid encoding a fusion protein, wherein the fusion protein includes a signal peptide from a non-coronavirus glycoprotein (Signal GP MARV), truncated amino acids 2-1213 derived from the S protein (S1+S2 truncated+K986P and V987P), and a transmembrane domain of the glycoprotein (GP TM), in a left-to-right orientation. A start codon is provided 5' to the Signal GP MARV-S protein (S1+S2 truncated+K986P and V987P)-GP TM fusion encoding nucleic acid in a left-to-right orientation. The insert may include a translation initiation sequence, for example a Kozak sequence, prior to the start codon of the Signal GP MARV-S protein (S1+S2 truncated+K986P and V987P)-GP TM fusion sequence. In addition, a nucleic acid sequence encoding a tag, for example a C-affinity tag, may be included at the 3' terminus of the fusion protein, prior to the stop codon. As exemplified, a nucleic acid sequence encoding a non-coronavirus matrix protein, for example Marburgvirus matrix protein VP40, is also inserted as, for example, a bicistronic sequence. The nucleic acid sequence encoding the matrix protein is operably linked to, for example, a pmH5 promoter and is oriented in a 3' to 5' orientation. Similar to the fusion protein, the matrix protein nucleic acid sequence can also include appropriate translation initiation sequences such as a Kozak sequence, as well as a nucleic acid sequence encoding a tag at the 3' terminus of the coding sequence prior to the stop codon.

FIG. 10S-10T-10U is an exemplary rMVA nucleic acid insert of SEQ ID NO: 129 encoding a glycoprotein (Signal GP MARV)-S protein truncated S1+S2 plus two proline substitutions at amino acids 981 and 982-transmembrane domain of the glycoprotein (GP TM) fusion protein and the MARC VP40 protein. Also exemplified and identified in the sequence are the vaccinia mH5 promoters, vaccinia P11 promoter, start codons, Kozak regulatory sequences, and c-tag sequences.

FIG. 10V-10W-10X is an exemplary rMVA nucleic acid insert of SEQ ID NO: 130 encoding a glycoprotein (Signal GP MARV)-S protein truncated S1+S2 plus two proline substitutions at amino acids 981 and 982-transmembrane domain of the glycoprotein (GP TM) fusion protein and the MARC VP40 protein. Also exemplified and identified in the sequence are the vaccinia mH5 promoters, vaccinia P11 promoter, SmaI restriction site, start codons, Kozak regulatory sequences, and c-tag sequences.

Figure 11A:
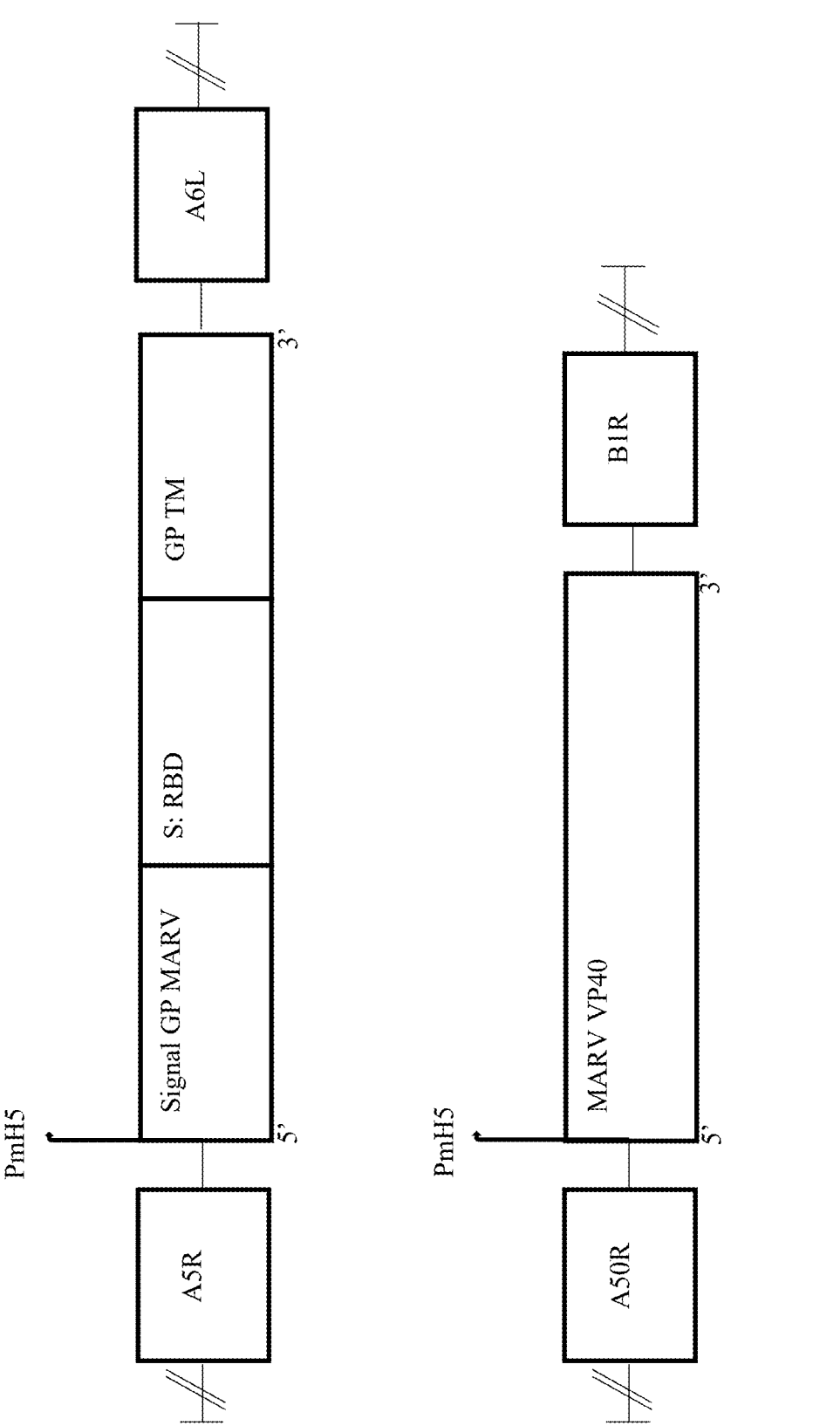

FIG. 11A provides an exemplary linear schematic of an exemplary recombinant MVA viral vector comprising a nucleic acid sequence encoding a glycoprotein (Signal GP MARV)-S protein RDB-transmembrane domain of the glycoprotein (GPTM) fusion protein inserted between MVA genes A5R and A6L, and a nucleic acid sequence encoding a non-coronavirus matrix protein inserted between MVA genes A50R and B1R. As exemplified, a mH5 promoter (pmH5) is operably linked to a nucleic acid encoding a fusion protein, wherein the fusion protein includes a signal peptide from a non-coronavirus glycoprotein (Signal GP MARV), S protein RBD region, and a transmembrane domain of the glycoprotein (GP TM), in a left-to-right orientation. A start codon is provided 5' to the glycoprotein-S RBD fusion encoding nucleic acid in a left-to-right orientation. The insert may include a translation initiation sequence, for example a Kozak sequence, prior to the start codon of the Signal GP MARV-S RBD-GP TM fusion sequence. In addition, a nucleic acid sequence encoding a tag, for example a C-affinity tag, may be included at the 3' terminus of the fusion protein, prior to the stop codon. As exemplified, a nucleic acid sequence encoding a non-coronavirus matrix protein, for example Marburgvirus matrix protein VP40, is inserted between MVA genes A50R and B1R. The nucleic acid sequence encoding the matrix protein is operably linked to, for example, a pmH5 promoter. Similar to the fusion protein, the matrix protein nucleic acid sequence can also include appropriate translation initiation sequences such as a Kozak sequence, as well as a nucleic acid sequence encoding a tag at the 3' terminus of the coding sequence prior to the stop codon.

Figure 11B:
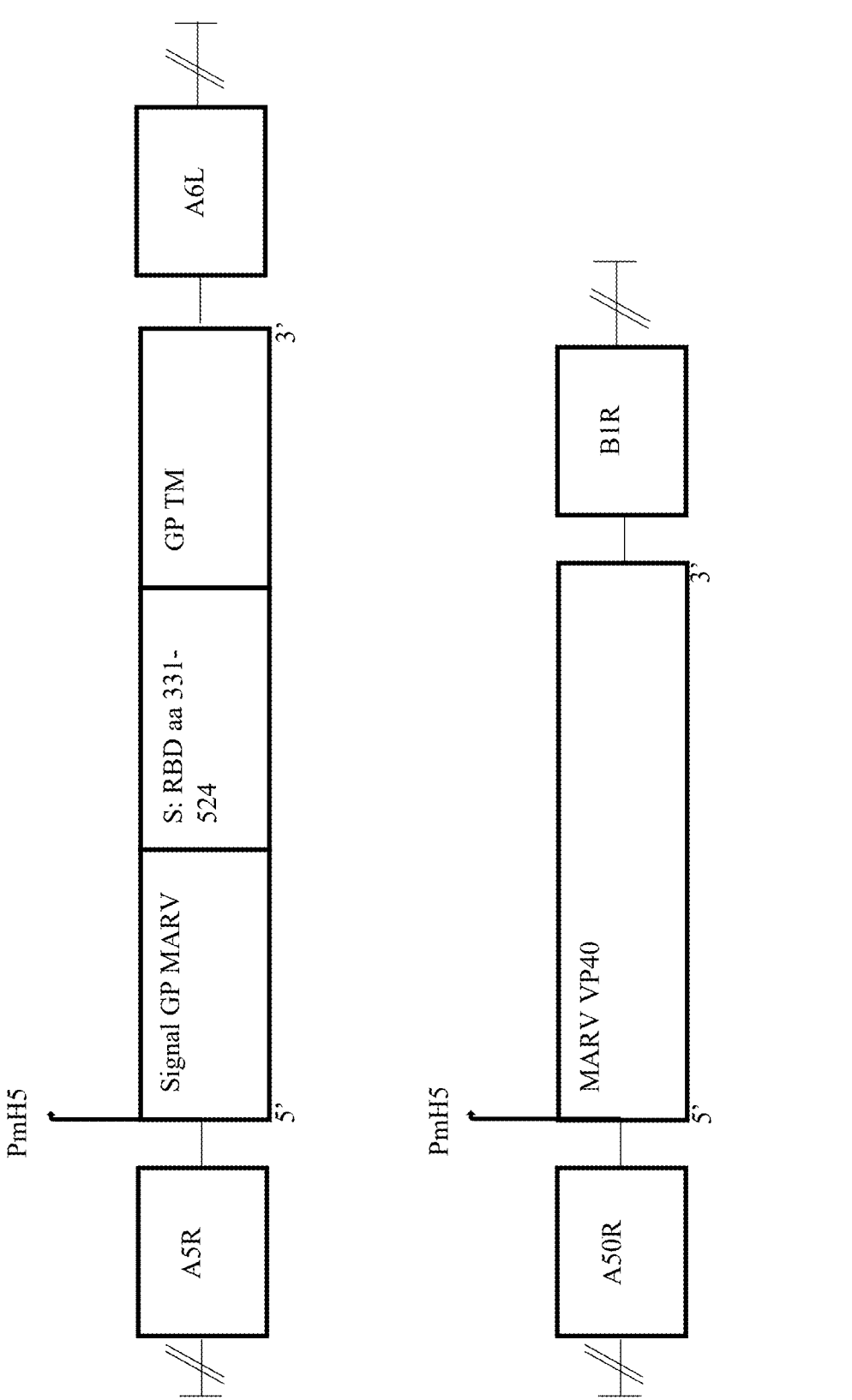

FIG. 11B provides an exemplary linear schematic of an exemplary recombinant MVA viral vector comprising a nucleic acid sequence encoding a glycoprotein (Signal GP MARV)-S protein RDB (331-524)-transmembrane domain of the glycoprotein (GP TM) fusion protein inserted between MVA genes A5R and A6L, and a nucleic acid sequence encoding a non-coronavirus matrix protein inserted between MVA genes A50R and B1R. As exemplified, a mH5 promoter (pmH5) is operably linked to a nucleic acid encoding a fusion protein, wherein the fusion protein includes a signal peptide from a non-coronavirus glycoprotein (Signal GP MARV), S protein RBD (331-524) region, and a transmembrane domain of the glycoprotein (GP TM), in a left-to-right orientation. A start codon is provided 5' to the glycoprotein-S RBD (331-524) fusion encoding nucleic acid in a left-to-right orientation. The insert may include a translation initiation sequence, for example a Kozak sequence, prior to the start codon of the Signal GP MARV-S RBD (331-524)-GP TM fusion sequence. In addition, a nucleic acid sequence encoding a tag, for example a C-affinity tag, may be included at the 3' terminus of the fusion protein, prior to the stop codon. As exemplified, a nucleic acid sequence encoding a non-coronavirus matrix protein, for example Marburgvirus matrix protein VP40, is inserted between MVA genes A50R and B1R. The nucleic acid sequence encoding the matrix protein is operably linked to, for example, a pmH5 promoter. Similar to the fusion protein, the matrix protein nucleic acid sequence can also include appropriate translation initiation sequences such as a Kozak sequence, as well as a nucleic acid sequence encoding a tag at the 3' terminus of the coding sequence prior to the stop codon.

FIG. 11C is an exemplary rMVA nucleic acid insert of SEQ ID NO: 133 encoding a glycoprotein (Signal GP MARV)-S protein RDB (331-524)-transmembrane domain of the glycoprotein (GP TM) fusion protein. Also exemplified and identified in the sequence are the vaccinia mH5 promoters, vaccinia P11 promoter, start codons, Kozak regulatory sequences, and c-tag sequences.

FIG. 11D is an exemplary rMVA nucleic acid insert of SEQ ID NO: 134 encoding a glycoprotein (Signal GP MARV)-S protein RDB (331-524)-transmembrane domain of the glycoprotein (GP TM) fusion protein. Also exemplified and identified in the sequence are the vaccinia mH5 promoters, vaccinia P11 promoter, start codons, Kozak regulatory sequences, Smal restriction site, and c-tag sequences.

Figure 11E:
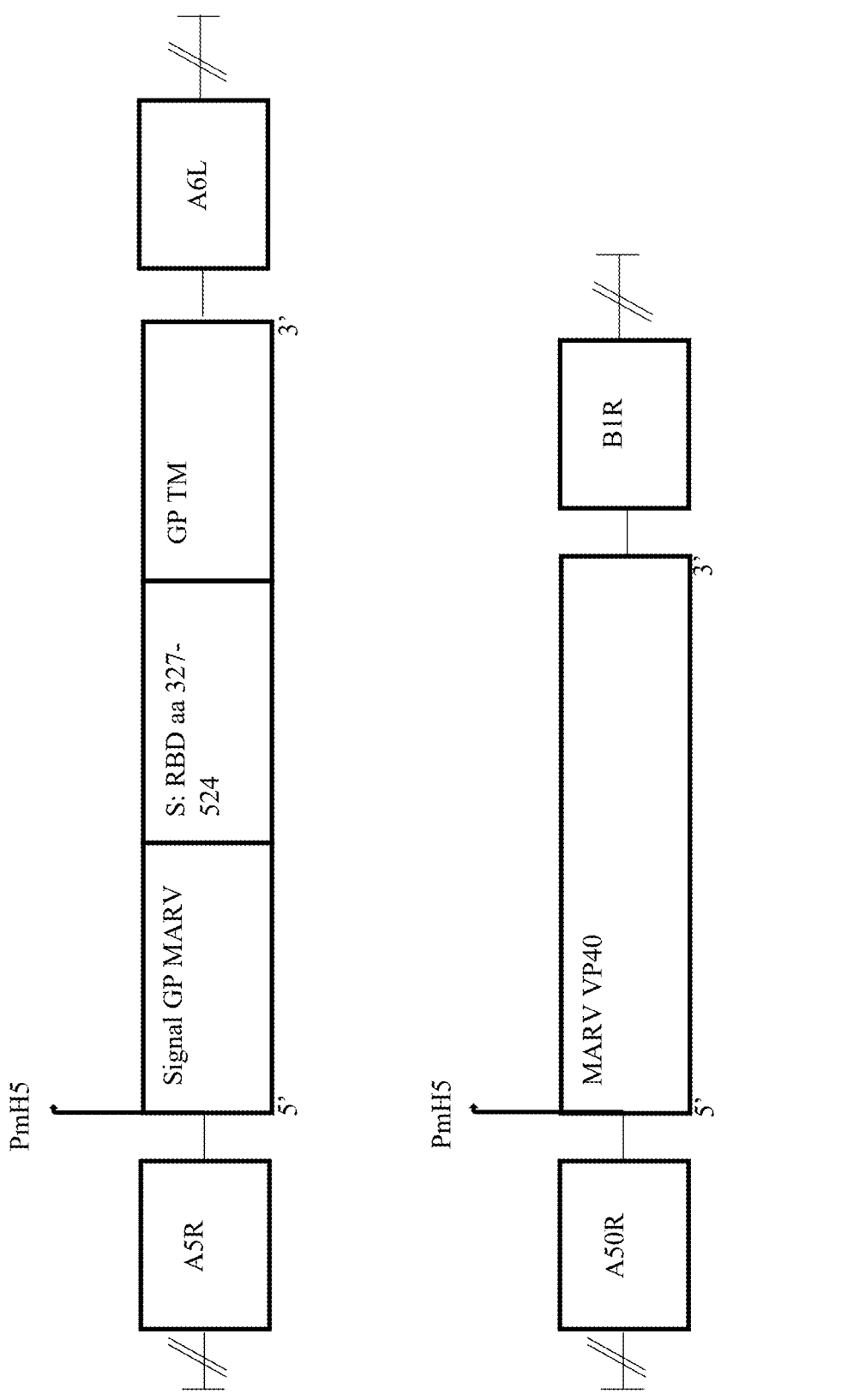

FIG. 11E provides an exemplary linear schematic of an exemplary recombinant MVA viral vector comprising a nucleic acid sequence encoding a glycoprotein (Signal GP MARV)-S protein RDB (327-524)-transmembrane domain of the glycoprotein (GP TM) fusion protein inserted between MVA genes A5R and A6L, and a nucleic acid sequence encoding a non-coronavirus matrix protein inserted between MVA genes A50R and B1R. As exemplified, a mH5 promoter (pmH5) is operably linked to a nucleic acid encoding a fusion protein, wherein the fusion protein includes a signal peptide from a non-coronavirus glycoprotein (Signal GP MARV), S protein RBD (327-524) region, and a transmembrane domain of the glycoprotein (GP TM), in a left-to-right orientation. A start codon is provided 5' to the glycoprotein-S RBD (327-524) fusion encoding nucleic acid in a left-to-right orientation. The insert may include a translation initiation sequence, for example a Kozak sequence, prior to the start codon of the Signal GP MARV-S RBD (327-524)-GP TM fusion sequence. In addition, a nucleic acid sequence encoding a tag, for example a C-affinity tag, may be included at the 3' terminus of the fusion protein, prior to the stop codon. As exemplified, a nucleic acid sequence encoding a non-coronavirus matrix protein, for example Marburgvirus matrix protein VP40, is inserted between MVA genes A50R and B1R. The nucleic acid sequence encoding the matrix protein is operably linked to, for example, a pmH5 promoter. Similar to the fusion protein, the matrix protein nucleic acid sequence can also include appropriate translation initiation sequences such as a Kozak sequence, as well as a nucleic acid sequence encoding a tag at the 3' terminus of the coding sequence prior to the stop codon.

FIG. 11F is an exemplary rMVA nucleic acid insert of SEQ ID NO: 131 encoding a glycoprotein (Signal GP MARV)-S protein RDB (327-524)-transmembrane domain of the glycoprotein (GP TM) fusion protein. Also exemplified and identified in the sequence are the vaccinia mH5 promoters, vaccinia P11 promoter, start codons, Kozak regulatory sequences, and c-tag sequences.

FIG. 11G is an exemplary rMVA nucleic acid insert of SEQ ID NO: 132 encoding a glycoprotein (Signal GP MARV)-S protein RDB (327-524)-transmembrane domain of the glycoprotein (GP TM) fusion protein. Also exemplified and identified in the sequence are the vaccinia mH5 promoters, vaccinia P11 promoter, start codons, Kozak regulatory sequences, SmaI restriction site, and c-tag sequences.

Figure 11H:
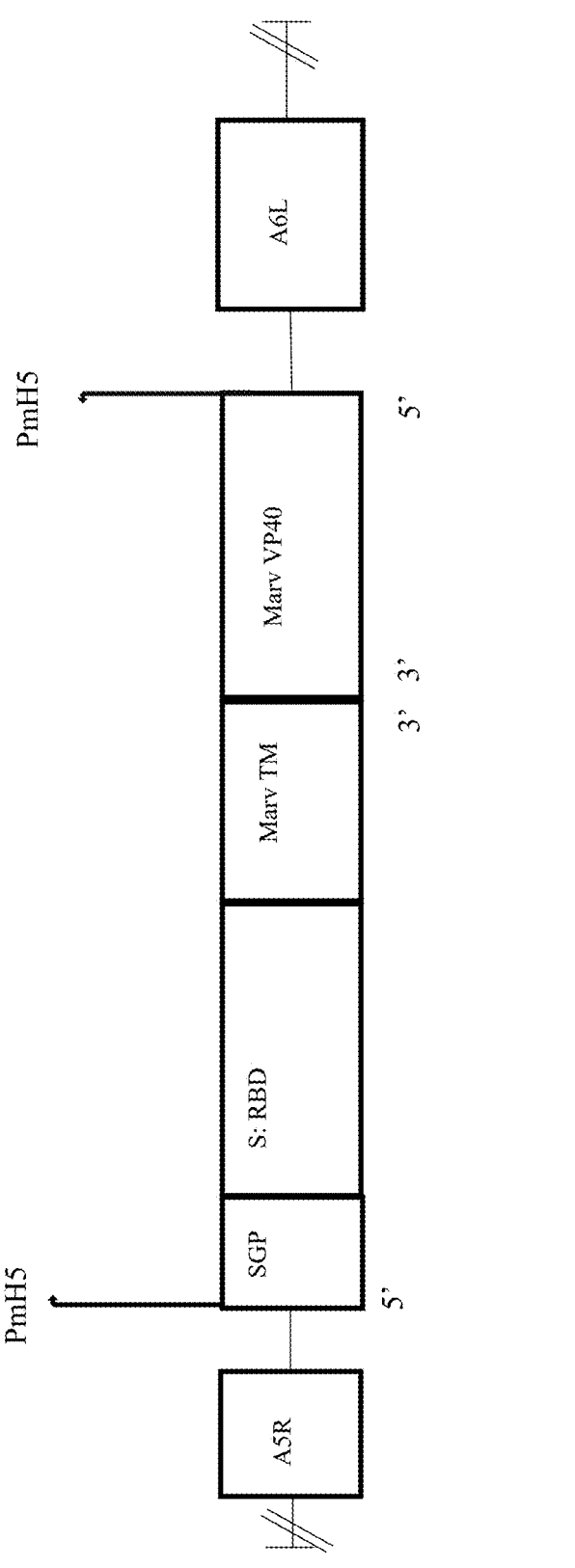

FIG. 11H provides an exemplary linear schematic of an exemplary recombinant MVA viral vector comprising a bicistronic nucleic acid sequence encoding a glycoprotein (Signal GP MARV)-S protein RDB-transmembrane domain of the glycoprotein (GP TM) fusion protein and a nucleic acid sequence encoding a non-coronavirus matrix protein inserted, for example, between MVA genes A5R and A6L. As exemplified, a mH5 promoter (pmH5) is operably linked to a nucleic acid encoding a fusion protein, wherein the fusion protein includes a signal peptide from a non-coronavirus glycoprotein (Signal GP MARV), S protein RBD region, and a transmembrane domain of the glycoprotein (GP TM), in a left-to-right orientation. A start codon is provided 5' to the glycoprotein-S RBD fusion encoding nucleic acid in a left-to-right orientation. The insert may include a translation initiation sequence, for example a Kozak sequence, prior to the start codon of the Signal GP MARV-S RBD-GP TM fusion sequence. In addition, a nucleic acid sequence encoding a tag, for example a C-affinity tag, may be included at the 3' terminus of the fusion protein, prior to the stop codon. In addition, the bicistronic nucleic acid sequence also encodes a non-coronavirus matrix protein, for example Marburgvirus matrix protein VP40. The nucleic acid sequence encoding the matrix protein is operably linked to, for example, a pmH5 promoter. Similar to the fusion protein, the matrix protein nucleic acid sequence can also include appropriate translation initiation sequences such as a Kozak sequence, as well as a nucleic acid sequence encoding a tag at the 3' terminus of the coding sequence prior to the stop codon.

Figure 11I:
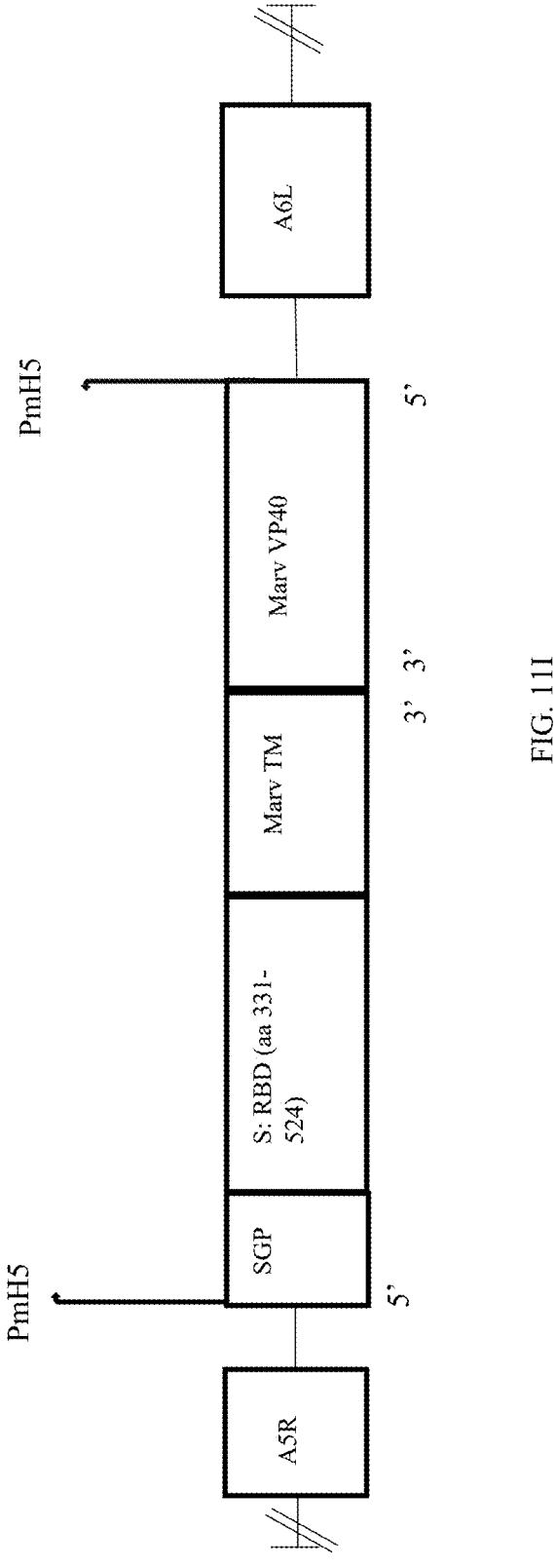

FIG. 11I provides an exemplary linear schematic of an exemplary recombinant MVA viral vector comprising a bicistronic nucleic acid sequence encoding a glycoprotein (Signal GP MARV)-S protein RDB (aa 331-524)-transmembrane domain of the glycoprotein (GP TM) fusion protein and a nucleic acid sequence encoding a non-coronavirus matrix protein inserted, for example, between MVA genes A5R and A6L. As exemplified, a mH5 promoter (pmH5) is operably linked to a nucleic acid encoding a fusion protein, wherein the fusion protein includes a signal peptide from a non-coronavirus glycoprotein (Signal GP MARV), S protein RBD (aa 331-524) region, and a transmembrane domain of the glycoprotein (GP TM), in a left-to-right orientation. A start codon is provided 5' to the glycoprotein-S RBD fusion encoding nucleic acid in a left-to-right orientation. The insert may include a translation initiation sequence, for example a Kozak sequence, prior to the start codon of the Signal GP MARV-S RBD (aa 331-524)-GP TM fusion sequence. In addition, a nucleic acid sequence encoding a tag, for example a C-affinity tag, may be included at the 3' terminus of the fusion protein, prior to the stop codon. In addition, the bicistronic nucleic acid sequence also encodes a non-coronavirus matrix protein, for example Marburgvirus matrix protein VP40. The nucleic acid sequence encoding the matrix protein is operably linked to, for example, a pmH5 promoter. Similar to the fusion protein, the matrix protein nucleic acid sequence can also include appropriate translation initiation sequences such as a Kozak sequence, as well as a nucleic acid sequence encoding a tag at the 3' terminus of the coding sequence prior to the stop codon.

FIG. 11J-11K is an exemplary rMVA nucleic acid insert of SEQ ID NO: 137 encoding a glycoprotein (Signal GP MARV)-S protein RDB (aa 331-524)-transmembrane domain of the glycoprotein (GP TM) fusion protein and the MARV VP40 protein. Also exemplified and identified in the sequence are the vaccinia mH5 promoters, vaccinia P11 promoter, start codons, Kozak regulatory sequences, and c-tag sequences.

Figure 11N:
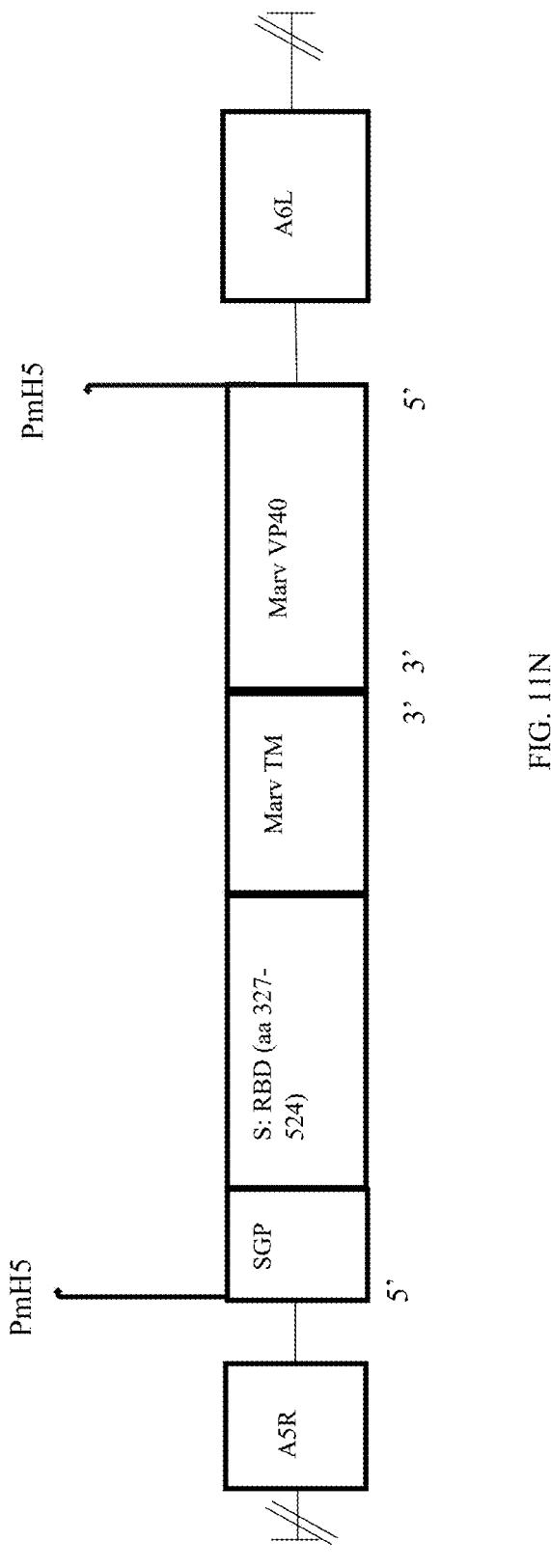

FIG. 11L-11M is an exemplary rMVA nucleic acid insert of SEQ ID NO: 138 encoding a glycoprotein (Signal GP MARV)-S protein RDB (aa 331-524)-transmembrane domain of the glycoprotein (GP TM) fusion protein and the MARV VP40 protein. Also exemplified and identified in the sequence are the vaccinia mH5 promoters, vaccinia P11 promoter, start codons, Kozak regulatory sequences, SmaI restriction site, and c-tag sequences FIG. 11N provides an exemplary linear schematic of an exemplary recombinant MVA viral vector comprising a bicistronic nucleic acid sequence encoding a glycoprotein (Signal GP MARV)-S protein RDB (aa 327-524)-transmembrane domain of the glycoprotein (GP TM) fusion protein and a nucleic acid sequence encoding a non-coronavirus matrix protein inserted, for example, between MVA genes A5R and A6L. As exemplified, a mH5 promoter (pmH5) is operably linked to a nucleic acid encoding a fusion protein, wherein the fusion protein includes a signal peptide from a non-coronavirus glycoprotein (Signal GP MARV), S protein RBD (aa 327-524) region, and a transmembrane domain of the glycoprotein (GP TM), in a left-to-right orientation. A start codon is provided 5' to the glycoprotein-S RBD fusion encoding nucleic acid in a left-to-right orientation. The insert may include a translation initiation sequence, for example a Kozak sequence, prior to the start codon of the Signal GP MARV-S RBD (aa 327-524)-GP TM fusion sequence. In addition, a nucleic acid sequence encoding a tag, for example a C-affinity tag, may be included at the 3' terminus of the fusion protein, prior to the stop codon. In addition, the bicistronic nucleic acid sequence also encodes a non-coronavirus matrix protein, for example Marburgvirus matrix protein VP40. The nucleic acid sequence encoding the matrix protein is operably linked to, for example, a pmH5 promoter. Similar to the fusion protein, the matrix protein nucleic acid sequence can also include appropriate translation initiation sequences such as a Kozak sequence, as well as a nucleic acid sequence encoding a tag at the 3' terminus of the coding sequence prior to the stop codon.

FIG. 11O-11P is an exemplary rMVA nucleic acid insert of SEQ ID NO: 135 encoding a glycoprotein (Signal GP MARV)-S protein RDB (aa 327-524)-transmembrane domain of the glycoprotein (GP TM) fusion protein and the MARV VP40 protein. Also exemplified and identified in the sequence are the vaccinia mH5 promoters, vaccinia P11 promoter, start codons, Kozak regulatory sequences, and c-tag sequences.

FIG. 11Q-11R is an exemplary rMVA nucleic acid insert of SEQ ID NO: 136 encoding a glycoprotein (Signal GP MARV)-S protein RDB (aa 327-524)-transmembrane domain of the glycoprotein (GP TM) fusion protein and the MARV VP40 protein. Also exemplified and identified in the sequence are the vaccinia mH5 promoters, vaccinia P11 promoter, start codons, Kozak regulatory sequences, SmaI restriction site, and c-tag sequences.

Figure 12A:
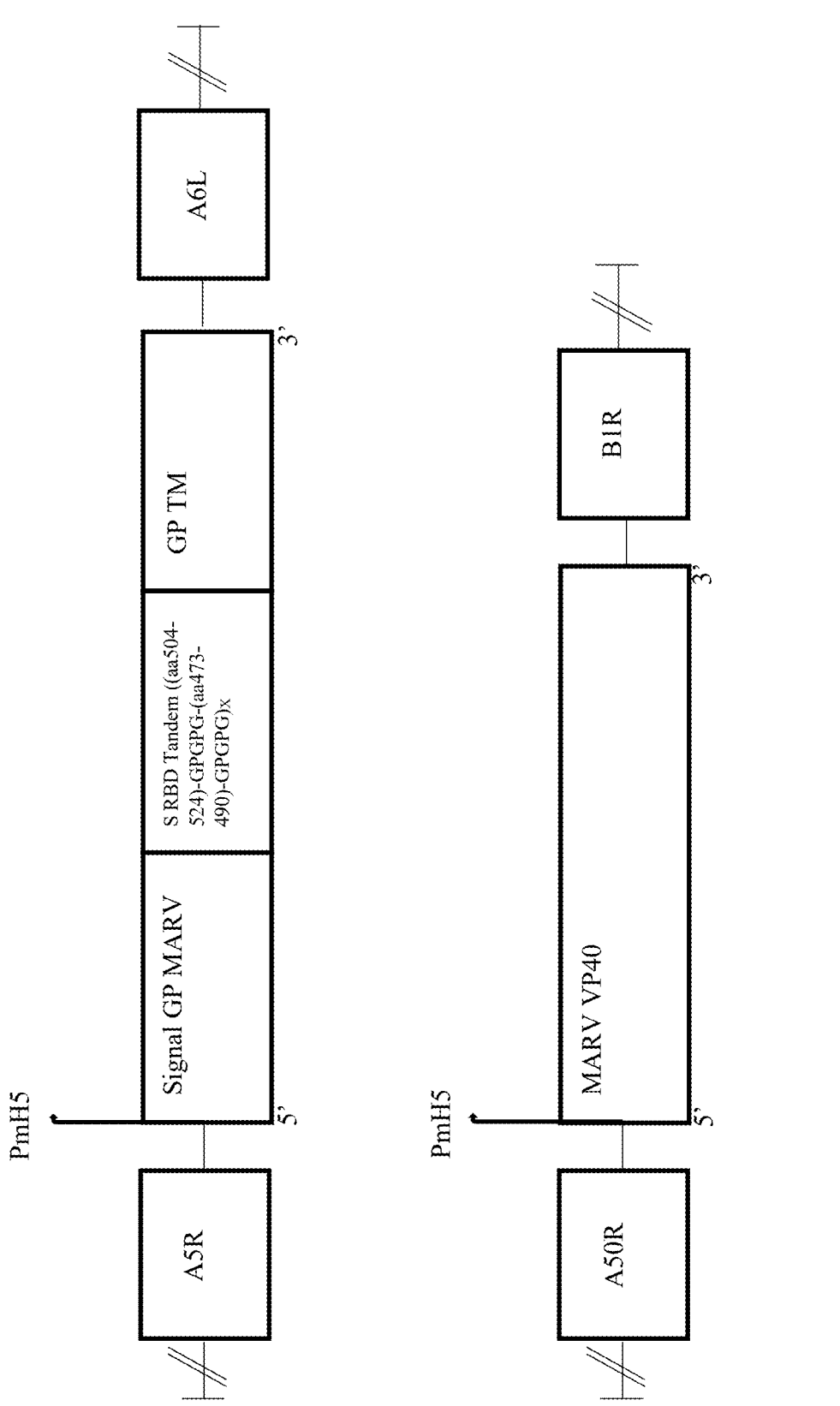

FIG. 12A provides an exemplary linear schematic of an exemplary recombinant MVA viral vector comprising a nucleic acid sequence encoding a glycoprotein (Signal GP MARV)-tandem repeat of S protein RBD derived amino acid-transmembrane domain of the glycoprotein (GP TM) fusion protein inserted between MVA genes A5R and A6L, and a nucleic acid sequence encoding a non-coronavirus matrix protein inserted between MVA genes A50R and B1R. As exemplified, a mH5 promoter (pmH5) is operably linked to a nucleic acid encoding a fusion protein, wherein the fusion protein includes a signal peptide from a non-coronavirus glycoprotein (Signal GP MARV), S RBD tandem repeat ((aa504-524)-GPGPG-(aa473-490)-GPGPG) 5, and a transmembrane domain of the glycoprotein (GP TM), in a left-to-right orientation. A start codon is provided 5' to the Signal GP MARV-S RBD tandem repeat-GP TM fusion encoding sequence. The insert may include a translation initiation sequence, for example a Kozak sequence, prior to the start codon of the Signal GP MARV-S RBD tandem repeat-GP TM fusion sequence. In addition, a nucleic acid sequence encoding a tag, for example a C-affinity tag, may be included at the 3' terminus of the fusion protein, prior to the stop codon. As exemplified, a nucleic acid sequence encoding a non-coronavirus matrix protein, for example Marburgvirus matrix protein VP40, is inserted between MVA genes A50R and B1R. The nucleic acid sequence encoding the matrix protein is operably linked to, for example, a mH5 promoter (pmH5). Similar to the fusion protein, the matrix protein nucleic acid sequence can also include appropriate translation initiation sequences such as a Kozak sequence, as well as a nucleic acid sequence encoding a tag at the 3' terminus of the coding sequence prior to the stop codon.

Figure 12D:
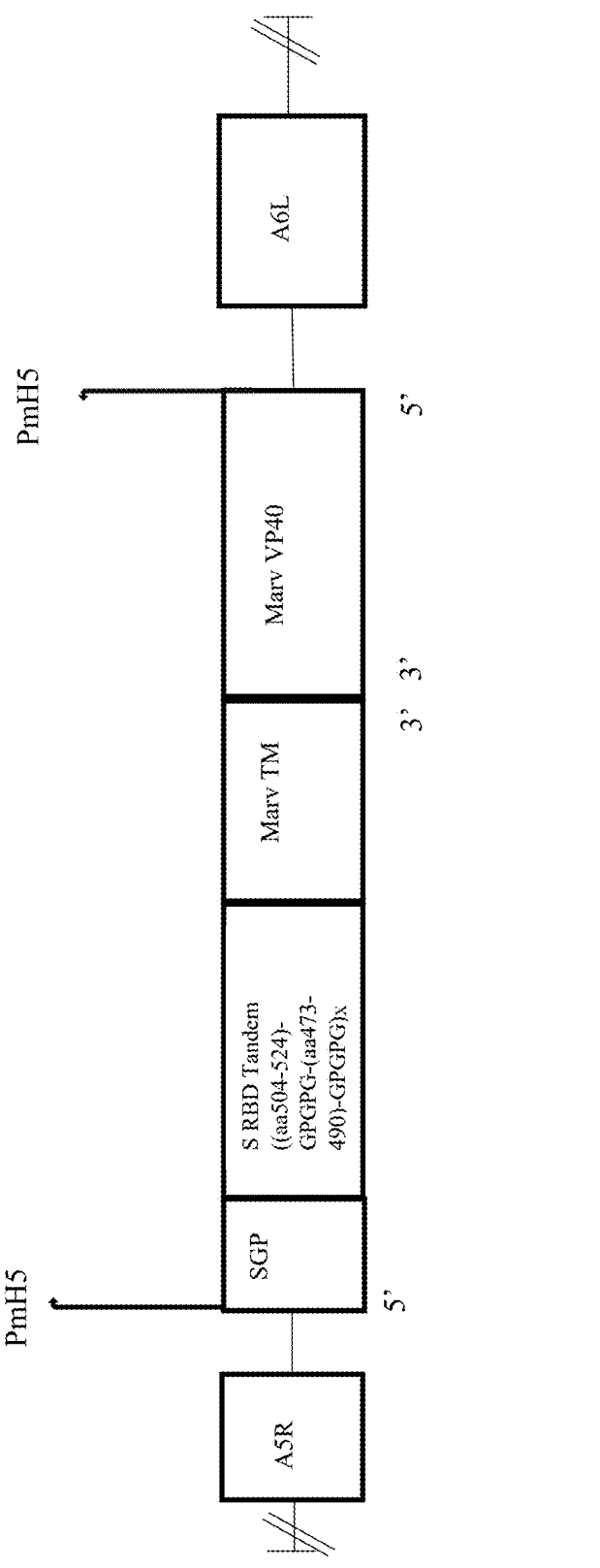

FIG. 12B is an exemplary rMVA nucleic acid insert of SEQ ID NO: 139 encoding a glycoprotein (Signal GP MARV)-tandem repeat of S protein RBD derived amino acid-transmembrane domain of the glycoprotein (GP TM) fusion protein. Also exemplified and identified in the sequence are the vaccinia mH5 promoters, vaccinia P11 promoter, start codons, Kozak regulatory sequences, and c-tag sequences FIG. 12C is an exemplary rMVA nucleic acid insert of SEQ ID NO: 140 encoding a glycoprotein (Signal GP MARV)-tandem repeat of S protein RBD derived amino acid-transmembrane domain of the glycoprotein (GP TM) fusion protein. Also exemplified and identified in the sequence are the vaccinia mH5 promoters, vaccinia P11 promoter, start codons, Kozak regulatory sequences, SmaI restriction site, and c-tag sequences FIG. 12D provides an exemplary linear schematic of an exemplary recombinant MVA viral vector comprising a bicistronic nucleic acid sequence encoding a glycoprotein (Signal GP MARV)-S protein RBD tandem repeat ((aa504-524)-GPGPG-(aa473-490)-GPGPG) 5)-transmembrane domain of the glycoprotein (GP TM) fusion protein and a nucleic acid sequence encoding a non-coronavirus matrix protein inserted, for example, between MVA genes A5R and A6L. As exemplified, a mH5 promoter (pmH5) is operably linked to a nucleic acid encoding a fusion protein, wherein the fusion protein includes a signal peptide from a non-coronavirus glycoprotein (Signal GP MARV), S protein RBD tandem repeat ((aa504-524)-GPGPG-(aa473-490)-GPGPG) 5) region, and a transmembrane domain of the glycoprotein (GP TM), in a left-to-right orientation. A start codon is provided 5' to the glycoprotein-S RBD fusion encoding nucleic acid in a left-to-right orientation. The insert may include a translation initiation sequence, for example a Kozak sequence, prior to the start codon of the Signal GP MARV-S protein RBD tandem repeat ((aa504-524)-GPGPG-(aa473-490)-GPGPG) 5)-GP TM fusion sequence. In addition, a nucleic acid sequence encoding a tag, for example a C-affinity tag, may be included at the 3' terminus of the fusion protein, prior to the stop codon. In addition, the bicistronic nucleic acid sequence also encodes a non-coronavirus matrix protein, for example Marburgvirus matrix protein VP40. The nucleic acid sequence encoding the matrix protein is operably linked to, for example, a pmH5 promoter. Similar to the fusion protein, the matrix protein nucleic acid sequence can also include appropriate translation initiation sequences such as a Kozak sequence, as well as a nucleic acid sequence encoding a tag at the 3' terminus of the coding sequence prior to the stop codon.

FIG. 12E-12F is an exemplary rMVA nucleic acid insert of SEQ ID NO: 141 encoding a glycoprotein (Signal GP MARV)-S protein RBD tandem repeat ((aa504-524)-GPGPG-(aa473-490)-GPGPG) 5)-transmembrane domain of the glycoprotein (GP TM) fusion protein and the MARV VP40 protein. Also exemplified and identified in the sequence are the vaccinia mH5 promoters, vaccinia P11 promoter, start codons, Kozak regulatory sequences, and c-tag sequences.

FIG. 12G-12H is an exemplary rMVA nucleic acid insert of SEQ ID NO: 142 encoding a glycoprotein (Signal GP MARV)-S protein RBD tandem repeat ((aa504-524)-GPGPG-(aa473-490)-GPGPG) 5)-transmembrane domain of the glycoprotein (GP TM) fusion protein and the MARV VP40 protein. Also exemplified and identified in the sequence are the vaccinia mH5 promoters, vaccinia P11 promoter, start codons, Kozak regulatory sequences, SmaI restriction site, and c-tag sequences.

Figure 13A:
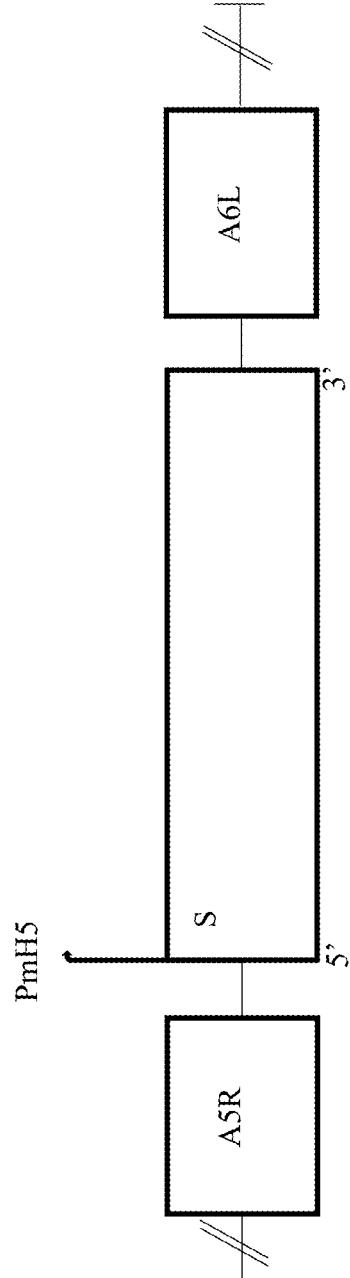

FIG. 13A provides an exemplary linear schematic of an exemplary recombinant MVA viral vector comprising a nucleic acid encoding a full-length S protein inserted between MVA genes A5R and A6L. As exemplified, a mH5 promoter (pmH5) is operably linked to a nucleic acid encoding the full-length SARS-CoV2 S protein in a left-to-right orientation. The insert may include a translation initiation sequence, for example a Kozak sequence, prior to the start codon of the S protein sequence as well as a nucleic acid sequence encoding a tag at the 3' terminus of the coding sequence prior to the stop codon.

FIG. 13B-13C is an exemplary rMVA nucleic acid insert of SEQ ID NO: 143 encoding a full-length S protein. Also exemplified and identified in the sequence are the vaccinia mH5 promoters, vaccinia P11 promoter, start codons, Kozak regulatory sequences, and c-tag sequences.

FIG. 13D-13E is an exemplary rMVA nucleic acid insert of SEQ ID NO: 144 encoding a full-length S protein. Also exemplified and identified in the sequence are the vaccinia mH5 promoters, vaccinia P11 promoter, start codons, Kozak regulatory sequences, SmaI restriction site, and c-tag sequences.

Figure 14A:
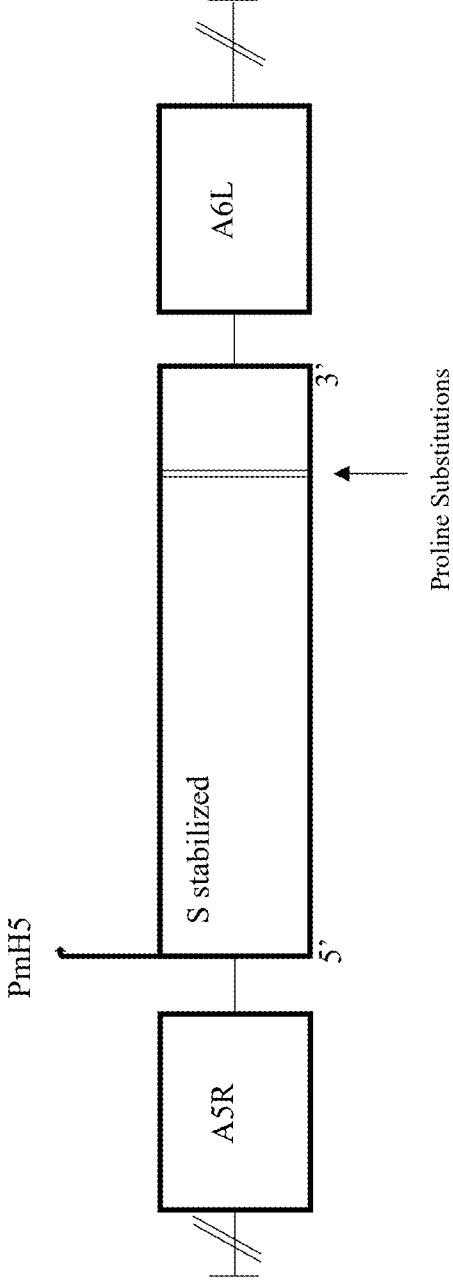

FIG. 14A provides an exemplary linear schematic of an exemplary recombinant MVA viral vector comprising a nucleic acid sequence encoding a stabilized S protein inserted between MVA genes A5R and A6L. As exemplified, a mH5 promoter (pmH5) is operably linked to a nucleic acid encoding the full-length SARS-CoV2 S stabilized protein in a left-to-right orientation. The insert may include a translation initiation sequence, for example a Kozak sequence, prior to the start codon of the S stabilized protein sequence, as well as a nucleic acid sequence encoding a tag at the 3' terminus of the coding sequence prior to the stop codon.

FIG. 14B-14C is an exemplary rMVA nucleic acid insert of SEQ ID NO: 145 encoding a full-length a stabilized S protein plus two proline substitutions at amino acids 981 and 982. Also exemplified and identified in the sequence are the vaccinia mH5 promoters, vaccinia P11 promoter, start codons, Kozak regulatory sequences, and c-tag sequences.

FIG. 14D-14E is an exemplary rMVA nucleic acid insert of SEQ ID NO: 146 encoding a full-length a stabilized S protein plus two proline substitutions at amino acids 981 and 982. Also exemplified and identified in the sequence are the vaccinia mH5 promoters, vaccinia P11 promoter, start codons, Kozak regulatory sequences, SmaI restriction site, and c-tag sequences.

Figure 15A:
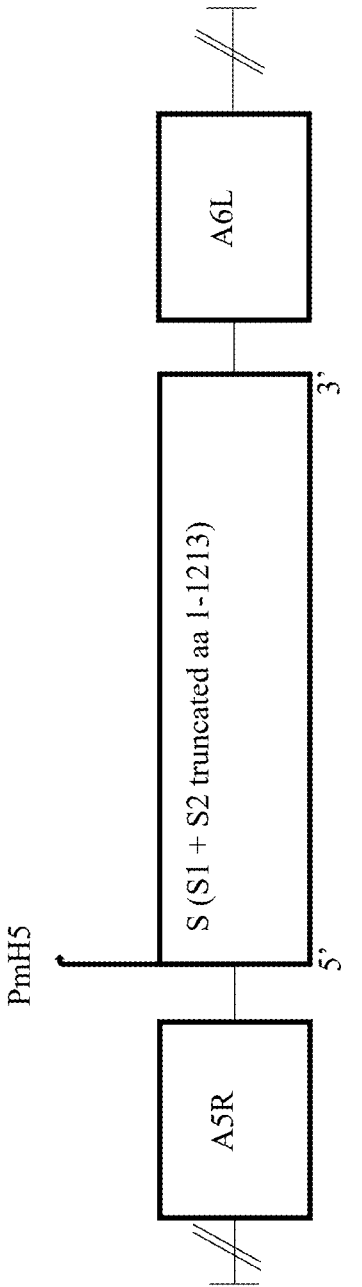

FIG. 15A provides an exemplary linear schematic of an exemplary recombinant MVA viral vector comprising a nucleic acid sequence encoding amino acid 1-1213 truncated S protein (S1+S2 truncated) inserted between, for example, MVA genes A5R and A6L. As exemplified, a mH5 promoter (pmH5) is operably linked to a nucleic acid encoding the full-length SARS-CoV2 S (S1+S2 truncated) protein in a left-to-right orientation. The insert may include a translation initiation sequence, for example a Kozak sequence, prior to the start codon of the S (S1+S2 truncated) protein sequence, as well as a nucleic acid sequence encoding a tag at the 3' terminus of the coding sequence prior to the stop codon.

FIG. 15B-15C is an exemplary rMVA nucleic acid insert of SEQ ID NO: 147 encoding amino acid 1-1213 truncated S protein (S1+S2 truncated). Also exemplified and identified in the sequence are the vaccinia mH5 promoters, vaccinia P11 promoter, start codons, Kozak regulatory sequences, and c-tag sequences.

FIG. 15D-15E is an exemplary rMVA nucleic acid insert of SEQ ID NO: 148 encoding amino acid 1-1213 truncated S protein (S1+S2 truncated). Also exemplified and identified in the sequence are the vaccinia mH5 promoters, vaccinia P11 promoter, start codons, Kozak regulatory sequences, SmaI restriction site, and c-tag sequences.

Figure 15F:
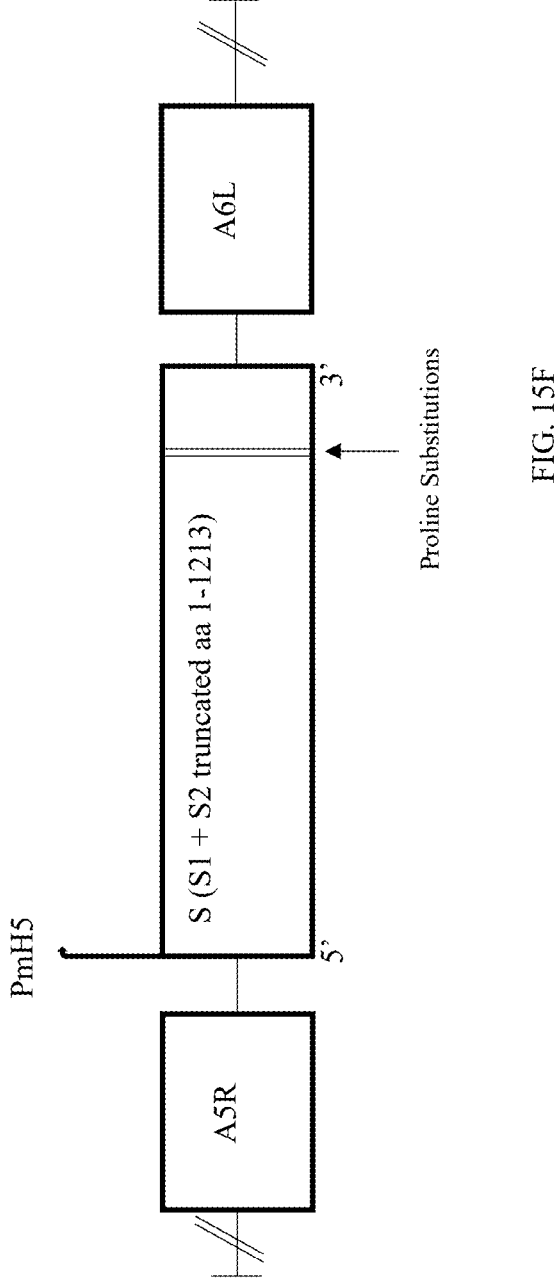

FIG. 15F provides an exemplary linear schematic of an exemplary recombinant MVA viral vector comprising a nucleic acid sequence encoding amino acid 1-1213 truncated S protein (S1+S2 truncated+K986P and V987P) inserted between, for example, MVA genes A5R and A6L. As exemplified, a mH5 promoter (pmH5) is operably linked to a nucleic acid encoding the full-length SARS-CoV2 S (S1+S2 truncated+K986P and V987P) protein in a left-to-right orientation. The insert may include a translation initiation sequence, for example a Kozak sequence, prior to the start codon of the S (S1+S2 truncated+K986P and V987P) protein sequence, as well as a nucleic acid sequence encoding a tag at the 3' terminus of the coding sequence prior to the stop codon.

FIG. 15G-15H is an exemplary rMVA nucleic acid insert of SEQ ID NO: 149 encoding amino acid 1-1213 truncated S protein (S1+S2 truncated) plus two substitutions at K986P and V987P. Also exemplified and identified in the sequence are the vaccinia mH5 promoters, vaccinia P11 promoter, start codons, Kozak regulatory sequences, and c-tag sequences.

FIG. 15I-15J is an exemplary rMVA nucleic acid insert of SEQ ID NO: 150 encoding amino acid 1-1213 truncated S protein (S1+S2 truncated) plus two substitutions at K986P and V987P. Also exemplified and identified in the sequence are the vaccinia mH5 promoters, vaccinia P11 promoter, start codons, Kozak regulatory sequences, SmaI restriction site, and c-tag sequences.

Figure 16:
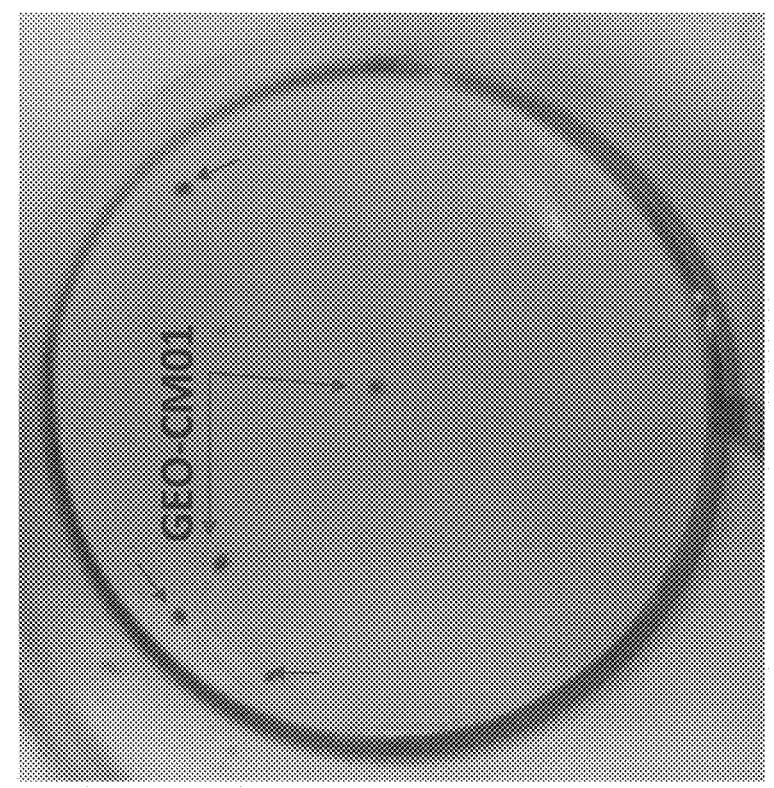

FIG. 16 is a picture of an immunocytochemistry assay of CEF cells infected with recombinant MVA construct GEO-CM01 expressing S, M, and E VLPs exposed to a primary mouse-anti-SARS-CoV-2 spike antibody and secondary anti-mouse HRP antibody and developed with AEC peroxidase substrate. Arrows indicate plaques staining positive for S protein expression.

Figure 17:
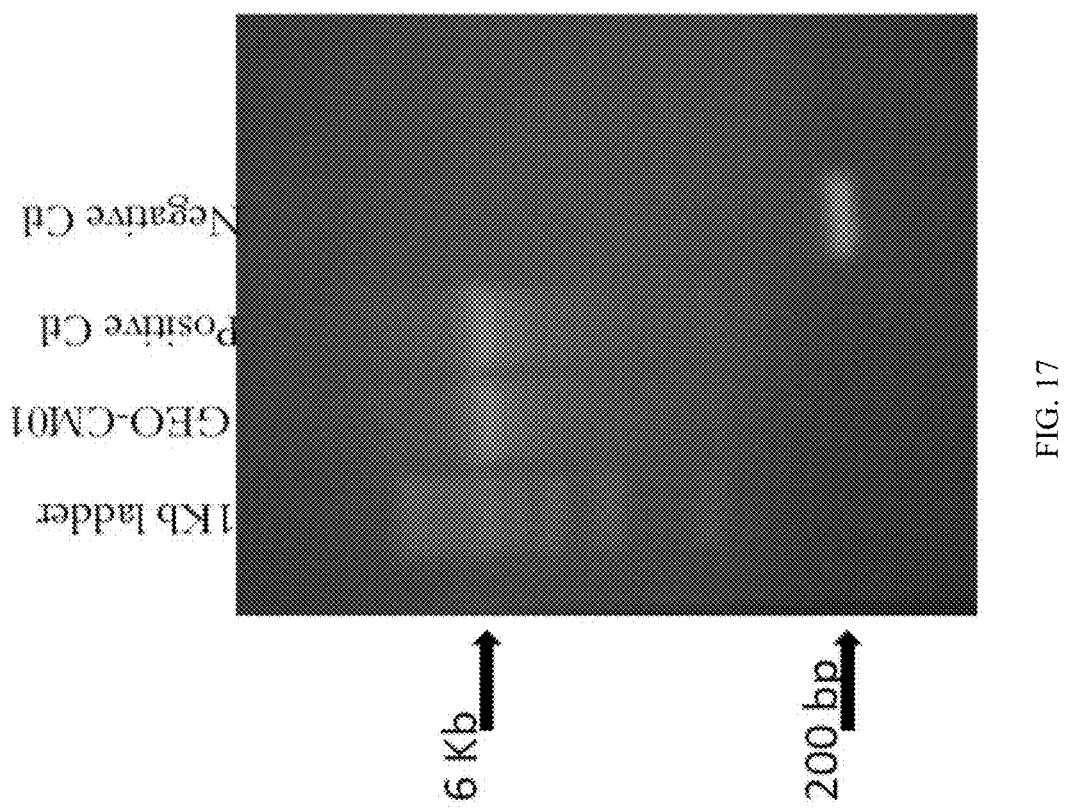

FIG. 17 is a PCR gel showing the amplification of the S protein antigen insert. GEO-CM01 represents recombinant MVA construct GEO-CM01 expressing S, M, and E VLPs; positive control was generated using 50 ng of DNA from the shuttle plasmid used to generate GEO-CM01 (positive control); and the negative control represents the MVA parental strain.

Figure 18:
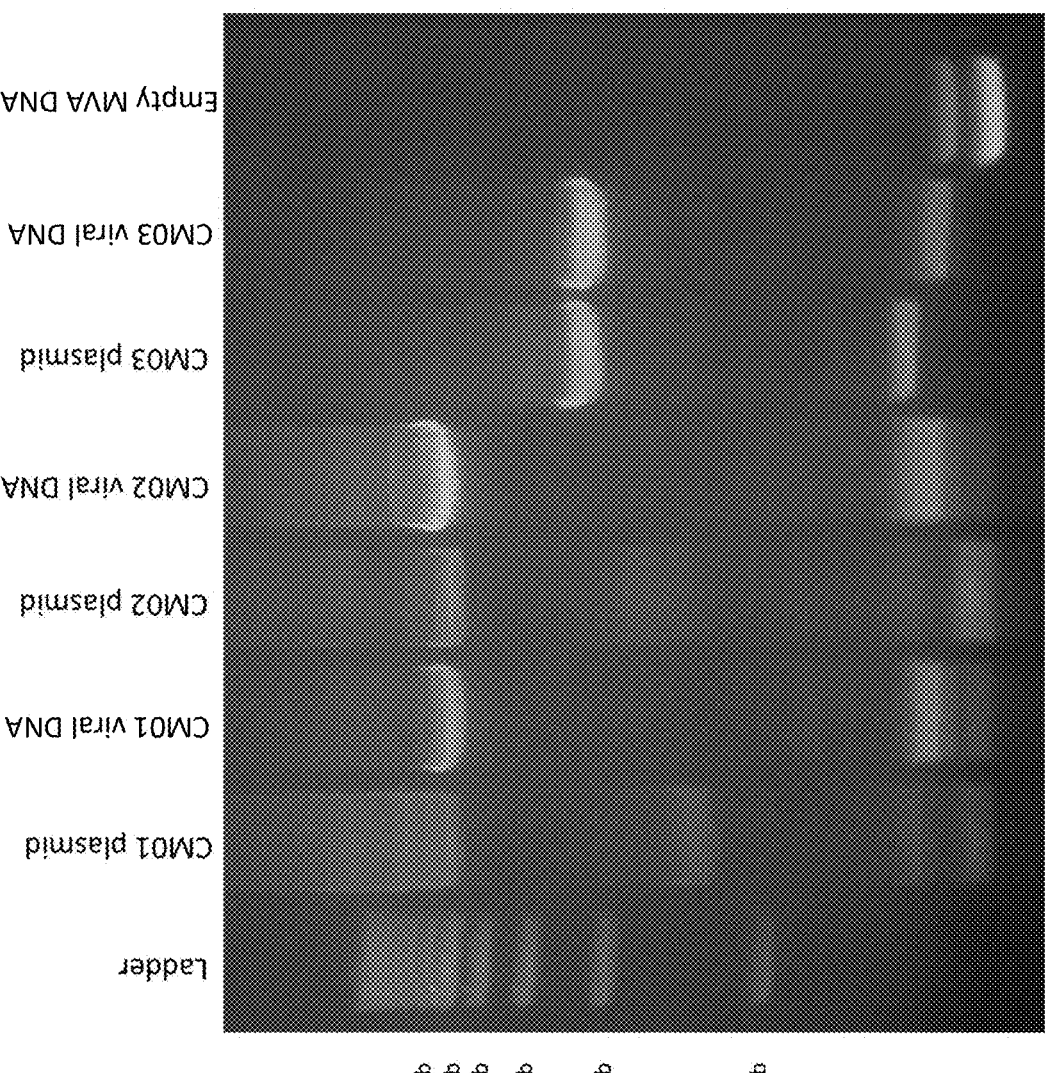

FIG. 18 is a PCR gel showing the amplification of the S protein antigen insert. CM01 viral DNA represents recombinant MVA construct GEO-CM01 expressing S, M, and E VLPs; CM01 plasmid represents a positive control generated using 50 ng of DNA from the shuttle plasmid used to generate GEO-CM01; CM02 viral DNA represents recombinant MVA construct GEO-CM02 expressing stabilized S, M, and E VLPs; CM02 plasmid represents a positive control generated using 50 ng of DNA from the shuttle plasmid used to generate GEO-CM02; CM03 viral DNA represents recombinant MVA construct GEO-CM03 expressing the RBD of the S protein, M, and E VLPs; CM03 plasmid represents a positive control generated using 50 ng of DNA from the shuttle plasmid used to generate GEO-CM03; and the empty MVA DNA represents the MVA parental strain as a negative control.

Figure 19:
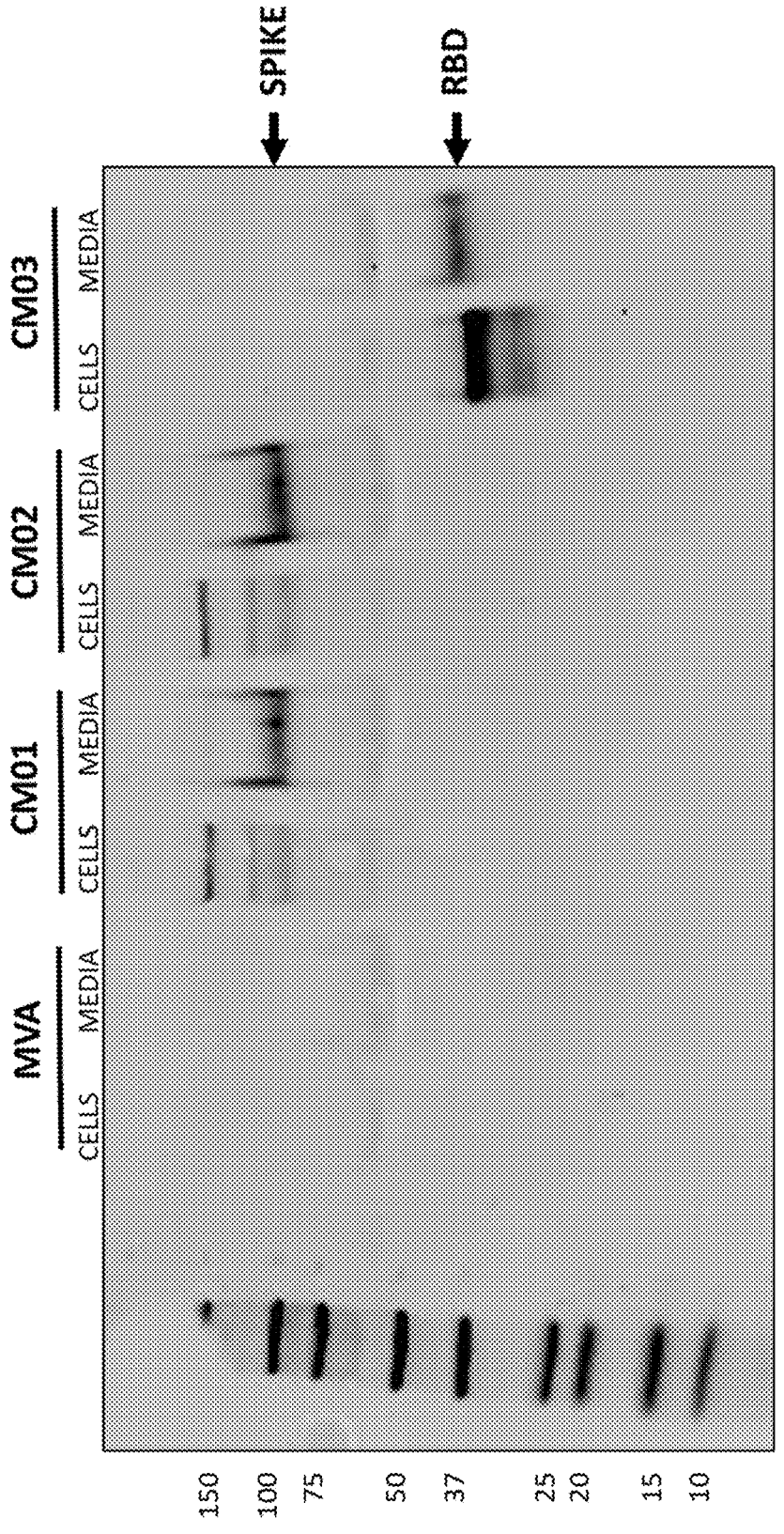

FIG. 19 is a Western blot of S protein antigen expression in cell lysate and supernatant of DF1 cells infected with recombinant MVA construct GEO-CM01 (Covid M01), GEO-CM02 (Covid M02), and GEO-CM03 (Covid M03), indicating the formation of virus-like particles.

Figure 20:
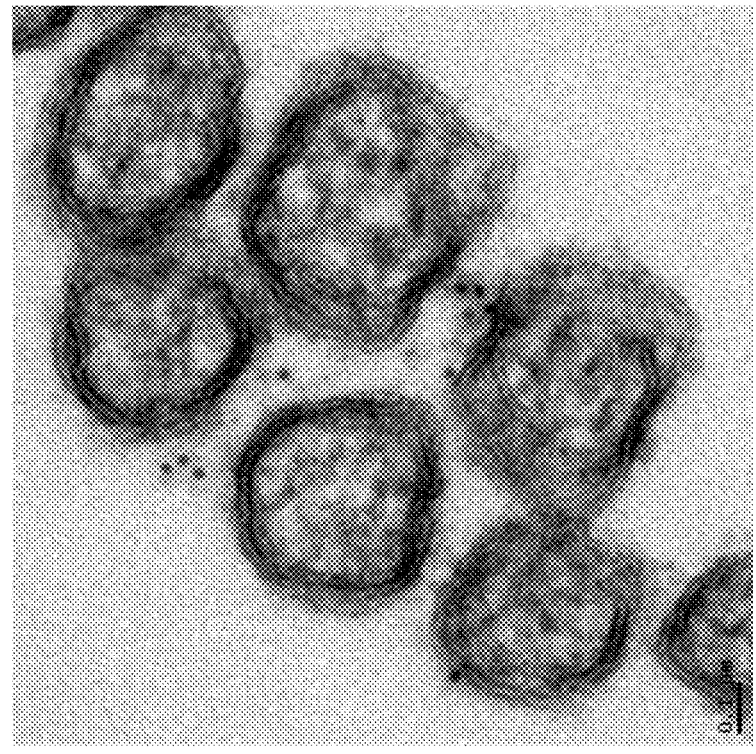
Figure 20:
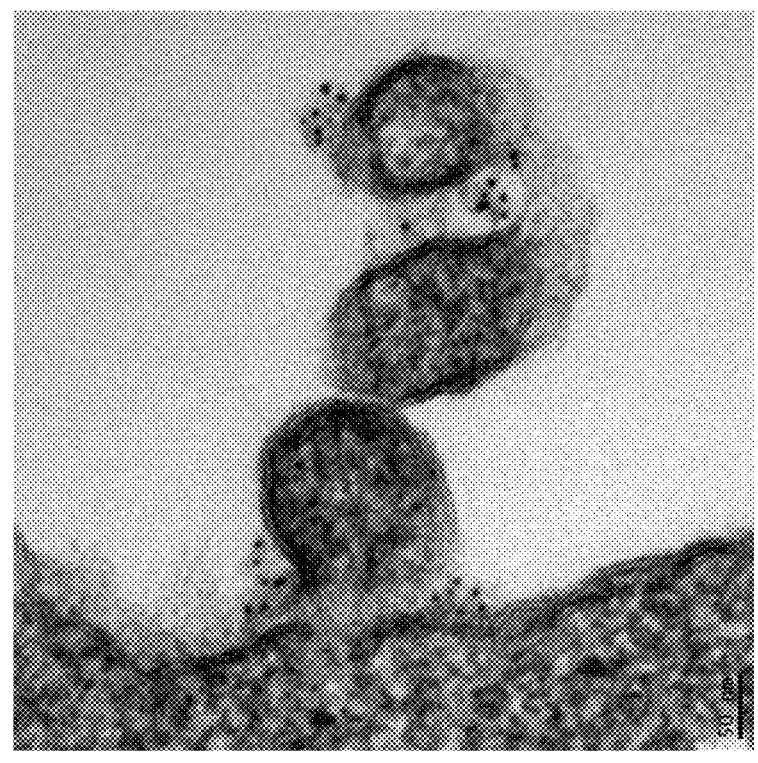

FIG. 20 is an electron microscopic image of the formation of a virus-like particle in GEO-CM01 infected DF1 cells.

Figure 21:
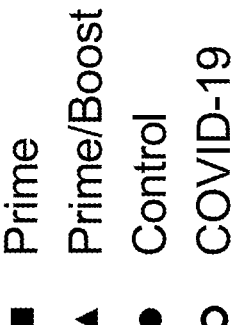
Figure 21:
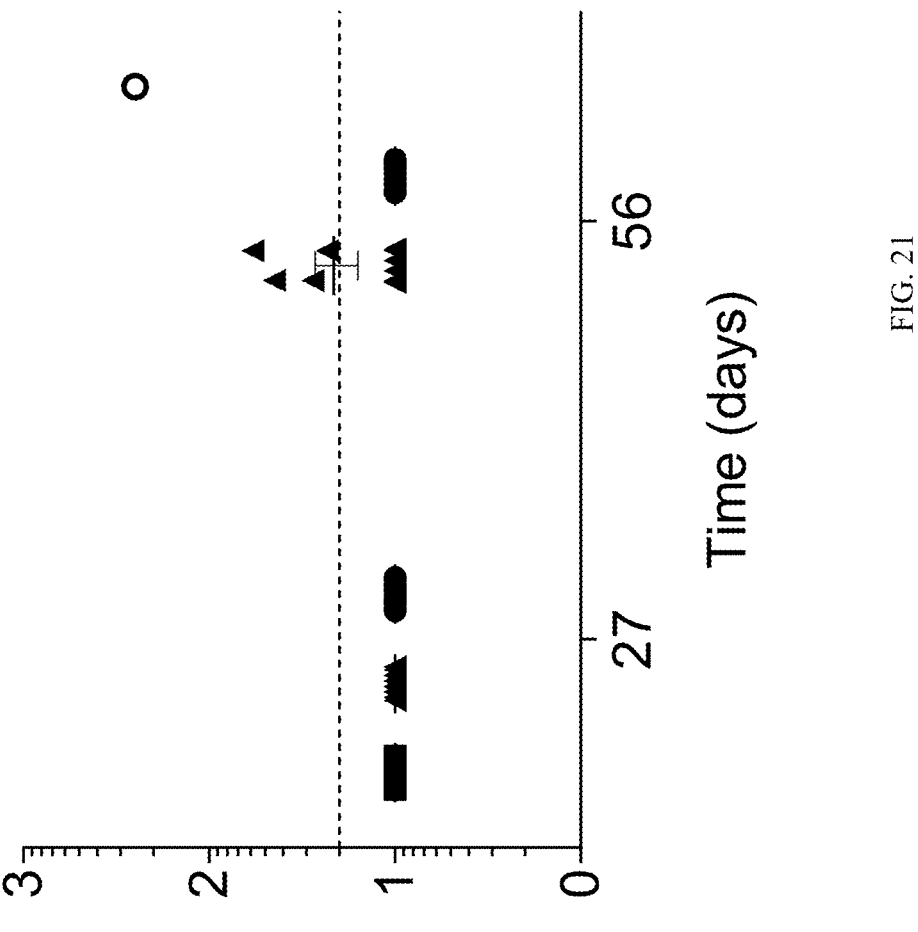

FIG. 21 is a schematic of a SARS-CoV2 neutralization assay. Serum from immunized animals was tested for its capacity to neutralize live SARS-CoV-2. Serial dilutions of serum were incubated with SARS-CoV-2 and then level of neutralization was determined by plaque assay.

Figure 22:
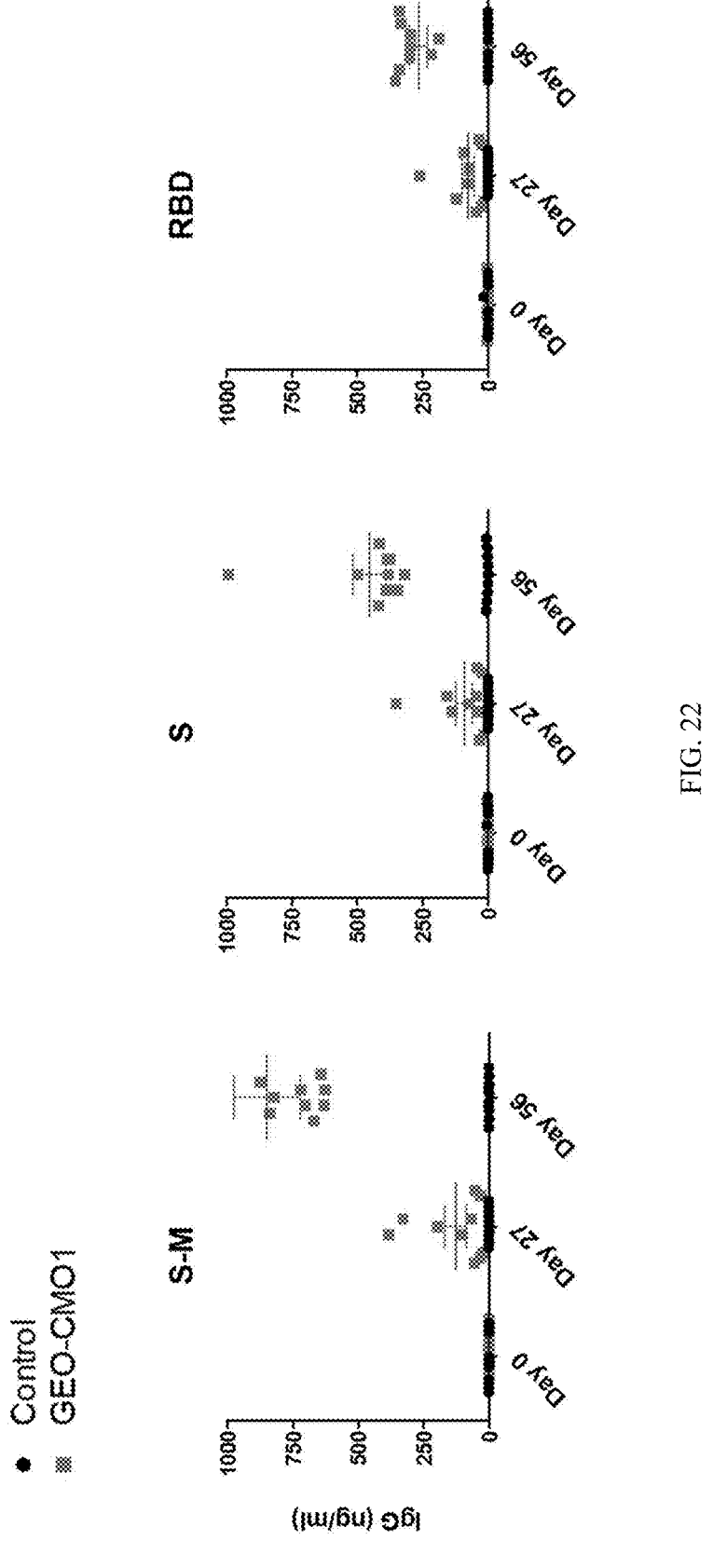
Figure 23:
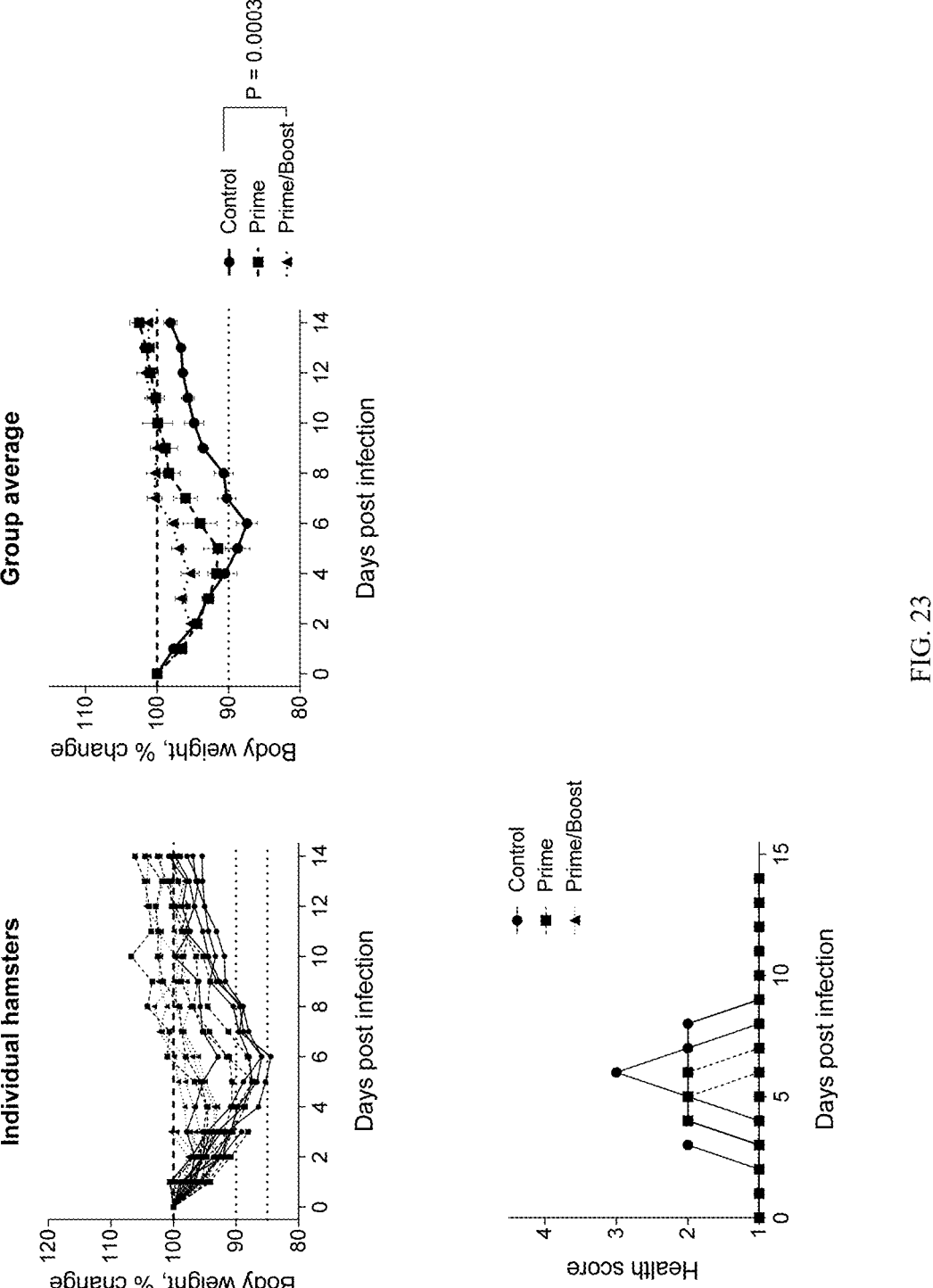

FIG. 22 is a schematic of an ELISA specific for antibody detection to recombinant Spike-Membrane fusion, Spike, and the receptor binding domain (RBD) of the S protein following immunization of golden hamsters, FIG. 23 is a schematic of body weight and health scores over time in a SARS-CoV2 post challenge in a prime/boost (GEO-CM01) vs. control test in golden hamsters. P=0.0003 Friendman's test followed by Dunn's multiple comparison test.

Figure 24:
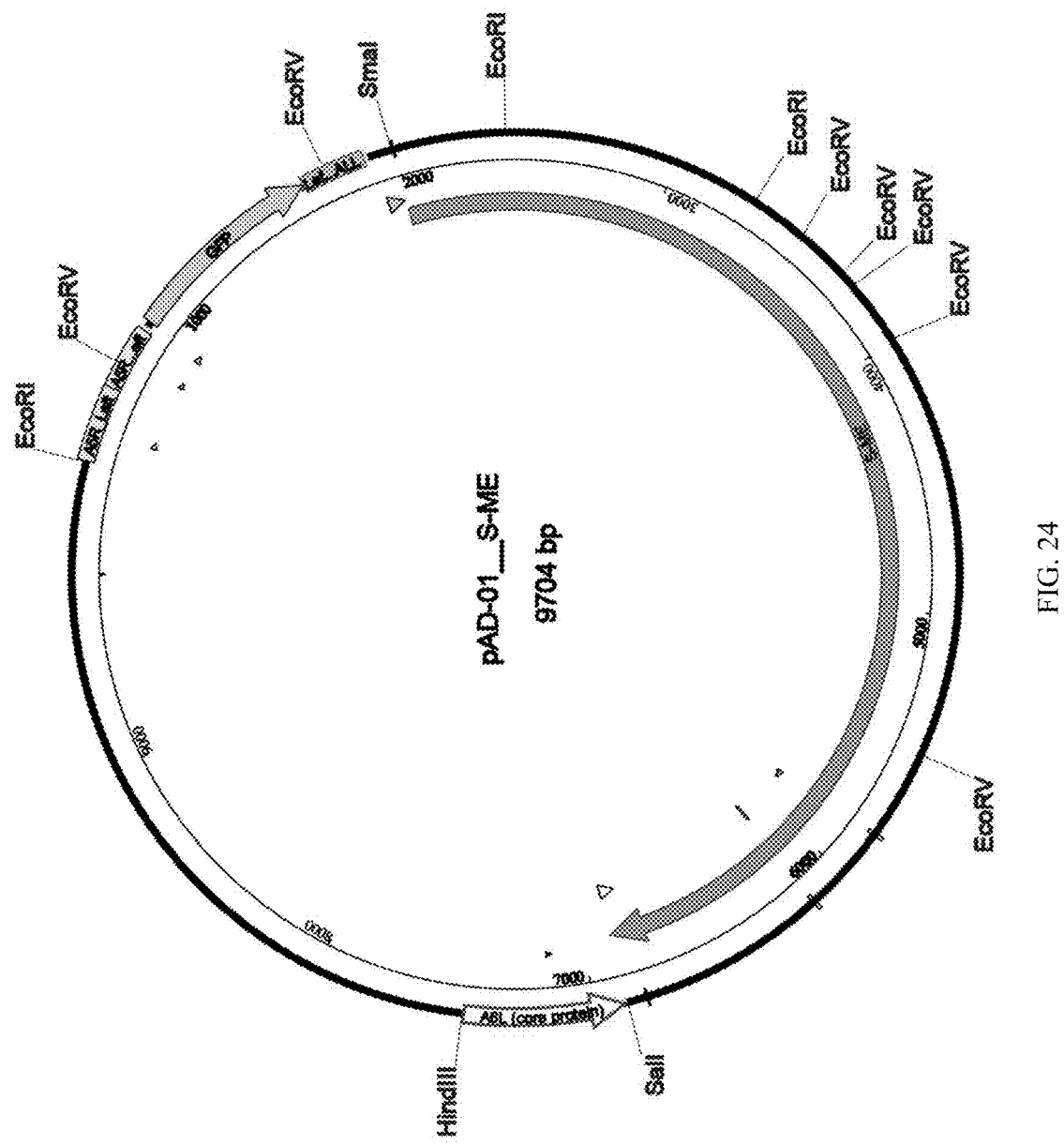

FIG. 24 is a shuttle vector map of pAD-1/S-ME.

Figure 25:
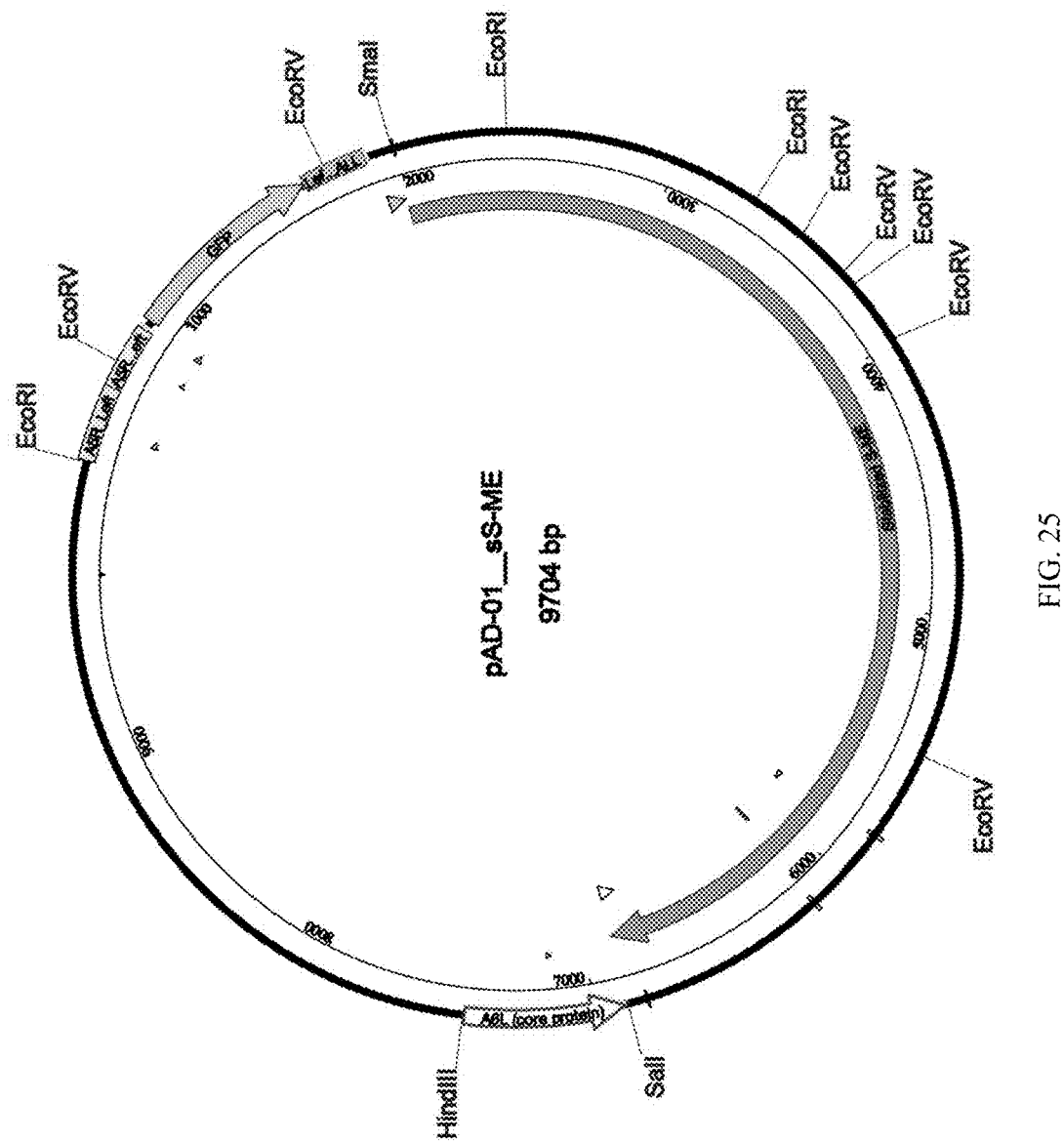

FIG. 25 is a shuttle vector map of pAD-1/sS-ME.

Figure 26:
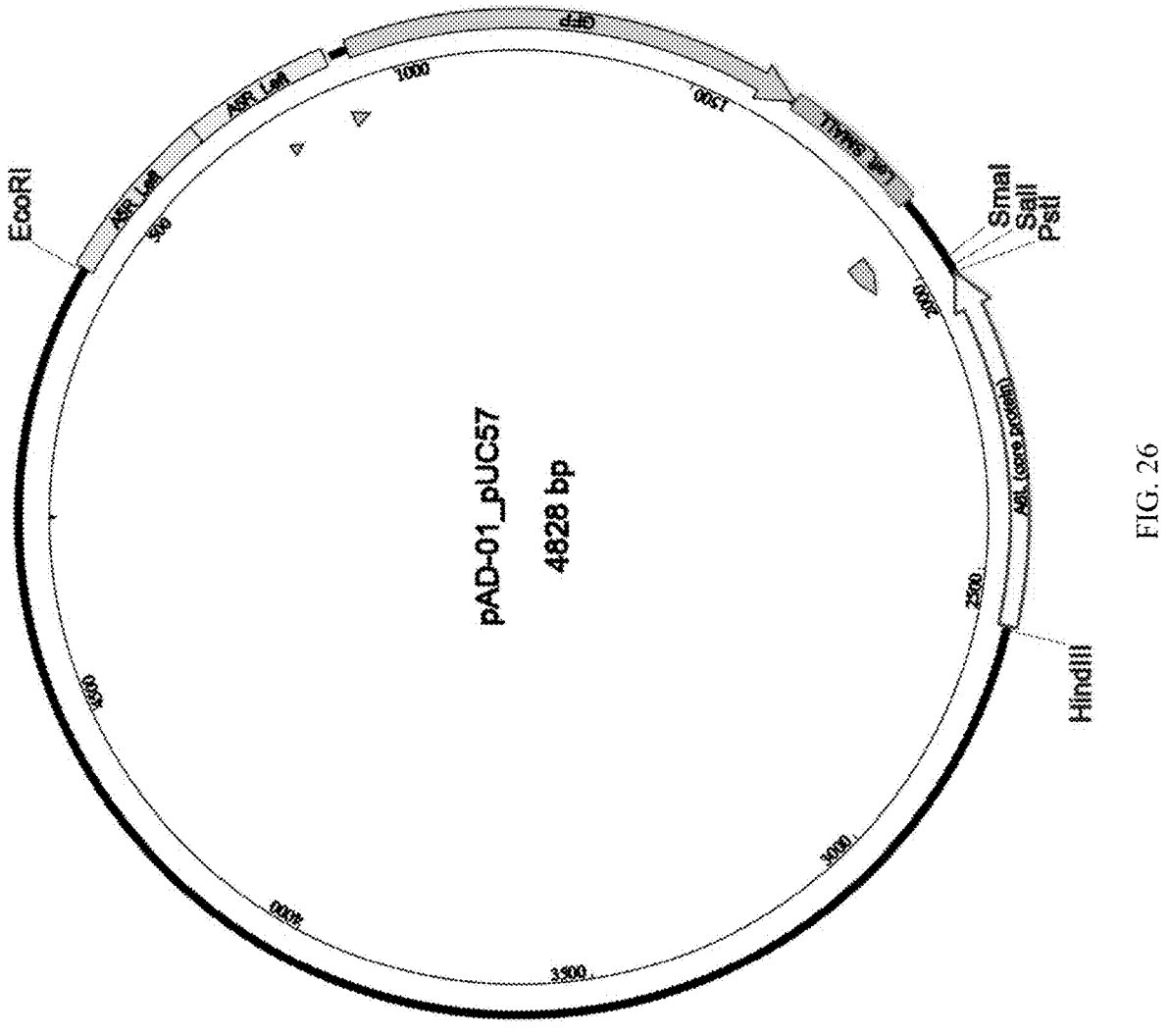

FIG. 26 is a shuttle vector map of pAD-1/pUC57.

Figure 27:
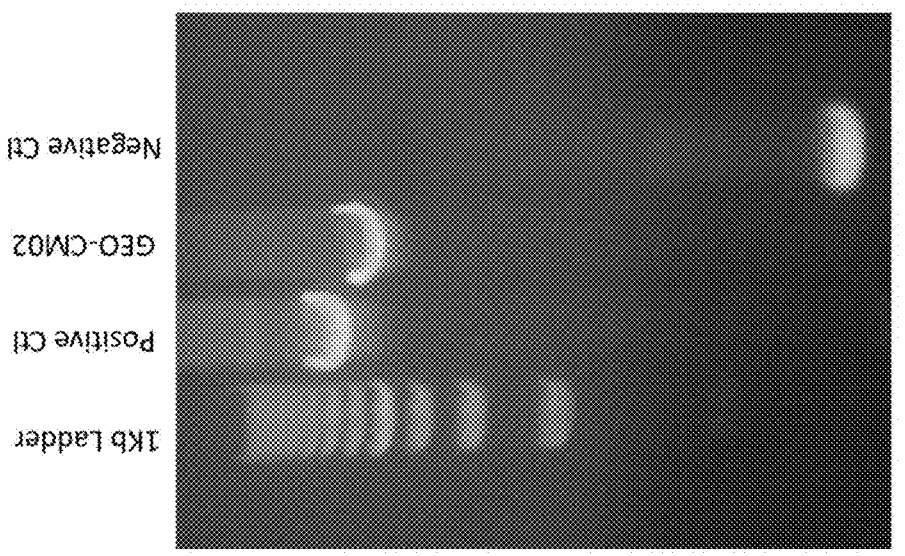

FIG. 27 is a PCR gel showing the amplification of the S protein antigen insert. GEO-CM02 represents recombinant MVA construct GEO-CM02 expressing stabilized S, M, and E VLPs; positive control was generated using 50 ng of DNA from the shuttle plasmid used to generate GEO-CM02 (positive control); and the negative control represents the MVA parental strain.

Figure 28:
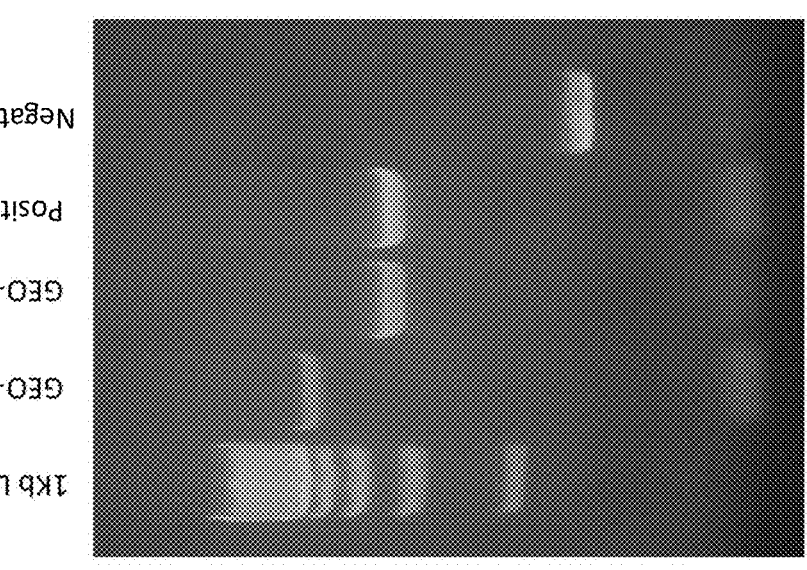

FIG. 28 is a PCR gel showing the amplification of the RBD antigen insert. GEO-CM03 represents recombinant MVA construct GEO-CM03 expressing stabilized RBD, M, and E VLPs; positive control was generated using 50 ng of DNA from the shuttle plasmid used to generate GEO-CM03 (positive control); and the negative control represents the MVA parental strain. The amplification product from GEO-CM01 is used as a comparative.

Figure 29:
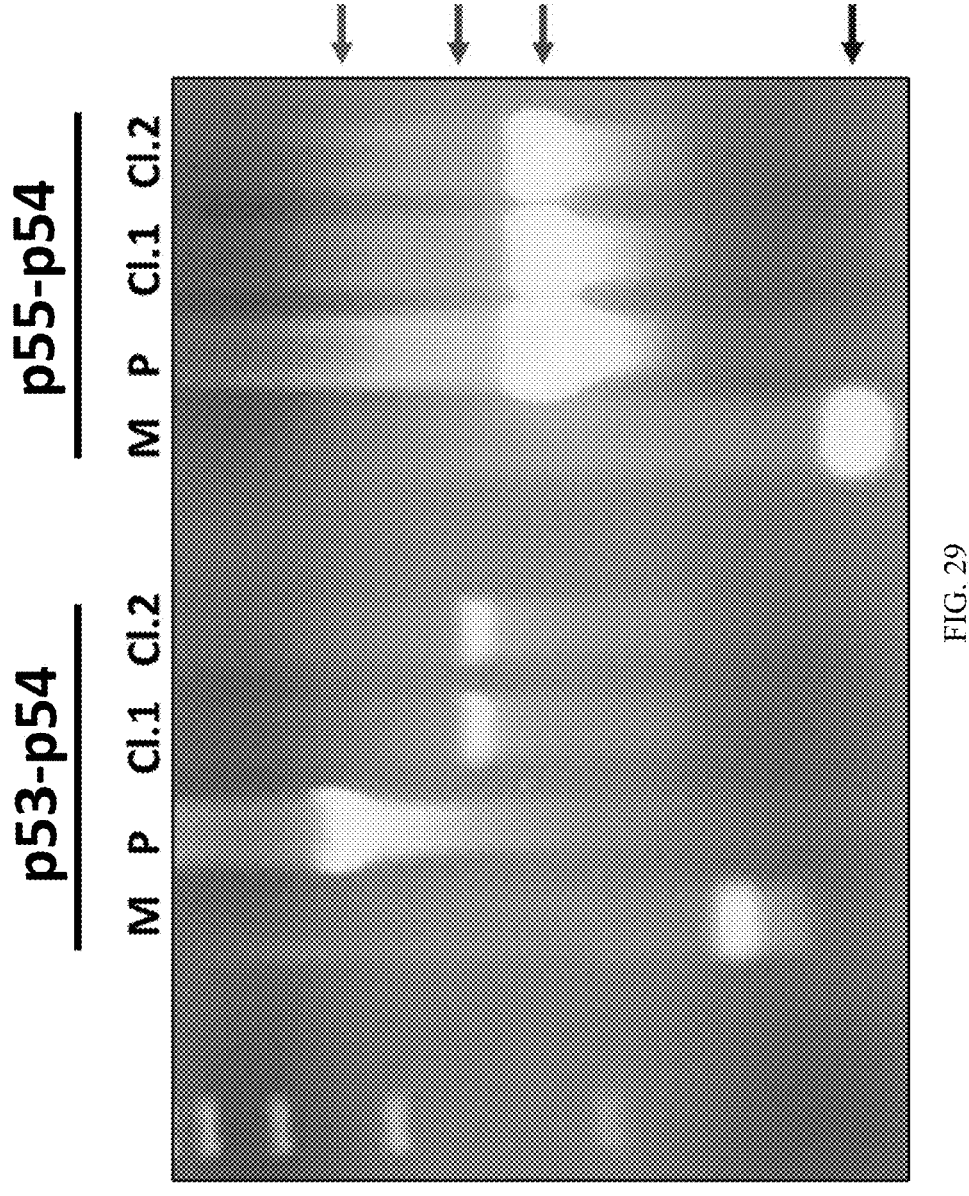

FIG. 29 is a PCR gel showing the amplification of the RBD antigen insert of GEO-CM03b represents recombinant MVA construct GEO-CM03b expressing RBD; positive control was generated using 50 ng of DNA from the shuttle plasmid used to generate GEO-CM03b (P=positive control); and the negative control represents the MVA parental strain (M). M=MVA parent; P=pGeo-MTRBD plasmid DNA; Cl.1=MVA-RBDVP40 clone #4/01; Cl.2=MVA-RBDVP40 clone #4/02. The expected PCR fragments are as follows: p53/p54: MVA parent (M)=647 bp; MVA-RBDVP40/GFP-2544 bp (upper arrow); MVA-RBDVP40-1558 bp (upper middle arrow); pGEO-MTRBD-2544 bp. P55/p54=MVA parent (M)=377 bp (lower arrow); MVA-RBDVP40/GFP-1288 bp (lower middle arrow); MVA-RBDVP40-1288 bp (lower middle arrow); pGEO-MTRBD-1288 bp (lower middle arrow).

DETAILED DESCRIPTION

Provided herein are vaccine compositions comprising a recombinant MVA viral vector capable of expressing one or more SARS-CoV2 (2019-novel coronavirus) antigens, fragments thereof, variants thereof, or a combination thereof. The vaccine can be used to protect against SARS-CoV2, thereby treating, preventing, and/or protecting against SARS-CoV2 based pathologies. The vaccine can significantly induce an immune response of a subject administered the vaccine, thereby protecting against and treating SARS-CoV2 infection.

The compositions and methods of the present invention can be used in a therapeutically effective amount to prevent infection in an unexposed person or to treat disease in a subject exposed to SARS-CoV2 in order to lessen the severity of the disease.

In some embodiments, the compositions and methods can be used as a booster vaccine, to increase or modify or alter immune responses induced by a prior SARS-CoV2 vaccine; such as an RNA vaccine or a DNA vaccine or a virus vectored vaccine, such as adenovirus vaccine vectors, or a protein-based vaccine or a vaccine comprised on a killed or inactivated preparation of SARS-CoV2, with or without an adjuvant, or an attenuated SARS-CoV2. In some embodiments, the compositions and methods can be used as a booster vaccine following infection and recovery from SARS-CoV2.

Ideal immunogenic compositions or vaccines have the characteristics of safety, efficacy, scope of protection and longevity. Compositions having fewer than all of these characteristics may still be useful in preventing SARS-CoV2 infection or limiting symptoms or disease progression in an exposed subject treated prior to the development of symptoms. In one embodiment the present invention provides a vaccine that permits at least partial, if not complete, protection after a single immunization.

The vaccine can induce a humoral immune response in the subject administered the vaccine. The induced humoral immune response can be specific for one or more of the rMVA expressed SARS-CoV2 antigenic epitopes or regions that are specific to SARS-CoV2 or conserved epitopes or segments that are also present in other coronaviruses. The induced humoral immune response can be reactive with the one or more expressed SARS-CoV2 antigens.

The humoral immune response induced by the vaccine can include an increased level of neutralizing antibodies associated with the subject administered the vaccine as compared to a subject not administered the vaccine. In addition, the humoral response induced by the vaccine can include an increased level of neutralizing antibodies for those who have been previously infected with SARS-CoV2, wherein the rMVA of the present invention acts as a booster. The humoral response induced by the vaccine can include an increased level of neutralizing antibodies for those who have been previously administered a different SARS-CoV2 vaccine, wherein the rMVA of the present invention acts as a booster. The neutralizing antibodies can be specific for the SARS-CoV2 antigens or fragments thereof expressed by the rMVA viral vector. The neutralizing antibodies can be reactive with the SARS-CoV2 antigens. The neutralizing antibodies can provide protection against and/or treatment of SARS-CoV2 infection and its associated pathologies in the subject administered the vaccine.

The humoral immune response induced by the vaccine can include an increased level of IgG antibodies associated with the subject administered the vaccine as compared to a subject not administered the vaccine. These IgG antibodies can be specific for at least one SARS-CoV2 antigens.

The vaccine can induce a cellular immune response in the subject administered the vaccine. The induced cellular immune response can be specific for the SARS-CoV2 antigens. The induced cellular immune response can be reactive to the SARS-CoV2 antigens. The induced cellular immune response can include eliciting a CD8+ T cell response. The elicited CD8+ T cell response can be reactive with the SARS-CoV2 antigenic epitopes or regions that are specific to SARS-CoV2 or conserved epitopes or segments that are also present in other coronaviruses.

The elicited CD8+ T cell response can be polyfunctional. The induced cellular immune response can include eliciting a CD8+ T cell response, in which the CD8+ T cells produce interferon-gamma (IFN-γ), tumor necrosis factor alpha (TNF-α), interleukin-2 (IL-2), or a combination of IFN-γ and TNF-α.

The induced cellular immune response can include an increased CD8+ T cell response associated with the subject administered the vaccine as compared to the subject not administered the vaccine. The induced cellular immune response can include an increased frequency of CD3+CD8+ T cells that produce IFN-γ. The induced cellular immune response can include an increased frequency of CD3+CD8+

T cells that produce TNF-α. The induced cellular immune response can include an increased frequency of CD3+CD8+ T cells that produce IL-2. The induced cellular immune response can include an increased frequency of CD3+CD8+ T cells that produce both IFN-γ and TNF-α.

The cellular immune response induced by the vaccine can include eliciting a CD4+ T cell response. The elicited CD4+ T cell response can be reactive with the SARS-CoV2 antigens. The elicited CD4+ T cell response can be polyfunctional. The induced cellular immune response can include eliciting a CD4+ T cell response, in which the CD4+ T cells produce IFN-γ, TNF-α, IL-2, or a combination of IFN-γ and TNF-α.

The induced cellular immune response can include an increased frequency of CD3+CD4+ T cells that produce IFN-γ. The induced cellular immune response can include an increased frequency of CD3+CD4+ T cells that produce TNF-α. The induced cellular immune response can include an increased frequency of CD3+CD4+ T cells that produce IL-2. The induced cellular immune response can include an increased frequency of CD3+CD4+ T cells that produce both IFN-γ and TNF-α.

In some embodiments, these increased cellular immune responses described above induced by the vaccine are in subjects who have been previously infected with SARS-CoV2, wherein the rMVA of the present invention acts as a booster. In some embodiments, these increased cellular immune responses described above induced by the vaccine are in subjects who have been previously administered a different SARS-CoV2 vaccine, wherein the rMVA of the present invention acts as a booster.

Definitions

Where a term is provided in the singular, the inventors also contemplate aspects of the invention described by the plural of that term. As used in this specification and in the appended claims, the singular forms "a", "an", and "the" include plural references unless the context clearly dictates otherwise, e.g., "a peptide" includes a plurality of peptides. Thus, for example, a reference to "a method" includes one or more methods, and/or steps of the type described herein, and/or which will become apparent to those persons skilled in the art upon reading this disclosure.

The term "adjuvant" as used herein means any molecule added to the vaccine described herein to enhance the immunogenicity of the composition.

The term "antigen" refers to a substance or molecule, such as a protein, or fragment thereof, that is capable of inducing an immune response.

"Coding sequence" or "encoding nucleic acid" or "nucleic acid sequence encoding" or the like, as used herein means the nucleic acids (RNA or DNA molecule) that comprise a nucleotide sequence which encodes a protein or fragment thereof. The coding sequence can further include initiation and termination signals operably linked to regulatory elements including a promoter and polyadenylation signal capable of directing expression in the cells of an individual or mammal to which the nucleic acid is administered.

The term "conservative amino acid substitution" refers to substitution of a native amino acid residue with a non-native residue such that there is little or no effect on the size, polarity, charge, hydrophobicity, or hydrophilicity of the amino acid residue at that position, and without resulting in substantially altered immunogenicity. For example, these may be substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Conservative amino acid modifications to the sequence of a polypeptide (and the corresponding modifications to the encoding nucleotides) may produce polypeptides having functional and chemical characteristics similar to those of a parental polypeptide.

The term "deletion" in the context of a polypeptide or protein refers to removal of codons for one or more amino acid residues from the polypeptide or protein sequence, wherein the regions on either side are joined together. The term deletion in the context of a nucleic acid refers to removal of one or more bases from a nucleic acid sequence, wherein the regions on either side are joined together.

The term "fragment" in the context of a proteinaceous agent refers to a peptide or polypeptide comprising an amino acid sequence of at least 2 contiguous amino acid residues, at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a peptide, polypeptide or protein. In one embodiment the fragment constitutes at least 10%, 20%, 30%, 40%, 50%, 60%, 70%, 80%, or 90% of the entire length of the reference polypeptide. In one embodiment, a fragment of a full-length protein retains activity of the full-length protein. In another embodiment, the fragment of the full-length protein does not retain the activity of the full-length protein.

The term "fragment" in the context of a nucleic acid refers to a nucleic acid comprising an nucleic acid sequence of at least 2 contiguous nucleotides, at least 5 contiguous nucleotides, at least 10 contiguous nucleotides, at least 15 contiguous nucleotides, at least 20 contiguous nucleotides, at least 25 contiguous nucleotides, at least 30 contiguous nucleotides, at least 35 contiguous nucleotides, at least 40 contiguous nucleotides, at least 50 contiguous nucleotides, at least 60 contiguous nucleotides, at least 70 contiguous nucleotides, at least contiguous 80 nucleotides, at least 90 contiguous nucleotides, at least 100 contiguous nucleotides, at least 125 contiguous nucleotides, at least 150 contiguous nucleotides, at least 175 contiguous nucleotides, at least 200 contiguous nucleotides, at least 250 contiguous nucleotides, at least 300 contiguous nucleotides, at least 350 contiguous nucleotides, or at least 380 contiguous nucleotides of the nucleic acid sequence encoding a peptide, polypeptide or protein. In one embodiment the fragment constitutes at least 10%, 20%, 30%, 40%, 50%, 60%, 70%, 80%, or 90% of the entire length of the reference nucleic acid sequence. In a preferred embodiment, a fragment of a nucleic acid encodes a peptide or polypeptide that retains activity of the full-length protein. In another embodiment, the fragment encodes a peptide or polypeptide that of the full-length protein does not retain the activity of the full-length protein.

As used herein, the phrase "heterologous sequence" refers to any nucleic acid, protein, polypeptide or peptide sequence which is not normally associated in nature with another nucleic acid or protein, polypeptide or peptide sequence of interest.

As used herein, the phrase "heterologous nucleic acid insert" refers to any nucleic acid sequence that has been or is to be inserted into the recombinant vectors described herein. The heterologous nucleic acid insert may refer to only the gene product encoding sequence or may refer to a sequence comprising a promoter, a gene product encoding sequence (for example membrane (M) protein, envelope (E) protein, spike(S) protein), and any regulatory sequences associated or operably linked therewith.

The term "homopolymer stretch" refers to a sequence comprising at least four of the same nucleotides uninterrupted by any other nucleotide, e.g., GGGG or TTTTTTT.

The term "inducing an immune response" means eliciting a humoral response (e.g., the production of antibodies) or a cellular response (e.g., the activation of T cells) directed against one or more SARS-CoV2 proteins or fragments thereof expressed by the rMVA in a subject to which the rMVA has been administered.

The term "modified vaccinia Ankara," "modified vaccinia Ankara," "Modified Vaccinia Ankara," or "MVA" refers to a highly attenuated strain of vaccinia virus developed by Dr. Anton Mayr by serial passage on chick embryo fibroblast cells; or variants or derivatives thereof. MVA is reviewed in Mayr, A. et al. 1975 Infection 3:6-14.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription.

The term "prevent," "preventing," and "prevention" refers to the inhibition of the development or onset of a condition (e.g., a SARS-CoV2 infection), or the prevention of the recurrence, onset, or development of one or more symptoms of a condition in a subject resulting from the administration of a therapy or the administration of a combination of therapies.

The term "prophylactically effective amount" refers to the amount of a composition (e.g., the recombinant MVA vector or pharmaceutical composition) which is sufficient to result in the prevention of the development, recurrence, or onset of a condition or a symptom thereof (e.g., a SARS-CoV2 infection) or symptom associated therewith or to enhance or improve the prophylactic effect(s) of another therapy.

The term "recombinant," with respect to a viral vector, means a vector (e.g., a viral genome) that has been manipulated in vitro, e.g., using recombinant nucleic acid techniques to express heterologous viral nucleic acid sequences.

The term "regulatory sequence" and "regulatory sequences" refers collectively to promoter sequences, polyadenylation signals, transcription termination sequences, upstream regulatory domains, origins of replication, internal ribosome entry sites ("IRES"), enhancers, and the like, which collectively provide for the transcription and translation of a coding sequence. Not all of these control sequences need always be present so long as the selected gene is capable of being transcribed and translated.

The term "shuttle vector" refers to a genetic vector (e.g., a DNA plasmid) that is useful for transferring genetic material from one host system into another. A shuttle vector can replicate alone (without the presence of any other vector) in at least one host (e.g., E. coli). In the context of MVA vector construction, shuttle vectors are usually DNA plasmids that can be manipulated in E. coli and then introduced into cultured cells infected with MVA vectors, resulting in the generation of new recombinant MVA vectors.

The term "silent mutation" means a change in a nucleotide sequence that does not cause a change in the primary structure of the protein encoded by the nucleotide sequence, e.g., a change from AAA (encoding lysine) to AAG (also encoding lysine).

The term "subject" means any mammal, including but not limited to, humans, domestic and farm animals, and zoo, sports, or pet animals, such as dogs, horses, cats, cows, rats, mice, guinea pigs and the like. Determination of those subjects "at risk" can be made by any objective or subjective determination by a diagnostic test or opinion of a subject or health care provider (e.g., genetic test, enzyme or protein marker, marker history, and the like).

The term "synonymous codon" refers to the use of a codon with a different nucleic acid sequence to encode the same amino acid, e.g., AAA and AAG (both of which encode lysine). Codon optimization changes the codons for a protein to the synonymous codons that are most frequently used by a vector or a host cell.

The term "therapeutically effective amount" means the amount of the composition (e.g., the recombinant MVA vector or pharmaceutical composition) that, when administered to a mammal for preventing or treating a virus, is sufficient to affect such prevention or treatment of the virus.

The term "treating" or "treat" refer to the eradication or control of a SARS-CoV2 infection, the reduction or amelioration of the progression, severity, and/or duration of a condition or one or more symptoms caused by the virus resulting from the administration of one or more therapies.

The term "vaccine" means material used to provoke an immune response and confer immunity after administration of the material to a subject. Such immunity may include a cellular or humoral immune response that occurs when the subject is exposed to the immunogen after vaccine administration.

The term "vaccine insert" refers to a nucleic acid sequence encoding a heterologous sequence that is operably linked to a promoter for expression when inserted into a recombinant vector. The heterologous sequence may encode a glycoprotein or matrix protein described herein.

The term "virus-like particles" or "VLP" refers to a structure which resembles a virus but is not infectious because it does not contain viral genetic material.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

SARS-CoV2 Antigens

Provided herein are recombinant modified vaccinia Ankara (rMVA) viral vectors comprising heterologous nucleic acid inserts encoding one or more SARS-CoV2 proteins, peptides, or fragments thereof, operably linked to a promoter compatible with poxvirus expression systems that, upon expression, are capable of inducing protective immunity without inducing the immuno-pathologies associated with previous MVA-related coronavirus vaccination strategies.

Coronaviruses belong to the family Coronaviridae in the order Nidovirales and are a large family of single-stranded enveloped RNA viruses. They can be classified into four genera: Alphacoronavirus, Betacoronavirus, Gammacoronavirus, and Deltacoronavirus (Perlman & Netland, Coronaviruses post-SARS: update on replication and pathogenesis. Nature Reviews Microbiology 2009; 7:439-450). The SARS-CoV2 belongs to the Betacoronavirus-genus, which also includes SARS-CoV, MERS-CoV, bat coronavirus HKU4, mouse hepatitis coronavirus (MHV), bovine coronavirus (BCoV), and human coronavirus OC43.

Coronaviruses have the largest genome among all RNA viruses, typically ranging from 27 to 32 kb. The genome is packed inside a helical capsid formed by the nucleocapsid protein (N) and further surrounded by an envelope. Associated with the viral envelope are at least three structural proteins: The membrane protein (M) and the envelope protein (E) are involved in virus assembly, whereas the spike protein(S) mediates virus entry into host cells. Among these structural proteins, the spike forms large protrusions from the virus surface, giving coronaviruses the appearance of having crowns (hence their name; corona in Latin means crown). In addition to mediating virus entry, the spike is a critical determinant of viral host range and tissue tropism and a major inducer of host immune responses.

The complete genome of the SARS-CoV2 has been sequenced, and has been assigned GenBank accession number MN908947.3. It consists of a single-stranded RNA sequence that is 29,903 base pairs. To date, 10 open reading frames (ORFs) have been identified, including genes encoding a structural membrane (M) protein, envelope (E) protein, and a spike(S) protein.

Spike(S) Protein

An envelope-anchored spike protein mediates coronavirus entry into host cells by first binding to a host receptor and then fusing viral and host membranes (Li F. 2016. Structure, Function, and Evolution of Coronavirus Spike Proteins. Annu Rev Virol 3:237-261). A defined receptor-binding domain (RBD) of SARS-CoV spike specifically recognizes its host receptor angiotensin-converting enzyme 2 (ACE2) (Li et al., 2003. Angiotensin-converting enzyme 2 is a functional receptor for the SARS coronavirus. Nature 426: 450-454). The overall sequence similarities between SARS-CoV2 spike and SARS-CoV spike are around 76%-78% for the whole protein, around 73%-76% for the RBD, and 50%-53% for the receptor binding motif (RBM), with the similarities between the two S proteins indicating the likelihood that ACE2 is the receptor for SARS-CoV2. See Wan et al., Receptor recognition by novel coronavirus from Wuhan: An analysis based on decade-long structural studies of SARS, J. Virol. doi: 10.1128/JVI.00127-20.

The coronavirus spike contains three segments: a large ectodomain, a single-pass transmembrane anchor, and a short intracellular tail. The ectodomain consists of a receptor-binding subunit S1 and a membrane-fusion subunit S2. Electron microscopy studies revealed that the spike is a clove-shaped trimer with three S1 heads and a trimeric S2 stalk. See, e.g., Kirchdoerfer et al., Pre-fusion structure of a human coronavirus spike protein. Nature. 2016 Mar. 3; 531 (7592): 118-21. During virus entry, S1 binds to a receptor on the host cell surface for viral attachment, and S2 fuses the host and viral membranes, allowing viral genomes to enter host cells. Receptor binding and membrane fusion are the initial and critical steps in the coronavirus infection cycle.

The amino acid sequence of the SARS-CoV2 spike(S) protein is 1273 amino acids in length. The S protein has been reported at GenBank Accession No. QHD43416, and is reproduced in Table 1 as SEQ ID NO: 1, along with its corresponding nucleic acid sequence (SEQ ID NO: 2), which has been reported at GenBank Accession No. MN908947.3, and is located at nucleic acids 21563-25384 of the SARS-CoV2 genome. In some embodiments, the rMVA comprises a nucleic acid sequence encoding SEQ ID NO: 1, or an amino acid sequence 80%, 85%, 90%, 95%, 98%, or 99% homologous thereto. In some embodiments, the nucleic acid for the full-length S protein inserted into the MVA viral vector has been optimized, as described below and for example, as provided in SEQ ID NO: 3, or a nucleic acid sequence 80%, 85%, 90%, 95%, 98%, or 99% homologous thereto. In certain embodiments, an additional nucleic acid sequence encoding a tag may be included in the nucleic acid sequence to be inserted into the rMVA, so that the tag is expressed at the C-terminus of the protein. In some embodiments, the nucleic acid sequence (GAGCCAGAGGCT) (SEQ ID NO: 4) encodes for the high affinity C-tag having the amino acid sequence EPEA (SEQ ID NO: 5).

TABLE 1

| SARS-CoV2 Spike Protein | |
| --- | --- |
| SEQ ID NO: 1- SARS-CoV2 full- length S protein | MFVFLVLLPLVSSQCVNLTTRTQLPPAYTNSFTRGVYYPDKVFRSSVLHSTQDLFL PFFSNVTWFHAIHVSGTNGTKRFDNPVLPFNDGVYFASTEKSNIIRGWIFGTTLDS KTQSLLIVNNATNVVIKVCEFQFCNDPFLGVYYHKNNKSWMESEFRVYSSANNC TFEYVSQPFLMDLEGKQGNFKNLREFVFKNIDGYFKIYSKHTPINLVRDLPQGFSA LEPLVDLPIGINITRFQTLLALHRSYLTPGDSSSGWTAGAAAYYVGYLQPRTFLLK YNENGTITDAVDCALDPLSETKCTLKSFTVEKGIYQTSNFRVQPTESIVRFPNITNL CPFGEVFNATRFASVYAWNRKRISNCVADYSVLYNSASFSTFKCYGVSPTKLNDL CFTNVYADSFVIRGDEVRQIAPGQTGKIADYNYKLPDDFTGCVIAWNSNNLDSKV GGNYNYLYRLFRKSNLKPFERDISTEIYQAGSTPCNGVEGFNCYFPLQSYGFQPTN GVGYQPYRVVVLSFELLHAPATVCGPKKSTNLVKNKCVNFNFNGLTGTGVLTES NKKFLPFQQFGRDIADTTDAVRDPQTLEILDITPCSFGGVSVITPGTNTSNQVAVL YQDVNCTEVPVAIHADQLTPTWRVYSTGSNVFQTRAGCLIGAEHVNNSYECDIPI GAGICASYQTQTNSPRRARSVASQSIIAYTMSLGAENSVAYSNNSIAIPTNFTISVT TEILPVSMTKTSVDCTMYICGDSTECSNLLLQYGSFCTQLNRALTGIAVEQDKNT QEVFAQVKQIYKTPPIKDFGGFNFSQILPDPSKPSKRSFIEDLLFNKVTLADAGFIK QYGDCLGDIAARDLICAQKFNGLTVLPPLLTDEMIAQYTSALLAGTITSGWTFGA GAALQIPFAMQMAYRFNGIGVTQNVLYENQKLIANQFNSAIGKIQDSLSSTASAL GKLQDVVNQNAQALNTLVKQLSSNFGAISSVLNDILSRLDKVEAEVQIDRLITGR LQSLQTYVTQQLIRAAEIRASANLAATKMSECVLGQSKRVDFCGKGYHLMSFPQ SAPHGVVFLHVTYVPAQEKNFTTAPAICHDGKAHFPREGVFVSNGTHWFVTQRN FYEPQIITTDNTFVSGNCDVVIGIVNNTVYDPLQPELDSFKEELDKYFKNHTSPDV DLGDISGINASVVNIQKEIDRLNEVAKNLNESLIDLQELGKYEQYIKWPWYIWLGF IAGLIAIVMVTIMLCCMTSCCSCLKGCCSCGSCCKFDEDDSEPVLKGVKLHYT |
| SEQ ID NO: 2- SARS-CoV2 nucleic acid sequence for full length S protein | ATGTTTGTTTTTCTTGTTTTATTGCCACTAGTCTCTAGTCAGTGTGTTAATCTTA CAACCAGAACTCAATTACCCCCTGCATACACTAATTCTTTCACACGTGGTGTT TATTACCCTGACAAAGTTTTCAGATCCTCAGTTTTACATTCAACTCAGGACTTG TTCTTACCTTTCTTTTCCAATGTTACTTGGTTCCATGCTATACATGTCTCTGGGA CCAATGGTACTAAGAGGTTTGATAACCCTGTCCTACCATTTAATGATGGTGTT TATTTTGCTTCCACTGAGAAGTCTAACATAATAAGAGGCTGGATTTTTGGTAC TACTTTAGATTCGAAGACCCAGTCCCTACTTATTGTTAATAACGCTACTAATGT TGTTATTAAAGTCTGTGAATTTCAATTTTGTAATGATCCATTTTTGGGTGTTTA TTACCACAAAAACAACAAAAGTTGGATGGAAAGTGAGTTCAGAGTTTATTCT AGTGCGAATAATTGCACTTTTGAATATGTCTCTCAGCCTTTTCTTATGGACCTT GAAGGAAACAGGGTAATTTCAAAAATCTTAGGGAATTTGTGTTTAAGAATA TTGATGGTTATTTTAAAATATATTCTAAGCACACGCCTATTAATTTAGTGCGTG ATCTCCCTCAGGGTTTTTCGGCTTTAGAACCATTGGTAGATTTGCCAATAGGT ATTAACATCACTAGGTTTCAAACTTTACTTGCTTTACATAGAAGTTATTTGACT CCTGGTGATTCTTCTTCAGGTTGGACAGCTGGTGCTGCAGCTTATTATGTGGGT TATCTTCAACCTAGGACTTTTCTATTAAAATATAATGAAAATGGAACCATTAC AGATGCTGTAGACTGTGCACTTGACCCTCTCTCAGAAACAAAGTGTACGTTGA |

TABLE 1-continued

SARS-CoV2 Spike Protein

```
AATCCTTCACTGTAGAAAAAGGAATCTATCAAACTTCTAACTTTAGAGTCCAA
CCAACAGAATCTATTGTTAGATTTCCTAATATTACAAACTTGTGCCCTTTTGGT
GAAGTTTTTAACGCCACCAGATTTGCATCTGTTTATGCTTGGAACAGGAAGAG
AATCAGCAACTGTGTTGCTGATTATTCTGTCCTATATAATTCCGCATCATTTTC
CACTTTTAAGTGTTATGGAGTGTCTCCTACTAAATTAAATGATCTCTGCTTTAC
TAATGTCTATGCAGATTCATTTGTAATTAGAGGTGATGAAGTCAGACAAATCG
CTCCAGGGCAAACTGGAAAGATTGCTGATTATAATTATAAATTACCAGATGAT
TTTACAGGCTGCGTTATAGCTTGGAATTCTAACAATCTTGATTCTAAGGTTGGT
GGTAATTATAATTACCTGTATAGATTGTTTAGGAAGTCTAATCTCAAACCTTTT
GAGAGAGATATTTCAACTGAAATCTATCAGGCCGGTAGCACACCTTGTAATG
GTGTTGAAGGTTTTAATTGTTACTTTCCTTTACAATCATATGGTTTCCAACCCA
CTAATGGTGTTGGTTACCAACCATACAGAGTAGTAGTACTTTCTTTTGAACTTC
TACATGCACCAGCAACTGTTTGTGGACCTAAAAAGTCTACTAATTTGGTTAAA
AACAAATGTGTCAATTTCAACTTCAATGGTTTAACAGGCACAGGTGTTCTTAC
TGAGTCTAACAAAAAGTTTCTGCCTTTCCAACAATTTGGCAGAGACATTGCTG
ACACTACTGATGCGTCCGTGATCCACAGACACTTGAGATTCTTGACATTACA
CCATGTTCTTTTGGTGGTGTCAGTGTTATAACACCAGGAACAAATACTTCTAA
CCAGGTTGCTGTTCTTTATCAGGATGTTAACTGCACAGAAGTCCCTGTTGC
TATTCATGCAGATCAACTTACTCCTACTTGGCGTGTTTATTCTACAGGTTCTAA
TGTTTTTTCAAACACGTGCAGGCTGTTTAATAGGGGCTGAACATGTCAACAACT
CATATGAGTGTGACATACCCATTGGTGCAGGTATATGCGCTAGTTATCAGACT
CAGACTAATTCTCCTCGGCGGGCACGTAGTGTAGCTAGTCAATCCATCATTGC
CTACACTATGTCACTTGGTGCAGAAAATTCAGTTGCTTACTCTAATAACTCTAT
TGCCATACCCACAAATTTTACTATTAGTGTTACCACAGAAATTCTACCAGTGT
CTATGACCAAGACATCAGTAGATTGTACAATGTACATTTGTGGTGATTCAACT
GAATGCAGCAATCTTTTGTTGCAATATGGCAGTTTTTGTACACAATTAAACCG
TGCTTTAACTGGAATAGCTGTTGAACAAGACAAAAACACCCAAGAAGTTTTTG
CACAAGTCAAACAAATTTACAAAACACCACCAATTAAAGATTTTGGTGGTTTT
AATTTTTCACAAATATTACCAGATCCATCAAAACCAAGCAAGAGGTCATTTAT
TGAAGATCTACTTTTTCAACAAAGTGACACTTGCAGATGCTGGCTTCATCAAAC
AATATGGTGATTGCCTTGGTGATATTGCTGCTAGAGACCTCATTTGTGCACAA
AAGTTTAACGGCCTTACTGTTTTGCCACCTTTGCTCACAGATGAAATGATTGCT
CAATACACTTCTGCACTGTTAGCGGGTACAATCACTTCTGGTTGGACCTTTGG
TGCAGGTGCTGCATTACAAATACCATTTGCTATGCAAATGGCTTATAGGTTTA
ATGGTATTGGAGTTACACAGAATGTTCTCTATGAGAACCAAAAATTGATTGCC
AACCAATTTAATAGTGCTATTGGCAAAATTCAAGACTCACTTTCTTCCACAGC
AAGTGCACTTGGAAAACTTCAAGATGTGGTCAACCAAAATGCACAAGCTTTA
AACACGCTTGTTAAACAACTTAGCTCCAATTTTGGTGCAATTTCAAGTGTTTTA
AATGATATCCTTTCACGTCTTGACAAAGTTGAGGCTGAAGTGCAAATTGATAG
GTTGATCACAGGCAGACTTCAAAGTTTGCAGACATATGTGACTCAACAATTAA
TTAGAGCTGCAGAAATCAGAGCTTCTGCTAATCTTGCTGCTACTAAAATGTCA
GAGTGTGTACTTGGACAATCAAAAAGAGTTGATTTTTGTGGAAAGGGCTATCA
TCTTATGTCCTTCCCTCAGTCAGCACCTCATGGTGTAGTCTTCTTGCATGTGAC
TTATGTCCCTGCACAAGAAAAGAACTTCACAACTGCTCCTGCCATTTGTCATG
ATGGAAAAGCACACTTTCCTCGTGAAGGTGTCTTTGTTTCAAATGGCACACAC
TGGTTTGTAACACAAAGGAATTTTTATGAACCACAAATCATTACTACAGACAA
CACATTTGTGTCTGGTAACTGTGATGTTGTAATAGGAATTGTCAACAACACAG
TTTATGATCCTTTGCAACCTGAATTAGACTCATTCAAGGAGGAGTTAGATAAA
TATTTTAAGAATCATACATCACCAGATGTTGATTTAGGTGACATCTCTGGCAT
TAATGCTTCAGTTGTAAACATTCAAAAAGAAATTGACCGCCTCAATGAGGTTG
CCAAGAATTTAAATGAATCTCTCATCGATCTCCAAGAACTTGGAAAGTATGAG
CAGTATATAAAAATGGCCATGGTACATTTGGCTAGGTTTTTATAGCTGGCTTGAT
TGCCATAGTAATGGTGACAATTATGCTTTGCTGTATGACCAGTTGCTGTAGTT
GTCTCAAGGGCTGTTGTTCTTGTGGATCCTGCTGCAAATTTGATGAAGACGAC
TCTGAGCCAGTGCTCAAAGGAGTCAAATTACATTACACA
```

SEQ ID NO: 3-
SARS-CoV2
optimized nucleic
acid sequence for
full length S protein

```
ATGTTCGTGTTCCTAGTCCTACTACCGCTAGTCTCTTCTCAGTGTGTAAACCTA
ACAACGAGAACACAACTACCACCGGCGTACACCAATTCTTTCACAAGAGGAG
TATATTACCCGGACAAGGTGTTCAGATCCTCCGTACTACATTCTACACAGGAC
CTATTCCTACCGTTCTTCTCTAACGTAACATGGTTCCACGCGATCCATGTCTCT
GGAACAAACGGAACGAAGAGATTCGATAACCCGGTCTTGCCGTTCAACGATG
GTGTATACTTTGCGTCCACCGAGAAGTCCAACATCATCAGAGGATGGATCTTC
GGAACCACCTTGGATTCTAAGACCCAGTCCTTGCTAATCGTCAACAACGCGAC
CAACGTCGTCATCAAAGTCTGCGAATTCCAGTTCTGTAACGACCCGTTCTTGG
GAGTCTACTACCACAAGAACAACAAGTCCTGGATGGAATCCGAGTTCAGAGT
CTACTCTTCCGCGAACAACTGCACCTTCGAATATGTATCTCAGCCGTTCCTAAT
GGACCTAGAGGGAAAGCAGGGAAACTTCAAGAACCTAAGAGAGTTCGTATTC
AAGAACATCGACGGATACTTCAAGATCTACTCCAAGCACACTCCGATCAACCT
AGTTAGAGATCTACCGCAAGGATTCTCTGCGCTAGAACCGTTAGTAGATTTGC
CGATCGGAATCAACATCACCAGATTCCAGACACTACTAGCGCTACACAGATCT
TACCTAACGCCGGGAGATTCTTCTTCTGGATGGACTGCTGGTGCTGCGGCTTA
TTATGTAGGATACCTACAGCCGAGAACCTTCCTATTGAAGTACAACGAAAAC
GGAACCATCACCGATGCCGTAGATTGTGCTCTAGATCCGCTATCCGAAACGAA
GTGCACCCTAAAGTCTTTCACCGTCGAGAAGGGAATCTACCAGACCTCCAACT
TTAGAGTACAGCCGACCGAATCCATCGTCAGATTTCCGAACATCACGAACCTA
TGTCCGTTCGGAGAAGTGTTCAACGCGACAAGATTTGCGTCGTCTATGCGTG
GAACAGAAAAAGAATCAGTAACTGCGTCGCGGACTACTCCGTCCTATACAAC
TCTGCCTCTTTCTCCACGTTCAAATGCTACGGTGTATCTCCGACAAAGCTAAA
```

TABLE 1-continued

SARS-CoV2 Spike Protein

```
CGATCTATGCTTCACCAACGTCTACGCGGACTCCTTCGTAATCAGAGGAGATG
AAGTTAGACAGATTGCGCCGGGACAAACTGGAAAGATCGCGGATTATAACTA
CAAGCTACCGGACGACTTCACCGGATGTGTAATTGCGTGGAATTCGAACAAC
CTAGACTCCAAAGTCGGAGGAAACTACAACTACTTGTACAGACTATTCAGAA
AGTCCAACCTAAAGCCGTTCGAGAGAGACATCTCCACCGAAATCTATCAGGC
TGGATCTACACCGTGTAATGGTGTCGAAGGATTCAACTGCTACTTCCCGCTAC
AGTCTTACGGATTTCAACCGACAAACGGTGTAGGATATCAGCCGTACAGAGT
CGTCGTACTATCCTTCGAACTACTACATGCTCCGGCGACAGTATGTGGACCGA
AAAAGTCTACCAACCTAGTCAAGAACAAATGCGTCAACTTTAACTTCAACGG
ACTAACCGGAACCGGTGTCCTAACCGAATCTAACAAGAAGTTTCTACCGTTCC
AGCAGTTCGGAAGAGATATCGCGGATACAACAGACGCTGTCAGAGATCCGCA
AACCTTGGAGATCCTAGATATCACACCGTGTTCTTTCGGTGGTGTCTCTGTAAT
TACTCCGGGAACGAACACCTCCAATCAAGTAGCGGTACTATACCAGGACGTG
AACTGTACAGAAGTACCGGTAGCTATTCACGCGGATCAACTAACACCAACTT
GGAGAGTGTACTCCACCGGATCTAACGTATTCCAAACAAGAGCGGGATGTCT
AATCGGAGCGGAACACGTAAACAACTCCTACGAATGTGATATCCCGATTGGA
GCGGGAATCTGTGCGTCTTACCAAACACAAACAAACTCTCCGAGAAGAGCGA
GATCTGTAGCCTCTCAATCTATTATCGCCTACACCATGTCCTTGGGAGCCGAA
AATTCTGTCGCGTACTCCAACAATTCTATCGCGATCCCGACAAACTTCACCAT
CTCTGTAACAACCGAGATCCTACCGGTGTCTATGACCAAGACATCTGTCGATT
GCACCATGTACATCTGCGGAGATTCCACCGAGTGCTCCAACCTACTACTACAG
TACGGATCTTTCTGTACCCAGCTAAACAGAGCGTTGACTGGAATCGCTGTAGA
GCAGGATAAGAACACTCAAGAGGTATTCGCGCAAGTCAAGCAGATCTATAAG
ACTCCGCCGATCAAGGACTTCGGAGGTTTCAACTTCTCTCAGATCTTGCCGGA
TCCGTCCAAACCGTCTAAGAGATCTTTCATCGAGGACCTACTATTCAACAAAG
TCACCCTAGCTGACGCGGGATTCATCAAACAATACGGAGATTGCTTGGGAGA
CATTGCGGCGAGAGATCTAATTTGCGCGCAGAAGTTTAACGGATTGACAGTA
CTACCGCCGCTACTAACCGATGAGATGATTGCGCAGTACACGTCTGCTCTATT
GGCGGGAACAATTACAAGTGGATGGACATTTGGAGCCGGTGCCGCTCTACAA
ATTCCGTTTGCTATGCAAATGGCGTACAGATTCAACGGAATCGGAGTAACCCA
GAACGTCTTGTACGAGAACCAGAAGCTAATCGCGAACCAGTTCAATTCCGCG
ATCGGAAAGATCCAGGACAGTCTATCTTCTACTGCTTCGGCGTTGGGAAAGCT
ACAGGATGTAGTAAATCAAAACGCGCAGGCGCTAAACACCTTGGTCAAGCAA
CTATCCTCTAACTTCGGAGCGATCTCGTCCGTCCTAAACGACATCTTATCCAG
ACTAGATAAGGTCGAAGCGGAGGTCCAGATCGATAGACTAATCACTGGAAGA
TTGCAGTCCCTACAGACCTACGTAACACAGCAACTAATTAGAGCGGCGGAGA
TTAGAGCCTCTGCTAATCTAGCTGCGACCAAGATGTCCGAATGTGTCTTGGGA
CAATCCAAGAGAGTGGACTTCTGCGGAAAGGGATACCACCTAATGTCTTTCCC
ACAATCTGCGCCGCATGGTGTCGTATTCCTACATGTAACATATGTGCCGGCGC
AAGAAAAGAACTTCACAACAGCTCCAGCGATCTGCCATGATGGAAAAGCTCA
TTTCCCGAGAGAGGGAGTCTTTGTCTCTAACGGAACTCATTGGTTCGTCACCC
AGAGAAACTTCTACGAGCCGCAGATCATCACCACCGACAACACATTCGTCTC
GGGAAACTGCGACGTGGTCATCGGAATCGTAAACAATACCGTCTACGATCCG
TTGCAGCCGGAACTAGACTCCTTCAAAGAAGAGTTGGACAAGTACTTCAAGA
ACCACACCTCTCCGGATGTGGACTTGGGAGATATCTCTGGAATCAACGCGTCC
GTCGTCAACATCCAGAAAGAAATCGATAGATTGAACGAGGTCGCGAAGAACT
TGAACGAGTCCCTAATCGACCTACAAGAGCTAGGAAAATACGAGCAGTACAT
CAAGTGGCCGTGGTACATCTGGCTAGGATTCATTGCTGGACTAATTGCGATCG
TCATGGTCACCATCATGCTATGCTGTATGACCTCCTGTTGCTCCTGTCTAAAGG
GATGTTGTTCCTGCGGATCCTGTTGCAAGTTCGATGAAGATGATAGTGAACCG
GTCCTAAAGGGTGTCAAGCTACACTACACA
```

In certain embodiments, the S protein is expressed as a full-length protein and contains one or more amino acid substitutions. In some embodiments, the S protein is expressed as a full-length protein and contains one or more substitutions selected from K417T, E484K or N501Y of SEQ ID NO: 1. In some embodiments, the S protein is expressed as a full-length protein and contains the following substitutions: K417T, E484K, and N501Y of SEQ ID NO:1. In some embodiments, the substitution is K417N. In some embodiments, the S protein is expressed as a full-length protein of SEQ ID NO: 6, or an amino acid sequence 80%, 85%, 90%, 95%, 98%, or 99% homologous thereto. In some embodiments, the S protein is expressed as a full-length protein and has a deletion of one or more spike protein amino acids H69, V70, or Y144, or combinations thereof, of SEQ ID NO: 1. In some embodiments, the S protein is expressed as a full-length protein and contains one or more substitutions selected from D614G, A570D, P681H, T716I, S982A, D1118H, K417N or K417T, D215G, A701V, L18F, R246I, Y453F, I692V, M1229I, N439K, A222V, S477N, or A376T, or combinations thereof, of SEQ ID NO:1. In some embodiments, the variant strain is a SARS-CoV2 virus which has a spike protein deletion at amino acids 242-244 of SEQ ID NO: 1. In some embodiments, the S protein is expressed as a full-length protein and contains the following deletions and substitutions: deletion of amino acids 69-70, deletion of amino acid Y144, amino acid substitution N501Y, amino acid substitution A570D, amino acid substitution D614G, amino acid substitution P681H, amino acid substitution T716I, amino acid substitution S982A, and amino acid substitution D1118H, or SEQ ID NO: 1. In some embodiments, the S protein is expressed as a full-length protein and contains the following deletions and substitutions: N501Y, K417N or K417T, E484K, D80A, A701V, L18F, and amino acid deletion at amino acids 242-244, of SEQ ID NO: 1. In some embodiments, the S protein is expressed as a full-length protein and contains one or more of the following substitutions: D614G; D936Y; P1263L; L5F; N439K; R211; D839Y; L54F; A879S; L18F; F1121L; R847K; T478I; A829T; Q675H; S477N; H49Y; T29I;

53

G769V; G1124V; V1176F; K1073N; P479S; S1252P; Y145 deletion; E583D; R214L; A1020V; Q1208H; D215G; H146Y; S98F; T95I; G1219C; A846V; I197V; R102I; V367F; T572I; A1078S; A831V; P1162L; T73I; A845S; G1219V; H245Y; L8V; Q675R; S254F; V483A; Q677H; D138H; D80Y; M1237T; D1146H; E654D; H655Y; S50L; S939F; S943P; G485R; Q613H; T76I; V341I; M153I; S221L; T859I; W258L; L242F; P681L; V289I; A520S; V1104L; V1228L; L176F; M1237I; T307I; T716I; L141; M1229I; A1087S; P26S; P330S; P384L; R765L; S940F; T323I; V826L; E1202Q; L1203F; L611F; V615I; A262S; A522V; A688V; A706V; A892S; E554D; Q836H; T1027I; T221; A222V; A27S; A626V; C1247F; K1191N; M731I; P26L; S1147L; S1252F; S255F; V1264L; V308L; D80A; I670L; P251L; P631S; *1274Q; A344S; A771S; A879T; D1084Y; D253G; H1101Y; L1200F; Q14H; Q239K; A623V; D215Y; E1150D; G476S; K77M; M177I; P812S; S704L; T51I; T547I; T791I; V1122L; Y145H; D574Y; G142D; G181V; I834T; N370S; P812L; S12F; T791P; V90F; W152L; A292S; A570V; A647S; A845V; D1163Y; G181R; L84I; L938F; P1143L; P809S; R78M; T1160I; V1133F; V213L; V615F; A831V; D839Y; D839N; D839E; S943P; P1263L; or V622F; and combinations thereof, of SEQ ID NO: 1.

TABLE 2

SARS-CoV2 Spike Protein Mutants

| | |
|---|---|
| SEQ ID NO: 6-<br>SARS-CoV2 full-<br>length S<br>protein-<br>K417T, E484K,<br>and N501Y | MFVFLVLLPLVSSQCVNLTTRTQLPPAYTN<br>SFTRGVYYPDKVFRSSVLHSTQDLFLPFFS<br>NVTWFHAIHVSGTNGTKRFDNPVLPFNDGV<br>YFASTEKSNIIRGWIFGTTLDSKTQSLLIV<br>NNATNVVIKVCEFQFCNDPFLGVYYHKNNK<br>SWMESEFRVYSSANNCTFEYVSQPFLMDLE<br>GKQGNFKNLREFVFKNIDGYFKIYSKHTPI<br>NLVRDLPQGFSALEPLVDLPIGINITRFQT<br>LLALHRSYLTPGDSSSGWTAGAAAYYVGYL<br>QPRTFLLKYNENGTITDAVDCALDPLSETK<br>CTLKSFTVEKGIYQTSNFRVQPTESIVRFP<br>NITNLCPFGEVFNATRFASVYAWNRKRISN<br>CVADYSVLYNSASFSTFKCYGVSPTKLNDL<br>CFTNVYADSFVIRGDEVRQIAPGQTGTIAD<br>YNYKLPDDFTGCVIAWNSNNLDSKVGGNYN<br>YLYRLFRKSNLKPFERDISTEIYQAGSTPC<br>NGVKGFNCYFPLQSYGFQPTYGVGYQPYRV<br>VVLSFELLHAPATVCGPKKSTNLVKNKCVN<br>FNFNGLTGTGVLTESNKKFLPFQQFGRDIA<br>DTTDAVRDPQTLEILDITPCSFGGVSVITP<br>GTNTSNQVAVLYQDVNCTEVPVAIHADQLT<br>PTWRVYSTGSNVFQTRAGCLIGAEHVNNSY<br>ECDIPIGAGICASYQTQTNSPRRARSVASQ<br>SIIAYTMSLGAENSVAYSNNSIAIPTNFTI<br>SVTTEILPVSMTKTSVDCTMYICGDSTECS<br>NLLLQYGSFCTQLNRALTGIAVEQDKNTQE<br>VFAQVKQIYKTPPIKDFGGFNFSQILPDPS<br>KPSKRSFIEDLLFNKVTLADAGFIKQYGDC |

54

TABLE 2-continued

SARS-CoV2 Spike Protein Mutants

```
LGDIAARDLICAQKFNGLTVLPPLLTDEMI
AQYTSALLAGTITSGWTFGAGAALQIPFAM
QMAYRFNGIGVTQNVLYENQKLIANQFNSA
IGKIQDSLSSTASALGKLQDVVNQNAQALN
TLVKQLSSNFGAISSVLNDILSRLDKVEAE
VQIDRLITGRLQSLQTYVTQQLIRAAEIRA
SANLAATKMSECVLGQSKRVDFCGKGYHLM
SFPQSAPHGVVFLHVTYVPAQEKNFTTAPA
ICHDGKAHFPREGVFVSNGTHWFVTQRNFY
EPQIITTDNTFVSGNCDVVIGIVNNTVYDP
LQPELDSFKEELDKYFKNHTSPDVDLGDIS
GINASVVNIQKEIDRLNEVAKNLNESLIDL
QELGKYEQYIKWPWYIWLGFIAGLIAIVMV
TIMLCCMTSCCSCLKGCCSCGSCCKFDEDD
SEPVLKGVKLHYT
```

In certain aspects, the S protein is expressed as a full-length protein and contains one or more amino acid proline substitutions that stabilize the S protein trimer in the prefusion conformation. In some embodiments, the S protein is expressed as a full-length protein and contains one or more proline substitutions at or near the boundary between a Heptad Repeat 1 (HR1) and a central helix of the promoters of the S ectodomain trimer. In some embodiments, the proline substitutions occur between amino acid residues 970 to 990 (GAISSVLNDILSRLDKVEAE) (SEQ ID NO: 7) of the promoters in the trimer. In some embodiments, the S protein is expressed as a full-length protein and contains two proline substitutions at amino acids K986 and V987 of SEQ ID NO: 1, as provided for in SEQ ID NO: 8 in Table 3 below, wherein the K986P and V987P substitutions are bolded and underlined, or an amino acid sequence 80%, 85%, 90%, 95%, 98%, or 99% homologous thereto. In some embodiments, the rMVA comprises SEQ ID NO: 9, which provides a nucleic acid sequence encoding the full-length S protein of SARS-CoV2 derived from the native SARS-CoV2 sequence with nucleic acid substitutions encoding for P986 and P987, or a nucleic acid sequence 80%, 85%, 90%, 95%, 98%, or 99% homologous thereto. In some embodiments, the rMVA comprises SEQ ID NO: 10, which provides an optimized nucleic acid sequence encoding the double proline substituted and stabilized SARS-CoV2 S protein, wherein the nucleic acid has been optimized as described below, or a nucleic acid sequence 80%, 85%, 90%, 95%, 98%, or 99% homologous thereto. In certain embodiments, an additional nucleic acid sequence encoding a tag may be included in the nucleic acid sequence to be inserted into the rMVA, so that the tag is expressed at the C-terminus of the protein. In some embodiments, the nucleic acid sequence (GAGCCAGAGGCT) (SEQ ID NO: 4) encodes for the high affinity C-tag having the amino acid sequence EPEA (SEQ ID NO: 5).

TABLE 3

Exemplary SARS-CoV2 Full-Length S Protein-Stabilized

| | |
|---|---|
| SEQ ID NO: 8-<br>SARS-CoV2 full-<br>length S protein-<br>stabilized with 2<br>proline<br>substitutions | MFVFLVLLPLVSSQCVNLTTRTQLPPAYTNSFTRGVYYPDKVFRSSVLHSTQDLFL<br>PFFSNVTWFHAIHVSGTNGTKRFDNPVLPFNDGVYFASTEKSNIIRGWIFGTTLDS<br>KTQSLLIVNNATNVVIKVCEFQFCNDPFLGVYYHKNNKSWMESEFRVYSSANNC<br>TFEYVSQPFLMDLEGKQGNFKNLREFVFKNIDGYFKIYSKHTPINLVRDLPQGFSA<br>LEPLVDLPIGINITRFQTLLALHRSYLTPGDSSSGWTAGAAAYYVGYLQPRTFLLK<br>YNENGTITDAVDCALDPLSETKCTLKSFTVEKGIYQTSNFRVQPTESIVRFPNITNL<br>CPFGEVFNATRFASVYAWNRKRISNCVADYSVLYNSASFSTFKCYGVSPTKLNDL<br>CFTNVYADSFVIRGDEVRQIAPGQTGKIADYNYKLPDDFTGCVIAWNSNNLDSKV<br>GGNYNYLYRLFRKSNLKPFERDISTEIYQAGSTPCNGVEGFNCYFPLQSYGFQPTN<br>GVGYQPYRVVVLSFELLHAPATVCGPKKSTNLVKNKCVNFNFNGLTGTGVLTES<br>NKKFLPFQQFGRDIADTTDAVRDPQTLEILDITPCSFGGVSVITPGTNTSNQVAVL<br>YQDVNCTEVPVAIHADQLTPTWRVYSTGSNVFQTRAGCLIGAEHVNNSYECDIPI |

TABLE 3-continued

Exemplary SARS-CoV2 Full-Length S Protein-Stabilized

GAGICASYQTQTNSPRRARSVASQSIIAYTMSLGAENSVAYSNNSIAIPTNFTISVT
TEILPVSMTKTSVDCTMYICGDSTECSNLLLQYGSFCTQLNRALTGIAVEQDKNT
QEVFAQVKQIYKTPPIKDFGGFNFSQILPDPSKPSKRSFIEDLLFNKVTLADAGFIK
QYGDCLGDIAARDLICAQKFNGLTVLPPLLTDEMIAQYTSALLAGTITSGWTFGA
GAALQIPFAMQMAYRFNGIGVTQNVLYENQKLIANQFNSAIGKIQDSLSSTASAL
GKLQDVVNQNAQALNTLVKQLSSNFGAISSVLNDILSRLDPPEAEVQIDRLITGRL
QSLQTYVTQQLIRAAEIRASANLAATKMSECVLGQSKRVDFCGKGYHLMSFPQS
APHGVVFLHVTYVPAQEKNFTTAPAICHDGKAHFPREGVFVSNGTHWFVTQRNF
YEPQIITTDNTFVSGNCDVVIGIVNNTVYDPLQPELDSFKEELDKYFKNHTSPDVD
LGDISGINASVVNIQKEIDRLNEVAKNLNESLIDLQELGKYEQYIKWPWYIWLGFI
AGLIAIVMVTIMLCCMTSCCSCLKGCCSCGSCCKFDEDDSEPVLKGVKLHYT

SEQ ID NO: 9-
SARS-CoV2 nucleic
acid sequence for
full length
S protein
with 2 proline
substitutions.

ATGTTTGTTTTTCTTGTTTTATTGCCACTAGTCTCTAGTCAGTGTGTTAATCTTA
CAACCAGAACTCAATTACCCCCTGCATACACTAATTCTTTCACACGTGGTGTT
TATTACCCTGACAAAGTTTTCAGATCCTCAGTTTTACATTCAACTCAGGACTTG
TTCTTACCTTTCTTTTCCAATGTTACTTGGTTCCATGCTATACATGTCTCTGGGA
CCAATGGTACTAAGAGGTTTGATAACCCTGTCCTACCATTTAATGATGGTGTT
TATTTTGCTTCCACTGAGAAGTCTAACATAATAAGAGGCTGGATTTTTGGTAC
TACTTTAGATTCGAAGACCCAGTCCCTACTTATTGTTAATAACGCTACTAATGT
TGTTATTAAAGTCTGTGAATTTCAATTTTGTAATGATCCATTTTTGGGTGTTTA
TTACCACAAAAACAACAAAGTTGGATGGAAAGTGAGTTCAGAGTTTATTCT
AGTGCGAATAATTGCACTTTTGAATATGTCTCTCAGCCTTTTCTTATGGACCTT
GAAGGAAAACAGGGTAATTTCAAAAATCTTAGGGAATTTGTGTTTAAGAATA
TTGATGGTTATTTTAAAATATATTCTAAGCACACGCCTATTAATTTAGTGCGTG
ATCTCCCTCAGGGTTTTTCGGCTTTAGAACCATTGGTAGATTGCCAATAGGT
ATTAACATCACTAGGTTTCAAACTTTACTTGCTTTACATAGAAGTTATTTGACT
CCTGGTGATTCTTCTTCAGGTTGGACAGCTGGTGCTGCAGCTTATTATGTGGGT
TATCTTCAACCTAGGACTTTTCTATTAAAATATAATGAAAATGGAACCATTAC
AGATGCTGTAGACTGTGCACTTGACCCTCTCTCAGAAACAAAGTGTACGTTGA
AATCCTTCACTGTAGAAAAAGGAATCTATCAAACTTCTAACTTTAGAGTCCAA
CCAACAGAATCTATTGTTAGATTTCCTAATATTACAAACTTGTGCCCTTTTGGT
GAAGTTTTTAACGCCACCAGATTTGCATCTGTTTATGCTTGGAACAGGAAGAG
AATCAGCAACTGTGTTGCTGATTATTCTGTCCTATATAATTCCGCATCATTTTC
CACTTTTAAGTGTTATGGAGTGTCTCCTACTAAATTAAATGATCTCTGCTTTAC
TAATGTCTATGCAGATTCATTTGTAATTAGAGGTGATGAAGTCAGACAAATCG
CTCCAGGGCAAACTGGAAAGATTGCTGATTATAATTATAAATTACCAGATGAT
TTTACAGGCTGCGTTATAGCTTGGAATTCTAACAATCTTGATTCTAAGGTTGGT
GGTAATTATAATTACCTGTATAGATTGTTTAGGAAGTCTAATCTCAAACCTTTT
GAGAGAGATATTTCAACTGAAATCTATCAGGCCGGTAGCACACCTTGTAATG
GTGTTGAAGGTTTTAATTGTTACTTTCCTTTACAATCATATGGTTTCCAACCCA
CTAATGGTGTTGGTTACCAACCATACAGAGTAGTAGTACTTTCTTTTGAACTTC
TACATGCACCAGCAACTGTTTGTGGACCTAAAAGTCTACTAATTTGGTTAAA
AACAAATGTGTCAATTTCAACTTCAATGGTTTAACAGGCACAGGTGTTCTTAC
TGAGTCTAACAAAAGTTTCTGCCTTTCCAACAATTTGGCAGAGACATTGCTG
ACACTACTGATGCTGTCCGTGATCCACAGACACTTGAGATTCTTGACATTACA
CCATGTTCTTTTGGTGGTGTCAGTGTTATAACACCAGGAACAAATACTTCTAA
CCAGGTTGCTGTTCTTTATCAGGATGTTAACTGCACAGAAGTCCCTGTTGC
TATTCATGCAGATCAACTTACTCCTACTTGGCGTGTTTATTCTACAGGTTCTAA
TGTTTTTTCAAACACGTGCAGGCTGTTTAATAGGGGCTGAACATGTCAACAACT
CATATGAGTGTGACATACCCATTGGTGCAGGTATATGCGCTAGTTATCAGACT
CAGACTAATTCTCCTCGGCGGGCACGTAGTGTAGCTAGTCAATCCATCATTGC
CTACACTATGTCACTTGGTGCAGAAAATTCAGTTGCTTACTCTAATAACTCTAT
TGCCATACCCACAAATTTTACTATTAGTGTTACCACAGAAATTCTACCAGTGT
CTATGACCAAGACATCAGTAGATTGTACAATGTACATTTGTGGTGATTCAACT
GAATGCAGCAATCTTTTGTTGCAATATGGCAGTTTTTGTACACAATTAAACCG
TGCTTTAACTGGAATAGCTGTTGAACAAGACAAAAACACCCAAGAAGTTTTTG
CACAAGTCAAACAAATTTACAAAACACCACCAATTAAAGATTTTGGTGGTTTT
AATTTTTCACAAATATTACCAGATCCATCAAAACCAAGCAAGAGGTCATTTAT
TGAAGATCTACTTTTCAACAAAGTGACACTTGCAGATGCTGGCTTCATCAAAC
AATATGGTGATTGCCTTGGTGATATTGCTGCTAGAGACCTCATTTGTGCACAA
AAGTTTAACGGCCTTACTGTTTTGCCACCTTTGCTCACAGATGAAATGATTGCT
CAATACACTTCTGCACTGTTAGCGGGTACAATCACTTCTGGTTGGACCTTTGG
TGCAGGTGCTGCATTACAAATACCATTTGCTATGCAAATGGCTTATAGGTTTA
ATGGTATTGGAGTTACACAGAATGTTCTCTATGAGAACCAAAAATTGATTGCC
AACCAATTTAATAGTGCTATTGGCAAAATTCAAGACTCACTTTCTTCCACAGC
AAGTGCACTTGGAAAACTTCAAGATGTGGTCAACCAAAATGCACAAGCTTTA
AACACGCTTGTTAAACAACTTAGCTCCAATTTTGGTGCAATTTCAAGTGTTTTA
AATGATATCCTTTCACGTCTTGACCCACCGGAGGCTGAAGTGCAAATTGATAG
GTTGATCACAGGCAGACTTCAAAGTTTGCAGACATATGTGACTCAACAATTAA
TTAGAGCTGCAGAAATCAGAGCTTCTGCTAATCTTGCTGCTACTAAAATGTCA
GAGTGTGTACTTGGACAATCAAAAAGAGTTGATTTTTGTGGAAAGGGCTATCA
TCTTATGTCCTTCCCTCAGTCAGCACCTCATGGTGTAGTCTTCTTGCATGTGAC
TTATGTCCCTGCACAAGAAAAGAACTTCACAACTGCTCCTGCCATTTGTCATG
ATGGAAAAGCACACTTTCCTCGTGAAGGTGTCTTTGTTTCAAATGGCACACAC
TGGTTTGTAACACAAAGGAATTTTTATGAACCACAAATCATTACTACAGACAA
CACATTTGTGTCTGGTAACTGTGATGTTGTAATAGGAATTGTCAACAACACAG
TTTATGATCCTTTGCAACCTGAATTAGACTCATTCAAGGAGGAGTTAGATAAA
TATTTTAAGAATCATACATCACCAGATGTTGATTTAGGTGACATCTCTGGCAT

TABLE 3-continued

Exemplary SARS-CoV2 Full-Length S Protein-Stabilized

|  |  |
|---|---|
|  | TAATGCTTCAGTTGTAAACATTCAAAAAGAAATTGACCGCCTCAATGAGGTTG<br>CCAAGAATTTAAATGAATCTCTCATCGATCTCCAAGAACTTGGAAAGTATGAG<br>CAGTATATAAAATGGCCATGGTACATTTGGCTAGGTTTTATAGCTGGCTTGAT<br>TGCCATAGTAATGGTGACAATTATGCTTTGCTGTATGACCAGTTGCTGTAGTT<br>GTCTCAAGGGCTGTTGTTCTTGTGGATCCTGCTGCAAATTTGATGAAGACGAC<br>TCTGAGCCAGTGCTCAAAGGAGTCAAATTACATTACACA |
| SEQ ID NO: 10-<br>SARS-CoV2 nucleic<br>acid sequence for<br>full length<br>S protein<br>with 2 proline<br>substitutions-<br>optimized. | ATGTTCGTGTTCCTAGTCCTACTACCGCTAGTCTCTTCTCAGTGTGTAAACCTA<br>ACAACGAGAACACAACTACCACCGGCGTACACCAATTCTTTCACAAGAGGAG<br>TATATTACCCGGACAAGGTGTTCAGATCCTCCGTACTACATTCTACACAGGAC<br>CTATTCCTACCGTTCTTCTCTAACGTAACATGGTTCCACGCGATCCATGTCTCT<br>GGAACAAACGGAACGAAGAGATTCGATAACCCGGTCTTGCCGTTCAACGATG<br>GTGTATACTTTGCGTCCACCGAGAAGTCCAACATCATCAGAGGATGGATCTTC<br>GGAACCACCTTGGATTCTAAGACCCAGTCCTTGCTAATCGTCAACAACGCGAC<br>CAACGTCGTCATCAAAGTCTGCGAATTCCAGTTCTGTAACGACCCGTTCTTGG<br>GAGTCTACTACCACAAGAACAACAAGTCCTGGATGGAATCCGAGTTCAGAGT<br>CTACTCTTCCGCGAACAACTGCACCTTCGAATATGTATCTCAGCCGTTCCTAAT<br>GGACCTAGAGGGAAAGCAGGGAAACTTCAAGAACCTAAGAGAGTTCGTATTC<br>AAGAACATCGACGGATACTTCAAGATCTACTCCAAGCACACTCCGATCAACCT<br>AGTTAGAGATCTACCGCAAGGATTCTCTGCGCTAGAACCGTTAGTAGATTTGC<br>CGATCGGAATCAACATCACCAGATTCCAGACACTACTAGCGCTACACAGATCT<br>TACCTAACGCCGGGAGATTCTTCTTCTGGATGGACTGCTGGTGCTGCGGCTTA<br>TTATGTAGGATACCTACAGCCGAGAACCTTCCTATTGAAGTACAACGAAAAC<br>GGAACCATCACCGATGCCGTAGATTGTGCTCTAGATCCGCTATCCGAAACGAA<br>GTGCACCCTAAAGTCTTTCACCGTCGAGAAGGGAATCTACCAGACCTCCAACT<br>TTAGAGTACAGCCGACCGAATCCATCGTCAGATTTCCGAACATCACGAACCTA<br>TGTCCGTTCGGAGAAGTGTTCAACGCGACAAGATTTGCGTCTGTCTATGCGTG<br>GAACAGAAAAGAATCAGTAACTGCGTCGCGGACTACTCCGTCCTATACAAC<br>TCTGCCTCTTTCTCCACGTTCAAATGCTACGGTGTATCTCCGACAAAGCTAAA<br>CGATCTATGCTTCACCAACGTCTACGCGGACTCCTTCGTAATCAGAGGAGATG<br>AAGTTAGACAGATTGCGCCGGGACAAACTGGAAAGATCGCGGATTATAACTA<br>CAAGCTACCGGACGACTTCACCGGATGTGTAATTGCGTGGAATTCGAACAAC<br>CTAGACTCCAAAGTCGGAGGAAACTACAACTACTTGTACAGACTATTCAGAA<br>AGTCCAACCTAAAGCCGTTCGAGAGAGACATCTCCACCGAAATCTATCAGGC<br>TGGATCTACACCGTGTAATGGTGTCGAAGGATTCAACTGCTACTTCCCGCTAC<br>AGTCTTACGGATTTCAACCGACAAACGGTGTAGGATATCAGCCGTACAGAGT<br>CGTCGTACTATCCTTCGAACTACTACATGCTCCGGCGACAGTATGTGGACCGA<br>AAAAGTCTACCAACCTAGTCAAGAACAAATGCGTCAACTTTAACTTCAACGG<br>ACTAACCGGAACCGGTGTCCTAACCGAATCTAACAAGAAGTTTCTACCGTTCC<br>AGCAGTTCGGAAGAGATATCGCGGATACAACAGACGCTGTCAGAGATCCGCA<br>AACCTTGGAGATCCTAGATATCACACCGTGTTCTTTCGGTGGTGTCTCTGTAAT<br>TACTCCGGGAACGAACACCTCCAATCAAGTAGCGGTACTATACCAGGACGTG<br>AACTGTACAGAAGTACCGGTAGCTATTCACGCGGATCAACTAACACCAACTT<br>GGAGAGTGTACTCCACCGGATCTAACGTATTCCAAACAAGAGCGGGATGTCT<br>AATCGGAGCGGAACACGTAAACAACTCCTACGAATGTGATATCCCGATTGGA<br>GCGGGAATCTGTGCGTCTTACCAAACACAAACAAACTCTCCGAGAAGAGCGA<br>GATCTGTAGCCTCTCAATCTATTATCGCCTACACCATGTCCTTGGGAGCCGAA<br>AATTCTGTCGCGTACTCCAACAATTCTATCGCGATCCCGACAAACTTCACCAT<br>CTCTGTAACAACCGAGATCCTACCGGTGTCTATGACCAAGACATCTGTCGATT<br>GCACCATGTACATCTGCGGAGATTCCACCGAGTGCTCCAACCTACTACTACAG<br>TACGGATCTTTCTGTACCCAGCTAAACAGAGCGTTGACTGGAATCGCTGTAGA<br>GCAGGATAAGAACACTCAAGAGGTATTCGCGCAAGTCAAGCAGATCTATAAG<br>ACTCCGCCGATCAAGGACTTCGGAGGTTTCAACTTCTCTCAGATCTTGCCGGA<br>TCCGTCCAAACCGTCTAAGAGATCTTTCATCGAGGACCTACTATTCAACAAG<br>TCACCCTAGCTGACGCGGGATTCATCAAACAATACGGAGATTGCTTGGGAGA<br>CATTGCGGCGAGAGATCTAATTTGCGCGCAGAAGTTTAACGGATTGACAGTA<br>CTACCGCCGCTACTAACCGATGAGATGATTGCGCAGTACACGTCTGCTCTATT<br>GGCGGGAACAATTACAAGTGGATGGACATTTGGAGCCGGTGCCGCTCTACAA<br>ATTCCGTTTGCTATGCAAATGGCGTACAGATTCAACGGAATCGGAGTAACCCA<br>GAACGTCTTGTACGAGAACCAGAAGCTAATCGCGAACCAGTTCAATTCCGCG<br>ATCGGAAAGATCCAGGACAGTCTATCTTCTACTGCTTCGGCGTTGGGAAAGCT<br>ACAGGATGTAGTAAATCAAAACGCGCAGGCGCTAAACACCTTGGTCAAGCAA<br>CTATCCTCTAACTTCGGAGCGATCTCGTCCGTCCTAAACGACATCTTATCCAG<br>ACTAGATCCACCGGAAGCGGAGGTCCAGATCGATAGACTAATCACTGGAAGA<br>TTGCAGTCCCTACAGACCTACGTAACACAGCAACTAATTAGACGGCGGAGA<br>TTAGAGCCTCTGCTAATCTAGCTGCGACCAAGATGTCCGAATGTGTCTTGGGA<br>CAATCCAAGAGAGTGGACTTCTGCGGAAAGGGATACCACCTAATGTCTTTCCC<br>ACAATCTGCGCCGCATGGTGTCGTATTCCTACATGTAACATATGTGCCGGCGC<br>AAGAAAAGAACTTCACAACAGCTCCAGCGATCTGCCATGATGGAAAAGCTCA<br>TTTCCCGAGAGAGGGAGTCTTTGTCTCTAACGGAACTCATTGGTTCGTCACCC<br>AGAGAAACTTCTACGAGCCGCAGATCATCACCACCGACAACACATTCGTCTC<br>GGGAAACTGCGACGTGGTCATCGGAATCGTAAACAATACCGTCTACGATCCG<br>TTGCAGCCGGAACTAGACTCCTTCAAAGAAGAGTTGGACAAGTACTTCAAGA<br>ACCACACCTCTCCGGATGTGGACTTGGGAGATATCTCTGGAATCAACGCGTCC<br>GTCGTCAACATCCAGAAAGAAATCGATAGATTGAACGAGGTCGCGAAGAACT<br>TGAACGAGTCCCTAATCGACCTACAAGAGCTAGGAAAATACGAGCAGTACAT<br>CAAGTGGCCGTGGTACATCTGGCTAGGATTCATTGCTGGACTAATTGCGATCG<br>TCATGGTCACCATCATGCTATGCTGTATGACCTCCTGTTGCTCCTGTCTAAAGG |

TABLE 3-continued

| Exemplary SARS-CoV2 Full-Length S Protein-Stabilized |
| --- |
| GATGTTGTTCCTGCGGATCCTGTTGCAAGTTCGATGAAGATGATAGTGAACCG GTCCTAAAGGGTGTCAAGCTACACTACACA |

In certain embodiments, the S protein is expressed as a full-length protein and contains one or more amino acid substitutions. In some embodiments, the S protein is expressed as a full-length protein and contains one or more substitutions selected from K417T, E484K or N501Y of SEQ ID NO: 8. In some embodiments, the S protein is expressed as a full-length protein and contains the following substitutions: K417T, E484K, and N501Y of SEQ ID NO:8 . . . . In some embodiments, the S protein is expressed as a full-length protein of SEQ ID NO: 11, or an amino acid sequence 89%, 85%, 90%, 95%, 98%, or 99% homologous thereto. In some embodiments, the rMVA comprises SEQ ID NO: 12, which provides an optimized nucleic acid sequence encoding the double proline substituted and stabilized SARS-CoV2 S protein with a K417T, E484K, and N501Y substitutions, wherein the nucleic acid has been optimized as described below, or a nucleic acid sequence 80%, 85%, 90%, 95%, 98%, or 99% homologous thereto. In some embodiments, the mutation is K417N.

In some embodiments, the S protein is expressed as a full-length protein and has a deletion of one or more spike protein amino acids H69, V70, or Y144, or combinations thereof, of SEQ ID NO: 8. In some embodiments, the S protein is expressed as a full-length protein and contains one or more substitutions selected from D614G, A570D, P681H, T716I, S982A, D1118H, K417N, K417T, D215G, A701V, L18F, R246I, Y453F, I692V, M1229I, N439K, A222V, S477N, or A376T, or combinations thereof, of SEQ ID NO: 8. In some embodiments, the spike protein includes a deletion at amino acids 242-244 of SEQ ID NO: 8. In some embodiments, the S protein is expressed as a full-length protein and contains the following deletions and substitutions: deletion of amino acids 69-70, deletion of amino acid Y144, amino acid substitution N501Y, amino acid substitution A570D, amino acid substitution D614G, amino acid substitution P681H, amino acid substitution T716I, amino acid substitution S982A, and amino acid substitution D1118H, or SEQ ID NO: 8. In some embodiments, the S protein is expressed as a full-length protein and contains the following deletions and substitutions: N501Y, K417N or K417T, E484K, D80A, A701V, L18F, and amino acid deletion at amino acids 242-244, of SEQ ID NO: 8. In some embodiments, the S protein is expressed as a full-length protein and contains one or more of the following substitutions: D614G; D936Y; P1263L; L5F; N439K; R21I; D839Y; L54F; A879S; L18F; F1121L; R847K; T478I; A829T; Q675H; S477N; H49Y; T29I; G769V; G1124V; V1176F; K1073N; P479S; S1252P; Y145 deletion; E583D; R214L; A1020V; Q1208H; D215G; H146Y; S98F; T95I; G1219C; A846V; I197V; R1021; V367F; T572I; A1078S; A831V; P1162L; T73I; A845S; G1219V; H245Y; L8V; Q675R; S254F; V483A; Q677H; D138H; D80Y; M1237T; D1146H; E654D; H655Y; S50L; S939F; S943P; G485R; Q613H; T76I; V341I; M153I; S221L; T859I; W258L; L242F; P681L; V289I; A520S; V1104L; V1228L; L176F; M1237I; T307I; T716I; L141; M1229I; A1087S; P26S; P330S; P384L; R765L; S940F; T323I; V826L; E1202Q; L1203F; L611F; V615I; A262S; A522V; A688V; A706V; A892S; E554D; Q836H; T1027I; T22I; A222V; A27S; A626V; C1247F; K1191N; M731I; P26L; S1147L; S1252F; S255F; V1264L; V308L; D80A; I670L; P251L; P631S; *1274Q; A344S; A771S; A879T; D1084Y; D253G; H1101Y; L1200F; Q14H; Q239K; A623V; D215Y; E1150D; G476S; K77M; M177I; P812S; S704L; T51I; T547I; T791I; V1122L; Y145H; D574Y; G142D; G181V; I834T; N370S; P812L; S12F; T791P; V90F; W152L; A292S; A570V; A647S; A845V; D1163Y; G181R; L84I; L938F; P1143L; P809S; R78M; T1160I; V1133F; V213L; V615F; A831V; D839Y; D839N; D839E; S943P; P1263L; or V622F; and combinations thereof, of SEQ ID NO: 8.

In some embodiment, the nucleic acid sequence encoding the stabilized S protein is SEQ ID NO: 12, or a nucleic acid sequence 80%, 85%, 90%, 95%, 98%, or 99% homologous thereto. SEQ ID NO: 12 provides an optimized nucleic acid sequence encoding the double proline substituted and stabilized SARS-CoV2 S protein, further comprising K417T, E484K, and N501T amino acid substitutions, wherein the nucleic acid has been optimized as described below. In certain embodiments, an additional nucleic acid sequence encoding a tag may be included in the nucleic acid sequence to be inserted into the rMVA, so that the tag is expressed at the C-terminus of the protein. In some embodiments, the nucleic acid sequence (GAGCCAGAGGCT) (SEQ ID NO: 4) encodes for the high affinity C-tag having the amino acid sequence EPEA (SEQ ID NO: 5).

TABLE 4

| Exemplary SARS-CoV2 Full-Length S Protein-Stabilized Mutant | |
| --- | --- |
| SEQ ID NO: 11-<br>SARS-CoV2 full-<br>length stabilized S<br>protein-K417T,<br>E484K, and N501Y | MFVFLVLLPLVSSQCVNLTTRTQLPPAYTNSFTRGVYYPDKVFRSSVLHSTQDLFL<br>PFFSNVTWFHAIHVSGTNGTKRFDNPVLPFNDGVYFASTEKSNIIRGWIFGTTLDS<br>KTQSLLIVNNATNVVIKVCEFQFCNDPFLGVYYHKNNKSWMESEFRVYSSANNC<br>TFEYVSQPFLMDLEGKQGNFKNLREFVFKNIDGYFKIYSKHTPINLVRDLPQGFSA<br>LEPLVDLPIGINITRFQTLLALHRSYLTPGDSSSGWTAGAAAYYVGYLQPRTFLLK<br>YNENGTITDAVDCALDPLSETKCTLKSFTVEKGIYQTSNFRVQPTESIVRFPNITNL<br>CPFGEVFNATRFASVYAWNRKRISNCVADYSVLYNSASFSTFKCYGVSPTKLNDL<br>CFTNVYADSFVIRGDEVRQIAPGQTGTIADYNYKLPDDFTGCVIAWNSNNLDSKV<br>GGNYNYLYRLFRKSNLKPFERDISTEIYQAGSTPCNGVKGFNCYFPLQSYGFQPT<br>YGVGYQPYRVVVLSFELLHAPATVCGPKKSTNLVKNKCVNFNFNGLTGTGVLTE<br>SNKKFLPFQQFGRDIADTTDAVRDPQTLEILDITPCSFGGVSVITPGTNTSNQVAVL<br>YQDVNCTEVPVAIHADQLTPTWRVYSTGSNVFQTRAGCLIGAEHVNNSYECDIPI<br>GAGICASYQTQTNSPRRARSVASQSIIAYTMSLGAENSVAYSNNSIAIPTNFTISVT<br>TEILPVSMTKTSVDCTMYICGDSTECSNLLLQYGSFCTQLNRALTGIAVEQDKNT<br>QEVFAQVKQIYKTPPIKDFGGFNFSQILPDPSKPSKRSFIEDLLFNKVTLADAGFIK |

TABLE 4-continued

Exemplary SARS-CoV2 Full-Length S Protein-Stabilized Mutant

QYGDCLGDIAARDLICAQKFNGLTVLPPLLTDEMIAQYTSALLAGTITSGWTFGA
GAALQIPFAMQMAYRFNGIGVTQNVLYENQKLIANQFNSAIGKIQDSLSSTASAL
GKLQDVVNQNAQALNTLVKQLSSNFGAISSVLNDILSRLDPPEAEVQIDRLITGRL
QSLQTYVTQQLIRAAEIRASANLAATKMSECVLGQSKRVDFCGKGYHLMSFPQS
APHGVVFLHVTYVPAQEKNFTTAPAICHDGKAHFPREGVFVSNGTHWFVTQRNF
YEPQIITTDNTFVSGNCDVVIGIVNNTVYDPLQPELDSFKEELDKYFKNHTSPDVD
LGDISGINASVVNIQKEIDRLNEVAKNLNESLIDLQELGKYEQYIKWPWYIWLGFI
AGLIAIVMVTIMLCCMTSCCSCLKGCCSCGSCCKFDEDDSEPVLKGVKLHYT

SEQ ID NO: 12-
SARS-CoV2 nucleic
acid sequence for
full length S protein
with 2 proline
substitutions, and
K417T, E484K, and
N501T amino acid
substitutions-
optimized ATGTTCGTGTTCCTAGTCCTACTACCGCTAGTCTCTTCTCAGTGTGTAAACCTA
ACAACGAGAACACAACTACCACCGGCGTACACCAATTCTTTCACAAGAGGAG
TATATTACCCGGACAAGGTGTTCAGATCCTCCGTACTACATTCTACACAGGAC
CTATTCCTACCGTTCTTCTCTAACGTAACATGGTTCCACGCGATCCATGTCTCT
GGAACAAACGGAACGAAGAGATTCGATAACCCGGTCTTGCCGTTCAACGATG
GTGTATACTTTGCGTCCACCGAGAAGTCCAACATCATCAGAGGATGGATCTTC
GGAACCACCTTGGATTCTAAGACCCAGTCCTTGCTAATCGTCAACAACGCGAC
CAACGTCGTCATCAAAGTCTGCGAATTCCAGTTCTGTAACGACCCGTTCTTGG
GAGTCTACTACCACAAGAACAACAAGTCCTGGATGGAATCCGAGTTCAGAGT
CTACTCTTCCGCGAACAACTGCACCTTCGAATATGTATCTCAGCCGTTCCTAAT
GGACCTAGAGGGAAAGCAGGGAAACTTCAAGAACCTAAGAGAGTTCGTATTC
AAGAACATCGACGGATACTTCAAGATCTACTCCAAGCACACTCCGATCAACCT
AGTTAGAGATCTACCGCAAGGATTCTCTGCGCTAGAACCGTTAGTAGATTTGC
CGATCGGAATCAACATCACCAGATTCCAGACACTACTAGCGCTACACAGATCT
TACCTAACGCCGGGAGATTCTTCTTCTGGATGGACTGCTGGTGCTGCGGCTTA
TTATGTAGGATACCTACAGCCGAGAACCTTCCTATTGAAGTACAACGAAAAC
GGAACCATCACCGATGCCGTAGATTGTGCTCTAGATCCGCTATCCGAAACGAA
GTGCACCCTAAAGTCTTTCACCGTCGAGAAGGGAATCTACCAGACCTCCAACT
TTAGAGTACAGCCGACCGAATCCATCGTCAGATTTCCGAACATCACGAACCTA
TGTCCGTTCGGAGAAGTGTTCAACGCGACAAGATTTGCGTCTGTCTATGCGTG
GAACAGAAAAGAATCAGTAACTGCGTCGCGGACTACTCCGTCCTATACAAC
TCTGCCTCTTTCTCCACGTTCAAATGCTACGGTGTATCTCCGACAAAGCTAAA
CGATCTATGCTTCACCAACGTCTACGCGGACTCCTTCGTAATCAGAGGAGATG
AAGTTAGACAGATTGCGCCGGGACAAACTGGAACGATCGCGGATTATAACTA
CAAGCTACCGGACGACTTCACCGGATGTGTAATTGCGTGGAATTCGAACAAC
CTAGACTCCAAAGTCGGAGGAAACTACAACTACTTGTACAGACTATTCAGAA
AGTCCAACCTAAAGCCGTTCGAGAGAGACATCTCCACCGAAATCTATCAGGC
TGGATCTACACCGTGTAATGGTGTCAAGGGATTCAACTGCTACTTCCCGCTAC
AGTCTTACGGATTTCAACCGACATACGGTGTAGGATATCAGCCGTACAGAGTC
GTCGTACTATCCTTCGAACTACTACATGCTCCGGCGACAGTATGTGGACCGAA
AAAGTCTACCAACCTAGTCAAGAACAAATGCGTCAACTTTAACTTCAACGGA
CTAACCGGAACCGGTGTCCTAACCGAATCTAACAAGAAGTTTCTACCGTTCCA
GCAGTTCGGAAGAGATATCGCGGATACAACAGACGCTGTCAGAGATCCGCAA
ACCTTGGAGATCCTAGATATCACACCGTGTTCTTTCGGTGGTGTCTCTGTAATT
ACTCCGGGAACGAACACCTCCAATCAAGTAGCGGTACTATACCAGGACGTGA
ACTGTACAGAAGTACCGGTAGCTATTCACGCGGATCAACTAACACCAACTTG
GAGAGTGTACTCCACCGGATCTAACGTATTCCAAACAAGAGCGGGATGTCTA
ATCGGAGCGGAACACGTAAACAACTCCTACGAATGTGATATCCCGATTGGAG
CGGGAATCTGTGCGTCTTACCAAACACAAACAAACTCTCCGAGAAGAGCGAG
ATCTGTAGCCTCTCAATCTATTATCGCCTACACCATGTCCTTGGGAGCCGAAA
ATTCTGTCGCGTACTCCAACAATTCTATCGCGATCCCGACAAACTTCACCATC
TCTGTAACAACCGAGATCCTACCGGTGTCTATGACCAAGACATCTGTCGATTG
CACCATGTACATCTGCGGAGATTCCACCGAGTGCTCCAACCTACTACTACAGT
ACGGATCTTTCTGTACCCAGCTAAACAGAGCGTTGACTGGAATCGCTGTAGAG
CAGGATAAGAACACTCAAGAGGTATTCGCGCAAGTCAAGCAGATCTATAAGA
CTCCGCCGATCAAGGACTTCGGAGGTTTCAACTTCTCTCAGATCTTGCCGGAT
CCGTCCAAACCGTCTAAGAGATCTTTCATCGAGGACCTACTATTCAACAAAGT
CACCCTAGCTGACGCGGGATTCATCAAACAATACGGAGATTGCTTGGGAGAC
ATTGCGGCGAGAGATCTAATTTGCGCGCAGAAGTTTAACGGATTGACAGTACT
ACCGCCGCTACTAACCGATGAGATGATTGCGCAGTACACGTCTGCTCTATTGG
CGGGAACAATTACAAGTGGATGGACATTTGGAGCCGGTGCCGCTCTACAAAT
TCCGTTTGCTATGCAAATGGCGTACCAGATTCAACGGAATCGGAGTAACCCAG
AACGTCTTGTACGAGAACCAGAAGCTAATCGCGAACCAGTTCAATTCCGCGA
TCGGAAAGATCCAGGACAGTCTATCTTCTACTGCTTCGGCGTTGGGAAAGCTA
CAGGATGTAGTAAATCAAAACGCGCAGGCGCTAAACACCTTGGTCAAGCAAC
TATCCTCTAACTTCGGAGCGATCTCGTCCGTCCTAAACGACATCTTATCCAGA
CTAGATCCACCGGAAGCGGAGGTCCAGATCGATAGACTAATCACTGGAAGAT
TGCAGTCCCTACGACCTACGTAACACAGCCAACTAATTAGAGCGGCGGAGAT
TAGAGCCTCTGCTAATCTAGCTGCGACCAAGATGTCCGAATGTGTCTTGGGAC
AATCCAAGAGAGTGGACTTCTGCGGAAAGGGATACCACCTAATGTCTTTCCCA
CAATCGCGCCGCATGGTGTCGTATTCCTACATGTAACATATGTGCCGGCGCA
AGAAAAGAACTTCACAACAGCTCCAGCGATCTGCCATGATGGAAAAGCTCAT
TTCCCGAGAGAGGGGAGTCTTTGTCTCTAACGGAACTCATTGGTTCGTCACCCA
GAGAAACTTCTACGAGCCGCAGATCATCACCACCGACAACACATTCGTCTCG
GGAAACTGCGACGTGGTCATCGGAATCGTAAACAATACCGTCTACGATCCGTT
GCAGCCGGAACTAGACTCCTTCAAAGAAGAGTTGGACAAGTACTTCAAGAAC
CACACCTCTCCGGATGTGGACTTGGGAGATATCTCTGGAATCAACGCGTCCGT
CGTCAACATCCAGAAAGAAATCGATAGATTGAACGAGGTCGCGAAGAACTTG
AACGAGTCCCTAATCGACCTACAAGAGCTAGGAAAATACGAGCAGTACATCA TABLE 4-continued Exemplary SARS-CoV2 Full-Length S Protein-Stabilized Mutant

```
AGTGGCCGTGGTACATCTGGCTAGGATTCATTGCTGGACTAATTGCGATCGTC
ATGGTCACCATCATGCTATGCTGTATGACCTCCTGTTGCTCCTGTCTAAAGGG
ATGTTGTTCCTGCGGATCCTGTTGCAAGTTCGATGAAGATGATAGTGAACCGG
TCCTAAAGGGTGTCAAGCTACACTACACA
```

In certain aspects, the SARS-CoV2 antigen expressed by the rMVA is a modified spike(S) protein, wherein the modified S protein comprises an S1+S2 truncated protein lacking the carboxy terminus of the protein. In some embodiments, the S1+S2 truncated protein comprises amino acids 1 to 1213 (SEQ ID NO: 13) of the SARS-CoV2 S protein, as provided for in Table 5, or an amino acid sequence 80%, 85%, 90%, 95%, 98%, or 99% homologous thereto. In some embodiments, the rMVA comprises SEQ ID NO: 15, which provides a nucleic acid sequence encoding the S1+S2 truncated protein derived from the native SARS-CoV2 sequence, or a nucleic acid sequence 80%, 85%, 90%, 95%, 98%, or 99% homologous thereto. In some embodiments, the rMVA comprises SEQ ID NO: 16, which provides an optimized nucleic acid sequence encoding the S1+S2 truncated protein, or a nucleic acid sequence 80%, 85%, 90%, 95%, 98%, or 99% homologous thereto. In some embodiments, the S1+S2 truncated protein comprises amino acids 1 to 1213 and two proline substitutions at amino acids 986 and 987 (SEQ ID NO: 14) of the SARS-CoV2 S protein, as provided for in Table 5, or an amino acid sequence 80%, 85%, 90%, 95%, 98%, or 99% homologous thereto. In some embodiments, the rMVA comprises SEQ ID NO: 17, which provides an optimized nucleic acid sequence encoding the S1+S2 truncated protein +K986P and V987P, or a nucleic acid sequence 80%, 85%, 90%, 95%, 98%, or 99% homologous thereto. In certain embodiments, an additional nucleic acid sequence encoding a tag may be included in the nucleic acid sequence to be inserted into the rMVA, so that the tag is expressed at the C-terminus of the protein. In some embodiments, the nucleic acid sequence (GAGCCAGAGGCT) (SEQ ID NO: 4) encodes for the high affinity C-tag having the amino acid sequence EPEA (SEQ ID NO: 5).

TABLE 5

Truncated S1 + S2 SARS-CoV2 Protein

| | |
|---|---|
| SEQ ID NO: 13-<br>SARS-CoV2<br>truncated S1 + S2<br>protein (aa 1-1213). | MFVFLVLLPLVSSQCVNLTTRTQLPPAYTNSFTRGVYYPDKVFRSSVLHSTQDLFL<br>PFFSNVTWFHAIHVSGTNGTKRFDNPVLPFNDGVYFASTEKSNIIRGWIFGTTLDS<br>KTQSLLIVNNATNVVIKVCEFQFCNDPFLGVYYHKNNKSWMESEFRVYSSANNC<br>TFEYVSQPFLMDLEGKQGNFKNLREFVFKNIDGYFKIYSKHTPINLVRDLPQGFSA<br>LEPLVDLPIGINITRFQTLLALHRSYLTPGDSSSGWTAGAAAYYVGYLQPRTFLLK<br>YNENGTITDAVDCALDPLSETKCTLKSFTVEKGIYQTSNFRVQPTESIVRFPNITNL<br>CPFGEVFNATRFASVYAWNRKRISNCVADYSVLYNSASFSTFKCYGVSPTKLNDL<br>CFTNVYADSFVIRGDEVRQIAPGQTGKIADYNYKLPDDFTGCVIAWNSNNLDSKV<br>GGNYNYLYRLFRKSNLKPFERDISTEIYQAGSTPCNGVEGFNCYFPLQSYGFQPTN<br>GVGYQPYRVVVLSFELLHAPATVCGPKKSTNLVKNKCVNFNFNGLTGTGVLTES<br>NKKFLPFQQFGRDIADTTDAVRDPQTLEILDITPCSFGGVSVITPGTNTSNQVAVL<br>YQDVNCTEVPVAIHADQLTPTWRVYSTGSNVFQTRAGCLIGAEHVNNSYECDIPI<br>GAGICASYQTQTNSPRRARSVASQSIIAYTMSLGAENSVAYSNNSIAIPTNFTISVT<br>TEILPVSMTKTSVDCTMYICGDSTECSNLLLQYGSFCTQLNRALTGIAVEQDKNT<br>QEVFAQVKQIYKTPPIKDFGGFNFSQILPDPSKPSKRSFIEDLLFNKVTLADAGFIK<br>QYGDCLGDIAARDLICAQKFNGLTVLPPLLTDEMIAQYTSALLAGTITSGWTFGA<br>GAALQIPFAMQMAYRFNGIGVTQNVLYENQKLIANQFNSAIGKIQDSLSSTASAL<br>GKLQDVVNQNAQALNTLVKQLSSNFGAISSVLNDILSRLDKVEAEVQIDRLITGR<br>LQSLQTYVTQQLIRAAEIRASANLAATKMSECVLGQSKRVDFCGKGYHLMSFPQ<br>SAPHGVVFLHVTYVPAQEKNFTTAPAICHDGKAHFPREGVFVSNGTHWFVTQRN<br>FYEPQIITTDNTFVSGNCDVVIGIVNNTVYDPLQPELDSFKEELDKYFKNHTSPDV<br>DLGDISGINASVVNIQKEIDRLNEVAKNLNESLIDLQELGKYEQYIKWP |
| SEQ ID NO: 14-<br>SARS-CoV2<br>truncated S1 + S2<br>protein + K986P and<br>V987P (aa 1-1213). | MFVFLVLLPLVSSQCVNLTTRTQLPPAYTNSFTRGVYYPDKVFRSSVLHSTQDLFL<br>PFFSNVTWFHAIHVSGTNGTKRFDNPVLPFNDGVYFASTEKSNIIRGWIFGTTLDS<br>KTQSLLIVNNATNVVIKVCEFQFCNDPFLGVYYHKNNKSWMESEFRVYSSANNC<br>TFEYVSQPFLMDLEGKQGNFKNLREFVFKNIDGYFKIYSKHTPINLVRDLPQGFSA<br>LEPLVDLPIGINITRFQTLLALHRSYLTPGDSSSGWTAGAAAYYVGYLQPRTFLLK<br>YNENGTITDAVDCALDPLSETKCTLKSFTVEKGIYQTSNFRVQPTESIVRFPNITNL<br>CPFGEVFNATRFASVYAWNRKRISNCVADYSVLYNSASFSTFKCYGVSPTKLNDL<br>CFTNVYADSFVIRGDEVRQIAPGQTGKIADYNYKLPDDFTGCVIAWNSNNLDSKV<br>GGNYNYLYRLFRKSNLKPFERDISTEIYQAGSTPCNGVEGFNCYFPLQSYGFQPTN<br>GVGYQPYRVVVLSFELLHAPATVCGPKKSTNLVKNKCVNFNFNGLTGTGVLTES<br>NKKFLPFQQFGRDIADTTDAVRDPQTLEILDITPCSFGGVSVITPGTNTSNQVAVL<br>YQDVNCTEVPVAIHADQLTPTWRVYSTGSNVFQTRAGCLIGAEHVNNSYECDIPI<br>GAGICASYQTQTNSPRRARSVASQSIIAYTMSLGAENSVAYSNNSIAIPTNFTISVT<br>TEILPVSMTKTSVDCTMYICGDSTECSNLLLQYGSFCTQLNRALTGIAVEQDKNT<br>QEVFAQVKQIYKTPPIKDFGGFNFSQILPDPSKPSKRSFIEDLLFNKVTLADAGFIK<br>QYGDCLGDIAARDLICAQKFNGLTVLPPLLTDEMIAQYTSALLAGTITSGWTFGA<br>GAALQIPFAMQMAYRFNGIGVTQNVLYENQKLIANQFNSAIGKIQDSLSSTASAL<br>GKLQDVVNQNAQALNTLVKQLSSNFGAISSVLNDILSRLDPPEAEVQIDRLITGRL<br>QSLQTYVTQQLIRAAEIRASANLAATKMSECVLGQSKRVDFCGKGYHLMSFPQS<br>APHGVVFLHVTYVPAQEKNFTTAPAICHDGKAHFPREGVFVSNGTHWFVTQRNF<br>YEPQIITTDNTFVSGNCDVVIGIVNNTVYDPLQPELDSFKEELDKYFKNHTSPDVD<br>LGDISGINASVVNIQKEIDRLNEVAKNLNESLIDLQELGKYEQYIKWP |

TABLE 5-continued

Truncated S1 + S2 SARS-CoV2 Protein

| | |
|---|---|
| SEQ ID NO: 15-<br>SARS-CoV2 nucleic<br>acid sequence for<br>truncated S1 + S2<br>protein (aa 1-1213). | ATGTTTGTTTTTCTTGTTTTATTGCCACTAGTCTCTAGTCAGTGTGTTAATCTTA<br>CAACCAGAACTCAATTACCCCCTGCATACACTAATTCTTTCACACGTGGTGTT<br>TATTACCCTGACAAAGTTTTCAGATCCTCAGTTTTACATTCAACTCAGGACTTG<br>TTCTTACCTTTCTTTTCCAATGTTACTTGGTTCCATGCTATACATGTCTCTGGGA<br>CCAATGGTACTAAGAGGTTTGATAACCCTGTCCTACCATTTAATGATGGTGTT<br>TATTTTGCTTCCACTGAGAAGTCTAACATAATAAGAGGCTGGATTTTTGGTAC<br>TACTTTAGATTCGAAGACCCAGTCCCTACTTATTGTTAATAACGCTACTAATGT<br>TGTTATTAAAGTCTGTGAATTTCAATTTTGTAATGATCCATTTTTGGGTGTTTA<br>TTACCACAAAAACAACAAAAGTTGGATGGAAAGTGAGTTCAGAGTTTATTCT<br>AGTGCGAATAATTGCACTTTTGAATATGTCTCTCAGCCTTTTCTTATGGACCTT<br>GAAGGAAAACAGGGTAATTTCAAAAATCTTAGGGAATTTGTGTTTAAGAATA<br>TTGATGGTTATTTTAAAATATATTCTAAGCACACGCCTATTAATTTAGTGCGTG<br>ATCTCCCTCAGGGTTTTTCGGCTTTAGAACCATTGGTAGATTTGCCAATAGGT<br>ATTAACATCACTAGGTTTCAAACTTTACTTGCTTTACATAGAAGTTATTTGACT<br>CCTGGTGATTCTTCTTCAGGTTGGACAGCTGGTGCTGCAGCTTATTATGTGGGT<br>TATCTTCAACCTAGGACTTTTCTATTAAAATATAATGAAAATGGAACCATTAC<br>AGATGCTGTAGACTGTGCACTTGACCCTCTCTCAGAAACAAAGTGTACGTTGA<br>AATCCTTCACTGTAGAAAAAGGAATCTATCAAACTTCTAACTTTAGAGTCCAA<br>CCAACAGAATCTATTGTTAGATTTCCTAATATTACAAACTTGTGCCCTTTTGGT<br>GAAGTTTTTAACGCCACCAGATTTGCATCTGTTTATGCTTGGAACAGGAAGAG<br>AATCAGCAACTGTGTTGCTGATTATTCTGTCCTATATAATTCCGCATCATTTTC<br>CACTTTTAAGTGTTATGGAGTGTCTCCTACTAAATTAAATGATCTCTGCTTTAC<br>TAATGTCTATGCAGATTCATTTGTAATTAGAGGTGATGAAGTCAGACAAATCG<br>CTCCAGGGCAAACTGGAAAGATTGCTGATTATAATTATAAATTACCAGATGAT<br>TTTACAGGCTGCGTTATAGCTTGGAATTCTAACAATCTTGATTCTAAGGTTGGT<br>GGTAATTATAATTACCTGTATAGATTGTTTAGGAAGTCTAATCTCAAACCTTTT<br>GAGAGAGATATTTCAACTGAAATCTATCAGGCCGGTAGCACACCTTGTAATG<br>GTGTTGAAGGTTTTAATTGTTACTTTCCTTTACAATCATATGGTTTCCAACCCA<br>CTAATGGTGTTGGTTACCAACCATACAGAGTAGTAGTACTTTCTTTTGAACTTC<br>TACATGCACCAGCAACTGTTTGTGGACCTAAAAAGTCTACTAATTTGGTTAAA<br>AACAAATGTGTCAATTTCAACTTCAATGGTTTAACAGGCACAGGTGTTCTTAC<br>TGAGTCTAACAAAAAGTTTCTGCCTTTCCAACAATTTGGCAGAGACATTGCTG<br>ACACTACTGATGCTGTCCGTGATCCACAGACACTTGAGATTCTTGACATTACA<br>CCATGTTCTTTTGGTGGTGTCAGTGTTATAACACCAGGAACAAATACTTCTAA<br>CCAGGTTGCTGTTCTTTATCAGGATGTTAACTGCACAGAAGTCCCTGTTGCTAT<br>TCATGCAGATCAACTTACTCCTACTTGGCGTGTTTATTCTACAGGTTCTAATGT<br>TTTTCAAACACGTGCAGGCTGTTTAATAGGGGCTGAACATGTCAACAACTCAT<br>ATGAGTGTGACATACCCATTGGTGCAGGTATATGCGCTAGTTATCAGACTCAG<br>ACTAATTCTCCTCGGCGGGCACGTAGTGTAGCTAGTCAATCCATCATTGCCTA<br>CACTATGTCACTTGGTGCAGAAAATTCAGTTGCTTACTCTAATAACTCTATTGC<br>CATACCCACAAATTTTACTATTAGTGTTACCACAGAAATTCTACCAGTGTCTA<br>TGACCAAGACATCAGTAGATTGTACAATGTACATTTGTGGTGATTCAACTGAA<br>TGCAGCAATCTTTTGTTGCAATATGGCAGTTTTTGTACACAATTAAACCGTGCT<br>TTAACTGGAATAGCTGTTGAACAAGACAAAAACACCCAAGAAGTTTTTGCAC<br>AAGTCAAACAAATTTACAAAACACCACCAATTAAAGATTTTGGTGGTTTTAAT<br>TTTTCACAAATATTACCAGATCCATCAAAACCAAGCAAGAGGTCATTTATTGA<br>AGATCTACTTTTCAACAAAGTGACACTTGCAGATGCTGGCTTCATCAAACAAT<br>ATGGTGATTGCCTTGGTGATATTGCTGCTAGAGACCTCATTTGTGCACAAAAG<br>TTTAACGGCCTTACTGTTTTGCCACCTTTGCTCACAGATGAAATGATTGCTCAA<br>TACACTTCTGCACTGTTAGCGGGTACAATCACTTCTGGTTGGACCTTTGGTGC<br>AGGTGCTGCATTACAAATACCATTTGCTATGCAAATGGCTTATAGGTTTAATG<br>GTATTGGAGTTACACAGAATGTTCTCTATGAGAACCAAAAATTGATTGCCAAC<br>CAATTTAATAGTGCTATTGGCAAAATTCAAGACTCACTTTCTTCCACAGCAAG<br>TGCACTTGGAAAACTTCAAGATGTGGTCAACCAAAATGCACAAGCTTTAAAC<br>ACGCTTGTTAAACAACTTAGCTCCAATTTTGGTGCAATTTCAAGTGTTTTAAAT<br>GATATCCTTTCACGTCTTGACAAAGTTGAGGCTGAAGTGCAAATTGATAGGTT<br>GATCACAGGCAGACTTCAAAGTTTGCAGACATATGTGACTCAACAATTAATTA<br>GAGCTGCAGAAATCAGAGCTTCTGCTAATCTTGCTGCTACTAAAATGTCAGAG<br>TGTGTACTTGGACAATCAAAAAGAGTTGATTTTTGTGGAAAGGGCTATCATCT<br>TATGTCCTTCCCTCAGTCAGCACCTCATGGTGTAGTCTTCTTGCATGTGACTTA<br>TGTCCCTGCACAAGAAAAGAACTTCACAACTGCTCCTGCCATTTGTCATGATG<br>GAAAAGCACACTTTCCTCGTGAAGGTGTCTTTGTTTCAAATGGCACACACTGG<br>TTTGTAACACAAAGGAATTTTTATGAACCACAAATCATTACTACAGACAACAC<br>ATTTGTGTCTGGTAACTGTGATGTTGTAATAGGAATTGTCAACAACACAGTTT<br>ATGATCCTTTGCAACCTGAATTAGACTCATTCAAGGAGGAGTTAGATAAAATAT<br>TTTAAGAATCATACATCACCAGATGTTGATTTAGGTGACATCTCTGGCATTAA<br>TGCTTCAGTTGTAAACATTCAAAAAGAAATTGACCGCCTCAATGAGGTTGCCA<br>AGAATTTAAATGAATCTCTCATCGATCTCCAAGAACTTGGAAAGTATGAGCAG<br>TATATAAAATGGCCA |
| SEQ ID NO: 16-<br>SARS-CoV2 nucleic<br>acid sequence for<br>truncated S1 + S2<br>protein (aa 1-1213). | ATGTTCGTGTTCCTAGTCCTACTACCGCTAGTCTCTTCTCAGTGTGTAAACCTA<br>ACAACGAGAACACAACTACCACCGGCGTACACCAATTCTTTCACAAGAGGAG<br>TATATTACCCGGACAAGGTGTTCAGATCCTCCGTACTACATTCTACACAGGAC<br>CTATTCCTACCGTTCTTCTCTAACGTAACATGGTTCCACGCGATCCATGTCTCT<br>GGAACAAACGGAACGAAGAGATTCGATAACCCGGTCTTGCCGTTCAACGATG<br>GTGTATACTTTGCGTCCACCGAGAAGTCCAACATCATCAGAGGATGGATCTTC<br>GGAACCACCTTGGATTCTAAGACCCAGTCCTTGCTAATCGTCAACAACGCGAC |

TABLE 5-continued

| Truncated S1 + S2 SARS-CoV2 Protein |
| --- |

|  | CAACGTCGTCATCAAAGTCTGCGAATTCCAGTTCTGTAACGACCCGTTCTTGG<br>GAGTCTACTACCACAAGAACAACAAGTCCTGGATGGAATCCGAGTTCAGAGT<br>CTACTCTTCCGCGAACAACTGCACCTTCGAATATGTATCTCAGCCGTTCCTAAT<br>GGACCTAGAGGGAAAGCAGGGAAACTTCAAGAACCTAAGAGAGTTCGTATTC<br>AAGAACATCGACGGATACTTCAAGATCTACTCCAAGCACACTCCGATCAACCT<br>AGTTAGAGATCTACCGCAAGGATTCTCTGCGCTAGAACCGTTAGTAGATTTGC<br>CGATCGGAATCAACATCACCAGATTCCAGACACTACTAGCGCTACACAGATCT<br>TACCTAACGCCGGGAGATTCTTCTTCTGGATGGACTGCTGGTGCTGCGGCTTA<br>TTATGTAGGATACCTACAGCCGAGAACCTTCCTATTGAAGTACAACGAAAAC<br>GGAACCATCACCGATGCCGTAGATTGTGCTCTAGATCCGCTATCCGAAACGAA<br>GTGCACCCTAAAGTCTTTCACCGTCGAGAAGGGAATCTACCAGACCTCCAACT<br>TTAGAGTACAGCCGACCGAATCCATCGTCAGATTTCCGAACATCACGAACCTA<br>TGTCCGTTCGGAGAAGTGTTCAACGCGACAAGATTTGCGTCTGTCTATGCGTG<br>GAACAGAAAAGAATCAGTAACTGCGTCGCGGACTACTCCGTCCTATACAAC<br>TCTGCCTCTTTCTCCACGTTCAAATGCTACGGTGTATCTCCGACAAAGCTAAA<br>CGATCTATGCTTCACCAACGTCTACGCGGACTCCTTCGTAATCAGAGGAGATG<br>AAGTTAGACAGATTGCGCCGGGACAAACTGGAAAGATCGCGGATTATAACTA<br>CAAGCTACCGGACGACTTCACCGGATGTGTAATTGCGTGGAATTCGAACAAC<br>CTAGACTCCAAAGTCGGAGGAAACTACAACTACTTGTACAGACTATTCAGAA<br>AGTCCAACCTAAAGCCGTTCGAGAGAGACATCTCCACCGAAATCTATCAGGC<br>TGGATCTACACCGTGTAATGGTGTCGAAGGATTCAACTGCTACTTCCCGCTAC<br>AGTCTTACGGATTTCAACCGACAAACGGTGTAGGATATCAGCCGTACAGAGT<br>CGTCGTACTATCCTTCGAACTACTACATGCTCCGGCGACAGTATGTGGACCGA<br>AAAAGTCTACCAACCTAGTCAAGAACAAATGCGTCAACTTTAACTTCAACGG<br>ACTAACCGGAACCGGTGTCCTAACCGAATCTAACAAGAAGTTTCTACCGTTCC<br>AGCAGTTCGGAAGAGATATCGCGGATACAACAGACGCTGTCAGAGATCCGCA<br>AACCTTGGAGATCCTAGATATCCACACCGTGTTCTTTCGGTGGTGTCTCTGTAAT<br>TACTCCGGGAACGAACACCTCCAATCAAGTAGCGGTACTATACCAGGACGTG<br>AACTGTACAGAAGTACCGGTAGCTATTCACGCGGATCAACTAACACCAACTT<br>GGAGAGTGTACTCCACCGGATCTAACGTATTCCAAACAAGAGCGGGATGTCT<br>AATCGGAGCGGAACACGTAAACAACTCCTACGAATGTGATATCCCGATTGGA<br>GCGGGAATCTGTGCGTCTTACCAAACACAAACAAACTCTCCGAGAAGAGCGA<br>GATCTGTAGCCTCTCAATCTATTATCGCCTACACCATGTCCTTGGGAGCCGAA<br>AATTCTGTCGCGTACTCCAACAATTCTATCGCGATCCCGACAAACTTCACCAT<br>CTCTGTAACAACCGAGATCCTACCGGTGTCTATGACCAAGACATCTGTCGATT<br>GCACCATGTACATCTGCGGAGATTCCACCGAGTGCTCCAACCTACTACTACAG<br>TACGGATCTTTCTGTACCCAGCTAAACAGAGCGTTGACTGGAATCGCTGTAGA<br>GCAGGATAAGAACACTCAAGAGGTATTCGCGCAAGTCAAGCAGATCTATAAG<br>ACTCCGCCGATCAAGGACTTCGGAGGTTTCAACTTCTCTCAGATCTTGCCGGA<br>TCCGTCCAAACCGTCTAAGAGATCTTTCATCGAGGACCTACTATTCAACAAAG<br>TCACCCTAGCTGACGCGGGATTCATCAAACAATACGGAGATTGCTTGGGAGA<br>CATTGCGGCGAGAGATCTAATTTGCGCGCAGAAGTTTAACGGATTGACAGTA<br>CTACCGCCGCTACTAACCGATGAGATGATTGCGCAGTACACGTCTGCTCTATT<br>GGCGGGAACAATTACAAGTGGATGGACATTTGGAGCCGGTGCCGCTCTACAA<br>ATTCCGTTTGCTATGCAAATGGCGTACAGATTCAACGGAATCGGAGTAACCCA<br>GAACGTCTTGTACGAGAACCAGAAGCTAATCGCGAACCAGTTCAATTCCGCG<br>ATCGGAAAGATCCAGGACAGTCTATCTTCTACTGCTTCGGCGTTGGGAAAGCT<br>ACAGGATGTAGTAAATCAAAACGCGCAGGCGCTAAACACCTTGGTCAAGCAA<br>CTATCCTCTAACTTCGGAGCGATCTCGTCCGTCCTAAACGACATCTTATCCAG<br>ACTAGATAAGGTCGAAGCGGAGGTCCAGATCGATAGACTAATCACTGGAAGA<br>TTGCAGTCCCTACAGACCTACGTAACACAGCAACTAATTAGAGCGGCGGAGA<br>TTAGAGCCTCTGCTAATCTAGCTGCGACCAAGATGTCCGAATGTGTCTTGGGA<br>CAATCCAAGAGAGTGGACTTCTGCGGAAAGGGATACCACCTAATGTCTTTCCC<br>ACAATCTGCGCCGCATGGTGTCGTATTCCTACATGTAACATATGTGCCGGCGC<br>AAGAAAAGAACTTCACAACAGCTCCAGCGATCTGCCATGATGGAAAAGCTCA<br>TTTCCCGAGAGAGGGAGTCTTTGTCTCTAACGGAACTCATTGGTTCGTCACCC<br>AGAGAAACTTCTACGAGCCGCAGATCATCACCACCGACAACACATTCGTCTC<br>GGGAAACTGCGACGTGGTCATCGGAATCGTAAACAATACCGTCTACGATCCG<br>TTGCAGCCGGAACTAGACTCCTTCAAAGAAGAGTTGGACAAGTACTTCAAGA<br>ACCACACCTCTCCGGATGTGGACTTGGGAGATATCTCTGGAATCAACGCGTCC<br>GTCGTCAACATCCAGAAAGAAATCGATAGATTGAACGAGGTCGCGAAGAACT<br>TGAACGAGTCCCTAATCGACCTACAAGAGCTAGGAAAATACGAGCAGTACAT<br>CAAGTGGCCG |
| SEQ ID NO: 17-<br>SARS-CoV2 nucleic<br>acid sequence for<br>truncated S1 + S2<br>protein<br>(aa 1-1213) +<br>K986P and V987P-<br>optimized. | ATGTTCGTGTTCCTAGTCCTACTACCGCTAGTCTCTTCTCAGTGTGTAAACCTA<br>ACAACGAGAACACAACTACCACCGGCGTACACCAATTCTTTCACAAGAGGAG<br>TATATTACCCGGACAAGGTGTTCAGATCCTCCGTACTACATTCTACACAGGAC<br>CTATTCCTACCGTTCTTCTCTAACGTAACATGGTTCCACGCGATCCCATGTCTCT<br>GGAACAAACGGAACGAAGAGATTCGATAACCCGGTCTTGCCGTTCAACGATG<br>GTGTATACTTTGCGTCCACCGAGAAGTCCAACATCATCAGAGGATGGATCTTC<br>GGAACCACCTTGGATTCTAAGACCCAGTCCTTGCTAATCGTCAACAACGCGAC<br>CAACGTCGTCATCAAAGTCTGCGAATTCCAGTTCTGTAACGACCCGTTCTTGG<br>GAGTCTACTACCACAAGAACAACAAGTCCTGGATGGAATCCGAGTTCAGAGT<br>CTACTCTTCCGCGAACAACTGCACCTTCGAATATGTATCTCAGCCGTTCCTAAT<br>GGACCTAGAGGGAAAGCAGGGAAACTTCAAGAACCTAAGAGAGTTCGTATTC<br>AAGAACATCGACGGATACTTCAAGATCTACTCCAAGCACACTCCGATCAACCT<br>AGTTAGAGATCTACCGCAAGGATTCTCTGCGCTAGAACCGTTAGTAGATTTGC<br>CGATCGGAATCAACATCACCAGATTCCAGACACTACTAGCGCTACACAGATCT |

TABLE 5-continued

Truncated S1 + S2 SARS-CoV2 Protein

```
TACCTAACGCCGGGAGATTCTTCTTCTGGATGGACTGCTGGTGCTGCGGCTTA
TTATGTAGGATACCTACAGCCGAGAACCTTCCTATTGAAGTACAACGAAAAC
GGAACCATCACCGATGCCGTAGATTGTGCTCTAGATCCGCTATCCGAAACGAA
GTGCACCCTAAAGTCTTTCACCGTCGAGAAGGGAATCTACCAGACCTCCAACT
TTAGAGTACAGCCGACCGAATCCATCGTCAGATTTCCGAACATCACGAACCTA
TGTCCGTTCGGAGAAGTGTTCAACGCGACAAGATTTGCGTCTGTCTATGCGTG
GAACAGAAAAGAATCAGTAACTGCGTCGCGGACTACTCCGTCCTATACAAC
TCTGCCTCTTTCTCCACGTTCAAATGCTACGGTGTATCTCCGACAAAGCTAAA
CGATCTATGCTTCACCAACGTCTACGCGGACTCCTTCGTAATCAGAGGAGATG
AAGTTAGACAGATTGCGCCGGGACAAACTGGAAAGATCGCGGATTATAACTA
CAAGCTACCGGACGACTTCACCGGATGTGTAATTGCGTGGAATTCGAACAAC
CTAGACTCCAAAGTCGGAGGAAACTACAACTACTTGTACAGACTATTCAGAA
AGTCCAACCTAAAGCCGTTCGAGAGAGACATCTCCACCGAAATCTATCAGGC
TGGATCTACACCGTGTAATGGTGTCGAAGGATTCAACTGCTACTTCCCGCTAC
AGTCTTACGGATTTCAACCGACAAACGGTGTAGGATATCAGCCGTACAGAGT
CGTCGTACTATCCTTCGAACTACTACATGCTCCGGCGACAGTATGTGGACCGA
AAAAGTCTACCAACCTAGTCAAGAACAAATGCGTCAACTTTAACTTCAACGG
ACTAACCGGAACCGGTGTCCTAACCGAATCTAACAAGAAGTTTCTACCGTTCC
AGCAGTTCGGAAGAGATATCGCGGATACAACAGACGCTGTCAGAGATCCGCA
AACCTTGGAGATCCTAGATATCACACCGTGTTCTTTCGGTGGTGTCTCTGTAAT
TACTCCGGGAACGAACACCTCCAATCAAGTAGCGGTACTATACCAGGACGTG
AACTGTACAGAAGTACCGGTAGCTATTCACGCGGATCAACTAACACCAACTT
GGAGAGTGTACTCCACCGGATCTAACGTATTCCAAACAAGAGCGGGATGTCT
AATCGGAGCGGAACACGTAAACAACTCCTACGAATGTGATATCCCGATTGGA
GCGGGAATCTGTGCGTCTTACCAAACACAAACAAACTCTCCGAGAAGAGCGA
GATCTGTAGCCTCTCAATCTATTATCGCCTACACCATGTCCTTGGGAGCCGAA
AATTCTGTCGCGTACTCCAACAATTCTATCGCGATCCCGACAAACTTCACCAT
CTCTGTAACAACCGAGATCCTACCGGTGTCTATGACCAAGACATCTGTCGATT
GCACCATGTACATCTGCGGAGATTCCACCGAGTGCTCCAACCTACTACTACAG
TACGGATCTTTCTGTACCCAGCTAAACAGAGCGTTGACTGGAATCGCTGTAGA
GCAGGATAAGAACACTCAAGAGGTATTCGCGCAAGTCAAGCAGATCTATAAG
ACTCCGCCGATCAAGGACTTCGGAGGTTTCAACTTCTCTCAGATCTTGCCGGA
TCCGTCCAAACCGTCTAAGAGATCTTTCATCGAGGACCTACTATTCAACAAAG
TCACCCTAGCTGACGCGGGATTCATCAAACAATACGGAGATTGCTTGGGAGA
CATTGCGGCGAGAGATCTAATTTGCGCGCAGAAGTTTAACGGATTGACAGTA
CTACCGCCGCTACTAACCGATGAGATGATTGCGCAGTACACGTCTGCTCTATT
GGCGGGAACAATTACAAGTGGATGGACATTTGGAGCCGGTGCCGCTCTACAA
ATTCCGTTTGCTATGCAAATGGCGTACAGATTCAACGGAATCGGAGTAACCCA
GAACGTCTTGTACGAGAACCAGAAGCTAATCGCGAACCAGTTCAATTCCGCG
ATCGGAAAGATCCAGGACAGTCTATCTTCTACTGCTTCGGCGTTGGGAAAGCT
ACAGGATGTAGTAAATCAAAACGCGCAGGCGCTAAACACCTTGGTCAAGCAA
CTATCCTCTAACTTCGGAGCGATCTCGTCCGTCCTAAACGACATCTTATCCAG
ACTAGATCCACCGGAAGCGGAGGTCCAGATCGATAGACTAATCACTGGAAG
ATTGCAGTCCCTACAGACCTACGTAACACAGCAACTAATTAGAGCGGCGGAG
ATTAGAGCCTCTGCTAATCTAGCTGCGACCAAGATGTCCGAATGTGTCTTGGG
ACAATCCAAGAGAGTGGACTTCTGCGGAAAGGGATACCACCTAATGTCTTTCC
CACCAATCTGCGCCGCATGGTGTCGTATTCCTACATGTAACATATGTGCCGGCG
CAAGAAAAGAACTTCACAACAGCTCCAGCGATCTGCCATGATGGAAAAGCTC
ATTTCCCGAGAGAGGGAGTCTTTGTCTCTAACGGAACTCATTGGTTCGTCACC
CAGAGAAACTTCTACGAGCCGCAGATCATCACCACCGACAACACATTCGTCTC
GGGAAACTGCGACGTGGTCATCGGAATCGTAAACAATACCGTCTACGATCCG
TTGCAGCCGGAACTAGACTCCTTCAAAGAAGAGTTGGACAAGTACTTCAAGA
ACCACACCTCTCCGGATGTGGACTTGGGAGATATCTCTGGAATCAACGCGTCC
GTCGTCAACATCCAGAAAGAAATCGATAGATTGAACGAGGTCGCGAAGAACT
TGAACGAGTCCCTAATCGACCTACAAGAGCTAGGAAAATACGAGCAGTACAT
CAAGTGGCCG
```

<hr/>

In certain aspects, the SARS-CoV2 antigen expressed by the rMVA is a modified spike(S) protein, wherein the modified S protein comprises an S1+S2 truncated protein lacking the carboxy terminus of the protein, and further comprises one or more amino acid substitutions or deletions. In some embodiments, the S1+S2 truncated protein comprises amino acids 1 to 1213 (SEQ ID NO: 18) of the SARS-CoV2 S protein with K417T, E484K, and N501Y substitutions, as provided for in Table 6, or an amino acid sequence 80%, 85%, 90%, 95%, 98%, or 99% homologous thereto. In some embodiments, the S1+S2 truncated protein comprises amino acids 1 to 1213 and two proline substitutions at amino acids 986 and 987, and amino acid substitutions K417T, E484K, and N501Y (SEQ ID NO: 19) of the SARS-CoV2 S protein, as provided for in Table 6, or an amino acid sequence 80%, 85%, 90%, 95%, 98%, or 99% homologous thereto.

In some embodiments, the S protein expressed by the rMVA is a modified spike(S) protein, wherein the modified S protein comprises an S1+S2 truncated protein lacking the carboxy terminus of the protein, and further comprises one or more substitutions selected from K417T, E484K or N501Y of SEQ ID NO: 13 or 14, or an amino acid sequence 80%, 85%, 90%, 95%, 98%, or 99% homologous thereto. In some embodiments, the mutation is K417N.

In some embodiments, the S protein expressed by the rMVA is a modified spike(S) protein, wherein the modified S protein comprises an S1+S2 truncated protein lacking the carboxy terminus of the protein, and further comprises a deletion of one or more spike protein amino acids H69, V70, or Y144, or combinations thereof, of SEQ ID NO: 13 or 14, or an amino acid sequence 80%, 85%, 90%, 95%, 98%, or 99% homologous thereto. In some embodiments, the S protein expressed by the rMVA is a modified spike(S) protein, wherein the modified S protein comprises an S1+S2 truncated protein lacking the carboxy terminus of the protein, and further comprises one or more substitutions selected from D614G, A570D, P681H, T716I, S982A, D1118H, K417N, K417T, D215G, A701V, L18F, R246I, Y453F, 1692V, M1229I, N439K, A222V, S477N, or A376T, or combinations thereof, of SEQ ID NO: 13 or 14. In some embodiments, the S protein expressed by the rMVA is a modified spike(S) protein, wherein the modified S protein comprises an S1+S2 truncated protein lacking the carboxy terminus of the protein, and further comprises a deletion at amino acids 242-244 of SEQ ID NO: 13 or 14. In some embodiments, the S protein expressed by the rMVA is a modified spike(S) protein, wherein the modified S protein comprises an S1+S2 truncated protein lacking the carboxy terminus of the protein, and further comprises the following deletions and substitutions: deletion of amino acids 69-70, deletion of amino acid Y144, amino acid substitution N501Y, amino acid substitution A570D, amino acid substitution D614G, amino acid substitution P681H, amino acid substitution T716I, amino acid substitution S982A, and amino acid substitution D1118H, of SEQ ID NO: 13 or 14. In some embodiments, the S protein expressed by the rMVA is a modified spike(S) protein, wherein the modified S protein comprises an S1+S2 truncated protein lacking the carboxy terminus of the protein, and further comprises the following deletions and substitutions: N501Y, K417N or K417T, E484K, D80A, A701V, L18F, and amino acid deletion at amino acids 242-244, of SEQ ID NO: 13 or 14. In some embodiments, the S protein expressed by the rMVA is a modified spike(S) protein, wherein the modified S protein comprises an S1+S2 truncated protein lacking the carboxy terminus of the protein, and further comprises one or more of the following substitutions: D614G; D936Y; P1263L; L5F; N439K; R211; D839Y; L54F; A879S; L18F; F1121L; R847K; T478I; A829T; Q675H; S477N; H49Y; T29I; G769V; G1124V; V1176F; K1073N; P479S; Y145 deletion; E583D; R214L; A1020V; Q1208H; D215G; H146Y; S98F; T95I; G1219C; A846V; I197V; R102I; V367F; T572I; A1078S; A831V; P1162L; T73I; A845S; H245Y; L8V; Q675R; S254F; V483A; Q677H; D138H; D80Y; D1146H; E654D; H655Y; S50L; S939F; S943P; G485R; Q613H; T76I; V341I; M153I; S221L; T859I; W258L; L242F; P681L; V289I; A520S; V1104L; L176F; T307I; T716I; L141; A1087S; P26S; P330S; P384L; R765L; S940F; T323I; V826L; E1202Q; L1203F; L611F; V615I; A262S; A522V; A688V; A706V; A892S; E554D; Q836H; T1027I; T221; A222V; A27S; A626V; K1191N; M731I; P26L; S1147L; S255F; V308L; D80A; I670L; P251L; P631S; A344S; A771S; A879T; D1084Y; D253G; H1101Y; L1200F; Q14H; Q239K; A623V; D215Y; E1150D; G476S; K77M; M177I; P812S; S704L; T51I; T547I; T791I; V1122L; Y145H; D574Y; G142D; G181V; I834T; N370S; P812L; S12F; T791P; V90F; W152L; A292S; A570V; A647S; A845V; D1163Y; G181R; L84I; L938F; P1143L; P809S; R78M; T1160I; V1133F; V213L; V615F; A831V; D839Y; D839N; D839E; S943P; or V622F; and combinations thereof, of SEQ ID NO: 13 or 14.

In certain embodiments, an additional nucleic acid sequence encoding a tag may be included in the nucleic acid sequence to be inserted into the rMVA, so that the tag is expressed at the C-terminus of the protein. In some embodiments, the nucleic acid sequence (GAGCCAGAGGCT) (SEQ ID NO: 4) encodes for the high affinity C-tag having the amino acid sequence EPEA (SEQ ID NO: 5).

TABLE 6

| Truncated S1 + S2 SARS-CoV2 Protein with | |
|---|---|
| SEQ ID NO: 18-SARS-CoV2 truncated S1 + S2 protein (aa 1-1213). K417T, E484K, and N501Y | MFVFLVLLPLVSSQCVNLTTRTQLPPAYTNSFTRGVYYPDKVFRSSVLHSTQDLFL PFFSNVTWFHAIHVSGTNGTKRFDNPVLPFNDGVYFASTEKSNIIRGWIFGTTLDS KTQSLLIVNNATNVVIKVCEFQFCNDPFLGVYYHKNNKSWMESEFRVYSSANNC TFEYVSQPFLMDLEGKQGNFKNLREFVFKNIDGYFKIYSKHTPINLVRDLPQGFSA LEPLVDLPIGINITRFQTLLALHRSYLTPGDSSSGWTAGAAAYYVGYLQPRTFLLK YNENGTITDAVDCALDPLSETKCTLKSFTVEKGIYQTSNFRVQPTESIVRFPNITNL CPFGEVFNATRFASVYAWNRKRISNCVADYSVLYNSASFSTFKCYGVSPTKLNDL CFTNVYADSFVIRGDEVRQIAPGQTGTIADYNYKLPDDFTGCVIAWNSNNLDSKV GGNYNYLYRLFRKSNLKPFERDISTEIYQAGSTPCNGVKGFNCYFPLQSYGFQPT YGVGYQPYRVVVLSFELLHAPATVCGPKKSTNLVKNKCVNFNFNGLTGTGVLTE SNKKFLPFQQFGRDIADTTDAVRDPQTLEILDITPCSFGGVSVITPGTNTSNQVAVL YQDVNCTEVPVAIHADQLTPTWRVYSTGSNVFQTRAGCLIGAEHVNNSYECDIPI GAGICASYQTQTNSPRRARSVASQSIIAYTMSLGAENSVAYSNNSIAIPTNFTISVT TEILPVSMTKTSVDCTMYICGDSTECSNLLLQYGSFCTQLNRALTGIAVEQDKNT QEVFAQVKQIYKTPPIKDFGGFNFSQILPDPSKPSKRSFIEDLLFNKVTLADAGFIK QYGDCLGDIAARDLICAQKFNGLTVLPPLLTDEMIAQYTSALLAGTITSGWTFGA GAALQIPFAMQMAYRFNGIGVTQNVLYENQKLIANQFNSAIGKIQDSLSSTASAL GKLQDVVNQNAQALNTLVKQLSSNFGAISSVLNDILSRLDKVEAEVQIDRLITGR LQSLQTYVTQQLIRAAEIRASANLAATKMSECVLGQSKRVD̅F̅CGKGYHLMSFPQ SAPHGVVFLHVTYVPAQEKNFTTAPAICHDGKAHFPREGVFVSNGTHWFVTQRN FYEPQIITTDNTFVSGNCDVVIGIVNNTVYDPLQPELDSFKEELDKYFKNHTSPDV DLGDISGINASVVNIQKEIDRLNEVAKNLNESLIDLQELGKYEQYIKWP |
| SEQ ID NO: 19-SARS-CoV2 truncated S1 + S2 protein + K986P and V987P (aa 1-1213) + K417T, E484K, and N501Y. | MFVFLVLLPLVSSQCVNLTTRTQLPPAYTNSFTRGVYYPDKVFRSSVLHSTQDLFL PFFSNVTWFHAIHVSGTNGTKRFDNPVLPFNDGVYFASTEKSNIIRGWIFGTTLDS KTQSLLIVNNATNVVIKVCEFQFCNDPFLGVYYHKNNKSWMESEFRVYSSANNC TFEYVSQPFLMDLEGKQGNFKNLREFVFKNIDGYFKIYSKHTPINLVRDLPQGFSA LEPLVDLPIGINITRFQTLLALHRSYLTPGDSSSGWTAGAAAYYVGYLQPRTFLLK YNENGTITDAVDCALDPLSETKCTLKSFTVEKGIYQTSNFRVQPTESIVRFPNITNL CPFGEVFNATRFASVYAWNRKRISNCVADYSVLYNSASFSTFKCYGVSPTKLNDL CFTNVYADSFVIRGDEVRQIAPGQTGTIADYNYKLPDDFTGCVIAWNSNNLDSKV GGNYNYLYRLFRKSNLKPFERDISTEIYQAGSTPCNGVKGFNCYFPLQSYGFQPT YGVGYQPYRVVVLSFELLHAPATVCGPKKSTNLVKNKCVNFNFNGLTGTGVLTE SNKKFLPFQQFGRDIADTTDAVRDPQTLEILDITPCSFGGVSVITPGTNTSNQVAVL YQDVNCTEVPVAIHADQLTPTWRVYSTGSNVFQTRAGCLIGAEHVNNSYECDIPI GAGICASYQTQTNSPRRARSVASQSIIAYTMSLGAENSVAYSNNSIAIPTNFTISVT |

TABLE 6-continued

Truncated S1 + S2 SARS-CoV2 Protein with

```
TEILPVSMTKTSVDCTMYICGDSTECSNLLLQYGSFCTQLNRALTGIAVEQDKNT
QEVFAQVKQIYKTPPIKDFGGFNFSQILPDPSKPSKRSFIEDLLFNKVTLADAGFIK
QYGDCLGDIAARDLICAQKFNGLTVLPPLLTDEMIAQYTSALLAGTITSGWTFGA
GAALQIPFAMQMAYRFNGIGVTQNVLYENQKLIANQFNSAIGKIQDSLSSTASAL
GKLQDVVNQNAQALNTLVKQLSSNFGAISSVLNDILSRLDPPEAEVQIDRLITGRL
QSLQTYVTQQLIRAAEIRASANLAATKMSECVLGQSKRVDFCGKGYHLMSFPQS
APHGVVFLHVTYVPAQEKNFTTAPAICHDGKAHFPREGVFVSNGTHWFVTQRNF
YEPQIITTDNTFVSGNCDVVIGIVNNTVYDPLQPELDSFKEELDKYFKNHTSPDVD
LGDISGINASVVNIQKEIDRLNEVAKNLNESLIDLQELGKYEQYIKWP
```

In certain aspects, the SARS-CoV2 antigen is a linear epitope of the S protein. In a particular embodiment, the linear epitope of the S protein is the receptor biding domain (RBD) of the SARS-CoV2 S protein. In some embodiments, the linear S epitope comprises amino acids 327 to 524 of the S protein (SEQ ID NO: 20), provided in Table 7 below, or an amino acid sequence 80%, 85%, 90%, 95%, 95%, or 99% homologous thereto. In some embodiments, the rMVA comprises SEQ ID NO: 22, which provides a nucleic acid sequence encoding the linear S epitope of amino acids 327 to 524 of the S Protein derived from the native sequence of SARS-CoV2, or a nucleic acid sequence 80%, 85%, 90%, 95%, 95%, or 99% homologous thereto. In some embodiments, the rMVA comprises SEQ ID NO: 24, which provides an optimized nucleic acid sequence encoding the linear S epitope of amino acids 327 to 524 of the S Protein, or a nucleic acid sequence 80%, 85%, 90%, 95%, 95%, or 99% homologous thereto. In some embodiments, the linear S epitope comprises amino acids 331 to 524 of the S protein (SEQ ID NO: 21), provided in Table 7 below, or an amino acid sequence 80%, 85%, 90%, 95%, 95%, or 99% homologous thereto. In some embodiments, the rMVA comprises SEQ ID NO: 23, which provides a nucleic acid sequence encoding the linear S epitope of amino acids 331 to 524 of the S Protein derived from the native sequence of SARS-CoV2, or a nucleic acid sequence 80%, 85%, 90%, 95%, 95%, or 99% homologous thereto. In some embodiments, the rMVA comprises SEQ ID NO: 24, which provides an optimized nucleic acid sequence encoding the linear S epitope of amino acids 331 to 524 of the S Protein, or a nucleic acid sequence 80%, 85%, 90%, 95%, 95%, or 99% homologous thereto. In some embodiments, the linear S epitope comprises amino acids 504 to 524 (SEQ ID NO: 26) of the RBD region of the SARS-CoV2 S protein, or an amino acid sequence 80%, 85%, 90%, 95%, 95%, or 99% homologous thereto. In some embodiments, the rMVA comprises SEQ ID NO: 27, which provides a nucleic acid sequence encoding the linear S epitope of amino acids 504 to 524 derived from the native sequence of SARS-CoV2, or a nucleic acid sequence 80%, 85%, 90%, 95%, 95%, or 99% homologous thereto. In some embodiments, the rMVA comprises SEQ ID NO: 28, which provides an optimized nucleic acid sequence encoding the linear S epitope of amino acids 504 to 524 of the RBD region of the SARS-CoV2 S protein, or a nucleic acid sequence 80%, 85%, 90%, 95%, 95%, or 99% homologous thereto. In some embodiments, the linear S epitope comprises amino acids 473 to 490 (SEQ ID NO: 29) of the RBD region of the SARS-CoV2 S protein, or an amino acid sequence 80%, 85%, 90%, 95%, 95%, or 99% homologous thereto. In some embodiments, the rMVA encodes SEQ ID NO:30, which provides a nucleic acid sequence encoding the linear S epitope of amino acids 473 to 490 derived from the native sequence of SARS-CoV2, or an amino acid sequence 80%, 85%, 90%, 95%, 95%, or 99% homologous thereto. In some embodiments, the rMVA comprises SEQ ID NO: 31, which provides an optimized nucleic acid sequence encoding the linear S epitope of amino acids 473 to 490 of the RBD region of the SARS-CoV2 S protein, or a nucleic acid sequence 80%, 85%, 90%, 95%, 95%, or 99% homologous thereto.

In some embodiments, the linear epitope of the S protein is a receptor biding domain (RBD) consensus sequence.

In certain embodiments, an additional nucleic acid sequence encoding a tag may be included in the nucleic acid sequence to be inserted into the rMVA, so that the tag is expressed at the C-terminus of the protein. In some embodiments, the nucleic acid sequence (GAGCCAGAGGCT) (SEQ ID NO: 4) encodes for the high affinity C-tag having the amino acid sequence EPEA (SEQ ID NO: 5).

In some embodiments, the S protein RBD linear epitope includes the amino acid methionine at the NH-terminus encoded by the nucleic acid sequence ATG.

TABLE 7

Exemplary SARS-CoV2 Linear S Protein RBD Epitopes

| | |
|---|---|
| SEQ ID NO: 20-<br>SARS-CoV2 S<br>protein RBD linear<br>epitope (aa 327-524) | VRFPNITNLCPFGEVFNATRFASVYAWNRKRISNCVADYSVLYNSASFSTFKCYG<br>VSPTKLNDLCFTNVYADSFVIRGDEVRQIAPGQTGKIADYNYKLPDDFTGCVIA<br>WNSNNLDSKVGGNYNYLYRLFRKSNLKPFERDISTEIYQAGSTPCNGVEGFNCY<br>FPLQSYGFQPTNGVGYQPYRVVVLSFELLHAPATV |
| SEQ ID NO: 21-<br>SARS-CoV2 S<br>protein RBD linear<br>epitope (aa 331-524) | NITNLCPFGEVFNATRFASVYAWNRKRISNCVADYSVLYNSASFSTFKCYGVSPT<br>KLNDLCFTNVYADSFVIRGDEVRQIAPGQTGKIADYNYKLPDDFTGCVIAWNSN<br>NLDSKVGGNYNYLYRLFRKSNLKPFERDISTEIYQAGSTPCNGVEGFNCYFPLQS<br>YGFQPTNGVGYQPYRVVVLSFELLHAPATV |
| SEQ ID NO: 22-<br>SARS-CoV2 nucleic<br>acid encoding S<br>protein RBD linear<br>epitope (aa 327-524) | GTTAGATTTCCTAATATTACAAACTTGTGCCCTTTTGGTGAAGTTTTTAACGC<br>CACCAGATTTGCATCTGTTTATGCTTGGAACAGGAAGAGAATCAGCAACTGT<br>GTTGCTGATTATTCTGTCCTATATAATTCCGCATCATTTTCCACTTTTAAGTGT<br>TATGGAGTGTCTCCTACTAAATTAAATGATCTCTGCTTTACTAATGTCTATGC<br>AGATTCATTTGTAATTAGAGGTGATGAAGTCAGACAAATCGCTCCAGGGCAA<br>ACTGGAAAGATTGCTGATTATAATTATAAATTACCAGATGATTTTACAGGCT |

TABLE 7-continued

Exemplary SARS-CoV2 Linear S Protein RBD Epitopes

| | GCGTTATAGCTTGGAATTCTAACAATCTTGATTCTAAGGTTGGTGGTAATTAT |
| | AATTACCTGTATAGATTGTTTAGGAAGTCTAATCTCAAACCTTTTGAGAGAG |
| | ATATTTCAACTGAAATCTATCAGGCCGGTAGCACACCTTGTAATGGTGTTGA |
| | AGGTTTTAATTGTTACTTTCCTTTACAATCATATGGTTTCCAACCCACTAATG |
| | GTGTTGGTTACCAACCATACAGAGTAGTAGTACTTTCTTTTGAACTTCTACAT |
| | GCACCAGCAACTGTTTGTGGACCTAAAAAGTCTACTAATTTGGTTAAAAACA |
| | AATGTGTCAAT |

| SEQ ID NO: 23- | AATATTACAAACTTGTGCCCTTTTGGTGAAGTTTTTAACGCCACCAGATTTGC |
| SARS-CoV2 nucleic | ATCTGTTTATGCTTGGAACAGGAAGAGAATCAGCAACTGTGTTGCTGATTAT |
| acid encoding S | TCTGTCCTATATAATTCCGCATCATTTTCCACTTTTAAGTGTTATGGAGTGTCT |
| protein RBD linear | CCTACTAAATTAAATGATCTCTGCTTTACTAATGTCTATGCAGATTCATTTGT |
| epitope (aa 331-524) | AATTAGAGGTGATGAAGTCAGACAAATCGCTCCAGGGCAAACTGGAAAGAT |
| | TGCTGATTATAATTATAAATTACCAGATGATTTTACAGGCTGCGTTATAGCTT |
| | GGAATTCTAACAATCTTGATTCTAAGGTTGGTGGTAATTATAATTACCTGTAT |
| | AGATTGTTTAGGAAGTCTAATCTCAAACCTTTTGAGAGAGATATTTCAACTG |
| | AAATCTATCAGGCCGGTAGCACACCTTGTAATGGTGTTGAAGGTTTTAATTG |
| | TTACTTTCCTTTACAATCATATGGTTTCCAACCCACTAATGGTGTTGGTTACC |
| | AACCATACAGAGTAGTAGTACTTTCTTTTGAACTTCTACATGCACCAGCAACT |
| | GTTTGTGGACCTAAAAAGTCTACTAATTTGGTTAAAAACAAATGTGTCAAT |

| SEQ ID NO: 24- | GTCAGATTTCCGAACATCACGAACCTATGTCCGTTCGGAGAAGTGTTCAACG |
| SARS-CoV2 nucleic | CGACAAGATTTGCGTCTGTCTATGCGTGGAACAGAAAAAGAATCAGTAACTG |
| acid encoding S | CGTCGCGGACTACTCCGTCCTATACAACTCTGCCTCTTTCTCCACGTTCAAAT |
| protein RBD linear | GCTACGGTGTATCTCCGACAAAGCTAAACGATCTATGCTTCACCAACGTCTA |
| epitope (aa 327-524)- | CGCGGACTCCTTCGTAATCAGAGGAGATGAAGTTAGACAGATTGCGCCGGG |
| optimized | ACAAACTGGAAAGATCGCGGATTATAACTACAAGCTACCGGACGACTTCACC |
| | GGATGTGTAATTGCGTGGAATTCGAACAACCTAGACTCCAAAGTCGGAGGA |
| | AACTACAACTACTTGTACAGACTATTCAGAAAGTCCAACCTAAAGCCGTTCG |
| | AGAGAGACATCTCCACCGAAATCTATCAGGCTGGATCTACACCGTGTAATGG |
| | TGTCGAAGGATTCAACTGCTACTTCCCGCTACAGTCTTACGGATTTCAACCGA |
| | CAAACGGTGTAGGATATCAGCCGTACAGAGTCGTCGTACTATCCTTCGAACT |
| | ACTACATGCTCCGGCGACAGTA |

| SEQ ID NO: 25- | AACATCACGAACCTATGTCCGTTCGGAGAAGTGTTCAACGCGACAAGATTTG |
| SARS-CoV2 nucleic | CGTCTGTCTATGCGTGGAACAGAAAAAGAATCAGTAACTGCGTCGCGGACTA |
| acid encoding S | CTCCGTCCTATACAACTCTGCCTCTTTCTCCACGTTCAAATGCTACGGTGTAT |
| protein RBD linear | CTCCGACAAAGCTAAACGATCTATGCTTCACCAACGTCTACGCGGACTCCTT |
| epitope (aa 331-524)- | CGTAATCAGAGGAGATGAAGTTAGACAGATTGCGCCGGGACAAACTGGAAA |
| optimized | GATCGCGGATTATAACTACAAGCTACCGGACGACTTCACCGGATGTGTAATT |
| | GCGTGGAATTCGAACAACCTAGACTCCAAAGTCGGAGGAAACTACAACTAC |
| | TTGTACAGACTATTCAGAAAGTCCAACCTAAAGCCGTTCGAGAGAGACATCT |
| | CCACCGAAATCTATCAGGCTGGATCTACACCGTGTAATGGTGTCGAAGGATT |
| | CAACTGCTACTTCCCGCTACAGTCTTACGGATTTCAACCGACAAACGGTGTA |
| | GGATATCAGCCGTACAGAGTCGTCGTACTATCCTTCGAACTACTACATGCTC |
| | CGGCGACAGTA |

| SEQ ID NO: 26- | YQPYRVVVLSFELLHAPATV |
| SARS-CoV2 S | |
| protein RBD linear | |
| epitope (aa 504 to | |
| 524) | |

| SEQ ID NO: 27- | TACCAACCATACAGAGTAGTAGTACTTTCTTTTGAACTTCTACATGCACCAGC |
| SARS-CoV2 nucleic | AACTGTT |
| acid encoding S | |
| protein RBD linear | |
| epitope (aa 504 to | |
| 524) | |

| SEQ ID NO: 28- | TATCAGCCGTACAGAGTCGTCGTACTATCCTTCGAACTACTACATGCTCCGGC |
| SARS-CoV2 nucleic | GACAGTA |
| acid encoding S | |
| protein RBD linear | |
| epitope (aa 504 to | |
| 524)-optimized | |

| SEQ ID NO: 29- | YQAGSTPCNGVEGFNCYF |
| SARS-CoV2 S | |
| protein RBD linear | |
| epitope (aa 473 to | |
| 490) | |

TABLE 7-continued

| Exemplary SARS-CoV2 Linear S Protein RBD Epitopes |
|---|

| | |
|---|---|
| SEQ ID NO: 30-<br>SARS-CoV2 nucleic<br>acid encoding S<br>protein RBD linear<br>epitope (aa 473 to<br>490) | TATCAGGCCGGTAGCACACCTTGTAATGGTGTTGAAGGTTTTAATTGTTACTT<br>T |
| SEQ ID NO: 31-<br>SARS-CoV2 nucleic<br>acid encoding S<br>protein RBD linear<br>epitope (aa 473 to<br>490)-optimized | TATCAGGCTGGATCTACACCGTGTAATGGTGTCGAAGGATTCAACTGCTACT<br>TC |

In some embodiments, the linear epitope of the S protein is the receptor biding domain (RBD) of the SARS-CoV2 S protein comprising one or more mutations or deletions. In some embodiments, the linear S epitope comprises amino acids 327 to 524 of the S protein (SEQ ID NO: 32), provided in Table 8 below, or an amino acid sequence 80%, 85%, 90%, 95%, 95%, or 99% homologous thereto. In some embodiments, the linear S epitope comprises amino acids expressed at the C-terminus of the protein. In some embodiments, the nucleic acid sequence (GAGCCAGAGGCT) (SEQ ID NO: 4) encodes for the high affinity C-tag having the amino acid sequence EPEA (SEQ ID NO: 5).

In some embodiments, the S protein RBD linear epitope includes the amino acid methionine at the NH-terminus encoded by the nucleic acid sequence ATG.

TABLE 8

| Exemplary SARS-CoV2 Linear S Protein RBD Epitopes with K417T, E484K, and N501Y mutations | |
|---|---|
| SEQ ID NO: 32-<br>SARS-CoV2 S<br>protein RBD linear<br>epitope (aa 327-524)<br>comprising K417T,<br>E484K, and N501Y | VRFPNITNLCPFGEVFNATRFASVYAWNRKRISNCVADYSVLYNSASFSTFKCYG<br>VSPTKLNDLCFTNVYADSFVIRGDEVRQIAPGQTGTIADYNYKLPDDFTGCVIA<br>WNSNNLDSKVGGNYNYLYRLFRKSNLKPFERDISTEIYQAGSTPCNGVKGFNCY<br>FPLQSYGFQPTYGVGYQPYRVVVLSFELLHAPATV |
| SEQ ID NO: 33-<br>SARS-CoV2 S<br>protein RBD linear<br>epitope (aa 331-524)<br>comprising K417T,<br>E484K, and N501Y | NITNLCPFGEVFNATRFASVYAWNRKRISNCVADYSVLYNSASFSTFKCYGVSPT<br>KLNDLCFTNVYADSFVIRGDEVRQIAPGQTGTIADYNYKLPDDFTGCVIAWNSN<br>NLDSKVGGNYNYLYRLFRKSNLKPFERDISTEIYQAGSTPCNGVKGFNCYFPLQS<br>YGFQPTYGVGYQPYRVVVLSFELLHAPATV |

331 to 524 of the S protein (SEQ ID NO: 33), provided in Table 8 below, or an amino acid sequence 80%, 85%, 90%, 95%, 95%, or 99% homologous thereto.

In some embodiments, the receptor biding domain (RBD) of the SARS-CoV2 S protein comprises one or more mutations or deletions selected from K417T, K417N, E484K, or N501Y substitutions.

In some embodiments, the S protein expressed by the rMVA is the receptor biding domain (RBD) of the SARS-CoV2 S protein comprising one or more substitutions selected from K417N, K417T, Y453F, N439K, S477N, or A376T, or combinations thereof, of SEQ ID NO: 20 or 21, or an amino acid sequence 80%, 85%, 90%, 95%, 95%, or 99% homologous thereto. In some embodiments, the S protein expressed by the rMVA is the receptor biding domain (RBD) of the SARS-CoV2 S protein comprising one or more of the following substitutions: N439K; T478I; S477N; P479S; V367F; V341I; P330S; P384L; A522V; and combinations thereof, of SEQ ID NO: 20 or 21, or an amino acid sequence 80%, 85%, 90%, 95%, 95%, or 99% homologous thereto.

In certain embodiments, an additional nucleic acid sequence encoding a tag may be included in the nucleic acid sequence to be inserted into the rMVA, so that the tag is In certain aspects, two or more linear epitopes of the S protein are encoded by the rMVA, wherein the two or more linear epitopes are separated by a spacer, for example a GPGPG spacer polypeptide. In some embodiments, the sequence inserted into the rMVA viral vector encodes linear epitopes separated by a spacer, wherein the linear epitopes include different S protein RBD peptides, for example (RBD Seq. 1-spacer-RBD Seq. 2), wherein RBD Seq. 1 is a first S protein RBD peptide, and RBD Seq. 2 is a second S protein RBD peptide. In some embodiments, the sequence inserted into the rMVA viral vector encodes a tandem repeat sequence, for example (RBD-spacer-RBD-spacer) x or (RBD Seq. 1-spacer-RBD Seq. 2-spacer) x, wherein x=2, 3, 4, 5, 6, 7, 8, 9, 10. In some embodiments, the RBD peptides are selected from one or more peptides derived from amino acids 331 to 524 of the SARS-CoV2 S protein. In some embodiments, the linear epitopes encoded by the rMVA are selected from the amino acids 504 to 524 and amino acids 473 to 490 of the SARS-CoV2 S protein. In some embodiments, the linear epitopes encoded by the rMVA are the amino acids 504 to 524 and amino acids 473 to 490 of the SARS-CoV2 S protein. In some embodiments, the sequence inserted into the MVA viral vector encodes a S protein RBD peptide containing tandem repeat sequence ((aa504-524)- spacer-(aa473-490)-spacer) x, wherein x=2, 3, 4, 5, 6, 7, 8, 9, 10. In some embodiments, x=3-7. In some embodiments, x=5. In some embodiments, the sequence inserted into the MVA viral vector encodes a S protein RBD peptide containing tandem repeat sequence ((aa504-524)-GPGPG-(aa473-490)-GPGPG) x, wherein x=2, 3, 4, 5, 6, 7, 8, 9, 10. In some embodiments, x=3-7. In some embodiments, x=5.

In some embodiments, the MVA comprises a nucleic acid sequence encoding the amino acid sequence of SEQ ID NO: 34 provided in Table 9 below, which provides an exemplary amino acid sequence encoding S protein RBD peptides in a tandem repeat sequence ((aa504-524)-GPGPG-(aa473-490)-GPGPG)x. In some embodiment, the MVA comprises a nucleic acid sequence of SEQ ID NO: 35, which provides a nucleic acid sequence which encodes the tandem repeat sequence ((aa504-524)-GPGPG-(aa473-490)-GPGPG) x derived from the native SARS-CoV2 genomic sequence encoding amino acids 504-524 and amino acids 473-490, and including a nucleic acid sequence encoding the linker amino acid sequence GPGPG. In some embodiments, the MVA comprises a nucleic acid sequence encoding the amino acid sequence of SEQ ID NO: 36, which provides an amino acid sequence of S protein RBD peptides in a tandem repeat sequence ((aa504-524)-GPGPG-(aa473-490)-GPGPG) x, wherein in x=5, and SEQ ID NO: 37 provides a nucleic acid sequence encoding same which has been optimized. In some embodiments, the MVA comprises a nucleic acid sequence encoding the amino acid sequence of SEQ ID NO: 38 provided in Table 9 below, which provides an exemplary amino acid sequence encoding S protein RBD peptides in a tandem repeat sequence ((aa504-524)-GPGPG-(aa473-490)-GPGPG) x, and further comprising the substitution E484K. In some embodiments, the MVA comprises a nucleic acid sequence encoding the amino acid sequence of SEQ ID NO: 39, which provides an amino acid sequence of S protein RBD peptides in a tandem repeat sequence ((aa504-524)-GPGPG-(aa473-490)-GPGPG) x, wherein in x=5, and further comprising the substitution E484K. In some embodiments, the S protein RBD tandem repeats include the amino acid methionine at the NH-terminus encoded by the nucleic acid sequence ATG.

TABLE 9

| SARS-CoV2SARS-CoV2 S Protein RBD Tandem Repeat Sequences | |
|---|---|
| SEQ ID NO: 34-amino acid sequence of SARS-CoV2 S Protein RBD Tandem Repeat Sequence. | (YQPYRVVVLSFELLHAPATVGPGPGYQAGSTPCNGVEGFNCYFGPGPG)x, wherein x = 2, 3, 4, 5, 6, 7, 8, 9, 10, or more than 10. |
| SEQ ID NO: 35-nucleic acid sequence of SARS-CoV2 S Protein RBD Tandem Repeat Sequence. | (TACCAACCATACAGAGTAGTAGTACTTTCTTTTGAACTTCTACATGCACCAGCAACTG TTGGTCCTGGACCCGGTTATCAGGCCGGTAGCACACCTTGTAATGGTGTTGAAGGTTTT AATTGTTACTTTGGTCCTGGACCCGGT)x, wherein x = 2, 3, 4, 5, 6, 7, 8, 9, 10, or more than 10. |
| SEQ ID NO: 36-amino acid sequence of SARS-CoV2 S Protein RBD Tandem Repeat Sequence, x = 5. | YQPYRVVVLSFELLHAPATVGPGPGYQAGSTPCNGVEGFNCYFGPGPGYQPYRVVVLSFE LLHAPATVGPGPGYQAGSTPCNGVEGFNCYFGPGPGYQPYRVVVLSFELLHAPATVGPGP GYQAGSTPCNGVEGFNCYFGPGPGYQPYRVVVLSFELLHAPATVGPGPGYQAGSTPCNG VEGFNCYFGPGPGYQPYRVVVLSFELLHAPATVGPGPGYQAGSTPCNGVEGFNCYFGPGP G |
| SEQ ID NO: 37-nucleic acid sequence of SARS-CoV2 S Protein RBD Tandem Repeat Sequence, x = 5; optimized | TATCAGCCGTACAGAGTCGTCGTACTATCCTTCGAACTACTACATGCTCCGGCGACAG TAGGTCCTGGACCCGGTTATCAGGCTGGATCTACACCGTGTAATGGTGTCGAAGGATT CAACTGCTACTTCGGTCCTGGACCCGGTTATCAGCCGTACAGAGTCGTCGTACTATCCT TCGAACTACTACATGCTCCGGCGACAGTAGGTCCTGGACCCGGTTATCAGGCTGGATC TACACCGTGTAATGGTGTCGAAGGATTCAACTGCTACTTCGGTCCTGGACCCGGTTAT CAGCCGTACAGAGTCGTCGTACTATCCTTCGAACTACTACATGCTCCGGCGACAGTAG GTCCTGGACCCGGTTATCAGGCTGGATCTACACCGTGTAATGGTGTCGAAGGATTCAA CTGCTACTTCGGTCCTGGACCCGGTTATCAGCCGTACAGAGTCGTCGTACTATCCTTCG AACTACTACATGCTCCGGCGACAGTAGGTCCTGGACCCGGTTATCAGGCTGGATCTAC ACCGTGTAATGGTGTCGAAGGATTCAACTGCTACTTCGGTCCTGGACCCGGTTATCAG CCGTACAGAGTCGTCGTACTATCCTTCGAACTACTACATGCTCCGGCGACAGTAGGTC CTGGACCCGGTTATCAGGCTGGATCTACACCGTGTAATGGTGTCGAAGGATTCAACTG CTACTTCGGTCCTGGACCCGGT |
| SEQ ID NO: 38-amino acid sequence of SARS-CoV2 S Protein RBD | (YQPYRVVVLSFELLHAPATVGPGPGYQAGSTPCNGVKGFNCYFGPGPG)x, wherein x = 2, 3, 4, 5, 6, 7, 8, 9, 10, or more than 10. |

TABLE 9-continued

| SARS-CoV2SARS-CoV2 S Protein RBD Tandem Repeat Sequences |
|---|

| Tandem Repeat Sequence (E484K) | |
|---|---|
| SEQ ID NO: 39-amino acid sequence of SARS-CoV2 S Protein RBD Tandem Repeat Sequence, x = 5 (E484K) | YQPYRVVVLSFELLHAPATVGPGPGYQAGSTPCNGVKGFNCYFGPGPGYQPYRVVVLSFE LLHAPATVGPGPGYQAGSTPCNGVKGFNCYFGPGPGYQPYRVVVLSFELLHAPATVGPGP GYQAGSTPCNGVKGFNCYFGPGPGYQPYRVVVLSFELLHAPATVGPGPGYQAGSTPCNG VKGFNCYFGPGPGYQPYRVVVLSFELLHAPATVGPGPGYQAGSTPCNGVKGFNCYFGPGP G |

Envelope (E) Protein

The E protein is the smallest of the major structural proteins. During the replication cycle of, for example SARS, E is abundantly expressed inside the infected cell, but only a small portion is incorporated into the virion envelope. Venkatagopalan et al., Coronavirus envelope (E) protein remains at the site of assembly. Virology. 2015; 478:75-85. The majority of the protein in SARS infections, for example, is localized at the site of intracellular trafficking, viz. the ER, Golgi, and ERGIC, where it participates in CoV assembly and budding. Nieto-Torres et al., Subcellular location and topology of severe acute respiratory syndrome coronavirus envelope protein. Virology. 2011; 415 (2): 69-82.

The amino acid sequence of the SARS-CoV2 envelope (E) protein is 75 amino acids in length. The E protein has example, as provided in SEQ ID NO: 42, or a nucleic acid 80%, 85%, 90%, 95%, 98%, or 99% homologous thereto.

In some embodiments, the nucleic acid inserted into the MVA viral vector encodes an amino acid of SEQ ID NO: 40, having one or more substitutions selected from S68F, L73F, P71L, S55F, R69I, T9I, V24M, D72H, T30I, S68C, V75L, V58F, V75F, or L21F, and combinations thereof, or an amino acid 80%, 85%, 90%, 95%, 98%, or 99% homologous thereto.

In certain embodiments, an additional nucleic acid sequence encoding a tag may be included in the nucleic acid sequence to be inserted into the rMVA, so that the tag is expressed at the C-terminus of the protein. In some embodiments, the nucleic acid sequence (GAGCCAGAGGCT) (SEQ ID NO: 4) encodes for the high affinity C-tag having the amino acid sequence EPEA (SEQ ID NO: 5).

TABLE 10

| SARS-CoV2 Envelope (E) Protein | |
|---|---|
| SEQ ID NO: 40-SARS-CoV2 E protein amino acid sequence | MYSFVSEETGTLIVNSVLLFLAFVVFLLVTLAILTALRLCAYCCNIVNVSLVKPSF YVYSRVKNLNSSRVPDLLV |
| SEQ ID NO: 41-SARS-CoV2 nucleic acid sequence for E protein | ATGTACTCATTCGTTTCGGAAGAGACAGGTACGTTAATAGTTAATAGCGTAC TTCTTTTTCTTGCTTTCGTGGTATTCTTGCTAGTTACACTAGCCATCCTTACTG CGCTTCGATTGTGTGCGTACTGCTGCAATATTGTTAACGTGAGTCTTGTAAAA CCTTCTTTTTACGTTTACTCTCGTGTTAAAAATCTGAATTCTTCTAGAGTTCCT GATCTTCTGGTC |
| SEQ ID NO: 42-SARS-CoV2 nucleic acid sequence for E protein-optimized | ATGTACTCCTTCGTGTCCGAAGAAACCGGAACCTTGATCGTCAACTCCGTCCT ACTATTCCTAGCGTTCGTCGTGTTCCTACTAGTAACCCTAGCTATCCTAACCG CGCTAAGACTATGTGCGTACTGCTGCAACATCGTCAACGTGTCCCTAGTGAA GCCGTCCTTCTACGTCTACTCCAGAGTCAAGAACCTAAACTCCTCTAGAGTCC CGGACCTACTAGTT | been reported at GenBank Accession number QHD43418, and is reproduced in Table 10 (SEQ ID NO: 40) along with its corresponding nucleic acid sequence (SEQ ID NO: 41), which has been reported at GenBank Accession No. MN908947.3, and is located at nucleic acids 26245 to 26472 of the SARS-CoV2 genome. In some embodiments, the nucleic acid inserted into the MVA viral vector encodes an amino acid of SEQ ID NO: 40, or an amino acid 80%, 85%, 90%, 95%, 98%, or 99% homologous thereto. In some embodiments, the nucleic acid inserted into the MVA viral vector is SEQ ID NO: 41, or a nucleic acid 80%, 85%, 90%, 95%, 98%, or 99% homologous thereto. In some embodiments, the nucleic acid sequence encoding the E protein inserted into the MVA viral vector has been optimized, for Membrane (M) Protein The coronavirus M protein is the most abundant structural protein and defines the shape of the viral envelope. Neuman et al., A structural analysis of M protein in coronavirus assembly and morphology. J Struct Biol. 2011; 174 (1): 11-22. It is also regarded as the central organizer of CoV assembly, interacting with all other major coronaviral structural proteins. Masters PS. The molecular biology of coronaviruses. Adv Virus Res. 2006; 66:193-292. Homotypic interactions between, for example, the SARS M proteins are the major driving force behind virion envelope formation but, alone, is not sufficient for virion formation. Neuman et al., J Struct Biol. 2011; 174 (1): 11-22; de Haan et al., Assembly of the coronavirus envelope: homotypic interactions between the M proteins. J Virol. 2000; 74 (11):

4967-78. With respect to, for example SARS, M and E make up the viral envelope and their interaction is sufficient for the production and release of VLPs. Mortola & Roy. Efficient assembly and release of SARS coronavirus-like particles by a heterologous expression system. FEBS Lett. 2004; 576 (1-2): 174-8.

The amino acid sequence of the SARS-CoV2 membrane (M) protein is 222 amino acids in length. The M protein has In certain embodiments, an additional nucleic acid sequence encoding a tag may be included in the nucleic acid sequence to be inserted into the rMVA, so that the tag is expressed at the C-terminus of the protein. In some embodiments, the nucleic acid sequence (GAGCCAGAGGCT) (SEQ ID NO: 4) encodes for the high affinity C-tag having the amino acid sequence EPEA (SEQ ID NO: 5).

TABLE 11

| SARS-CoV2 M Protein | |
|---|---|
| SEQ ID NO: 43-<br>SARS-CoV2 M<br>protein amino acid<br>sequence. | MADSNGTITVEELKKLLEQWNLVIGFLFLTWICLLQFAYANRNRFLYIIKLIFLWL<br>LWPVTLACFVLAAVYRINWITGGIAIAMACLVGLMWLSYFIASFRLFARTRSMW<br>SFNPETNILLNVPLHGTILTRPLLESELVIGAVILRGHLRIAGHHLGRCDIKDLPKEI<br>TVATSRTLSYYKLGASQRVAGDSGFAAYSRYRIGNYKLNTDHSSSSDNIALLVQ |
| SEQ ID NO: 44-<br>SARS-CoV2 nucleic<br>acid sequence for M<br>protein. | ATGGCAGATTCCAACGGTACTATTACCGTTGAAGAGCTTAAAAAGCTCCTTG<br>AACAATGGAACCTAGTAATAGGTTTCCTATTCCTTACATGGATTTGTCTTCTA<br>CAATTTGCCTATGCCAACAGGAATAGGTTTTTGTATATAATTAAGTTAATTTT<br>CCTCTGGCTGTTATGGCCAGTAACTTTAGCTTGTTTTGTGCTTGCTGCTGTTTA<br>CAGAATAAATTGGATCACCGGTGGAATTGCTATCGCAATGGCTTGTCTTGTA<br>GGCTTGATGTGGCTCAGCTACTTCATTGCTTCTTTCAGACTGTTTGCGCGTAC<br>GCGTTCCATGTGGTCATTCAATCCAGAAACTAACATTCTTCTCAACGTGCCAC<br>TCCATGGCACTATTCTGACCAGACCGCTTCTAGAAAGTGAACTCGTAATCGG<br>AGCTGTGATCCTTCGTGGACATCTTCGTATTGCTGGACACCATCTAGGACGCT<br>GTGACATCAAGGACCTGCCTAAAGAAATCACTGTTGCTACATCACGAACGCT<br>TTCTTATTACAAATTGGGAGCTTCGCAGCGTGTAGCAGGTGACTCAGGTTTTG<br>CTGCATACAGTCGCTACAGGATTGGCAACTATAAATTAAACACAGACCATTC<br>CAGTAGCAGTGACAATATTGCTTTGCTTGTACAG |
| SEQ ID NO: 45-<br>SARS-CoV2 nucleic<br>acid sequence for M<br>protein-optimized | ATGGCGGATTCTAACGGAACCATCACCGTCGAAGAGTTGAAGAAGCTACTA<br>GAGCAGTGGAACCTAGTCATCGGATTCCTATTCCTAACCTGGATCTGCCTACT<br>ACAGTTCGCGTACGCGAACAGGAACAGATTCTTGTACATCATCAAGCTAATC<br>TTCCTATGGCTACTATGGCCGGTCACCTTGGCCTGCTTCGTTCTAGCTGCGGT<br>CTACAGAATCAACTGGATCACAGGTGGAATCGCGATCGCTATGGCTTGTCTA<br>GTAGGACTAATGTGGCTATCCTACTTCATCGCCTCCTTCAGACTATTCGCGAG<br>AACCAGATCTATGTGGTCGTTCAACCCGGAGACGAACATCCTATTGAACGTA<br>CCGCTACATGGAACCATCCTAACCAGACCGCTATTGGAATCCGAATTGGTTA<br>TCGGAGCGGTCATCCTAAGAGGACATCTAAGAATTGCGGGACACCACCTAG<br>GAAGATGTGACATCAAGGACCTACCGAAGGAGATCACCGTAGCGACCTCTA<br>GAACCCTATCGTACTATAAGTTGGGAGCCTCTCAAAGAGTCGCGGGAGATTC<br>TGGATTTGCGGCGTATTCTAGATACAGAATCGGGAACTACAAGCTAAACACC<br>GACCACTCCTCCAGTTCCGATAATATCGCTCTACTAGTCCAG |

40 been reported at GenBank Accession No. QHD43419, reproduced below in Table 11 as SEQ ID NO: 43, and its nucleic acid sequence, which is located at nucleic acids 26523 to 27191 of the SARS-CoV2 genome has been reported at GenBank Accession No. MN908947.3, and is reproduced below as SEQ ID NO: 44.

In some embodiments, the nucleic acid sequence inserted into the MVA viral vector encodes an amino acid of SEQ ID NO: 43, or an amino acid 80%, 85%, 90%, 95%, 98%, or 99% homologous thereto. In some embodiments, the nucleic acid sequence inserted into the MVA viral vector is SEQ ID NO: 44, or a nucleic acid 80%, 85%, 90%, 95%, 98%, or 99% homologous thereto. In some embodiments, the nucleic acid sequence encoding the M protein inserted into the MVA viral vector has been optimized, for example, as provided in SEQ ID NO: 45, or a nucleic acid 80%, 85%, 90%, 95%, 98%, or 99% homologous thereto.

In some embodiments, the nucleic acid sequence inserted into the MVA viral vector encodes an amino acid of SEQ ID NO: 43, further comprising one or more substitutions selected from T175M, D3G, V23L, W31C, A2V, V70F, W75L, M1091, 152T, L46F, V70I, D3Y, K162N, H125Y, K15R, D209Y, R146H, R158C, L87F, A2S, A69S, S214I, T208I, L124F, or S4F, and combinations thereof, or an amino acid 80%, 85%, 90%, 95%, 98%, or 99% homologous thereto.

Modified Vaccinia Ankara (MVA) Viral Vector

As provided herein, a nucleic acid sequence encoding one or more SARS-CoV2 antigens or antigenic fragments thereof are inserted into the vaccinia virus strain modified vaccinia Ankara (MVA), which, when administered to the subject, is capable of expressing the one or more SARS-CoV2 antigens or antigenic fragments in the cells of a subject. The term "modified vaccinia Ankara," "modified vaccinia ankara," "Modified Vaccinia Ankara," or "MVA" refers to a highly attenuated strain of vaccinia virus developed by Dr. Anton Mayr by serial passage on chick embryo fibroblast cells; or variants or derivatives thereof. MVA is reviewed in (Mayr, A. et al. 1975 Infection 3:6-14; Swiss U.S. Pat. No. 568,392). The complete genomic sequence of MVA is available as Genbank Accession No. U94848.

Modified vaccinia Ankara (MVA) has been generated by long-term serial passages of the Ankara strain of vaccinia virus (CVA) on chicken embryo fibroblasts (for review see Mayr, A. et al. 1975 Infection 3:6-14; Swiss U.S. Pat. No. 568,392). The MVA virus is publicly available from American Type Culture Collection as ATCC No. VR-1508. MVA is distinguished by its great attenuation, as demonstrated by diminished virulence and reduced ability to replicate in primate cells, while maintaining good immunogenicity. The MVA virus has been analyzed to determine alterations in the genome relative to the parental CVA strain. Six major deletions of genomic DNA (deletion I, II, III, IV, V, and VI) totaling 31,000 base pairs have been identified (Meyer, H. et al. 1991 J Gen Virol 72:1031-1038). The resulting MVA virus is host cell restricted to avian cells.

MVA replication in human cells has been found to be blocked late in infection preventing the assembly to mature infectious virions. Nevertheless, MVA is able to express viral and recombinant heterologous genes at high levels even in non-permissive cells (Sutter, G. and Moss, B. 1992 PNAS USA 89:10847-10851). Recombinant MVA can be prepared as set out hereinafter. In general, a DNA-construct which contains a DNA-sequence which codes for one or more SARS-CoV2 (heterologous) polypeptides flanked by MVA DNA sequences adjacent to a predetermined insertion site (as described further below) can be introduced into cells infected with MVA (for example chicken embryo fibroblast (CEF) cell, to allow homologous recombination. Once the DNA-construct has been introduced into the eukaryotic cell and the foreign DNA has recombined with the viral DNA, it is possible to isolate the desired recombinant MVA. The DNA-construct to be inserted can be linear or circular. A plasmid or polymerase chain reaction product is preferred. Such methods of making recombinant MVA vectors are described in, e.g., U.S. Pat. No. 9,453,239 incorporated by reference herein.

For the expression of a heterologous DNA sequence or gene, it is necessary for regulatory sequences such as promoters, which are required for the transcription of the gene, to be present on the DNA. Because MVA is a cytoplasmic virus, suitable promoters include those derived from naturally occurring poxviral promoters. Poxviral genes, promoters, and transcription factors are divided into early, intermediate, and late classes, depending on their expression timing during poxvirus infections. See, e.g., Assarsson et al., Kinetic analysis of a complete poxvirus transcriptome reveals an immediate-early class of genes. PNAS 2008; 105 (6): 2140-2145. Yang Zet al., Genome-wide analysis of the 5' and 3' ends of vaccinia virus early mRNAs delineates regulatory sequences of annotated and anomalous transcripts. J Virol. 2011; 85 (12): 5897-5909. MVA replication in most mammalian cells (non-permissive cells) ceases during the assembly of progeny virions after all stages of expression occur. This supports the utility of all promoter classes, including late promoters, for controlling transgene expression. Sancho et al., The block in assembly of modified vaccinia virus Ankara in Hela cells reveals new insights into vaccinia virus morphogenesis. J Virol. 2002; 76 (16): 8318-8334; Geiben-Lynn et al., Kinetics of recombinant adenovirus type 5, vaccinia virus, modified vaccinia ankara virus, and DNA antigen expression in vivo and the induction of memory T-lymphocyte responses. Clin Vaccine Immunol. 2008; 15 (4): 691-696. Some poxviral promoters have both early and late elements, allowing their open-reading frames (ORFs) or recombinant antigens to be expressed early in the virus infection and late after the viral genome replication, respectively. Broyles SS, Vaccinia virus transcription. J Gen Virol. 2003; 84 (Pt 9): 2293-2303. Poxviral promoters can be utilised cross-strain. See Prideaux et al., Comparative analysis of vaccinia virus promoter activity in fowlpox and vaccinia virus recombinants. Virus Res. 1990; 16 (1): 43-57; Tripathy et al., Regulation of foreign gene in fowlpox virus by a vaccinia virus promoter. Avian Dis. 1990; 34 (1): 218-220. Such regulatory sequences are known to those skilled in the art, and include for example the p11 promoter, which drives expression of the 11 k protein encoded by the F17R ORF (Wittek et al., Mapping of a gene coding for a major late structural polypeptide on the vaccinia virus genome. J Virol. 1984; 49 (2): 371-378); the p7.5 promoter (Cochran et al., In vitro mutagenesis of the promoter region for a vaccinia virus gene: evidence for tandem early and late regulatory signals. J Virol. 1985; 54 (1): 30-37); the pI1L promoter (Schmitt et al., Sequence and transcriptional analysis of the vaccinia virus HindIII I fragment. J Virol. 1988; 62 (6): 1889-1897); the pTK promoter (Weir and Moss, Determination of the promoter region of an early vaccinia virus gene encoding thymidine kinase. Virology. 1987; 158 (1): 206-210); the pF7L promoter (Coupar et al., Effect of in vitro mutations in a vaccinia virus early promoter region monitored by herpes simplex virus thymidine kinase expression in recombinant vaccinia virus. J Gen Virol. 1987; 68 (Pt 9): 2299-2309); the pH5 promoter (Perkus et al., Cloning and expression of foreign genes in vaccinia virus, using a host range selection system. J Virol. 1989; 63 (9): 3829-3836); the short synthetic promoter pSyn (Chakrabarti et al., Compact, synthetic, vaccinia virus early/late promoter for protein expression. Biotechniques. 1997; 23 (6): 1094-1097; Hammond et al., A synthetic vaccinia virus promoter with enhanced early and late activity. J Virol Methods. 1997; 66 (1): 135-1380); the pH5 promoter (Wyatt et al., Development of a replication-deficient recombinant vaccinia virus vaccine effective against parainfluenza virus 3 infection in an animal model. Vaccine. 1996; 14 (15): 1451-1458); the pmH5 promoter (Wyatt et al., Development of a replication-deficient recombinant vaccinia virus vaccine effective against parainfluenza virus 3 infection in an animal model. Vaccine. 1996; 14 (15): 1451-1458); the pHyb promoter (Sancho et al., The block in assembly of modified vaccinia virus Ankara in Hela cells reveals new insights into vaccinia virus morphogenesis. J Virol. 2002; 76 (16): 8318-8334); the LEO promoter (Wyatt et al., Correlation of immunogenicities and in vitro expression levels of recombinant modified vaccinia virus Ankara HIV vaccines. Vaccine. 2008; 26 (4): 486-493); the pB8 promoter (Orubu et al., Expression and cellular immunogenicity of a transgenic antigen driven by endogenous poxviral early promoters at their authentic loci in MVA. PLOS One. 2012; 7 (6): e40167); the pF11 promoter (Orubu et al., Expression and cellular immunogenicity of a transgenic antigen driven by endogenous poxviral early promoters at their authentic loci in MVA. PLOS One. 2012; 7 (6): e40167).

In some embodiments, the promoter is a pmH5 promoter. In some embodiments, the comprises SEQ ID NO: promoter 154 (AAAAATTGAAAATAAATACAAAGGTTCTT-GAGGGTTGTGTTAAATTGAAAGCGAGA AATAAT-CATAA).

In some embodiments, the promoter is a p11 promoter. In some embodiments, the promoter comprises SEQ ID NO: 155 (TTTCATTTTGTTTTTTTTCTATGCTATAA).

The DNA-construct can be introduced into the MVA infected cells by transfection, for example by means of calcium phosphate precipitation (Graham et al. 1973 Virol 52:456-467; Wigler et al. 1979 Cell 16:777-785), by means of electroporation (Neumann et al. 1982 EMBO J. 1:841-845), by microinjection (Graessmann et al. 1983 Meth Enzymol 101:482-492), by means of liposomes (Straubinger et al. 1983 Meth Enzymol 101:512-527), by means of spheroplasts (Schaffher 1980 PNAS USA 77:2163-2167) or by other methods known to those skilled in the art.

The present MVA vector design and methods of manufacture are useful in producing effective MVA vaccine vectors for eliciting effective T-cell and antibody immune responses against SARS-CoV2. In some embodiments, the MVA vaccine vectors described herein are capable of eliciting effective immune responses and antibody production after a single homologous prime boost.

In some embodiments, the present invention provides recombinant viral vector (e.g., an MVA vector) comprising one or more nucleic acid sequences encoding a SARS-CoV2 protein or immunogenic fragments thereof. The viral vector (e.g., an MVA vector) may be constructed using conventional techniques known to one of skill in the art. The one or more heterologous SARS-CoV2 gene inserts encode a polypeptide having desired immunogenicity, i.e., a polypeptide that can induce an immune reaction, cellular immunity and/or humoral immunity, in vivo by administration thereof. In the introduction of a gene encoding a polypeptide having immunogenicity, an appropriate promoter may be operatively linked upstream of the gene encoding a polypeptide having desired immunogenicity.

One or more nucleic acid sequences may be optimized for use in an MVA vector. Optimization includes codon optimization, which employs silent mutations to change selected codons from the native sequences into synonymous codons that are optimally expressed by the host-vector system. Other types of optimization include the use of silent mutations to interrupt homopolymer stretches or transcription terminator motifs. Each of these optimization strategies can improve the stability of the gene, improve the stability of the transcript, or improve the level of protein expression from the sequence. In exemplary embodiments, the number of homopolymer stretches in the heterologous DNA insert sequence will be reduced to stabilize the construct. A silent mutation may be provided for anything similar to a vaccinia termination signal.

In exemplary embodiments, the sequences are codon optimized for expression in MVA; sequences with runs of >5 deoxyguanosines, >5 deoxycytidines, >5 deoxyadenosines, and >5 deoxythymidines are interrupted by silent mutation to minimize loss of expression due to frame shift mutations.

In particular, the nucleic acid for insertion can be optimized by codon optimizing the original DNA sequence. For example, the "Invitrogen GeneArt Gene Software" can be used to codon optimize the DNA sequence. To fully optimize the gene sequence, homopolymer sequences (G/C or T/A rich areas) are interrupted via silent mutation(s). To the extent present in the nucleic acid insert sequence, the MVA transcription terminator (T5NT (UUUUUNU)) is interrupted via silent mutation(s). Further optimizations can include, for example, adding a Kozak sequence (GCCACC/ATG), adding a second stop codon, and adding a vaccinia virus transcription terminator, specifically "TTTTTAT", or variations and/or combinations thereof.

The DNA insert encoding the one or more SARS-CoV2 proteins or fragments thereof can be inserted into the MVA genome at any suitable location, for example, a natural deletion site, a modified natural deletion site, in a non-essential MVA gene, for example the MVA thymidine kinase locus, or in an intergenic region between essential or non-essential MVA genes. Suitable insertion sites have been described, for example, in U.S. Pat. Nos. 6,998,252, 9,133,478, Ober et al., Immunogenicity and safety of defective vaccinia virus lister: comparison with modified vaccinia virus Ankara. J. Virol., August 2002 (pg. 7713-7723), U.S. Pat. Nos. 9,133,480, 8,288,125, each of which is incorporated herein by reference.

In some embodiments, the SARS-CoV2 peptide encoding sequence is inserted into a natural deletion site, for example a deletion site selected from the natural deletion sites I, II, III, IV, V or VI, a modified natural deletion site, for example the restructured and modified deletion III site between the MVA genes A50R and B1R (see, e.g., U.S. Pat. No. 9,133, 480), between non-essential MVA genes, between essential MVA genes, for example I8R and G1L or A5R and A6L or other suitable insertion site, in a non-essential locus, for example in the MVA TK locus, or a combination thereof.

Recombinant Modified Vaccinia Ankara (rMVA) Vaccine Constructs

Provided herein are recombinant modified vaccinia Ankara (rMVA) viral vectors comprising heterologous nucleic acid inserts encoding one or more SARS-CoV2 proteins, peptides, or fragments thereof, operably linked to a promoter compatible with poxvirus expression systems that, upon expression, are capable of inducing protective immunity without inducing the immuno-pathologies associated with previous rMVA-related coronavirus vaccination strategies.

SARS-CoV/2 S-E-M VLPs

In one aspect, the recombinant MVA vaccine expresses the M and E proteins of SARS-CoV2, and the SARS-CoV2 S protein, or a fragment or variant thereof, as provided further below. Upon expression in a host cell, the SARS-CoV2 are capable of forming a non-infectious virus-like particle (VLP), enhancing epitope display, and inducing potent anti-viral immune responses.

Figure 1A:
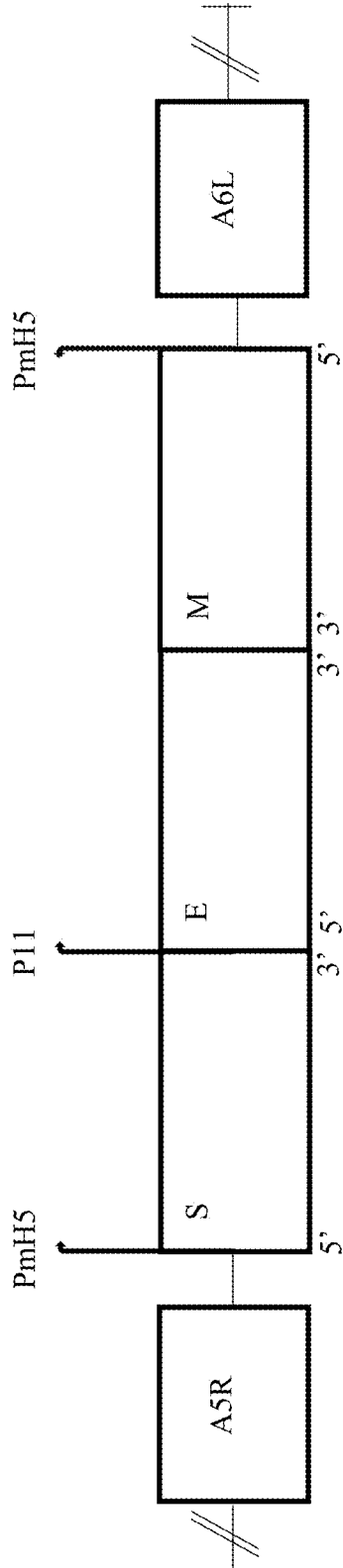
FIG. 1A provides an exemplary linear schematic of an exemplary recombinant MVA viral vector comprising an insert comprising a nucleic acid encoding a full-length S, E, and M protein between, for example, MVA genes A5R and A6L. As exemplified, a mH5 promoter (pmH5) is operably linked to a nucleic acid encoding the full-length SARS-CoV2 S protein in a left-to-right orientation. The insert may include a translation initiation sequence, for example a Kozak sequence, prior to the start codon of the S protein sequence. In addition, a nucleic acid sequence encoding a tag, for example a C-affinity tag, may be included at the 3' terminus of the S protein, prior to the stop codon. As exemplified, adjacent to the S protein is a nucleic acid sequence encoding the full-length E protein, in a left to right orientation, which is operably linked to, for example, a p11 promoter. Similar to the S protein, the E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a mH5 promoter (pmH5). The M protein nucleic acid sequence can also include appropriate translation initiation sequences such as a Kozak sequence, as well as a nucleic acid sequence encoding a tag at the 3' terminus of the coding sequence prior to the stop codon.

In some embodiments, an rMVA viral vector is provided which encodes the spike(S) protein (or fragment thereof), the envelope (E) protein, and the membrane (M) protein of the SARS-CoV2, wherein, upon expression of the S, E, and M protein, a VLP is formed. In some embodiments, the nucleic acid is arranged so that the S, E, and M encoding sequences are linearly adjacent. A linear representation of a single MVA insert encoding an S, E, and M protein suitable for forming a VLP upon expression is provided for in FIG. 1A. In some embodiments, the S protein is expressed as a full-length protein, for example, as provided for in SEQ ID NO: 1, the E protein is expressed as a full-length protein, as provided for in SEQ ID NO: 40, and the M protein is expressed as a full-length protein, as provided for in SEQ ID NO: 43, or sequences at least 70%, 75%, 80%, 85%, 90%, or 95% homologous thereto. In some embodiments, provided herein is a plasmid or MVA viral vector comprising a nucleic acid sequence encoding SEQ ID NOS: 1, 40, and 43, or sequences at least 70%, 75%, 80%, 85%, 90%, or 95% homologous thereto. In some embodiments, the S protein is expressed as a full-length protein, for example, as provided for in SEQ ID NO: 6, the E protein is expressed as a full-length protein, as provided for in SEQ ID NO: 40, and the M protein is expressed as a full-length protein, as provided for in SEQ ID NO: 43, or sequences at least 70%, 75%, 80%, 85%, 90%, or 95% homologous thereto. In some embodiments, provided herein is a plasmid or MVA viral vector comprising a nucleic acid sequence encoding SEQ ID NOS: 6, 40, and 43, or sequences at least 70%, 75%, 80%, 85%, 90%, or 95% homologous thereto. In some embodiments, provided herein is a nucleic acid sequence comprising SEQ ID NOS: 2, 41, and 44 or a sequence at least 70%, 75%, 80%, 85%, 90%, or 95% homologous thereto. In some embodiments, provided herein is a nucleic acid encoding the full-length S, E, and M proteins, wherein the nucleic acid has been optimized for expression in the MVA viral vector, for example as provided in SEQ ID NOS: 3, 42, and 45. In some embodiments, the nucleic acid sequence encodes for an additional amino acid sequence such as a tag, for example a C-terminus tag such as EPEA suitable for detection of the expressed proteins in an assay. The nucleic acid sequences may further comprise suitable promoter sequences such as, for example but not limited to, those derived from pmH5, p11, pSyn, pHyb, or any other suitable promoter sequence known in the art. In addition, the nucleic acid sequence for insertion may further include suitable translation initiation sequences, such as for example, a Kozak consensus sequence. In addition, the nucleic acid sequence can include appropriate stop codons, for example TAA, TAG, or TGA, or combinations or multiples thereof, at the 3'end of the nucleic acid sequence following the last amino acid sequence of each protein or tag. Furthermore, the nucleic acid sequence can include a vaccinia virus termination sequence 3' of the last stop codon of each encoded protein. In addition, the nucleic acid sequence for insertion may further include restriction enzyme sites useful for generating shuttle vectors for ease of insertion of the antigenic sequence. Exemplary nucleic acid sequences comprising the adjacent coding sequences of the full-length S, E, and M proteins are provided below in as SEQ ID NOS: 46, 47, or 156. In some embodiments, the rMVA comprises a nucleic acid sequence of SEQ ID NO: 46 (FIG. 1B-1C-1D), or a sequence at least 70%, 75%, 80%, 85%, 90%, 95%, or 99% homologous thereto. In some embodiments, the rMVA comprises a nucleic acid sequence of SEQ ID NO: 47 (FIG. 1E-1F-1G), or a sequence at least 70%, 75%, 80%, 85%, 90%, 95%, or 99% homologous thereto. In some embodiments, the rMVA comprises a nucleic acid sequence of SEQ ID NO: 156 (FIG. 1H-1I-1J), or a sequence at least 70%, 75%, 80%, 85%, 90%, 95%, or 99% homologous thereto.

Figure 2A:
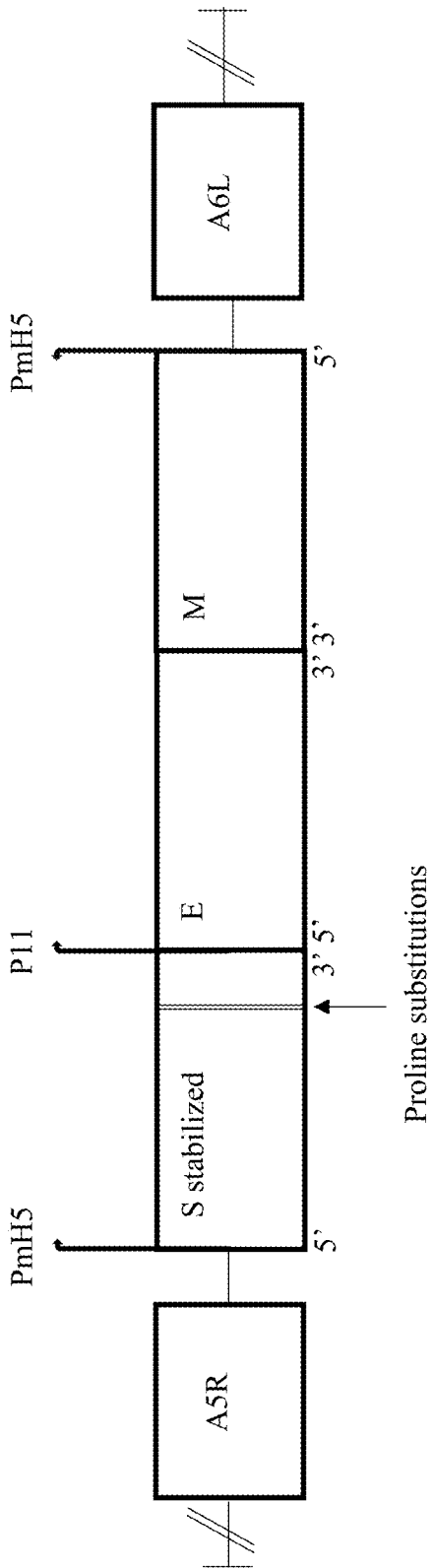
FIG. 2A provides an exemplary linear schematic of an exemplary recombinant MVA viral vector comprising a nucleic acid insert encoding a stabilized S protein, an E protein, and an M protein between, for example, MVA genes A5R and A6L. As exemplified, a mH5 promoter (pmH5) is operably linked to a nucleic acid encoding the full-length SARS-CoV2 S stabilized protein in a left-to-right orientation. The insert may include a translation initiation sequence, for example a Kozak sequence, prior to the start codon of the S stabilized protein sequence. In addition, a nucleic acid sequence encoding a tag, for example a C-affinity tag, may be included at the 3' terminus of the S stabilized protein, prior to the stop codon. As exemplified, adjacent to the S stabilized protein is a nucleic acid sequence encoding the full-length E protein, in a left to right orientation, which is operably linked to, for example, a p11 promoter. Similar to the S stabilized protein, the E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a pmH5 promoter. The M protein nucleic acid sequence can also include appropriate translation initiation sequences such as a Kozak sequence, as well as a nucleic acid sequence encoding a tag at the 3' terminus of the coding sequence prior to the stop codon.

Alternatively, an rMVA viral vector is provided which encodes the spike(S) protein, the envelope (E) protein, and the membrane (M) protein of the SARS-CoV2, wherein the S protein has been stabilized with one or more amino acid proline substitutions that stabilize the S protein trimer in the prefusion conformation, and wherein upon expression, the proteins form a VLP. In some embodiments, the nucleic acid is arranged so that the stabilized S, E, and M encoding sequences are linearly adjacent. In some embodiments, the S protein is expressed as a full-length protein and contains one or more proline substitutions at or near the boundary between a Heptad Repeat 1 (HR1) and a central helix of the promoters of the S ectodomain trimer. In some embodiments, the proline substitutions occur between amino acid residues 970 to 990 of the promoters in the trimer. In some embodiments, the S protein is expressed as a full-length protein and contains two proline substitutions at amino acids K986 and V987. A linear representation of a single MVA insert encoding a stabilized S, an E, and an M protein suitable for forming a VLP upon expression is provided for in FIG. 2A. In some embodiments, the S protein is expressed as a full-length protein comprising two proline substitutions at amino acids 986 and 987 of the S protein, for example, as provided for in SEQ ID NO: 8, the E protein is expressed as a full-length protein, as provided for in SEQ ID NO: 40, and the M protein is expressed as a full-length protein, as provided for in SEQ ID NO: 43, or sequences at least 75%, 80%, 85%, 90%, or 95% homologous thereto. In some embodiments, provided herein is a plasmid or MVA viral vector containing a nucleic acid sequence encoding SEQ ID NOS: 8, 40, and 43, or sequences at least 75%, 80%, 85%, 90%, or 95% homologous thereto. In some embodiments, the S protein is expressed as a full-length protein comprising two proline substitutions at amino acids 986 and 987 of the S protein, for example, as provided for in SEQ ID NO: 11, the E protein is expressed as a full-length protein, as provided for in SEQ ID NO: 40, and the M protein is expressed as a full-length protein, as provided for in SEQ ID NO: 43, or sequences at least 75%, 80%, 85%, 90%, or 95% homologous thereto. In some embodiments, provided herein is a plasmid or MVA viral vector containing a nucleic acid sequence encoding SEQ ID NOS: 11, 40, and 43, or sequences at least 75%, 80%, 85%, 90%, or 95% homologous thereto. In some embodiments, provided herein is a nucleic acid sequence comprising SEQ ID NOS: 9, 41, and 44, or sequences at least 75%, 80%, 85%, 90%, or 95% homologous thereto. In some embodiments, provided herein is a nucleic acid encoding the full-length proline substituted S protein, the E protein, and M protein, wherein the nucleic acid has been optimized for expression in the MVA viral vector, for example as provided in SEQ ID NOS: 10, 42, and 45, or sequences at least 75%, 80%, 85%, 90%, or 95% homologous thereto. In some embodiments, provided herein is a nucleic acid encoding the full-length proline substituted S protein, the E protein, and M protein, wherein the nucleic acid has been optimized for expression in the MVA viral vector, for example as provided in SEQ ID NOS: 12, 42, and 45, or sequences at least 75%, 80%, 85%, 90%, or 95% homologous thereto. In some embodiments, the nucleic acid sequence encodes for an additional amino acid sequence such as a tag, for example a C-terminus tag such as EPEA. The nucleic acid sequences may further comprise suitable promoter sequences such as, for example but not limited to, those derived from pmH5, p11, pSyn, pHyb, or any other suitable promoter sequence. In addition, the nucleic acid sequence for insertion may further include suitable translation initiation sequences, such as for example, a Kozak consensus sequence. In addition, the nucleic acid sequence can include appropriate stop codons, for example TAA, TAG, or TGA, or combinations or multiples thereof, at the 3'end of the nucleic acid sequence following the last amino acid sequence of the protein or tag. Furthermore, the nucleic acid sequence can include a vaccinia virus termination sequence 3' of the last stop codon of each encoded protein. In addition, the nucleic acid sequence for insertion may further include restriction enzyme sites useful for generating shuttle vectors for ease of insertion of the antigenic sequence. Exemplary nucleic acid sequences for insertion encoding the full-length stabilized S protein, the E protein, and the M protein are provided below as SEQ ID NOS: 48, 49, 50, or 156. In some embodiments, the rMVA comprises a nucleic acid sequence of SEQ ID NO: 48 (FIG. 2B-2C-2D), or a sequence at least 70%, 75%, 80%, 85%, 90%, 95%, or 99% homologous thereto. In some embodiments, the rMVA comprises a nucleic acid sequence of SEQ ID NO: 49 (FIG. 2E-2F-2G), or a sequence at least 70%, 75%, 80%, 85%, 90%, 95%, or 99% homologous thereto. In some embodiments, the rMVA comprises a nucleic acid sequence of SEQ ID NO: 50 (2H-2I-2J), or a sequence at least 70%, 75%, 80%, 85%, 90%, 95%, or 99% homologous thereto. In some embodiments, the rMVA comprises a nucleic acid sequence of SEQ ID NO: 157 (2K-2L-2M), or a sequence at least 70%, 75%, 80%, 85%, 90%, 95%, or 99% homologous thereto. In some embodiments, the rMVA comprises a nucleic acid sequence of SEQ ID NO: 159 (2N-2O-2P), or a sequence at least 70%, 75%, 80%, 85%, 90%, 95%, or 99% homologous thereto. In some embodiments, the rMVA comprises a nucleic acid sequence of SEQ ID NO: 160 (2Q-2R-2S), or a sequence at least 70%, 75%, 80%, 85%, 90%, 95%, or 99% homologous thereto.

Figure 3A:
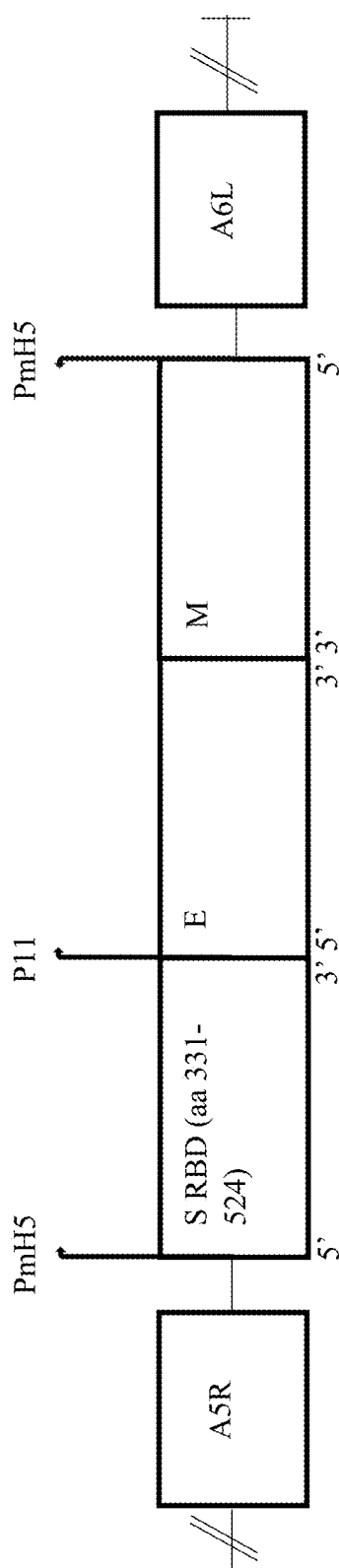
FIG. 3A provides an exemplary linear schematic of an exemplary recombinant MVA viral vector comprising a nucleic acid sequence encoding an RBD (aa 331-524) region of the S protein, an E protein, and an M protein inserted between, for example, MVA genes A5R and A6L. As exemplified, a mH5 promoter (pmH5) is operably linked to a nucleic acid encoding amino acids 331 to 524 of the S protein in a left-to-right orientation. The insert may include a translation initiation sequence, for example a Kozak sequence, prior to a start codon inserted 5' of the S RBD (aa 331-524) protein sequence. In addition, a nucleic acid sequence encoding a tag, for example a C-affinity tag, may be included at the 3' terminus of the S RBD (aa 331-524) protein, prior to the stop codon. As exemplified, adjacent to the S RBD (aa 331-524) protein is a nucleic acid sequence encoding the full-length E protein, in a left to right orientation, which is operably linked to, for example, a p11 promoter. Similar to the S RBD (aa 331-524) protein, the E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a mH5 promoter (pmH5). The M protein nucleic acid sequence can also include appropriate translation initiation sequences such as a Kozak sequence, as well as a nucleic acid sequence encoding a tag at the 3' terminus of the coding sequence prior to the stop codon.
Figure 3D:
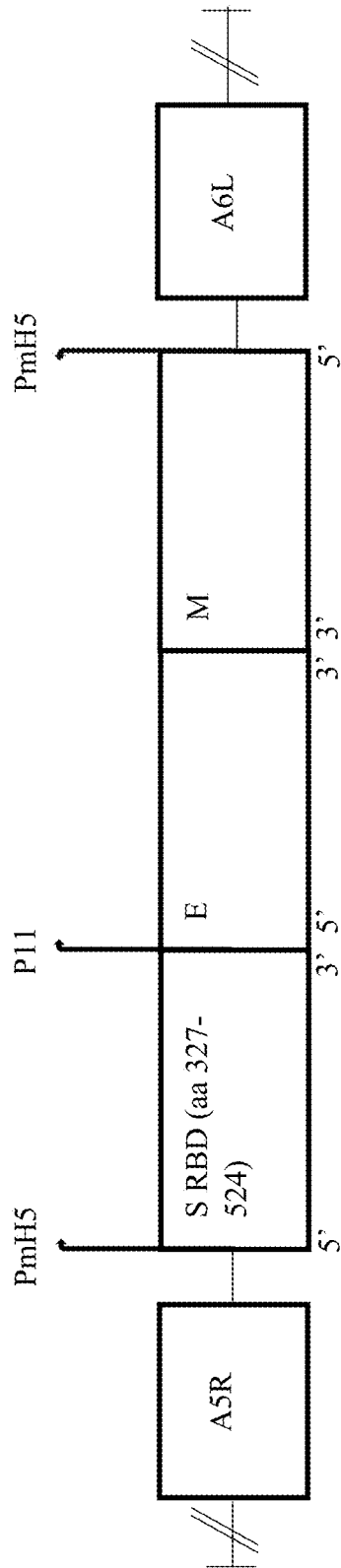
FIG. 3D provides an exemplary linear schematic of an exemplary recombinant MVA viral vector comprising a nucleic acid sequence encoding an RBD (aa 327-524) region of the S protein, an E protein, and an M protein inserted between, for example, MVA A5R and A6L. As exemplified, a mH5 promoter (pmH5) is operably linked to a nucleic acid encoding amino acids 327 to 524 of the S protein in a left-to-right orientation. The insert may include a translation initiation sequence, for example a Kozak sequence, prior to a start codon inserted 5' of the S RBD (aa 327-524) protein sequence. In addition, a nucleic acid sequence encoding a tag, for example a C-affinity tag, may be included at the 3' terminus of the S RBD (aa 327-524) protein, prior to the stop codon. As exemplified, adjacent to the S RBD (aa 327-524) protein is a nucleic acid sequence encoding the full-length E protein, in a left to right orientation, which is operably linked to, for example, a p11 promoter. Similar to the S RBD (aa 327-524) protein, the E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a mH5 promoter (pmH5). The M protein nucleic acid sequence can also include appropriate translation initiation sequences such as a Kozak sequence, as well as a nucleic acid sequence encoding a tag at the 3' terminus of the coding sequence prior to the stop codon.

Alternatively, an rMVA viral vector is provided which encodes a partial spike(S) protein, the envelope (E) protein, and the membrane (M) protein of the SARS-CoV2, wherein the partial S protein is the receptor biding domain (RBD) of the SARS-CoV2 S protein. In some embodiments, the linear S epitope comprises amino acids 327 to 524 of the S protein, and optionally further comprises an initial methionine amino acid residue at the NH-terminus. In some embodiments, the RBD sequence is a coronavirus consensus sequence. In some embodiments, the nucleic acid is arranged so that the S RBD, E, and M encoding sequences are linearly adjacent. A linear representation of a single MVA insert encoding a partial S protein encoding amino acids 327 to 524, an E protein, and an M protein suitable for forming a VLP upon expression is provided for in FIG. 3D. In some embodiments, the partial S protein is expressed as provided for in SEQ ID NO: 20, the E protein is expressed as a full-length protein, as provided for in SEQ ID NO: 40, and the M protein is expressed as a full-length protein, as provided for in SEQ ID NO: 43, or sequences at least 70%, 75%, 80%, 85%, 90%, or 95% homologous thereto. In some embodiments, provided herein is a plasmid or MVA viral vector containing a nucleic acid sequence encoding SEQ ID NOS: 22, 40, and 43, or sequences at least 70%, 75%, 80%, 85%, 90%, or 95% homologous thereto. In some embodiments, provided herein is a nucleic acid sequence comprising SEQ ID NOS: 24, 41, and 44, or sequences at least 70%, 75%, 80%, 85%, 90%, or 95% homologous thereto. In some embodiments, provided herein is a nucleic acid encoding the partial S protein, the E protein, and M protein, wherein the nucleic acid has been optimized for expression in the MVA viral vector, for example as provided in SEQ ID NOS: 24, 42, and 45, or sequences at least 70%, 75%, 80%, 85%, 90%, or 95% homologous thereto. In some embodiments, the partial S protein is expressed as provided for in SEQ ID NO: 32, the E protein is expressed as a full-length protein, as provided for in SEQ ID NO: 40, and the M protein is expressed as a full-length protein, as provided for in SEQ ID NO: 43, or sequences at least 70%, 75%, 80%, 85%, 90%, or 95% homologous thereto.

In some embodiments, the nucleic acid sequence encodes for an additional amino acid sequence such as a tag, for example a C-terminus tag such as EPEA suitable for use during assay detection. The nucleic acid sequences may further comprise suitable promoter sequences such as those derived from pmH5, p11, pSyn, pHyb, or any other suitable promoter sequence. In addition, the nucleic acid sequence for insertion may further include suitable translation initiation sequences, such as for example, a Kozak consensus sequence. In addition, the nucleic acid sequence can include appropriate stop codons, for example TAA, TAG, or TGA, or combinations or multiples thereof, at the 3'end of the nucleic acid sequence following the last amino acid sequence of the protein or tag. Furthermore, the nucleic acid sequence can include a vaccinia virus termination sequence 3' of the last stop codon of each encoded protein. In addition, the nucleic acid sequence for insertion may further include restriction enzyme sites useful for generating shuttle vectors for ease of insertion of the antigenic sequence. Exemplary nucleic acid sequences for insertion encoding the S protein RBD region, the E protein, and the M protein are provided as SEQ ID NOS: 51 or 52. In some embodiments, the rMVA comprises a nucleic acid sequence of SEQ ID NO: 51 (FIG. 3E), or a sequence at least 70%, 75%, 80%, 85%, 90%, 95%, or 99% homologous thereto. In some embodiments, the rMVA comprises a nucleic acid sequence of SEQ ID NO: 52 (FIG. 3F), or a sequence at least 70%, 75%, 80%, 85%, 90%, 95%, or 99% homologous thereto.

Alternatively, in some embodiments, the linear S epitope comprises amino acids 331 to 524 of the S protein, and optionally further comprises a methionine at the NH-terminus of the RBD. In some embodiments, the nucleic acid is arranged so that the S RBD (aa 331-524), E, and M encoding sequences are linearly adjacent. A linear representation of a single MVA insert encoding a partial S protein encoding amino acids 331 to 524, an E protein, and an M protein suitable for forming a VLP upon expression is provided for in FIG. 3A. In some embodiments, the partial S protein is expressed as provided for in SEQ ID NO: 21, the E protein is expressed as a full-length protein, as provided for in SEQ ID NO: 40, and the M protein is expressed as a full-length protein, as provided for in SEQ ID NO: 43, or sequences at least 70%, 75%, 80%, 85%, 90%, or 95% homologous thereto. In some embodiments, provided herein is a plasmid or MVA viral vector containing a nucleic acid sequence encoding SEQ ID NOS: 23, 40, and 43, or sequences at least 70%, 75%, 80%, 85%, 90%, or 95% homologous thereto. In some embodiments, provided herein is a nucleic acid sequence comprising SEQ ID NOS: 25, 41, and 44, or sequences at least 70%, 75%, 80%, 85%, 90%, or 95% homologous thereto. In some embodiments, provided herein is a nucleic acid encoding the partial S protein, the E protein, and M protein, wherein the nucleic acid has been optimized for expression in the MVA viral vector, for example as provided in SEQ ID NOS: 25, 42, and 45, or sequences at least 70%, 75%, 80%, 85%, 90%, or 95% homologous thereto. In some embodiments, the partial S protein is expressed as provided for in SEQ ID NO: 33, the E protein is expressed as a full-length protein, as provided for in SEQ ID NO: 40, and the M protein is expressed as a full-length protein, as provided for in SEQ ID NO: 43, or sequences at least 70%, 75%, 80%, 85%, 90%, or 95% homologous thereto.

In some embodiments, the nucleic acid sequence encodes for an additional amino acid sequence such as a tag, for example a C-terminus tag such as EPEA suitable for use during assay detection. The nucleic acid sequences may further comprise suitable promoter sequences such as, for example but not limited to, those derived from pmH5, p11, pSyn, pHyb, or any other suitable promoter sequence. In addition, the nucleic acid sequence for insertion may further include suitable translation initiation sequences, such as for example, a Kozak consensus sequence. In addition, the nucleic acid sequence can include appropriate stop codons, for example TAA, TAG, or TGA, or combinations or multiples thereof, at the 3'end of the nucleic acid sequence following the last amino acid sequence of the protein or tag. Furthermore, the nucleic acid sequence can include a vaccinia virus termination sequence 3' of the last stop codon of each encoded protein. In addition, the nucleic acid sequence for insertion may further include restriction enzyme sites useful for generating shuttle vectors for ease of insertion of the antigenic sequence. Exemplary nucleic acid sequences for insertion encoding the S protein RBD (aa 331-524) region, the E protein, and the M protein are provided as SEQ ID NOS: 53 or 54. In some embodiments, the rMVA comprises a nucleic acid sequence of SEQ ID NO: 53 (FIG. 3B), or a sequence at least 70%, 75%, 80%, 85%, 90%, 95%, or 99% homologous thereto. In some embodiments, the rMVA comprises a nucleic acid sequence of SEQ ID NO: 54 (FIG. 3C), or a sequence at least 70%, 75%, 80%, 85%, 90%, 95%, or 99% homologous thereto.

Figure 3G:
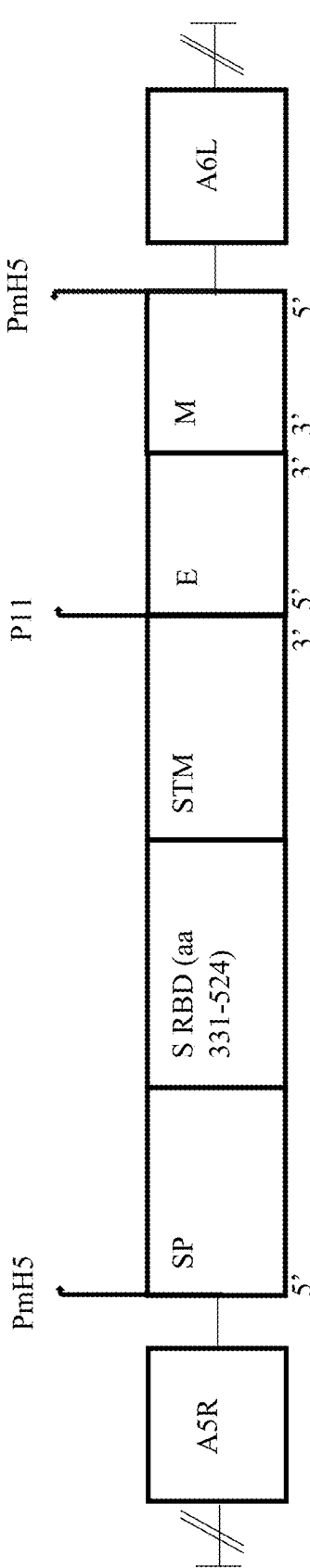
FIG. 3G provides an exemplary linear schematic of an exemplary recombinant MVA viral vector comprising a nucleic acid sequence encoding a S protein signal peptide (SP)-S protein RBD (aa 331-524)-S protein transmembrane domain (STM) fusion protein, an E protein, and an M protein inserted between, for example, MVA A5R and A6L. As exemplified, a mH5 promoter (pmH5) is operably linked to a nucleic acid encoding a fusion protein, wherein the fusion protein includes a S protein signal peptide derived from amino acids 1-13 of the S protein (SP), an S protein RBD (aa 331-524) peptide, and a transmembrane domain derived from amino acids 1214-1273 of the S protein (STM), in a left-to-right orientation. A start codon is provided 5' to the SP-S RBD (aa 331-524)-STM fusion encoding nucleic acid. The insert may include a translation initiation sequence, for example a Kozak sequence, prior to the start codon of the signal peptide encoding sequence. In addition, a nucleic acid sequence encoding a tag, for example a C-affinity tag, may be included at the 3' terminus of the SP-S RBD (aa 331-524)-STM fusion, prior to the stop codon. As exemplified, adjacent to the SP-S RBD (aa 331-524)-STM fusion encoding sequence is a nucleic acid sequence encoding the full-length E protein, in a left to right orientation, which is operably linked to, for example, a p11 promoter. The E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a mH5 promoter (pmH5). The M protein nucleic acid sequence can also include appropriate translation initiation sequences such as a Kozak sequence, as well as a nucleic acid sequence encoding a tag at the 3' terminus of the coding sequence prior to the stop codon.
Figure 3H:
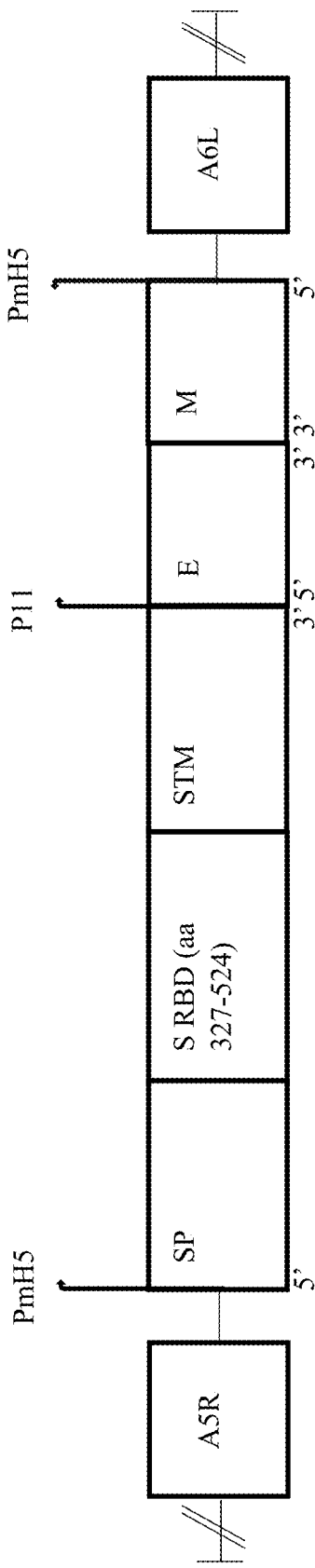
FIG. 3H provides an exemplary linear schematic of an exemplary recombinant MVA viral vector comprising a nucleic acid sequence encoding a S protein signal peptide (SP)-S protein RBD (aa 327-524)-S protein transmembrane domain (STM) fusion protein, an E protein, and an M protein inserted between, for example, MVA genes A5R and A6L. As exemplified, a mH5 promoter (pmH5) is operably linked to a nucleic acid encoding a fusion protein, wherein the fusion protein includes a S protein signal peptide derived from amino acids 1-13 of the S protein (SP), an S protein RBD (aa 327-524) peptide, and a transmembrane domain derived from amino acids 1214-1273 of the S protein (STM), in a left-to-right orientation. A start codon is provided 5' to the SP-S RBD (aa 327-524)-STM fusion encoding nucleic acid. The insert may include a translation initiation sequence, for example a Kozak sequence, prior to the start codon of the signal peptide encoding sequence. In addition, a nucleic acid sequence encoding a tag, for example a C-affinity tag, may be included at the 3' terminus of the SP-S RBD (aa 327-524)-STM fusion, prior to the stop codon. As exemplified, adjacent to the SP-S RBD (aa 327-524)-STM fusion encoding sequence is a nucleic acid sequence encoding the full-length E protein, in a left to right orientation, which is operably linked to, for example, a p11 promoter. The E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a mH5 promoter (pmH5). The M protein nucleic acid sequence can also include appropriate translation initiation sequences such as a Kozak sequence, as well as a nucleic acid sequence encoding a tag at the 3' terminus of the coding sequence prior to the stop codon.
Figure 3Q:
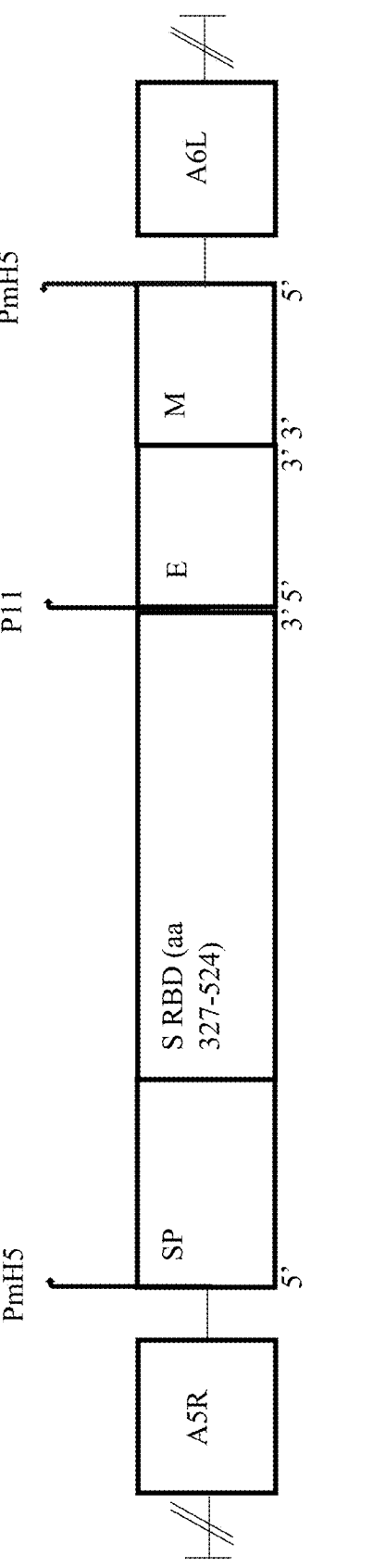
FIG. 3Q provides an exemplary linear schematic of an exemplary recombinant MVA viral vector comprising a nucleic acid sequence encoding a S protein signal peptide (SP)-S protein RBD (aa 327-524) fusion protein, an E protein, and an M protein inserted between, for example, MVA genes A5R and A6L. As exemplified, a mH5 promoter (pmH5) is operably linked to a nucleic acid encoding a fusion protein, wherein the fusion protein includes a S protein signal peptide derived from amino acids 1-13 of the S protein (SP) and an S protein RBD (aa 327-524) peptide in a left-to-right orientation. A start codon is provided 5' to the SP-S RBD (aa 327-524) fusion encoding nucleic acid. The insert may include a translation initiation sequence, for example a Kozak sequence, prior to the start codon of the signal peptide encoding sequence. In addition, a nucleic acid sequence encoding a tag, for example a C-affinity tag, may be included at the 3' terminus of the SP-S RBD (aa 327-524), prior to the stop codon. As exemplified, adjacent to the SP-S RBD (aa 327-524) fusion encoding sequence is a nucleic acid sequence encoding the full-length E protein, in a left to right orientation, which is operably linked to, for example, a p11 promoter. The E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a mH5 promoter (pmH5). The M protein nucleic acid sequence can also include appropriate translation initiation sequences such as a Kozak sequence, as well as a nucleic acid sequence encoding a tag at the 3' terminus of the coding sequence prior to the stop codon.
Figure 3R:
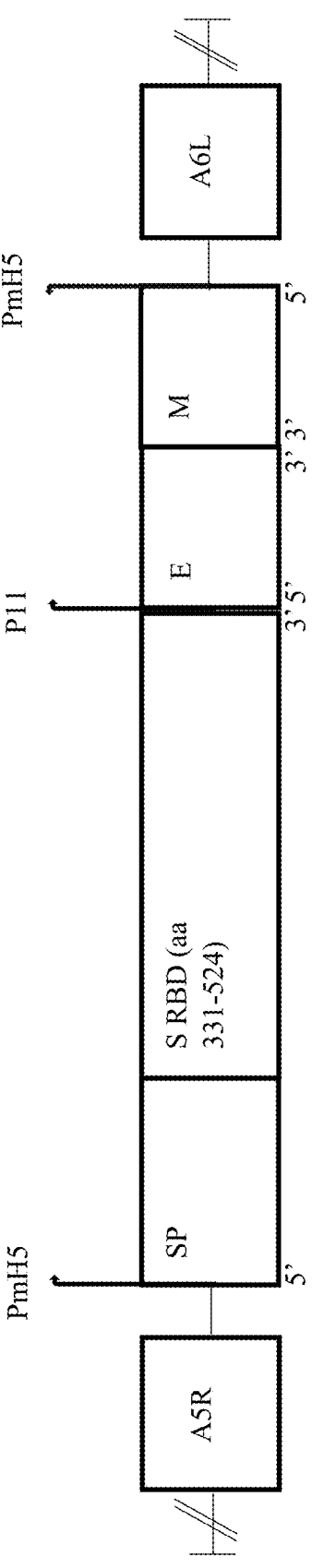
FIG. 3R provides an exemplary linear schematic of an exemplary recombinant MVA viral vector comprising a nucleic acid sequence encoding a S protein signal peptide (SP)-S protein RBD (aa 331-524) fusion protein, an E protein, and an M protein inserted between, for example, MVA genes A5R and A6L. As exemplified, a mH5 promoter (pmH5) is operably linked to a nucleic acid encoding a fusion protein, wherein the fusion protein includes a S protein signal peptide derived from amino acids 1-13 of the S protein (SP) and an S protein RBD (aa 331-524) peptide in a left-to-right orientation. A start codon is provided 5' to the SP-S RBD (aa 331-524) fusion encoding nucleic acid. The insert may include a translation initiation sequence, for example a Kozak sequence, prior to the start codon of the signal peptide encoding sequence. In addition, a nucleic acid sequence encoding a tag, for example a C-affinity tag, may be included at the 3' terminus of the SP-S RBD (aa 331-524), prior to the stop codon. As exemplified, adjacent to the SP-S RBD (aa 331-524) fusion encoding sequence is a nucleic acid sequence encoding the full-length E protein, in a left to right orientation, which is operably linked to, for example, a p11 promoter. The E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a mH5 promoter (pmH5). The M protein nucleic acid sequence can also include appropriate translation initiation sequences such as a Kozak sequence, as well as a nucleic acid sequence encoding a tag at the 3' terminus of the coding sequence prior to the stop codon.
Figure 3S:
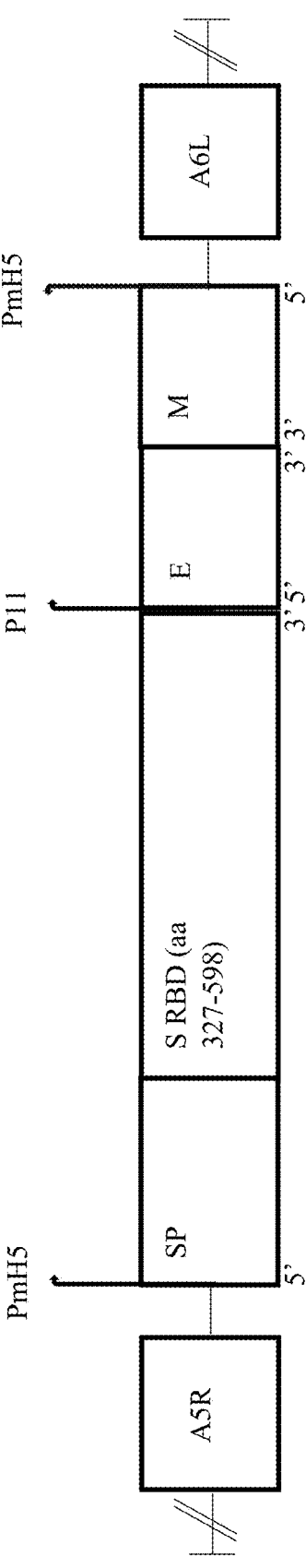
FIG. 3S provides an exemplary linear schematic of an exemplary recombinant MVA viral vector comprising a nucleic acid sequence encoding a S protein signal peptide (SP)-S protein RBD (aa 327-598) fusion protein, an E protein, and an M protein inserted between, for example, MVA genes A5R and A6L. As exemplified, a mH5 promoter (pmH5) is operably linked to a nucleic acid encoding a fusion protein, wherein the fusion protein includes a S protein signal peptide derived from amino acids 1-13 of the S protein (SP) and an S protein RBD (aa 327-598) peptide in a left-to-right orientation. A start codon is provided 5' to the SP-S RBD (aa 327-598) fusion encoding nucleic acid. The insert may include a translation initiation sequence, for example a Kozak sequence, prior to the start codon of the signal peptide encoding sequence. In addition, a nucleic acid sequence encoding a tag, for example a C-affinity tag, may be included at the 3' terminus of the SP-S RBD (aa 327-598), prior to the stop codon. As exemplified, adjacent to the SP-S RBD (aa 327-598) fusion encoding sequence is a nucleic acid sequence encoding the full-length E protein, in a left to right orientation, which is operably linked to, for example, a p11 promoter. The E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a mH5 promoter (pmH5). The M protein nucleic acid sequence can also include appropriate translation initiation sequences such as a Kozak sequence, as well as a nucleic acid sequence encoding a tag at the 3' terminus of the coding sequence prior to the stop codon.
Figure 3T:
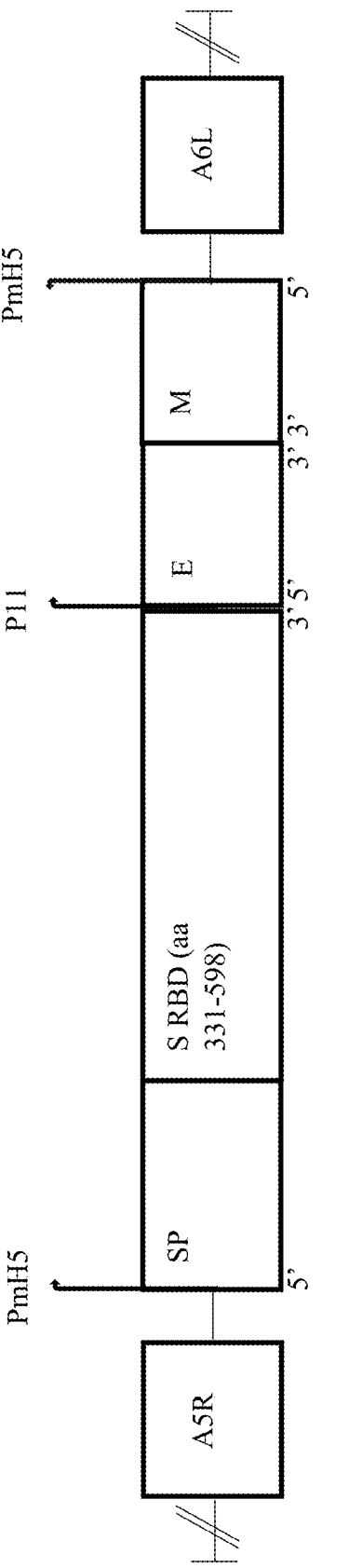
FIG. 3T provides an exemplary linear schematic of an exemplary recombinant MVA viral vector comprising a nucleic acid sequence encoding a S protein signal peptide (SP)-S protein RBD (aa 331-598) fusion protein, an E protein, and an M protein inserted between, for example, MVA genes A5R and A6L. As exemplified, a mH5 promoter (pmH5) is operably linked to a nucleic acid encoding a fusion protein, wherein the fusion protein includes a S protein signal peptide derived from amino acids 1-13 of the S protein (SP) and an S protein RBD (aa 331-598) peptide in a left-to-right orientation. A start codon is provided 5' to the SP-S RBD (aa 331-598) fusion encoding nucleic acid. The insert may include a translation initiation sequence, for example a Kozak sequence, prior to the start codon of the signal peptide encoding sequence. In addition, a nucleic acid sequence encoding a tag, for example a C-affinity tag, may be included at the 3' terminus of the SP-S RBD (aa 331-598), prior to the stop codon. As exemplified, adjacent to the SP-S RBD (aa 331-598) fusion encoding sequence is a nucleic acid sequence encoding the full-length E protein, in a left to right orientation, which is operably linked to, for example, a p11 promoter. The E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a mH5 promoter (pmH5). The M protein nucleic acid sequence can also include appropriate translation initiation sequences such as a Kozak sequence, as well as a nucleic acid sequence encoding a tag at the 3' terminus of the coding sequence prior to the stop codon.

In some embodiments, an rMVA viral vector is provided which encodes a partial spike(S) protein, the envelope (E) protein, and the membrane (M) protein of the SARS-CoV2, wherein the partial S protein is the receptor biding domain (RBD) of the SARS-CoV2 S protein, and wherein the RBD binding protein is flanked on its NH-terminus by a S protein signal peptide derived from amino acids 1 to 13 of the S protein, and flanked on its carboxy terminus by a S protein transmembrane domain derived from amino acids 1214 to 1273, or a fragment thereof. The flanking S protein signal peptide (SP) is provided below in Table 12 as SEQ ID NO: 55, and its nucleic acid sequence is provided as SEQ ID NO: 56. An optimized nucleic acid sequence of the SP is provided in SEQ ID NO: 59. The S protein transmembrane domain (STM) is provided below in Table 8 as SEQ ID NO: 57, and its nucleic acid sequence is provided as SEQ ID NO: 58, and an optimized nucleic acid sequence provided as SEQ ID NO: 60. In some embodiments, the linear S epitope comprises amino acids 327 to 524 of the S protein, flanked by the SP and STM. The SP-RBD (aa 327-524)-STM peptide is provided in SEQ ID NO: 61. In some embodiments, the linear S epitope comprises amino acids 331 to 524 of the S protein, flanked by the SP and STM. The SP-RBD (aa 331-524)-STM peptide is provided in SEQ ID NO: 62. In some embodiments, the nucleic acid is arranged so that the S SP-RBD-TM, E, and M encoding sequences are linearly adjacent. A linear representation of a single MVA insert encoding a partial S protein encoding amino acids 1-13 (SP), 331 to 524 (RBD), and 1214-1273 (STM), an E protein, and an M protein suitable for forming a VLP upon expression is provided for in FIG. 3G. A linear representation of a single MVA insert encoding a partial S protein encoding amino acids 1-13 (SP), 327 to 524 (RBD), and 1214-1273 (STM), an E protein, and an M protein suitable for forming a VLP upon expression is provided for in FIG. 3H. In some embodiments, the partial S protein SP-RBD (aa 327-524)-STM is expressed as provided for in SEQ ID NO: 61, the E protein is expressed as a full-length protein, as provided for in SEQ ID NO: 40, and the M protein is expressed as a full-length protein, as provided for in SEQ ID NO: 43, or sequences at least 70%, 75%, 80%, 85%, 90%, or 95% homologous thereto. In some embodiments, the partial S protein SP-RBD (aa 331-524)-STM is expressed as provided for in SEQ ID NO: 62, the E protein is expressed as a full-length protein, as provided for in SEQ ID NO: 40, and the M protein is expressed as a full-length protein, as provided for in SEQ ID NO: 43, or sequences at least 70%, 75%, 80%, 85%, 90%, or 95% homologous thereto. In some embodiments, provided herein is a plasmid or MVA viral vector containing a nucleic acid sequence encoding SEQ ID NOS: 61 or 62, 40, and 43, or sequences at least 70%, 75%, 80%, 85%, 90%, or 95% homologous thereto. In some embodiments, provided herein is a plasmid or MVA viral vector containing a nucleic acid sequence encoding SEQ ID NOS: 67 or 68, 40, and 43, or sequences at least 70%, 75%, 80%, 85%, 90%, or 95% homologous thereto. In some embodiments, provided herein is a nucleic acid sequence comprising SEQ ID NOS: 63 or 64, 41, and 44, or sequences at least 70%, 75%, 80%, 85%, 90%, or 95% homologous thereto. In some embodiments, provided herein is a nucleic acid encoding the partial S protein, the E protein, and M protein, wherein the nucleic acid has been optimized for expression in the MVA viral vector, for example as provided in SEQ ID NOS: 65 or 66, 42, and 45, or sequences at least 70%, 75%, 80%, 85%, 90%, or 95% homologous thereto. In some embodiments, the nucleic acid sequence encodes for an additional amino acid sequence such as a tag, for example a C-terminus tag such as EPEA suitable for use during assay detection. The nucleic acid sequences may further comprise suitable promoter sequences such as, for example but not limited to, those derived from pmH5, p11, pSyn, pHyb, or any other suitable promoter sequence. In addition, the nucleic acid sequence for insertion may further include suitable translation initiation sequences, such as for example, a Kozak consensus sequence. In addition, the nucleic acid sequence can include appropriate stop codons, for example TAA, TAG, or TGA, or combinations or multiples thereof, at the 3'end of the nucleic acid sequence following the last amino acid sequence of the protein or tag. Furthermore, the nucleic acid sequence can include a vaccinia virus termination sequence 3' of the last stop codon of each encoded protein. In addition, the nucleic acid sequence for insertion may further include restriction enzyme sites useful for generating shuttle vectors for ease of insertion of the antigenic sequence. Exemplary nucleic acid sequences for insertion encoding the S protein SP-RBD (327-524)-STM region, the E protein, and the M protein are provided as SEQ ID NOS: 69 or 70. Exemplary nucleic acid sequences for insertion encoding the S protein SP-RBD (331-524)-STM region, the E protein, and the M protein are provided as SEQ ID NOS: 71 or 72. In some embodiments, the rMVA comprises a nucleic acid sequence selected from SEQ ID NO: 69 (FIG. 3I-3J), 70 (FIG. 3K-3L), 71 (FIG. 3M-3N), or 72 (FIG. 3O-3P), or a sequence at least 70%, 75%, 80%, 85%, 90%, 95%, or 99% homologous thereto.

In an alternate embodiment, the nucleic acid insert encodes a linear S epitope which further comprises a signal peptide, the E protein, and the M protein (see, e.g., FIG. 3Q, FIG. 3R, FIG. 3S, FIG. 3T). The S protein signal peptide can comprise or be derived from, for example, amino acids 1-13 (MFVFLVLLPLVSS) (SEQ ID NO: 55) of the SARS-CoV2 S protein. In some embodiments, the S protein encoded comprises an RBD consensus sequence. In some embodiments, the RBD consensus sequence further comprises an S protein signal peptide, for example derived from SEQ ID NO: 55. In some embodiments, the rMVA expresses the linear RBD epitope comprising amino acids 327-524. In some embodiments, the rMVA expresses the amino acid sequences comprising SEQ ID NOS: 55 and 20, or sequences at least 70%, 75%, 80%, 85%, 90%, or 95% homologous thereto. In some embodiments, the rMVA expresses the linear RBD epitope comprising amino acids 331-524. In some embodiments, the rMVA expresses the amino acid sequences comprising SEQ ID NOS: 55 and 21, or sequences at least 70%, 75%, 80%, 85%, 90%, or 95% homologous thereto. In some embodiments, the rMVA expresses the linear RBD epitope comprising amino acids 327-598. In some embodiments, the rMVA expresses the amino acid sequences comprising SEQ ID NOS: 55 and 161, or sequences at least 70%, 75%, 80%, 85%, 90%, or 95% homologous thereto. In some embodiments, the rMVA expresses the linear RBD epitope comprising amino acids 331-598. In some embodiments, the rMVA expresses the amino acid sequences comprising SEQ ID NOS: 55 and 162, or sequences at least 70%, 75%, 80%, 85%, 90%, or 95% homologous thereto. In some embodiments, the RBD peptide comprises substitutions K417T, E484K, and N501Y. In some embodiments, the rMVA expresses the amino acid sequences comprising SEQ ID NOS: 55 and 32, or sequences at least 70%, 75%, 80%, 85%, 90%, or 95% homologous thereto. In some embodiments, the rMVA expresses the amino acid sequences comprising SEQ ID NOS: 55 and 33, or sequences at least 70%, 75%, 80%, 85%, 90%, or 95% homologous thereto. In some embodiments, the rMVA expresses the amino acid sequences comprising SEQ ID NOS: 55 and 163, or sequences at least 70%, 75%, 80%, 85%, 90%, or 95% homologous thereto. In some embodiments, the rMVA expresses the amino acid sequences comprising SEQ ID NOS: 55 and 164, or sequences at least 70%, 75%, 80%, 85%, 90%, or 95% homologous thereto. In some embodiments, the rMVA encodes an amino acid sequence comprising SEQ ID NOS: 55, 20, 40, and 43, or sequences at least 70%, 75%, 80%, 85%, 90%, or 95% homologous thereto. In some embodiments, the rMVA encodes an amino acid sequence of SEQ ID NO: 55, 21, 40, and 43, or sequences at least 70%, 75%, 80%, 85%, 90%, or 95% homologous thereto. In some embodiments, the rMVA encodes amino acid sequences of SEQ ID NOS: 55, 32, 40, and 43 or sequences at least 70%, 75%, 80%, 85%, 90%, or 95% homologous thereto. In some embodiments, the rMVA encodes amino acid sequences comprising SEQ ID NOS: 55, 33, 40, and 43, or sequences at least 70%, 75%, 80%, 85%, 90%, or 95% homologous thereto. In some embodiments, the rMVA encodes amino acid sequences comprising SEQ ID NOS: 55, 161, 40, and 43, or sequences at least 70%, 75%, 80%, 85%, 90%, or 95% homologous thereto. In some embodiments, the rMVA encodes amino acid sequences comprising SEQ ID NOS: 55, 162, 40, and 43, or sequences at least 70%, 75%, 80%, 85%, 90%, or 95% homologous thereto. In some embodiments, the rMVA encodes amino acid sequences comprising SEQ ID NOS: 55, 163, 40, and 43, or sequences at least 70%, 75%, 80%, 85%, 90%, or 95% homologous thereto. In some embodiments, the rMVA encodes amino acid sequences comprising SEQ ID NOS: 164, 33, 40, and 43, or sequences at least 70%, 75%, 80%, 85%, 90%, or 95% homologous thereto. In some embodiments, the nucleic acid sequence encodes for an additional amino acid sequence such as a tag, for example a C-terminus tag such as EPEA suitable for use during assay detection. The nucleic acid sequences may further comprise suitable promoter sequences such as, for example but not limited to, those derived from pmH5, p11, pSyn, pHyb, or any other suitable promoter sequence. In addition, the nucleic acid sequence for insertion may further include suitable translation initiation sequences, such as for example, a Kozak consensus sequence. In addition, the nucleic acid sequence can include appropriate stop codons, for example TAA, TAG, or TGA, or combinations or multiples thereof, at the 3'end of the nucleic acid sequence following the last amino acid sequence of the protein or tag. Furthermore, the nucleic acid sequence can include a vaccinia virus termination sequence 3' of the last stop codon of each encoded protein. In addition, the nucleic acid sequence for insertion may further include restriction enzyme sites useful for generating shuttle vectors for ease of insertion of the antigenic sequence. In some embodiments, the rMVA comprises SEQ ID NO: 158 (FIG. 3U-3V), or a sequence at least 70%, 75%, 80%, 85%, 90%, 95%, or 99% homologous thereto.

TABLE 12

| SP Peptide, TM Peptide, SP-RBD-STM Peptide Sequences | |
| --- | --- |
| SEQ ID NO: 55-<br>S protein signal<br>peptide amino<br>acids 1 to 13 | MFVFLVLLPLVSS |
| SEQ ID NO: 56-<br>S protein signal<br>peptide nucleic<br>acid sequence | ATGTTTGTTTTTCTTGTTTTATTGCCACTAGTCTCTAGT |
| SEQ ID NO: 57-<br>S protein<br>transmembrane<br>domain amino<br>acids 1214 to 1273 | WYIWLGFIAGLIAIVMVTIMLCCMTSCCSCLKGCCSCGSCCKFDEDDSEPVLKGVK<br>LHYT |
| SEQ ID NO: 58-<br>S protein<br>transmembrane<br>domain nucleic<br>acid sequence | TGGTACATTTGGCTAGGTTTTATAGCTGGCTTGATTGCCATAGTAATGGTGACAA<br>TTATGCTTTGCTGTATGACCAGTTGCTGTAGTTGTCTCAAGGGCTGTTGTTCTTG<br>TGGATCCTGCTGCAAATTTGATGAAGACGACTCTGAGCCAGTGCTCAAAGGAGT<br>CAAATTACATTACACA |
| SEQ ID NO: 59-<br>S protein signal<br>peptide nucleic<br>acid sequence-<br>optimized | ATGTTCGTGTTCCTAGTCCTACTACCGCTAGTCTCTTCT |
| SEQ ID NO: 60-<br>S protein<br>transmembrane<br>domain nucleic<br>acid sequence-<br>optimized | TGGTACATCTGGCTAGGATTCATTGCTGGACTAATTGCGATCGTCATGGTCACC<br>ATCATGCTATGCTGTATGACCTCCTGTTGCTCCTGTCTAAAGGGATGTTGTTCCT<br>GCGGATCCTGTTGCAAGTTCGATGAAGATGATAGTGAACCGGTCCTAAAGGGTG<br>TCAAGCTACACTACACA |
| Seq. ID No. 61-<br>SP-RBD (aa 327-<br>524)-STM peptide<br>amino acid<br>sequence | MFVFLVLLPLVSSVRFPNITNLCPFGEVFNATRFASVYAWNRKRISNCVADYSVLYN<br>SASFSTFKCYGVSPTKLNDLCFTNVYADSFVIRGDEVRQIAPGQTGKIADYNYKLPD<br>DFTGCVIAWNSNNLDSKVGGNYNYLYRLFRKSNLKPFERDISTEIYQAGSTPCNGV<br>EGFNCYFPLQSYGFQPTNGVGYQPYRVVVLSFELLHAPATVWYIWLGFIAGLIAIV<br>MVTIMLCCMTSCCSCLKGCCSCGSCCKFDEDDSEPVLKGVKLHYT |
| Seq. ID No. 62-<br>SP-RBD (aa 331-<br>524)-STM peptide<br>amino acid<br>sequence | MFVFLVLLPLVSSNITNLCPFGEVFNATRFASVYAWNRKRISNCVADYSVLYNSASF<br>STFKCYGVSPTKLNDLCFTNVYADSFVIRGDEVRQIAPGQTGKIADYNYKLPDDFTG<br>CVIAWNSNNLDSKVGGNYNYLYRLFRKSNLKPFERDISTEIYQAGSTPCNGVEGFN<br>CYFPLQSYGFQPTNGVGYQPYRVVVLSFELLHAPATVWYIWLGFIAGLIAIVMVTIM<br>LCCMTSCCSCLKGCCSCGSCCKFDEDDSEPVLKGVKLHYT |

TABLE 12-continued

SP Peptide, TM Peptide, SP-RBD-STM Peptide Sequences

| | |
|---|---|
| SEQ ID NO: 63-<br>SP-RBD(aa 327-<br>524)-STM peptide<br>nucleic acid<br>sequence | ATGTTTGTTTTTCTTGTTTTATTGCCACTAGTCTCTAGTGTTAGATTTCCTAATAT<br>TACAGTTAGATTTCCTAATATTACAAACTTGTGCCCTTTTGGTGAAGTTTTTAAC<br>GCCACCAGATTTGCATCTGTTTATGCTTGGAACAGGAAGAGAATCAGCAACTGT<br>GTTGCTGATTATTCTGTCCTATATAATTCCGCATCATTTTCCACTTTTAAGTGTTA<br>TGGAGTGTCTCCTACTAAATTAAATGATCTCTGCTTTACTAATGTCTATGCAGAT<br>TCATTTGTAATTAGAGGTGATGAAGTCAGACAAATCGCTCCAGGGCAAACTGGA<br>AAGATTGCTGATTATAATTATAAATTACCAGATGATTTTACAGGCTGCGTTATA<br>GCTTGGAATTCTAACAATCTTGATTCTAAGGTTGGTGGTAATTATAATTACCTGT<br>ATAGATTGTTTAGGAAGTCTAATCTCAAACCTTTTGAGAGAGATATTTCAACTG<br>AAATCTATCAGGCCGGTAGCACACCTTGTAATGGTGTTGAAGGTTTTAATTGTT<br>ACTTTCCTTTACAATCATATGGTTTCCAACCCACTAATGGTGTTGGTTACCAACC<br>ATACAGAGTAGTAGTACTTTCTTTTGAACTTCTACATGCACCAGCAACTGTTTGT<br>GGACCTAAAAAGTCTACTAATTTGGTTAAAAACAAATGTGTCAATTGGTACATT<br>TGGCTAGGTTTTATAGCTGGCTTGATTGCCATAGTAATGGTGACAATTATGCTTT<br>GCTGTATGACCAGTTGCTGTAGTTGTCTCAAGGGCTGTTGTTCTTGTGGATCCTG<br>CTGCAAATTTGATGAAGACGACTCTGAGCCAGTGCTCAAAGGAGTCAAATTACA<br>TTACACA |
| SEQ ID NO: 64-<br>SP-RBD(aa 331-<br>524)-STM peptide<br>nucleic acid<br>sequence | ATGTTTGTTTTTCTTGTTTTATTGCCACTAGTCTCTAGTAATATTACAAACTTGTG<br>CCCTTTTGGTGAAGTTTTTAACGCCACCAGATTTGCATCTGTTTATGCTTGGAAC<br>AGGAAGAGAATCAGCAACTGTGTTGCTGATTATTCTGTCCTATATAATTCCGCA<br>TCATTTTCCACTTTTAAGTGTTATGGAGTGTCTCCTACTAAATTAAATGATCTCT<br>GCTTTACTAATGTCTATGCAGATTCATTTGTAATTAGAGGTGATGAAGTCAGAC<br>AAATCGCTCCAGGGCAAACTGGAAAGATTGCTGATTATAATTATAAATTACCAG<br>ATGATTTTACAGGCTGCGTTATAGCTTGGAATTCTAACAATCTTGATTCTAAGGT<br>TGGTGGTAATTATAATTACCTGTATAGATTGTTTAGGAAGTCTAATCTCAAACCT<br>TTTGAGAGAGATATTTCAACTGAAATCTATCAGGCCGGTAGCACACCTTGTAAT<br>GGTGTTGAAGGTTTTAATTGTTACTTTCCTTTACAATCATATGGTTTCCAACCCA<br>CTAATGGTGTTGGTTACCAACCATACAGAGTAGTAGTACTTTCTTTTGAACTTCT<br>ACATGCACCAGCAACTGTTTGTGGACCTAAAAAGTCTACTAATTTGGTTAAAAA<br>CAAATGTGTCAATTGGTACATTTGGCTAGGTTTTATAGCTGGCTTGATTGCCATA<br>GTAATGGTGACAATTATGCTTTGCTGTATGACCAGTTGCTGTAGTTGTCTCAAGG<br>GCTGTTGTTCTTGTGGATCCTGCTGCAAATTTGATGAAGACGACTCTGAGCCAGT<br>GCTCAAAGGAGTCAAATTACATTACACA |
| SEQ ID NO: 65-<br>SP-RBD(aa 327-<br>524)-STM peptide<br>nucleic acid<br>sequence<br>optimized | ATGTTCGTGTTCCTAGTCCTACTACCGCTAGTCTCTTCTGTCAGATTTCCGAACA<br>TCACGAACCTATGTCCGTTCGGAGAAGTGTTCAACGCGACAAGATTTGCGTCTG<br>TCTATGCGTGGAACAGAAAAAGAATCAGTAACTGCGTCGCGGACTACTCCGTCC<br>TATACAACTCTGCCTCTTTCTCCACGTTCAAATGCTACGGTGTATCTCCGACAAA<br>GCTAAACGATCTATGCTTCACCAACGTCTACGCGGACTCCTTCGTAATCAGAGG<br>AGATGAAGTTAGACAGATTGCGCCGGGACAAACTGGAAAGATCGCGGATTATA<br>ACTACAAGCTACCGGACGACTTCACCGGATGTGTAATTGCGTGGAATTCGAACA<br>ACCTAGACTCCAAAGTCGGAGGAAACTACAACTACTTGTACAGACTATTCAGAA<br>AGTCCAACCTAAAGCCGTTCGAGAGAGACATCTCCACCGAAATCTATCAGGCTG<br>GATCTACACCGTGTAATGGTGTCGAAGGATTCAACTGCTACTTCCCGCTACAGT<br>CTTACGGATTTCAACCGACAAACGGTGTAGGATATCAGCCGTACAGAGTCGTCG<br>TACTATCCTTCGAACTACTACATGCTCCGGCGACAGTATGGTACATCTGGCTAG<br>GATTCATTGCTGGACTAATTGCGATCGTCATGGTCACCATCATGCTATGCTGTAT<br>GACCTCCTGTTGCTCCTGTCTAAAGGGATGTTGTTCCTGCGGATCCTGTTGCAAG<br>TTCGATGAAGATGATAGTGAACCGGTCCTAAAGGGTGTCAAGCTACACTACACA |
| SEQ ID NO: 66-<br>SP-RBD(aa 331-<br>524)-STM peptide<br>nucleic acid<br>sequence<br>optimized | ATGTTCGTGTTCCTAGTCCTACTACCGCTAGTCTCTTCTAACATCACGAACCTAT<br>GTCCGTTCGGAGAAGTGTTCAACGCGACAAGATTTGCGTCTGTCTATGCGTGGA<br>ACAGAAAAAGAATCAGTAACTGCGTCGCGGACTACTCCGTCCTATACAACTCTG<br>CCTCTTTCTCCACGTTCAAATGCTACGGTGTATCTCCGACAAAGCTAAACGATCT<br>ATGCTTCACCAACGTCTACGCGGACTCCTTCGTAATCAGAGGAGATGAAGTTAG<br>ACAGATTGCGCCGGGACAAACTGGAAAGATCGCGGATTATAACTACAAGCTAC<br>CGGACGACTTCACCGGATGTGTAATTGCGTGGAATTCGAACAACCTAGACTCCA<br>AAGTCGGAGGAAACTACAACTACTTGTACAGACTATTCAGAAAGTCCAACCTAA<br>AGCCGTTCGAGAGAGACATCTCCACCGAAATCTATCAGGCTGGATCTACACCGT<br>GTAATGGTGTCGAAGGATTCAACTGCTACTTCCCGCTACAGTCTTACGGATTTCA<br>ACCGACAAACGGTGTAGGATATCAGCCGTACAGAGTCGTCGTACTATCCTTCGA<br>ACTACTACATGCTCCGGCGACAGTATGGTACATCTGGCTAGGATTCATTGCTGG<br>ACTAATTGCGATCGTCATGGTCACCATCATGCTATGCTGTATGACCTCCTGTTGC<br>TCCTGTCTAAAGGGATGTTGTTCCTGCGGATCCTGTTGCAAGTTCGATGAAGAT<br>GATAGTGAACCGGTCCTAAAGGGTGTCAAGCTACACTACACA |
| Seq. ID No. 67-<br>SP-RBD (aa 327-<br>524)-STM peptide<br>amino acid<br>sequence (K417T,<br>E484K, N501Y) | MFVFLVLLPLVSSVRFPNITNLCPFGEVFNATRFASVYAWNRKRISNCVADYSVLYN<br>SASFSTFKCYGVSPTKLNDLCFTNVYADSFVIRGDEVRQIAPGQTGTIADYNYKLPD<br>DFTGCVIAWNSNNLDSKVGGNYNYLYRLFRKSNLKPFERDISTEIYQAGSTPCNGV<br>KGFNCYFPLQSYGFQPTYGVGYQPYRVVVLSFELLHAPATVWYIWLGFIAGLIAIV<br>MVTIMLCCMTSCCSCLKGCCSCGSCCKFDEDDSEPVLKGVKLHYT |
| Seq. ID No. 68-<br>SP-RBD (aa 331-<br>524)-STM peptide | MFVFLVLLPLVSSNITNLCPFGEVFNATRFASVYAWNRKRISNCVADYSVLYNSASF<br>STFKCYGVSPTKLNDLCFTNVYADSFVIRGDEVRQIAPGQTGTIADYNYKLPDDFTG<br>CVIAWNSNNLDSKVGGNYNYLYRLFRKSNLKPFERDISTEIYQAGSTPCNGVKGFN |

TABLE 12-continued

| SP Peptide, TM Peptide, SP-RBD-STM Peptide Sequences |
|---|

| amino acid sequence (K417T, E484K, N501Y) | CYFPLQSYGFQPTYGVGYQPYRVVVLSFELLHAPATVWYIWLGFIAGLIAIVMVTIM LCCMTSCCSCLKGCCSCGSCCKFDEDDSEPVLKGVKLHYT |
|---|---|
| SEQ ID NO: 161 SP-RBD (aa 327-598)peptide amino acid Sequence | MFVFLVLLPLVSSVRFPNITNLCPFGEVFNATRFASVYAWNRKRISNCVADYSVLYN SASFSTFKCYGVSPTKLNDLCFTNVYADSFVIRGDEVRQIAPGQTGIADYNYKLPD DFTGCVIAWNSNNLDSKVGGNYNYLYRLFRKSNLKPFERDISTEIYQAGSTPCNGV KGFNCYFPLQSYGFQPTYGVGYQPYRVVVLSFELLHAPATVCGPKKSTNLVKNKC VNFNFNGLTGTGVLTESNKKFLPFQQFGRDIADTTDAVRDPQTLEILDITPCSFGGVS |
| SEQ ID NO: 162 SP-RBD (aa 331-598) peptide amino acid Sequence | MFVFLVLLPLVSSNITNLCPFGEVFNATRFASVYAWNRKRISNCVADYSVLYNSASF STFKCYGVSPTKLNDLCFTNVYADSFVIRGDEVRQIAPGQTGKIADYNYKLPDDFTG CVIAWNSNNLDSKVGGNYNYLYRLFRKSNLKPFERDISTEIYQAGSTPCNGVEGFN CYFPLQSYGFQPTNGVGYQPYRVVVLSFELLHAPATVCGPKKSTNLVKNKCVNFNF NGLTGTGVLTESNKKFLPFQQFGRDIADTTDAVRDPQTLEILDITPCSFGGVS |
| SEQ ID NO: 163 SP-RBD (aa 327-598) peptide amino acid Sequence (K417T, E484K, N501Y) | MFVFLVLLPLVSSVRFPNITNLCPFGEVFNATRFASVYAWNRKRISNCVADYSVLYN SASFSTFKCYGVSPTKLNDLCFTNVYADSFVIRGDEVRQIAPGQTGKIADYNYKLPD DFTGCVIAWNSNNLDSKVGGNYNYLYRLFRKSNLKPFERDISTEIYQAGSTPCNGV EGFNCYFPLQSYGFQPTNGVGYQPYRVVVLSFELLHAPATVCGPKKSTNLVKNKCV NFNFNGLTGTGVLTESNKKFLPFQQFGRDIADTTDAVRDPQTLEILDITPCSFGGVS |
| SEQ ID NO: 164 SP-RBD (aa 331-598) peptide amino acid Sequence (K417T, E484K, N501Y) | MFVFLVLLPLVSSNITNLCPFGEVFNATRFASVYAWNRKRISNCVADYSVLYNSASF STFKCYGVSPTKLNDLCFTNVYADSFVIRGDEVRQIAPGQTGTIADYNYKLPDDFTG CVIAWNSNNLDSKVGGNYNYLYRLFRKSNLKPFERDISTEIYQAGSTPCNGVKGFN CYFPLQSYGFQPTYGVGYQPYRVVVLSFELLHAPATVWYIWLGFIAGLIAIVMVTIM LCCMTSCCSCLKGCCSCGSCCKFDEDDSEPVLKGVKLHYTCGPKKSTNLVKNKCV NFNFNGLTGTGVLTESNKKFLPFQQFGRDIADTTDAVRDPQTLEILDITPCSFGGVS |

Alternatively, an rMVA viral vector is provided which encodes a tandem repeat sequence, the envelope (E) protein, and the membrane (M) protein of the SARS-CoV2, wherein the tandem repeat sequence is derived from linear epitopes of the S protein RBD domain. In some embodiments, the tandem repeat is for example (RBD-spacer-RBD-spacer) x or (RBD Seq. 1-spacer-RBD Seq. 2-spacer) x, wherein RBD is any S protein RBD peptide, RBD Seq. 1 is a first S protein RBD peptide, and RBD Seq. 2 is a second S protein RBD peptide, and wherein x=2, 3, 4, 5, 6, 7, 8, 9, or 10. In some embodiments, the tandem repeat optionally comprises a methionine amino acid at the NH-terminus. In some embodiments, the RBD peptides are selected from one or more peptides derived from amino acids 331 to 524 of the SARS-CoV2 S protein or 327-524 of the SARS-CoV2 S protein. In some embodiments, the linear epitopes encoded by the rMVA are selected from the amino acids 504 to 524 and amino acids 473 to 490 of the SARS-CoV2 S protein. In some embodiments, the linear epitopes encoded by the rMVA are the amino acids 504 to 524 and amino acids 473 to 490 of the SARS-CoV2 S protein. In some embodiments, the sequence inserted into the MVA viral vector encodes a S protein RBD peptide containing tandem repeat sequence ((aa504-524)-spacer-(aa473-490)-spacer) x, wherein x=2, 3, 4, 5, 6, 7, 8, 9, or 10. In some embodiments, x=3-7. In some embodiments, x=5.

Figure 4A:
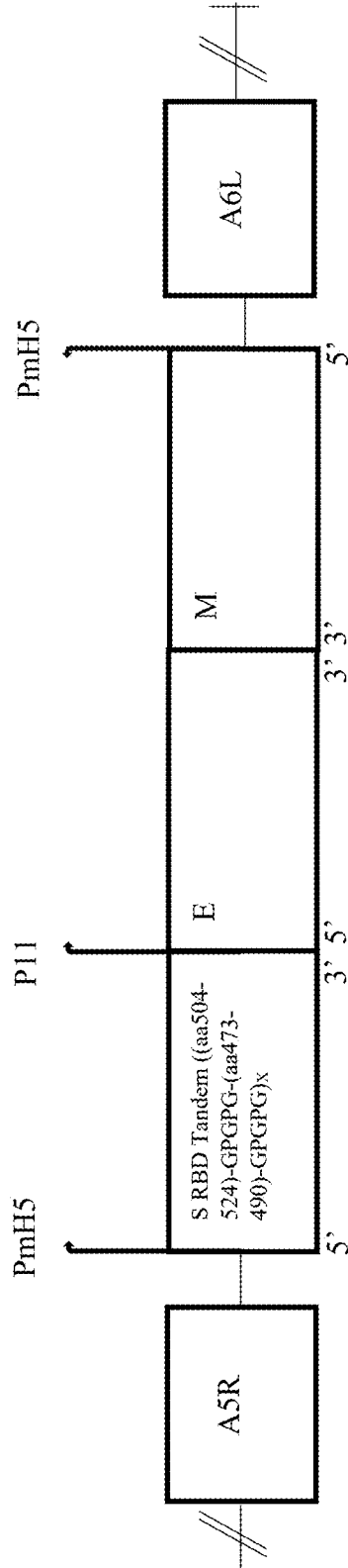
FIG. 4A provides an exemplary linear schematic of an exemplary recombinant MVA viral vector comprising a nucleic acid sequence encoding a tandem repeat of S protein RBD derived amino acids, an E protein, and an M protein inserted between, for example, MVA genes A5R and A6L. As exemplified, a mH5 promoter (pmH5) is operably linked to a nucleic acid encoding the S RBD tandem repeat ((aa504-524)-GPGPG-(aa473-490)-GPGPG) 5, in a left-to-right orientation. A start codon is provided 5' to the S RBD tandem repeat. The insert may include a translation initiation sequence, for example a Kozak sequence, prior to the start codon of the S RBD tandem repeat sequence. In addition, a nucleic acid sequence encoding a tag, for example a C-affinity tag, may be included at the 3' terminus of the S RBD tandem repeat protein, prior to the stop codon. As exemplified, adjacent to the S RBD tandem repeat protein is a nucleic acid sequence encoding the full-length E protein, in a left to right orientation, which is operably linked to, for example, a p11 promoter. Similar to the S RBD tandem repeat, the E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a pmH5 promoter. The M protein nucleic acid sequence can also include appropriate translation initiation sequences such as a Kozak sequence, as well as a nucleic acid sequence encoding a tag at the 3' terminus of the coding sequence prior to the stop codon.

In some embodiments, the nucleic acid is arranged so that the tandem repeat, E, and M encoding sequences are linearly adjacent. A linear representation of a single MVA insert encoding a tandem repeat, an E protein, and an M protein suitable for forming a VLP upon expression is provided for in FIG. 4A. In some embodiments, the tandem repeat is expressed as provided for in SEQ ID NO: 34, further optionally comprising a methionine at the NH-terminus, wherein x is 2-10, the E protein is expressed as a full-length protein, as provided for in SEQ ID NO: 40, and the M protein is expressed as a full-length protein, as provided for in SEQ ID NO: 43, or sequences at least 70%, 75%, 80%, 85%, 90%, or 95% homologous thereto. In some embodiments, provided herein is a plasmid or MVA viral vector containing a nucleic acid sequence encoding SEQ ID NO: 34, wherein x is 2-10 or more than 10, SEQ ID NO: 40, and SEQ ID NO: 43, or sequences at least 70%, 75%, 80%, 85%, 90%, or 95% homologous thereto. In some embodiments, provided herein is a plasmid or MVA viral vector containing a nucleic acid sequence encoding SEQ ID NO: 38, wherein x is 2-10 or more than 10, SEQ ID NO: 40, and SEQ ID NO: 43, or sequences at least 70%, 75%, 80%, 85%, 90%, or 95% homologous thereto. In some embodiments, provided herein is a plasmid or MVA viral vector containing a nucleic acid sequence encoding SEQ ID NO: 39, wherein x is 2-10 or more than 10, SEQ ID NO: 40, and SEQ ID NO: 43, or sequences at least 70%, 75%, 80%, 85%, 90%, or 95% homologous thereto. In some embodiments, provided herein is a nucleic acid sequence comprising SEQ ID NO: 35, wherein x is 2-10 or more than 10, SEQ ID NO: 41, and SEQ ID NO: 44, or sequences at least 70%, 75%, 80%, 85%, 90%, or 95% homologous thereto. In some embodiments, provided herein is a nucleic acid sequence comprising SEQ ID NO: 36, SEQ ID NO: 41, and SEQ ID NO: 44, or sequences at least 70%, 75%, 80%, 85%, 90%, or 95% homologous thereto. In some embodiments, provided herein is a nucleic acid encoding a tandem repeat, the E protein, and M protein, wherein the nucleic acid has been optimized for expression in the MVA viral vector, for example as provided in SEQ ID NOS: 37, 42, and 45, or sequences at least 70%, 75%, 80%, 85%, 90%, or 95% homologous thereto. In some embodiments, the nucleic acid sequence encodes for an additional amino acid sequence such as a tag, for example a C-terminus tag such as EPEA suitable for use during assay detection. The nucleic acid sequences may further comprise suitable promoter sequences such as, for example but not limited to, those derived from pmH5, p11, pSyn, pHyb, or any other suitable promoter sequence. In addition, the nucleic acid sequence for insertion may further include suitable translation initiation sequences, such as for example, a Kozak consensus sequence. In addition, the nucleic acid sequence can include appropriate stop codons, for example TAA, TAG, or TGA, or combinations or multiples thereof, at the 3'end of the nucleic acid sequence following the last amino acid sequence of the protein or tag. Furthermore, the nucleic acid sequence can include a vaccinia virus termination sequence 3' of the last stop codon of each encoded protein. In addition, the nucleic acid sequence for insertion may further include restriction enzyme sites useful for generating shuttle vectors for ease of insertion of the antigenic sequence. Exemplary nucleic acid sequences for insertion encoding the tandem repeat, the E protein, and the M protein is provided as SEQ ID NOS: 73 or 74. In some embodiments, the rMVA comprises a nucleic acid sequence of SEQ ID NO: 73 (FIG. 4B-4C), or a sequence at least 70%, 75%, 80%, 85%, 90%, 95%, or 99% homologous thereto. In some embodiments, the rMVA comprises a nucleic acid sequence of SEQ ID NO: 74 (FIG. 4D-4E), or a sequence at least 70%, 75%, 80%, 85%, 90%, 95%, or 99% homologous thereto.

Alternatively, an rMVA viral vector is provided which encodes a tandem repeat sequence, the envelope (E) protein, and the membrane (M) protein of the SARS-CoV2, wherein the tandem repeat sequence is derived from linear epitopes of the S protein RBD domain, and is flanked on its NH-terminus by a SP peptide, for example, SEQ ID NO: 55, and flanked on its carboxy terminus by an STM, for example SEQ ID NO: 57. In some embodiments, the tandem repeat is for example (RBD-spacer-RBD-spacer) x or (RBD Seq. 1-spacer-RBD Seq. 2-spacer) x, wherein RBD is any S protein RBD peptide, RBD Seq. 1 is a first S protein RBD peptide, and RBD Seq. 2 is a second S protein RBD peptide, and wherein x=2, 3, 4, 5, 6, 7, 8, 9, or 10. In some embodiments, the RBD peptides are selected from one or more peptides derived from amino acids 331 to 524 of the SARS-CoV2 S protein or from amino acids 327 to 524 of the SARS-CoV2 S protein. In some embodiments, the linear epitopes encoded by the rMVA are selected from the amino acids 504 to 524 and amino acids 473 to 490 of the SARS-CoV2 S protein. In some embodiments, the linear epitopes encoded by the rMVA are the amino acids 504 to 524 and amino acids 473 to 490 of the SARS-CoV2 S protein. In some embodiments, the sequence inserted into the MVA viral vector encodes a S protein RBD peptide containing tandem repeat sequence ((aa504-524)-spacer-(aa473-490)-spacer) x, wherein x=2, 3, 4, 5, 6, 7, 8, 9, or 10. In some embodiments, x=3-7. In some embodiments, x=5.

Figure 4F:
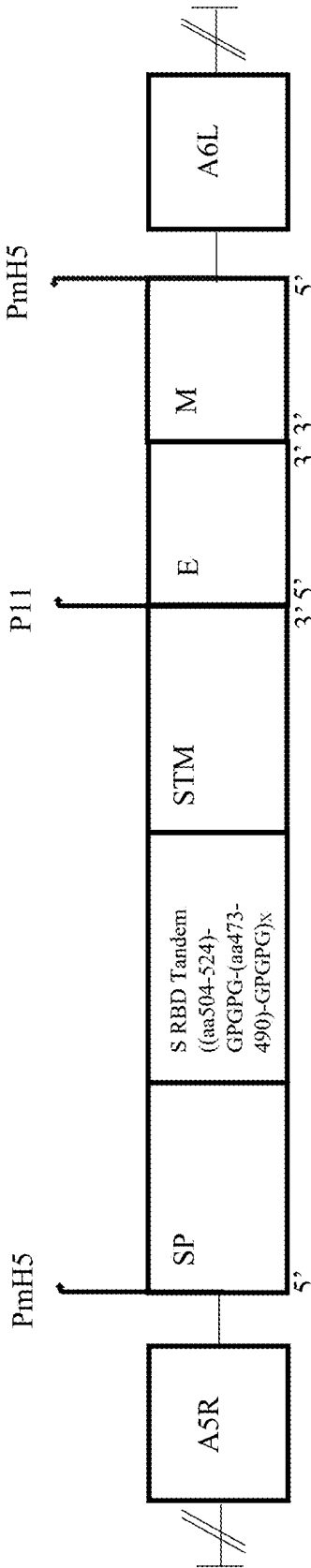
FIG. 4F provides an exemplary linear schematic of an exemplary recombinant MVA viral vector comprising a nucleic acid sequence encoding a signal peptide of the S protein amino acids 1-13 (SP)-S protein RBD tandem repeat-S protein transmembrane domain (STM) fusion protein, an E protein, and an M protein inserted between, for example, MVA genes A5R and A6L. As exemplified, a mH5 promoter (pmH5) is operably linked to a nucleic acid encoding a fusion protein, wherein the fusion protein includes a signal peptide derived from amino acids 1-13 of the S protein (SP), an S protein RBD tandem repeat peptide, and a transmembrane domain derived from amino acids 1214-1273 of the S protein (STM), in a left-to-right orientation. A start codon is provided 5' to the SP-S RBD tandem repeat-STM fusion encoding nucleic acid. The insert may include a translation initiation sequence, for example a Kozak sequence, prior to the start codon of the signal peptide encoding sequence. In addition, a nucleic acid sequence encoding a tag, for example a C-affinity tag, may be included at the 3' terminus of the SP-S RBD tandem repeat-STM fusion, prior to the stop codon. As exemplified, adjacent to the SP-S RBD tandem repeat-STM fusion encoding sequence is a nucleic acid sequence encoding the full-length E protein, in a left to right orientation, which is operably linked to, for example, a p11 promoter. The E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a mH5 promoter (pmH5). The M protein nucleic acid sequence can also include appropriate translation initiation sequences such as a Kozak sequence, as well as a nucleic acid sequence encoding a tag at the 3' terminus of the coding sequence prior to the stop codon.
Figure 5A:
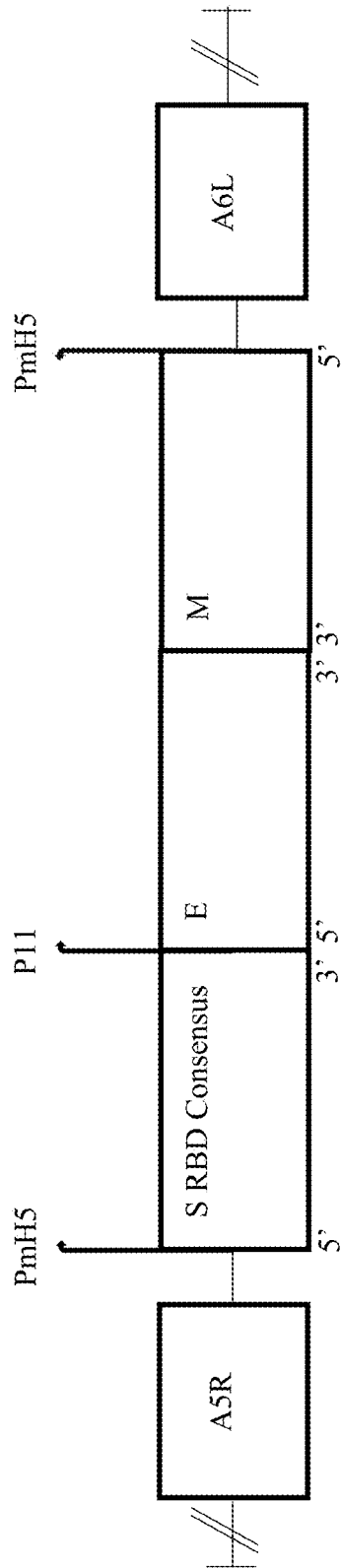
FIG. 5A provides an exemplary linear schematic of an exemplary recombinant MVA viral vector comprising a nucleic acid sequence encoding an S protein RBD consensus sequence, an E protein, and an M protein inserted between, for example, MVA genes A5R and A6L. As exemplified, a mH5 promoter (pmH5) is operably linked to a nucleic acid encoding the S RBD consensus protein in a left-to-right orientation. A start codon is provided 5' to the S RBD consensus encoding nucleic acid. The insert may include a translation initiation sequence, for example a Kozak sequence, prior to the start codon of the S RBD consensus protein encoding sequence. In addition, a nucleic acid sequence encoding a tag, for example a C-affinity tag, may be included at the 3' terminus of the S RBD consensus protein, prior to the stop codon. As exemplified, adjacent to the S RBD consensus protein encoding sequence is a nucleic acid sequence encoding the full-length E protein, in a left to right orientation, which is operably linked to, for example, a p11 promoter. Similar to the S RBD consensus protein, the E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a mH5 promoter (pmH5). The M protein nucleic acid sequence can also include appropriate translation initiation sequences such as a Kozak sequence, as well as a nucleic acid sequence encoding a tag at the 3' terminus of the coding sequence prior to the stop codon.
Figure 5B:
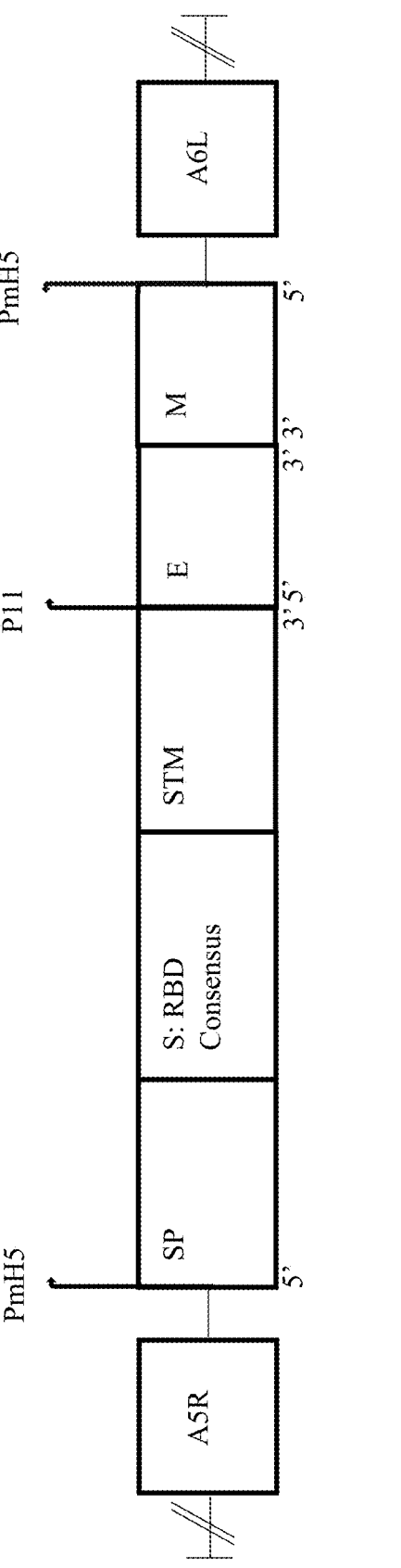
FIG. 5B provides an exemplary linear schematic of an exemplary recombinant MVA viral vector comprising a nucleic acid sequence encoding a signal peptide of the S protein amino acids 1-13 (SP)-S protein RBD consensus-S protein transmembrane domain (STM) fusion protein, an E protein, and an M protein inserted between, for example, MVA genes A5R and A6L. As exemplified, a mH5 promoter (pmH5) is operably linked to a nucleic acid encoding a fusion protein, wherein the fusion protein includes a signal peptide derived from amino acids 1-13 of the S protein (SP), an S protein RBD consensus peptide, and a transmembrane domain derived from amino acids 1214-1273 of the S protein (STM), in a left-to-right orientation. A start codon is provided 5' to the SP-S RBD consensus-STM fusion encoding nucleic acid. The insert may include a translation initiation sequence, for example a Kozak sequence, prior to the start codon of the signal peptide encoding sequence. In addition, a nucleic acid sequence encoding a tag, for example a C-affinity tag, may be included at the 3' terminus of the SP-S RBD consensus-STM fusion, prior to the stop codon. As exemplified, adjacent to the SP-S RBD consensus-STM fusion encoding sequence is a nucleic acid sequence encoding the full-length E protein, in a left to right orientation, which is operably linked to, for example, a p11 promoter. The E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a mH5 promoter (pmH5). The M protein nucleic acid sequence can also include appropriate translation initiation sequences such as a Kozak sequence, as well as a nucleic acid sequence encoding a tag at the 3' terminus of the coding sequence prior to the stop codon.

In some embodiments, the nucleic acid is arranged so that the SP-tandem repeat-TM, E, and M encoding sequences are linearly adjacent. A linear representation of a single MVA insert encoding a SP-tandem repeat-TM, an E protein, and an M protein suitable for forming a VLP upon expression is provided for in FIG. 4F. In some embodiments, the SP-tandem repeat-TM is expressed as provided for in SEQ ID NO: 75, wherein x is 2-10, the E protein is expressed as a full-length protein, as provided for in SEQ ID NO: 40, and the M protein is expressed as a full-length protein, as provided for in SEQ ID NO: 43, or sequences at least 70%, 75%, 80%, 85%, 90%, or 95% homologous thereto. In some embodiments, provided herein is a plasmid or MVA viral vector containing a nucleic acid sequence encoding SEQ ID NO: 77, SEQ ID NO: 40, and SEQ ID NO: 43, or sequences at least 70%, 75%, 80%, 85%, 90%, or 95% homologous thereto. In some embodiments, provided herein is a nucleic acid sequence comprising SEQ ID NO: 76, wherein x is 2-10, SEQ ID NO: 41, and SEQ ID NO: 44, or sequences at least 70%, 75%, 80%, 85%, 90%, or 95% homologous thereto. In some embodiments, provided herein is a nucleic acid sequence comprising SEQ ID NO: 78, SEQ ID NO: 41, and SEQ ID NO: 44, or sequences at least 70%, 75%, 80%, 85%, 90%, or 95% homologous thereto. In some embodiments, provided herein is a nucleic acid encoding a SP-tandem repeat-TM, the E protein, and M protein, wherein the nucleic acid has been optimized for expression in the MVA viral vector, for example as provided in SEQ ID NOS: 76 or 78, 42, and 45, or sequences at least 70%, 75%, 80%, 85%, 90%, or 95% homologous thereto.

In some embodiments, the SP-tandem repeat-TM is expressed as provided for in SEQ ID NO: 79, wherein x is 2-10, the E protein is expressed as a full-length protein, as provided for in SEQ ID NO: 40, and the M protein is expressed as a full-length protein, as provided for in SEQ ID NO: 43, or sequences at least 70%, 75%, 80%, 85%, 90%, or 95% homologous thereto. In some embodiments, provided herein is a plasmid or MVA viral vector containing a nucleic acid sequence encoding SEQ ID NO: 80, SEQ ID NO: 40, and SEQ ID NO: 43, or sequences at least 70%, 75%, 80%, 85%, 90%, or 95% homologous thereto.

In some embodiments, the nucleic acid sequence encodes for an additional amino acid sequence such as a tag, for example a C-terminus tag such as EPEA suitable for use during assay detection. The nucleic acid sequences may further comprise suitable promoter sequences such as, for example but not limited to, those derived from pmH5, p11, pSyn, pHyb, or any other suitable promoter sequence. In addition, the nucleic acid sequence for insertion may further include suitable translation initiation sequences, such as for example, a Kozak consensus sequence. In addition, the nucleic acid sequence can include appropriate stop codons, for example TAA, TAG, or TGA, or combinations or multiples thereof, at the 3'end of the nucleic acid sequence following the last amino acid sequence of the protein or tag. Furthermore, the nucleic acid sequence can include a vaccinia virus termination sequence 3' of the last stop codon of each encoded protein. In addition, the nucleic acid sequence for insertion may further include restriction enzyme sites useful for generating shuttle vectors for ease of insertion of the antigenic sequence. Exemplary nucleic acid sequences for insertion encoding the tandem repeat, the E protein, and the M protein are provided as SEQ ID NOS: 81 or 82. In some embodiments, the rMVA comprises a nucleic acid sequence selected from SEQ ID NO: 81 (FIG. 4G-4H), or a sequence at least 70%, 75%, 80%, 85%, 90%, 95%, or 99% homologous thereto. In some embodiments, the rMVA comprises a nucleic acid sequence selected from SEQ ID NO: 82 (FIG. 4I-4J), or a sequence at least 70%, 75%, 80%, 85%, 90%, 95%, or 99% homologous thereto.

TABLE 13

| SP-RBD Tandem Repeat-TM | |
|---|---|
| SEQ ID NO: 75-amino acid sequence of SARS- | MFVFLVLLPLVSS(YQPYRVVVLSFELLHAPATVGPGPGYQAGSTPCNGVEGFNCYFGPG PG)xWYIWLGFIAGLIAIVMVTIMLCCMTSCCSCLKGCCSCGSCCKFDEDDSEPVLKGVKL HYT, wherein x = 2, 3, 4, 5, 6, 7, 8, 9, or 10. |

TABLE 13-continued

SP-RBD Tandem Repeat-TM

| | |
|---|---|
| CoV2 S Protein SP-RBD Tandem Repeat-TM Sequence. | |
| SEQ ID NO: 76-nucleic acid sequence of SARS-CoV2 S Protein SP-RBD Tandem Repeat-TM Sequence. | ATGTTTGTTTTTCTTGTTTTATTGCCACTAGTCTCTAGT(TACCAACCATACAGAGTAG TAGTACTTTCTTTTGAACTTCTACATGCACCAGCAACTGTTGGTCCTGGACCCGGTTA TCAGGCCGGTAGCACACCTTGTAATGGTGTTGAAGGTTTTAATTGTTACTTTGGTCCT GGACCCGGT)xTGGTACATTTGGCTAGGTTTTATAGCTGGCTTGATTGCCATAGTAATG GTGACAATTATGCTTTGCTGTATGACCAGTTGCTGTAGTTGTCTCAAGGGCTGTTGTT CTTGTGGATCCTGCTGCAAATTTGATGAAGACGACTCTGAGCCAGTGCTCAAAGGAG TCAAATTACATTACACA<br>wherein x = 2, 3, 4, 5, 6, 7, 8, 9, or 10. |
| SEQ ID NO: 77-amino acid sequence of SARS-CoV2 S Protein SP-RBD Tandem Repeat Sequence, x = 5-TM | MFVFLVLLPLVSSYQPYRVVVLSFELLHAPATVGPGPGYQAGSTPCNGVEGFNCYFGPGP GYQPYRVVVLSFELLHAPATVGPGPGYQAGSTPCNGVEGFNCYFGPGPGYQPYRVVVLS FELLHAPATVGPGPGYQAGSTPCNGVEGFNCYFGPGPGYQPYRVVVLSFELLHAPATVG PGPGYQAGSTPCNGVEGFNCYFGPGPGYQPYRVVVLSFELLHAPATVGPGPGYQAGSTP CNGVEGFNCYFGPGPGWYIWLGFIAGLIAIVMVTIMLCCMTSCCSCLKGCCSCGSCCKFD EDDSEPVLKGVKLHYT |
| SEQ ID NO: 78-nucleic acid sequence of SARS-CoV2 S Protein RED Tandem Repeat Sequence, x = 5; optimized | ATGTTCGTGTTCCTAGTCCTACTACCGCTAGTCTCTTCTTATCAGCCGTACAGAGTCGT CGTACTATCCTTCGAACTACTACATGCTCCGGCGACAGTAGGTCCTGGACCCGGTTAT CAGGCTGGATCTACACCGTGTAATGGTGTCGAAGGATTCAACTGCTACTTCGGTCCTG GACCCGGTTATCAGCCGTACAGAGTCGTCGTACTATCCTTCGAACTACTACATGCTCC GGCGACAGTAGGTCCTGGACCCGGTTATCAGGCTGGATCTACACCGTGTAATGGTGT CGAAGGATTCAACTGCTACTTCGGTCCTGGACCCGGTTATCAGCCGTACAGAGTCGTC GTACTATCCTTCGAACTACTACATGCTCCGGCGACAGTAGGTCCTGGACCCGGTTATC AGGCTGGATCTACACCGTGTAATGGTGTCGAAGGATTCAACTGCTACTTCGGTCCTGG ACCCGGTTATCAGCCGTACAGAGTCGTCGTACTATCCTTCGAACTACTACATGCTCCG GCGACAGTAGGTCCTGGACCCGGTTATCAGGCTGGATCTACACCGTGTAATGGTGTC GAAGGATTCAACTGCTACTTCGGTCCTGGACCCGGTTATCAGCCGTACAGAGTCGTC GTACTATCCTTCGAACTACTACATGCTCCGGCGACAGTAGGTCCTGGACCCGGTTATC AGGCTGGATCTACACCGTGTAATGGTGTCGAAGGATTCAACTGCTACTTCGGTCCTGG ACCCGGTTGGTACATCTGGCTAGGATTCATTGCTGGACTAATTGCGATCGTCATGGTC ACCATCATGCTATGCTGTATGACCTCCTGTTGCTCCTGTCTAAAGGGATGTTGTTCCT GCGGATCCTGTTGCAAGTTCGATGAAGATGATAGTGAACCGGTCCTAAAGGGTGTCA AGCTACACTACACA |
| SEQ ID NO: 79-amino acid sequence of SARS-CoV2 S Protein SP-RBD Tandem Repeat-TM Sequence (E484K) | MFVFLVLLPLVSS(YQPYRVVVLSFELLHAPATVGPGPGYQAGSTPCNGVKGFNCYFGPG PG)xWYIWLGFIAGLIAIVMVTIMLCCMTSCCSCLKGCCSCGSCCKFDEDDSEPVLKGVKL HYT, wherein x = 2, 3, 4, 5, 6, 7, 8, 9, or 10. |
| SEQ ID NO: 80-amino acid sequence of SARS-CoV2 S Protein SP-RBD Tandem Repeat Sequence, x = 5-TM (E484K) | MFVFLVLLPLVSSYQPYRVVVLSFELLHAPATVGPGPGYQAGSTPCNGVEGFNCYFGPGP GYQPYRVVVLSFELLHAPATVGPGPGYQAGSTPCNGVKGFNCYFGPGPGYQPYRVVVLS FELLHAPATVGPGPGYQAGSTPCNGVEGFNCYFGPGPGYQPYRVVVLSFELLHAPATVG PGPGYQAGSTPCNGVEGFNCYFGPGPGYQPYRVVVLSFELLHAPATVGPGPGYQAGSTP CNGVEGFNCYFGPGPGWYIWLGFIAGLIAIVMVTIMLCCMTSCCSCLKGCCSCGSCCKFD EDDSEPVLKGVKLHYT |

Figure 6A:
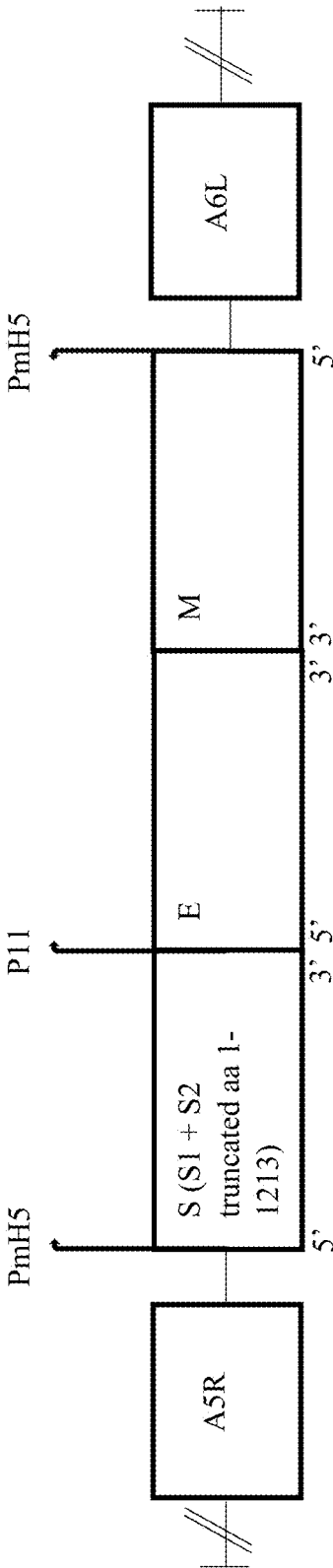
FIG. 6A provides an exemplary linear schematic of an exemplary recombinant MVA viral vector comprising a nucleic acid encoding truncated amino acids 1-1213 derived from the S protein (S1+S2 truncated), an E protein, and M protein inserted between, for example, MVA genes A5R and A6L. As exemplified, a mH5 promoter (pmH5) is operably linked to a nucleic acid encoding truncated amino acids 1-1213 derived from the S protein (S1+S2 truncated), in a left-to-right orientation. The insert may include a translation initiation sequence, for example a Kozak sequence, prior to the start codon of the S (S1+S2 truncated) protein sequence. In addition, a nucleic acid sequence encoding a tag, for example a C-affinity tag, may be included at the 3' terminus of the S protein (S1+S2 truncated), prior to the stop codon. As exemplified, adjacent to the S protein (S1+S2 truncated) is a nucleic acid sequence encoding the full-length E protein, left-to-right orientation, which is operably linked to, for example, a p11 promoter. Similar to the S protein (S1+S2 truncated), the E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a mH5 promoter (pmH5). The M protein nucleic acid sequence can also include appropriate translation initiation sequences such as a Kozak sequence, as well as a nucleic acid sequence encoding a tag at the 3' terminus of the coding sequence prior to the stop codon.
Figure 6H:
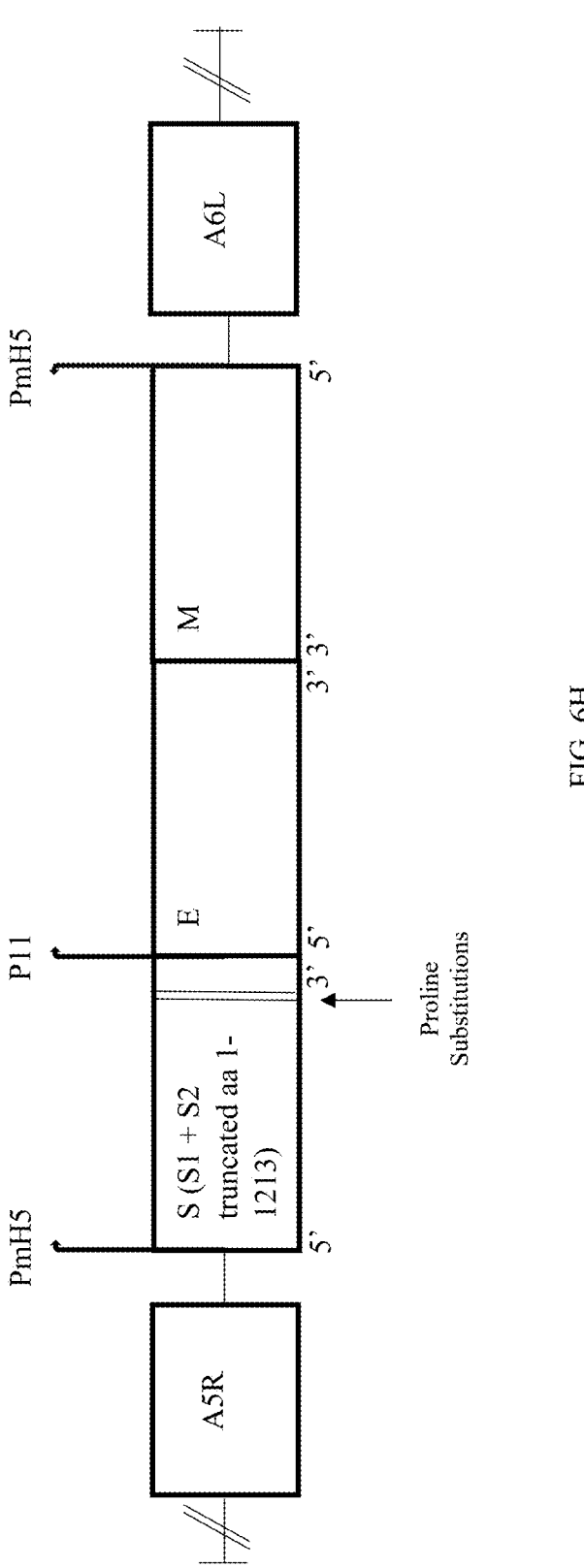
FIG. 6H provides an exemplary linear schematic of an exemplary recombinant MVA viral vector comprising a nucleic acid encoding truncated amino acids 1-1213 derived from the S protein (S1+S2 truncated) with two proline substitutions at amino acids 981 and 982, an E protein, and M protein inserted between, for example, MVA genes A5R and A6L. As exemplified, a mH5 promoter (pmH5) is operably linked to a nucleic acid encoding truncated amino acids 1-1213 derived from the S protein (S1+S2 truncated+ K986P and V987P), in a left-to-right orientation. The insert may include a translation initiation sequence, for example a Kozak sequence, prior to the start codon of the S (S1+S2 truncated+K986P and V987P) protein sequence. In addition, a nucleic acid sequence encoding a tag, for example a C-affinity tag, may be included at the 3' terminus of the S protein (S1+S2 truncated+K986P and V987P), prior to the stop codon. As exemplified, adjacent to the S protein (S1+S2 truncated+K986P and V987P) is a nucleic acid sequence encoding the full-length E protein, left-to-right orientation, which is operably linked to, for example, a p11 promoter. Similar to the S protein (S1+S2 truncated+K986P and V987P), the E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a mH5 promoter (pmH5). The M protein nucleic acid sequence can also include appropriate translation initiation sequences such as a Kozak sequence, as well as a nucleic acid sequence encoding a tag at the 3' terminus of the coding sequence prior to the stop codon.

Alternatively, an rMVA viral vector is provided which encodes a modified, truncated form of the spike(S) protein, the envelope (E) protein, and the membrane (M) protein of the SARS-CoV2, wherein the truncated S protein comprises a S1+S2 region and lacks the carboxy terminus, and wherein upon expression, the proteins form a VLP. In some embodiments, the nucleic acid is arranged so that the truncated S, E, and M encoding sequences are linearly adjacent. In some embodiments, the truncated S protein comprises amino acids 1 to 1213 (SEQ ID NO: 13). A linear representation of a single MVA insert encoding a truncated S, an E, and an M protein suitable for forming a VLP upon expression is provided for in FIG. 6A. In some embodiments, the truncated S protein contains two proline substitutions at amino acids 986 and 987, for example, as exemplified in FIG. 6H. In some embodiments, the truncated S protein is expressed as provided for in SEQ ID NO: 13 or 14 or 18 or 19, the E protein is expressed as a full-length protein, as provided for in SEQ ID NO: 40, and the M protein is expressed as a full length protein, as provided for in SEQ ID NO: 43, or sequences at least 75%, 80%, 85%, 90%, or 95% homologous thereto. In some embodiments, provided herein is a plasmid or MVA viral vector containing a nucleic acid sequence encoding SEQ ID NOS: 13 or 14 or 18 or 19, 40, and 43, or sequences at least 75%, 80%, 85%, 90%, or 95% homologous thereto. In some embodiments, provided herein is a nucleic acid sequence comprising SEQ ID NOS: 15 or 17, 41, and 44, or sequences at least 75%, 80%, 85%, 90%, or 95% homologous thereto. In some embodiments, provided herein is a nucleic acid encoding the truncated S protein, the E protein, and M protein, wherein the nucleic acid has been optimized for expression in the MVA viral vector, for example as provided in SEQ ID NOS: 16 or 17, 42, and 45, or sequences at least 75%, 80%, 85%, 90%, or 95% homologous thereto. In some embodiments, the nucleic acid sequence encodes for an additional amino acid sequence such as a tag, for example a C-terminus tag such as EPEA. The nucleic acid sequences may further comprise suitable promoter sequences such as, for example but not limited to, those derived from pmH5, p11, pSyn, pHyb, or any other suitable promoter sequence. In addition, the nucleic acid sequence for insertion may further include suitable translation initiation sequences, such as for example, a Kozak consensus sequence. In addition, the nucleic acid sequence can include appropriate stop codons, for example TAA, TAG, or TGA, or combinations or multiples thereof, at the 3'end of the nucleic acid sequence following the last amino acid sequence of the protein or tag. Furthermore, the nucleic acid sequence can include a vaccinia virus termination sequence 3' of the last stop codon of each encoded protein. In addition, the nucleic acid sequence for insertion may further include restriction enzyme sites useful for generating shuttle vectors for ease of insertion of the antigenic sequence. Exemplary nucleic acid sequence for insertion encoding the truncated S protein, the E protein, and the M protein are provided below as SEQ ID NO: 83 or 84. Exemplary nucleic acid sequence for insertion encoding the truncated S protein +K986P and V987P, the E protein, and the M protein are provided below as SEQ ID NO: 85 or 86. In some embodiments, the rMVA comprises a nucleic acid sequence selected from SEQ ID NOS: 83 (FIG. 6B-6C-6D), 84 (FIG. 6E-6F-6G), 85 (FIG. 6I-6J-6K), or 86 (FIG. 6L-6M-6N), or a sequence at least 70%, 75%, 80%, 85%, 90%, 95%, or 99% homologous thereto.

S Fragment-GP Fusion VLPs

In an alternative aspect, provided herein is a rMVA viral vector designed to express one or more SARS-CoV2 S protein antigenic peptides as an in-frame fusion protein, wherein the fusion protein comprises a signal sequence of an envelope glycoprotein (GPS), SARS-CoV2 S protein or protein fragment, a transmembrane domain of an envelope glycoprotein (GPTM), and, optionally, a cytosolic domain of an envelope glycoprotein (GPCD), wherein the envelope glycoprotein is not derived from a coronavirus. The rMVA viral vector is further designed to express a matrix protein from the same virus the envelope glycoprotein was derived from. By providing the SARS-CoV2 S protein fragment as a fusion with a GP protein, the S protein fragment-GP fusion can form a VLP with the rMVA expressed matrix protein. In some embodiments, the rMVA viral vector further expresses the membrane (M) protein and the envelope (E) protein of the SARS-CoV2, which, when expressed, are capable of forming a separate VLP. Thus, from a single rMVA viral vector, two VLPs are capable of being produced displaying antigenic epitopes of the SARS-CoV2.

Suitable glycoproteins and matrix proteins for use in the present invention include, but are not limited to, those derived from: a Filoviridae, for example Marburg virus, Ebola virus, or Sudan virus; a Retroviridae, for example human immunodeficiency virus type 1 (HIV-1); an Arenaviridaea, for example Lassa virus; a Flaviviridae, for example Dengue virus and Zika virus.

In particular embodiments, the glycoprotein and matrix proteins are derived from Marburg virus (MARV). In particular embodiments, the glycoprotein is derived from the MARV GP protein (Genbank accession number AFV31202.1). The amino acid sequence of the MARV GP protein is provided as SEQ ID NO: 87 in Table 14 below. In particular embodiments, the MARV GPS domain comprises amino acids 1 to 19 of the glycoprotein (MWTTCFFIS-LILIQGIKTL) (SEQ ID NO: 88, which can be encoded by, for example the MVA optimized nucleic acid sequence of SEQ ID NO: 89), the GPTM domain comprises amino acid sequences 644-673 of the glycoprotein (WWTSDWGVLTNLGILLLLSIAVLIALSCICRIFT-KYIG) (SEQ ID NO: 90, which can be encoded by, for example the MVA optimized nucleic acid sequence of SEQ ID NO: 91).

The MARV VP40 amino acid sequence is available at GenBank accession number JX458834, and provided below in Table 14 as SEQ ID NO: 92, which can be encoded by, for example, the MVA optimized nucleic acid sequence of SEQ ID NO: 93. In some embodiments, the nucleic acid inserted into the rMVA is Seq.ID. No. 94, or a nucleic acid sequence 70%, 75%, 80%, 85%, 90%, 95% or more homologous thereto.

TABLE 14

MARV Glycoprotein Domains for use in S Protein Fusion Constructs

| | |
|---|---|
| SEQ ID NO: 87-<br>GP MARV amino<br>acid sequence | MWTTCFFISLILIQGIKTLPILEIASNDQPQNVDSVCSGTLQKTEDVHLMGFTLSGQK<br>VADSPLEASKRWAFRTGVPPKNVEYTEGEEAKTCYNISVTDPSGKSLLLDPPTNVR<br>DYPKCKTIHHIQGQNPHAQGIALHLWGAFFLYDRIASTTMYRGKVFTEGNIAAMIV<br>NKTVHKMIFSRQGQGYRHMNLTSTNKYWTSSNGTQTNDTGCFGTLQEYNSTKNQ<br>TCAPSKTPPPPPTAHPEIKPTSTPTDATRLNTTNPNSDDEDLTTSGSGSGEQEPYTTS<br>DAVTKQGLSSTMPPTLSPQPGTPQQGGNNTNHSQDAATELDNTNTTAQPPMPSHN<br>TTTISTNNTSKHNLSTLSEPPQNTTNPNTQSMATENEKTSAPPKTTLPPTESPTTEKS<br>TNNTKSPTTMEPNTTNGHFTSPSSTPNSTTQHLIYFRRKRSILWREGDMFPFLDGLI<br>NAPIDFDPVPNTKTIFDESSSSGASAEEDQHASSNISLTLSYLPHTSENTAYSGENEN<br>DCDAELRIWSVQEDDLAAGLSWIPFFGPGIEGLYTAGLIKNQNNLVCRLRRLANQT<br>AKSLELLLRVTTEERTFSLINRHAIDFLLTRWGGTCKVLGPDCCIGIEDLSRNISEQI<br>DQIKKDEQKEGTGWGLGGKWWTSDWGVLTNLGILLLLSIAVLIALSCICRIFTKYI<br>G |

TABLE 14-continued

| MARV Glycoprotein Domains for use in S Protein Fusion Constructs |
|---|

| SEQ ID NO: 88-<br>Signal peptide<br>amino acid<br>sequence of GP<br>MARV | MWTTCFFISLILIQGIKTL |
|---|---|
| SEQ ID NO: 89-<br>Signal peptide<br>nucleic acid<br>sequence of GP<br>MARV-optimized | ATGTGGACGACCTGCTTCTTCATCTCCCTAATCCTAATCCAGGGAATCAAGACC<br>CTA |
| SEQ ID NO: 90-<br>Transmembrane<br>domain amino acid<br>sequence of GP<br>MARV | WWTSDWGVLTNLGILLLLSIAVLIALSCICRIFTKYIG |
| SEQ ID NO: 91-<br>Transmembrane<br>domain nucleic<br>acid sequence of<br>GP MARV-<br>optimized | TGGTGGACATCTGACTGGGGAGTCCTAACGAACCTAGGAATCCTACTACTATT<br>GTCGATCGCGGTCCTAATCGCGCTATCCTGTATCTGTAGAATCTTCACCAAGTA<br>CATCGGA |
| SEQ ID NO: 92-<br>MARVVP 40<br>amino acid<br>sequence | MASSSNYNTYMQYLNPPPYADHGANQLIPADQLSNQHGITPNYVGDLNLDDQFK<br>GNVCHAFTLEAIIDISAYNERTVKGVPAWLPLGIMSNFEYPLAHTVAALLTGSYTIT<br>QFTHNGQKFVRVNRLGTGIPAHPLRMLREGNQAFIQNMVIPRNFSTNQFTYNLTNL<br>VLSVQKLPDDAWRPSKDKLIGNTMHPAISIHPNLPPIVLPTVKKQAYRQHKNPNNG<br>PLLAISGILHQLRVEKVPEKTSLFRISLPADMFSVKEGMMKKRGESSPVVYFQAPEN<br>FPLNGFNNRQVVLAYANPTLSAI |
| SEQ ID NO: 93-<br>MARVVP 40<br>nucleic acid<br>sequence<br>optimized | ATGGCGTCTAGTTCTAATTATAATACTTATATGCAATATCTAAATCCACCACCA<br>TATGCGGATCATGGTGCTAATCAACTAATTCCAGCGGATCAACTATCTAATCAA<br>CATGGAATTACACCAAATTATGTTGGAGATCTAAATCTAGATGATCAGTTTAA<br>AGGAAATGTTTGTCATGCGTTTACACTAGAAGCGATTATTGATATTTCTGCGTA<br>TAATGAAAGAACAGTAAAAGGTGTACCAGCTTGGCTACCACTAGGAATTATGT<br>CTAATTTTGAATATCCACTAGCGCATACAGTAGCGGCGCTATTGACAGGATCTT<br>ATACAATTACACAGTTTACACATAATGGACAAAAGTTTGTTAGAGTAAATAGA<br>CTAGGAACTGGAATACCAGCGCATCCACTAAGAATGCTAAGAGAAGGAAATC<br>AAGCTTTTATTCAAAATATGGTTATTCCAAGAAATTTCTCTACAAATCAGTTTA<br>CTTATAATCTAACTAATCTAGTACTATCTGTACAAAAGCTACCAGATGATGCTT<br>GGAGACCATCTAAAGATAAACTAATTGGAAATACAATGCATCCAGCGATTTCT<br>ATTCATCCAAATCTACCACCAATAGTACTACCAACTGTAAAGAAACAAGCGTA<br>TAGACAACATAAGAATCCAAATAATGGACCACTATTGGCGATTTCTGGAATTC<br>TACATCAACTAAGAGTAGAAAAGGTACCAGAAAAGACATCTTTGTTTAGAATT<br>TCTCTACCAGCGGATATGTTTTCTGTAAAAGAAGGAATGATGAAGAAAAGAGG<br>AGAATCTTCTCCAGTAGTATATTTTCAAGCGCCAGAAAATTTTCCATTGAATGG<br>TTTTAATAATAGACAAGTAGTACTAGCGTATGCGAATCCAACACTATCTGCGAT<br>ATAATAA |
| SEQ ID NO: 94-<br>Marburg VP40<br>Optimized mH5<br>Vaccinia Promoter | AAAAATTGAAAATAAATACAAAGGTTCTTGAGGGTTGTGTTAAATTGAAAGCG<br>AGAAATAATCATAAATGGCGTCTAGTTCTAATTATAATACTTATATGCAATATC<br>TAAATCCACCACCATATGCGGATCATGGTGCTAATCAACTAATTCCAGCGGAT<br>CAACTATCTAATCAACATGGAATTACACCAAATTATGTTGGAGATCTAAATCTA<br>GATGATCAGTTTAAAGGAAATGTTTGTCATGCGTTTACACTAGAAGCGATTATT<br>GATATTTCTGCGTATAATGAAAGAACAGTAAAAGGTGTACCAGCTTGGCTACC<br>ACTAGGAATTATGTCTAATTTTGAATATCCACTAGCGCATACAGTAGCGGCGCT<br>ATTGACAGGATCTTATACAATTACACAGTTTACACATAATGGACAAAAGTTTGT<br>TAGAGTAAATAGACTAGGAACTGGAATACCAGCGCATCCACTAAGAATGCTAA<br>GAGAAGGAAATCAAGCTTTTATTCAAAATATGGTTATTCCAAGAAATTTCTCTA<br>CAAATCAGTTTACTTATAATCTAACTAATCTAGTACTATCTGTACAAAAGCTAC<br>CAGATGATGCTTGGAGACCATCTAAAGATAAACTAATTGGAAATACAATGCAT<br>CCAGCGATTTCTATTCATCCAAATCTACCACCAATAGTACTACCAACTGTAAAG<br>AAACAAGCGTATAGACAACATAAGAATCCAAATAATGGACCACTATTGGCGAT<br>TTCTGGAATTCTACATCAACTAAGAGTAGAAAAGGTACCAGAAAAGACATCTT<br>TGTTTAGAATTTCTCTACCAGCGGATATGTTTTCTGTAAAAGAAGGAATGATGA<br>AGAAAAGAGGAGAATCTTCTCCAGTAGTATATTTTCAAGCGCCAGAAAATTTT<br>CCATTGAATGGTTTTAATAATAGACAAGTAGTACTAGCGTATGCGAATCCAAC<br>ACTATCTGCGATATAATAATAATAATTTTTAT |

In one alternative, a rMVA viral vector is provided which encodes for an S protein or protein fragment fused with a GP protein, the E protein from SARS-CoV2, the M protein from SARS-CoV2, and a matrix protein. In some embodiments, the S protein or protein fragment-GP fusion, E, and M protein encoding nucleic acid sequences are inserted in a single insertion site in the rMVA, and the MARV VP40 encoding nucleic acid sequence is inserted at a separated insertion site. In some embodiments, the S protein or protein fragment-GP fusion, E, and M protein, and MARV VP40 encoding nucleic acid sequences are inserted in a single insertion site in the rMVA.

Figure 7B:
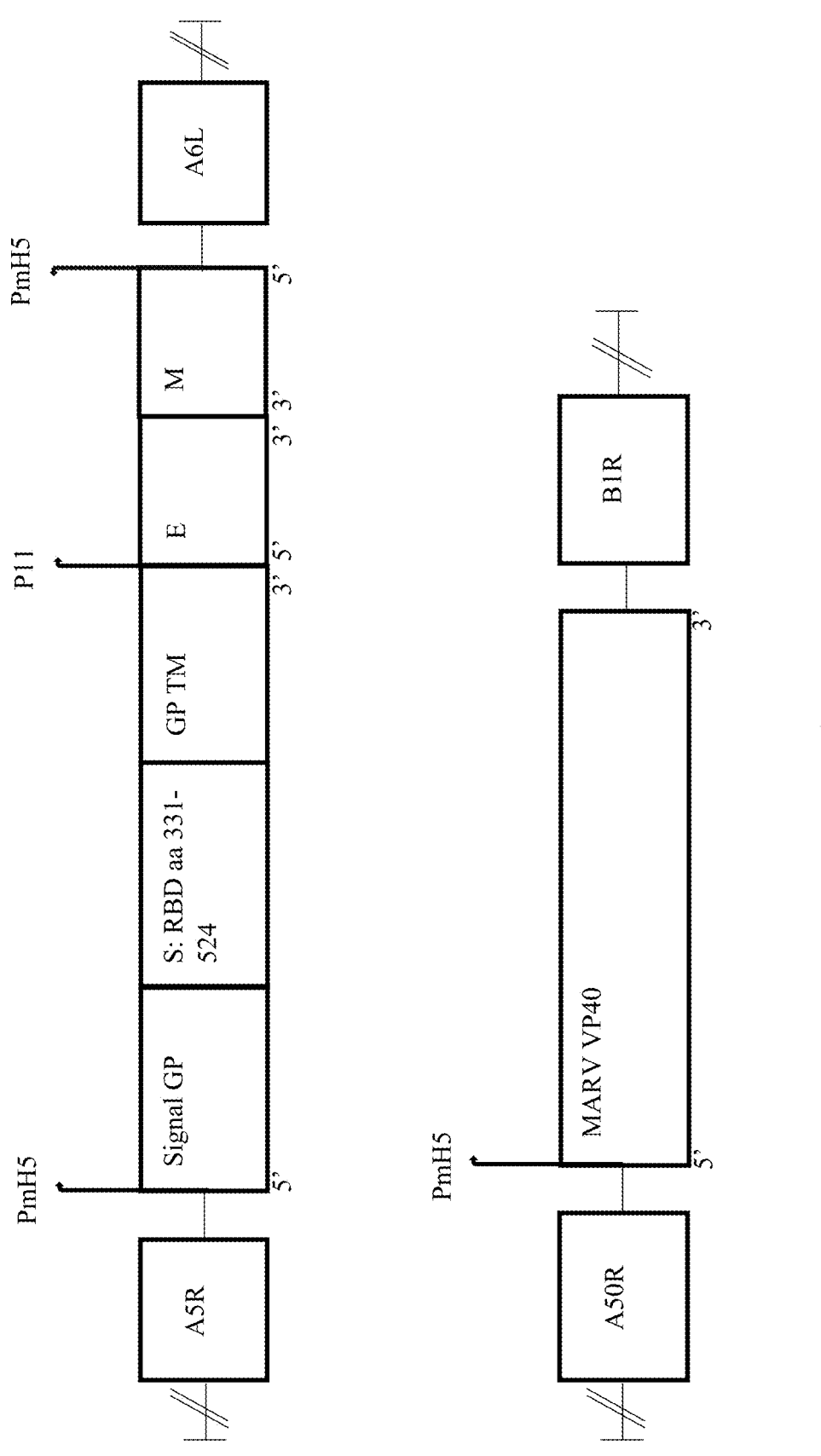
FIG. 7B provides an exemplary linear schematic of an exemplary recombinant MVA viral vector comprising a nucleic acid sequence encoding a signal glycoprotein (Signal GP)-S protein RBD (aa 331-524) consensus-glycoprotein transmembrane domain sequence (GP TM) fusion protein, an E protein, and an M protein inserted between MVA genes A5R and A6L. As exemplified, a mH5 promoter (pmH5) is operably linked to a nucleic acid encoding a fusion protein, wherein the fusion protein includes a signal peptide from a non-coronavirus signal glycoprotein (Signal GP), an S protein RBD (aa 331-524) consensus peptide, and a transmembrane domain of the glycoprotein (GP TM), in a left-to-right orientation. A start codon is provided 5' to the Signal GP-S RBD (aa 331-524) consensus-GP TM fusion encoding nucleic acid. The insert may include a translation initiation sequence, for example a Kozak sequence, prior to the start codon of the signal peptide encoding sequence. In addition, a nucleic acid sequence encoding a tag, for example a C-affinity tag, may be included at the 3' terminus of the Signal GP-S RBD (aa 331-524) consensus-GP TM fusion, prior to the stop codon. As exemplified, adjacent to the Signal GP-S RBD (aa 331-524) consensus-GP TM fusion encoding sequence is a nucleic acid sequence encoding the full-length E protein, in a left-to-right orientation, which is operably linked to, for example, a p11 promoter. The E protein nucleic acid sequence can also include appropriate translation initiation sequences such as a Kozak sequence, as well as a nucleic acid sequence encoding a tag at the 3' terminus of the coding sequence prior to the stop codon. As exemplified, the insert further includes a nucleic acid sequence encoding a full-length M protein. As exemplified, the M protein coding sequence is oriented in a right-to-left orientation, wherein the 3' end of the E protein coding sequence is adjacent to the 3' end of the M protein coding sequence. As exemplified, the M protein coding sequence is operably linked to a mH5 promoter (pmH5). The M protein nucleic acid sequence can also include appropriate translation initiation sequences such as a Kozak sequence, as well as a nucleic acid sequence encoding a tag at the 3' terminus of the coding sequence prior to the stop codon. As exemplified, a nucleic acid sequence encoding a non-coronavirus matrix protein, for example Marburgvirus matrix protein VP40, is inserted between, for example, MVA genes A50R and B1R. The nucleic acid sequence encoding the matrix protein is operably linked to, for example, a mH5 promoter (pmH5). Similar to the fusion protein, the matrix protein nucleic acid sequence can also include appropriate translation initiation sequences such as a Kozak sequence, as well as a nucleic acid sequence encoding a tag at the 3' terminus of the coding sequence prior to the stop codon.
Figure 7G:
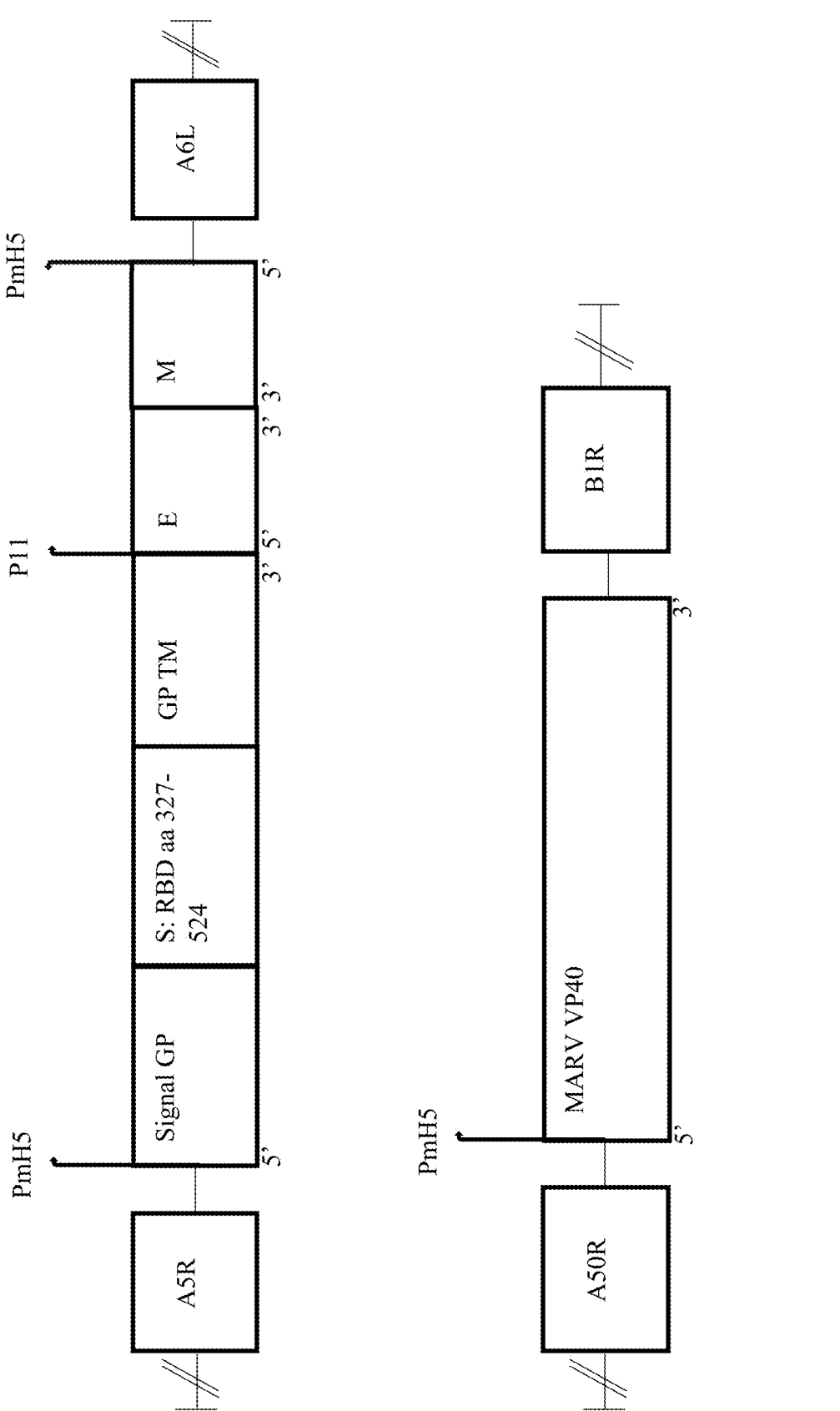
FIG. 7G provides an exemplary linear schematic of an exemplary recombinant MVA viral vector comprising a nucleic acid sequence encoding a signal glycoprotein (Signal GP)-S protein RBD (aa 327-524) consensus-glycoprotein transmembrane domain sequence (GP TM) fusion protein, an E protein, and an M protein inserted between, for example, MVA genes A5R and A6L. As exemplified, a mH5 promoter (pmH5) is operably linked to a nucleic acid encoding a fusion protein, wherein the fusion protein includes a signal peptide from a non-coronavirus signal glycoprotein (Signal GP), an S protein RBD (aa 327-524) consensus peptide, and a transmembrane domain of the glycoprotein (GP TM), in a left-to-right orientation. A start codon is provided 5' to the Signal GP-S RBD (aa 327-524) consensus-GP TM fusion encoding nucleic acid. The insert may include a translation initiation sequence, for example a Kozak sequence, prior to the start codon of the signal peptide encoding sequence. In addition, a nucleic acid sequence encoding a tag, for example a C-affinity tag, may be included at the 3' terminus of the Signal GP-S RBD (aa 327-524) consensus-GP TM fusion, prior to the stop codon.

In some embodiments, the S protein fragment-GP fusion protein comprises an S protein receptor biding domain (RBD). In some embodiments, the RBD peptide is derived from amino acids 327 to 524 of the S protein. In some embodiments, the RBD peptide is derived from amino acids 331 to 524 of the S protein. In some embodiments, the RBD is a consensus coronavirus sequence. The RBD peptide is flanked on its NH-terminus side by a signal peptide derived from amino acids 1-19 of the MARV glycoprotein (SEQ ID NO: 88), and on its carboxy-terminus side by the transmembrane domain of the MARV glycoprotein (SEQ ID NO: 90). The GPS-RBD (aa 327-524)-GPTM peptide expressed is provided in SEQ ID NO: 95 in Table 15 below, which can be encoded by, for example, an MVA optimized nucleic acid sequence for example provided in SEQ ID NO: 97. The GPS-RBD (aa 331-524)-GPTM peptide expressed is provided in SEQ ID NO: 96 in Table 15 below, which can be encoded by, for example, an MVA optimized nucleic acid sequence for example provided in SEQ ID NO: 98. In some embodiments, the nucleic acid is arranged so that the GPS-RBD-GPTM, E, and M encoding sequences are linearly adjacent. A linear representation of a rMVA comprising a MARV VP 40 insert and a separate, single MVA insert encoding GPS-RBD-TM, an E protein, and an M protein suitable for forming a VLP upon expression is provided for in FIG. 7A. A linear representation of a rMVA comprising a MARV VP 40 insert and a separate, single MVA insert encoding GPS-RBD (aa 331-524)-TM, an E protein, and an M protein suitable for forming a VLP upon expression is provided for in FIG. 7B. A linear representation of a rMVA comprising a MARV VP 40 insert and a separate, single MVA insert encoding GPS-RBD (aa 327-524)-TM, an E protein, and an M protein suitable for forming a VLP upon expression is provided for in FIG. 7G. In some embodiments, GPS-RBD-GPTM is expressed as provided for in SEQ ID NO: 95 (RBD aa 327-524) or SEQ ID NO: 96 (RBD aa 331-524) or SEQ ID NO: 99 (RBD aa 327-524, E484K) or SEQ ID NO: 100 (RBD aa 331-524; E484K), the E protein is expressed as a full-length protein, as provided for in SEQ ID NO: 40, the M protein is expressed as a full-length protein, as provided for in SEQ ID NO: 43, and the MARV VP protein is expressed as provided for in SEQ ID NO: 92, or sequences at least 70%, 75%, 80%, 85%, 90%, or 95% homologous thereto. In some embodiments, provided herein is a plasmid or MVA viral vector containing a nucleic acid sequence encoding SEQ ID NOS: 95 or 96 or 99 or 100, 40, 43, and 92, or sequences at least 70%, 75%, 80%, 85%, 90%, or 95% homologous thereto. In some embodiments, provided herein is a nucleic acid sequence comprising SEQ ID NOS: 97 or 98, 41, and 44, or sequences at least 70%, 75%, 80%, 85%, 90%, or 95% homologous thereto. In some embodiments, provided herein is a nucleic acid encoding the GPS-RBD-GPTM, the E protein, and M protein, wherein the nucleic acid has been optimized for expression in the MVA viral vector, for example as provided in SEQ ID NOS: 97 or 98, 42, and 45, or sequences at least 70%, 75%, 80%, 85%, 90%, or 95% homologous thereto. In some embodiments, the nucleic acid sequence encodes for an additional amino acid sequence such as a tag, for example a C-terminus tag such as EPEA suitable for use during assay detection. The nucleic acid sequences may further comprise suitable promoter sequences such as those derived from pmH5, p11, pSyn, pHyb, or any other suitable promoter sequence. In addition, the nucleic acid sequence for insertion may further include suitable translation initiation sequences, such as for example, a Kozak consensus sequence. In addition, the nucleic acid sequence can include appropriate stop codons, for example TAA, TAG, or TGA, or combinations or multiples thereof, at the 3'end of the nucleic acid sequence following the last amino acid sequence of the protein or tag. Furthermore, the nucleic acid sequence can include a vaccinia virus termination sequence 3' of the last stop codon of each encoded protein. In addition, the nucleic acid sequence for insertion may further include restriction enzyme sites useful for generating shuttle vectors for ease of insertion of the antigenic sequence. Exemplary nucleic acid sequences for insertion encoding the GPS-RBD-GPTM, the E protein, and the M protein are provided as SEQ ID NOS: 101, 102, 103, and 104. In some embodiments, the rMVA comprises a nucleic acid sequence selected from SEQ ID NOS: 101 (FIG. 7H-7I), 102 (FIG. 7J-7K), 103 (FIG. 7C-7D), or 104 (FIG. 7E-7F), or a sequence at least 70%, 75%, 80%, 85%, 90%, 95%, or 99% homologous thereto. In some embodiments, the rMVA further comprises a nucleic acid sequence of SEQ ID NO: 93 or 94, or a sequence at least 70%, 75%, 80%, 85%, 90%, or 95% homologous thereto.

TABLE 15

| GPS-RBD-GPTM Fusions | |
| --- | --- |
| SEQ ID NO: 95-GPS-RBD (aa 327-524)-GPTM Fusion Peptide amino acid sequence | MWTTCFFISLILIQGIKTLVRFPNITNLCPFGEVFNATRFASVYAWNRKRIS NCVADYSVLYNSASFSTFKCYGVSPTKLNDLCFTNVYADSFVIRGDEVRQ IAPGQTGKIADYNYKLPDDFTGCVIAWNSNNLDSKVGGNYNYLYRLFRK SNLKPFERDISTEIYQAGSTPCNGVEGFNCYFPLQSYGFQPTNGVGYQPYR VVVLSFELLHAPATVWWTSDWGVLTNLGILLLLSIAVLIALSCICRIFTKYI G |
| SEQ ID NO: 96-GPS-RBD (aa 331-524)-GPTM Fusion Peptide amino acid sequence | MWTTCFFISLILIQGIKTLNITNLCPFGEVFNATRFASVYAWNRKRISNCVA DYSVLYNSASFSTFKCYGVSPTKLNDLCFTNVYADSFVIRGDEVRQIAPGQ TGKIADYNYKLPDDFTGCVIAWNSNNLDSKVGGNYNYLYRLFRKSNLKP FERDISTEIYQAGSTPCNGVEGFNCYFPLQSYGFQPTNGVGYQPYRVVVLS FELLHAPATVWWTSDWGVLTNLGILLLLSIAVLIALSCICRIFTKYIG |
| SEQ ID NO: 97-GPS-RBD (aa 327-524)-GPTM Fusion Peptide nucleic acid sequence-optimized | ATGTGGACGACCTGCTTCTTCATCTCCCTAATCCTAATCCAGGGAATCA AGACCCTAGTCAGATTTCCGAACATCACGAACCTATGTCCGTTCGGAG AAGTGTTCAACGCGACAAGATTTGCGTCTGTCTATGCGTGGAACAGAA AAAGAATCAGTAACTGCGTCGCGGACTACTCCGTCCTATACAACTCTG CCTCTTTCTCCACGTTCAAATGCTACGGTGTATCTCCGACAAAGCTAAA CGATCTATGCTTCACCAACGTCTACGCGGACTCCTTCGTAATCAGAGG AGATGAAGTTAGACAGATTGCGCCGGGACAAACTGGAAAGATCGCGG ATTATAACTACAAGCTACCGGACGACTTCACCGGATGTGTAATTGCGT |

TABLE 15-continued

GPS-RBD-GPTM Fusions

|  |  |
| --- | --- |
|  | GGAATTCGAACAACCTAGACTCCAAAGTCGGAGGAAACTACAACTAC<br>TTGTACAGACTATTCAGAAAGTCCAACCTAAAGCCGTTCGAGAGAGAC<br>ATCTCCACCGAAATCTATCAGGCTGGATCTACACCGTGTAATGGTGTC<br>GAAGGATTCAACTGCTACTTCCCGCTACAGTCTTACGGATTTCAACCG<br>ACAAACGGTGTAGGATATCAGCCGTACAGAGTCGTCGTACTATCCTTC<br>GAACTACTACATGCTCCGGCGACAGTATGGTGGACATCTGACTGGGGA<br>GTCCTAACGAACCTAGGAATCCTACTACTATTGTCGATCGCGGTCCTA<br>ATCGCGCTATCCTGTATCTGTAGAATCTTCACCAAGTACATCGGA |
| SEQ ID NO: 98-GPS-RBD<br>(aa 331-524)-GPTM Fusion<br>Peptide nucleic acid<br>sequence-optimized | ATGTGGACGACCTGCTTCTTCATCTCCCTAATCCTAATCCAGGGAATCA<br>AGACCCTAAACATCACGAACCTATGTCCGTTCGGAGAAGTGTTCAACG<br>CGACAAGATTTGCGTCTGTCTATGCGTGGAACAGAAAAAGAATCAGTA<br>ACTGCGTCGCGGACTACTCCGTCCTATACAACTCTGCCTCTTTCTCCAC<br>GTTCAAATGCTACGGTGTATCTCCGACAAAGCTAAACGATCTATGCTT<br>CACCAACGTCTACGCGGACTCCTTCGTAATCAGAGGAGATGAAGTTAG<br>ACAGATTGCGCCGGGACAAACTGGAAAGATCGCGGATTATAACTACA<br>AGCTACCGGACGACTTCACCGGATGTGTAATTGCGTGGAATTCGAACA<br>ACCTAGACTCCAAAGTCGGAGGAAACTACAACTACTTGTACAGACTAT<br>TCAGAAAGTCCAACCTAAAGCCGTTCGAGAGAGACATCTCCACCGAA<br>ATCTATCAGGCTGGATCTACACCGTGTAATGGTGTCGAAGGATTCAAC<br>TGCTACTTCCCGCTACAGTCTTACGGATTTCAACCGACAAACGGTGTA<br>GGATATCAGCCGTACAGAGTCGTCGTACTATCCTTCGAACTACTACAT<br>GCTCCGGCGACAGTATGGTGGACATCTGACTGGGGAGTCCTAACGAAC<br>CTAGGAATCCTACTACTATTGTCGATCGCGGTCCTAATCGCGCTATCCT<br>GTATCTGTAGAATCTTCACCAAGTACATCGGA |
| SEQ ID NO: 99-GPS-RBD<br>(aa 327-524)-GPTM Fusion<br>Peptide amino acid sequence<br>(K417T; E484K; N501Y) | MWTTCFFISLILIQGIKTLVRFPNITNLCPFGEVFNATRFASVYAWNRKRIS<br>NCVADYSVLYNSASFSTFKCYGVSPTKLNDLCFTNVYADSFVIRGDEVRQ<br>IAPGQTGTIADYNYKLPDDFTGCVIAWNSNNLDSKVGGNYNYLYRLFRKS<br>NLKPFERDISTEIYQAGSTPCNGVKGFNCYFPLQSYGFQPTYGVGYQPYRV<br>VVLSFELLHAPATVWWTSDWGVLTNLGILLLLSIAVLIALSCICRIFTKYIG |
| SEQ ID NO: 100-GPS-<br>RBD (aa 331-524)-GPTM<br>Fusion Peptide amino acid<br>sequence (K417T; E484K;<br>N501Y) | MWTTCFFISLILIQGIKTLNITNLCPFGEVFNATRFASVYAWNRKRISNCVA<br>DYSVLYNSASFSTFKCYGVSPTKLNDLCFTNVYADSFVIRGDEVRQIAPGQ<br>TGTIADYNYKLPDDFTGCVIAWNSNNLDSKVGGNYNYLYRLFRKSNLKP<br>FERDISTEIYQAGSTPCNGVKGFNCYFPLQSYGFQPTYGVGYQPYRVVVLS<br>FELLHAPATVWWTSDWGVLTNLGILLLLSIAVLIALSCICRIFTKYIG |

35

In one alternative, a rMVA viral vector is provided which encodes for an S protein peptide fused with a GP protein, the E protein from SARS-CoV2, the M protein from SARS-CoV2, and a matrix protein, wherein the S protein fragment-GP fusion protein comprises an S protein tandem repeat sequence. The S protein tandem repeat sequence is flanked on its NH-terminus side by a signal peptide derived from amino acids 1-19 of the MARV glycoprotein (SEQ ID NO: 88), and on its carboxy-terminus side by the transmembrane domain of the MARV glycoprotein (SEQ ID NO: 90). In some embodiments, the tandem repeat is for example (RBD-spacer-RBD-spacer) x or (RBD Seq. 1-spacer-RBD Seq. 2-spacer) x, wherein RBD is any S protein RBD peptide, RBD Seq. 1 is a first S protein RBD peptide, and RBD Seq. 2 is a second S protein RBD peptide, and wherein X=2, 3, 4, 5, 6, 7, 8, 9, or 10. In some embodiments, the RBD peptides are selected from one or more peptides derived from amino acids 331 to 524 of the SARS-CoV2 S protein. In some embodiments, the linear epitopes encoded by the rMVA are selected from the amino acids 504 to 524 and amino acids 473 to 490 of the SARS-CoV2 S protein. In some embodiments, the linear epitopes encoded by the rMVA are the amino acids 504 to 524 and amino acids 473 to 490 of the SARS-CoV2 S protein. In some embodiments, the tandem repeat sequence is ((aa504-524)-spacer-(aa473-490)-spacer) x, wherein x=2, 3, 4, 5, 6, 7, 8, 9, or 10. In some embodiments, x=3-7. In some embodiments, x=5. An exemplary amino acid sequence comprising a GPS-tandem repeat-GPTM is provided for in Table 16 as SEQ ID NO: 105, which can be encoded by the MVA optimized nucleic acid sequence of SEQ ID NO: 106. An exemplary amino acid sequence comprising a GPS-tandem repeat-GPTM, wherein x=5 for the tandem repeat, is provided for in Table 16 as SEQ ID NO: 107, which can be encoded by the MVA optimized nucleic acid sequence of SEQ ID NO: 108.

In some embodiments, the nucleic acid is arranged so that the GPS-tandem repeat-GPTM peptide, E, and M encoding sequences are linearly adjacent. A linear representation of a rMVA comprising a MARV VP 40 insert and a separate, single MVA insert encoding GPS-tandem repeat-GPTM peptide, an E protein, and M protein suitable for forming a VLP upon expression is provided for in FIG. 8A. In some embodiments, GPS-tandem repeat-GPTM peptide is expressed as provided for in SEQ ID NO: 105 or 107 or 109 or 110, the E protein is expressed as a full-length protein, as provided for in SEQ ID NO: 40, the M protein is expressed as a full-length protein, as provided for in SEQ ID NO: 43, and the MARV VP protein is expressed as provided for in SEQ ID NO: 92, or sequences at least 70%, 75%, 80%, 85%, 90%, or 95% homologous thereto. In some embodiments, provided herein is a plasmid or MVA viral vector containing a nucleic acid sequence encoding SEQ ID NOS: 105 or 107 or 109 or 110, 40, and 43, and 92, or sequences at least 70%, 75%, 80%, 85%, 90%, or 95% homologous thereto. In some embodiments, provided herein is a nucleic acid sequence comprising SEQ ID NOS: 106 or 108, 41, and 44, or sequences at least 70%, 75%, 80%, 85%, 90%, or 95% homologous thereto. In some embodiments, provided herein is a nucleic acid encoding the GPS-tandem repeat-GPTM peptide, the E protein, and M protein, wherein the nucleic acid has been optimized for expression in the MVA viral vector, for example as provided in SEQ ID NOS: 106 or 108, 42, and 45, or sequences at least 70%, 75%, 80%, 85%, 90%, or 95% homologous thereto. In some embodiments, the nucleic acid sequence encodes for an additional amino acid sequence such as a tag, for example a C-terminus tag such as EPEA suitable for use during assay detection. The nucleic acid sequences may further comprise suitable promoter sequences such as, for example but not limited to, those derived from pmH5, p11, pSyn, pHyb, or any other suitable promoter sequence. In addition, the nucleic acid sequence for insertion may further include suitable translation initiation sequences, such as for example, a Kozak consensus sequence. In addition, the nucleic acid sequence can include appropriate stop codons, for example TAA, TAG, or TGA, or combinations or multiples thereof, at the 3'end of the nucleic acid sequence following the last amino acid sequence of the protein or tag. Furthermore, the nucleic acid sequence can include a vaccinia virus termination sequence 3' of the last stop codon of each encoded protein. In addition, the nucleic acid sequence for insertion may further include restriction enzyme sites useful for generating shuttle vectors for ease of insertion of the antigenic sequence. Exemplary nucleic acid sequences for insertion encoding the GPS-tandem repeat-GPTM peptide, the E protein, and the M protein are provided as SEQ ID NO: 111 and 112. In some embodiments, the rMVA comprises a nucleic acid sequence selected from SEQ ID NO: 111 (FIG. 8B-8C) or 112 (FIG. 8D-8E), or a sequence at least 70%, 75%, 80%, 85%, 90%, 95%, or 99% homologous thereto. In some embodiments, the rMVA further comprises a nucleic acid sequence of SEQ ID NO: 93 or 94, or a sequence at least 70%, 75%, 80%, 85%, 90%, or 95% homologous thereto.

TABLE 16

| GPS-RBD Tandem Repeat-GPTM | |
|---|---|
| SEQ ID NO: 105-GPS-RBD Tandem Repeat-GPTM amino acid sequence | MWTTCFFISLILIQGIKTL(YQPYRVVVLSFELLHAPATVGPGPGYQAGSTPC NGVEGFNCYFGPGPG)xWWTSDWGVLTNLGILLLLSIAVLIALSCICRIFTKY IG<br>wherein x = 2, 3, 4, 5, 6, 7, 8, 9, or 10. |
| SEQ ID NO: 106-GPS-RBD Tandem Repeat-GPTM nucleic acid sequence-optimized | ATGTGGACGACCTGCTTCTTCATCTCCCTAATCCTAATCCAGGGAATCA AGACCCTA(TACCAACCATACAGAGTAGTAGTACTTTCTTTTGAACTTCT ACATGCACCAGCAACTGTTGGTCCTGGACCCGGTTATCAGGCCGGTAGC ACACCTTGTAATGGTGTTGAAGGTTTTAATTGTTACTTTGGTCCTGGACC CGGT)xTGGTGGACATCTGACTGGGGAGTCCTAACGAACCTAGGAATCC TACTACTATTGTCGATCGCGGTCCTAATCGCGCTATCCTGTATCTGTAGA ATCTTCACCAAGTACATCGGA<br>wherein x = 2, 3, 4, 5, 6, 7, 8, 9, or 10. |
| SEQ ID NO: 107-GPS-RBD Tandem Repeat-GPTM amino acid sequence, wherein x = 5 | MWTTCFFISLILIQGIKTLYQPYRVVVLSFELLHAPATVGPGPGYQAGSTPC NGVEGFNCYFGPGPGYQPYRVVVLSFELLHAPATVGPGPGYQAGSTPCNG VEGFNCYFGPGPGYQPYRVVVLSFELLHAPATVGPGPGYQAGSTPCNGVE GFNCYFGPGPGYQPYRVVVLSFELLHAPATVGPGPGYQAGSTPCNGVEGF NCYFGPGPGYQPYRVVVLSFELLHAPATVGPGPGYQAGSTPCNGVEGFNC YFGPGPGWWTSDWGVLTNLGILLLLSIAVLIALSCICRIFTKYIG |
| SEQ ID NO: 108-GPS-RED Tandem Repeat-GPTM nucleic acid sequence-optimized, wherein x = 5 | ATGTGGACGACCTGCTTCTTCATCTCCCTAATCCTAATCCAGGGAATCA AGACCCTATATCAGCCGTACAGAGTCGTCGTACTATCCTTCGAACTACT ACATGCTCCGGCGACAGTAGGTCCTGGACCCGGTTATCAGGCTGGATCT ACACCGTGTAATGGTGTCGAAGGATTCAACTGCTACTTCGGTCCTGGAC CCGGTTATCAGCCGTACAGAGTCGTCGTACTATCCTTCGAACTACTACA TGCTCCGGCGACAGTAGGTCCTGGACCCGGTTATCAGGCTGGATCTACA CCGTGTAATGGTGTCGAAGGATTCAACTGCTACTTCGGTCCTGGACCCG GTTATCAGCCGTACAGAGTCGTCGTACTATCCTTCGAACTACTACATGC TCCGGCGACAGTAGGTCCTGGACCCGGTTATCAGGCTGGATCTACACCG TGTAATGGTGTCGAAGGATTCAACTGCTACTTCGGTCCTGGACCCGGTT ATCAGCCGTACAGAGTCGTCGTACTATCCTTCGAACTACTACATGCTCC GGCGACAGTAGGTCCTGGACCCGGTTATCAGGCTGGATCTACACCGTGT AATGGTGTCGAAGGATTCAACTGCTACTTCGGTCCTGGACCCGGTTATC AGCCGTACAGAGTCGTCGTACTATCCTTCGAACTACTACATGCTCCGGC GACAGTAGGTCCTGGACCCGGTTATCAGGCTGGATCTACACCGTGTAAT GGTGTCGAAGGATTCAACTGCTACTTCGGTCCTGGACCCGGTTGGTGGA CATCTGACTGGGGAGTCCTAACGAACCTAGGAATCCTACTACTATTGTC GATCGCGGTCCTAATCGCGCTATCCTGTATCTGTAGAATCTTCACCAAG TACATCGGA |
| SEQ ID NO: 109-GPS-RED Tandem Repeat-GPTM amino acid sequence (E484K) | MWTTCFFISLILIQGIKTL(YQPYRVVVLSFELLHAPATVGPGPGYQAGSTPC NGVKGFNCYFGPGPG)xWWTSDWGVLTNLGILLLLSIAVLIALSCICRIFTK YIG<br>wherein x = 2, 3, 4, 5, 6, 7, 8, 9, or 10. |
| SEQ ID NO: 110-GPS-RED Tandem Repeat-GPTM amino acid sequence, wherein x = 5 (E484K) | MWTTCFFISLILIQGIKTLYQPYRVVVLSFELLHAPATVGPGPGYQAGSTPC NGVKGFNCYFGPGPGYQPYRVVVLSFELLHAPATVGPGPGYQAGSTPCNG VKGFNCYFGPGPGYQPYRVVVLSFELLHAPATVGPGPGYQAGSTPCNGVK GFNCYFGPGPGYQPYRVVVLSFELLHAPATVGPGPGYQAGSTPCNGVKGF NCYFGPGPGYQPYRVVVLSFELLHAPATVGPGPGYQAGSTPCNGVKGFNC YFGPGPGWWTSDWGVLTNLGILLLLSIAVLIALSCICRIFTKYIG |

In one alternative, a rMVA viral vector is provided which encodes for a modified S protein peptide fused with a GP protein, the E protein from SARS-CoV2, the M protein from SARS-CoV2, and a matrix protein, wherein the modified S protein comprises an S1+S2 truncated protein lacking the carboxy terminus of the protein. In some embodiments, the S1+S2 truncated protein comprises amino acids 2 to 1213 of the S protein. In some embodiments, the S1+S2 truncated protein comprises amino acids 2 to 1213 of the S protein, and a proline substitution at amino acid 986 and/or 987 (S1+S2 truncated+K986P and V987P). In some embodiments, the truncated S protein-GP fusion, E, and M protein encoding nucleic acid sequences are inserted in a single insertion site in the rMVA, and the MARV VP40 encoding nucleic acid sequence is inserted at a separated insertion site.

In some embodiments, the truncated S protein-GP fusion protein comprises amino acids 2-1213 of the S Protein. The truncated S protein is flanked on its NH-terminus side by a signal peptide derived from amino acids 1-19 of the MARV glycoprotein (SEQ ID NO: 88), and on its carboxy-terminus side by the transmembrane domain of the MARV glycoprotein (SEQ ID NO: 90). The GPS-truncated S protein-GPTM peptide expressed is provided in SEQ ID NO: 113 in Table 17 below, which can be encoded by, for example, an MVA optimized nucleic acid sequence for example provided in SEQ ID NO: 115. The GPS-truncated S protein+K986P and V987P)-GPTM peptide expressed is provided in SEQ ID NO: 114 in Table 17 below, which can be encoded by, for example, an MVA optimized nucleic acid sequence for example provided in SEQ ID NO: 116. The GPS-truncated S protein-GPTM peptide expressed is provided in SEQ ID NO: 117 in Table 17 below, which further includes substitution K417T, E484K, and N501Y. The GPS-truncated S protein+K986P, V987P, K417T, E484K, and N501Y)-GPTM peptide expressed is provided in SEQ ID NO: 118 in Table 17 below. In some embodiments, the nucleic acid is arranged so that the GPS-truncated S-GPTM, E, and M encoding sequences are linearly adjacent. A linear representation of a rMVA comprising a MARV VP 40 insert and a separate, single MVA insert encoding GPS-truncated S-TM, an E protein, and an M protein suitable for forming a VLP upon expression is provided for in FIG. 9A. In some embodiments, the nucleic acid is arranged so that the GPS-truncated S+K986P and V987P-GPTM, E, and M encoding sequences are linearly adjacent. A linear representation of a rMVA comprising a MARV VP 40 insert and a separate, single MVA insert encoding GPS-truncated S+K986P and V987P-TM, an E protein, and an M protein suitable for forming a VLP upon expression is provided for in FIG. 9H. In some embodiments, GPS-Truncated S-GPTM is expressed as provided for in SEQ ID NO: 113 or SEQ ID NO: 114 or SEQ ID NO: 117 or SEQ ID NO: 118, the E protein is expressed as a full-length protein, as provided for in SEQ ID NO: 40, the M protein is expressed as a full-length protein, as provided for in SEQ ID NO: 43, and the MARV VP protein is expressed as provided for in SEQ ID NO: 92, or sequences at least 70%, 75%, 80%, 85%, 90%, or 95% homologous thereto. In some embodiments, provided herein is a plasmid or MVA viral vector containing a nucleic acid sequence encoding SEQ ID NOS: 113 or 114 or 117 or 118, 40, and 43, and 92, or sequences at least 70%, 75%, 80%, 85%, 90%, or 95% homologous thereto. In some embodiments, provided herein is a nucleic acid sequence comprising SEQ ID NOS: 115 or 116, 41, and 44, or sequences at least 70%, 75%, 80%, 85%, 90%, or 95% homologous thereto. In some embodiments, provided herein is a nucleic acid encoding the GPS-truncated S-GPTM, the E protein, and M protein, wherein the nucleic acid has been optimized for expression in the MVA viral vector, for example as provided in SEQ ID NOS: 115 or 116, 42, and 45, or sequences at least 70%, 75%, 80%, 85%, 90%, or 95% homologous thereto. In some embodiments, the nucleic acid sequence encodes for an additional amino acid sequence such as a tag, for example a C-terminus tag such as EPEA suitable for use during assay detection. The nucleic acid sequences may further comprise suitable promoter sequences such as those derived from pmH5, p11, pSyn, pHyb, or any other suitable promoter sequence. In addition, the nucleic acid sequence for insertion may further include suitable translation initiation sequences, such as for example, a Kozak consensus sequence. In addition, the nucleic acid sequence can include appropriate stop codons, for example TAA, TAG, or TGA, or combinations or multiples thereof, at the 3'end of the nucleic acid sequence following the last amino acid sequence of the protein or tag. Furthermore, the nucleic acid sequence can include a vaccinia virus termination sequence 3' of the last stop codon of each encoded protein. In addition, the nucleic acid sequence for insertion may further include restriction enzyme sites useful for generating shuttle vectors for ease of insertion of the antigenic sequence. Exemplary nucleic acid sequences for insertion encoding the GPS-truncated S-GPTM or GPS-truncated S+K986P and V987P), the E protein, and the M protein are provided as SEQ ID NOS: 119, 120, 121, or 122. In some embodiments, the rMVA comprises a nucleic acid sequence selected from SEQ ID NO: 119 (FIG. 9B-9C-9D), 120 (FIG. 9E-9F-9G), 121 (FIG. 9I-9J-9K), or 122 (FIG. 9L-9M-9N), or a sequence at least 70%, 75%, 80%, 85%, 90%, 95%, or 99% homologous thereto. In some embodiments, the rMVA further comprises a nucleic acid sequence of SEQ ID NO: 93 or 94, or a sequence at least 70%, 75%, 80%, 85%, 90%, or 95% homologous thereto.

TABLE 17

| GPS-Truncated S-GPTM | |
|---|---|
| SEQ ID NO: 113-GPS-truncated S-GPTM amino acid sequence | MWTTCFFISLILIQGIKTLFVFLVLLPLVSSQCVNLTTRTQLPPAYTNSFTRGV YYPDKVFRSSVLHSTQDLFLPFFSNVTWFHAIHVSGTNGTKRFDNPVLPFND GVYFASTEKSNIIRGWIFGTTLDSKTQSLLIVNNATNVVIKVCEFQFCNDPFLG VVYHKNNKSWMESEFRVYSSANNCTFEYVSQPFLMDLEGKQGNFKNLREFV FKNIDGYFKIYSKHTPINLVRDLPQGFSALEPLVDLPIGINITRFQTLLALHRSY LTPGDSSSGWTAGAAAYYVGYLQPRTFLLKYNENGTITDAVDCALDPLSETK CTLKSFTVEKGIYQTSNFRVQPTESIVRFPNITNLCPFGEVFNATRFASVYAWN RKRISNCVADYSVLYNSASFSTFKCYGVSPTKLNDLCFTNVYADSFVIRGDEV RQIAPGQTGKIADYNYKLPDDFTGCVIAWNSNNLDSKVGGNYNYLYRLFRK SNLKPFERDISTEIYQAGSTPCNGVEGFNCYFPLQSYGFQPTNGVGYQPYRVV VLSFELLHAPATVCGPKKSTNLVKNKCVNFNFNGLTGTGVLTESNKKFLPFQ QFGRDIADTTDAVRDPQTLEILDITPCSFGGVSVITPGTNTSNQVAVLYQDVN CTEVPVAIHADQLTPTWRVYSTGSNVFQTRAGCLIGAEHVNNSYECDIPIGAG |

TABLE 17-continued

GPS-Truncated S-GPTM

|  |  |
|---|---|
|  | ICASYQTQTNSPRRARSVASQSIIAYTMSLGAENSVAYSNNSIAIPTNFTISVTT EILPVSMTKTSVDCTMYICGDSTECSNLLLQYGSFCTQLNRALTGIAVEQDKN TQEVFAQVKQIYKTPPIKDFGGFNFSQILPDPSKPSKRSFIEDLLFNKVTLADA GFIKQYGDCLGDIAARDLICAQKFNGLTVLPPLLTDEMIAQYTSALLAGTITS GWTFGAGAALQIPFAMQMAYRFNGIGVTQNVLYENQKLIANQFNSAIGKIQD SLSSTASALGKLQDVVNQNAQALNTLVKQLSSNFGAISSVLNDILSRLDKVE AEVQIDRLITGRLQSLQTYVTQQLIRAAEIRASANLAATKMSECVLGQSKRVD FCGKGYHLMSFPQSAPHGVVFLHVTYVPAQEKNFTTAPAICHDGKAHFPREG VFVSNGTHWFVTQRNFYEPQIITTDNTFVSGNCDVVIGIVNNTVYDPLQPELD SFKEELDKYFKNHTSPDVDLGDISGINASVVNIQKEIDRLNEVAKNLNESLIDL QELGKYEQYIKWPWWTSDWGVLTNLGILLLLSIAVLIALSCICRIFTKYIG |
| SEQ ID NO: 114-GPS-truncated S + K986P and V987P-GPTM amino acid sequence | MWTTCFFISLILIQGIKTLFVFLVLLPLVSSQCVNLTTRTQLPPAYTNSFTRGV YYPDKVFRSSVLHSTQDLFLPFFSNVTWFHAIHVSGTNGTKRFDNPVLPFND GVYFASTEKSNIIRGWIFGTTLDSKTQSLLIVNNATNVVIKVCEFQFCNDPFLG VYYHKNNKSWMESEFRVYSSANNCTFEYVSQPFLMDLEGKQGNFKNLREFV FKNIDGYFKIYSKHTPINLVRDLPQGFSALEPLVDLPIGINITRFQTLLALHRSY LTPGDSSSGWTAGAAAYYVGYLQPRTFLLKYNENGTITDAVDCALDPLSETK CTLKSFTVEKGIYQTSNFRVQPTESIVRFPNITNLCPFGEVFNATRFASVYAWN RKRISNCVADYSVLYNSASFSTFKCYGVSPTKLNDLCFTNVYADSFVIRGDEV RQIAPGQTGKIADYNYKLPDDFTGCVIAWNSNNLDSKVGGNYNYLYRLFRK SNLKPFERDISTEIYQAGSTPCNGVEGFNCYFPLQSYGFQPTNGVGYQPYRVV VLSFELLHAPATVCGPKKSTNLVKNKCVNFNFNGLTGTGVLTESNKKFLPFQ QFGRDIADTTDAVRDPQTLEILDITPCSFGGVSVITPGTNTSNQVAVLYQDVN CTEVPVAIHADQLTPTWRVYSTGSNVFQTRAGCLIGAEHVNNSYECDIPIGAG ICASYQTQTNSPRRARSVASQSIIAYTMSLGAENSVAYSNNSIAIPTNFTISVTT EILPVSMTKTSVDCTMYICGDSTECSNLLLQYGSFCTQLNRALTGIAVEQDKN TQEVFAQVKQIYKTPPIKDFGGFNFSQILPDPSKPSKRSFIEDLLFNKVTLADA GFIKQYGDCLGDIAARDLICAQKFNGLTVLPPLLTDEMIAQYTSALLAGTITS GWTFGAGAALQIPFAMQMAYRFNGIGVTQNVLYENQKLIANQFNSAIGKIQD SLSSTASALGKLQDVVNQNAQALNTLVKQLSSNFGAISSVLNDILSRLDPPEA EVQIDRLITGRLQSLQTYVTQQLIRAAEIRASANLAATKMSECVLGQSKRVDF CGKGYHLMSFPQSAPHGVVFLHVTYVPAQEKNFTTAPAICHDGKAHFPREG VFVSNGTHWFVTQRNFYEPQIITTDNTFVSGNCDVVIGIVNNTVYDPLQPELD SFKEELDKYFKNHTSPDVDLGDISGINASVVNIQKEIDRLNEVAKNLNESLIDL QELGKYEQYIKWPWWTSDWGVLTNLGILLLLSIAVLIALSCICRIFTKYIG |
| SEQ ID NO: 115-GPS-truncated S-GPTM nucleic acid sequence-optimized | ATGTGGACGACCTGCTTCTTCATCTCCCTAATCCTAATCCAGGGAATCAAG ACCCTATTCGTGTTCCTAGTCCTACTACCGCTAGTCTCTTCTCAGTGTGTA AACCTAACAACGAGAACACAACTACCACCGGCGTACACCAATTCTTTCAC AAGAGGAGTATATTACCCGGACAAGGTGTTCAGATCCTCCGTACTACATT CTACACAGGACCTATTCCTACCGTTCTTCTCTAACGTAACATGGTTCCACG CGATCCATGTCTCTGGAACAAACGGAACGAAGAGATTCGATAACCCGGTC TTGCCGTTCAACGATGGTGTATACTTTGCGTCCACCGAGAAGTCCAACAT CATCAGAGGATGGATCTTCGGAACCACCTTGGATTCTAAGACCCAGTCCT TGCTAATCGTCAACAACGCGACCAACGTCGTCATCAAAGTCTGCGAATTC CAGTTCTGTAACGACCCGTTCTTGGGAGTCTACTACCACAAGAACAACAA GTCCTGGATGGAATCCGAGTTCAGAGTCTACTCTTCCGCGAACAACTGCA CCTTCGAATATGTATCTCAGCCGTTCCTAATGGACCTAGAGGGAAAGCAG GGAAACTTCAAGAACCTAAGAGAGTTCGTATTCAAGAACATCGACGGAT ACTTCAAGATCTACTCCAAGCACACTCCGATCAACCTAGTTAGAGATCTA CCGCAAGGATTCTCTGCGCTAGAACCGTTAGTAGATTTGCCGATCGGAAT CAACATCACCAGATTCCAGACACTACTAGCGCTACACAGATCTTACCTAA CGCCGGGAGATTCTTCTTCTGGATGGACTGCTGGTGCTGCGGCTTATTATG TAGGATACCTACAGCCGAGAACCTTCCTATTGAAGTACAACGAAAACGGA ACCATCACCGATGCCGTAGATTGTGCTCTAGATCCGCTATCCGAAACGAA GTGCACCCTAAAGTCTTTCACCGTCGAGAAGGGAATCTACCAGACCTCCA ACTTTAGAGTACAGCCGACCGAATCCATCGTCAGATTTCCGAACATCACG AACCTATGTCCGTTCGGAGAAGTGTTCAACGCGACAAGATTTGCGTCTGT CTATGCGTGGAACAGAAAAAGAATCAGTAACTGCGTCGCGGACTACTCCG TCCTATACAACTCTGCCTCTTTCTCCACGTTCAAATGCTACGGTGTATCTC CGACAAAGCTAAACGATCTATGCTTCACCAACGTCTACGCGGACTCCTTC GTAATCAGAGGAGATGAAGTTAGACAGATTGCGCCGGGACAAACTGGAA AGATCGCGGATTATAACTACAAGCTACCGGACGACTTCACCGGATGTGTA ATTGCGTGGAATTCGAACAACCTAGACTCCAAAGTCGGAGGAAACTACA ACTACTTGTACAGACTATTCAGAAAGTCCAACCTAAAGCCGTTCGAGAGA GACATCTCCACCGAAATCTATCAGGCTGGATCTACACCGTGTAATGGTGT CGAAGGATTCAACTGCTACTTCCCGCTACAGTCTTACGGATTTCAACCGA CAAACGGTGTAGGATATCAGCCGTACAGAGTCGTCGTACTATCCTTCGAA CTACTACATGCTCCGGCGACAGTATGTGGACCGAAAAAGTCTACCAACCT AGTCAAGAACAAATGCGTCAACTTTAACTTCAACGGACTAACCGGAACCG GTGTCCTAACCGAATCTAACAAGAAGTTTCTACCGTTCCAGCAGTTCGGA AGAGATATCGCGGATACAACAGACGCTGTCAGAGATCCGCAAACCTTGG AGATCCTAGATATCACACCGTGTTCTTTCGGTGGTGTCTCTGTAATTACTC CGGGAACGAACACCTCCAATCAGTAGCGGTACTATACCAGGACGTGAA CTGTACAGAAGTACCGGTAGCTATTCACGCGGATCAACTAACACCAACTT GGAGAGTGTACTCCACCGGATCTAACGTATTCCAAACAAGAGCGGGATGT CTAATCGGAGCGGAACACGTAAACAACTCCTACGAATGTGATATCCCGAT |

TABLE 17-continued

GPS-Truncated S-GPTM

|  |  |
|---|---|
|  | TGGAGCGGGAATCTGTGCGTCTTACCAAACACAAACAAACTCTCCGAGAA<br>GAGCGAGATCTGTAGCCTCTCAATCTATTATCGCCTACACCATGTCCTTGG<br>GAGCCGAAAATTCTGTCGCGTACTCCAACAATTCTATCGCGATCCCGACA<br>AACTTCACCATCTCTGTAACAACCGAGATCCTACCGGTGTCTATGACCAA<br>GACATCTGTCGATTGCACCATGTACATCTGCGGAGATTCCACCGAGTGCT<br>CCAACCTACTACTACAGTACGGATCTTTCTGTACCCAGCTAAACAGAGCG<br>TTGACTGGAATCGCTGTAGAGCAGGATAAGAACACTCAAGAGGTATTCGC<br>GCAAGTCAAGCAGATCTATAAGACTCCGCCGATCAAGGACTTCGGAGGTT<br>TCAACTTCTCTCAGATCTTGCCGGATCCGTCCAAACCGTCTAAGAGATCTT<br>TCATCGAGGACCTACTATTCAACAAAGTCACCCTAGCTGACGCGGGATTC<br>ATCAAACAATACGGAGATTGCTTGGGAGACATTGCGGCGAGAGATCTAAT<br>TTGCGCGCAGAAGTTTAACGGATTGACAGTACTACCGCCGCTACTAACCG<br>ATGAGATGATTGCGCAGTACACGTCTGCTCTATTGGCGGGAACAATTACA<br>AGTGGATGGACATTTGGAGCCGGTGCCGCTCTACAAATTCCGTTTGCTAT<br>GCAAATGGCGTACAGATTCAACGGAATCGGAGTAACCCAGAACGTCTTGT<br>ACGAGAACCAGAAGCTAATCGCGAACCAGTTCAATTCCGCGATCGGAAA<br>GATCCAGGACAGTCTATCTTCTACTGCTTCGGCGTTGGGAAAGCTACAGG<br>ATGTAGTAAATCAAAACGCGCAGGCGCTAAACACCTTGGTCAAGCAACTA<br>TCCTCTAACTTCGGAGCGATCTCGTCCGTCCTAAACGACATCTTATCCAGA<br>CTAGATAAGGTCGAAGCGGAGGTCCAGATCGATAGACTAATCACTGGAA<br>GATTGCAGTCCCTACAGACCTACGTAACACAGCAACTAATTAGAGCGGCG<br>GAGATTAGAGCCTCTGCTAATCTAGCTGCGACCAAGATGTCCGAATGTGT<br>CTTGGGACAATCCAAGAGAGTGGACTTCTGCGGAAAGGGATACCACCTA<br>ATGTCTTTCCCACAATCTGCGCCGCATGGTGTCGTATTCCTACATGTAACA<br>TATGTGCCGGCGCAAGAAAAGAACTTCACAACAGCTCCAGCGATCTGCCA<br>TGATGGAAAAGCTCATTTCCCGAGAGAGGGAGTCTTTGTCTCTAACGGAA<br>CTCATTGGTTCGTCACCCAGAGAAACTTCTACGAGCCGCAGATCATCACC<br>ACCGACAACACATTCGTCTCGGGAAACTGCGACGTGGTCATCGGAATCGT<br>AAACAATACCGTCTACGATCCGTTGCAGCCGGAACTAGACTCCTTCAAAG<br>AAGAGTTGGACAAGTACTTCAAGAACCACACCTCTCCGGATGTGGACTTG<br>GGAGATATCTCTGGAATCAACGCGTCCGTCGTCAACATCCAGAAAGAAAT<br>CGATAGATTGAACGAGGTCGCGAAGAACTTGAACGAGTCCCTAATCGACC<br>TACAAGAGCTAGGAAAATACGAGCAGTACATCAAGTGGCCGTGGTGGAC<br>ATCTGACTGGGGAGTCCTAACGAACCTAGGAATCCTACTACTATTGTCGA<br>TCGCGGTCCTAATCGCGCTATCCTGTATCTGTAGAATCTTCACCAAGTACA<br>TCGGA |
| SEQ ID NO: 116-GPS-<br>truncated S-GPTM<br>nucleic acid sequence-<br>optimized | ATGTGGACGACCTGCTTCTTCATCTCCCTAATCCTAATCCAGGGAATCAAG<br>ACCCTATTCGTGTTCCTAGTCCTACTACCGCTAGTCTCTTCTCAGTGTGTA<br>AACCTAACAACGAGAACACAACTACCACCGGCGTACACCAATTCTTTCAC<br>AAGAGGAGTATATTACCCGGACAAGGTGTTCAGATCCTCCGTACTACATT<br>CTACACAGGACCTATTCCTACCGTTCTTCTCTAACGTAACATGGTTCCACG<br>CGATCCATGTCTCTGGAACAAACGGAACGAAGAGATTCGATAACCCGGTC<br>TTGCCGTTCAACGATGGTGTATACTTTGCGTCCACCGAGAAGTCCAACAT<br>CATCAGAGGATGGATCTTCGGAACCACCTTGGATTCTAAGACCCAGTCCT<br>TGCTAATCGTCAACAACGCGACCAACGTCGTCATCAAAGTCTGCGAATTC<br>CAGTTCTGTAACGACCCGTTCTTGGGAGTCTACTACCACAAGAACAACAA<br>GTCCTGGATGGAATCCGAGTTCAGAGTCTACTCTTCCGCGAACAACTGCA<br>CCTTCGAATATGTATCTCAGCCGTTCCTAATGGACCTAGAGGGAAAGCAG<br>GGAAACTTCAAGAACCTAAGAGAGTTCGTATTCAAGAACATCGACGGAT<br>ACTTCAAGATCTACTCCAAGCACACTCCGATCAACCTAGTTAGAGATCTA<br>CCGCAAGGATTCTCTGCGCTAGAACCGTTAGTAGATTTGCCGATCGGAAT<br>CAACATCACCAGATTCCAGACACTACTAGCGCTACACAGATCTTACCTAA<br>CGCCGGGAGATTCTTCTTCTGGATGGACTGCTGGTGCTGCGGCTTATTATG<br>TAGGATACCTACAGCCGAGAACCTTCCTATTGAAGTACAACGAAAACGGA<br>ACCATCACCGATGCCGTAGATTGTGCTCTAGATCCGCTATCCGAAACGAA<br>GTGCACCCTAAAGTCTTTCACCGTCGAGAAGGGAATCTACCAGACCTCCA<br>ACTTTAGAGTACAGCCGACCGAATCCATCGTCAGATTTCCGAACATCACG<br>AACCTATGTCCGTTCGGAGAAGTGTTCAACGCGACAAGATTGCGTCTGT<br>CTATGCGTGGAACAGAAAAAGAATCAGTAACTGCGTCGCGGACTACTCCG<br>TCCTATACAACTCTGCCTCTTTCTCCACGTTCAAATGCTACGGTGTATCTC<br>CGACAAAGCTAAACGATCTATGCTTCACCAACGTCTACGCGGACTCCTTC<br>GTAATCAGAGGAGATGAAGTTAGACAGATTGCGCCGGGACAAACTGGAA<br>AGATCGCGGATTATAACTACAAGCTACCGGACGACTTCACCGGATGTGTA<br>ATTGCGTGGAATTCGAACAACCTAGACTCCAAAGTCGGAGGGAAACTACA<br>ACTACTTGTACAGACTATTCAGAAAGTCCAACCTAAAGCCGTTCGAGAGA<br>GACATCTCCACCGAAATCTATCAGGCTGGATCTACACCGTGTAATGGTGT<br>CGAAGGATTCAACTGCTACTTCCCGCTACAGTCTTACGGATTTCAACCGA<br>CAAACGGTGTAGGATATCAGCCGTACAGAGTCGTCGTACTATCCTTCGAA<br>CTACTACATGCTCCGGCGACAGTATGTGGACCGAAAAAGTCTACCAACCT<br>AGTCAAGAACAAATGCGTCAACTTTAACTTCAACGGACTAACCGGAACCG<br>GTGTCCTAACCGAATCTAACAAGAAGTTTCTACCGTTCCAGCAGTTCGGA<br>AGAGATATCGCGGATACAACAGACGCGTGTCAGAGATCCGCAAACCTTGG<br>AGATCCTAGATATCACACCGTGTTCTTTCGGTGGTGTCTCTGTAATTACTC<br>CGGGAACGAACACCTCCAATCAGTAGCGGTACTATACCAGGACGTGAA<br>CTGTACAGAAGTACCGGTAGCTATTCACGCGGATCAACTAACACCAACTT<br>GGAGAGTGTACTCCACCGGATCTAACGTATTCCAAACAAGAGCGGGATGT<br>CTAATCGGAGCGGAACACGTAAACAACTCCTACGAATGTGATATCCCGAT |

TABLE 17-continued

GPS-Truncated S-GPTM

```
TGGAGCGGGAATCTGTGCGTCTTACCAAACACAAACAAACTCTCCGAGAA
GAGCGAGATCTGTAGCCTCTCAATCTATTATCGCCTACACCATGTCCTTGG
GAGCCGAAAATTCTGTCGCGTACTCCAACAATTCTATCGCGATCCCGACA
AACTTCACCATCTCTGTAACAACCGAGATCCTACCGGTGTCTATGACCAA
GACATCTGTCGATTGCACCATGTACATCTGCGGAGATTCCACCGAGTGCT
CCAACCTACTACTACAGTACGGATCTTTCTGTACCCAGCTAAACAGAGCG
TTGACTGGAATCGCTGTAGAGCAGGATAAGAACACTCAAGAGGTATTCGC
GCAAGTCAAGCAGATCTATAAGACTCCGCCGATCAAGGACTTCGGAGGTT
TCAACTTCTCTCAGATCTTGCCGGATCCGTCCAAACCGTCTAAGAGATCTT
TCATCGAGGACCTACTATTCAACAAAGTCACCCTAGCTGACGCGGGATTC
ATCAAACAATACGGAGATTGCTTGGGAGACATTGCGGCGAGAGATCTAAT
TTGCGCGCAGAAGTTTAACGGATTGACAGTACTACCGCCGCTACTAACCG
ATGAGATGATTGCGCAGTACACGTCTGCTCTATTGGCGGGAACAATTACA
AGTGGATGGACATTTGGAGCCGGTGCCGCTCTACAAATTCCGTTTGCTAT
GCAAATGGCGTACAGATTCAACGGAATCGGAGTAACCCAGAACGTCTTGT
ACGAGAACCAGAAGCTAATCGCGAACCAGTTCAATTCCGCGATCGGAAA
GATCCAGGACAGTCTATCTTCTACTGCTTCGGCGTTGGGAAAGCTACAGG
ATGTAGTAAATCAAAACGCGCAGGCGCTAAACACCTTGGTCAAGCAACTA
TCCTCTAACTTCGGAGCGATCTCGTCCGTCCTAAACGACATCTTATCCAGA
CTAGATCCACCGGAAGCGGAGGTCCAGATCGATAGACTAATCACTGGAA
GATTGCAGTCCCTACAGACCTACGTAACACAGCAACTAATTAGAGCGGCG
GAGATTAGAGCCTCTGCTAATCTAGCTGCGACCAAGATGTCCGAATGTGT
CTTGGGACAATCCAAGAGAGTGGACTTCTGCGGAAAGGGATACCACCTA
ATGTCTTTCCCACAATCTGCGCCGCATGGTGTCGTATTCCTACATGTAACA
TATGTGCCGGCGCAAGAAAAGAACTTCACAACAGCTCCAGCGATCTGCCA
TGATGGAAAAGCTCATTTCCCGAGAGAGGGAGTCTTTGTCTCTAACGGAA
CTCATTGGTTCGTCACCCAGAGAAACTTCTACGAGCCGCAGATCATCACC
ACCGACAACACATTCGTCTCGGGAAACTGCGACGTGGTCATCGGAATCGT
AAACAATACCGTCTACGATCCGTTGCAGCCGGAACTAGACTCCTTCAAAG
AAGAGTTGGACAAGTACTTCAAGAACCACACCTCTCCGGATGTGGACTTG
GGAGATATCTCTGGAATCAACGCGTCCGTCGTCAACATCCAGAAAGAAAT
CGATAGATTGAACGAGGTCGCGAAGAACTTGAACGAGTCCCTAATCGACC
TACAAGAGCTAGGAAAATACGAGCAGTACATCAAGTGGCCGTGGTGGAC
ATCTGACTGGGGAGTCCTAACGAACCTAGGAATCCTACTACTATTGTCGA
TCGCGGTCCTAATCGCGCTATCCTGTATCTGTAGAATCTTCACCAAGTACA
TCGGA
```

| SEQ ID NO: 117-GPS-truncated S-GPTM amino acid sequence (K417T; E484K; N501Y) | MWTTCFFISLILIQGIKTLFVFLVLLPLVSSQCVNLTTRTQLPPAYTNSFTRGV YYPDKVFRSSVLHSTQDLFLPFFSNVTWFHAIHVSGTNGTKRFDNPVLPFND GVYFASTEKSNIIRGWIFGTTLDSKTQSLLIVNNATNVVIKVCEFQFCNDPFLG VYYHKNNKSWMESEFRVYSSANNCTFEYVSQPFLMDLEGKQGNFKNLREFV FKNIDGYFKIYSKHTPINLVRDLPQGFSALEPLVDLPIGINITRFQTLLALHRSY LTPGDSSSGWTAGAAAYYVGYLQPRTFLLKYNENGTITDAVDCALDPLSETK CTLKSFTVEKGIYQTSNFRVQPTESIVRFPNITNLCPFGEVFNATRFASVYAWN RKRISNCVADYSVLYNSASFSTFKCYGVSPTKLNDLCFTNVYADSFVIRGDEV RQIAPGQTGTIADYNYKLPDDFTGCVIAWNSNNLDSKVGGNYNYLYRLFRKS NLKPFERDISTEIYQAGSTPCNGVKGFNCYFPLQSYGFQPTYGVGYQPYRVV VLSFELLHAPATVCGPKKSTNLVKNKCVNFNFNGLTGTGVLTESNKKFLPFQ QFGRDIADTTDAVRDPQTLEILDITPCSFGGVSVITPGTNTSNQVAVLYQDVN CTEVPVAIHADQLTPTWRVYSTGSNVFQTRAGCLIGAEHVNNSYECDIPIGAG ICASYQTQTNSPRRARSVASQSIIAYTMSLGAENSVAYSNNSIAIPTNFTISVTT EILPVSMTKTSVDCTMYICGDSTECSNLLLQYGSFCTQLNRALTGIAVEQDKN TQEVFAQVKQIYKTPPIKDFGGFNFSQILPDPSKPSKRSFIEDLLFNKVTLADA GFIKQYGDCLGDIAARDLICAQKFNGLTVLPPLLTDEMIAQYTSALLAGTITS GWTFGAGAALQIPFAMQMAYRFNGIGVTQNVLYENQKLIANQFNSAIGKIQD SLSSTASALGKLQDVVNQNAQALNTLVKQLSSNFGAISSVLNDILSRLDKVE AEVQIDRLITGRLQSLQTYVTQQLIRAAEIRASANLAATKMSECVLGQSKRVD FCGKGYHLMSFPQSAPHGVVFLHVTYVPAQEKNFTTAPAICHDGKAHFPREG VFVSNGTHWFVTQRNFYEPQIITTDNTFVSGNCDVVIGIVNNTVYDPLQPELD SFKEELDKYFKNHTSPDVDLGDISGINASVVNIQKEIDRLNEVAKNLNESLIDL QELGKYEQYIKWPWWTSDWGVLTNLGILLLLSIAVLIALSCICRIFTKYIG |
| --- | --- |
| SEQ ID NO: 118-GPS-truncated S + K986P and V987P-GPTM amino acid sequence (K417T; E484K; N501Y) | MWTTCFFISLILIQGIKTLFVFLVLLPLVSSQCVNLTTRTQLPPAYTNSFTRGV YYPDKVFRSSVLHSTQDLFLPFFSNVTWFHAIHVSGTNGTKRFDNPVLPFND GVYFASTEKSNIIRGWIFGTTLDSKTQSLLIVNNATNVVIKVCEFQFCNDPFLG VYYHKNNKSWMESEFRVYSSANNCTFEYVSQPFLMDLEGKQGNFKNLREFV FKNIDGYFKIYSKHTPINLVRDLPQGFSALEPLVDLPIGINITRFQTLLALHRSY LTPGDSSSGWTAGAAAYYVGYLQPRTFLLKYNENGTITDAVDCALDPLSETK CTLKSFTVEKGIYQTSNFRVQPTESIVRFPNITNLCPFGEVFNATRFASVYAWN RKRISNCVADYSVLYNSASFSTFKCYGVSPTKLNDLCFTNVYADSFVIRGDEV RQIAPGQTGTIADYNYKLPDDFTGCVIAWNSNNLDSKVGGNYNYLYRLFRKS NLKPFERDISTEIYQAGSTPCNGVKGFNCYFPLQSYGFQPTYGVGYQPYRVV VLSFELLHAPATVCGPKKSTNLVKNKCVNFNFNGLTGTGVLTESNKKFLPFQ QFGRDIADTTDAVRDPQTLEILDITPCSFGGVSVITPGTNTSNQVAVLYQDVN CTEVPVAIHADQLTPTWRVYSTGSNVFQTRAGCLIGAEHVNNSYECDIPIGAG ICASYQTQTNSPRRARSVASQSIIAYTMSLGAENSVAYSNNSIAIPTNFTISVTT EILPVSMTKTSVDCTMYICGDSTECSNLLLQYGSFCTQLNRALTGIAVEQDKN TQEVFAQVKQIYKTPPIKDFGGFNFSQILPDPSKPSKRSFIEDLLFNKVTLADA |

TABLE 17-continued

GPS-Truncated S-GPTM

```
GFIKQYGDCLGDIAARDLICAQKFNGLTVLPPLLTDEMIAQYTSALLAGTITS
GWTFGAGAALQIPFAMQMAYRFNGIGVTQNVLYENQKLIANQFNSAIGKIQD
SLSSTASALGKLQDVVNQNAQALNTLVKQLSSNFGAISSVLNDILSRLDPPEA
EVQIDRLITGRLQSLQTYVTQQLIRAAEIRASANLAATKMSECVLGQSKRVDF
CGKGYHLMSFPQSAPHGVVFLHVTYVPAQEKNFTTAPAICHDGKAHFPREG
VFVSNGTHWFVTQRNFYEPQIITTDNTFVSGNCDVVIGIVNNTVYDPLQPELD
SFKEELDKYFKNHTSPDVDLGDISGINASVVNIQKEIDRLNEVAKNLNESLIDL
QELGKYEQYIKWPWWTSDWGVLTNLGILLLLSIAVLIALSCICRIFTKYIG
```

In an alternative aspect, provided herein is a rMVA viral vector designed to express one or more SARS-CoV2 S protein antigenic peptides as an in-frame fusion protein, wherein the fusion protein comprises a signal sequence of an envelope glycoprotein (GPS), SARS-CoV2 S protein fragment, a transmembrane domain of an envelope glycoprotein (GPTM), and a cytosolic domain of an envelope glycoprotein (GPCD), wherein the envelope glycoprotein is not derived from a coronavirus. The rMVA viral vector is further designed to express a matrix protein from the same virus the envelope glycoprotein was derived from. By providing the SARS-CoV2 S protein fragment as a fusion with a GP protein, the S protein fragment-GP fusion can form a VLP with the rMVA expressed matrix protein.

Suitable glycoproteins and matrix proteins for use in the present invention include, but are not limited to, those derived from: a Filoviridae, for example Marburg virus, Ebola virus, or Sudan virus; a Retroviridae, for example human immunodeficiency virus type 1 (HIV-1); an Arenaviridaea, for example Lassa virus; a Flaviviridae, for example Dengue virus and Zika virus. In particular embodiments, the glycoprotein and matrix proteins are derived from Marburg virus (MARV). In particular embodiments, the glycoprotein is derived from the MARV GP protein (Genbank accession number AFV31202.1). The amino acid sequence of the MARV GP protein is provided as SEQ ID NO: 87 in Table 14. In particular embodiments, the MARV GPS domain comprises amino acids 1 to 19 of the glycoprotein (MWTTCFFISLILIQGIKTL) (SEQ ID NO: 88), which can be encoded by, for example the MVA optimized nucleic acid sequence of SEQ ID NO: 89), the GPTM domain comprises amino acid sequences 644-673 of the glycoprotein (WWTSDWGVLTNLGILLLLSIA-VLIALSCICRIFTKYIG) (SEQ ID NO: 90, which can be encoded by, for example the MVA optimized nucleic acid sequence of SEQ ID NO: 91).

The MARV VP40 amino acid sequence is available at Genbank accession number JX458834, and provided in Table 14 as SEQ ID NO: 92, which can be encoded by, for example, the MVA optimized nucleic acid sequence of SEQ ID NO: 93. In some embodiments, the nucleic acid sequence encoding the viral matrix protein can be contained as a bicistronic sequence with the GPS-S protein or protein fragment-GPTM nucleic acid sequence, or contained on a separate nucleic acid sequence inserted at a separate location within the MVA genome.

In one alternative, a rMVA viral vector is provided which encodes for a modified S protein peptide fused with a GP protein, wherein the modified S protein comprises an S1+S2 truncated protein lacking the carboxy terminus of the protein, and also encodes a matrix protein, for example the MARV VP40 protein. In some embodiments, the S1+S2 truncated protein comprises amino acids 2 to 1213 of the S protein. In some embodiments, the S1+S2 truncated protein comprises amino acids 2 to 1213 of the S protein and one or more proline substitutions, for example, K986P and/or V987P. In some embodiments, the truncated S protein-GP fusion and the MARV VP40 encoding nucleic acid sequence are inserted at a separated insertion site. In some embodiments, the truncated S protein-GP fusion and the MARV VP40 encoding nucleic acid sequence are inserted as a bicistronic sequence in the MVA genome.

In some embodiments, the truncated S protein-GP fusion protein comprises amino acids 2-1213 of the S Protein. The truncated S protein is flanked on its NH-terminus side by a signal peptide derived from amino acids 1-19 of the MARV glycoprotein (SEQ ID NO: 88), and on its carboxy-terminus side by the transmembrane domain of the MARV glycoprotein (SEQ ID NO: 90). The GPS-truncated S protein-GPTM peptide expressed is provided in SEQ ID NO: 113 or 114 in Table 17, which can be encoded by, for example, an MVA optimized nucleic acid sequence for example provided in SEQ ID NOS: 115 or 116. Alternatively, the GPS-truncated S protein-GPTM peptide expressed is provided in SEQ ID NOS: 117 or 118 in Table 17. A linear representation of a rMVA comprising a MARV VP 40 insert and a separate, single MVA insert encoding GPS-truncated S-TM, is provided for in FIG. 10A. A linear representation of a rMVA comprising a MARV VP 40 insert and a separate, single MVA insert encoding GPS-truncated S +K986P and V987P-TM, is provided for in FIG. 10F. In some embodiments, GPS-truncated S-GPTM is expressed as provided for in SEQ ID NOS: 113 or 114 or 117 or 118, and the MARV VP protein is expressed as provided for in SEQ ID NO: 92, or sequences at least 70%, 75%, 80%, 85%, 90%, or 95% homologous thereto. In some embodiments, provided herein is a plasmid or MVA viral vector containing nucleic acid sequences encoding SEQ ID NOS: 113 or 114 or 117 or 118, and 92, or sequences at least 70%, 75%, 80%, 85%, 90%, or 95% homologous thereto. In some embodiments, provided herein is a nucleic acid sequence comprising SEQ ID NOS: 70A or 70B or sequences at least 70%, 75%, 80%, 85%, 90%, or 95% homologous thereto. In some embodiments, provided herein is a nucleic acid encoding the GPS-truncated S-GPTM, wherein the nucleic acid has been optimized for expression in the MVA viral vector, for example as provided in SEQ ID NOS: 115 or 116 or sequences at least 70%, 75%, 80%, 85%, 90%, or 95% homologous thereto. In some embodiments, the nucleic acid sequence encodes for an additional amino acid sequence such as a tag, for example a C-terminus tag such as EPEA suitable for use during assay detection. The nucleic acid sequences may further comprise suitable promoter sequences such as, for example but not limited to, those derived from pmH5, p11, pSyn, pHyb, or any other suitable promoter sequence. In addition, the nucleic acid sequence for insertion may further include suitable translation initiation sequences, such as for example, a Kozak consensus sequence. In addition, the nucleic acid sequence can include appropriate stop codons, for example TAA, TAG, or TGA, or combinations or multiples thereof, at the 3'end of the nucleic acid sequence following the last amino acid sequence of the protein or tag. Furthermore, the nucleic acid sequence can include a vaccinia virus termination sequence 3' of the last stop codon of each encoded protein. In addition, the nucleic acid sequence for insertion may further include restriction enzyme sites useful for generating shuttle vectors for ease of insertion of the antigenic sequence. Exemplary nucleic acid sequences for insertion encoding the GPS-truncated S-GPTM is provided as SEQ ID NOS: 123, 124, 125, or 126. In some embodiments, the rMVA comprises a nucleic acid sequence selected from SEQ ID NOS: 123 (FIG. 10B-10C), 124 (FIG. 10D-10E), 125 (FIG. 10G-10H), or 126 (FIG. 10I-10J), or a sequence at least 70%, 75%, 80%, 85%, 90%, 95%, or 99% homologous thereto. In some embodiments, the rMVA further comprises a nucleic acid sequence of SEQ ID NOS: 93 or 94, or a sequence at least 70%, 75%, 80%, 85%, 90%, or 95% homologous thereto.

In some embodiments, the truncated S protein-GP fusion and the MARV VP40 encoding nucleic acid sequence are inserted as a bicistronic sequence in the MVA genome. A linear representation of a rMVA comprising a MARV VP 40 insert and GPS-truncated S-TM as a bicistronic nucleic acid is provided for in FIG. 10K. A linear representation of a rMVA comprising a MARV VP 40 insert GPS-truncated S+K986P and V987P-TM as a bicistronic nucleic acid is provided for in FIG. 10R. Exemplary nucleic acid sequences for insertion encoding the GPS-truncated S or truncated S+K986P and V987P-GPTM/VP40 is provided as SEQ ID NOS: 127, 128, 129, or 130. In some embodiments, the rMVA comprises a nucleic acid sequence selected from SEQ ID NO: 127 (FIG. 10L-10M-10N), 128 (FIG. 10O-10P-10Q), 129 (FIG. 10S-10T-10U), or 130 (FIG. 10V-10W-10X), or a sequence at least 70%, 75%, 80%, 85%, 90%, 95%, or 99% homologous thereto.

In one alternative, a rMVA viral vector is provided which encodes for a S protein receptor binding domain (RBD) peptide fused with a GP protein, and also encodes a matrix protein, for example, the MARV VP40 protein. In some embodiments, the RBD-GP fusion and the MARV VP40 encoding nucleic acid sequence are inserted at a separated insertion site, as exemplified in FIG. 11A. In some embodiments, the RBD GP fusion are inserted as a bicistronic sequence in the MVA genome as exemplified in FIG. 11H.

In some embodiments, the RBD peptide is derived from amino acids 327 to 524 of the S protein. In some embodiments, the RBD peptide is derived from amino acids 331 to 524 of the S protein. In some embodiments, the RBD is a consensus coronavirus sequence. The RBD peptide is flanked on its NH-terminus side by a signal peptide derived from amino acids 1-19 of the MARV glycoprotein (SEQ ID NO: 88), and on its carboxy-terminus side by the transmembrane domain of the MARV glycoprotein (SEQ ID NO: 90). The GPS-RBD (aa 327-524)-GPTM peptide expressed is provided in SEQ ID NO: 95 in Table 15, which can be encoded by, for example, an MVA optimized nucleic acid sequence for example provided in SEQ ID NO: 97. The GPS-RBD (aa 331-524)-GPTM peptide expressed is provided in SEQ ID NO: 96 in Table 15, which can be encoded by, for example, an MVA optimized nucleic acid sequence for example provided in SEQ ID NO: 98. Alternatively, the GPS-RBD (aa327-524)-GPTM peptide expressed is provided in SEQ ID NO: 99. Alternatively, the GPS-RBD (aa327-524)-GPTM peptide expressed is provided in SEQ ID NO: 100. A linear representation of a rMVA comprising a MARV VP 40 insert and a separate GPS-RBD-TM insert suitable for forming a VLP upon expression is provided for in FIG. 11a. A linear representation of a rMVA comprising a MARV VP 40 insert and a separate GPS-RBD (aa 331-524)-TM insert suitable for forming a VLP upon expression is provided for in FIG. 11b. A linear representation of a rMVA comprising a MARV VP 40 insert and a separate GPS-RBD (aa 327-524)-TM insert suitable for forming a VLP upon expression is provided for in FIG. 11E. In some embodiments, GPS-RBD-GPTM is expressed as provided for in SEQ ID NOS: 95 or 99 (RBD (aa 327-524) or 96 or 100 (RBD (aa 331-524) and the MARV VP protein is expressed as provided for in SEQ ID NO: 92, or sequences at least 70%, 75%, 80%, 85%, 90%, or 95% homologous thereto. In some embodiments, provided herein is a plasmid or MVA viral vector containing a nucleic acid sequence encoding SEQ ID NOS: 95 or 96 or 99 or 100 and 92, or sequences at least 70%, 75%, 80%, 85%, 90%, or 95% homologous thereto. In some embodiments, provided herein is a nucleic acid sequence comprising SEQ ID NOS: 97 or 98, or sequences at least 70%, 75%, 80%, 85%, 90%, or 95% homologous thereto. In some embodiments, provided herein is a nucleic acid encoding the GPS-RBD-GPTM, wherein the nucleic acid has been optimized for expression in the MVA viral vector, for example as provided in SEQ ID NOS: 97 or 98, or sequences at least 70%, 75%, 80%, 85%, 90%, or 95% homologous thereto. In some embodiments, the nucleic acid sequence encodes for an additional amino acid sequence such as a tag, for example a C-terminus tag such as EPEA suitable for use during assay detection. The nucleic acid sequences may further comprise suitable promoter sequences such as, for example but not limited to, those derived from pmH5, p11, pSyn, pHyb, or any other suitable promoter sequence. In addition, the nucleic acid sequence for insertion may further include suitable translation initiation sequences, such as for example, a Kozak consensus sequence. In addition, the nucleic acid sequence can include appropriate stop codons, for example TAA, TAG, or TGA, or combinations or multiples thereof, at the 3'end of the nucleic acid sequence following the last amino acid sequence of the protein or tag. Furthermore, the nucleic acid sequence can include a vaccinia virus termination sequence 3' of the last stop codon of each encoded protein. In addition, the nucleic acid sequence for insertion may further include restriction enzyme sites useful for generating shuttle vectors for ease of insertion of the antigenic sequence. Exemplary nucleic acid sequences for insertion encoding the GPS-RBD-GPTM is provided as SEQ ID NO: 131, 132, 133, or 134. In some embodiments, the rMVA comprises a nucleic acid sequence selected from SEQ ID NOS: 131 (FIG. 11F), 132 (FIG. 11G), 133 (FIG. 11C), or 134 (FIG. 11D), or a sequence at least 70%, 75%, 80%, 85%, 90%, 95%, or 99% homologous thereto. In some embodiments, the rMVA further comprises a nucleic acid sequence of SEQ ID NO: 93 or 94, or a sequence at least 70%, 75%, 80%, 85%, 90%, or 95% homologous thereto.

In some embodiments, the RBD-GP fusion and the MARV VP40 encoding nucleic acid sequence are inserted as a bicistronic sequence in the MVA genome. A linear representation of a rMVA comprising a MARV VP 40 insert and GPS-RBD (aa 331-325)-TM as a bicistronic nucleic acid is provided for in FIG. 11I. A linear representation of a rMVA comprising a MARV VP 40 insert and GPS-RBD (aa 327-325)-TM as a bicistronic nucleic acid is provided for in FIG. 11N. Exemplary nucleic acid sequences for insertion encoding the GPS-RBD-GPTM-VP40 is provided as SEQ ID NOS: 135 (FIG. 11O-11P) and 136 (FIG. 11Q-11R) (RBD (aa 327-524)) or 137 (FIG. 11J-11K) and 138 (FIG. 11L-11M) (RBD (aa 331-524)) In some embodiments, the rMVA comprises a nucleic acid sequence selected from SEQ ID NOS: 135, 136, 137, or 138, or a sequence at least 70%, 75%, 80%, 85%, 90%, 95%, or 99% homologous thereto.

In one alternative, a rMVA viral vector is provided which encodes for an S protein peptide fused with a GP protein and also encodes a viral matrix protein, for example a MARV VP40 protein. In some embodiments, the S protein tandem repeat sequence is flanked on its NH-terminus side by a signal peptide derived from amino acids 1-19 of the MARV glycoprotein (SEQ ID NO: 88), and on its carboxy-terminus side by the transmembrane domain of the MARV glycoprotein (SEQ ID NO: 90). In some embodiments, the tandem repeat is for example (RBD-spacer-RBD-spacer) x or (RBD Seq. 1-spacer-RBD Seq. 2-spacer) x, wherein RBD is any S protein RBD peptide, RBD Seq. 1 is a first S protein RBD peptide, and RBD Seq. 2 is a second S protein RBD peptide, and wherein x=2, 3, 4, 5, 6, 7, 8, 9, or 10. In some embodiments, the RBD peptides are selected from one or more peptides derived from amino acids 331 to 524 or 327 to 524 of the SARS-CoV2 S protein. In some embodiments, the linear epitopes encoded by the rMVA are selected from the amino acids 504 to 524 and amino acids 473 to 490 of the SARS-CoV2 S protein. In some embodiments, the linear epitopes encoded by the rMVA are the amino acids 504 to 524 and amino acids 473 to 490 of the SARS-CoV2 S protein. In some embodiments, the tandem repeat sequence is ((aa504-524)-spacer-(aa473-490)-spacer) x, wherein x=2, 3, 4, 5, 6, 7, 8, 9, or 10. In some embodiments, x=3-7. In some embodiments, x=5. An exemplary amino acid sequence comprising a GPS-tandem repeat-GPTM is provided for in Table 16 as SEQ ID NO: 105, which can be encoded by the MVA optimized nucleic acid sequence of SEQ ID NO: 106. Alternatively, an exemplary amino acid sequence comprising a GPS-tandem repeat-GPTM is provided for in Table 16 as SEQ ID NO: 109. An exemplary amino acid sequence comprising a GPS-tandem repeat-GPTM, wherein x=5 for the tandem repeat, is provided for in Table 16 as SEQ ID NO: 107, which can be encoded by the MVA optimized nucleic acid sequence of SEQ ID NO: 108. An alternative exemplary amino acid sequence comprising a GPS-tandem repeat-GPTM, wherein x=5 for the tandem repeat, is provided for in Table 16 as SEQ ID NO: 110.

A linear representation of a rMVA comprising a MARV VP 40 insert and a separate, single MVA insert encoding GPS-tandem repeat-GPTM peptide suitable for forming a VLP upon expression is provided for in FIG. 12A. In some embodiments, GPS-tandem repeat-GPTM peptide is expressed as provided for in SEQ ID NO: 64 or 66, and the MARV VP protein is expressed as provided for in SEQ ID NO: 59, or sequences at least 70%, 75%, 80%, 85%, 90%, or 95% homologous thereto. In some embodiments, provided herein is a plasmid or MVA viral vector containing nucleic acid sequences encoding SEQ ID NOS: 105 or 106 or 109 or 110, and 92, or sequences at least 70%, 75%, 80%, 85%, 90%, or 95% homologous thereto. In some embodiments, provided herein is a nucleic acid sequence comprising SEQ ID NOS: 106 or 108, or sequences at least 70%, 75%, 80%, 85%, 90%, or 95% homologous thereto. In some embodiments, provided herein is a nucleic acid encoding the GPS-tandem repeat-GPTM peptide, wherein the nucleic acid has been optimized for expression in the MVA viral vector, for example as provided in SEQ ID NOS: 106 or 108 or 109 or 110, or sequences at least 70%, 75%, 80%, 85%, 90%, or 95% homologous thereto. In some embodiments, the nucleic acid sequence encodes for an additional amino acid sequence such as a tag, for example a C-terminus tag such as EPEA suitable for use during assay detection. The nucleic acid sequences may further comprise suitable promoter sequences such as, for example but not limited to, those derived from pmH5, p11, pSyn, pHyb, or any other suitable promoter sequence. In addition, the nucleic acid sequence for insertion may further include suitable translation initiation sequences, such as for example, a Kozak consensus sequence. In addition, the nucleic acid sequence can include appropriate stop codons, for example TAA, TAG, or TGA, or combinations or multiples thereof, at the 3'end of the nucleic acid sequence following the last amino acid sequence of the protein or tag. Furthermore, the nucleic acid sequence can include a vaccinia virus termination sequence 3' of the last stop codon of each encoded protein. In addition, the nucleic acid sequence for insertion may further include restriction enzyme sites useful for generating shuttle vectors for ease of insertion of the antigenic sequence. Exemplary nucleic acid sequences for insertion encoding the GPS-tandem repeat-GPTM peptide are provided as SEQ ID NOS: 139 and 140. In some embodiments, the rMVA comprises a nucleic acid sequence selected from SEQ ID NO: 139 (FIG. 12B) or 140 (FIG. 12C), or a sequence at least 70%, 75%, 80%, 85%, 90%, 95%, or 99% homologous thereto. In some embodiments, the rMVA further comprises a nucleic acid sequence of SEQ ID NOS: 93 or 94, or a sequence at least 70%, 75%, 80%, 85%, 90%, or 95% homologous thereto.

In some embodiments, the GPS-tandem repeat-GPTM and the MARV VP40 encoding nucleic acid sequence are inserted as a bicistronic sequence in the MVA genome. A linear representation of a rMVA comprising a MARV VP 40 insert and GPS-tandem repeat-GPTM as a bicistronic nucleic acid is provided for in FIG. 12D. Exemplary nucleic acid sequences for insertion encoding the GPS-tandem repeat-GPTM-VP40 are provided as SEQ ID NOS: 141 and 142. In some embodiments, the rMVA comprises a nucleic acid sequence selected from SEQ ID NOS: 141 (FIG. 12E-12F) or 142 (FIG. 12G-12H), or a sequence at least 70%, 75%, 80%, 85%, 90%, or 95% homologous thereto.

In some embodiments, an rMVA viral vector is provided which encodes only the spike(S) protein (or fragment thereof). A linear representation of a single MVA insert encoding an S protein is provided for in FIG. 13A. In some embodiments, the S protein is expressed as a full-length protein, for example, as provided for in SEQ ID NOS: 1 or 6, or sequences at least 70%, 75%, 80%, 85%, 90%, or 95% homologous thereto. In some embodiments, provided herein is a plasmid or MVA viral vector comprising a nucleic acid sequence encoding SEQ ID NO: 1, or sequences at least 70%, 75%, 80%, 85%, 90%, or 95% homologous thereto. In some embodiments, provided herein is a plasmid or MVA viral vector comprising a nucleic acid sequence encoding SEQ ID NO: 6, or sequences at least 70%, 75%, 80%, 85%, 90%, or 95% homologous thereto. In some embodiments, provided herein is a nucleic acid encoding the full-length S protein, wherein the nucleic acid has been optimized for expression in the MVA viral vector, for example as provided in SEQ ID NO: 3. In some embodiments, the nucleic acid sequence encodes for an additional amino acid sequence such as a tag, for example a C-terminus tag such as EPEA suitable for detection of the expressed proteins in an assay. The nucleic acid sequences may further comprise suitable promoter sequences such as, for example but not limited to, those derived from pmH5, p11, pSyn, pHyb, or any other suitable promoter sequence known in the art. In addition, the nucleic acid sequence for insertion may further include suitable translation initiation sequences, such as for example, a Kozak consensus sequence. In addition, the nucleic acid sequence can include appropriate stop codons, for example TAA, TAG, or TGA, or combinations or multiples thereof, at the 3'end of the nucleic acid sequence following the last amino acid sequence of each protein or tag. Furthermore, the nucleic acid sequence can include a vaccinia virus termination sequence 3' of the last stop codon of each encoded protein. In addition, the nucleic acid sequence for insertion may further include restriction enzyme sites useful for generating shuttle vectors for ease of insertion of the antigenic sequence. Exemplary nucleic acid sequences comprising the adjacent coding sequences of the full-length S protein are provided below in as SEQ ID NOS: 143 (FIG. 13B-13C) and 144 (FIG. 13D-13E). In some embodiments, the rMVA comprises a nucleic acid sequence selected from SEQ ID NOS: 143 or 144, or a sequence at least 70%, 75%, 80%, 85%, 90%, or 95% homologous thereto.

Alternatively, an rMVA viral vector is provided which encodes the spike(S) protein, wherein the S protein has been stabilized with one or more amino acid proline substitutions that stabilize the S protein trimer in the prefusion conformation. In some embodiments, the S protein is expressed as a full-length protein and contains one or more proline substitutions at or near the boundary between a Heptad Repeat 1 (HR1) and a central helix of the promoters of the S ectodomain trimer. In some embodiments, the proline substitutions occur between amino acid residues 970 to 990 of the promoters in the trimer. In some embodiments, the S protein is expressed as a full-length protein and contains two proline substitutions at amino acids K986 and V987. A linear representation of a single MVA insert encoding a stabilized S protein is provided for in FIG. 14A. In some embodiments, the S protein is expressed as a full-length protein comprising two proline substitutions at amino acids 986 and 987 of the S protein, for example, as provided for in SEQ ID NO: 8 or 11, or sequences at least 75%, 80%, 85%, 90%, or 95% homologous thereto. In some embodiments, provided herein is a plasmid or MVA viral vector containing a nucleic acid sequence encoding SEQ ID NO: 8 or 11 or sequences at least 75%, 80%, 85%, 90%, or 95% homologous thereto. In some embodiments, provided herein is a nucleic acid sequence comprising SEQ ID NO: 9 or sequences at least 75%, 80%, 85%, 90%, or 95% homologous thereto. In some embodiments, provided herein is a nucleic acid encoding the full-length proline substituted S protein, wherein the nucleic acid has been optimized for expression in the MVA viral vector, for example as provided in SEQ ID NOS: 10 or 12, or sequences at least 75%, 80%, 85%, 90%, or 95% homologous thereto. In some embodiments, the nucleic acid sequence encodes for an additional amino acid sequence such as a tag, for example a C-terminus tag such as EPEA. The nucleic acid sequences may further comprise suitable promoter sequences such as, for example but not limited to, those derived from pmH5, p11, pSyn, pHyb, or any other suitable promoter sequence. In addition, the nucleic acid sequence for insertion may further include suitable translation initiation sequences, such as for example, a Kozak consensus sequence. In addition, the nucleic acid sequence can include appropriate stop codons, for example TAA, TAG, or TGA, or combinations or multiples thereof, at the 3'end of the nucleic acid sequence following the last amino acid sequence of the protein or tag. Furthermore, the nucleic acid sequence can include a vaccinia virus termination sequence 3' of the last stop codon of each encoded protein.

In addition, the nucleic acid sequence for insertion may further include restriction enzyme sites useful for generating shuttle vectors for ease of insertion of the antigenic sequence. Exemplary nucleic acid sequences for insertion encoding the full-length stabilized S protein are provided below as SEQ ID NOS: 145 and 146. In some embodiments, the rMVA comprises a nucleic acid sequence selected from SEQ ID NOS: 145 (FIG. 14B-14C) or 146 FIG. 14D-14E), or a sequence at least 70%, 75%, 80%, 85%, 90%, 95%, or 99% homologous thereto.

Alternatively, an rMVA viral vector is provided which encodes a modified, truncated form of the spike(S) protein, wherein the truncated S protein comprises a S1+S2 region and lacks the carboxy terminus. In some embodiments, the truncated S protein comprises amino acids 1 to 1213 (SEQ ID NO: 13 or SEQ ID NO: 18). In some embodiments, the truncated S protein contains two proline substitutions at amino acids 986 and 987 (SEQ ID NO: 14 or SEQ ID NO: 19). A linear representation of a single MVA insert encoding a truncated S protein is provided for in FIG. 15A. A linear representation of a single MVA insert encoding a truncated S protein+K986P and V987P is provided for in FIG. 15F. In some embodiments, the truncated S protein is expressed as provided for in SEQ ID NOS: 13, 14, 18, or 19, or sequences at least 75%, 80%, 85%, 90%, or 95% homologous thereto. In some embodiments, provided herein is a plasmid or MVA viral vector containing a nucleic acid sequence encoding SEQ ID NOS: 13, 14, 18, or 19, or sequences at least 75%, 80%, 85%, 90%, or 95% homologous thereto. In some embodiments, provided herein is a nucleic acid sequence comprising SEQ ID NO: 15, or sequences at least 75%, 80%, 85%, 90%, or 95% homologous thereto. In some embodiments, provided herein is a nucleic acid encoding the truncated S protein, wherein the nucleic acid has been optimized for expression in the MVA viral vector, for example as provided in SEQ ID NOS: 16 or 17, or sequences at least 75%, 80%, 85%, 90%, or 95% homologous thereto. In some embodiments, the nucleic acid sequence encodes for an additional amino acid sequence such as a tag, for example a C-terminus tag such as EPEA. The nucleic acid sequences may further comprise suitable promoter sequences such as, for example but not limited to, those derived from pmH5, p11, pSyn, pHyb, or any other suitable promoter sequence. In addition, the nucleic acid sequence for insertion may further include suitable translation initiation sequences, such as for example, a Kozak consensus sequence. In addition, the nucleic acid sequence can include appropriate stop codons, for example TAA, TAG, or TGA, or combinations or multiples thereof, at the 3'end of the nucleic acid sequence following the last amino acid sequence of the protein or tag. Furthermore, the nucleic acid sequence can include a vaccinia virus termination sequence 3' of the last stop codon of each encoded protein. In addition, the nucleic acid sequence for insertion may further include restriction enzyme sites useful for generating shuttle vectors for ease of insertion of the antigenic sequence. Exemplary nucleic acid sequences for insertion encoding the truncated S protein are provided below as SEQ ID NOS: 147 (FIG. 15B-15C), 148 (FIG. 15D-15E), 149 (FIG. 15G-15H), or 150 (FIG. 15I-15J). In some embodiments, the rMVA comprises a nucleic acid sequence selected from SEQ ID NOS: 147, 148, 149, or 150, or a sequence at least 70%, 75%, 80%, 85%, 90%, 95%, or 99% homologous thereto.

Pharmaceutical Compositions

The recombinant viral vectors of the present invention are readily formulated as pharmaceutical compositions for veterinary or human use, either alone or in combination. The pharmaceutical composition may comprise a pharmaceutically acceptable diluent, excipient, carrier, or adjuvant.

In one embodiment, the present invention is a vaccine effective to protect against and/or treat a SARS-CoV2 infection comprising a recombinant MVA vector that expresses at least one SARS-CoV2 antigenic polypeptide or an immunogenic fragment thereof. The vaccine composition may comprise one or more additional therapeutic agents.

The pharmaceutical composition may comprise 1, 2, 3, 4 or more than 4 different recombinant MVA vectors.

As used herein, the phrase "pharmaceutically acceptable carrier" encompasses any of the standard pharmaceutical carriers, such as those suitable for parenteral administration, such as, for example, by intramuscular, intraarticular (in the joints), intravenous, intradermal, intraperitoneal, and subcutaneous routes. Examples of such formulations include aqueous and non-aqueous, isotonic sterile injection solutions, which contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. One exemplary pharmaceutically acceptable carrier is physiological saline.

Other physiologically acceptable diluents, excipients, carriers, or adjuvants and their formulations are known to those skilled in the art.

In some embodiments, adjuvants are used as immune response enhancers. In various embodiments, the immune response enhancer is selected from the group consisting of alum-based adjuvants, oil based adjuvants, Specol, RIBI, TiterMax, Montanide ISA50 or Montanide ISA 720, GM-CSF, nonionic block copolymer-based adjuvants, dimethyl dioctadecyl ammoniumbromide (DDA) based adjuvants AS-1, AS-2, Ribi Adjuvant system based adjuvants, QS21, Quil A, SAF (Syntex adjuvant in its microfluidized form (SAF-m), dimethyl-dioctadecyl ammonium bromide (DDA), human complement based adjuvants m. vaccae, ISCOMS, MF-59, SBAS-2, SBAS-4, Enhanzyn®, RC-529, AGPs, MPL-SE, QS7, Escin; Digitonin; *Gypsophila*; and *Chenopodium quinoa* saponins.

The compositions utilized in the methods described herein can be administered by a route selected from, e.g., parenteral, intramuscular, intraarterial, intravascular, intravenous, intraperitoneal, subcutaneous, dermal, transdermal, ocular, inhalation, buccal, sublingual, perilingual, nasal, topical administration, and oral administration. The preferred method of administration can vary depending on various factors (e.g., the components of the composition being administered and the severity of the condition being treated). Formulations suitable for oral administration may consist of liquid solutions, such as an effective amount of the composition dissolved in a diluent (e.g., water, saline, or PEG-400), capsules, sachets or tablets, each containing a predetermined amount of the vaccine. The pharmaceutical composition may also be an aerosol formulation for inhalation, e.g., to the bronchial passageways. Aerosol formulations may be mixed with pressurized, pharmaceutically acceptable propellants (e.g., dichlorodifluoromethane, propane, or nitrogen).

For the purposes of this invention, pharmaceutical compositions suitable for delivering a therapeutic or biologically active agent can include, e.g., tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, injectables, implants, sprays, or aerosols. Any of these formulations can be prepared by well-known and accepted methods of art. See, for example, Remington: The Science and Practice of Pharmacy (21 st ed.), ed. A. R. Gennaro, Lippincott Williams & Wilkins, 2005, and Encyclopedia of Pharmaceutical Technology, ed. J. Swarbrick, Informa Healthcare, 2006, each of which is hereby incorporated by reference.

The immunogenicity of the composition (e.g., vaccine) may be significantly improved if the composition of the present invention is co-administered with an immunostimulatory agent or adjuvant. Suitable adjuvants well-known to those skilled in the art include, e.g., aluminum phosphate, aluminum hydroxide, QS21, Quil A (and derivatives and components thereof), calcium phosphate, calcium hydroxide, zinc hydroxide, glycolipid analogs, octodecyl esters of an amino acid, muramyl dipeptides, polyphosphazene, lipoproteins, ISCOM-Matrix, DC-Choi, DDA, cytokines, and other adjuvants and derivatives thereof.

Formulations suitable for oral administration can consist of (a) liquid solutions, such as an effective amount of the vaccine dissolved in diluents, such as water, saline or PEG 400; (b) capsules, sachets or tablets, each containing a predetermined amount of the vaccine, as liquids, solids, granules or gelatin; (c) suspensions in an appropriate liquid; (d) suitable emulsions; and (e) polysaccharide polymers such as chitins. The vaccine, alone or in combination with other suitable components, may also be made into aerosol formulations to be administered via inhalation, e.g., to the bronchial passageways. Aerosol formulations can be placed into pressurized acceptable propellants, such as dichlorodifluoromethane, propane, nitrogen, and the like.

Suitable formulations for rectal administration include, for example, suppositories, which consist of the vaccine with a suppository base. Suitable suppository bases include natural or synthetic triglycerides or paraffin hydrocarbons. In addition, it is also possible to use gelatin rectal capsules which consist of a combination of the vaccine with a base, including, for example, liquid triglycerides, polyethylene glycols, and paraffin hydrocarbons. The vaccines of the present invention may also be co-administered with cytokines to further enhance immunogenicity. The cytokines may be administered by methods known to those skilled in the art, e.g., as a nucleic acid molecule in plasmid form or as a protein or fusion protein.

This invention also provides kits comprising the vaccines of the present invention. For example, kits comprising a vaccine and instructions for use are within the scope of this invention.

Methods of Use

The compositions of the invention can be used as vaccines for inducing an immune response to SARS-CoV2.

In exemplary embodiments, the present invention provides a method of preventing a SARS-CoV2 infection to a subject in need thereof (e.g., an unexposed subject), said method comprising administering the composition of the present invention to the subject in a prophylactically effective amount. The result of the method is that the subject is partially or completely immunized against the virus.

In exemplary embodiments, the present invention provides a method of treating a SARS-CoV2 infection in a subject in need thereof (e.g., an exposed subject, such as a subject who has been recently exposed but is not yet symptomatic, or a subject who has been recently exposed and is only mildly symptomatic), said method comprising administering the composition of the present invention to the subject in a therapeutically effective amount. The result of treatment is a subject that has an improved therapeutic profile.

A subject to be treated according to the methods described herein (e.g., a subject infected with SARS-CoV2) may be one who has been diagnosed by a medical practitioner as having such a condition. Diagnosis may be performed by any suitable means. A subject in whom the development of an infection is being prevented may or may not have received such a diagnosis. One skilled in the art will understand that a subject to be treated according to the present invention may have been identified using standard tests or may have been identified, without examination, as one at high risk due to the presence of one or more risk factors (e.g., exposure to SARS-CoV2, etc.).

Prophylactic treatment may be administered, for example, to a subject not yet exposed to or infected by SARS-CoV2 but who is susceptible to, or otherwise at risk of exposure or infection with a SARS-CoV2.

Therapeutic treatment may be administered, for example, to a subject already exposed to or infected by SARS-CoV2 who is not yet ill, or showing symptoms or infection, suffering from a disorder in order to improve or stabilize the subject's condition (e.g., a patient already infected with SARS-CoV2). The result is an improved therapeutic profile. In some instances, as compared with an equivalent untreated control, treatment may ameliorate a disorder or a symptom thereof by, e.g., 5%, 10%, 20%, 30%, 40%, 50%, 60%, 70%, 80%, 90%, 95%, or 100% as measured by any standard technique. In some instances, treating can result in the inhibition of viral replication, a decrease in viral titers or viral load, eradication or clearing of the virus. In other embodiments, treatment may result in amelioration of one or more symptoms of the infection, including any symptom identified above. According to this embodiment, confirmation of treatment can be assessed by detecting an improvement in or the absence of symptoms.

In other embodiments, treatment may result in reduction or elimination of the ability of the subject to transmit the infection to another, uninfected subject. Confirmation of treatment according to this embodiment is generally assessed using the same methods used to determine amelioration of the disorder, but the reduction in viral titer or viral load necessary to prevent transmission may differ from the reduction in viral titer or viral load necessary to ameliorate the disorder.

In one embodiment, the present invention is a method of inducing an immune response in a subject (e.g., a human) by administering to the subject a recombinant viral vector that encodes at least one gene from SARS-CoV2. The immune response may be a cellular immune response or a humoral immune response, or a combination thereof.

In a particular embodiment, the present invention is a method of inducing an immune response in a subject (e.g., a human) by administering to the subject a recombinant viral vector that encodes at least one gene from SARS-CoV2. The immune response may be a cellular immune response or a humoral immune response, or a combination thereof.

In one embodiment, the immune response is a broadly neutralizing antibody response.

In a particular embodiment, the present invention is a method of inducing an immune response in a subject (e.g., a human) by administering to the subject a recombinant viral vector that encodes at least one gene from SARS-CoV2. In certain embodiments, the recombinant viral vector encodes at least two genes from a SARS-CoV2. The immune response may be a cellular immune response or a humoral immune response, or a combination thereof.

In another embodiment, the invention features a method of treating SARS-CoV2 infection in a subject (e.g., a human) by administering to the subject a recombinant viral vector that encodes at least one gene from SARS-CoV2. The subject being treated may not have, but is at risk of developing, an infection by SARS-CoV2.

The composition may be administered, e.g., by injection (e.g., intramuscular, intraarterial, intravascular, intravenous, intraperitoneal, or subcutaneous).

It will be appreciated that more than one route of administering the vaccines of the present invention may be employed either simultaneously or sequentially (e.g., boosting). In addition, the vaccines of the present invention may be employed in combination with traditional immunization approaches such as employing protein antigens, vaccinia virus and inactivated virus, as vaccines. Thus, in one embodiment, the vaccines of the present invention are administered to a subject (the subject is "primed" with a vaccine of the present invention) and then a different vaccine is administered (the subject is "boosted" with a different vaccine). In another embodiment, a different vaccine is first administered to the subject followed by administration of a vaccine of the present invention. In yet another embodiment, a different vaccine and a vaccine of the present invention are co-administered. In some embodiments, the different vaccine is mRNA-1273 (Moderna, Inc.), AZD-1222 (AstraZeneca and University of Oxford), BNT162 (Pfizer and BioNTech), CoronaVac (Sinovac), NVX-CoV 2372 (NovoVax), SCB-2019 (Sanofi and GSK), ZyCoV-D (Zydus Cadila), or CoVaxin (Bharat Biotech).

While not to be bound by any specific mechanism, it is believed that upon inoculation with a pharmaceutical composition as described herein, the immune system of the host responds to the vaccine by producing antibodies, both secretory and serum, specific for SARS-CoV2 proteins; and by producing a cell-mediated immune response specific for SARS-CoV2. As a result of the vaccination, the host becomes at least partially or completely immune to SARS-CoV2 infection, or resistant to developing moderate or severe disease caused by SARS-CoV2 infection.

In one aspect, methods are provided to alleviate, reduce the severity of, or reduce the occurrence of, one or more of the symptoms (e.g., fever, severe headache, muscle pain, malaise, extreme asthenia, conjunctivitis, popular rash, dysphagia, nausea, vomiting, bloody diarrhea followed by diffuse hemorrhages, delirium, shock, jaundice, thrombocytopenia, lymphocytopenia, neutrophilia, focal necrosis in various organs (e.g., kidneys and liver), and acute respiratory distress) associated with SARS-CoV2 infection comprising administering an effective amount of a pharmaceutical composition comprising a recombinant MVA viral vector that comprises a SARS-CoV2 protein or fragment thereof.

In one embodiment, administration is repeated at least twice, at least 3 times, at least 4 times, at least 5 times, at least 6 times, at least 7 times, at least 8 times, or more than 8 times.

In one embodiment, administration is repeated twice.

In one embodiment, about 2-8, about 4-8, or about 6-8 administrations are provided.

In one embodiment, about 1-4-week, 2-4 week, 3-4 week, 1 week, 2 weeks, 3 weeks, 4 weeks or more than 4 week intervals are provided between administrations.

In one specific embodiment, a 4-week interval is used between 2 administrations.

The invention includes methods of prevention and treatment of a SARS-CoV2 infection, including drug resistant and multidrug resistant forms of the virus and related disease states, conditions, or complications of the viral infection, including pneumonia, such as 2019 novel coronavirus-infected pneumonia (NCIP), acute lung injury (ALI), and acute respiratory distress syndrome (ARDS). Additional non-limiting complications include hypoxemic respiratory failure, acute respiratory failure (ARF), acute liver injury, acute cardiac injury, acute kidney injury, septic shock, disseminated intravascular coagulation, blood clots, multisystem inflammatory syndrome, chronic fatigue, rhabdomyolysis, and cytokine storm.

In another alternative embodiment, a method to prevent transmission is provided that includes administering an effective amount of one or more of the rMVA viral vectors described herein to humans to induce a sufficient immune response that prevents transmission of SARS-CoV2.

The invention is directed to a method of treating a SARS-CoV2 infection, including drug resistant and multidrug resistant forms of the virus and related disease states, conditions, or complications of the viral infection, including pneumonia, such as 2019 novel coronavirus-infected pneumonia (NCIP), acute lung injury (ALI), and acute respiratory distress syndrome (ARDS). Additional non-limiting complications include hypoxemic respiratory failure, acute respiratory failure (ARF), acute liver injury, acute cardiac injury, acute kidney injury, septic shock, disseminated intravascular coagulation, blood clots, multisystem inflammatory syndrome, chronic fatigue, rhabdomyolysis, and cytokine storm.

In one embodiment, the administration of a rMVA described herein results in a reduction in the incidence of progressive respiratory insufficiency (PRI) as measured by greater than or equal to a 1-tier or even a 2-tier or more increase in respiratory support methods required to maintain satisfactory oxygenation (SpO2>93%) using the 6-tier hierarchical levels of respiratory support methods described below, wherein the subject has acquired a SARS-CoV2 infection but has previously been, or will be, administered a rMVA viral vector described herein.

The scale of increasing respiratory support levels includes:

Level 1: Normal oxygenation on room air (SpO2>93%), no need for supplemental O2

Level 2: Persistent hypoxemia on room air (SpO2>93) with requirement for low-level supplemental O2 by nasal cannular or mask (up to 2 L/min) to maintain SpO2>93

Level 3: Requirement for higher levels of passive supplemental O2 by nasal cannular or mask (up to 2 L/min) to maintain SpO2>93

Level 4: Requirement for oxygenation by positive-pressure devices, e.g., Continuous Positive Airway Pressure (CPAP) or Bi-level Positive Airway Pressure (BiPAP) or other non-invasive positive-pressure respiratory support methods to main satisfactory oxygenation and/or ventilation Level 5: Requires invasive respiratory support (intubated mechanical ventilation or ECMO)

Level 6: Death

In one embodiment, the reduction in PRI is an increase from level 5 to level 3, level 5 to level 2, or level 5 to level 1 in comparison to a non-immunized subject. In one embodiment, the reduction in PRI is an increase from level 4 to level 2 or level 4 to level 1 in comparison to a non-immunized subject. In one embodiment, the reduction in PRI is an increase from level 3 to level 1 in comparison to a non-immunized subject.

In one embodiment, the administration of rMVA viral vector described herein reduces the median time to Clinical Recovery (status 6, 7, or 8 in the NIAID Clinical Status scale using an adapted National Institute of Allergy and Infectious Diseases (NIAID) ordinal scale of Clinical Status) by at least 3, 4, 5, or more days. In one embodiment, the administration of a rMVA viral vector described herein results in an improvement as measured by the adapted ordinal scale of Clinical Status in a subject that develops a SARS-CoV2 infection.

From most severe disease to progressively less severe disease, the stages of the adapted ordinal scale of overall Clinical Status are defined as follows:

1. Death
2. Hospitalized, on invasive mechanical ventilation or ECMO
3. Hospitalized, on non-invasive ventilation or high flow oxygen devices
4. Hospitalized, requiring supplemental oxygen
5. Hospitalized, not requiring supplemental oxygen-requiring ongoing medical care (COVID-19 related or otherwise)
6. Hospitalized, not requiring supplemental oxygen; no longer requires close medical care for COVID-19
7. Not hospitalized, but with limitation on activities and needing close outpatient care for COVID-19 manifestations
8. Not hospitalized, no limitations on activities, no need for continued close medical care In one embodiment, the administration of a rMVA viral vector described herein reduces the median time to Clinical Recovery (status 6, 7, or 8 in the NIAID Clinical Status scale using an adapted National Institute of Allergy and Infectious Diseases (NIAID) ordinal scale of Clinical Status) by at least 5 days, at least 6 days, at least 7 days, at least 8 days, at least 9 days, or at least 10 days compared to a non-immunized subject.

In one embodiment, the administration of a rMVA viral vector described herein reduces the duration of hospitalization for a patient infected with the SARS-CoV-2 virus compared to a non-immunized subject.

In one embodiment, the administration of a rMVA viral vector described herein reduces the time to sustained non-detectable SARS-CoV-2 virus in the nose and/or throat in a patient infected with the SARS-CoV-2 virus compared to a non-immunized subject.

In one embodiment, the administration of a rMVA viral vector described herein reduces respiratory failure or death compared to a non-immunized subject.

Dosage

The vaccines are administered in a manner compatible with the dosage formulation, and in such amount as will be therapeutically effective, immunogenic and protective. The quantity to be administered depends on the subject to be treated, including, for example, the capacity of the immune system of the individual to synthesize antibodies, and, if needed, to produce a cell-mediated immune response. Precise amounts of active ingredient required to be administered depend on the judgment of the practitioner and may be monitored on a patient-by-patient basis. However, suitable dosage ranges are readily determinable by one skilled in the art and generally range from about $5.0 \chi 10^6$ $TCID_{50}$ to about $5.0 \chi 10^9$ $TCID_{50}$. The dosage may also depend, without limitation, on the route of administration, the patient's state of health and weight, and the nature of the formulation.

The pharmaceutical compositions of the invention are administered in such an amount as will be therapeutically effective, immunogenic, and/or protective against a pathogenic species of ebolavirus. The dosage administered depends on the subject to be treated (e.g., the manner of administration and the age, body weight, capacity of the immune system, and general health of the subject being treated). The composition is administered in an amount to provide a sufficient level of expression that elicits an immune response without undue adverse physiological effects. Preferably, the composition of the invention is a heterologous viral vector that includes one or more polypeptides of the SARS-CoV2 or a nucleic acid molecule encoding one or more genes of SARS-CoV2, and is administered at a dosage of, e.g., between $1.0\chi10^4$ and $9.9\chi10^{12}$ $TCID_{50}$ of the viral vector, preferably between $1.0\chi105$ $TCID_{50}$ and $1.0\chi10^{11}$ $TCID_{50}$ pfu, more preferably between $1.0\chi10^6$ and $1.0\chi10^{10}$ $TCID_{50}$ pfu, or most preferably between $5.0\chi10^6$ and $5.0\chi10^9$ $TCID_{50}$. The composition may include, e.g., at least $5.0\chi106$ $TCID_{50}$ of the viral vector (e.g., $1.0\chi10^8$ $TCID_{50}$ of the viral vector). A physician or researcher can decide the appropriate amount and dosage regimen.

The composition of the method may include, e.g., between $1.0\chi10^4$ and $9.9\chi10^{12}$ $TCID_{50}$ of the viral vector, preferably between $1.0\chi10^5$ $TCID_{50}$ and $1.0\chi10^{11}$ $TCID_{50}$ pfu, more preferably between $1.0\chi10^6$ and $1.0\chi10^{10}$ $TCID_{50}$ pfu, or most preferably between $5.0\chi10^6$ and $5.0\chi10^9$ $TCID_{50}$. The composition may include, e.g., at least $5.0\chi106$ $TCID_{50}$ of the viral vector (e.g., $1.0\chi10^8$ $TCID_{50}$ of the viral vector). The method may include, e.g., administering the composition to the subject two or more times.

The invention also features a method of inducing an immune response to SARS-CoV2 in a subject (e.g., a human) that includes administering to the subject an effective amount of a recombinant viral vector that encodes at least one gene from SARS-CoV2. The subject being treated may not have, but is at risk of developing, an infection by an arenavirus. Alternatively, the subject may already be infected with a SARS-CoV2. The composition may be administered, e.g., by injection (e.g., intramuscular, intraarterial, intravascular, intravenous, intraperitoneal, or subcutaneous).

The term "effective amount" is meant the amount of a composition administered to improve, inhibit, or ameliorate a condition of a subject, or a symptom of a disorder, in a clinically relevant manner (e.g., improve, inhibit, or ameliorate infection by arenavirus or provide an effective immune response to infection by SARS-CoV2). Any improvement in the subject is considered sufficient to achieve treatment. Preferably, an amount sufficient to treat is an amount that prevents the occurrence or one or more symptoms of SARS-CoV2 or is an amount that reduces the severity of, or the length of time during which a subject suffers from, one or more symptoms of SARS-CoV2 infection (e.g., by at least 10%, 20%, or 30%, more preferably by at least 50%, 60%, or 70%, and most preferably by at least 80%, 90%, 95%, 99%, or more, relative to a control subject that is not treated with a composition of the invention). A sufficient amount of the pharmaceutical composition used to practice the methods described herein (e.g., the treatment of SARS-CoV2 infection) varies depending upon the manner of administration and the age, body weight, and general health of the subject being treated. Ultimately, the prescribers or researchers will decide the appropriate amount and dosage.

In some instances, it may be desirable to combine the immunogenic SARS-CoV2 compositions of the present invention with immunogenic compositions which induce protective responses to other agents, particularly other viruses. For example, the vaccine compositions of the present invention can be administered simultaneously, separately or sequentially with other genetic immunization vaccines such as those for influenza (Ulmer, J. B. et al., Science 259:1745-1749 (1993); Raz, E. et al., PNAS (USA) 91:9519-9523 (1994)), malaria (Doolan, D. L. et al., J. Exp. Med. 183:1739-1746 (1996); Sedegah, M. et al., PNAS (USA) 91:9866-9870 (1994)), and tuberculosis (Tascon, R. C. et al., Nat. Med. 2:888-892 (1996)).

Administration

As used herein, the term "administering" refers to a method of giving a dosage of a pharmaceutical composition of the invention to a subject. The compositions utilized in the methods described herein can be administered by a route selected from, e.g., parenteral, dermal, transdermal, ocular, inhalation, buccal, sublingual, perilingual, nasal, rectal, topical administration, and oral administration. Parenteral administration includes intravenous, intraperitoneal, subcutaneous, intraarterial, intravascular, and intramuscular administration. The preferred method of administration can vary depending on various factors (e.g., the components of the composition being administered, and the severity of the condition being treated).

Administration of the pharmaceutical compositions (e.g., vaccines) of the present invention can be by any of the routes known to one of skill in the art. Administration may be by, e.g., intramuscular injection. The compositions utilized in the methods described herein can also be administered by a route selected from, e.g., parenteral, dermal, transdermal, ocular, inhalation, buccal, sublingual, perilingual, nasal, rectal, topical administration, and oral administration. Parenteral administration includes intravenous, intraperitoneal, subcutaneous, and intramuscular administration. The preferred method of administration can vary depending on various factors, e.g., the components of the composition being administered, and the severity of the condition being treated.

In addition, single or multiple administrations of the compositions of the present invention may be given to a subject. For example, subjects who are particularly susceptible to SARS-CoV2 infection may require multiple treatments to establish and/or maintain protection against the virus. Levels of induced immunity provided by the pharmaceutical compositions described herein can be monitored by, e.g., measuring amounts of neutralizing secretory and serum antibodies. The dosages may then be adjusted or repeated as necessary to maintain desired levels of protection against viral infection.

Combinations

The rMVA vaccines described herein can be administered in addition to the current standard of care for patients suffering from SARS-CoV2, or in combination or alternation with any other compound or therapy that the healthcare provider deems beneficial to the patient, as described in more detail below. The combination and/or alternation therapy can be preventative, therapeutic, adjunctive, or palliative.

The method also comprises administering to a host in need thereof, typically a human, an effective amount of an rMVA described herein optionally in combination with at least one additional bioactive agent, for example, an additional anti-viral agent, further optionally in combination with a pharmaceutically acceptable carrier additive and/or excipient.

In some embodiments, the rMVA described herein can be administered in combination or alternation with an additional SARS-CoV2 vaccination. In some embodiments, the additional vaccination can be selected from an mRNA-based vaccine, an adenovirus vaccine, a non-replicating vaccine, a DNA vaccine, a live attenuated vaccine, a plant-based adjuvant vaccine, a multipope peptide-based vaccine, an inactivated virus, and a peptide vaccine, or combinations thereof. Additional vaccines suitable for use with the rMVA viral vectors and methods described herein include, but are not limited to, mRNA-1273 (MODERNA COVID-19 VACCINE; Moderna, Inc.), AZD-1222 (COVIDSHIELD; Astra-Zeneca and University of Oxford), BNT162 (COMIRNATY; Pfizer and BioNTech), Sputnik V (Gamaleya Research Institute, Acellena Contract Drug Research and Development), CoronaVac (Sinovac), NVX-CoV 2372 (NovoVax), SCB-2019 (Sanofi and GSK), ZyCoV-D (Zydus Cadila), BBIBP-CorV (Beijing Institute of Biological Products; China National Pharmaceutical Group (Sinopharm)), EpiVacCorona (Federal Budgetary Research Institution State Research Center of Virology and Biotechnology), Convidicea (CanSino Biologics), Covid-19 Vaccine (Wuhan Institute of Biological Products; China National Pharmaceutical Group (Sinopharm), JNJ-78436735 (Johnson & Johnson), ZF2001) Anhui Zhifei Longcom Biopharmaceutical, Institute of Microbiology of the Chinese Academy of Sciences), CVnCoV (CureVac; GSK), INO-4800 (Inovio Pharmaceuticals), VIR-7831 (Medicago; GSK; Dynavax), Covid-19 adenovirus bases vaccine (ImmunityBio; NantKwest), UB-612 (COVAXX), or CoVaxin (Bharat Biotech), or combinations thereof.

TherMVA viral vectors described herein can be administered on top of the current standard of care for COVID patients, or in combination or alternation with any other compound or therapy that the healthcare provider deems beneficial for the patient. The combination and/or alternation therapy can be therapeutic, adjunctive, or palliative.

In some embodiments, the rMVA viral vector is administered with an anti-infective agent, for example a NS5B inhibitor including, but not limited to remdesivir, a protease inhibitor such as lopinavir or ritonavir, previously approved for HIV, may also be administered. In some embodiments, the anti-infective is selected from favipiravir, fingolimod (Gilenya), methylprednisolone, bevacizumab (Avastin), Actemra (tocilizumab), umifenovir, losartan and the monoclonal antibody combination of REGN3048 and REGN3051, ribavirin, AT-527 (Atea Pharmaceuticals, described in U.S. Pat. No. 10,519,186, incorporated by reference herein) or AT-511 (Atea Pharmaceuticals, described in U.S. Pat. No. 10,519,186, incorporated by reference herein). Any of these drugs or vaccines can be used in combination or alternation with the rMVA provided herein to treat or prevent a SARS-CoV2 viral infection susceptible to such.

Embodiments

At least the following embodiments are provided herein:
1. A recombinant modified vaccinia Ankara (rMVA) viral vector comprising a heterologous nucleic acid sequence encoding a Spike(S) protein, peptide fragment, or variant thereof, a Membrane (M) protein, and an Envelope (E) protein derived from severe acute respiratory syndrome-coronavirus 2 (SARS-CoV2) operably linked to a promoter compatible with poxvirus expression systems, wherein, upon expression in a host cell, the S protein, peptide fragment, or variant thereof, M protein, and E protein are capable of together forming a virus like particle.
2. The rMVA of embodiment 1, wherein the heterologous nucleic acid sequence encodes a full-length S protein.
3. The rMVA of embodiments 1 or 2, wherein the full-length S protein comprises an amino acid sequence of SEQ ID NO: 1, or a sequence at least 95% homologous thereto.
4. The rMVA of embodiment 3, wherein the full-length S protein comprises the amino acid sequence of SEQ ID NO: 1.
5. The rMVA of embodiments 1-2, wherein the heterologous nucleic acid sequence encoding the S protein comprises SEQ ID NO: 3, or a sequence at least 95% homologous thereto.
6. The rMVA of embodiment 5, wherein the heterologous nucleic acid sequence encoding the full-length S protein comprises SEQ ID NO: 3.
7. The rMVA of embodiments 1 or 2, wherein the full-length S protein comprises an amino acid sequence of SEQ ID NO: 6, or a sequence at least 95% homologous thereto.
8. The rMVA of embodiment 7, wherein the full-length S protein comprises the amino acid sequence of SEQ ID NO: 6.
9. The rMVA of embodiments 1-8, wherein the E protein comprises an amino acid sequence of SEQ ID NO: 40, or a sequence at least 95% homologous thereto.
10. The rMVA of embodiment 9, wherein the E protein comprises the amino acid sequence of SEQ ID NO: 40.
11. The rMVA of embodiments 1-10, wherein the heterologous nucleic acid sequence encoding the E protein comprises SEQ ID NO: 42, or a sequence at least 95% homologous thereto.
12. The rMVA of embodiment 11, wherein the heterologous nucleic acid sequence encoding the E protein comprises SEQ ID NO: 42.
13. The rMVA of embodiments 1-12, wherein the M protein comprises an amino acid sequence of SEQ ID NO: 43, or a sequence at least 95% homologous thereto.
14. The rMVA of embodiment 13, wherein the M protein comprises the amino acid sequence of SEQ ID NO: 43.
15. The rMVA of embodiments 1-14, wherein the heterologous nucleic acid sequence encoding the M protein comprises SEQ ID NO: 45, or a sequence at least 95% homologous thereto.
16. The rMVA of embodiment 15, wherein the heterologous nucleic acid sequence encoding the E protein comprises SEQ ID NO: 45.
17. The rMVA of embodiment 1, wherein the heterologous nucleic acid sequence encodes amino acid sequences comprising SEQ ID NOS: 1, 40, and 43, or sequences at least 95% homologous thereto.
18. The rMVA of embodiment 17, wherein the heterologous nucleic acid sequence encodes amino acid sequences comprising SEQ ID NOS: 1, 40, and 43.
19. The rMVA of embodiment 1, wherein the heterologous nucleic acid sequence comprises SEQ ID NOS: 3, 42, and 45, or sequences at least 95% homologous thereto.

20. The rMVA of embodiments 19, wherein the heterologous nucleic acid sequence comprises SEQ ID NOS: 3, 42, and 45.

21. The rMVA of embodiment 1, wherein the heterologous nucleic acid sequence encodes amino acid sequences comprising SEQ ID NOS: 6, 40, and 43, or sequences at least 95% homologous thereto.

22. The rMVA of embodiment 21, wherein the heterologous nucleic acid sequence encodes amino acid sequences comprising SEQ ID NOS: 6, 40, and 43.

23. The rMVA of embodiments 1-22, wherein the S protein comprises one or more amino acid substitutions selected from K986P, V987P, K417T, K417N, E484K, or N501Y.

24. The rMVA of embodiment 23, wherein the S protein comprises the amino substitutions K417T, E484K, and N501Y.

25. The rMVA of embodiments 1-24, wherein the heterologous nucleic acid sequence encoding the S protein, E protein, and M protein is operably linked to one or more promoters compatible with poxvirus expression systems selected from a p11 promoter, pmH5 promoter, pH5 promoter, p7.5 promoter, pSyn, and pHyb.

26. The rMVA of embodiment 25, wherein the promoter is p7.5 promoter.

27. The rMVA of embodiment 26, wherein the promoter is a pmH5 promoter.

28. The rMVA of embodiment 26, wherein the promoter is a p11 promoter.

29. The rMVA of embodiment 27, wherein the promoter is SEQ ID NO: 154.

30. The rMVA of embodiment 28, wherein the promoter is SEQ ID NO: 155.

31. The rMVA of embodiment 1, wherein the rMVA heterologous nucleic acid sequence comprises a nucleic acid sequence selected from SEQ ID NO: 46, 47, 156.

32. A recombinant modified vaccinia Ankara (rMVA) viral vector comprising a heterologous nucleic acid sequence encoding a stabilized Spike(S) protein, peptide fragment, or variant thereof, a Membrane (M) protein, and an Envelope (E) protein derived from severe acute respiratory syndrome-coronavirus 2 (SARS-CoV2) operably linked to a promoter compatible with poxvirus expression systems, wherein, upon expression in a host cell, the stabilized S protein, peptide fragment, or variant thereof, M protein, and E protein are capable of together forming a virus like particle.

33. The rMVA of embodiments 32, wherein the heterologous nucleic acid sequence encodes a full-length stabilized S protein.

34 The rMVA of embodiments 32 or 33, wherein the full-length stabilized S protein comprises an amino acid sequence of SEQ ID NO: 8, or a sequence at least 95% homologous thereto.

35. The rMVA of embodiment 34, wherein the full-length stabilized S protein comprises the amino acid sequence of SEQ ID NO: 8.

36. The rMVA of embodiments 32-33, wherein the heterologous nucleic acid sequence encoding the stabilized S protein comprises SEQ ID NO: 10, or a sequence at least 95% homologous thereto.

37. The rMVA of embodiment 36, wherein the heterologous nucleic acid sequence encoding the full-length stabilized S protein comprises SEQ ID NO: 10.

38. The rMVA of embodiments 32 or 33, wherein the full-length stabilized S protein comprises an amino acid sequence of SEQ ID NO: 11, or a sequence at least 95% homologous thereto.

39. The rMVA of embodiment 38, wherein the full-length stabilized S protein comprises the amino acid sequence of SEQ ID NO: 11.

40. The rMVA of embodiments 32-39, wherein the E protein comprises an amino acid sequence of SEQ ID NO: 40, or a sequence at least 95% homologous thereto.

41. The rMVA of embodiment 40, wherein the E protein comprises the amino acid sequence of SEQ ID NO: 40.

42. The rMVA of embodiment 32-41, wherein the heterologous nucleic acid sequence encoding the E protein comprises SEQ ID NO: 42, or a sequence at least 95% homologous thereto. 43. The rMVA of embodiment 42, wherein the heterologous nucleic acid sequence encoding the E protein comprises SEQ ID NO: 42.

44. The rMVA of embodiments 32-43, wherein the M protein comprises an amino acid sequence of SEQ ID NO: 43, or a sequence at least 95% homologous thereto.

45. The rMVA of embodiment 4, wherein the M protein comprises the amino acid sequence of SEQ ID NO: 43.

46. The rMVA of embodiments 32-45, wherein the heterologous nucleic acid sequence encoding the M protein comprises SEQ ID NO: 45, or a sequence at least 95% homologous thereto.

47. The rMVA of embodiment 46, wherein the heterologous nucleic acid sequence encoding the E protein comprises SEQ ID NO: 45.

48. The rMVA of embodiment 32, wherein the heterologous nucleic acid sequence encodes amino acid sequences comprising SEQ ID NOS: 8, 40, and 43, or sequences at least 95% homologous thereto.

49. The rMVA of embodiment 48, wherein the heterologous nucleic acid sequence encodes amino acid sequences comprising SEQ ID NOS: 8, 40, and 43.

50. The rMVA of embodiment 32, wherein the heterologous nucleic acid sequence comprises SEQ ID NOS: 10, 42, and 45, or sequences at least 95% homologous thereto.

51. The rMVA of embodiment 50, wherein the heterologous nucleic acid sequence comprises SEQ ID NOS: 10, 42, and 45.

52. The rMVA of embodiment 32, wherein the heterologous nucleic acid sequence encodes amino acid sequences comprising SEQ ID NOS: 11, 40, and 43, or sequences at least 95% homologous thereto.

53. The rMVA of embodiment 52, wherein the heterologous nucleic acid sequence encodes amino acid sequences comprising SEQ ID NOS: 11, 40, and 43.

54. The rMVA of embodiment 32, wherein the heterologous nucleic acid sequence comprises SEQ ID NOS: 12, 42, and 45, or sequences at least 95% homologous thereto.

55. The rMVA of embodiment 54, wherein the heterologous nucleic acid sequence comprises SEQ ID NOS: 12, 42, and 45.

56. The rMVA of embodiments 32-55, wherein the heterologous nucleic acid sequence encoding the S protein, E protein, and M protein is operably linked to one or more promoters compatible with poxvirus expression systems selected from a p11 promoter, pmH5 promoter, pH5 promoter, p7.5 promoter, pSyn, and pHyb.

57. The rMVA of embodiment 56, wherein the promoter is p7.5 promoter.

58. The rMVA of embodiment 56, wherein the promoter is a pmH5 promoter.

59. The rMVA of embodiment 56, wherein the promoter is a p11 promoter.

60. The rMVA of embodiment 58, wherein the promoter is SEQ ID NO: 154.

61. The rMVA of embodiment 59, wherein the promoter is SEQ ID NO: 155.

62. The rMVA of embodiment 32, wherein the rMVA heterologous nucleic acid sequence is selected from nucleic acid sequences comprising SEQ ID NO: 48, 49, 50, 157, 159, 160, or a nucleic acid sequence at least 95% homologous thereto.

63. A recombinant modified vaccinia Ankara (rMVA) viral vector comprising a heterologous nucleic acid sequence encoding a linear epitope of the Spike(S) protein receptor binding domain (RBD), a Membrane (M) protein, and an Envelope (E) protein derived from severe acute respiratory syndrome-coronavirus 2 (SARS-CoV2) operably linked to a promoter compatible with poxvirus expression systems, wherein, upon expression in a host cell, the linear epitope, M protein, and E protein are capable of together forming a virus like particle.

64. The rMVA of embodiment 63, wherein the heterologous nucleic acid sequence encodes amino acids 331-524 of the S protein RBD domain.

65. The rMVA of embodiments 63 or 64, wherein the S protein RBD comprises an amino acid sequence of SEQ ID NO: 21, or a sequence at least 95% homologous thereto.

66. The rMVA of embodiment 65, wherein the S protein RBD comprises an amino acid sequence of SEQ ID NO: 21.

67. The rMVA of embodiments 63-66, wherein the heterologous nucleic acid sequence encoding the S protein RBD comprises SEQ ID NO: 24, or a sequence at least 95% homologous thereto.

68. The rMVA of embodiment 67, wherein the heterologous nucleic acid sequence encoding the S protein RBD comprises SEQ ID NO: 24.

69. The rMVA of embodiment 63, wherein the heterologous nucleic acid sequence encodes amino acids 327-524 of the S protein RBD domain.

70. The rMVA of embodiments 63 or 69, wherein the S protein RBD comprises an amino acid sequence of SEQ ID NO: 20, or a sequence at least 95% homologous thereto.

71. The rMVA of embodiment 70, wherein the S protein RBD comprises an amino acid sequence of SEQ ID NO: 20.

72. The rMVA of embodiments 63 or 69-71, wherein the heterologous nucleic acid sequence encoding the S protein RBD comprises SEQ ID NO: 25, or a sequence at least 95% homologous thereto.

73. The rMVA of embodiment 72, wherein the heterologous nucleic acid sequence encoding the S protein RBD comprises SEQ ID NO: 25.

74. The rMVA of embodiment 63, wherein the RBD domain comprises one or more substitutions selected from K417N, K417T, E484K, or N501Y.

75. The rMVA of embodiment 74, wherein the RBD domain comprises the substitutions K417T, E484K, and N501Y.

76. The rMVA of embodiment 63, wherein the S protein RBD comprises an amino acid sequence of SEQ ID NO: 33, or a sequence at least 95% homologous thereto.

77. The rMVA of embodiment 77, wherein the S protein RBD comprises an amino acid sequence of SEQ ID NO: 33.

78. The rMVA of embodiment 63, wherein the S protein RBD comprises an amino acid sequence of SEQ ID NO: 32, or a sequence at least 95% homologous thereto.

79. The rMVA of embodiment 78, wherein the S protein RBD comprises an amino acid sequence of SEQ ID NO: 32.

80. The rMVA of embodiments 63-79, wherein the E protein comprises an amino acid sequence of SEQ ID NO: 40, or a sequence at least 95% homologous thereto.

81. The rMVA of embodiment 80, wherein the E protein comprises the amino acid sequence of SEQ ID NO: 40.

82. The rMVA of embodiments 63-81, wherein the heterologous nucleic acid sequence encoding the E protein comprises SEQ ID NO: 42, or a sequence at least 95% homologous thereto. 83. The rMVA of embodiment 82, wherein the heterologous nucleic acid sequence encoding the E protein comprises SEQ ID NO: 42.

84. The rMVA of embodiments 62-83, wherein the M protein comprises an amino acid sequence of SEQ ID NO: 43, or a sequence at least 95% homologous thereto.

85. The rMVA of embodiment 84, wherein the M protein comprises the amino acid sequence of SEQ ID NO: 43.

86. The rMVA of embodiment 63-85, wherein the heterologous nucleic acid sequence encoding the M protein comprises SEQ ID NO: 45, or a sequence at least 95% homologous thereto.

87. The rMVA of embodiment 86, wherein the heterologous nucleic acid sequence encoding the E protein comprises SEQ ID NO: 45.

88. The rMVA of embodiment 63, wherein the heterologous nucleic acid sequence encodes amino acid sequences comprising SEQ ID NOS: 20, 40, and 43, or sequences at least 95% homologous thereto.

89. The rMVA of embodiment 88, wherein the heterologous nucleic acid sequence encodes amino acid sequences comprising SEQ ID NOS: 20, 40, and 43.

90. The rMVA of embodiment 63, wherein the heterologous nucleic acid sequence comprises SEQ ID NOS: 24, 42, and 45, or sequences at least 95% homologous thereto.

91. The rMVA of embodiment 90, wherein the heterologous nucleic acid sequence comprises SEQ ID NOS: 24, 42, and 45.

92. The rMVA of embodiment 63, wherein the heterologous nucleic acid sequence encodes amino acid sequences comprising SEQ ID NOS: 21, 40, and 43, or sequences at least 95% homologous thereto.

93. The rMVA of embodiment 92, wherein the heterologous nucleic acid sequence encodes amino acid sequences comprising SEQ ID NOS: 21, 40, and 43.

94. The rMVA of embodiment 63, wherein the heterologous nucleic acid sequence comprises SEQ ID NOS: 25, 42, and 45, or sequences at least 95% homologous thereto.

95. The rMVA of embodiment 63, wherein the heterologous nucleic acid sequence comprises SEQ ID NOS: 25, 42, and 45.

96. The rMVA of embodiments 63-95, wherein the S RBD domain which further comprises a signal peptide and a transmembrane peptide derived from the S protein.

97. The rMVA of embodiment 96, wherein the S signal peptide comprises SEQ ID NO: 55.

98. The rMVA of embodiments 96 or 97, wherein the S transmembrane peptide comprises SEQ ID NO: 57.

99. The rMVA of embodiments 63-98, wherein the heterologous nucleic acid sequence encoding the S protein, E protein, and M protein is operably linked to one or more promoters compatible with poxvirus expression systems selected from a p11 promoter, pmH5 promoter, pH5 promoter, p7.5 promoter, pSyn, and pHyb.

100. The rMVA of embodiment 99, wherein the promoter is p7.5 promoter.

101. The rMVA of embodiment 99, wherein the promoter is a pmH5 promoter.

102. The rMVA of embodiment 99, wherein the promoter is a p11 promoter.

103. The rMVA of embodiment 101, wherein the promoter comprises SEQ ID NO: 154.

104. The rMVA of embodiment 102, wherein the promoter comprises SEQ ID NO: 155.

105. The rMVA of embodiment 63, wherein the rMVA heterologous nucleic acid sequence is selected from the sequences comprising SEQ ID NO: 51, 52, 53, or 54, or a nucleic acid sequence at least 95% homologous thereto.

106. A recombinant modified vaccinia Ankara (rMVA) viral vector comprising a heterologous nucleic acid sequence encoding a linear epitope of the Spike(S) protein receptor binding domain (RBD), a Membrane (M) protein, and an Envelope (E) protein derived from severe acute respiratory syndrome-coronavirus 2 (SARS-CoV2) operably linked to a promoter compatible with poxvirus expression systems, wherein the linear S epitope RBD domain further comprises a signal peptide and a transmembrane peptide derived from the S protein, wherein, upon expression in a host cell, the linear S epitope RBD domain, M protein, and E protein are capable of together forming a virus like particle.

107. The rMVA of embodiment 106, wherein the S signal peptide comprises SEQ ID NO: 55.

108. The rMVA of embodiments 106 or 107, wherein the S transmembrane peptide comprises SEQ ID NO: 57.

109. The rMVA of embodiments 106-108, wherein the heterologous nucleic acid sequence encodes amino acids 327-524 of the S protein RBD domain.

110. The rMVA of embodiments 106-109, wherein the S protein RBD comprises an amino acid sequence of SEQ ID NO: 61, or a sequence at least 95% homologous thereto.

111. The rMVA of embodiment 110, wherein the S protein RBD comprises an amino acid sequence of SEQ ID NO: 61.

112. The rMVA of embodiments 106-110, wherein the S protein RBD is encoded by a nucleic acid comprising SEQ ID NO: 65, or a sequence at least 95% homologous thereto.

113. The rMVA of embodiment 112, wherein the S protein RBD is encoded by a nucleic acid comprising SEQ ID NO: 65.

114. The rMVA of embodiments 106-108, wherein the heterologous nucleic acid sequence encodes amino acids 327-524 of the S protein RBD domain.

115. The rMVA of embodiments 106-108, and 114, wherein the S protein RBD comprises an amino acid sequence of SEQ ID NO: 62, or a sequence at least 95% homologous thereto.

116. The rMVA of embodiment 115, wherein the S protein RBD comprises an amino acid sequence of SEQ ID NO: 62.

117. The rMVA of embodiments 114-117, wherein the heterologous nucleic acid sequence encoding the S protein RBD comprises SEQ ID NO: 66, or a sequence at least 95% homologous thereto.

118. The rMVA of embodiment 117, wherein the heterologous nucleic acid sequence encoding the S protein RBD comprises SEQ ID NO: 66.

119. The rMVA of embodiment 106, wherein the RBD domain comprises one or more substitutions selected from K417N, K417T, E484K, or N501Y.

120. The rMVA of embodiment 119, wherein the RBD domain comprises the substitutions K417T, E484K, and N501Y.

121. The rMVA of embodiment 106, wherein the S protein RBD comprises an amino acid sequence of SEQ ID NO: 67, or a sequence at least 95% homologous thereto.

122. The rMVA of embodiment 106, wherein the S protein RBD comprises an amino acid sequence of SEQ ID NO: 67.

123. The rMVA of embodiment 106, wherein the S protein RBD comprises an amino acid sequence of SEQ ID NO: 68, or a sequence at least 95% homologous thereto.

124. The rMVA of embodiment 123, wherein the S protein RBD comprises an amino acid sequence of SEQ ID NO: 68.

125. The rMVA of embodiments 106-124, wherein the E protein comprises an amino acid sequence of SEQ ID NO: 40, or a sequence at least 95% homologous thereto.

126. The rMVA of embodiment 125, wherein the E protein comprises the amino acid sequence of SEQ ID NO: 40.

127. The rMVA of embodiments 106-126, wherein the heterologous nucleic acid sequence encoding the E protein comprises SEQ ID NO: 42, or a sequence at least 95% homologous thereto.

128. The rMVA of embodiment 127, wherein the heterologous nucleic acid sequence encoding the E protein comprises SEQ ID NO: 42.

129. The rMVA of embodiments 106-128, wherein the M protein comprises an amino acid sequence of SEQ ID NO: 43, or a sequence at least 95% homologous thereto.

130. The rMVA of embodiment 129, wherein the M protein comprises the amino acid sequence of SEQ ID NO: 43.

131. The rMVA of embodiments 106-130, wherein the heterologous nucleic acid sequence encoding the M protein comprises SEQ ID NO: 45, or a sequence at least 95% homologous thereto. 132. The rMVA of embodiment 131, wherein the heterologous nucleic acid sequence encoding the E protein comprises SEQ ID NO: 45.

133. The rMVA of embodiment 106, wherein the heterologous nucleic acid sequence encodes an amino acid sequence comprising SEQ ID NOS: 61, 40, and 43, or sequences at least 95% homologous thereto.

134. The rMVA of embodiment 133, wherein the heterologous nucleic acid sequence encodes an amino acid sequence comprising SEQ ID NOS: 61, 40, and 43.

135. TherMVA of embodiment 106, wherein the heterologous nucleic acid sequence comprises SEQ ID NOS: 65, 42, and 45, or sequences at least 95% homologous thereto.

136. The rMVA of embodiment 135, wherein the heterologous nucleic acid sequence comprises SEQ ID NOS: 65, 42, and 45.

137. The rMVA of embodiment 106, wherein the heterologous nucleic acid sequence encodes an amino acid sequence comprising SEQ ID NOS: 62, 40, and 43, or sequences at least 95% homologous thereto.

138. The rMVA of embodiment 137, wherein the heterologous nucleic acid sequence encodes an amino acid sequence comprising SEQ ID NOS: 62, 40, and 43.

139. The rMVA of embodiment 106, wherein the heterologous nucleic acid sequence comprises SEQ ID NOS: 66, 42, and 45, or sequences at least 95% homologous thereto.

140. The rMVA of embodiment 139, wherein the heterologous nucleic acid sequence comprises SEQ ID NOS: 66, 42, and 45.

141. The rMVA of embodiment 106, wherein the heterologous nucleic acid sequence encodes an amino acid sequence comprising SEQ ID NOS: 67, 40, and 43, or sequences at least 95% homologous thereto.

142. The rMVA of embodiment 141, wherein the heterologous nucleic acid sequence encodes an amino acid sequence comprising SEQ ID NOS: 67, 40, and 43.

143. The rMVA of embodiment 106, wherein the heterologous nucleic acid sequence encodes an amino acid sequence comprising SEQ ID NOS: 68, 40, and 43, or sequences at least 95% homologous thereto.

144. The rMVA of embodiment 144, wherein the heterologous nucleic acid sequence encodes an amino acid sequence comprising SEQ ID NOS: 68, 40, and 43.

145. The rMVA of embodiments 106-144, wherein the heterologous nucleic acid sequence encoding the S protein, E protein, and M protein is operably linked to one or more promoters compatible with poxvirus expression systems selected from a p11 promoter, pmH5 promoter, pH5 promoter, p7.5 promoter, pSyn, and pHyb.

146. The rMVA of embodiment 145, wherein the promoter is p7.5 promoter.

147. The rMVA of embodiment 145, wherein the promoter is a pmH5 promoter.

148. The rMVA of embodiment 145, wherein the promoter is a p11 promoter.

149. The rMVA of embodiment 147, wherein the promoter comprises SEQ ID NO: 154.

150. The rMVA of embodiment 148, wherein the promoter comprises SEQ ID NO: 155.

151. The rMBA embodiment 106, wherein the rMVA heterologous nucleic acid sequence is selected from a sequences comprising SEQ ID NO: 69, 70, 71, or 72, or a nucleic acid sequence at least 95% homologous thereto.

152. A recombinant modified vaccinia Ankara (rMVA) viral vector comprising one or more heterologous nucleic acid sequences encoding i) a linear epitope of the Spike(S) protein receptor binding domain (RBD) fusion peptide derived from the RBD domain of SARS-CoV2, wherein the fusion peptide comprises an a) envelope glycoprotein signal peptide of Marburgvirus, b) the linear epitope of the RBD domain, and c) an envelope glycoprotein transmembrane domain, and ii) a Marburgvirus matrix protein, operably linked to a promoter compatible with poxvirus expression systems, wherein, upon expression in a host cell, the RBD fusion peptide and matrix protein are capable of together forming a virus like particle.

153. The rMVA of embodiment 152, wherein glycoprotein signal peptide comprises the amino acid sequence of SEQ ID NO: 88, or a sequence at least 95% homologous thereto.

154. The rMVA of embodiments 152 or 153, wherein the glycoprotein transmembrane domain comprises SEQ ID NO: 90, or a sequence at least 95% homologous thereto.

155. The rMVA of embodiments 152-154, wherein the matrix protein is the VP40 protein.

156. The rMVA of embodiment 155, wherein the VP40 protein comprises the amino acid sequence of SEQ ID NO: 92, or a sequence at least 95% homologous thereto.

157. The rMVA of embodiment 156, wherein the VP40 protein is encoded by a nucleic acid comprising SEQ ID NO: 93, or a sequence at least 95% homologous thereto.

158. The rMVA of embodiments 152-157, wherein the heterologous nucleic acid sequence encodes amino acids 327-524 of the S protein RBD domain.

159. The rMVA of embodiment 158, wherein the RBD fusion peptide is encoded by a nucleic acid comprising SEQ ID NO: 97.

160. The rMVA of embodiments 152-157, wherein the heterologous nucleic acid sequence encodes amino acids 331-524 of the S protein RBD domain.

161. The rMVA of embodiment 160, wherein the RBD fusion peptide comprises an amino acid sequence of SEQ ID NO: 96, or a sequence at least 95% homologous thereto.

162. The rMVA of embodiment 161, wherein the RBD fusion peptide comprises an amino acid sequence of SEQ ID NO: 96.

163. The rMVA of embodiments 160-162, wherein the heterologous nucleic acid sequence encoding the RBD fusion peptide comprises SEQ ID NO: 98, or a sequence at least 95% homologous thereto.

164. The rMVA of embodiment 163, wherein the heterologous nucleic acid sequence encoding the RBD fusion peptide comprises SEQ ID NO: 98.

165. The rMVA of embodiments 152-157, wherein the RBD domain comprises one or more substitutions selected from K417N, K417T, E484K, or N501Y.

166. The rMVA of embodiment 165, wherein the RBD domain comprises the substitutions K417T, E484K, and N501Y.

167. The rMVA of embodiments 152-157, wherein the RBD fusion peptide comprises an amino acid sequence of SEQ ID NO: 99, or a sequence at least 95% homologous thereto.

168. The rMVA of embodiment 167, wherein the RBD fusion peptide comprises an amino acid sequence of SEQ ID NO: 99.

169. The rMVA of embodiments 152-157, wherein the RBD fusion peptide comprises an amino acid sequence of SEQ ID NO: 100, or a sequence at least 95% homologous thereto.

170. The rMVA of embodiment 169, wherein the RBD fusion peptide comprises an amino acid sequence of SEQ ID NO: 99.

171. The rMVA of embodiments 152-173, wherein the heterologous nucleic acid sequence encoding the S protein, E protein, and M protein is operably linked to one or more promoters compatible with poxvirus expression systems selected from a p11 promoter, pmH5 promoter, pH5 promoter, p7.5 promoter, pSyn, and pHyb.

172. The rMVA of embodiment 171, wherein the promoter is p7.5 promoter.

173. The rMVA of embodiment 171, wherein the promoter is a pmH5 promoter.

174. The rMVA of embodiment 171, wherein the promoter is a p11 promoter.

175. The rMVA of embodiment 173, wherein the promoter comprises SEQ ID NO: 154.

176. The rMVA of embodiment 174, wherein the promoter comprises SEQ ID NO: 155.

177. The rMVA of embodiments 152-176, wherein the rMVA heterologous nucleic acid sequence is selected from a sequence comprising SEQ ID NO: 131, 132, 133, 134, 135, 136, 137, or 138, or a nucleic acid sequence at least 95% homologous thereto.

178. A recombinant modified vaccinia Ankara (rMVA) viral vector comprising one or more heterologous nucleic acid sequences encoding i) a linear epitope of the Spike(S) protein receptor binding domain (RBD) fusion peptide derived from the RBD domain of SARS-CoV2, wherein the fusion peptide comprises an a) a signal peptide of the S protein and the linear epitope of the RBD domain, and c) an envelope glycoprotein transmembrane domain, ii) the M protein of SARS-CoV2, and iii) a E protein of SARS-CoV2, operably linked to a promoter compatible with poxvirus expression systems, wherein, upon expression in a host cell, the RBD fusion peptide, E, and M proteins are capable of together forming a virus like particle.

179. TherMVA of embodiment 178, wherein signal peptide comprises the amino acid sequence of SEQ ID NO: 55, or a sequence at least 95% homologous thereto.

180. The rMVA of embodiments 178-179, wherein the heterologous nucleic acid sequence encodes amino acids 327-524 of the S protein RBD domain.

181. The rMVA of embodiment 180, wherein the RBD fusion peptide comprises an amino acid sequence comprising SEQ ID NOS: 55 and 20, or a sequence at least 95% homologous thereto. 182. The rMVA of embodiments 178-179, wherein the heterologous nucleic acid sequence encodes amino acids 331-524 of the S protein RBD domain.

183. The rMVA of embodiment 182, wherein the RBD fusion peptide comprises an amino acid sequence of SEQ ID NOS: 55 and 21, or a sequence at least 95% homologous thereto.

184. The rMVA of embodiment 161, wherein the RBD fusion peptide comprises an amino acid sequence of SEQ ID NOS: 55 and 21.

185. The rMVA of embodiments 178-179, wherein the heterologous nucleic acid sequence encodes amino acids 327-598 of the S protein RBD domain.

186. The rMVA of embodiment 185, wherein the RBD fusion peptide comprises an amino acid sequence of SEQ ID NOS: 55 and 161, or a sequence at least 95% homologous thereto.

187. The rMVA of embodiment 186, wherein the RBD fusion peptide comprises an amino acid sequence of SEQ ID NOS: 55 and 161.

188. The rMVA of embodiments 178-179, wherein the heterologous nucleic acid sequence encodes amino acids 331-598 of the S protein RBD domain.

189. The rMVA of embodiment 185, wherein the RBD fusion peptide comprises an amino acid sequence of SEQ ID NOS: 55 and 162, or a sequence at least 95% homologous thereto.

190. The rMVA of embodiment 189, wherein the RBD fusion peptide comprises an amino acid sequence of SEQ ID NOS: 55 and 162.

191. The rMVA of embodiments 178-190, wherein the RBD domain comprises one or more substitutions selected from K417N, K417T, E484K, or N501Y.

192. The rMVA of embodiment 191, wherein the RBD domain comprises the substitutions K417T, E484K, and N501Y.

193. The rMVA of embodiment 192, wherein the heterologous nucleic acid sequence encodes amino acids 327-524 of the S protein RBD domain.

194. The rMVA of embodiment 193, wherein the RBD fusion peptide comprises an amino acid sequence comprising SEQ ID NOS: 55 and 32, or a sequence at least 95% homologous thereto.

195. The rMVA of embodiment 191, wherein the heterologous nucleic acid sequence encodes amino acids 331-524 of the S protein RBD domain.

196. The rMVA of embodiment 195, wherein the RBD fusion peptide comprises an amino acid sequence of SEQ ID NOS: 55 and 33, or a sequence at least 95% homologous thereto.

197. The rMVA of embodiment 196, wherein the RBD fusion peptide comprises an amino acid sequence of SEQ ID NOS: 55 and 33.

198. The rMVA of embodiment 191, wherein the heterologous nucleic acid sequence encodes amino acids 327-598 of the S protein RBD domain.

199. The rMVA of embodiment 198, wherein the RBD fusion peptide comprises an amino acid sequence of SEQ ID NOS: 55 and 163, or a sequence at least 95% homologous thereto.

200. The rMVA of embodiment 199, wherein the RBD fusion peptide comprises an amino acid sequence of SEQ ID NOS: 55 and 163.

201. The rMVA of embodiment 191, wherein the heterologous nucleic acid sequence encodes amino acids 331-598 of the S protein RBD domain.

202. The rMVA of embodiment 201, wherein the RBD fusion peptide comprises an amino acid sequence of SEQ ID NOS: 55 and 164, or a sequence at least 95% homologous thereto.

203. The rMVA of embodiment 202, wherein the RBD fusion peptide comprises an amino acid sequence of SEQ ID NOS: 55 and 164.

204. The rMVA of embodiments 179-203, wherein the heterologous nucleic acid sequence encoding the S protein, E protein, and M protein is operably linked to one or more promoters compatible with poxvirus expression systems selected from a p11 promoter, pmH5 promoter, pH5 promoter, p7.5 promoter, pSyn, and pHyb.

205. The rMVA of embodiment 204, wherein the promoter is p7.5 promoter.

206. The rMVA of embodiment 204, wherein the promoter is a pmH5 promoter.

207. The rMVA of embodiment 204, wherein the promoter is a p11 promoter.

208. The rMVA of embodiment 206, wherein the promoter comprises SEQ ID NO: 154.

209. The rMVA of embodiment 207, wherein the promoter comprises SEQ ID NO: 155.

210. The rMVA of embodiments 179-209, wherein the rMVA heterologous nucleic acid sequence comprises SEQ ID NO: 158, or a nucleic acid sequence at least 95% homologous thereto.

211. A method of reducing or preventing a SARS-CoV2 infection in a human comprising administering an effective amount of an rMVA viral vector of any of embodiments 1-181.

212. The method of embodiment 211, wherein the rMVA is administered as a prophylactic primary vaccination.

213. The method of embodiment 211, wherein the rMVA is administered as a boost vaccination.

214. The method of embodiment 213, wherein the human has previously been administered a SARS-CoV2 vaccine.

215. The method of embodiment 214, wherein the previous vaccine is selected from an mRNA-based vaccine, an adenovirus vaccine, a non-replicating vaccine, a DNA vaccine, a live attenuated vaccine, a plant-based adjuvant vaccine, a multipope peptide-based vaccine, an inactivated virus, a peptide vaccine, 216. The method of embodiment 214, wherein the previous vaccine is selected from mRNA-1273 (MODERNA COVID-19 VACCINE; Moderna, Inc.), AZD-1222 (COVIDSHIELD; AstraZeneca and University of Oxford), BNT162 (COMIRNATY; Pfizer and BioNTech), Sputnik V (Gamaleya Research Institute, Acellena Contract Drug Research and Development), Corona Vac (Sinovac), NVX-CoV 2372 (NovoVax), SCB-2019 (Sanofi and GSK), ZyCoV-D (Zydus Cadila), BBIBP-CorV (Beijing Institute of Biological Products; China National Pharmaceutical Group (Sinopharm)), EpiVacCorona (Federal Budgetary Research Institution State Research Center of Virology and Biotechnology), Convidicea (CanSino Biologics), Covid-19 Vaccine (Wuhan Institute of Biological Products; China National Pharmaceutical Group (Sinopharm), JNJ-78436735 (Johnson & Johnson), ZF2001) Anhui Zhifei Longcom Biopharmaceutical, Institute of Microbiology of the Chinese Academy of Sciences), CVnCoV (CureVac; GSK), INO-4800 (Inovio Pharmaceuticals), VIR-7831 (Medicago; GSK; Dynavax), Covid-19 adenovirus bases vaccine (ImmunityBio; NantKwest), UB-612 (COVAXX), or CoVaxin (Bharat Biotech).

217. The method of embodiment 213, wherein the human has previously been infected with SARS-CoV2.

218. The method of embodiment 211, wherein the rMVA is administered as both a prime and a boost vaccine.

219. The method of embodiments 213-216, wherein the rMVA is administered as a boost vaccine 2 or more times.

219. The method of embodiment 216, wherein the rMVA boost is administered 4 or more weeks after the prime vaccination.

The claimed invention is further described by way of the following non-limiting examples. Further aspects and embodiments of the present invention will be apparent to those of ordinary skill in the art, in view of the above disclosure and following experimental exemplification, included by way of illustration and not limitation, and with reference to the attached figures.

EXAMPLES

Example 1: Construction of S Protein-E-M rMVA Viral Vector GEO-CM01

A recombinant MVA vaccine candidate (GEO-CM01) was constructed using the S, M, and E proteins from the COVID-19 Wuhan seafood market pneumonia virus (GenBank Accession number MT039888.1). SEQ ID NO: 156 was inserted into parental attenuated strain Modified Vaccinia Ankara, MVA 1974/NIH Clone 1 (ATCC #PTA-5095), which was developed by Dr. Bernard Moss of the National Institute of Allergy and Infectious Diseases (NIAID), Laboratory of Viral Diseases (LVD), using the pAD-1/S-ME shuttle vector (FIG. 24) for insertion between two vaccinia genes, A5R and A6L. The pAD-1/S-ME shuttle vector was derived from the pAD-1/pUC57 shuttle vector (FIG. 26). The inserted sequence was codon optimized for MVA. Silent mutations were introduced to interrupt homo-polymer sequences (>4G/C and >4A/T), which reduces RNA polymerase errors that possibly lead to frameshifts. The sequences were edited for vaccinia-specific terminators to remove motifs that could lead to premature termination. The modified H5 early/late promoter was used to drive transcription of the S and M inserts, while the p11 promoter was used to drive transcription of the E insert. The rMVA were made by homologous recombination and serial plaque purification in chicken embryo fibroblasts. Briefly, the pAD-1/S-ME was transfected into primary chicken embryonic fibroblasts (CEF) cells that were infected with parental MVA. The recombinant virus was obtained from supernatants and lysates, then subjected to multiple rounds of plaque purification using reporter gene screening.

To verify insertion of SEQ ID NO: 156 into the parental strain, PCR amplification of the nucleic acid sequence expressing the S protein was performed. The antigen insert was amplified using 50 ng of DNA from the shuttle plasmid pAD-1/S-ME used to generate GEO-CM01 (positive control), GEO-CM01, MVA parental (negative control) in 25 ul reactions with 10 mM of primers: forward primer p55 (5'-AGATCGGAGATGACTGCGATG-3') (SEQ ID NO: 151) and reverse primer p54 (5'-CGATGGTAGGTCAGAT-TGTCC-3') (SEQ ID NO: 152). Reactions were visualized by loading 10 ul of the PCR reaction on a 1% agarose gel stained with ethidium bromide. As shown in FIG. 17 and FIG. 18, the PCR of GEO-CM01 rMVA generated the appropriate signal (5384 base pairs).

To verify expression of SME VLPs, CEF cells were infected with GEO-CM01 and 48 hours later analyzed by immunocytochemistry. Briefly, cells were fixed with 1:1 Methanol: Acetone, stained with primary mouse anti-SARS-CoV-2 spike antibody (GeneTex #GTX632604) and secondary anti-mouse HRP, and developed with AEC peroxidase substrate, which mediates a colorimetric readout of plaques. Positive staining plaques were identified (See FIG. 16).

To further confirm antigen expression in GEO-CM01, Western blot analysis of GEO-CM01 antigen expression was performed. DF1 cells were infected at a low m.o.i. (0.5) with GEO-CM01 or MVA parental. Two days following infection, cell lysate and supernatant were harvested and equal volumes were subjected to SDS-PAGE, transferred to PVDF membrane and probed with an anti-SARS-CoV-2 Spike/RBD (rabbit) antibody (Sino Biologicals, #40592-T62) and secondary anti-rabbit IgG (FIG. 19). Membranes were visualized on an Odyssey infrared scanner. As shown in FIG. 19, DF1 cell lysate and supernatant of GEO-CM01 infection show expression of the spike protein.

Electron microscopic (EM) images were taken of virus-like particle formation in DF1 cells that had been infected with GEO-CM01 (FIG. 20).

Example 2—Animal Protection Challenges Using GEO-CM01

The initial preclinical efficacy of GEO-CM01 was determined using a hamster model. The studies were carried out in strict accordance with the recommendations described in the Guide for the Care and Use of Laboratory Animals of the National Research Council. All efforts were made to minimize animal suffering and all procedures involving potential pain were performed with the appropriate anesthetic or analgesic. The number of hamsters used was scientifically justified based on statistical analyses of virological and immunological outcomes.

Seven-week-old golden Syrian female hamsters (Envigo) were anesthetized with 5% isoflurane prior to immunization and blood collections and with ketamine/xylazine prior to the SARS-CoV-2 challenge. Hamsters (N=10 per group) were vaccinated once or twice at a 29-day interval with the MVA-SME vaccine (GEO-CM01) at a dose of $10^8$ $TCID_{50}$ per animal via the intramuscular route (100 ul delivered as 50 ul per hind leg), while the control group received saline. Vena cava blood collections were performed four days prior to the first immunization and on 27 days post immunization (days 27 and 56). On day 59, vaccinated and control animals were exposed intranasally to the targeted dose of 105 PFU of passage 5 of isolate SARS-CoV-2 USA-WA1/2020. Animals were monitored daily for weight loss and signs of disease. Five animals in each group were euthanized by overdose of injectable anesthetics (ketamine/xylazine) 3 days post challenge for viral load determination. Remaining animals were euthanized 14 days post infection by overdose of ketamine/xylazine.

Sera collected from animals were tested for neutralizing capabilities against SARS-CoV-2. Briefly, serum samples were heat-inactivated (30 minutes at 56° C.). 10-fold diluted sera were further diluted in a 2-fold serial fashion, and 60 ul of each serum dilution was mixed with 60 ul of SARS-CoV-2-mNG (200 PFU). The serum/virus mixtures were incubated for 1 hr at 37° C. 100 ul of the serum/virus mixtures were then transferred to Vero E6 cell monolayers in black flat-bottom 96-well plates and incubated for 2 days at 37° C. Virus fluorescence was measured with a Cytation Hybrid Multi-Mode reader at 488 nm (Biotek Instruments). Results of the ability of GEO-CM01 to induce neutralizing are shown in FIG. 21 and FIG. 22. Results demonstrate the dilution at which there was a 50% reduction in SARS-CoV-2 plaque formation (FIG. 21). Half of the animals that received a prime/boost dose of GEO-CM01 generated antibodies that neutralized SARS-CoV-2, indicating the capability of GEO-CM01 to elicit neutralizing antibodies to SARS-CoV-2 in a golden hamster model.

Serum from GEO-CM01 immunized animals was analyzed by ELISA for levels of antibody specific to recombinant Spike-Membrane (S-M) fusion, Spike(S) and the receptor binding domain (RBD) proteins (FIG. 22). Following single-dose immunization (Day 27), detectable levels of antibodies to S-M, S and RBD are observed. A further increase in the levels of binding antibody to these proteins is observed following prime-boost vaccination, indicating that GEO-CM01 induces robust antibodies to Spike, including RBD, and Membrane proteins in a golden hamster model.

Animals were vaccinated in a single-dose or prime-boost regimen, challenged with SARS-CoV-2, then monitored for morbidity. Body weight and health scores were recorded daily following challenge (FIG. 23). Single-dose immunization modestly protects animals from clinical disease and weight loss, whereas prime-boost immunization offers complete protection from clinical disease and significantly reduces weight loss following SARS-CoV-2 challenge, indicating that vaccination with GEO-CM01 significantly reduces morbidity, protecting animals from disease following SARS-CoV-2 challenge in a golden hamster model.

Example 3—Construction of Stabilized S Protein-E-M rMVA Viral Vector GEO-CM02

A recombinant MVA vaccine candidate (GEO-CM02) was constructed using a stabilized S protein and the M, and E proteins from the COVID-19 Wuhan seafood market pneumonia virus (GenBank Accession number MT039888.1). SEQ ID NO: 157 was inserted into parental attenuated strain Modified Vaccinia Ankara, MVA 1974/NIH Clone 1 (ATCC #PTA-5095), which was developed by Dr. Bernard Moss of the National Institute of Allergy and Infectious Diseases (NIAID), Laboratory of Viral Diseases (LVD), using the pAD-1/sS-ME shuttle vector (FIG. 25) for insertion between two vaccinia genes, A5R and A6L. The pAD-1/sS-ME shuttle vector was derived from the pAD-1/pUC57 shuttle vector (FIG. 26). The inserted sequence was codon optimized for MVA. Silent mutations were introduced to interrupt homo-polymer sequences (>4G/C and >4A/T), which reduces RNA polymerase errors that possibly lead to frameshifts. The sequences were edited for vaccinia-specific terminators to remove motifs that could lead to premature termination. The modified H5 early/late promoter was used to drive transcription of the S and M inserts, while the p11 promoter was used to drive transcription of the E insert. The rMVA were made by homologous recombination and serial plaque purification in chicken embryo fibroblasts. Briefly, the pAD-1/sS-ME was transfected into primary chicken embryonic fibroblasts (CEF) cells that were infected with parental MVA. The recombinant virus was obtained from supernatants and lysates, then subjected to multiple rounds of plaque purification using reporter gene screening.

To verify insertion of SEQ ID NO: 157 into the parental strain, PCR amplification of the nucleic acid sequence expressing the stabilized S protein was performed. The antigen insert was amplified using 50 ng of DNA from the shuttle plasmid pAD-1/sS-ME used to generate GEO-CM02 (positive control), GEO-CM02, MVA parental (negative control) in 25 ul reactions with 10 mM of primers: forward primer p55 (5'-AGATCGGAGATGACTGCGATG-3') (SEQ ID NO: 151) and reverse primer p54 (5'-CGATGGTAGGTCAGATTGTCC-3') (SEQ ID NO: 152). Reactions were visualized by loading 10 ul of the PCR reaction on a 1% agarose gel stained with ethidium bromide. As shown in FIGS. 18 and 31, the PCR of GEO-CM02 rMVA generated the appropriate signal (5384 base pairs).

To further confirm antigen expression in GEO-CM02, Western blot analysis of GEO-CM02 antigen expression was performed. DF1 cells were infected at a low m.o.i. (0.5) with GEO-CM02 or MVA parental. Two days following infection, cell lysate and supernatant were harvested and equal volumes were subjected to SDS-PAGE, transferred to PVDF membrane and probed with anti-SARS-CoV-2 Spike/RBD (rabbit) antibody (Sino Biologicals, #40592-T62) and secondary anti-rabbit IgG (FIG. 20).

Example 4—Animal Protection Challenges Using GEO-CM02

The initial preclinical efficacy of GEO-CM02 is being determined using a hamster model.

Hamsters were initially immunized intramuscularly using 108 PFU of GEO-CM02 on day 0 and day 29 (prime/boost group) or on day 29 only (prime group). The hamsters will be administered SARS-CoV-2 intranasal on Day 59. A group of hamsters will be sacrificed at day 3 post challenge (day 62) and a group will be sacrificed at day 14 post challenge (day 73).

The SARS-CoV2 antibodies will be analyzed by ELISA, and neutralization capacity of the antibodies will be determined. The lungs will be harvested for histopathology and examination of viral loads.

Example 5—Construction of SP-RBD-E/M rMVA Viral Vector

A recombinant MVA vaccine candidate (GEO-CM03) was constructed using the RBD sequence of the S protein (aa 327-527), the M, and E proteins from the COVID-19 Wuhan seafood market pneumonia virus (GenBank Accession number MT039888.1). The RBD sequence was flanked on its N-terminus by the signal peptide of the S protein, and on its Carboxy-terminus by the transmembrane region of the S protein, thus allowing the formation of a VLP displaying the RBD on the VLP surface upon expression. SEQ ID NO: 158 was inserted into parental attenuated strain Modified Vaccinia Ankara, MVA 1974/NIH Clone 1 (ATCC #PTA-5095), which was developed by Dr. Bernard Moss of the National Institute of Allergy and Infectious Diseases (NIAID), Laboratory of Viral Diseases (LVD), using the pAD-1/SP-RBD-TM/E/M shuttle vector for insertion between two vaccinia genes, A5R and A6L. The pAD-1/SP-RBD/E/M shuttle vector was derived from the pAD-1/pUC57 shuttle vector (FIG. 26). The inserted sequence was codon optimized for MVA. Silent mutations were introduced to interrupt homopolymer sequences (>4G/C and >4A/T), which reduces RNA polymerase errors that possibly lead to frameshifts. The sequences were edited for vaccinia-specific terminators to remove motifs that could lead to premature termination. The modified H5 early/late promoter was used to drive transcription of the SP-RBD fusion and M inserts, while the p11 promoter was used to drive transcription of the E insert. The rMVA were made by homologous recombination and serial plaque purification in chicken embryo fibroblasts. Briefly, the pAD-1/SP-RBD-E/M was transfected into primary chicken embryonic fibroblasts (CEF) cells that were infected with parental MVA. The recombinant virus was obtained from supernatants and lysates, then subjected to multiple rounds of plaque purification using reporter gene screening.

To verify insertion of SEQ ID NO: 158 into the parental strain, PCR amplification of the nucleic acid sequence expressing the RBD insert was performed. The antigen insert was amplified using 50 ng of DNA from the shuttle plasmid used to generate GEO-CM03 (positive control), GEO-CM03, MVA parental (negative control) in 25 ul reactions with 10 mM of primers: forward primer p55 (5'-AGATCGGAGATGACTGCGATG-3') (SEQ ID NO: 151) and reverse primer p54 (5'-CGATGGTAGGTCAGAT-TGTCC-3') (SEQ ID NO: 152). Reactions were visualized by loading 10 ul of the PCR reaction on a 1% agarose gel stained with ethidium bromide. As shown in FIGS. 18 and 31, the PCR of GEO-CM03 rMVA generated the appropriate signal (2422 base pairs).

To further confirm antigen expression in GEO-CM03, Western blot analysis of GEO-CM03 antigen expression was performed. DF1 cells were infected at a low m.o.i. (0.5) with GEO-CM03 or MVA parental. Two days following infection, cell lysate and supernatant were harvested and equal volumes were subjected to SDS-PAGE, transferred to PVDF membrane and probed with anti-SARS-CoV-2 Spike/RBD (rabbit) antibody (Sino Biologicals, #40592-T62) and secondary anti-rabbit IgG (FIG. 20).

Example 6—Animal Protection Challenges Using GEO-CM03

The initial preclinical efficacy of GEO-CM03 is being determined using a hamster model. Hamsters were initially immunized intramuscularly using 108 PFU of GEO-CM02 on day 0 and day 29 (prime/boost group) or on day 29 only (prime group). The hamsters will be administered SARS-CoV-2 intranasal on Day 59. A group of hamsters will be sacrificed at day 3 post challenge (day 62) and a group will be sacrificed at day 14 post challenge (day 73).

The SARS-CoV2 antibodies will be analyzed by ELISA, and neutralization capacity of the antibodies will be determined. The lungs will be harvested for histopathology and examination of viral loads.

Example 7—Construction of MarvGP-RBD and MARV VP40 rMVA Viral Vector

A recombinant MVA vaccine candidate (GEO-CM03b) was constructed using sequences from the COVID-19 Wuhan seafood market pneumonia virus (accession number MT039888.1) and Marburg virus (MARV) Marburg marburgvirus isolate MARV/*H.sapiens*-tc/COD/2000/24 DRC, ACCESSION JX458834). SEQ ID NO: 134 was inserted into parental attenuated strain Modified Vaccinia Ankara, MVA 1974/NIH Clone 1 (ATCC #PTA-5095), which was developed by Dr. Bernard Moss of the National Institute of Allergy and Infectious Diseases (NIAID), Laboratory of Viral Diseases (LVD).

The COVID-19 spike gene receptor binding domain was fused between the signal sequence of Marburg virus glycoprotein at the amino terminus and the transmembrane domain and cytoplasmic tail of Marburg virus glycoprotein at the carboxy terminus (SignalMARV-RBDCOVID-TM-MARV). SignalMARV-RBDCOVID-TMMARV were subcloned into the pLW76 shuttle vector for insertion between two essential vaccinia genes, A5R and A6L. The MARV matrix protein (SEQ ID NO: 92), VP40, was subcloned into the pAD2/67 shuttle vector for insertion between two essential vaccinia genes, A50R and B1R. The inserted sequences were codon optimized for MVA (SEQ ID NO: 94). Silent mutations were introduced to interrupt homo-polymer sequences (>4G/C and >4A/T), which reduce RNA polymerase errors that possibly lead to frameshifts. The sequences were edited for vaccinia-specific terminators to remove motifs that could lead to premature termination. The modified H5 early/late promoter was used to drive transcription of gene inserts. The recombinants were made by homologous recombination and serial plaque purification. Briefly, the recombinant plasmid was transfected into primary chicken embryonic fibroblasts that have been infected with parental MVA. The recombinant virus was obtained from supernatants and lysates, then subjected to multiple rounds of plaque purification using reporter gene screening.

To verify insertion of SEQ ID NO: 134 into the parental strain, PCR amplification of the nucleic acid sequence expressing the RBD insert was performed. The antigen insert was amplified using 50 ng of DNA from the shuttle plasmid MTRDB used to generate GEO-CM03b (positive control), GEO-CM03b, MVA parental (negative control) in 25 ul reactions with 10 mM of primers: forward primer p55 (5'-AGATCGGAGATGACTGCGATG-3') (SEQ ID NO:

151) and reverse primer p54 (5'-CGATGGTAGGTCAGAT-TGTCC-3') (SEQ ID NO: 152) or forward primer p53 (5'-CAGAAGTTAATAAGCGTATAGCCATC-3') (SEQ ID NO: 153) and reverse primer p54. Reactions were visualized by loading 10 ul of the PCR reaction on a 1% agarose gel stained with ethidium bromide. As shown in FIG. 28, the PCR of GEO-CM03b rMVA generated the appropriate signal (p54/p55-1288 base pairs; p54/p53-1558 base pairs-see middle two arrows).

SEQUENCE LISTING

```
Sequence total quantity: 164
SEQ ID NO: 1              moltype = AA   length = 1273
FEATURE                   Location/Qualifiers
source                    1..1273
                          mol_type = protein
                          organism = synthetic construct
SEQUENCE: 1
MFVFLVLLPL VSSQCVNLTT RTQLPPAYTN SFTRGVYYPD KVFRSSVLHS TQDLFLPFFS   60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA 1020
SANLAATKMS ECVLGQSKRV DFCGKGYHLM SFPQSAPHGV VFLHVTYVPA QEKNFTTAPA 1080
ICHDGKAHFP REGVFVSNGT HWFVTQRNFY EPQIITTDNT FVSGNCDVVI GIVNNTVYDP 1140
LQPELDSFKE ELDKYFKNHT SPDVDLGDIS GINASVVNIQ KEIDRLNEVA KNLNESLIDL 1200
QELGKYEQYI KWPWYIWLGF IAGLIAIVMV TIMLCCMTSC CSCLKGCCSC GSCCKFDEDD 1260
SEPVLKGVKL HYT                                                    1273

SEQ ID NO: 2              moltype = DNA   length = 3819
FEATURE                   Location/Qualifiers
source                    1..3819
                          mol_type = other DNA
                          organism = synthetic construct
SEQUENCE: 2
atgtttgttt ttcttgtttt attgccacta gtctctagtc agtgtgttaa tcttacaacc   60
agaactcaat taccccctgc atacactaat tctttcacac gtggtgttta ttaccctgac  120
aaagttttca gatcctcagt tttacattca actcaggact tgttcttacc tttctttttc  180
aatgttactt ggttccatgc tatacatgtc tctgggacca atggtactaa gaggtttgat  240
aaccctgtcc taccatttaa tgatggtgtt tattttgctt ccactgagaa gtctaacata  300
ataagaggct ggatttttgg tactacttta gattcgaaga cccagtccct acttattgtt  360
aataacgcta ctaatgttgt tattaaagtc tgtgaatttc aattttgtaa tgatccattt  420
ttgggtgttt attaccacaa aaacaacaaa agttggatgg aaagtgagtt cagagtttat  480
tctagtgcga ataattgcac ttttgaatat gtctctcagc ctttttctat ggaccttgaa  540
ggaaaacagg gtaatttcaa aaatcttagg gaatttgtgt ttaagaatat tgatggttat  600
tttaaaatat attctaagca cacgcctatt aatttagtgc gtgatctccc tcagggtttt  660
tcggctttag aaccattggt agatttgcca ataggtatta acatcactag gtttcaaact  720
ttacttgctt tacatagaag ttatttgact cctggtgatt cttcttcagg ttggacagct  780
ggtgctgcag cttattatgt gggttatctt caacctagga cttttctatt aaaatataat  840
gaaaatggaa ccattacaga tgctgtagac tgtgcacttg accctctctc agaaacaaag  900
tgtacgttga aatccttcac tgtagaaaaa ggaatctatc aaacttctaa ctttagagtc  960
caaccaacag aatctattgt tagatttcct aatattacaa acttgtgccc ttttggtgaa 1020
gtttttaacg ccaccagatt tgcatctgtt tatgcttgga acaggaagag aatcagcaac 1080
tgtgttgctg attattctgt cctatataat tccgcatcat tttccacttt taagtgttat 1140
ggagtgtctc ctactaaatt aaatgatctc tgctttacta atgtctatgc agattcattt 1200
gtaattagag gtgatgaagt cagacaaatc gctcagggc aaactggaaa gattgctgat 1260
tataattata aattaccaga tgattttaca ggctgcgtta tagcttggaa ttctaacaat 1320
cttgattcta aggttggtgg taattataat tacctgtata gattgtttag gaagtctaat 1380
ctcaaacctt ttgagagaga tatttcaact gaaatctatc aggccggtag cacaccttgt 1440
aatggtgttg aaggttttaa ttgttacttt cctttacaat catatggttt ccaacccact 1500
aatggtgttg gttaccaacc atacagagta gtagtacttt cttttgaact tctacatgca 1560
ccagcaactg tttgtggacc taaaaagtct actaatttgg ttaaaaacaa atgtgtcaat 1620
ttcaacttca atggtttaac aggcacaggt gttcttactg agtctaacaa aaagtttctg 1680
cctttccaac aatttggcag agacattgct gacactactg atgctgtccg tgatccacag 1740
```

```
acacttgaga ttcttgacat tacaccatgt tcttttggtg gtgtcagtgt tataacacca   1800
ggaacaaata cttctaacca ggttgctgtt ctttatcagg atgttaactg cacagaagtc   1860
cctgttgcta ttcatgcaga tcaacttact cctacttggc gtgtttattc tacaggttct   1920
aatgtttttc aaacacgtgc aggctgttta ataggggctg aacatgtcaa caactcatat   1980
gagtgtgaca tacccattgg tgcaggtata tgcgctagtt atcagactca gactaattct   2040
cctcggcggg cacgtagtgt agctagtcaa tccatcattg cctacactat gtcacttggt   2100
gcagaaaatt cagttgctta ctctaataac tctattgcca tacccacaaa ttttactatt   2160
agtgttacca cagaaattct accagtgtct atgaccaaga catcagtaga ttgtacaatg   2220
tacatttgtg gtgattcaac tgaatgcagc aatcttttgt tgcaatatgg cagtttttgt   2280
acacaattaa accgtgcttt aactggaata gctgttgaac aagacaaaaa cacccaagaa   2340
gtttttgcac aagtcaaaca aatttacaaa acaccaccaa ttaaagattt tggtggtttt   2400
aatttttcac aaatattacc agatccatca aaaccaagca agaggtcatt tattgaagat   2460
ctactttca acaaagtgac acttgcagat gctggcttca tcaaacaata tggtgattgc   2520
cttggtgata ttgctgctag agacctcatt tgtgcacaaa agtttaacgg ccttactgtt   2580
ttgccacctt tgctcacaga tgaaatgatt gctcaataca cttctgcact gttagcgggt   2640
acaatcactt ctggttggac ctttggtgca ggtgctgcat tacaaatacc atttgctatg   2700
caaatggctt ataggtttaa tggtattgga gttacacaga atgttctcta tgagaaccaa   2760
aaattgattg ccaaccaatt taatagtgct attggcaaaa ttcaagactc actttcttcc   2820
acagcaagtg cacttggaaa acttcaagat gtggtcaacc aaaatgcaca agctttaaac   2880
acgcttgtta aacaacttag ctccaatttt ggtgcaattt caagtgtttt aaatgatatc   2940
ctttcacgtc ttgacaaagt tgaggctgaa gtgcaaattg ataggttgat cacaggcaga   3000
cttcaaagtt gcagacata tgtgactcaa caattaatta gagctgcgaa aatcagagct   3060
tctgctaatc ttgctgctac taaaatgtca gagtgtgtac ttggacaatc aaaaagagtt   3120
gattttgtg gaaagggcta tcatcttatg tccttccctc agtcagcacc tcatggtgta   3180
gtcttcttgc atgtgactta tgtccctgca caagaaaaga acttcacaac tgctcctgcc   3240
atttgtcatg atggaaaagc acactttcct cgtgaaggtg tctttgtttc aaatggcaca   3300
cactggtttg taacacaaag gaattttat gaaccacaaa tcattactac agacaacaca   3360
tttgtgtctg gtaactgtga tgttgtaata ggaattgtca acaacacagt ttatgatcct   3420
ttgcaacctg aattagactc attcaaggag gagttagata aatattttaa gaatcataca   3480
tcaccagatg ttgatttagg tgacatctct ggcattaagt cttcagttgt aaacattcaa   3540
aaagaaattg accgcctcaa tgaggttgcc aagaatttaa atgaatctct catcgatctc   3600
caagaacttg gaaagtatga gcagtatata aaatggccat ggtacatttg gctaggtttt   3660
atagctggct tgattgccat agtaatggtg acaattatgc tttgctgtat gaccagttgc   3720
tgtagttgtc tcaagggctg ttgttcttgt ggatcctgct gcaaatttga tgaagacgac   3780
tctgagccag tgctcaaagg agtcaaatta cattacaca                           3819
```

```
SEQ ID NO: 3                moltype = DNA   length = 3819
FEATURE                     Location/Qualifiers
source                      1..3819
                            mol_type = other DNA
                            organism = synthetic construct
SEQUENCE: 3
atgttcgtgt tcctagtcct actaccgcta gtctcttctc agtgtgtaaa cctaacaacg   60
agaacacaac taccaccggc gtacaccaat tctttcacaa gaggagtata ttacccggac   120
aaggtgttca gatcctccgt actacattct acacaggacc tattcctacc gttcttctct   180
aacgtaacat ggttccacgc gatccatgtc tctggaacaa acggaacgaa gagattcgat   240
aacccggtct tgccgttcaa cgatggtgta tactttgcgt ccaccgagaa gtccaacatc   300
atcagaggat ggatcttcgg aaccaccttg gattctaaga cccagtcctt gctaatcgtc   360
aacaacgcga ccaacgtcgt catcaaagtc tgcgaattcc agttctgtaa cgacccgttc   420
ttgggagtct actaccacaa gaacaacaag tcctggatgg aatccgagtt cagagtctac   480
tcttccgcga caactgcac cttcgaatat gtatctcagc cgttcctaat ggacctagag   540
ggaaagcagg gaaacttcaa gaacctaaga gagttcgtat tcaagaacat cgacggatac   600
ttcaagatct actccaagca cactccgatc aacctagtta gagatctacc gcaaggattc   660
tctgcgctag aaccgttagt agatttgccg atcggaatca acatcaccag attccagaca   720
ctactacaga tacacagatc ttacctaacg ccgggagatt cttcttctgg atggactgct   780
ggtgctgcgg cttattatgt aggatacca cagccgagaa ccttcctatt gaagtacaac   840
gaaaacggaa ccatcaccga tgccgtagat tgtgctctag atccgctatc cgaaacgaag   900
tgcaccctaa agtctttcac cgtcgagaag ggaatctacc agacctccaa ctttagagta   960
cagccgaccg aatccatcgt cagatttccg aacatcacga acctatgtcc gttcggagaa   1020
gtgttcaacg cgacaagatt tgcgtctgtc tatgcgtgga acagaaaaag aatcagtaac   1080
tgcgtcgcgg actactccgt cctatacaac tctgcctctt tctccacgtt caaatgctac   1140
ggtgtatctc cgacaaagct aaacgatcta tgcttcacca acgtctacgc ggactccttc   1200
gtaatcagag gagatgaagt tagacagatt gcgccgggac aaactggaaa gatcgcggat   1260
tataactaca agctaccgga cgacttcacc ggatgtgtaa ttgcgtggaa ttcgaacaac   1320
ctagactcca agtcggagg aaactacaac tacttgtaca gactattcag aaagtccaac   1380
ctaaagccgt tcgagagaga catctccacc gaaatctatc aggctggatc tacaccgtgt   1440
aatggtgtcg aaggattcaa ctgctacttc ccgctacagt cttacggatt caaccgaca   1500
aacggtgtag gatatcagcc gtacagagtc gtcgtactat ccttcgaact actacatgct   1560
ccggcgacag tatgtggacc gaaaaagtct accaacctag tcaagaacaa atgcgtcaac   1620
tttaacttca acggactaac cggaaccggt gtcctaaccg aatctaacaa gaagtttcta   1680
ccgttccagc agttcggaag agatatcgcg gatacaacag acgctgtcag agatccgcaa   1740
accttggaga tcctagatat cacaccgtgt tctttcggtg gtgtctctgt aattactccg   1800
ggaacgaaca cctccaatca gtagcggta ctataccagg acgtgaactg tacagaagta   1860
ccggtagcta ttcacgcgga tcaactaaca ccaacttgga gagtgtactc caccggatct   1920
aacgtattcc aaacaagagc gggatgctca atcggagcgg aacacgtaaa caactcctac   1980
gaatgtgata tcccgattgg agcgggaatc tgtgcgtctt accaaacaca aacaaactct   2040
ccgagaagag cgagatctgt agcctctcaa tctattatcg cctacaccat gtccttggga   2100
gccgaaaatt ctgtcgcgta ctccaacaat tctatcgcga tcccgacaaa cttcaccatc   2160
tctgtaacaa ccgagatcct accggtgtct atgaccaaga catctgtcga ttgcaccatg   2220
```

```
tacatctgcg gagattccac cgagtgctcc aacctactac tacagtacgg atctttctgt  2280
acccagctaa acagagcgtt gactggaatc gctgtagagc aggataagaa cactcaagag  2340
gtattcgcgc aagtcaagca gatctataag actccgccga tcaaggactt cggaggtttc  2400
aacttctctc agatcttgcc ggatccgtcc aaaccgtcta agagatcttt catcgaggac  2460
ctactattca acaaagtcac cctagctgac gcgggattca tcaaacaata cggagattgc  2520
ttgggagaca ttgcggcgag agatctaatt tgcgcgcaga agtttaacgg attgacagta  2580
ctaccgccgc tactaaccga tgagatgatt gcgcagtaca cgtctgctct attggcggga  2640
acaattacaa gtggatggac atttggagcc ggtgccgctc tacaaattcc gtttgctatg  2700
caaatggcgt acagattcaa cggaatcgga gtaacccaga acgtcttgta cgagaaccag  2760
aagctaatcg cgaaccagtt caattccgcg atcggaaaga tccaggacag tctatcttct  2820
actgcttcgg cgttgggaaa gctacaggat gtagtaaatc aaaacgcgca ggcgctaaac  2880
accttggtca agcaactatc ctctaacttc ggacgatct cgtccgtcct aaacgacatc  2940
ttatccagac tagataaggt cgaagcggag gtccagatcg atagactaat cactggaaga  3000
ttgcagtccc tacagaccta cgtaacacag caactaatta gagcggcgga gattagagcc  3060
tctgctaatc tagctgcgac caagatgtcc gaatgtgtct tgggacaatc caagagagtg  3120
gacttctgcg gaaagggata ccacctaatg tctttccac aatctgcgcc gcatggtgtc  3180
gtattcctac atgtaacata tgtgccggcg caagaaaaga acttcacaac agctccagcg  3240
atctgccatg atggaaaagc tcatttcccg agagagggag tctttgtctc taacggaact  3300
cattggttcg tcacccagag aaacttctac gagccgcaga tcatcaccac cgacaacaca  3360
ttcgtctcgg gaaactgcga cgtggtcatc ggaatcgtaa acaataccgt ctacgatccg  3420
ttgcagccgg aactagactc cttcaaagaa gagttggaca agtacttcaa gaaccacacc  3480
tctccggatg tggacttggg agatatctct ggaatcaacg cgtccgtcgt caacatccag  3540
aaagaaatcg atagattgaa cgaggtcgcg aagaacttga acgagtccct aatcgaccta  3600
caagagctag gaaaatacga gcagtacatc aagtggccgt ggtacatctg gctaggattc  3660
attgctggac taattgcgat cgtcatggtc accatcatgc tatgctgtat gacctcctgt  3720
tgctcctgtc taaagggatg ttgttcctgc ggatcctgtt gcaagttcga tgaagatgat  3780
agtgaaccgg tcctaaaggg tgtcaagcta cactacaca                         3819
```

```
SEQ ID NO: 4                moltype = DNA  length = 12
FEATURE                     Location/Qualifiers
source                      1..12
                            mol_type = other DNA
                            organism = synthetic construct
SEQUENCE: 4
gagccagagg ct                                                       12

SEQ ID NO: 5                moltype = AA  length = 4
FEATURE                     Location/Qualifiers
source                      1..4
                            mol_type = protein
                            organism = synthetic construct
SEQUENCE: 5
EPEA                                                                4

SEQ ID NO: 6                moltype = AA  length = 1273
FEATURE                     Location/Qualifiers
source                      1..1273
                            mol_type = protein
                            organism = synthetic construct
SEQUENCE: 6
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGTIAD  420
YNYKLPDDFT GCVIAWNSNN LDSKVGGNYN YLRLFRKSN LKPFERDIST EIYQAGSTPC  480
NGVKGFNCYF PLQSYGFQPT YGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VPLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                     1273

SEQ ID NO: 7                moltype = AA  length = 20
FEATURE                     Location/Qualifiers
source                      1..20
                            mol_type = protein
                            organism = synthetic construct
SEQUENCE: 7
```

```
GAISSVLNDI LSRLDKVEAE                                                  20

SEQ ID NO: 8           moltype = AA   length = 1273
FEATURE                Location/Qualifiers
source                 1..1273
                       mol_type = protein
                       organism = synthetic construct
SEQUENCE: 8
MFVFLVLLPL VSSQCVNLTT RTQLPPAYTN SFTRGVYYPD KVFRSSVLHS TQDLFLPFFS    60
NVTWFHAIHV SGTNGTKRFD NPVLPFNDGV YFASTEKSNI IRGWIFGTTL DSKTQSLLIV    120
NNATNVVIKV CEFQFCNDPF LGVYYHKNNK SWMESEFRVY SSANNCTFEY VSQPFLMDLE    180
GKQGNFKNLR EFVFKNIDGY FKIYSKHTPI NLVRDLPQGF SALEPLVDLP IGINITRFQT    240
LLALHRSYLT PGDSSSGWTA GAAAYYVGYL QPRTFLLKYN ENGTITDAVD CALDPLSETK    300
CTLKSFTVEK GIYQTSNFRV QPTESIVRFP NITNLCPFGE VFNATRFASV YAWNRKRISN    360
CVADYSVLYN SASFSTFKCY GVSPTKLNDL CFTNVYADSF VIRGDEVRQI APGQTGKIAD    420
YNYKLPDDFT GCVIAWNSNN LDSKVGGNYN YLYRLFRKSN LKPFERDIST EIYQAGSTPC    480
NGVEGFNCYF PLQSYGFQPT NGVGYQPYRV VVLSFELLHA PATVCGPKKS TNLVKNKCVN    540
FNFNGLTGTG VLTESNKKFL PFQQFGRDIA DTTDAVRDPQ TLEILDITPC SFGGVSVITP    600
GTNTSNQVAV LYQDVNCTEV PVAIHADQLT PTWRVYSTGS NVFQTRAGCL IGAEHVNNSY    660
ECDIPIGAGI CASYQTQTNS PRRARSVASQ SIIAYTMSLG AENSVAYSNN SIAIPTNFTI    720
SVTTEILPVS MTKTSVDCTM YICGDSTECS NLLLQYGSFC TQLNRALTGI AVEQDKNTQE    780
VFAQVKQIYK TPPIKDFGGF NFSQILPDPS KPSKRSFIED LLFNKVTLAD AGFIKQYGDC    840
LGDIAARDLI CAQKFNGLTV LPPLLTDEMI AQYTSALLAG TITSGWTFGA GAALQIPFAM    900
QMAYRFNGIG VTQNVLYENQ KLIANQFNSA IGKIQDSLSS TASALGKLQD VVNQNAQALN    960
TLVKQLSSNF GAISSVLNDI LSRLDPPEAE VQIDRLITGR LQSLQTYVTQ QLIRAAEIRA    1020
SANLAATKMS ECVLGQSKRV DFCGKGYHLM SFPQSAPHGV VFLHVTYVPA QEKNFTTAPA    1080
ICHDGKAHFP REGVFVSNGT HWFVTQRNFY EPQIITTDNT FVSGNCDVVI GIVNNTVYDP    1140
LQPELDSFKE ELDKYFKNHT SPDVDLGDIS GINASVVNIQ KEIDRLNEVA KNLNESLIDL    1200
QELGKYEQYI KWPWYIWLGF IAGLIAIVMV TIMLCCMTSC CSCLKGCCSC GSCCKFDEDD    1260
SEPVLKGVKL HYT                                                       1273

SEQ ID NO: 9           moltype = DNA   length = 3819
FEATURE                Location/Qualifiers
source                 1..3819
                       mol_type = other DNA
                       organism = synthetic construct
SEQUENCE: 9
atgtttgttt ttcttgtttt attgccacta gtctctagtc agtgtgttaa tcttacaacc    60
agaactcaat taccccctgc atacactaat tctttcacac gtggtgttta ttaccctgac    120
aaagttttca gatcctcagt tttacattca actcaggact tgttcttacc tttctttttcc    180
aatgttactt ggttccatgc tatacatgtc tctgggacca atggtactaa gaggtttgat    240
aaccctgtcc taccatttaa tgatggtgtt tattttgctt ccactgagaa gtctaacata    300
ataagaggct ggatttttgg tactacttta gattcgaaga cccagtccct acttattgtt    360
aataacgcta ctaatgttgt tattaaagtc tgtgaatttc aattttgtaa tgatccattt    420
ttgggtgttt attaccacaa aaacaacaaa agttggatgg aaagtgagtt cagagtttat    480
tctagtgcga ataattgcac ttttgaatat gtctctcagc ctttttcttat ggaccttgaa    540
ggaaaacagg gtaatttcaa aaatcttagg gaatttgtct ttaagaatat tgatggttat    600
tttaaaatat attctaagca cacgcctatt aatttagtgc gtgatctccc tcagggtttt    660
tcggctttag aaccattggt agatttgcca ataggtatta acatcactag gtttcaaact    720
ttacttgctt tacatagaag ttatttgact cctggtgatt cttcttcagg ttggacagct    780
ggtgctgcag cttattatgt gggttatctt caacctagga ctttttctat taaaatataat    840
gaaaatggaa ccattacaga tgctgtagac tgtgcacttg accctctctc agaaacaaag    900
tgtacgttga atccttcac tgtagaaaaa ggaatctatc aaacttctaa ctttagagtc    960
caaccaacag aatctattgt tagatttcct aatattacaa acttgtgccc ttttggtgaa    1020
gtttttaacg ccaccagatt tgcatctgtt tatgcttgga acaggaagag aatcagcaac    1080
tgtgttgctg attattctgt cctatataat tccgcatcat tttccacttt taagtgttat    1140
ggagtgtctc ctactaaatt aaatgatctc tgctttacta tgtctatgc agattcattt    1200
gtaattagag gtgatgaagt cagacaaatc gctccagggc aaactggaaa gattgctgat    1260
tataattata aattaccaga tgatttttaca ggctgcgtta tagcttggaa ttctaacaat    1320
cttgattcta aggttggtgg taattataat tacctgtata gattgtttag gaagtctaat    1380
ctcaaacctt ttgagagaga tatttcaact gaaatctatc aggccggtag cacaccttgt    1440
aatggtgttg aaggttttaa ttgttacttt ccttttacaat catatggttt ccaacccact    1500
aatggtgttg gttaccaacc atacagagta gtagtacttt cttttgaact tctacatgca    1560
ccagcaactg tttgtggacc taaaaagtct actaatttgg ttaaaaacaa atgtgtcaat    1620
ttcaacttca atggtttaac aggcacaggt gttcttactg agtctaacaa aaagtttctg    1680
cctttccaac aatttggcag agacattgct gacactactg atgctgtccg tgatccacag    1740
acacttgaga ttcttgacat tacaccatgt tcttttggtg gtgtcagtgt tataacacca    1800
ggaacaaata cttctaacca ggttgctgtt ctttatcagg atgttaactg cacagaagtc    1860
cctgttgcta ttcatgcaga tcaacttact cctacttggc gtgtttattc tacaggttct    1920
aatgtttttc aaacacgtgc aggctgttta ataggggctg aacatgtcaa caactcatat    1980
gagtgtgaca tacccattgg tgcaggtata tgcgctagtt atcagactca gactaattct    2040
cctcggcggg cacgtagtgt agctagtcaa tccatcattg cctacactat gtcacttggt    2100
gcagaaaatt cagttgctta ctctaataac tctattgcca tacccacaaa ttttactatt    2160
agtgttacca cagaaattct catcagtgtc atgaccaaga cattaactgg ttgtacaagt    2220
tacatttgtg gtgattcaac tgaatgcagc aatcttttgt tgcaatatgg cagtttttgt    2280
acacaattaa accgtgcttt aactggaata gctgttgaac aagacaaaaa cacccaagaa    2340
gtttttgcac aagtcaaaca aatttacaaa acaccaccaa ttaaagattt tggtggtttt    2400
aattttttcac aaatattacc agatccatca aaaccaagca gaggtcatt tattgaagat    2460
ctacttttca acaaagtgac acttgcagat gctggcttca tcaaacaata tggtgattgc    2520
```

-continued

```
cttggtgata ttgctgctag agacctcatt tgtgcacaaa agtttaacgg ccttactgtt  2580
ttgccacctt tgctcacaga tgaaatgatt gctcaataca cttctgcact gttagcgggt  2640
acaatcactt ctggttggac ctttggtgca ggtgctgcat tacaaatacc atttgctatg  2700
caaatggctt ataggtttaa tggtattgga gttacacaga atgttctcta tgagaaccaa  2760
aaattgattg ccaaccaatt taatagtgct attggcaaaa ttcaagactc actttcttcc  2820
acagcaagtg cacttggaaa acttcaagat gtggtcaacc aaaatgcaca agctttaaac  2880
acgcttgtta aacaacttag ctccaatttt ggtgcaattt caagtgtttt aaatgatatc  2940
ctttcacgtc ttgacccacc ggaggctgaa gtgcaaattg ataggttgat cacaggcaga  3000
cttcaaagtt tgcagacata tgtgactcaa caattaatta gagctgcgaa aatcagagct  3060
tctgctaatc ttgctgctac taaaatgtca gagtgtgtac ttggacaatc aaaaagagtt  3120
gattttgtg gaaagggcta tcatcttatg tccttccctc agtcagcacc tcatggtgta  3180
gtcttcttgc atgtgactta tgtccctgca caagaaaaga acttcacaac tgctcctgcc  3240
atttgtcatg atggaaaagc acactttcct cgtgaaggtg tctttgtttc aaatggcaca  3300
cactggtttg taacacaaag gaatttttat gaaccacaaa tcattactac agacaacaca  3360
tttgtgtctg gtaactgtga tgttgtaata ggaattgtca acaacacagt ttatgatcct  3420
ttgcaacctg aattagactc attcaaggag gagttagata aatatttaa gaatcataca  3480
tcaccagatg ttgatttagg tgacatctct ggcattaatg cttcagttgt aaacattcaa  3540
aaagaaattg accgcctcaa tgaggttgcc aagaatttaa atgaatctct catcgatctc  3600
caagaacttg gaaagtatga gcagtatata aaatggccat ggtacatttg gctaggtttt  3660
atagctggct tgattgccat agtaatggtg acaattatgc tttgctgtat gaccagttgc  3720
tgtagttgtc tcaagggctg ttgttcttgt ggatcctgct gcaaatttga tgaagacgac  3780
tctgagccag tgctcaaagg agtcaaatta cattacaca  3819
```

```
SEQ ID NO: 10            moltype = DNA   length = 3819
FEATURE                  Location/Qualifiers
source                   1..3819
                         mol_type = other DNA
                         organism = synthetic construct
SEQUENCE: 10
atgttcgtgt tcctagtcct actaccgcta gtctcttctc agtgtgtaaa cctaacaacg  60
agaacacaac taccaccggc gtacaccaat tctttcacaa gaggagtata ttacccggac  120
aaggtgttca gatcctccgt actacattct acacaggacc tattcctacc gttcttctct  180
aacgtaacat ggttccacgc gatccatgtc tctggaacaa acggaacgaa gagattcgat  240
aacccggtct tgccgttcaa cgatggtgta tactttgcgt ccaccgagaa gtccaacatc  300
atcagaggat ggatcttcgg aaccaccttg gattctaaga cccagtcctt gctaatcgtc  360
aacaacgcga ccaacgtcgt catcaaagtc tgcgaattcc agttctgtaa cgacccgttc  420
ttgggagtct actaccacaa gaacaacaag tcctggatgg aatccgagtt cagagtctac  480
tcttccgcga caactgcac cttcgaatat gtatctcagc cgttcctaat ggacctagag  540
ggaaagcagg gaaacttcaa gaacctaaga gagttcgtat tcaagaacat cgacggatac  600
ttcaagatct actccaagca cactccgatc aacctagtta gagatctacc gcaaggattc  660
tctgcgctag aaccgttagt agatttgccg atcggaatca acatcaccag attccagaca  720
ctactagcgc tacacagatc ttacctaacg ccgggagatt cttcttctgg atggactgct  780
ggtgctgcgg cttattatgt aggataccta cagccgaaca cctcctatt gaagtacaac  840
gaaaacggaa ccatcaccga tgccgtagat tgtgctctag atccgctatc cgaaacgaag  900
tgcaccctaa agtctttcac cgtcgagaag ggaatctacc agacctccaa ctttagagta  960
cagccgaccg aatccatcgt cagatttccg aacatcacga acctatgtcc gttcggagaa  1020
gtgttcaacg cgacaagatt tgcgtctgtc tatgcgtgga acagaaaaag aatcagtaac  1080
tgcgtcgcgg actactccgt cctatacaac tctgcctctt tctccacgtt caaatgctac  1140
ggtgtatctc cgacaaagct aaacgatcta tgcttcacca acgtctacgc ggactccttc  1200
gtaatcagag gagatgaagt tagacagatt gcgccgggac aaactggaaa gatcgcggat  1260
tataactaca agctaccgga cgacttcacc ggatgtgtaa ttgcgtggaa ttcgaacaac  1320
ctagactcca aagtcggagg aaactacaac tacttgtaca gactattcag aaagtccaac  1380
ctaaagccgt tcgagagaga catctccacc gaaatctatc aggctggatc tacaccgtgt  1440
aatggtgtcg aaggattcaa ctgctacttc ccgctacagt cttacggatt tcaaccgaca  1500
aacggtgtag gatatcagcc gtacagagtc gtcgtactat ccttcgaact actacatgct  1560
ccggcgacag tatgtggacc gaaaaagtct accaacctag tcaagaacaa atgcgtcaac  1620
tttaacttca acggactaac cggaaccggt gtcctaaccg aatctaacaa gaagtttcta  1680
ccgttccagc agttcggaag agatatcgcg gatacaacag acgctgtcag agatccgcaa  1740
accttggaga tcctagatat cacaccgtgt tctttcggtg gtgtctctgt aattactccg  1800
ggaacgaaca cctccaatca agtagcggta ctataccagg acgtgaactg tacagaagta  1860
ccggtagcta ttcacgcgga tcaactaaca ccaacttgga gagtgactc caccggatct  1920
aacgtattcc aaacaagagc gggatgtcta atcggagcgg aacacgtaaa caactcctac  1980
gaatgtgata tcccgattgg agcgggaatc tgtgcgtctt accaaacaca aacaaatct  2040
ccgagaagag cgagatctgt agcctctcaa tctattacg cctacaccat gtccttggga  2100
gccgaaaatt ctgtcgcgta ctccaacaat tctatcgcga tcccgacaaa cttcaccatc  2160
tctgtaacaa ccgagatcct accggtgtct atgaccaaga catctgtcga ttgcaccatg  2220
tacatctgcg gagattccac cgagtgctcc aacctactac tacagtacgg atctttctgt  2280
acccagctaa acagagcgtt gactggaatc gctgtagagc aggataagaa cactcaagag  2340
gtattcgcgc aagtcaagca gatctataag actccgccga tcaaggactt cggaggtttc  2400
aacttctctc agatcttgcc ggatccgtcc aaaccgtcta agagatcttt catcgaggac  2460
ctactattca acaaagtcac cctagctgac gcgggattca tcaaacaata cggagattgc  2520
ttgggagaca ttgcggcgag agatctaatt tgcgcgcaga gtttaacgg attgacagta  2580
ctaccgccgc tactaaccga tgagatgatt gcgcagtaca cgtctgctct attggcggga  2640
acaattacaa gtggatggac atttggagcc ggtgccgctc tacaaattcc gtttgctatg  2700
caaatggcgt acagattcaa cggaatcgga gtaacccaga cgtcttgta cgagaaccag  2760
aagctaatcg cgaaccagtt caattccgcg atcggaaaga tccaggacag tctatcttct  2820
actgcttcgg cgttgggaaa gctacaggat gtagtaaatc aaaacgcgca ggcgctaaac  2880
accttggtca agcaactatc ctctaacttc ggagcgatcg cgtccgtcct aaacgacatc  2940
ttatccgac tagatccacc ggaagcggag gtccagatcg atagactaat cactggaaga  3000
```

```
ttgcagtccc tacagaccta cgtaacacag caactaatta gagcggcgga gattagagcc  3060
tctgctaatc tagctgcgac caagatgtcc gaatgtgtct tgggacaatc caagagagtg  3120
gacttctgcg gaaagggata ccacctaatg tctttcccac aatctgcgcc gcatggtgtc  3180
gtattcctac atgtaacata tgtgccggcg caagaaaaga acttcacaac agctccagcg  3240
atctgccatg atggaaaagc tcatttcccg agagagggag tctttgtctc taacggaact  3300
cattggttcg tcacccagag aaacttctac gagccgcaga tcatcaccac cgacaacaca  3360
ttcgtctcgg gaaactgcga cgtggtcatc ggaatcgtaa acaataccgt ctacgatccg  3420
ttgcagccgg aactagactc cttcaaagaa gagttggaca agtacttcaa gaaccacacc  3480
tctccggatg tggacttggg agatatctct ggaatcaacg cgtccgtcgt caacatccga  3540
aaagaaatcg atagattgaa cgaggtcgcg aagaacttga acgagtccct aatcgaccta  3600
caagagctag gaaaatacga gcagtacatc aagtggccgt ggtacatctg gctaggattc  3660
attgctggac taattgcgat cgtcatggtc accatcatgc tatgctgtat gacctcctgt  3720
tgctcctgtc taaagggatg ttgttcctgc ggatcctgtt gcaagttcga tgaagatgat  3780
agtgaaccgg tcctaaaggg tgtcaagcta cactacaca  3819
```

```
SEQ ID NO: 11              moltype = AA   length = 1273
FEATURE                    Location/Qualifiers
source                     1..1273
                           mol_type = protein
                           organism = synthetic construct
SEQUENCE: 11
MFVFLVLLPL VSSQCVNLTT RTQLPPAYTN SFTRGVYYPD KVFRSSVLHS TQDLFLPFFS   60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGTIAD  420
YNYKLPDDFT GCVIAWNSNN LDSKVGGNYN YLYRLFRKSN LKPFERDIST EIYQAGSTPC  480
NGVKGFNCYF PLQSYGFQPT YGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDPPEAE VQIDRLITGR LQSLQTYVTQ QLIRAAEIRA 1020
SANLAATKMS ECVLGQSKRV DFCGKGYHLM SFPQSAPHGV VFLHVTYVPA QEKNFTTAPA 1080
ICHDGKAHFP REGVFVSNGT HWFVTQRNFY EPQIITTDNT FVSGNCDVVI GIVNNTVYDP 1140
LQPELDSFKE ELDKYFKNHT SPDVDLGDIS GINASVVNIQ KEIDRLNEVA KNLNESLIDL 1200
QELGKYEQYI KWPWYIWLGF IAGLIAIVMV TIMLCCMTSC CSCLKGCCSC GSCCKFDEDD 1260
SEPVLKGVKL HYT                                                    1273
```

```
SEQ ID NO: 12              moltype = DNA   length = 3819
FEATURE                    Location/Qualifiers
source                     1..3819
                           mol_type = other DNA
                           organism = synthetic construct
SEQUENCE: 12
atgttcgtgt tcctagtcct actaccgcta gtctcttctc agtgtgtaaa cctaacaacg   60
agaacacaac taccaccggc gtacaccaat tctttcacaa gaggagtata ttacccggac  120
aaggtgttca gatcctccgt actacattct acacaggacc tattcctacc gttcttctct  180
aacgtaacat ggtccacgc gatccatgtc tctggaacaa acggaacgaa gagattcgat  240
aacccggtct tgccgttcaa cgatggtgta tactttgcgt ccaccgagaa gtccaacatc  300
atcagaggat ggatcttcgg aaccaccttg gattctaaga cccagtcctt gctaatcgtc  360
aacaacgcga ccaacgtcgt catcaaagtc tgcgaattcc agttctgtaa cgaccgttc  420
ttgggagtct actaccacaa gaacaacaag tcctggatgg aatccgagtt cagagtctac  480
tcttccgcga caactgcac cttcgaatat gtatctgtac cgttcctaat ggacctagag  540
ggaaagcagg gaaacttcaa gaacctaaga gagttcgtat tcaagaacat cgacggatac  600
ttcaagatct actccaagca cactccgatc aacctagtta gagatctacc gcaaggattc  660
tctgcgctag aaccgttagt agatttgccg atcggaatca acatcaccag attccagaca  720
ctactagcgc tacacagatc ttacctaacg ccgggagatt cttcttctgg atggactgct  780
ggtgctgcg cttattatgt aggatacctt cagccgagac ccttcctatt gaagtacaac  840
gaaaacggaa ccatcaccga tgccgtagat tgtgctctag atccgctatc cgaaacgaag  900
tgcaccctaa agtctttcac cgtcgagaag ggaatctacc agacctccaa ctttagagta  960
cagccgaccg aatccatcgt cagatttccg aacatcacga acctatgtcc gttcggagaa 1020
gtgttcaacg cgacaagatt tgcgtctgtc tatgcgtgga cagaaaaag aatcagtaac 1080
tgcgtcgcg actactccgt cctatacaac tctgcctctt tctccacgtt caaatgctac 1140
ggtgtatctc cgacaaagct aaacgatcta tgcttcacca acgtctacgc ggactccttc 1200
gtgtaatcagag gagatgaagt tagacagatt gcgccgggac aaactggaac gatcgcggat 1260
tataactaca agctaccgga cgacttcacc ggatgtgtaa ttgcgtggaa ttcgaacaac 1320
ctagactcca agtcggagg aaactacaac tacttgtaca gactattcag aaagtccaac 1380
ctaaagccgt tcgagagaga catctccacc gaaatctatc aggctggatc tacaccgtgt 1440
aatggtgtca agggattcaa ctgctacttc ccgctacagt cttacggatt tcaaccgaca 1500
tacggtgtag gatatcagcc gtacagagtc gtcgtactat ccttcgaact actacatgct 1560
ccggcgacat atgtggacc gaaaaagtct accaacctag tcaagaacaa atgcgtcaac 1620
tttaacttca acggactaac cggaaccggt gtcctaaccg aatctaacaa gaagtttcta 1680
ccgttccagc agttcggaag agatatcgcg gatacaacag acgctgtcag agatccgcaa 1740
```

-continued

```
accttggaga tcctagatat cacaccgtgt tctttcggtg gtgtctctgt aattactccg  1800
ggaacgaaca cctccaatca agtagcggta ctataccagg acgtgaactg tacagaagta  1860
ccggtagcta ttcacgcgga tcaactaaca ccaacttgga gagtgtactc caccggatct  1920
aacgtattcc aaacaagagc gggatgtcta atcggagcgg aacacgtaaa caactcctac  1980
gaatgtgata tcccgattgg agcgggaatc tgtgcgtctt accaaacaca aacaaactct  2040
ccgagaagag cgagatctgt agcctctcaa tctattatcg cctacaccat gtccttggga  2100
gccgaaaatt ctgtcgcgta ctccaacaat tctatcgcga tcccgacaaa cttcaccatc  2160
tctgtaacaa ccgagatcct accggtgtct atgaccaaga catctgtcga ttgcaccatg  2220
tacatctgcg gagattccac cgagtgctcc aacctactac tacagtacgg atctttctgt  2280
acccagctaa acagagcgtt gactggaatc gctgtagagc aggataagaa cactcaagag  2340
gtattcgcgc aagtcaagca gatctataag actccgccga tcaaggactt cggaggtttc  2400
aacttctctc agatcttgcc ggatccgtcc aaaccgtcta agagatcttt catcgaggac  2460
ctactattca acaaagtcac cctagctgac gcgggattca tcaaacaata cggagattgc  2520
ttgggagaca ttgcggcgag agatctaatt tgcgcgcaga agtttaacgg attgacagta  2580
ctaccgccgc tactaaccga tgagatgatt gcgcagtaca cgtctgctct attggcggga  2640
acaattacaa gtggatggac atttggagcc ggtgccgctc tacaaattcc gtttgctatg  2700
caaatggcgt acagattcaa cggaatcgga gtaacccaga acgtcttgta cgagaaccag  2760
aagctaatcg cgaaccagtt caattccgcg atcggaaaga tccggacagt ctatctttct  2820
actgcttcgg cgttgggaaa gctacaggat gtagtaaatc aaaacgcgca ggcgctaaac  2880
accttggtca agcaactatc ctctaacttc ggagcgatct cgtccgtcct aaacgacatc  2940
ttatccgac tagatccacc ggaagcggag gtccagatcg atagactaat cactggaaga  3000
ttgcagtccc tacagaccta cgtaacacag caactaatta cagcggcgga gattagagca  3060
tctgctaatc tagctgcgac caagatgtcc gaatgtgtct tgggacaatc caagagagtg  3120
gacttctgcg gaaagggata ccacctaatg tctttcccac aatctgcgcc gcatggtgtc  3180
gtattcctac atgtaacata tgtgccggcg caagaaaaga acttcacaac agctccagcg  3240
atctgccatg atggaaaagc tcatttcccg agagaggcag tctttgtctc taacggaact  3300
cattggttcg tcacccagag aaacttctac gagccgcaga tcatcaccac cgacaacaca  3360
ttcgtctcgg gaaactgcga cgtggtcatc ggaatcgtaa acaataccgt ctacgatccg  3420
ttgcagccgg aactagactc cttcaaagaa gagttggaca agtacttcaa gaaccacacc  3480
tctccggatg tggacttggg agatatctct ggaatcaacg cgtccgtcgt caacatccag  3540
aaagaaatcg atagattgaa cgaggtcgcg aagaacttga acgagtccct aatcgaccta  3600
caagagctag gaaaatacga gcagtacatc aagtggccgt ggtacatctg gctaggattc  3660
attgctggac taattgcgat cgtcatggtc accatcatgc tatgctgtat gacctcctgt  3720
tgctcctgtc taaagggatg ttgttcctgc ggatcctgtt gcaagttcga tgaagatgat  3780
agtgaaccgg tcctaaaggg tgtcaagcta cactacaca            3819
```

SEQ ID NO: 13             moltype = AA  length = 1213
FEATURE                   Location/Qualifiers
source                    1..1213
                          mol_type = protein
                          organism = synthetic construct
SEQUENCE: 13
```
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWP                                       1213
```

SEQ ID NO: 14             moltype = AA  length = 1213
FEATURE                   Location/Qualifiers
source                    1..1213
                          mol_type = protein
                          organism = synthetic construct
SEQUENCE: 14
```
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
```

```
FNFNGLTGTG VLTESNKKFL PFQQFGRDIA DTTDAVRDPQ TLEILDITPC SFGGVSVITP   600
GTNTSNQVAV LYQDVNCTEV PVAIHADQLT PTWRVYSTGS NVFQTRAGCL IGAEHVNNSY   660
ECDIPIGAGI CASYQTQTNS PRRARSVASQ SIIAYTMSLG AENSVAYSNN SIAIPTNFTI   720
SVTTEILPVS MTKTSVDCTM YICGDSTECS NLLLQYGSFC TQLNRALTGI AVEQDKNTQE   780
VFAQVKQIYK TPPIKDFGGF NFSQILPDPS KPSKRSFIED LLFNKVTLAD AGFIKQYGDC   840
LGDIAARDLI CAQKFNGLTV LPPLLTDEMI AQYTSALLAG TITSGWTFGA GAALQIPFAM   900
QMAYRFNGIG VTQNVLYENQ KLIANQFNSA IGKIQDSLSS TASALGKLQD VVNQNAQALN   960
TLVKQLSSNF GAISSVLNDI LSRLDPPEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWP                                                     1213

SEQ ID NO: 15           moltype = DNA  length = 3639
FEATURE                 Location/Qualifiers
source                  1..3639
                        mol_type = other DNA
                        organism = synthetic construct
SEQUENCE: 15
atgtttgttt ttcttgtttt attgccacta gtctctagtc agtgtgttaa tcttacaacc    60
agaactcaat taccccctgc atacactaat tctttcacac gtggtgttta ttaccctgac   120
aaagttttca gatcctcagt tttacattca actcaggact tgttcttacc tttctttttcc   180
aatgttactt ggttccatgc tatacatgtc tctgggacca atggtactaa gaggtttgat   240
aaccctgtcc taccatttaa tgatggtgtt tatttttgctt ccactgagaa gtctaacata   300
ataagaggct ggattttttgg tactacttta gattcgaaga cccagtccct acttattgtt   360
aataacgcta ctaatgttgt tattaaagtc tgtgaatttc aattttgtaa tgatccattt   420
ttgggtgttt attaccacaa aaacaacaaa agttggatgg aaagtgagtt cagagtttat   480
tctagtgcga ataattgcac ttttgaatat gtctctcagc cttttcttat ggaccttgaa   540
ggaaaacagg gtaatttcaa aaatcttagg gaatttgtgt ttaagaatat tgatggttat   600
tttaaaatat attctaagca cacgcctatt aatttagtgc gtgatctccc tcagggttct   660
tcggctttag aaccattggt agatttgcca ataggtatta acatcactag gtttcaaact   720
ttacttgctt tacatagaag ttatttgact cctggtgatt cttcttcagg ttggacagct   780
ggtgctgcag cttattatgt gggttatctt caacctagga ctttctatt aaaatataat   840
gaaaatggaa ccattacaga tgctgtagac tgtgcacttg accctctctc agaaacaaag   900
tgtacgttga aatccttcac tgtagaaaaa ggaatctatc aaacttctaa ctttagagtc   960
caaccaacag aatctattgt tagatttcct aatattacaa acttgtgccc ttttggtgaa  1020
gttttttaacg ccaccagatt tgcatctgtt tatgcttgga acaggaagag aatcagcaac  1080
tgtgttgctg attattctgt cctatataat tccgcatcat tttccacttt taagtgttat  1140
ggagtgtctc ctactaaatt aaatgatctc tgctttacta atgtctatgc agattcattt  1200
gtaattagag gtgatgaagt cagacaaatc gctccagggc aaactggaaa gattgctgat  1260
tataattata aattaccaga tgattttaca ggctgcgtta tagcttggaa ttctaacaat  1320
cttgattcta aggttggtgg taattataat tacctgtata gattgtttag gaagtctaat  1380
ctcaaacctt ttgagagaga tatttcaact gaaatctatc aggccggtag cacaccttgt  1440
aatggtgttg aaggttttaa ttgttacttt ccttttacaat catatggttt ccaacccact  1500
aatggtgttg gttaccaacc atacagagta gtagtacttt cttttgaact tctacatgca  1560
ccagcaactg tttgtggacc taaaaagtct actaatttgg ttaaaaacaa atgtgtcaat  1620
ttcaacttca atggtttaac aggcacaggt gttcttactg agtctaacaa aaagtttctg  1680
cctttccaac aatttggcag agacattgct gacactactg atgctgtccg tgatccacag  1740
acacttgaga ttcttgacat tacaccatgt tcttttggtg gtgtcagtgt tataacacca  1800
ggaacaaata cttctaacca ggttgctgtt ctttatcagg atgttaactg cacagaagtc  1860
cctgttgcta ttcatgcaga tcaacttact cctacttggc gtgtttattc tacaggttct  1920
aatgtttttc aaacacgtgc aggctgttta ataggggctg aacatgtcaa caactcatat  1980
gagtgtgaca tacccattgg tgcaggtata tgcgctagtt atcagactca gactaattct  2040
cctcggcggg cacgtagtgt agctagtcaa tccatcattg cctacactat gtcacttggt  2100
gcagaaaatt cagttgctta ctctaataac tctattgcca tacccacaaa ttttactatt  2160
agtgttacca cagaaattct accagtgtct atgaccaaga catcagtaga ttgtacaatg  2220
tacatttgtg gtgattcaac tgaatgcagc aatcttttgt tgcaatatgg cagtttttgt  2280
acacaattaa accgtgcttt aactggaata gctgttgaac aagacaaaaa cacccaagaa  2340
gtttttgcac aagtcaaaca aatttacaaa acaccaccaa ttaaagattt tggtggtttt  2400
aattttttcac aaatattacc agatccatca aaaccaagca gaggtcatt tattgaagat  2460
ctacttttca acaaagtgac acttgcagat gctggcttca tcaaacaata tggtgattgc  2520
cttggtgata ttgctgctag agacctcatt tgtgcacaaa agtttaacgg ccttactgtt  2580
ttgccaccttt tgctcacaga tgaaatgatt gctcaataca cttctgcact gttagcgggt  2640
acaatcactt ctggttggac ctttggtgca ggtgctgcat tacaaatacc atttgctatg  2700
caaatggctt ataggtttaa tggtattgga gttacacaga tgttctcta tgagaaccaa  2760
aaattgattg ccaaccaatt taatagtgct attggcaaaa ttcaagactc actttcttcc  2820
acagcaagtg cacttggaaa acttcaagat gtggtcaacc aaaatgcaca gcttttaaac  2880
acgcttgtta aacaacttag ctccaatttt ggtgcaattt caagtgtttt aaatgatatc  2940
ctttcacgtc ttgacaaagt tgaggctgaa gtgcaaattg ataggttgat cacaggttatg  3000
cttcaaagtt tgcagacata tgtgactcaa caattaatta gagctgcaga aatcagagct  3060
tctgctaatc ttgctgctac taaaatgtca gagtgtgtac ttggacaatc aaaaagagtt  3120
gatttttgtg aaagggctat catcttatg tccttccctc agtcagcacc tcatggtgta  3180
gtcttcttgc atgtgactta tgtccctgca caagaaaaga cttcacaac tgctcctgcc  3240
atttgtcatg atggaaaagc acactttcct cgtgaaggtg tctttgtttc aaatggcaca  3300
cactggtttg taacacaaag gaatttttat gaaccacaaa tcattactac agacaacaca  3360
tttgtgtctg gtaactgtga tgttgtaata ggaattgtca caacacagt ttatgatcct  3420
ttgcaacctg aattagactc attcaaggag gagttagata atattttaa gaatcataca  3480
tcaccagatg ttgatttagg tgacatctct ggcattaatg cttcagttgt aaacattcaa  3540
aaagaaattg accgcctcaa tgaggttgcc aagaatttaa atgaatctct catcgatctc  3600
```

```
caagaacttg gaaagtatga gcagtatata aaatggcca                                  3639

SEQ ID NO: 16          moltype = DNA   length = 3639
FEATURE                Location/Qualifiers
source                 1..3639
                       mol_type = other DNA
                       organism = synthetic construct SEQUENCE: 16
atgttcgtgt tcctagtcct actaccgcta gtctcttctc agtgtgtaaa cctaacaacg     60
agaacacaac taccaccggc gtacaccaat tctttcacaa gaggagtata ttacccggac    120
aaggtgttca gatcctccgt actacattct acacaggacc tattcctacc gttcttctct    180
aacgtaacat ggttccacgc gatccatgtc tctggaacaa acggaacgaa gagattcgat    240
aacccggtct tgccgttcaa cgatggtgta tactttgcgt ccaccgagaa gtccaacatc    300
atcagaggat ggatcttcgg aaccaccttg gattctaaga cccagtcctt gctaatcgtc    360
aacaacgcga ccaacgtcgt catcaaagtc tgcgaattcc agttctgtaa cgacccgttc    420
ttgggagtct actaccacaa gaacaacaag tcctggatgg aatccgagtt cagagtctac    480
tcttccgcga acaactgcac cttcgaatat gtatctcagc cgttcctaat ggacctagag    540
ggaaagcagg gaaacttcaa gaacctaaga gagttcgtat tcaagaacat cgacggatac    600
ttcaagatct actccaagca cactccgatc aacctagtta gagatctacc gcaaggattc    660
tctgcgctag aaccgttagt agatttgccg atcggaatca acatcaccag attccagaca    720
ctactagcgc tacacagatc ttacctaacg ccgggagatt cttcttctgg atggactgct    780
ggtgctgcgg cttattatgt aggataccta cagccgagaa ccttcctatt gaagtacaac    840
gaaaacggaa ccatcaccga tgccgtagat tgtgctctag atccgctatc cgaaacgaag    900
tgcaccctaa agtctttcac cgtcgagaag ggaatctacc agacctccaa ctttagagta    960
cagccgaccg aatccatcgt cagatttccg aacatcacga acctatgtcc gttcggagaa   1020
gtgttcaacg cgacaagatt tgcgtctgtc tatgcgtgga acagaaaaag aatcagtaac   1080
tgcgtcgcgg actactccgt cctatacaac tctgcctctt tctccacgtt caaatgctac   1140
ggtgtatctc cgacaaagct aaacgatcta tgcttcacca acgtctacgc ggactccttc   1200
gtaatcagag gagatgaagt tagacagatt gcgccgggac aaactggaaa gatcgcggat   1260
tataactaca agctaccgga cgacttcacc ggatgtgtaa ttgcgtggaa ttcgaacaac   1320
ctagactcca aagtcggagg aaactacaac tacttgtaca gactattcag aaagtccaac   1380
ctaaagccgt tcgagagaga catctccacc gaaatctatc aggctggatc tacaccgtgt   1440
aatggtgtcg aaggattcaa ctgctacttc ccgctacagt cttacggatt tcaaccgaca   1500
aacggtgtag gatatcagcc gtacagagtc gtcgtactat ccttcgaact actacatgct   1560
ccggcgacag tatgtggacc gaaaaagtct accaacctag tcaagaacaa atgcgtcaac   1620
tttaacttca acggactaac cggaaccggt gtcctaaccg aatctaacaa gaagtttcta   1680
ccgttccagc agttcggaag agatatcgcg gatacaacag acgctgtcag agatccgcaa   1740
accttggaga tcctagatat cacaccgtgt tctttcggtg gtgtctctgt aattactccg   1800
ggaacgaaca cctccaatca agtagcggta ctataccagg acgtgaactg tacagaagta   1860
ccggtagcta ttcacgcgga tcaactaaca ccaacttgga gagtgtactc caccggatct   1920
aacgtattcc aaacaagagc gggatgtcta atcggagcgg aacacgtaaa caactcctac   1980
gaatgtgata tcccgattgg agcgggaatc tgtgcgtctt accaaacaca aacaaactct   2040
ccgagaagag cgagatctgt agcctctcaa tctattacgg cctacaccat gtccttggga   2100
gccgaaaatt ctgtcgcgta ctccaacaat tctatcgcga tcccgacaaa cttcaccatc   2160
tctgtaacaa ccgagatcct accggtgtct atgaccaaga catctgtcga ttgcaccatg   2220
tacatctgcg gagattccac cgagtgctcc aacctactac tacagtacgg atctttctgt   2280
acccagctaa acagagcgtt gactggaatc gctgtagagc aggataagaa cactcaagag   2340
gtattcgcgc aagtcaagca gatctataag actccgccga tcaaggactt cggaggtttc   2400
aacttctctc agatcttgcc ggatccgtcc aaaccgtcta agagatcttt catcgaggac   2460
ctactattca acaaagtcac cctagctgac gcgggattca tcaaacaata cggagattgc   2520
ttgggagaca ttgcggcgag agatctaatt tgcgcgcaga agtttaacgg attgacagta   2580
ctaccgccgc tactaaccga tgagatgatt gcgcagtaca cgtctgctct attggcggga   2640
acaattacaa gtggatggac atttggagcc ggtgccgctc tacaaattcc gtttgctatg   2700
caaatggcgt acagattcaa cggaatcgga gtaacccaga acgtcttgta cgagaaccag   2760
aagctaatcg cgaaccagtt caattccgcg atcggaaaga tccaggacag tctatcttct   2820
actgcttcgg cgttgggaaa gctacaggat gtagtaaatc aaaacgcgca ggcgctaaac   2880
accttggtca gcaactatc ctctaacttc ggacgcgatct cgtccgtcct aaacgacatc   2940
ttatccagac tagataaggt cgaagcggag gtccagatcg atagactaat cactggaaga   3000
ttgcagtccc tacagaccta cgtaacacag caactaatta gagcggcgga gattagagcc   3060
tctgctaatc tagctgcgac caagatgtcc gaatgtgtct tgggacaatc caagagagtg   3120
gacttctgcg gaaagggata ccacctaatg tctttccac aatctgcgcc gcatggtgtc   3180
gtattcctac atgtaacata tgtgccggcg caagaaaaga acttcacaac agctccagcg   3240
atctgccatg atggaaaagc tcatttcccg agagagggag tctttgtctc taacggaact   3300
cattggttcg tcacccagag aaacttctac gagccgcaga tcatccacac cgacaacaca   3360
ttcgtctcgg gaaactgcga cgtggtcatc ggaatcgtaa acaataccgt ctacgatccg   3420
ttgcagccgg aactagactc cttcaaagaa gagttggaca gtacttcaa gaaccacacc   3480
tctccggatg tggacttggg agatatctct ggaatcaacg cgtccgtcgt caacatccag   3540
aaagaaatcg atagattgaa cgaggtcgcg aagaacttga cgagtccct aatcgaccta   3600
caagagctag gaaaatacga gcagtacatc aagtggccg                           3639

SEQ ID NO: 17          moltype = DNA   length = 3639
FEATURE                Location/Qualifiers
source                 1..3639
                       mol_type = other DNA
                       organism = synthetic construct SEQUENCE: 17
atgttcgtgt tcctagtcct actaccgcta gtctcttctc agtgtgtaaa cctaacaacg     60
agaacacaac taccaccggc gtacaccaat tctttcacaa gaggagtata ttacccggac    120
aaggtgttca gatcctccgt actacattct acacaggacc tattcctacc gttcttctct    180
```

-continued

```
aacgtaacat ggttccacgc gatccatgtc tctggaacaa acggaacgaa gagattcgat  240
aacccggtct tgccgttcaa cgatggtgta tactttgcgt ccaccgagaa gtccaacatc  300
atcagaggat ggatcttcgg aaccaccttg gattctaaga cccagtcctt gctaatcgtc  360
aacaacgcga ccaacgtcgt catcaaagtc tgcgaattcc agttctgtaa cgacccgttc  420
ttgggagtct actaccacaa gaacaacaag tcctggacta aatccgagtt cagagtctac  480
tcttccgcga acaactgcac cttcgaatat gtatctcagc cgttcctaat ggacctagag  540
ggaaagcagg gaaacttcaa gaacctaaga gagttcgtat tcaagaacat cgacggatac  600
ttcaagatct actccaagca cactccgatc aacctagtta gagatctacc gcaaggattc  660
tctgcgctag aaccgttagt agatttgccg atcggaatca acatcaccag attccagaca  720
ctactagcgc tacacagatc ttacctaacg ccgggagatt cttcttctgg atggactgct  780
ggtgctgcgg cttattatgt aggataccta cagccgagaa ccttcctatt gaagtacaac  840
gaaaacggaa ccatcaccga tgccgtagat tgtgctctag atccgctatc cgaaacgaag  900
tgcaccctaa agtctttcac cgtcgagaag ggaatctacc agacctccaa ctttagagta  960
cagccgaccg aatccatcgt cagatttccg aacatcacga acctatgtcc gttcggagaa 1020
gtgttcaacg cgacaagatt tgcgtctgtc tatgcgtgga acagaaaaag aatcagtaac 1080
tgcgtcgcgg actactccgt cctatacaac tctgcctctt tctccacgtt caaatgctac 1140
ggtgtatctc cgacaaagct aaacgatcta tgcttcacca acgtctacgc ggactccttc 1200
gtaatcagag gagatgaagt tagacagatt gcgccgggac aaactggaaa gatcgcggat 1260
tataactaca agctaccgga cgacttcacc ggatgtgtaa ttgcgtggaa ttcgaacaac 1320
ctagactcca aagtcggagg aaaactacaa cacttgtaca gactattcag aaagtccaac 1380
ctaaagccgt tcgagagaga catctccacc gaaatctatc aggctggatc tacaccgtgt 1440
aatggtgtcg aaggattcaa ctgctacttc ccgctacagt cttacggatt tcaaccgaca 1500
aacggtgtag gatatcagcc gtacagagtc gtcgtactat ccttcgaact actacatgct 1560
ccggcgacag tatgtggacc gaaaaagtct accaacctag tcaagaacaa atgcgtcaac 1620
tttaacttca acggactaac cggaaccggt gtcctaaccg aatctaacaa gaagtttcta 1680
ccgttccagc agttcggaag agatatcgcg gatacaacag acgctgtcag agatccgtaa 1740
accttggaga tcctagatat cacaccgtgt tctttcggtg gtgtctctgt aattactccg 1800
ggaacgaaca cctccaatca agtagcggta ctataccagg acgtgaactg tacagaagta 1860
ccggtagcta ttcacgcgga tcaactaaca ccaacttgga gagtgtactc caccggatct 1920
aacgtattcc aaacaagagc gggatgtcta atcggagcgg aacacgtaaa caactcctac 1980
gaatgtgata tcccgattgg agcgggaatc tgtgcgtctt accaaacaca aacaaactct 2040
ccgagaagag cgagatctgt agcctctcaa tctattatcg cctacaccat gtccttggga 2100
gccgaaaatt ctgtcgcgta ctccaacaat tctatcgcga tcccgacaaa cttcaccatc 2160
tctgtaacaa ccgagatcct accggtgtct atgaccaaga catctgtcga ttgcaccatg 2220
tacatctgcg gagattccac cgagtgctcc aacctactac tacagtacgg atctttctgt 2280
acccagctaa acagagcgtt gactggaatc gctgtagagc aggataagaa cactcaagag 2340
gtattcgcgc aagtcaagca gatctataag actccgccga tcaaggactt cggaggtttc 2400
aacttctctc agatcttgcc ggatccgtcc aaaccgtcta agagatcttt catcgaggac 2460
ctactattca caaagtcac cctagctgac gcgggattca tcaaacaata cggagattgc 2520
ttgggagaca ttgcggcgag agatctaatt tgcgcgcaga gtttaacggg attgacagta 2580
ctaccgccgc tactaaccga tgagatgatt gcgcagtaca cgtctgctct attggcggga 2640
acaattacaa gtggatggac atttggagcc ggtgccgctc tacaaattcc gtttgctatg 2700
caaatggcag acagattcaa cggaatcgga gtaaccaaga acgtcttgta cgagaaccag 2760
aagctaatcg cgaaccagtt caattccgcg atcggaaaga tccaggacag tctatcttct 2820
actgcttcgg cgttgggaaa gctacaggat gtagtaaatc aaaacgcgca ggcgctaaac 2880
accttggtca agcaactatc ctctaacttc ggagcgatct cgtccgtcct aaacgacatc 2940
ttatccagac tagatccacc ggaagcggag gtccagatcg atagactaat cactggaaga 3000
ttgcagtccc tacagaccta cgtaacacag caactaatta gagcggcgga gattagagcc 3060
tctgctaatc tagctgcgac caagatgtcc gaatgtgtct ggggacaatc caagagagtg 3120
gacttctgcg gaaagggata ccacctaatg tctttcccac aatctgcgcc gcatggtgtc 3180
gtattcctac atgtaacata tgtgccggcg caagaaaaga acttcacaac agctccagcg 3240
atctgccatg atggaaaagc tcatttcccg agagagggag tctttgtctc taacggaact 3300
cattggttcg tcacccagag aaacttctac gagccgcaga tcatcaccac cgacaacaca 3360
ttcgtctcgg gaaactgcga cgtggtcatc ggaatcgtaa acaataccgt ctacgatccg 3420
ttgcagccgg aactagactc cttcaaagaa gagttggaca agtacttcaa gaaccacacc 3480
tctccggatg tggacttggg agatatctct ggaatcaacg cgtccgtcgt caacatccag 3540
aaagaaatcg atagattgaa cgaggtcgcg aagaacttga acgagtccct aatcgaccta 3600
caagagctag gaaaatacga gcagtacatc aagtggccg                         3639
```

```
SEQ ID NO: 18          moltype = AA  length = 1213
FEATURE                Location/Qualifiers
source                 1..1213
                       mol_type = protein
                       organism = synthetic construct
SEQUENCE: 18
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV 120
NNATNVVIKV CEFQFCNDPF LGVYYHKNNK SWMESEFRVY SSANNCTFEY VSQPFLMDLE 180
GKQGNFKNLR EFVFKNIDGY FKIYSKHTPI NLVRDLPQGF SALEPLVDLP IGINITRFQT 240
LLALHRSYLT PGDSSSGWTA GAAAYYVGYL QPRTFLLKYN ENGTITDAVD CALDPLSETK 300
CTLKSFTVEK GIYQTSNFRV QPTESIVRFP NITNLCPFGE VFNATRFASV YAWNRKRISN 360
CVADYSVLYN SASFSTFKCY GVSPTKLNDL CFTNVYADSF VIRGDEVRQI APGQTGTIAD 420
YNYKLPDDFT GCVIAWNSNN LDSKVGGNYN YLYRLFRKSN LKPFERDIST EIYQAGSTPC 480
NGVKGFNCYF PLQSYGFQPT YGVGYQPYRV VVLSFELLHA PATVCGPKKS TNLVKNKCVN 540
FNFNGLTGTG VLTESNKKFL PFQQFGRDIA DTTDAVRDPQ TLEILDITPC SFGGVSVITP 600
GTNTSNQVAV LYQDVNCTEV PVAIHADQLT PTWRVYSTGS NVFQTRAGCL IGAEHVNNSY 660
ECDIPIGAGI CASYQTQTNS PRRARSVASQ SIIAYTMSLG AENSVAYSNN SIAIPTNFTI 720
SVTTEILPVS MTKTSVDCTM YICGDSTECS NLLLQYGSFC TQLNRALTGI AVEQDKNTQE 780
VFAQVKQIYK TPPIKDFGGF NFSQILPDPS KPSKRSFIED LLFNKVTLAD AGFIKQYGDC 840
```

```
LGDIAARDLI CAQKFNGLTV LPPLLTDEMI AQYTSALLAG TITSGWTFGA GAALQIPFAM   900
QMAYRFNGIG VTQNVLYENQ KLIANQFNSA IGKIQDSLSS TASALGKLQD VVNQNAQALN   960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWP                                                     1213

SEQ ID NO: 19              moltype = AA   length = 1213
FEATURE                    Location/Qualifiers
source                     1..1213
                           mol_type = protein
                           organism = synthetic construct
SEQUENCE: 19
MFVFLVLLPL VSSQCVNLTT RTQLPPAYTN SFTRGVYYPD KVFRSSVLHS TQDLFLPFFS   60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGTIAD  420
YNYKLPDDFT GCVIAWNSNN LDSKVGGNYN YLYRLFRKSN LKPFERDIST EIYQAGSTPC  480
NGVKGFNCYF PLQSYGFQPT YGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDPPEAE VQIDRLITGR LQSLQTYVTQ QLIRAAEIRA 1020
SANLAATKMS ECVLGQSKRV DFCGKGYHLM SFPQSAPHGV VFLHVTYVPA QEKNFTTAPA 1080
ICHDGKAHFP REGVFVSNGT HWFVTQRNFY EPQIITTDNT FVSGNCDVVI GIVNNTVYDP 1140
LQPELDSFKE ELDKYFKNHT SPDVDLGDIS GINASVVNIQ KEIDRLNEVA KNLNESLIDL 1200
QELGKYEQYI KWP                                                    1213

SEQ ID NO: 20              moltype = AA   length = 198
FEATURE                    Location/Qualifiers
source                     1..198
                           mol_type = protein
                           organism = synthetic construct
SEQUENCE: 20
VRFPNITNLC PFGEVFNATR FASVYAWNRK RISNCVADYS VLYNSASFST FKCYGVSPTK   60
LNDLCFTNVY ADSFVIRGDE VRQIAPGQTG KIADYNYKLP DDFTGCVIAW NSNNLDSKVG  120
GNYNYLYRLF RKSNLKPFER DISTEIYQAG STPCNGVEGF NCYFPLQSYG FQPTNGVGYQ  180
PYRVVVLSFE LLHAPATV                                                198

SEQ ID NO: 21              moltype = AA   length = 194
FEATURE                    Location/Qualifiers
source                     1..194
                           mol_type = protein
                           organism = synthetic construct
SEQUENCE: 21
NITNLCPFGE VFNATRFASV YAWNRKRISN CVADYSVLYN SASFSTFKCY GVSPTKLNDL   60
CFTNVYADSF VIRGDEVRQI APGQTGKIAD YNYKLPDDFT GCVIAWNSNN LDSKVGGNYN  120
YLYRLFRKSN LKPFERDIST EIYQAGSTPC NGVEGFNCYF PLQSYGFQPT NGVGYQPYRV  180
VVLSFELLHA PATV                                                    194

SEQ ID NO: 22              moltype = DNA   length = 642
FEATURE                    Location/Qualifiers
source                     1..642
                           mol_type = other DNA
                           organism = synthetic construct
SEQUENCE: 22
gttagatttc ctaatattac aaacttgtgc ccttttggtg aagttttaa cgccaccaga   60
tttgcatctg tttatgcttg gaacaggaag agaatcagca actgtgttgc tgattattct  120
gtcctatata attccgcatc attttccact tttaagtgtt atggagtgtc tcctactaaa  180
ttaaatgatc tctgctttac taatgtctat gcagattcat ttgtaattag aggtgatgaa  240
gtcagacaaa tcgctccagg gcaaactgga aagattgtt attataatta taaattacca  300
gatgatttta caggctgcgt tatagcttgg aattctaaca atcttgattc taaggttggt  360
ggtaattata attacctgta tagattgttt aggaagtcta atctcaaacc ttttgagaga  420
gatatttcaa ctgaaatcta tcaggccggt agcacacctt gtaatggtgt tgaaggtttt  480
aattgttact ttcctttaca atcatatggt ttccaaccca ctaatggtgt tggttaccaa  540
ccatacagag tagtagtact ttcttttgaa cttcacatg caccagcaac tgtttgtgga  600
cctaaaaagt ctactaattg gggttaaaac aaatgtgtca at                     642

SEQ ID NO: 23              moltype = DNA   length = 630
FEATURE                    Location/Qualifiers
source                     1..630
```

```
                              mol_type = other DNA
                              organism = synthetic construct
SEQUENCE: 23
aatattacaa acttgtgccc ttttggtgaa gtttttaacg ccaccagatt tgcatctgtt   60
tatgcttgga acaggaagag aatcagcaac tgtgttgctg attattctgt cctatataat  120
tccgcatcat tttccacttt taagtgttat ggagtgtctc ctactaaatt aaatgatctc  180
tgctttacta atgtctatgc agattcattt gtaattagag gtgatgaagt cagacaaatc  240
gctccagggc aaactggaaa gattgctgat tataattata aattaccaga tgattttaca  300
ggctgcgtta tagcttggaa ttctaacaat cttgattcta aggttggtgg taattataat  360
tacctgtata gattgtttag gaagtctaat ctcaaacctt ttgagagaga tatttcaact  420
gaaatctatc aggccggtag cacaccttgt aatggtgttg aaggttttaa ttgttacttt  480
cctttacaat catatggttt ccaacccact aatggtgttg gttaccaacc atacagagta  540
gtagtacttt cttttgaact tctacatgca ccagcaactg tttgtggacc taaaaagtct  600
actaatttgg ttaaaaacaa atgtgtcaat                                   630

SEQ ID NO: 24          moltype = DNA   length = 594
FEATURE                Location/Qualifiers
source                 1..594
                       mol_type = other DNA
                       organism = synthetic construct
SEQUENCE: 24
gtcagatttc cgaacatcac gaacctatgt ccgttcggag aagtgttcaa cgcgacaaga   60
tttgcgtctg tctatgcgtg gaacagaaaa agaatcagta actgcgtcgc ggactactcc  120
gtcctataca actctgcctc tttctccacg ttcaaatgct acggtgtatc tccgacaaag  180
ctaaacgatc tatgcttcac caacgtctac gcggactcct cgtaatcag aggagatgaa   240
gttagacaga ttgcgccggg acaaactgga aagatcgcgg attataacta caagctaccg  300
gacgacttca ccggatgtgt aattgcgtgg aattcgaaca acctagactc caaagtcgga  360
ggaaactaca actacttgta cagactattc agaaagtcca acctaaagcc gttcgagaga  420
gacatctcca ccgaaatcta tcaggctgga tctacaccgt gtaatggtgt cgaaggattc  480
aactgctact ccccgctaca gtcttacgga tttcaaccga caaacggtgt aggatatcag  540
ccgtacagag tcgtcgtact atccttcgaa ctactacatg ctccggcgac agta        594

SEQ ID NO: 25          moltype = DNA   length = 582
FEATURE                Location/Qualifiers
source                 1..582
                       mol_type = other DNA
                       organism = synthetic construct
SEQUENCE: 25
aacatcacga acctatgtcc gttcggagaa gtgttcaacg cgacaagatt tgcgtctgtc   60
tatgcgtgga acagaaaaag aatcagtaac tgcgtcgcgg actactccgt cctatacaac  120
tctgcctctt tctccacgtt caaatgctac ggtgtatctc cgacaaagct aaacgatcta  180
tgcttcacca acgtctacgc ggactccttc gtaatcagag gagatgaagt tagacagatt  240
gcgccgggac aaactggaaa gatcgcggat tataacaca agctaccgga cgacttcacc    300
ggatgtgtaa ttgcgtggaa ttcgaacaac ctagactcca aagtcggagg aaactacaac  360
tacttgtaca gactattcag aaagtccaac ctaaagccgt cgagagaga catctccacc    420
gaaatctatc aggctggatc tacaccgtgt aatggtgtcg aaggattcaa ctgctacttc  480
ccgctacagt cttacggatt tcaaccgaca aacggtgtag gatatcagcc gtacagagtc  540
gtcgtactat ccttcgaact actacatgct ccggcgacag ta                     582

SEQ ID NO: 26          moltype = AA   length = 20
FEATURE                Location/Qualifiers
source                 1..20
                       mol_type = protein
                       organism = synthetic construct
SEQUENCE: 26
YQPYRVVVLS FELLHAPATV                                               20

SEQ ID NO: 27          moltype = DNA   length = 60
FEATURE                Location/Qualifiers
source                 1..60
                       mol_type = other DNA
                       organism = synthetic construct
SEQUENCE: 27
taccaaccat acagagtagt agtactttct tttgaacttc tacatgcacc agcaactgtt   60

SEQ ID NO: 28          moltype = DNA   length = 60
FEATURE                Location/Qualifiers
source                 1..60
                       mol_type = other DNA
                       organism = synthetic construct
SEQUENCE: 28
tatcagccgt acagagtcgt cgtactatcc ttcgaactac tacatgctcc ggcgacagta   60

SEQ ID NO: 29          moltype = AA   length = 18
FEATURE                Location/Qualifiers
source                 1..18
                       mol_type = protein
                       organism = synthetic construct
SEQUENCE: 29
```

```
YQAGSTPCNG VEGFNCYF                                                18

SEQ ID NO: 30              moltype = DNA   length = 54
FEATURE                   Location/Qualifiers
source                    1..54
                          mol_type = other DNA
                          organism = synthetic construct
SEQUENCE: 30
tatcaggccg gtagcacacc ttgtaatggt gttgaaggtt ttaattgtta cttt        54

SEQ ID NO: 31              moltype = DNA   length = 54
FEATURE                   Location/Qualifiers
source                    1..54
                          mol_type = other DNA
                          organism = synthetic construct
SEQUENCE: 31
tatcaggctg gatctacacc gtgtaatggt gtcgaaggat tcaactgcta cttc        54

SEQ ID NO: 32              moltype = AA   length = 198
FEATURE                   Location/Qualifiers
source                    1..198
                          mol_type = protein
                          organism = synthetic construct
SEQUENCE: 32
VRFPNITNLC PFGEVFNATR FASVYAWNRK RISNCVADYS VLYNSASFST FKCYGVSPTK   60
LNDLCFTNVY ADSFVIRGDE VRQIAPGQTG TIADYNYKLP DDFTGCVIAW NSNNLDSKVG   120
GNYNYLYRLF RKSNLKPFER DISTEIYQAG STPCNGVKGF NCYFPLQSYG FQPTYGVGYQ   180
PYRVVVLSFE LLHAPATV                                                198

SEQ ID NO: 33              moltype = AA   length = 194
FEATURE                   Location/Qualifiers
source                    1..194
                          mol_type = protein
                          organism = synthetic construct
SEQUENCE: 33
NITNLCPFGE VFNATRFASV YAWNRKRISN CVADYSVLYN SASFSTFKCY GVSPTKLNDL   60
CFTNVYADSF VIRGDEVRQI APGQTGTIAD YNYKLPDDFT GCVIAWNSNN LDSKVGGNYN   120
YLYRLFRKSN LKPFERDIST EIYQAGSTPC NGVKGFNCYF PLQSYGFQPT YGVGYQPYRV   180
VVLSFELLHA PATV                                                    194

SEQ ID NO: 34              moltype = AA   length = 48
FEATURE                   Location/Qualifiers
source                    1..48
                          mol_type = protein
                          organism = synthetic construct
REPEAT                    1..48
                          note = 2, 3, 4, 5, 6, 7, 8, 9, 10, or more than 10 REPEATS
SEQUENCE: 34
YQPYRVVVLS FELLHAPATV GPGPGYQAGS TPCNGVEGFN CYFGPGPG              48

SEQ ID NO: 35              moltype = DNA   length = 144
FEATURE                   Location/Qualifiers
source                    1..144
                          mol_type = other DNA
                          organism = synthetic construct
repeat_region             1..144
                          note = 2, 3, 4, 5, 6, 7, 8, 9, 10, or more than 10 REPEATS
SEQUENCE: 35
taccaaccat acagagtagt agtactttct tttgaacttc tacatgcacc agcaactgtt   60
ggtcctggac ccggttatca ggccggtagc acaccttgta atggtgttga aggttttaat   120
tgttactttg gtcctggacc cggt                                        144

SEQ ID NO: 36              moltype = AA   length = 240
FEATURE                   Location/Qualifiers
source                    1..240
                          mol_type = protein
                          organism = synthetic construct
SEQUENCE: 36
YQPYRVVVLS FELLHAPATV GPGPGYQAGS TPCNGVEGFN CYFGPGPGYQ PYRVVVLSFE   60
LLHAPATVGP GPGYQAGSTP CNGVEGFNCY FGPGPGYQPY RVVVLSFELL HAPATVGPGP   120
GYQAGSTPCN GVEGFNCYFG PGPGYQPYRV VVLSFELLHA PATVGPGPGY QAGSTPCNGV   180
EGFNCYFGPG PGYQPYRVVV LSFELLHAPA TVGPGPGYQA GSTPCNGVEG FNCYFGPGPG   240

SEQ ID NO: 37              moltype = DNA   length = 720
FEATURE                   Location/Qualifiers
source                    1..720
                          mol_type = other DNA
                          organism = synthetic construct
SEQUENCE: 37
```

```
tatcagccgt acagagtcgt cgtactatcc ttcgaactac tacatgctcc ggcgacagta   60
ggtcctggac ccggttatca ggctggatct acaccgtgta atggtgtcga aggattcaac  120
tgctacttcg gtcctggacc cggttatcag ccgtacagag tcgtcgtact atccttcgaa  180
ctactacatg ctccggcgac agtaggtcct ggacccggtt atcaggctgg atctacaccg  240
tgtaatggtg tcgaaggatt caactgctac ttcggtcctac gacccggtta tcagccgtac  300
agagtcgtcg tactatcctt cgaactacta catgctccgg cgacagtagg tcctggaccc  360
ggttatcagg ctggatctac accgtgtaat ggtgtcgaag gattcaactg ctacttcggt  420
cctggacccg gttatcagcc gtacagagtc gtcgtactat ccttcgaact actacatgct  480
ccggcgacag taggtcctgg acccggttat caggctggat ctacaccgtg taatggtgtc  540
gaaggattca actgctactt cggtcctgga cccggttatc agccgtacag agtcgtcgta  600
ctatccttcg aactactaca tgctccggcg acagtaggtc ctggacccgg ttatcaggct  660
ggatctacac cgtgtaatgg tgtcgaagga ttcaactgct acttcggtcc tggacccggt  720
```

SEQ ID NO: 38               moltype = AA   length = 48
FEATURE                     Location/Qualifiers
source                      1..48
                            mol_type = protein
                            organism = synthetic construct
REPEAT                      1..48
                            note = 2, 3, 4, 5, 6, 7, 8, 9, 10, or more than 10 REPEATS
SEQUENCE: 38
YQPYRVVVLS FELLHAPATV GPGPGYQAGS TPCNGVKGFN CYFGPGPG                  48

SEQ ID NO: 39               moltype = AA   length = 240
FEATURE                     Location/Qualifiers
source                      1..240
                            mol_type = protein
                            organism = synthetic construct
SEQUENCE: 39
YQPYRVVVLS FELLHAPATV GPGPGYQAGS TPCNGVKGFN CYFGPGPGYQ PYRVVVLSFE    60
LLHAPATVGP GPGYQAGSTP CNGVKGFNCY FGPGPGYQPY RVVVLSFELL HAPATVGPGP   120
GYQAGSTPCN GVKGFNCYFG PGPGYQPYRV VVLSFELLHA PATVGPGPGY QAGSTPCNGV   180
KGFNCYFGPG PGYQPYRVVV LSFELLHAPA TVGPGPGYQA GSTPCNGVKG FNCYFGPGPG   240

SEQ ID NO: 40               moltype = AA   length = 75
FEATURE                     Location/Qualifiers
source                      1..75
                            mol_type = protein
                            organism = synthetic construct
SEQUENCE: 40
MYSFVSEETG TLIVNSVLLF LAFVVFLLVT LAILTALRLC AYCCNIVNVS LVKPSFYVYS    60
RVKNLNSSRV PDLLV                                                     75

SEQ ID NO: 41               moltype = DNA   length = 225
FEATURE                     Location/Qualifiers
source                      1..225
                            mol_type = other DNA
                            organism = synthetic construct
SEQUENCE: 41
atgtactcat tcgtttcgga agagacaggt acgttaatag ttaatagcgt acttcttttt    60
cttgctttcg tggtattctt gctagttaca ctagccatcc ttactgcgct tcgattgtgt   120
gcgtactgct gcaatattgt taacgtgagt cttgtaaaac cttcttttta cgtttactct   180
cgtgttaaaa atctgaattc ttctagagtt cctgatcttc tggtc                   225

SEQ ID NO: 42               moltype = DNA   length = 225
FEATURE                     Location/Qualifiers
source                      1..225
                            mol_type = other DNA
                            organism = synthetic construct
SEQUENCE: 42
atgtactcct tcgtgtccga agaaaccgga accttgatcg tcaactccgt cctactattc    60
ctagcgttcg tcgtgttcct actagtaacc ctagctatcc taaccgcgct aagactatgt   120
gcgtactgct gcaacatcgt caacgtgtcc ctagtgaagc cgtccttcta cgtctactcc   180
agagtcaaga acctaaactc ctctagagtc ccggacctac tagtt                   225

SEQ ID NO: 43               moltype = AA   length = 222
FEATURE                     Location/Qualifiers
source                      1..222
                            mol_type = protein
                            organism = synthetic construct
SEQUENCE: 43
MADSNGTITV EELKKLLEQW NLVIGFLFLT WICLLQFAYA NRNRFLYIIK LIFLWLLWPV    60
TLACFVLAAV YRINWITGGI AIAMACLVGL MWLSYFIASF RLFARTRSMW SFNPETNILL   120
NVPLHGTILT RPLLESELVI GAVILRGHLR IAGHHLGRCD IKDLPKEITV ATSRTLSYYK   180
LGASQRVAGD SGFAAYSRYR IGNYKLNTDH SSSSDNIALL VQ                      222

SEQ ID NO: 44               moltype = DNA   length = 666
FEATURE                     Location/Qualifiers
source                      1..666

-continued

```
                        mol_type = other DNA
                        organism = synthetic construct
SEQUENCE: 44
atggcagatt ccaacggtac tattaccgtt gaagagctta aaaagctcct tgaacaatgg     60
aacctagtaa taggtttcct attccttaca tggatttgtc ttctacaatt tgcctatgcc    120
aacaggaata ggtttttgta tataattaag ttaattttcc tctggctgtt atggccagta    180
actttagctt gttttgtgct tgctgctgtt tacagaataa aattggatcac cggtggaatt    240
gctatcgcaa tggcttgtct tgtaggcttg atgtggctca gctacttcat tgcttctttc    300
agactgtttg cgcgtacgcg ttccatgtgg tcattcaatc cagaaactaa cattcttctc    360
aacgtgccac tccatggcac tattctgacc agaccgcttc tagaaagtga actcgtaatc    420
ggagctgtga tccttcgtgg acatcttcgt attgctggac accatctagg acgctgtgac    480
atcaaggacc tgcctaaaga aatcactgtt gctacatcac gaacgctttc ttattacaaa    540
ttgggagctt cgcagcgtgt agcaggtgac tcaggttttg ctgcatacag tcgctacagg    600
attggcaact ataaattaaa cacagaccat tccagtagca gtgacaatat tgctttgctt    660
gtacag                                                                666

SEQ ID NO: 45          moltype = DNA   length = 666
FEATURE                Location/Qualifiers
source                 1..666
                       mol_type = other DNA
                       organism = synthetic construct
SEQUENCE: 45
atggcggatt ctaacggaac catcaccgtc gaagagttga agaagctact agagcagtgg     60
aacctagtca tcggattcct attcctaacc tggatctgcc tactacagtt cgcgtacgcg    120
aacaggaaca gattcttgta catcatcaag ctaatcttcc tatggctact atggccggtc    180
accttggcct gcttcgttct agctgcggtc tacagaatca attggatcac aggtggaatc    240
gcgatcgcta tggcttgtct agtaggacta atgtggctat cctacttcat cgcctccttc    300
agactattcg cgagaaccag atctatgtgg tcgttcaacc cggagacgaa catcctattg    360
aacgtaccgc tacatggaac catcctaacc agaccgctat tggaatccga attggttatc    420
ggagcggtca tcctaagagg acatctaaga attgcgggac accacctagg aagatgtgac    480
atcaaggacc taccgaagga gatcaccgta gcgacctcta gaaccctatc gtactataag    540
ttgggagcct ctcaaagagt cgcgggagat tctggatttg cggcgtattc tagatacaga    600
atcgggaact acaagctaaa caccgaccac tcctccagtt ccgataatat cgctctacta    660
gtccag                                                                666

SEQ ID NO: 46          moltype = DNA   length = 4959
FEATURE                Location/Qualifiers
source                 1..4959
                       mol_type = other DNA
                       organism = synthetic construct
SEQUENCE: 46
aaaaattgaa aataaataca aaggttcttg agggttgtgt taaattgaaa gcgagaaata     60
atcataagcc accatgttcg tgttcctagt cctactaccg ctagtctctt ctcagtgtgt    120
aaacctaaca acgagaacac aactaccacc ggcgtacacc aattctttca caagaggagt    180
atattacccg gacaaggtgt tcagatcctc cgtactacat tctacacagg acctattcct    240
accgttcttc tctaacgtaa catggttcca cgcgatccat gtctctggaa caaacggaac    300
gaagagattc gataacccgg tcttgccgtt caacgatggt gtatactttg cgtccaccga    360
gaagtccaac atcatcagag gatggatctt cggaaccacc ttggattcta agacccagtc    420
cttgctaatc gtcaacaacg cgaccaacgt cgtcatcaaa gtctcgcgaat tccagttctg    480
taacgacccg ttcttgggag tctactacca caagaacaac aagtcctgga tggaatccga    540
gttcagagtc tactcttccg cgaacaactg caccttcgaa tatgtatctc agccgttcct    600
aatggaccta gagggaaagc agggaaactt caagaaccta agagagttcg tattcaagaa    660
catcgacgga tacttcaaga tctactccaa gcacactccg atcaacctag ttagagatct    720
accgcaagga ttctctgcgc tagaaccgtt agtagatttg ccgatcggaa tcaacatcac    780
cagattccag acactactag cgctacacag atcttaccta acgccgggag attcttcttc    840
tggatggact gctggtgctg cggcttatta tgtaggatac ctacagccga gaaccttcct    900
attgaagtac aacgaaaacg gaaccatcac cgatgccgta gattgtgctc tagatccgct    960
atccgaaacg aagtgcaccc taaagtcttt caccgtcgag aagggaatct accagacctc   1020
caactttaga gtacagccga ccgaatccat cgtcagattt cgtgaacatca cggaacctatg   1080
tccgttcgga gaagtgttca acgcgacaag atttgcgtct gtctatgcgt ggaacagaaa   1140
aagaatcagt aactgcgtcg cggactactc cgtcctatac aactctgcct ctttctccac   1200
gttcaaatgc tacggtgtat ctccgacaaa gctaaacgat ctatgcttca ccaacgtcta   1260
cgcggactcc ttcgtaatca gaggagatga agttagacag attgcgccgg gacaaactgg   1320
aaagatcgcg gattataact acaagctacc ggacgacttc accggatgtg taattgcggg   1380
gaattcgaac aacctagact ccaaagtcgg aggaaactac aactacttgt acagactatt   1440
cagaaagtcc aacctaaagc cgttcgagag agacatctcc accgaaatct atcaggctgg   1500
atctacaccg tgtaatggtg tcgaaggatt caactgctac ttcccgctac agtcttacgg   1560
atttcaaccg acaaacggtg taggatatca gccgtacaga gtcgtcgtac tatccttcga   1620
actactacat gctccggccga cagtatgtgg accgaaaaag tctaccaacc tagtcaagaa   1680
caaatgcgtc aactttaact tcaacggact aaccggaacc ggtgtcctaa ccgaatctaa   1740
caagaagttt ctaccgttcc agcagttcgg aagagatatc gcggatacaa cagacgctgt   1800
cagagatccg caaaccttgg agatcctaga tatcacaccg tgttctttcg gtggtgtctc   1860
tgtaattact ccgggaacga acacctccaa tcaagtagcg gtactatacc aggacgtgaa   1920
ctgtacagaa gtaccggtag ctattcacgc ggatcaacta acaccaactt ggagagtgta   1980
ctccaccgga tctaacgtat tccaaacaag agcggatgt ctaatcggag cggaacacgt   2040
aaacaactcc tacgaatgtg atatcccgat tggagcggga atctgtcgt cttaccaaac   2100
acaaacaaac tctccgagaa gagcgagatc tgtagcctct caatctatta tcgcctacac   2160
catgtccttg ggagccgaaa attctgtcgc gtactccaac aattctatcg cgatcccgac   2220
aaacttcacc atctctgtaa caaccgagat cctaccggtg tctatgacca agacatctgt   2280
```

```
cgattgcacc atgtacatct gcggagattc caccgagtgc tccaacctac tactacagta  2340
cggatctttc tgtacccagc taaacagagc gttgactgga atcgctgtag agcaggataa  2400
gaacactcaa gaggtattcg cgcaagtcaa gcagatctat aagactccgc cgatcaagga  2460
cttcggaggt ttcaacttct ctcagatctt gccggatccg tccaaaccgt ctaagagatc  2520
tttcatcgag gacctactat tcaacaaagt caccctagct gacgcgggat tcatcaaaca  2580
atacggagat tgcttgggag acattgcggc gagagatcta atttgcgcgc agaagtttaa  2640
cggattgaca gtactaccgc cgctactaac cgatgagatg attgcgcagt acacgtctgc  2700
tctattggcg ggaacaatta caagtggatg gacatttgga gccggtgccg ctctacaaat  2760
tccgttttgct atgcaaatgg cgtacagatt caacggaatc ggagtaaccc agaacgtctt  2820
gtacgagaac cagaagctaa tcgcgaacca gttcaattcc gcgatcggaa agatccagga  2880
cagtctatct tctactgctt cggcgttggg aaagctacag gatgtagtaa atcaaaacgc  2940
gcaggcgcta aacaccttgg tcaagcaact atcctctaac ttcggagcga tctcgtccgt  3000
cctaaacgac atcttatcca gactagataa ggtcgaagcg gaggtccaga tcgatagact  3060
aatcactgga agattgcagt ccctacagac ctacgtaaca cagcaactaa ttagagcggc  3120
ggagattaga gcctctgcta atctagctgc gaccaagatg tccgaatgtg tcttgggaca  3180
atccaagaga gtggacttct gcggaaaggg ataccaccta atgtctttcc cacaatctgc  3240
gccgcatggt gtcgtattcc tacatgtaac atatgtgccg gcgcaagaaa agaacttcac  3300
aacagctcca gcgatctgcc atgatggaaa agctcatttc ccgagagagg gagtctttgt  3360
ctctaacgga actcattggt tcgtcaccca gagaaacttc tacgagccgc agatcatcac  3420
caccgacaac acattcgtct cgggaaactg cgacgtggtc atcggaatcg taaacaatac  3480
cgtctacgat ccgttgcagc cggaactaga ctccttcaaa gaagagttgg acaagtactt  3540
caagaaccac acctctccgg atgtggactt gggagatatc tctggaatca acgcgtccgt  3600
cgtcaacatc cagaaagaaa tcgatagatt gaacgaggtc gcgaagaact tgaacgagtc  3660
cctaatcgac ctacaagagc taggaaaata cgagcagtac atcaagtggc cgtggtacat  3720
ctggctagga ttcattgctg gactaattgc gatcgtcatg gtcaccatca tgctatgctg  3780
tatgacctcc tgttgctcct gtctaaaggg atgttgttcc tgcggatcct gttgcaagtt  3840
cgatgaagat gatagtgaac cggtcctaaa gggtgtcaag ctacactaca cagagccaga  3900
ggcttaataa tttttatctt tcattttgtt tttttctatg ctataagcca ccatgctactc  3960
cttcgtgtcc gaagaaaccg gaaccttgat cgtcaactcc gtcctactat tcctagcgtt  4020
cgtcgtgttc ctactagtaa ccctagctat cctaaccgcg ctaagactat gtgcgtactg  4080
ctgcaacatc gtcaacgtgt ccctagtgaa gccgtccttc tacgtctact ccagagtcaa  4140
gaacctaaac tcctctagag tcccggacct actagttgag ccagaggctt aataaataaa  4200
aattattaag cctctggctc ctggactagt agagcgatat tatcggaact ggaggagtgg  4260
tcggtgttta gcttgtagtt cccgattctg tatctagaat acgccgcaaa tccagaatct  4320
cccgcgactc tttgagaggc tcccaactta tagtacgata gggttctaga ggtcgctacg  4380
gtgatctcct tcggtaggtc cttgatgtca catcttccta ggtggtgtcc cgcaattctt  4440
agatgtcctc ttaggatgac cgctccgata accaattcgg attccaatag cggtctggtt  4500
aggatggttc catgtagcgg tacgttcaat aggatgttcg tctccgggtt gaacgaccac  4560
atagatctgg ttctcgcgaa tagtctgaag gaggcgatga agtaggatag ccacattagt  4620
cctactagac aagccatagc gatcgcgatt ccacctgtga tccagttgat tctgtagacc  4680
gcagctagaa cgaagcaggc caaggtgacc ggccatagta gccataggaa gattagcttg  4740
atgatgtaca agaatctgtt cctgttcgcg tacgcgaact gtagtaggca gatccaggtt  4800
aggaatagga atccgatgac taggttccac tgctctagta gcttcttcaa ctcttcgacg  4860
gtgatggttc cgttagaatc cgccatggtg gcttatgatt atttctcgct ttcaatttaa  4920
cacaaccctc aagaaccttt gtatttattt tcaattttt                         4959
```

SEQ ID NO: 47          moltype = DNA   length = 4965
FEATURE                Location/Qualifiers
source                 1..4965
                       mol_type = other DNA
                       organism = synthetic construct
SEQUENCE: 47

```
aaaaattgaa aataaataca aaggttcttg agggttgtgt taaattgaaa gcgagaaata    60
atcataaccc ggggccacca tgttcgtgtt cctagtccta ctaccgctag tctcttctca   120
gtgtgtaaac ctaacaacga gaacacaact accaccggcg tacaccaatt ctttcacaag   180
aggagtatat tacccggaca aggtgttcag atcctccgta ctacattcta cacaggacct   240
attcctaccg ttcttctcta acgtaacatg gttccacgcg atccatgtct ctggaacaaa   300
cggaacgaag agattcgata acccggtctt gccgttcaac gatggtgtat actttgcgtc   360
caccgagaag tccaacatca tcagaggatg gatcttcgga accaccttgg attctaagac   420
ccagtccttg ctaatcgtca acaacgcgac caacgtcgtc atcaaagtct gcgaattcca   480
gttctgtaac gacccgttct tgggagtcta ctaccacaag aacaacaagt cctggatgga   540
atccgagttc agagtctact cttccgcgaa caactgcacc ttcgaatatg tatctcagcc   600
gttcctaatg gacctagagg gaaagcaggg aaacttcaag aacctaagag agttcgtatt   660
caagaacatc gacggatact tcaagatcta ctccaagcac actccgatca acctagtag   720
agatctaccg caaggattct ctgcgctaga accgttagta gatttgccga tcggaatcaa   780
catcaccaga ttccagacac tactagcgct acacagatct tacctaacgc cgggagattc   840
ttcttctgga tggactgctg gtgctgcggc ttattatgta ggataccac agccgagaac   900
cttcctattg aagtacaacg aaaacggaac catcaccgat gccgtagatt gtgctctaga   960
tccgctatcc gaaacgaagt gcaccctaaa gtctttcacc gtcgagaagg gaatctacca  1020
gacctccaac tttagagtac agccgaccga atccatcgtc agatttccga acatcacgaa  1080
cctatgtccg ttcggagaag tgttcaacgc gacaagattt gcgtctgtct atgcgtggaa  1140
cagaaaaaga atcagtaact gcgtcgcgga ctactccgtc ctatacaact ctgcctcttt  1200
ctccacgttc aaatgctacg gtgtatctcc gacaaagcta aacgatctat gcttcaccaa  1260
cgtctacgcg gactccttcg taatcagagg agatgaagtt cagccggaga gccgccggaga  1320
aactggaaag atcgcggatt ataactacaa gctaccggac gacttcaccg gatgtgtaat  1380
tgcgtggaat tcgaacaacc tagactccaa agtcggagga aactacaact acttgtacag  1440
actattcaga aagtccaacc taaagccgtt cgagagagac atctccaccg aaatctatca  1500
ggctggatct acaccgtgta atggtgtcga aggattcaac tgctacttcc cgctacagtc  1560
ttacggattt caaccgacaa acggtgtagg atatcagccg tacagagtcg tcgtactatc  1620
```

```
cttcgaacta ctacatgctc cggcgacagt atgtggaccg aaaaagtcta ccaacctagt  1680
caagaacaaa tgcgtcaact ttaacttcaa cggactaacc ggaaccggtg tcctaaccga  1740
atctaacaag aagtttctac cgttccagca gttcggaaga gatatcgcgg atacaacaga  1800
cgctgtcaga gatccgcaaa ccttggagat cctagatatc acaccgtgtt ctttcggtgg  1860
tgtctctgta attactccgg gaacgaacac ctccaatcaa gtagcggtac tataccagga  1920
cgtgaactgt acagaagtac cggtagctat tcacgcggat caactaacac caacttggag  1980
agtgtactcc accggatcta acgtattcca aacaagagcg ggatgtctaa tcggagcgga  2040
acacgtaaac aactcctacg aatgtgatat cccgattgga gcgggaatct gtgcgtctta  2100
ccaaacacaa acaaactctc cgagaagagc gagatcgta gcctctcaat ctattatcgc  2160
ctacaccatg tccttgggag ccgaaaattc tgtcgcgtac tccaacaatt ctatcgcgat  2220
cccgacaaac ttcaccatct ctgtaacaac cgagatccta ccggtgtcta tgaccaagac  2280
atctgtcgat tgcaccatgt acatctgcgg agattccacc gagtgctcca acctactact  2340
acagtacgga tctttctgta cccagctaaa cagagcgttg actggaatcg ctgtagagca  2400
ggataagaac actcaagagg tattcgcgca agtcaagcag atctataaga ctccgccgat  2460
caaggacttc ggaggtttca acttctctca gatcttgccg gatccgtcca aaccgtctaa  2520
gagatctttc atcgaggacc tactattcaa caaagtcacc ctagctgacg cgggattcat  2580
caaacaatac ggagattgct tgggagacat tgcggcgaga gatctaattt gcgcgcagaa  2640
gtttaacgga ttgacagtac taccgccgct actaaccgat gagatgattg cgcagtacac  2700
gtctgctcta ttggcgggaa caattacaag tggatggaca tttggagccg gtgccgctct  2760
acaaattccg tttgctatgc aaatggcgta cagattcaac ggaatcggag taacccagaa  2820
cgtcttgtac gagaaccaga agctaatcgc gaaccagttc aattccgcga tcggaaagat  2880
ccaggacagt ctatcttcta ctgcttcggc gttgggaaag ctacaggatg tagtaaatca  2940
aaacgcgcag gcgctaaaca ccttggtcaa gcaactatcc tctaacttcg gagcgatctc  3000
gtccgtcgta aacgacatct tatccagact agataaggtc gaagcggagg tccagatcga  3060
tagactaatc actggaagat tgcagtccct acagacctac gtaacacagc aactaattag  3120
agcggcggag attagagcct ctgctaatct agctgcgacc aagatgtccg aatgtgtctt  3180
gggacaatcc aagagagtgg acttctgcgg aaagggatac cacctaatgt ctttcccaca  3240
atctgcgccg catggtgtcg tattcctaca tgtaacatat gtgccggcgc aagaaaagaa  3300
cttcacaaca gctccagcga tctgccatga tggaaaagct catttcccga gagagggagt  3360
ctttgtctct aacggaactc attggttcgt cacccagaga aacttctacg agccgcagat  3420
catcaccacc gacaacacat tcgtctcggg aaactgcgac gtggtcatcg gaatcgtaaa  3480
caataccgtc tacgatccgt tgcagccgga actagactcc ttcaaagaag agttggacaa  3540
gtacttcaag aaccacacct ctccggatgt ggacttggga gatatctctg gaatcaacgc  3600
gtccgtcgtc aacatccaga aagaaatcga tagattgaac gaggtcgcga agaacttgaa  3660
cgagtcccta atcgacctac aagagctagg aaaatacgag cagtacatca agtggccgtg  3720
gtacatctgg ctaggattca ttgctggact aattgcgatc gtcatggtca ccatcatgct  3780
atgctgtatg acctcctgtt gctcctgtct aaagggatgt tgttcctgcg gatcctgttg  3840
caagttcgat gaagatgata gtgaaccggt cctaaagggt gtcaagctac actacacaga  3900
gccagaggct taataatttt tatctttcat tttgttttt tctatgctat aagccaccat  3960
gtactccttc gtgtccgaag aaaccggaac cttgatcgtc aactccgtcc tactattcct  4020
agcgttcgtc gtgttcctac tagtaaccct agctatccta accgcgctaa gactatgtgc  4080
gtactgctgc aacatcgtca acgtgtccct agtgaagccg tccttctacg tctactccag  4140
agtcaagaac ctaaactcct ctagagtccc ggacctacta gttgagccag aggcttaata  4200
aataaaaatt attaagcctc tggctcctgg actagtagag cgatattatc ggaactggag  4260
gagtggtcgg tgtttagctt gtagttcccg attctgtatc tagaatacgc cgcaaatcca  4320
gaatctcccg cgactctttg agaggctccc aacttatagt acgatagggt tctagaggtc  4380
gctacggtga tctccttcgg taggtccttg atgtcacatc ttcctaggtg gtgtcccgca  4440
attcttagat gtcctcttag gatgaccgct ccgataacca attcggattc caatagcggt  4500
ctggttagga tggttccatg tagcggtacg ttcaatagga tgttcgtctc cgggttgaac  4560
gaccacatag atctggttct cgcgaatagt ctgaaggagg cgatgaagta ggatagccac  4620
attagtccta ctagacaagc catagcgatc gcgattccac ctgtgatcca gttgattctg  4680
tagaccgcag ctagaacgaa gcaggccaag gtgaccggcc atagtagcca taggaagatt  4740
agcttgatga tgtacaagaa tctgttcctg ttcgcgtacg cgaactgtag taggcagatc  4800
caggttagga ataggaatcc gatgactagg ttccactgct ctagtagctt cttcaactct  4860
tcgacggtga tggttccgtt agaatccgcc atggtggctt atgattattt ctcgctttca  4920
atttaacaca accctcaaga acctttgtat ttattttcaa ttttt            4965
```

```
SEQ ID NO: 48              moltype = DNA  length = 4959
FEATURE                    Location/Qualifiers
source                     1..4959
                           mol_type = other DNA
                           organism = synthetic construct
SEQUENCE: 48
aaaaattgaa aataaataca aaggttcttg agggttgtgt taaattgaaa gcgagaaata  60
atcataagcc accatgttcg tgttcctagt cctactaccg ctagtctctt ctcagtgtgt  120
aaacctaaca acgagaacac aactaccacc ggcgtacacc aattctttca caagaggagt  180
atattacccg gacaaggtgt tcagatcctc cgtactacat tctacacagg acctattcct  240
accgttcttc tctaacgtaa catggttcca cgcgatccat gtctctggaa caaacggaac  300
gaagagattc gataaccggg tcttgccgtt caacgatggt gtatactttg cgtccaccga  360
gaagtccaac atcatcagag gatgggatctt cggaaccacc ttggattcta agacccagtc  420
cttgctaatc gtcaacaacg cgaccaacgt cgtcatcaaa gtctgcgaat ccagttctg  480
taacgacccg ttcttgggag tctactacca caagaacaac aagtcctgga tggaatccga  540
gttcagagtc tactcttccg cgaacaactg caccttcgaa tatgtatctc agccgttcct  600
aatggaccta gagggaaagc agggaaactt caagaaccta gaagagttcg tattcaagaa  660
catcgacgga tacttcaaga tctactccaa gcacactccg atcaacctag ttagagatct  720
accgcaagga ttctctgcgc tagaaccgtt agtagatttg ccgatcggaa tcaacatcac  780
cagattccag acactactag cgctacacag atcttaccta acgccgggag attcttcttc  840
tggatggact gctggtgctg cggcttatta tgtaggatac ctacagccga gaaccttcct  900
attgaagtac aacgaaaacg gaaccatcac cgatgccgta gattgtgctc tagatccgct  960
```

```
atccgaaacg aagtgcaccc taaagtcttt caccgtcgag aagggaatct accagacctc  1020
caactttaga gtacagccga ccgaatccat cgtcagattt ccgaacatca cgaacctatg  1080
tccgttcgga gaagtgttca acgcgacaag atttgcgtct gtctatgcgt ggaacagaaa  1140
aagaatcagt aactgcgtcg cggactactc cgtcctatac aactctgcct ctttctccac  1200
gttcaaatgc tacggtgtat ctccgacaaa gctaaacgat ctatgcttca ccaacgtcta  1260
cgcggactcc ttcgtaatca gaggagatga agttagacag attgcgccgg gacaaactgg  1320
aaagatcgcg gattataact acaagctacc ggacgacttc accggatgtg taattgcgtg  1380
gaattcgaac aacctagact ccaaagtcgg aggaaactac aactacttgt acagactatt  1440
cagaaagtcc aacctaaagc cgttcgagag agacatctcc accgaaatct atcaggctgg  1500
atctacaccg tgtaatggtg tcgaaggatt caactgctac ttcccgctac agtcttacgg  1560
atttcaaccg acaaacggtg taggatatca gccgtacaga gtcgtcgtac tatccttcga  1620
actactacat gctccggcga cagtatgtgg accgaaaaag tctaccaacc tagtcaagaa  1680
caaatgcgtc aactttaact tcaacggact aaccggaacc ggtgtcctaa ccgaatctaa  1740
caagaagttt ctaccgttcc agcagttcgg aagagatatc gcggatacaa cagacgctgt  1800
cagagatccg caaaccttgg agatcctaga tatcacaccg tgttctttcg gtggtgtctc  1860
tgtaattact ccgggaacga acacctccaa tcaagtagcg gtactatacc aggacgtgaa  1920
ctgtacagaa gtaccggtag ctattcacgc ggatcaacta acaccaactt ggagagtgta  1980
ctccaccgga tctaacgtat tccaaacaag agcgggatgt ctaatcggag cggaacacgt  2040
aaacaactcc tacgaatgtg atatcccgat tggagcggga atctgtgcgt cttaccaaac  2100
acaaacaaac tctccgagaa gagcgagatc tgtagcctct caatctatta tcgcctacac  2160
catgtccttg ggagccgaaa attctgtcgc gtactccaac aattctatcg cgatcccgac  2220
aaacttcacc atctctgtaa caaccgagat cctaccggtg tctatgacca agacatctgt  2280
cgattgcacc atgtacatct gcggagattc caccgagtgc tccaacctac tactacagta  2340
cggatctttc tgtacccagc taaacagagc gttgactgga atcgctgtag agcaggataa  2400
gaacactcaa gaggtattcg cgcaagtcaa gcagatctat aagactccgc cgatcaagga  2460
cttcggaggt ttcaacttct ctcagatctt gccggatccg tccaaaccgt ctaagagatc  2520
tttcatcgag gacctactat tcaacaaagt caccctagct gacgcgggat tcatcaaaca  2580
atacggagat tgcttgggag acattgcggc gagagatcta atttgcgcgc agaagtttaa  2640
cggattgaca gtactaccgc cgctactaac cgatgagatg attgcgcagt acacgtctgc  2700
tctattggcg ggaacaatta caagtggatg gacatttgga gccggtgccg ctctacaaat  2760
tccgtttgct atgcaaatgg cgtacagatt caacggaatc ggagtaaccc agaacgtctt  2820
gtacgagaac cagaagctaa tcgcgaacca gttcaattcc gcgatcggaa agatccagga  2880
cagtctatct tctactgctt cggcgttggg aaagctacag gatgtagtaa atcaaaacgc  2940
gcaggcgcta aacaccttgg tcaagcaact atcctctaac ttcggagcga tctcgtccgt  3000
cctaaacgac atcttatcca gactagatcc accggaagcg gaggtccaga tcgatagact  3060
aatcactgga agattgcagt ccctacgac ctacgtaaca cagcaactaa ttagagcggc  3120
ggagattaga gcctctgcta atctagctgc gaccaagatg tccgaatgtg tcttgggaca  3180
atccaagaga gtggacttct gcggaaaggg ataccaccta atgtctttcc cacaatctgc  3240
gccgcatggt gtcgtattcc tacatgtaac atatgtgccg gcgcaagaaa agaacttcac  3300
aacagctcca gcgatctgcc atgatggaaa agctcatttc ccgagagagg gagtctttgt  3360
ctctaacgga actcattggt tcgtcaccca gagaaacttc tacgagccgc agatcatcac  3420
caccgacaac acattcgtct cgggaaactg cgacgtggtc atcggaatcg taaacaatac  3480
cgtctacgat ccgttgcagc cggaactaga ctccttcaaa gagagttggg acaagtactt  3540
caagaaccac acctctccgg atgtggactt gggagatatc tctggaatca acgcgtccgt  3600
cgtcaacatc cagaaagaaa tcgatagatt gaacgaggtc gcgaagaact tgaacgagtc  3660
cctaatcgac ctacaagagc taggaaaata cgagcagtac atcaagtggc cgtggtacat  3720
ctggctagga ttcattgctg gactaattgc gatcgtcatg tgctaccatc tgctatgctg  3780
tatgacctcc tgttgctcct gtctaaaggg atgttgttcc tgcggatcct gttgcaagtt  3840
cgatgaagat gatagtgaac cggtcctaaa gggtgtcaag ctacactaca cagagccaga  3900
ggcttaataa tttttatctt tcattttgtt tttttctatg ctataagcca ccatgtactc  3960
cttcgtgtcc gaagaaaccg gaaccttgat cgtcaactcc gtcctactat tcctagcgt  4020
cgtcgtgttc ctactagtaa ccctagctat cctaaccgcg ctaagactat gtgcgtactg  4080
ctgcaacatc gtcaacgtgt ccctagtgaa gccgtccttc tacgtctact ccagagtcaa  4140
gaacctaaac tcctctagag tcccggacct actagttgag ccagaggctt aataaataaa  4200
aattattaag cctctggctc ctggactagt agagcgatat tatcggaact ggaggagtgg  4260
tcggtgttta gcttgtagtt cccgattctg tatctagaat acgccgcaaa tccagaatct  4320
cccgcgactc tttgagaggc tcccaactta tagtacgata gggttctaga ggtcgctacg  4380
gtgatctcct tcggtaggtc cttgatgtca catcttccta ggtggtgtcc cgcaattctt  4440
agatgtcctc ttaggatgac cgctccgata accaattcga attccaatag cggtctggtt  4500
aggatggttc catgtagcgg tacgttcaat aggatgttcg tctccgggtt gaacgaccac  4560
atagatctgg ttctcgcgaa tagtctgaag gaggcgatga agtaggatag ccacattagt  4620
cctactagac aagccatagc gatcgcgatt ccacctgtga tccagttgat tctgtagacc  4680
gcagctagaa cgaagcaggc caaggtgacc ggccatagta gccataggaa gattagcttg  4740
atgatgtaca agaatctgtt cctgttcgcg tacgcgaact gtagtaggca gatccaggtt  4800
aggaatagga atccgatgac taggttccac tgctctagta gcttcttcaa ctcttcgacg  4860
gtgatggttc cgttagaatc cgccatggtg gcttatgatt atttctcgct ttcaatttaa  4920
cacaaccctc aagaacctt gtatttattt tcaattttt                          4959
```

```
SEQ ID NO: 49         moltype = DNA   length = 4965
FEATURE               Location/Qualifiers
source                1..4965
                      mol_type = other DNA
                      organism = synthetic construct
SEQUENCE: 49
aaaaattgaa aataaataca aaggttcttg agggttgtgt taaattgaaa gcgagaaata  60
atcataaccc ggggccacca tgttcgtgtt cctagtccta ctaccgctag tctcttctca  120
gtgtgtaaac ctaacaacga gaacacaact accaccggcg tacaccaatt ctttcacaag  180
aggagtatat tacccggaca aggtgttcag atcctccgta ctacattcta cacaggacct  240
attcctaccg ttcttctcta acgtaacatg gttccacgcg atccatgtct ctggaacaaa  300
```

-continued

```
cggaacgaag agattcgata acccggtctt gccgttcaac gatggtgtat actttgcgtc  360
caccgagaag tccaacatca tcagaggatg gatcttcgga accaccttgg attctaagac  420
ccagtccttg ctaatcgtca acaacgcgac caacgtcgtc atcaaagtct gcgaattcca  480
gttctgtaac gacccgttct tgggagtcta ctaccacaag aacaacaagt cctggatgga  540
atccgagttc agagtctact cttccgcgaa caactgcac ttcgaatatg tatctcagcc  600
gttcctaatg gacctagagg gaaagcaggg aaacttcaag aacctaagag agttcgtatt  660
caagaacatc gacggatact tcaagatcta ctccaagcac actccgatca acctagttag  720
agatctaccg caaggattct ctgcgctaga accgttagta gatttgccga tcggaatcaa  780
catcaccaga ttccagacac tactagcgct acacagatct tacctaacgc cgggagattc  840
ttcttctgga tggactgctg gtgctgcggc ttattatgta ggatacctac agccgagaac  900
cttcctattg aagtacaacg aaaacggaac catcaccgat gccgtagatt gtgctctaga  960
tccgctatcc gaaacgaagt gcaccctaaa gtctttcacc gtcgagaagg gaatctacca 1020
gacctccaac tttagagtac agccgaccga atccatcgtc agatttccga acatcacgaa 1080
cctatgtccg ttcggagaag tgttcaacgc gacaagattt gcgtctgtct atgcgtggaa 1140
cagaaaaaga atcagtaact gcgtcgcgga ctactccgtc ctatacaact ctgcctcttt 1200
ctccacgttc aaatgctacg gtgtatctcc gacaaagcta aacgatctat gcttcaccaa 1260
cgtctacgcg gactccttcg taatcagagg agatgaagtt agacagattg cgccgggaca 1320
aactggaaag atcgcggatt ataactacaa gctaccggac gacttcaccg gatgtgtaat 1380
tgcgtggaat tcgaacaacc tagactccaa agtcggagga aactacaact acttgtacag 1440
actattcaga aagtccaacc taaagccgtt cgagagagac atctccaccg aaatctatca 1500
ggctggatct acaccgtgta atggtgtcga aggattcaac tgctacttcc cgctacagtc 1560
ttacggattt caaccgacaa acggtgtagg atatcagccg tacagagtcg tcgtactatc 1620
cttcgaacta ctacatgctc cggcgacagt atgtggaccg aaaaagtcta ccaacctagt 1680
caagaacaaa tgcgtcaact ttaacttcaa cggactaacc ggaaccgtg tcctaaccga 1740
atctaacaag aagtttctac cgttccagca gttcggaaga gatatcgcgg atacaacaga 1800
cgctgtcaga gatccgcaaa ccttggagat cctagatatc acaccgtgtt ctttcggttg 1860
tgtctctgta attactccgg gaacgaacac ctccaatcaa gtagcggtac tataccagga 1920
cgtgaactgt acagaagtac cggtagctat tcacgcggat caactaacac caacttggag 1980
agtgtactcc accggatcta acgtattcca aacaagagcg ggatgtctaa tcggagcgga 2040
acacgtaaac aactcctacg aatgtgtat cccgattgga gcggaaatct gtgcgtctta 2100
ccaaacacaa acaaactctc cgagaagagc gagatctgta gcctctcaat ctattatcgc 2160
ctacaccatg tccttgggag ccgaaaattc tgtcgcgtac tccaacaatt ctatcgcgat 2220
cccgacaaac ttcaccatct ctgtaacaac cgagatccta ccggtgtcta tgaccaagac 2280
atctgtcgat tgcaccatgt acatctgcgg agattccacc gagtgctcca acctactact 2340
acagtacgga tctttctgta cccagctaaa cagagcgttg actggaatcg ctgtagagca 2400
ggataagaac actcaagagg tattcgcgca agtcaagcag atctataaga ctccgccgat 2460
caaggacttc ggaggtttca acttctctca gatcttgccg gatccgtcca aaccgtctaa 2520
gagatctttc atcgaggacc tactattcaa caaagtcacc ctagctgacg cgggattcat 2580
caaacaatac ggagattgct tgggagacat tgcggcgaga gatctaattt gcgcgcagaa 2640
gtttaacgga ttgacagtac taccgccgct actaaccgat gagatgattg cgcagtacac 2700
gtctgctcta ttggcgggaa caattacaag tggatggaca tttggagccg gtgccgctct 2760
acaaattccg tttgctatgc aaatggcgta cagattcaac ggaatcggag taacccagaa 2820
cgtcttgtac gagaaccaga agctaatcgc gaaccagttc aattccgcga tcggaaagat 2880
ccaggacagt ctatcttcta ctgcttcggc gttgggaaag ctacaggatg tagtaaatca 2940
aaacgcgcag gcgctaaaca ccttggtcaa gcaactatcc tctaacttcg gagcgatctc 3000
gtccgtccta aacgacatct tatccagact agatccaccg gaagcggagg tccagatcga 3060
tagactaatc actggaagat tgcagtccct acagacctac gtaacacagc aactaattag 3120
agcggcggag attagagcct ctgctaatct agctgcgacc aagatgtccg aatgtgtctt 3180
gggacaatcc aagagagtgg acttctgcgg aaagggatac cacctaatgt ctttcccaca 3240
atctgcgccg catggtgtcg tattcctaca tgtaacatat gtgccggcgc aagaaaagaa 3300
cttcacaaca gctccagcga tctgccatga tggaaaagct catttcccga gagagggaat 3360
ctttgtctct aacggaactc attggttcgt cacccagaga aacttctacg agccgcagat 3420
catcaccacc gacaacacat tcgtctcggg aaactgcgac gtggtcatcg gaatcgtaaa 3480
caataccgtc tacgatccgt tgcagccgga actagactcc ttcaaagaag agttggacaa 3540
gtacttcaag aaccacacct ctccggatgt ggacttggga gatatctctg gaatcaacgc 3600
gtccgtcgtc aacatccaga aagaaatcga tagattgaac gaggtcgcga agaacttgaa 3660
cgagtccta atcgacctac aagagctagg aaaaatacgag cagtacatca agtggccgtg 3720
gtacatctgg ctaggattca ttgctggact aattgcgatc gtcatggtca ccatcatgct 3780
atgctgtatg acctcctgtt gctcctgtct aaagggatgt tgttcctgcg gatcctgttg 3840
caagttcgat gaagatgata gtgaaccggt cctaaagggt gtcaagctac actacacaga 3900
gccagaggct taataatttt tatctttcat tttgtttttt tctatgctat aagccaccat 3960
gtactccttc gtgtccgaag aaaccggaac cttgatcgtc aactccgtcc tactattcct 4020
agcgttcgtc gtgttcctac tagtaaccct agctatccta accgcgctaa gactatgtgc 4080
gtactgctgc aacatcgtca acgtgtccct agtgaagccg tccttctacg tctactccag 4140
agtcaagaac ctaaactcct ctagagtccc ggacctacta gttgagccag aggcttaata 4200
aataaaaatt attaagcctc tggctcctgg actagtagag cgatattatc ggaactggag 4260
gagtggtcgg tgtttagctt gtagttcccg attctgtatc tagaatacgc cgcaaatcca 4320
gaatctcccg cgactctttg agaggctccc aacttatagt acgataggt tctagaggtc 4380
gctacggtga tctccttcgg taggtccttg atgtcacatc ttcctaggtg gtgtcccgca 4440
attcttagat gtcctcttag gatgaccgct ccgataacca attcggattc caatagcggt 4500
ctggttagga tggttccatg tagcggtacg ttcaatagga tgttcgtctc cgggttgaac 4560
gaccacatag atctggttct cgcgaatagt ctgaaggagg cgatgaagta ggatagccac 4620
attagtccta ctagacaagc catagcgatc gcgattccac ctgtgatcca gttgattctg 4680
tagaccgcag ctagaacgaa gcaggccaag gtgaccggcc atagtagcca taggaagatt 4740
agcttgatga tgtacaagaa tctgttcctg ttcgcgtacg cgaactgtag taggcagatc 4800
caggttagga ataggaatcc gatgactagg ttccactgct ctagtagctt cttcaactct 4860
tcgacggtga tggttccgtt agaatccgcc atggtggctt atgattattt ctcgctttca 4920
atttaacaca accctcaaga acctttgtat ttattttcaa tttttt          4965
```

```
SEQ ID NO: 50          moltype = DNA   length = 4966
FEATURE                Location/Qualifiers
source                 1..4966
                       mol_type = other DNA
                       organism = synthetic construct
SEQUENCE: 50
aaaaattgaa aataaataca aaggttcttg agggttgtgt taaattgaaa gcgagaaata   60
atcataaccc ggggccacca tgttcgtgtt cctagtccta ctaccgctag tctcttctca   120
gtgtgtaaac ctaacaacga gaacacaact accaccggcg tacaccaatt ctttcacaag   180
aggagtatat tacccggaca aggtgttcag atcctccgta ctacattcta cacaggacct   240
attcctaccg ttcttctcta acgtaacatg gttccacgcg atccatgtct ctggaacaaa   300
cggaacgaag agattcgata acccggtctt gccgttcaac gatggtgtat actttgcgtc   360
caccgagaag tccaacatca tcagaggatg gatcttcgga accaccttgg attctaagac   420
ccagtccttg ctaatcgtca acaacgcgac caacgtcgtc atcaaagtct gcggaattcca   480
gttctgtaac gacccgttct tgggagtcta ctaccacaag aacaacaagt cctggatgga   540
atccgagttc agagtctact cttccgcgaa caactgcacc ttcgaatatg tatctcagcc   600
gttcctaatg gacctagagg gaaagcaggg aaacttcaag aacctaagag agttcgtatt   660
caagaacatc gacggatact tcaagatcta ctccaagcac actccgatca acctagttag   720
agatctaccg caaggattct ctgcgctaga accgttagta gatttgccga tcggaatcaa   780
catcaccaga ttccagacac tactagcgct acacagatct tacctaacgc cgggagattc   840
ttcttctgga tggactgctg gtgctgcggc ttattatgta ggatacctac agccgagaac   900
cttcctattg aagtacaacg aaaacggaac catcaccgat gccgtagatt gtgctctaga   960
tccgctatcc gaaacgaagt gcaccctaaa gtctttcacc gtcgagaagg aatctacca   1020
gacctccaac tttagagtac agccgaccga atccatcgtc agatttccga acatcacgaa   1080
cctatgtccg ttcggagaag tgttcaacgc gacaagattt gcgtctgtct atgcgtggaa   1140
cagaaaaaga atcagtaact gcgtcgcgga ctactccgtc ctatacaact ctgcctcttt   1200
ctccacgttc aaatgctacg gtgtatctcc gacaaagcta aacgatctat gcttcaccaa   1260
cgtctacgcg gactccttcg taatcagagg agatgaagtt agacagattg cgccgggaca   1320
aactggaacg atcgcggatt ataactacaa gctaccggac gacttcaccg gatgtgtaat   1380
tgcgtggaat tcgaacaacc tagactccaa agtcggagga aactacaact acttgtacag   1440
actattcaga aagtccaacc taaagccgtt cgagagagac atctccaccg aaatctatca   1500
ggctggatct acaccgtgta atggtgtcaa gggattcaac tgctacttcc cgctacagtc   1560
ttacggattt caaccgacat acggtgtagg atatcagccg tacagagtcg tcgtactatc   1620
cttcgaacta ctacatgctc cggcgacagt atgtggaccg aaaaagtcta ccaacctagt   1680
caagaacaaa tgcgtcaact ttaacttcaa cggactaacc ggaaccggtg tcctaaccga   1740
atctaacaag aagtttctac cgttccagca gttcggaaga gatatcgcgg atacaacaga   1800
cgctgtcaga gatccgcaaa ccttggagat cctagatatc acaccgtgtt ctttcggtgg   1860
tgtctctgta attactccgg gaacgaacac ctccaatcaa gtagcggtac tataccagga   1920
cgtgaactgt acagaagtac cggtagctat tcacgcggat caactaacac caacttggag   1980
agtgtactcc accggatcta acgtattcca aacaagagcg ggatgtctaa tcggagcgga   2040
acacgtaaac aactcctacg aatgtgtat cccgattgga gcgggaatct gtgcgtctta   2100
ccaaacacaa acaaactctc cgagaagagc gagatctgta gcctctcaat ctattatcgc   2160
ctacaccatg tccttgggag ccgaaaattc tgtcgcgtac tccaacaatt ctatcgcgat   2220
cccgacaaac ttcaccatct ctgtaacaac cgagatccta ccggtgtcta tgaccaaagc   2280
atctgtcgat tgcaccatgt acatctgcgg agattccacc gagtgctcca acctactact   2340
acagtacgga tctttctgta cccagctaaa cagagcgttg actggaatcg ctgtagagca   2400
ggataagaac actcaagagg tattcgcgca agtcaagcag atctataaga ctccgccgat   2460
caaggacttc ggaggtttca acttctctca gatcttgccg gatccgtcca aaccgtctaa   2520
gagatctttc atcgaggacc tactattcaa caaagtcacc ctagctgacg cgggattcat   2580
caaacaatac ggagattgct tgggagacat tgcggcgaga gatctaattt gcgcgcagaa   2640
gtttaacgga ttgacagtac taccgccgct actaaccgat gagatgattg cgcagtacac   2700
gtctgctcta ttggcgggaa caattacaag tggatggaca tttggagccg gtgccgctct   2760
acaaattccg tttgctatgc aaatggcgta cagattcaac ggaatcggag taacccagaa   2820
cgtcttgtac gagaaccaga agctaatcgc gaaccagttc aattccgcga tcggaaagat   2880
ccaggacagt ctatcttcta ctgcttcggc gttgggaaag ctacaggatg tagtaaatca   2940
aaacgcgcag gcgctaaaca ccttggtcaa gcaactatcc tctaacttcg gagcgatctc   3000
gtccgtccta aacgacatct tatccagact agatccaccg gaagcggagg tccagatcga   3060
tagactaatc actggaagat tgcagtccct acagacctac gtaacacagc aactaattag   3120
agcggcggag attagagcct ctgctaatct agctgcgacc aagatgtccg aatgtgtctt   3180
gggacaatcc aagagagtgg acttctgcgg aaagggatac cacctaatgt ctttcccaca   3240
atctgcgccg catggtgtcg tattcctaca tgtaacatat gtgccggcgc aagaaaagaa   3300
cttcacaaca gctccagcga tctgccatga tggaaaagct catttcccga gagagggagt   3360
ctttgtctct aacggaactc attggttcgt caccccagaga aacttctacg agccgcagat   3420
catcaccacc gacaacacat tcgtctcggg aaactgcgac gtggtcatcg gaatcgtaaa   3480
caataccgtc tacgatccgt tgcagccgga actagactcc ttcaaagaag agttggacaa   3540
gtacttcaag aaccacacct ctccggatgt ggacttggga gatatctctg gaatcaacgc   3600
gtccgtcgtc aacatccaga agaaatcga tagattgaac gaggtcgcga agaacttgaa   3660
cgagtcccta atcgacctac aagagctagg aaaatacgac cagtacatca agtggccgtg   3720
gtacatctgg ctaggattca ttgctggact aattgcgatc gtcatggtca ccatcatgct   3780
atgctgtatg acctcctgtt gctcctgtct aaagggatgt tgttcctgcg gattcctgtt   3840
gcaagttcga tgaagatgat agtgaaccgg tcctaaaggg tgtcaagcta cactacacag   3900
agccagaggc ttaataattt ttatctttca ttttgttttt ttctatgcta taagccacca   3960
tgtactcctt cgtgtccgaa gaaaccggaa ccttgatcgt caactccgtc ctactattcc   4020
tagcgtcgt cgtgttccta ctagtaaccc tagctatcct aaccgcgcta agactatgtg   4080
cgtactgctg caacatcgtc aacgtgtccc tagtgaagcc gtccttctac gtctactcca   4140
gagtcaagaa cctaaactcc tctagagtcc cggacctact agttgagcca gaggcttaat   4200
aaataaaat tattaagcct ctggctcctg gactagtaga gcgatattat cggaactgga   4260
ggagtggtcg gtgtttagct tgtagttccc gattctgtat ctagaatacg ccgcaaatcc   4320
agaatctccc gcgactcttt gagaggctcc caacttatag tacgataggg ttctagaggt   4380
```

-continued

```
cgctacggtg atctccttcg gtaggtcctt gatgtcacat cttcctaggt ggtgtcccgc   4440
aattcttaga tgtcctctta ggatgaccgc tccgataacc aattcggatt ccaatagcgg   4500
tctggttagg atggttccat gtagcggtac gttcaatagg atgttcgtct ccgggttgaa   4560
cgaccacata gatctggttc tcgcgaatag tctgaaggag gcgatgaagt aggatagcca   4620
cattagtcct actagacaag ccatagcgat cgcgattcca cctgtgatcc agttgattct   4680
gtagaccgca gctagaacga agcaggccaa ggtgaccggc catagtagcc ataggaagat   4740
tagcttgatg atgtacaaga atctgttcct gttcgcgtac gcgaactgta gtaggcagat   4800
ccaggttagg aataggaatc cgatgactag gttccactgc tctagtagct tcttcaactc   4860
ttcgacggtg atggttccgt tagaatccgc catggtggct tatgattatt tctcgctttc   4920
aatttaacac aaccctcaag aacctttgta tttattttca attttt              4966

SEQ ID NO: 51             moltype = DNA  length = 1737
FEATURE                   Location/Qualifiers
source                    1..1737
                          mol_type = other DNA
                          organism = synthetic construct
SEQUENCE: 51
aaaaattgaa aataaataca aaggttcttg agggttgtgt taaattgaaa gcgagaaata   60
atcataagcc accatggtca gatttccgaa catcacgaac ctatgtccgt tcggagaagt   120
gttcaacgcg acaagatttg cgtctgtcta tgcgtggaac agaaaaagaa tcagtaactg   180
cgtcgcggac tactccgtcc tatacaactc tgcctctttc tccacgttca aatgctacgg   240
tgtatctccg acaaagctaa acgatctatg cttcaccaac gtctacgcgg actccttcgt   300
aatcagagga gatgaagtta gacagattgc gccgggacaa actggaaaga tcgcggatta   360
taactacaag ctaccggacg acttcaccgg atgtgtaatt gcgtggaatt cgaacaacct   420
agactccaaa gtcggaggaa actacaacta cttgtacaga ctattcagaa agtccaacct   480
aaagccgttc gagagagaca tctccaccga aatctatcag gctggatcta caccgtgtaa   540
tggtgtcgaa ggattcaact gctacttccc gctacagtct tacggatttc aaccgacaaa   600
cggtgtagga tatcagccgt acagagtcgt cgtactatcc ttcgaactac tacatgctcc   660
ggcgacagta gagccggaag cttaataatt tttatctttc attttgtttt tttctatgct   720
ataagccacc atgtactcct tcgtgtccga agaaaccgga accttgatcg tcaactccgt   780
cctactattc ctagcgttcg tcgtgttcct actagtaacc ctagctatcc taaccgcgct   840
aagactatgt gcgtactgct gcaacatcgt caacgtgtcc ctagtgaagc cgtccttcta   900
cgtctactcc agagtcaaga acctaaactc ctctagagtc ccggacctac tagttgagcc   960
agaggcttaa taaataaaaa ttattaagcc tctggctcct ggactagtag agcgatatta   1020
tcggaactgg aggagtgggtc ggtgtttagc ttgtagttcc cgattctgta tctagaaatc   1080
gccgcaaatc cagaatctcc cgcgactctt tgagaggctc ccaacttata gtacgatagg   1140
gttctagagg tcgctacggt gatctccttc ggtaggtcct tgatgtcaca tcttcctagg   1200
tggtgtcccg caattcttag atgtcctctt aggatgaccg ctccgataac caattcggat   1260
tccaatagcg gtctggttag gatggttcca tgtagcggta cgttcaatag gatgttcgtc   1320
tccgggttga acgaccacat agatctggtt ctcgcgaata gtctgaagga ggcgatgaag   1380
taggatagcc acattagtcc tactagacaa gccatagcga tcgcgattcc acctgtgatc   1440
cagttgattc tgtagaccgc agctagaacg aagcaggcca aggtgaccgg ccatagtagc   1500
cataggaaga ttagcttgat gatgtacaag aatctgttcc tgttcgcgta cgcgaactgt   1560
agtaggcaga tccaggttag gaataggaat ccgatgacta ggttccactg ctctagtagc   1620
ttcttcaact cttcgacggt gatggttccg ttagaatccg ccatggtggc ttatgattat   1680
ttctcgcttt caatttaaca aaccctcaa gaacctttgt atttattttc aattttt     1737

SEQ ID NO: 52             moltype = DNA  length = 1743
FEATURE                   Location/Qualifiers
source                    1..1743
                          mol_type = other DNA
                          organism = synthetic construct
SEQUENCE: 52
aaaaattgaa aataaataca aaggttcttg agggttgtgt taaattgaaa gcgagaaata   60
atcataaccc ggggccacca tggtcagatt tccgaacatc acgaacctat gtccgttcgg   120
agaagtgttc aacgcgacaa gatttgcgtc tgtctatgcg tggaacagaa aaagaatcag   180
taactgcgtc gcggactact ccgtcctata caactctgcc tctttctcca cgttcaaatg   240
ctacggtgta tctccgacaa agctaaacga tctatgcttc accaacgtct acgcggactc   300
cttcgtaatc agaggagatg aagttagaca gattgcgccg ggacaaactg gaaagatcga   360
ggattataac tacaagctac cggacgactt caccggatgt gtaattgcgt ggaattcgaa   420
caacctagac tccaaagtcg gaggaaacta caactacttg tacagactat tcagaaagtc   480
caacctaaag ccgttcgaga gagacatctc caccgaaatc tatcaggctg atctacacc   540
gtgtaatggt gtcgaaggat tcaactgcta cttcccgcta cagtcttacg gatttcaacc   600
gacaaacggt gtaggatatc agccgtacag agtcgtcgta ctatccttcg aactactaca   660
tgctccggcg acagtagagc cggaagctta ataattttta tctttcattt tgtttttttc   720
tatgctataa gccaccatgt actccttcgt gtccgaagaa accggaacct tgatcgtcaa   780
ctccgtccta ctattcctag cgttcgtcgt gttcctacta gtaaccctag ctatcctaac   840
cgcgctaaga ctatgtgcgt actgctgcaa catcgtcaac gtgtccctag tgaagccgtc   900
cttctacgtc tactccagag tcaagaacct aaactcctct agagtcccgg acctactagt   960
tgagccagag gcttaataaa taaaaattat taagcctctg gctcctggac tagtagagcg   1020
atattatcgg aactgaggga gtgggtcggtg tttagcttgt agttcccgat tctgtatcta   1080
gaatacgccg caaatccaga atctcccgcg actctttgag aggctccaa cttatagtac   1140
gatagggttc tagaggtcgc tacggtgatc tccttcggta ggtccttgat gtcacatctt   1200
cctaggtggt gtcccgcaat tcttagatgt cctcttagga tgaccgctcc gataaccaat   1260
tcggattcca atagcggtct ggttaggatg gttccatgta gcggtacgtt caataggatg   1320
ttcgtctccg ggttgaacga ccacatagat ctggttctcg cgaatagtct gaaggaggcg   1380
atgaagtagg atagccacat tagtcctact agacaagcca tagcgatcgc gattccacct   1440
gtgatccagt tgattctgta gaccgcagct agaacgaagc aggccaaggt gaccggccat   1500
agtagccata ggaagattag cttgatgatg tacaagaatc tgttcctgtt cgcgtacgcg   1560
```

```
aactgtagta ggcagatcca ggttaggaat aggaatccga tgactaggtt ccactgctct   1620
agtagcttct tcaactcttc gacggtgatg gttccgttag aatccgccat ggtggcttat   1680
gattatttct cgctttcaat ttaacacaac cctcaagaac ctttgtattt attttcaatt   1740
ttt                                                                  1743

SEQ ID NO: 53            moltype = DNA  length = 1725
FEATURE                  Location/Qualifiers
source                   1..1725
                         mol_type = other DNA
                         organism = synthetic construct
SEQUENCE: 53
aaaaattgaa aataaataca aaggttcttg agggttgtgt taaattgaaa gcgagaaata   60
atcataagcc accatgaaca tcacgaacct atgtccgttc ggagaagtgt tcaacgcgac   120
aagatttgcg tctgtctatg cgtggaacag aaaaagaatc agtaactgcg tcgcggacta   180
ctccgtccta tacaactctg cctctttctc cacgttcaaa tgctacggtg tatctccgac   240
aaagctaaac gatctatgct tcaccaacgt ctacgcggac tccttcgtaa tcagaggaga   300
tgaagttaga cagattgcgc cgggacaaac tggaaagatc gcggattata actacaagct   360
accggacgac ttcaccggat gtgtaattgc gtggaattcg aacaacctag actccaaagt   420
cggaggaaac tacaactact tgtacagact attcagaaag tccaacctaa agccgttcga   480
gagagacatc tccaccgaaa tctatcaggc tggatctaca ccgtgtaatg gtgtcgaagg   540
attcaactgc tacttccgc tacagtctta cggatttcaa ccgacaaacg gtgtaggata   600
tcagccgtac agagtcgtcg tactatcctt cgaactacta catgctccgg cgacagtaga   660
gccggaagct taataatttt tatctttcat tttgtttttt tctatgctat aagccaccat   720
gtactccttc gtgtccgaag aaaccggaac cttgatcgtc aactccgtcc tactattcct   780
agcgttcgtc gtgttcctac tagtaaccct agctatccta accgcgctaa gactatgtgc   840
gtactgctgc aacatcgtca acgtgtccct agtgaagccg tccttctacg tctactccag   900
agtcaagaac ctaaactcct ctagagtccc ggacctacta gttgagccag aggcttaata   960
aataaaaatt attaagcctc tggctcctgg actagtagag cgatattatc ggaactggag   1020
gagtggtcgg tgtttagctt gtagttcccg attctgtatc tagaatacgc cgcaaatcca   1080
gaatctcccg cgactctttg agaggctccc aacttatagt acgatagggt tctagaggtc   1140
gctacggtga tctccttcgg taggtccttg atgtcacatc ttcctaggtg gtgtcccgca   1200
attcttagat gtcctcttag gatgaccgct ccgataacca attcggattc caatagcggt   1260
ctggttagga tggttccatg tagcggtacg ttcaatagga tgttcgtctc cgggttgaac   1320
gaccacatag atctggttct cgcgaatagt ctgaaggagg cgatgaagta ggatagccac   1380
attagtccta ctagacaagc catagcgatc gcgattccac ctgtgatcca gttgattctg   1440
tagaccgcag ctagaacgaa gcaggccaag gtgaccggcc atagtagcca taggaagatt   1500
agcttgatga tgtacaagaa tctgttcctg ttcgcgtacg cgaactgtag taggcagatc   1560
caggttagga ataggaatcc gatgactagg ttccactgct ctagtagctt cttcaactct   1620
tcgacggtga tggttccgtt agaatccgcc atggtggctt atgattattt ctcgctttca   1680
atttaacaca acccttcaaga accttgtat ttattttcaa tttt               1725

SEQ ID NO: 54            moltype = DNA  length = 1731
FEATURE                  Location/Qualifiers
source                   1..1731
                         mol_type = other DNA
                         organism = synthetic construct
SEQUENCE: 54
aaaaattgaa aataaataca aaggttcttg agggttgtgt taaattgaaa gcgagaaata   60
atcataaccc ggggccacca tgaacatcac gaacctatgt ccgttcggag aagtgttcaa   120
cgcgacaaga tttgcgtctg tctatgcgtg gaacagaaaa agaatcagta actgcgtcgc   180
ggactactcc gtcctataca actctgcctc tttctccacg ttcaaatgct acggtgtatc   240
tccgacaaag ctaaacgatc tatgcttcac caacgtctac gcggactcct tcgtaatcag   300
aggagatgaa gttagacaga ttgcgccggg acaaactgga aagatcgcgg attataacta   360
caagctaccg gacgacttca ccggatgtgt aattgcgtgg aattcgaaca acctagactc   420
caaagtcgga ggaaactaca actacttgta cagactattc agaaagtcca acctaaagcc   480
gttcgagaga gacatctcca ccgaaatcta tcaggctgga tctacaccgt gtaatggtgt   540
cgaaggattc aactgctact tccgctaca gtcttacgga tttcaaccga caaacggtgt   600
aggatatcag ccgtacagag tcgtcgtact atccttcgaa ctactacatg ctccggcgac   660
agtagagccg gaagcttaat aattttttatc tttcattttg tttttttcta tgctataagc   720
caccatgtac tccttcgtgt ccgaagaaac cggaacctta tcgtcaact ccgtcctact   780
attcctagcg ttcgtcgtgt tcctactagt aaccctagct atcctaaccg cgctaagact   840
atgtgcgtac tgctgcaaca tcgtcaacgt gtccctagtg aagccgtcct tctacgtcta   900
ctccagagtc aagaacctaa actcctctag agtcccggac ctactagttg agccagaggc   960
ttaataaata aaaattatta agcctctggc tcctggacta gtagagcgat attatcggaa   1020
ctggaggagt ggtcggtgtt tagcttgtag ttcccgattc tgtatctaga atacgccgca   1080
aatccagaat ctcccgcgac tctttgagag gctcccaact atagtacga tagggttcta   1140
gaggtcgcta cggtgatctc cttcggtagg tccttgatgt cacatcttcc taggtggtgt   1200
cccgcaattc ttagatgtcc tcttaggatg accgctccga taaccaattc ggattccaat   1260
agcggtctgg ttaggatggt tccatgtagc ggtacgttca ataggatgtt cgtctccggg   1320
ttgaacgacc acatagatct ggttctcgcg aatagtctga aggaggcgat gaagtaggat   1380
agccacatta gtcctactag acaagccata gcgatcgcga ttccacctgt gatccagttg   1440
attctgtaga ccgcagctag aacgaagcag gccaaggtga ccggccatag tagccatagg   1500
aagattagct tgatgatgta caagaatctg ttcctgttcg cgtacgcgaa ctgtagtagg   1560
cagatccagg ttaggaatag gaatccgatg actaggttcc actgctctag tagcttcttc   1620
aactcttcga cggtgatggt tccgttagaa tccgccatgg tggcttatga ttatttctcg   1680
ctttcaattt aacacaaccc tcaagaacct ttgtatttat tttcaatttt t           1731

SEQ ID NO: 55            moltype = AA  length = 13
FEATURE                  Location/Qualifiers
```

```
source                  1..13
                        mol_type = protein
                        organism = synthetic construct
SEQUENCE: 55
MFVFLVLLPL VSS                                                         13

SEQ ID NO: 56           moltype = DNA   length = 39
FEATURE                 Location/Qualifiers
source                  1..39
                        mol_type = other DNA
                        organism = synthetic construct
SEQUENCE: 56
atgtttgttt ttcttgtttt attgccacta gtctctagt                            39

SEQ ID NO: 57           moltype = AA   length = 60
FEATURE                 Location/Qualifiers
source                  1..60
                        mol_type = protein
                        organism = synthetic construct
SEQUENCE: 57
WYIWLGFIAG LIAIVMVTIM LCCMTSCCSC LKGCCSCGSC CKFDEDDSEP VLKGVKLHYT      60

SEQ ID NO: 58           moltype = DNA   length = 180
FEATURE                 Location/Qualifiers
source                  1..180
                        mol_type = other DNA
                        organism = synthetic construct
SEQUENCE: 58
tggtacattt ggctaggttt tatagctggc ttgattgcca tagtaatggt gacaattatg     60
ctttgctgta tgaccagttg ctgtagttgt ctcaaggggc gttgttcttg tggatcctgc    120
tgcaaatttg atgaagacga ctctgagcca gtgctcaaag gagtcaaatt acattacaca    180

SEQ ID NO: 59           moltype = DNA   length = 39
FEATURE                 Location/Qualifiers
source                  1..39
                        mol_type = other DNA
                        organism = synthetic construct
SEQUENCE: 59
atgttcgtgt tcctagtcct actaccgcta gtctcttct                            39

SEQ ID NO: 60           moltype = DNA   length = 180
FEATURE                 Location/Qualifiers
source                  1..180
                        mol_type = other DNA
                        organism = synthetic construct
SEQUENCE: 60
tggtacatct ggctaggatt cattgctgga ctaattgcga tcgtcatggt caccatcatg     60
ctatgctgta tgacctcctg ttgctcctgt ctaaagggat gttgttcctg cggatcctgt    120
tgcaagttcg atgaagatga tagtgaaccg gtcctaaagg gtgtcaagct acactacaca    180

SEQ ID NO: 61           moltype = AA   length = 271
FEATURE                 Location/Qualifiers
source                  1..271
                        mol_type = protein
                        organism = synthetic construct
SEQUENCE: 61
MFVFLVLLPL VSSVRFPNIT NLCPFGEVFN ATRFASVYAW NRKRISNCVA DYSVLYNSAS     60
FSTFKCYGVS PTKLNDLCFT NVYADSFVIR GDEVRQIAPG QTGKIADYNY KLPDDFTGCV    120
IAWNSNNLDS KVGGNYNYLY RLFRKSNLKP FERDISTEIY QAGSTPCNGV EGFNCYFPLQ    180
SYGFQPTNGV GYQPYRVVVL SFELLHAPAT VWYIWLGFIA GLIAIVMVTI MLCCMTSCCS    240
CLKGCCSCGS CCKFDEDDSE PVLKGVKLHY T                                   271

SEQ ID NO: 62           moltype = AA   length = 267
FEATURE                 Location/Qualifiers
source                  1..267
                        mol_type = protein
                        organism = synthetic construct
SEQUENCE: 62
MFVFLVLLPL VSSNITNLCP FGEVFNATRF ASVYAWNRKR ISNCVADYSV LYNSASFSTF     60
KCYGVSPTKL NDLCFTNVYA DSFVIRGDEV RQIAPGQTGK IADYNYKLPD DFTGCVIAWN    120
SNNLDSKVGG NYNYLYRLFR KSNLKPFERD ISTEIYQAGS TPCNGVEGFN CYFPLQSYGF    180
QPTNGVGYQP YRVVVLSFEL LHAPATVWYI WLGFIAGLIA IVMVTIMLCC MTSCCSCLKG    240
CCSCGSCCKF DEDDSEPVLK GVKLHYT                                        267

SEQ ID NO: 63           moltype = DNA   length = 882
FEATURE                 Location/Qualifiers
source                  1..882
                        mol_type = other DNA
                        organism = synthetic construct
```

```
SEQUENCE: 63
atgtttgttt ttcttgtttt attgccacta gtctctagtg ttagatttcc taatattaca    60
gttagatttc ctaatattac aaacttgtgc ccttttggtg aagtttttaa cgccaccaga   120
tttgcatctg tttatgcttg gaacaggaag agaatcagca actgtgttgc tgattattct   180
gtcctatata attccgcatc attttccact tttaagtgtt atggagtgtc tcctactaaa   240
ttaaatgatc tctgctttac taatgtctat gcagattcat ttgtaattag aggtgatgaa   300
gtcagacaaa tcgctccagg gcaaactgga aagattgctg attataatta taaattacca   360
gatgatttta caggctgcgt tatagcttgg aattctaaca atcttgattc taaggttggt   420
ggtaattata attacctgta tagattgttt aggaagtcta atctcaaacc ttttgagaga   480
gatatttcaa ctgaaatcta tcaggccggt agcacacctt gtaatggtgt tgaaggtttt   540
aattgttact ttcctttaca atcatatggt ttccaaccca ctaatggtgt tggttaccaa   600
ccatacagag tagtagtact ttcttttgaa cttctacatg caccagcaac tgtttgtgga   660
cctaaaaagt ctactaattt ggttaaaaac aaatgtgtca attggtacat ttggctaggt   720
tttatagctg gcttgattgc catagtaatg gtgacaatta tgctttgctg tatgaccagt   780
tgctgtagtt gtctcaaggg ctgttgttct tgtggatcct gctgcaaatt tgatgaagac   840
gactctgagc cagtgctcaa aggagtcaaa ttacattaca ca                     882

SEQ ID NO: 64        moltype = DNA   length = 849
FEATURE              Location/Qualifiers
source               1..849
                     mol_type = other DNA
                     organism = synthetic construct
SEQUENCE: 64
atgtttgttt ttcttgtttt attgccacta gtctctagta atattacaaa cttgtgccct    60
tttggtgaag ttttttaacgc caccagattt gcatctgttt atgcttggaa caggaagaga   120
atcagcaact gtgttgctga ttattctgtc ctatatatt ccgcatcatt ttccactttt    180
aagtgttatg gagtgtctcc tactaaatta aatgatctct gctttactaa tgtctatgca   240
gattcatttg taattagagg tgatgaagtc agacaaatcg ctccagggca aactggaaag   300
attgctgatt ataattataa attaccagat gattttacag gctgcgttat agcttggaat   360
tctaacaatc ttgattctaa ggttggtggt aattataatt acctgtatag attgtttagg   420
aagtctaatc tcaaaccttt tgagagagat atttcaactg aaatctatca ggccggtagc   480
acaccttgta atggtgttga aggttttaat tgttactttc ctttacaatc atatggtttc   540
caacccacta atggtgttgg ttaccaacca tacagagtag tagtactttc ttttgaactt   600
ctacatgcac cagcaactgt ttgtggacct aaaaagtcta ctaatttggt taaaaacaaa   660
tgtgtcaatt ggtacatttg gctaggtttt atagctggct tgattgccat agtaatggtg   720
acaattatgc tttgctgtat gaccagttgc tgtagttgtc tcaagggctg ttgttcttgt   780
ggatcctgct gcaaatttga tgaagacgac tctgagccag tgctcaaagg agtcaaatta   840
cattacaca                                                          849

SEQ ID NO: 65        moltype = DNA   length = 813
FEATURE              Location/Qualifiers
source               1..813
                     mol_type = other DNA
                     organism = synthetic construct
SEQUENCE: 65
atgttcgtgt tcctagtcct actaccgcta gtctcttctg tcagatttcc gaacatcacg    60
aacctatgtc cgttcggaga agtgttcaac gcgacaagat ttgcgtctgt ctatgcgtgg   120
aacagaaaaa gaatcagtaa ctgcgtcgcg gactactccg tcctatacaa ctctgcctct   180
ttctccacgt tcaaatgcta cggtgtatct ccgacaaagc taaacgatct atgcttcacc   240
aacgtctacg cggactcctt cgtaatcaga ggagatgaag ttagacagat tgcgccggga   300
caaactggaa agatcgcgga ttataactac aagctaccgg acgacttcac cggatgtgta   360
attgcgtgga attcgaacaa cctagactcc aaagtcggag gaaactacaa ctacttgtac   420
agactattca gaaagtccaa cctaaagccg ttcgagagag acatctccac cgaaatctat   480
caggctggat ctacaccgtg taatggtgtc gaaggattca actgctactt cccgctacag   540
tcttacggat ttcaaccgac aaacggtgta ggatatcaac cgtacagagt cgtcgtacta   600
tccttcgaac tactacatgc tccggcgaca gtatggtaca tctggctagg attccattgct   660
ggactaattg cgatcgtcat ggtcaccatc atgctatgct gtatgacctc ctgttgctcc   720
tgtctcaaagg gatgttgttc ctgcggatcc tgttgcaagt tcgatgaaga tgatagtgaa   780
ccggtcctaa agggtgtcaa gctacactac aca                               813

SEQ ID NO: 66        moltype = DNA   length = 801
FEATURE              Location/Qualifiers
source               1..801
                     mol_type = other DNA
                     organism = synthetic construct
SEQUENCE: 66
atgttcgtgt tcctagtcct actaccgcta gtctcttcta acatcacgaa cctatgtccg    60
ttcggagaag tgttcaacgc gacaagattt gcgtctgtct atgcgtggaa cagaaaaaga   120
atcagtaact gcgtcgcgga ctactccgtc tatacaact ctgcctcttt ctccacgttc    180
aaatgctacg gtgtatctcc gacaaagcta aacgatctat gcttcaccaa cgtctacgcg   240
gactccttcg taatcagagg agatgaagtt agacagattg cgccgggaca aactggaaag   300
atcgcggatt ataactacaa gctaccggac gacttcaccg gatgtgtaat tgcgtggaat   360
tcgaacaacc tagactccaa gtcggagga aactacaact acttgtacag actattcaga    420
aagtccaaca aagccgtt cgagagagac atctccacca aatctatca ggctggatct      480
acaccgtgta atggtgtcga aggattcaac tgctacttcc gctacagtc ttacggattt     540
caaccgacaa acggtgtagg atatcagccg tacagagtcg tcgtactatc cttcgaacta   600
ctacatgctc ggcgacagt atggtacatc tggctaggat tcattgctgg actaattgcg    660
atcgtcatgg tcaccatcat gctatgctgt atgacctcct gttgctcctg tctaaaggga   720
tgttgttcct gcggatcctg ttgcaagttc gatgaagatg atagtgaacc ggtcctaaag   780
```

-continued

```
ggtgtcaagc tacactacac a                                              801

SEQ ID NO: 67              moltype = AA  length = 271
FEATURE                    Location/Qualifiers
source                     1..271
                           mol_type = protein
                           organism = synthetic construct
SEQUENCE: 67
MFVFLVLLPL VSSVRFPNIT NLCPFGEVFN ATRFASVYAW NRKRISNCVA DYSVLYNSAS     60
FSTFKCYGVS PTKLNDLCFT NVYADSFVIR GDEVRQIAPG QTGTIADYNY KLPDDFTGCV    120
IAWNSNNLDS KVGGNYNYLY RLFRKSNLKP FERDISTEIY QAGSTPCNGV KGFNCYFPLQ    180
SYGFQPTYGV GYQPYRVVVL SFELLHAPAT VWYIWLGFIA GLIAIVMVTI MLCCMTSCCS    240
CLKGCCSCGS CCKFDEDDSE PVLKGVKLHY T                                   271

SEQ ID NO: 68              moltype = AA  length = 267
FEATURE                    Location/Qualifiers
source                     1..267
                           mol_type = protein
                           organism = synthetic construct
SEQUENCE: 68
MFVFLVLLPL VSSNITNLCP FGEVFNATRF ASVYAWNRKR ISNCVADYSV LYNSASFSTF     60
KCYGVSPTKL NDLCFTNVYA DSFVIRGDEV RQIAPGDFEV IADYNYKLPD DFTGCVIAWN    120
SNNLDSKVGG NYNYLYRLFR KSNLKPFERD ISTEIYQAGS TPCNGVKGFN CYFPLQSYGF    180
QPTYGVGYQP YRVVVLSFEL LHAPATVWYI WLGFIAGLIA IVMVTIMLCC MTSCCSCLKG    240
CCSCGSCCKF DEDDSEPVLK GVKLHYT                                        267

SEQ ID NO: 69              moltype = DNA  length = 1953
FEATURE                    Location/Qualifiers
source                     1..1953
                           mol_type = other DNA
                           organism = synthetic construct
SEQUENCE: 69
aaaaattgaa aataaataca aaggttcttg agggttgtgt taaattgaaa gcgagaaata     60
atcataagcc accatgttcg tgttcctagt cctactaccg ctagtctctt ctgtcagatt    120
tccgaacatc acgaacctat gtccgttcgg agaagtgttc aacgcgacaa gatttgcgtc    180
tgtctatgcg tggaacagaa aaagaatcag taactgcgtc gcggactact ccgtcctata    240
caactctgcc tctttctcca cgttcaaatg ctacggtgta tctccgacaa agctaaacga    300
tctatgcttc accaacgtct acgcggactc cttcgtaatc agaggagatg aagttagaca    360
gattgcgccg ggacaaactg gaaagatcgc ggattataac tacaagctac cggacgactt    420
caccggatgt gtaattgcgt ggaattcgaa caacctagac tccaaagtcg gaggaaacta    480
caactacttg tacagactat tcagaaagtc caacctaaag ccgttcgaga gagacatctc    540
caccgaaatc tatcaggctg gatctacacc gtgtaatggt gtcgaaggat tcaactgcta    600
cttcccgcta cagtcttacg gatttcaacc gacaaacggt gtaggtatcc agcgtacag     660
agtcgtcgta ctatccttcg aactactaca tgctccggcg acagtatggt acatctggct    720
aggattcatt gctggactaa ttgcgatcgt catggtcacc atcatgctat gctgtatgac    780
ctcctgttgc tcctgtctaa agggatgttg ttcctgcgga tcctgttgca agttcgatga    840
agatgatagt gaaccggtcc taaagggtgt caagctacac tacacagagc cggaagctta    900
ataatttttta tctttcattt tgtttttttc tatgctataa gccaccatgt actccttcgt    960
gtccgaagaa accggaacct tgatcgtcaa ctccgtccta ctattcctag cgttcgtcgt   1020
gttcctacta gtaaccctag ctatcctaac cgcgctaaga ctatgtgcgt actgctgcaa   1080
catcgtcaac tgtgtccctag tgaagccgtc cttctacgtc tactccagag tcaagaacct   1140
aaactcctct agagtcccgg acctactagt tgagccagag gcttaataaa taaaaattat   1200
taagcctctg gctcctggac tagtagagcg atattatcgg aactggagga gtggtcggtg   1260
tttagcttgt agttcccgat tctgtatcta gaatacgccg caaatccaga atctcccgcg   1320
actctttgag aggctcccaa cttatagtac gatagggttc tagaggtcgc tacggtgatc   1380
tccttcggta ggtccttgat gtcacatctt cctaggtggt gtcccgcaat tcttagatgt   1440
cctcttagga tgaccgctcc gataaccaat tcggattcca atagcggtct ggttaggatg   1500
gttccatgta gcggtacgtt caataggatg ttcgtctccg ggttaacga ccacatagat    1560
ctggttctcg cgaatagtct gaaggaggcg atgaagtagg atagccacat tagtcctact   1620
agacaagcca tagcgatcgc gattccacct gtgatccagt tgattctgta gaccgcagct   1680
agaacgaagc aggccaaggt gaccggccat agtagccata ggaagattag cttgatgatg   1740
tacaagaatc tgttcctgtt cgcgtacgcg aactgtagta ggcagatcca ggttaggaat   1800
aggaatccga tgactaggtt ccactgctct agtagcttct tcaactcttc gacggtgatg   1860
gttccgttag aatccgccat ggtggcttat gattatttct cgctttcaat ttaacacaac   1920
cctcaagaac ctttgtattt attttcaatt ttt                                1953

SEQ ID NO: 70              moltype = DNA  length = 1959
FEATURE                    Location/Qualifiers
source                     1..1959
                           mol_type = other DNA
                           organism = synthetic construct
SEQUENCE: 70
aaaaattgaa aataaataca aaggttcttg agggttgtgt taaattgaaa gcgagaaata     60
atcataaccc gggggccacca tgttcgtgtt cctagtccta ctaccgctag tctcttctgt    120
cagatttccg aacatcacga acctatgtcc gttcggagaa gtgttcaacg cgacaagatt    180
tgcgtctgtc tatgcgtgga acagaaaaag aatcagtaac tgcgtcgcgg actactccgt    240
cctatacaac tctgcctctt tctccacgtt caaatgctac ggtgtatctc gacaaagct     300
aaacgatcta tgcttcacca cgtctacgc ggactccttc gtaatcagag agatgaagt     360
tagacagatt gcgccgggac aaactggaaa gatcgcggat tataactaca agctaccgga    420
```

-continued

```
cgacttcacc ggatgtgtaa ttgcgtggaa ttcgaacaac ctagactcca aagtcggagg   480
aaactacaac tacttgtaca gactattcag aaagtccaac ctaaagccgt tcgagagaga   540
catctccacc gaaatctatc aggctggatc tacaccgtgt aatggtgtcg aaggattcaa   600
ctgctacttc ccgctacagt cttacggatt tcaaccgaca aacggtgtag gatatcagcc   660
gtacagagtc gtcgtactat ccttcgaact actacatgct ccggcgacag tatggtacat   720
ctggctagga ttcattgctg gactaattgc gatcgtcatg gtcaccatca tgctatgctg   780
tatgacctcc tgttgctcct gtctaaaggg atgttgttcc tgcggatcct gttgcaagtt   840
cgatgaagat gatagtgaac cggtcctaaa gggtgtcaag ctacactaca cagagccgga   900
agcttaataa tttttatctt tcattttgtt tttttctatg ctataagcca ccatgtactc   960
cttcgtgtcc gaagaaaccg gaaccttgat cgtcaactcc gtcctactat tcctagcgtt   1020
cgtcgtgttc ctactagtaa ccctagctat cctaaccgcg ctaagactat gtgcgtactg   1080
ctgcaacatc gtcaacgtgt ccctagtgaa gccgtccttc tacgtctact ccagagtcaa   1140
gaacctaaac tcctctagag tcccggacct actagttgag ccagaggctt aataaataaa   1200
aattattaag cctctggctc ctggactagt agagcgatat tatcggaact cggaggagtg   1260
tcggtgttta gcttgtagtt cccgattctg tatctagaat acgccgcaaa tccagaatct   1320
cccgcgactc tttgagaggc tcccaactta tagtacgata gggttctaga ggtcgctacg   1380
gtgatctcct tcggtaggtc cttgatgtca catcttccta ggtggtgtcc cgcaattctt   1440
agatgtcctc ttaggatgac cgctccgata accaattcgg attccaatag cggtctggtt   1500
aggatggttc catgtagcgg tacgttcaat aggatgttcg tctccgggtt gaacgaccac   1560
atagatctgg ttctcgcgaa tagtctgaag gaggcgatga agtaggatag ccacattagt   1620
cctactagac aagccatagc gatcgcgatt ccacctgtga tccagttgat tctgtagacc   1680
gcagctagaa cgaagcaggc caaggtgacc ggccatagta gccataggaa gattagcttg   1740
atgatgtaca agaatctgtt cctgttcgcg tacgcgaact gtagtaggca gatccaggtt   1800
aggaatagga atccgatgac taggttccac tgctctagta gcttcttcaa ctcttcgacg   1860
gtgatggttc cgttagaatc cgccatggtg gcttatgatt atttctcgct ttcaatttaa   1920
cacaaccctc aagaaccttt gtatttattt tcaattttt                          1959
```

SEQ ID NO: 71          moltype = DNA  length = 1941
FEATURE                Location/Qualifiers
source                 1..1941
                       mol_type = other DNA
                       organism = synthetic construct

SEQUENCE: 71

```
aaaaattgaa aataaataca aaggttcttg agggttgtgt taaattgaaa gcgagaaata   60
atcataagcc accatgttcg tgttcctagt cctactaccg ctagtctctt ctaacatcac   120
gaacctatgt ccgttcggag aagtgttcaa cgcgacaaga tttgcgtctg tctatgcgtg   180
gaacagaaaa agaatcagta actgcgtcgc ggactactcc gtcctataca actctgcctc   240
tttctccacg ttcaaatgct acggtgtatc tccgacaaag ctaaacgatc tatgcttcac   300
caacgtctac gcggactcct tcgtaatcag aggagatgaa gttagacaga ttgcgccgag   360
acaaactgga aagatcgcgg attataacta caagctaccg gacgacttca ccggatgtgt   420
aattgcgtgg aattcgaaca acctagactc caaagtcgga ggaaactaca actacttgta   480
cagactattc agaaagtcca acctaaagcc gttcgagaga gacatctcca ccgaaatcta   540
tcaggctgga tctacaccgt gtaatggtgt gtcgaaggattc aactgctact tcccgctaca   600
gtcttacgga tttcaaccga caaacggtgt aggatatcag ccgtacagag tcgtcgtact   660
atccttcgaa ctactacatg ctccggcgac agtatggtac atctggctag gattcattgc   720
tggactaatt gcgatcgtca tggtcaccat catgctatgc tgtatgacct cctgttgctc   780
ctgtctaaag ggatgttgtt cctgcggatc ctgttgcaag ttcgatgaag atgatagtga   840
accggtccta aagggtgtca agctacacta cacagagccg gaagcttaat aatttttatc   900
tttcattttg tttttttcta tgctataagc caccatgtac tccttcgtgt ccgaagaaac   960
cggaaccttg atcgtcaact ccgtcctact attcctagcg ttcgtcgtgt tcctactagt   1020
aaccctagct atcctaaccg cgctaagact atgtgcgtac tgctgcaaca tcgtcaacgt   1080
gtccctagtg aagccgtcct tctacgtcta ctccagagtc aagaacctaa actcctctag   1140
agtcccggac ctactagttg agccagaggc ttaataaata aaaattatta gcctctggc   1200
tcctggacta gtagagcgat attatcggaa ctggaggagt ggtcggtgtt tagcttgtag   1260
ttcccgattc tgtatctaga atacgccgca aatccagaat ctcccgcgac tctttgagag   1320
gctcccaact tatagtacga tagggttcta gaggtcgcta cggtgatctc cttcggtagg   1380
tccttgatgt cacatcttcc taggtggtgt cccgcaattc ttagatgtcc tcttaggatg   1440
accgctccga taaccaattc ggattccaat agcggtctgg ttaggatggt tccatgtagc   1500
ggtacgttca ataggatgtt cgtctccggg ttgaacgacc acatagatct ggttctcgcg   1560
aatagtctga ggaggcgat gaagtaggat agccacatta tccctactag acaagccata   1620
gcgatcgcga ttccacctgt gatccagttg attctgtaga ccgcagctag aacgaagcag   1680
gccaaggtga ccggccatag tagccatagg aagattagct tgatgatgta caagaatctg   1740
ttcctgttcg cgtacgcgaa ctgtagtagg cagatccagg ttaggaatag gaatccgatg   1800
actaggttcc actgctctag tagcttcttc aactcttcga cggtgatggt tccgttagaa   1860
tccgccatgg tggcttatga ttatttctcg ctttcaattt aacacaaccc tcaagaacct   1920
ttgtatttat tttcaatttt t                                             1941
```

SEQ ID NO: 72          moltype = DNA  length = 1947
FEATURE                Location/Qualifiers
source                 1..1947
                       mol_type = other DNA
                       organism = synthetic construct

SEQUENCE: 72

```
aaaaattgaa aataaataca aaggttcttg agggttgtgt taaattgaaa gcgagaaata   60
atcataaccc ggggccacca tgttcgtgtt cctagtccta ctaccgctag tctcttctaa   120
catcacgaac ctatgtccgt tcggagaagt gttcaacgcg acaagatttg cgtctgtcta   180
tgcgtggaac agaaaaagaa tcagtaactg cgtcgcggac tactccgtcc tatacaactc   240
tgcctctttc tccacgttca aatgctacgg tgtatctccg acaaagctaa acgatctatg   300
cttcaccaac gtctacgcgg actccttcgt aatcagagga gatgaagtta gacagattgc   360
```

```
gccgggacaa actggaaaga tcgcggatta taactacaag ctaccggacg acttcaccgg  420
atgtgtaatt gcgtggaatt cgaacaacct agactccaaa gtcggaggaa actacaacta  480
cttgtacaga ctattcagaa agtccaacct aaagccgttc gagagagaca tctccaccga  540
aatctatcag gctggatcta caccgtgtaa tggtgtcgaa ggattcaact gctacttccc  600
gctacagtct tacggatttc aaccgacaaa cggtgtagga tatcagccgt acagagtcgt  660
cgtactatcc ttcgaactac tacatgctcc ggcgacagta tggtacatct ggctaggatt  720
cattgctgga ctaattgcga tcgtcatggt caccatcatg ctatgctgta tgacctcctg  780
ttgctcctgt ctaaagggat gttgttcctg cggatcctgt tgcaagttcg atgaagatga  840
tagtgaaccg gtcctaaagg gtgtcaagct acactacaca gagccggaag cttaataatt  900
tttatctttc attttgtttt tttctatgct ataagccacc atgtactcct tcgtgtccga  960
agaaaccgga accttgatcg tcaactccgt cctactattc ctagcgttcg tcgtgttcct  1020
actagtaacc ctagctatcc taaccgcgct aagactatgt gcgtactgct gcaacatcgt  1080
caacgtgtcc ctagtgaagc cgtccttcta cgtctactcc agagtcaaga acctaaactc  1140
ctctagagtc ccggacctac tagttgagcc agaggcttaa taaataaaaa ttattaagcc  1200
tctggctcct ggactagtag agcgatatta tcggaactgg aggagtggtc ggtgtttagc  1260
ttgtagttcc cgattctgta tctagaatac gccgcaaatc cagaatctcc cgcgactctt  1320
tgagaggctc ccaacttata gtacgatagg gttctagagg tcgctacggt gatctccttc  1380
ggtaggtcct tgatgtcaca tcttcctagg tggtgtcccg caattcttag atgtcctctt  1440
aggatgaccg ctccgataac caattcggat tccaatagcg gtctggttag gatggttcca  1500
tgtagcggta cgttcaatag gatgttcgtc tccgggttga acgaccacat agatctggtt  1560
ctcgcgaata gtctgaagga ggcgatgaag taggatagcc acattagtcc tactagacaa  1620
gccatagcga tcgcgattcc acctgtgatc cagttgattc tgtagaccg agctagaacg  1680
aagcaggcca aggtgaccgg ccatagtagc cataggaaga ttagcttgat gatgtacaag  1740
aatctgttcc tgttcgcgta cgcgaactgt agtaggcaga tccaggttag gaataggaat  1800
ccgatgacta ggttccactg ctctagtagc ttcttcaact cttcgacggt gatggttccg  1860
ttagaatccg ccatggtggc ttatgattat ttctcgcttt caatttaaca caaccctcaa  1920
gaacctttgt atttattttc aatttt                                       1947
```

SEQ ID NO: 73          moltype = DNA  length = 1902
FEATURE                Location/Qualifiers
source                 1..1902
                       mol_type = other DNA
                       organism = synthetic construct
SEQUENCE: 73

```
aaaaattgaa aataaataca aaggttcttg agggttgtgt taaattgaaa gcgagaaata  60
atcataagcc accatgtgga cgacctgctt cttcatctcc ctaatcctaa tccagggaat  120
caagacccta tatcagccgt acagagtcgt cgtactatcc ttcgaactac tacatgctcc  180
ggcgacagta ggtcctggac ccggttatca ggctggatct acaccgtgta atggtgtcga  240
aggattcaac tgctacttcg gtcctggacc cggttatcag ctacagagt cgtcgtact  300
atccttcgaa ctactacatg ctccggcgac agtaggtcct ggacccggtt atcaggctgg  360
atctacaccg tgtaatggtg tcgaaggatt caactgctac ttcggtcctg gacccggtta  420
tcagccgtac agagtcgtcg tactatcctt cgaactacta catgctccgg cgacagtagg  480
tcctggaccc ggttatcagg ctggatctac accgtgtcag gattcaactg  540
ctacttcggt cctggacccg gttatcagcc gtacagagtc gtcgtactat ccttcgaact  600
actacatgct ccggcgacag taggtcctgg acccggttat caggctggat ctacaccgtg  660
taatggtgtc gaaggattca actgctactt cggtcctgga cccggttatc agccgtacag  720
agtcgtcgta ctatccttcg aactactaca tgctccggcg acagtaggtc ctggaccctg  780
ttatcaggct ggatctacac cgtgtaatgg tgtcgaagga ttcaactgct acttcgagcc  840
ggaagcttaa taatttttat cttttcatttt gttttttttct atgctataag ccaccatgta  900
ctccttcgtg tccgaagaaa ccggaacctt gatcgtcaac tccgtcctac tattcctagc  960
gttcgtcgtg ttcctactag taaccctagc tatcctaacc gcgctaagac tatgtgctg  1020
ctgctgcaac atcgtcaacg tgtccctagt gaagccgtcc ttctacgtct actccagagt  1080
caagaaccta aactcctcta gagtcccgga cctactagtt gagccagagg cttaataaat  1140
aaaaattatt aagcctctgg ctcctggact agtagagcga tattatcgga actgaggag  1200
tggtcggtgt ttagcttgta gttcccgatt ctgtatctag aatacgccg aaatccagaa  1260
tctcccgcga ctctttgaga ggctcccaac ttatagtacg ataggggtct agaggtcgct  1320
acggtgatct ccttcggtag gtccttgatg tcacatcttc ctaggtggtg tccgcaatt  1380
cttagatgtc ctcttaggat gaccgctccg ataaccaatt cggattccaa tagcggtctg  1440
gttaggatgg ttccatgtag cggtacgttc aataggatgt tcgtctccgg gttgaacgac  1500
cacatagatc tggttctcgc gaatagtctg aaggaggcga tgaagtagga tagcacatt  1560
agtcctacta gacaagccat agcgatcgcg attccacctg tgatccagtt gattctgtag  1620
accgcagcta gaacgaagca ggccaaggtg accggccata gtagccatag gaagattagc  1680
ttgatgatgt acaagaatct gttcctgttc gcgtacgcga actgtagtag gcagatccag  1740
gttaggaata ggaatccgat gactaggttc cactgctcta caactcttcg  1800
acggtgatgg ttccgttaga atccgccatg gtggcttatg attattttctc gctttcaatt  1860
taacacaacc ctcaagaacc tttgtatttta ttttcaattt tt                    1902
```

SEQ ID NO: 74          moltype = DNA  length = 1908
FEATURE                Location/Qualifiers
source                 1..1908
                       mol_type = other DNA
                       organism = synthetic construct
SEQUENCE: 74

```
aaaaattgaa aataaataca aaggttcttg agggttgtgt taaattgaaa gcgagaaata  60
atcataaccc ggggccacca tgtggacgac ctgcttcttc atctccctaa tcctaatcca  120
gggaatcaag accctatatc agccgtacag agtcgtcgta ctatccttcg aactactaca  180
tgctccggcg acagtaggtc ctggacccgg ttatcaggct ggatctacac cgtgtaatgg  240
tgtcgaagga ttcaactgct acttcggtcc tggacccggt tatcagccgt acagagtcgt  300
cgtactatcc ttcgaactac tacatgctcc ggcgacagta ggtcctggac ccggttatca  360
```

```
ggctggatct acaccgtgta atggtgtcga aggattcaac tgctacttcg gtcctggacc   420
cggttatcag ccgtacagag tcgtcgtact atccttcgaa ctactacatg ctccggcgac   480
agtaggtcct ggacccggtt atcaggctgg atctacaccg tgtaatggtg tcgaaggatt   540
caactgctac ttcggtcctg acccggtta tcagccgtac agagtcgtcg tactatcctt   600
cgaactacta catgctccgg cgacagtagg tcctggacta ggttatcagg ctggatctac   660
accgtgtaat ggtgtcgaag gattcaactg ctacttcggt cctggacccg gttatcagcc   720
gtacagagtc gtcgtactat ccttcgaact actacatgct ccggcgacag taggtcctgg   780
acccggttat caggctggat ctacaccgtg taatggtgtc gaaggattca actgctactt   840
cgagccggaa gcttaataat tttttatcttt catttttgttt ttttctatgc tataagccac   900
catgtactcc ttcgtgtccg aagaaaccgg aaccttgatc gtcaactccg tcctactatt   960
cctagcgttc gtcgtgttcc tactagtaac cctagctatc ctaaccgcgc taagactatg  1020
tgcgtactgc tgcaacatcg tcaacgtgtc cctagtgaag ccgtccttct acgtctactc  1080
cagagtcaag aacctaaact cctctagagt cccggaccta ctagttgagc cagaggctta  1140
ataaaataaaa attattaagc ctctggctcc tggactagta gagcgatatt atcggaactg  1200
gaggagtggt cggtgtttag cttgtagttc ccgattctgt atctagaata cgccgcaaat  1260
ccagaatctc ccgcgactct ttgagaggct cccaacttat agtacgatag ggttctagag  1320
gtcgctacgg tgatctcctt cggtaggtcc ttgatgtcac atcttcctag gtggtgtccc  1380
gcaattctta gatgtcctct taggatgacc gctccgataa ccaattcgga ttccaatagc  1440
ggtctggtta ggatggttcc atgtagcggt acgttcaata ggatgttcgt ctccgggttg  1500
aacgaccaca tagatctggt tctcgcgaat agtctgaagg aggcgatgaa gtaggatagc  1560
cacattagtc ctactagaca agccatagcg atcgcgattc cacctgtgat ccagttgatt  1620
ctgtagaccg cagctagaac gaagcaggcc aaggtgaccg gccatagtag ccataggaag  1680
attagcttga tgatgtacaa gaatctgttc ctgttcgcgt acgcgaactg tagtaggcag  1740
atccaggtta ggaataggaa tccgatgact aggttccact gctctagtag cttcttcaac  1800
tcttcgacgg tgatggttcc gttagaatcc gccatggtgg cttatgatta tttctcgctt  1860
tcaatttaac acaaccctca agaacctttg tatttattttt caattttt             1908
```

```
SEQ ID NO: 75          moltype = AA   length = 121
FEATURE                Location/Qualifiers
source                 1..121
                       mol_type = protein
                       organism = synthetic construct
REPEAT                 14..61
                       note = 2, 3, 4, 5, 6, 7, 8, 9, 10, or more than 10 REPEATS
SEQUENCE: 75
MFVFLVLLPL VSSYQPYRVV VLSFELLHAP ATVGPGPGYQ AGSTPCNGVE GFNCYFGPGP  60
GWYIWLGFIA GLIAIVMVTI MLCCMTSCCS CLKGCCSCGS CCKFDEDDSE PVLKGVKLHY  120
T                                                                   121
```

```
SEQ ID NO: 76          moltype = DNA   length = 363
FEATURE                Location/Qualifiers
source                 1..363
                       mol_type = other DNA
                       organism = synthetic construct
repeat_region          40..183
                       note = 2, 3, 4, 5, 6, 7, 8, 9, 10, or more than 10 REPEATS
SEQUENCE: 76
atgtttgttt ttcttgtttt attgccacta gtctctagtt accaaccata cagagtagta   60
gtactttctt ttgaacttct acatgcacca gcaactgttg gtcctggacc cggttatcag  120
gccggtagca caccttgtaa tggtgttgaa ggttttaatt gttactttgg tcctggaccc  180
ggttggtaca tttggctagg tttttatagct ggcttgttg ccatagtaat ggtgacaatt  240
atgctttgct gtatgaccag ttgctgtagt tgtctcaagg gctgttgttc ttgtggatcc  300
tgctgcaaat ttgatgaaga cgactctgag ccagtgctca aaggagtcaa attacattac  360
aca                                                                 363
```

```
SEQ ID NO: 77          moltype = AA   length = 313
FEATURE                Location/Qualifiers
source                 1..313
                       mol_type = protein
                       organism = synthetic construct
SEQUENCE: 77
MFVFLVLLPL VSSYQPYRVV VLSFELLHAP ATVGPGPGYQ AGSTPCNGVE GFNCYFGPGP  60
GYQPYRVVVL SFELLHAPAT VGPGPGYQAG STPCNGVEGF NCYFGPGPGY QPYRVVVLSF  120
ELLHAPATVG PGPGYQAGST PCNGVEGFNC YFGPGPGYQP YRVVVLSFEL LHAPATVGPG  180
PGYQAGSTPC NGVEGFNCYF GPGPGYQPYR VVVLSFELLH APATVGPGPG YQAGSTPCNG  240
VEGFNCYFGP GPGWYIWLGF IAGLIAIVMV TIMLCCMTSC CSCLKGCCSC GSCCKFDEDD  300
SEPVLKGVKL HYT                                                      313
```

```
SEQ ID NO: 78          moltype = DNA   length = 939
FEATURE                Location/Qualifiers
source                 1..939
                       mol_type = other DNA
                       organism = synthetic construct
SEQUENCE: 78
atgttcgtgt tcctagtcct actaccgcta gtctcttctt atcagccgta cagagtcgtc   60
gtactatcct tcgaactact acatgctccg gcgacagtag gtcctggacc cggttatcag  120
gctggatcta caccgtgtaa tggtgtcgaa ggattcaact gctacttcgg tcctggaccc  180
ggttatcagc cgtacagagt cgtcgtacta tccttcgaac tactacatgc tccggcgaca  240
gtaggtcctg gacccggtta tcaggctgga tctacaccgt gtaatggtgt cgaaggattc  300
```

```
aactgctact tcggtcctgg acccggttat cagccgtaca gagtcgtcgt actatccttc    360
gaactactac atgctccggc gacagtaggt cctggacccg gttatcaggc tggatctaca    420
ccgtgtaatg gtgtcgaagg attcaactgc tacttcggtc ctggacccgg ttatcagccg    480
tacagagtcg tcgtactatc cttcgaacta ctacatgctc cggcgacagt aggtcctgga    540
cccggttatc aggctggatc tacaccgtgt aatggtgtcg aaggattcaa ctgctacttc    600
ggtcctggac ccggttatca gccgtacaga gtcgtcgtac tatccttcga actactacat    660
gctccggcga cagtaggtcc tggacccggt tatcaggctg atctacaccc gtgtaatggt    720
gtcgaaggat tcaactgcta cttcggtcct ggacccggtt ggtacatctg ctaggattca    780
attgctggac taattgcgat cgtcatggtc accatcatgc tatgctgtat gacctcctgt    840
tgctcctgtc taaagggatg ttgttcctgc ggatcctgt gcaagttcga tgaagatgat    900
agtgaaccgg tcctaaaggg tgtcaagcta cactacaca                          939
```

SEQ ID NO: 79          moltype = AA   length = 121
FEATURE                Location/Qualifiers
source                 1..121
                       mol_type = protein
                       organism = synthetic construct
REPEAT                 14..61
                       note = 2, 3, 4, 5, 6, 7, 8, 9, 10, or more than 10 REPEATS
SEQUENCE: 79
MFVFLVLLPL VSSYQPYRVV VLSFELLHAP ATVGPGPGYQ AGSTPCNGVK GFNCYFGPGP    60
GWYIWLGFIA GLIAIVMVTI MLCCMTSCCS CLKGCCSCGS CCKFDEDDSE PVLKGVKLHY   120
T                                                                  121

SEQ ID NO: 80          moltype = AA   length = 313
FEATURE                Location/Qualifiers
source                 1..313
                       mol_type = protein
                       organism = synthetic construct
SEQUENCE: 80
MFVFLVLLPL VSSYQPYRVV VLSFELLHAP ATVGPGPGYQ AGSTPCNGVE GFNCYFGPGP    60
GYQPYRVVVL SFELLHAPAT VGPGPGYQAG STPCNGVKGF NCYFGPGPGY QPYRVVVLSF   120
ELLHAPATVG PGPGYQAGST PCNGVEGFNC YFGPGPGYQP YRVVVLSFEL LHAPATVGPG   180
PGYQAGSTPC NGVEGFNCYF GPGPGYQPYR VVVLSFELLH APATVGPGPG YQAGSTPCNG   240
VEGFNCYFGP GPGWYIWLGF IAGLIAIVMV TIMLCCMTSC CSCLKGCCSC GSCCKFDEDD   300
SEPVLKGVKL HYT                                                     313

SEQ ID NO: 81          moltype = DNA   length = 2097
FEATURE                Location/Qualifiers
source                 1..2097
                       mol_type = other DNA
                       organism = synthetic construct
SEQUENCE: 81
```
```
aaaaattgaa aataaataca aaggttcttg agggttgtgt taaattgaaa gcgagaaata    60
atcataagcc accatgttcg tgttcctagt cctactaccg ctagtctctt cttatcagcc   120
gtacagagtc gtcgtactat ccttcgaact actacatgct ccggcgacag taggtcctgg   180
acccggttat caggctggat ctacaccgtg taatggtgtc gaaggattca actgctactt   240
cggtcctgga cccggttatc agccgtacag agtcgtcgta ctatccttcg aactactaca   300
tgctccggcg acagtaggtc ctggacccgg ttatcaggct ggatctacac cgtgtaatgg   360
tgtcgaagga ttcaactgct acttcggtcc tggacccggt ggtcctggac ccggttatca   420
gccgtacaga gtcgtcgtac tatccttcga actactacat gctccggcga cagtaggtcc   480
tggacccggt tatcaggctg atctacacc gtgtaatgg gtcgaaggat tcaactgcta   540
cttcggtcct ggacccggtt atcagccgta cagagtcgtc gtactatcct tcgaactact   600
acatgctccg gcgacagtag gtcctggacc cggttatcag gctggatcta caccgtgtaa   660
tggtgtcgaa ggattcaact gctacttcgg tcctggaccc ggtggtcctg gacccggtta   720
tcagccgtac agagtcgtcg tactatcctt cgaactacta catgctccgg cgacagtagg   780
tcctggaccc ggttatcagg ctggatctac accgtgtaat aatggtgtcg aaggattcaa   840
ctgctacttc tggtacatct ggctaggatt cattgctgga ctaattgcga tcgtcatggt   900
caccatcatg ctatgctgta tgacctcctg ttgctcctgt ctaaagggat gttgttcctg   960
cggatcctgt tgcaagttcg atgaagatga tagtgaaccg gtcctaaagg tgtgtcaagc   1020
acactacaca gagccggaag cttaataatt tttatctttc attttgtttt tttctatgct   1080
ataagccacc atgtactcct tcgtgtccga agaaaccgga accttgatcg tcaactccgt   1140
cctactattc ctagcgttcg tcgtgttcct actagtaacc ctagctatcc taaccgcgct   1200
aagactatgt gcgtactgct gcaacatcgt caacgtgtcc ctagtgaagc cgtccttcta   1260
cgtctactcc agagtcaaga acctaaactc ctctagagtc ccggacctac tagttgagcc   1320
agaggcttaa taaataaaaa ttattaagcc tctggctcct ggactagtag agcgatatta   1380
tcggaactgg aggagtggtc ggtgtttagc ttgtagttcc cgattctgta tctagaatac   1440
gccgcaaatc cagaatctcc cgcgactctt tgagaggctc ccaacttata gtacgatagg   1500
gttctagagg tcgctacggt gatctccttc ggtaggtcct tgatgtcaca tcttcctagg   1560
tggtgtcccg caattcttag atgtcctctt aggatgaccg ctccgataac caattcggat   1620
tccaatagcg gtctggttag gatggttcca tgtagcggta cgttcaatag gatgttcgtc   1680
tccgggttga acgaccacat agatctggtt ctcgcgaata gtctgaagga ggcgatgaag   1740
taggatagcc acattagtcc tactagacaa gccatagcga tcgcgattcc acctgtgatc   1800
cagttgattc tgtagaccgc agctagaacg aagcaggcca aggtgaccgg ccatagtagc   1860
cataggaaga ttagcttgat gatgtacaag aatctgttcc tgttcgcgta cgcgaactgc   1920
agtaggcaga tccaggttag gaataggaat ccgatgacta ggtccactg ctctagtagc   1980
ttcttcaact cttcgacggt gatggttccg ttagaatccg ccatggtggc ttatgattat   2040
ttctcgcttt caatttaaca caaccctcaa gaacctttgt atttatttc aattttt      2097
```

```
SEQ ID NO: 82           moltype = DNA   length = 2103
FEATURE                 Location/Qualifiers
source                  1..2103
                        mol_type = other DNA
                        organism = synthetic construct
SEQUENCE: 82
aaaaattgaa aataaataca aaggttcttg agggttgtgt taaattgaaa gcgagaaata    60
atcataaccc ggggccacca tgttcgtgtt cctagtccta ctaccgctag tctcttctta   120
tcagccgtac agagtcgtcg tactatcctt cgaactacta catgctccgg cgacagtagg   180
tcctggaccc ggttatcagg ctggatctac accgtgtaat ggtgtcgaag gattcaactg   240
ctacttcggt cctggacccg gttatcagcc gtacagagtc gtcgtactat ccttcgaact   300
actacatgct ccggcgacag taggtcctgg acccggttat caggctggat ctacaccgtg   360
taatggtgtc gaaggattca actgctactt cggtcctgga cccggtggtc ctggacccgg   420
ttatcagccg tacagagtcg tcgtactatc cttcgaacta ctacatgctc cggcgacagt   480
aggtcctgga cccggttatc aggctggatc tacaccgtg aatggtgtcg aaggattcaa   540
ctgctacttc ggtcctggac ccggttatca gccgtacaga gtcgtcgtac tatccttcga   600
actactacat gctccggcga cagtaggtcc tggacccggt tatcaggctg gatctacacc   660
gtgtaatggt gtcgaaggat tcaactgcta cttcggtgct ggacccggtg gtcctggacc   720
cggttatcag ccgtacagag tcgtcgtact atccttcgaa ctactacatg ctccggcgac   780
agtaggtcct ggacccggtt atcaggctgg atctacaccg tgtaataatg gtgtcgaagg   840
attcaactgc tacttctggt acatctggct aggattcatt gctggactaa ttgcgatcgt   900
catggtcacc atcatgctat gctgtatgac ctcctgttgc tcctgtctaa agggatgttg   960
ttcctgcgga tcctgttgca agttcgatga agatgatagt gaaccggtcc taaagggtgt  1020
caagctacac tacacagagc cggaagctta ataattttta tctttcattt tgttttttc   1080
tatgctataa gccaccatgt actccttcgt gtccgaagaa accggaacct tgatcgtcaa  1140
ctccgtccta ctattcctag cgttcgtcgt gttcctacta gtaaccctag ctatcctaac  1200
cgcgctaaga ctatgtgcgt actgctgcaa catcgtcaac gtgtccctag tgaagccgtc  1260
cttctacgtc tactccagag tcaagaacct aaactcctct agagtcccgg acctactagt  1320
tgagccagag gcttaataaa taaaaattat taagcctctg gctcctggac tagtagagcg  1380
atattatcgg aactggagga gtggtcggtg tttagcttgt agttcccgat tctgtatcta  1440
gaatacgccg caaatccaga atctcccgcg actctttgag aggctcccaa cttatagtac  1500
gatagggttc tagaggtcgc tacggtgatc tccttcggta ggtccttgat gtcacatctt  1560
cctaggtggt gtcccgcaat tcttagatgt cctcttagga tgaccgctcc gataaccaat  1620
tcggattcca atagcggtct ggttaggatg gttccatgta gcggtacgtt caataggatg  1680
ttcgtctccg ggttgaacga ccacatagat ctggttctcg cgaatagtct gaaggaggcg  1740
atgaagtagg atagccacat tagtcctact agacaagcca tagcgatcgc gattccacct  1800
gtgatccagt tgattctgta gaccgcagct agaacgaagc aggccaaggt gaccggccat  1860
agtagccata ggaagattag cttgatgatg tacaagaatc tgttcctgtt cgcgtacgcg  1920
aactgtagta ggcagatcca ggttaggaat aggaatccga tgactaggtt ccactgctct  1980
agtagcttct tcaactcttc gacggtgatg gttccgttag aatccgccat ggtggcttat  2040
gattatttct cgctttcaat ttaacacaac cctcaagaac ctttgtattt attttcaatt  2100
ttt                                                                2103

SEQ ID NO: 83           moltype = DNA   length = 4779
FEATURE                 Location/Qualifiers
source                  1..4779
                        mol_type = other DNA
                        organism = synthetic construct
SEQUENCE: 83
aaaaattgaa aataaataca aaggttcttg agggttgtgt taaattgaaa gcgagaaata    60
atcataagcc accatgttcg tgttcctagt cctactaccg ctagtctctt ctcagtgtgt   120
aaacctaaca acgagaacac aactaccacc ggcgtacacc aattctttca caagaggagt   180
atattacccg gacaaggtgt tcagatcctc cgtactacat tctacacagg acctattcct   240
accgttcttc tctaacgtaa catggttcca cgcgatccat gtctctggaa caaacggaac   300
gaagagattc gataacccgg tcttgccgtt caacgatggt gtatactttg cgtccaccga   360
gaagtccaac atcatcagag gatggatctt cggaaccacc ttggattcta agacccagtc   420
cttgctaatc gtcaacaacg cgaccaacgt cgtcatcaaa gtctgcgaat tccagttctg   480
taacgacccg ttcttgggag tctactacca caagaacaac aagtcctgga tggaatccga   540
gttcagagtc tactcttccg cgaacaactg caccttcgaa tatgtatctc agccgttcct   600
aatggaccta gagggaaagc agggaaactt caagaaccta agagagttcg tattcaagaa   660
catcgacgga tacttcaaga tctactccaa gcacactccg atcaacctag ttagagatct   720
accgcaagga ttctctgcgc tagaaccgtt agtagatttg ccgatcggaa tcaacatcac   780
cagattccag acactactag cgctacacag atcttaccta acgccgggag attcttcttc   840
tggatggact gctggtgctg cggcttatta tgtaggatac ctacagccga gaaccttcct   900
attgaagtac aacgaaaacg gaaccatcac cgatgccgta gattgtgctc tagatccgct   960
atccgaaacg aagtgcaccc taaagtcttt caccgtcgag aagggaatct accagacctc  1020
caactttaga gtacagccga ccgaatccat cgtcagattt ccgaacatca cgaacctatg  1080
tccgttcgga gaagtgttca acgcgacaag atttgcgtct gtctatgcgt ggaacagaaa  1140
aagaatcagt aactgcgtcg cggactactc cgtcctatac aactctgcct ctttctccac  1200
gttcaaatgc tacggtgtat ctccgacaaa gctaaacgat ctatgcttca ccaacgtcta  1260
cgcggactcc ttcgtaatca gaggagatga agttagacag attgcgccgg acaaactgg   1320
aaagatcgcg gattataact acaagctacc ggacgacttc accggatgtg taattgcgtg  1380
gaattcgaac aacctagact ccaaagtcgg aggaaactac aactacttgt acagactatt  1440
cagaaagtcc aacctaaagc cgttcgagag agacatctcc accgaaatct atcaggctgg  1500
atctacaccg tgtaatggtg tcgaaggatt caactgctac ttcccgctac agtcttacgg  1560
atttcaaccg acaaacggtg taggatatca gccgtacaga gtcgtcgtac tatccttcga  1620
actactacat gctccggcga cagtatgtgg accgaaaaag tctaccaacc tagtcaagaa  1680
caaatgcgtc aactttaact tcaacggact aaccggaacc ggtgtcctaa ccgaatctaa  1740
caagaagttt ctaccgttcc agcagttcgg aagagatatc gcggatacaa cagacgctgt  1800
```

```
cagagatccg caaaccttgg agatcctaga tatcacaccg tgttctttcg gtggtgtctc    1860
tgtaattact ccgggaacga acacctccaa tcaagtagcg gtactatacc aggacgtgaa    1920
ctgtacagaa gtaccggtag ctattcacgc ggatcaacta acaccaactt ggagagtgta    1980
ctccaccgga tctaacgtat tccaaacaag agcgggatgt ctaatcggag cggaacacgt    2040
aaacaactcc tacgaatgtg atatcccgat tggagcggga atctgtgcgt cttaccaaac    2100
acaaacaaac tctccgagaa gagcgagatc tgtagcctct caatctatta tcgcctacac    2160
catgtccttg ggagccgaaa attctgtcgc gtactccaac aattctatcg cgatcccgac    2220
aaacttcacc atctctgtaa caaccgagat cctaccggtg tctatgacca agacatctgt    2280
cgattgcacc atgtacatct gcggagattc caccgagtgc tccaacctac tactacagta    2340
cggatctttc tgtacccagc taaacagagc gttgactgga atcgctgtag agcaggataa    2400
gaacactcaa gaggtattcg cgcaagtcaa gcagatctat aagactccgc cgatcaagga    2460
cttcggaggt ttcaacttct ctcagatctt gccggatccg tccaaaccgt ctaagagatc    2520
tttcatcgag gacctactat tcaacaaagt caccctagct gacgcgggat tcatcaaaca    2580
atacggagat tgcttgggag acattgcggc gagagatcta atttgcgcgc agaagtttaa    2640
cggattgaca gtactaccgc cgctactaac cgatgagatg attgcgcagt acacgtctgc    2700
tctattggcg ggaacaatta caagtggatg gacatttgga gccggtgccg ctctacaaat    2760
tccgtttgct atgcaaatgg cgtacagatt caacggaatc ggagtaaccc agaacgtctt    2820
gtacgagaac cagaagctaa tcgcgaacca gttcaattcc gcgatcggaa agatccagga    2880
cagtctatct tctactgctt cggcgttggg aaagctacag gatgtagtaa atcaaaacgc    2940
gcaggcgcta aacaccttgg tcaagcaact atcctctaac ttcggagcga tctcgtccgt    3000
cctaaacgac atcttatcca gactagataa ggtcgaagcg gaggtccaga tcgatagact    3060
aatcactgga agattgcagt ccctacagac ctacgtaaca gcaactaa ttagagcggc    3120
ggagattaga gcctctgcta atctagctgc gaccaagatg tccgaatgtg tcttgggaca    3180
atccaagaga gtggacttct gcggaaaggg ataccaccta atgtctttcc cacaatctgc    3240
gccgcatggt gtcgtattcc tacatgtaac atatgtgccg gcgcaagaaa agaacttcac    3300
aacagctcca gcgatctgcc atgatggaaa agctcatttc ccgagagagg gagtctttgt    3360
ctctaacgga actcattggt tcgtcaccca gagaaacttc tacgagccgc agatcatcac    3420
caccgacaac acattcgtct cgggaaactg cgacgtggtc atcggaatcg taaacaaatac    3480
cgtctacgat ccgttgcagc cggaactaga ctccttcaaa gaagagttgg acaagtactt    3540
caagaaccac acctctccgg atgtggactt gggagatatc tctggaatca acgcgtccgt    3600
cgtcaacatc cagaaagaaa tcgatagatt gaacgaggtc gcgaagaact tgaacgagtc    3660
cctaatcgac ctacaagagc taggaaaata cgagcagtac atcaagtggc cggagccgga    3720
agcttaataa tttttatctt tcattttgtt tttttctatg ctataagcca ccatgtactc    3780
cttcgtgtcc gaagaaaccg gaaccttgat cgtcaactcc gtcctactat tcctagccgt    3840
cgtcgtgttc ctactagtaa ccctagctat cctaaccgcg ctaagactat gtgcgtactg    3900
ctgcaacatc gtcaacgtgt ccctagtgaa gccgtccttc tacgtctact ccagagtcaa    3960
gaacctaaac tcctctagag tcccggacct actagttgag ccagaggctt aataaataaa    4020
aattattaag cctctggctc ctggactagt agagcgatat tatcggaact ggaggagtgg    4080
tcggtgttta gcttgtagtt cccgattctg tatctagaat acgccgcaaa tccagaatct    4140
cccgcgactc tttgagaggc tcccaactta tagtacgata gggttctaga ggtcgctacg    4200
gtgatctcct tcggtaggtc cttgatgtca catcttccta ggtggtgtcc cgcaattctt    4260
agatgtcctc ttaggatgac cgctccgata accaattcgg attccaatag cggtctggtt    4320
aggatggttc catgtagcgg tacgttcaat aggatgttcg tctccgggtt gaacgaccac    4380
atagatctgg ttctcgcgaa tagtctgaag gaggcgatga agtaggatag ccacattagt    4440
cctactagac aagccatagc gatcgcgatt ccacctgtga tccagttgat tctgtagacc    4500
gcagctagaa cgaagcaggc caaggtgacc ggccatagta gccataggaa gattagcttg    4560
atgatgtaca agaatctgtt cctgttcgcg tacgcgaact gtagtgagca gatccaggtt    4620
aggaatagga atccgatgac taggttccac tgctctagta gcttcttcaa ctcttcgacg    4680
gtgatggttc cgttagaatc cgccatggtg gcttatgatt atttctcgct ttcaatttaa    4740
cacaaccctc aagaacctct gtatttattt tcaattttt                          4779
```

```
SEQ ID NO: 84         moltype = DNA   length = 4785
FEATURE               Location/Qualifiers
source                1..4785
                      mol_type = other DNA
                      organism = synthetic construct
SEQUENCE: 84
aaaaattgaa aataaataca aaggttcttg agggttgtgt taaattgaaa gcgagaaata    60
atcataaccc ggggccacca tgttcgtgtt cctagtccta ctaccgctag tctcttctca    120
gtgtgtaaac ctaacaacga gaacacaact accaccggcg tacaccaatt cttttcacaag   180
aggagtatat tacccggaca aggtgttcag atcctccgta ctacattcta cacaggacct    240
attcctaccg ttcttctcta acgtaacatg gttccacgcg atccatgtct ctggaacaaa    300
cggaacgaag agattcgata acccggtgtt gccgttcaac gatggtgtat actttgcgtc    360
caccgagaag tccaacatca tcagaggatg gatcttcgga accacccttgg attctaagac    420
ccagtccttg ctaatcgtca caacgcgac caacgtcgtc atcaaagtct gcgaattcca    480
gttctgtaac gacccgttct tgggagtcta ctaccacaag aacaacaagt cctggatgga    540
atccgagttc agagtctact cttccgcgaa caactgcacc ttcgaatatg tatctcagcc    600
gttcctaatg gacctagagg gaaagcaggg aaacttcaag aacctaagag agttcgtatt    660
caagaacatc acggcgatact tcaagatcta ctccaagcac actccgatca acctagttag    720
agatctaccg caaggattct ctgcgctaga accgttagta gatttgccga tcggaatcaa    780
catcaccaga ttccagacac tactagcgct acacagatct tacctaacgc cgggagattc    840
ttcttctgga tggactgctg gtgctgcggc ttattatgta ggatacctac agccgagaac    900
cttcctattg aagtacaacg aaaacggaac catcaccgat gccgtagatt gtgctctaga    960
tccgctatcc gaaacgaagt gcaccctaaa gtctttcacc gtcgagaagg gaatctacca    1020
gacctccaac tttagagtac agccgaccga atccatcgtc agattccgaa acatcacgaa    1080
cctatgtccg ttcggagaag tgttcaacgc gacaagattt gcgtctgtct atgcgtggaa    1140
cagaaaaaga atcagtaact gcgtcgcgga ctactccgtc ctatacaact ctgcctcttt    1200
ctccacgttc aaatgctacg gtgtatctcc gacaaagcta aacgatctat gcttcaccaa    1260
cgtctacgcg gactccttcg taatcagagg agatgaagtt agacagattg cgccgggaca    1320
```

```
aactggaaag atcgcggatt ataactacaa gctaccggac gacttcaccg gatgtgtaat   1380
tgcgtggaat tcgaacaacc tagactccaa agtcggagga aactacaact acttgtacag   1440
actattcaga aagtccaacc taaagccgtt cgagagagac atctccaccg aaatctatca   1500
ggctggatct acaccgtgta atggtgtcga aggattcaac tgctacttcc cgctacagtc   1560
ttacggattt caaccgacaa acggtgtagg atatcagccg tacagagtcg tcgtactatc   1620
cttcgaacta ctacatgctc cggcgacagt atgtggaccg aaaaagtcta ccaacctagt   1680
caagaacaaa tgcgtcaact ttaacttcaa cggactaacc ggaaccggtg tcctaaccga   1740
atctaacaag aagtttctac cgttccagca gttcggaaga gatatcgcgg atacaacaga   1800
cgctgtcaga gatccgcaaa ccttggagat cctagatatc acaccgtgtt ctttcggtgg   1860
tgtctctgta attactccgg gaacgaacac ctccaatcaa gtagcggtac tataccagga   1920
cgtgaactgt acagaagtac cggtagctat tcacgcggat caactaacac caacttggag   1980
agtgtactcc accggatcta acgtattcca aacaagagcg ggatgtctaa tcggagcgga   2040
acacgtaaac aactcctacg aatgtgatat cccgattgga gcgggaatct gtgcgtctta   2100
ccaaacacaa acaaactctc cgagaagagc gagatctgta gcctctcaat ctattatcgc   2160
ctacaccatg tccttgggag ccgaaaattc tgtcgcgtac tccaacaatt ctatcgcgat   2220
cccgacaaac ttcaccatct ctgtaacaac cgagatccta ccggtgtcta tgaccaagac   2280
atctgtcgat tgcaccatgt acatctgcgg agattccacc gagtgctcca acctactact   2340
acagtacgga tctttctgta cccagctaaa cagagcgttg actggaatcg ctgtagagca   2400
ggataagaac actcaagagg tattcgcgca agtcaagcag atctataaga ctccgccgat   2460
caaggacttc ggaggtttca acttctctca gatcttgccg gatccgtcca aaccgtctaa   2520
gagatctttc atcgaggacc tactattcaa caaagtcacc ctagctgacg cgggattcat   2580
caaacaatac ggagattgct tgggagacat tgcggcgaga gctcaattt gcgcgcagaa   2640
gtttaacgga ttgacagtac taccgccgct actaaccgat gagatgattg cgcagtacac   2700
gtctgctcta ttggcgggaa caattacaag tggatggaca tttggagccg gtgccgctct   2760
acaaattccg tttgctatgc aaatggcgta cagattcaac ggaatcggag taacccagaa   2820
cgtcttgtac gagaaccaga agctaatcgc gaaccagttc aattccgcga tcggaaagat   2880
ccaggacagt ctatcttcta ctgcttcggc gttgggaaag ctacaggatg tagtaaatca   2940
aaacgcgcag gcgctaaaca ccttggtcaa gcaactatcc tctaacttcg gagcgatctc   3000
gtccgtccta aacgacatct tatccagact agataaggtc gaagcggagg tccagatcga   3060
tagactaatc actggaagat tgcagtccct acagacctac gtaacacagc aactaattag   3120
agcggcggag attagagcct ctgctaatct agctgcgacc aagatgtccg aatgtgtctt   3180
gggacaatcc aagagagtgg acttctgcgg aaagggatac cacctaatgt ctttcccaca   3240
atctgcgccg catggtgtcg tattcctaca tgtaacatat gtgccggcgc aagaaaagaa   3300
cttcacaaca gctccagcga tctgcacatga tggaaaagct catttcccga gagagggaat   3360
ctttgtctct aacggaactc attggttcgt cacccagaga aacttctacg agccgcagat   3420
catcaccacc gacaacacat tcgtctcggg aaactgcgac gtggtcatcg gaatcgtaaa   3480
caataccgtc tacgatccgt tgcagccgga actagactcc ttcaaagaag agttggacaa   3540
gtacttcaag aaccacacct ctccggatgt ggacttggga gatatctctg gaatcaacgc   3600
gtccgtcgtc aacatccaga aagaaatcga tagattgaac gaggtcgcga agaacttgaa   3660
cgagtcccta atcgacctac aagagctagg aaaaatacgag cagtacatca agtggccgga   3720
gccggaagct taataatttt tatctttcat tttgttttt tctatgctat aagccaccat   3780
gtactccttc gtgtccgaag aaaccggaac cttgatcgtc aactccgtcc tactattcct   3840
agcgttcgtc gtgttcctac tagtaaccct agctatccta accgcgctaa gactatgtgc   3900
gtactgctgc aacatcgtca acgtgtccct agtgaagccg tccttctacg tctactccag   3960
agtcaagaac ctaaactcct ctagagtccc ggacctacta gttgagccag aggcttaata   4020
aataaaaatt attaagcctc tggctcctgg actagtagag cgatattatc ggaactggag   4080
gagtggtcgg tgtttagctt gtagttcccg attctgtatc tagaatacgc gcaaatcca   4140
gaatctcccg cgactctttg agaggctccc aacttatagt acgatagggt tctagaggtc   4200
gctacggtga tctccttcgg taggtccttg atgtcacatc ttcctaggtg gtgtcccgca   4260
attcttagat gtcctcttag gatgaccgct ccgataacca attcggattc caatagcggt   4320
ctggttagga tggttccatg tagcggtacg ttcaatagga tgttcgtctc cgggttgaac   4380
gaccacatag atctggttct cgcgaatagt ctgaaggagg cgatgaagta ggatagccac   4440
attagtccta ctagacaagc catagcgatc gcgattccac ctgtgatcca gttgattctg   4500
tagaccgcag ctagaacgaa gcaggccaag gtgaccggcc atagtagcca taggaagatt   4560
agcttgatga tgtacaagaa tctgttcctg ttcgcgtacg cgaactgtag taggcagatc   4620
caggttagga ataggaatcc gatgactagg ttccactgct ctagtagctt cttcaactct   4680
tcgacggtga tggttccgtt agaatccgcc atggtggctt atgattattt ctcgctttca   4740
atttaacaca accctcaaga acctttgtat ttattttcaa ttttt           4785
```

```
SEQ ID NO: 85          moltype = DNA   length = 4779
FEATURE                Location/Qualifiers
source                 1..4779
                       mol_type = other DNA
                       organism = synthetic construct
SEQUENCE: 85
aaaaattgaa aataaataca aaggttcttg agggttgtgt taaattgaaa gcgagaaata   60
atcataagcc accatgttcg tgttcctagt cctactaccg ctagtctctt ctcagtgtgt   120
aaacctaaca acgagaacac aactaccacc ggcgtacacc aattctttca caagaggagt   180
atattacccg gacaaggtgt tcagatcctc cgtactacat tctacacagg acctattcct   240
accgttcttc tctaacgtaa catggttcca cgcgatccat gtctctggaa caaacggaac   300
gaagagattc gataacccgg tcttgccgtt caacgatggt gtatactttg cgtccaccga   360
gaagtccaac atcatcagag gatggatctt cggaaccacc ttggattcta agacccagtc   420
cttgctaatc gtcaacaacg cgaccaacgt cgtcatcaaa gtctgcgaat ccagttctg   480
taacgaccga ttcttgggag tctactacca caagaacaac aagtcctgga tggaatccga   540
gttcagagtc tactcttccg cgaacaactg caccttcgaa tatgtatctc agccgttcct   600
aatggaccta gagggaaagc agggaaactt caagaaccta agagagttcg tattcaagaa   660
catcgacgga tacttcaaga tctactccaa gcacactccg atcaacctag ttagagatct   720
accgcaagga ttctctgcgc tagaaccgtt agtagatttg ccgatcggaa tcaacatcac   780
cagattccag acactactag cgctacacag atcttaccta acgccgggag attcttcttc   840
```

```
tggatggact gctggtgctg cggcttatta tgtaggatac ctacagccga gaaccttcct    900
attgaagtac aacgaaaacg gaaccatcac cgatgccgta gattgtgctc tagatccgct    960
atccgaaacg aagtgcaccc taaagtcttt caccgtcgag aagggaatct accagacctc   1020
caactttaga gtacagccga ccgaatccat cgtcagattt ccgaacatca cgaacctatg   1080
tccgttcgga gaagtgttca acgcgacaag atttgcgtct gtctatgcgt ggaacagaaa   1140
aagaatcagt aactgcgtcg cggactactc cgtcctacac aactctgcct ctttctccac   1200
gttcaaatgc tacggtgtat ctccgacaaa gctaaacgat ctatgcttca ccaacgtcta   1260
cgcggactcc ttcgtaatca gaggagatga agttagacag attgcgccgg acaaactgg    1320
aaagatcgcg gattataact acaagctacc ggacgacttc accggatgtg taattgcgtg   1380
gaattcgaac aacctagact ccaaagtcgg aggaaactac aactacttgt acagactatt   1440
cagaaagtcc aacctaaagc cgttcgagag agacatctcc accgaaatct atcaggctgg   1500
atctacaccg tgtaatggtg tcgaaggatt caactgctac ttcccgctac agtcttacgg   1560
atttcaaccg acaaacggtg taggatatca gccgtacaga gtcgtcgtac tatccttcga   1620
actactacat gctccggcga cagtatgtgg accgaaaaag tctaccaacc tagtcaagaa   1680
caaatgcgtc aactttaact tcaacggact aaccggaacc ggtgtcctaa ccgaatctaa   1740
caagaagttt ctaccgttcc agcagttcgg aagagatatc gcggatacaa cagacgctgt   1800
cagagatccg caaaccttgg agatcctaga tatcacaccg tgttctttcg gtggtgtctc   1860
tgtaattact ccgggaacga acacctccaa tcaagtagcg gtactatacc aggacgtgaa   1920
ctgtacagaa gtaccggtag ctattcacgc ggatcaacta acaccaactt ggagagtgta   1980
ctccaccgga tctaacgtat tccaaacaag agcgggatgt ctaatcggag cggaacacgt   2040
aaacaactcc tacgaatgtg atatcccgat tggagcggga atctgtgcgt cttaccaaac   2100
acaaacaaac tctccgagaa gagcgagatc tgtagcctct caatctatta tcgcctacac   2160
catgtccttg ggagccgaaa attctgtcgc gtactccaac aattctatcg cgatcccgac   2220
aaacttcacc atctctgtaa caaccgagat cctaccggtg tctatgacca agacatctgt   2280
cgattgcacc atgtacatct gcggagattc caccgagtgc tccaacctac tactacagta   2340
cggatctttc tgtacccagc taaacagagc gttgactgga atcgctgtag agcaggataa   2400
gaacactcaa gaggtattcg cgcaagtcaa gcagatctat aagactccgc cgatcaagga   2460
cttcggaggt ttcaacttct ctcagatctt gccggatccg tccaaaccgt ctaagagatc   2520
tttcatcgag gacctactat tcaacaaagt caccctagct gacgcgggat tcatcaaaca   2580
atacggagat tgcttgggag acattgcggc gagagatcta atttgcgcgc agaagtttaa   2640
cggattgaca gtactaccgc cgctactaac cgatgagatg attgcgcagt acacgtctgc   2700
tctattggcg ggaacaatta caagtggatg gacatttgga gccggtgccg ctctacaaat   2760
tccgtttgct atgcaaatgg cgtacagatt caacggaatc ggagtaaccc agaacgtctt   2820
gtacgagaac cagaagctaa tcgcgaacca gttcaattcc gcgatcggaa agatccagga   2880
cagtctatct tctactgctt cggcgttggg aaagctacag gatgtagtaa atcaaaacgc   2940
gcaggcgcta aacaccttgg tcaagcaact atcctctaac ttcggagcga tctcgtccgt   3000
cctaaacgac atcttatcca gactagatcc accggaagcg gaggtccaga tcgatagact   3060
aatcactgga agattgcagt ccctacagac ctacgtaaca cagcaactaa ttagagcggc   3120
ggagattaga gcctctgcta atctagctgc gaccaagatg tccgaatgtg tcttgggaca   3180
atccaagaga gtggacttct gcggaaaggg ataccaccta atgtctttcc cacaatctgc   3240
gccgcatggt gtcgtattcc tacatgtaac atatgtgccg gcgcaagaaa agaacttcac   3300
aacagctcca gcgatctgcc atgatggaaa agctcatttc ccgagagagg gagtctttgt   3360
ctctaacgga actcattggt tcgtcaccca gagaaactct tacgagccgc agatcatcac   3420
caccgacaac acattcgtct cgggaaactg cgacgtggtc atcggaatcg taaacaatac   3480
cgtctacgat ccgttgcagc cggaactaga ctccttcaaa gaagagttgg acaagtactt   3540
caagaaccac acctctccgg atgtggactt gggagatatc tctggaatca acgcgtccgt   3600
cgtcaacatc cagaaagaaa tcgatagatt gaacggagtc gcaagaaact tgaacgagtc   3660
cctaatcgac ctacaagagc taggaaaata cgagcagtca atcaagtggc cggagccgga   3720
agcttaataa tttttatctt tcattttgtt tttttctatg ctataagcca ccatgtactc   3780
cttcgtgtcc gaagaaaccg gaaccttgat cgtcaactcc gtcctactat tcctagccgtt   3840
cgtcgtgttc ctactagtaa ccctagctat cctaaccgcg ctaagactct gtgctgactg   3900
ctgcaacatc gtcaacgtgt ccctagtgaa gccgtccttc tacgtctact ccagagtcaa   3960
gaacctaaac tcctctagag tcccggacct actagttgag ccagaggctt aataaataaa   4020
aattattaag cctctggctc ctggactagt agagcgatat tatcggaact ggaggagtgg   4080
tcggtgttta gcttgtagtt cccgattctg tatctagaat acgccgcaaa tccagaatct   4140
cccgcgactc tttgagaggc tcccaactta tagtacgata gggttctaga ggtcgctacg   4200
gtgatctcct tcggtaggtc cttgatgtca catcttccta ggtggtgtcc cgcaattctt   4260
agatgtcctc ttaggatgac cgctccgata accaattcgg attccaatag cggtctggtt   4320
aggtaggttc catgtagcgg tacgttcaat aggatgttcg tctccgggtt gaacgaccac   4380
atagatctgg ttctcgcgaa tagtctgaag gaggcgatga agtaggatag ccacattagt   4440
cctactagac aagccatagc gatcgcgatt ccacctgtga tccagttgat tctgtagacc   4500
gcagctagaa cgaagcaggc caaggtgacc ggccatagta gccataggaa gattagcttg   4560
atgatgtaca agaatctgtt cctgttcgcg tacgcgaact gtagtaggca gatccaggtt   4620
aggaatagga atccgatgac taggttccac tgctctagta gcttcttcaa tcttccgacg   4680
gtgatggttc cgttagaatc cgccatggtg gcttatgatt atttctcgct ttcaatttaa   4740
cacaacccctc aagaacctttt gtatttattt tcaatttttt              4779
```

```
SEQ ID NO: 86         moltype = DNA   length = 4785
FEATURE               Location/Qualifiers
source                1..4785
                      mol_type = other DNA
                      organism = synthetic construct
SEQUENCE: 86
aaaaattgaa aataaataca aaggttcttg agggttgtgt taaattgaaa gcgagaaata    60
atcataaccc ggggccacca tgttcgtgtt cctagtccta ctaccgctag tctcttctca   120
gtgtgtaaac ctaacaacga gaacacaact accaccggcg tacaccaatt ctttcacaag   180
aggagtatat tacccggaca aggtgttcag atcctccgta ctacattcta cacaggacct   240
attcctaccg ttcttctcta acgtaacatg gttccacgcg atccatgtct ctggaacaaa   300
cggaacgaag agattcgata acccggtctt gccgttcaac gatggtgtat actttgcgtc   360
```

```
caccgagaag tccaacatca tcagaggatg gatcttcgga accaccttgg attctaagac  420
ccagtccttg ctaatcgtca acaacgcgac caacgtcgtc atcaaagtct gcgaattcca  480
gttctgtaac gacccgttct tgggagtcta ctaccacaag aacaacaagt cctggatgga  540
atccgagttc agagtctact cttccgcgaa caactgcacc ttcgaatatg tatctcagcc  600
gttcctaatg gacctagagg gaaagcaggg aaacttcaag aacctaagag agttcgtatt  660
caagaacatc gacggatact tcaagatcta ctccaagcac actccgatca acctagttag  720
agatctaccg caaggattct ctgcgctaga accgttagta gatttgccga tcggaatcaa  780
catcaccaga ttccagacac tactagcgct acacagatct tacctaacgc cgggagattc  840
ttcttctgga tggactgctg gtgctgcggc ttattatgta ggatacctac agccgagaac  900
cttcctattg aagtacaacg aaaacggaac catcaccgat gccgtagatt gtgctctaga  960
tccgctatcc gaaacgaagt gcaccctaaa gtctttcacc gtcgagaagg gaatctacca 1020
gacctccaac tttagagtac agccgaccga atccatcgtc agatttccga acatcacgaa 1080
cctatgtccg ttcggagaag tgttcaacgc gacaagattt gcgtctgtct atgcgtggaa 1140
cagaaaaaga atcagtaact gcgtcgcgga ctactccgtc ctatacaact ctgcctcttt 1200
ctccacgttc aaatgctacg gtgtatctcc gacaaagcta aacgatctat gcttccaccaa 1260
cgtctacgcg gactccttcg taatcagagg agatgaagtt agacagattg cgccgggaca 1320
aactggaaag atcgcggatt ataactacaa gctaccggac gacttcaccg gatgtgtaat 1380
tgcgtggaat tcgaacaacc tagactccaa agtcggaagga aactacaact acttgtacag 1440
actattcaga aagtccaacc taaagccgtt cgagagagac atctccaccg aaatctatca 1500
ggctggatct acaccgtgta atggtgtcga aggattcaac tgctacttcc cgctacagtc 1560
ttacggattt caaccgacaa acggtgtagg atatcagccg tacagagtcg tcgtactatc 1620
cttcgaacta ctacatgctc cggcgacagt atgtggaccg aaaaagtcta ccaacctagt 1680
caagaacaaa tgcgtcaact ttaacttcaa cggactaacc ggaaccggtg tcctaaccga 1740
atctaacaag aagtttctac cgttccagca gttcggaaga gatatcgcgg atacaacaga 1800
cgctgtcaga gatccgcaaa ccttggagat cctagatatc acaccgtgtt ctttcggtgg 1860
tgtctctgta attactccgg gaacgaacac ctccaatcaa gtagcggtac tataccagga 1920
cgtgaactgt acagaagtac cggtagctat tcacgcggat caactaacac caacttggag 1980
agtgtactcc accggatcta acgtattcca aacaagagcg ggatgtctaa tcggagcgga 2040
acacgtaaac aactcctacg aatgtgatat cccgattgga gcgggaatct gtgcgtctta 2100
ccaaacacaa acaaactctc cgagaagagc gagatctgta gcctctcaat ctattatcgc 2160
ctacaccatg tccttgggag ccgaaaattc tgtcgcgtac tccaacaatt ctatcgcgat 2220
cccgacaaac ttcaccatct ctgtaacaac cgagatccta ccggtgtcta tgaccaagac 2280
atctgtcgat tgcaccatgt acatctgcgg agattccacc gagtgctcca acctactact 2340
acagtacgga tctttctgta cccagctaaa cagagcgttg actggaatcg ctgtagagca 2400
ggataagaac actcaagagg tattcgcgca agtcaagcag atctataaga ctccgccgat 2460
caaggacttc ggaggtttca acttctctca gatcttgccg gatccgtcca aaccgtctaa 2520
gagatctttc atcgaggacc tactattcaa caaagtcacc ctagctgacg cgggattcat 2580
caaacaatac ggagattgct tgggagacat tgcggcgaga gatctaattt gcgcgcagaa 2640
gtttaacgga ttgacagtac taccgccgct actaaccgat gagatgattg cgcagtacac 2700
gtctgctcta ttggcgggaa caattacaag tggatggaca tttggagccg gtgccgctct 2760
acaaattccg tttgctatgc aaatggcgta cagattcaac ggaatcggag taacccagaa 2820
cgtcttgtac gagaaccaga agctaatcgc gaaccagttc aattccgcga tcggaaagat 2880
ccaggacagt ctatcttcta ctgcttcgcg gttgggaaag ctacaggatg tagtaaatca 2940
aaacgcgcag gcgctaaaca ccttggtcaa gcaactatcc tctaacttcg gagcgatctc 3000
gtccgtccta aacgacatct tatccagact agatccaccg gaagcggagg tccagatcga 3060
tagactaatc actggaagat tgcagtccct acagacctac gtaacacagc aactaattag 3120
agcggcggag attagagcct ctgctaatct agctgcgacc aagatgtccg aatgtgtctt 3180
gggacaatcc aagagagtgg acttctgcgg aaagggatac cacctaatgt ctttcccaca 3240
atctgcgccg catggtgtcg tattcctaca tgtaacatat gtgccggcgc aagaaaagaa 3300
cttcacaaca gctccagcga tctgccatga tggaaaagct catttcccga gagagggagt 3360
ctttgtctct aaccagaactc attggttcgt cacccagaga aacttctacg agccgcagat 3420
catcaccacc gacaacacat tcgtctcggg aaactgcgac gtggtcatcg gaatcgtaaa 3480
caataccgtc tacgatccgt tgcagccgga actagactcc ttcaaagaag agttggacaa 3540
gtacttcaag aaccacacct ctccggatgt ggacttggga gatatctctg gaatcaacgc 3600
gtccgtcgtc aacatccaga aagaaatcga tagattgaac gaggtcgcga agaacttgaa 3660
cgagtcccta atcgacctac aagagctagg aaaaatacgag cagtacatca agtggccgga 3720
gccggaagct taataatttt tatctttcat tttgttttttt tctatgctat aagccaccat 3780
gtactccttc gtgtccgaag aaaccggaac cttgatcgtc aactccgtcc tactattcct 3840
agcgttcgtc gtgttcctac tagtaacccct agctatccta accgcgctaa gactatgtgc 3900
gtactgctgc aacatcgtca acgtgtccct agtgaagccg tccttctacg tctactccag 3960
agtcaagaac ctaaactcct ctagagtccc ggacctacta gttgagccag aggcttaata 4020
aataaaaatt attaagcctc tggctcctgg actagtagag cgatattatc ggaactggag 4080
gagtggtcgg tgtttagctt gtagttcccg attctgtatc tagaatacgc cgcaaatcca 4140
gaatctcccg cgactctttg agaggctccc aacttatagt acgatagggt tctagaggtc 4200
gctacggtga tctccttcgg taggtccttg atgtcacatc ttcctaggtg gtgtcccgca 4260
attcttagat gtcctcttag gatgaccgct ccgataacca attcggattc caatagcggt 4320
ctggttagga tggttccatg tagcggtacg ttcaatagga tgttcgtctc cgggttgaac 4380
gaccacatag atctggttct cgcgaatagt ctgaaggagg cgatgaagta ggatagccac 4440
attagtccta ctagacaagc catagcgatc gcgattccac cctgtgatcca gttgattctg 4500
tagaccgcag ctagaacgaa gcaggccaag gtgaccggcc atagtagcca taggaagatt 4560
agcttgatga tgtacaagaa tctgttcctg ttcgcgtacg cgaactgtag taggcagatc 4620
caggttagga ataggaatcc gatgactagg ttccactgct ctagtagctt cttcaactct 4680
tcgacggtga tggttccgtt agaatccgcc atggtggctt atgattattt ctcgctttca 4740
atttaacaca accctcaaga acctttgtat ttattttcaa ttttt        4785
```

SEQ ID NO: 87          moltype = AA  length = 681
FEATURE                Location/Qualifiers
source                 1..681
                       mol_type = protein

```
                                 organism = synthetic construct
SEQUENCE: 87
MWTTCFFISL ILIQGIKTLP ILEIASNDQP QNVDSVCSGT LQKTEDVHLM GFTLSGQKVA    60
DSPLEASKRW AFRTGVPPKN VEYTEGEEAK TCYNISVTDP SGKSLLLDPP TNVRDYPKCK   120
TIHHIQGQNP HAQGIALHLW GAFFLYDRIA STTMYRGKVF TEGNIAAMIV NKTVHKMIFS   180
RQGQGYRHMN LTSTNKYWTS SNGTQTNDTG CFGTLQEYNS TKNQTCAPSK TPPPPPTAHP   240
EIKPTSTPTD ATRLNTTNPN SDDEDLTTSG SGSGEQEPYT TSDAVTKQGL SSTMPPTLSP   300
QPGTPQQGGN NTNHSQDAAT ELDNTNTTAQ PPMPSHNTTT ISTNNTSKHN LSTLSEPPQN   360
TTNPNTQSMA TENEKTSAPP KTTLPPTESP TTEKSTNNTK SPTTMEPNTT NGHFTSPSST   420
PNSTTQHLIY FRRKRSILWR EGDMFPFLDG LINAPIDFDP VPNTKTIFDE SSSSGASAEE   480
DQHASSNISL TLSYLPHTSE NTAYSGENEN DCDAELRIWS VQEDDLAAGL SWIPFFGPGI   540
EGLYTAGLIK NQNNLVCRLR RLANQTAKSL ELLLRVTTEE RTFSLINRHA IDFLLTRWGG   600
TCKVLGPDCC IGIEDLSRNI SEQIDQIKKD EQKEGTGWGL GGKWWTSDWG VLTNLGILLL   660
LSIAVLIALS CICRIFTKYI G                                            681

SEQ ID NO: 88              moltype = AA  length = 19
FEATURE                    Location/Qualifiers
source                     1..19
                           mol_type = protein
                           organism = synthetic construct
SEQUENCE: 88
MWTTCFFISL ILIQGIKTL                                                19

SEQ ID NO: 89              moltype = DNA  length = 57
FEATURE                    Location/Qualifiers
source                     1..57
                           mol_type = other DNA
                           organism = synthetic construct
SEQUENCE: 89
atgtggacga cctgcttctt catctcccta atcctaatcc agggaatcaa gaccccta     57

SEQ ID NO: 90              moltype = AA  length = 38
FEATURE                    Location/Qualifiers
source                     1..38
                           mol_type = protein
                           organism = synthetic construct
SEQUENCE: 90
WWTSDWGVLT NLGILLLLSI AVLIALSCIC RIFTKYIG                           38

SEQ ID NO: 91              moltype = DNA  length = 114
FEATURE                    Location/Qualifiers
source                     1..114
                           mol_type = other DNA
                           organism = synthetic construct
SEQUENCE: 91
tggtggacat ctgactgggg agtcctaacg aacctaggaa tcctactact attgtcgatc    60
gcggtcctaa tcgcgctatc ctgtatctgt agaatcttca ccaagtacat cgga         114

SEQ ID NO: 92              moltype = AA  length = 303
FEATURE                    Location/Qualifiers
source                     1..303
                           mol_type = protein
                           organism = synthetic construct
SEQUENCE: 92
MASSSNYNTY MQYLNPPPYA DHGANQLIPA DQLSNQHGIT PNYVGDLNLD DQFKGNVCHA    60
FTLEAIIDIS AYNERTVKGV PAWLPLGIMS NFEYPLAHTV AALLTGSYTI TQFTHNGQKF   120
VRVNRLGTGI PAHPLRMLRE GNQAFIQNMV IPRNFSTNQF TYNLTNLVLS VQKLPDDAWR   180
PSKDKLIGNT MHPAISIHPN LPPIVLPTVK KQAYRQHKNP NNGPLLAISG ILHQLRVEKV   240
PEKTSLFRIS LPADMFSVKE GMMKKRGESS PVVYFQAPEN FPLNGFNNRQ VVLAYANPTL   300
SAI                                                                303

SEQ ID NO: 93              moltype = DNA  length = 915
FEATURE                    Location/Qualifiers
source                     1..915
                           mol_type = other DNA
                           organism = synthetic construct
SEQUENCE: 93
atggcgtcta gttctaatta taatacttat atgcaatatc taaatccacc accatatgcg    60
gatcatggtg ctaatcaact aattccagcg gatcaactat ctaatcaaca tggaattaca   120
ccaaattatg ttggagatct aaatctagat gatcagttta aaggaaatgt ttgtcatgcg   180
tttacactag aagcgattat tgatatttct gcgtataatg aaagaacagt aaaaggtgta   240
ccagcttggc taccactagg aattatgtct aattttgaat atccactagc gcatacagta   300
gcggcgctat tgacaggatc ttatacaatt acacagttta cacataatgg acaaaagttt   360
gttagagtaa atagactagg aactggaata ccagcgcatc cactaagaat gctaagagaa   420
ggaaatcaag cttttattca aaatatggtt attccaagaa atttctctac aaatcagttt   480
acttataatc taactaatct agtactatct gtacaaaagc taccagatga tgcttggaga   540
ccatctaaag ataaactaat tggaaataca atgcatccag cgatttctat tcatccaaat   600
ctaccaccaa tagtactacc aactgtaaag aaacaagcgt atagacaaca taagaatcca   660
aataatggac cactattggc gatttctgga attctacatc aactaagagt agaaaaggta   720
```

-continued

```
ccagaaaaga catctttgtt tagaatttct ctaccagcgg atatgttttc tgtaaaagaa  780
ggaatgatga agaaaagagg agaatcttct ccagtagtat attttcaagc gccagaaaat  840
tttccattga atggttttaa taatagacaa gtagtactag cgtatgcgaa tccaacacta  900
tctgcgatat aataa                                                    915

SEQ ID NO: 94          moltype = DNA   length = 995
FEATURE                Location/Qualifiers
source                 1..995
                       mol_type = other DNA
                       organism = synthetic construct
SEQUENCE: 94
aaaaattgaa aataaataca aaggttcttg agggttgtgt taaattgaaa gcgagaaata  60
atcataaatg gcgtctagtt ctaattataa tacttatatg caatatctaa atccaccacc  120
atatgcggat catggtgcta atcaactaat tccagcggat caactatcta atcaacatgg  180
aattacacca aattatgttg gagatctaaa tctagatgat cagtttaaag gaaatgtttg  240
tcatgcgttt acactagaag cgattattga tatttctgcg tataatgaaa gaacagtaaa  300
aggtgtacca gcttggctac cactaggaat tatgtctaat tttgaatatc cactagcgca  360
tacagtagcg gcgctattga caggatctta tacaattaca cagtttacac ataatggaca  420
aaagtttgtt agagtaaata gactaggaac tggaatacca gcgcatccac taagaatgct  480
aagagaagga aatcaagctt ttattcaaaa tatggttatt ccaagaaatt tctctacaaa  540
tcagtttact tataatctaa ctaatctagt actatctgta caaaagctac cagatgatgc  600
ttggagacca tctaaagata aactaattgg aaatacaatg catccagcga tttctattca  660
tccaaatcta ccaccaatag tactaccaac tgtaaagaaa caagcgtata gacaacataa  720
gaatccaaat aatggaccac tattggcgat ttctggaatt ctacatcaac taagagtaga  780
aaaggtacca gaaaagacat ctttgtttag aatttctcta ccagcggata tgttttctgt  840
aaaagaagga atgatgaaga aaagaggaga atcttctcca gtagtatatt ttcaagcgcc  900
agaaaatttt ccattgaatg gttttaataa tagacaagta gtactagcgt atgcgaatcc  960
aacactatct gcgataataa ataataatt tttat               995

SEQ ID NO: 95          moltype = AA   length = 255
FEATURE                Location/Qualifiers
source                 1..255
                       mol_type = protein
                       organism = synthetic construct
SEQUENCE: 95
MWTTCFFISL ILIQGIKTLV RFPNITNLCP FGEVFNATRF ASVYAWNRKR ISNCVADYSV  60
LYNSASFSTF KCYGVSPTKL NDLCFTNVYA DSFVIRGDEV RQIAPGQTGK IADYNYKLPD  120
DFTGCVIAWN SNNLDSKVGG NYNYLYRLFR KSNLKPFERD ISTEIYQAGS TPCNGVEGFN  180
CYFPLQSYGF QPTNGVGYQP YRVVVLSFEL LHAPATVWWT SDWGVLTNLG ILLLLSIAVL  240
IALSCICRIF TKYIG                                                    255

SEQ ID NO: 96          moltype = AA   length = 251
FEATURE                Location/Qualifiers
source                 1..251
                       mol_type = protein
                       organism = synthetic construct
SEQUENCE: 96
MWTTCFFISL ILIQGIKTLN ITNLCPFGEV FNATRFASVY AWNRKRISNC VADYSVLYNS  60
ASFSTFKCYG VSPTKLNDLC FTNVYADSFV IRGDEVRQIA PGQTGKIADY NYKLPDDFTG  120
CVIAWNSNNL DSKVGGNYNY LYRLFRKSNL KPFERDISTE IYQAGSTPCN GVEGFNCYFP  180
LQSYGFQPTN GVGYQPYRVV VLSFELLHAP ATVWWTSDWG VLTNLGILLL LSIAVLIALS  240
CICRIFTKYI G                                                        251

SEQ ID NO: 97          moltype = DNA   length = 765
FEATURE                Location/Qualifiers
source                 1..765
                       mol_type = other DNA
                       organism = synthetic construct
SEQUENCE: 97
atgtggacga cctgcttctt catctcccta atcctaatcc agggaatcaa gaccctagtc  60
agatttccga acatcacgaa cctatgtccg ttcggagaag tgttcaacgc gacaagattt  120
gcgtctgtct atgcgtggaa cagaaaaaga atcagtaact gcgtcgcgga ctactccgtc  180
ctatacaact ctgcctcttt ctccacgttc aaatgctacg gtgtatctcc gacaaagcta  240
aacgatctat gcttccacaa cgtctacgcg gactccttcg taatcagagg agatgaagtt  300
agacagattg cgccgggaca aactggaaag atcgcggatt ataactacaa gctaccggac  360
gacttcaccg gatgtgtaat tgcgtggaat tcgaacaacc tagactccaa agtcggagga  420
aactacaact acttgtacag actattcaga aagtccaacc taaagccgtt cgagagagac  480
atctccaccg aaatctatca ggctggatct acaccgtgta atggtgtcga aggattcaac  540
tgctacttcc cgctacagtc ttacggattt caaccgacaa acggtgtagg atatcagccg  600
tacagagtcg tcgtactatc cttcgaacta ctacatgctc cggcgacagt atggtggaca  660
tctgactggg gagtcctaac gaacctagga atcctactac tattgtcgat cgcggtccta  720
atcgcgctat cctgtatctg tagaatcttc accaagtaca tcgga         765

SEQ ID NO: 98          moltype = DNA   length = 753
FEATURE                Location/Qualifiers
source                 1..753
                       mol_type = other DNA
                       organism = synthetic construct
SEQUENCE: 98
```

-continued

```
atgtggacga cctgcttctt catctcccta atcctaatcc agggaatcaa gaccctaaac   60
atcacgaacc tatgtccgtt cggagaagtg ttcaacgcga caagatttgc gtctgtctat  120
gcgtggaaca gaaaaagaat cagtaactgc gtcgcggact actccgtcct atacaactct  180
gcctctttct ccacgttcaa atgctacggt gtatctccga caaagctaaa cgatctatgc  240
ttcaccaacg tctacgcgga ctccttcgta atcagaggag atgaagttag acagattgcg  300
ccgggacaaa ctggaaagat cgcggattat aactacaagc taccggacga cttcaccgga  360
tgtgtaattg cgtggaattc gaacaaccta gactccaaag tcggaggaaa ctacaactac  420
ttgtacagac tattcagaaa gtccaaccta aagccgttcg agagagacat ctccaccgaa  480
atctatcagg ctggatctac accgtgtaat ggtgtcgaag gattcaactg ctacttcccg  540
ctacagtctt acggatttca accgacaaac ggtgtaggat atcagccgta cagagtcgtc  600
gtactatcct tcgaactact acatgctccg gcgacagtat ggtggacatc tgactgggga  660
gtcctaacga acctaggaat cctactacta ttgtcgatcg cggtcctaat cgcgctatcc  720
tgtatctgta gaatcttcac caagtacatc gga                              753
```

```
SEQ ID NO: 99          moltype = AA   length = 255
FEATURE                Location/Qualifiers
source                 1..255
                       mol_type = protein
                       organism = synthetic construct
SEQUENCE: 99
MWTTCFFISL ILIQGIKTLV RFPNITNLCP FGEVFNATRF ASVYAWNRKR ISNCVADYSV   60
LYNSASFSTF KCYGVSPTKL NDLCFTNVYA DSFVIRGDEV RQIAPGQTGT IADYNYKLPD  120
DFTGCVIAWN SNNLDSKVGG NYNYLYRLFR KSNLKPFERD ISTEIYQAGS TPCNGVKGFN  180
CYFPLQSYGF QPTYGVGYQP YRVVVLSFEL LHAPATVWWT SDWGVLTNLG ILLLLSIAVL  240
IALSCICRIF TKYIG                                                   255
```

```
SEQ ID NO: 100         moltype = AA   length = 251
FEATURE                Location/Qualifiers
source                 1..251
                       mol_type = protein
                       organism = synthetic construct
SEQUENCE: 100
MWTTCFFISL ILIQGIKTLN ITNLCPFGEV FNATRFASVY AWNRKRISNC VADYSVLYNS   60
ASFSTFKCYG VSPTKLNDLC FTNVYADSFV IRGDEVRQIA PGQTGTIADY NYKLPDDFTG  120
CVIAWNSNNL DSKVGGNYNY LYRLFRKSNL KPFERDISTE IYQAGSTPCN GVKGFNCYFP  180
LQSYGFQPTY GVGYQPYRVV VLSFELLHAP ATVWWTSDWG VLTNLGILLL LSIAVLIALS  240
CICRIFTKYI G                                                       251
```

```
SEQ ID NO: 101         moltype = DNA   length = 1905
FEATURE                Location/Qualifiers
source                 1..1905
                       mol_type = other DNA
                       organism = synthetic construct
SEQUENCE: 101
aaaaattgaa aataaataca aaggttcttg agggttgtgt taaattgaaa gcgagaaata   60
atcataagcc accatgtgga cgacctgctt cttcatctcc ctaatcctaa tccagggaat  120
caagacccta gtcagatttc gaacatcac gaacctatgt ccgttcggag aagtgttcaa  180
cgcgacaaga tttgcgtctg tctatgcgtg gaacagaaaa agaatcagta actgcgtcgc  240
ggactactcc gtcctataca actctgcctc tttctccacg ttcaaatgct acggtgtatc  300
tccgacaaag ctaaacgatc tatgcttcac caacgtctac gcggactcct cgtaatcag  360
aggagatgaa gttagacaga ttgcgccggg acaaactgga aagatcgcgg attataacta  420
caagctaccg gacgacttca ccggatgtgt aattgcgtgg aattcgaaca acctagactc  480
caaagtcgga ggaaactaca actacttgta cagactattc agaaagtcca acctaaagcc  540
gttcgagaga gacatctcca ccgaaatcta tcaggctgga tctacaccgt gtaatggtgt  600
cgaaggattc aactgctact tcccgctaca gtcttacgga tttcaaccga caaacggtgt  660
aggatatcag ccgtacagag tcgtcgtact atccttcgaa ctactacatg ctccggcgac  720
agtatggtgg acctccgatt ggggagtact aacaaaccta ggaatcctac tactattgtc  780
gatcgcggtc ctaatcgcgc tatcctgtat ctgtagaatc ttcaccaagt acatcggaga  840
gccggaagct taataatttt tatctttcat tttgtttttt tctatgctat aagccaccat  900
gtactccttc gtgtccgaag aaacggaac cttgatcgtc aactccgtcc tactattcct  960
agcgttcgtc gtgttcctac tagtaaccct agctatccta accgcgctaa gactatgtgc 1020
gtactgctgc aacatcgtca acgtgtccct agtgaagccg tccttctacg tctactccag 1080
agtcaagaac ctaaactcct ctagagtccc ggacctacta gttgagccag aggcttaata 1140
aataaaaatt attaagcctc tggctcctgg actagtagag cgatattatc ggaactggag 1200
gagtggtcgg tgtttagctt gtagttcccg attctgtatc tagaatacgc cgcaaatcca 1260
gaatctcccg cgactctttg agaggctccc aacttatagt acgatagggt tctagaggtc 1320
gctacggtga tctccttcgg taggtccttg atgtcacatc ttcctaggtg gtgtcccgca 1380
attcttagat gtcctcttag gatgaccgct ccgataacca attcggattc caatagcggt 1440
ctggttagga tggttccatg tagcggtacg ttcaatagga tgttcgtctc cgggttgaac 1500
gaccacatag atctggttct cgcgaatagt ctgaaggagg cgatgaagta ggatagccac 1560
attagtccta ctagacaagc catagcgatc gcgattccac ctgtgatcca gttgattctg 1620
tagaccgcag ctagaacgaa gcaggccaag gtgaccggcc atagtagcca taggaagatt 1680
agcttgatga tgtacaagaa tctgttcctg ttcgcgtacg cgaactgtag taggcagatc 1740
caggttagga ataggaatcc gatgactagg ttccactgct ctagtagctt cttcaactct 1800
tcgacggtga tggttccgtt agaatccgcc atggtggctt atgattattt ctcgctttca 1860
atttaacaca accctcaaga acctttgtat ttattttcaa ttttt                1905
```

```
SEQ ID NO: 102         moltype = DNA   length = 1911
FEATURE                Location/Qualifiers
```

-continued

```
source                  1..1911
                        mol_type = other DNA
                        organism = synthetic construct
SEQUENCE: 102
aaaaattgaa aataaataca aaggttcttg agggttgtgt taaattgaaa gcgagaaata   60
atcataaccc ggggccacca tgtggacgac ctgcttcttc atctccctaa tcctaatcca   120
gggaatcaag accctagtca gatttccgaa catcacgaac ctatgtccgt tcggagaagt   180
gttcaacgcg acaagatttg cgtctgtcta tgcgtggaac agaaaaagaa tcagtaactg   240
cgtcgcggac tactccgtcc tatacaactc tgcctctttc tccacgttca aatgctacgg   300
tgtatctccg acaaagctaa acgatctatg cttcaccaac gtctacgcgg actccttcgt   360
aatcagagga gatgaagtta gacagattgc gccgggacaa actggaaaga tcgcggatta   420
taactacaag ctaccggacg acttcaccgg atgtgtaatt gcgtggaatt cgaacaacct   480
agactccaaa gtcggaggaa actacaacta cttgtacaga ctattcagaa agtccaacct   540
aaagccgttc gagagagaca tctccaccga aatctatcag gctggatcta caccgtgtaa   600
tggtgtcgaa ggattcaact gctacttccc gctacagtct tacggatttc aaccgacaaa   660
cggtgtagga tatcagccgt acagagtcgt cgtactatcc ttcgaactac tacatgctcc   720
ggcgacagta tggtggacct ccgattgggg agtactaaca aacctaggaa tcctactact   780
attgtcgatc gcggtcctaa tcgcgctatc ctgtatctgt agaatcttca ccaagtacat   840
cggagagccg gaagcttaat aatttttatc tttcattttg ttttttttcta tgctataagc   900
caccatgtac tccttcgtgt ccgaagaaac cggaaccttg atcgtcaact ccgtcctact   960
attcctagcg ttcgtcgtgt tcctactagt aaccctagct atcctaaccg cgctaagact   1020
atgtgcgtac tgctgcaaca tcgtcaacgt gtccctagtg aagccgtcct tctacgtcta   1080
ctccagagtc aagaacctaa actcctctag agtcccggac ctactagttg agccagaggc   1140
ttaataaata aaaattatta agcctctggc tcctggacta gtagagcgat attatcggaa   1200
ctggaggagt ggtcggtgtt tagcttgtag ttcccgattc tgtatctaga atacgccgca   1260
aatccagaat ctcccgcgac tctttgagag gctcccaact tatagtacga taggttcta   1320
gaggtcgcta cggtgatctc cttcggtagg tccttgatgt cacatcttcc taggtggtgt   1380
cccgcaattc ttagatgtcc tcttaggatg accgctccga taaccaattc ggattccaat   1440
agcggtctgg ttaggatggt tccatgtagc ggtacgttca ataggatgtt cgtctccggg   1500
ttgaacgacc acatagatct ggttctcgcg aatagtctga aggaggcgat gaagtaggat   1560
agccacatta gtcctactag acaagccata gcgatcgcga ttccacctgt gatccagttg   1620
attctgtaga ccgcagctag aacgaagcag gccaaggtga ccggccatag tagccatagg   1680
aagattagct tgatgatgta caagaatctg ttcctgttcg cgtacgcgaa ctgtagtagg   1740
cagatccagg ttaggaatag gaatccgatg actaggtcc actgctctag tagcttcttc   1800
aactcttcga cggtgatggt tccgttagaa tccgccatgg tggcttatga ttatttctcg   1860
ctttcaattt aacacaaccc tcaagaacct ttgtatttat tttcaatttt t           1911

SEQ ID NO: 103        moltype = DNA  length = 1893
FEATURE               Location/Qualifiers
source                1..1893
                      mol_type = other DNA
                      organism = synthetic construct
SEQUENCE: 103
aaaaattgaa aataaataca aaggttcttg agggttgtgt taaattgaaa gcgagaaata   60
atcataagcc accatgtgga cgacctgctt cttcatctcc ctaatcctaa tccagggaat   120
caagacccta aacatcacga acctatgtcc gttcggagag tgttcaacg cgacaagatt    180
tgcgtctgtc tatgcgtgga acagaaaaag aatcagtaac tgcgtcgcgg actactccgt    240
cctatacaac tctgcctctt tctccacgtt caaatgctac ggtgtatctc cgacaaagct    300
aaacgatcta tgcttcacca cgtctacgc ggactccttc gtaatcagag gagatgaagt     360
tagacagatt gcgccgggac aaactggaaa gatcgcggat tataactaca gctaccgga     420
cgacttcacc ggatgtgtaa ttgcgtggaa ttcgaacaac ctagactcca aagtcggagg    480
aaactacaac tacttgtaca gactattcag aaagtccaac ctaaagccgt tcgagagaga    540
catctccacc gaaatctatc aggctggatc tacaccgtgt aatggtgtcg aaggattcaa    600
ctgctacttc ccgctacagt cttacggatt tcaaccgaca aacggtgtag gatatcagcc    660
gtacagagtc gtcgtactat ccttcgaact actacatgct ccggcgacag tatggtggac    720
ctccgattgg ggagtactaa caaacctagg aatcctacta ctattgtcga tcgcggtcct    780
aatcgcgcta tcctgtatct gtagaatctt caccaagtac atcggagagc cggaagctta    840
ataatttta tctttcattt tgtttttttc tatgctataa gccaccatgt actccttcgt     900
gtccgaagaa accggaacct tgatcgtcaa ctccgtccta ctattcctag cgttcgtcgt    960
gttcctacta gtaaccctag ctatcctaac cgcgctaaga ctatgtgcgt actgctgcaa    1020
catcgtcaac gtgtccctag tgaagccgtc cttctacgtc tactccagag tcaagaacct    1080
aaactcctct agagtcccgg acctactagt tgagccagag gcttaataaa taaaaattat    1140
taagcctctg gctcctggac tagtagagcg atattatcgg aactggagga gtggtcggtg    1200
tttagcttgt agttcccgat tctgtatcta gaatacgccg caaatccaga atctcccgat    1260
actctttgag aggctcccaa cttatagtac gataggttc tagaggtcgc tacggtgatc      1320
tccttcggta ggtccttgat gtcacatctt cctaggtggt gtcccgcaat cttagatgt     1380
cctcttagga tgaccgctcc gataaccaat tcggattcca atagcggtct ggttaggatg    1440
gttccatgta gcggtacgtt caataggatg ttcgtctccg gttgaacga ccacatagat     1500
ctggttctcg cgaatagtct gaaggaggcg atgaagtagg atagccacat tagtcctact    1560
agacaagcca tagcgatcgc gattccacct gtgatccagt tgattctgta ccgcagct     1620
agaacgaagc aggccaaggt gaccggccat agtagccata ggaagattag cttgatgatg    1680
tacaagaatc tgttcctgtt cgcgtacgcg aactgtagta ggcagatcca ggttaggaat    1740
aggaatccga tgactaggtt ccactgctct agtagcttct tcaactcttc gacggtgatg    1800
gttccgttag aatccgccat ggtggcttat gattatttct cgctttcaat ttaacacaac    1860
cctcaagaac ctttgtattt attttcaatt ttt                                 1893

SEQ ID NO: 104        moltype = DNA  length = 1899
FEATURE               Location/Qualifiers
source                1..1899
```

```
                         mol_type = other DNA
                         organism = synthetic construct
SEQUENCE: 104
aaaaattgaa aataaataca aaggttcttg agggttgtgt taaattgaaa gcgagaaata  60
atcataaccc ggggccacca tgtggacgac ctgcttcttc atctccctaa tcctaatcca  120
gggaatcaag accctaaaca tcacgaacct atgtccgttc ggagaagtgt tcaacgcgac  180
aagatttgcg tctgtctatg cgtggaacag aaaaagaatc agtaactgcg tcgcggacta  240
ctccgtccta tacaactctg cctctttctc cacgttcaaa tgctacggtg tatctccgac  300
aaagctaaac gatctatgct tcaccaacgt ctacgcggac tccttcgtaa tcagaggaga  360
tgaagttaga cagattgcgc cgggacaaac tggaaagatc gcggattata actacaagct  420
accggacgac ttcaccggat gtgtaattgc gtggaattcg aacaacctag actccaaagt  480
cggaggaaac tacaactact tgtacagact attcagaaag tccaacctaa agccgttcga  540
gagagacatc tccaccgaaa tctatcaggc tggatctaca ccgtgtaatg gtgtcgaagg  600
attcaactgc tacttcccgc tacagtctta cggatttcaa ccgacaaacg gtgtaggata  660
tcagccgtac agagtcgtcg tactatcctt cgaactacta catgctccgg cgacagtatg  720
gtggacctcc gattggggag tactaacaaa cctaggaatc ctactactat tgtcgatcgc  780
ggtcctaatc gcgctatcct gtatctgtag aatcttcacc aagtacatcg gagagccgga  840
agcttaataa ttttttatctt tcattttgtt tttttctatg ctataagcca ccatgtactc  900
cttcgtgtcc gaagaaaccg gaaccttgat cgtcaactcc gtcctactat tcctagcgtt  960
cgtcgtgttc ctactagtaa ccctagctat cctaaccgcg ctaagactat gtgcgtactg  1020
ctgcaacatc gtcaacgtgt ccctagtgaa gccgtccttc tacgtctact ccagagtcaa  1080
gaacctaaac tcctctagag tcccggacct actagttgag ccagaggctt aataaataaa  1140
aattattaag cctctggctc ctggactagt agagcgatat tatcggaact ggaggagtgg  1200
tcggtgttta gcttgtagtt cccgattctg tatctagaat acgccgcaaa tccagaatct  1260
cccgcgactc tttgagaggc tcccaactta tagtacgata gggttctaga ggtcgctacg  1320
gtgatctcct tcggtaggtc cttgatgtca catcttccta ggtggtgtcc cgcaattctt  1380
agatgtcctc ttaggatgac cgctccgata accaattcgg attccaatag cggtctggtt  1440
aggatggttc catgtagcgg tacgttcaat aggatgttcg tctccgggtt gaacgaccac  1500
atagatctgg ttctcgcgaa tagtctgaag gaggcgatga agtaggatag ccacattagt  1560
cctactagac aagccatagc gatcgcgatt ccacctgtga tccagttgat tctgtagacc  1620
gcagctagaa cgaagcaggc caaggtgacc ggccatagta gccataggaa gattagcttg  1680
atgatgtaca agaatctgtt cctgttcgcg tacgcgaact gtagtaggca gatccaggtt  1740
aggaatagga atccgatgac taggttccac tgctctagta gcttcttcaa ctcttcgacg  1800
gtgatggttc cgttagaatc cgccatggtg gcttatgatt atttctcgct ttcaatttaa  1860
cacaaccctc aagaaccttt gtatttattt tcaattttt                         1899

SEQ ID NO: 105            moltype = AA  length = 105
FEATURE                   Location/Qualifiers
source                    1..105
                          mol_type = protein
                          organism = synthetic construct
REPEAT                    20..67
                          note = 2, 3, 4, 5, 6, 7, 8, 9, or 10 REPEATS
SEQUENCE: 105
MWTTCFFISL ILIQGIKTLY QPYRVVVLSF ELLHAPATVG PGPGYQAGST PCNGVEGFNC  60
YFGPGPGWWT SDWGVLTNLG ILLLLSIAVL IALSCICRIF TKYIG                 105

SEQ ID NO: 106            moltype = DNA  length = 315
FEATURE                   Location/Qualifiers
source                    1..315
                          mol_type = other DNA
                          organism = synthetic construct
repeat_region             58..201
                          note = 2, 3, 4, 5, 6, 7, 8, 9, or 10 REPEATS
SEQUENCE: 106
atgtggacga cctgcttctt catctcccta atcctaatcc agggaatcaa gaccctatac  60
caaccataca gagtagtagt actttctttt gaacttctac atgcaccagc aactgttggt  120
cctgacccg gttatcaggc cggtagcaca ccttgtaatg gtgttgaagg ttttaattgt  180
tactttggtc ctgacccgg ttggtggaca tctgactggg gagtcctaac gaacctagga  240
atcctactac tattgtcgat cgcggtccta atcgcgctat cctgtatctg tagaatcttc  300
accaagtaca tcgga                                                  315

SEQ ID NO: 107            moltype = AA  length = 297
FEATURE                   Location/Qualifiers
source                    1..297
                          mol_type = protein
                          organism = synthetic construct
SEQUENCE: 107
MWTTCFFISL ILIQGIKTLY QPYRVVVLSF ELLHAPATVG PGPGYQAGST PCNGVEGFNC  60
YFGPGPGYQP YRVVVLSFEL LHAPATVGPG PGYQAGSTPC NGVEGFNCYF GPGPGYQPYR  120
VVVLSFELLH APATVGPGPG YQAGSTPCNG VEGFNCYFGP GPGYQPYRVV VLSFELLHAP  180
ATVGPGPGYQ AGSTPCNGVE GFNCYFGPGP GYQPYRVVVL SFELLHAPAT VGPGPGYQAG  240
STPCNGVEGF NCYFGPGPGW WTSDWGVLTN LGILLLLSIA VLIALSCICR IFTKYIG    297

SEQ ID NO: 108            moltype = DNA  length = 891
FEATURE                   Location/Qualifiers
source                    1..891
                          mol_type = other DNA
                          organism = synthetic construct
```

```
SEQUENCE: 108
atgtggacga cctgcttctt catctcccta atcctaatcc agggaatcaa gaccctatat  60
cagccgtaca gagtcgtcgt actatccttc gaactactac atgctccggc gacagtaggt  120
cctggacccg gttatcaggc tggatctaca ccgtgtaatg gtgtcgaagg attcaactgc  180
tacttcggtc ctggaccCgg ttatcagccg tacagagtcg ttgctactatc cttcgaacta  240
ctacatgctc cggcgacagt aggtcctgga cccggttatc aggctggatc tacaccgtgt  300
aatggtgtcg aaggattcaa ctgctacttc ggtcctggac ccggttatca gccgtacaga  360
gtcgtcgtac tatccttcga actactacat gctccggcga cagtaggtcc tggacccggt  420
tatcaggctg gatctacacc gtgtaatggt gtcgaaggat tcaactgcta cttcggtcct  480
ggacccggtt atcagccgta cagagtcgtc gtactatcct tcgaactact acatgctccg  540
gcgacagtag gtcctggacc cggttatcag gctggatcta caccgtgtaa tggtgtcgaa  600
ggattcaact gctacttcgg tcctggaccc ggttatcagc cgtacagagt cgtcgtacta  660
tccttcgaac tactacatgc tccggcgaca gtaggtcctg gacccggtta tcaggctgga  720
tctacaccgt gtaatggtgt cgaaggattc aactgctact tcggtcctgg acccggttgg  780
tggacatctg actgggggagt cctaacgaac ctaggaatcc tactactatt gtcgatcgcg  840
gtcctaatcg cgctatcctg tatctgtaga atcttcacca agtacatcgg a          891

SEQ ID NO: 109        moltype = AA  length = 105
FEATURE               Location/Qualifiers
source                1..105
                      mol_type = protein
                      organism = synthetic construct
REPEAT                20..67
                      note = 2, 3, 4, 5, 6, 7, 8, 9, or 10 REPEATS
SEQUENCE: 109
MWTTCFFISL ILIQGIKTLY QPYRVVVLSF ELLHAPATVG PGPGYQAGST PCNGVKGFNC  60
YFGPGPGWWT SDWGVLTNLG ILLLLSIAVL IALSCICRIF TKYIG                 105

SEQ ID NO: 110        moltype = AA  length = 297
FEATURE               Location/Qualifiers
source                1..297
                      mol_type = protein
                      organism = synthetic construct
SEQUENCE: 110
MWTTCFFISL ILIQGIKTLY QPYRVVVLSF ELLHAPATVG PGPGYQAGST PCNGVKGFNC  60
YFGPGPGYQP YRVVVLSFEL LHAPATVGPG PGYQAGSTPC NGVKGFNCYF GPGPGYQPYR  120
VVVLSFELLH APATVGPGPG YQAGSTPCNG VKGFNCYFGP GPGYQPYRVV VLSFELLHAP  180
ATVGPGPGYQ AGSTPCNGVK GFNCYFGPGP GYQPYRVVVL SFELLHAPAT VGPGPGYQAG  240
STPCNGVKGF NCYFGPGPGW WTSDWGVLTN LGILLLLSIA VLIALSCICR IFTKYIG     297

SEQ ID NO: 111        moltype = DNA  length = 2083
FEATURE               Location/Qualifiers
source                1..2083
                      mol_type = other DNA
                      organism = synthetic construct
SEQUENCE: 111
aaaaattgaa aataaataca aaggttcttg agggttgtgt taaattgaaa gcgagaaata  60
atcataagcc accatgtgga cgacctgctt cttcatctcc ctaatcctaa tccagggaat  120
caagacccta tggacgacct gcttcttcat ctccctaatc ctaatccagg gaatcaagac  180
cctatatcag ccgtacagag tcgtcgtact atccttcgaa ctactacatg ctccggcgac  240
agtaggtcct ggacccggtt atcaggctgg atctacaccg tgtaatggtg tcgaaggatt  300
caactgctac ttcggtcctg gacccggtta tcagcgtac agagtcgtcg tactatcctt  360
cgaactacta catgctccgg cgacagtagg tcctggaccc ggttatcagg ctggatctac  420
accgtgtaat ggtgtcgaag gattcaactg ctacttcggt cctggacccg gttatcagcc  480
gtacagagtc gtcgtactat ccttcgaact actacatg ccggcgacag taggtcctgg  540
acccggttat caggctggat ctacaccgtg taatggtgtc gaaggattca actgctactt  600
cggtcctgga cccggttatc agccgtacag agtcgtcgta ctatccttcg aactactaca  660
tgctccggcg acagtaggtc ctggacccgg ttatcaggct ggatctacac cgtgtaatgg  720
tgtcgaagga ttcaactgct acttcggtcc tggacccggt tatcagccgt acagagtcgt  780
cgtactatcc ttcgaactac tacatgctcc ggcgacagta ggtcctggac ccggttatca  840
ggctggatct acaccgtgta atggtgtcga aggattcaac tgctacttct ggtggacatc  900
tgactgggga gtcctaacga acctaggaat cctactacta ttgtcgatcg cggtcctaat  960
cgcgctatcc tgtatctgta gaatcttcac caagtacatc ggagagccgg aagcttaata  1020
attttta attatttta tctttcattt tgtttttttc tatgctataa gccaccatgt  1080
actccttcgt gtccgaagaa accggaacct tgatcgtcaa ctccgtccta ctattcctag  1140
cgttcgtcgt gttcctacta gtaacccta ctatcctaac cgcgctaaga ctatgtgcgt  1200
actgctcaa catcgtcaac gtgtccctag tgaagccgtc cttctacgtc tactccagag  1260
tcaagaacct aaactcctct agagtcccgg acctactagt tgagccagag gcttaataaa  1320
taaaaattat taagcctctg gctcctggac tagtagagcg atattatcgg aactggagga  1380
gtggtcggtg tttagcttgt agttcccgat tctgtatcta gaatacgccg caaatccaga  1440
atctcccgcg actctttgag aggctcccaa cttatagtac gataggttc tagaggtcgc  1500
tacggtgatc tccttcggta ggtccttgat gtcacatctt cctaggtggt gtcccgcaat  1560
tcttagatgt cctcttagga tgaccgctcc gataaccaat tcggattcca atagcggtct  1620
ggttaggtga gttccatgta gcggtacgtt caataggatg ttcgtctccg ggttgaacga  1680
ccacatagat ctggttctcg cgaatagtct gaaggaggcg atgaagtagg atagccacat  1740
tagtcctact agacaagcca tagcgatcgc gattccacct gtgatccagt tgattctgta  1800
gaccgcagct agaacgaagc aggccaaggt gaccggccat agtagccata ggaagattag  1860
cttgatgatg tacaagaatc tgttcctgtt cgcgtacgcg aactgtagta ggcagatcca  1920
ggttaggaat aggaatccga tgactaggtt ccactgctct agtagcttct tcaactcttc  1980
```

```
gacggtgatg gttccgttag aatccgccat ggtggcttat gattatttct cgctttcaat  2040
ttaacacaac cctcaagaac ctttgtattt attttcaatt ttt                    2083

SEQ ID NO: 112          moltype = DNA  length = 2089
FEATURE                 Location/Qualifiers
source                  1..2089
                        mol_type = other DNA
                        organism = synthetic construct
SEQUENCE: 112
aaaaattgaa ataaatacaa aaggttcttg agggttgtgt taaattgaaa gcgagaaata  60
atcataaccc ggggccacca tgtggacgac ctgcttcttc atctccctaa tcctaatcca  120
gggaatcaag accctatgga cgacctgctt cttcatctcc ctaatcctaa tccagggaat  180
caagaccagta tatcagccgt acagagtcgt cgtactatcc ttcgaactac tacatgctcc  240
ggcgacagta ggtcctggac ccggttatca ggctggatc acaccgtgta atggtgtcga  300
aggattcaac tgctacttcg gtcctggacc cggttatcag ccgtacagag tcgtcgtact  360
atccttcgaa ctactacatg ctccggcgac agtaggtcct ggacccggtt atcaggctgg  420
atctacaccg tgtaatggtg tcgaaggatt caactgctac ttcggtcctg gacccggtta  480
tcagccgtac agagtcgtcg tactatcctt cgaactacta catgctccgg cgacagtagg  540
tcctggaccc ggttatcagg ctggatctac accgtgtaat ggtgtcgaag gattcaactg  600
ctacttcggt cctggacccg gttatcagcc gtacagagtc gtcgtactat ccttcgaact  660
actacatgct ccggcgacag taggtcctgg acccggttat caggctggat ctacaccgtg  720
taatggtgtc gaaggattca actgctactt cggtcctgga cccggttacag accgtacag  780
agtcgtcgta ctatccttcg aactactaca tgctccggcg acagtaggtc ctggacccgg  840
ttatcaggct ggatctacac cgtgtaatgg tgtcgaagga ttcaactgct acttctggtg  900
gacatctgac tggggagtcc taacgaacct aggaatccta ctactattgt cgatcgcggt  960
cctaatcgcg ctatcctgta tctgtagaat cttcaccaag tacatcggag agccggaagc  1020
ttaataattt ttattaataa ttttatctt tcatttttgtt ttttctatg ctataagcca  1080
ccatgtactc cttcgtgtcc gaagaaaccg gaaccttgat cgtcaactcc gtcctactat  1140
tcctagcgtt cgtcgtgttc ctactagtaa ccctagctat cctaaccgcg ctaagactat  1200
gtgcgtactg ctgcaaacatc gtcaacgtgt ccctagtgaa gccgtccttc tacgtctact  1260
ccagagtcaa gaacctaaac tcctctagag tcccggacct actagttgag ccagaggctt  1320
aataaataaa aattattaag cctctggctc ctggactagt agagcgatat tatcggaact  1380
ggaggagtgg tcggtgttta gcttgtagtt cccgattctg tatctagaat acgccgcaaa  1440
tccagaatct cccgcgactc tttgagaggc tcccaactta tagtacgata gggttctaga  1500
ggtcgctacg gtgatctcct tcggtaggtc cttgatgtca catcttccta ggtggtgtcc  1560
cgcaattctt agatgtcctc ttaggatgac cgctccgata accaattcgg attccaatag  1620
cggtctggtt aggatggttc catgtagcgg tacgttcaat aggatgttcg tctccgggtt  1680
gaacgaccac atagatctgg ttctcgcgaa tagtctgaag gaggcgatga agtaggatag  1740
ccacattagt cctactagac aagccatagc gatcgcgatt ccacctgtga tccagttgat  1800
tctgtagacc gcagctagaa cgaagcaggc caaggtgacc ggccatagta gccataggaa  1860
gattagcttg atgatgtaca agaatctgtt cctgttcgcg tacgcgaact gtagtaggca  1920
gatccaggtt aggaatagga atccgatgac taggttccac tgctctagta gcttcttcaa  1980
ctcttcgacg gtgatggttc cgttagaatc cgccatggtg gcttatgatt atttctcgct  2040
ttcaatttaa cacaaccctc aagaaccttt gtatttattt tcaattttt            2089

SEQ ID NO: 113          moltype = AA  length = 1269
FEATURE                 Location/Qualifiers
source                  1..1269
                        mol_type = protein
                        organism = synthetic construct
SEQUENCE: 113
MWTTCFFISL ILIQGIKTLF VFLVLLPLVS SQCVNLTTRT QLPPAYTNSF TRGVYYPDKV  60
FRSSVLHSTQ DLFLPFFSNV TWFHAIHVSG TNGTKRFDNP VLPFNDGVYF ASTEKSNIIR  120
GWIFGTTLDS KTQSLLIVNN ATNVVIKVCE FQFCNDPFLG VYYHKNNKSW MESEFRVYSS  180
ANNCTFEYVS QPFLMDLEGK QGNFKNLREF VFKNIDGYFK IYSKHTPINL VRDLPQGFSA  240
LEPLVDLPIG INITRFQTLL ALHRSYLTPG DSSSGWTAGA AAYYVGYLQP RTFLLKYNEN  300
GTITDAVDCA LDPLSETKCT LKSFTVEKGI YQTSNFRVQP TESIVRFPNI TNLCPFGEVF  360
NATRFASVYA WNRKRISNCV ADYSVLYNSA SFSTFKCYGV SPTKLNDLCF TNVYADSFVI  420
RGDEVRQIAP GQTGKIADYN YKLPDDFTGC VIAWNSNNLD SKVGGNYNYL YRLFRKSNLK  480
PFERDISTEI YQAGSTPCNG VEGFNCYFPL QSYGFQPTNG VGYQPYRVVV LSFELLHAPA  540
TVCGPKKSTN LVKNKCVNFN FNGLTGTGVL TESNKKFLPF QQFGRDIADT TDAVRDPQTL  600
EILDITPCSF GGVSVITPGT NTSNQVAVLY QDVNCTEVPV AIHADQLTPT WRVYSTGSNV  660
FQTRAGCLIG AEHVNNSYEC DIPIGAGICA SYQTQTNSPR RARSVASQSI IAYTMSLGAE  720
NSVAYSNNSI AIPTNFTISV TTEILPVSMT KTSVDCTMYI CGDSTECSNL LLQYGSFCTQ  780
LNRALTGIAV EQDKNTQEVF AQVKQIYKTP PIKDFGGFNF SQILPDPSKP SKRSFIEDLL  840
FNKVTLADAG FIKQYGDCLG DIAARDLICA QKFNGLTVLP PLLTDEMIAQ YTSALLAGTI  900
TSGWTFGAGA ALQIPFAMQM AYRFNGIGVT QNVLYENQKL IANQFNSAIG KIQDSLSSTA  960
SALGKLQDVV NQNAQALNTL VKQLSSNFGA ISSVLNDILS RLDKVEAEVQ IDRLITGRLQ  1020
SLQTYVTQQL IRAAEIRASA NLAATKMSEC VLGQSKRVDF CGKGYHLMSF PQSAPHGVVF  1080
LHVTYVPAQE KNFTTAPAIC HDGKAHFPRE GVFVSNGTHW FVTQRNFYEP QIITTDNTFV  1140
SGNCDVVIGI VNNTVYDPLQ PELDSFKEEL DKYFKNHTSP DVDLGDISGI NASVVNIQKE  1200
IDRLNEVAKN LNESLIDLQE LGKYEQYIKW PWWTSDWGVL TNLGILLLLS IAVLIALSCI  1260
CRIFTKYIG                                                         1269

SEQ ID NO: 114          moltype = AA  length = 1269
FEATURE                 Location/Qualifiers
source                  1..1269
                        mol_type = protein
                        organism = synthetic construct
```

-continued

```
SEQUENCE: 114
MWTTCFFISL ILIQGIKTLF VFLVLLPLVS SQCVNLTTRT QLPPAYTNSF TRGVYYPDKV    60
FRSSVLHSTQ DLFLPFFSNV TWFHAIHVSG TNGTKRFDNP VLPFNDGVYF ASTEKSNIIR   120
GWIFGTTLDS KTQSLLIVNN ATNVVIKVCE FQFCNDPFLG VYYHKNNKSW MESEFRVYSS   180
ANNCTFEYVS QPFLMDLEGK QGNFKNLREF VFKNIDGYFK IYSKHTPINL VRDLPQGFSA   240
LEPLVDLPIG INITRFQTLL ALHRSYLTPG DSSSGWTAGA AAYYVGYLQP RTFLLKYNEN   300
GTITDAVDCA LDPLSETKCT LKSFTVEKGI YQTSNFRVQP TESIVRFPNI TNLCPFGEVF   360
NATRFASVYA WNRKRISNCV ADYSVLYNSA SFSTFKCYGV SPTKLNDLCF TNVYADSFVI   420
RGDEVRQIAP GQTGKIADYN YKLPDDFTGC VIAWNSNNLD SKVGGNYNYL YRLFRKSNLK   480
PFERDISTEI YQAGSTPCNG VEGFNCYFPL QSYGFQPTNG VGYQPYRVVV LSFELLHAPA   540
TVCGPKKSTN LVKNKCVNFN FNGLTGTGVL TESNKKFLPF QQFGRDIADT TDAVRDPQTL   600
EILDITPCSF GGVSVITPGT NTSNQVAVLY QDVNCTEVPV AIHADQLTPT WRVYSTGSNV   660
FQTRAGCLIG AEHVNNSYEC DIPIGAGICA SYQTQTNSPR RARSVASQSI IAYTMSLGAE   720
NSVAYSNNSI AIPTNFTISV TTEILPVSMT KTSVDCTMYI CGDSTECSNL LLQYGSFCTQ   780
LNRALTGIAV EQDKNTQEVF AQVKQIYKTP PIKDFGGFNF SQILPDPSKP SKRSFIEDLL   840
FNKVTLADAG FIKQYGDCLG DIAARDLICA QKFNGLTVLP PLLTDEMIAQ YTSALLAGTI   900
TSGWTFGAGA ALQIPFAMQM AYRFNGIGVT QNVLYENQKL IANQFNSAIG KIQDSLSSTA   960
SALGKLQDVV NQNAQALNTL VKQLSSNFGA ISSVLNDILS RLDPPEAEVQ IDRLITGRLQ  1020
SLQTYVTQQL IRAAEIRASA NLAATKMSEC VLGQSKRVDF CGKGYHLMSF PQSAPHGVVF  1080
LHVTYVPAQE KNFTTAPAIC HDGKAHFPRE GVFVSNGTHW FVTQRNFYEP QIITTDNTFV  1140
SGNCDVVIGI VNNTVYDPLQ PELDSFKEEL DKYFKNHTSP DVDLGDISGI NASVVNIQKE  1200
IDRLNEVAKN LNESLIDLQE LGKYEQYIKW PWWTSDWGVL TNLGILLLLS IAVLIALSCI  1260
CRIFTKYIG                                                         1269

SEQ ID NO: 115          moltype = DNA  length = 3807
FEATURE                 Location/Qualifiers
source                  1..3807
                        mol_type = other DNA
                        organism = synthetic construct
SEQUENCE: 115
atgtggacga cctgcttctt catctcccta atcctaatcc agggaatcaa gaccctattc    60
gtgttcctag tcctactacc gctagtctct tctcagtgtg taaacctaac aacgagaaca   120
caactaccac cggcgtacac caattctttc acaagaggag tatattaccc ggacaaggtg   180
ttcagatcct ccgtactaca ttctacacag gacctattcc taccgttctt ctctaacgta   240
acatggttcc acgcgatcca tgtctctgga acaaacgaaa cgaagagatt cgataacccg   300
gtcttgccgt tcaacgatgg tgtatacttt gcgtccaccg agaagtccaa catcatcaga   360
ggatggatct tcggaaccac cttggattct aagacccagt ccttgctaat cgtcaacaac   420
gcgaccaacg tcgtcatcaa agtctgcgaa ttccagttct gtaacgaccc gttcttggga   480
gtctactacc acaagaacaa caagtcctgg atggaatccg agttcagagt ctactcttcc   540
gcgaacaact gcaccttcga atatgtatct cagccgttcc taatggacct agagggaaag   600
cagggaaact tcaagaacct aagagagttc gtattcaaga acatcgacgg atacttcaag   660
atctactcca agcacactcc gatcaaccta gttagagatc taccgcaagg attctctgcg   720
ctagaaccgt tagtagattt gccgatcgga atcaacatca ccagattcca gacactacta   780
gcgctacaca gatcttacct aacgccggga gattcttctt ctggatggac tgctggtgct   840
gcggcttatt atgtaggata cctacagccg agaaccttcc tattgaagta caacgaaaac   900
ggaaccatca ccgatgccgt agattgtgct ctagatccgc tatccgaaac gaagtgcacc   960
ctaaagtctt tcaccgtcga gaagggaatc taccagacct ccaactttag agtacagccg  1020
accgaatcca tcgtcagatt tccgaacatc acgaacctat gtccgttcgg agaagtgttc  1080
aacgcgacaa gatttgcgtc tgtctatgcg tggaacagaa aaagaatcag taactgcgtc  1140
gcggactact ccgtcctata caactctgcc tctttctcca cgttcaaatg ctacggtgta  1200
tctccgacaa agctaaacga tctatgcttc accaacgtct acgcggactc cttcgtaatc  1260
agaggagatg aagttagaca gattgcgccg ggacaaactg gaaagatcgc ggattataac  1320
tacaagctac cggacgactt caccggatgt gtaattgcgt ggaattcgaa caacctagac  1380
tccaaagtcg gaggaaacta caactacttg tacagactat tcagaaagtc caacctaaag  1440
ccgttcgaga gagacatctc caccgaaatc tatcaggctg gatctacacc gtgtaatggt  1500
gtcgaaggat tcaactgcta cttcccgcta cagtcttacg gatttcaacc gacaaacggt  1560
gtaggatatc agccgtacag agtcgtcgta ctatccttcg aactactaca tgctccggcg  1620
acagtatgtg gaccgaaaaa gtctaccaac ctagtcaaga caaatgcgt caactttaac  1680
ttcaacggac taaccggaac cggtgtccta accgaatcta acaagaagtt tctaccgttc  1740
cagcagttcg gaagagatat cgcggataca acagacgctg tcagagatcc gcaaaccttg  1800
gagatcctag atatcacacc gtgttctttc ggtggtgtct ctgtaattac tccgggaacg  1860
aacacctcca tcaagtagc ggtactatac caggacgtga actgtacaga gtaccggta  1920
gctattcacg cggatcaact aacaccaact tggagagtgt actccaccgg atctaacgta  1980
ttccaaacaa gagcgggatg tctaatcgga gcggaacacg taaacaactc ctacgaatgt  2040
gatatcccga ttggagcggg aatctgtgcg tcttaccaaa cacaaacaa ctctccgaga  2100
agagcgagat ctgtagcctc tcaatctatt atcgcctaca ccatgtcctt gggagccgaa  2160
aattctgtcg cgtactccaa caattctatc gcgatcccga caaacttcac catctctgta  2220
acaaccgaga tcctaccggt gtctatgacc aagacatcg tcgattgcac catgtacatc  2280
tgcggagatt ccaccgagtg ctccaaccta ctactacagt acggatctt ctgtaccag  2340
ctaaacagag cgttgactgg aatcgctgta gagcaggata gaacactca agaggtattc  2400
gcgcaagtca agcagatcta taagactccg ccgatcaagg acttcggagg tttcaacttc  2460
tctcagatct tgccggatcc gtccaaaccg tctaagagat cttttcatcga ggacctacta  2520
ttcaacaaag tcaccctagc tgacgcggga ttcatcaaac aatacggaga ttgcttggga  2580
gacattgcgg cgagagatct aatttgcgcg cagaagttta cggattgac agtactaccg  2640
ccgctactaa ccgatgagat gattgcgcag tacacgtctg tctctattggc gggaacaatt  2700
acaagtggat ggacatttgg agccggtgcc gctctacaaa ttccgtttgc tatgcaaatg  2760
gcgtacagat tcaacggaat cggagtaacc cagaacgtct gtacgagaa ccagaagcta  2820
atcgcgaacc agttcaattc cgcgatcgga aagatccagg acagtctatc ttctactgct  2880
tcggcgttgg gaaagctaca ggatgtagta aatcaaaacg cgcaggcgct aaacaccttg  2940
```

```
gtcaagcaac tatcctctaa cttcggagcg atctcgtccg tcctaaacga catcttatcc   3000
agactagata aggtcgaagc ggaggtccag atcgatagac taatcactgg aagattgcag   3060
tccctacaga cctacgtaac acagcaacta attagagcgg cggagattag agcctctgct   3120
aatctagctg cgaccaagat gtccgaatgt gtcttgggac aatccaagag agtggacttc   3180
tgcggaaagg gataccacct aatgtctttc ccacaatctg cgccgcatgg tgtcgtattc   3240
ctacatgtaa catatgtgcc ggcgcaagaa aagaacttca caacagctcc agcgatctgc   3300
catgatggaa aagctcattt cccgagagag ggagtctttg tctctaacgg aactcattgg   3360
ttcgtcaccc agagaaactt ctacgagccg cagatcatca ccaccgacaa cacattcgtc   3420
tcgggaaact gcgacgtggt catcggaatc gtaaacaata ccgtctacga tccgttgcag   3480
ccggaactag actccttcaa agaagagttg gacaagtact tcaagaacca cacctctccg   3540
gatgtggact tgggagatat ctctggaatc aacgcgtccg tcgtcaacat ccagaaagaa   3600
atcgatagat tgaacgaggt cgcgaagaac ttgaacgagt ccctaatcga cctacaagag   3660
ctaggaaaat acgagcagta catcaagtgg ccgtggtgga catctgactg gggagtccta   3720
acgaacctag gaatcctact actattgtcg atcgcggtcc taatcgcgct atcctgtatc   3780
tgtagaatct tcaccaagta catcgga                                        3807
```

```
SEQ ID NO: 116              moltype = DNA  length = 3807
FEATURE                    Location/Qualifiers
source                     1..3807
                           mol_type = other DNA
                           organism = synthetic construct
SEQUENCE: 116
atgtggacga cctgcttctt catctcccta atcctaatcc agggaatcaa gaccctattc   60
gtgttcctag tcctactacc gctagtctct tctcagtgtg taaacctaac aacgagaaca   120
caactaccac cggcgtacac caattctttc acaagaggag tatattaccc ggacaaggtg   180
ttcagatcct ccgtactaca ttctacacag gacctattcc taccgttctt ctctaacgta   240
acatggttcc acgcgatcca tgtctctgga acaaacggaa cgaagagatt cgataacccg   300
gtcttgccgt tcaacgatgg tgtatacttt gcgtccaccg agaagtccaa catcatcaga   360
ggatggatct tcggaaccac cttggattct aagacccagt ccttgctaat cgtcaacaac   420
gcgaccaacg tcgtcatcaa agtctgcgaa ttccagttct gtaacgaccc gttcttggga   480
gtctactacc acaagaacaa caagtcctgg atggaatccg agttcagagt ctactcttcc   540
gcgaacaact gcaccttcga atatgtatct cagccgttcc taatggacct agagggaaag   600
cagggaaact tcaagaacct aagagagttc gtattcaaga acatcgacgg atacttcaag   660
atctactcca agcacactcc gatcaaccta gttagagatc taccgcaagg attctctgcg   720
ctagaaccgt tagtagattt gccgatcgga atcaacatca ccagattcca gacactacta   780
gcgctacaca gatcttacct aacgccggga gattcttctt ctggatggac tgctggtgct   840
gcggcttatt atgtaggata cctacagccg agaaccttcc tattgaagta caacgaaaac   900
ggaaccatca ccgatgccgt agattgtgct ctagatccgc tatccgaaac gaagtgcacc   960
ctaaagtctt tcaccgtcga gaagggaatc taccagacct ccaactttag agtacagccg   1020
accgaatcca tcgtcagatt tccgaacatc acgaacctat gtccgttcgg agaagtgttc   1080
aacgcgacaa gatttgcgtc tgtctatgcg tggaacagaa aaagaatcag taactgcgtc   1140
gcggactact ccgtcctata caactctgcc tctttctcca cgttcaaatg ctacggtgta   1200
tctccgacaa agctaaacga tctatgcttc accaacgtct acgcggactc cttcgtaatc   1260
agaggagatg aagttagaca gattgcgccg ggacaaactg gaaagatcgc ggattataac   1320
tacaagctac cggacgactt caccggatgt gtaattgcgt ggaattcgaa caacctagac   1380
tccaaagtcg gaggaaacta caactacttg tacagactat tcagaaagtc caacctaaag   1440
ccgttcgaga gagacatctc caccgaaatc tatcaggctg gatctacacc gtgtaatggt   1500
gtcgaaggat tcaactgcta cttcccgcta cagtcttacg gatttcaacc gacaaacggt   1560
gtaggatatc agccgtacag agtcgtcgta ctatccttcg aactactaca tgctccggcg   1620
acagtatgtg gaccgaaaaa gtctaccaac ctagtcaaga caaatgcgt caactttaac   1680
ttcaacggac taaccggaac cggtgtccta accgaatcta acagaagtt tctaccgttc   1740
cagcagttcg gaagagatat cgcggataca acagacgctg tcagagatcc gcaaaccttg   1800
gagatcctag atatcacacc gtgttctttc ggtggtgtct ctgtaattac tccgggaacg   1860
aacacctcca tcaagtagc ggtactatac caggacgtga actgtacaga agtaccggta   1920
gctattcacg cggatcaact aacaccaact tggagagtgt actccaccgg atctaacgta   1980
ttccaaacaa gagcgggatg tctaatcgga gcgaacacg taaacaactc ctacgaatgt   2040
gatatcccga ttggagcggg aatctgtgcg tcttaccaaa cacaaacaaa ctctccgaga   2100
agagcgagat ctgtagcctc tcaatctatt atcgcctaca ccatgtcctt gggagccgaa   2160
aattctgtcg cgtactccaa caattctatc gcgatcccga caaacttcac catctctgta   2220
acaaccgaga tcctaccggt gtcatgacc aagacatctg tcgattgcac catgtacatc   2280
tgcggagatt ccaccgagtg ctccaaccta ctactacagt acggatcttt ctgtacccag   2340
ctaaacagag cgttgactgg aatcgctgta gagcaggata gaacactca agaggtattc   2400
gcgcaagtca agcagatcta taagactccg ccgatcaag acttcggagg tttcaacttc   2460
tctcagatct tgccggatcc gtccaaaccg tctaagagat ctttcatcga ggacctacta   2520
ttcaacaaag tcaccctagc tgacgcggga ttcatcaaac aatacggaga ttgcttggga   2580
gacattgcgg cgagagatct aatttgcgcg cagaagttta acggattgac agtactaccg   2640
ccgctactaa ccgatgagat gattgcgcag tacacgtctg ctctattggc gggaacaatt   2700
acaagtggat ggacatttgg agccggtgcc gctctacaaa ttccgtttgt tctgcaaatg   2760
gcgtacagat tcaacggaat cggagtaacc cagaacgtct tgtacgagaa ccagaagcta   2820
atcgcgaacc agttcaattc cgcgatcgga aagatccagg acagtctatc ttctactgct   2880
tcggcgttgg gaaagctaca ggatgtagta aatcaaaacg cgcaggcgct aaacaccttg   2940
gtcaagcaac tatcctctaa cttcggagcg atctcgtccg tcctaaacga catcttatcc   3000
agactagatc caccggaagc ggaggtccag atcgatagac taatcactgg aagattgcag   3060
tccctacaga cctacgtaac acagcaacta attagagcgg cggagattag agcctctgct   3120
aatctagctg cgaccaagat gtccgaatgt gtcttgggac aatccaagag agtggacttc   3180
tgcggaaagg gataccacct aatgtctttc ccacaatctg cgccgcatgg tgtcgtattc   3240
ctacatgtaa catatgtgcc ggcgcaagaa aagaacttca caacagctcc agcgatctgc   3300
catgatggaa aagctcattt cccgagagag ggagtctttg tctctaacgg aactcattgg   3360
ttcgtcaccc agagaaactt ctacgagccg cagatcatca ccaccgacaa cacattcgtc   3420
```

```
tcgggaaact gcgacgtggt catcggaatc gtaaacaata ccgtctacga tccgttgcag   3480
ccggaactag actccttcaa agaagagttg gacaagtact tcaagaacca cacctctccg   3540
gatgtggact tgggagatat ctctggaatc aacgcgtccg tcgtcaacat ccagaaagaa   3600
atcgatagat tgaacgaggt cgcgaagaac ttgaacgagt ccctaatcga cctacaagag   3660
ctaggaaaat acgagcagta catcaagtgg ccgtggtgga catctgactg gggagtccta   3720
acgaacctag gaatcctact actattgtcg atcgcggtcc taatcgcgct atcctgtatc   3780
tgtagaatct tcaccaagta catcgga                                        3807

SEQ ID NO: 117          moltype = AA   length = 1269
FEATURE                 Location/Qualifiers
source                  1..1269
                        mol_type = protein
                        organism = synthetic construct
SEQUENCE: 117
MWTTCFFISL ILIQGIKTLF VFLVLLPLVS SQCVNLTTRT QLPPAYTNSF TRGVYYPDKV   60
FRSSVLHSTQ DLFLPFFSNV TWFHAIHVSG TNGTKRFDNP VLPFNDGVYF ASTEKSNIIR   120
GWIFGTTLDS KTQSLLIVNN ATNVVIKVCE FQFCNDPFLG VYYHKNNKSW MESEFRVYSS   180
ANNCTFEYVS QPFLMDLEGK QGNFKNLREF VFKNIDGYFK IYSKHTPINL VRDLPQGFSA   240
LEPLVDLPIG INITRFQTLL ALHRSYLTPG DSSSGWTAGA AAYYVGYLQP RTFLLKYNEN   300
GTITDAVDCA LDPLSETKCT LKSFTVEKGI YQTSNFRVQP TESIVRFPNI TNLCPFGEVF   360
NATRFASVYA WNRKRISNCV ADYSVLYNSA SFSTFKCYGV SPTKLNDLCF TNVYADSFVI   420
RGDEVRQIAP GQTGTIADYN YKLPDDFTGC VIAWNSNNLD SKVGGNYNYL YRLFRKSNLK   480
PFERDISTEI YQAGSTPCNG VKGFNCYFPL QSYGFQPTYG VGYQPYRVVV LSFELLHAPA   540
TVCGPKKSTN LVKNKCVNFN FNGLTGTGVL TESNKKFLPF QQFGRDIADT TDAVRDPQTL   600
EILDITPCSF GGVSVITPGT NTSNQVAVLY QDVNCTEVPV AIHADQLTPT WRVYSTGSNV   660
FQTRAGCLIG AEHVNNSYEC DIPIGAGICA SYQTQTNSPR RARSVASQSI IAYTMSLGAE   720
NSVAYSNNSI AIPTNFTISV TTEILPVSMT KTSVDCTMYI CGDSTECSNL LLQYGSFCTQ   780
LNRALTGIAV EQDKNTQEVF AQVKQIYKTP PIKDFGGFNF SQILPDPSKP SKRSFIEDLL   840
FNKVTLADAG FIKQYGDCLG DIAARDLICA QKFNGLTVLP PLLTDEMIAQ YTSALLAGTI   900
TSGWTFGAGA ALQIPFAMQM AYRFNGIGVT QNVLYENQKL IANQFNSAIG KIQDSLSSTA   960
SALGKLQDVV NQNAQALNTL VKQLSSNFGA ISSVLNDILS RLDKVEAEVQ IDRLITGRLQ   1020
SLQTYVTQQL IRAAEIRASA NLAATKMSEC VLGQSKRVDF CGKGYHLMSF PQSAPHGVVF   1080
LHVTYVPAQE KNFTTAPAIC HDGKAHFPRE GVFVSNGTHW FVTQRNFYEP QIITTDNTFV   1140
SGNCDVVIGI VNNTVYDPLQ PELDSFKEEL DKYFKNHTSP DVDLGDISGI NASVVNIQKE   1200
IDRLNEVAKN LNESLIDLQE LGKYEQYIKW PWWTSDWGVL TNLGILLLLS IAVLIALSCI   1260
CRIFTKYIG                                                            1269

SEQ ID NO: 118          moltype = AA   length = 1269
FEATURE                 Location/Qualifiers
source                  1..1269
                        mol_type = protein
                        organism = synthetic construct
SEQUENCE: 118
MWTTCFFISL ILIQGIKTLF VFLVLLPLVS SQCVNLTTRT QLPPAYTNSF TRGVYYPDKV   60
FRSSVLHSTQ DLFLPFFSNV TWFHAIHVSG TNGTKRFDNP VLPFNDGVYF ASTEKSNIIR   120
GWIFGTTLDS KTQSLLIVNN ATNVVIKVCE FQFCNDPFLG VYYHKNNKSW MESEFRVYSS   180
ANNCTFEYVS QPFLMDLEGK QGNFKNLREF VFKNIDGYFK IYSKHTPINL VRDLPQGFSA   240
LEPLVDLPIG INITRFQTLL ALHRSYLTPG DSSSGWTAGA AAYYVGYLQP RTFLLKYNEN   300
GTITDAVDCA LDPLSETKCT LKSFTVEKGI YQTSNFRVQP TESIVRFPNI TNLCPFGEVF   360
NATRFASVYA WNRKRISNCV ADYSVLYNSA SFSTFKCYGV SPTKLNDLCF TNVYADSFVI   420
RGDEVRQIAP GQTGTIADYN YKLPDDFTGC VIAWNSNNLD SKVGGNYNYL YRLFRKSNLK   480
PFERDISTEI YQAGSTPCNG VKGFNCYFPL QSYGFQPTYG VGYQPYRVVV LSFELLHAPA   540
TVCGPKKSTN LVKNKCVNFN FNGLTGTGVL TESNKKFLPF QQFGRDIADT TDAVRDPQTL   600
EILDITPCSF GGVSVITPGT NTSNQVAVLY QDVNCTEVPV AIHADQLTPT WRVYSTGSNV   660
FQTRAGCLIG AEHVNNSYEC DIPIGAGICA SYQTQTNSPR RARSVASQSI IAYTMSLGAE   720
NSVAYSNNSI AIPTNFTISV TTEILPVSMT KTSVDCTMYI CGDSTECSNL LLQYGSFCTQ   780
LNRALTGIAV EQDKNTQEVF AQVKQIYKTP PIKDFGGFNF SQILPDPSKP SKRSFIEDLL   840
FNKVTLADAG FIKQYGDCLG DIAARDLICA QKFNGLTVLP PLLTDEMIAQ YTSALLAGTI   900
TSGWTFGAGA ALQIPFAMQM AYRFNGIGVT QNVLYENQKL IANQFNSAIG KIQDSLSSTA   960
SALGKLQDVV NQNAQALNTL VKQLSSNFGA ISSVLNDILS RLDPPEAEVQ IDRLITGRLQ   1020
SLQTYVTQQL IRAAEIRASA NLAATKMSEC VLGQSKRVDF CGKGYHLMSF PQSAPHGVVF   1080
LHVTYVPAQE KNFTTAPAIC HDGKAHFPRE GVFVSNGTHW FVTQRNFYEP QIITTDNTFV   1140
SGNCDVVIGI VNNTVYDPLQ PELDSFKEEL DKYFKNHTSP DVDLGDISGI NASVVNIQKE   1200
IDRLNEVAKN LNESLIDLQE LGKYEQYIKW PWWTSDWGVL TNLGILLLLS IAVLIALSCI   1260
CRIFTKYIG                                                            1269

SEQ ID NO: 119          moltype = DNA   length = 4947
FEATURE                 Location/Qualifiers
source                  1..4947
                        mol_type = other DNA
                        organism = synthetic construct
SEQUENCE: 119
aaaaattgaa aataaataca aaggttcttg agggttgtgt taaattgaaa gcgagaaata   60
atcataagcc accatgtgga cgacctgctt cttcatctcc ctaatcctaa tccagggaat   120
caagacccta ttcgtgttcc tagtcctact accgctagtc tcttctcagt gtgtaaacct   180
aacaacgaga acacaactac caccggcgta caccaattct ttcacaagag gagtatatta   240
cccgacaag gtgttcagat cctccgtact acattctaca caggacctat tcctaccgtt   300
cttctctaac gtaacatggt tccacgcgat ccatgtctct ggaacaaacg gaacgaagag   360
attcgataac ccggtcttgc cgttcaacga tggtgtatac tttgcgtcca ccgagaagtc   420
```

-continued

```
caacatcatc agaggatgga tcttcggaac caccttggat tctaagaccc agtccttgct   480
aatcgtcaac aacgcgacca acgtcgtcat caaagtctgc gaattccagt tctgtaacga   540
cccgttcttg ggagtctact accacaagaa caacaagtcc tggatggaat ccgagttcag   600
agtctactct tccgcgaaca actgcacctt cgaatatgta tctcagccgt tcctaatgga   660
cctagaggga aagcagggaa acttcaagaa cctaagagag ttcgtattca agaacatcga   720
cggatacttc aagatctact ccaagcacac tccgatcaac ctagttagag atctaccgca   780
aggattctct gcgctagaac cgttagtaga tttgccgatc ggaatcaaca tcaccagatt   840
ccagacacta ctagcgctac acagatctta cctaacgccg ggagattctt cttctggatg   900
gactgctggt gctgcggctt attatgtagg atacctacag ccgagaacct tcctattgaa   960
gtacaacgaa aacggaacca tcaccgatgc cgtagattgt gctctagatc cgctatccga   1020
aacgaagtgc accctaaagt cttttcaccgt cgagaaggga atctaccaga cctccaactt   1080
tagagtacag ccgaccgaat ccatcgtcag atttccgaac atcacgaacc tatgtccgtt   1140
cggagaagtg ttcaacgcga caagatttgc gtctgtctat gcgtggaaca gaaaaagaat   1200
cagtaactgc gtcgcggact actccgtcct atacaactct gcctctttct ccacgttcaa   1260
atgctacggt gtatctccga caaagctaaa cgatctatgc ttcaccaacg tctacgcgga   1320
ctccttcgta atcagaggag atgaagttag acagattgcg ccgggacaaa ctggaaagat   1380
cgcggattat aactacaagc taccggacga cttcaccgga tgtgtaattg cgtggaattc   1440
gaacaaccta gactccaaag tcggaggaaa ctacaactac ttgtacagac tattcagaaa   1500
gtccaaccta aagccgttcg agagagacat ctccaccgaa atctatcagg ctggatctac   1560
accgtgtaat ggtgtcgaag gattcaactg ctacttcccg ctacagtctt acggatttca   1620
accgacaaac ggtgtaggat atcagccgta cagagtcgtc gtactatcct tcgaactact   1680
acatgctccg gcgacagtat gtggaccgaa aaagtctacc aacctagtca gaacaaatg   1740
cgtcaacttt aacttcaacg gactaaccgg aaccggtgtc ctaaccgaat ctaacaagaa   1800
gtttctaccg ttccagcagt tcggaagaga tatcgcggat acaacagacg ctgtcagaga   1860
tccgcaaacc ttggagatcc tagatatcac accgtgttct ttcggtggtg tctctgtaat   1920
tactccggga acgaacacct ccaatcaagt agcggtacta taccaggacg tgaactgtac   1980
agaagtaccg gtagctattc acgcggatca actaacacca acttggagag tgtactccac   2040
cggatctaac gtattccaaa caagagcggg atgtctaatc ggagcggaac acgtaaacaa   2100
ctcctacgaa tgtgatatcc cgattggagc gggaatctgt gcgtcttacc aaacacaaac   2160
aaactctccg agaagagcga gatctgtagc ctctcaatct attatcgcct acaccatgtc   2220
cttgggagcc gaaaattctg tcgcgtactc caacaattct atcgcgatcc cgacaaactt   2280
caccatctct gtaacaaccg agatcctacc ggtgtctatg accaagacat ctgtcgattg   2340
caccatgtac atctgcggag attccaccga gtgctccaac ctactactac agtacggatc   2400
tttctgtacc cagctaaaca gagcgttgac tggaatcgct gtagagcagg ataagaacac   2460
tcaagaggta ttcgcgcaag tcaagcagat ctataagact ccgccgatca aggacttcgg   2520
aggtttcaac ttctctcaga tcttgccgga tccgtccaaa ccgtctaaga gatctttcat   2580
cgaggaccta ctattcaaca aagtcaccct agctgacgcg ggattcatca aacaatacgg   2640
agattgcttg ggagacattg cggcgagaga tctaatttgc gcgcagaagt ttaacggatt   2700
gacagtacta ccgccgctac taaccgatga gatgattgcg cagtacacgt ctgctctatt   2760
ggcgggaaca attacaagtg gatggacatt tggagccggt gccgctctac aaattccgtt   2820
tgctatgcaa atggcgtaca gattcaacgg aatcggagta acccagaacg tcttgtacga   2880
gaaccagaag ctaatcgcga accagttcaa ttccgcgatc ggaaagatcc aggacagtct   2940
atcttctact gcttcggcgt tgggaaagct acaggatgta gtaaatcaaa acgcgcaggc   3000
gctaaacacc ttggtcaagc aactatcctc taacttcgga gcgatctcgt ccgtcctaaa   3060
cgacatctta tccagactag ataaggtcga agcggaggtc cagatcgata gactaatcac   3120
tggaagattg cagtccctac agacctacgt aacacagcaa ctaattagag cggcggagat   3180
tagagcctct gctaatctag ctgcgaccaa gatgtccgaa tgtgtcttgg gacaatccaa   3240
gagagtggac ttctgcggaa agggatacca cctaatgtct ttcccacaat ctgcgccgca   3300
tggtgtcgta ttcctacatg taacatatgt gccggcgcaa gaaaagaact tcacaacagc   3360
tccagcgatc tgccatgatg gaaaaagctca tttcccgaga gagggagtct ttgtctctaa   3420
cggaactcat tggttcgtca cccagagaaa cttctacgag ccgcagatca tcaccaccga   3480
caacacattc gtctcgggaa actgcgacgt ggtcatcgga atcgtaaaca ataccgtcta   3540
cgatccgttg cagccggaac tagactcctt caaagaagag ttggacaagt acttcaagaa   3600
ccacacctct ccggatgtgg acttgggaga tatctctgga atcaacgcgt ccgtcgtcaa   3660
catccagaaa gaaatcgata gattgaacga ggtcgcgaag aacttgaacg agtccctaat   3720
cgacctacaa gagctaggaa aatacgagca gtacatcaag tggccgtggt ggacatctga   3780
ctggggagtc ctaacgaacc taggaatcct actactattg tcgatcgcgg tcctaatcgc   3840
gctatcctgt atctgtagaa tcttcaccaa gtacatcgga gagccggaag cttaataatt   3900
tttatcttttc atttttgtttt tttctatgct ataagccacc atgtactcct tcgtgtccga   3960
agaaaccgga accttgatcg tcaactccgt cctactattc ctagcgttcg tcgtgttcct   4020
actagtaacc ctagctatcc taaccgcgct aagactatgt gcgtactgct gcaacatcgt   4080
caacgtgtcc ctagtgaagc cgtccttcta cgtctactcc agagtcaaga acctaaactc   4140
ctctagagtc ccggacctac tagttgagcc agaggcttaa taaataaaaa ttattaagaa   4200
tctggctcct ggactagtag agcgatatta tcggaactgg aggatggtc ggtgtttagc   4260
ttgtagttcc cgattctgta tctagaatac gccgcaaatc cagaatctcc cgcgactctt   4320
tgagaggctc ccaacttata gtacgatagg gttctagagg tcgctacggt gatctccttc   4380
ggtaggtcct tgatgtcaca tcttcctagg tggtgtcccg caattcttag atgtcctctt   4440
aggatgaccg ctccgataac caattcggat tccaatagcg gtctggttag gatggttcca   4500
tgtagcggta cgttcaatag gatgttcgtc tccgggttga acgaccacat agatctggtt   4560
ctcgcgaata gtctgaagga ggcgatgaag taggatagcc acattagtcc tactagacaa   4620
gccatagcga tcgcgattcc acctgtgatc cagttgattc tgtagaccgc agctagaacg   4680
aagcaggcca aggtgaccgg ccatagtagc cataggaaga ttagcttgat gatgtacaag   4740
aatctgttcc tgttcgcgta cgcgaactgt agtaggcaga tccaggttag gaataggaat   4800
ccgatgacta ggttccactg ctctagtagc ttcttcaact cttcgacggt gatggttccg   4860
ttagaatccg ccatggtggc ttatgattat ttctcgcttt caatttaaca caaccctcaa   4920
gaacctttgt atttatttct aattttt                                       4947
```

SEQ ID NO: 120       moltype = DNA  length = 4953
FEATURE              Location/Qualifiers -continued

```
source                  1..4953
                        mol_type = other DNA
                        organism = synthetic construct
SEQUENCE: 120
aaaaattgaa aataaataca aaggttcttg agggttgtgt taaattgaaa gcgagaaata  60
atcataaccc ggggccacca tgtggacgac ctgcttcttc atctccctaa tcctaatcca  120
gggaatcaag accctattcg tgttcctagt cctactaccg ctagtctctt ctcagtgtgt  180
aaaacctaaca acgagaacac aactaccacc ggcgtacacc aattctttca caagaggagt  240
atattacccg gacaaggtgt tcagatcctc cgtactacat tctacacagg acctattcct  300
accgttcttc tctaacgtaa catggttcca cgcgatccat gtctctggaa caaacggaac  360
gaagagattc gataacccgg tcttgccgtt caacgatggt gtatactttg cgtccaccga  420
gaagtccaac atcatcagag gatggatctt cggaaccacc ttggattcta agacccagtc  480
cttgctaatc gtcaacaacg cgaccaacgt cgtcatcaaa gtctgcgaat tccagttctg  540
taacgacccg ttcttgggag tctactacca caagaacaac aagtcctgga tggaatccga  600
gttcagagtc tactcttccg cgaacaactg caccttcgaa tatgtatctc agccgttcct  660
aatggaccta gagggaaagc agggaaactt caagaaccta agagagttcg tattcaagaa  720
catcgacgga tacttcaaga tctactccaa gcacactccg atcaacctag ttagagatct  780
accgcaagga ttctctgcgc tagaaccgtt agtagatttg ccgatcggaa tcaaacatcac  840
cagattccag acactactag cgctacacag atcttaccta acgccgggag attcttcttc  900
tggatggact gctggtgctg cggcttatta tgtaggatac ctacagccga gaaccttcct  960
attgaagtac aacgaaaacg gaaccatcac cgatgccgta gattgtgctc tagatccgct  1020
atccgaaacg aagtgcaccc taaagtcttt caccgtcgaa aagggaatct accagaccct  1080
caactttaga gtacagccga ccgaatccat cgtcagattt ccgaacatca cgaacctatg  1140
tccgttcgga gaagtgttca acgcgacaag atttgcgtct gtctatgcgt ggaacagaaa  1200
aagaatcagt aactgcgtcg cggactactc cgtcctatac aactctgcct ctttctccac  1260
gttcaaatgc tacggtgtat ctccgacaaa gctaaacgat ctatgcttca ccaacgtca  1320
cgcggactcc ttcgtaatca gaggagatga agttagacag attgcgccgg gacaaactgg  1380
aaagatcgcg gattataact acaagctacc ggacgacttc accggatgtg taattgcgtg  1440
gaattcgaac aacctagact ccaaagtcgg aggaaactac aactacttgt acagactatt  1500
cagaaagtcc aacctaaagc cgttcgagag agacatctcc accgaaatct atcaggctgg  1560
atctacaccg tgtaatggtg tcgaaggatt caactgctac ttcccgctac agtcttacgg  1620
atttcaaccg acaaacggtg taggatatca gccgtacaga gtcgtcgtac tatccttcga  1680
actactacat gctccggcga cagtatgtgg accgaaaaag tctaccaacc tagtcaagaa  1740
caaatgcgtc aactttaact tcaacggact aaccggaacc ggtgtcctaa ccgaatctaa  1800
caagaagttt ctaccgttcc agcagttcgg aagagatatc gcggatacaa cagacgctgt  1860
cagagatccg caaaccttgg agatcctaga tatcacaccg tgttctttcg gtggtgtctc  1920
tgtaattact ccgggaacga acacctccaa tcaagtagcg gtactatacc aggacgtgaa  1980
ctgtacagaa gtaccggtag ctattcacgc ggatcaacta acaccaactt ggagagtgta  2040
ctccaccgga tctaacgtat tccaaacaag agcgggatgt ctaatcggag cggaacacgt  2100
aaacaactcc tacgaatgtg atatcccgat tggagcggga atctgtgcgt cttaccaaac  2160
acaaacaaac tctccgagaa gagcgagatc tgtagcctct caatctatta tcgcctacac  2220
catgtccttg ggagccgaaa attctgtcgc gtactccaac aattctatcg cgatcccgac  2280
aaacttcacc atctctgtaa caaccgagat cctaccggtg tctatgacca agacatctgt  2340
cgattgcacc atgtacatct gcggagattc caccgagtgc tccaacctac tactacagta  2400
cggatctttc tgtacccagc taaacagagc gttgactgga atcgctgtag agcaggataa  2460
gaacactcaa gaggtattcg cgcaagtcaa gcagatctat aagactccgc cgatcaagga  2520
cttcggaggt ttcaacttct ctcagatctt gccggatccg tccaaaccgt ctaagagatc  2580
tttcatcgag gacctactat tcaacaaagt caccctagct gacgcgggat tcatcaaaca  2640
atacggagat tgcttgggag acattgcggc gagagatcta atttgcgcgc agaagtttaa  2700
cggattgaca gtactaccgc cgctactaac cgatgagatg attgcgcagt acacgtctgc  2760
tctattggcg ggaacaatta caagtggatg gacatttgga gccggtgccg ctctacaaat  2820
tccgtttgct atgcaaatgg cgtacagatt caacggaatc ggagtaaccc agaacgtctt  2880
gtacgagaac cagaagctaa tcgcgaacca gttcaattcc gcgatcggaa agatccagga  2940
cagtctatct tctactgctt cggcgttggg aaagctacag gatgtagtaa atcaaaacgc  3000
gcaggcgcta aacaccttgg tcaagcaact atcctctaac ttcggagcga tctcgtccgt  3060
cctaaacgac atcttatcca gactagataa ggtcgaagcg gaggtccaga tcgatagact  3120
aatcactgga agattgcagt ccctacgac ctacgtaaca cagcaactaa ttagagcggc  3180
ggagattaga gcctctgcta atctagctgc gaccaagatg tccgaatgtg tcttgggaca  3240
atccaagaga gtggacttct gcggaaaggg ataccaccta atgtctttcc cacaatctgt  3300
gccgcatggt gtcgtattcc tacatgtaac atatgtgccg gtgcaagaa agaacttcac  3360
aacagctcca gcgatctgcc atgatggaaa agctcatttc ccgagagagg gagtctttgt  3420
ctctaacgga actcattggt tcgtcaccca gagaaacttc tacgagccgc agatcatcac  3480
caccgacaac acattcgtct cgggaaactg cgacgtggtc atcggaatcg taaacaatac  3540
cgtctacgat ccgttgcagc cggaactaga ctccttcaaa gaagagttga acaagtacct  3600
caagaaccac acctctccgg atgtggactt gggagatatc tctggaatca acgcgtccgt  3660
cgtcaacatc cagaaagaaa tcgatagatt gaacgaggtc gcgaagaact tgaacgagtc  3720
cctaatcgac ctacaagagc taggaaaata cgagcagtac atcaagtggc cgtggtggac  3780
atctgactgg ggagtcctaa cgaacctagg aatcctacta ctattgtcga tcgcggtcct  3840
aatcgcgcta tcctgtatct gtagaatctt caccaagtac atcggagagc cggaagctta  3900
ataattttta tctttcattt tgtttttttc tatgctataa gccaccatgt actccttcgt  3960
gtccgaagaa accggaacct tgatcgtcaa ctccgtccta ctattcctag cgttcgtcgt  4020
gttcctacta gtaaccctag ctatcctaac cgcgctaaga ctatgtgcgt actgctgcaa  4080
catcgtcaac gtgtccctag tgaagccgtc cttctacgtc tactccagag tcaagaacct  4140
aaactcctct agagtcccgg acctactagt tgagccagac gcttaataaa taaaaattat  4200
taagcctctg gctcctcggac tagtagagcg atattatcgg aactggagga gtggtcggtg  4260
tttagcttgt agttccgat tctgtatcta gaatacgccg caaatccaga atctcccgcg  4320
actctttgag aggctcccaa cttatagtac gatagggttc tagaggtcgc tacggtgatc  4380
tccttcggta ggtccttgat gtcacatctt cctaggtggt gtcccgcaat tcttagatgt  4440
cctcttagga tgaccgctcc gataaccaat tcggattcca atagcggtct ggttaggatg  4500
```

```
gttccatgta gcggtacgtt caataggatg ttcgtctccg ggttgaacga ccacatagat  4560
ctggttctcg cgaatagtct gaaggaggcg atgaagtagg atagccacat tagtcctact  4620
agacaagcca tagcgatcgc gattccacct gtgatccagt tgattctgta gaccgcagct  4680
agaacgaagc aggccaaggt gaccggccat agtagccata ggaagattag cttgatgatg  4740
tacaagaatc tgttcctgtt cgcgtacgcg aactgtagta ggcagatcca ggttaggaat  4800
aggaatccga tgactaggtt ccactgctct agtagcttct tcaactcttc gacggtgatg  4860
gttccgttag aatccgccat ggtggcttat gattatttct cgctttcaat ttaacacaac  4920
cctcaagaac ctttgtattt attttcaatt ttt                               4953
```

```
SEQ ID NO: 121              moltype = DNA  length = 4947
FEATURE                     Location/Qualifiers
source                      1..4947
                            mol_type = other DNA
                            organism = synthetic construct
SEQUENCE: 121
aaaaattgaa aataaataca aaggttcttg agggttgtgt taaattgaaa gcgagaaata  60
atcataagcc accatgtgga cgacctgctt cttcatctcc ctaatcctaa tccagggaat  120
caagacccta ttcgtgttcc tagtcctact accgctagtc tcttctcagt gtgtaaacct  180
aacaacgaga acacaactac caccggcgta caccaattct ttcacaagag gagtatatta  240
cccgacaag gtgttcagat cctccgtact acattctaca caggacctat tcctaccgtt  300
cttctctaac gtaacatggt tccacgcgat ccatgtctct ggaacaaacg gaacgaagag  360
attcgataac ccggtcttgc cgttcaacga tggtgtatac tttgcgtcca ccgagaagtc  420
caacatcatc agaggatgga tcttcggaac caccttggat tctaagaccc agtccttgct  480
aatcgtcaac aacgcgacca acgtcgtcat caaagtctgc gaattccagt tctgtaacga  540
cccgttcttg ggagtctact accacaagaa caacaagtcc tggatggaat ccgagttcag  600
agtctactct tccgcgaaca actgcacctt cgaatatgta tctcagccgt tcctaatgga  660
cctagaggga aagcagggaa acttcaagaa cctaagagag ttcgtattca agaacatcga  720
cggatacttc aagatctact ccaagcacac tccgatcaac ctagttagag atctaccgca  780
aggattctct gcgctagaac cgttagtaga tttgccgatc ggaatcaaca tcaccagatt  840
ccagacacta ctagcgctac acagatctta cctaacgccg ggagattctt cttctggatg  900
gactgctggt gctgcggctt attatgtagg ataccacag ccgagaacct tcctattgaa  960
gtacaacgaa aacggaacca tcaccgatgc cgtagattgt gctctagatc cgctatccga  1020
aacgaagtgc accctaaagt ctttcaccgt cgagaaggga atctaccaga cctccaactt  1080
tagagtacag ccgaccgaat ccatcgtcag atttccgaac atcacgaacc tatgtccgtt  1140
cggagaagtg ttcaacgcga caagatttgc gtctgtctat gcgtggaaca gaaaaagaat  1200
cagtaactgc gtcgcggact actccgtcct atacaactct gcctcttct ccacgttcaa  1260
atgctacggt gtatctccga caaagctaaa cgatctatgc ttcaccaacg tctacgcgga  1320
ctccttcgta atcagaggag atgaagttag acagattgcg ccgggacaaa ctggaaagat  1380
cgcggattat aactacaagc taccggacga cttcaccgga tgtgtaattg cgtggaattc  1440
gaacaaccta gactccaaag tcggaggaaa ctacaactac ttgtacagac tattcagaaa  1500
gtccaaccta aagccgttcg agagagacat ctccaccgaa atctatcagg ctggatctac  1560
accgtgtaat ggtgtcgaag gattcaactg ctacttcccg ctacagtctt acggatttca  1620
accgacaaac ggtgtaggat atcagccgta cagagtcgtc gtactatcct tcgaactact  1680
acatgctccg gcgacagtat gtggaccgaa aaagtctacc aacctagtca agaacaaatg  1740
cgtcaacttt aacttcaacg gactaaccgg aaccggtgtc ctaaccgaat ctaacaagaa  1800
gtttctaccg ttccagcagt tcggaagaga tatcgcggat acaacagacg ctgtcagaga  1860
tccgcaaacc ttggagatcc tagatatcac accgtgttct ttcggtggtg tctctgtaat  1920
tactccggga acgaacacct ccaatcaagt agcggtacta taccaggacg tgaactgtac  1980
agaagtaccg gtagctattc acgcggatca actaacacca acttggagag tgtactccac  2040
cggatctaac gtattccaaa caagagcggg atgtctaatc ggagcggaac acgtaaacaa  2100
ctcctacgaa tgtgatatcc cgattggagc gggaatctgt ggcgtcttacc aaacacaaac  2160
aaactctccg agaagagcga gatctgtagc ctctcaatct attatcgcct acaccatgtc  2220
cttgggagcc gaaaattctg tcgcgtactc caacaattct atcgcgatcc cgacaaactt  2280
caccatctct gtaacaaccg agatcctacc ggtgtctatg accaagacat ctgtcgattg  2340
caccatgtac atctgcggag attccaccga gtgctccaac ctactactac agtacggatc  2400
tttctgtacc cagctaaaca gagcgttgac tggaatcgct gtagagcagg ataagaacac  2460
tcaagaggta ttcgcgcaag tcaagcagat ctataagact ccgccgatca aggacttcgg  2520
aggtttcaac ttctctcaga tcttgccgga tccgtccaaa ccgtctaaga gatctttcat  2580
cgaggaccta ctattcaaca aagtcaccct agctgacgcg ggattcatca aacaatacgg  2640
agattgcttg ggagacattg cggcgagaga tctaatttgc gcgcagaagt ttaacggatt  2700
gacagtacta ccgccgctac taaccgatga gatgattgcg cagtacacgt ctgctctatt  2760
ggcgggaaca attacaagtg gatggacatt tggagccggt gccgctctac aaattccgtt  2820
tgctatgcaa atggcgtaca gattcaacgg aatcggagta acccagaacg tcttgtacga  2880
gaaccagaac ctaatcgcga accagttcaa ttccgcgatc aggaaagatc aggacagtct  2940
atcttctact gcttcggcgt tgggaaagct acaggatgta gtaaatcaaa acgcgcaggc  3000
gctaaacacc ttggtcaagc aactatcctc taacttcgga gcgatctcgt ccgtcctaaa  3060
cgacatctta tccagactag atccaccgga agcggaggtc cagatcgata gactaatcac  3120
tggaagattg cagtccctac agacctacgt aacacagcaa ctaattagag cggcggagat  3180
tagagcctct gctaatctag ctgcgaccaa gatgtccgaa tgtgtcttgg gacaatccaa  3240
gagagtggac ttctgtcggaa agggatacca cctaatgtct ttcccacaat ctgcgccgca  3300
tggtgtcgta ttcctacatg taacatatgt gccggcgcaa gaaaagaact tcacaacagc  3360
tccagcgatc tgccatgatg gaaaagctca tttcccgaga gagggagtct ttgtctctaa  3420
cggaactcat tggttcgtca cccagagaaa cttctacgag ccgcagatca tcaccaccga  3480
caacacattc gtctcgggaa actgcgacgt ggtcatcgga atcgtaaaca ataccgtcta  3540
cgatccgttg cagccggaac tagactcctt caaagaagag ttggacaagt acttcaagaa  3600
ccacacctct ccggatgtgg acttgggaga tatctctgga atcaacgcgt ccgtcgtcaa  3660
catccagaaa gaaatcgata gattgaacga ggtcgcgaag aacttgaacg agtccctaat  3720
cgacctacaa gagctaggaa aatacgagca gtacatcaag tggccgtggt ggacatctga  3780
ctggggagtc ctaacgaacc taggaatcct actactattg tcgatcgcgg tcctaatcgc  3840
```

-continued

```
gctatcctgt atctgtagaa tcttcaccaa gtacatcgga gagccggaag cttaataatt    3900
tttatctttc attttgtttt tttctatgct ataagccacc atgtactcct tcgtgtccga    3960
agaaaccgga accttgatcg tcaactccgt cctactattc ctagcgttcg tcgtgttcct    4020
actagtaacc ctagctatcc taaccgcgct aagactatgt gcgtactgct gcaacatcgt    4080
caacgtgtcc ctagtgaagc cgtccttcta cgtctactcc agagtcaaga acctaaactc    4140
ctctagagtc ccggacctac tagttgagcc agaggcttaa taaataaaaa ttattaagcc    4200
tctggctcct ggactagtag agcgatatta tcggaactgg aggagtgggtc ggtgtttagc    4260
ttgtagttcc cgattctgta tctagaatac gccgcaaatc cagaatctcc cgcgactctt    4320
tgagaggctc ccaacttata gtacgatagg gttctagagg tcgctacggt gatctccttc    4380
ggtaggtcct tgatgtcaca tcttcctagg tggtgtcccg caattcttag atgtcctctt    4440
aggatgaccg ctccgataac caattcggat tccaatagcg gtctggttag gatggttcca    4500
tgtagcggta cgttcaatag gatgttcgtc tccgggttga acgaccacat agatctggtt    4560
ctcgcgaata gtctgaagga ggcgatgaag taggatagcc acattagtcc tactagacaa    4620
gccatagcga tcgcgattcc acctgtgatc cagttgattc tgtagaccgc agctagaacg    4680
aagcaggcca aggtgaccgg ccatagtagc cataggaaga ttagcttgat gatgtacaag    4740
aatctgttcc tgttcgcgta cgcgaactgt agtaggcaga tccaggttag gaataggaat    4800
ccgatgacta ggttccactg ctctagtagc ttcttcaact cttcgacggt gatggttccg    4860
ttagaatccg ccatggtggc ttatgattat ttctcgcttt caatttaaca caaccctcaa    4920
gaacctttgt atttattttc aattttt                                         4947
```

```
SEQ ID NO: 122          moltype = DNA  length = 4953
FEATURE                 Location/Qualifiers
source                  1..4953
                        mol_type = other DNA
                        organism = synthetic construct
SEQUENCE: 122
aaaaattgaa aataaataca aaggttcttg agggttgtgt taaattgaaa gcgagaaata    60
atcataaccc ggggccacca tgtggacgac ctgcttcttc atctccctaa tcctaatcca    120
gggaatcaag accctattcg tgttcctagt cctactaccg ctagtctctt ctcagtgtgt    180
aaacctaaca acgagaacac aactaccacc ggcgtacacc aattctttca caagaggagt    240
atattacccg gacaaggtgt tcagatcctc cgtactacat tctacacagg acctattcct    300
accgttcttc tctaacgtaa catggttcca cgcgatccat gtctctggaa caaacggaac    360
gaagagattc gataacccgg tcttgccgtt caacgatggt gtatactttg cgtccaccga    420
gaagtccaac atcatcagag gatggatctt cggaaccacc ttggattcta agacccagtc    480
cttgctaatc gtcaacaacg cgaccaacgt cgtcatcaaa gtctgcgaat tccagttctg    540
taacgacccg ttcttgggag tctactacca caagaacaac aagtcctgga tggaatccga    600
gttcagagtc tactcttccg cgaacaactg caccttcgaa tatgtatctc agccgttcct    660
aatggaccta gagggaaagc agggaaactt caagaaccta agagagttcg tattcaagaa    720
catcgacga tacttcaaga tctactccaa gcacactccg atcaacctag ttagagatct    780
accgcaagga ttctctgcgc tagaaccgtt agtagatttg ccgatcggaa tcaacatcac    840
cagattccag acactactag cgctacacag atcttaccta acgccgggag attcttcttc    900
tggatggact gctggtgctg cggcttatta tgtaggatac ctacagccga gaaccttcct    960
attgaagtac aacgaaaacg gaaccatcac cgatgccgta gattgtgctc tagatccgct    1020
atccgaaacg aagtgcaccc taaagtcttt caccgtcgag aagggaatct accagacctc    1080
caactttaga gtacagccga ccgaatccat cgtcagattt ccgaacatca cgaacctatg    1140
tccgttcgga gaagtgttca acgcgacaag atttgcgtct gtctatgcgt ggaacagaaa    1200
aagaatcagt aactgcgtcg cggactactc cgtcctatac aactctgcct ctttctccac    1260
gttcaaatgc tacggtgtat ctccgacaaa gctaaacgat ctatgcttca ccaacgtcta    1320
cgcggactcc ttcgtaatca gaggagatga agttagacag attgcgccgg gacaaactgg    1380
aaagatcgcg gattataact acaagctacc ggacgacttc accggatgtg taattgcgtg    1440
gaattcgaac aacctagact ccaaagtcgg aggaaactac aactacttgt acagactatt    1500
cagaaagtcc aacctaaagc cgttcgagag agacatctcc accgaaatct atcaggctgg    1560
atctacaccg tgtaatggtg tcgaaggatt caactgctac ttcccgctac agtcttacgg    1620
atttcaaccg acaaacggtg taggatatca gccgtacaga gtcgtcgtac tatccttcga    1680
actactacat gctccggcga cagtatgtgg accgaaaaag tctaccaacc tagtcaagaa    1740
caaatgcgtc aactttaact tcaacggact aaccggaacc ggtgtcctaa ccgaatctaa    1800
caagaagttt ctaccgttcc agcagttcgg aagagatatc gcggatacaa cagacgctgt    1860
cagagatccg caaaccttgg agatcctaga tatcacaccg tgttctttcg gtggtgtctc    1920
tgtaattact ccgggaacga acacctccaa tcaagtgacg gtatatacca aggacgtgaa    1980
ctgtacagaa gtaccggtag ctattcacgc ggatcaacta acaccaactt ggagagtgta    2040
ctccaccgga tctaacgtat tccaaacaag agcgggatgt ctaatcggag cggaacacgt    2100
aaacaactcc tacgaatgtg atatcccgat tggagcggga atctgtgcgt cttaccaaac    2160
acaaacaaac tctccgagaa gagcgagatc tgtagcctct caatctatta tcgcctcacac   2220
catgtccttg ggagccgaaa attctgtcgc gtactccaac aattctatcg cgatcccgac    2280
aaacttcacc atctctgtaa caaccgagat cctaccggtg tctatgacca agacatctgt    2340
cgattgcacc atgtacatct gcggagatte caccgagtgc tccaacctac tactacagta    2400
cggatctttc tgtacccagc taaacagagc gttgactgga atcgctgtag agcaggataa    2460
gaacactcaa gaggtattcg cgcaagtcaa gcagatctat aagactccgc cgatcaagga    2520
cttcggaggt ttcaacttct ctcagatctt gccggatccg tccaaaccgt ctaagagatc    2580
tttcatcgag gacctactat tcaacaaagt caccctagct gacgcgggat tcatcaaaca    2640
atacggagat tgctttgggag acattgcggc gagagatcta atttgcgcgc agaagtttaa    2700
cggattgaca gtactaccgc cgctactaac cgatgagatg attgcgcagt acacgtctgc    2760
tctattggcg ggaacaatta caagtggatg gacatttgga gccggtgccg ctctacaaat    2820
tccgtttgct atgcaaatgg cgtacagatt caacggaatc ggagataccc agaacgtctt    2880
gtacgagaac cagaagctaa tcgcgaacca gttcaattcc gcgatcggaa agatccagga    2940
cagtctatct tctactgctt cggcgttggg aaagctacag gatgtagtaa atcaaaacgc    3000
gcaggcgcta aacaccttgg tcaagcaact atcctctaac ttcggagcga tctcgtccgt    3060
cctaaacgac atcttatcca gactagatcc accggaagcg gaggtccaga tcgatagact    3120
aatcactgga agattgcagt ccctacagac ctacgtaaca cagcaactaa ttagagcggc    3180
```

```
ggagattaga gcctctgcta atctagctgc gaccaagatg tccgaatgtg tcttgggaca   3240
atccaagaga gtggacttct gcggaaaggg ataccaccta atgtctttcc cacaatctgc   3300
gccgcatggt gtcgtattcc tacatgtaac atatgtgccg gcgcaagaaa agaacttcac   3360
aacagctcca gcgatctgcc atgatggaaa agctcatttc ccgagagagg gagtctttgt   3420
ctctaacgga actcattggt tcgtcaccca gagaaacttc tacgagccgc agatcatcac   3480
caccgacaac acattcgtct cgggaaactg cgacgtggtc atcggaatcg taaacaatac   3540
cgtctacgat ccgttgcagc cggaactaga ctccttcaaa gaagagttgg acaagtactt   3600
caagaaccac acctctccgg atgtggactt gggagatatc tctggaatca acgcgtccgt   3660
cgtcaacatc cagaaagaaa tcgatagatt gaacgaggtc gcgaagaact tgaacgagtc   3720
cctaatcgac ctacaagagc taggaaaata cgagcagtac atcaagtggc cgtggtggac   3780
atctgactgg ggagtcctaa cgaacctagg aatcctacta ctattgtcga tcgcggtcct   3840
aatcgcgcta tcctgtatct gtagaatctt caccaagtac atcggagagc cggaagctta   3900
ataatttta tctttcattt tgtttttttc tatgctataa gccaccatgt actccttcgt   3960
gtccgaagaa accggaacct tgatcgtcaa ctccgtccta ctattcctag cgttcgtcgt   4020
gttcctacta gtaaccctag ctatcctaac cgcgctaaga ctatgtgcgt actgctgcaa   4080
catcgtcaac gtgtccctag tgaagccgtc cttctacgtc tactccagag tcaagaacct   4140
aaactcctct agagtcccgg acctactagt tgagccagag gcttaataaa taaaaattat   4200
taagcctctg gctcctggac tagtagagcg atattatcgg aactggagga gtggtcggtg   4260
tttagcttgt agttcccgat tctgtatcta gaatacgccg caaatccaga atctcccgcg   4320
actctttgag aggctcccaa cttatagtac gatagggttc tagaggtcgc tacggtgatc   4380
tccttcggta ggtccttgat gtcacatctt cctaggtggt gtcccgcaat tcttagatgt   4440
cctcttagga tgaccgctcc gataaccaat tcggattcca atagcggtct ggttaggatg   4500
gttccatgta gcggtacgtt caataggatg ttcgtctccg ggttgaacga ccacatagat   4560
ctggttctcg cgaatagtct gaaggaggcg atgaagtagg atagccacat tagtcctact   4620
agacaagcca tagcgatcgc gattccacct gtgatccagt tgattctgta gaccgcagct   4680
agaacgaagc aggccaaggt gaccggccat agtagccata ggaagattag cttgatgatg   4740
tacaagaatc tgttcctgtt cgcgtacgcg aactgtagta ggcagatcca ggttaggaat   4800
aggaatccga tgactaggtt ccactgctct agtagcttct tcaactcttc gacggtgatg   4860
gttccgttag aatccgccat ggtggcttat gattatttct cgctttcaat ttaacacaac   4920
cctcaagaac ctttgtattt attttcaatt ttt                                4953
```

```
SEQ ID NO: 123          moltype = DNA  length = 3905
FEATURE                 Location/Qualifiers
source                  1..3905
                        mol_type = other DNA
                        organism = synthetic construct
SEQUENCE: 123
aaaaattgaa aataaataca aaggttcttg agggttgtgt taaattgaaa gcgagaaata   60
atcataagcc accatgtgga cgacctgctt cttcatctcc ctaatcctaa tccagggaat   120
caagaccctt ttcgtgttcc tagtcctact accgctagtc tcttctcagt gtgtaaacct   180
aacaacgaga acacaactac caccggcgta caccaattct ttcacaagag gagtatatta   240
cccggacaag gtgttcagat cctccgtact acattctaca caggacctat tcctaccgtt   300
cttctctaac gtaacatggt tccacgcgat ccatgtctct ggaacaaacg gaacgaagag   360
attcgataac ccggtcttgc cgttcaacga tggtgtatac tttgcgtcca ccgagaagtc   420
caacatcatc agaggatgga tcttcggaac caccttggat tctaagaccc agtccttgct   480
aatcgtcaac aacgcgacca acgtcgtcat caaagtctgc gaattccagt tctgtaacga   540
cccgttcttg ggagtctact accacaagaa caacaagtcc tggatggaat ccgagttcag   600
agtctactct tccgcgaaca actgcacctt cgaatatgta tctcagccgt tcctaatgga   660
cctagaggga aagcagggaa acttcaagaa cctaagagag ttcgtattca agaacatcga   720
cggatacttc aagatctact ccaagcacac tccgatcaac ctagttagag atctaccgca   780
aggattctct gcgctagaac cgttagtaga tttgccgatc ggaatcaaca tcaccagatt   840
ccagacacta ctagcgctac acagatctta cctaacgccg ggagattctt cttctggatg   900
gactgctggt gctgcggctt attatgtagg atacctacag ccgagaacct tcctattgaa   960
gtacaacgaa aacggaacca tcaccgatgc cgtagattgt gctctagatc cgctatccga   1020
aacgaagtgc accctaaagt cttcaccgt cgagaaggga atctaccaga cctccaactt   1080
tagagtacag ccgaccgaat ccatcgtcag atttccgaac atcacgaacc tatgtccgtt   1140
cggagaagtg ttcaacgcga caagatttgc gtctgtctat gcgtggaaca gaaaaagaat   1200
cagtaactgc gtcgcggact actccgtcct atacaactct gcctctttct ccacgttcaa   1260
atgctacggt gtatctccga caaagctaaa cgatctatgc ttcaccaacg tctacgcgga   1320
ctccttcgta atcagaggag atgaagttag acagattgcg ccgggacaaa ctggaaagat   1380
cgcggattat aactacaagc taccggacga cttcaccgga tgtgtaattg cgtggaattc   1440
gaacaaccta gactccaaag tcggaggaaa ctacaactac ttgtacgac tattcagaaa    1500
gtccaaccta aagccgttcg agagagacat ctccaccgaa atctatcagg ctggatctac   1560
accgtgtaat ggtgtccgaag gattcaactg ctacttcccg ctacagtctt acggatttca   1620
accgacaaac ggtgtaggat atcagccgta cagagtcgtc gtactatcct cgaactact   1680
acatgctccg gcgacagtat gtggaccgaa aaagtctacc aacctagtca agaacaaatg   1740
cgtcaacttt aacttcaacg gactaaccgg aaccggtgtc ctaaccgaat ctaacaagaa   1800
gtttctaccg ttccagcagt tcggaagaga tatcgcggat acaacagacg ctgtcagaga   1860
tccgcaaacc ttggagatcc tagatatcac accgtgttct ttcggtggtg tctctgtaat   1920
tactccggga acgaacacct ccaatcaagt agcggtacta taccaggacg tgaactgtac   1980
agaagtaccg gtagctattc acgcggatca actaacacca acttggagag tgtactccac   2040
cggatctaac gtattccaaa caagagcggg atgtctaatc ggagcggaac acgtaaacaa   2100
ctcctacgaa tgtgatatcc cgattggagc gggaatctgt gcgtcttacc aaacacaaac   2160
aaactcctcg agaagagcga gatctgtagc ctctcaatct attatcgcct acaccatgtc   2220
cttgggagcc gaaaattctg tcgcgtactc caacaattcc atcgcgatcc cgacaaactt   2280
caccatctct gtaacaaccg agatcctacc ggtgtctatg accaagacat ctgtcgattg   2340
caccatgtac atctgcggag attccaccga gtgctccaac ctactactac agtacgatc    2400
tttctgtacc cagctaaaca gagcgttgac tggaatcgct gtagagcagg ataagaacac   2460
tcaagaggta ttcgcgcaag tcaagcagat ctataagact ccgccgatca aggacttcgg   2520
```

-continued

```
aggtttcaac ttctctcaga tcttgccgga tccgtccaaa ccgtctaaga gatctttcat   2580
cgaggaccta ctattcaaca aagtcaccct agctgacgcg ggattcatca aacaatacgg   2640
agattgcttg ggagacattg cggcgagaga tctaatttgc gcgcagaagt ttaacggatt   2700
gacagtacta ccgccgctac taaccgatga gatgattgcg cagtacacgt ctgctctatt   2760
ggcgggaaca attacaagtg gatggacatt tggagccggt gccgctctac aaattccgtt   2820
tgctatgcaa atggcgtaca gattcaacgg aatcggagta acccagaacg tcttgtacga   2880
gaaccagaag ctaatcgcga accagttcaa ttccgcgatc ggaaagatcc aggacagtct   2940
atcttctact gcttcggcgt tgggaaagct acaggatgta gtaaatcaaa acgcgcaggc   3000
gctaaacacc ttggtcaagc aactatcctc taacttcgga gcgatctcgt ccgtcctaaa   3060
cgacatctta tccagactag ataaggtcga agcggaggtc cagatcgata gactaatcac   3120
tggaagattg cagtccctac agacctacgt aacacagcaa ctaattagag cggcggagat   3180
tagagcctct gctaatctag ctgcgaccaa gatgtccgaa tgtgtcttgg acaatccaa    3240
gagagtggac ttctgcggaa agggatacca cctaatgtct ttcccacaat ctgcgccgca   3300
tggtgtcgta ttcctacatg taacatatgt gccggccgaa gaaaagaact tcacaacagc   3360
tccagcgatc tgccatgatg gaaaagctca tttcccgaga gagggagtct ttgtctctaa   3420
cggaactcat tggttcgtca cccagagaaa cttctacgag ccgcagatca tcaccaccga   3480
caacacattc gtctcgggaa actgcgacgt ggtcatcgga atcgtaaaca ataccgtcta   3540
cgatccgttg cagccggaac tagactcctt caaagaagag ttggacaagt acttcaagaa   3600
ccacacctct ccggatgtgg acttgggaga tatctctgga atcaacgcgt ccgtcgtcaa   3660
catccagaaa gaaatcgata gattgaacga ggtcgcgaag aacttgaacg agtccctaat   3720
cgacctacaa gagctaggaa aatacgagca gtacatcaag tggccgtggt ggacatctga   3780
ctggggagtc ctaacgaacc taggaatcct actactattg tcgatcgcgg tcctaatcgc   3840
gctatcctgt atctgtagaa tcttcaccaa gtacatcgga gagccggaag cttaataatt   3900
tttat                                                                 3905
```

```
SEQ ID NO: 124        moltype = DNA   length = 3911
FEATURE               Location/Qualifiers
source                1..3911
                      mol_type = other DNA
                      organism = synthetic construct
SEQUENCE: 124
aaaaattgaa aataaataca aaggttcttg agggttgtgt taaattgaaa gcgagaaata   60
atcataaccc ggggccacca tgtggacgac ctgcttcttc atctccctaa tcctaatcca   120
gggaatcaag accctattcg tgttcctagt cctactaccg ctagtctctt ctcagtgtgt   180
aaacctaaca acgagaacac aactaccacc ggcgtacacc aattctttca caagaggagt   240
atattacccg gacaaggtgt tcagatcctc cgtactacat tctacacagg acctattcct   300
accgttcttc tctaacgtaa catggttcca cgcgatccat gtctctggaa caaacggaac   360
gaagagattc gataacccgg tcttgccgtt caacgatggt gtatactttg cgtccaccga   420
gaagtccaac atcatcagag gatggatctt cggaaccacc ttggattcta agacccagtc   480
cttgctaatc gtcaacaacg cgaccaacgt cgtcatcaaa gtctgcgaat tccagttctg   540
taacgacccg ttcttgggag tctactacca caagaacaac aagtcctgga tggaatccga   600
gttcagagtc tactcttccg cgaacaactg caccttcgaa tatgtatctc agccgttcct   660
aatggaccta gagggaaagc agggaaactt caagaaccta agagagttcg tattcaagaa   720
catcgacgga tacttcaaga tctactccaa gcacactccg atcaacctag ttagagatct   780
accgcaagga ttctctgcgc tagaaccgtt agtagatttg ccgatcggaa tcaacatcac   840
cagattccag acactactag cgctacacag atcttaccta acgccgggag attcttcttc   900
tggatggact gctggtgctg cggcttatta tgtaggatac ctacagccga gaaccttcct   960
attgaagtac aacgaaaacg gaaccatcac cgatgccgta gattgtgctc tagatccgct  1020
atccgaaacg aagtgcaccc taaagtcttt caccgtcgag aagggaatct accagacctc  1080
caactttaga gtacagccga ccgaatccat cgtcagattt ccgaacatca cgaacctatg  1140
tccgttcgga gaagtgttca acgcgacaag atttgcgtct gtctatgcgt ggaacagaaa  1200
aagaatcagt aactgcgtcg cggactactc cgtcctatac aactctgcct ctttctccac  1260
gttcaaatgc tacggtgtat ctccgacaaa gctaaacgat ctatgcttca ccaacgtcta  1320
cgcggactcc ttcgtaatca gaggagatga agttagacag attgcgccgg acaaactgg   1380
aaagatcgcg gattataact acaagctacc ggacgacttc accggatgtg taattgcgtg  1440
gaattcgaac aacctagact ccaaagtcgg aggaaactac aactacttgt acagactatt  1500
cagaaagtcc aacctaaagc cgttcgagag agacatctcc accgaaatct atcaggctgg  1560
atctacaccg tgtaatggtg tcgaaggatt caactgctac ttcccgctac agtcttacgg  1620
atttcaaccg acaaacggtg taggatatca gccgtacaga gtcgtcgtac tatccttcga  1680
actactacat gctccggcga cagtatgtgg accgaaaaag tctaccaacc tagtcaagaa  1740
caaatgcgtc aactttaact tcaacggact aaccggaacc ggtgtcctaa ccgaatctaa  1800
caagaagttt ctaccgttcc agcagttcgg aagagatatc gcggatacaa cagacgctgt  1860
cagagatccg caaaccttgg agatcctaga tatcacaccg tgttctttcg gtggtgtctc  1920
tgtaattact ccgggaacga acacctccaa tcaagtagcg aagacgtgaa  1980
ctgtacagaa gtaccggtag ctattcacgc ggatcaacta acaccaactt ggagagtgta  2040
ctccaccgga tctaacgtat tccaaacaag agcgggatgt ctaatcggag cggaacacgt  2100
aaacaactcc tacgaatgtg atatcccgat tggagcggga atctgtgcgt cttaccaaac  2160
acaaacaaac tctccgagaa gagcgagatc tgtagcctct caatctatta tcgcctacac  2220
catgtccttg ggagccgaaa attctgtcgc gtactccaac aattctatcg cgatcccgac  2280
aaacttcacc atctctgtaa caaccgagat cctaccggtg tctatgacca agacatctgt  2340
cgattgcacc atgtacatct gcggagattc caccgagtgc tccaacctac tactacagta  2400
cggatctttc tgtacccagc taaacagagc gttgactgga atcgctgtag agcaggataa  2460
gaacactcaa gaggtattcg cgcaagtcaa gcagatctat aagactccgc cgatcaagga  2520
cttcggaggt ttcaacttct ctcagatctt gccggatccg tccaaaccgt ctaagagatc  2580
tttcatcgag gacctactat tcaacaaagt caccctagct gacgcgggat tcatcaaaca  2640
atacggagat tgcttgggag acattgcggc gagagatcta atttgcgcgc agaagtttaa  2700
cggattgaca gtactaccgc cgctactaac cgatgagatg attgcgcagt acacgtctgc  2760
tctattggcg ggaacaatta caagtggatg gacatttgga gccggtgccg ctctacaaat  2820
tccgtttgct atgcaaatgg cgtacagatt caacggaatc ggagtaaccc agaacgtctt  2880
```

-continued

```
gtacgagaac cagaagctaa tcgcgaacca gttcaattcc gcgatcggaa agatccagga   2940
cagtctatct tctactgctt cggcgttggg aaagctacag gatgtagtaa atcaaaacgc   3000
gcaggcgcta aacaccttgg tcaagcaact atcctctaac ttcggagcga tctcgtccgt   3060
cctaaacgac atcttatcca gactagataa ggtcgaagcg gaggtccaga tcgatagact   3120
aatcactgga agattgcagt ccctacagac ctacgtaaca cagcaactaa ttagagcggc   3180
ggagattaga gcctctgcta atctagctgc gaccaagatg tccgaatgtg tcttgggaca   3240
atccaagaga gtggacttct gcggaaaggg ataccaccta atgtctttcc cacaatctgc   3300
gccgcatggt gtcgtattcc tacatgtaac atatgtgccg gcgcaagaaa agaacttcac   3360
aacagctcca gcgatctgcc atgatggaaa agctcatttc ccgagagagg gagtctttgt   3420
ctctaacgga actcattggt tcgtcaccca gagaaacttc tacgagccgc agatcatcac   3480
caccgacaac acattcgtct cgggaaactg cgacgtggtc atcggaatcg taaacaatac   3540
cgtctacgat ccgttgcagc cggaactaga ctccttcaaa gaagagttgg acaagtactt   3600
caagaaccac acctctccgg atgtggactt gggagatatc tctggaatca acgcgtccgt   3660
cgtcaacatc cagaaagaaa tcgatagatt gaacgagcgc gcgaagaact tgaacgagtc   3720
cctaatcgac ctacaagagc taggaaaata cgagcagtac atcaagtggc cgtggtggac   3780
atctgactgg ggagtcctaa cgaacctagg aatcctacta ctattgtcga tcgcggtcct   3840
aatcgcgcta tcctgtatct gtagaatctt caccaagtac atcggagagc cggaagctta   3900
ataatttta t                                                         3911
```

SEQ ID NO: 125          moltype = DNA  length = 3905
FEATURE                 Location/Qualifiers
source                  1..3905
                        mol_type = other DNA
                        organism = synthetic construct
SEQUENCE: 125
```
aaaaattgaa aataaataca aaggttcttg agggttgtgt taaattgaaa gcgagaaata   60
atcataagcc accatgtgga cgacctgctt cttcatctcc ctaatcctaa tccagggaat   120
caagacccta ttcgtgttcc tagtcctact accgctagtc tcttctcagt gtgtaaacct   180
aacaacgaga acacaactac caccggcgta caccaattct ttcacaagag gagtatatta   240
cccggacaag gtgttcagat cctccgtact acattctaca caggacctat tcctaccgtt   300
cttctctaac gtaacatggt tccacgcgat ccatgtctct ggaacaaacg gaacgaagag   360
attcgataac ccggtcttgc cgttcaacga tggtgtatac tttgcgtcca ccgagaagtc   420
caacatcatc agaggatgga tcttcggaac caccttggat tctaagaccc agtccttgct   480
aatcgtcaac aacgcgacca acgtcgtcat caaagtctgc gaattccagt tctgtaacga   540
cccgttcttg ggagtctact accacaagaa caacaagtcc tggatggaat ccgagttcaa   600
agtctactct tccgcgaaca actgcacctt cgaatatgta tctcagccgt tcctaatgga   660
cctagaggga aagcagggaa acttcaagaa cctaagagag ttcgtattca agaacatcga   720
cggatacttc aagatctact ccaagcacac tccgatcaac ctagttagag atctaccgca   780
aggattctct gcgctagaac cgttagtaga tttgccgatc ggaatcaaca tcaccagatt   840
ccagacacta ctagcgctac acagatctta cctaacgccg ggagattctt cttctgggatg  900
gactgctggt gctgcggctt attatgtagg atacctacag ccgagaacct tcctattgaa   960
gtacaacgaa aacggaacca tcaccgatgc cgtagattgt gctctagatc cgctatccga   1020
aacgaagtgc accctaaagt ctttcaccgt cgagaaggga atctaccaga cctccaactt   1080
tagagtacag ccgaccgaat ccatcgtcag atttccgaac atcacgaacc tatgtccgtt   1140
cggagaagtg ttcaacgcga caagatttgc gtctgtctat gcgtggaaca gaaaaagaat   1200
cagtaactgc gtcgcggact actccgtcct atacaactct gcctctttct ccacgttcaa   1260
atgctacggt gtatctccga caaagctaaa cgatctatgc ttcaccaacg tctacgcgga   1320
ctccttcgta atcagaggag atgaagttag acagattgcg ccgggacaaa ctggaaagat   1380
cgcggattat aactacaagc taccggacga cttcaccgga tgtgtaattg cgtggaattc   1440
gaacaaccta gactccaaag tcggaggaaa ctacaactac ttgtacagac tattcagaaa   1500
gtccaaccta aagccgttcg agagagacat ctccaccgaa atctatcagg ctggatctac   1560
accgtgtaat ggtgtcgaag gattcaactg ctacttcccg ctacagtctt acggatttca   1620
accgacaaac ggtgtaggat atcagccgta cagagtcgtc gtactatcct tcgaactact   1680
acatgctccg gcgacagtat gtggaccgaa aaagtctacc aacctagtca agaacaaatg   1740
cgtcaacttt aacttcaacg gactaaccgg aaccggtgtc ctaaccgaat ctaacaagaa   1800
gtttctaccg ttccagcagt tcggaagaga tatcgcggat acaacagacg ctgtcagaga   1860
tccgcaaacc ttggagatcc tagatatcac accgtgttct ttcggtggtg tctctgtaat   1920
tactccggga acgaacacct ccaatcaagt agcggtacta taccaggacg tgaactgtac   1980
agaagtaccg gtagctattc acgcggatca actaacacca acttggagag tgtactccac   2040
cggatctaac gtattccaaa caagagcggg atgtctaatc ggagcggaac acgtaaacaa   2100
ctcctacgaa tgtgatatcc cgattggagc gggaatctgt gcgtcttacc aaacacaaac   2160
aaactctccg agaagagcga gatctgtagc ctctcaatct attatcgcct acaccatgtc   2220
cttgggagcc gaaaattctg tcgcgtactc caacaattct atcgcgatcc cgacaaactt   2280
caccatctct gtaacaaccg agatcctacc ggtgtcatca accaagacat ctgtcgattg   2340
caccatgtac atctgcggag attccaccga gtgctccaac ctactactac agtacggatc   2400
tttctgtacc cagctaaaca gagcgttgac tggaatcgct gtagagcagg ataagaaac    2460
tcaagaggta ttcgcgcaag tcaagcagat ctataagact ccgccgatca aggacttcgg   2520
aggtttcaac ttctctcaga tcttgccgga tccgtccaaa ccgtctaaga gatctttcat   2580
cgaggaccta ctattcaaca aagtcaccct agctgacgcg ggattcatca aacaatacgg   2640
agattgcttg ggagacattg cggcgagaga tctaatttgc gcgcagaagt ttaacggatt   2700
gacagtacta ccgccgctac taaccgatga gatgattgcg cagtacacgt ctgctctatt   2760
ggcgggaaca attacaagtg gatggacatt tggagccggt gccgctctac aaattccgtt   2820
tgctatgcaa atggcgtaca gattcaacgg aatcggagta acccagaacg tcttgtacga   2880
gaaccagaag ctaatcgcga accagttcaa ttccgcgatc gaaagatcc aggacagtcgt   2940
atcttctact gcttcggcgt tgggaaagct acaggatgta gtaaatcaaa acgcgcaggc   3000
gctaaacacc ttggtcaagc aactatcctc taacttcgga gcgatctcgt ccgtcctaaa   3060
cgacatctta tccagaccac cgaaggtcga agcggaggtc cagatcgata gactaatcac   3120
tggaagattg cagtccctac agacctacgt aacacagcaa ctaattagag cggcggagat   3180
tagagcctct gctaatctag ctgcgaccaa gatgtccgaa tgtgtcttgg gacaatccaa   3240
```

-continued

```
gagagtggac ttctgcggaa agggatacca cctaatgtct ttcccacaat ctgcgccgca   3300
tggtgtcgta ttcctacatg taacatatgt gccggcgcaa gaaaagaact tcacaacagc   3360
tccagcgatc tgccatgatg gaaaagctca tttcccgaga gagggagtct ttgtctctaa   3420
cggaactcat tggttcgtca cccagagaaa cttctacgag ccgcagatca tcaccaccga   3480
caacacattc gtctcgggaa actgcgacgt ggtcatcgaa atcgtaaaca ataccgtcta   3540
cgatccgttg cagccggaac tagactcctt caaagaagag ttggacaagt acttcaagaa   3600
ccacacctct ccggatgtgg acttgggaga tatctctgga atcaacgcgt ccgtcgtcaa   3660
catccagaaa gaaatcgata gattgaacga ggtcgcgaag aacttgaacg agtccctaat   3720
cgacctacaa gagctaggaa aatacgagca gtacatcaag tggccgtggt ggacatctga   3780
ctgggggagtc ctaacgaacc taggaatcct actactattg tcgatcgcgg tcctaatcgc   3840
gctatcctgt atctgtagaa tcttcaccaa gtacatcgga gagccggaag cttaataatt   3900
tttat                                                                3905
```

SEQ ID NO: 126          moltype = DNA  length = 3911
FEATURE                 Location/Qualifiers
source                  1..3911
                        mol_type = other DNA
                        organism = synthetic construct
SEQUENCE: 126

```
aaaaattgaa aataaataca aaggttcttg agggttgtgt taaattgaaa gcgagaaata   60
atcataaccc ggggccacca tgtggacgac ctgcttcttc atctccctaa tcctaatcca   120
gggaatcaag accctattcg tgttcctagt cctactaccg ctagtctctt ctcagtgtgt   180
aaacctaaca acgagaacac aactaccacc ggcgtacacc aattctttca caagaggagt   240
atattacccg gacaaggtgt tcagatcctc cgtactacat tctacacagg acctattcct   300
accgttcttc tctaacgtaa catggttcca cgcgatccat gtctctggaa caaacggaac   360
gaagagattc gataacccgg tcttgccgtt caacgatggt gtatactttg cgtccaccga   420
gaagtccaac atcatcagag gatggatctt cggaaccacc ttggattcta agacccagtc   480
cttgctaatc gtcaacaacg cgaccaacgt cgtcatcaaa gtctgcgaat tccagttctg   540
taacgacccg ttcttgggag tctactacca caagaacaac aagtcctgga tggaatccga   600
gttcagagtc tactcttccg cgaacaactg caccttcgaa tatgtatctc agccgttcct   660
aatggaccta gagggaaagc agggaaactt caagaaccta agagagttcg tattcaagaa   720
catcgacgga tacttcaaga tctactccaa gcacactccg atcaacctag ttagagatct   780
accgcaagga ttctctgcgc tagaaccgtt agtagatttg ccgatcggaa tcaacatcac   840
cagattccag acactactag cgctacacag atcttaccta acgccgggag attcttcttc   900
tggatggact gctggtgctg cggcttatta tgtaggatac ctacagccga gaaccttcct   960
attgaagtac aacgaaaacg gaaccatcac cgatgccgta gattgtgctc tagatccgct   1020
atccgaaacg aagtgcaccc taaagtcttt caccgtcgag aagggaatct accagacctc   1080
caactttaga gtacagccga ccgaatccat cgtcagattt ccgaacatca cgaacctatg   1140
tccgttcgga gaagtgttca acgcgacaag atttgcgtct gtctatgcgt ggaacagaaa   1200
aagaatcagt aactgcgtcg cggactactc cgtcctatac aactctgcct ctttctccac   1260
gttcaaatgc tacggtgtat ctccgacaaa gctaaacgat ctatgcttca ccaacgtcta   1320
cgcggactcc ttcgtaatca gaggagatga agttagacag attgcgccgg acaaactgg    1380
aaagatcgcg gattataact acaagctacc ggacgacttc accggatgtg taattgcgta   1440
gaattcgaac aacctagact ccaaagtcgg aggaaactac aactacttgt acagactatt   1500
cagaaagtcc aacctaaagc cgttcgagag agacatctcc accgaaatct atcaggctgg   1560
atctacaccg tgtaatggtg tcgaaggatt caactgctac ttcccgctac agtcttacg    1620
atttcaaccg acaaacggtg taggatatca gccgtacaga gtcgtcgtac tatccttcga   1680
actactacat gctccggcga cagtatgtgg accgaaaaag tctaccaacc tagtcaagaa   1740
caaatgcgtc aactttaact tcaacggact aaccggaacc ggtgtcctaa ccgaatctaa   1800
caagaagttt ctaccgttcc agcagttcgg aagagatatc gcggatacaa cagacgctgt   1860
cagagatccg caaaccttgg agatcctaga tatcacaccg tgttctttcg gtggtgtctc   1920
tgtaattact ccgggaacga acacctccaa tcaagtagcg gtactatacc aggacgtgaa   1980
ctgtacagaa gtaccggtag ctattcacgc ggatcaacta acaccaactt ggagagtgta   2040
ctccaccgga tctaacgtat tccaaacaag agcgggatgt ctaatcggag cggaacacgt   2100
aaacaactcc tacgaatgtg atatcccgat tgggagcggaa atctgtgcgt cttaccaaac   2160
acaaacaaac tctccgagaa gagcgagatc tgtagcctct caatctatta tcgcctacac   2220
catgtccttg ggagccgaaa attctgtcgc gtactccaac aattctatcg cgatcccgac   2280
aaacttcacc atctctgtaa caaccgagat cctaccggtg tctatgacca agacatctgt   2340
cgattgcacc atgtacatct gcggagattc caccgagtgc tccaacctac tactacagta   2400
cggatctttc tgtacccagc taaacagagc gttgactgga atcgctgtag agcaggataa   2460
gaacactcaa gaggtattcg cgcaagtcaa gcagatctat aagactccgc cgatcaagga   2520
cttcggaggt ttcaacttct ctcagatctt gccggatccg tccaaaccgt ctaagagatc   2580
tttcatcgag gacctactat tcaacaaagt caccctagct gacgcgggat tcatcaaaca   2640
atacggagat tgcttgggag acattgcggc gagagatcca atttgcgcgc agaagtttaa   2700
cggattgaca gtactaccgc cgctactaac cgatgagatg attgcgcagt acacgtctgc   2760
tctattggcg ggaacaatta caagtggatg gacatttgga gccggtgccg ctctacaaat   2820
tccgtttgct atgcaaatgg cgtacagatt caacggaatc ggagtaaccc agaacgtctt   2880
gtacgagaac cagaagctaa tcgcgaacca gttcaattcc gcgatcggaa agatccagga   2940
cagtctatct tctactgctt cggcgttggg aaagctacag gatgtagtaa atcaaaacgc   3000
gcaggcgcta aacaccttgg tcaagcaact atcctctaac ttcggagcga tctcgtccgg   3060
cctaaacgac atcttatcca gactagatcc accggaagcg gaggtccaga tcgatagact   3120
aatcactgga agattgcagt ccctacgac ctacgtaaca cagcaactaa ttagagcggc   3180
ggagattaga gcctctgcta atctagctgc gaccaagatg tccgaatgtg tcttgggaca   3240
atccaagaga gtggacttct gcggaaaggg ataccaccca atgtctttcc cacaatcgta   3300
gccgcatgg gtcgtattcc tacatgtaac atatgtgccg cgcaagaaa agaacttcac   3360
aacagctcca gcgatctgcc atgatggaaa agctcatttc cgagagagg gagtctttgt   3420
ctctaacgga actcattggt tcgtcaccca gagaaacttc tacgagccgc agatcatcac   3480
caccgacaac acattcgtct cgggaaactg cgacgtggtc atcggaatcg taaacaatac   3540
cgtctacgat ccgttgcagc cggaactaga ctcccttcaaa gaagagttgg acaagtactt   3600
```

```
caagaaccac acctctccgg atgtggactt gggagatatc tctggaatca acgcgtccgt  3660
cgtcaacatc cagaaagaaa tcgatagatt gaacgaggtc gcgaagaact tgaacgagtc  3720
cctaatcgac ctacaagagc taggaaaata cgagcagtac atcaagtggc cgtggtggac  3780
atctgactgg ggagtcctaa cgaacctagg aatcctacta ctattgtcga tcgcggtcct  3840
aatcgcgcta tcctgtatct gtagaatctt caccaagtac atcggagagc cggaagctta  3900
ataattttta t                                                        3911

SEQ ID NO: 127             moltype = DNA   length = 4910
FEATURE                    Location/Qualifiers
source                     1..4910
                           mol_type = other DNA
                           organism = synthetic construct
SEQUENCE: 127
aaaaattgaa aataaataca aaggttcttg agggttgtgt taaattgaaa gcgagaaata   60
atcataagcc accatgtgga cgacctgctt cttcatctcc ctaatcctaa tccagggaat  120
caagacccta ttcgtgttcc tagtcctact accgctagtc tcttctcagt gtgtaaacct  180
aacaacgaga acacaactac caccggcgta caccaattct ttcacaagag gagtatatta  240
cccggacaag gtgttcagat cctccgtact acattctaca caggacctat tcctaccgtt  300
cttctctaac gtaacatggt tccacgcgat ccatgtctct ggaacaaacg gaacgaagag  360
attcgataac ccggtcttgc cgttcaacga tggtgtatac tttgcgtcca ccgagaagtc  420
caacatcatc agaggatgga tcttcggaac caccttggat tctaagaccc agtccttgct  480
aatcgtcaac aacgcgacca acgtcgtcat caaagtctgc gaattccagt tctgtaacga  540
cccgttcttg ggagtctact accacaagaa caacaagtcc tggatggaat ccgagttcag  600
agtctactct tccgcgaaca actgcacctt cgaatatgta tctcagccgt tcctaatgga  660
cctagaggga aagcagggaa acttcaagaa cctaagagag ttcgtattca agaacatcga  720
cggatacttc aagatctact ccaagcacac tccgatcaac ctagttagag atctaccgca  780
aggattctct gcgctagaac cgttagtaga tttgccgatc ggaatcaaca tcaccagatt  840
ccagacacta ctagcgctac acagatctta cctaacgccg ggagattctt cttctggatg  900
gactgctggt gctgcggctt attatgtagg atacctacag ccgagaacct tcctattgaa  960
gtacaacgaa aacggaacca tcaccgatgc cgtagattgt gctctagatc cgctatccga 1020
aacgaagtgc accctaaagt cttttcaccgt cgagaaggga atctaccaga cctccaactt 1080
tagagtacag ccgaccgaat ccatcgtcag atttccgaac atcacgaacc tatgtccgtt 1140
cggagaagtg ttcaacgcga caagatttgc gtctgtctat gcgtggaaca gaaaaagaat 1200
cagtaactgc gtcgcggact actccgtcct atacaactct gcctctttct ccacgttcaa 1260
atgctacggt gtatctccga caaagctaaa cgatctatgc ttcaccaacg tctacgcgga 1320
ctccttcgta atcagaggag atgaagttag acagattgcg ccgggacaaa ctggaaagat 1380
cgcggattat aactacaagc taccggacga cttcaccgga tgtgtaattg cgtggaattc 1440
gaacaaccta gactccaaag tcggaggaaa ctacaactac ttgtacagac tattcagaaa 1500
gtccaaccta aagccgttcg agagagacat ctccaccgaa atctatcagg ctggatctac 1560
accgtgtaat ggtgtcgaag gattcaactg ctacttcccg ctacagtctt acggatttca 1620
accgacaaac ggtgtaggat atcagccgta cagagtcgtc gtactatcct tcgaactact 1680
acatgctccg gcgacagtat gtggaccgaa aaagtctacc aacctagtca agaacaaatg 1740
cgtcaacttt aacttcaacg gactaaccgg aaccggtgtc ctaaccgaat ctaacaagaa 1800
gtttctaccg ttccagcagt tcggaagaga tatcgcggat acaacagacg ctgtcagaga 1860
tccgcaaacc ttggagatcc tagatatcac accgtgttct ttcggtggtg tctctgtaat 1920
tactccggga acgaacacct ccaatcaagt agcggtacta taccaggacg tgaactgtac 1980
agaagtaccg gtagctattc acgcgggatca actaacacca acttggagag tgtactccac 2040
cggatctaac gtattccaaa caagagcggg atgtctaatc ggagcggaac acgtaaacaa 2100
ctcctacgaa tgtgatatcc cgattggagc gggaatctgt gcgtcttacc aaacacaaac 2160
aaactctccg agaagagcga gatctgtagc ctctcaatct attatcgcct acaccatgtc 2220
cttgggagcc gaaaattctg tcgcgtactc caacaattct atcgcgatcc cgacaaactt 2280
caccatctct gtaacaaccg agatcctacc ggtgtctatg accaagacat ctgtcgattg 2340
caccatgtac atctgcggag attccaccga gtgctccaac ctactactac agtacggatc 2400
tttctgtacc cagctaaaca gagcgttgac tggaatcgct gtagagcagg ataagaacac 2460
tcaagaggta ttcgcgcaag tcaagcagat ctataagact ccgccgatca aggacttcgg 2520
aggtttcaac ttctctcaga tcttgccgga tccgtccaaa ccgtctaaga gatctttcat 2580
cgaggaccta ctattcaaca aagtcaccct agctgacgcg ggattcatca aacaatacgg 2640
agattgcttg ggagacattg cggcgagaga tctaatttgc gcgcagaagt ttaacggatt 2700
gacagtacta ccgccgctac taaccgatga gatgattgcg cagtacacgt ctgctctatt 2760
ggcgggaaca attacaagtg gatggacatt tggagccggt gccgctctac aaattccgtt 2820
tgctatgcaa atggcgtaca gattcaacgg aatcggagta acccagaacg tcttgtacga 2880
gaaccagaag ctaatcgcga accagttcaa ttccgcgatc ggaaagatcc aggacagtct 2940
atcttctact gcttcggcgt tgggaaagct acaggatgta gtaaatcaaa acgcgcaggc 3000
gctaaacacc ttggtcaagc aactatcctc taacttcgga gcgatctgt ccgtcctaaa 3060
cgacatctta tccagactag ataaggtcga agcggaggtc cagatcgata gactaatcac 3120
tggaagattg cagtccctac agacctacgt aacacagcaa ctaattagag cggcggagat 3180
tagagcctct gctaatctag ctgcgaccaa gatgtccgaa tgtgtcttgg gacaatccaa 3240
gagagtggac ttctgcggaa agggatacca cctaatgtct ttcccacaat ctgcgccgca 3300
tggtgtcgta ttcctacatg taacatatgt gccgggcgaa gaaaagaact tcaacaacagc 3360
tccagcgatc tgccatgatg gaaaagctca tttcccggaga gagggagtct ttgtctctaa 3420
cggaactcat tggttcgtca cccagagaaa cttctacgag ccgcagatca tcaccaccga 3480
caacacattc gtctcgggaa actgcgacgt ggtcatcgga atcgtaaaca ataccgtcta 3540
cgatccgttg cagccggaac tagactcctt caaagaagag ttggacaagt acttcaagaa 3600
ccacacctct ccggatgtgg acttgggaga tatctctgga atcaacgcgt ccgtcaacatc 3660
catcagaaa gaaatcgata gattgaacga ggtcgcgaag aacttgaacg agtccctaat 3720
cgacctacaa gagctaggaa aatacgagca gtacatcaag tggccgtggt ggacatctga 3780
ctggggagtc ctaacgaacc taggaatcct actactattg tcgatcgcgg tcctaatcgc 3840
gctatccgt atctgtagaa tcttcaccaa gtacatcgga gagccggaag cttaataatt 3900
tttatctgca ggtcgactta ttatatcgca gatagtgttg gattcgcata cgctagtact 3960
```

```
acttgtctat tattaaaacc attcaatgga aaattttctg gcgcttgaaa atatactact   4020
ggagaagatt ctcctctttt cttcatcatt ccttctttta cagaaaacat atccgctggt   4080
agagaaattc taaacaaaga tgtctttct ggtacctttt ctactcttag ttgatgtaga     4140
attccagaaa tcgccaatag tggtccatta tttggattct tatgttgtct atacgcttgt   4200
ttcttacag ttggtagtac tattggtggt agatttggat gaatagaaat cgctggatgc     4260
attgtatttc caattagttt atctttagat ggtctccaag catcatctgg tagctttgt     4320
acagatagta ctagattagt tagattataa gtaaactgat ttgtagagaa atttcttgga   4380
ataaccatat tttgaataaa agcttgattt ccttctctta gcattcttag tggatgcgct   4440
ggtattccag ttcctagtct atttactcta acaaactttt gtccattatg tgtaaactgt   4500
gtaattgtat aagatcctgt caatagcgcc gctactgtat gcgctagtgg atattcaaaa   4560
ttagacataa ttcctagtgg tagccaagct ggtacacctt ttactgttct ttcattatac   4620
gcagaaatat caataatcgc ttctagtgta aacgcatgac aaacatttcc tttaaactga   4680
tcatctagat ttagatctcc aacataattt ggtgtaattc catgttgatt agatagttga   4740
tccgctggaa ttagttgatt agcaccatga tccgcatatg gtggtggatt tagatattgc   4800
atataagtat tataattaga actagacgcc atcccgggct tatttatgat tatttctcgc   4860
tttcaattta acacaaccct caagaacctt tgtatttatt ttcaattttt               4910
```

SEQ ID NO: 128          moltype = DNA  length = 4916
FEATURE                 Location/Qualifiers
source                  1..4916
                        mol_type = other DNA
                        organism = synthetic construct
SEQUENCE: 128

```
aaaaattgaa aataaataca aaggttcttg agggttgtgt taaattgaaa gcgagaaata   60
atcataaccc ggggccacca tgtggacgac ctgcttcttc atctccctaa tcctaatcca     120
gggaatcaag accctattcg tgttcctagt cctactaccg ctagtctctt ctcagtgtgt   180
aaacctaaca acgagaacac aactaccacc ggcgtacacc aattctttca caagaggagt   240
atattacccg gacaaggtgt tcagatcctc cgtactacat tctacacagg acctattcct   300
accgttcttc tctaacgtaa catggttcca cgcgatccat gtctctggaa caaacggaac   360
gaagagattc gacaacccgg tcttgccgtt caacgatggt gtatactttg cgtccaccga   420
gaagtccaac atcatcagag gatggatctt cggaaccacc ttggattcta agacccagtc   480
cttgctaatc gtcaacaacg cgaccaacgt cgtcatcaaa gtctgcgaat tccagttctg   540
taacgacccg ttcttgggag tctactacca caagaacaac aagtcctgga tggaatccga   600
gttcagagtc tactcttccg cgaacaactg caccttcgaa tatgtatctc agccgttcct   660
aatggaccta gagggaaagc agggaaactt caagaaccta agagagttcg tattcaagaa   720
catcgacgga tacttcaaga tctactccaa gcacactccg atcaacctag ttagagatct   780
accgcaagga ttctctgcgc tagaaccgtt agtagatttg ccgatcggaa tcaacatcac   840
cagattccag acactactag cgctacacag atcttaccta acgccgggag attcttcttc   900
tggatggact gctggtgctg cggcttatta tgtaggatac ctacagccga gaaccttcct   960
attgaagtac aacgaaaacg gaaccatcac cgatgccgta gattgtgctc tagatccgct   1020
atccgaaacg aagtgcaccc taaagtcttt caccgtcgag aagggaatct accagacctc   1080
caactttaga gtacagccga ccgaatccat cgtcagattt ccgaacatca cgaacctatg   1140
tccgttcgga gaagtgttca acgcgacaag atttgcgtct gtctatgcgt ggaacagaaa   1200
aagaatcagt aactgcgtcg cggactactc cgtcctatac aactctgcct ctttctccac   1260
gttcaaatgc tacggtgtat ctccgacaaa gctaaacgat ctatgcttca ccaacgtcta   1320
cgcggactcc ttcgtaatca gaggagatga agttagacag attgcgccgg gacaaactgg   1380
aaagatcgcg gattataact acaagctacc ggacgacttc accggatggt taattgcgtg   1440
gaattcgaac aacctagact ccaaagtcgg aggaaactac aactacttgt acagactatt   1500
cagaaagtcc aacctaaagc cgttcgagag agacatctcc accgaaatct atcaggctgg   1560
atctacaccg tgtaatggtg tcgaaggatt caactgctac ttcccgctac agtcttacgg   1620
atttcaaccg acaaacggtg taggatatca gccgtacaga gtcgtcgtac tatccttcga   1680
actactacat gctccggcga cagtatgtgg accgaaaaag tctaccaacc tagtcaagaa   1740
caaatgcgtc aactttaact tcaacggact aaccggaacc ggtgtcctaa ccgaatctaa   1800
caagaagttt ctaccgttcc agcagttcgg aagagatatc gcggatacaa cagacgctgt   1860
cagagatccg caaaccttgg agatcctaga tatcacaccg tgttctttcg gtggtgtctc   1920
tgtaattact ccgggaacga acacctccaa tcaagtagcg gtactatacc aggacgtgaa   1980
ctgtacagaa gtaccggtag ctattcacgc ggatcaacta acaccaactt ggagagtgta   2040
ctccaccgga tctaacgtat tccaaacaag agcgggatgt ctaatcggag cggaacacgt   2100
aaacaactcc tacgaatgtg atatcccgat tggagcggga atctgtgcgt cttaccaaac   2160
acaaacaaac tctccgagaa gagcgagatc tgtagcctct caatctatta tcgcctacac   2220
catgtccttg ggagccgaaa attctgtcgc gtactccaac aattctatcg cgatcccgac   2280
aaacttcacc atctctgtaa caaccgagat cctaccggtg tctatgacca agacatctgt   2340
cgattgcacc atgtacatct gcggagattc caccgagtgc tccaacctac tactacagta   2400
cggatctttc tgtacccagc taaacagagc gttgactgga atcgctgcg agcaggataa   2460
gaacactcaa gaggtattcg cgcaagtcaa gcagatctat aagactccgc cgatcaagga   2520
cttcggaggt ttcaacttct ctcagatctt gccggatccg tccaaaccgt ctaagagatc   2580
tttcatcgag gacctactat tcaacaaagt caccctagct gacgcgggat tcatcaaaca   2640
atacggagat tgcttgggag acattgcggc gagagatcta atttgcgcgc agaagtttaa   2700
cggattgaca gtactaccgc cgctactaac cgatgagatg attgcgcagt acacgtctgc   2760
tctattggcg ggaacaatta caagtggatg gacatttgga gccggtgccg ctctacaaat   2820
tccgtttgct atgcaaatgg cgtacagatt caacggaatc ggagtaaccc agaacgtctt   2880
gtacgagaac cagaagctaa tcgcgaacca gttcaattcc gcgatcggaa agatccagga   2940
cagtctatct tctactgctt cggcgttggg aaagctacag gatgtagtaa atcaaaacgc   3000
gcaggcgcta aacaccttgg tcaagcaact atcctctaac ttcggtgcga tctgtccgt   3060
cctaaacgac atcttatcca gactagataa ggtcgaagcg gaggtccaga tcgtagact    3120
aatcactgga agattgcagt ccctacgac ctacgtaaca cagcaactaa ttagagcggc   3180
ggagattaga gcctctgcta atctagctgc gaccaagatg tccgaatgtg tcttgggaca   3240
atccaagaga gtggacttct gcggaaaggg ataccaccta atgtctttcc cacaatctgc   3300
gccgcatggt gtcgtattcc tacatgtaac atatgtgccg gcgcaagaaa agaacttcac   3360
```

-continued

```
aacagctcca gcgatctgcc atgatggaaa agctcatttc ccgagagagg gagtctttgt  3420
ctctaacgga actcattggt tcgtcaccca gagaaacttc tacgagccgc agatcatcac  3480
caccgacaac acattcgtct cgggaaactg cgacgtggtc atcggaatcg taaacaatac  3540
cgtctacgat ccgttgcagc cggaactaga ctccttcaaa gaagagttgg acaagtactt  3600
caagaaccac acctctccgg atgtggactt gggagatatc tctggaatca acgcgtccgt  3660
cgtcaacatc cagaaagaaa tcgatagatt gaacgaggtc gcgaagaact tgaacgagtc  3720
cctaatcgac ctacaagagc taggaaaata cgagcagtac atcaagtggc cgtggtggac  3780
atctgactgg ggagtcctaa cgaacctagg aatcctacta ctattgtcga tcgcggtcct  3840
aatcgcgcta tcctgtatct gtagaatctt caccaagtac atcggagagc cggaagctta  3900
ataatttta tctgcaggtc gacttattat atcgcagata gtgttggatt cgcatacgct  3960
agtactactt gtctattatt aaaaccattc aatggaaaat tttctggcgc ttgaaaatat  4020
actactggag aagattctcc tcttttcttc atcattcctt cttttacaga aaacatatcc  4080
gctggtagag aaattctaaa caaagatgtc ttttctggta ccttttctac tcttagttga  4140
tgtagaattc cagaaatcgc caatagtggt ccattcttatg gattcttatg ttgtctatac  4200
gcttgtttct ttacagttgg tagtactatt ggtggtagat ttggatgaat agaaatcgct  4260
ggatgcattg tatttccaat tagtttatct ttagatggtc tccaagcatc atctggtagc  4320
ttttgtacag atagtactag attagttaga ttataagtaa actgatttgt agagaaattt  4380
cttggaataa ccatattttg aataaaagct tgatttcctt ctcttagcat tcttagtgga  4440
tgcgctggta ttccagttcc tagtctattt actctaacaa acttttgtcc attatgtgta  4500
aactgtgtaa ttgtataaga tcctgtcaat agcgccgcta ctgtatgcgc tagtgtgatat  4560
tcaaaattag acataattcc tagtggtagc caagctggta cacctttac tgttctttca  4620
ttatacgcag aaatatcaat aatcgcttct agtgtaaacg catgacaaac atttcctta  4680
aactgatcat ctagatttag atctccaaca taatttggtg taattccatg ttgattagat  4740
agttgatccg ctggaattag ttgattagca ccatgatccg catatggtgg tggatttaga  4800
tattgcatat aagtattata attagaacta gacgccatcc cgggcttatt tatgattatt  4860
tctcgctttc aatttaacac aaccctcaag aacctttgta tttattttca attttt  4916
```

```
SEQ ID NO: 129          moltype = DNA  length = 4910
FEATURE                 Location/Qualifiers
source                  1..4910
                        mol_type = other DNA
                        organism = synthetic construct
SEQUENCE: 129
aaaaattgaa aataaataca aaggttcttg agggttgtgt taaattgaaa gcgagaaata  60
atcataagcc accatgtgga cgacctgctt cttcatctcc ctaatcctaa tccaggaat  120
caagacccta ttcgtgttcc tagtcctact accgctagtc tcttctcagt gtgtaaacct  180
aacaacgaga acacaactac caccggcgta caccaattct ttcacaagag gagtatatta  240
cccggacaag gtgttcagat cctccgtact acattctaca caggacctat tcctaccgtt  300
cttctctaac gtaacatggt tccacgcgat ccatgtctct ggaacaaacg gaacgaagag  360
attcgataac ccggtcttgc cgttcaacga tggtgtatac tttgcgtcca ccgagaagtc  420
caacatcatc agaggatgga tcttcggaac caccttggat tctaagaccc agtccttgct  480
aatcgtcaac aacgcgacca acgtcgtcat caaagtctgc gaattccagt tctgtaacga  540
cccgttcttg ggagtctact accacaagaa caacaagtcc tggatggaat cgcgagttcag  600
agtctactct tccgcgaaca actgcacctt cgaatatgta tctcagccgt tcctaatgga  660
cctagaggga aagcagggaa acttcaagaa cctaagagag ttcgtattca agaacatcga  720
cggatacttc aagatctact ccaagcacac tccgatcaac ctagttagag atctaccgca  780
aggattctct gcgctagaac cgttagtaga tttgccgatc ggaatcaaca tcaccagatt  840
ccagacacta ctagcgctac acagatctta cctaacgccg ggagattctt cttctgatg  900
gactgctggt gctgcggctt attatgtagg atacctacag ccgagaacct tcctattgaa  960
gtacaacgaa aacggaacca tcaccgatgc cgtagattgt gctctagatc cgctatccga  1020
aacgaagtgc accctaaagt cttttcaccgt cgagaaggga atctaccaga cctccaactt  1080
tagagtacag ccgaccgaat ccatcgtcag atttccgaac atcacgaacc tatgtccgtt  1140
cggagagtg ttcaacgcga caagatttgc gtctgtctat gcgtggaaca gaaaaagaat  1200
cagtaactgc gtcgcggact actccgtcct atacaactct gcctctttct ccacgttcaa  1260
atgctacggt gtatctccga caaagctaaa cgatctatgc ttcaccaacg tctacgcgga  1320
ctccttcgta atcagaggag atgaagttag acagattgcg ccgggacaaa ctggaaagat  1380
cgcggattat aactacaagc taccggacga cttcaccgga tgtgtaattg cgtggaattc  1440
gaacaaccta gactccaaag tcggaggaaa ctacaactac ttgtacagac tattcagaaa  1500
gtccaaccta aagccgttcg agagagacat ctccaccgaa atctatcagg ctggatctac  1560
accgtgtaat ggtgtcgaag gattcaactg ctacttcccg ctacagtctt acggatttca  1620
accgacaaac ggtgtaggat atcagccgta cagagtcgtc gtactatcct tcgaactact  1680
acatgctccg gcgacagtat gtggaccgaa aaagtctacc aacctagtca agaacaaatg  1740
cgtcaacttt aacttcaacg gactaaccgg aaccggtgtc ctaaccgaat ctaacaagaa  1800
gtttctaccg ttccagcagt tcggaagaga tatcgcgagt acaacgacgc ctgtcagaga  1860
tccgcaaacc ttggagatcc tagatatcac accgtgttct ttcggtggtg tctctgtaat  1920
tactccggga acgaacacct ccaatcaagt agcggtacta taccaggacg tgaactgtac  1980
agaagtaccg gtagctattc acgcggatca actaacacca acttggagag tgtactccac  2040
cggatctaac gtattccaaa caagagcggg atgtctaatc ggacggaac acgtaaacaa  2100
ctcctacgaa tgtgatatcc cgattggagc gggaatctgt ggcgtcttacc aaacacaaac  2160
aaactctccg agaagagcga gatctgtagc ctctcaatct attatcgcct acaccatgtc  2220
cttgggagcc gaaaattctg tcgcgtactc caacaattct atcgcgatcc cgacaaactt  2280
caccatctct gtaacaaccg agatcctacc ggtgtctatg accaagacat ctgtcgattg  2340
caccatgtac atctgcggag attccaccga gtgctccaac ctactactac agtacggatc  2400
tttctgtacc cagctaaaca gagcgttgac tggaatcgct ggagagagg ataagaacac  2460
tcaagaggta ttcgcgcaag tcaagcagat ctataagact ccgccgatca aggacttcgg  2520
aggttcaac ttctctcaga tcttgccgga tccgtccaaa ccgtctaaga atctttcat  2580
cgaggaccta ctattcaaca aagtcaccct agctgacgcg ggattcatca acaatacgg  2640
agattgcttg ggagacattg cggcgagaga tctaatttgc gcgcagaagt ttaacggatt  2700
gacagtacta ccgccgctac taaccgatga gatgattgcg cagtacacgt ctgctctatt  2760
```

```
ggcgggaaca attacaagtg gatggacatt tggagccggt gccgctctac aaattccgtt  2820
tgctatgcaa atggcgtaca gattcaacgg aatcggagta acccagaacg tcttgtacga  2880
gaaccagaag ctaatcgcga accagttcaa ttccgccgatc ggaaagatcc aggacagtct  2940
atcttctact gcttcggcgt tgggaaagct acaggatgta gtaaatcaaa acgcgcaggc  3000
gctaaacacc ttggtcaagc aactatcctc taacttcgga gcgatctcgt ccgtcctaaa  3060
cgacatctta tccagactag atccaccgga agcggaggtc cagatcgata gactaatcac  3120
tggaagattg cagtccctac agacctacgt aacacagcaa ctaattagag cggcggagat  3180
tagagcctct gctaatctag ctgcgaccaa gatgtccgaa tgtgtcttgg gacaatccaa  3240
gagagtggac ttctgcggaa agggatacca cctaatgtct ttcccacaat ctgcgccgca  3300
tggtgtcgta ttcctacatg taacatatgt gccggcgcaa gaaaagaact tcacaacagc  3360
tccagcgatc tgccatgatg gaaaagctca tttcccgaga gagggagtct ttgtctctaa  3420
cggaactcat tggttcgtca cccagagaaa cttctacgag ccgcagatca tcaccaccga  3480
caacacattc gtctcgggaa actgcgacgt ggtcatcgga atcgtaaaca ataccgtcta  3540
cgatccgttg cagccggaac tagactcctt caaagaagag ttggacaagt acttcaagaa  3600
ccacacctct ccggatgtgg acttgggaga tatctctgga atcaacgcgt ccgtcgtcaa  3660
catccagaaa gaaatcgata gattgaacga ggtcgcgaag aacttgaacg agtccctaat  3720
cgacctacaa gagctaggaa aatacgagca gtacatcaag tggccgtggt ggacatctga  3780
ctggggagtc ctaacgaacc taggaatcct actactattg tcgatcgcgg tcctaatcgc  3840
gctatcctgt atctgtagaa tcttcaccaa gtacatcgga gagccggaag cttaataatt  3900
tttatctgca ggtcgactta ttatatcgca gatagtgttg gattcgcata cgctagtact  3960
acttgtctat tattaaaacc attcaatgga aaatttctg gcgcttgaaa atatactact  4020
ggagaagatt ctcctctttt cttcatcatt ccttctttta cagaaaacat atccgctagt  4080
agagaaattc taaacaaaga tgtctttttct ggtacctttt ctactcttag ttgatgtaga  4140
attccagaaa tcgccaatag tggtccatta tttggattct tatgttgtct atacgcttgt  4200
ttctttacag ttggtagtac tattggtggt agatttggat gaatagaaat cgctggatgc  4260
attgtatttc caattagttt atctttagat ggtctccaag catcatctgg tagcttttgt  4320
acagatagta ctagattagt tagattataa gtaaactgat ttgtagagaa atttcttgga  4380
ataaccatat tttgaataaa agcttgattt ccttctctta gcattcttag tggatgcgct  4440
ggtattccag ttcctagtct atttactcta acaaacttt gtccattatg tgtaaactgt  4500
gtaattgtat aagatcctgt caatagcgcc gctactgtat gcgctagtgg atattcaaaa  4560
ttagacataa ttcctagtgg tagccaagct ggtacacctt ttactgttct ttcattatac  4620
gcagaaatat caataatcgc ttctagtgta aacgcatgac aaacatttcc tttaaactga  4680
tcatctagat ttagatctcc aacataattt ggtgtaattc catgttgatt agatagttga  4740
tccgctggaa ttagttgatt agcaccatga tccgcatatg gtggtggatt tagatattgc  4800
atataagtat tataattaga actagacgcc atcccgggct tatttatgat tatttctcgc  4860
tttcaattta acacaacct caagaacctt tgtatttatt ttcaattttt  4910
```

```
SEQ ID NO: 130            moltype = DNA  length = 4916
FEATURE                   Location/Qualifiers
source                    1..4916
                          mol_type = other DNA
                          organism = synthetic construct
SEQUENCE: 130
aaaaattgaa aataaataca aaggttcttg agggttgtgt taaattgaaa gcgagaaata  60
atcataaccc ggggccacca tgtggacgac ctgcttcttc atctccctaa tcctaatcca  120
gggaatcaag accctattcg tgttcctagt cctactaccg ctagtctctt ctcagtgtgt  180
aaacctaaca acgagaacac aactaccacc ggcgtacaca aattctttca caagaggagt  240
atattacccg gacaaggtgt tcagatcctc cgtactacat tctacacagg acctattcct  300
accgttcttc tctaacgtaa catggttcca cgcgatccat gtctctggaa caaacggaac  360
gaagagattc gataacccgg tcttgccgtt caacgatggt gtatactttg cgtccaccga  420
gaagtccaac atcatcagag gatggatctt cggaaccacc ttggattcta agacccagtt  480
cttgctaatc gtcaacaacg cgaccaacgt cgtcatcaaa gtctgcgaat tccagttctg  540
taacgacccg ttcttgggag tctactacca caagaacaac aagtcctgga tggaatccga  600
gttcagagtc tactcttccg cgaacaactg caccttcgaa tatgtatctc agccgttcct  660
aatggaccta gagggaaagc agggaaactt caagaaccta agagagttcg tattcaagaa  720
catccacgtg tacttcaaga tctactccaa gcacactccg atcaacctag ttagagatct  780
accgcaagga ttctctgcgc tagaaccgtt agtagatttg ccgatcggaa tcaacatcac  840
cagattccag acactactag cgctacacag atcttaccta acgccgggag attcttcttc  900
tggatggact gctggtgctg cggcttatta tgtaggatac ctacagccga gaaccttct  960
attgaagtac aacgaaaacg gaaccatcac cgatgccgta gattgtgctc tagatccgct  1020
atccgaaacg aagtgcaccc taaagtcttt caccgtcgag aagggaatct accagacctc  1080
caactttaga gtacagccga ccgaatccat cgtcagattt ccgaacatca cgaacctatg  1140
tccgttcgga gaagtgttca acgcgacaag atttgcgtct gtctatgcgt ggaacagaaa  1200
aagaatcagt aactgcgtcg cggactactc cgtcctatac aactctgcct ctttctccac  1260
gttcaaatgc tacggtgtat ctccgacaaa gctaaacgat ctatgcttca ccaacgtcta  1320
cgcggactcc ttcgtaatca gaggagatga agttagacag attgcgccgg gacaaactgg  1380
aaagatcgcg gattataact acaagctacc ggacgacttc accggatgtg taattgcgtg  1440
gaattcgaac aaacctagact ccaaagtcgg aggaaactac aactacttgt acagactatt  1500
cagaaagtcc aacctaaagc cgttcgagag agacatctca accgaaatct atcaggctgg  1560
atctacaccg tgtaatggtg tcgaaggatt caactgctac ttcccgctac agtcttacgg  1620
atttcaaccg acaaacggtg taggatatca gccgtacaga gtcgtcgtac tatccttcga  1680
actactacat gctccggcga cagtatgtgg accgaaaaag tctaccaacc tagtcaagaa  1740
caaatgcgtc aactttaact tcaacggact aaccggaacc ggtgtcctaa ccgaatctaa  1800
caagaagttt ctaccgttcc agcagttcgg aagagatatc cggagtacaa cagacgctgt  1860
cagagatccg caaaccttgg agatcctaga tatcacaccg tgttctttcg gtggtgtctc  1920
tgtaattact ccgggaacga acacctccaa tcaagtagcg gtactatacc aggacgtgaa  1980
ctgtacagaa gtaccggtag ctattcacgc ggatcaacta acaccaactt ggagagtgta  2040
ctccaccgga tctaacgtat tccaaacaag agcgggatgt ctaatcggag cggaacacgt  2100
aaacaactcc tacgaatgtg atatcccgat tggagcggga atctgtgcgt cttaccaaac  2160
```

```
acaaacaaac tctccgagaa gagcgagatc tgtagcctct caatctatta tcgcctacac  2220
catgtccttg ggagccgaaa attctgtcgc gtactccaac aattctatcg cgatcccgac  2280
aaacttcacc atctctgtaa caaccgagat cctaccggtg tctatgacca agacatctgt  2340
cgattgcacc atgtacatct gcggagattc caccgagtgc tccaacctac tactacagta  2400
cggatctttc tgtacccagc taaacagagc gttgactgga atcgctgtag agcaggataa  2460
gaacactcaa gaggtattcg cgcaagtcaa gcagatctat aagactccgc cgatcaagga  2520
cttcggaggt ttcaacttct ctcagatctt gccggatccg tccaaaccgt ctaagagatc  2580
tttcatcgag gacctactat tcaacaaagt caccctagct gacgcgggat tcatcaaaca  2640
atacggagat tgcttgggag acattgcggc gagagatca atttgcgcgc agaagtttaa  2700
cggattgaca gtactaccgc cgctactaac cgatgagatg attgcgcagt acacgtctgc  2760
tctattggcg ggaacaatta caagtggatg gacatttgga gccggtgccg ctctacaaat  2820
tccgtttgct atgcaaatgg cgtacagatt caacggaatc ggagtaaccc agaacgtctt  2880
gtacgagaac cagaagctaa tcgcgaacca gttcaattcc gcgatcggaa agatccagga  2940
cagtctatct tctactgctt cggcgttggg aaagctacag gatgtagtaa atcaaaacgc  3000
gcaggcgcta aacaccttgg tcaagcaact atcctctaac ttcggagcga tctcgtccgt  3060
cctaaacgac atcttatcca gactagatcc accggaagcg gaggtccaga tcgatagact  3120
aatcactgga agattgcagt ccctacgac ctacgtaaca cagcaactaa ttagagcggc  3180
ggagattaga gcctctgcta atctagctgc gaccaagatg tccgaatgtg tcttgggaca  3240
atccaagaga gtggacttct gcggaaaggg ataccaccta atgtctttcc cacaatctgc  3300
gccgcatggt gtcgtattcc tacatgtaac atatgtgccg gcgcaagaaa agaacttcac  3360
aacagctcca gcgatctgcc atgatggaaa agctcatttc ccgagagagg gagtctttgt  3420
ctctaacgga actcattggt tcgtcaccca gagaaacttc tacgagccgc agatcatcac  3480
caccgacaac acattcgtct cgggaaactg cgacgtggtc atcggaatcg taaacaaatac  3540
cgtctacgat ccgttgcagc cggaactaga ctccttcaaa gaagagttgg acaagtactt  3600
caagaaccac acctctccgg atgtggactt gggagatatc tctggaatca acgcgtccgt  3660
cgtcaacatc cagaaagaaa tcgatagatt gaacgagctg gcgaagaact tgaacgagtc  3720
cctaatcgac ctacaagagc taggaaaata cgagcagtac atcaagtggc cgtggtggac  3780
atctgactgg ggagtcctaa cgaacctagg aatcctacta ctattgtcga tcgcggtcct  3840
aatcgcgcta tcctgtatct gtagaatctt caccaagtac atcggagagc cggaagctta  3900
ataatttta tctgcaggtc gacttattat atcgcagata gtgttggatt cgcatacgct  3960
agtactactt gtctattatt aaaaccattc aatggaaaat tttctggcgc ttgaaaatat  4020
actactggag aagattctcc tcttttcttc atcattcctt cttttacaga aaacatatcc  4080
gctggtagag aaattctaaa caaagatgtc ttttctggta cctttctac tcttagttga  4140
tgtagaattc cagaaatcgc caatagtggt ccattatttg gattcttatg ttgtctatac  4200
gcttgtttct ttacagttgg tagtactatt ggtggtagat ttggatgaat agaaatcgct  4260
ggatgcattg tatttccaat tagtttatct ttagatggtc tccaagcatc atctggtagc  4320
ttttgtacag atagtactag attagttaga ttataagtaa actgatttgt agagaaattt  4380
cttggaataa ccatattttg aataaaagct tgatttcctt ctcttagcat tcttagtgga  4440
tgcgctggta ttccagttcc tagtctattt actctaacaa acttttgtcc attatgtga  4500
aactgtgtaa ttgtataaga tcctgtcaat agcgccgcta ctgtatgcgc tagtggatat  4560
tcaaaattag acataattcc tagtggtagc caagctggta caccttttac tgttctttca  4620
ttatacgcag aaatatcaat aatcgcttct agtgtaaacg catgacaaac atttccttta  4680
aactgatcat ctagatttag atctccaaca taatttggtg taattccatg ttgattagat  4740
agttgatccg ctggaattag ttgattagca ccatgatccg catatggtgg tggatttaga  4800
tattgcatat aagtattata attagaacta gacgccatcc cgggcttatt tatgattatt  4860
tctcgctttc aatttaacac aaccctcaag aacctttgta tttattttca attttt       4916
```

SEQ ID NO: 131          moltype = DNA   length = 863
FEATURE                 Location/Qualifiers
source                  1..863
                        mol_type = other DNA
                        organism = synthetic construct
SEQUENCE: 131
```
aaaaattgaa aataaataca aaggttcttg agggttgtgt taaattgaaa gcgagaaata  60
atcataagcc accatgtgga cgacctgctt cttcatctcc ctaatcctaa tccagggaat  120
caagacccta gtcagatttc cgaacatcac gaacctatgt ccgttcggag aagtgttcaa  180
cgcgacaaga tttgcgtctg tctatgcgtg gaacagaaaa agaatcagta actgcgtcgc  240
ggactactcc gtcctataca actctgcctc tttctccacg ttcaaatgct acggtgtatc  300
tccgacaaag ctaaacgatc tatgcttcac caacgtctac gcggactcct tcgtaatcag  360
aggagatgaa gttagacaga ttgcgccggg acaaactgga aagatcgcgg attataacta  420
caagctaccg gacgacttca ccggatgtgt aattgcgtgg aattcgaaca acctagactc  480
caaagtcgga ggaaactaca actacttgta cagactattc agaaagtcca acctaaagcc  540
gttcgagaga gacatctcca ccgaaatcta tcaggctgga tctacaccgt gtaatggtgt  600
cgaaggattc aactgctact ccccgctaca gtcttacgga tttcaaccga caaacggtat  660
aggatatcag ccgtacagag tcgtcgtact atccttcgaa ctactacatg ctccggcgac  720
agtatggtgg acctccgatt ggggagtact aacaaaccta ggaatcctac tactattgtc  780
gatcgcggtc ctaatcgcgc tatcctgtat ctgtagaatc ttcaccaagt acatcggaga  840
gccggaagct taataatttt tat                                           863
```

SEQ ID NO: 132          moltype = DNA   length = 869
FEATURE                 Location/Qualifiers
source                  1..869
                        mol_type = other DNA
                        organism = synthetic construct
SEQUENCE: 132
```
aaaaattgaa aataaataca aaggttcttg agggttgtgt taaattgaaa gcgagaaata  60
atcataaccc ggggccacca tgtggacgac ctgcttcttc atctccctaa tcctaatcca  120
gggaatcaag accctagtca gatttccgaa catcacgaac ctatgtccgt tcggagaagt  180
gttcaacgcg acaagatttg cgtctgtcta tgcgtggaac agaaaaagaa tcagtaactg  240
```

```
cgtcgcggac tactccgtcc tatacaactc tgcctctttc tccacgttca aatgctacgg    300
tgtatctccg acaaagctaa acgatctatg cttcaccaac gtctacgcgg actccttcgt    360
aatcagagga gatgaagtta gacagattgc gccgggacaa actggaaaga tcgcggatta    420
taactacaag ctaccggacg acttcaccgg atgtgtaatt gcgtggaatt cgaacaacct    480
agactccaaa gtcggaggaa actacaacta cttgtacaga ctattcagaa agtccaacct    540
aaagccgttc gagagagaca tctccaccga aatctatcag gctggatcta caccgtgtaa    600
tggtgtcgaa ggattcaact gctacttccc gctacagtct tacggatttc aaccgacaaa    660
cggtgtagga tatcagccgt acagagtcgt cgtactatcc ttcgaactac tacatgctcc    720
ggcgacagta tggtggacct ccgattgggg agtactaaca aacctaggaa tcctactact    780
attgtcgatc gcggtcctaa tcgcgctatc ctgtatctgt agaatcttca ccaagtacat    840
cggagagccg gaagcttaat aattttat                                        869

SEQ ID NO: 133            moltype = DNA  length = 851
FEATURE                   Location/Qualifiers
source                    1..851
                          mol_type = other DNA
                          organism = synthetic construct
SEQUENCE: 133
aaaaattgaa aataaataca aaggttcttg agggttgtgt taaattgaaa gcgagaaata    60
atcataagcc accatgtgga cgacctgctt cttcatctcc ctaatcctaa tccagggaat    120
caagacccta aacatcacga acctatgtcc gttcggagaa gtgttcaacg cgacaagatt    180
tgcgtctgtc tatgcgtgga acagaaaaag aatcagtaac tgcgtcgcgg actactccgt    240
cctatacaac tctgcctctt tctccacgtt caaatgctac ggtgtatctc cgacaaagct    300
aaacgatcta tgcttcacca acgtctacgc ggactccttc gtaatcagag gagatgaagt    360
tagacagatt gcgccgggac aaactggaaa gatcgcggat tataactaca agctaccgga    420
cgacttcacc ggatgtgtaa ttgcgtggaa ttcgaacaac ctagactcca aagtcggagg    480
aaactacaac tacttgtaca gactattcag aaagtccaac ctaaagccgt tcgagagaga    540
catctccacc gaaatctatc aggctggatc tacaccgtgt aatggtgtcg aaggattcaa    600
ctgctacttc ccgctacagt cttacggatt tcaaccgaca aacggtgtag gatatcagcc    660
gtacagagtc gtcgtactat ccttcgaact actacatgct ccggcgacag tatggtggac    720
ctccgattgg ggagtactaa caaacctagg aatcctacta ctattgtcga tcgcggtcct    780
aatcgcgcta tcctgtatct gtagaatctt caccaagtac atcggagagc cggaagctta    840
ataattttta t                                                          851

SEQ ID NO: 134            moltype = DNA  length = 861
FEATURE                   Location/Qualifiers
source                    1..861
                          mol_type = other DNA
                          organism = synthetic construct
SEQUENCE: 134
aaaaattgaa aataaataca aaggttcttg agggttgtgt taaattgaaa gcgagaaata    60
atcataaata acccggggcc accatgtgga cgacctgctt cttcatctcc ctaatcctaa    120
tccagggaat caagacccta aacatcacga acctatgtcc gttcggagaa gtgttcaacg    180
cgacaagatt tgcgtctgtc tatgcgtgga acagaaaaag aatcagtaac tgcgtcgcgg    240
actactccgt cctatacaac tctgcctctt tctccacgtt caaatgctac ggtgtatctc    300
cgacaaagct aaacgatcta tgcttcacca acgtctacgc ggactccttc gtaatcagag    360
gagatgaagt tagacagatt gcgccgggac aaactggaaa gatcgcggat tataactaca    420
agctaccgga cgacttcacc ggatgtgtaa ttgcgtggaa ttcgaacaac ctagactcca    480
aagtcggagg aaactacaac tacttgtaca gactattcag aaagtccaac ctaaagccgt    540
tcgagagaga catctccacc gaaatctatc aggctggatc tacaccgtgt aatggtgtcg    600
aaggattcaa ctgctacttc ccgctacagt cttacggatt tcaaccgaca aacggtgtag    660
gatatcagcc gtacagagtc gtcgtactat ccttcgaact actacatgct ccggcgacag    720
tatggtggac ctccgattgg ggagtactaa caaacctagg aatcctacta ctattgtcga    780
tcgcggtcct aatcgcgcta tcctgtatct gtagaatctt caccaagtac atcggagagc    840
cggaagctta ataattttta t                                               861

SEQ ID NO: 135            moltype = DNA  length = 1868
FEATURE                   Location/Qualifiers
source                    1..1868
                          mol_type = other DNA
                          organism = synthetic construct
SEQUENCE: 135
aaaaattgaa aataaataca aaggttcttg agggttgtgt taaattgaaa gcgagaaata    60
atcataagcc accatgtgga cgacctgctt cttcatctcc ctaatcctaa tccagggaat    120
caagacccta gtcagatttc cgaacatcac gaacctatgt ccgttcggag aagtgttcaa    180
cgcgacaaga tttgcgtctg tctatgcgtg gaacagaaaa agaatcagta actgcgtcgc    240
ggactactcc gtcctataca actctgcctc tttctccacg ttcaaatgct acggtgtatc    300
tccgacaaag ctaaacgatc tatgcttcac caacgtctac gcggactcct tcgtaatcag    360
aggagatgaa gttagacaga ttgcgccggg acaaactgga aagatcgcgg attataacta    420
caagctaccg gacgacttca ccggatgtgt aattgcgtgg aattcgaaca acctagactc    480
caaagtcgga ggaaactaca actacttgta cagactattc agaaagtcca acctaaagcc    540
gttcgagaga gacatctcca ccgaaatcta tcaggctgga tctacaccgt gtaatggtgt    600
cgaaggattc aactgctact tcccgctaca gtcttacgga tttcaaccga caaacggtgt    660
aggatatcag ccgtacagag tcgtcgtact atccttcgaa ctactacatg ctccggcgac    720
agtatggtgg acctccgatt ggggagtact aacaaaccta ggaatcctac tactattgtc    780
gatcgcggtc ctaatcgcgc tatcctgtat ctgtagaatc ttcaccaagt acatcggaga    840
gccgaagct taataatttt tatctgcagg tcgacttatt atatcgcaga tagtgttgga    900
ttcgcatacg ctagtactac ttgtctatta ttaaaaccat tcaatggaaa attttctggc    960
gcttgaaaat atactactgg agaagattct cctcttttct tcatcattcc ttcttttaca   1020
```

-continued

```
gaaaacatat ccgctggtag agaaattcta aacaaagatg tcttttctgg tacctttttct   1080
actcttagtt gatgtagaat tccagaaatc gccaatagtg gtccattatt tggattctta   1140
tgttgtctat acgcttgttt ctttacagtt ggtagtacta ttggtggtag atttggatga   1200
atagaaatcg ctggatgcat tgtatttcca attagtttat ctttagatgg tctccaagca   1260
tcatctggta gcttttgtac agatagtact agattagtta gattataagt aaactgattt   1320
gtagagaaat ttcttggaat aaccatattt tgaataaaag cttgatttcc ttctcttagc   1380
attcttagtg gatgcgctgg tattccagtt cctagtctat ttactctaac aaacttttgt   1440
ccattatgtg taaactgtgt aattgtataa gatcctgtca atagcgccgc tactgtatgc   1500
gctagtggat attcaaaatt agacataatt cctagtggta gccaagctgg tacacctttt   1560
actgttcttt cattatacgc agaaatatca ataatcgctt ctagtgtaaa cgcatgacaa   1620
acatttcctt taaactgatc atctagattt agatctccaa cataaatttgg tgtaattcca   1680
tgttgattag atagttgatc cgctggaatt agttgattag caccatgatc cgcatatggt   1740
ggtggattta gatattgcat ataagtatta taattgaaac tagacgccat cccgggctta   1800
tttatgatta tttctcgctt tcaatttaac acaaccctca agaacctttg tatttatttt   1860
caatttt                                                                1868

SEQ ID NO: 136        moltype = DNA   length = 1874
FEATURE               Location/Qualifiers
source                1..1874
                      mol_type = other DNA
                      organism = synthetic construct
SEQUENCE: 136
aaaaattgaa aataaataca aaggttcttg agggttgtgt taaattgaaa gcgagaaata   60
atcataaccc ggggccacca tgtggacgac ctgcttcttc atctccctaa tcctaatcca   120
gggaatcaag accctagtca gatttccgaa catcacgaac ctatgtccgt tcggagaagt   180
gttcaacgcg acaagatttg cgtctgtcta tgcgtggaac agaaaaagaa tcagtaactg   240
cgtcgcggac tactccgtcc tatacaactc tgcctctttc tccacgttca aatgctacgg   300
tgtatctccg acaaagctaa acgatctatg cttcaccaac gtctacgcgg actccttcgt   360
aatcagagga gatgaagtta gacagattgc gccgggacaa actggaaaga tcgcggatta   420
taactacaag ctaccggacg acttcaccgg atgtgtaatt gcgtggaatt cgaacaacct   480
agactccaaa gtcggaggaa actacaacta cttgtacaga ctattcagaa agtccaacct   540
aaagccgttc gagagagaca tctccaccga aatctatcag gctggatcta caccgtgtaa   600
tggtgtcgaa ggattcaact gctacttccc gctacagtct tacggatttc aaccgacaaa   660
cggtgtagga tatcagccgt acagagtcgt cgtactatcc ttcgaactac tacatgctgt   720
ggcgacagta tggtggacct ccgattgggg agtactaaca aacctaggaa tcctactact   780
attgtcgatc gcggtcctaa tcgcgctatc ctgtatctgt agaatcttca ccaagtacat   840
cggagagccg gaagcttaat aatttttatc tgcaggtcga cttattatat cgcagatagt   900
gttggattcg catacgctag tactacttgt ctattattaa aaccattcaa tggaaaattt   960
tctggcgctt gaaaatatac tactggagaa gattctcctc ttttcttcat cattccttct   1020
tttacagaaa acatatccgc tggtagagaa attctaaaca aagatgtctt ttctggtacc   1080
ttttctactc ttagttgatg tagaattcca gaaatcgcca atagtggtcc attatttgga   1140
ttcttatgtt gtctatacgc ttgtttcttt acagttggta gtactattgg tggtagattt   1200
ggatgaatag aaatcgctgg atgcattgta tttccaatta gttatcttt agatggtctc   1260
caagcatcat ctggtagctt ttgtacagat agtactagat tagttagatt ataagtaaac   1320
tgatttgtag agaaatttct tggaataacc atattttgaa taaaagcttg atttccttct   1380
cttagcattc ttagtggatg cgctggtatt ccagttccta gtcatttac tctaacaaac   1440
ttttgtccat tatgtgtaaa ctgtgtaatt gtataagatc ctgtcaatag cgccgctact   1500
gtatgcgcta gtggatattc aaaattagac ataattccta gtggtagcca agctggtaca   1560
cctttactg ttctttcatt atacgcagaa atatcaataa tcgcttctag tgtaaacgca   1620
tgacaaacat ttcctttaaa ctgatcatct agatttagat ctccaacata atttggtgta   1680
attccatgtt gattagatag ttgatccgct ggaattagtt gattagcacc atgatccgct   1740
catatggtggtg gatttagata ttgcatataa gtattataat tgaaactaga cgccatcccg   1800
ggcttatttta tgattatttc tcgctttcaa tttaacacaa ccctcaagaa cctttgtatt   1860
tattttcaat tttt                                                         1874

SEQ ID NO: 137        moltype = DNA   length = 1856
FEATURE               Location/Qualifiers
source                1..1856
                      mol_type = other DNA
                      organism = synthetic construct
SEQUENCE: 137
aaaaattgaa aataaataca aaggttcttg agggttgtgt taaattgaaa gcgagaaata   60
atcataagcc accatgtgga cgacctgctt cttcatctcc ctaatcctaa tccagggaat   120
caagaccctga aacatcacga acctatgtcc gttcggggaac gtgttcaacg gacaagatt   180
tgcgtctgtc tatgcgtgga acagaaaaag aatcagtaac tgcgtcgcgg actactccgt   240
cctatacaac tctgcctctt tctccacgtt caaatgctac ggtgtatctc cgacaaagct   300
aaacgatcta tgcttcacca cgtctacgc ggactccttc gtaatcagag gagatgaagt   360
tagacagatt gcgccgggac aaactggaaa gatcgcggat tataactaca agctaccgga   420
cgacttcacc ggatgtgtaa ttgcgtggaa ttcgaacaac ctagactcca agtcggagg   480
aaactacaac tacttgtaca gactattcag aaagtccaac ctaaagccgt tcgagagaga   540
catctccacc gaaatctatc aggctggatc tacaccgtgt aatggtgtcg aaggattcaa   600
ctgctacttc ccgctacagt cttacggatt tcaaccgaca aacggtgtag gatatcagcc   660
gtacagagtc gtcgtactat ccttcgaact actacatgct ccggcgacag tatggtggac   720
ctccgattgg ggagtactaa caaacctagg aatcctacta cattgtcga tcgcatacgct   780
aatcgcgcta tcctgtatct gtagaatctt caccaagtac atcggagagc cggaagctta   840
ataatttta tctgcaggtc gacttattat atcgcagata gtgttggatt cgcatacgct   900
agtactactt gtctattatt aaaaccattc aatggaaaat tttctggcgc ttgaaaatat   960
actactggag aagattctcc tctttttctc atcattcctt cttttacaga aacacatatcc   1020
gctggtagag aaattctaaa caaagatgtc ttttctggta cctttctac tcttagttga   1080
```

-continued

```
tgtagaattc cagaaatcgc caatagtggt ccattatttg gattcttatg ttgtctatac   1140
gcttgtttct ttacagttgg tagtactatt ggtggtagat ttggatgaat agaaatcgct   1200
ggatgcattg tatttccaat tagtttatct ttagatggtc tccaagcatc atctggtagc   1260
ttttgtacag atagtactag attagttaga ttataagtaa actgatttgt agagaaattt   1320
cttggaataa ccatattttg aataaaagct tgatttcctt ctcttagcat tcttagtgga   1380
tgcgctggta ttccagttcc tagtctattt actctaacaa acttttgtcc attatgtgta   1440
aactgtgtaa ttgtataaga tcctgtcaat agcgccgcta ctgtatgcgc tagtggatat   1500
tcaaaattag acataattcc tagtggtagc caagctggta cacctttttac tgttctttca   1560
ttatacgcag aaatatcaat aatcgcttct agtgtaaacg catgacaaac atttccttta   1620
aactgatcat ctagatttag atctccaaca taatttggtg taattccatg ttgattagat   1680
agttgatccg ctggaattag ttgattagca ccatgatccg catatggtgg tggatttaga   1740
tattgcatat aagtattata attagaacta gacgccatcc cgggcttatt tatgattatt   1800
tctcgctttc aatttaacac aaccctcaag aacctttgta tttatttca attttt       1856
```

SEQ ID NO: 138          moltype = DNA  length = 1862
FEATURE                 Location/Qualifiers
source                  1..1862
                        mol_type = other DNA
                        organism = synthetic construct
SEQUENCE: 138
```
aaaaattgaa aataaataca aaggttcttg agggttgtgt taaattgaaa gcgagaaata   60
atcataaccc ggggccacca tgtggacgac ctgcttcttc atctccctaa tcctaatcca   120
gggaatcaag accctaaaca tcacgaacct atgtccgttc ggagaagtgt tcaacgcgac   180
aagatttgcg tctgtctatg cgtggaacag aaaaagaatc agtaactgcg tcgcggacta   240
ctccgtccta tacaactctg cctctttctc cacgttcaaa tgctacggtg tatctccgac   300
aaagctaaac gatctatgct tcaccaacgt ctacgcggac tccttcgtaa tcagaggaga   360
tgaagttaga cagattgcgc cgggacaaac tggaaagatc gcggattata actacaagct   420
accggacgac ttcaccggat gtgtaattgc gtggaattcg aacaacctag actccaaagt   480
cggaggaaac tacaactact tgtacagact attcagaaag tccaacctaa agccgttcga   540
gagagacatc tccaccgaaa tctatcaggc tggatctcaa ccgtgtaatg gtgtcgaagg   600
attcaactgc tacttccgc tacagtctta cggatttcaa ccgacaaacg gtgtaggata   660
tcagccgtac agagtcgtcg tactatcctt cgaactacta catgctccgg cgacagtatg   720
gtggacctcc gattggggag tactaacaaa cctaggaatc ctactactat tgtcgatcgc   780
ggtcctaatc gcgctatcct gtatctgtag aatcttcacc aagtacatcg gagagccgga   840
agcttaataa tttttatctg caggtcgact tattatatcg cagatagtgt tggattcgca   900
tacgctagta ctacttgtct attattaaaa ccattcaatg gaaaatttc tggcgcttga   960
aaatatacta ctggagaaga ttctcctctt ttcttcatca ttccttcttt tacagaaaac   1020
atatccgctg gtagagaaat tctaaacaaa gatgtctttt ctggtacctt ttctactctt   1080
agttgatga gaattccaga aatcgccaat agtggtccat tatttggatt cttatgttgt   1140
ctatacgctt gtttctttac agttggtagt actattggtg gtagatttgg atgaatagaa   1200
atcgctggat gcattgtatt tccaattagt ttatctttag atggtctcca agcatcatct   1260
ggtagctttt gtacagatag tactagatta gttagattat aagtaaactg atttgtagag   1320
aaatttcttg gaataaccat attttgaata aagcttgat ttccttctct tagcattctt   1380
agtggatgcg ctggtattcc agttcctagt ctatttactc taacaaactt ttgtccatta   1440
tgtgtaaact gtgtaattgt ataagatcct gtcaatagcg ccgctactgt atgcgctagt   1500
ggatattcaa aattagacat aattcctagt ggtagccaag ctggtacacc ttttactgtt   1560
ctttcattat acgcagaaat caataatc gcttctagt gttaaacgca tgacaaac   1620
cctttaaact gatcatctag atttagatct ccaacataat ttggtgtaat tccatgttga   1680
ttagatagtt gatccgctgg aattagttga ttagcaccat gatccgcata tggtggtgga   1740
tttagatatt gcatataagt attataatta gaactagacg ccatcccggg cttatttatg   1800
attatttctc gctttcaatt taacacaacc ctcaagaacc tttgtattta ttttcaattt   1860
tt                                                                 1862
```

SEQ ID NO: 139          moltype = DNA  length = 1041
FEATURE                 Location/Qualifiers
source                  1..1041
                        mol_type = other DNA
                        organism = synthetic construct
SEQUENCE: 139
```
aaaaattgaa aataaataca aaggttcttg agggttgtgt taaattgaaa gcgagaaata   60
atcataagcc accatgtgga cgacctgctt cttcatctcc ctaatcctaa tccagggaat   120
caagacccta tggacgacct gcttcttcat ctccctaatc ctaatccagg gaatcaagac   180
cctatatcag ccgtacagag tcgtcgtact atccttcgaa ctactacatg ctccggcgac   240
agtaggtcct ggacccggtt atcaggctgg atctacaccg tgtaatggtg tcgaaggatt   300
caactgctac ttcggtcctg gacccggtta tcagccgtac agagtcgtcg tactatcctt   360
cgaactacta catgctccgg cgacagtagg tcctggaccc ggttatcagg ctggatctac   420
accgtgtaat ggtgtcgaag gattcaactg ctacttcggt cctggacccg gttatcagcc   480
gtacagagtc gtcgtactat ccttcgaact actacatgct ccggcgacag taggtcctgg   540
acccggttat caggctggat ctacaccgtg taatggtgtc gaaggattca actgctactt   600
cggtcctgga cccggttatc agccgtacag agtcgtcgta ctatccttcg aactactaca   660
tgctccggcg acagtaggtc ctggacccgg ttatcaggct ggatctacac cgtgtaatgg   720
tgtcgaagga ttcaactgct acttcggtcc tggacccggt atcagccgt acagagtcgt   780
cgtactatcc ttcgaactac tacatgctcc ggcgacagta ggtcctggac ccggttatca   840
ggctggatct acaccgtgta atggtgtcga aggattcaac tgctacttct ggtggacatc   900
ggctggatct acaccgtgta atggtgtcga aggattcaac tgctacttct ggtggacatc   960
tgactgggga gtcctaacga acctaggaat cctactacta ttgtcgatcg cggtcctaat   960
cgcgctatcc tgtatctgta gaatcttcac caagtacatc ggagagccgg aagcttaata   1020
attttatta ataatttta t                                              1041
```

SEQ ID NO: 140          moltype = DNA  length = 1047

```
FEATURE               Location/Qualifiers
source                1..1047
                      mol_type = other DNA
                      organism = synthetic construct
SEQUENCE: 140
aaaaattgaa aataaataca aaggttcttg agggttgtgt taaattgaaa gcgagaaata   60
atcataaccc ggggccacca tgtggacgac ctgcttcttc atctccctaa tcctaatcca  120
gggaatcaag accctatgga cgacctgctt cttcatctcc ctaatcctaa tccagggaat  180
caagaccta tatcagccgt acagagtcgt cgtactatcc ttcgaactac tacatgctcc   240
ggcgacagta ggtcctggac ccggttatca ggctggatct acaccgtgta atggtgtcga  300
aggattcaac tgctacttcg gtcctggacc cggttatcag ccgtacagag tcgtcgtact  360
atccttcgaa ctactacatg ctccggcgac agtaggtcct ggacccggtt atcaggctgg  420
atctacaccg tgtaatggtg tcgaaggatt caactgctac ttcggtcctg gacccggtta  480
tcagccgtac agagtcgtcg tactatcctt cgaactacta catgctccgg cgacagtagg  540
tcctggaccc ggttatcagg ctggatctac accgtgtaat ggtgtcgaag gattcaactg  600
ctacttcggt cctggacccg gttatcagcc gtacagagtc gtcgtactat ccttcgaact  660
actacatgct ccggcgacag taggtcctgg acccggttat caggctggat ctacaccgtg  720
taatggtgtc gaaggattca actgctactt cggtcctgga cccggttatc agccgtacag  780
agtcgtcgta ctatccttcg aactactaca tgctccggcg acagtaggtc ctggacccgg  840
ttatcaggct ggatctacac cgtgtaatgg tgtcgaagga ttcaactgct acttctggtg  900
gacatctgac tggggagtcc taacgaacct aggaatccta ctactattgt cgatcgcggt  960
cctaatcgcg ctatcctgta tctgtagaat cttcaccaag tacatcggag agccggaagc 1020
ttaataattt ttattaataa tttttat                                     1047

SEQ ID NO: 141        moltype = DNA   length = 2046
FEATURE               Location/Qualifiers
source                1..2046
                      mol_type = other DNA
                      organism = synthetic construct
SEQUENCE: 141
aaaaattgaa aataaataca aaggttcttg agggttgtgt taaattgaaa gcgagaaata   60
atcataagcc accatgtgga cgacctgctt cttcatctcc ctaatcctaa tccagggaat  120
caagaccta tggacgacct gcttcttcat ctccctaatc ctaatccagg gaatcaagac  180
cctatatcag ccgtacagag tcgtcgtact atccttcgaa ctactacatg ctccggcgac  240
agtaggtcct ggacccggtt atcaggctgg atctacaccg tgtaatggtg tcgaaggatt  300
caactgctac ttcggtcctg gacccggtta tcagccgtac agagtcgtcg tactatcctt  360
cgaactacta catgctccgg cgacagtagg tcctggaccc ggttatcagg ctggatctac  420
accgtgtaat ggtgtcgaag gattcaactg ctacttcggt cctggacccg gttatcagcc  480
gtacagagtc gtcgtactat ccttcgaact actacatgct ccggcgacag taggtcctgg  540
acccggttat caggctggat ctacaccgtg taatggtgtc gaaggattca actgctactt  600
cggtcctgga cccggttatc agccgtacag agtcgtcgta ctatccttcg aactactaca  660
tgctccggcg acagtaggtc ctggacccgg ttatcaggct ggatctacac cgtgtaatgg  720
tgtcgaagga ttcaactgct acttcggtcc tggacccggt tatcagccgt acagagtcgt  780
cgtactatcc ttcgaactac tacatgctcc ggcgacagta ggtcctggac ccggttatca  840
ggctggatct acaccgtgta atggtgtcga aggattcaac tgctacttct ggtggacatc  900
tgactgggga gtcctaacga acctaggaat cctactacta ttgtcgatcg cggtcctaat  960
cgcgctatcc tgtatctgta gaatcttcac caagtacatc ggagagccgg aagcttaata 1020
atttttatta ataattttta tctgcaggtc gacttattat atcgcagata gtgttggatt 1080
cgcatacgct agtactactt gtctattatt aaaaccattc aatggaaaat tttctggcgc 1140
ttgaaaatat actactggag aagattctcc tcttttcttc atcattcctt cttttacaga 1200
aaacatatcc gctggtagag aaattctaaa caaagatgtt ttttctggta ccttttctac 1260
tcttagttga tgtagaattc cagaaatcgc caatagtggt ccattatttg gattcttatg 1320
ttgtctatac gcttgtttct ttacagttgg tagtactatt ggtggtagat ttggatgaat 1380
agaaatcgct ggatgcattg tatttccaat tagtttatct ttagatggtc tccaagcatc 1440
atctgtagc ttttgtacag atagtactag attagttaga ttataagtaa actgatttgt 1500
agagaaattt cttggaataa ccatattttg aataaaagct tgatttcctt ctcttagcat 1560
tcttagtgga tgcgctggta ttccagttcc tagtctattt actctaacaa acttttgtcc 1620
attatgtgta aactgtgtaa ttgtataaga tcctgtcaat agcgccgcta ctgtatgcgc 1680
tagtggatat tcaaaattag acataattcc tagtggtagc caagctggta caccttttac 1740
tgttctttca ttatacgcag aaatatcaat aatcgcttct agtgtaaacg catgacaaac 1800
atttccttta aactgatcat ctagatttag atctccaaca taatttggtg taattccatg 1860
ttgattagat agttgatccg ctggaattag ttgattagca ccatgatccg catatggtgg 1920
tggatttaga tattgcatat aagtattata attagaacta gacgccatcc cgggcttatt 1980
tatgattatt tctcgctttc aatttaacac aacccctcaag aacctttgta tttattttca 2040
attttt                                                            2046

SEQ ID NO: 142        moltype = DNA   length = 2052
FEATURE               Location/Qualifiers
source                1..2052
                      mol_type = other DNA
                      organism = synthetic construct
SEQUENCE: 142
aaaaattgaa aataaataca aaggttcttg agggttgtgt taaattgaaa gcgagaaata   60
atcataaccc ggggccacca tgtggacgac ctgcttcttc atctccctaa tcctaatcca  120
gggaatcaag accctatgga cgacctgctt cttcatctcc ctaatcctaa tccagggaat  180
caagaccta tatcagccgt acagagtcgt cgtactatcc ttcgaactac tacatgctcc   240
ggcgacagta ggtcctggac ccggttatca ggctggatct acaccgtgta atggtgtcga  300
aggattcaac tgctacttcg gtcctggacc cggttatcag ccgtacagag tcgtcgtact  360
atccttcgaa ctactacatg ctccggcgac agtaggtcct ggacccggtt atcaggctgg  420
```

-continued

```
atctacaccg tgtaatggtg tcgaaggatt caactgctac ttcggtcctg gaccggtta   480
tcagccgtac agagtcgtcg tactatcctt cgaactacta catgctccgg cgacagtagg   540
tcctggaccc ggttatcagg ctggatctac accgtgtaat ggtgtcgaag gattcaactg   600
ctacttcggt cctggacccg gttatcagcc gtacagagtc gtcgtactat ccttcgaact   660
actacatgct ccggcgacag taggtcctgg acccggttgg caggctggat ctacaccgtg   720
taatggtgtc gaaggattca actgctactt cggtcctgga cccggttatc agccgtacag   780
agtcgtcgta ctatccttcg aactactaca tgctccggcg acagtaggtc ctggacccgg   840
ttatcaggct ggatctacac cgtgtaatgg tgtcgaagga ttcaactgct acttctggtg   900
gacatctgac tggggagtcc taacgaacct aggaatccta ctactattgt cgatcgcggt   960
cctaatcgcg ctatcctgta tctgtagaat cttcaccaag tacatcggag agccggaagc   1020
ttaataattt ttattaataa ttttttatctg caggtcgact tattatatcg cagatagtgt   1080
tggattcgca tacgctagta ctacttgtct attattaaaa ccattcaatg gaaaattttc   1140
tggcgcttga aaatatacta ctggagaaga ttctcctctt ttcttcatca ttccttcttt   1200
tacagaaaac atatccgctg gtagagaaat tctaaacaaa gatgtctttt ctggtacctt   1260
ttctactctt agttgatgta gaattccaga aatcgccaat agtggtccat tatttggatt   1320
cttatgttgt ctatacgctt gtttctttac agttggtagt actattggtg gtagatttgg   1380
atgaatagaa atcgctggat gcattgtatt tccaattagt ttatctttag atggtctcca   1440
agcatcatct ggtagctttt gtacagatag tactagatta gttagattat aagtaaactg   1500
atttgtagag aaatttcttg gaataaccat attttgaata aaagcttgat ttccttctct   1560
tagcattctt agtggatgcg ctggtattcc agttcctagt ctatttactc taacaaactt   1620
ttgtccatta tgtgtaaact gtgtaattgt ataagatcct gtcaatagcg ccgctactgt   1680
atgcgctagt ggatattcaa aattagacat aattcctagt ggtagccaag ctggtacacc   1740
ttttactgtt ctttcattat acgcagaaat atcaataatc gcttctagtg taaacgcatg   1800
acaaacattt cctttaaact gatcatctag atttagatct ccaacataat ttggtgtaat   1860
tccatgttga ttagatagtt gatccgctgg aattagttga ttagcaccat gatccgcata   1920
tggtggtgga tttagatatt gcatataagt attataatta gaactagacg ccatcccggg   1980
cttatttatg attatttctc gctttcaatt taacacaacc ctcaagaacc tttgtattta   2040
ttttcaattt tt                                                       2052
```

```
SEQ ID NO: 143          moltype = DNA  length = 3917
FEATURE                 Location/Qualifiers
source                  1..3917
                        mol_type = other DNA
                        organism = synthetic construct
SEQUENCE: 143
aaaaattgaa aataaataca aaggttcttg agggttgtgt taaattgaaa gcgagaaata   60
atcataagcc accatgttcg tgttcctagt cctactaccg ctagtctctt ctcagtgtgt   120
aaacctaaca acgagaacac aactaccacc ggcgtacacc aattctttca caagaggagt   180
atattcccg gacaaggtgt tcagatcctc cgtactacat tctacacagg acctattcct   240
accgttcttc tctaacgtaa catggttcca cgcgatccat gtctctggaa caaacggaac   300
gaagagattc gataacccgg tcttgccgtt caacgatggt gtatactttg cgtccaccga   360
gaagtccaac atcatcagag gatggatctt cggaaccacc ttggattcta agacccagtc   420
cttgctaatc gtcaacaacg cgaccaacgt cgtcatcaaa gtctgcgaat tccagttctg   480
taacgcaccg ttcttgggag tctactacca caagaacaac aagtcctgga tggaatccga   540
gttcagagtc tactcttccg cgaacaactg caccttcgaa tatgtatctc agccgttcct   600
aatgaccta gagggaaagc agggaaactt caagaaccta agagagttcg tattcaagaa   660
catcgacgga tacttcaaga tctactccaa gcacactccg atcaacctag ttagagatct   720
accgcaagga ttctctgcgc tagaaccgtt agtagatttg ccgatcggaa tcaacatcac   780
cagattccag acactactag cgctacacag atcttaccta acgccgggag attcttcttc   840
tggatggact gctggtgctg cggcttatta tgtaggatac ctacagccga gaaccttcct   900
attgaagtac aacgaaaacg gaaccatcac cgatgccgta gattgtgctc tagatccgat   960
atccgaaacg aagtgcaccc taaagtcttt caccgtcgag aagggaatct accagacctc   1020
caactttaga gtacagccga ccgaatccat cgtcagattt ccgaacatca cgaacctatg   1080
tccgttcgga gaagtgttca acgcgacaag atttgcgtct gtctatgcgt ggaacagaaa   1140
aagaatcagt aactgcgtcg cggactactc cgtcctatac aactctgcct ctttctccac   1200
gttcaaatgc tacggtgtat ctccgacaaa gctaaacgat ctatgcttca ccaacgtcta   1260
cgcggactcc ttcgtaatca gaggagatga agttagacag attgcgccgg gacaaactgg   1320
aaagatcgcg gattataact acaagctacc ggacgacttc accggatgtg taattgcgtg   1380
gaattcgaac aacctagact ccaaagtcgg aggaaactac aactacttgt acagactatt   1440
cagaaagtcc aacctaaagc cgttcgagag agacatctcc accgaaatct atcaggctgg   1500
atctacaccg tgtaatggtg tcgaaggatt caactgctac ttcccgctac agtcttacgg   1560
atttcaaccg acaaacggtg taggatatca gccgtacaga gtcgtcgtac tatccttcga   1620
actactacat gctccggcga cagtatgtgg accgaaaaag tctaccaacc tagtcaagaa   1680
caaatggtc aactttaact tcaacggact aaccggaacc ggtgtcctaa ccgaatctaa   1740
caagaagttt ctaccgttcc agcagttcgg aagagatatc gcggatacaa cagacgctgt   1800
cagagatccg caaaccttgg agatcctaga tatcacaccg tgttctttcg gtggtgtctc   1860
tgtaattact ccgggaacga acacctccaa tcaagtagcg gtactatacc aggacgtgaa   1920
ctgtacagaa gtaccggtag ctattcacgc ggatcaacta acaccaactt gggagagtgta   1980
ctccaccgga tctaacgtat tccaaacaag agcgggatgt ctaatcggag cggaacacgt   2040
aaacaactcc tacgaatgtg atatcccgat tggagcggga atctgtgcgt cttaccaaac   2100
acaaacaaac tctccgagaa gagcgagatc tgtagcctct caatctatta tcgcctacac   2160
catgtccttg ggagccgaaa attctgtcgc gtactccaac aattctatcg cgatcccgac   2220
aaacttcacc atctctgtaa caaccgagat cctaccggtc tctatgacca agacatctgt   2280
cgattgacc atgtacatct gcgggagattc caccgagtgc tccaacctac tactacagta   2340
cggatctttc tgtacccagc taaacagagc gttgactgga atcgctgtag agcaggataa   2400
gaacactcaa gaggtattcg cgcaagtcaa gcagatctat aagactccgc cgatcaagga   2460
cttcggaggt ttcaacttct ctcagatctt gccggatccg tccaaccgt ctaagagatc   2520
tttcatcgag gacctactat tcaacaaagt caccctagct gacgcgggat tcatcaaaca   2580
atacggagat tgcttgggag acattgcggc gagagatcta atttgcgcgc agaagtttaa   2640
```

```
cggattgaca gtactaccgc cgctactaac cgatgagatg attgcgcagt acacgtctgc  2700
tctattggcg ggaacaatta caagtggatg gacatttgga gccggtgccg ctctacaaat  2760
tccgtttgct atgcaaatgg cgtacagatt caacggaatc ggagtaaacc agaacgtctt  2820
gtacgagaac cagaagctaa tcgcgaacca gttcaattcc gcgatcggaa agatccagga  2880
cagtctatct tctactgctt cggcgttggg aaagctacag gatgtagtaa atcaaaacgc  2940
gcaggcgcta aacaccttgg tcaagcaact atcctctaac ttcggagcga tctcgtccgt  3000
cctaaacgac atcttatcca gactagataa ggtcgaagcg gaggtccaga tcgatagact  3060
aatcactgga agattgcagt ccctacagac ctacgtaaca cagcaactaa ttagagcggc  3120
ggagattgaa gcctctgcta atctagctgc gaccaagatg tccgaatgtg tcttgggaca  3180
atccaagaga gtggacttct gcggaaaggg ataccaccta atgtctttcc cacaatctgc  3240
gccgcatggt gtcgtattcc tacatgtaac atatgtgccg gcgcaagaaa agaacttcac  3300
aacagctcca gcgatctgcc atgatggaaa agctcatttc ccgagagagg gagtctttgt  3360
ctctaacgga actcattggt tcgtcaccca gagaaacttc tacgagccgc agatcatcac  3420
caccgacaac acattcgtct cgggaaactg cgacgtggtc atcggaatcg taaacaatac  3480
cgtctacgat ccgttgcagc cggaactaga ctccttcaaa gaagagttgg acaagtactt  3540
caagaaccac acctctccgg atgtggactt gggagatatc tctggaatca acgcgtccgt  3600
cgtcaacatc cagaaagaaa tcgatagatt gaacgaggtc gcgaagaact tgaacgagtc  3660
cctaatcgac ctacaagagc taggaaaata cgagcagtac atcaagtggc cgtggtacat  3720
ctggctagga ttcattgctg gactaattgc gatcgtcatg gtcaccatca tgctatgctg  3780
tatgacctcc tgttgctcct gtctaaaggg atgttgttcc tgcggatcct gttgcaagtt  3840
cgatgaagat gatagtgaac cggtcctaaa gggtgtcaag ctacactaca cagagccaga  3900
ggcttaataa tttttat                                                  3917
```

```
SEQ ID NO: 144        moltype = DNA   length = 3923
FEATURE               Location/Qualifiers
source                1..3923
                      mol_type = other DNA
                      organism = synthetic construct SEQUENCE: 144
aaaaattgaa aataaataca aaggttcttg agggttgtgt taaattgaaa gcgagaaata  60
atcataaccc ggggccacca tgttcgtgtt cctagtccta ctaccgctag tctcttctca  120
gtgtgtaaac ctaacaacga gaacacaact accaccggcg tacaccaatt ctttcacaag  180
aggagtatat tacccggaca aggtgttcag atcctccgta ctacattcta cacaggacct  240
attcctaccg ttcttctcta acgtaacatg gttccacgcg atccatgtct ctggaacaaa  300
cggaacgaag agattcgata acccggtctt gccgttcaac gatggtgtat actttgcgtc  360
caccgagaag tccaacatca tcagaggatg gatcttcgga accaccttgg attctaagac  420
ccagtccttg ctaatcgtca acaacgcgac caacgtcgtc atcaaagtct gcgaattcca  480
gttctgtaac gacccgttct tgggagtcta ctaccacaag aacaacaagt cctggatgga  540
atccgagttc agagtctact cttccgcgaa caactgcacc ttcgaatatg tatctcagcc  600
gttcctaatg gacctagagg gaaagcaggg aaacttcaag aacctaagag agttcgtatt  660
caagaacatc gacggatact tcaagatcta ctccaagcac actccgatca acctagttag  720
agatctaccg caaggattct ctgcgctaga accgttagta gatttgccga tcggaatcaa  780
catcaccaga ttccagacac tactagcgct acacagatct tacctaacgc cgggagattc  840
ttcttctgga tggactgctg gtgctgcggc ttattatgta ggatacctac agccgagaac  900
cttcctattg aagtacaacg aaaacggaac catcaccgat gccgtagatt gtgctctaga  960
tccgctatcc gaaacgaagt gcaccctaaa gtctttcacc gtcgagaagg gaatctacca  1020
gacctccaac tttagagtac agccgaccga atccatcgtc agatttccga acatcacgaa  1080
cctatgtccg ttcggagaag tgttcaacgc gacaagattt gcgtctgtct atgcgtggaa  1140
cagaaaaaga atcagtaact gcgtcgcgga ctactccgtc ctatacaact ctgcctcttt  1200
ctccacgttc aaatgctacg gtgtatctcc gacaaagcta aacgatctat gcttcaccaa  1260
cgtctacgcg gactccttcg taatcagagg agatgaagtt agacagattg cgccgggaca  1320
aactggaaag atcgcggatt ataactacaa gctaccggac gacttcaccg gatgtgtaat  1380
tgcgtggaat tcgaacaacc tagactccaa agtcggagga aactacaact acttgtacag  1440
actattcaga aagtccaacc taaagccgtt cgagagagac atctccaccg aaatctatca  1500
ggctggatct acaccgtgta atggtgtcga aggattcaac tgctacttcc cgctacagtc  1560
ttacggattt caaccgacaa acggtgtagg atatcagccg tacagagtcg tcgtactatc  1620
cttcgaacta ctacatgctc cggcgacagt atgtggaccg aaaaagtcta ccaacctagt  1680
caagaacaaa tgcgtcaact ttaacttcaa cggactaacc ggaaccggtg tcctaaccga  1740
atctaacaag aagtttctac cgttccagca gttcggaaga gatatcgcgg atacaacaga  1800
cgctgtcaga gatccgcaaa ccttggagat cctagatatc acaccgtgtt ctttcggtgg  1860
tgtctctgta attactccgg gaacgaacac ctccaatcaa gtagcggtac tataccagga  1920
cgtgaactgt acagaagtac cggtagctat tcacgcggat caactaacac caacttggag  1980
agtgtactcc accggatcta acgtattcca aacaagagcg ggatgtctaa tcggagcgga  2040
acacgtaaac aactcctacg aatgtgatat cccgattgga gcggaaatct gtgcgtctta  2100
ccaaacacaa acaaactctc cgagaagagc gagatctgta gcctctcaat ctattatcgc  2160
ctacaccatg tccttgggag ccgaaaattc tgtcgcgtac tccaacaatt ctatcgcgat  2220
cccgacaaac ttcaccatct ctgtaacaac cgagatccta ccggtgtcta tgaccaagac  2280
atctgtcgat tgcaccatgt acatctgcgg agattccacc gagtgctcca acctactact  2340
acagtacgga tctttctgta cccagctaaa cagagcgttg actggaatcc ctgtagagca  2400
ggataagaac actcaagagg tattcgcgca agtcaagcag atctataaga ctccgccgat  2460
caaggacttc ggaggtttca acttctctca gatcttgccg gatccgtcca aaccgtctaa  2520
gagatctttc atcgaggacc tactattcaa caaagtcacc ctagctgacg cgggattcat  2580
caaacaatac ggagattgct gggagacat tgcggcgaga gatctaattt gcgcgcagaa  2640
gtttaacgga ttgacagtac taccgccgct actaaccgat gagatgattg cgcagtacat  2700
gtctgctcta ttggcgggaa caattacaag tggatggaca tttggagccg gtgccgctct  2760
acaaattccg tttgctatgc aaatggcgta cagattcaac ggaatcggag taaacccagaa  2820
cgtcttgtac gagaaccaga gctaatcgc gaaccagttc aattccgcga tcggaaagat  2880
ccaggacagt ctatcttcta ctgcttcggc gttgggaaag ctacaggatg tagtaaatca  2940
aaacgcgcag gcgctaaaca ccttggtcaa gcaactatcc tctaacttcg gagcgatctc  3000
```

-continued

```
gtccgtccta aacgacatct tatccagact agataaggtc gaagcggagg tccagatcga   3060
tagactaatc actggaagat tgcagtccct acagacctac gtaacacagc aactaattag   3120
agcggcggag attagagcct ctgctaatct agctgcgacc aagatgtccg aatgtgtctt   3180
gggacaatcc aagagagtgg acttctgcgg aaagggatac cacctaatgt ctttcccaca   3240
atctgcgccg catggtgtcg tattcctaca tgtaacatat gtgccggcgc aagaaaagaa   3300
cttcacaaca gctccagcga tctgccatga tggaaaagct catttcccga gagagggagt   3360
ctttgtctct aacggaactc attggttcgt cacccagaga aacttctacg agccgcagat   3420
catcaccacc gacaacacat tcgtctcggg aaactgcgac gtggtcatcg gaatcgtaaa   3480
caataccgtc tacgatccgt tgcagccgga actagactcc ttcaaagaag agttggacaa   3540
gtacttcaag aaccacacct ctccggatgc ggacttggga gatatctctg gaatcaacgc   3600
gtccgtcgtc aacatccaga aagaaatcga tagattgaac gaggtcgcga agaacttgaa   3660
cgagtcccta atcgacctac aagagctagg aaaatacgag cagtacatca agtggccgtg   3720
gtacatctgg ctaggattca ttgctggact aattgcgatc gtcatggtca ccatcatgct   3780
atgctgtatg acctcctgtt gctcctgtct aaagggatgt tgttcctgcg gatcctgttg   3840
caagttcgat gaagatgata gtgaaccggt cctaaagggt gtcaagctac actacacaga   3900
gccagaggct taataatttt tat                                            3923
```

SEQ ID NO: 145       moltype = DNA  length = 3917
FEATURE             Location/Qualifiers
source              1..3917
                    mol_type = other DNA
                    organism = synthetic construct
SEQUENCE: 145

```
aaaaattgaa aataaataca aaggttcttg agggttgtgt taaattgaaa gcgagaaata   60
atcataagcc accatgttcg tgttcctagt cctactaccg ctagtctctt ctcagtgtgt   120
aaacctaaca acgagaacac aactaccacc ggcgtacacc aattctttca caagaggagt   180
atattacccg gacaaggtgt tcagatcctc cgtactacat tctacacagg acctattcct   240
accgttcttc tctaacgtaa catggttcca cgcgatccat gtctctggaa caaacggaac   300
gaagagattc gataacccgg tcttgccgtt caacgatggt gtatactttg cgtccaccga   360
gaagtccaac atcatcagag gatggatctt cggaaccacc ttggattcta agacccagtc   420
cttgctaatc gtcaacaacg cgaccaacgt cgtcatcaaa gtctgcgaat tccagttctg   480
taacgacccg ttcttgggag tctactacca caagaacaac aagtcctgga tggaatccga   540
gttcagagtc tactcttccg cgaacaactg caccttcgaa tatgtatctc agccgttcct   600
aatggaccta gagggaaagc agggaaactt caagaaccta agagagttcg tattcaagaa   660
catcgacgga tacttcaaga tctactccaa gcacactccg atcaacctag ttagagatct   720
accgcaagga ttctctgcgc tagaaccgtt agtagatttg ccgatcggaa tcaacatcac   780
cagattccag acactactag cgctacacag atcttaccta acgccgggag attcttcttc   840
tggatggact gctggtgctg cggcttatta tgtaggatac ctacagccga gaaccttcct   900
attgaagtac aacgaaaacg gaaccatcac cgatgccgta gattgtgctc tagatccgct   960
atccgaaacg aagtgcaccc taaagtcttt caccgtcgag aagggaatct accagacctc   1020
caactttaga gtacagccga ccgaatccat cgtcagattt ccgaacatca cgaacctatg   1080
tccgttcgga gaagtgttca acgcgacaag atttgcgtct gtctatgcgt ggaacagaaa   1140
aagaatcagt aactgcgtcg cggactactc cgtcctatac aactctgcct ctttctccac   1200
gttcaaatgc tacggtgtat ctccgacaaa gctaaacgat ctatgcttca ccaacgtcta   1260
cgcggactcc ttcgtaatca gaggagatga agttagacag attgcgccgg gacaaactgg   1320
aaagatcgcg gattataact acaagctacc ggacgacttc accggatgtg taattgcgtg   1380
gaattcgaac aacctagact ccaaagtcgg aggaaactac aactacttgt acagactatt   1440
cagaaagtcc aacctaaagc cgttcgagag agacatctcc accgaaatct atcaggctgg   1500
atctacaccg tgtaatggtg tcgaaggatt caactgctac ttcccgctac agtcttacgg   1560
atttcaaccg acaaacggtg taggatatca gccgtacaga gtcgtcgtac tatccttcga   1620
actactacat gctccggcga cagtatgtgg accgaaaaag tctaccaacc tagtcaagaa   1680
caaatgcgtc aactttaact tcaacggact aaccggaacc ggtgtcctaa ccgaatctaa   1740
caagaagttt ctaccgttcc agcagttcgg aagagatatc gcggatacaa cagacgctgt   1800
cagagatccg caaaccttgg agatcctaga tatcacaccg tgttctttcg gtggtgtctc   1860
tgtaattact ccgggaacga acacctccaa tcaagtagcg gtactatacc aggacgtgaa   1920
ctgtacagaa gtaccggtag ctattcacgc ggatcaacta acaccaactt ggagagtgta   1980
ctccaccgga tctaacgtat tccaaacaag agcgggatgt ctaatcggag cggaacacgt   2040
aaacaactcc tacgaatgtg atatcccgat tgggagcggga atctgtgcgt cttaccaaac   2100
acaacaaac tctccgagaa gagcgagatc tgtagcctct caatctatta tcgcctacac   2160
catgtccttg ggagccgaaa attctgtcgc gtactccaac aattctatcg cgatcccgac   2220
aaacttcacc atctctgtaa caaccgagat cctaccggtg tctatgacca agacatctgt   2280
cgattgcacc atgtacatct gcggagattc caccgagtgc tccaacctac tactacagta   2340
cggatctttc tgtacccagc taaacagagc gttgactgga atcgctgtag agcaggataa   2400
gaacactcaa gaggtattcg cgcaagtcaa gcagatctat aagactccgc cgatcaaggta   2460
cttcggaggt ttcaacttct ctcagatctt gccggatccg tccaaaccgt ctaagagatc   2520
tttcatcgag gacctactat tcaacaaagt caccctagct gacgcgggat tcatcaaaca   2580
atacggagat tgcttgggag acattgcggc gagagatcta atttgcgcgc agaagtttaa   2640
cggattgaca gtactaccgc cgctactaac cgatgagagt attgcgcagt acacgtctgc   2700
tctattggcg ggaacaatta caagtggatg gacatttgga gccggtgccg ctctacaaat   2760
tccgtttgct atgcaaatgg cgtacagatt caacggaatc ggagtaaccc agaacgtctt   2820
gtacgagaac cagaagctaa tcgcgaacca gttcaattcc gcgatcggaa agatccagga   2880
cagtctatct tctactgctt cggcgttggg aaagctacag gatgtagtaa atcaaaacgc   2940
gcaggcgcta aacaccttgg tcaagcaact atcctctaac ttcggagcga tctcgtccgt   3000
cctaaacgat atcttatcca gactagatcc accggaacgg aggtccaga tcgatagact   3060
aatcactgga gagattgcagt ccctacgac ctacgtaaca cagcaactaa ttagagcggc   3120
ggagattaga gcctctgcta atctagctgc gaccaagatg tccgaatgtg tcttgggaca   3180
atccaagaga gtggacttct gcggaaaggg ataccaccta atgtctttcc cacaatctgc   3240
gccgcatggt gtcgtattcc tacatgtaac atatgtgccg gcgcaagaaa agaacttcac   3300
aacagctcca gcgatctgcc atgatggaaa agctcatttc cgagagagg gagtctttgt   3360
```

```
ctctaacgga actcattggt tcgtcaccca gagaaacttc tacgagccgc agatcatcac  3420
caccgacaac acattcgtct cgggaaactg cgacgtggtc atcggaatcg taaacaatac  3480
cgtctacgat ccgttgcagc cggaactaga ctccttcaaa gaagagttgg acaagtactt  3540
caagaaccac acctctccgg atgtggactt gggagatatc tctggaatca acgcgtccgt  3600
cgtcaacatc cagaaagaaa tcgatagatt gaacgagact gcgaagaact tgaacgagtc  3660
cctaatcgac ctacaagagc taggaaaata cgagcagtac atcaagtggc cgtggtacat  3720
ctggctagga ttcattgctg gactaattgc gatcgtcatg gtcaccatca tgctatgctg  3780
tatgacctcc tgttgctcct gtctaaaggg atgttgttcc tgcggatcct gttgcaagtt  3840
cgatgaagat gatagtgaac cggtcctaaa gggtgtcaag ctacactaca cagagccaga  3900
ggcttaataa tttttat                                                  3917
```

```
SEQ ID NO: 146              moltype = DNA  length = 3923
FEATURE                     Location/Qualifiers
source                      1..3923
                            mol_type = other DNA
                            organism = synthetic construct
SEQUENCE: 146
aaaaattgaa aataaataca aaggttcttg agggttgtgt taaattgaaa gcgagaaata  60
atcataaccc ggggccacca tgttcgtgtt cctagtccta ctaccgctag tctcttctca  120
gtgtgtaaac ctaacaacga gaacacaact accaccggcg tacaccaatt ctttcacaag  180
aggagtatat tacccggaca aggtgttcag atcctccgta ctacattcta cacaggacct  240
attcctaccg ttcttctcta acgtaacatg gttccacgcg atccatgtct ctggaacaaa  300
cggaacgaag agattcgata acccggtctt gccgttcaac gatggtgtat actttgcgtc  360
caccgagaag tccaacatca tcagaggatg gatcttcgga accaccttgg attctaagac  420
ccagtccttg ctaatcgtca acaacgcgac caacgtcgtc atcaaagtct gcgaattcca  480
gttctgtaac gacccgttct tgggagtcta ctaccacaag aacaacaagt cctggatcga  540
atccgagttc agagtctact cttccgcgaa caactgcacc ttcgaatatg tatctcagcc  600
gttcctaatg gacctagagg gaaagcaggg aaacttcaag aacctaagag agttcgtatt  660
caagaacatc gacggatact tcaagatcta ctccaagcac actccgatca acctagttag  720
agatctaccg caaggattct ctgcgctaga accgttagta gatttgccga tcggaatcaa  780
catcaccaga ttccagacac tactagcgct acacagatct tacctaacgc cgggagattc  840
ttcttctgga tggactgctg gtgctgcggc ttattatgta ggatacctac agccgagaac  900
cttcctattg aagtacaacg aaaacggaac catcaccgat gccgtagatt gtgctctaga  960
tccgtatcc gaaacgaagt gcaccctaaa gtctttcacc gtcgagaagg gaatctacca  1020
gacctccaac tttagagtac agccgaccga atccatcgtc agatttccga acatcacgaa  1080
cctatgtccg ttcggagaag tgttcaacgc gacaagattt gcgtctgtct atgcgtggaa  1140
cagaaaaaga atcagtaact gcgtcgcgga ctactccgtc ctatacaact ctgcctcttt  1200
ctccacgttc aaatgctacg gtgtatctcc gacaaagcta aacgatctat gcttccaccaa  1260
cgtctacgcg gactccttcg taatcagagg agatgaagtt agacagattg cgccgggaca  1320
aactggaaag atcgcggatt ataactacaa gctaccggac gacttcaccg gatgtgtaat  1380
tgcgtggaat tcgaacaacc tagactccaa agtcggagga aactacaact acttgtacag  1440
actattcaga aagtccaacc taaagccgtt cgagagagac atctccaccg aaatctatca  1500
ggctggatct acaccgtgta atggtgtcga aggattcaac tgctacttcc cgctacagtc  1560
ttacggattt caaccgacaa acggtgtagg atatcagccg tacagagtcg tcgtactatc  1620
cttcgaacta ctacatgctc cggcgacagt atgtggaccg aaaaagtcta ccaacctagt  1680
caagaacaaa tgcgtcaact ttaacttcaa cggactaacc ggaaccggtg tcctaaccga  1740
atctaacaag aagtttctac cgttccagca gttcggaaga gatatcgcgg atacaacaga  1800
cgctgtcaga gatccgcaaa ccttggagat cctagatatc acaccgtgtt ctttcggtgg  1860
tgtctctgta attactccgg gaacgaacac ctccaatcaa gtagcggtac tataccagga  1920
cgtgaactgt acagaagtac cggtagctat tcacgcggat caactaacac caacttggag  1980
agtgtactcc accggatcta acgtattcca aacaagagcg ggatgtctaa tcggagcgga  2040
acacgtaaac aactcctacg aatgtgatat cccgattgga gcgggaatct gtgcgtctta  2100
ccaaacacaa acaaactctc cgagaagagc gagatctgta gcctctcaat ctattatcgc  2160
ctacaccatg tccttgggag ccgaaaattc tgtcgcgtac tccaacaatt ctatcgcgat  2220
cccgacaaac ttcaccatct ctgtaacaac cgagatccta ccggtgtcta tgaccaagac  2280
atctgtcgat tgcaccatgt acatctgcgg agattccacc gagtgctcca acctactact  2340
acagtacgga tctttctgta cccagctaaa cagagcgttg actggaatcg ctgtagagca  2400
ggataagaac actcaagagg tattcgcgca agtcaagcag atctataaga ctccgccgat  2460
caaggacttc ggaggtttca acttctctca gatcttgccg gatccgtcca aacgtctaa  2520
gagatctttc atcgaggacc tactattcaa caaagtcacc ctagctgacg cgggattcat  2580
caaacaatac ggagattgct tgggagacat tgcggcgaga gatctaattt gcgcgcagaa  2640
gtttaacgga ttgacagtac taccgccgct actaaccgat gagatgattg cgcagtacac  2700
gtctgctcta ttggcgggaa caattacaag tggatggaca tttggagccg gtgccgctct  2760
acaaattccg tttgctatgc gaaatggcgta cagattcaac ggaatcggag taacccagaa  2820
cgtcttgtac gagaaccaga agctaatcgc gaaccagttc aattccgcga tcggaaagat  2880
ccaggacagt ctatcttcta ctgcttcgc gttgggaaag ctacaggatg tagtaaatca  2940
aaacgcgcag cgctaaaca ccttggtcaa gcaactatcc tctaacttcg gagcgatctc  3000
gtccgtccta aacgacatct tatccagact agatccaccg gaagcggagg tccagatcga  3060
tagactaatc actggaagat tgcagtccct acagacctac gtaaccacga aactaattag  3120
agcggcggag attagagcct ctgctaatct agctgcgacc aagatgtccg aatgtgtctt  3180
gggacaatcc aagagagtgg acttctgcgg aaagggatac cacctaatgt ctttcccaca  3240
atctgcgccg catggtgtcg tattcctaca tgtaacatat gtgccggcgc aagaaaagaa  3300
cttcacaaca gctccagcga tctgccatga tggaaaagct catttcccga gagagggagt  3360
ctttgtctct aacgaaactc attggttcgt cacccagaaa aacttctacg agccagat  3420
catcaccacc gacaacacat tcgtctcggg aaactgcgac gtggtcatcg gaatcgtaaa  3480
caataccgtc tacgatccgt tgcagccgga actagactcc ttcaaagaag agttggacaa  3540
gtacttcaag aaccacacct ctccggatgt ggacttggga gatatctctg gaatcaacgc  3600
gtccgtcgtc aacatccaga agaaatcga tagattgaac gaggtcgcga agaacttgaa  3660
cgagtcccta atcgacctac aagagctagg aaaatacag cagtacatca gtggccgtg  3720
```

```
gtacatctgg ctaggattca ttgctggact aattgcgatc gtcatggtca ccatcatgct  3780
atgctgtatg acctcctgtt gctcctgtct aaagggatgt tgttcctgcg gatcctgttg  3840
caagttcgat gaagatgata gtgaaccggt cctaaagggt gtcaagctac actacacaga  3900
gccagaggct taataatttt tat                                          3923
```

```
SEQ ID NO: 147          moltype = DNA   length = 3737
FEATURE                 Location/Qualifiers
source                  1..3737
                        mol_type = other DNA
                        organism = synthetic construct
SEQUENCE: 147
aaaaattgaa aataaataca aaggttcttg agggttgtgt taaattgaaa gcgagaaata  60
atcataagcc accatgttcg tgttcctagt cctactaccg ctagtctctt ctcagtgtgt  120
aaacctaaca acgagaacac aactaccacc ggcgtacacc aattctttca caagaggagt  180
atattacccg gacaaggtgt tcagatcctc cgtactacat tctacacagg acctattcct  240
accgttcttc tctaacgtaa catggttcca cgcgatccat gtctctggaa caaacggaac  300
gaagagattc gataacccgg tcttgccgtt caacgatggt gtatactttg cgtccaccga  360
gaagtccaac atcatcagag gatggatctt cggaaccacc ttggattcta agacccagtc  420
cttgctaatc gtcaacaacg cgaccaacgt cgtcatcaaa gtctgcgaat tccagttctg  480
taacgacccg ttcttgggag tctactacca caagaacaac aagtcctgga tggaatccga  540
gttcagagtc tactcttccg cgaacaactg caccttcgaa tatgtatctc agccgttcct  600
aatggaccta gagggaaagc agggaaactt caagaaccta agagagttcg tattccaagaa  660
catcgacgga tacttcaaga tctactccaa gcacactccg atcaacctag ttagagatct  720
accgcaagga ttctctgcgc tagaaccgtt agtagatttg ccgatcggaa tcaacatcac  780
cagattccag acactactag cgctacacag atcttaccta acgccgggag attcttcttc  840
tggatggact gctggtgctg cggcttatta tgtaggatac ctacagccga gaaccttcct  900
attgaagtac aacgaaaacg gaaccatcac cgatgccgta gattgtgctc tagatccgtc  960
atccgaaacg aagtgcaccc taaagtcttt caccgtcgag aagggaatct accagacctc  1020
caactttaga gtacagccga ccgaatccat cgtcagattt ccgaacatca cgaacctatg  1080
tccgttcgga gaagtgttca acgcgacaag atttgcgtct gtctatgcgt ggaacagaaa  1140
aagaatcagt aactgcgtcg cggactactc cgtcctatac aactctgcct ctttctccac  1200
gttcaaatgc tacggtgtat ctccgacaaa gctaaacgat ctatgcttca ccaacgtcta  1260
cgcggactcc ttcgtaatca gaggagatga agttagacag attgcgccgg gacaaactgg  1320
aaagatcgcg gattataact acaagctacc ggacgacttc accggatgtg taattgcgtg  1380
gaattcgaac aacctagact ccaaagtcgg aggaaactac aactacttgt acagactatt  1440
cagaaagtcc aacctaaagc cgttcgagag agacatctcc accgaaatct atcaggctgg  1500
atctacaccg tgtaatggtg tcgaaggatt caactgctac ttcccgctac agtcttacgg  1560
atttcaaccg acaaacggtg taggatatca gccgtacaga gtcgtcgtac tatccttcga  1620
actactacat gctccggcga cagtatgtgg accgaaaaag tctaccaacc tagtcaagaa  1680
caaatgcgtc aactttaact tcaacggact aaccggaacc ggtgtcctaa ccgaatctaa  1740
caagaagttt ctaccgttcc agcagttcgg aagagatatc gcggatacaa cagacgctgt  1800
cagagatccg caaaccttgg agatcctaga tatcacaccg tgttctttcg gtggtgtctc  1860
tgtaattact ccgggaacga acacctccaa tcaagtagcg gaggacgtgaa  1920
ctgtacagaa gtaccggtag ctattcacgc ggatcaacta acaccaactt ggagagtgta  1980
ctccaccgga tctaacgtat tccaaacaag agcgggatgt ctaatcggag cggaacacgt  2040
aaacaactcc tacgaatgtg atatcccgat tggagcggga atctgtgcgt cttaccaaac  2100
acaacaaac tctccgagaa gagcgagatc tgtagcctct caatctatta tcgcctacac  2160
catgtccttg ggagccgaaa attctgtcgc gtactccaac aattctatcg cgatcccgac  2220
aaacttcacc atctctgtaa caaccgagat cctaccggtg tctatgacca agacatctgt  2280
cgattgcacc atgtacatct gcggagattc caccgagtgc tccaacctac tactacagta  2340
cggatctttc tgtacccagc taaacagagc gttgactgga atcgctgtag agcaggataa  2400
gaacactcaa gaggtattcg cgcaagtcaa gcagatctat aagactccgc cgatcaagga  2460
cttcggaggt ttcaacttct ctcagatctt gccggatccg tccaaaccgt ctaagagatc  2520
tttcatcgag gacctactat tcaacaaagt caccctagct gacgcgggat tcatcaaaca  2580
atacggagat tgcttgggag acattgcggc gagagatcta atttgcgcgc agaagtttaa  2640
cggattgaca gtactaccgc cgctactaac cgatgagatg attgcgcagt acacgtctgt  2700
tctattggcg ggaacaatta caagtggatg gacatttgga gccggtgccg ctctacaaat  2760
tccgtttgct atgcaaatgg cgtacagatt caacggaatc ggagtaaccc agaacgtctt  2820
gtacgagaac cagaagctaa tcgcgaacca gttcaattcc gcgatcggaa agatccagga  2880
cagtctatct tctactgctt cggcgttggg aaaagctacag gatgtagtaa atcaaaacgc  2940
gcaggcgcta aacaccttgg tcaagcaact atcctctaac ttcggagcga tctcgtccgt  3000
cctaaacgac atcttatcca gactagataa ggtcgaagcg gaggtccaga tcgatagact  3060
aatcactgga agattgcagt ccctacgac ctacgtaaca cagcaactaa ttagagcggc  3120
ggagattgaa gcctctgcta atctagctgc gaccaagatg tccgaatgtg tcttgggaca  3180
atccaagaga gtggacttct gcggaaaggg ataccaccta atgtctttcc cacaatctgc  3240
gccgcatggt gtcgtattcc tacatgtaac atatgtgccg gcgcaagaaa agaacttcac  3300
aacagctcca gcgatctgcc atgatggaaa agctcatttc ccgagagagg gagtctttgt  3360
ctctaacgga actcattggt tcgtcaccca gagaaacttc tacgagccgc agatcatcac  3420
caccgacaac acattcgtct cgggaaactg cgacgtggtc atcggaatcg taaacaatac  3480
cgtctacgat ccgttgcagc cggaactaga ctccttcaaa gaagagttgg acaagtactt  3540
caagaaccac acctctccgg atgtggactt gggagatatc tctggaatca acgcgtccgt  3600
cgtcaacatc cagaaagaaa tcgatagatt gaacgaggtc gcgaagaact tgaacgagtc  3660
cctaatcgac ctacaagagc taggaaaata cgagcagtac atcaagtggc cggagccgga  3720
agcttaataa ttttttat                                                3737
```

```
SEQ ID NO: 148          moltype = DNA   length = 3743
FEATURE                 Location/Qualifiers
source                  1..3743
                        mol_type = other DNA
```

-continued

```
                            organism = synthetic construct
SEQUENCE: 148
aaaaattgaa aataaataca aaggttcttg agggttgtgt taaattgaaa gcgagaaata    60
atcataaccc ggggccacca tgttcgtgtt cctagtccta ctaccgctag tctcttctca   120
gtgtgtaaac ctaacaacga gaacacaact accaccggcg tacaccaatt ctttcacaag   180
aggagtatat tacccggaca aggtgttcag atcctccgta ctacattcta cacaggacct   240
attcctaccg ttcttctcta acgtaacatg gttccacgcg atccatgtct ctggaacaaa   300
cggaacgaag agattcgata acccggtctt gccgttcaac gatggtgtat actttgcgtc   360
caccgagaag tccaacatca tcagaggatg gatcttcgga accaccttgg attctaaagac  420
ccagtccttg ctaatcgtca acaacgcgac caacgtcgtc atcaaagtct gcgaattcca   480
gttctgtaac gacccgttct tgggagtcta ctaccacaag aacaacaagt cctggatgga   540
atccgagttc agagtctact cttccgcgaa caactgcacc ttcgaatatg tatctcagcc   600
gttcctaatg gacctagagg gaaagcaggg aaacttcaag aacctaagag agttcgtatt   660
caagaacatc gacggatact tcaagatcta ctccaagcac actccgatca acctagttag   720
agatctaccg caaggattct ctgcgctaga accgttagta gatttgccga tcggaatcaa   780
catcaccaga ttccagacac tactagcgct acacagatct tacctaacgc cgggagattc   840
ttcttctgga tggactgctg gtgctgcggc ttattatgta ggatacctac agccgagaac   900
cttcctattg aagtacaacg aaaacggaac catcaccgat gccgtagatt gtgctctaga   960
tccgctatcc gaaacgaagt gcaccctaaa gtctttcacc gtcgagaagg aatctacca   1020
gacctccaac tttagagtac agccgaccga atccatcgtc agatttccga acatcacgaa  1080
cctatgtccg ttcggagaag tgttcaacgc gacaagattt gcgtctgtct atgcgtggaa  1140
cagaaaaaga atcagtaact gcgtcgcgga ctactccgtc ctatacaact ctgcctcttt  1200
ctccacgttc aaatgctacg gtgtatctcc gacaaagcta aacgatctat gcttcaccaa  1260
cgtctacgcg gactccttcg taatcagagg agatgaagtt agacagattg cgccgggaca  1320
aactggaaag atcgcggatt ataactacaa gctaccggac gacttcaccg gatgtgtaat  1380
tgcgtggaat tcgaacaacc tagactccaa agtcggagga aactacaact acttgtacag  1440
actattcaga aagtccaacc taaagccgtt cgagagagac atctccaccg aaatctcatca  1500
ggctggatct acaccgtgta atggtgtcga aggattcaac tgctacttcc cgctacagtc  1560
ttacggattt caaccgacaa acggtgtagg atatcagccg tacagagtcg tcgtactatc  1620
cttcgaacta ctacatgctc cggcgacagt atgtggaccg aaaaagtcta ccaacctagt  1680
caagaacaaa tgcgtcaact ttaacttcaa cggactaacc ggaaccggtg tcctaaccga  1740
atctaacaag aagtttctac cgttccagca gttcggaaga gatatcgcgg atacaacaga  1800
cgctgtcaga gatccgcaaa ccttggagat cctagatatc acaccgtgtt ctttcggtgg  1860
tgtctctgta attactccgg gaacgaacac ctccaatcaa gtagcggtac tataccagga  1920
cgtgaactgt acagaagtac cggtagctat tcacgcggat caactaacac caacttggag  1980
agtgtactcc accggatcta acgtattcca aacaagagcg ggatgtctaa tcggagcgga  2040
acacgtaaac aactcctacg aatgtgatat cccgattgga gcgggaatct gtgcgtctta  2100
ccaaacacaa acaaactctc cgagaagagc gagatctgta gcctctcaat ctattatcgc  2160
ctacaccatg tccttgggag ccgaaaattc tgtcgcgtac tccaacaatt ctatcgcgat  2220
cccgacaaac ttcaccatct ctgtaacaac cgagatccta ccggtgtcta tgaccaagac  2280
atctgtcgat tgcaccatgt acatctgcgg agattccacc gagtgctcca acctactact  2340
acagtacgga tctttctgta cccagctaaa cagagcgttg actggaatcg ctgtagagca  2400
ggataagaac actcaagagg tattcgcgca agtcaagcag atctataaga ctccgccgat  2460
caaggacttc ggaggtttca acttctctca gatcttgccg gatccgtcca aaccgtctaa  2520
gagatctttc atcgaggacc tactattcaa caaagtcacc ctagctgacg cgggattcat  2580
caaacaatac ggagattgct tgggagacat tgcggcgaga gatctaattt gcgcgcagaa  2640
gtttaacgga ttgacagtac taccgccgct actaaccgat gagatgattg cgcagtacac  2700
gtctgctcta ttggcgggaa caattacaag tggatggaca tttggagccg gtgccgctct  2760
acaaattccg tttgctatgc aaatggcgta cagattcaac ggaatcggag taacccagaa  2820
cgtcttgtac gagaaccaga agctaatcgc gaaccagttc aattccgcga tcggaaagat  2880
ccaggacagt ctatcttcta ctgcttcggc gttgggaaag ctacaggatg tagtaaatca  2940
aaacgcgcag gcgctaaaca ccttggtcaa gcaactatcc tctaacttcg gagcgatctc  3000
gtccgtccta aacgacatct tatccagact agataaggtc gaagcggagg tccagatcga  3060
tagactaatc actggaagat tgcagtccct acagacctac gtaacacagc aactaattag  3120
agcggcggag attagagcct ctgctaatct agctgcgaac aagatgtccg aatgtgtctt  3180
gggacaatcc aagagagtgg acttctgcgg aaagggatac cacctaatgt ctttcccaca  3240
atctgcgccg catggtgtcg tattcctaca tgtaacatat gtgccggcgc aagaaaagaa  3300
cttcacaaca gctccagcga tctgccatga tggaaaagct catttcccga gagagggagt  3360
ctttgtctct aacggaactc attggttcgt caccagaga aacttctacg agccgcagat  3420
catcaccacc gacaacacat tcgtctcggg aaactgcgac gtggtcatcg gaatcgtaaa  3480
caataccgtc tacgatccgt tgcagccgga actagactcc ttcaaagaag agttggacaa  3540
gtacttcaag aaccacacct ctccggatgt ggacttggga gatatctctg gaatcaacgc  3600
gtccgtcgtc aacatccaga aagaaatcga tagattgaac gaggtcgcga agaacttgaa  3660
cgagtcccta atcgacctac aagagctagg aaaaatacga cagtacatca gtggccgga   3720
gccggaagct taataatttt tat                                          3743

SEQ ID NO: 149          moltype = DNA   length = 3737
FEATURE                 Location/Qualifiers
source                  1..3737
                        mol_type = other DNA
                        organism = synthetic construct
SEQUENCE: 149
aaaaattgaa aataaataca aaggttcttg agggttgtgt taaattgaaa gcgagaaata    60
atcataagcc accatgttcg tgttcctagt cctactaccg ctagtctctt ctcagtgtgt   120
aaacctaaca acgagaacac aactaccacc ggcgtacacc aattctttca caagaggagt   180
atattacccg gacaaggtgt tcagatcctc cgtactacat tctacacagg acctattcct   240
accgttcttc tctaacgtaa catggttcca cgcgatccat gtctctggaa caaacggaac   300
gaagagattc gataacccgg tcttgccgtt caacgatggt gtatactttg cgtccaccga   360
gaagtccaac atcatcagag gatggatctt cggaaccacc ttggattcta agaccagtc   420
```

-continued

```
cttgctaatc gtcaacaacg cgaccaacgt cgtcatcaaa gtctgcgaat tccagttctg    480
taacgacccg ttcttgggag tctactacca caagaacaac aagtcctgga tggaatccga    540
gttcagagtc tactcttccg cgaacaactg caccttcgaa tatgtatctc agccgttcct    600
aatggaccta gagggaaagc agggaaactt caagaaccta agagagttcg tattcaagaa    660
catcgacgga tacttcaaga tctactccaa gcacactccg atcaacctag ttagagatct    720
accgcaagga ttctctgcgc tagaaccgtt agtagatttg ccgatcggaa tcaacatcac    780
cagattccag acactactag cgctacacag atcttaccta acgccgggag attcttcttc    840
tggatggact gctggtgctg cggcttatta tgtaggatac ctacagccga gaaccttcct    900
attgaagtac aacgaaaacg gaaccatcac cgatgccgta gattgtgctc tagatccgat    960
atccgaaacg aagtgcaccc taaagtcttt caccgtcgag aagggaatct accagacctc   1020
caactttaga gtacagccga ccgaatccat cgtcagattt ccgaacatca cgaacctatg   1080
tccgttcgga gaagtgttca acgcgacaag atttgcgtct gtctatgcgt ggaacagaaa   1140
aagaatcagt aactgcgtcg cggactactc cgtcctatac aactctgcct ctttctccac   1200
gttcaaatgc tacggtgtat ctccgacaaa gctaaacgat ctatgcttca ccaacgtcta   1260
cgcggactcc ttcgtaatca gaggagatga agttagacag attgcgccgg gacaaactgg   1320
aaagatcgcg gattataact acaagctacc ggacgacttc accggatgtg taattgcgtg   1380
gaattcgaac aacctagact ccaaagtcgg aggaaactac aactacttgt acagactatt   1440
cagaaagtcc aacctaaagc cgttcgagag agacatctcc accgaaatct atcaggctgg   1500
atctacaccg tgtaatggtg tcgaaggatt caactgctac ttcccgctac agtcttacgg   1560
atttcaaccg acaaacggtg taggatatca gccgtacaga gtcgtcgtac tatccttcga   1620
actactacat gctccggcga cagtatgtgg accgaaaaag tctaccaacc tagtcaagaa   1680
caaatgcgtc aactttaact tcaacggact aaccggaacc ggtgtcctaa ccgaatctaa   1740
caagaagttt ctaccgttcc agcagttcgg aagagatatc gcggatacaa cagacgctgt   1800
cagagatccg caaaccttgg agatcctaga tatcacaccg tgttctttcg gtggtgtctc   1860
tgtaattact ccgggaacga acacctccaa tcaagtagcg gtactatacc aggacgtgaa   1920
ctgtacagaa gtaccggtag ctattcacgc ggatcaacta acaccaactt ggagagtgta   1980
ctccaccgga tctaacgtat tccaaacaag agcgggatgt ctaatcggag cggaacacgt   2040
aaacaactcc tacgaatgtg atatcccgat tggagcggga atctgtgcgt cttaccaaac   2100
acaaacaaac tctccgagaa gagcgagatc tgtagcctct caatctatta tcgcctacac   2160
catgtccttg ggagccgaaa attctgtcgc gtactccaac aattctatcg cgatcccgac   2220
aaacttcacc atctctgtaa caaccgagat cctaccggtg tctatgacca agacatctgt   2280
cgattgcacc atgtacatct gcggagattc caccgagtgc tccaacctac tactacagta   2340
cggatctttc tgtacccagc taaacagagc gttgactgga atcgctgtag agcaggataa   2400
gaacactcaa gaggtattcg cgcaagtcaa gcagatctat aagactccgc cgatcaagga   2460
cttcggaggt ttcaacttct ctcagatctt gccggatccg tccaaaccgt ctaagagatc   2520
tttcatcgag gacctactat tcaacaaagt caccctagct gacgcgggat tcatcaaaca   2580
atacggagat tgcttgggag acattgcggc gagagatcta atttgcgcgc agaagtttaa   2640
cggattgaca gtactaccgc cgctactaac cgatgagatg attgcgcagt cacgtctgc    2700
tctattgggc ggaacaatta caagtggatg gacatttgga gccggtgccg ctctacaaat   2760
tccgtttgct atgcaaatgg cgtacagatt caacggaatc ggagtaaccc agaacgtctt   2820
gtacgagaac cagaagctaa tcgcgaacca gttcaattcc gcgatcggaa agatccagga   2880
cagtctatct tctactgctt cggcgttggg aaagctacag gatgtagtaa atcaaaacg    2940
gcaggcgcta aacaccttgg tcaagcaact atcctctaac ttcggagcga tctcgtccgt   3000
cctaaacgac atcttatcca gactagatcc accggaagcg gaggtccaga tcgatagact   3060
aatcactgga agattgcagt ccctacgac ctacgtaaca cagcaactaa ttagagcggc    3120
ggagattaga gcctctgcta atctagctgc gaccaagatg tccgaatgtg tcttgggaca   3180
atccaagaga gtggacttct gcggaaaggg ataccaccta atgtctttcc cacaatctgc   3240
gccgcatggt gtcgtattcc tacatgtaac atatgtgccg gcgcaagaaa agaacttcac   3300
aacagctcca gcgatctgcc atgatggaaa agctcatttc ccgagagagg gagtctttgt   3360
ctctaacgga actcattggt tcgtcaccca gagaaacttc tacgagccgc agatcatcac   3420
caccgacaac acattcgtct cgggaaactg cgacgtggtc atcggaatcg taaacaatac   3480
cgtctacgat ccgttgcagc cggaactaga ctccttcaaa gaagagttgg acaagtactt   3540
caagaaccac acctctccgg atgtggactt gggagatatc tctggaatca acgcgtccgt   3600
cgtcaacatc cagaaagaaa tcgatagatt gaacgaggtc gcgaagaact tgaacgagtc   3660
cctaatcgac ctacaagagc taggaaaata cgagcagtac atcaagtggc cggagccgga   3720
agcttaataa tttttat                                                  3737
```

```
SEQ ID NO: 150            moltype = DNA   length = 3743
FEATURE                   Location/Qualifiers
source                    1..3743
                          mol_type = other DNA
                          organism = synthetic construct
SEQUENCE: 150
aaaaattgaa aataaataca aaggttcttg agggttgtgt aaattgaaa gcgagaaata     60
atcataaccc ggggccacca tgttcgtgtt cctagtccta ctaccgctag tctcttctca    120
gtgtgtaaac ctaacaacga gaacacaact accaccggcg tacaccaatt ctttcacaag    180
aggagtatat taccccggaca aggtgttcag atcctccgta ctacattcta cacaggacct    240
attcctaccg ttcttctcta acgtaacatg gttcacgcg atccatgtct ctggaacaaa     300
cggaacgaag agattcgata acccggtctt gccgttcaac gatggtgtat actttgcgtc    360
caccgagaag tccaacatca tcagaggatg gatcttcgga accaccttgg attctaaagac   420
ccagtccttg ctaatcgtca caacgcgac caacgtcgtc atcaaagtct gcgaattcca     480
gttctgtaac gacccgttct tgggagtcta ctaccacaag aacaacaagt cctggatgga    540
atccgagttc agagtctact cttccgcgaa caactgcacc ttcgaatatg tatctcagcc    600
gttcctaatg gacctagagg gaaagcaggg aaacttaag aacctaagag agttcgtatt     660
caagaacatc gacggatact tcaagatcta ctccaagcac actccgatca acctagttag    720
agatctaccg caaggattct ctgcgctaga accgttagta gatttgccga tcggaatcaa    780
catcaccaga ttccagacac tactagcgct acacagatct tacctaacgc cgggagattc    840
ttcttctgga tggactgctg gtgctgcggc ttattatgta ggatacctac agccgagaac    900
cttcctattg aagtacaacg aaaacggaac catcaccgat gccgtagatt gtgctctaga    960
```

-continued

```
tccgctatcc gaaacgaagt gcaccctaaa gtctttcacc gtcgagaagg gaatctacca   1020
gacctccaac tttagagtac agccgaccga atccatcgtc agatttccga acatcacgaa   1080
cctatgtccg ttcggagaag tgttcaacgc gacaagattt gcgtctgtct atgcgtggaa   1140
cagaaaaaga atcagtaact gcgtcgcgga ctactccgtc ctatacaact ctgcctcttt   1200
ctccacgttc aaatgctacg gtgtatctcc gacaaagcta aacgatctat gcttcaccaa   1260
cgtctacgcg gactccttcg taatcagagg agatgaagtt agacagattg cgccgggaca   1320
aactggaaag atcgcggatt ataactacaa gctaccggac gacttcaccg gatgtgtaat   1380
tgcgtggaat tcgaacaacc tagactccaa agtcggagga aactacaact acttgtacag   1440
actattcaga aagtccaacc taaagccgtt cgagagagac atctccaccg aaatctatca   1500
ggctggatct acaccgtgta atggtgtcga aggattcaac tgctacttcc cgctacagtc   1560
ttacggattt caaccgacaa acggtgtagg atatcagccg tacagagtcg tcgtactatc   1620
cttcgaacta ctacatgctc cggcgacagt atgtggaccg aaaaagtcta ccaacctagt   1680
caagaacaaa tgcgtcaact ttaacttcaa cggactaacc ggaaccggtg tcctaaccga   1740
atctaacaag aagtttctac cgttccagca gttcggaaga gatatcgcgg atacaacaga   1800
cgctgtcaga gatccgcaaa ccttggagat cctagatatc acaccgtgtt ctttcggtgg   1860
tgtctctgta attactccgg gaacgaacac ctccaatcaa gtagcggtac tataccagga   1920
cgtgaactgt acagaagtac cggtagctat tcacgcggat caactaacac caacttggag   1980
agtgtactcc accggatcta acgtattcca aacaagagcg ggatgtctaa tcggagcgga   2040
acacgtaaac aactcctacg aatgtgatat cccgattgga gcgggaatct gtgcgtctta   2100
ccaaacacaa acaaactctc cgagaagagc gagatctgta gcctctcaat ctattatcgc   2160
ctacaccatg tccttgggag ccgaaaattc tgtcgcgtac tccaacaatt ctatcgcgat   2220
cccgacaaac ttcaccatct ctgtaacaac cgagatccta ccggtgtcta tgaccaagac   2280
atctgtcgat tgcaccatgt acatctgcgg agattccacc gagtgctcca acctactact   2340
acagtacgga tctttctgta cccagctaaa cagagcgttg actggaatcg ctgtagagca   2400
ggataagaac actcaagagg tattcgcgca agtcaagcag atctataaga ctccgccgat   2460
caaggacttc ggaggtttca acttctctca gatcttgccg gatccgtcca aaccgtctaa   2520
gagatctttc atcgaggacc tactattcaa caaagtcacc ctagctgacg cgggattcat   2580
caaacaatac ggagattgct tgggagacat tgcggcgaga gatctaattt gcgcgcagaa   2640
gtttaacgga ttgacagtac taccgccgct actaaccgat gagatgattg cgcagtacac   2700
gtctgctcta ttggcgggaa caattacaag tggatgacca tttggagccg gtgccgctct   2760
acaaattccg tttgctatgc aaatggcgta cagattcaac ggaatcggag taacccagaa   2820
cgtcttgtac gagaaccaga agctaatcgc gaaccagttc aattccgcga tcggaaagat   2880
ccaggacagt ctatcttcta ctgcttcggc gttgggaaag ctacaggatg tagtaaatca   2940
aaacgcgcag gcgctaaaca ccttggtcaa gcaactactc tctaacttcg gagcgatctc   3000
gtccgtccta aacgacatct tatccagact agatccaccg gaagcggagg tccagatcga   3060
tagactaatc actggaagat tgcagtccct acagacctac gtaacacagc aactaattag   3120
agcggcggag attagagcct ctgctaatct agctgcgacc aagatgtccg aatgtgtctt   3180
gggacaatcc aagagagtgg acttctgcgg aaagggatac cacctaatgt ctttccccaca  3240
atctgccgcg catggtgtcg tattcctaca tgtaacatat gtgccggcgc aagaaaagaa   3300
cttcacaaca gctccagcga tctgccatga tggaaaagct catttcccga gagagggagt   3360
ctttgtctct aacggaactc attggttcgt cacccagaga aacttctacg agccgcagat   3420
catcaccacc gacaacacat tcgtctcggg aaactgcgac gtggtcatcg gaatcgtaaa   3480
caataccgtc tacgatccgt tgcagccgga actagactcc ttcaaagaag agttggacaa   3540
gtacttcaag aaccacacct ctccggatgt ggacttggga gatatctctg gaatcaacgc   3600
gtccgtcgtc aacatccaga aagaaatcga tagattgaac gaggtcgcga agaacttgaa   3660
cgagtcccta atcgacctac aagagctagg aaaaatacgag cagtacatca gtggccggga  3720
gccggaagct taataatttt tat                                            3743
```

```
SEQ ID NO: 151          moltype = DNA   length = 21
FEATURE                 Location/Qualifiers
source                  1..21
                        mol_type = other DNA
                        organism = synthetic construct
SEQUENCE: 151
agatcggaga tgactgcgat g                                                21

SEQ ID NO: 152          moltype = DNA   length = 21
FEATURE                 Location/Qualifiers
source                  1..21
                        mol_type = other DNA
                        organism = synthetic construct
SEQUENCE: 152
cgatggtagg tcagattgtc c                                                21

SEQ ID NO: 153          moltype = DNA   length = 26
FEATURE                 Location/Qualifiers
source                  1..26
                        mol_type = other DNA
                        organism = synthetic construct
SEQUENCE: 153
cagaagttaa taagcgtata gccatc                                           26

SEQ ID NO: 154          moltype = DNA   length = 67
FEATURE                 Location/Qualifiers
source                  1..67
                        mol_type = other DNA
                        organism = synthetic construct
SEQUENCE: 154
aaaaattgaa aataaataca aaggttcttg agggttgtgt taaattgaaa gcgagaaata    60
```

```
atcataa                                                                67

SEQ ID NO: 155          moltype = DNA  length = 28
FEATURE                 Location/Qualifiers
source                  1..28
                        mol_type = other DNA
                        organism = synthetic construct
SEQUENCE: 155
tttcattttg tttttttcta tgctataa                                         28

SEQ ID NO: 156          moltype = DNA  length = 4982
FEATURE                 Location/Qualifiers
source                  1..4982
                        mol_type = other DNA
                        organism = synthetic construct
SEQUENCE: 156
aaaaattgaa aataaataca aaggttcttg agggttgtgt taaattgaaa gcgagaaata   60
atcataaata agcccggggc caccatgttc gtgttcctag tcctactacc gctagtctct  120
tctcagtgtg taaacctaac aacgagaaca caactaccac cggcgtacac caattctttc  180
acaagaggag tatattaccc ggacaaggtg ttcagatcct ccgtactaca ttctacacag  240
gacctattcc taccgttctt ctctaacgta acatggttcc acgcgatcca tgtctctgga  300
acaaacggaa cgaagagatt cgataaaccg gtcttgaccc tcaacgatgg tgtatacttt  360
gcgtccaccg agaagtccaa catcatcaga ggatggatct tcggaaccac cttggattct  420
aagacccagt ccttgctaat cgtcaacaac gcgaccaacg tcgtcatcaa agtctgcgaa  480
ttccagttct gtaacgaccc gttcttggga gtctactacc acaagaacaa caagtcctgg  540
atggaatccg agttcagagt ctactcttcc gcgaacaact gcaccttcga atatgtatct  600
cagccgttcc taatggacct agagggaaag cagggaaact tcaagaacct aagagagttc  660
gtattcaaga acatcgacgg atacttcaag atctactcca agcacactcc gatcaaccta  720
gttagagatc taccgcaagg attctctgcg ctagaaccgt tagtagattt gccgatcgga  780
atcaacatca ccagattcca gacactacta gcgctacaca gatcttacct aacgccggga  840
gattcttctt ctggatggac tgctggtgct gcggcttatt atgtaggata cctacagccg  900
agaaccttcc tattgaagta caacgaaaac ggaaccatca ccgatgccgt agattgtgct  960
ctagatccgc tatccgaaac gaagtgcacc ctaaagtctt tcaccgtcga gaagggaatc 1020
taccagacct ccaactttag agtacagccg accgaatcca tcgtcagatt tccgaacatc 1080
acgaacctat gtccgttcgg agaagtgttc aacgcgacaa gatttgcgtc tgtctatgcg 1140
tggaacagaa aaagaatcag taactgcgtc gcggactact ccgtcctata caactctgcc 1200
tctttctcca cgttcaaatg ctacggtgta tctccgacaa agctaaacga tctatgcttc 1260
accaacgtct acgcggactc cttcgtaatc agaggagatg aagttagaca gattgcgccg 1320
ggacaaactg gaaagatcgc ggattataac tacaagctac cggacgactt caccggatgt 1380
gtaattgcgt ggaattcgaa caacctagac tccaaagtcg gaggaaaacta caactacttg 1440
tacagactat tcagaaagtc caacctaaag ccgttcgaga gagacatctc caccgaaatc 1500
tatcaggctg gatctacacc gtgtaatggt gtcgaaggat tcaactgcta cttcccgcta 1560
cagtcttacg gatttcaacc gacaaacggt gtaggatatc agccgtacag agtcgtcgta 1620
ctatccttcg aactactaca tgctccggcg acagtatgtg gaccgaaaaa gtctaccaac 1680
ctagtcaaga acaaatgcgt caactttaac ttcaacggac taaccggaac cggtgtccta 1740
accgaatcta acaagaagtt tctaccgttc cagcagttcg gaagagatat cgcggataca 1800
acagacgctg tcagagatcc gcaaaccttg gagatcctag atatcacacc gtgttctttc 1860
ggtggtgtct ctgtaattac tccgggaacg aacacctcca tcaagtagc ggtactatac 1920
caggacgtga actgtacaga agtaccggta gctattcacg cggatcaact aacaccaact 1980
tggagagtgt actccaccgg atctaacgta ttccaaacaa gagcgggatg tctaatcgga 2040
gcggaacacg taaacaactc ctacgaatgt gatatccgta ttggagcggg aatctgtgcg 2100
tcttaccaaa cacaaacaaa ctctccgaga gagcgagat ctgtagcctc tcaatctatt 2160
atcgcctaca ccatgtcctt gggagccgaa aattctgtcg cgtactccaa caattctatc 2220
gcgatcccga caaacttcac catctctgta acaaccgaga tcctaccggt gtctatgacc 2280
aagacatctg tcgattgcac catgtacatc tgcggagatt ccaccgagtg ctccaaccta 2340
ctactacagt acggatcttt ctgtacccag ctaaacagag cgttgactgg aatcgctgta 2400
gagcaggata agaacactca agaggtattc gcgcaagtca agcagatcta taagactccg 2460
ccgatcaagg acttcggagg tttcaacttc tctcagatct tgccggatcc gtccaaaccg 2520
tctaagagat ctttcatcga ggacctacta ttcaacaaag tcaccctagc tgacgcggga 2580
ttcatcaaac aatacggaga ttgcttggga gacattgcgg cgagagatat aatttcgcag 2640
cagaagttta acggattgac agtactaccg ccgctactaa ccgatgagat gattgcgcag 2700
tacacgtctg ctctattggc gggaacaatt acaagtggat ggacatttgg agccggtgcc 2760
gctctacaaa ttccgtttgc tatgcaaatg gcgtacagat tcaacggaat cggagtaacc 2820
cagaacgtct tgtacgagaa ccagaagcta atcgcgaacc agttcaattc cgcgatcgga 2880
aagatccagg acagtctatc ttctactgct tcggcgttgg gaaagctaca ggatgtagta 2940
aatcaaaacg cgcaggcgct aaacaccttg gtcaagcaac tatcctctaa cttcggagcg 3000
atctcgtccg tcctaaacga catcttatcc agactagata aggtcgaagc ggaggtccag 3060
atcgatagac taatcactgg aagattgcag tccctacaga cctacgtaac acagcaacta 3120
attagagcgg cggagattag agcctctgct aatctagctg cgaccaagat gtccgaatgt 3180
gtcttgggac aatccaagag agtggacttc tgcggaaagg gataccacct aatgtctttc 3240
ccacaatctg cgccgcatgg tgtcgtattc ctacatgtaa catatgtgcc ggcgcaagaa 3300
aagaacttca caacagctcc agcgatctgc catgatggaa aagctcattt cccgagagag 3360
ggagtctttg tctctaacgg aactcattgg ttcgtcaccc agagaaactt ctacgagccg 3420
cagatcatca ccaccgacaa cacattcgtc tcgggaaact gcgacgtggt catcggaatc 3480
gtaaacaata ccgtctacga tccgttgcag ccggaactag actccttcaa gaagagttg 3540
gacaagtact tcaagaacca cacctctccg gatgtggact tgggagatat ctctggaatc 3600
aacgcgtccg tcgtcaacat ccagaaagaa atcgatagat tgaacgaggt cgcgaagaac 3660
ttgaacgagt ccctaatcga cctacaagag ctaggaaaat acgagcagta catcaagtgg 3720
ccgtggtaca tctggctagg attcattgct ggactaattg cgatcgtcat ggtcaccatc 3780
```

```
atgctatgct gtatgacctc ctgttgctcc tgtctaaagg gatgttgttc ctgcggatcc  3840
tgttgcaagt tcgatgaaga tgatagtgaa ccggtcctaa agggtgtcaa gctacactac  3900
acagagccag aggcttaata attttatgt cgacctttca ttttgttttt ttctatgcta  3960
taagccacca tgtactcctt cgtgtccgaa gaaaccggaa ccttgatcgt caactccgtc  4020
ctactattcc tagcgttcgt cgtgttccta ctagtaaccc tagctatcct aaccgcgcta  4080
agactatgtg cgtactgctg caacatcgtc aacgtgtccc tagtgaagcc gtccttctac  4140
gtctactcca gagtcaagaa cctaaactcc tctagagtcc cggacctact agttgagcca  4200
gaggcttaat aaataaaaat tattaagcct ctggctcctg gactagtaga gcgatattat  4260
cggaactgga ggagtggtcg gtgtttagct tgtagttccc gattctgtat ctagaatacg  4320
ccgcaaatcc agaatctccc gcgactcttt gagaggctcc caacttatag tacgatagg  4380
ttctagaggt cgctacggtg atctccttcg gtaggtcctt gatgtcacat cttcctaggt  4440
ggtgtccgc aattcttaga tgtcctctta ggatgaccgc tccgataacc aattcggatt  4500
ccaatagcgg tctggttagg atggttccat gtagcggtac gttcaatagg atgttcgtct  4560
ccgggttgaa cgaccacata gatctggttc tcgcgaatag tctgaaggag gcgatgaagt  4620
aggatagcca cattagtcct actagacaag ccatagcgat cgcgattcca cctgtgatcc  4680
agttgattct gtagaccgca gctagaacga agcaggccaa ggtgaccggc catagtagcc  4740
ataggaagat tagcttgatg atgtacaaga atctgttcct gttcgcgtac gcgaactgta  4800
gtaggcagat ccaggttagg aataggaatc cgatgactag gttccactgc tctagtagct  4860
tcttcaactc ttcgacggtg atggttccgt tagaatccgc catggtggct tatgattatt  4920
tctcgctttc aatttaacac aaccctcaag aacctttgta tttattttca attttctgc  4980
ag                                                                 4982
```

```
SEQ ID NO: 157            moltype = DNA   length = 4982
FEATURE                   Location/Qualifiers
source                    1..4982
                          mol_type = other DNA
                          organism = synthetic construct
SEQUENCE: 157
aaaaattgaa aataaataca aaggttcttg agggttgtgt taaattgaaa gcgagaaata  60
atcataaata agcccggggc caccatgttc gtgttcctag tcctactacc gctagtctct  120
tctcagtgtg taaacctaac aacgagaaca caactaccac cggcgtacac caattctttc  180
acaagaggag tatattaccc ggacaaggtg ttcagatcct ccgtactaca ttctacacag  240
gacctattcc taccgttctt ctctaacgta acatggttcc acgcgatcca tgtctctgga  300
acaaacggaa cgaagagatt cgataaacccg gtcttgccgt tcaacgatgg tgtatacttt  360
gcgtccaccg agaagtccaa catcatccga ggatggatct tcggaaccac cttggattct  420
aagacccagt ccttgctaat cgtcaacaac gcgaccaacg tcgtcatcaa agtctgcgaa  480
ttccagttct gtaacgaccc gttcttggga gtctactacc acaagaacaa caagtcctgg  540
atggaatccg agttcagagt ctactcttcc gcgaacaact gcaccttcga atatgtatct  600
cagccgttcc taatggacct agagggaaag cagggaaact tcaagaacct aagagagttc  660
gtattcaaga acatcgacgg atacttcaag atctactcca agcacactcc gatcaaccta  720
gttagagatc taccgcaagg attctctgcg ctagaaccgt tagtagattt gccgatcgga  780
atcaacatca ccagattcca gacactacta gcgctacaca gatcttacct aacgccggga  840
gattcttctt ctggatggac tgctggtgct gcggcttatt atgtaggata cctacagccg  900
agaaccttcc tattgaagta caacgaaaac ggaaccatca ccgatgccgt agattgtgct  960
ctagatccgc tatccgaaac gaagtgcacc ctaaagtctt tcaccgtcga gaagggaatc  1020
taccagacct ccaactttag agtacagccg accgaatcca tcgtcagatt tccgaacatc  1080
acgaacctat gtccgttcgg agaagtgttc aacgcgacaa gatttgcgtc tgtctatgcc  1140
tggaacagaa aaagaatcag taactgcgtc gcggactact ccgtcctata caactctgcc  1200
tctttctcca cgttcaaatg ctacggtgta tctccgacaa agctaaacga tctatgcttc  1260
accaacgtct acgcggactc cttcgtaatc agaggagatg aagttagaca gattgcgccg  1320
ggacaaactg gaaagatcgc ggattataac tacaagctac cggacgactt caccggatgt  1380
gtaattgcgt ggaattcgaa caacctagac tccaaagtcg gaggaaaacta caactacttg  1440
tacagactat tcagaaagtc caacctaaag ccgttcgaga gagacatctc caccgaaatc  1500
tatcaggctg gatctacacc gtgtaatggt gtcgaaggat tcaactgcta cttcccgcta  1560
cagtcttacg gatttcaacc gacaaacggt gtaggatatc agccgtacag agtcgtcgta  1620
ctatccttcg aactactaca tgctccggcg acagtatgtg gaccgaaaaa gtctaccaac  1680
ctagtcaaga acaaatgcgt caactttaac ttcaacggac taaccggaac cggtgtccta  1740
accgaatcta acaagaagtt tctaccgttc cagcagttcg gaagagatat cgcggataca  1800
acagacgctg tcagagatcc gcaaaaccttg gagatcctag atatcacacc gtgttctttc  1860
ggtggtgtct ctgtaattac tccgggaacg aacacctcca atcaagtagc ggtactatac  1920
caggacgtga actgtacaga agtaccggta gctattcacg cggatcaact aacaccaact  1980
tggagagtga actccaccgg atctaacgta ttccaaacaa gagcgggatg tctaatcgga  2040
gcggaacacg taaacaactc ctacgaatgt gatatcccga ttggagcggg aatctgtgcg  2100
tcttaccaaa cacaaacaaa ctctccgaga agagcgagat cgtagcctc tcaatctatt  2160
atcgcctaca ccatgtcctt gggagccgaa aattctgtcg cgtactccaa caattctatc  2220
gcgatcccga caaacttcac catctctgta acaaccgaga tcctaccggt gtctatgacc  2280
aagacatctg tcgattgcac catgtacatc tgcggagatt ccaccgagtg ctccaaccta  2340
ctactacagt acggatctttt ctgtacccag ctaaacagag cgttgactgg aatcgctgta  2400
gagcaggata agaacactca agaggtattc gcgcaagtca agcagatcta taagactccg  2460
ccgatcaagg acttcggagg tttcaacttc tctcagatct tgccggatcc gtccaaaccg  2520
tctaagagat ctttcatcga ggacctacta ttcaacaaag tcacccctagc tgacgcggga  2580
ttcatcaaac aatacggaga ttgcttggga gacattgcgg cgagagatct aatttgcgcg  2640
cagaagttta acggattgac agtactaccg ccgctactaa ccgatgagat gattgcgcag  2700
tacacgtctg ctctattggc gggaacaatt acaagtggat ggacatttgg agcgggtgcc  2760
gctctacaaa ttccgtttgc tatgcaaatg gcgtacagat tcaacggaat cggagtaacc  2820
cagaacgtct gtacgagaa ccagaagcta atcgcgaacc agttcaattc cgcgatcgga  2880
aagatccagg acagtctatc ttctactgct tcggcgttgg gaaagctaca ggatgtagta  2940
aatcaaaacg cgcaggcgct aaacaccttg gtcaagcaac tatcctctaa cttcggagcg  3000
atctcgtccg tcctaaacga catcttatcc agactagatc caccggaagc ggaggtccag  3060
```

```
atcgatagac taatcactgg aagattgcag tccctacaga cctacgtaac acagcaacta   3120
attagagcgg cggagattag agcctctgct aatctagctg cgaccaagat gtccgaatgt   3180
gtcttgggac aatccaagag agtggacttc tgcggaaagg gataccacct aatgtctttc   3240
ccacaatctg cgccgcatgg tgtcgtattc ctacatgtaa catatgtgcc ggcgcaagaa   3300
aagaacttca caacagctcc agcgatctgc catgatggaa aagctcattt cccgagagag   3360
ggagtctttg tctctaacgg aactcattgg ttcgtcaccc agagaaactt ctacgagccg   3420
cagatcatca ccaccgacaa cacattcgtc tcgggaaact gcgacgtggt catcggaatc   3480
gtaaacaata ccgtctacga tccgttgcag ccggaactag actccttcaa agaagagttg   3540
gacaagtact tcaagaacca cacctctccg gatgtggact tgggagatat ctctggaatc   3600
aacgcgtccg tcgtcaacat ccagaaagaa atcgatagat tgaacgaggt cgcgaagaac   3660
ttgaacgagt ccctaatcga cctacaagag ctaggaaaat acgagcagta catcaagtgg   3720
ccgtggtaca tctggctagg attcattgct ggactaattg cgatcgtcat ggtcaccatc   3780
atgctatgct gtatgacctc ctgttgctcc tgtctaaagg gatgttgttc ctgccggatcc   3840
tgttgcaagt tcgatgaaga tgatagtgaa ccggtcctaa aggtgtcaa gctacactac   3900
acagagccag aggcttaata attttttatgt cgacctttca ttttgttttt ttctatgcta   3960
taagccacca tgtactcctt cgtgtccgaa gaaaccggaa ccttgatcgt caactccgtc   4020
ctactattcc tagcgttcgt cgtgttccta ctagtaaccc tagctatcct aaccgcgcta   4080
agactatgtg cgtactgctg caacatcgtc aacgtgtccc tagtgaagcc gtccttctac   4140
gtctactcca gagtcaagaa cctaaactcc tctagagtcc cggacctact agttgagcca   4200
gaggcttaat aaataaaaat tattaagcct ctggctcctg gactagtaga gcgatattat   4260
cggaactgga ggagtggtcg gtgtttagct tgtagttccc gattctgtat ctagaatacg   4320
ccgcaaatcc agaatctccc gcgactcttt gagaggctcc caacttatag tacgataggg   4380
ttctagaggt cgctacggtg atctccttcg gtaggtcctt gatgtcacat cttcctaggt   4440
ggtgtcccgc aattcttaga tgtcctctta ggatgaccgc tccgataacc aattcggatt   4500
ccaatagcgg tctggttagg atggttccat gtagcggtac gttcaatagg atgttcgtct   4560
ccgggttgaa cgaccacata gatctggttc tcgcgaatag tctgaaggag gcgatgaagt   4620
aggatagcca cattagtcct actagacaag ccatagcgat cgcgattcca cctgtgatcc   4680
agttgattct gtagaccgca gctagaacga agcaggccaa ggtgaccggc catagtagcc   4740
ataggaagat tagcttgatg atgtacaaga atctgttcct gttcgcgtac gcgaactgta   4800
gtaggcagat ccaggttagg aataggaatc cgatgactag gttccactgc tctagtagct   4860
tcttcaactc ttcgacggtg atggttccgt tagaatccgc catggtggct tatgattatt   4920
tctcgctttc aatttaacac aaccctcaag aacctttgta tttattttca atttttctgc   4980
ag                                                                   4982

SEQ ID NO: 158          moltype = DNA  length = 2018
FEATURE                 Location/Qualifiers
source                  1..2018
                        mol_type = other DNA
                        organism = synthetic construct
SEQUENCE: 158
aaaaattgaa aataaataca aaggttcttg agggttgtgt taaattgaaa gcgagaaata   60
atcataaata agcccggggc caccatgttc gtgttcctag tcctactacc gctagtctct   120
tctgtcagat ttccgaacat cacgaaccta tgtccgttcg gagaagtgtt caacgcgaca   180
agatttgcgt ctgtctatgc gtggaacaga aaaagaatca gtaactgcgt cgcggactac   240
tccgtcctat acaactctgc ctctttctcc acgttcaaat gctacggtgt atctccgaca   300
aagctaaacg atctatgctt caccaacgtc tacgcggact ccttcgtaat cagaggagat   360
gaagttagac agattgcgcc gggacaaact ggaaagatcg cggattataa ctacaagcta   420
ccggacgact tcaccggatg tgtaattgcg tggaattcga acaacctaga ctccaaagtc   480
ggaggaaact acaactactt gtacagacta ttcagaaagt ccaacctaaa gccgttcgag   540
agagacatct ccaccgaaat ctatcaggct ggatctacac cgtgtaatgg tgtcgaagga   600
ttcaactgct acttcccgct acagtcttac ggatttcaac cgacaaacgg tgtaggatat   660
cagccgtaca gagtcgtcgt actatccttc gaactactac atgctccggc gacagtatgt   720
ggaccgaaaa agtctaccaa cctagtcaag aacaaatgcg tcaactttaa cttcaacgga   780
ctaaccggaa ccggtgtcct aaccgaatct aacaagaagt ttctaccgtt ccagcagttc   840
ggaagagata tcgcggatac aacagacgct gtcagagatc cgcaaacctt ggagatccta   900
gatatcacac cgtgttcttt cggtggtgtc tctgtaattg agccagaggc ttaataattt   960
ttatgtcgac ctttcatttt gttttttct atgctataag ccaccatgta ctccttcgtg   1020
tccgaagaaa ccggaacctt gatcgtcaac tccgtcctac tattcctagc gttcgtcgtg   1080
ttctactag taaccctagc tatcctaacc gcgctaagac tatgtgcgta ctgctgcaac   1140
atcgtcaacg tgtccctagt gaagccgtcc ttctacgtct actccagagt caagaaccta   1200
aactcctcta gagtcccgga cctactagtt gagccagagg cttaataaat aaaaattatt   1260
aagcctctgg ctcctggact agtagagcga tattatcgga actggaggag tggtcggtgt   1320
ttagcttgta gttcccgatt ctgtatctag aatacgccgc aaatccagaa tctcccgcga   1380
ctctttgaga ggctcccaac ttatagtacg atagggttct agaggtcgct acggtgatgg   1440
ccttcggtag gtccttgatg tcacatcttc ctaggtggtg tcccgcaatt cttagatgtc   1500
ctcttaggat gaccgctccg ataaccaatt cggattccaa tagcggtctg gttaggatgg   1560
ttccatgtag cggtacgttc aataggatgt tcgtctccgg gttgaacgac cacatagatc   1620
tggttctcgc gaatagtctg aaggagcga tgaagtagga tagccacatt agtcctacta   1680
gacaagccat agcgatcgcg attccacctg tgatccagtt gattctgtag accgcagctag   1740
gaacgaagca ggccaaggtg accggccata gtagccatag gaagattagc ttgatgatgt   1800
acaagaatct gttcctgttc gcgtacgcga actgtagtag gcagatccag gttaggaata   1860
ggaatccgat gactaggttc cactgctcta gtagcttctt caactcttcg acggtgatgg   1920
ttccgttaga atccgccatg gtggcttatg attatttctc gctttcaatt taacacaacc   1980
ctcaagaacc tttgtatttt ttttcaattt ttctgcag                          2018

SEQ ID NO: 159          moltype = DNA  length = 4982
FEATURE                 Location/Qualifiers
source                  1..4982
                        mol_type = other DNA
```

-continued

```
                       organism = synthetic construct
SEQUENCE: 159
aaaaattgaa aataaataca aaggttcttg agggttgtgt taaattgaaa gcgagaaata   60
atcataaaat acccggggcc accatgttcg tgttcctagt cctactaccg ctagtctctt  120
ctcagtgtgt aaacctaaca acgagaacac aactaccacc ggcgtacacc aattctttca  180
caagaggagt atattacccg gacaaggtgt tcagatcctc cgtactacat tctacacagg  240
acctattcct accgttcttc tctaacgtaa catggttcca cgcgatccat gtctctggaa  300
caaacggaac gaagagattc gataacccgg tcttgccgtt caacgatggt gtatactttg  360
cgtccaccga gaagtccaac atcatcagag gatggatctt cggaaccacc ttggattcta  420
agacccagtc cttgctaatc gtcaacaacg cgaccaacgt cgtcatcaaa gtctgcgaat  480
tccagttctg taacgacccg ttcttgggag tctactacca caagaacaac aagtcctgga  540
tggaatccga gttcagagtc tactcttccg cgaacaactg caccttcgaa tatgtatctc  600
agccgttcct aatggaccta gagggaaagc agggaaactt caagaaccta agagagttcg  660
tattcaagaa catcgacgga tacttcaaga tctactccga gcacactccg atcaacctag  720
ttagagatct accgcaagga ttctctgcgc tagaaccgtt agtagatttg ccgatcggaa  780
tcaacatcac cagattccag acactactag cgctacacag atcttaccta acgccgggag  840
attcttcttc tggatggact gctggtgctg cggcttatta tgtaggatac ctacagccga  900
gaaccttcct attgaagtac aacgaaaacg gaaccatcac cgatgccgta gattgtgctc  960
tagatccgct atccgaaacg aagtgcaccc taaagtcttt caccgtcgag aagggaatct 1020
accagacctc caactttaga gtacagccga ccgaatccat cgtcagattt ccgaacatca 1080
cgaacctatg tccgttcgga gaagtgttca acgcgacaag atttgcgtct gtctatgcgt 1140
ggaacagaaa aagaatcagt aactgcgtcg cggactactc cgtcctatac aactctgcct 1200
ctttctccac gttcaaatgc tacggtgtat ctccgacaaa gctaaacgat ctatgcttca 1260
ccaacgtcta cgcggactcc ttcgtaatca gaggagatga agttagacag attgcgccgg 1320
gacaaactgg aacgatcgcg gattataact acaagctacc ggacgacttc accggatgtg 1380
taattgcgtg gaattcgaac aacctagact ccaaagtcgg aggaaactac aactacttgt 1440
acagactatt cagaaagtcc aacctaaagc cgttcgagag agacatctcc accgaaatct 1500
atcaggctgg atctacaccg tgtaatggtg tcaagggatt caactgctac ttcccgctac 1560
agtcttacgg atttcaaccg acatacggtg taggatatca gccgtacaga gtcgtcgtac 1620
tatccttcga actactacat gctccggcga cagtatgtgg accgaaaaag tctaccaacc 1680
tagtcaagaa caaatgcgtc aactttaact tcaacggact aaccggaacc ggtgtcctaa 1740
ccgaatctaa caagaagttt ctaccgttcc agcagttcgg aagagatatc gcggatacaa 1800
cagacgctgt cagagatccg caaaccttgg agatcctaga tatcacaccg tgttctttcg 1860
gtggtgtctc tgtaattact ccgggaacga acacctccaa tcaagtagcg gtactatacc 1920
aggacgtgaa ctgtacagaa gtaccggtag ctattcacgc ggatcaacta acaccaactt 1980
ggagagtgta ctccaccgga tctaacgtat tccaaacaag agcgggatgt ctaatcggag 2040
cggaacacgt aaacaactcc tacgaatgtg atatcccgat tggagcggga atctgtgcgt 2100
cttaccaaac acaaacaaac tctccgagaa gagcgagatc tgtagcctct caatctatta 2160
tcgcctacac catgtccttg ggagccgaaa attctgtcgc gtactccaac aattctatcg 2220
cgatcccgac aaacttcacc atctctgtaa caaccgagat cctaccggtg tctatgacca 2280
agacatctgt cgattgcacc atgtacatct gcggagattc caccgagtgc tccaacctac 2340
tactacagta cggatctttc tgtacccagc taaacagagc gttgactgga atcgctgtag 2400
agcaggataa gaacactcaa gaggtattcg cgcaagtcaa gcagatctat aagactccgc 2460
cgatcaagga cttcggaggt ttcaacttct ctcagatctt gccggatccg tccaaaccgt 2520
ctaagagatc tttcatcgag gacctactat tcaacaaagt caccctagct gacgcgggat 2580
tcatcaaaca atacggagat tgcttgggag acattgcggc gagagatcta atttgcgcgc 2640
agaagtttaa cggattgaca gtactaccgc cgctactaac cgatgagatg attgcgcagt 2700
acacgtctgc tctattggcg ggaacaatta caagtggatg gacatttgga gccggtgccg 2760
ctctacaaat tccgtttgct atgcaaatgg cgtacagatt caacggaatc ggagtaaccc 2820
agaacgtctt gtacgagaac cagaagctaa tcgcgaacca gttcaattcc gcgatcggaa 2880
agatccagga cagtctatct tctactgctt cggcgttggg aaagctacag gatgtagtaa 2940
atcaaaacgc gcaggcgcta aacaccttgg tcaagcaact atcctctaac ttcggagcga 3000
tctcgtccgt cctaaacgac atcttatcca gactagatcc accggaagcg gaggtccaga 3060
tcgatagact aatcactgga agattgcagt ccctacagac ctacgtaaca cagcaactaa 3120
ttagagcggc ggagattaga gcctctgcta atctagctgc gaccaagatg tccgaatgtg 3180
tcttgggaca atccaagaga gtggacttct gcggaaaggg ataccaccta atgtctttcc 3240
cacaatctgc gccgcatggt gtcgtattcc tacatgtaac atatgtgccg gcgcaagaaa 3300
agaacttcac aacagctcca gcgatctgcc atgatggaaa agctcatttc ccgagagagg 3360
gagtctttgt ctctaacgga actcattggt tcgtcaccca gagaaacttc tacgagccgc 3420
agatcatcac caccgacaac acattcgtct cgggaaactg cgacgtggtc atcggaatcg 3480
taaacaatac cgtctacgat ccgttgcagc cggaactaga ctccttcaaa gaagagttgg 3540
acaagtactt caagaaccac acctctccgg atgtggactt gggagatatc tctggaatca 3600
acgcgtccgt cgtcaacatc cagaaagaaa tcgatagatt gaacgaggtc gcgaagaact 3660
tgaacgagtc cctaatcgac ctacaagagc taggaaaata cgagcagtac atcaagtggc 3720
cgtggtacat ctggctagga ttcattgctg gactaattgc gatcgtcatg gtcaccatca 3780
tgctatgctg tatgacctcc tgttgctcct gtctaaaggg atgttgttcc tgcggattcc 3840
tgttgcaagt tcgatgaaga tgatagtgaa ccggtcctaa agggtgtcaa gctacactac 3900
acagagccag aggcttaata atttttatgt cgacctttca ttttgttttt ttctatgcta 3960
taagccacca tgtactcctt cgtgtccgaa gaaaccggaa ccttgatcgt caactccgtc 4020
ctactattcc tagcgttcgt cgtgttccta ctagtaaccc tagctatcct aaccgcgcta 4080
agactatgtg cgtactgctg caacatcgtc aacgtgtccc tagtgaagcc gtccttctac 4140
gtctactcca gagtcaagaa cctaaactcc tctagagtcc cggacctact agttgagcca 4200
gaggcttaat aaataaaaat tattaagcct ctggctcctg gactagtaga gcgatattat 4260
cggaactgga ggagtggtcg gtgtttagct tgtagttccc gattctgtat ctagaatacg 4320
ccgcaaatcc agaatctccc gcgactcttt gagaggctcc caacttatag tacgataggg 4380
ttctagaggt cgctacggtg atctcccttcg gtaggtcctt gatgtcacat cttcctaggt 4440
ggtgtcccgc aattcttaga tgtcctctta ggatgaccgc tccgtaaccc aattcggatt 4500
ccaatagcgg tctggttagg atggttccat gtagcggtac gttcaatagg atgttcgtct 4560
ccgggttgaa cgaccacata gatctggttc tcgcgaatag tctgaaggag gcgatgaagt 4620
```

-continued

```
aggatagcca cattagtcct actagacaag ccatagcgat cgcgattcca cctgtgatcc   4680
agttgattct gtagaccgca gctagaacga agcaggccaa ggtgaccggc catagtagcc   4740
ataggaagat tagcttgatg atgtacaaga atctgttcct gttcgcgtac gcgaactgta   4800
gtaggcagat ccaggttagg aataggaatc cgatgactag gttccactgc tctagtagct   4860
tcttcaactc ttcgacggtg atggttccgt tagaatccgc catggtggct tatgattatt   4920
tctcgctttc aatttaacac aaccctcaag aacctttgta tttattttca atttttctgc   4980
ag                                                                   4982

SEQ ID NO: 160         moltype = DNA  length = 5000
FEATURE                Location/Qualifiers
source                 1..5000
                       mol_type = other DNA
                       organism = synthetic construct
SEQUENCE: 160
aaaaattgaa aataaataca aaggttcttg agggttgtgt taaattgaaa gcgagaaata   60
atcataaata agcccggggc caccatgttc gtgttcctag tcctactacc gctagtctct   120
tctcagtgtg taaacctaac aacgagaaca caactaccac cggcgtacac caattctttc   180
acaagaggag tatattaccc ggacaaggtg ttcagatcct ccgtactaca ttctacacag   240
gacctattcc taccgttctt ctctaacgta acatggttcc acgcgatcca tgtctctgga   300
acaaacggaa cgaagagatt cgataacccg gtcttgccgt tcaacgatgg tgtatacttt   360
gcgtccaccg agaagtccaa catcatcaga ggatggatct tcggaaccac cttggattct   420
aagacccagt ccttgctaat cgtcaacaac gcgaccaacg tcgtcatcaa agtctgcgaa   480
ttccagttct gtaacgaccc gttcttggga gtcactaccc acaagaacaa caagtcctgg   540
atggaatccg agttcagagt ctactcttcc gcgaacaact gcaccttcga atatgtatct   600
cagccgttcc taatggacct agagggaaag cagggaaact tcaagaacct aagagagttc   660
gtattcaaga acatcgacgg atacttcaag atctactcca agcacactcc gatcaaccta   720
gttagagatc taccgcaagg attctctgcg ctagaaccgt tagtagattt gccgatcgga   780
atcaacatca ccagattcca gacactacta gcgctacaca gatcttacct aacgccggga   840
gattcttctt ctggatggac tgctggtgct gcggcttatt atgtaggata cctacagccg   900
agaaccttcc tattgaagta caacgaaaac ggaaccatca ccgatgccgt agattgtgct   960
ctagatccgc tatccgaaac gaagtgcacc ctaaagtctt tcaccgtcga gaagggaatc   1020
taccagacct ccaactttag agtacagccg accgaatcca tcgtcagatt tccgaacatc   1080
acgaacctat gtccgttcgg agaagtgttc aacgcgacaa gatttgcgtc tgtctatgcg   1140
tggaacagaa aaagaatcag taactgcgtc gcggactact ccgtcctata caactctgcc   1200
tctttctcca cgttcaaatg ctacggtgta tctccgacaa agctaaacga tctatgcttc   1260
accaacgtct acgcggactc cttcgtaatc agaggagatg aagttagaca gattcgcccg   1320
ggacaaactg gaacgatcgc ggattataac tacaagctac cggacgactt caccggatgt   1380
gtaattgcgt ggaattcgaa caacctagac tccaaagtcg gaggaaacta caactacttg   1440
tacagactat tcagaaagtc caacctaaag ccgttcgaga gagacatctc caccgaaatc   1500
tatcaggctg gatctacacc gtgtaatggt gtcaagggat tcaactgcta cttcccgcta   1560
cagtcttacg gatttcaacc gacatacggt gtaggatatc agccgtacag agtcgtcgta   1620
ctatccttcg aactactaca tgctccggcg acagtatgtg gaccgaaaaa gtctaccaac   1680
ctagtcaaga acaaatgcgt caactttaac ttcaacggac taaccggaac cggtgtccta   1740
accgaatcta acaagaagtt tctaccgttc cagcagttcg gaagagatat cgcggataca   1800
acagacgctg tcagagatcc gcaaaccttg gagatcctag atatcacacc gtgttctttc   1860
ggtggtgtct ctgtaattac tccgggaacg aacacctcca tcaagtagc ggtactatac   1920
caggacgtga actgtacaga agtaccggta gctattcacg cggatcaact aacaccaact   1980
tggagagtgt actccaccgg atctaacgta ttccaaacaa gagcgggatg tctaatcgga   2040
gcggaacacg taaacaactc ctacgaatgt gatatcccga ttggagcggg aatctgtgcg   2100
tcttaccaaa cacaaacaaa ctctccgaga agagcgagat ctgtagcctc tcaatctatt   2160
atcgcctaca ccatgtcctt gggagccgaa aattctgtcg cgtactccaa caattcatc   2220
gcgatcccga caaacttcac catctctgta acaaccgaga tcctaccggt gtctatgacc   2280
aagacatctg tcgattgcac catgtacatc tgcggagatt ccaccgagtg ctccaaccta   2340
ctactacagt acggatcttt ctgtacccag ctaaacagag cgttgactgg aatcgctgta   2400
gagcaggata agaacactca agaggtattc gcgcaagtca agcagatcta taagactccg   2460
ccgatcaagg acttcggagg tttcaacttc tctcagatct tgcctgatcc gtccaaaccg   2520
tctaagagat ctttcatcga ggacctacta ttcaacaaag tcaccctagc tgacgcggga   2580
ttcatcaaac aatacggaga ttgcttggga gacattgcgg cgagagatct aatttgcgcg   2640
cagaagttta acggattgac agtactaccg ccgctactaa ccgatgagat gattgcgcag   2700
tacacgtctg ctctattggc gggaacaatt acaagtggat ggacatttgg agccggtgcc   2760
gctctacaaa ttccgtttgc tatgcaaatg gcgtacagat tcaacggaat cggagtaacc   2820
cagaacgtct tgtacgagaa ccagaagcta atcgcgaacc agttcaattc cgcgatcggt   2880
aagatccagg acagtctatc ttctactgct tcggcgttgg gaaagctaca ggatgtagta   2940
aatcaaaacg cgcaggcgct aaacaccttg gtcaagcaac tatcctctaa cttcggagcg   3000
atctcgtccg tcctaaacga catcttatcc agactagatc caccggaagc ggaggtccag   3060
atcgatagac taatcactgg aagattgcag tccctacaga cctacgtaac acagcaacta   3120
attagagcgg cggagattag agcctctgct aatctagctg cagccaagat gtccgaatgt   3180
gtcttgggac aatccaagag agtggacttc tgcggaaagg gataccacct aatgtctttc   3240
ccacaatctg cgccgcatgg tgtcgtattc ctacatgtaa catatgtgcc ggcgcaagaa   3300
aagaacttca caacagctcc agcgatctgc catgatggaa aagctcattt cccgagagag   3360
ggagtctttg tctctaacgg aactcattgg ttcgtcaccc agagaaactt ctacgagccg   3420
cagatcatca ccaccgacaa cacattcgtc tcgggaaaat gcgacgtggt catcggaatc   3480
gtaaacaata ccgtctacga tccgttgcag ccggaactag actccttcaa agaagagttg   3540
gacaagtact tcaagaacca cacctctccg gatgtggact tgggagatat ctctggaatc   3600
aacgcgtccg tcgtcaacat ccagaaagaa atcgatagat tgaacgaggt cgcgaagaac   3660
ttgaacgagt ccctaatcga cctacaagag ctaggaaaat acgagcagta catcaagtgg   3720
ccgtggtaca tctggctagg attcattgct ggactaattg cgatcgtcat ggtcaccatc   3780
```

-continued

```
atgctatgct gtatgacctc ctgttgctcc tgtctaaagg gatgttgttc ctgcggatcc   3840
tgttgcaagt tcgatgaaga tgatagtgaa ccggtcctaa agggtgtcaa gctacactac   3900
acataataat ttttatgcgg ccgcgagctc cgcttttat agtaagtttt tcacccataa    3960
ataataaata caataattaa tttctcgtaa aagtagaaaa tatattctaa tttattgcac   4020
ggtgccacca tggcggattc taacggaacc atcaccgtcg aagagttgaa gaagctacta   4080
gagcagtgga acctagtcat cggattccta ttcctaacct ggatctgcct actacagttc   4140
gcgtacgcga acaggaacag attcttgtac atcatcaagc taatcttcct atggctacta   4200
tggccggtca ccttggcctg cttcgttcta gctgcggtct acagaatcaa ctggatcaca   4260
ggtggaatcg cgatcgctat ggcttgtcta gtaggactaa tgtggctatc ctacttcatc   4320
gcctccttca gactattcgc gagaaccaga tctatgtggt cgttcaaccc gggacgaac    4380
atcctattga acgtaccgct acatggaacc atcctaacca gaccgctatt ggaatccgaa   4440
ttggttatcg gagcggtcat cctaagagga catctaagaa ttgcgggaca ccacctagga   4500
agatgtgaca tcaaggacct accgaaggag atcaccgtag cgacctctag aaccctatcg   4560
tactataagt tgggagcctc tcaaagagtc gcgggagatt ctggatttgc ggcgtattct   4620
agatacagaa tcgggaacta caagctaaac accgaccact cctccagttc cgataatatc   4680
gctctactag tccagtaata attttatat gcatccgcgg tttcattttg ttttttttcta   4740
tgctataaat gccaccatgt actccttcgt gtccgaagaa accggaacct tgatcgtcaa   4800
ctccgtccta ctattcctag cgttcgtcgt gttcctacta gtaaccctag ctatcctaac   4860
cgcgctaaga ctatgtgcgt actgctgcaa catcgtcaac gtgtccctag tgaagccgtc   4920
cttctacgtc tactccagag tcaagaacct aaactcctct agagtcccgg acctactagt   4980
ttaataattt ttatgtcgac                                               5000
```

```
SEQ ID NO: 161           moltype = AA  length = 283
FEATURE                  Location/Qualifiers
source                   1..283
                         mol_type = protein
                         organism = synthetic construct
SEQUENCE: 161
MFVFLVLLPL VSSVRFPNIT NLCPFGEVFN ATRFASVYAW NRKRISNCVA DYSVLYNSAS   60
FSTFKCYGVS PTKLNDLCFT NVYADSFVIR GDEVRQIAPG QTGTIADYNY KLPDDFTGCV   120
IAWNSNNLDS KVGGNYNYLY RLFRKSNLKP FERDISTEIY QAGSTPCNGV KGFNCYFPLQ   180
SYGFQPTYGV GYQPYRVVVL SFELLHAPAT VCGPKKSTNL VKNKCVNFNF NGLTGTGVLT   240
ESNKKFLPFQ QFGRDIADTT DAVRDPQTLE ILDITPCSFG GVS                     283
```

```
SEQ ID NO: 162           moltype = AA  length = 279
FEATURE                  Location/Qualifiers
source                   1..279
                         mol_type = protein
                         organism = synthetic construct
SEQUENCE: 162
MFVFLVLLPL VSSNITNLCP FGEVFNATRF ASVYAWNRKR ISNCVADYSV LYNSASFSTF   60
KCYGVSPTKL NDLCFTNVYA DSFVIRGDEV RQIAPGQTGK IADYNYKLPD DFTGCVIAWN   120
SNNLDSKVGG NYNYLYRLFR KSNLKPFERD ISTEIYQAGS TPCNGVEGFN CYFPLQSYGF   180
QPTNGVGYQP YRVVVLSFEL LHAPATVCGP KKSTNLVKNK CVNFNFNGLT GTGVLTESNK   240
KFLPFQQFGR DIADTTDAVR DPQTLEILDI TPCSFGGVS                          279
```

```
SEQ ID NO: 163           moltype = AA  length = 283
FEATURE                  Location/Qualifiers
source                   1..283
                         mol_type = protein
                         organism = synthetic construct
SEQUENCE: 163
MFVFLVLLPL VSSVRFPNIT NLCPFGEVFN ATRFASVYAW NRKRISNCVA DYSVLYNSAS   60
FSTFKCYGVS PTKLNDLCFT NVYADSFVIR GDEVRQIAPG QTGKIADYNY KLPDDFTGCV   120
IAWNSNNLDS KVGGNYNYLY RLFRKSNLKP FERDISTEIY QAGSTPCNGV EGFNCYFPLQ   180
SYGFQPTNGV GYQPYRVVVL SFELLHAPAT VCGPKKSTNL VKNKCVNFNF NGLTGTGVLT   240
ESNKKFLPFQ QFGRDIADTT DAVRDPQTLE ILDITPCSFG GVS                     283
```

```
SEQ ID NO: 164           moltype = AA  length = 339
FEATURE                  Location/Qualifiers
source                   1..339
                         mol_type = protein
                         organism = synthetic construct
SEQUENCE: 164
MFVFLVLLPL VSSNITNLCP FGEVFNATRF ASVYAWNRKR ISNCVADYSV LYNSASFSTF   60
KCYGVSPTKL NDLCFTNVYA DSFVIRGDEV RQIAPGQTGT IADYNYKLPD DFTGCVIAWN   120
SNNLDSKVGG NYNYLYRLFR KSNLKPFERD ISTEIYQAGS TPCNGVKGFN CYFPLQSYGF   180
QPTYGVGYQP YRVVVLSFEL LHAPATVWYI WLGFIAGLIA IVMVTIMLCC MTSCCSCLKG   240
CCSCGSCCKF DEDDSEPVLK GVKLHYTCGP KKSTNLVKNK CVNFNFNGLT GTGVLTESNK   300
KFLPFQQFGR DIADTTDAVR DPQTLEILDI TPCSFGGVS                          339
```

What is claimed is:

1. A recombinant modified vaccinia Ankara (rMVA) viral vector comprising a heterologous nucleic acid sequence encoding a Spike(S) protein, a Membrane (M) protein, and an Envelope (E) protein derived from severe acute respiratory syndrome-coronavirus 2 (SARS-CoV2) operably linked to one or more promoters compatible with poxvirus expression systems.

2. The rMVA of claim 1, wherein the S protein comprises the amino acid sequence of SEQ ID NO: 1, or an amino acid sequence at least 95% homologous thereto.

3. The rMVA of claim 1, wherein the S protein comprises the amino acid sequence of SEQ ID NO: 6, or an amino acid sequence at least 95% homologous thereto.

4. The rMVA of claim 1, wherein the M protein comprises an amino acid sequence of SEQ ID NO: 43, or an amino acid sequence at least 95% homologous thereto.

5. The rMVA of claim 1, wherein the E protein comprises an amino acid sequence of SEQ ID NO: 40, or an amino acid sequence at least 95% homologous thereto.

6. The rMVA of claim 1, wherein the rMVA heterologous nucleic acid sequence comprises a nucleic acid sequence selected from the group consisting of SEQ ID NOs: 46, 47, and 156, or a nucleic acid sequence at least 95% homologous thereto.

7. The rMVA of claim 1, wherein the promoters are selected from the group consisting of a p11 promoter, pmH5 promoter, pH5 promoter, p7.5 promoter, pSyn promoter, pHyb promoter, and a combination thereof.

8. A method of inducing an immune response in a human comprising administering an effective amount of an rMVA viral vector of claim 1 to the human.

9. A recombinant modified vaccinia Ankara (rMVA) viral vector comprising a heterologous nucleic acid sequence encoding a stabilized Spike(S) protein comprising proline substitutions corresponding to amino acid positions K986 and V987 of SEQ ID NO: 8, a Membrane (M) protein, and an Envelope (E) protein derived from severe acute respiratory syndrome-coronavirus 2 (SARS-CoV2) operably linked to a promoter compatible with poxvirus expression systems.

10. The rMVA of claim 9, wherein the stabilized S protein comprises the amino acid sequence of SEQ ID NO:8, or an amino acid sequence at least 95% homologous thereto.

11. The rMVA of claim 9, wherein the stabilized S protein comprises the amino acid sequence of SEQ ID NO:11, or an amino acid sequence at least 95% homologous thereto.

12. The rMVA of claim 9, wherein the M protein comprises an amino acid sequence of SEQ ID NO: 43, or an amino acid sequence at least 95% homologous thereto.

13. The rMVA of claim 9, wherein the E protein comprises an amino acid sequence of SEQ ID NO: 40, or an amino acid sequence at least 95% homologous thereto.

14. The rMVA of claim 9, wherein the rMVA heterologous nucleic acid sequence comprises a nucleic acid sequence selected from the group consisting of SEQ ID NOs: 48, 49, 50, 157, 159, or 160, and a nucleic acid sequence at least 95% homologous thereto.

15. The rMVA of claim 9, wherein the promoters are selected from the group consisting of a p11 promoter, pmH5 promoter, pH5 promoter, p7.5 promoter, pSyn promoter, pHyb promoter, and a combination thereof.

16. A method of inducing an immune response in a human comprising administering an effective amount of an rMVA viral vector of claim 9 to the human.

17. The rMVA of claim 1, wherein, upon expression in a host cell, the S protein, M protein, and E protein are capable of together forming a virus-like particle (VLP).

18. The rMVA of claim 10, wherein, upon expression in a host cell, the stabilized S protein, M protein, and E protein are capable of together forming a Virus-like particle (VLP).

19. The rMVA of claim 2, wherein the S protein comprises one or more amino acid substitutions selected from the group consisting of K417T, K417N, E484K, N501Y, and a combination thereof, wherein K417T, K417N, E484K, N501Y correspond to amino acid positions 417, 484, and 501 of SEQ ID NO: 1.

20. The rMVA of claim 10, wherein the stabilized S protein comprises one or more amino acid substitutions selected from the group consisting of K417T, K417N, E484K, N501Y, and a combination thereof, wherein K417T, K417N, E484K, N501Y correspond to amino acid positions 417, 484, and 501 of SEQ ID NO: 8.

21. The rMVA of claim 2, wherein the S protein comprises the amino acid sequence of SEQ ID NO:1.

22. The rMVA of claim 3, wherein the S protein comprises the amino acid sequence of SEQ ID NO:6.

23. The rMVA of claim 4, wherein the M protein comprises an amino acid sequence of SEQ ID NO:43.

24. The rMVA of claim 5, wherein the E protein comprises an amino acid sequence of SEQ ID NO:40.

25. The rMVA of claim 10, wherein the stabilized S protein comprises the amino acid sequence of SEQ ID NO:8.

26. The rMVA of claim 11, wherein the stabilized S protein comprises the amino acid sequence of SEQ ID NO:11.

27. The rMVA of claim 12, wherein the M protein comprises an amino acid sequence of SEQ ID NO:43.

28. The rMVA of claim 13, wherein the E protein comprises an amino acid sequence of SEQ ID NO:40.

* * * * *